United States Patent
Smith et al.

(10) Patent No.: US 12,089,426 B2
(45) Date of Patent: Sep. 10, 2024

(54) PHOTOACTIVE COMPOUNDS FOR VAPOR DEPOSITED ORGANIC PHOTOVOLTAIC DEVICES

(71) Applicant: Ubiquitous Energy, Inc., Redwood City, CA (US)

(72) Inventors: Austin Smith, Redwood City, CA (US); Matthew E. Sykes, Chicago, IL (US); Vineet Kumar, Fremont, CA (US); Douglas R. Robello, Webster, NY (US); John A. Love, Mountain View, CA (US); Ajara Safko, Redwood City, CA (US); Selvam Subramaniyam, High Point, NC (US); Richa Pandey, Sunnyvale, CA (US); Miles C. Barr, Redwood City, CA (US)

(73) Assignee: Ubiquitous Energy, Inc., Redwood City, CA (US)

( * ) Notice: Subject to any disclaimer, the term of this patent is extended or adjusted under 35 U.S.C. 154(b) by 0 days.

(21) Appl. No.: 17/519,360

(22) Filed: Nov. 4, 2021

(65) Prior Publication Data
US 2022/0149298 A1    May 12, 2022

Related U.S. Application Data

(60) Provisional application No. 63/109,722, filed on Nov. 4, 2020, provisional application No. 63/140,744, filed
(Continued)

(51) Int. Cl.
*H10K 30/20* (2023.01)
*C07D 495/04* (2006.01)
(Continued)

(52) U.S. Cl.
CPC ........... *H10K 30/20* (2023.02); *C07D 495/04* (2013.01); *C07D 495/10* (2013.01);
(Continued)

(58) Field of Classification Search
CPC .............. H01L 51/424; H01L 51/0008; H01L 51/0058; H01L 51/0068; H01L 51/0069;
(Continued)

(56) References Cited

U.S. PATENT DOCUMENTS 3,598,582 A    8/1971 Herrick et al.
4,164,431 A    8/1979 Tang
(Continued)

FOREIGN PATENT DOCUMENTS

CN    105646559 A  *  6/2016
CN    110964036 A     4/2020
(Continued)

OTHER PUBLICATIONS

Hui Huang, "Very Large Silacylic Substituent Effects on Response in Silole-Based Polymer Transistors" Chem. Mater. 2011, 23, 2185-2200 (Year: 2011).*

(Continued)

*Primary Examiner* — Michael Y Sun
(74) *Attorney, Agent, or Firm* — Kilpatrick Townsend & Stockton LLP

(57) ABSTRACT

Photoactive compounds are disclosed. The disclosed compounds can exhibit molecular structural elements tending to increase the evaporability of the compounds, such as by including geometric core disruption by use of conformationally restricted side groups instead of freely rotatable side groups or use of indandione moieties instead of dicyanomethyleneindanone moieties. The disclosed photoactive compounds include those with an imine-bridging linking moiety, which can shift the optical properties to a more red-shifted (Continued)

absorbance as compared to compounds with an alkene-bridging linking moiety. The disclosed photoactive compounds can be used in organic photovoltaic devices, such as visibly transparent or opaque photovoltaic devices.

24 Claims, 33 Drawing Sheets

Related U.S. Application Data on Jan. 22, 2021, provisional application No. 63/141,387, filed on Jan. 25, 2021, provisional application No. 63/140,758, filed on Jan. 22, 2021, provisional application No. 63/141,390, filed on Jan. 25, 2021, provisional application No. 63/275,311, filed on Nov. 3, 2021.

(51) Int. Cl.
| | |
|---|---|
| C07D 495/10 | (2006.01) |
| C07D 495/14 | (2006.01) |
| C07D 495/20 | (2006.01) |
| C07D 495/22 | (2006.01) |
| C07F 7/08 | (2006.01) |
| H10K 71/16 | (2023.01) |
| H10K 85/40 | (2023.01) |
| H10K 85/60 | (2023.01) |
| H10K 30/82 | (2023.01) |

(52) U.S. Cl.
CPC ......... *C07D 495/14* (2013.01); *C07D 495/20* (2013.01); *C07D 495/22* (2013.01); *C07F 7/0816* (2013.01); *H10K 71/16* (2023.02); *H10K 85/40* (2023.02); *H10K 85/626* (2023.02); *H10K 85/655* (2023.02); *H10K 85/656* (2023.02); *H10K 85/657* (2023.02); *H10K 85/6576* (2023.02); *H10K 30/82* (2023.02); *H10K 71/164* (2023.02)

(58) Field of Classification Search
CPC ............. H01L 51/0071; H01L 51/0074; H01L 51/0094; H01L 51/001; H01L 51/442; H01L 51/4253; C07D 495/04; C07D 495/10; C07D 495/14; C07D 495/20; C07D 495/22; C07F 7/0816; Y02E 10/549
See application file for complete search history.

(56) References Cited

U.S. PATENT DOCUMENTS

| | | | |
|---|---|---|---|
| 2004/0028943 | A1 | 2/2004 | Hartmann et al. |
| 2012/0211082 | A1 | 8/2012 | Akiyama et al. |
| 2013/0167931 | A1 | 7/2013 | Hildebrandt et al. |
| 2013/0324685 | A1 | 12/2013 | Aso et al. |
| 2014/0144509 | A1 | 5/2014 | Fadhel et al. |
| 2015/0090994 | A1 | 4/2015 | Kim et al. |
| 2017/0155047 | A1 | 6/2017 | Dorok et al. |
| 2018/0366668 | A1 | 12/2018 | Barr et al. |
| 2022/0140266 | A1 | 5/2022 | Smith et al. |
| 2022/0149298 | A1 | 5/2022 | Smith et al. |
| 2022/0242881 | A1 | 8/2022 | Kumar et al. |

FOREIGN PATENT DOCUMENTS

| | | | | |
|---|---|---|---|---|
| GB | 2001499.9 | | 5/2021 | |
| WO | 2014026244 | A1 | 2/2014 | |
| WO | WO-2014026244 | A1 * | 2/2014 | ........... C07D 407/10 |
| WO | 2015044377 | A1 | 4/2015 | |
| WO | 2018065350 | A1 | 4/2018 | |
| WO | 2018232358 | A1 | 12/2018 | |
| WO | 2019221386 | A1 | 11/2019 | |
| WO | 2021156605 | A1 | 8/2021 | |

OTHER PUBLICATIONS

Masaya Hirade "Effects of Intramolecular Donor-Acceptor Interactions on Bimolecular Recombination in Small-Molecule Organic Photovoltaic Cells" J. Phys. Chem. C 2013, 117, 4986-4991 (Year: 2013).*
Rocío Domínguez "Cyclopentadithiophene-based co-oligomers for solution-processed organic solar cells" Dyes and Pigments 143 (2017) 112-122 (Year: 2017).*
T. Benincori "Steric Control of Conductivity in Highly Conjugated Polythiophenes" Chem. Mater. 2001, 13, 1665-1673 (Year: 2001).*
Weixuan Zeng "Prediction of Oscillator Strength and Transition Dipole Moments with the Nuclear Ensemble Approach for Thermally Activated Delayed Fluorescence Emitters" (Year: 2019).*
PCT/US2021/058125, "International Search Report and Written Opinion", Mar. 15, 2022, 11 pages.
Gao, et al., "A New Nonfullerene Acceptor with Near Infrared Absorption for High Performance Ternary-Blend Organic Solar Cells with Efficiency Over 13%", Advanced Science, vol. 5, Mar. 25, 2018, pp. 1-6.
Lee, et al., "Bandgap Narrowing in Non-Fullerene Acceptors: Single Atom Substitution Leads to High Optoelectronic Response Beyond 1000 nm", Advanced Energy Materials, vol. 8, No. 24, Jun. 28, 2018, pp. 1-20.
Lin, et al., "A Low-Energy-Gap Organic Dye for High-Performance Small-Molecule Organic Solar Cells", Journal of the American Chemical Society, vol. 133, Sep. 9, 2011, pp. 15822-15825.
Lin, et al., "An Electron Acceptor Challenging Fullerenes for Efficient Polymer Solar Cells", Advanced Materials, vol. 27, No. 7, Jan. 7, 2015, pp. 1170-1174.
Meng, et al., "Organic and Solution-Processed Tandem Solar Cells with 17.3% Efficiency", Science, vol. 361, No. 6407, Sep. 14, 2018, pp. 1094-1098.
Pang, et al., "Alkyl Chain Length Effects of Polymer Donors on the Morphology and Device Performance of Polymer Solar Cells with Different Acceptors", Advanced Energy Materials, vol. 9, No. 30, Jul. 9, 2019, 40 pages.
PCT/US2021/058125, "Invitation to Pay Additional Fees and, Where Applicable Protest Fee", Jan. 21, 2022, 2 pages.
Shalev, et al., "Effect of Crystal Density on Sublimation Properties of Molecular Organic Semiconductors", Organic Electronics, vol. 14, No. 1, Jan. 2013, pp. 94-99.
Shi, et al., "Terthieno[3,2-b]Thiophene (6T) Based Low Band-Gap Fused-Ring Electron Acceptor for High Efficiency Solar Cell with a High Short-Circuit Current Density and Low Open-Circuit Voltage Loss", Advanced Energy Materials, vol. 8, No. 12, Jan. 19, 2018, 23 pages.
Yu, et al., "Diffusion-Limited Crystallization: A Rationale for the Thermal Stability of Non-Fullerene Solar Cells", ACS Applied Materials & Interfaces, vol. 11, No. 24, Jun. 7, 2019, pp. 21766-21774.
Zhang, et al., "Panchromatic Ternary Photovoltaic Cells Using a Nonfullerene Acceptor Synthesized Using C—H Functionalization", Chemistry of Materials, vol. 30, No. 2, Jan. 3, 2018, pp. 309-313.
PCT/US2022/013413, "International Search Report and Written Opinion", Apr. 8, 2022, 10 pages.
U.S. Appl. No. 17/519,361, "Non-Final Office Action", Nov. 10, 2022, 13 pages.
Baert, et al., "A Bridged Low Band Gap A-D-A Quaterthiophene as Efficient Donor for Organic Solar Cells", Journal of Materials Chemistry, Nov. 12, 2014.
U.S. Appl. No. 17/519,361, "Non-Final Office Action", Jul. 20, 2023, 24 pages.
Leitner, et al., "Influence of Alkyl Chain Length in S,N-Heteropentacenes on the Performance of Organic Solar Cells", Materials Chemistry Frontiers, vol. 2, 2018, pp. 959-968.

(56) References Cited

OTHER PUBLICATIONS

"Dipolar Bond", Compendium of Chemical Terminology, 2nd edition, Gold Book, 2012, 712 page.
Cho, "Skewed Starlight Suggests Particle Masses Changed Over Eons", Science, vol. 312, No. 5772, 2006, p. 348.
Kast, et al., "Acceptor-Substituted S,N-Heteropentacenes of Different Conjugation Length: Structure-Property Relationships and Solar Cell Performance", Advanced Functional Materials, Apr. 30, 2015, pp. 3414-3424.
March, "Advanced Organic Chemistry: Reactions, Mechanisms and Structure", 4th edition, 1992, pp. 293-293.
PCT/US2021/058125, "International Preliminary Report on Patentability", May 19, 2023, 8 pages.
Ukhin, et al., "Uncommon Condensations of 1, 2, 3-triketone 2-oximes with O-Phenylenediamine", Mendeleev Communications, vol. 29, No. 1, 2019, pp. 111-113.
Xian, et al., "Efficient Exciton Dissociation Enabled by the End Group Modification in Non-Fullerene Acceptors", The Journal of Physical Chemistry, vol. 124, No. 14, Mar. 16, 2020, pp. 7691-7698.
U.S. Appl. No. 17/519,364, "Final Office Action", Aug. 30, 2023, 21 pages.
Peltier, et al., "N-Cyanoimine as an Electron-Withdrawing Functional Group for Organic Semiconductors: Example of Dihydroindacenodithiophene Positional Isomers", Journal of Materials Chemistry C, vol. 6, 2018, pp. 13197-13210.

\* cited by examiner

FIG. 39A (3900): TPBi (50 nm) / Ag (8 nm) / TPBi:C$_{60}$ (75:25)(5 nm) / ClAlPc:IX (50:50)(40 nm) / p-6P (5 nm) / MoO$_3$ (8 nm) / ITO / Glass Substrate

FIG. 39B (3901): TPBi (50 nm) / Ag (8 nm) / TPBi:C$_{60}$ (75:25)(5 nm) / TAPC:XIII:C$_{60}$ (10:10:80)(40 nm) / p-6P (5 nm) / MoO$_3$ (8 nm) / ITO / Glass Substrate

FIG. 39C (3902): TPBi (50 nm) / Ag (8 nm) / TPBi:C$_{60}$ (75:25)(5 nm) / XVII (5 nm) / SubNc:XVII (50:50)(10 nm) / SubNc (5 nm) / MoO$_3$ (8 nm) / ITO / Glass Substrate

FIG. 39D (3903): TPBi (50 nm) / Ag (8 nm) / TPBi:C$_{60}$ (75:25)(5 nm) / LXXV:C$_{70}$ (30:70)(15 nm) / p-6P (5 nm) / MoO$_3$ (8 nm) / ITO / Glass Substrate

PHOTOACTIVE COMPOUNDS FOR VAPOR DEPOSITED ORGANIC PHOTOVOLTAIC DEVICES

CROSS-REFERENCE TO RELATED APPLICATIONS

This application claims the benefit of and priority to U.S. Provisional Application No. 63/109,722, filed on Nov. 4, 2020, U.S. Provisional Application No. 63/140,744, filed on Jan. 22, 2021, and U.S. Provisional Application No. 63/141,387, filed on Jan. 25, 2021, U.S. Provisional Application No. 63/140,758, filed on Jan. 22, 2021, U.S. Provisional Application No. 63/141,390, filed on Jan. 25, 2021, and U.S. Provisional Application No. 63/275,311, filed on Nov. 3, 2021, which are hereby incorporated by reference in their entireties.

FIELD

This application relates generally to the field of optically active materials and devices, and, more particularly, to photoactive materials for use in organic photovoltaic devices, photovoltaic devices, and methods for making photovoltaic devices.

BACKGROUND

The surface area necessary to take advantage of solar energy remains an obstacle to offsetting a significant portion of non-renewable energy consumption. For this reason, low-cost, transparent, organic photovoltaic (OPV) devices that can be integrated onto window panes in homes, skyscrapers, and automobiles are desirable. For example, window glass utilized in automobiles and architecture are typically 70-80% and 55-90% transmissive, respectively, to the visible spectrum, e.g., light with wavelengths from about 450 to 650 nanometers (nm). The limited mechanical flexibility, high module cost and, more importantly, the band-like absorption of inorganic semiconductors limit their potential utility to transparent solar cells.

In contrast, the optical characteristics of organic and molecular semiconductors results in absorption spectra that are highly structured with absorption minima and maxima that are uniquely distinct from the band absorption of their inorganic counterparts. However, a variety of organic and molecular semiconductors exist, but many of exhibit strong absorption in the visible spectrum and thus are not optimal for use in window glass-based photovoltaics.

Fullerene electron acceptors, such as $C_{60}$ and $C_{70}$, have been used historically in different organic photovoltaic solar cell architectures. However, due to the absorbance overlap in the visible region and issues with cost and purification, there has been interest in the development of NFAs (Non-Fullerene Acceptors). One class of NFAs is based on the molecule ITIC (3,9-bis(2-methylene-(3-(1,1-dicyanomethylene)-indanone))-5,5,11,11-tetrakis(4-hexylphenyl)-dithieno[2,3-d:2',3'-d']-s-indaceno[1,2-b:5,6-b']dithiophene), which contains an indacenedithione[3,2-b]thiophene core (IT), with four 4-hexylphenyl groups, and capped with 2-(3-oxo-2,3-dihydroinden-1-ylidene)malononitrile (INCN) groups. This and related ITIC-style acceptors are generally regarded as high performing NFA materials, but they cannot be deposited through physical vapor deposition. All known examples of devices containing ITIC-style acceptors are produced through solution-based processing. Solution based ITIC-style material containing devices have set world record performances for opaque organic photovoltaics, but challenges exist for manufacturing at scale using solution-based processing.

SUMMARY

Described herein are materials, methods, and systems related to organic photovoltaic devices and, in some cases, especially useful for visibly transparent organic photovoltaic devices as well as partially transparent organic photovoltaic devices and opaque organic photovoltaic devices. More particularly, the present description provides photoactive compounds, such as useful as acceptor molecules or donor molecules, and methods and systems incorporating the disclosed compounds as a photoactive material of a photovoltaic device.

The disclosed photoactive compounds include those having a formula of A-D-A, A-pi-D-A, or A-pi-D-pi-A, where A is an electron acceptor moiety, pi is a π-bridging moiety, and D is an electron donor moiety. In some cases, photoactive compounds may have a formula of A-D or A-pi-D. Variations on A, D, and pi moieties are described herein, but these moieties may be selected so as to provide an absorption and electrochemical character suitable for use as an electron donor molecule or an electron acceptor in an organic photovoltaic device. The disclosed photoactive compounds may be suitable for purification using sublimation and for deposition on a surface using a vacuum deposition process, like vacuum thermal evaporation. For example, their sublimation temperature may be lower than the temperature at which they thermally decompose. The identity, molecular weight, and structures of the A, D, and pi moieties may impact the volatility of the photoactive compounds in various ways, as described in further detail below.

In some examples, the D moiety in a photoactive compound may comprise a fused aromatic ring structure, such as containing one or more 5-membered rings and/or one or more 6-membered rings, with the rings optionally being carbocyclic rings or heterocyclic rings, such as containing one or more heteroatoms, like O, S, Se, N, Si, or Ge. The D moiety may also include one or more side groups, which may be referred to as Z groups or Z moieties. These Z groups may be bonded to carbon atoms in the fused ring structure, and optionally with multiple Z groups bonded to the same carbon atom, which may be a quaternary center, such as a quaternary C, Si, or Ge. Example Z groups may be alkyl groups, alkenyl group, or phenyl group, which may be substituted or unsubstituted. In some cases, two Z groups can form a ring.

In some examples, the Z groups may be referred to as planarity disrupting moieties or disrupting moieties, in that these groups may extend out from the plane of a fused aromatic ring structure and include a structure that conformationally or sterically locks the atoms of the Z group in a fixed position out-of-plane with the fused aromatic ring structure. This out-of-plane conformational can disrupt the crystal packing structure, for example, altering properties of the photoactive compound relating to melting, sublimation, or vapor pressure. In some cases, the disruption can make the photoactive compound more suitable for deposition using physical vapor deposition processes or for purifying by sublimation. In other cases, the Z groups may not result in significant disruption to the planar configuration of the fused aromatic ring structure.

In some examples, the A moiety in a photoactive compound may comprise an indanone, an indandione, an indanthione, an indandithione, a dicyanomethyleneindanone, or a bis(dicyanomethylidene)indan. In some cases, indandiones may be referred to as indanediones. In some cases, indanthiones may be referred to as thioxoindanone. In some cases, indandithiones may be referred to as indanedithiones. In some cases, dicyanomethyleneindanones may be referred to as malononitrile indanones. In some cases bis(dicyanomethylidene)indans may be referred to as dimalononitrile indanes. Other A moieties may also or alternatively be included in a photoactive compound, such as A moieties comprising five-membered and/or six-membered rings, which may include one or more heteroatoms, such as thiophene or other heterocyclic rings. In other examples, an A moiety may comprise a vinylic cyano-ester linked compound.

Optionally, the A moiety may be bonded to a D moiety or a pi moiety by a carbon-carbon bond (carbon linkage) or include a nitrogen atom and be bonded to a D moiety or a pi moiety by a nitrogen carbon bond (imine linkage). Use of an imine-linked A moiety may alter the spectroscopic properties of the photoactive compound, such as inducing a red-shift as compared to the same compound but using a carbon linkage instead of an imine linkage.

In some examples, the pi moiety may comprise an aromatic or heteroaromatic structure including one or more 5-membered rings and/or one or more 6-membered rings, with a bi-radical structure, providing a link between an A moiety and the D moiety. Examples of pi moieties may include, but are not limited to, thiophenes and fused thiophenes.

As noted above, the photoactive compounds may be suitable for deposition using vacuum deposition techniques like vacuum thermal evaporation. In some cases, the molecular weight of the photoactive compounds may impact the volatility of the compounds, as compounds that have a very high molecular weight may end up thermally decomposing before they evaporate or sublime. In some examples, an upper limit on the molecular weight of a photoactive compound may be about 1200 atomic mass units.

Photovoltaic devices incorporating the photoactive compounds, methods of making the photoactive compounds, and methods of making photovoltaic devices incorporating the photoactive compounds are also described herein.

These and other examples, embodiments, and aspects of the invention along with many advantages and features are described in more detail in conjunction with the text below and attached figures.

BRIEF DESCRIPTION OF THE DRAWINGS

FIG. 39A, FIG. 39B, FIG. 39C, and FIG. 39D provides schematic illustrations of example photovoltaic device structures.

DETAILED DESCRIPTION

The present disclosure relates to photoactive compounds, which may be useful as electron acceptor compounds or electron donor compounds, photovoltaic devices incorporating the disclosed photoactive compounds as photoactive materials, and methods of making and using photovoltaic devices. The disclosed photoactive compounds possess properties, such as relatively low molecular weights, relatively high vapor pressures, or the like, that allow for the compounds to be purified and/or deposited using vapor phase techniques such as sublimation, vacuum thermal evaporation, and physical vapor deposition. In addition, the photoactive compounds exhibit strong absorption, allowing for use in organic photovoltaic devices. In some cases, the photoactive compounds exhibit absorption of light more strongly in the near-infrared and/or ultraviolet regions and less strongly in the visible region, permitting their use in visibly transparent photovoltaic devices. In other cases, the photoactive compounds are useful in transparent and opaque photovoltaic devices.

Figure 1:
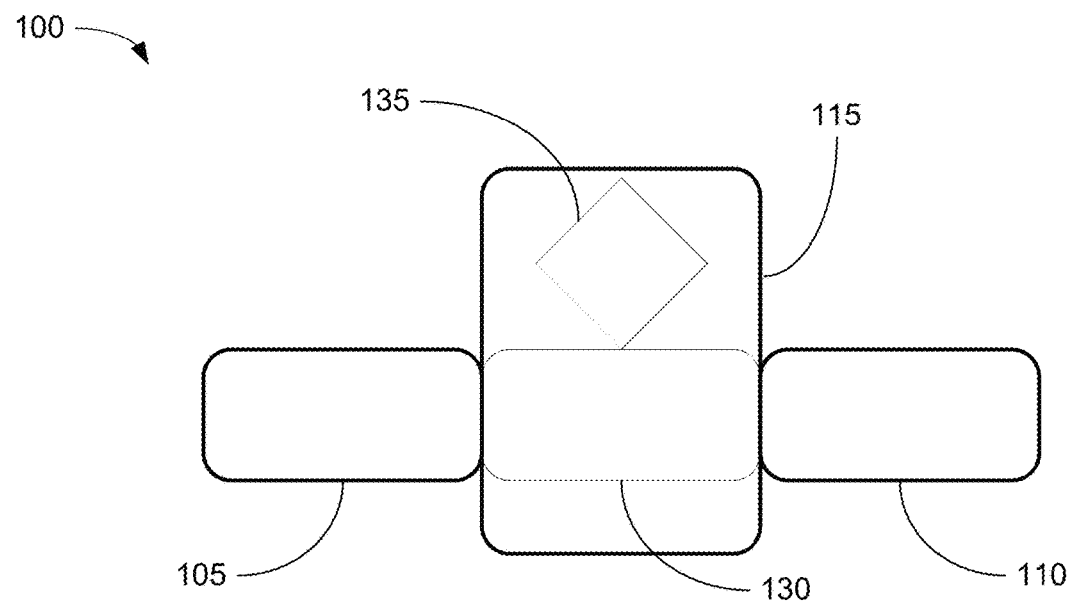
FIG. 1 provides a schematic representation of a photoactive compound in accordance with some examples.

The disclosed photoactive compounds include those with specific features that may provide advantages for use as electron acceptors but may also be useful as electron donors in some cases depending on the pairing of the photoactive compounds with other compounds in an organic photovoltaic device. The disclosed compounds may exhibit a molecular structure where different moieties or sub-structures are bonded to one another, such as electron donor moieties (D), electron acceptor moieties (A), and π-bridging moieties (pi). These components may be arranged in any suitable arrangement to form a photoactive compound. Moreover, each of the different components may include certain structural/compositional features that can impact various properties of the photoactive compound, such as the band gap, the sublimation enthalpy, the sublimation temperature, or the crystal packing density, for example For example, some of the disclosed compounds may exhibit a structure or have formula of A-D-A or A-D. FIG. 1 provides a schematic representation of a photoactive compound 100 having an A-D-A structure. FIG. 1 shows a first electron acceptor moiety 105, a second electron acceptor moiety 110, and an electron donor moiety 115 between first electron acceptor moiety 105 and second electron acceptor moiety 110. In cases where the photoactive compound 100 has an A-D structure, second electron acceptor moiety 110 may not be present and electron donor moiety 115 may include a small group, such as a hydrogen atom, an alkyl group, an alkylene group, or the like, at the position where second electron acceptor moiety 110 would otherwise be present. Optionally, the first electron acceptor moiety 105 and the second electron acceptor moiety 110 can be the same. Optionally, the first electron acceptor moiety 105 and the second electron acceptor moiety 110 can be different.

Figure 2:
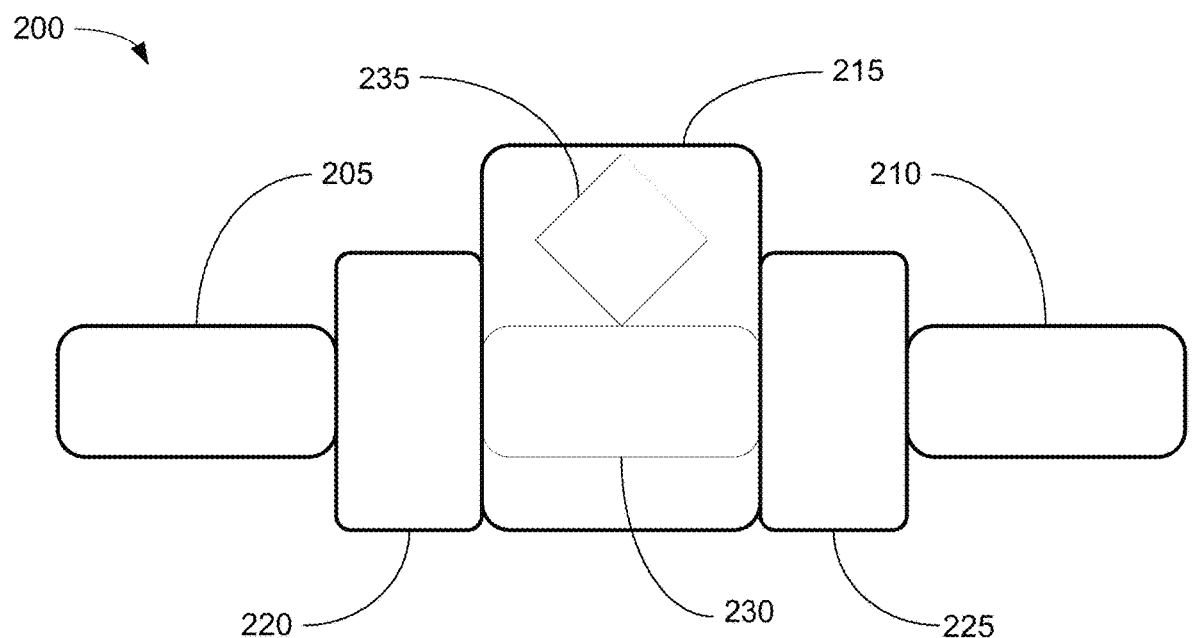
FIG. 2 provides a schematic representation of another photoactive compound in accordance with some examples.

In some cases, π-bridging moieties may be positioned between A and D moieties, such that the disclosed compounds may exhibit a structure or have formula of A-pi-D-A, A-pi-D-pi-A, or A-pi-D. FIG. 2 provides a schematic representation of a photoactive compound 200 having an A-pi-D-pi-A structure. FIG. 2 shows a first electron acceptor moiety 205, a second electron acceptor moiety 210, an electron donor moiety 215, a first π-bridging moiety 220, and a second π-bridging moiety 225. As shown, first π-bridging moiety 220 is positioned between first electron acceptor moiety 205 and electron donor moiety 215, and second π-bridging moiety 225 is positioned between electron donor moiety 215 and second electron acceptor moiety 210. In cases where the photoactive compound 200 has an A-pi-D-A structure, second π-bridging moiety 225 may not be present. In cases where the photoactive compound 200 has an A-pi-D structure, second electron acceptor moiety 210 may not be present and electron donor moiety 215 may include a small group, such as a hydrogen atom, an alkyl group, an alkylene group, or the like, at the position where second electron acceptor moiety 210 would otherwise be present. In some examples, second π-bridging moiety 225 may also not be present. Optionally, the first electron acceptor moiety 205 and the second electron acceptor moiety 210 can be the same. Optionally, the first electron acceptor moiety 205 and the second electron acceptor moiety 210 can be different. Optionally, the first π-bridging moiety 220 and the second π-bridging moiety 225 can be the same. Optionally, the first π-bridging moiety 220 and the second π-bridging moiety 225 can be different.

As depicted, electron donor moiety 115 and 215 can have various subcomponents, which may contribute certain features. For example, electron donor moiety 115 or 215 can comprise a central core 130 or 230 and a side group 135 or 235. In some electron donors, central core 130 or 230 may have or exhibit an electron rich planar molecular structure, such as where one or more carbon atoms, and optionally one or more heteroatoms, are arranged in a plane. In some cases, central core 130 or 230 may comprise an aromatic or heteroaromatic structure, optionally including one or more 5-membered rings, one or more 6-membered rings, or one or more 5-membered rings and one or more 6-membered rings, such as in a fused ring configuration.

Side group 135 or 235 may comprise any suitable organic group, optionally including one or more heteroatoms. In some cases, side group 135 or 235 may adopt any molecular arrangement, such as by including bonds allowing for free rotation. In other cases, however, the atoms making up side group 135 or 235 may have a bonding configuration locking the atoms in a particular geometry. For example, side group 135 or 235 may be or comprise one or more planarity disrupting moieties that are conformationally locked in a configuration out of plane to central core 130 or 230. Without wishing to be bound by any theory, the inclusion of a side group that is a planarity disrupting moiety can impact the ability of molecules of photoactive compound 100 or 200 to form tightly packed crystals in the bulk, as the planarity disrupting moieties can provide a molecular structure that forces an overall non-planar molecular geometry. Such a configuration can result in a decrease in crystal packing density, for example. Other properties, such as enthalpy of melting, evaporation, or sublimation, melting temperature, boiling temperature, or sublimation temperature may also be impacted. Thus, by including planarity disrupting moieties in the chemical structure, photoactive compound 100 or 200 can be more suitable for purification using sublimation processes or more suitable for deposition by gas phase deposition processes, like vacuum thermal evaporation. In some cases, use of a planarity disrupting moiety can increase the evaporability of the photoactive compound, such as to a level greater than a comparable photoactive compounds having the same electron acceptor moieties, pi-bridging moieties (if present), and central core, but including side group(s) that are not a planarity disrupting moiety but that have the same or about the same molecular weight.

Electron donor groups 105, 110, 205 or 220 can have various subcomponents, which may contribute certain features. For example, in some cases, one or more of electron acceptor groups 105, 110, 205, or 220 can comprise a specific composition, such as an indandione, an aryl-substituted indandione, an indanthione, an aryl-substituted indanthione, an indandithione, or an aryl-substituted indandithione. These compositions may contrast with other electron acceptor groups that may be used for some photoactive molecules, such as dicyanomethyleneindanone or bis(dicyanomethylidene)indan groups, which contain dicyanovinyl groups or $=C(CN)_2$ groups. However, such a configuration is not limiting and some electron acceptor groups may comprise indandione, aryl-substituted indandione, indanthione, aryl-substituted indanthione, indandithione, aryl-substituted indandithione, dicyanomethyleneindanone, or bis(dicyanomethylidene)indan groups or other electron acceptor groups. In some specific cases of a photoactive compound having two A components, one A can comprise a dicyanovinyl containing group and the other A can contain an indandione, an aryl-substituted indandione, a indanthione, an aryl-substituted indanthione, an indandithione, or an aryl-substituted indandithione. Photoactive compounds incorporating one or more indandione, aryl-substituted indandione, indanthione, aryl-substituted indanthione, indandithione, aryl-substituted indandithione groups as electron acceptor groups may be more suitable for purification by sublimation or more suitable for vapor deposition, such as using a thermal evaporation technique, than comparable photoactive compounds containing only dicyanomethyleneindanone, or bis(dicyanomethylidene)indan groups. For example, in some cases, use of an indandione, indanthione, or indandithione groups as electron acceptor groups can increase the volatility of the photoactive compound, such as to a level greater than a comparable photoactive compound having the same pi-bridging moieties (if present) and central core, but including dicyanomethyleneindanone or bis(dicyanomethylidene)indan groups instead of indandione, indanthione, or indandithione groups. In some cases, even substitution of one dicyanomethyleneindanone or bis(dicyanomethylidene)indan group for an indandione, indanthione, or indandithone group can result in a significant increase in the volatility.

As another example, electron acceptor groups 105, 110, 205, or 220 can comprise a specific linking structure at the point where electron acceptor groups 105, 110, 205, or 220 is bonded to electron donor groups 115 or 215 or π-bridging groups 220 or 225. For example, in some cases electron acceptor groups 105, 110, 205, or 220 can comprise an imine bond, $=N-$, as a linking group, where the single bond corresponds to a bond to an adjacent A or pi group and the double bond corresponds to a bond to another portion of the electron acceptor group. In other cases, electron acceptor groups 105, 110, 205, or 220 can comprise an alkene bond, $=CH-$, as a linking group, where the single bond corresponds to a bond to an adjacent A or pi group and the double bond corresponds to a bond to another portion of the electron acceptor group. Inclusion of an imine bond can be useful for modifying the band gap or absorption maximum of the photoactive compound 100 or 200. For example, in some cases inclusion of an imine bond can result in a redshift in the band gap or a redshift in the absorption maximum of a photoactive compound, as compared to a photoactive compound with an otherwise identical structure but containing an alkene bond instead of the imine bond. Preparation of photoactive compounds containing an imine bond may require a different synthetic route than used for preparing photoactive compounds lacking an imine bond.

In some examples, for purification and use of the disclosed photoactive compounds, a very high molecular weight may be undesirable, such as about 1200 amu or higher, about 1150 amu or higher, about 1100 amu or higher, about 1050 amu or higher, about 1000 amu or higher, about 950 amu or higher, about 900 amu or higher, or between 900 amu and 2000 amu or a subrange thereof. Some compounds with very high molecular weights may have limited volatilities and useful methods of purifying and using photoactive compounds may employ an evaporation or sublimation-based method. In addition, the photoactive compounds may be deposited as part of a photovoltaic device using a thermal evaporation technique and compounds of very high molecular weight may be difficult to deposit using thermal evaporation. In various examples, the photoactive compounds described herein have a molecular weight of 200 amu to 1200 amu, less than or about 1200 amu, less than or about 1150 amu, less than or about 1100 amu, less than or about 1050 amu, less than or about 1000 amu, less than or about 950 amu, less than or about 900 amu, less than or about 850 amu, less than or about 800 amu, less than or about 750 amu, less than or about 700 amu, less than or about 650 amu, less than or about 600 amu, less than or about 550 amu, less than or about 500 amu, less than or about 450 amu, less than or about 400 amu, less than or about 350 amu, less than or about 300 amu, less than or about 250 amu, or less than or about 200 amu.

To achieve desired optical properties, photoactive compounds may exhibit a molecular electronic structure where photons of light are absorbed, which results in promotion of an electron to a higher molecular orbital, with an energy difference matching that of the absorbed photon, which may result in generation of an electron-hole pair or exciton, which can subsequently separate into distinct electrons and holes, such as at an interface with another material. Compounds exhibiting extended aromaticity or extended conjugation may be beneficial, as compounds with extended aromaticity or extended conjugation may exhibit electronic absorption with energies matching that of near-infrared, visible, and/or ultraviolet photons. In addition to conjugation and aromaticity, absorption features may be modulated by inclusion of heteroatoms in the organic structure of the visibly transparent photoactive compounds, such as oxygen, nitrogen, or sulfur atoms.

In general the terms and phrases used herein have their art-recognized meaning, which can be found by reference to standard texts, journal references and contexts known to those skilled in the art. The following definitions are provided to clarify their specific use in the context of the invention.

As used herein, "maximum absorption strength" refers to the largest absorption value in a particular spectral region, such as the ultraviolet band (e.g., from 200 nm to 450 nm or from 280 nm to 450 nm), the visible band (e.g., from 450 nm to 650 nm), or the near-infrared band (e.g., from 650 nm to 1400 nm), of a particular molecule, for example. In some examples, a maximum absorption strength may correspond to an absorption strength of an absorption feature that is a local or absolute maximum, such as an absorption band or peak, and may be referred to as a peak absorption. In some examples, a maximum absorption strength in a particular band may not correspond to a local or absolute maximum but may instead correspond to the largest absorption value in the particular band. Such a configuration may occur, for example, when an absorption feature spans multiple bands (e.g., visible and near-infrared), and the absorption values from the absorption feature that occur within one band are smaller than those occurring within the adjacent band, such as when the peak of the absorption feature is located within the near-infrared band but a tail of the absorption feature extends to the visible band. In some examples, a photoactive compound described herein may having an absorption peak at a wavelength greater than about 650 nanometers (e.g., in the near-infrared), and the photoactive compound's absorption peak may be greater in magnitude than the photoactive compound's absorption at any wavelength between about 450 and 650 nanometers.

In various examples, disclosed compositions or compounds are isolated or purified. Optionally, an isolated or purified compound is at least partially isolated or purified as would be understood in the art. In some examples, a disclosed composition or compound has a chemical purity of 80%, optionally for some applications 90%, optionally for some applications 95%, optionally for some applications 99%, optionally for some applications 99.9%, optionally for some applications 99.99%, and optionally for some applications 99.999% pure. Purification of the disclosed compositions or compounds may be performed using any desirable technique. Purification by chromatography, vacuum sublimation, and/or crystallization may be particularly useful techniques.

Compounds disclosed herein optionally contain one or more ionizable groups. Ionizable groups include groups from which a proton can be removed (e.g., —COOH) or added (e.g., amines) and groups which can be quaternized (e.g., amines). All possible ionic forms of such molecules and salts thereof are intended to be included individually in the disclosure herein. With regard to salts of the compounds described herein, it will be appreciated that a wide variety of available counter-ions may be selected that are appropriate for preparation of salts for a given application. In specific applications, the selection of a given anion or cation for preparation of a salt can result in increased or decreased solubility of that salt.

The disclosed compounds optionally contain one or more chiral centers. Accordingly, this disclosure includes racemic mixtures, diastereomers, enantiomers, tautomers and mixtures enriched in one or more stereoisomer. Disclosed compounds including chiral centers encompass the racemic forms of the compound as well as the individual enantiomers and non-racemic mixtures thereof.

As used herein, the terms "group" and "moiety" may refer to a functional group of a chemical compound. Groups of the disclosed compounds refer to an atom or a collection of atoms that are a part of the compound. Groups of the disclosed compounds may be attached to other atoms of the compound via one or more covalent bonds. Groups may also be characterized with respect to their valence state. The present disclosure includes groups characterized as monovalent, divalent, trivalent, etc. valence states. Optionally, the term "substituent" may be used interchangeably with the terms "group" and "moiety." Groups may also be characterized with respect to their ability to donate or receive an electron, and such characterization may, in some examples, refer to a relative character of the group to donate or receive an electron as compared to other groups.

As is customary and well known in the art, hydrogen atoms in chemical formulas disclosed herein are not always explicitly shown, for example, hydrogen atoms bonded to the carbon atoms of aliphatic, aromatic, alicyclic, carbocyclic, and/or heterocyclic rings are not always explicitly shown in the formulas recited. The structures provided herein, for example in the context of the description of any specific formulas and structures recited, are intended to convey the chemical composition of disclosed compounds of methods and compositions. It will be appreciated that the structures provided do not indicate the specific positions of atoms and bond angles between atoms of these compounds. As used herein, a wavy line at an end of a bond in a structure or formula represents the position where the indicated moiety connects or can be connected to another moiety. For example, a wavy line in an A moiety can be paired to a wavy line in a D or pi moiety to form an A-D moiety or an A-pi moiety. In some cases, a wavy line in a D moiety may correspond to a hydrogen atom. For example, for A-D or A-pi-D compounds, some D moieties described herein are shown with two wavy lines, one of which can connect to a hydrogen atom.

As used herein, the terms "alkylene" and "alkylene group" are used synonymously and refer to a divalent group derived from an alkyl group as defined herein. The present disclosure includes compounds having one or more alkylene groups. Alkylene groups in some compounds function as attaching and/or spacer groups. Disclosed compounds optionally include substituted and/or unsubstituted $C_1$-$C_{20}$ alkylene, $C_1$-$C_{10}$ alkylene, or $C_1$-$C_5$ alkylene groups.

As used herein, the terms "cycloalkylene" and "cycloalkylene group" are used synonymously and refer to a divalent group derived from a cycloalkyl group as defined herein. The present disclosure includes compounds having one or more cycloalkylene groups. Cycloalkylene groups in some compounds function as attaching and/or spacer groups. Disclosed compounds optionally include substituted and/or unsubstituted $C_3$-$C_{20}$ cycloalkylene, $C_3$-$C_{10}$ cycloalkylene, or $C_3$-$C_5$ cycloalkylene groups.

As used herein, the terms "arylene" and "arylene group" are used synonymously and refer to a divalent group derived from an aryl group as defined herein. The present disclosure includes compounds having one or more arylene groups. In some examples, an arylene is a divalent group derived from an aryl group by removal of hydrogen atoms from two intra-ring carbon atoms of an aromatic ring of the aryl group. Arylene groups in some compounds function as attaching and/or spacer groups. Arylene groups in some compounds function as chromophore, fluorophore, aromatic antenna, dye, and/or imaging groups. Disclosed compounds optionally include substituted and/or unsubstituted $C_5$-$C_{30}$ arylene, $C_5$-$C_{20}$ arylene, or $C_5$-$C_{10}$ arylene groups.

As used herein, the terms "heteroarylene" and "heteroarylene group" are used synonymously and refer to a divalent group derived from a heteroaryl group as defined herein. The present disclosure includes compounds having one or more heteroarylene groups. In some examples, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as attaching and/or spacer groups. Heteroarylene groups in some compounds function as chromophore, aromatic antenna, fluorophore, dye, and/or imaging groups. Disclosed compounds optionally include substituted and/or unsubstituted $C_5$-$C_{30}$ heteroarylene, $C_5$-$C_{20}$ heteroarylene, or $C_5$-$C_{10}$ heteroarylene.

As used herein, the terms "alkenylene" and "alkenylene group" are used synonymously and refer to a divalent group derived from an alkenyl group as defined herein. The present disclosure includes compounds having one or more alkenylene groups. Alkenylene groups in some compounds function as attaching and/or spacer groups. Disclosed compounds optionally include substituted and/or unsubstituted $C_2$-$C_{20}$ alkenylene, $C_2$-$C_{10}$ alkenylene, or $C_2$-$C_5$ alkenylene groups.

As used herein, the terms "cycloalkenylene" and "cycloalkenylene group" are used synonymously and refer to a divalent group derived from a cycloalkenyl group as defined herein. The present disclosure includes compounds having one or more cycloalkenylene groups. Cycloalkenylene groups in some compounds function as attaching and/or spacer groups. Disclosed compounds optionally include substituted and/or unsubstituted $C_3$-$C_{20}$ cycloalkenylene, $C_3$-$C_{10}$ cycloalkenylene, or $C_3$-$C_5$ cycloalkenylene groups.

As used herein, the terms "alkynylene" and "alkynylene group" are used synonymously and refer to a divalent group derived from an alkynyl group as defined herein. The present disclosure includes compounds having one or more alkynylene groups. Alkynylene groups in some compounds function as attaching and/or spacer groups. Disclosed compounds optionally include substituted and/or unsubstituted $C_2$-$C_{20}$ alkynylene, $C_2$-$C_{10}$ alkynylene, or $C_2$-$C_5$ alkynylene groups.

As used herein, the term "halo" refers to a halogen group, such as a fluoro (—F), chloro (—Cl), bromo (—Br), or iodo (—I).

The term "heterocyclic" refers to ring structures containing at least one other kind of atom, in addition to carbon, in the ring. Examples of such atoms include oxygen, sulfur, selenium, tellurium, nitrogen, phosphorus, silicon, germanium, boron, aluminum, and, in some cases, a transition metal. Examples of heterocyclic rings include, but are not limited to, pyrrolidinyl, piperidyl, imidazolidinyl, tetrahydrofuranyl, tetrahydrothienyl, furanyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl, and tetrazolyl groups. Atoms of heterocyclic rings can be bonded to a wide range of other atoms and functional groups, for example, provided as substituents. Heterocyclic rings include aromatic heterocycles and non-aromatic heterocycles.

The term "carbocyclic" refers to ring structures containing only carbon atoms in the ring. Carbon atoms of carbocyclic rings can be bonded to a wide range of other atoms and functional groups, for example, provided as substituents. Carbocyclic rings include aromatic carbocyclic rings and non-aromatic carbocyclic rings.

The term "alicyclic" refers to a ring that is not an aromatic ring. Alicyclic rings include both carbocyclic and heterocyclic rings.

The term "aliphatic" refers to non-aromatic hydrocarbon compounds and groups. Aliphatic groups generally include carbon atoms covalently bonded to one or more other atoms, such as carbon and hydrogen atoms. Aliphatic groups may, however, include a non-carbon atom, such as an oxygen atom, a nitrogen atom, a sulfur atom, etc., in place of a carbon atom. Non-substituted aliphatic groups include only hydrogen substituents. Substituted aliphatic groups include non-hydrogen substituents, such as halo groups and other substituents described herein. Aliphatic groups can be straight chain, branched, or cyclic. Aliphatic groups can be saturated, meaning only single bonds join adjacent carbon (or other) atoms. Aliphatic groups can be unsaturated, meaning one or more double bonds or triple bonds join adjacent carbon (or other) atoms.

Alkyl groups include straight-chain, branched, and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 3-10 carbon atoms, including an alkyl group having one or more rings. Cycloalkyl groups include those having a 3-, 4-, 5-, 6-, 7-, 8-, 9-, or 10-member carbon ring(s) and particularly those having a 3-, 4-, 5-, 6-, or 7-member ring(s). The carbon rings in cycloalkyl groups can also carry alkyl groups. Cycloalkyl groups can include bicyclic and tricycloalkyl groups. Alkyl groups are optionally substituted. Substituted alkyl groups include, among others, those which are substituted with aryl groups, which in turn can be optionally substituted. Specific alkyl groups include methyl, ethyl, n-propyl, iso-propyl, cyclopropyl, n-butyl, branched butyl, cyclobutyl, n-pentyl, branched-pentyl, cyclopentyl, n-hexyl, branched hexyl, and cyclohexyl groups, all of which are optionally substituted. Substituted alkyl groups include fully-halogenated or semi-halogenated alkyl groups, such as alkyl groups having one or more hydrogens replaced with one or more fluorine atoms, chlorine atoms, bromine atoms and/or iodine atoms. Substituted alkyl groups include fully-fluorinated or semi-fluorinated alkyl groups, such as alkyl groups having one or more hydrogens replaced with one or more fluorine atoms. Substituted alkyl groups include alkyl groups substituted with one or more methyl, ethyl, halogen (e.g., fluoro), or trihalomethyl (e.g., trifluoromethyl) groups.

An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy, pentoxy, hexoxy, and heptoxy. Alkoxy groups include substituted alkoxy groups wherein the alkyl portion of the groups is substituted as provided herein in connection with the description of alkyl groups. As used herein MeO— refers to $CH_3O$—.

Alkenyl groups include straight-chain, branched, and cyclic alkenyl groups. Alkenyl groups include those having 1, 2, or more double bonds and those in which two or more of the double bonds are conjugated double bonds. Alkenyl groups include those having from 2 to 20 carbon atoms. Alkenyl groups include small alkenyl groups having 2 to 4 carbon atoms. Alkenyl groups include medium length alkenyl groups having from 5-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9-, or 10-member carbon ring(s) and particularly those having a 3-, 4-, 5-, 6-, or 7-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully-halogenated or semi-halogenated alkenyl groups, such as alkenyl groups having one or more hydrogens replaced with one or more fluorine atoms, chlorine atoms, bromine atoms, and/or iodine atoms. Substituted alkenyl groups include fully-fluorinated or semi-fluorinated alkenyl groups, such as alkenyl groups having one or more hydrogen atoms replaced with one or more fluorine atoms. Substituted alkenyl groups include alkenyl groups substituted with one or more methyl, ethyl, halogen (e.g., fluoro), or trihalomethyl (e.g., trifluoromethyl) groups.

Aryl groups include groups having one or more 5-, 6- or 7-member aromatic and/or heterocyclic aromatic rings. The term heteroaryl specifically refers to aryl groups having at least one 5-, 6-, or 7-member heterocyclic aromatic rings. Aryl groups can contain one or more fused aromatic and heteroaromatic rings or a combination of one or more aromatic or heteroaromatic rings and one or more non-aromatic rings that may be fused or linked via covalent bonds. Heterocyclic aromatic rings can include one or more N, O, or S atoms in the ring, among others. Heterocyclic aromatic rings can include those with one, two or three N atoms, those with one or two O atoms, and those with one or two S atoms, or combinations of one or two or three N, O, or S atoms, among others. Aryl groups are optionally substituted. Substituted aryl groups include among others those which are substituted with alkyl or alkenyl groups, which groups in turn can be optionally substituted. Specific aryl groups include phenyl, biphenyl groups, pyrrolidinyl, imidazolidinyl, tetrahydrofuranyl, tetrahydrothienyl, furanyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semi-halogenated aryl groups, such as aryl groups having one or more hydrogens replaced with one or more fluorine atoms, chlorine atoms, bromine atoms and/or iodine atoms. Substituted aryl groups include fully fluorinated or semi-fluorinated aryl groups, such as aryl groups having one or more hydrogens replaced with one or more fluorine atoms. Aryl groups include, but are not limited to, aromatic group-containing or heterocyclic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene, or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently bonded configuration in the disclosed compounds at any suitable point of attachment. In examples, aryl groups contain between 5 and 30 carbon atoms. In examples, aryl groups contain one aromatic or heteroaromatic six-membered ring and one or more additional five- or six-membered aromatic or heteroaromatic ring. In examples, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents. Substituted aryl groups include aryl groups substituted with one or more methyl, ethyl, halogen (e.g., fluoro), or trihalomethyl (e.g., trifluoromethyl) groups.

Arylalkyl and alkylaryl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl and arylalkyl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully-halogenated or semi-halogenated arylalkyl groups, such as arylalkyl groups having one or more alkyl and/or aryl groups having one or more hydrogens replaced with one or more fluorine atoms, chlorine atoms, bromine atoms, and/or iodine atoms.

As to any of the groups described herein which contain one or more substituents, it is understood that such groups do not contain any substitution or substitution patterns which are sterically impractical and/or synthetically non-feasible. In addition, the disclosed compounds include all stereochemical isomers arising from the substitution of these compounds. Optional substitution of alkyl groups includes substitution with one or more alkenyl groups, aryl groups, or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl, or aryl group includes substitution with one or more of the following substituents, among others:
  halogen, including fluorine, chlorine, bromine, or iodine;
  pseudohalides, including —CN;
  —COOR where R is a hydrogen or an alkyl group or an aryl group or, more specifically, where R is a methyl, ethyl, propyl, butyl, or phenyl group, all of which are optionally substituted;

—COR where R is a hydrogen or an alkyl group or an aryl group or, more specifically, where R is a methyl, ethyl, propyl, butyl, or phenyl group, all of which are optionally substituted;

—CON(R)$_2$ where each R, independently of each other R, is a hydrogen or an alkyl group or an aryl group or, more specifically, where R is a methyl, ethyl, propyl, butyl, or phenyl group, all of which are optionally substituted; and where R and R can optionally form a ring which can contain one or more double bonds and can contain one or more additional carbon atoms;

—OCON(R)$_2$ where each R, independently of each other R, is a hydrogen or an alkyl group or an aryl group and, more specifically, where R is a methyl, ethyl, propyl, butyl, or phenyl group, all of which are optionally substituted; and where R and R can optionally form a ring which can contain one or more double bonds and can contain one or more additional carbon atoms;

—N(R)$_2$ where each R, independently of each other R, is a hydrogen, or an alkyl group, or an acyl group or an aryl group or, more specifically, where R is a methyl, ethyl, propyl, butyl, phenyl, or acetyl group, all of which are optionally substituted; and where R and R can optionally form a ring which can contain one or more double bonds and can contain one or more additional carbon atoms;

—SR, where R is hydrogen or an alkyl group or an aryl group or, more specifically, where R is hydrogen, methyl, ethyl, propyl, butyl, or a phenyl group, all of which are optionally substituted;

—SO$_2$R, or —SOR where R is an alkyl group or an aryl group or, more specifically, where R is a methyl, ethyl, propyl, butyl, or phenyl group, all of which are optionally substituted;

—OCOOR where R is an alkyl group or an aryl group;

—SO$_2$N(R)$_2$ where each R, independently of each other R, is a hydrogen, an alkyl group, or an aryl group, all of which are optionally substituted, and wherein R and R can optionally form a ring which can contain one or more double bonds and can contain one or more additional carbon atoms;

—OR where R is H, an alkyl group, an aryl group, or an acyl group, all of which are optionally substituted. In a particular example R can be an acyl, yielding —OCOR" where R" is a hydrogen or an alkyl group or an aryl group and more specifically where R" is methyl, ethyl, propyl, butyl, or phenyl groups, all of which are optionally substituted.

Specific substituted alkyl groups include haloalkyl groups, particularly trihalomethyl groups and specifically trifluoromethyl groups. Specific substituted aryl groups include mono-, di-, tri, tetra- and penta-halo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

The term "electron acceptor" refers to a chemical composition that can accept an electron from another structure or compound. The term electron acceptor may be used, in some cases, in a relative sense to identify a characteristic of a compound or a subgroup thereof as having a stronger affinity for receiving an additional electron as compared to another compound or a subgroup. In an organic photovoltaic, an electron acceptor may be a compound having an ability to receive electrons from an electron donor. An electron acceptor may be a photoactive compound that generates an electron-hole pair (exciton) upon photoabsorption of light and which can transfer generated holes to an electron donor.

The term "electron donor" refers to a chemical composition that can donate an electron to another structure or compound. The term electron donor may be used, in some cases, in a relative sense to identify a characteristic of a compound or a subgroup thereof as having a weaker affinity for receiving an additional electron as compared to another compound or a subgroup. In an organic photovoltaic, an electron donor may be a compound having an ability to transfer electrons to an electron acceptor. An electron donor may be a photoactive compound that generates an electron-hole pair (exciton) upon photoabsorption of light and which can transfer generated electrons to an electron acceptor.

A "planarity disrupting moiety" or "disrupting moiety" refers to moiety or subgroup of a compound with an atomic arrangement (e.g., of non-hydrogen atoms, like carbon atoms and/or heteroatoms) that deviates from the arrangement of atoms (e.g., a planar arrangement of non-hydrogen atoms, like carbon atoms and/or heteroatoms) of another part of the compound. In one example, a compound can include a planar moiety, where all or most of the non-hydrogen atoms (e.g., carbon and/or heteroatoms), and optionally hydrogen atoms, fall within a plane in the chemical structure of the atoms, and also include a planarity disrupting moiety with atoms (e.g., non-hydrogen atoms like carbon and/or heteroatoms) that extend outside of or deviate significantly from the plane of the other portion of the compound, such as where the atoms are conformationally locked in a configuration out of plane of the rest of the compound. In some examples, a planarity disrupting moiety is referred to herein as a Z group. In some cases when a compound disclosed herein contains multiple planarity disrupting moiety attachment sites (e.g., multiple Z groups), two planarity disrupting moieties can comprise the same substructure; such a configuration may be referred to herein as Z and Z forming a ring. In some cases, a planarity disrupting moiety is bonded to a quaternary center, which may be carbon or a heteroatom (e.g., Si or Ge). In some cases, a quaternary center can be a component of two separate but joined ring structures, also referred to as a spiro compound. The presence of a planarity disrupting moiety in a compound can impact bulk properties, such as a crystallographic packing efficiency or density, which can be evident from or influence other molecular properties, such as vapor pressure, enthalpy of melting, enthalpy of fusion, enthalpy of sublimation, or yield through purification by sublimation. In examples, donor moieties, D, containing one or more planarity disrupting moieties may be referred to herein as core disrupted moieties. Similarly, photoactive compounds comprising donor moieties, D, containing one or more planarity disrupting moieties may be referred to herein as core disrupted photoactive compounds.

A "π-bridging moiety" or a "pi-bridging moiety" refers to moiety or subgroup of a compound providing extended conjugation of π- or, optionally, p-electrons and linking between different portions of the compound by way of a bivalent structure. Extended conjugation may occur when bonds in a chemical compound are in an alternating configuration of single-bonds and multiple-bonds (e.g., double- or triple-bonds). In some cases, extended conjugation may contribute additional electrons to an aromatic system.

The term "conformationally locked" refers to a configuration where atoms of a compound or group are in a bonded arrangement limiting free rotation or movement of components thereof. A conformationally locked group may have a limited number of arrangement that atoms of the group can adopt. As one example, a spiro group may be conformationally locked in that the atoms making up the two ring structures of the group are not able to freely rotate relative to one another; such a configuration contrasts with a group where free rotation of sub-groups the group can occur. Examples of groups that are not conformationally locked may include some alkyl groups, such as a methyl group, an ethyl group, a propyl group, or a butyl group), where methyl groups (—$CH_3$), ethyl groups (—$CH_2CH_3$), or the like, can undergo rotation. In some cases, sterics may limit rotation of some groups. In some cases, a conformationally locked group that is in a configuration that is out of plane of another component of the compound may not be able to be positioned in the plane due to the bonding arrangement of atoms in the conformationally locked group.

As used herein, the terms visible transparency, visibly transparent, and the like refer to an optical property of a material that exhibits an overall absorption, average absorption, or maximum absorption in the visible band of 0%-70%, such as less than or about 70%, less than or about 65%, less than or about 60%, less than or about 55%, less than or about 50%, less than or about 45%, less than or about 40%, less than or about 35%, less than or about 30%, less than or about 25%, or less than or about 20%. Stated another way, visibly transparent materials may transmit 30%-100% of incident visible light, such as greater than or about 80% of incident visible light, greater than or about 75% of incident visible light, greater than or about 70% of incident visible light, greater than or about 65% of incident visible light, greater than or about 60% of incident visible light, greater than or about 55% of incident visible light, greater than or about 50% of incident visible light, greater than or about 45% of incident visible light, greater than or about 40% of incident visible light, greater than or about 35% of incident visible light, or greater than or about 30% of incident visible light. Visibly transparent materials are generally considered at least partially see-through (e.g., not completely opaque) when viewed by a human. Optionally, visibly transparent materials may be colorless (e.g., not exhibiting strong visible absorption features that would provide an appearance of a particular color) when viewed by a human.

As used herein, the term "visible" refers to a band of electromagnetic radiation for which the human eye is sensitive. For example, visible light may refer to light having wavelengths between about 450 nm and about 650 nm.

The term "near-infrared" or "NIR" refers to a band of electromagnetic radiation having wavelengths longer than those for which the human eye is sensitive. For example, near-infrared light may refer to light having wavelengths greater than 650 nm, such as between about 650 nm and about 1400 nm or between about 650 nm and 2000 nm.

The term "ultraviolet" or "UV" refers to a band of electromagnetic radiation having wavelengths shorter than those for which the human eye is sensitive. For example, ultraviolet light may refer to light having wavelengths less than 450 nm, such as between about 200 nm and about 450 nm or between about 280 nm and 450 nm.

Figure 3A:
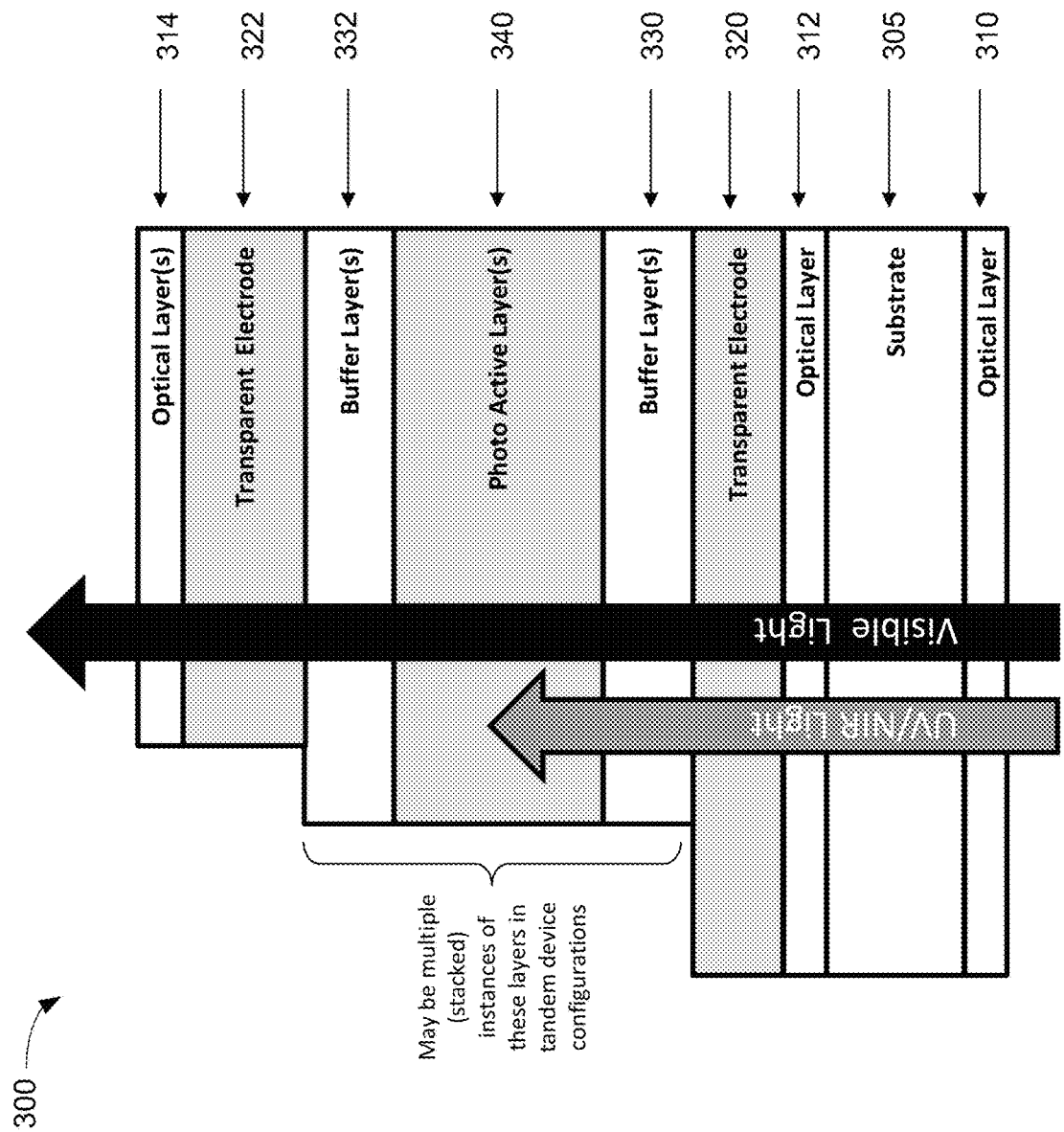
FIG. 3A is a simplified schematic diagram illustrating a visibly transparent photovoltaic device according to some examples.

The disclosed compounds can be used in any application, though the specific application described herein is for use as photoactive compounds in an organic photovoltaic device, such as electron acceptor compounds or electron donor compounds. In some examples, the disclosed compounds are paired with a counterpart photoactive material (e.g., an electron donor material or an electron acceptor material) to form heterojunction structures comprising an electron donor compound and a counterpart electron acceptor material or comprising an electron acceptor compound and a counterpart electron donor material, as further described below, for use in generating and separating electron-hole pairs for converting electromagnetic radiation (e.g., ultraviolet light, visible light, and/or near-infrared light) into useful electrical energy (e.g., voltage/current). In a specific example, the photovoltaic device incorporating one or more of the disclosed photoactive compounds is a visibly transparent photovoltaic device. In other examples, the photovoltaic device incorporating one or more of the disclosed photoactive compounds is a partially transparent photovoltaic device, a colored partially transparent photovoltaic device, or an opaque photovoltaic device FIG. 3A is a simplified schematic diagram illustrating a photovoltaic device according to some examples. As illustrated in FIG. 3A, the photovoltaic device 300 includes a number of layers and elements discussed more fully below. As discussed in relation to FIG. 4, the photovoltaic device 300 may be visibly transparent, which indicates that the photovoltaic device absorbs optical energy at wavelengths outside the visible wavelength band of 450 nm to 650 nm, for example, while substantially transmitting visible light inside the visible wavelength band. As illustrated in FIG. 3A, UV and/or NIR light is absorbed in the layers and elements of the photovoltaic device while visible light is transmitted through the device, though in some cases, such as in a partially transparent photovoltaic device or an opaque photovoltaic device, visible light may be absorbed, such as by a photoactive layer.

Substrate 305, which can be glass or other visibly transparent materials providing sufficient mechanical support to the other layers and structures illustrated, supports optical layers 310 and 312. These optical layers can provide a variety of optical properties, including antireflection (AR) properties, wavelength selective reflection or distributed Bragg reflection properties, index matching properties, encapsulation, or the like. Optical layers may advantageously be visibly transparent. An additional optical layer 314 can be utilized, for example, as an AR coating, an index matching later, a passive infrared or ultraviolet absorption layer, etc. Optionally, optical layers may be transparent to ultraviolet and/or near-infrared light or transparent to at least a subset of wavelengths in the ultraviolet and/or near-infrared bands. Depending on the configuration, additional optical layer 314 may also be a passive visible absorption layer or a neutral filter, for example. Example substrate materials include various glasses and rigid or flexible polymers. Multilayer substrates may also be utilized. Substrates may have any suitable thickness to provide the mechanical support needed for the other layers and structures, such as, for example, thicknesses from 1 mm to 20 mm. In some cases, the substrate may be or comprise an adhesive film to allow application of the photovoltaic device 300 to another structure, such as a window pane, display device, etc.

It will be appreciated that, although some of the devices described herein exhibit visible transparency, photovoltaic devices are also disclosed herein that are not fully visibly transparent, as some of the photoactive compounds described herein may exhibit visible absorption. In the case of a visibly transparent photovoltaic device that overall exhibits visible transparency, such as a transparency in the 450-650 nm range greater than 30%, greater than 40%, greater than 50%, greater than 60%, greater than 70%, or up to or approaching 100%, certain materials taken individually may exhibit absorption in portions of the visible spectrum. Optionally, each individual material or layer in a visibly transparent photovoltaic device has a high transparency in the visible range, such as greater than 30% (e.g., between 30% and 100%). It will be appreciated that transmission or absorption may be expressed as a percentage and may be dependent on the material's absorbance properties, a thickness or path length through an absorbing material, and a concentration of the absorbing material, such that a material with an absorbance in the visible spectral region may still exhibit a low absorption or high transmission if the path length through the absorbing material is short and/or the absorbing material is present in low concentration.

As described herein and below, various photoactive materials in various photoactive layers advantageously can exhibit minimal absorption in the visible region (e.g., less than 20%, less than 30%, less than 40%, less than 50%, less than 60%, or less than 70%), and instead exhibit high absorption in the near-infrared and/or ultraviolet regions (e.g., an absorption peak of greater than 50%, greater than 60%, greater than 70%, or greater than 80%). For some applications, absorption in the visible region may be as large as 70%. Various configurations of other materials, such as the substrate, optical layers, and buffer layers, may be useful for allowing these materials to provide overall visible transparency, even though the materials may exhibit some amount of visible absorption. For example, a thin film of a metal may be included in a transparent electrode, such as a metal that exhibits visible absorption, like Ag or Cu; when provided in a thin film configuration, however, the overall transparency of the film may be high. Similarly, materials included in an optical or buffer layer may exhibit absorption in the visible range but may be provided at a concentration or thickness where the overall amount of visible light absorption is low, providing visible transparency.

The photovoltaic device 300 also includes a set of transparent electrodes 320 and 322 with a photoactive layer 340 positioned between electrodes 320 and 322. These electrodes, which can be fabricated using ITO, thin metal films, or other suitable visibly transparent materials, provide electrical connection to one or more of the various layers illustrated. For example, thin films of copper, silver, or other metals may be suitable for use as a visibly transparent electrode, even though these metals may absorb light in the visible band. When provided as a thin film, however, such as a film having a thickness of 1 nm to 200 nm (e.g., about 5 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, about 150 nm, about 155 nm, about 160 nm, about 165 nm, about 170 nm, about 175 nm, about 180 nm, about 185 nm, about 190 nm, or about 195 nm), an overall transmittance of the thin film in the visible band may remain high, such as greater than 30%, greater than 40%, greater than 50%, greater than 60%, greater than 70%, greater than 80%, or greater than 90%. Advantageously, thin metal films, when used as transparent electrodes, may exhibit lower absorption in the ultraviolet band than other semiconducting materials that may be useful as a transparent electrode, such as ITO, as some semiconducting transparent conducting oxides exhibit a band gap that occurs in the ultraviolet band and thus are highly absorbing or opaque to ultraviolet light. In some cases, however, an ultraviolet absorbing transparent electrode may be used, such as to screen at least a portion of the ultraviolet light from underlying components, as ultraviolet light may degrade certain materials.

A variety of deposition techniques may be used to generate a transparent electrode, including vacuum deposition techniques, such as atomic layer deposition, chemical vapor deposition, physical vapor deposition, vacuum thermal evaporation, sputter deposition, epitaxy, etc. Solution-based deposition techniques, such as spin-coating, may also be used in some cases. In addition, various components, such as transparent electrodes, may be patterned using techniques known in the art of microfabrication, including lithography, lift off, etching, etc.

Buffer layers 330 and 332 and photoactive layer 340 are utilized to implement the electrical and optical properties of the photovoltaic device. These layers can be layers of a single material or can include multiple sub-layers as appropriate to the particular application. Thus, the term "layer" is not intended to denote a single layer of a single material but can include multiple sub-layers of the same or different materials. In some cases, layers may partially or completely overlap. In some examples, buffer layer 330, photoactive layer(s) 340 and buffer layer 332 are repeated in a stacked configuration to provide tandem device configurations, such as including multiple heterojunctions. In some examples, the photoactive layer(s) include electron donor materials and electron acceptor materials, also referred to as donors and acceptors. These donors and acceptors can, in some cases, be visibly transparent, but absorb outside the visible wavelength band to provide the photoactive properties of the device. In the case of partially transparent and opaque photovoltaic devices, the donors and/or acceptors can absorb in the visible region.

Useful buffer layers include those that function as electron transport layers, electron blocking layers, hole transport layers, hole blocking layers, exciton blocking layers, optical spacers, physical buffer layers, charge recombination layers, or charge generation layers. Buffer layers may exhibit any suitable thickness to provide the buffering effect desired and may optionally be present or absent. Useful buffer layers, when present, may have thicknesses from 1 nm to 1 μm. Various materials may be used as buffer layers, including fullerene materials, carbon nanotube materials, graphene materials, metal oxides, such as molybdenum oxide, titanium oxide, zinc oxide, etc., polymers, such as poly(3,4-ethylenedioxythiophene), polystyrene sulfonic acid, polyaniline, etc., copolymers, polymer mixtures, and small molecules, such as bathocuproine. Buffer layers may be applied using a deposition process (e.g., vacuum thermal evaporation) or a solution processing method (e.g., spin-coating).

Figure 3B:
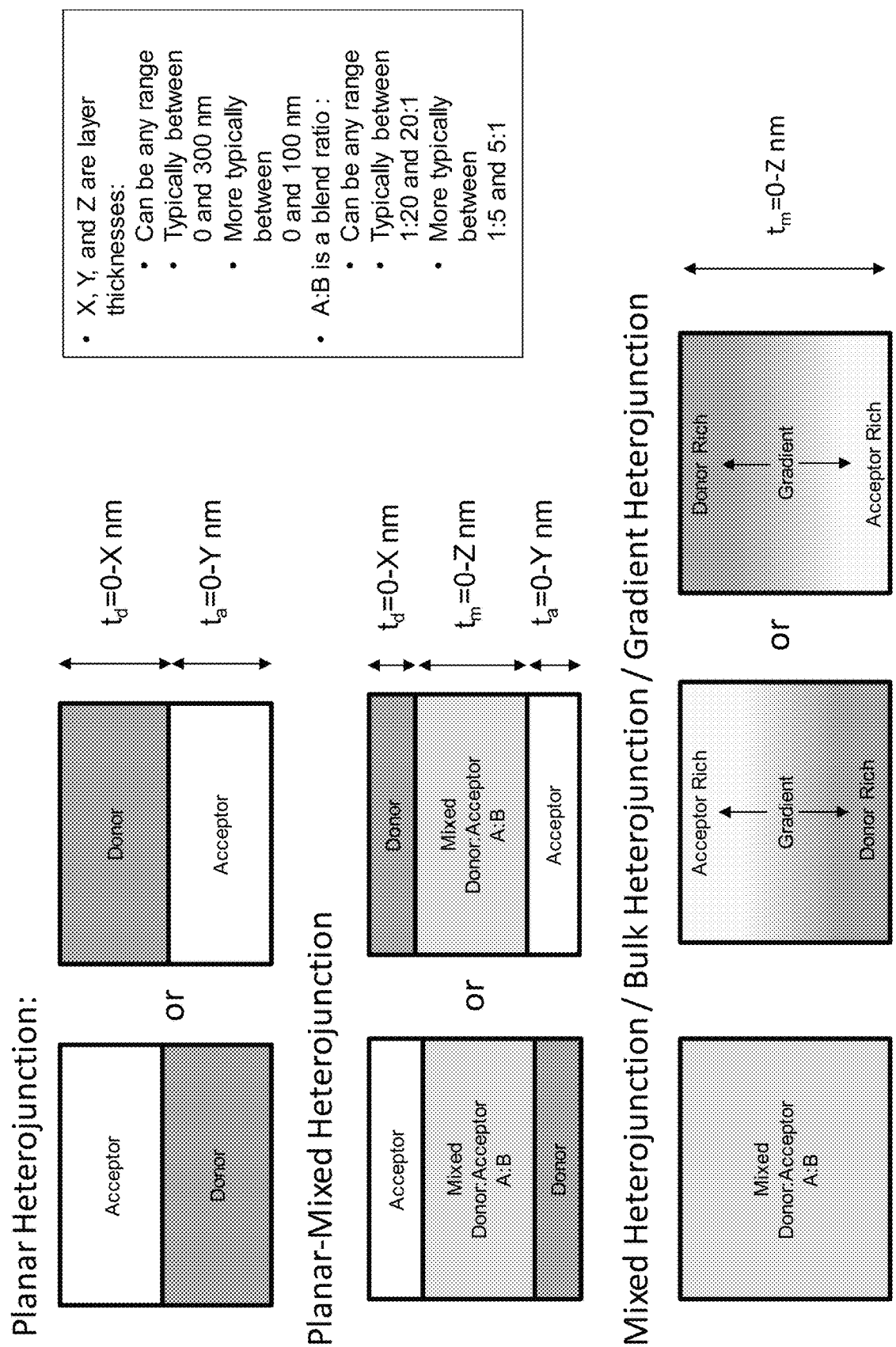
FIG. 3B provides an overview of various configurations of photoactive layer(s) in visibly transparent photovoltaic devices according to some examples.

FIG. 3B depicts an overview of various example single junction configurations for photoactive layer 340. Photoactive layer 340 may optionally correspond to mixed donor/acceptor (bulk heterojunction) configurations, planar donor/acceptor configurations, planar and mixed donor/acceptor configurations, or gradient donor/acceptor configurations. Various materials may be used as the photoactive layers 340, such as visibly transparent materials that absorb in the ultraviolet band or the near-infrared band but that only absorb minimally, if at all, in the visible band. In this way, the photoactive material may be used to generate electron-hole pairs for powering an external circuit by way of ultraviolet and/or near-infrared absorption, leaving the visible light relatively unperturbed to provide visible transparency. In other cases, however, photoactive layers 340 may include materials that absorb in the visible region. As illustrated, photoactive layer 340 may comprise a planar heterojunction including separate donor and acceptor layers. Photoactive layer 340 may alternatively comprise a planar-mixed heterojunction structure including separate acceptor and donor layers and a mixed donor-acceptor layer. Photoactive layers 340 may alternatively comprise a mixed heterojunction structure including a fully mixed acceptor-donor layer or those including a mixed donor-acceptor layer with various relative concentration gradients.

Photoactive layers 340 may have any suitable thickness and may have any suitable concentration or composition of photoactive materials to provide a desired level of transparency and ultraviolet/near-infrared absorption characteristics. Example thicknesses of a photoactive layer may range from about 1 nm to about 1 µm, about 1 nm to about 300 nm, or about 1 nm to about 100 nm. In some cases, photoactive layers 340 may be made up of individual sub-layers or mixtures of layers to provide suitable photovoltaic power generation characteristics, as illustrated in FIG. 3B. The various configurations depicted in FIG. 3B may be used and dependent on the particular donor and acceptor materials used in order to provide advantageous photovoltaic power generation. For example, some donor and acceptor combinations may benefit from particular configurations, while other donor and acceptor combinations may benefit from other particular configurations. Donor materials and acceptor materials may be provided in any ratio or concentration to provide suitable photovoltaic power generation characteristics. For mixed layers, the relative concentration of donors to acceptors is optionally between about 20 to 1 and about 1 to 20. Optionally, the relative concentration of donors to acceptors is optionally between about 5 to 1 and about 1 to 5. Optionally, donors and acceptors are present in a 1 to 1 ratio.

It will be appreciated that, in various examples, photovoltaic device 300 comprises transparent electrode 320, photoactive layer(s) 340, and transparent electrode 322, and that any one or more of substrate 305, optical layers 310, 312, and 314, and/or buffer layers 330 and 332 may be optionally included or excluded.

As described more fully herein, disclosed examples can employ photoactive compounds for one or more of the buffer layers, optical layers, and/or the photoactive layers. These compounds can include suitably functionalized versions for modification of the electrical and/or optical properties of the core structure. As an example, the disclosed compounds can include functional groups that decrease the absorption properties in the visible wavelength band between 450 nm to 650 nm and increase the absorption properties in the NIR band at wavelengths greater than 650 nm.

As an example, the disclosed photoactive compounds are useful as an electron acceptor materials or electron donor materials and may be paired with suitable counterpart materials of the opposite character, such as counterpart electron donor materials or counterpart electron acceptor materials, in order to provide a useful heterojunction-based photoactive layer in the photovoltaic device. Example electron donor photoactive materials or electron acceptor photoactive materials may be visibly transparent. In cases of partially transparent or opaque photovoltaic devices, the photoactive materials can absorb light in the visible region.

In examples, the chemical structure of the photoactive compounds can be functionalized with one or more directing groups, such as electron donating groups, electron withdrawing groups, or substitutions about or to a core metal atom or group, in order to provide desirable electrical characteristics to the material. For example, in some examples, the photoactive compounds are functionalized with amine groups, phenol groups, alkyl groups, phenyl groups, or other electron donating groups to improve the ability of the material to function as an electron donor in a photovoltaic device. As another example, the photoactive compounds may be functionalized with cyano groups, halogens, sulfonyl groups, or other electron withdrawing groups to improve the ability of the material to function as an electron acceptor in a photovoltaic device.

In examples, the photoactive compounds are functionalized to provide desirable optical characteristics. For example, the photoactive compounds may be functionalized with an extended conjugation to redshift the absorption profile of the material. It will be appreciated that conjugation may refer to a delocalization of pi electrons in a molecule and may be characterized by alternating single and multiple bonds in a molecular chemical structure, and/or the presence of aromatic structures. For example, functionalizations that extend the electron conjugation may include fusing one or more aromatic groups to the molecular structure of the material. Other functionalizations that may provide extended conjugation include alkene functionalization, such as by a vinyl group, aromatic or heteroaromatic functionalization, carbonyl functionalization, such as by an acyl group, sulfonyl functionalization, nitro functionalization, cyano functionalization, etc. It will be appreciated that various molecular functionalizations may impact both the optical and the electrical properties of the photoactive compounds.

It will be appreciated that device function may be impacted by the morphology of the active layers in the solid state. Separation of electron donors and acceptors into discrete domains, with dimensions on the scale of the exciton diffusion length and large interfacial areas, can be advantageous for achieving high device efficiency. Advantageously, the molecular framework of the photoactive materials can be tailored to control the morphology of the materials. For example, the introduction of functional groups as described herein can have large impacts to the morphology of the material in the solid state, regardless of whether such modifications impact the energetics or electronic properties of the material. Such morphological variations can be observed in pure materials and when a particular material is blended with a corresponding donor or acceptor. Useful functionalities to control morphology include, but are not limited to, addition of alkyl chains, conjugated linkers, fluorinated alkanes, bulky groups (e.g., tert-butyl, phenyl, naphthyl or cyclohexyl), as well as more complex coupling procedures designed to force parts of the structure out of the plane of the molecule to inhibit excessive crystallization.

In examples, other molecular structural characteristics may provide desirable electrical and optical properties in the photoactive compounds. For example, the photoactive compounds may exhibit portions of the molecule that may be characterized as electron donating while other portions of the molecule may be characterized as electron accepting. Without wishing to be bound by any theory, molecules including alternating electron donating and electron accepting portions may result in redshifting the absorption characteristics of the molecule as compared to similar molecules lacking alternating electron donating and electron accepting portions. For example, alternating electron donating and electron accepting portions may decrease or otherwise result in a lower energy gap between a highest occupied molecular orbital and a lowest unoccupied molecular orbital. Organic donor and/or acceptor groups may be useful as R-group substituents, such as on any aryl, aromatic, heteroaryl, heteroaromatic, alkyl, or alkenyl group, in the visibly transparent photoactive compounds described herein. Example acceptor and donor groups are described below in more detail.

In examples, the photoactive compounds may exhibit symmetric structures, such as structures having two or more points of symmetry. Symmetric structures may include those where a core group is functionalized on opposite sides by the same groups, or where two of the same core groups are fused or otherwise bonded to one another. In other examples, the photoactive compounds may exhibit asymmetric structures, such as structures having fewer than two points of symmetry. Asymmetric structures may include those where a core group is functionalized on opposite sides by different groups or where two different core groups are fused or otherwise bonded to one another.

When the materials described herein are incorporated as a photoactive layer in a photovoltaic device, for example as an electron acceptor or an electron donor, the layer thicknesses can be controlled to vary device output, absorbance, or transmittance. For example, increasing the donor or acceptor layer thickness can increase the light absorption in that layer. In some cases, increasing a concentration of donor/acceptor materials in a donor or acceptor layer may similarly increase the light absorption in that layer. However, in some examples, a concentration of donor/acceptor materials may not be adjustable, such as when active material layers comprise pure or substantially pure layers of donor/acceptor materials or pure or substantially pure mixtures of donor/acceptor materials. Optionally, donor/acceptor materials may be provided in a solvent or suspended in a carrier, such as a buffer layer material, in which case the concentration of donor/acceptor materials may be adjusted. In some examples, the donor layer concentration is selected where the current produced is maximized. In some examples, the acceptor layer concentration is selected where the current produced is maximized.

However, the charge collection efficiency can decrease with increasing donor or acceptor thickness due to the increased "travel distance" for the charge carriers. Therefore, there may be a trade-off between increased absorption and decreasing charge collection efficiency with increasing layer thickness. It can thus be advantageous to select materials as described herein that have a high absorption coefficient and/or concentration to allow for increased light absorption per thickness. In some examples, the donor layer thickness is selected where the current produced is maximized. In some examples, the acceptor layer thickness is selected where the current produced is maximized.

In addition to the individual photoactive layer thicknesses formed from materials described herein, the thickness and composition of the other layers in the transparent photovoltaic device can also be selected to enhance absorption within the photoactive layers. The other layers (buffer layers, electrodes, etc.), are typically selected based on their optical properties (index of refraction and extinction coefficient) in the context of the thin film device stack and resulting optical cavity. For example, a near-infrared absorbing photoactive layer can be positioned in the peak of the optical field for the near-infrared wavelengths where it absorbs to maximize absorption and resulting current produced by the device. This can be accomplished by spacing the photoactive layer at an appropriate distance from the electrode using a second photoactive layer and/or optical layers as spacer. A similar scheme can be used for ultraviolet or visible absorbing photoactive layers. In many cases, the peaks of the longer wavelength optical fields will be positioned further from the more reflective of the two transparent electrodes compared to the peaks of the shorter wavelength optical fields. Thus, when using separate donor and acceptor photoactive layers, the donor and acceptor can be selected to position the more red absorbing (longer wavelength) material further from the more reflective electrode and the more blue absorbing (shorter wavelength) closer to the more reflective electrode.

In some examples, optical layers may be included to increase the intensity of the optical field at wavelengths where the donor absorbs in the donor layer to increase light absorption and hence, increase the current produced by the donor layer. In some examples, optical layers may be included to increase the intensity of the optical field at wavelengths where the acceptor absorbs in the acceptor layer to increase light absorption and hence, increase the current produced by the acceptor layer. In some examples, optical layers may be used to improve the transparency of the stack by either decreasing visible absorption or visible reflection. Further, the electrode material and thickness may be selected to enhance absorption outside the visible range within the photoactive layers, while preferentially transmitting light within the visible range.

Optionally, enhancing spectral coverage of a photovoltaic device is achieved by the use of a multi-cell series stack of photovoltaic devices, referred to as tandem cells, which may be included as multiple stacked instances of buffer layer 330, photoactive layer 340, and buffer layer 332, as described with reference to FIG. 3A. This architecture includes more than one photoactive layer, which are typically separated by a combination of buffer layer(s) and/or thin metal layers, for example. In this architecture, the currents generated in each subcell flow in series to the opposing electrodes and therefore, the net current in the cell is limited by the smallest current generated by a particular subcell, for example. The open circuit voltage (VOC) is equal to the sum of the VOCs of the subcells. By combining sub-cells fabricated with different donor-acceptors pairs which absorb in different regions of the solar spectrum, a significant improvement in efficiency relative to a single junction cell can be achieved.

Additional description related to the materials utilized in one or more of the buffer layers and the photoactive layers, including donor layers and/or acceptor layers, are provided below.

Figure 4:
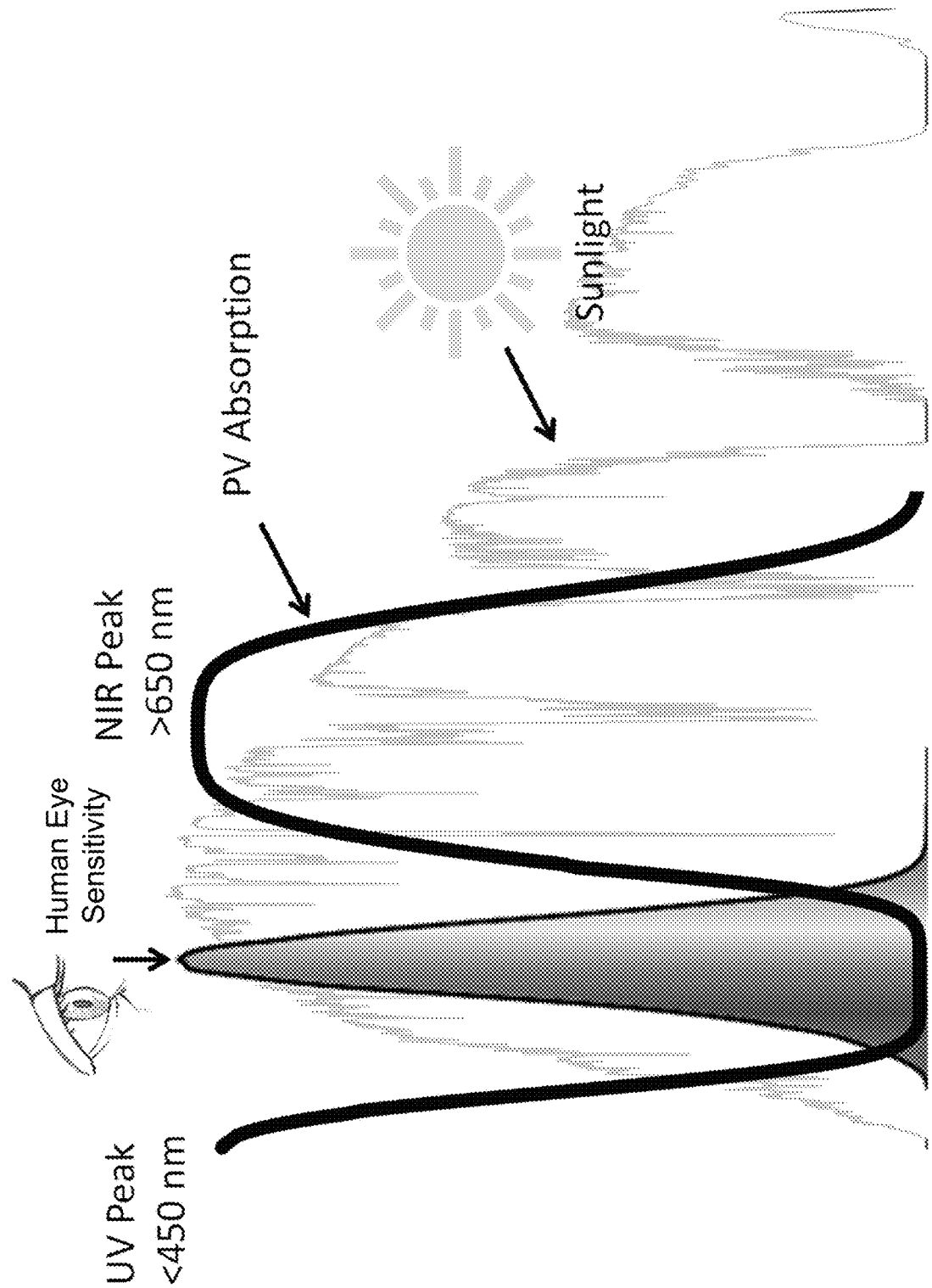
FIG. 4 is simplified plot illustrating the solar spectrum, human eye sensitivity, and exemplary transparent photovoltaic device absorption as a function of wavelength.

FIG. 4 is simplified plot illustrating the solar spectrum, human eye sensitivity, and exemplary visibly transparent photovoltaic device absorption as a function of wavelength. As illustrated in FIG. 4, examples of visibly transparent photovoltaic devices can utilize photovoltaic structures that have low absorption in the visible wavelength band between about 450 nm and about 650 nm but absorb in the UV and NIR bands, e.g., outside the visible wavelength band, enabling visibly transparent photovoltaic operation. The ultraviolet band or ultraviolet region may be described, in examples, as wavelengths of light of between about 200 nm and 450 nm. It will be appreciated that useful solar radiation at ground level may have limited amounts of ultraviolet less than about 280 nm and, thus, the ultraviolet band or ultraviolet region may be described as wavelengths of light of between about 280 nm and 450 nm, in some examples. The near-infrared band or near-infrared region may be described, in examples, as wavelengths of light of between about 650 nm and 1400 nm. Various compositions described herein may exhibit absorption including a NIR peak with a maximum absorption strength in the visible region that is smaller than that in the NIR region.

Figure 5:
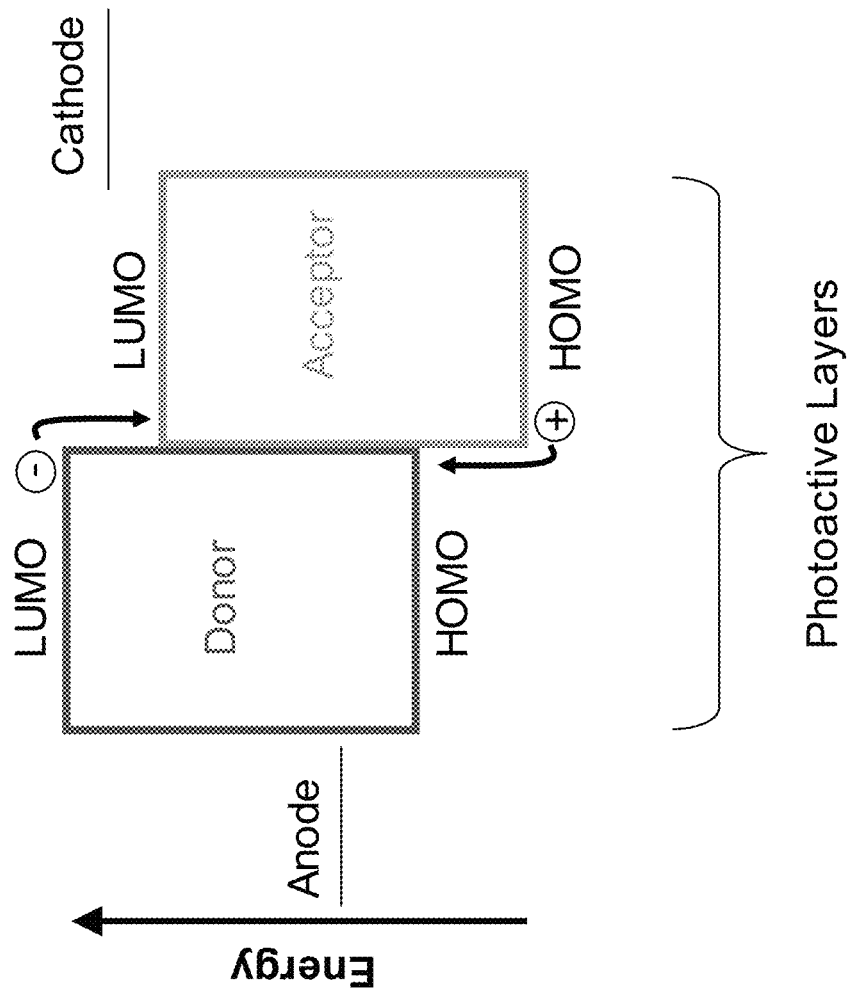
FIG. 5 is a simplified energy level diagram for a visibly transparent photovoltaic device according to some examples.

FIG. 5 provides a schematic energy level diagram overview for operation of an example organic photovoltaic device, such as visibly transparent photovoltaic device 300. For example, in such a photovoltaic device, various photoactive materials may exhibit electron donor or electron acceptor characteristics, depending on their properties and the types of materials that are used for buffer layers, counterpart materials, electrodes, etc. As depicted in FIG. 5, each of the donor and acceptor materials have a highest occupied molecular orbital (HOMO) and a lowest unoccupied molecular orbital (LUMO). A transition of an electron from the HOMO to the LUMO may be imparted by absorption of photons. The energy between the HOMO and the LUMO (the HOMO-LUMO gap) of a material represents approximately the energy of the optical band gap of the material. For the electron donor and electron acceptor materials useful with the transparent photovoltaic devices provided herein, the HOMO-LUMO gap for the electron donor and electron acceptor materials preferably falls outside the energy of photons in the visible range. For example, the HOMO-LUMO gap may be in the ultraviolet region or the near-infrared region, depending on the photoactive materials. In some cases, the HOMO-LUMO gap may be in the visible region or overlap with the visible region and the ultraviolet region or overlap with the visible region and the near-infrared region, such as for partially transparent or opaque photovoltaic devices. It will be appreciated that the HOMO is comparable to the valence band in conventional conductors or semiconductors, while the LUMO is comparable to the conduction band in conventional conductors or semiconductors.

The narrow absorption spectrum of many organic molecules, such as organic semiconductors, can make it difficult to absorb the entire absorption spectra using a single molecular species. Therefore, electron donor and acceptor molecules are generally paired to afford a complementary absorption spectrum and increase spectral coverage of light absorption. Additionally, the donor and acceptor molecules are selected such that their energy levels (HOMO and LUMO) lie favorably with respect to one another. The difference in the LUMO level of donor and acceptor provides a driving force for dissociation of electron-hole pairs (excitons) created on the donor whereas the difference in the HOMO levels of donor and acceptors provides driving force for dissociation of electron-hole pairs (excitons) created on the acceptor. In some examples, it may be useful for the acceptor to have high electron mobility to efficiently transport electrons to an adjacent buffer layer. In some examples, it may be useful for the donor to have high hole mobility to efficiently transport holes to the buffer layer. Additionally, in some examples, it may be useful to increase the difference in the LUMO level of the acceptor and the HOMO level of the donor to increase the open circuit voltage (VOC), since VOC has been shown to be directly proportional to the difference between LUMO of the acceptor and HOMO of the donor. Such donor-acceptor pairings within the photoactive layer may be accomplished by appropriately pairing one of the materials described herein with a complementary material, which could be a different photoactive compound described herein or a completely separate material system.

The buffer layer adjacent to the donor, generally referred to as the anode buffer layer or hole transport layer, is selected such that HOMO level or valence band (in the case of inorganic materials) of the buffer layer is aligned in the energy landscape with the HOMO level of the donor to transport holes from the donor to the anode (transparent electrode). In some examples, it may be useful for the buffer layer to have high hole mobility. The buffer layer adjacent to the acceptor, generally referred to as the cathode buffer layer or electron transport layer, is selected such that LUMO level or conduction band (in the case of inorganic materials) of the buffer layer is aligned in the energy landscape with the LUMO level of the acceptor to transport electrons from the acceptor to the cathode (transparent electrode). In some examples, it may be useful for the buffer layer to have high electron mobility.

Figure 6A:
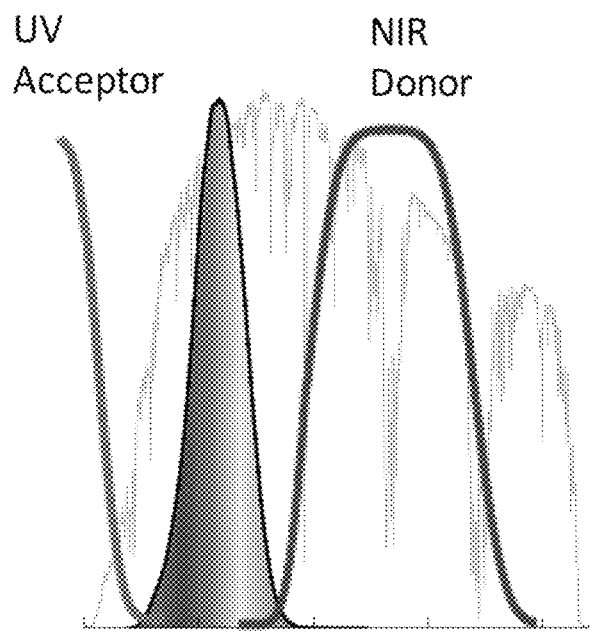
FIG. 6A, FIG. 6B, FIG. 6C, and FIG. 6D provide plots showing example absorption profiles for different electron acceptor and electron donor configurations, which can comprise the photoactive layers.
Figure 6B:
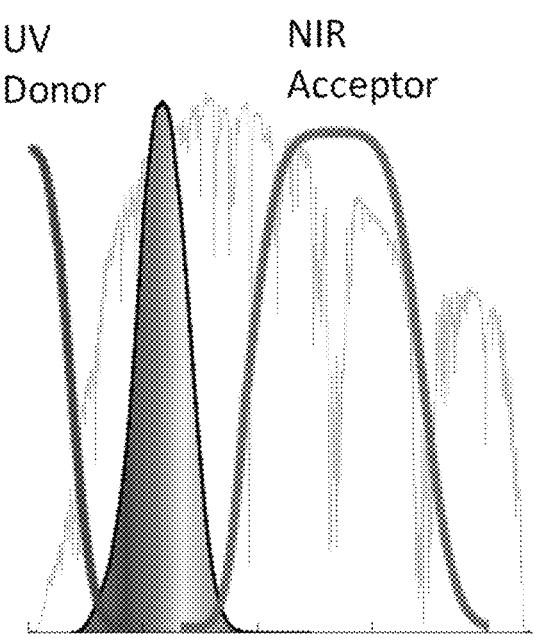

FIG. 6A, FIG. 6B, FIG. 6C, and FIG. 6D provide plots showing example absorption bands for different electron donor and electron acceptor configurations useful with visibly transparent photovoltaic devices. In FIG. 6A, the donor material exhibits absorption in the NIR, while the acceptor material exhibits absorption in the UV. FIG. 6B depicts the opposite configuration, where the donor material exhibits absorption in the UV, while the acceptor material exhibits absorption in the NIR.

Figure 6C:
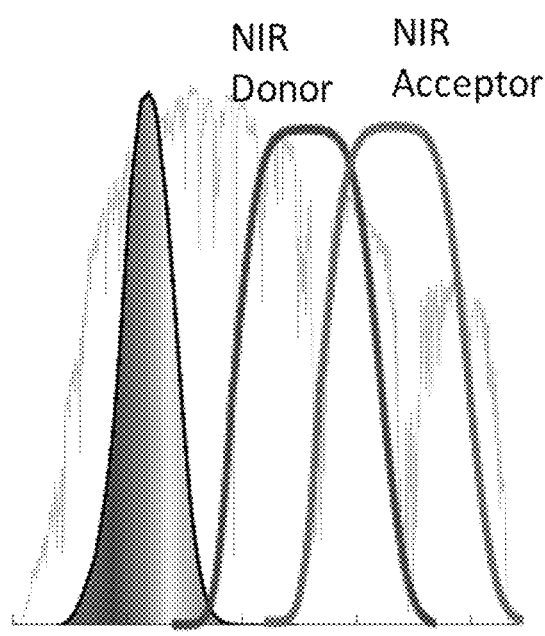
Figure 6D:
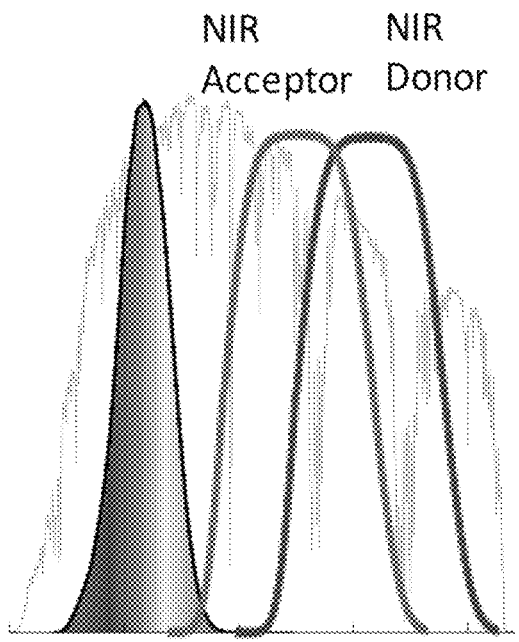

FIG. 6C depicts an additional configuration, where both the donor and acceptor materials exhibit absorption in the NIR. As illustrated in the figures, the solar spectrum exhibits significant amounts of useful radiation in the NIR with only relatively minor amounts in the ultraviolet, making the configuration depicted in FIG. 6C useful for capturing a large amount of energy from the solar spectrum. It will be appreciated that other examples are contemplated where both the donor and acceptor materials exhibit absorption in the NIR, such as depicted in FIG. 6D where the acceptor is blue shifted relative to the donor, opposite the configuration depicted in FIG. 6C, where the donor is blue shifted relative to the acceptor.

Figure 7:
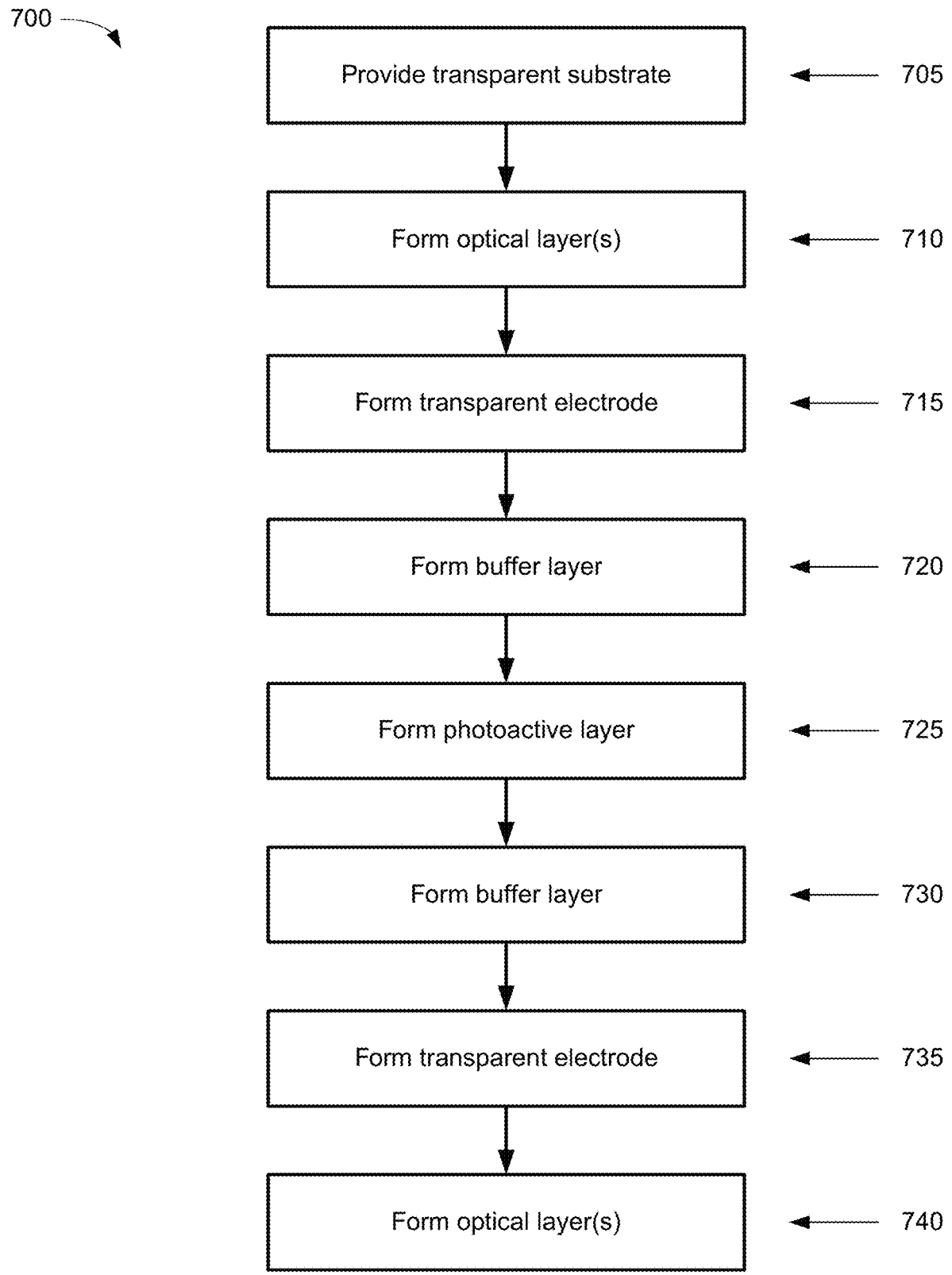
FIG. 7 provides an overview of a method of making visibly transparent photovoltaic devices according to some examples.

The present disclosure also provides methods for making photovoltaic devices, such as photovoltaic device 300. For example, FIG. 7 provides an overview of a method 700 for making a photovoltaic device in accordance with some examples. Method 700 begins at block 705, where a transparent substrate is provided. It will be appreciated that useful transparent substrates include visibly transparent substrates, such as glass, plastic, quartz, and the like. Flexible and rigid substrates are useful with various examples. Optionally, the transparent substrate is provided with one or more optical layers preformed on top and/or bottom surfaces.

At block 710, one or more optical layers are optionally formed on or over the transparent substrate, such as on top and/or bottom surfaces of the transparent substrate. Optionally, the one or more optical layers are formed on other materials, such as an intervening layer or material, such as a transparent conductor. Optionally, the one or more optical layers are positioned adjacent to and/or in contact with the visibly transparent substrate. It will be appreciated that formation of optical layers is optional, and some examples may not include optical layers adjacent to and/or in contact with the transparent substrate. Optical layers may be formed using a variety of methods including, but not limited to, one or more chemical deposition methods, such as plating, chemical solution deposition, spin coating, dip coating, chemical vapor deposition, plasma enhanced chemical vapor deposition, and atomic layer deposition, or one or more physical deposition methods, such as vacuum thermal evaporation, electron beam evaporation, molecular beam epitaxy, sputtering, pulsed laser deposition, ion beam deposition, and electrospray deposition. It will be appreciated that useful optical layers include visibly transparent optical layers. Useful optical layers include those that provide one or more optical properties including, for example, antireflection properties, wavelength selective reflection or distributed Bragg reflection properties, index matching properties, encapsulation, or the like. Useful optical layers may optionally include optical layers that are transparent to ultraviolet and/or near-infrared light. Depending on the configuration, however, some optical layers may optionally provide passive infrared and/or ultraviolet absorption. Optionally, an optical layer may include a visibly transparent photoactive compound described herein.

At block 715, a transparent electrode is formed. As described above, the transparent electrode may correspond to an indium tin oxide thin film or other transparent conducting film, such as thin metal films (e.g., Ag, Cu, etc.), multilayer stacks comprising thin metal films (e.g., Ag, Cu, etc.) and dielectric materials, or conductive organic materials (e.g., conducting polymers, etc.). It will be appreciated that transparent electrodes include visibly transparent electrodes. Transparent electrodes may be formed using one or more deposition processes, including vacuum deposition techniques, such as atomic layer deposition, chemical vapor deposition, physical vapor deposition, vacuum thermal evaporation, sputter deposition, epitaxy, etc. Solution based deposition techniques, such as spin-coating, may also be used in some cases. In addition, transparent electrodes may be patterned by way of microfabrication techniques, such as lithography, lift off, etching, etc.

At block 720, one or more buffer layers are optionally formed, such as on the transparent electrode. Buffer layers may be formed using a variety of methods including, but not limited to, one or more chemical deposition methods, such as a plating, chemical solution deposition, spin coating, dip coating, chemical vapor deposition, plasma enhanced chemical vapor deposition, and atomic layer deposition, or one or more physical deposition methods, such as vacuum thermal evaporation, electron beam evaporation, molecular beam epitaxy, sputtering, pulsed laser deposition, ion beam deposition, and electrospray deposition. It will be appreciated that useful buffer layers include visibly transparent buffer layers. Useful buffer layers include those that function as electron transport layers, electron blocking layers, hole transport layers, hole blocking layers, optical spacers, physical buffer layers, charge recombination layers, or charge generation layers. In some cases, the disclosed visibly transparent photoactive compounds may be useful as a buffer layer material. For example, a buffer layer may optionally include a visibly transparent photoactive compound described herein.

At block 725, one or more photoactive layers are formed, such as on a buffer layer or on a transparent electrode. As described above, photoactive layers may comprise electron acceptor layers and electron donor layers or co-deposited layers of electron donors and acceptors. Useful photoactive layers include those comprising the photoactive compounds described herein. Photoactive layers may be formed using a variety of methods including, but not limited to, one or more chemical deposition methods, such as a plating, chemical solution deposition, spin coating, dip coating, chemical vapor deposition, plasma enhanced chemical vapor deposition, and atomic layer deposition, or one or more physical deposition methods, such as vacuum thermal evaporation, electron beam evaporation, molecular beam epitaxy, sputtering, pulsed laser deposition, ion beam deposition, and electrospray deposition.

In some examples, photoactive compounds useful for photoactive layers may be deposited using a vacuum deposition technique, such as vacuum thermal evaporation. Vacuum deposition may take place in a vacuum chamber, such as at pressures of between about $10^{-5}$ Torr and about $10^{-8}$ Torr. In one example, vacuum deposition may take place at a pressure of about $10^{-7}$ Torr. As noted above, various deposition techniques may be applied. In some examples, thermal evaporation is used. Thermal evaporation may include heating a source of the material (e.g., the visibly transparent photoactive compound) to be deposited to a temperature of between 150° C. and 500° C. The temperature of the source of material may be selected so as to achieve a thin film growth rate of between about 0.01 nm/s and about 1 nm/s. For example, a thin film growth rate of 0.1 nm/s may be used. These growth rates are useful to generate thin films having thicknesses of between about 1 nm and 500 nm over the course of minutes to hours. It will be appreciated that various properties (e.g., the molecular weight, volatility, thermal stability) of the material being deposited may dictate or influence the source temperature or maximum useful source temperature. For example, a thermal decomposition temperature of the material being deposited may limit the maximum temperature of the source. As another example, a material being deposited that is highly volatile may require a lower source temperature to achieve a target deposition rate as compared to a material that is less volatile, where a higher source temperature may be needed to achieve the target deposition rate. As the material being deposited is evaporated from the source, it may be deposited on a surface (e.g., substrate, optical layer, transparent electrode, buffer layer, etc.) at a lower temperature. For example the surface may have a temperature from about 10° C. to about 100° C. In some cases, the temperature of the surface may be actively controlled. In some cases, the temperature of the surface may not be actively controlled.

At block 730, one or more buffer layers are optionally formed, such as on the photoactive layer. The buffer layers formed at block 730 may be formed similar to those formed at block 720. It will be appreciated that blocks 720, 725, and 730 may be repeated one or more times, such as to form a multilayer stack of materials including a photoactive layer and, optionally, various buffer layers.

At block 735, a second transparent electrode is formed, such as on a buffer layer or on a photoactive layer. Second transparent electrode may be formed using techniques applicable to formation of first transparent electrode at block 715.

At block 740, one or more additional optical layers are optionally formed, such as on the second transparent electrode.

It should be appreciated that the specific steps illustrated in FIG. 7 provide a particular method of making a photovoltaic device according to various examples. Other sequences of steps may also be performed according to alternative examples. For example, alternative examples may perform the steps outlined above in a different order. Moreover, the individual steps illustrated in FIG. 7 may include multiple sub-steps that may be performed in various sequences as appropriate to the individual step. Furthermore, additional steps may be added or removed depending on the particular applications. It will be appreciated that many variations, modifications, and alternatives may be used.

Method 700 may optionally be extended to correspond to a method for generating electrical energy. For example, a method for generating electrical energy may comprise providing a photovoltaic device, such as by making a photovoltaic device according to method 700. Methods for generating electrical energy may further comprise exposing the photovoltaic device to visible, ultraviolet and/or near-infrared light to drive the formation and separation of electron-hole pairs, as described above with reference to FIG. 5, for example, for generation of electrical energy. The photovoltaic device may include the photoactive compounds described herein as photoactive materials, buffer materials, and/or optical layers.

Turning now to further details on photoactive compounds, in some examples, the photoactive compounds described herein comprises a molecular composition having a structure A-D-A, A-pi-D-A, A-pi-D-pi-A, A-D, or A-pi-D, wherein each "A" moiety is an electron acceptor moiety, the "D" moiety is an electron donor moiety, and the "pi" moiety is a π-bridging moiety. Advantageously, the photoactive compounds can have molecular weights making them suitable for physical vapor deposition techniques, such as molecular weights from 200 amu to 1200 amu, for example, such as from 200 amu to 900 amu, from 200 amu to 950 amu, from 200 amu to 1000 amu, from 200 amu to 1050 amu, from 200 amu to 1100 amu. The photoactive compounds can exhibit thermal decomposition temperatures from 150° C. to 500° C. or greater than 500° C. and/or sublimation temperatures of 150° C. to 450° C. at pressures from 0.2 Torr to $10^{-7}$ Torr. These characteristics can aid or impart stability making the photoactive compounds suitable for use in physical vapor deposition processes.

The photoactive compounds can exhibit optical properties, as described above, such as where the photoactive compound exhibits absorption in the ultraviolet, visible, and/or infrared regions. In some cases, the compounds exhibit a bandgap of from 0.5 eV to 4.0 eV. For visibly transparent photoactive compounds, the bandgap may be from 0.5 eV to 1.9 eV or from 2.7 eV to 4.0 eV.

Each of the different A, pi, and D moieties in the photoactive compounds can impact the absorption profile and the volatility. Without limitation, each "A" moiety in a photoactive compound can be independently selected from:

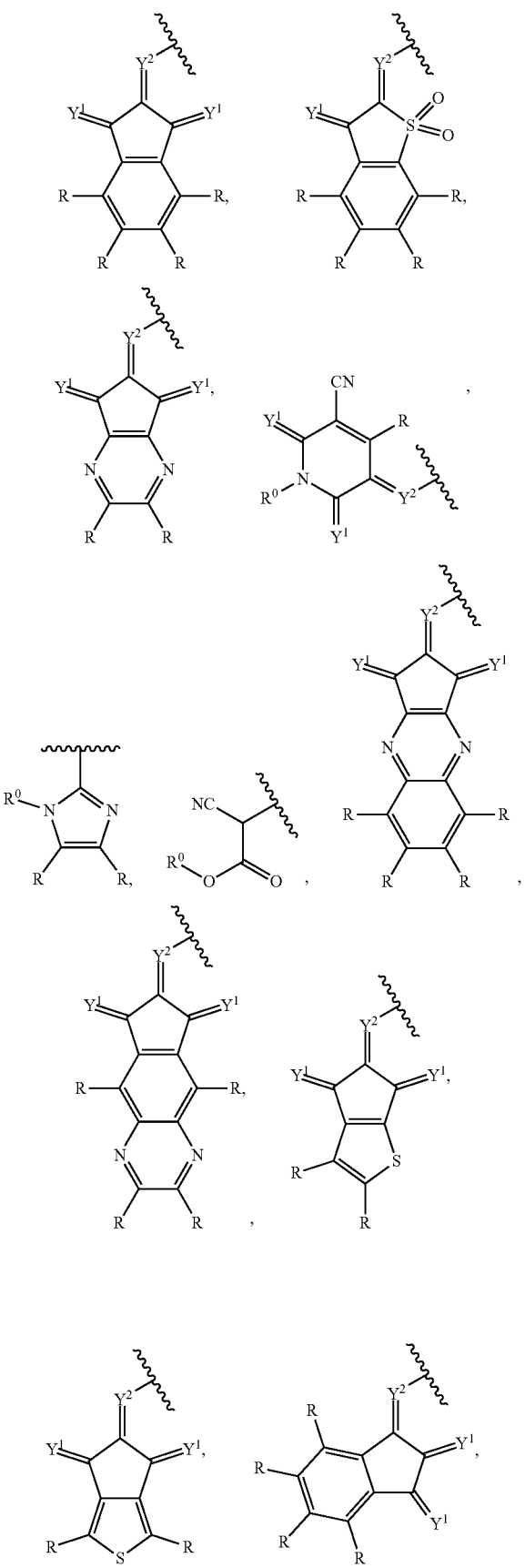
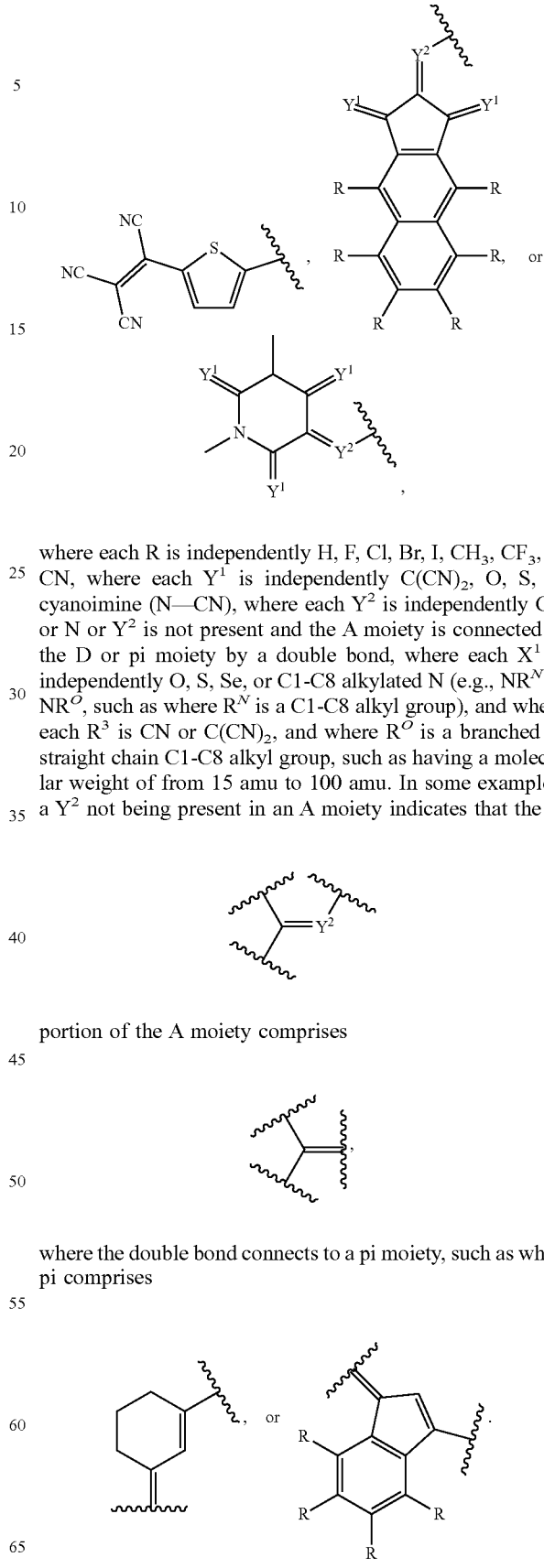

where each R is independently H, F, Cl, Br, I, $CH_3$, $CF_3$, or CN, where each $Y^1$ is independently $C(CN)_2$, O, S, or cyanoimine (N—CN), where each $Y^2$ is independently CH or N or $Y^2$ is not present and the A moiety is connected to the D or pi moiety by a double bond, where each $X^1$ is independently O, S, Se, or C1-C8 alkylated N (e.g., $NR^N$ or $NR^O$, such as where $R^N$ is a C1-C8 alkyl group), and where each $R^3$ is CN or $C(CN)_2$, and where $R^O$ is a branched or straight chain C1-C8 alkyl group, such as having a molecular weight of from 15 amu to 100 amu. In some examples, a $Y^2$ not being present in an A moiety indicates that the portion of the A moiety comprises where the double bond connects to a pi moiety, such as when pi comprises In some cases, it may be desirable for at least one $Y^1$ in a photoactive compound to be O or S, and not $C(CN)_2$. Although use of O instead of $C(CN)_2$ as a $Y^1$ in an A moiety can reduce a molecular weight by about 48 amu, the resultant photoactive compounds can exhibit larger increases in vapor pressure and volatility than are expected for just this change in molecular weight. Similarly, the use of S instead of $C(CN)_2$ as a $Y^1$ in an A moiety can reduce a molecular weight by about 32 amu, but the resultant photoactive compounds can exhibit larger increases in vapor pressure and volatility than are expected for just this change in molecular weight.

In some cases, it may be desirable for at least one $Y^2$ in a photoactive compound to be N, and not CH or a double-bond linkage. Such A moieties may be referred to as having a structure of

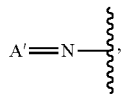

where A' is an imine-linked electron acceptor moiety, which may be or comprise a heterocycle, which may be substituted or unsubstituted. In some examples, A may be an imine-linked indandione, an imine-linked dicyanomethyleneindanone, an imine-linked bis(dicyanomethylidene)indan, or an imine-linked dicyanovinylene. Use of N as a $Y^2$ instead of CH or a double-bond linkage can result in an increase in molecular weight by about 1 amu, but other properties can change, also. For example, use of N as a $Y^2$ instead of CH or a double-bond linkage can result in a change in the optical properties of the photoactive compound. As one example, a redshift in the absorption maximum, such as by 50-100 nm can be achieved by using imine-linking between the A moiety and the D moiety or a pi moiety. In another example, a decrease in the band gap can be achieved, such as by about 0.25 eV to 0.75 eV, by using imine-linking between the A moiety and the D moiety or a pi moiety.

Without limitation, each "pi" moiety in a photoactive compound can be independently selected from:

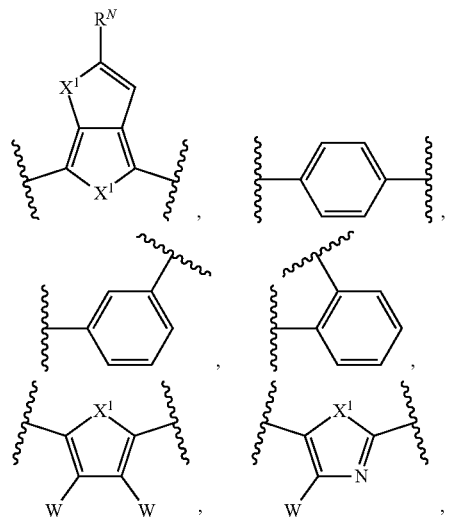

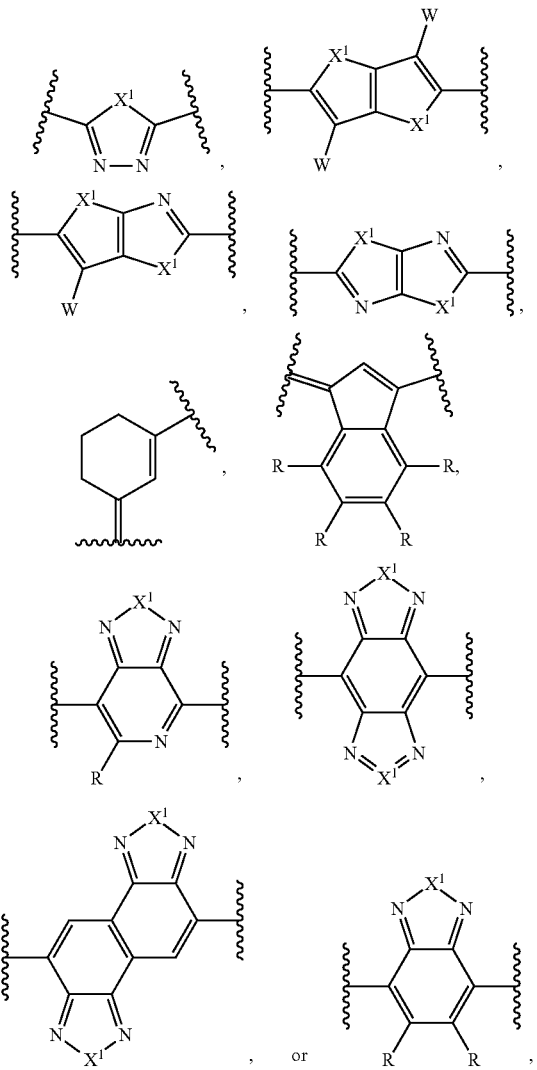

where each $X^1$ is independently O, S, Se, or C1-C8 alkylated N (e.g., $NR^N$ or $NR^O$, such as where R) is a C1-C8 alkyl group), each R is independently H, F, Cl, Br, I, $CH_3$, $CF_3$, or CN, each W is independently H, F, or a branched or straight chain C1-C8 alkyl group or a branched or straight chain C1-C8 alkoxy group, and each $R^N$ is independently a branched, cyclic, or straight chain alkyl or ester group having a molecular weight of from 15 amu to 100 amu. In other examples, longer conjugated pi systems can be used, such as where one or more carbon chains containing alternating double and single bonds are included at the position of the wavy line in the structures shown. In other examples, longer fused ring systems can be used, such as containing 3, 4, or 5 fused 5-membered rings, such as

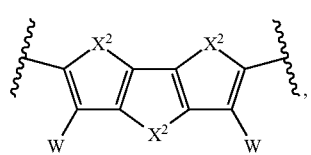

-continued

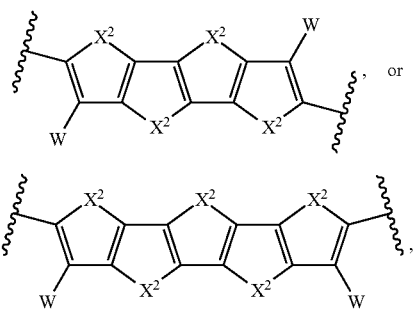
or where each $X^2$ is independently O, S, Se, NH, $NR^N$, $CH_2$, or $C(R^N)_2$ and each W is independently H, F, or a branched or straight chain C1-C8 alkyl group or a branched or straight chain C1-C8 alkoxy group. Including pi moieties in the photoactive compounds can, for example, result in a change in optical properties of the photoactive compound. As one example, a redshift in the absorption maximum can be achieved by longer and longer pi moieties between the A moiety and the D moiety. It will be appreciated, however, that inclusion of a pi moiety in a photoactive compound can result in an increase in the molecular weight of the compound, as compared to a compound comprising the same A and D moieties but not including a pi moiety. As one example, a pi moiety comprising a single 5-membered ring where $X^2$ is N can add about 64 amu to the molecular weight. For each additional fused 5-membered ring where $X^2$ is N, about 38 amu more will be added to the molecular weight. For example, a pi moiety comprising two fused 5-membered rings where X' is N can add about 102 amu to the molecular weight. In some cases, the redshifted absorption maximum can be beneficial despite the increase in the molecular weight and the associated reduction in vapor pressure and volatility. In other cases, the redshifted absorption maximum may not offset the increase in the molecular weight and the associated reduction in vapor pressure and volatility.

Without limitation, each "D" moiety in a photoactive compound can be independently selected from:

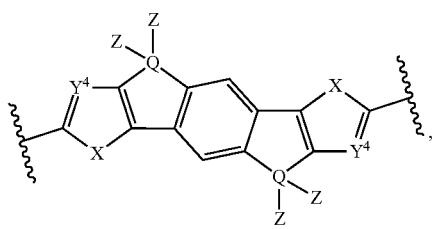

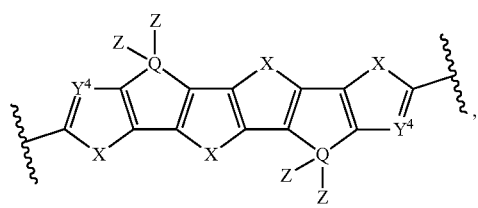

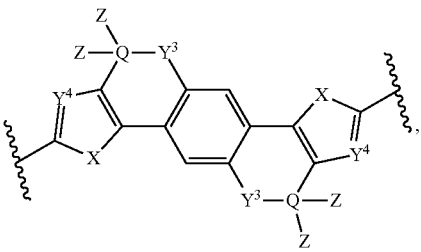

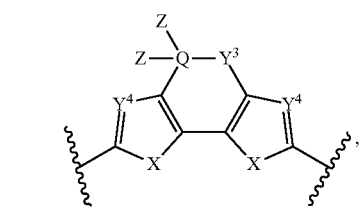

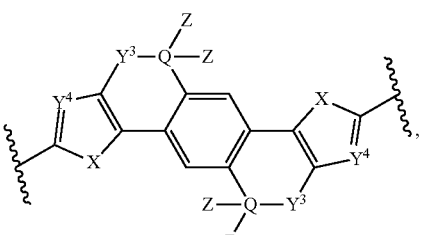

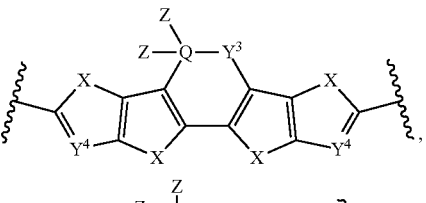

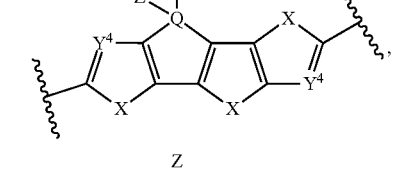

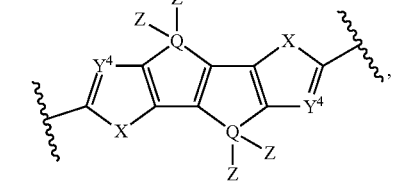

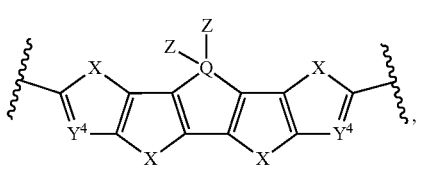

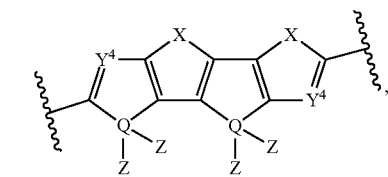

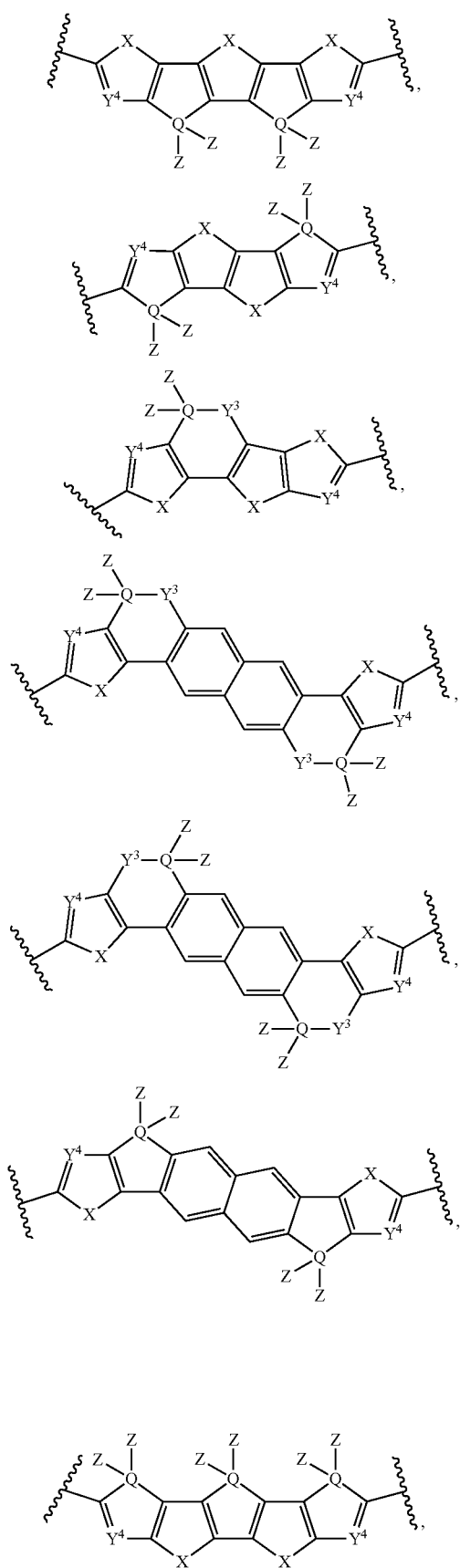
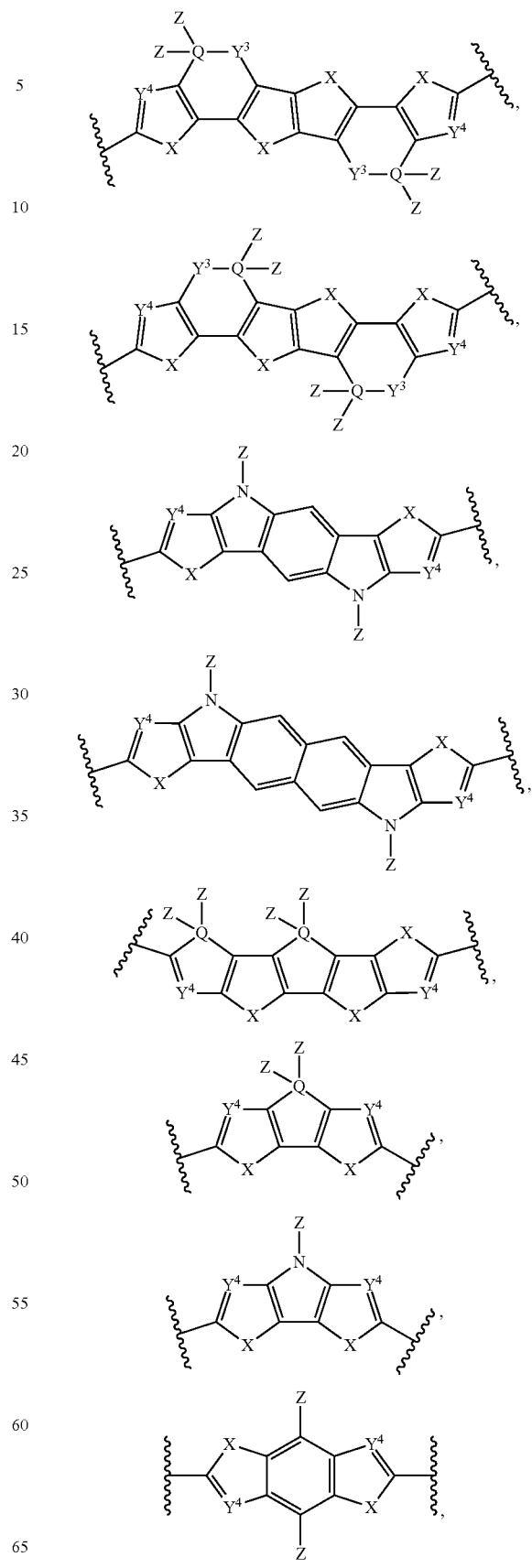

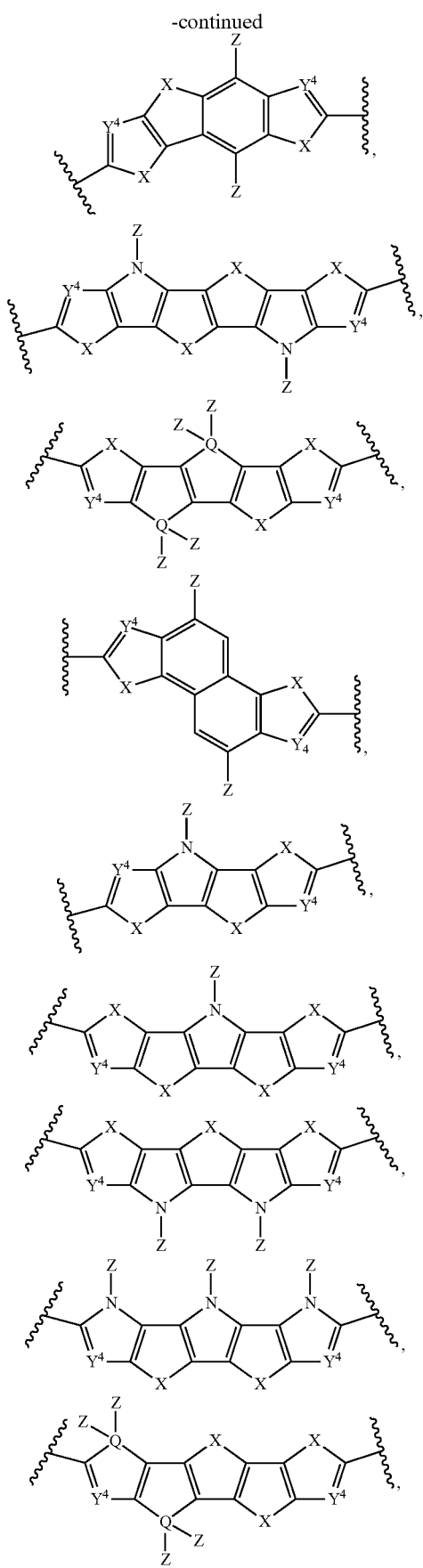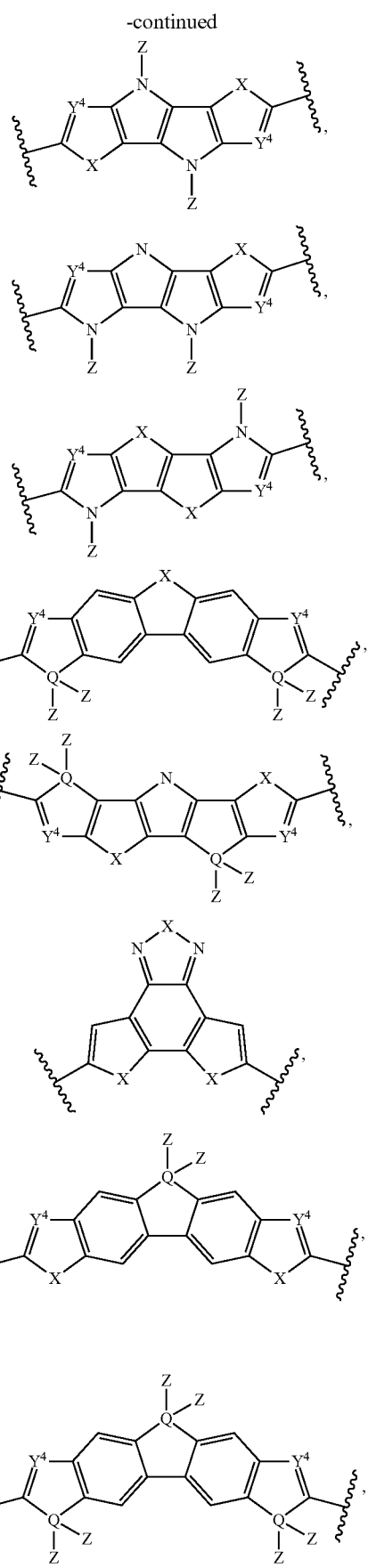

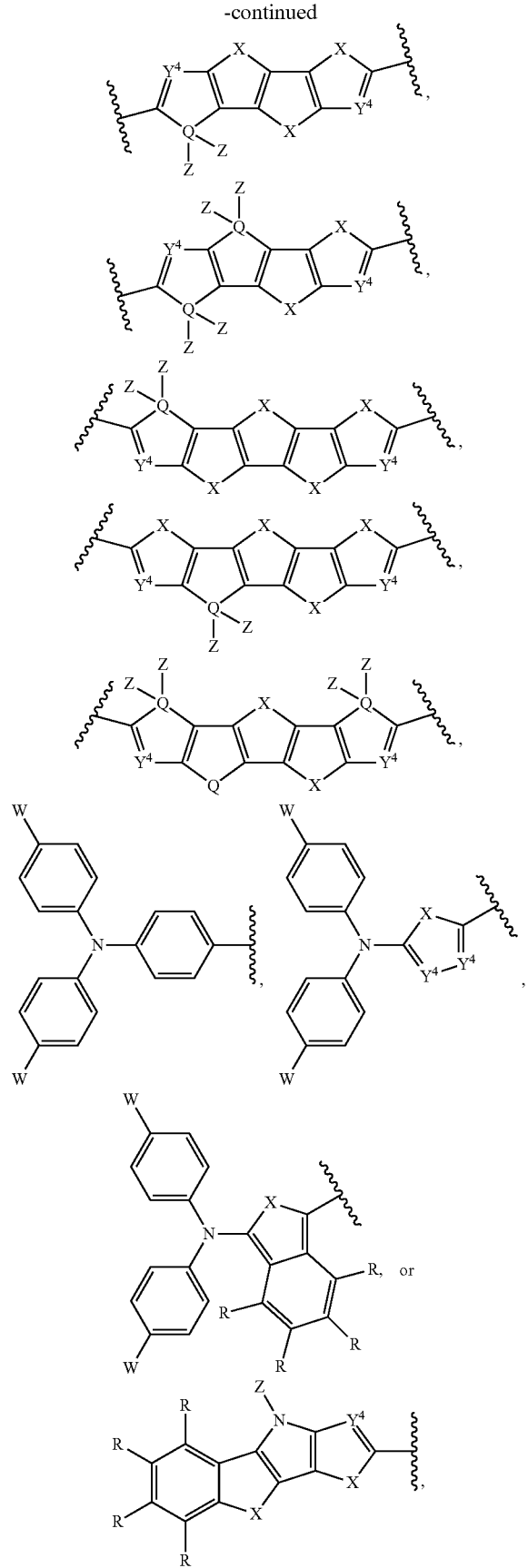

where each X is independently O, S, Se, NH, $NR^N$, $CH_2$, $C(R^N)_2$, $Si(R^N)_2$, or $Ge(R^N)_2$, each $R^N$ is independently a branched, cyclic, or straight chain alkyl or ester group having a molecular weight of from 15 amu to 100 amu, each W is independently H, F, or a branched or straight chain C1-C8 alkyl group or a branched or straight chain C1-C8 alkoxy group, each R is independently H, F, Cl, Br, I, $CH_3$, $CF_3$, or CN, each Z is independently a side group, such as $R^N$, or a planarity disrupting moiety, $Y^3$ is independently O or S, and $Y^4$ is independently CH, N, or $CR^N$.

A variety of side groups Z can be used. In some examples, one or more Zs are independently a substituted (e.g., halogen substituted) or unsubstituted alkyl group, a substituted (e.g., halogen substituted) or unsubstituted alkenyl group, an unsubstituted or methyl, ethyl, halogen, or trihalomethyl substituted cycloalkyl group, an unsubstituted or methyl, ethyl, halogen, or trihalomethyl substituted cycloalkenyl group, an unsubstituted or methyl, ethyl, halogen, or trihalomethyl substituted cyclopentadienyl group, or an unsubstituted or methyl, ethyl, halogen, or trihalomethyl substituted phenyl group. Optionally, Z contains one or more halogen or trihalomethyl substituents. Optionally, two Zs together form an unsubstituted or methyl, ethyl, halogen, or trihalomethyl substituted cycloalkyl group, an unsubstituted or methyl, ethyl, halogen, or trihalomethyl substituted cycloalkenyl group, an unsubstituted or methyl, ethyl, halogen, or trihalomethyl substituted cyclopentadienyl group, or an unsubstituted or methyl, ethyl, halogen, or trihalomethyl substituted phenyl group. In some examples, two Zs together form a group containing fused 5-membered rings that are unsubstituted or methyl, ethyl, halogen, or trihalomethyl substituted, fused 6-membered rings that are unsubstituted or methyl, ethyl, halogen, or trihalomethyl substituted, or fused 5-membered and 6-membered rings that are unsubstituted or methyl, ethyl, halogen, or trihalomethyl substituted. In some examples, two Zs together form a heterocyclic group or fused heterocyclic group. Optionally, one or more Z may be a hydrogen atom. Optionally, one or more Z may be 2-methylbutyl.

In some cases, each D moiety can include a planar central core with one or more side groups Z. In the examples given above, each D moiety may contain a planar fused ring central core structure comprising an aromatic, heteroaromatic, polycyclic aromatic, or polycyclic heteroaromatic moiety containing one or more 5-membered and/or 6-membered rings in which the ring structure comprises carbon and optionally one or more heteroatoms. In some cases, the atom that one or more side groups Z are bonded to is a quaternary center, Q. For example, the D moiety may comprise

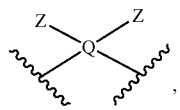

wherein Q is a quaternary center, which may be C, Si, or Ge, for example. The presence of a quaternary center may be useful for conformationally locking the one or more side groups Z in a configuration where they are positioned out of plane to the central core. In specific examples, a D moiety may comprise one or more of the following groups or a heterocyclic analog thereof:

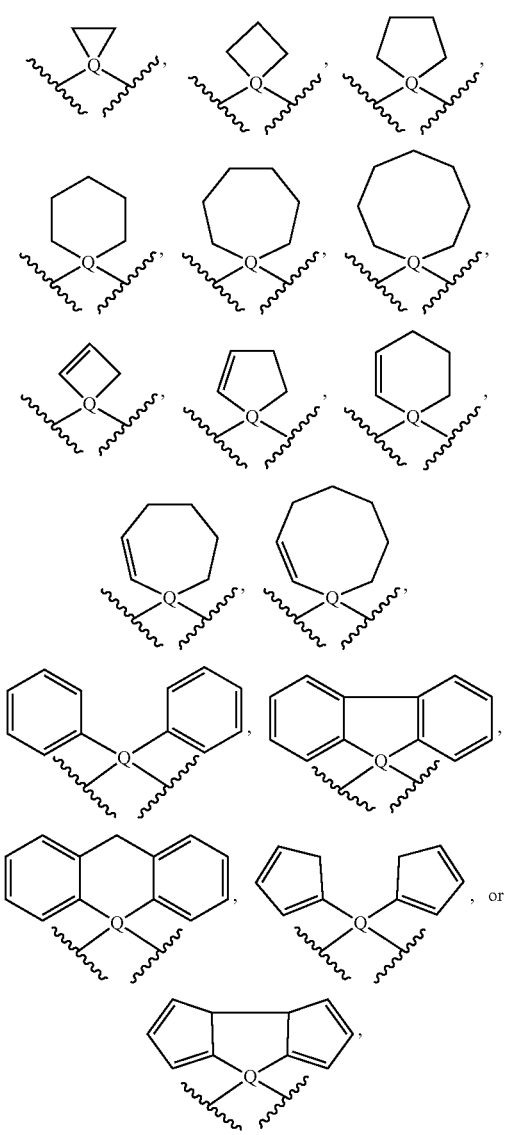

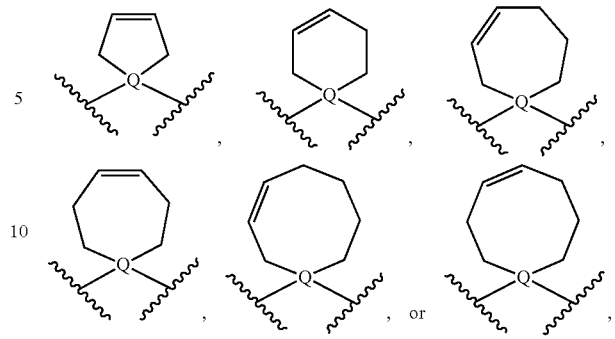

each of which is unsubstituted or substituted with one or more methyl, ethyl, halogen (e.g. fluoro), or trihalomethyl (e.g., trifluoromethyl) groups, or heterocyclic analogs thereof. Although a single configuration is shown for various different sized alkene rings in these examples, isomers where the double bond is in a different position are also contemplated herein, such as optionally substituted with one or more methyl, ethyl, halogen (e.g. fluoro), or trihalomethyl (e.g., trifluoromethyl) groups, or heterocyclic analogs thereof. Inclusion of side groups comprising a ring group containing a quaternary carbon atom Q, as shown, may allow the electron donor molecule to exhibit a spiro structure.

Inclusion of a side group (or groups) Z that is conformationally locked out of plane to the central core may provide advantageous properties to the photoactive compound, such as an increase in the sublimation yield. For example, photoactive compounds containing side groups that are conformationally locked out of plane to the central core (e.g., core disrupted photoactive compounds) may exhibit larger vapor pressures and lower sublimation temperatures as compared to other compounds containing side groups that are not conformationally locked out of plane to the central core (e.g., photoactive compounds lacking core disruption), such as despite exhibiting the same, nearly the same, or comparable molecular weights (e.g., within 2 or 3 amu of one another). Without wishing to be bound by any theory, inclusion of side groups that are conformationally locked out of plane to the central core of a photoactive compound can result in disrupting the bulk crystal packing efficiency of the photoactive compound, making the crystallized structure less energetically favorable than photoactive compounds with more tightly packed crystal structures. In this way, the core disrupted photoactive compounds may exhibit relatively smaller heats of fusion, evaporation, and/or sublimation, making it relatively easier to evaporate these compounds into the gas phase. As such, the sublimation yield of a photoactive compound including side groups that are conformationally locked out of plane to the central core may be greater than that of a similar photoactive compound with side groups that are not conformationally locked out of plane to the central core.

A variety of different photoactive compounds can be formulated and used according to the above description. Some specific example photoactive compounds include those having a formula of:

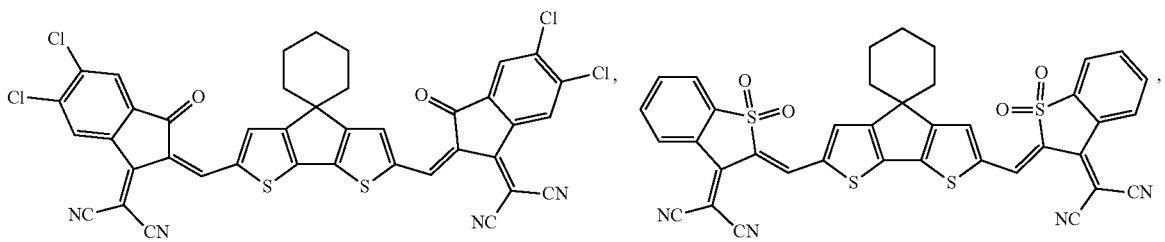

-continued
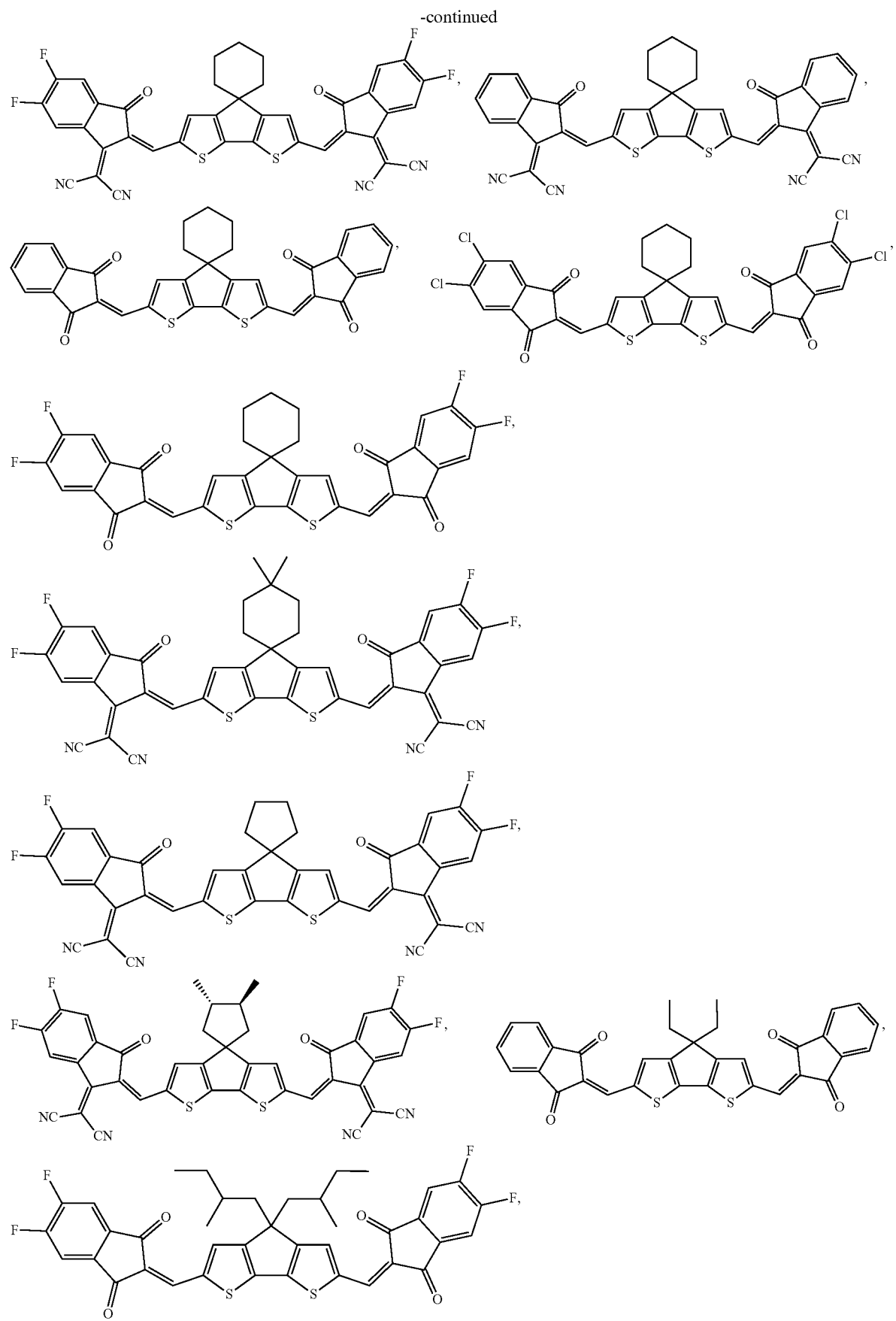

-continued
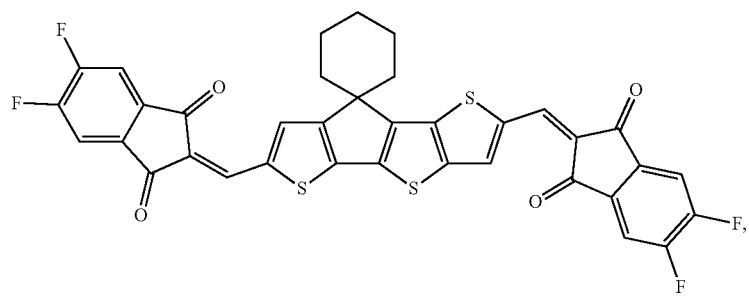
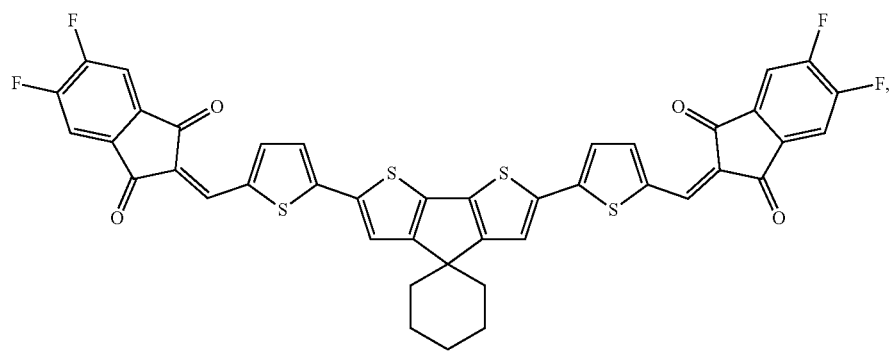
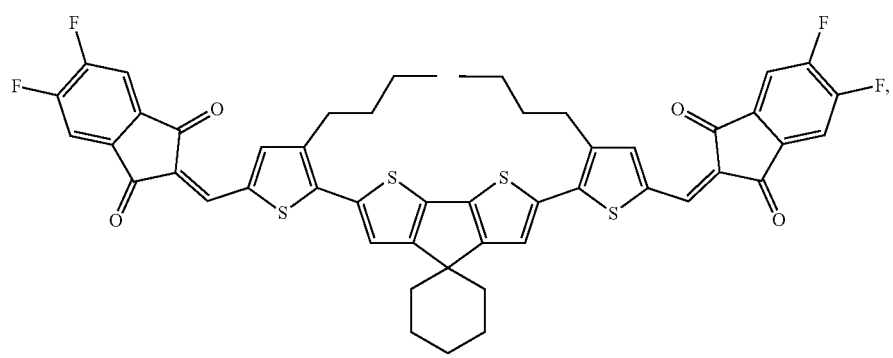
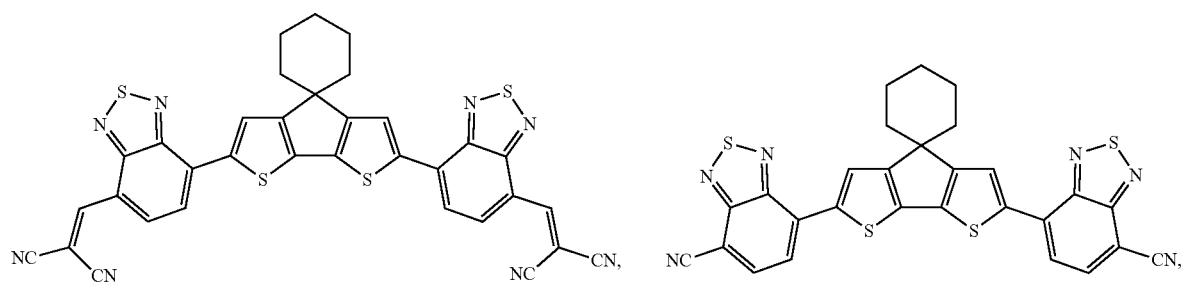
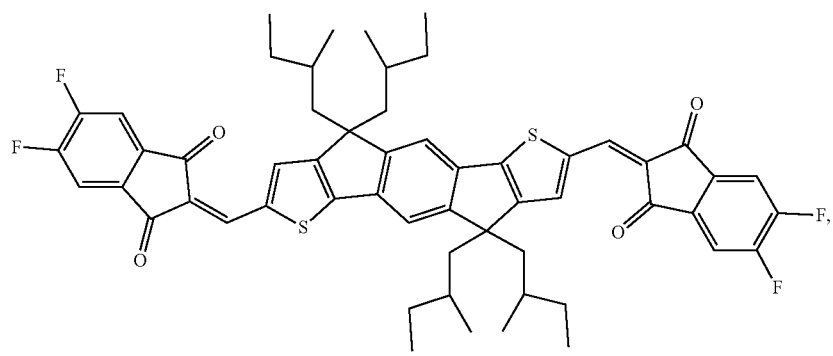

-continued
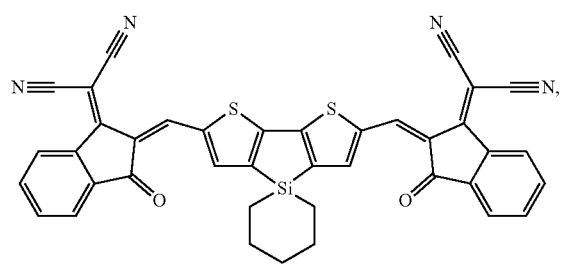 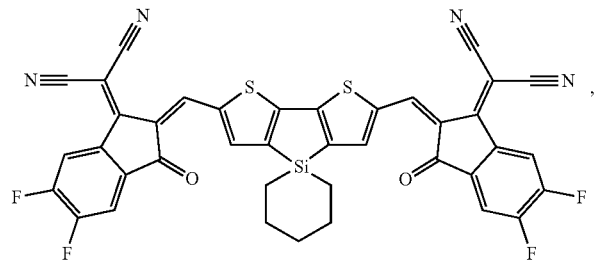
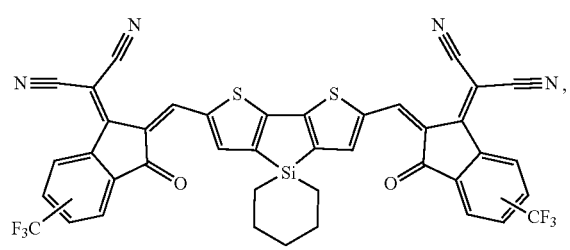 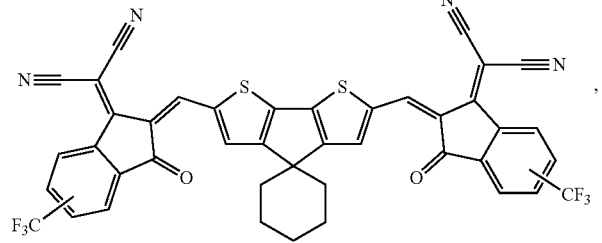
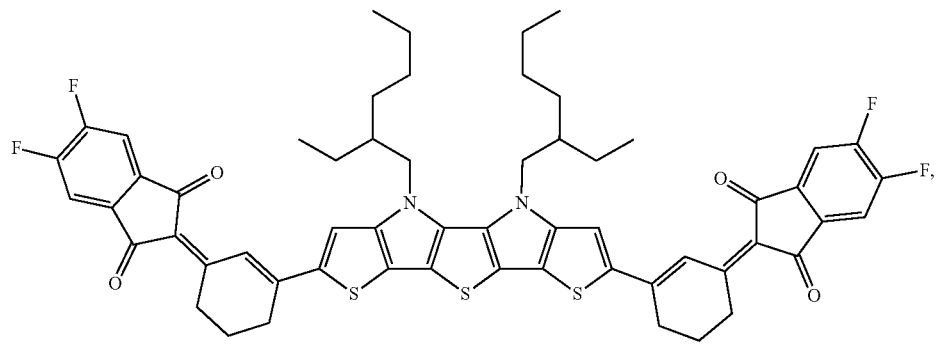
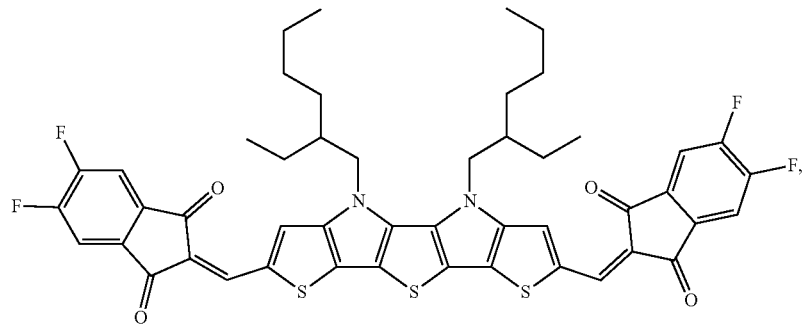
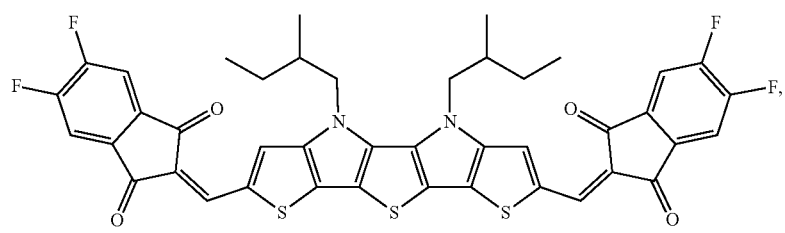
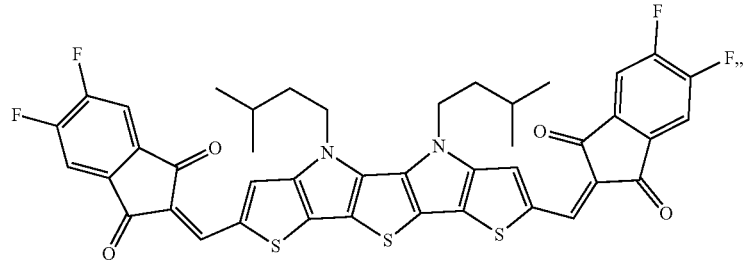

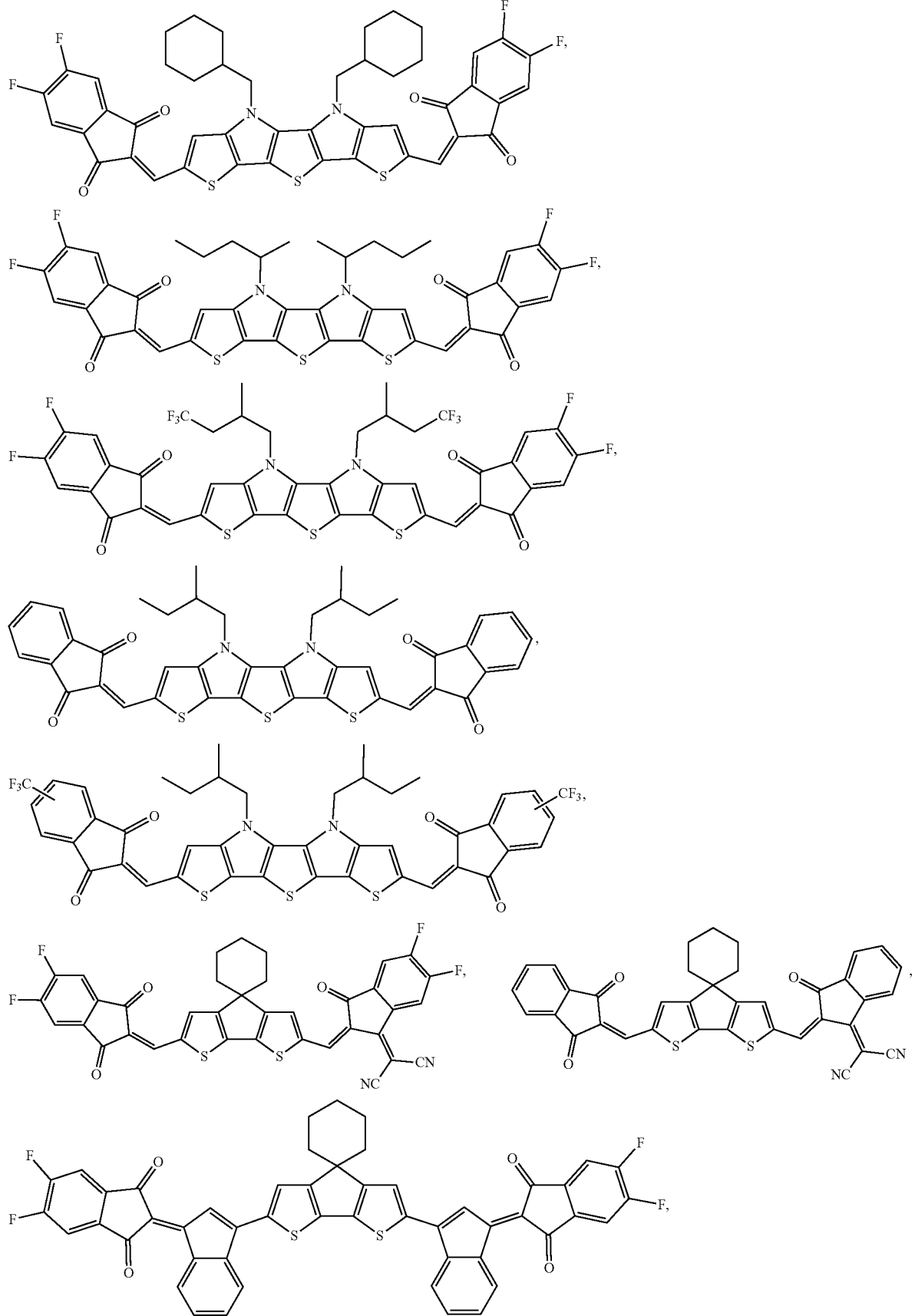

-continued
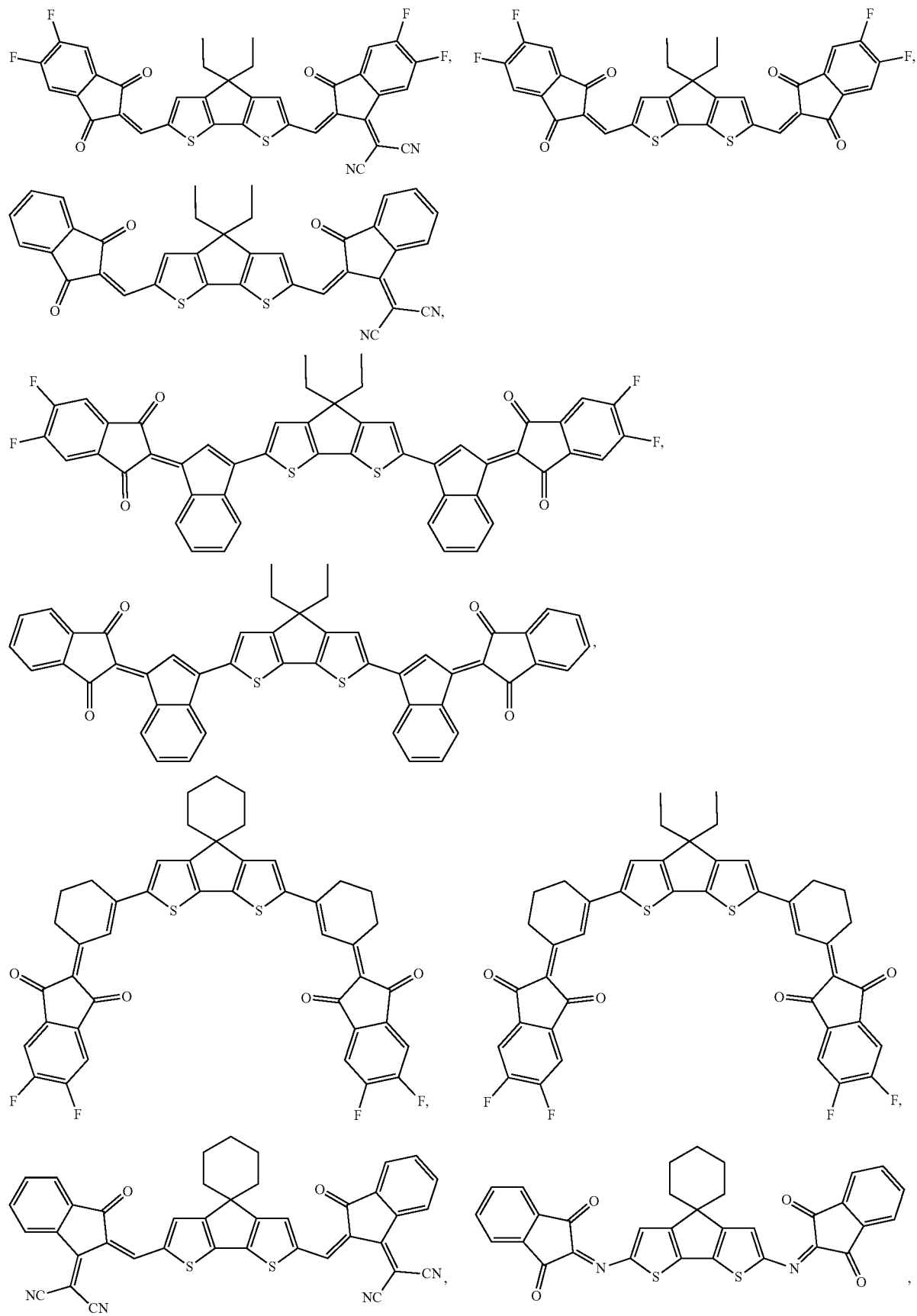

-continued
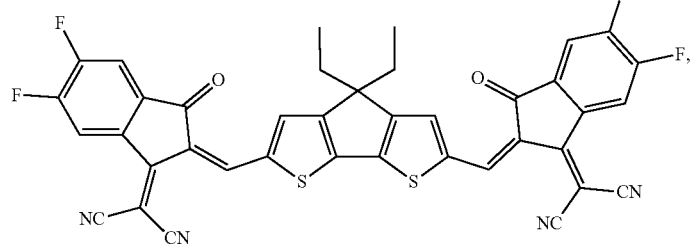
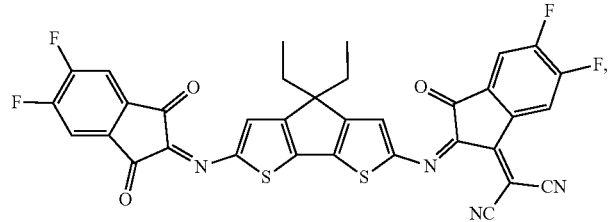
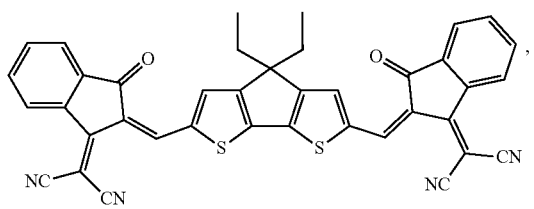
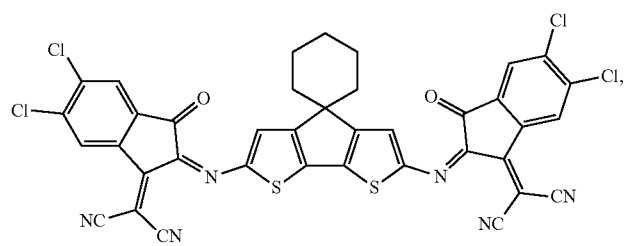
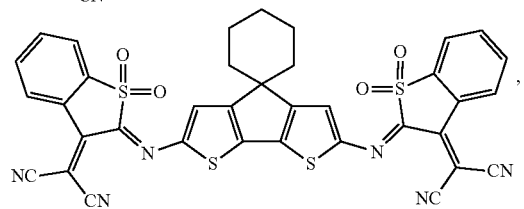
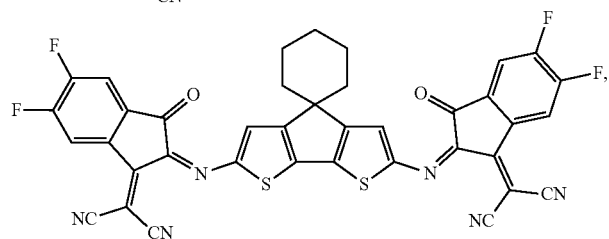
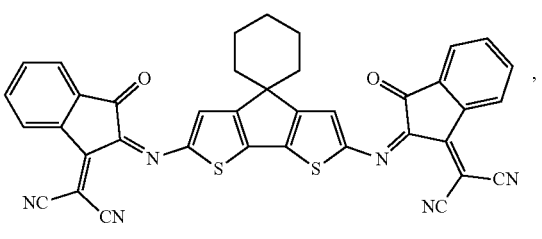
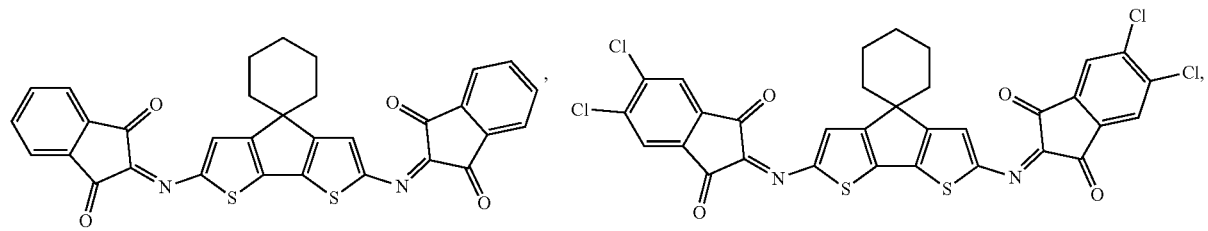
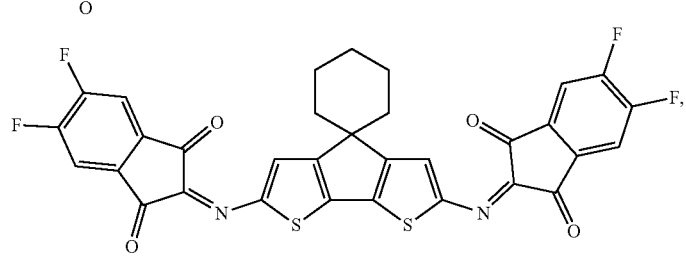
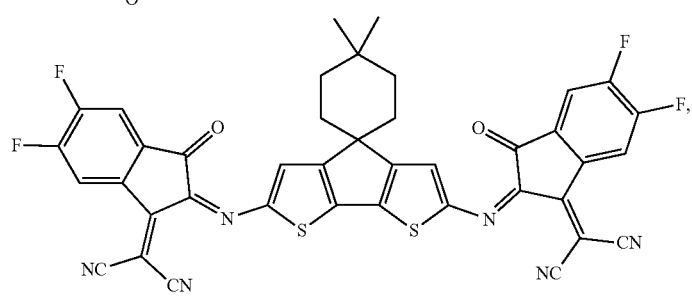

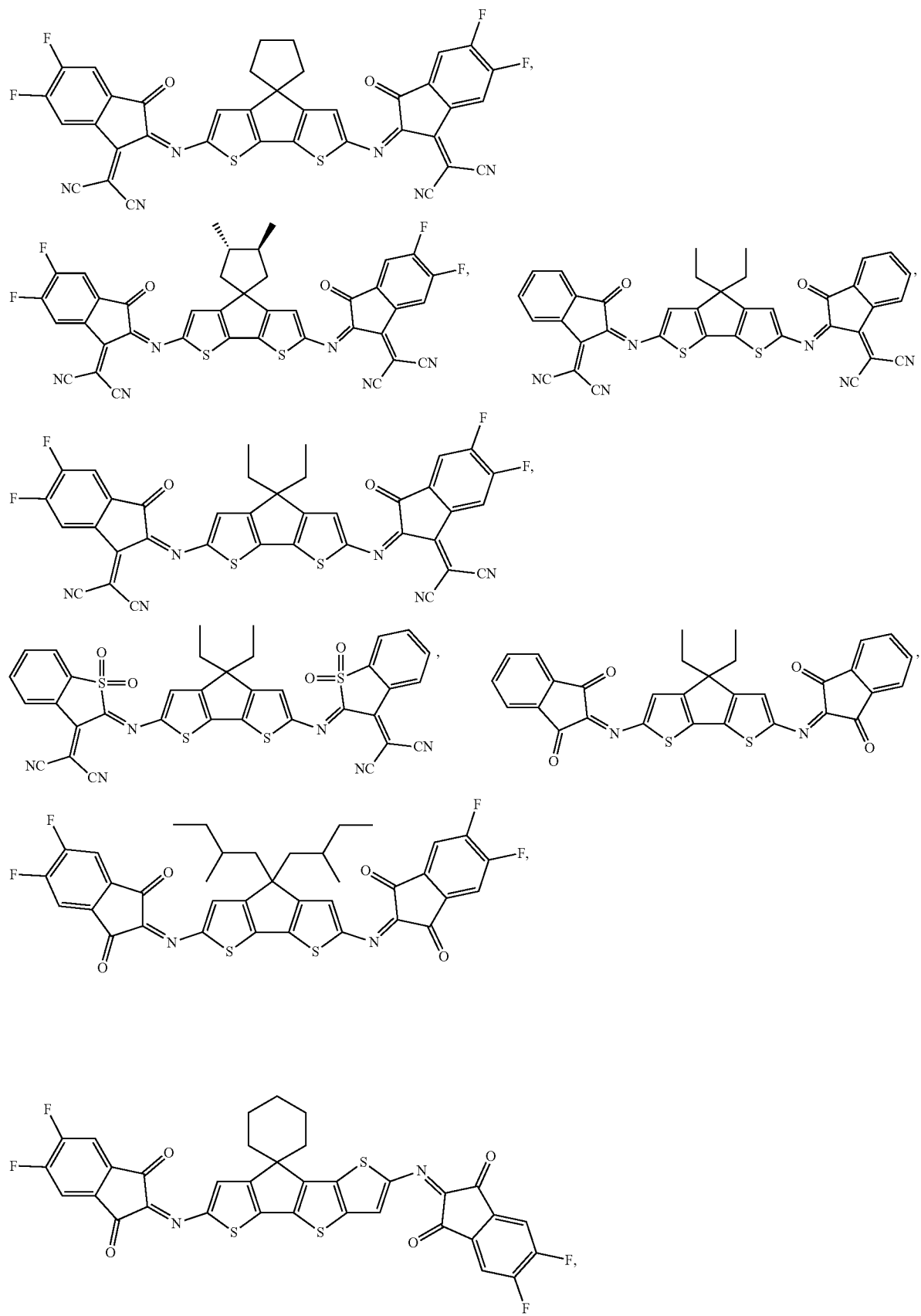

-continued
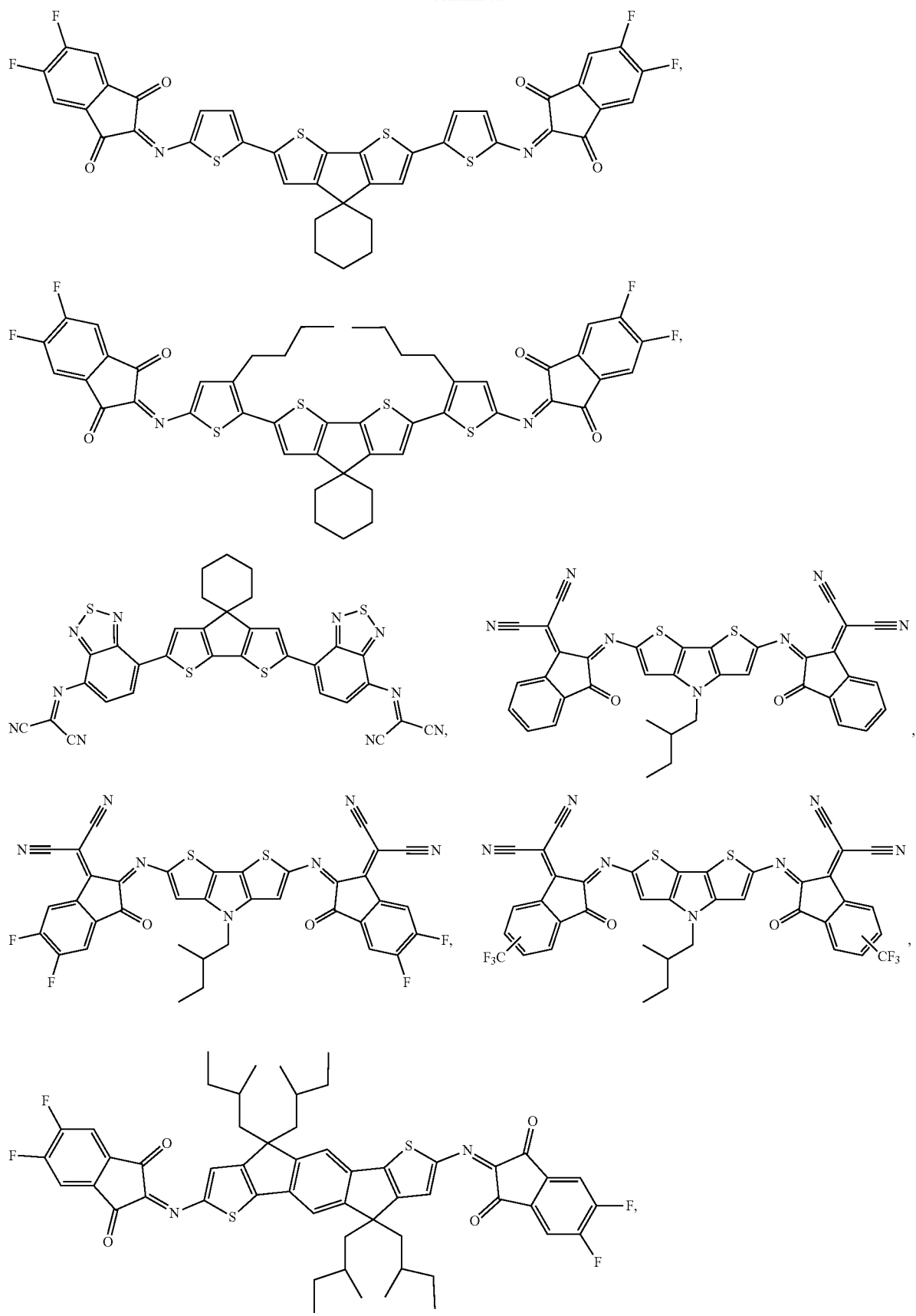

-continued
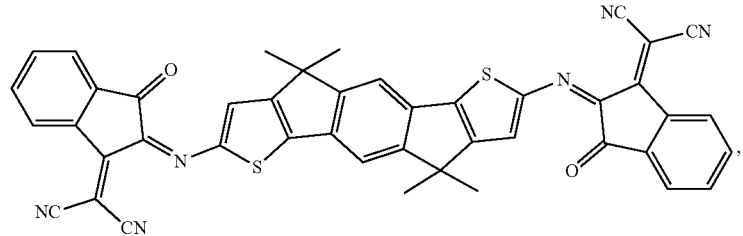
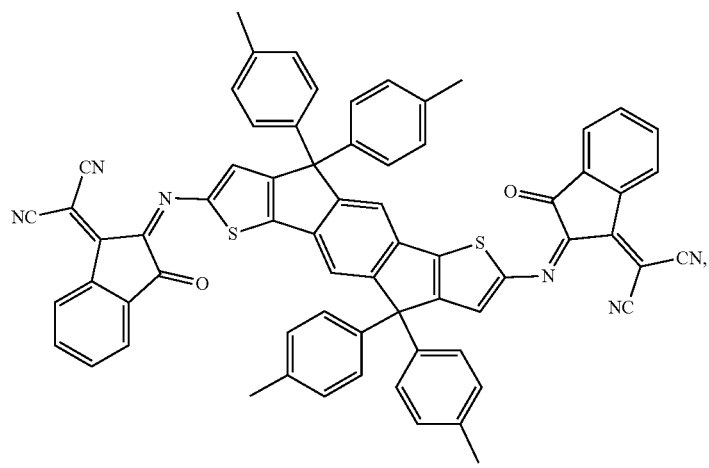
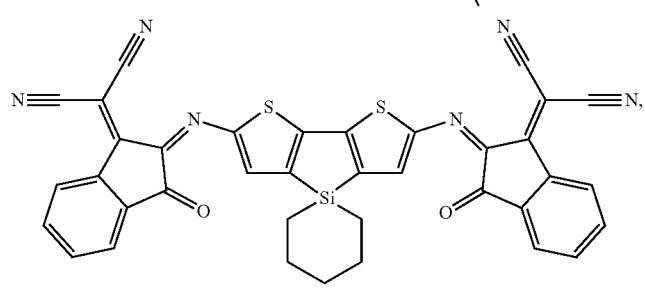
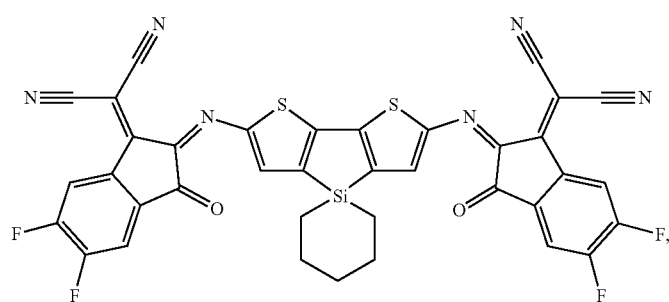
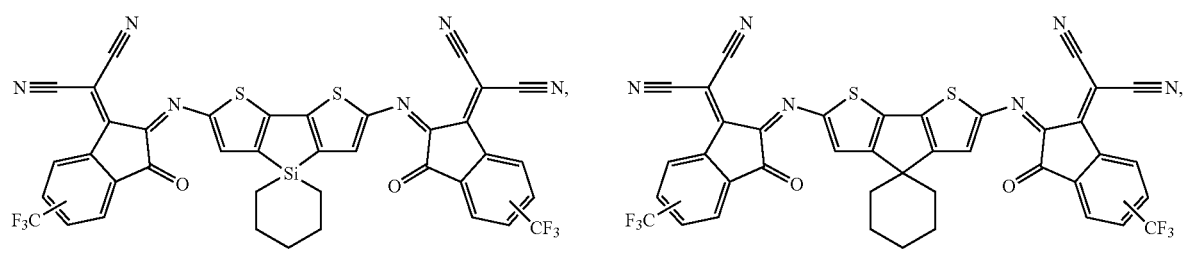

-continued
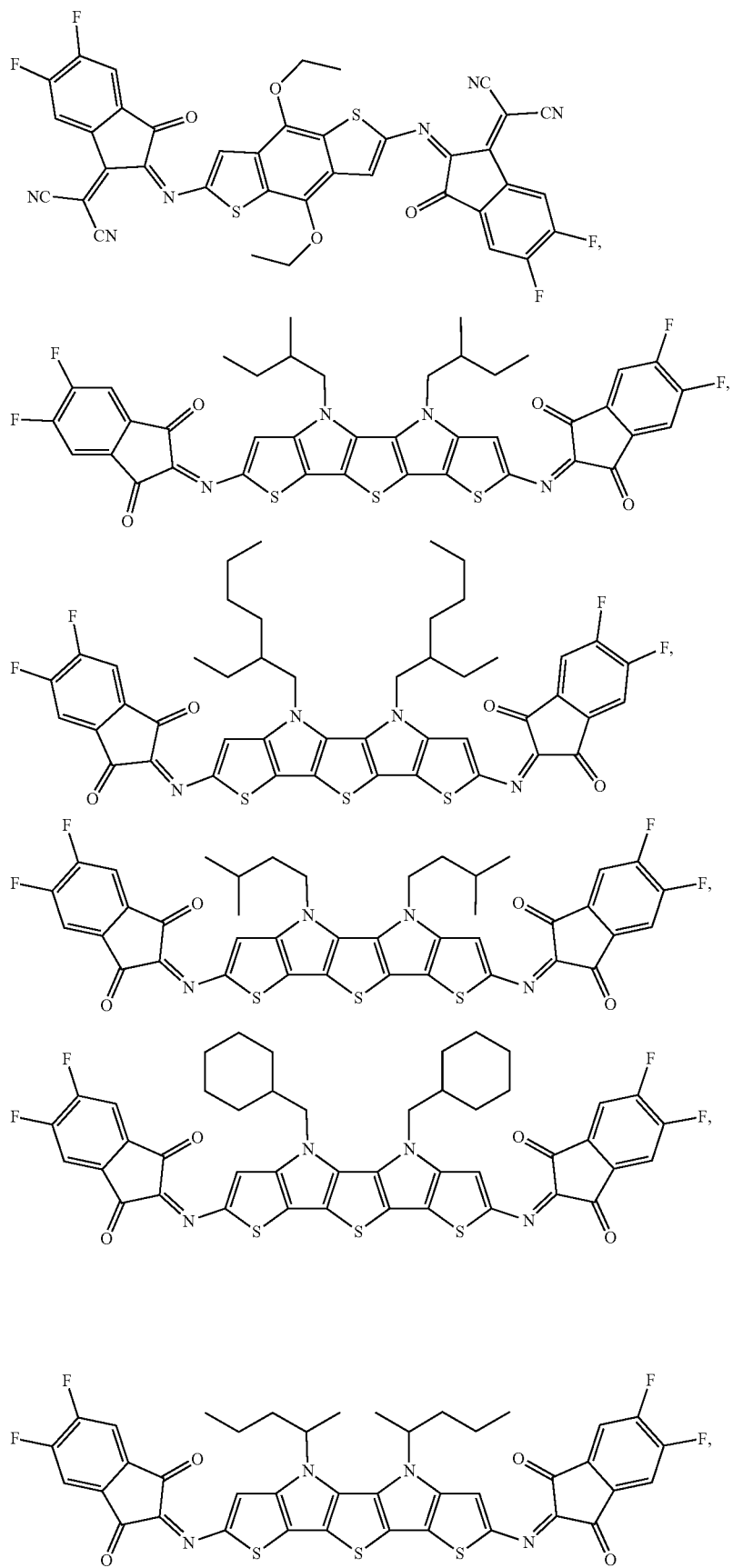

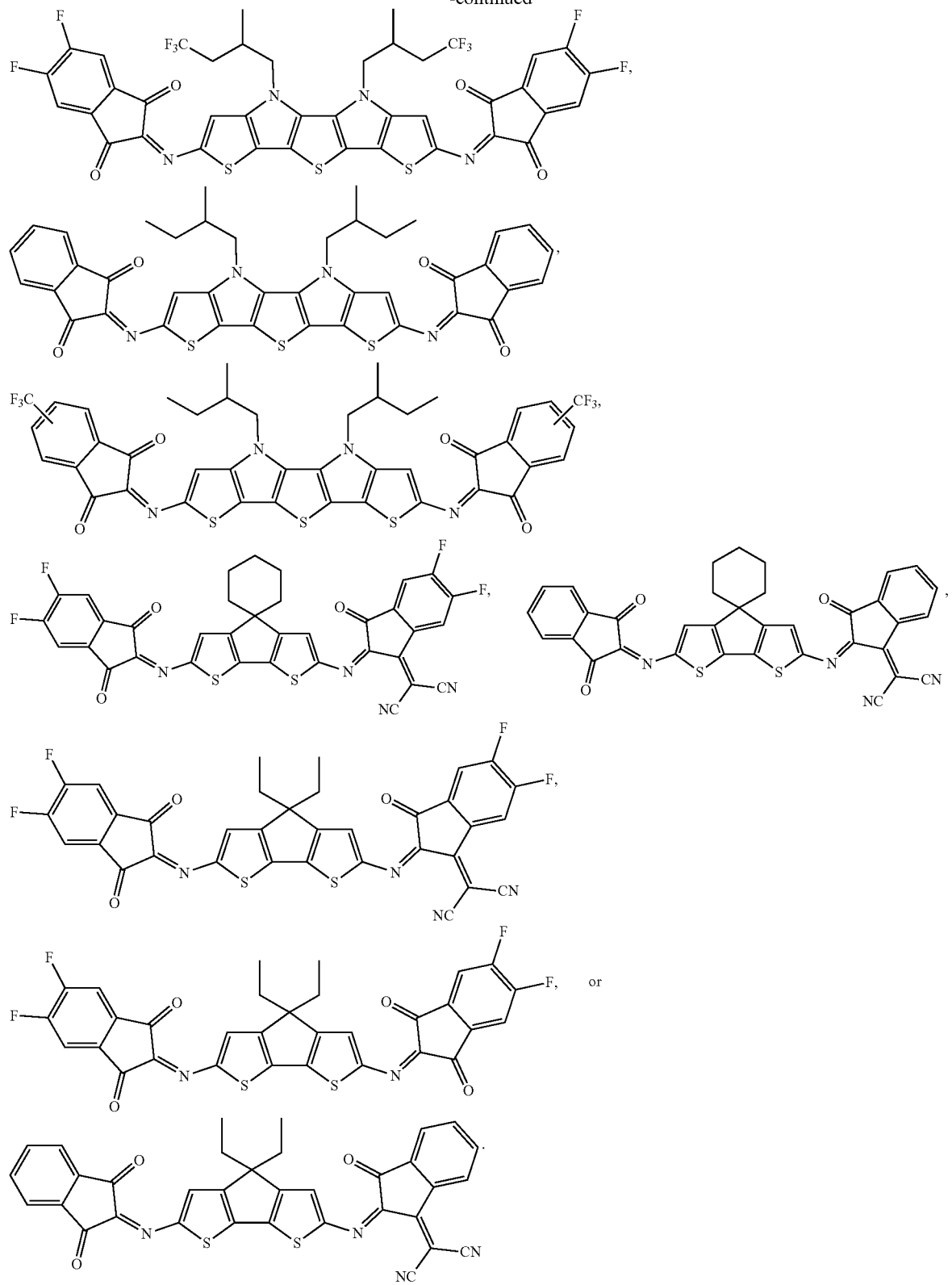
It will be appreciated that a variety of other photoactive compounds comprising various combinations of the disclosed A, D, and pi moieties are also contemplated.
For example, additional photoactive compounds include those having any of the following formulas, such as where any indicated Z groups are optionally 2-methylbutyl:

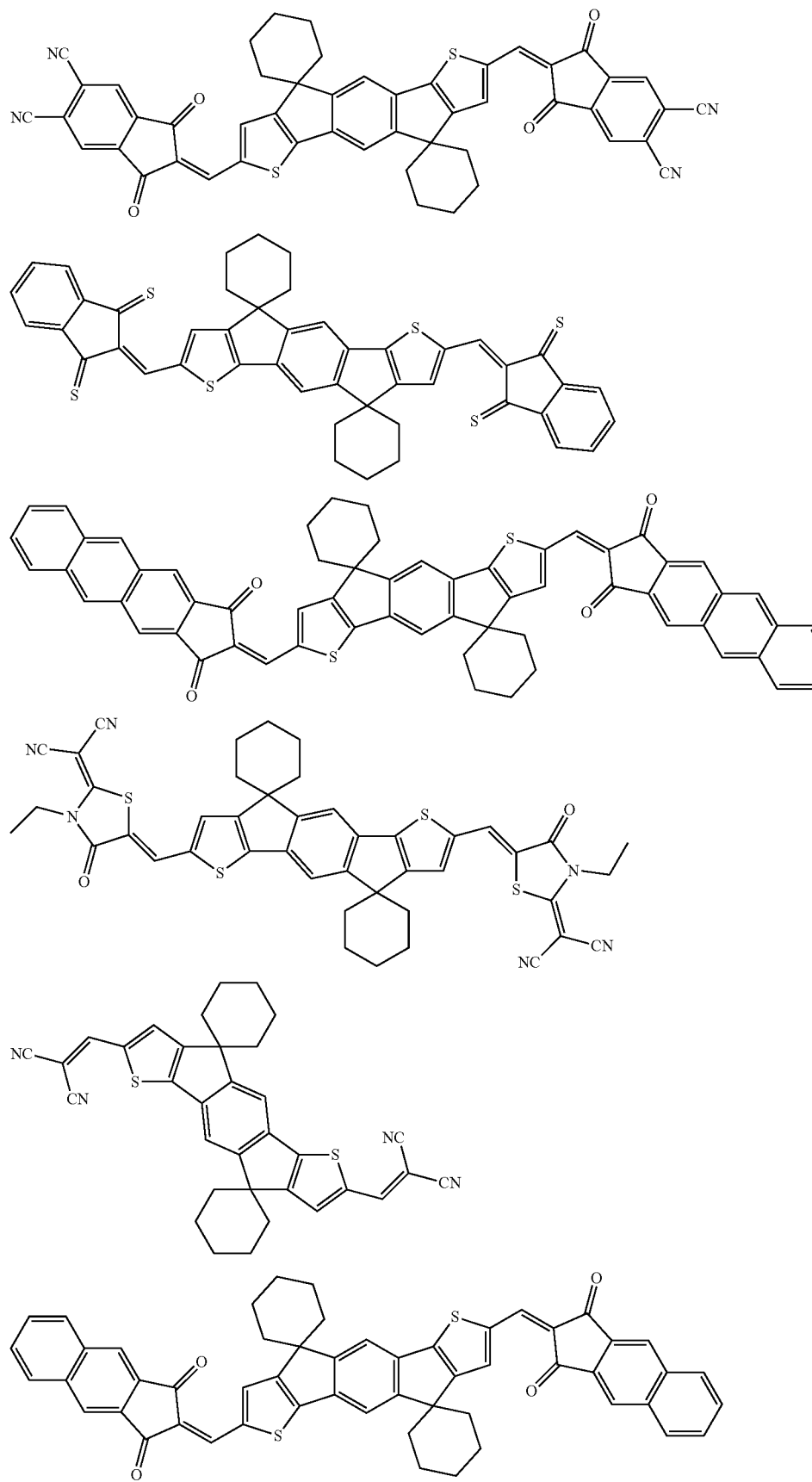

-continued
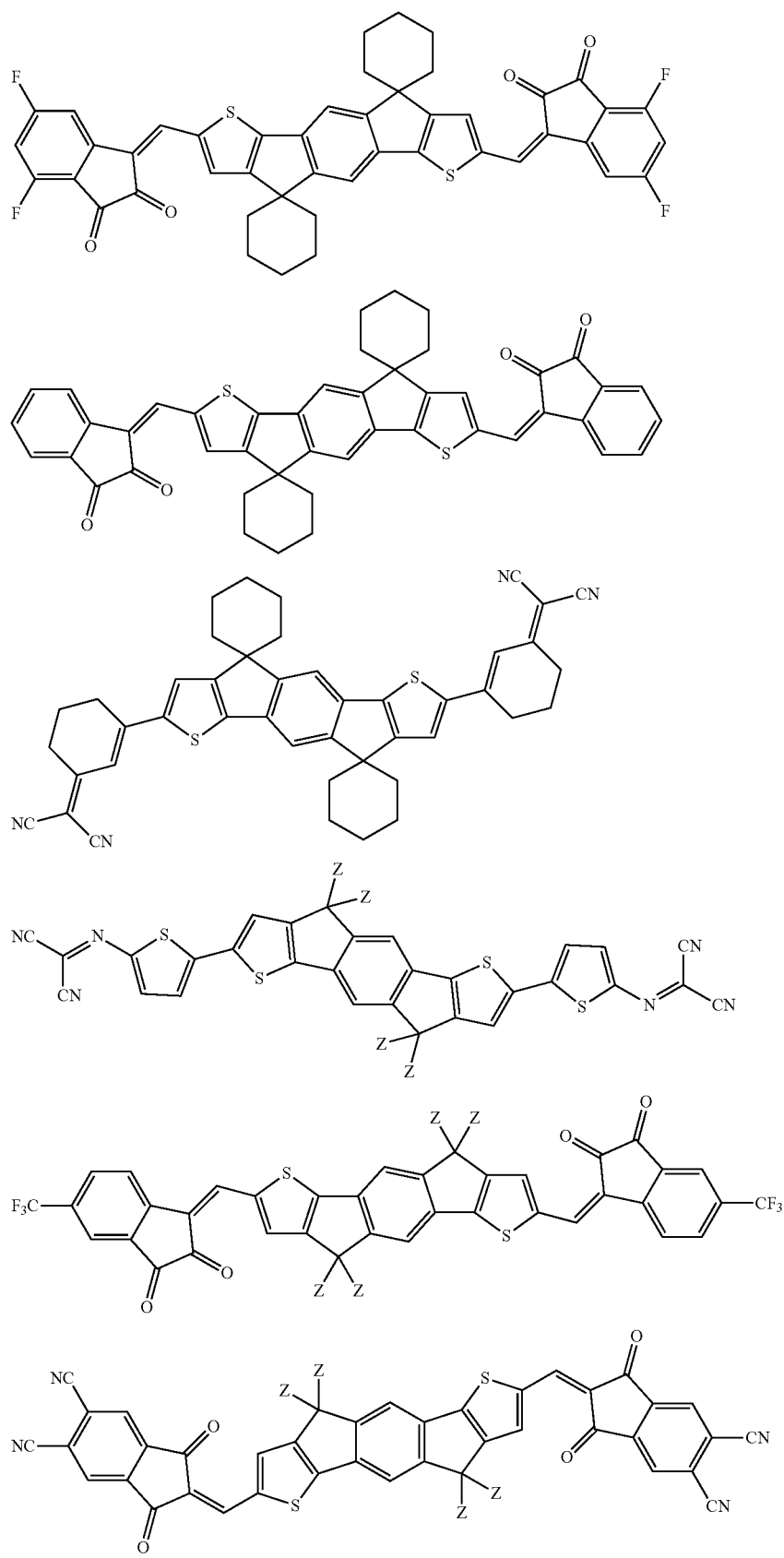

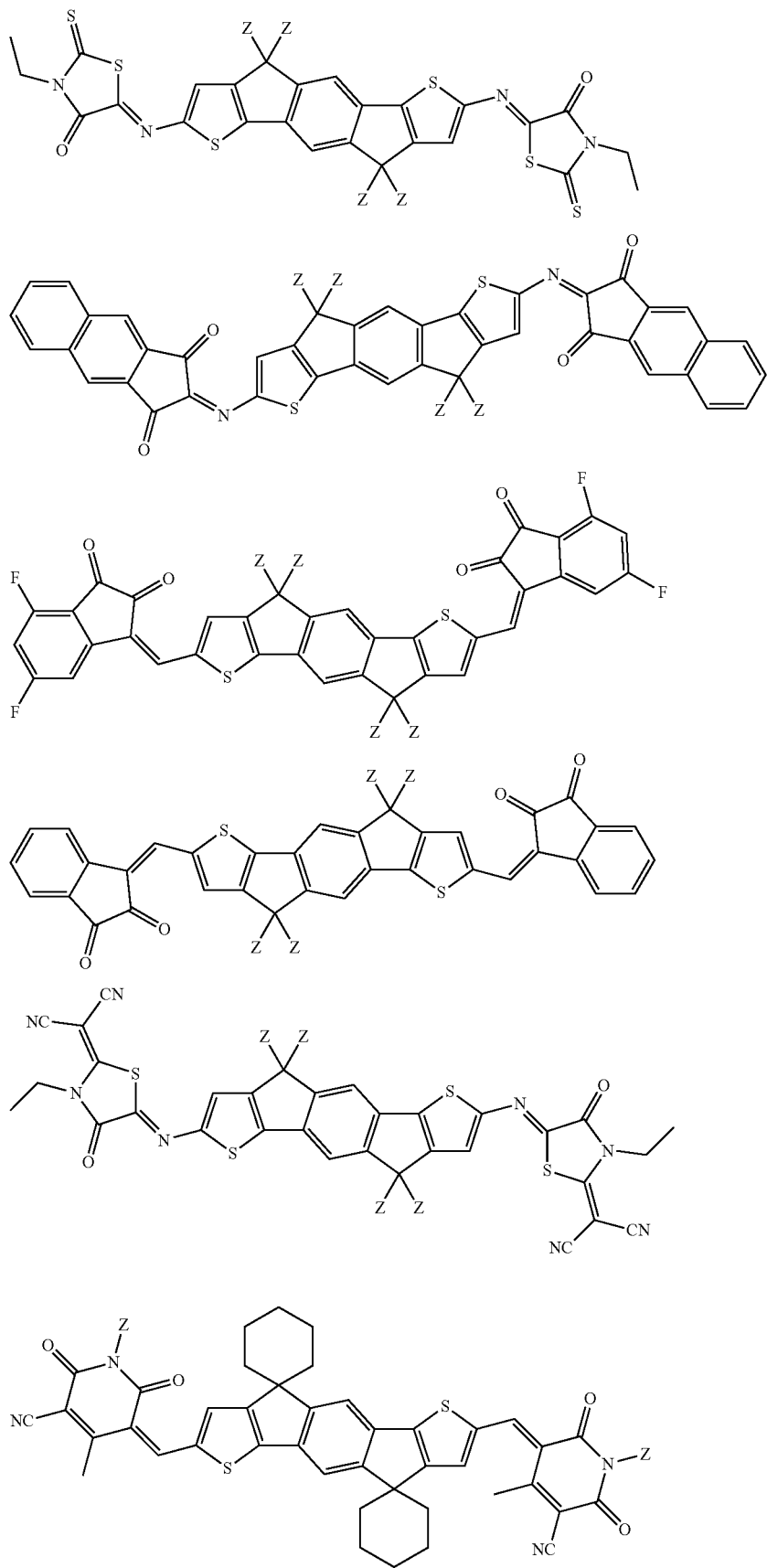

-continued
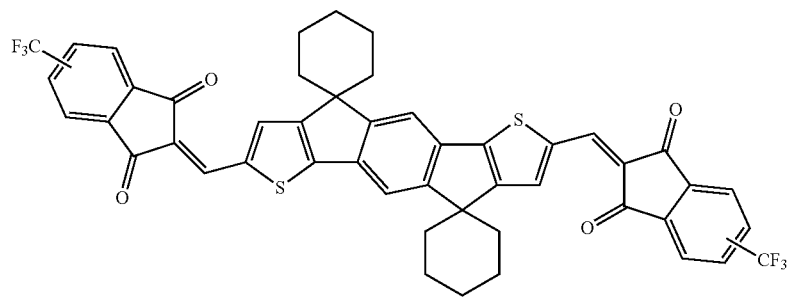
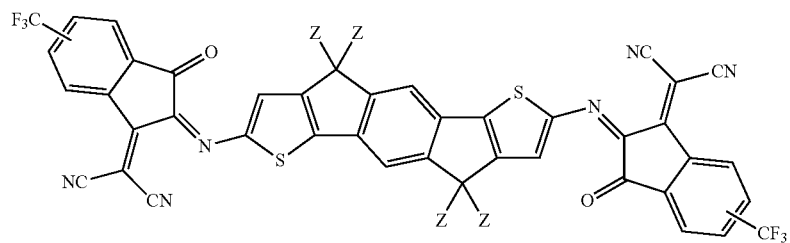
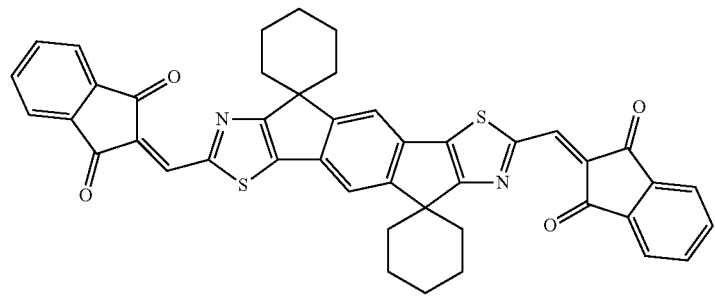
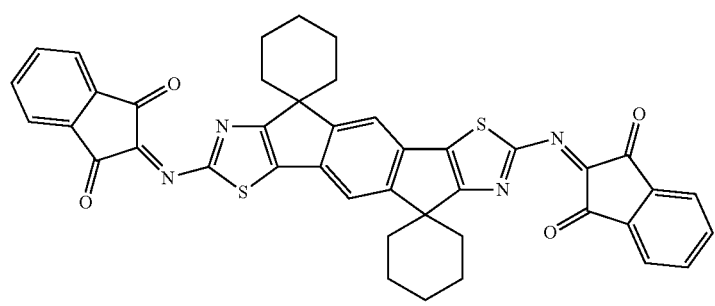
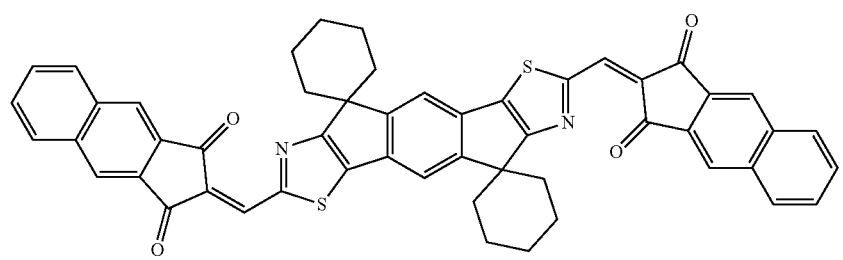
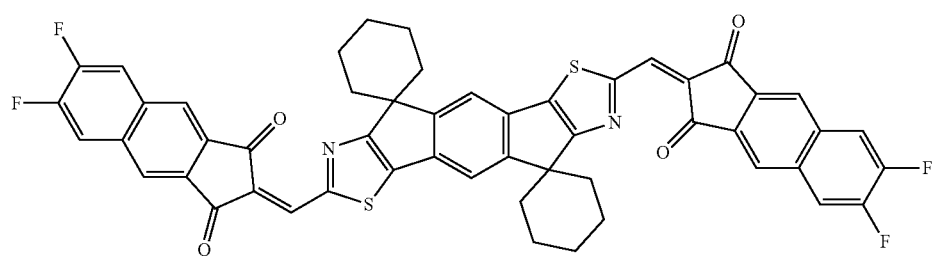

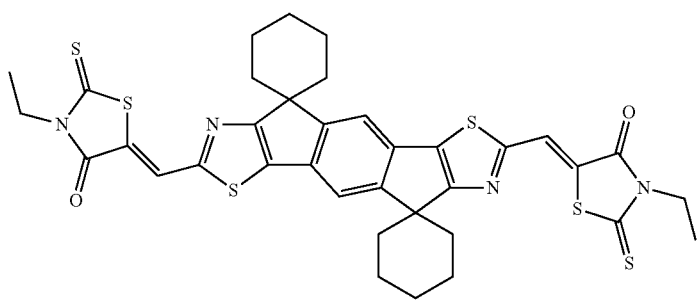
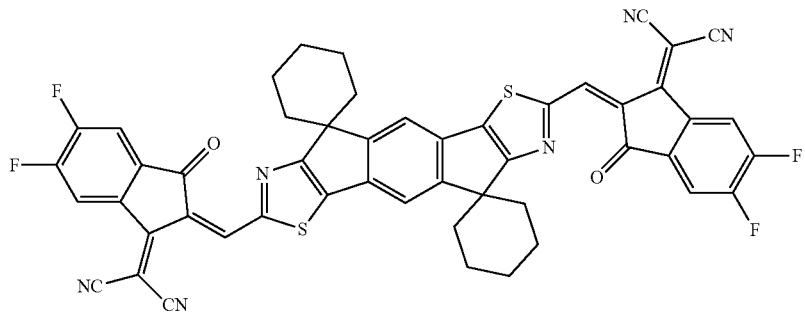
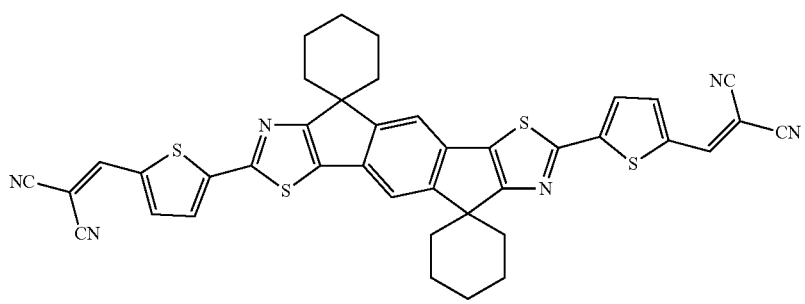
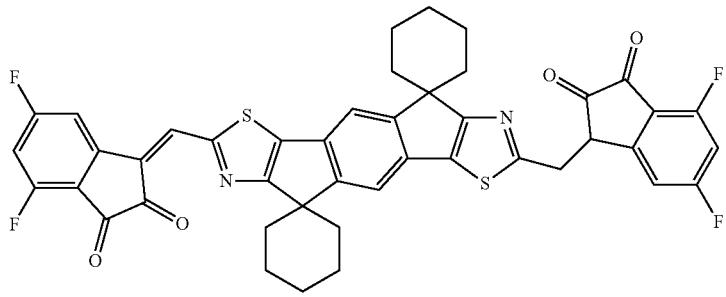
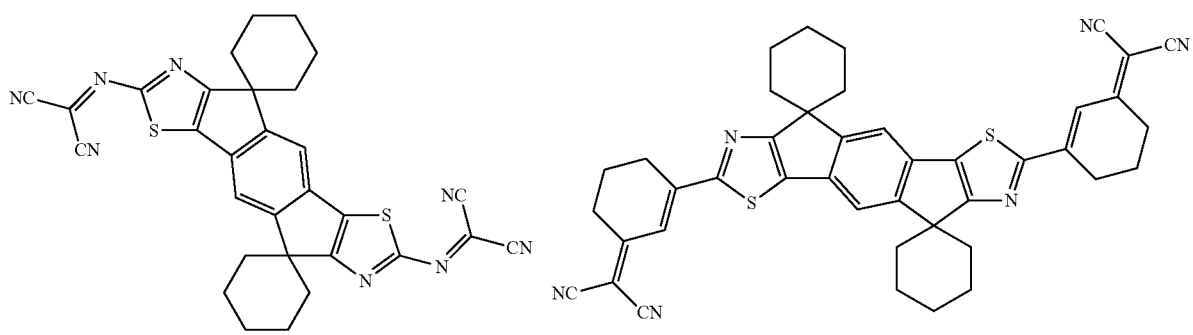

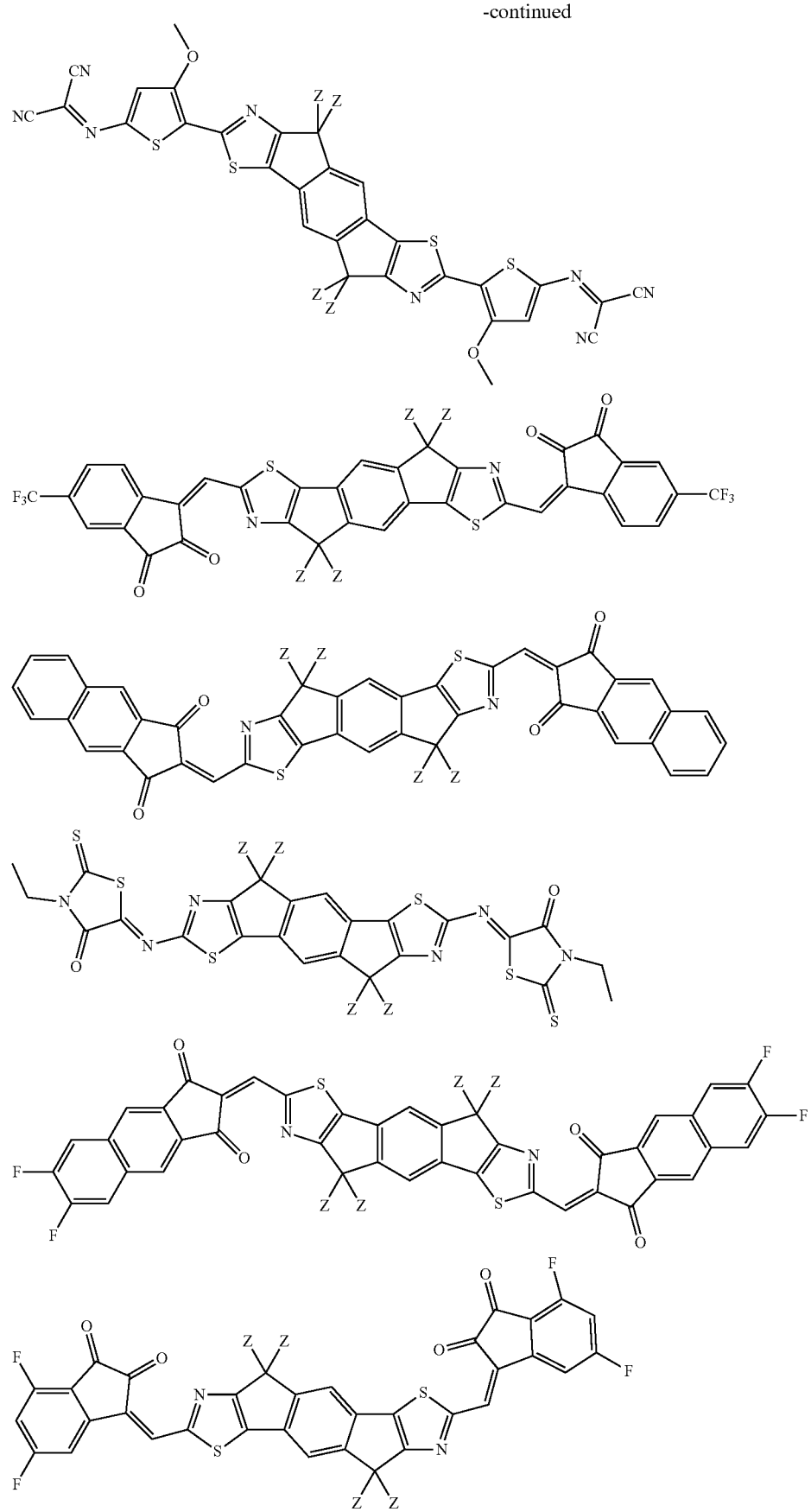

-continued
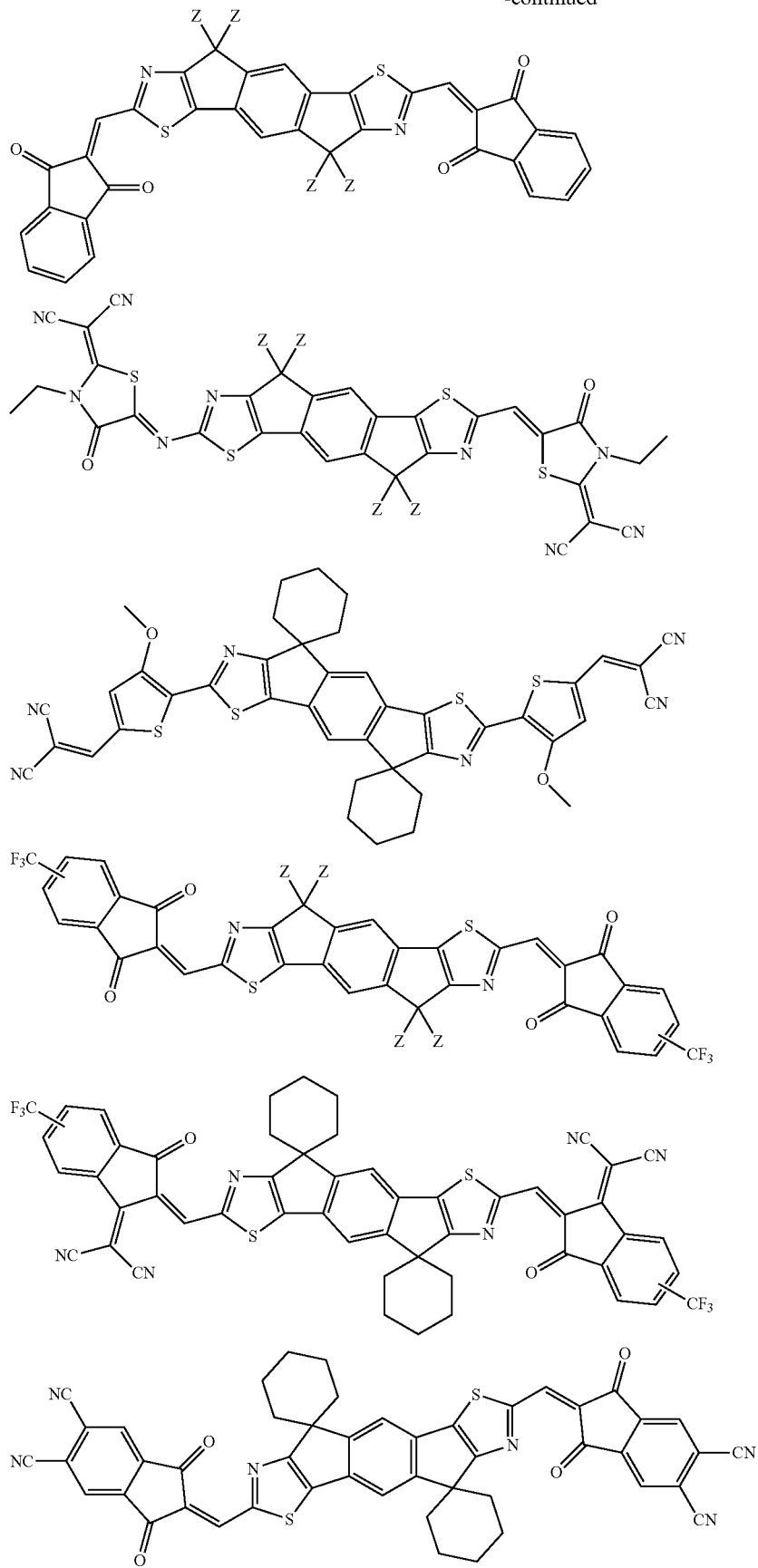

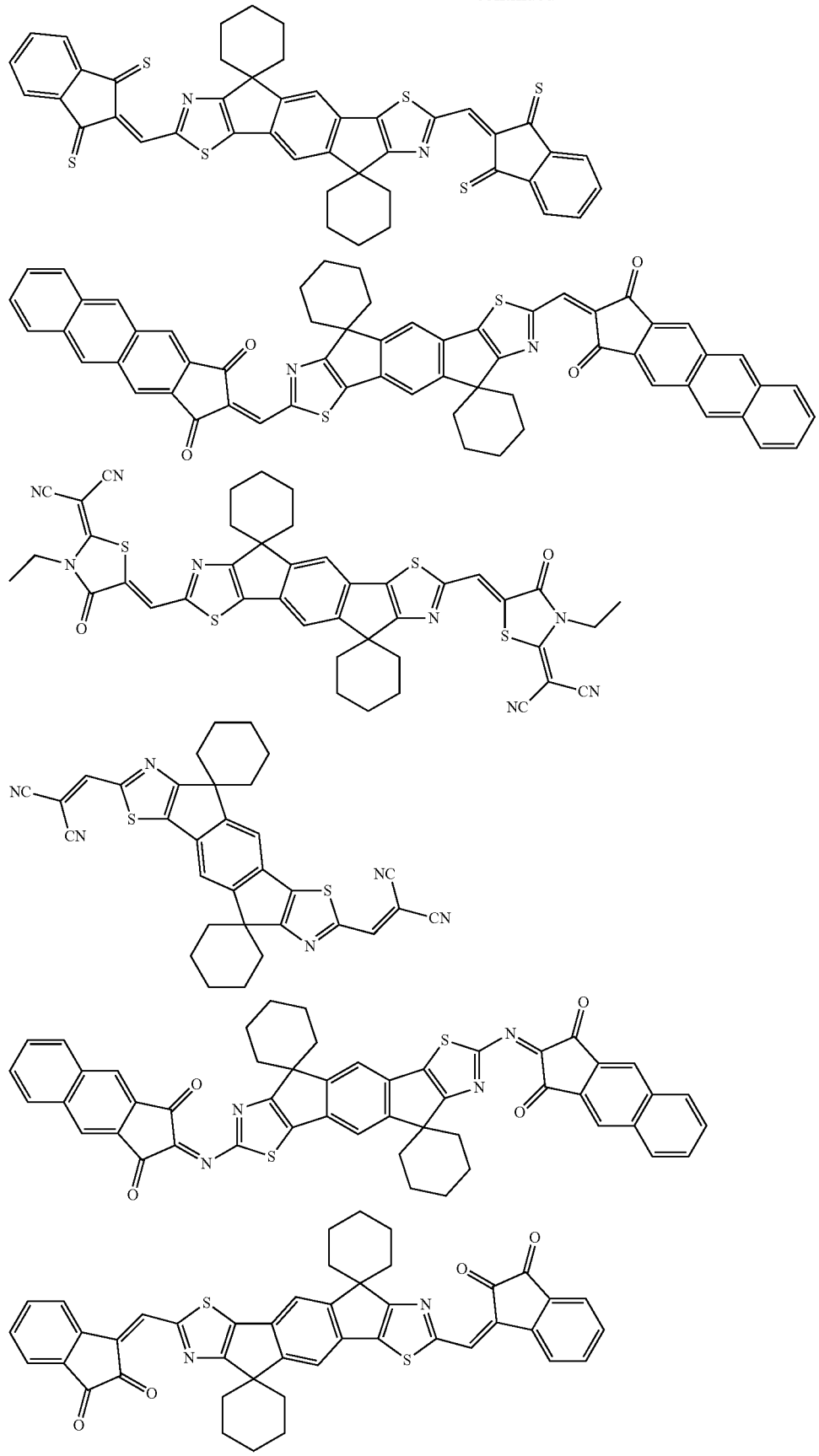

-continued
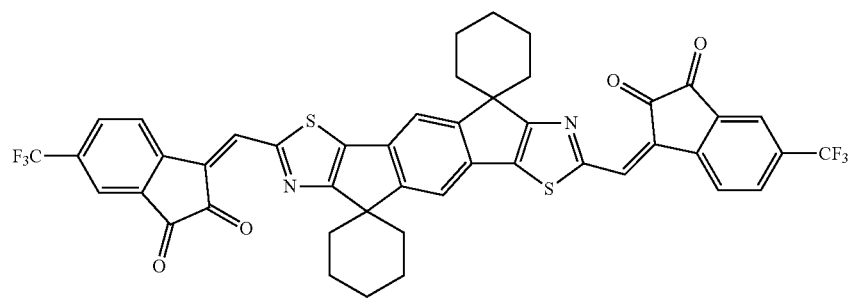
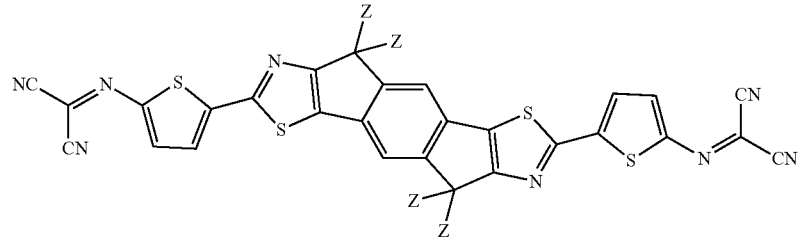
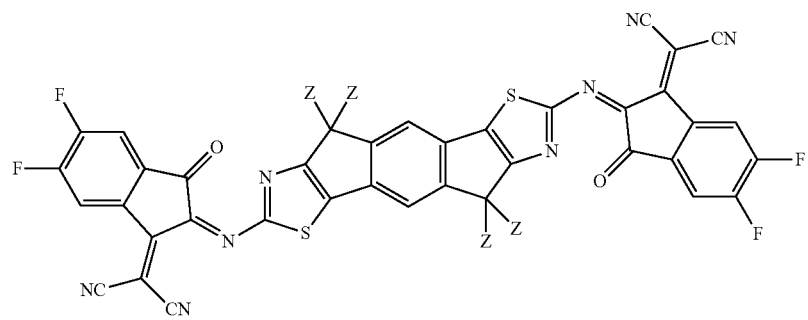
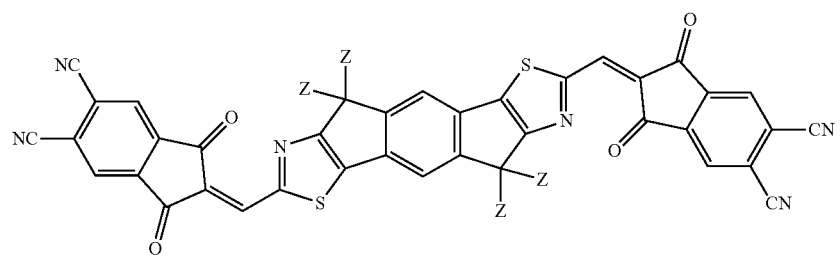
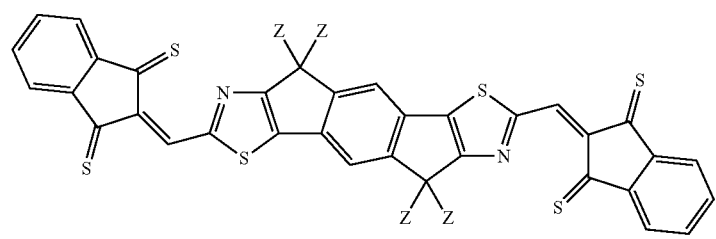
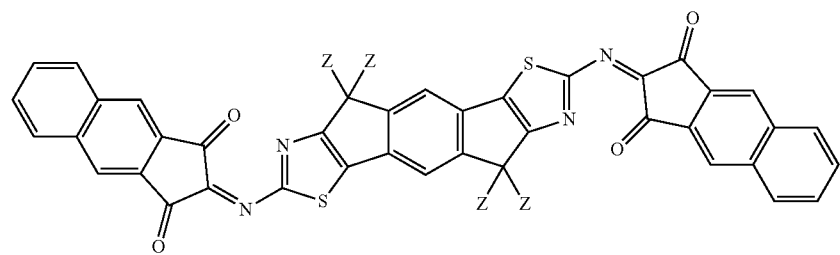

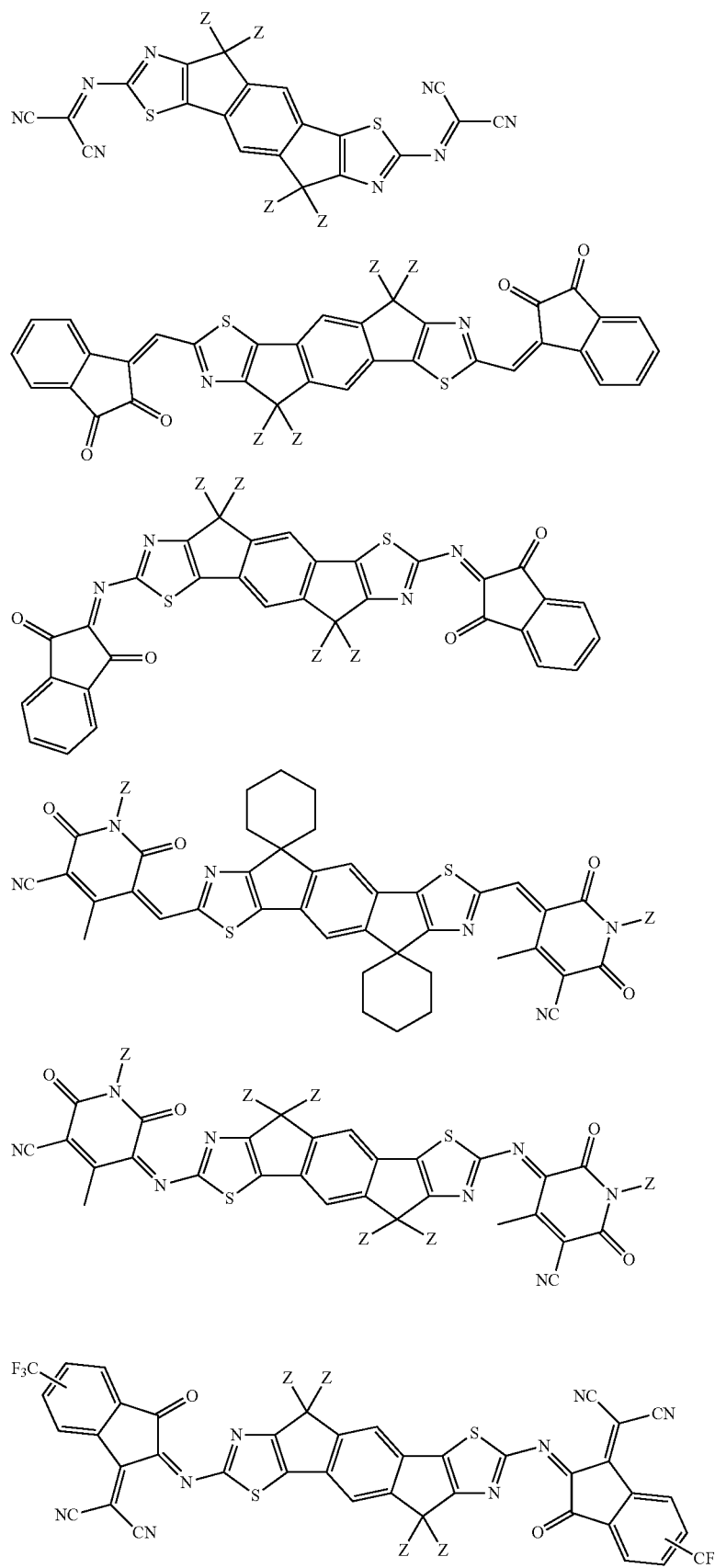

-continued
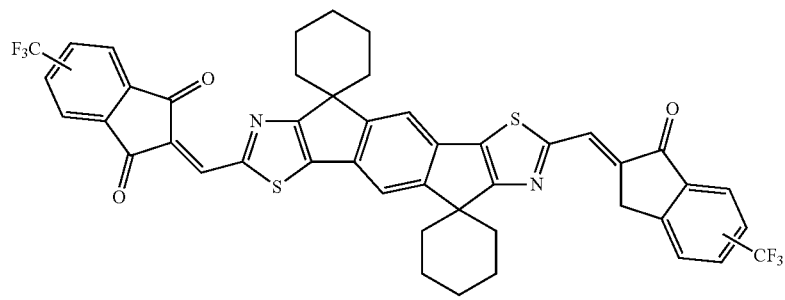
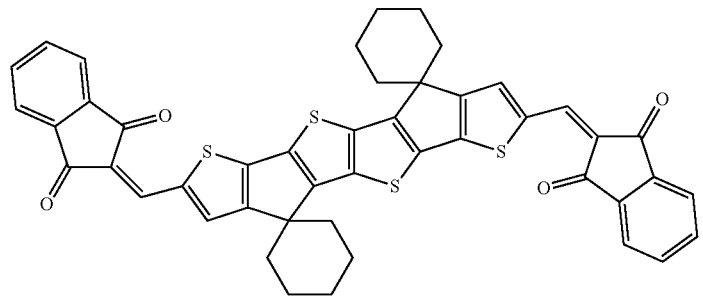
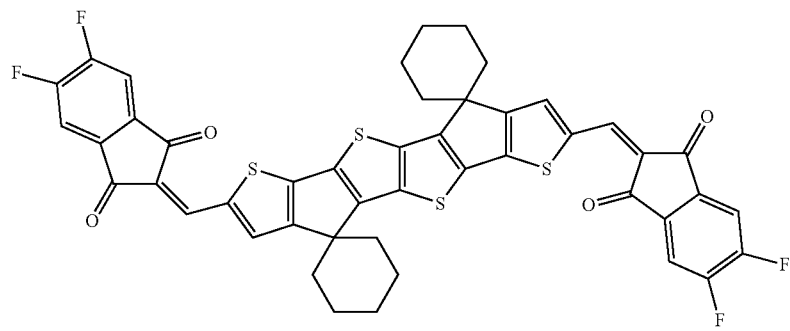
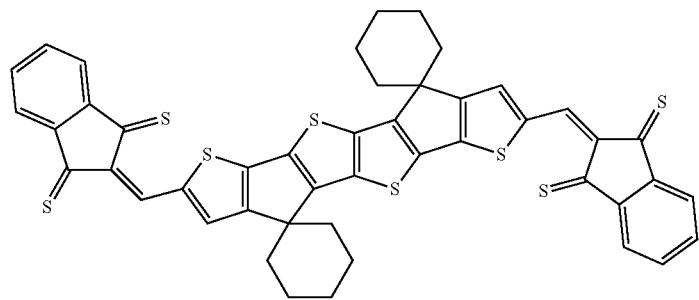
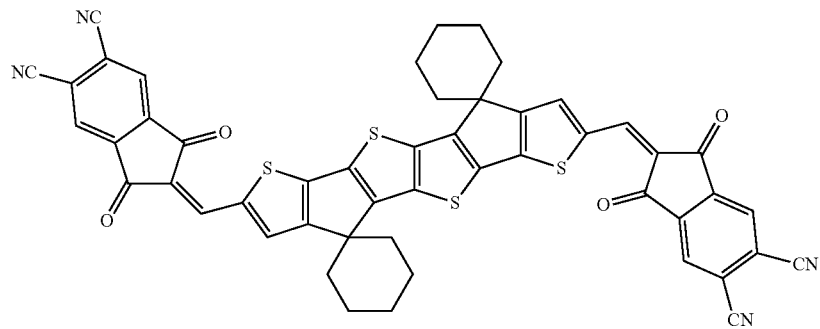

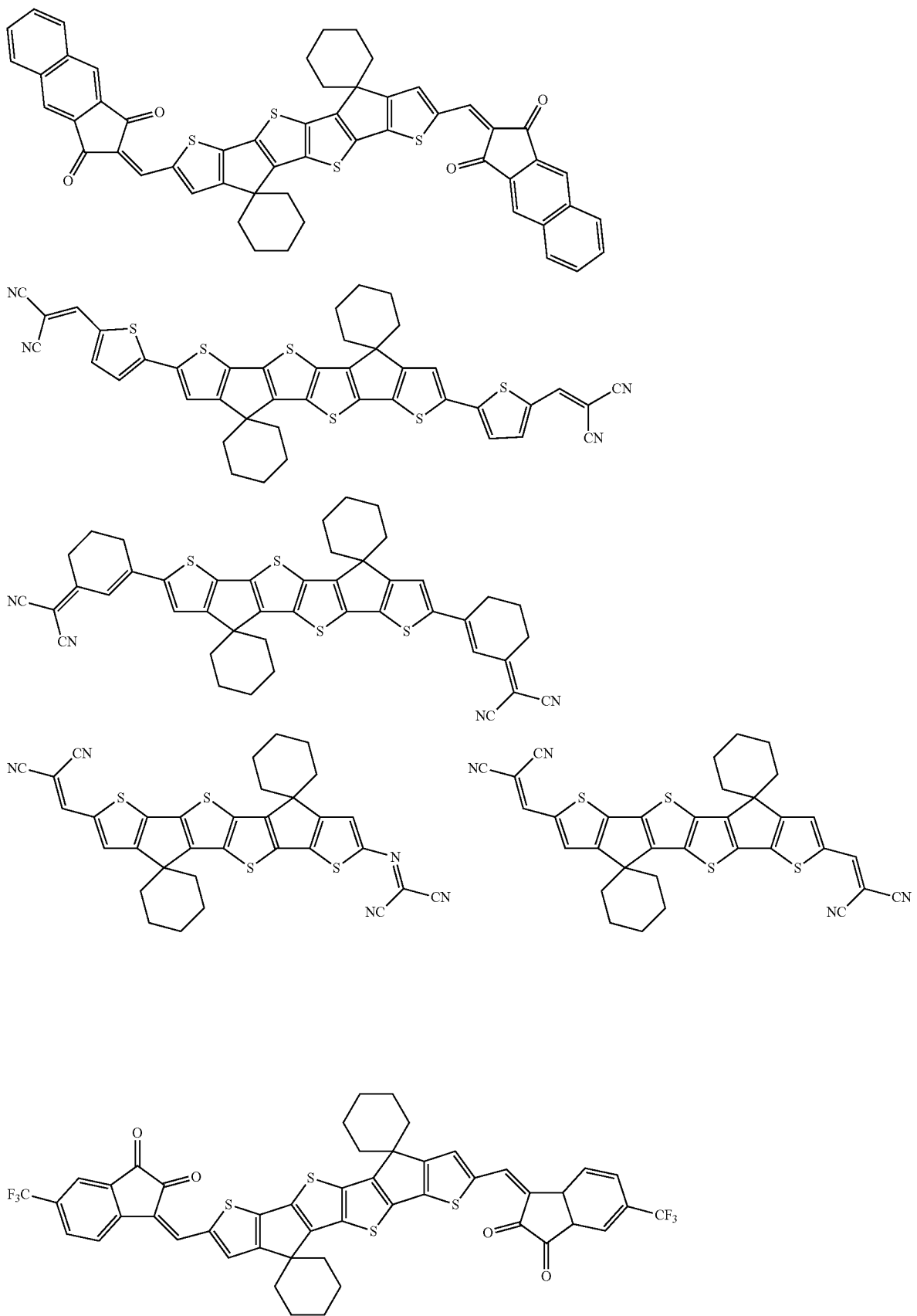

-continued
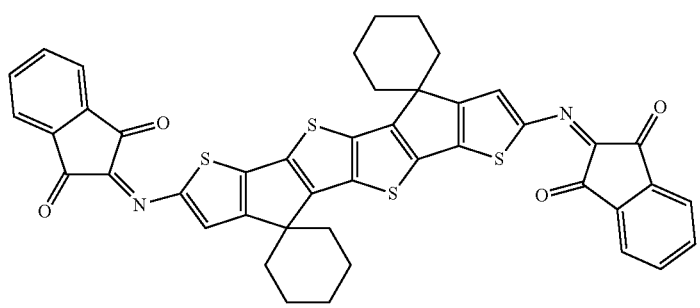
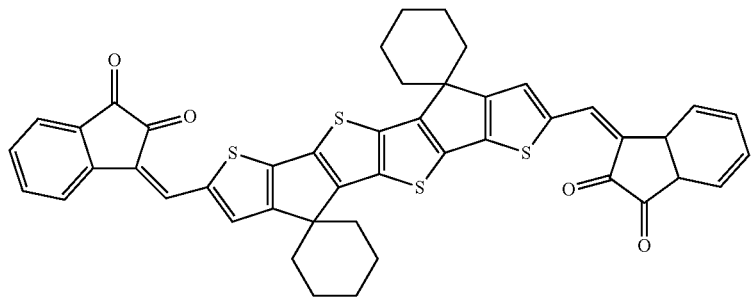
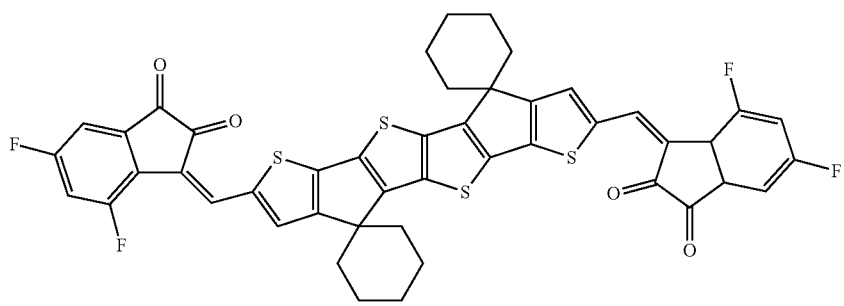
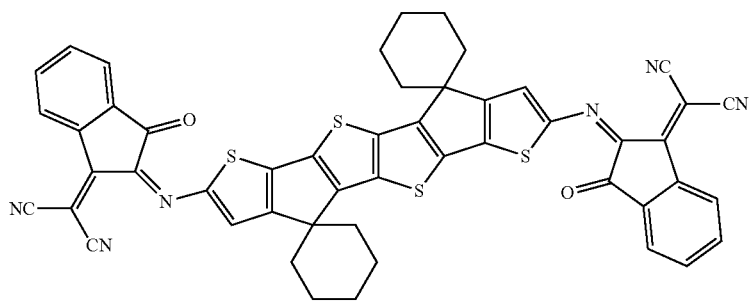
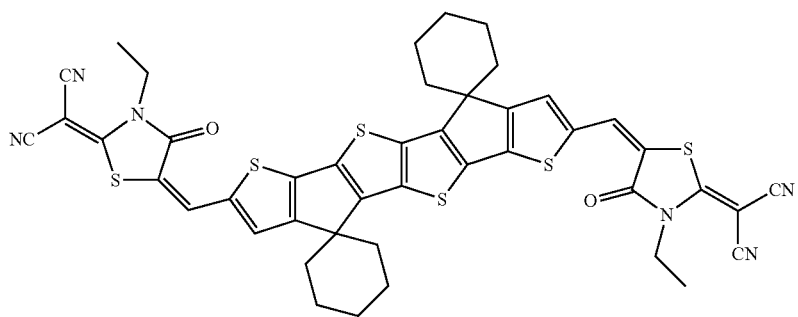

-continued
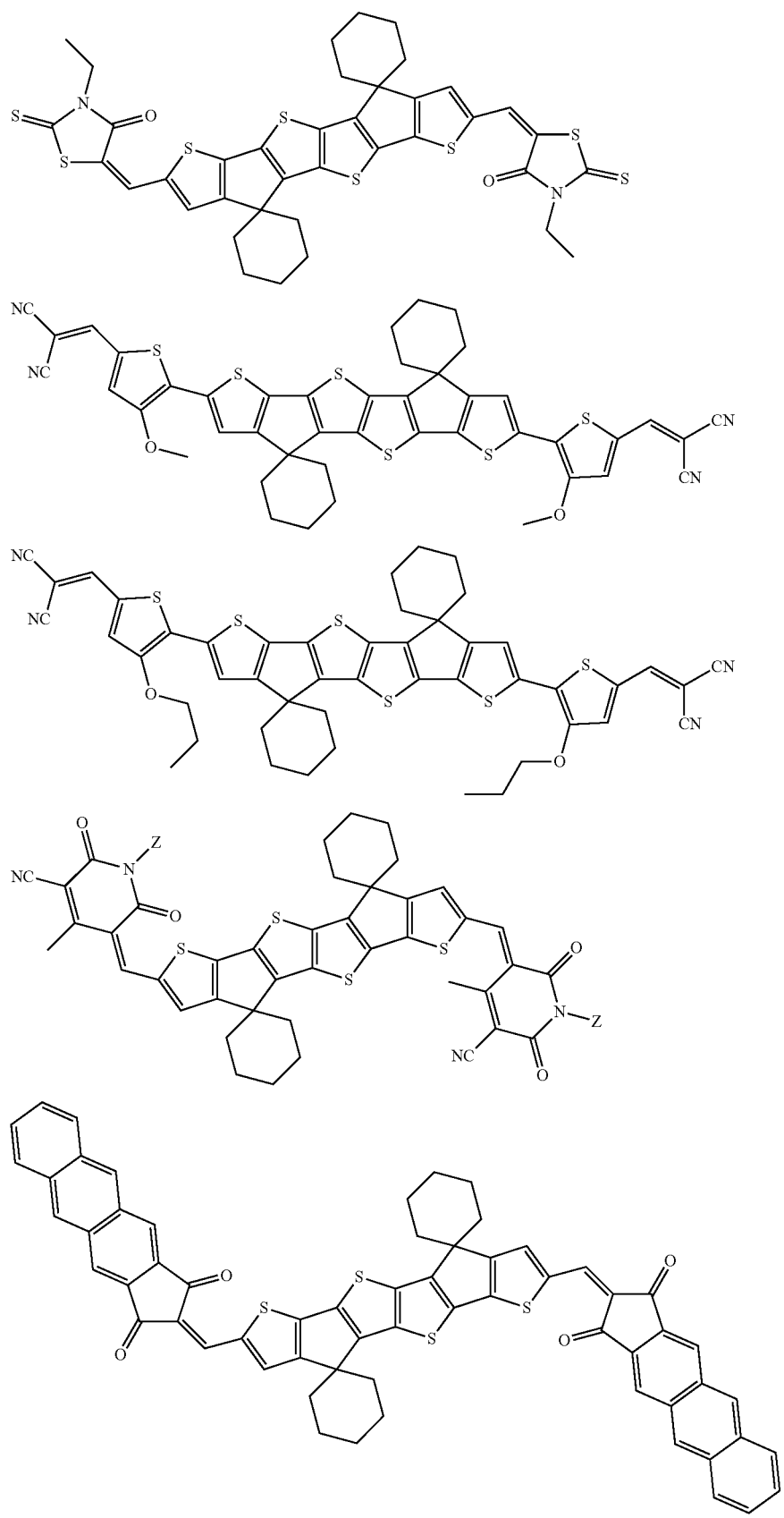

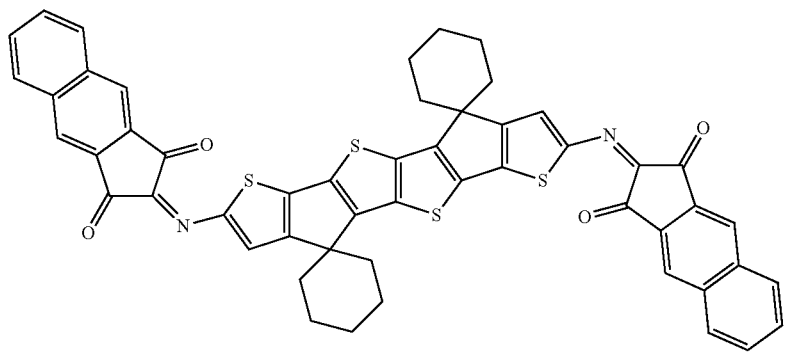
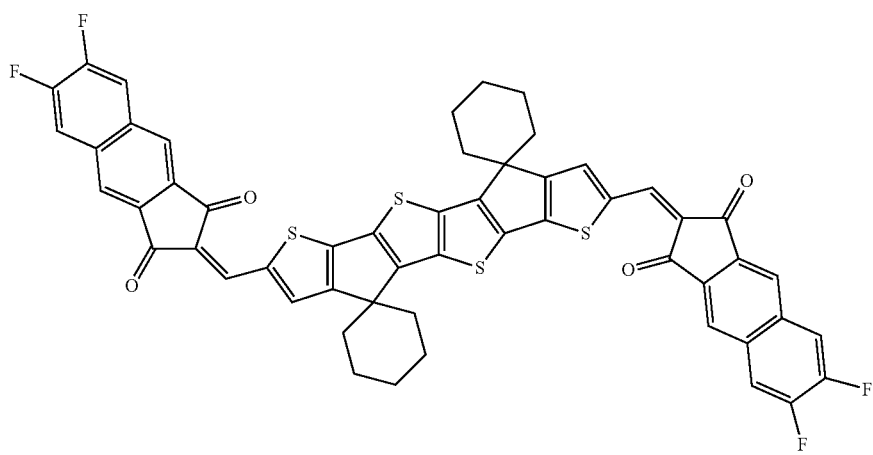
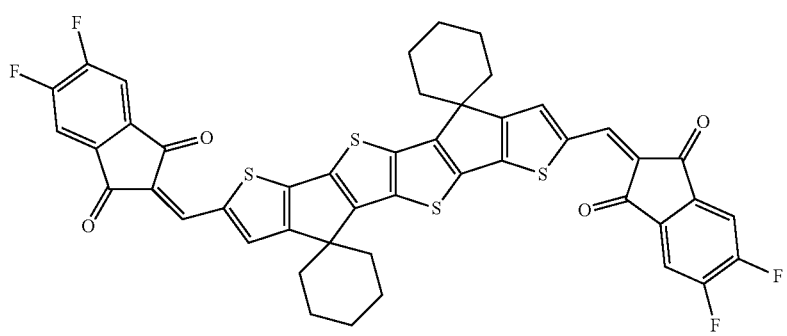
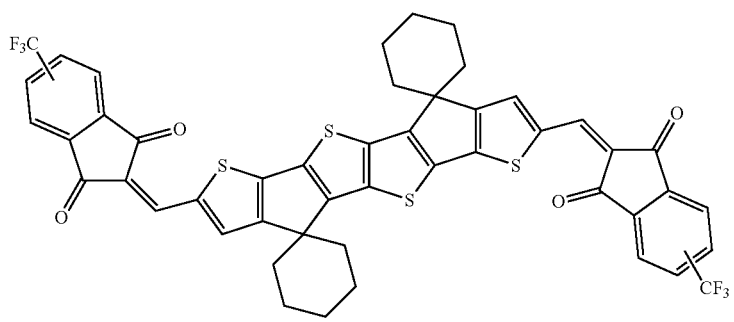

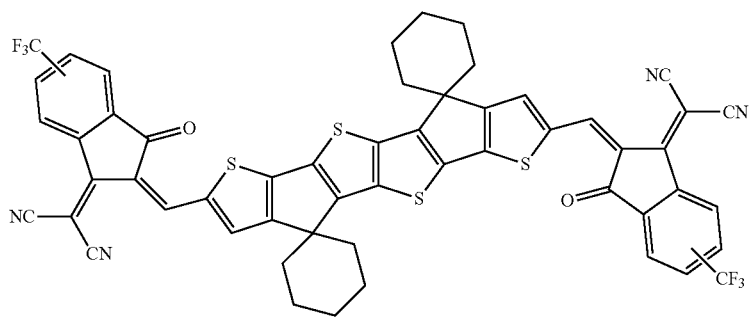
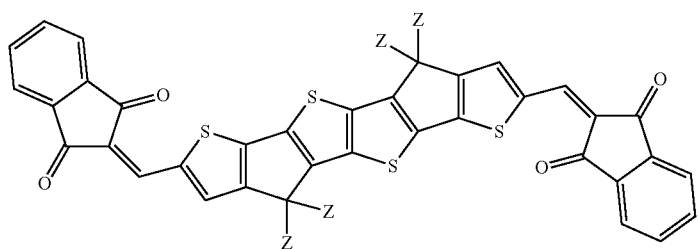
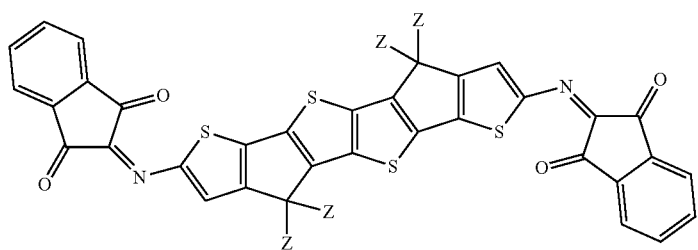
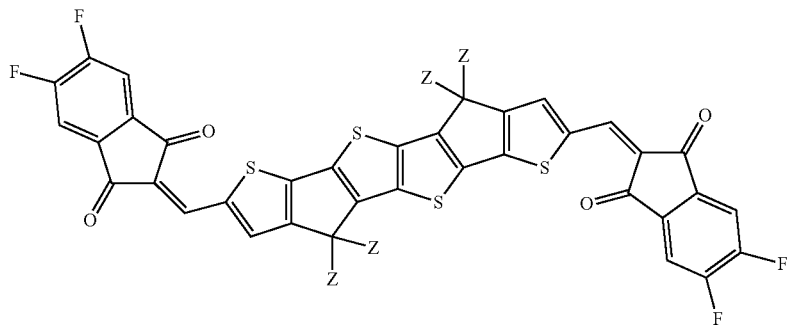
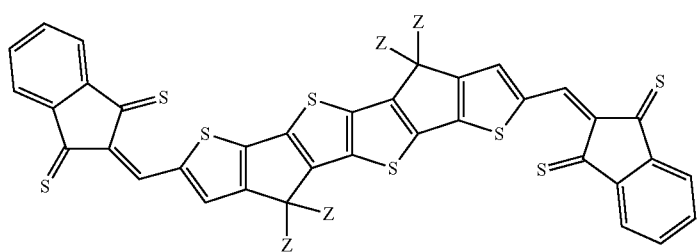
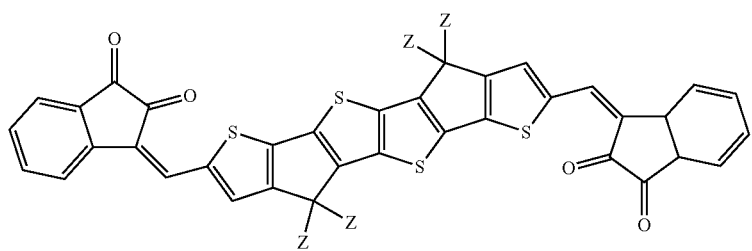

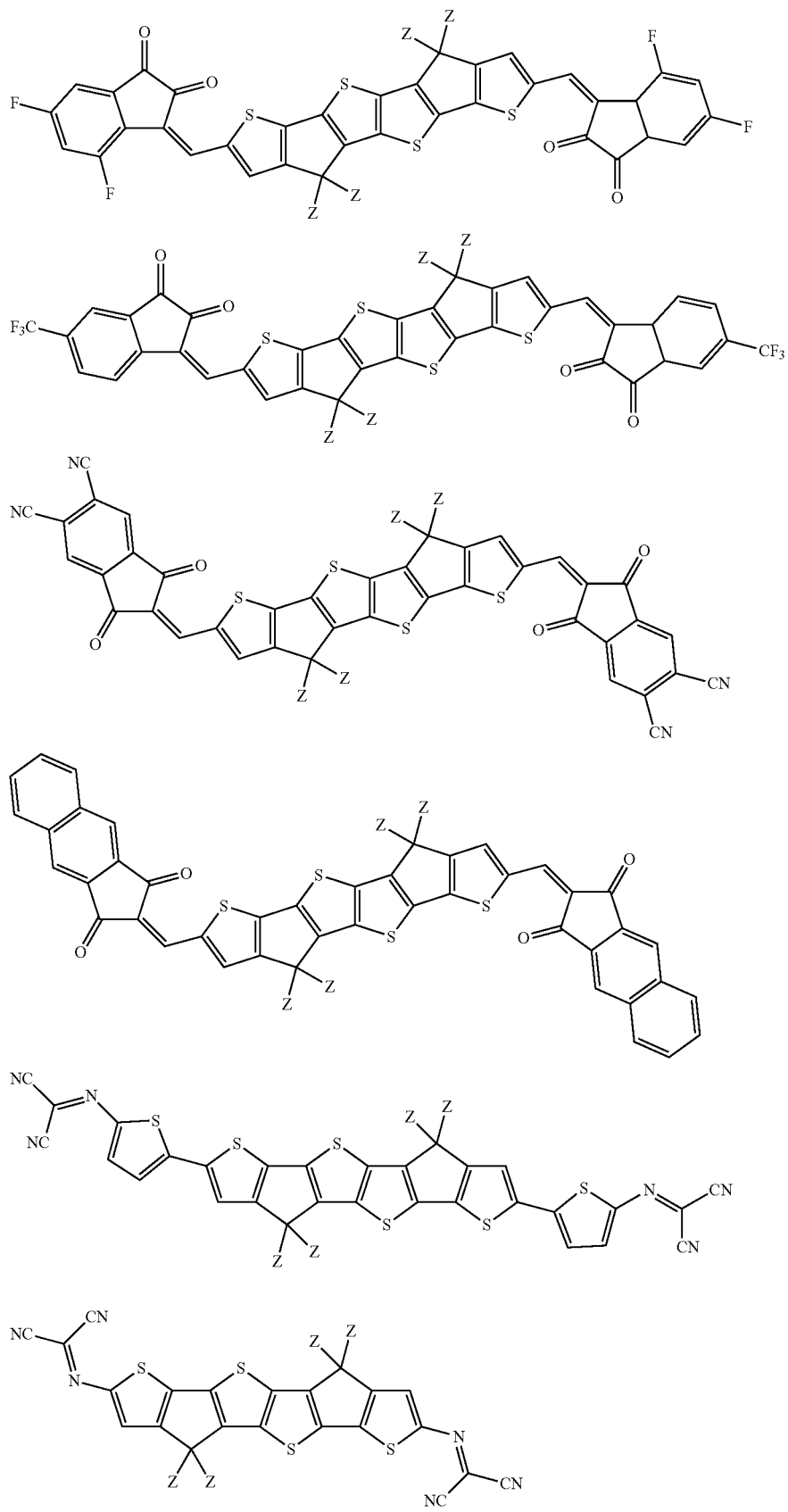

-continued
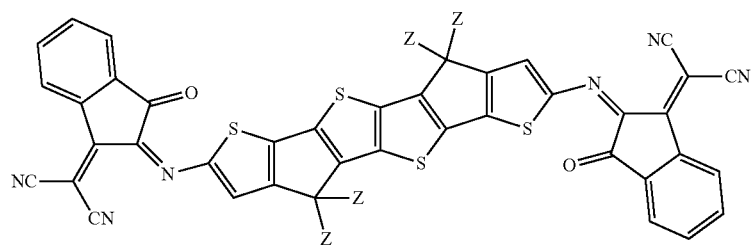
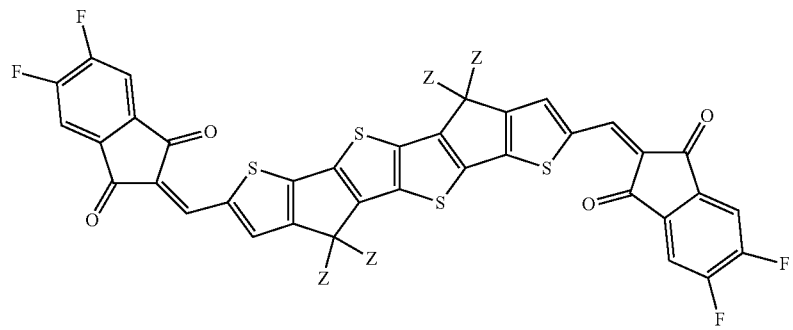
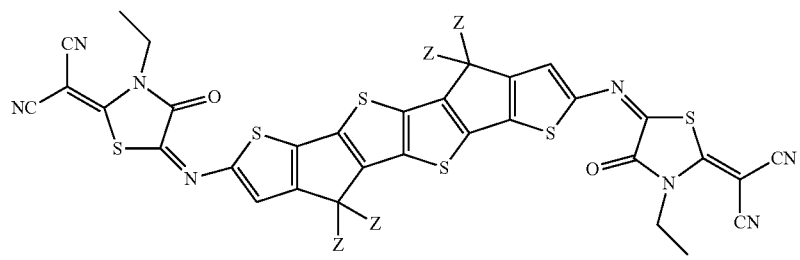
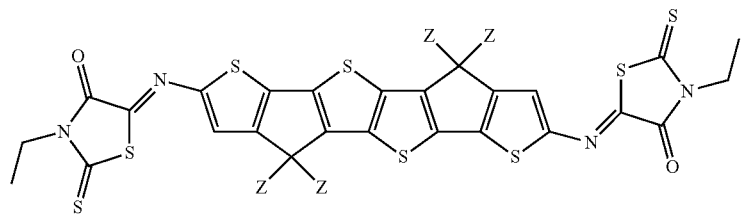
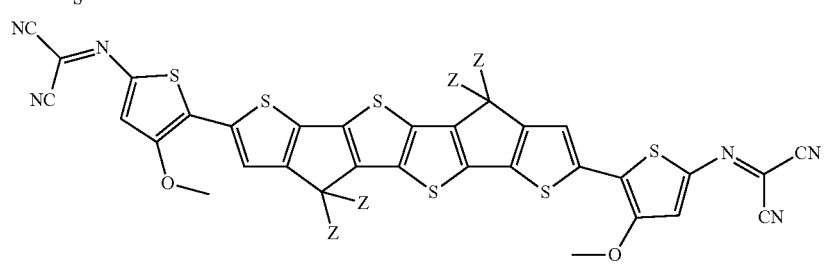
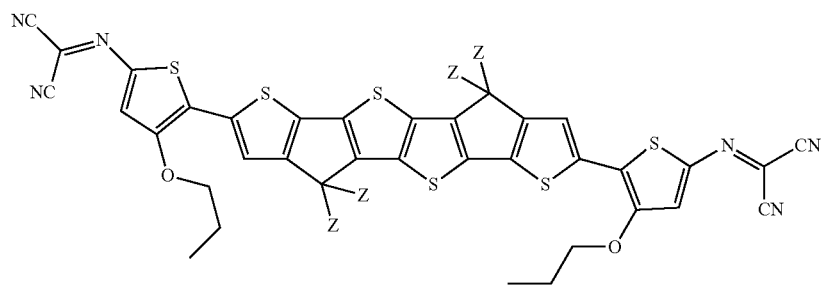

-continued
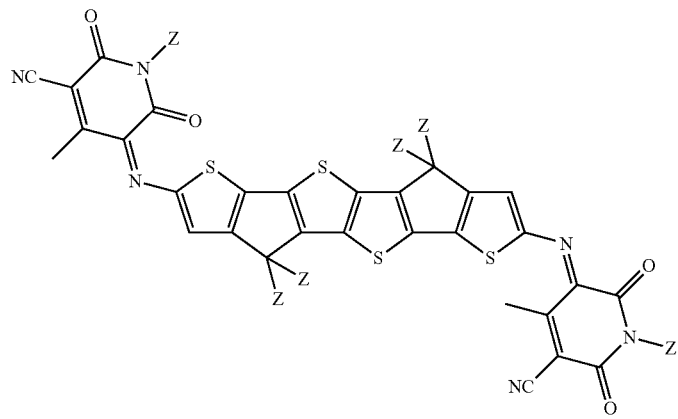
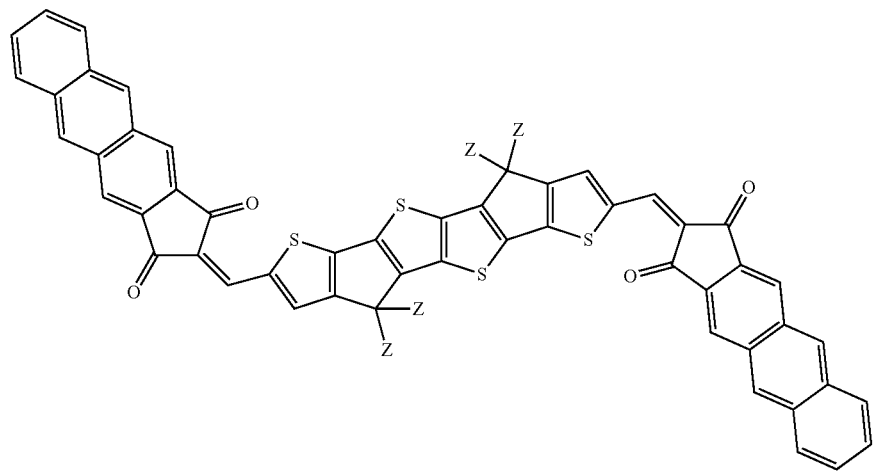
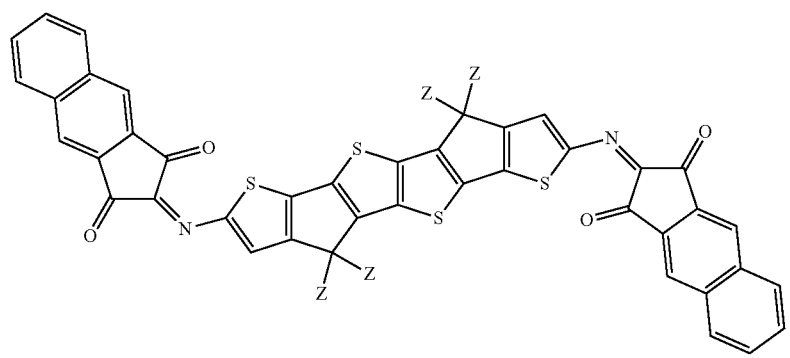
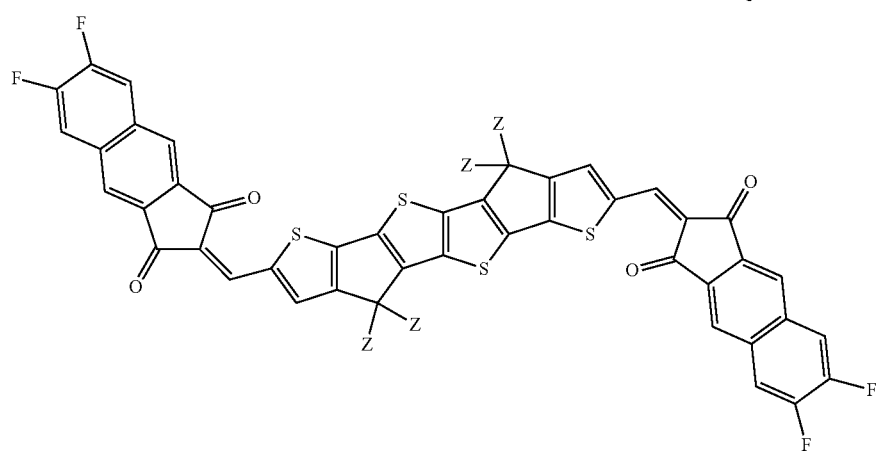

-continued
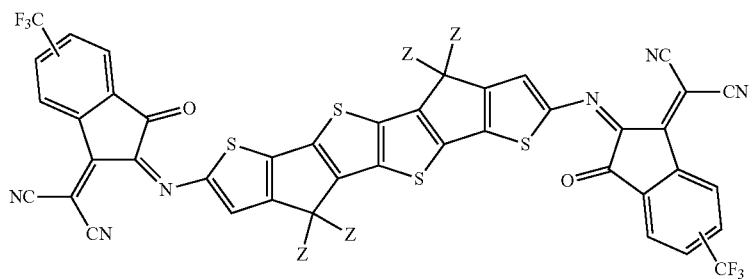
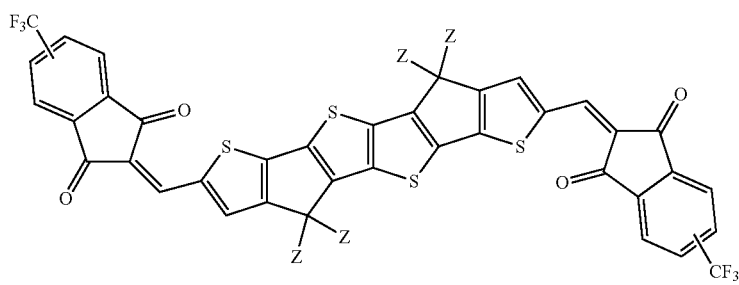
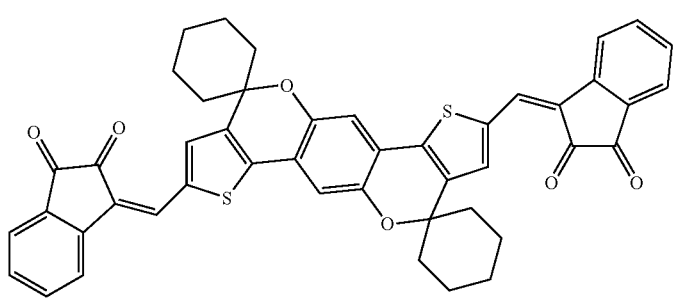
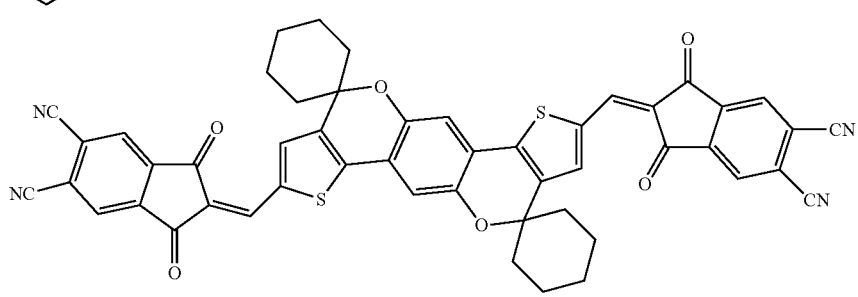
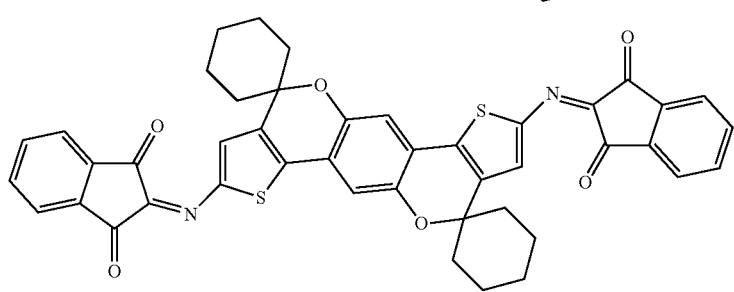
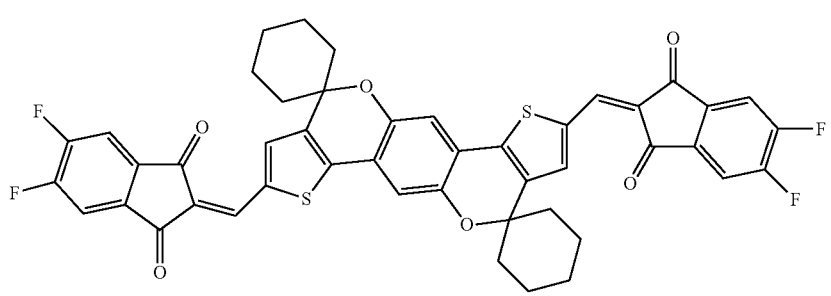

-continued
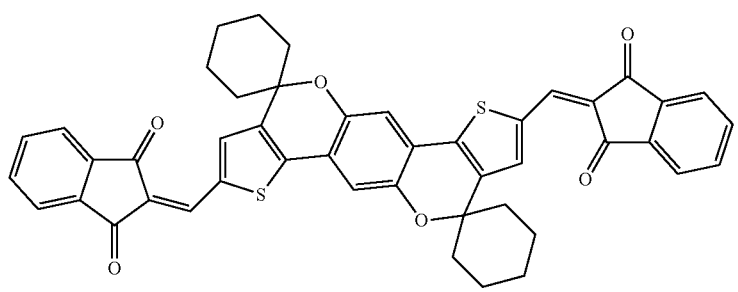
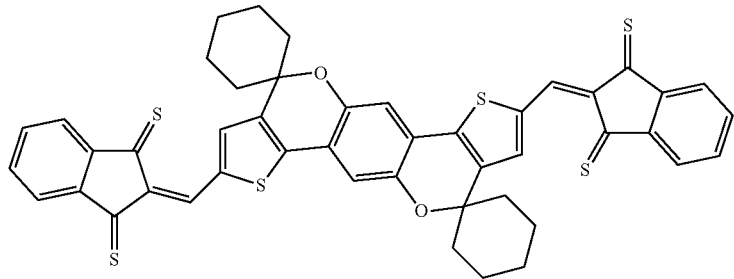
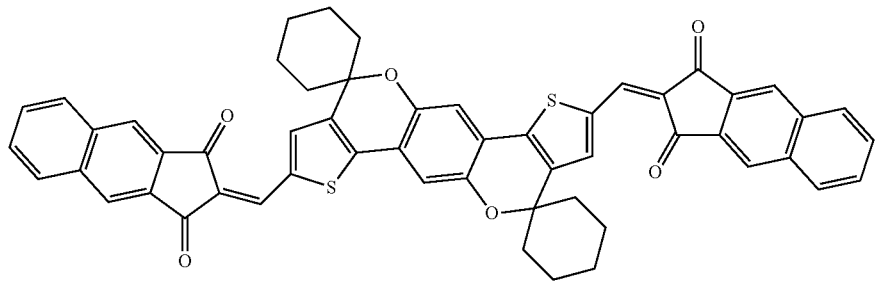
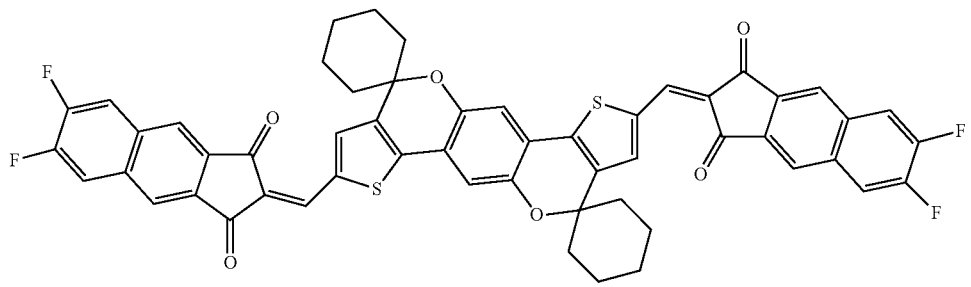
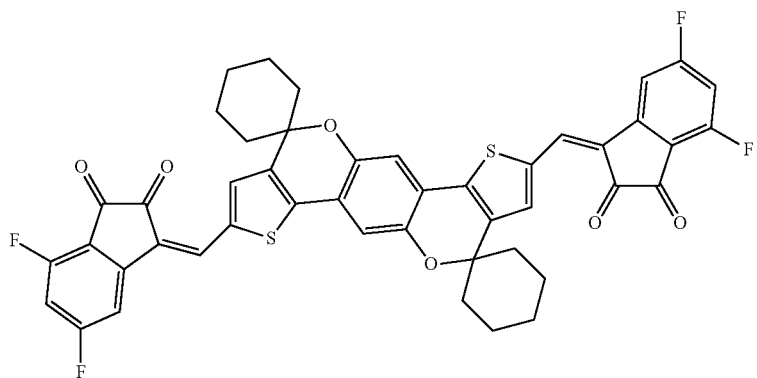

-continued
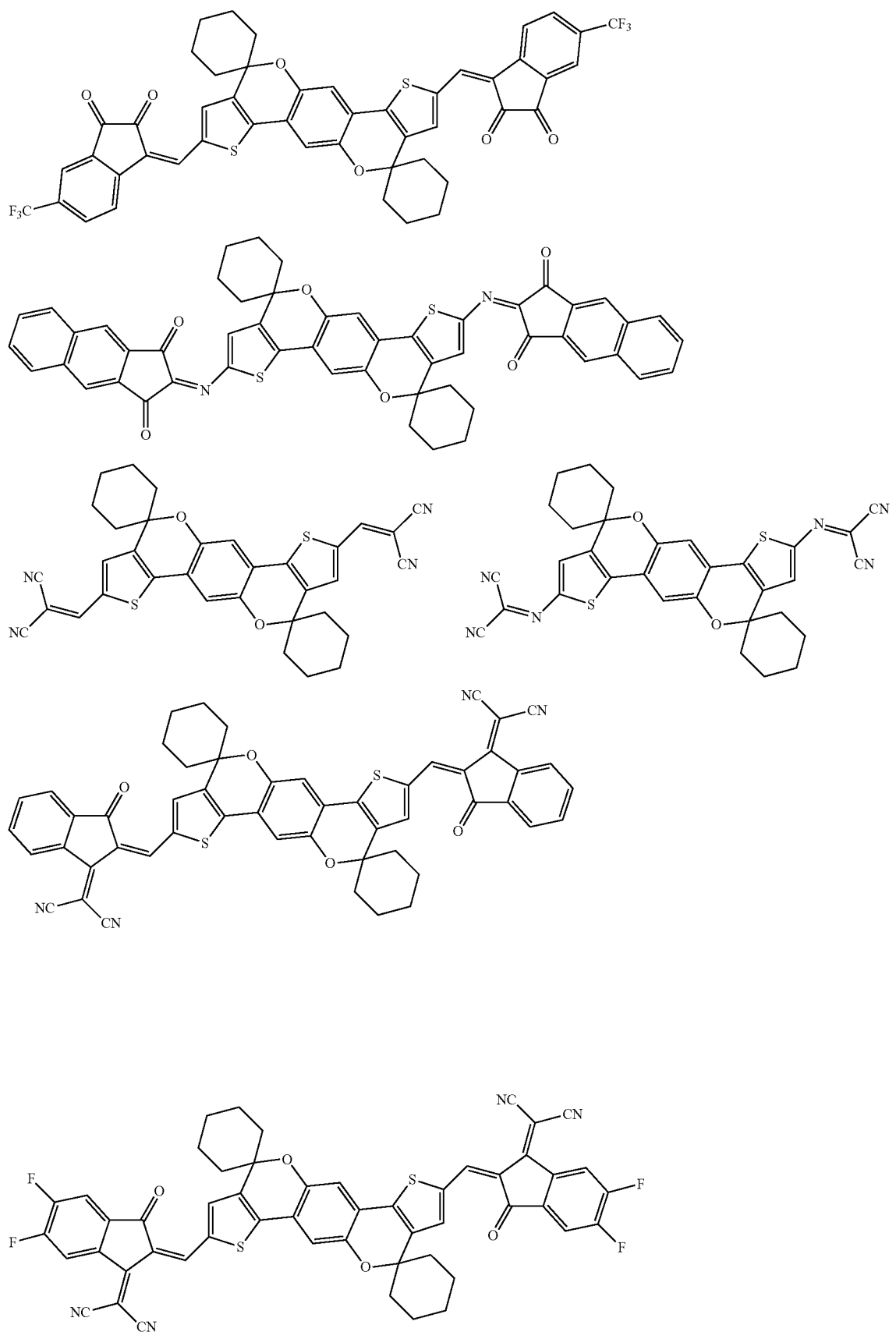

-continued
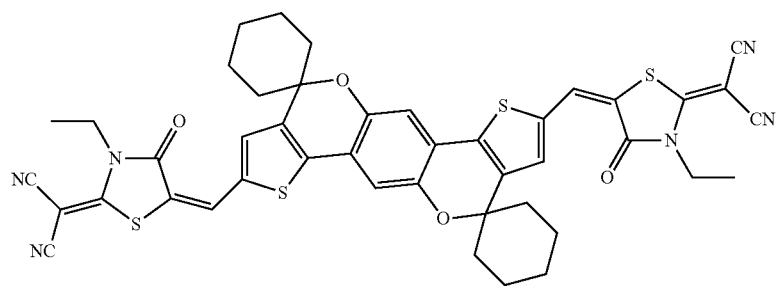
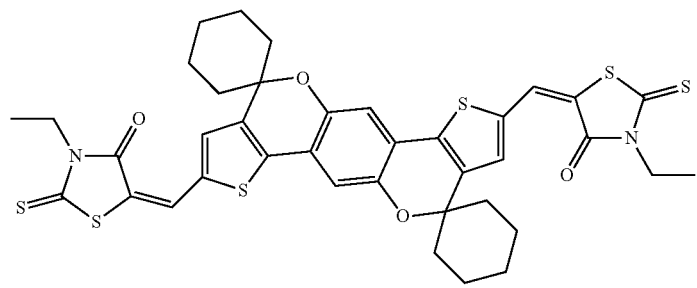
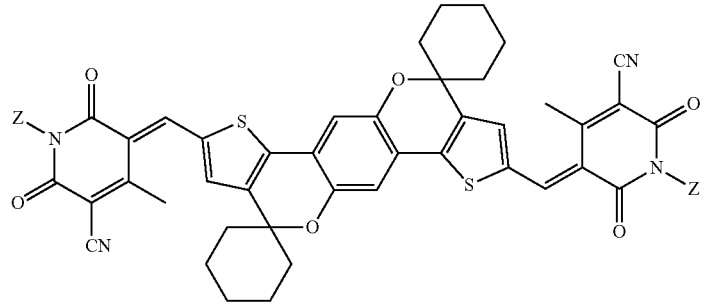
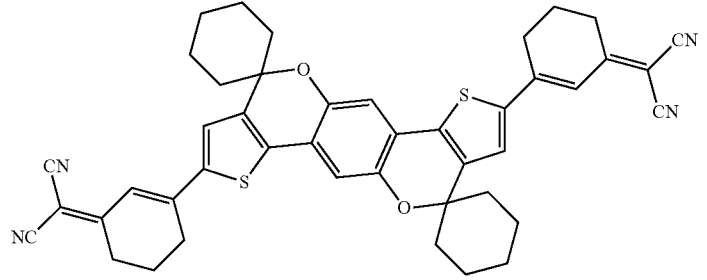
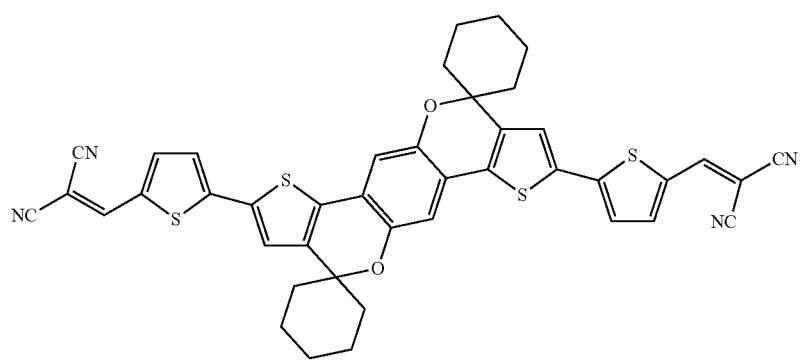

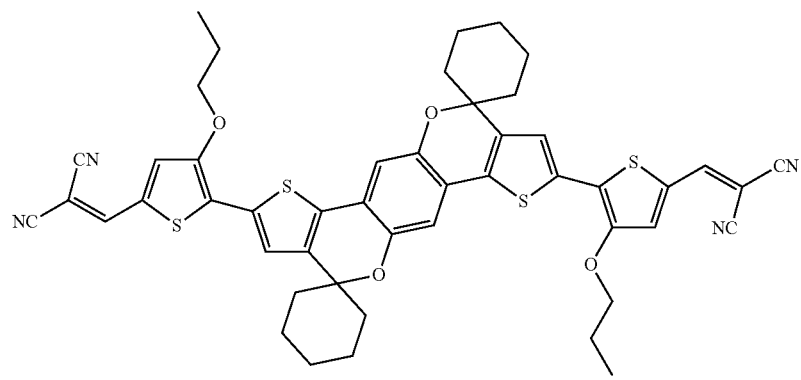
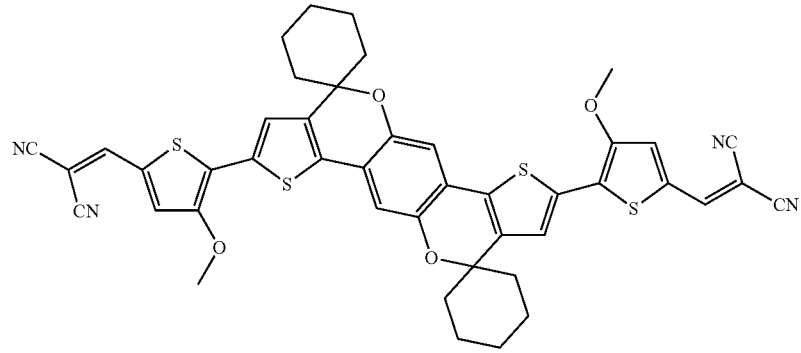
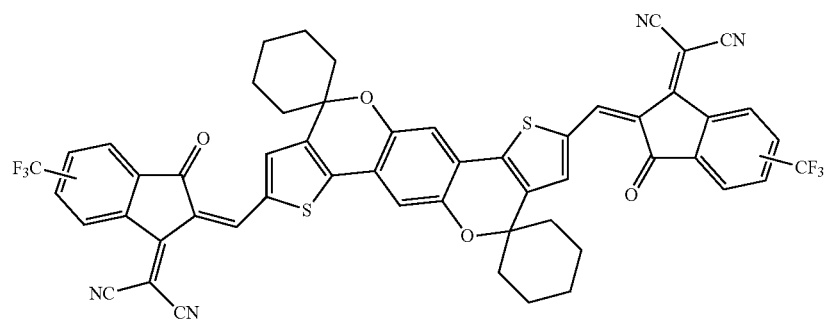
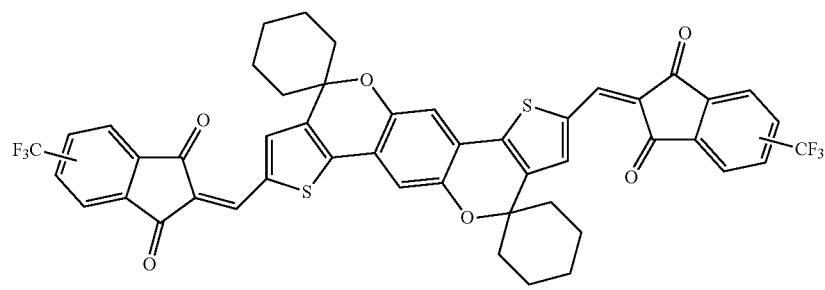
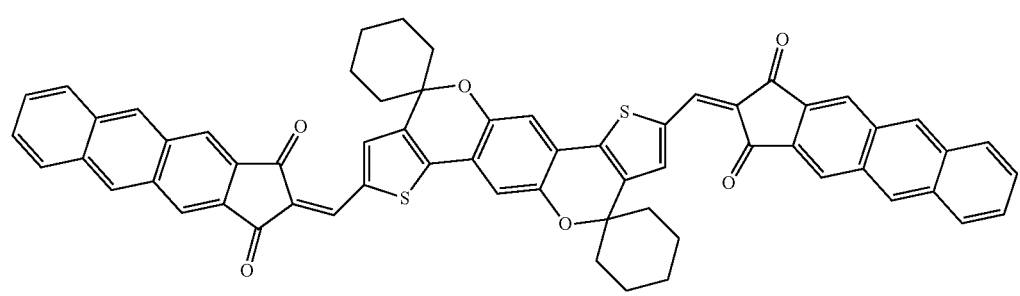

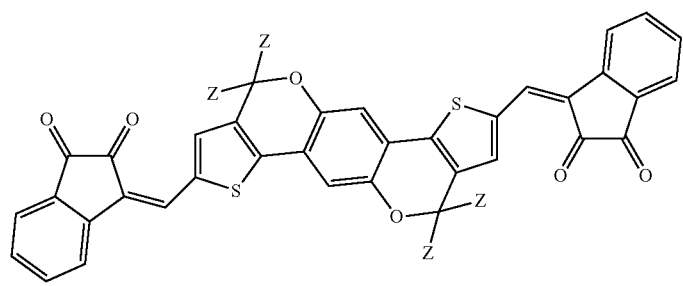
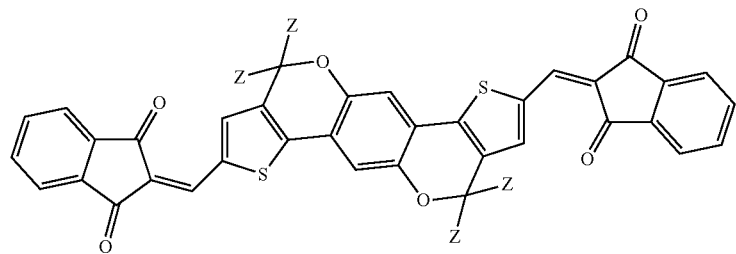
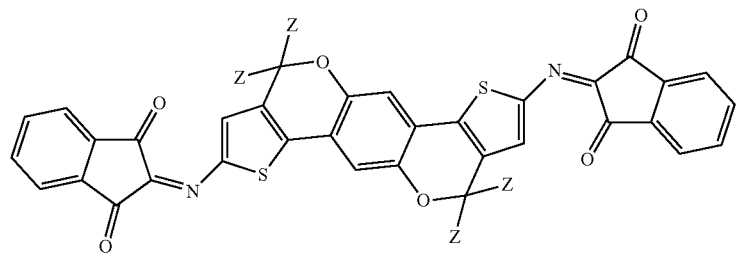
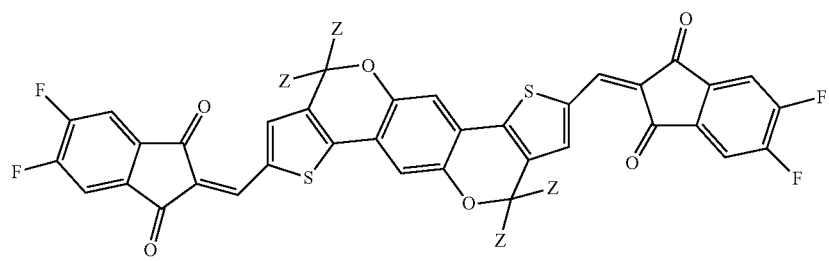
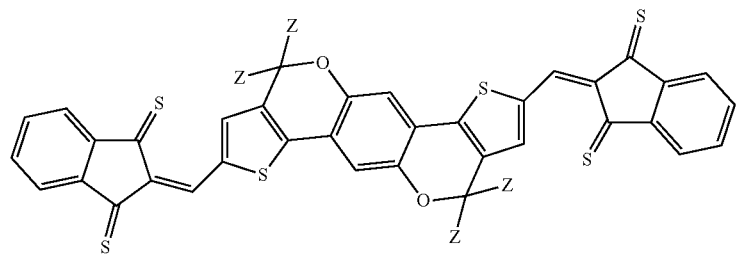
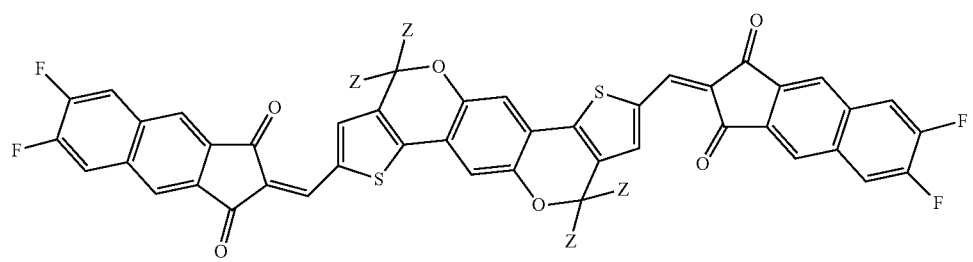

-continued
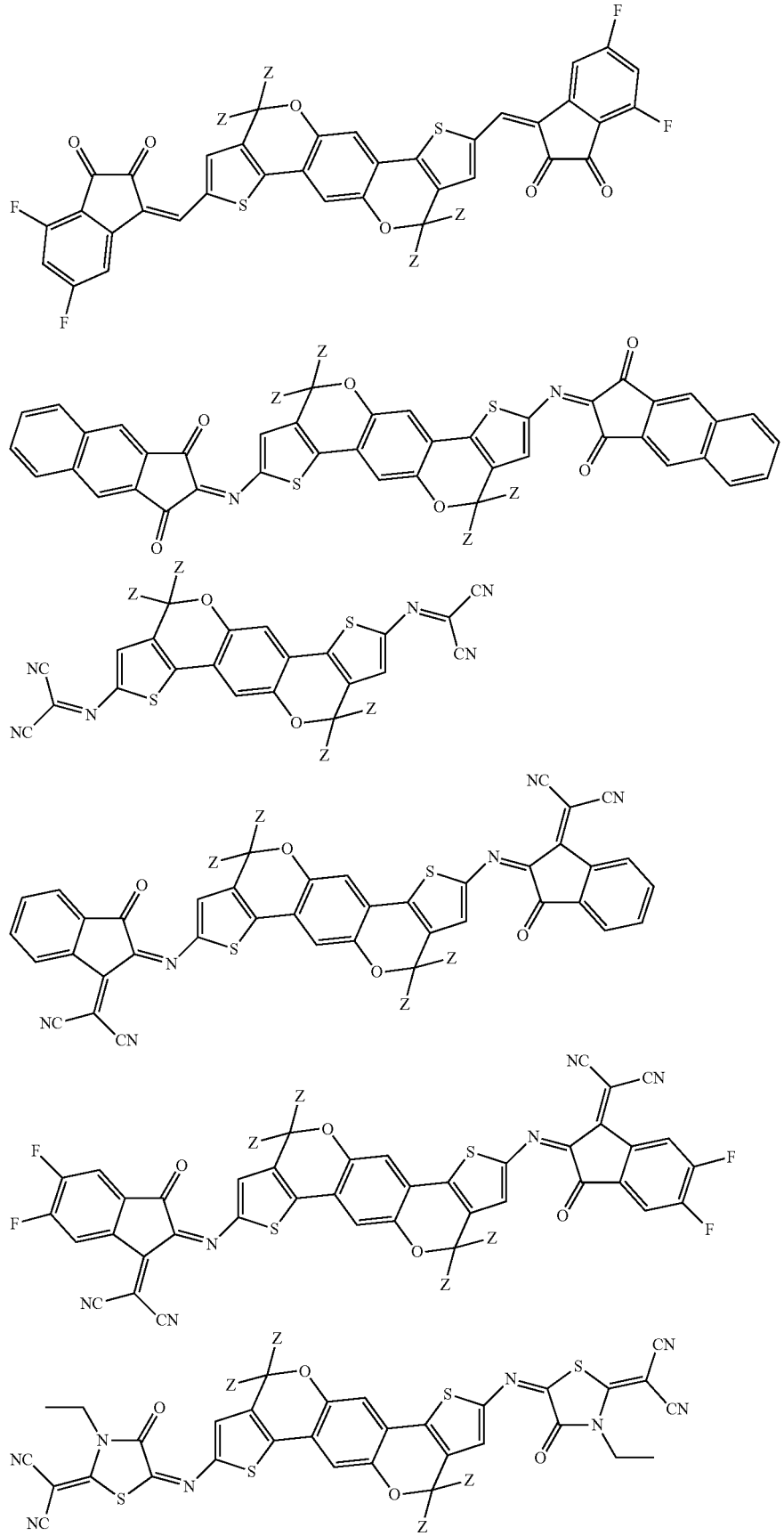

-continued
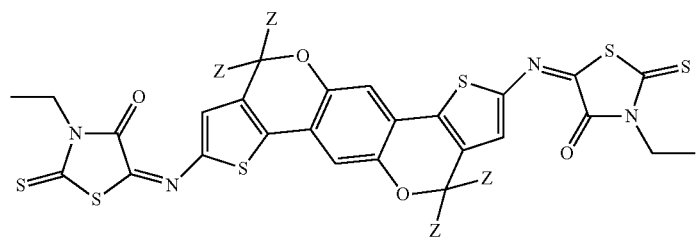
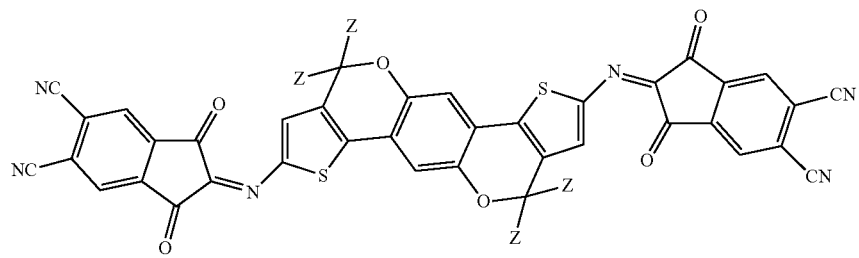
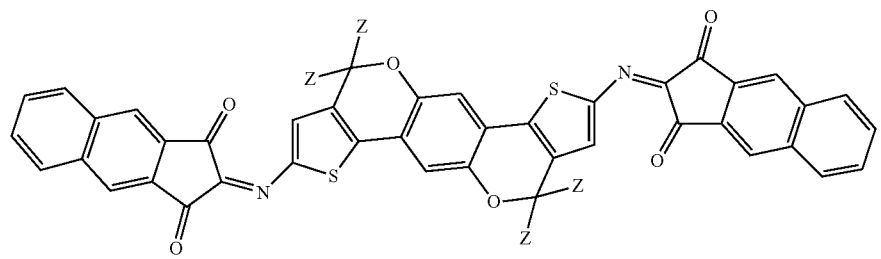
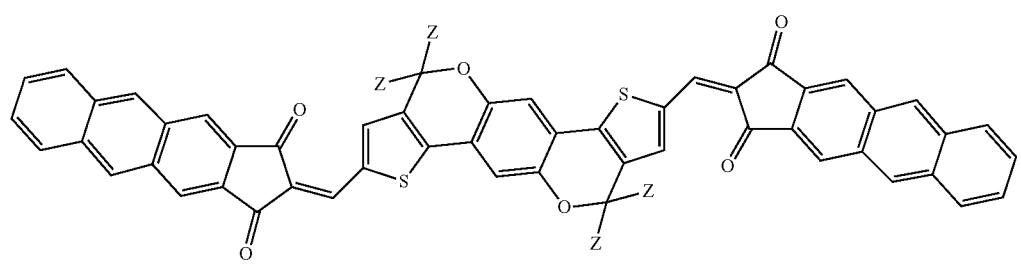
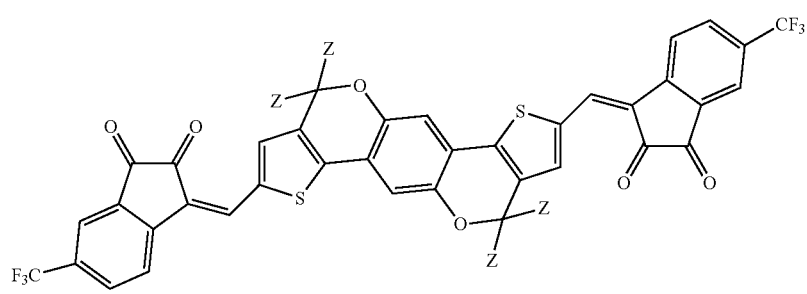
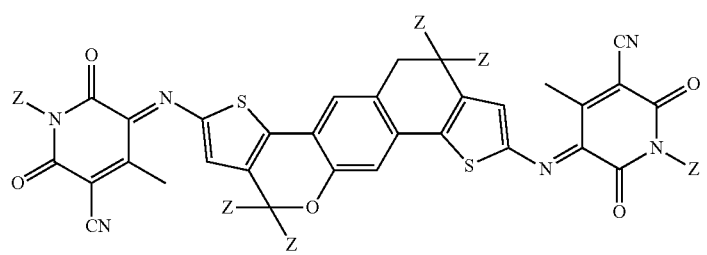

-continued
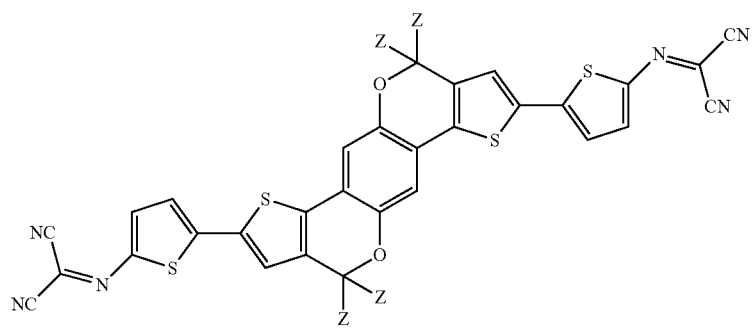
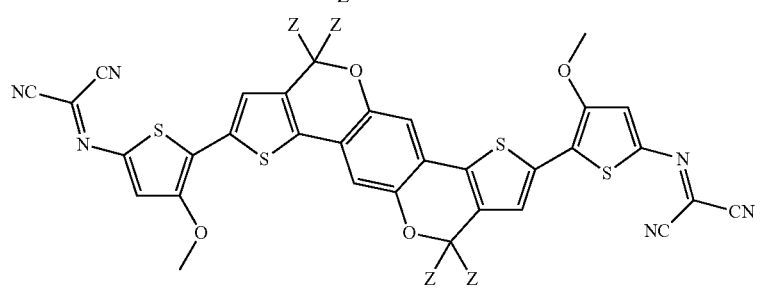
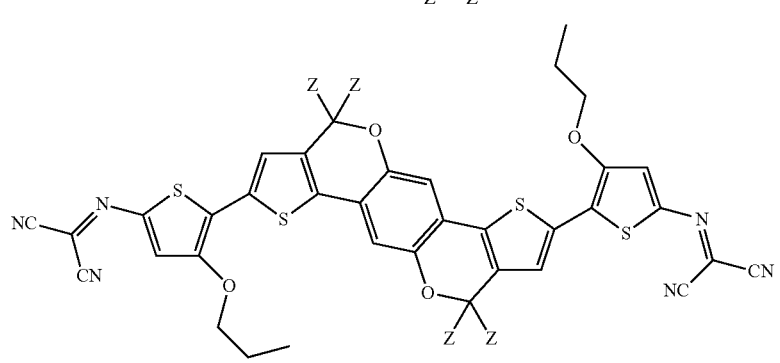
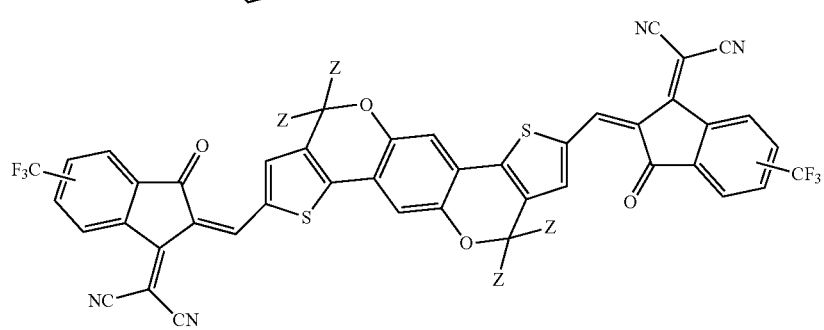
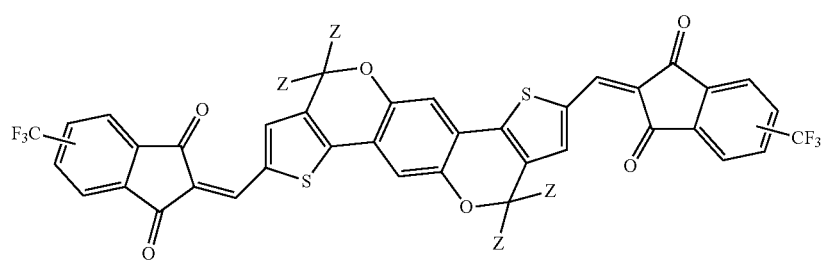

-continued
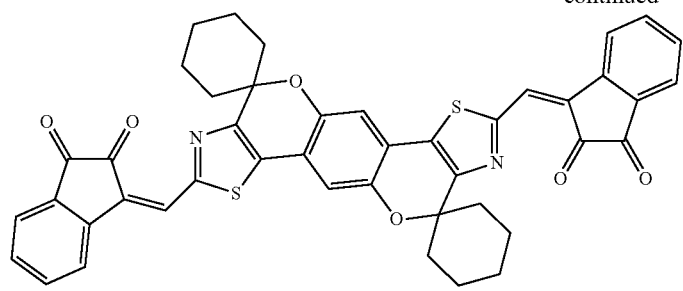
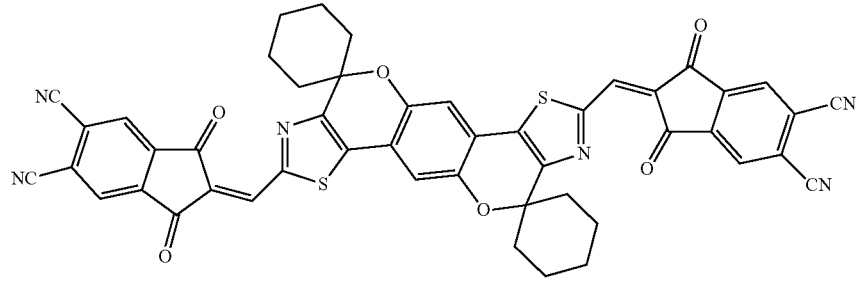
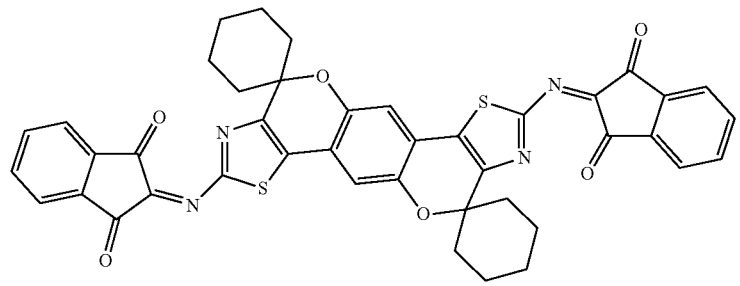
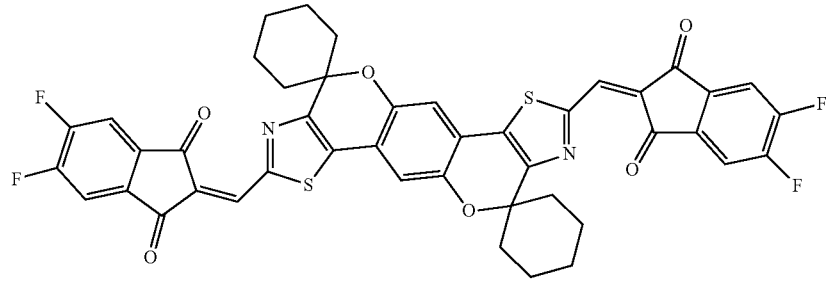
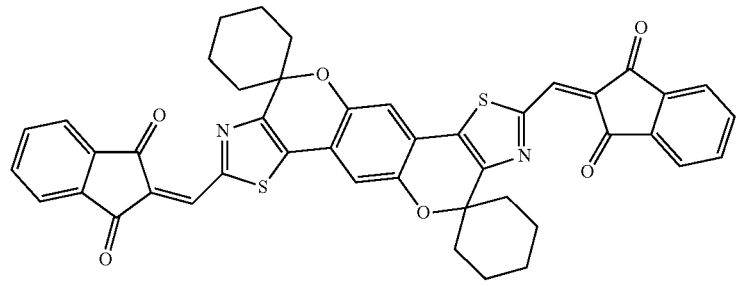
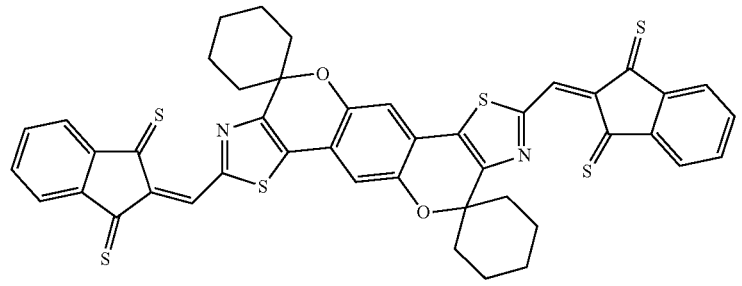

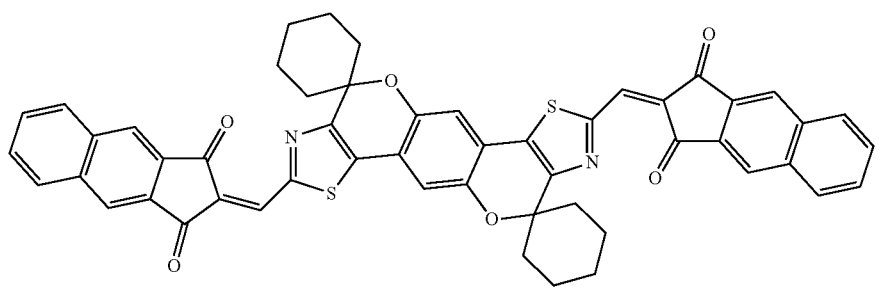
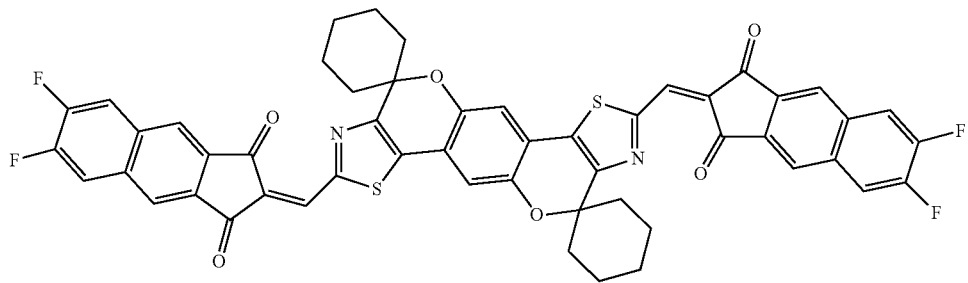
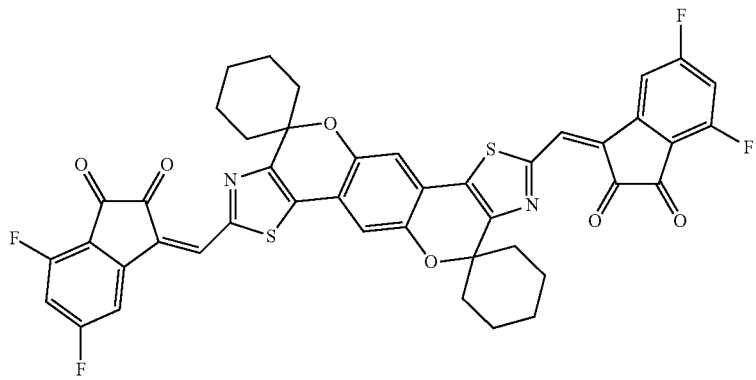
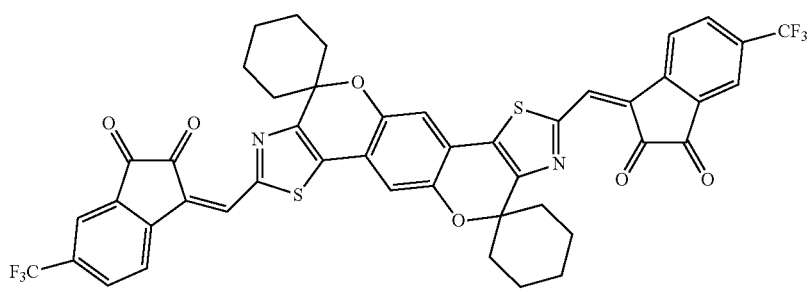
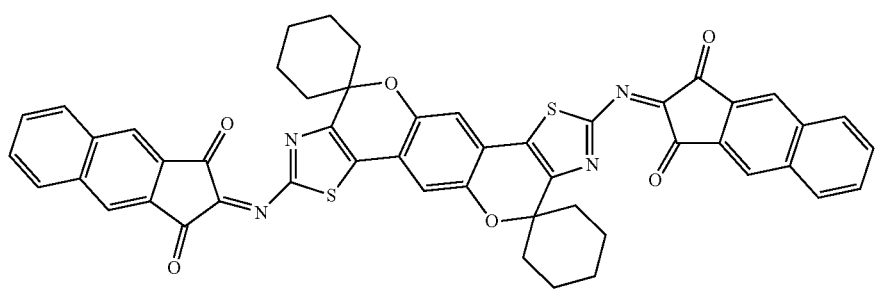

127 128
-continued
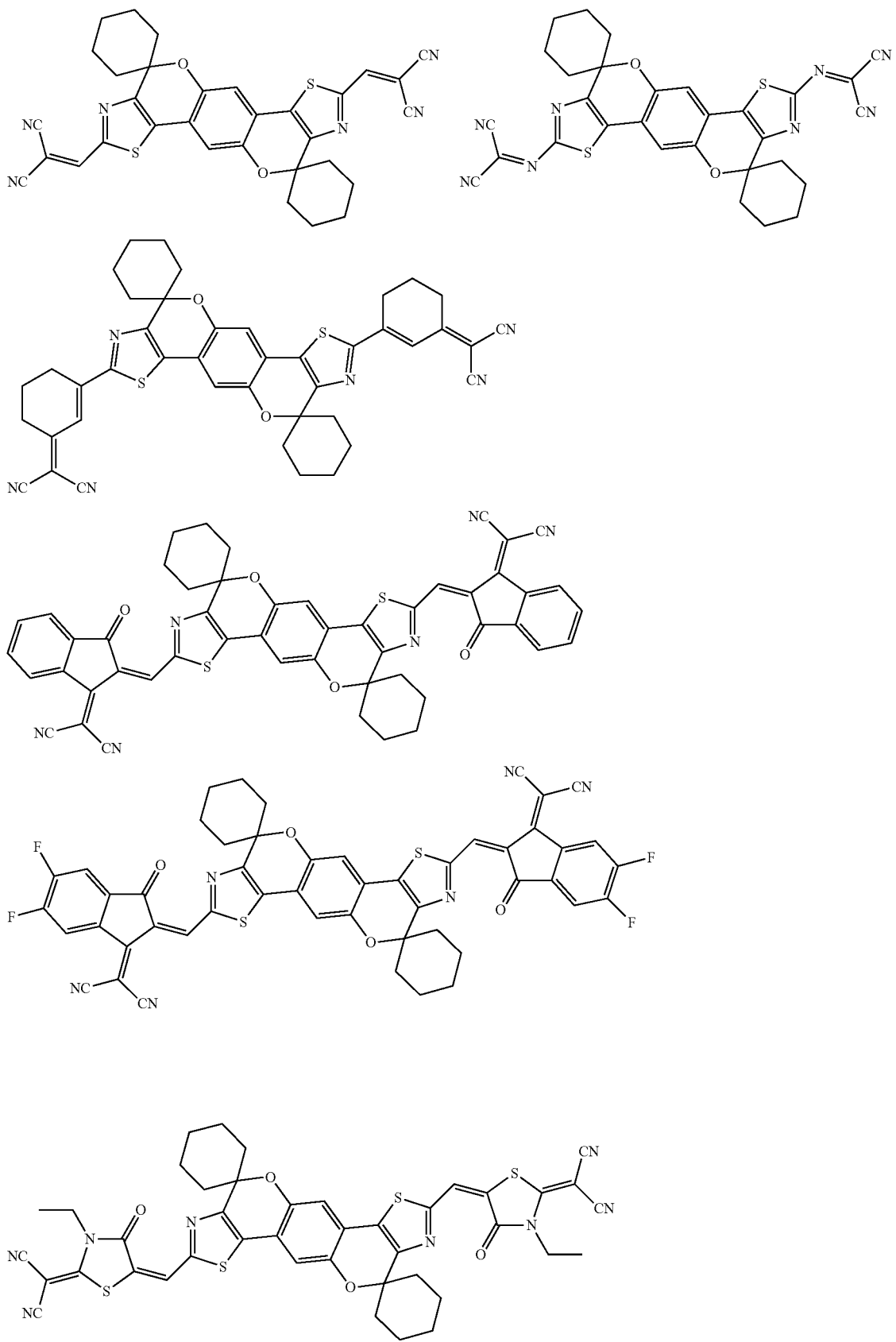

-continued
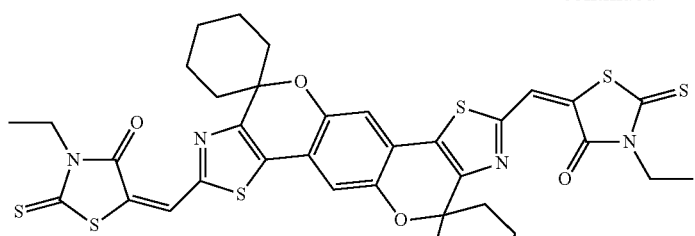
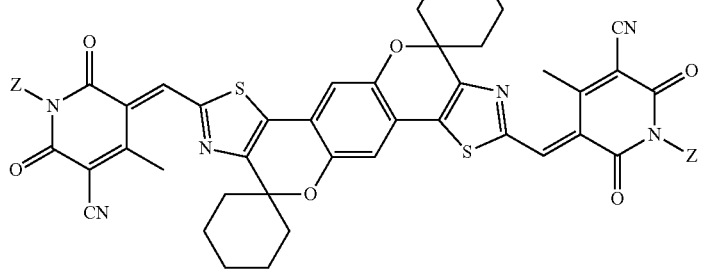
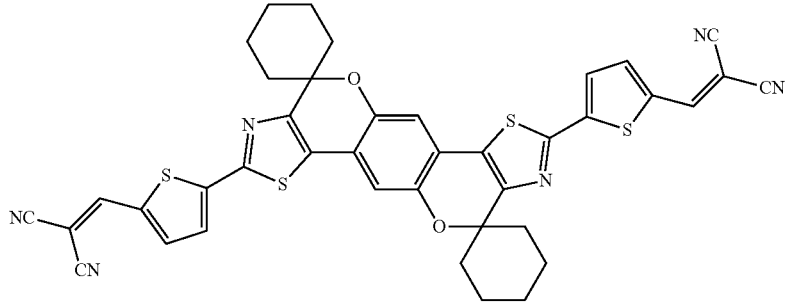
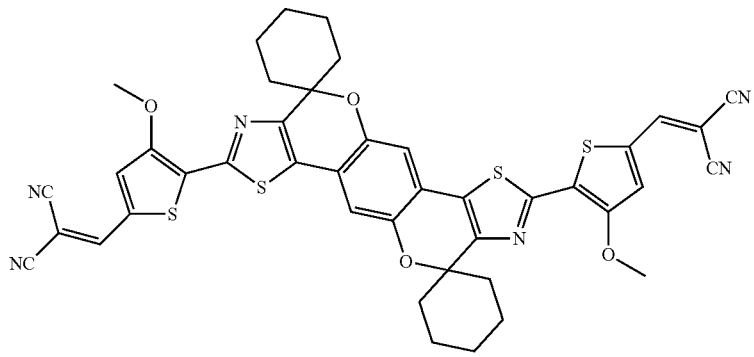
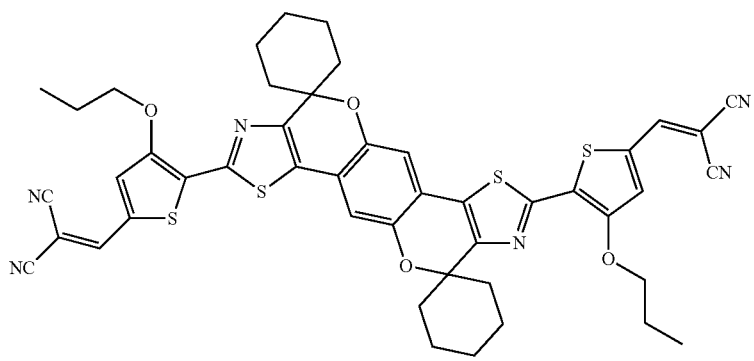

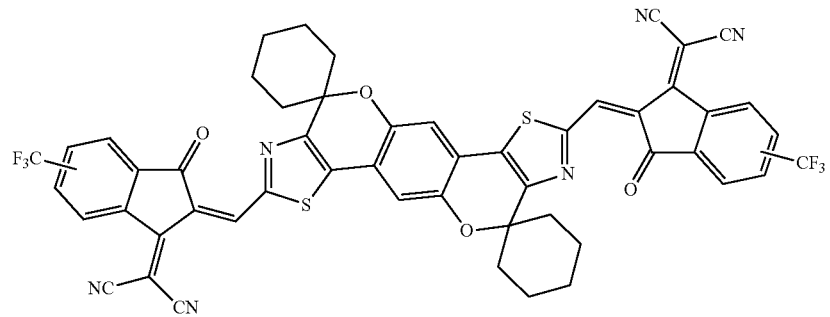
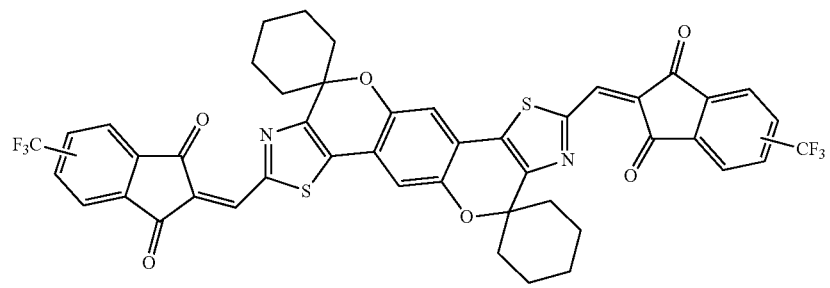
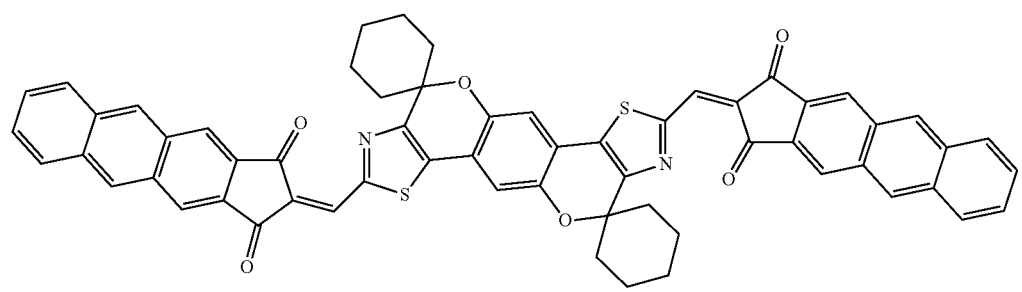
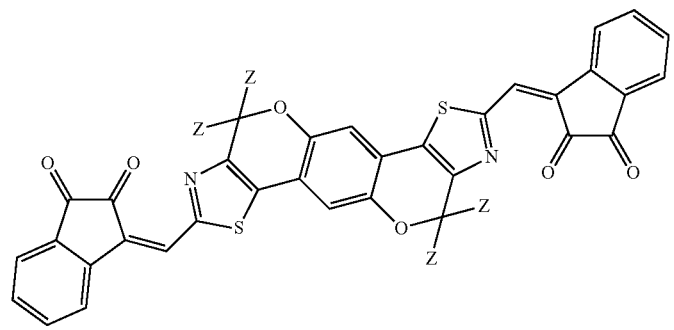
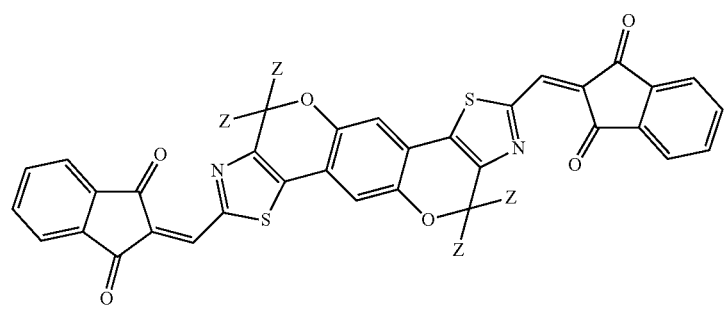

-continued
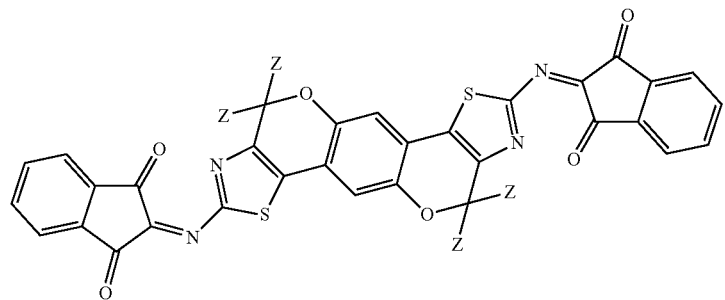
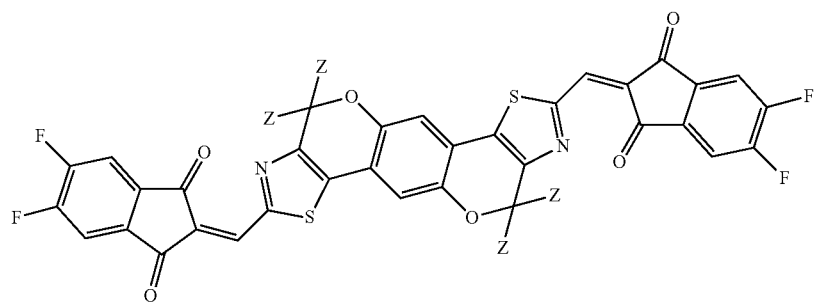
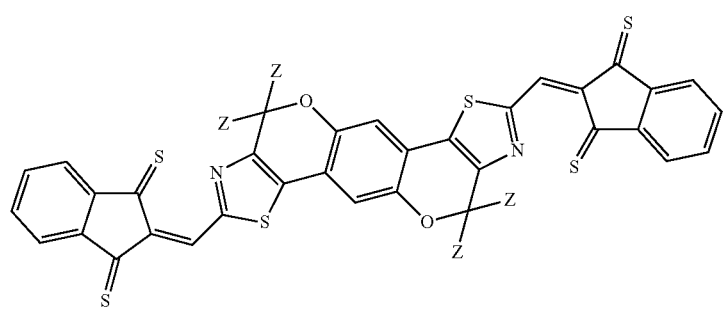
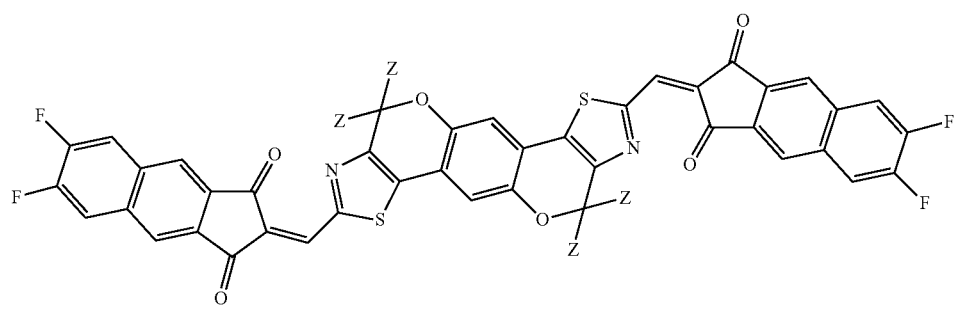
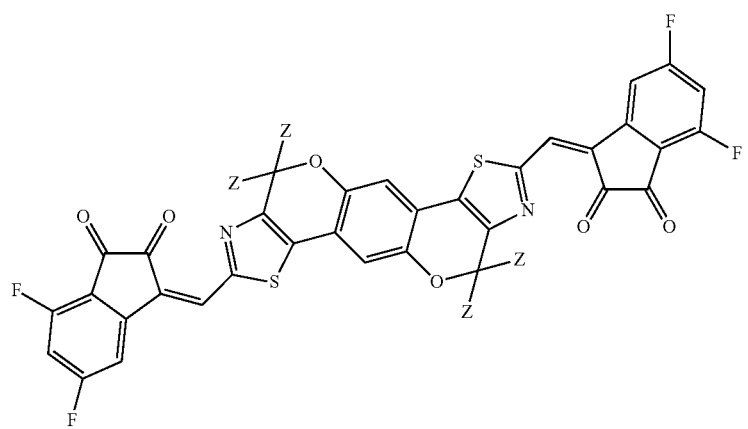

-continued
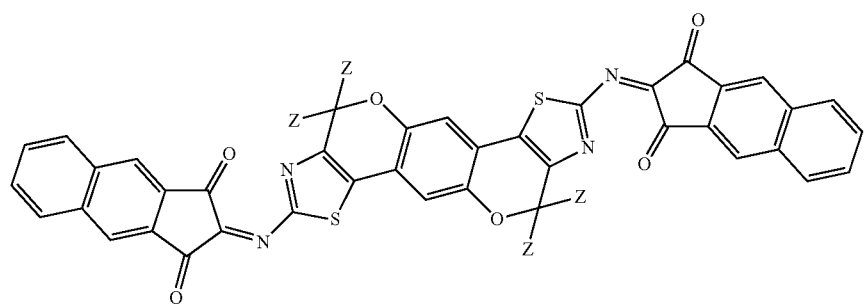
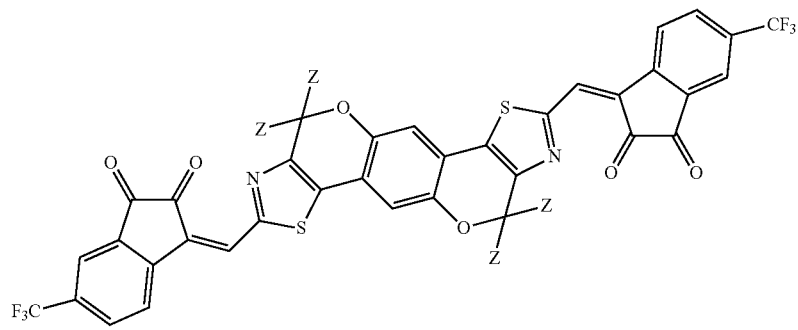
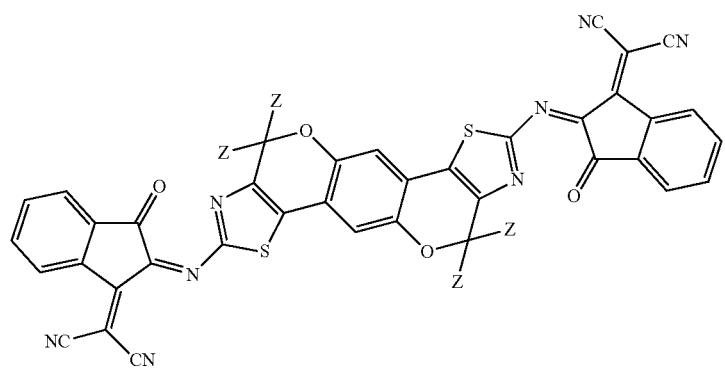
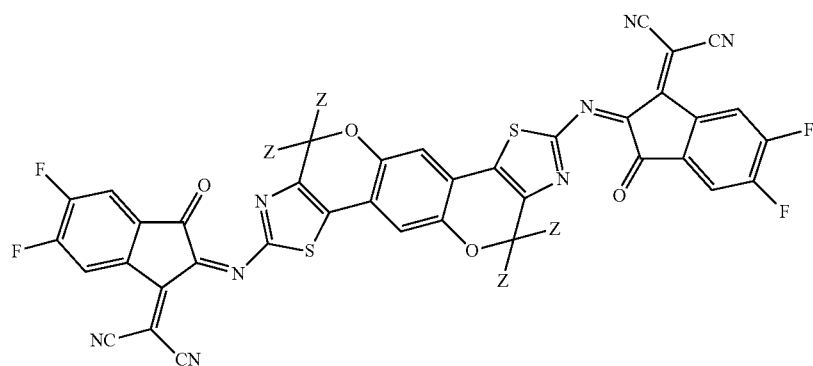
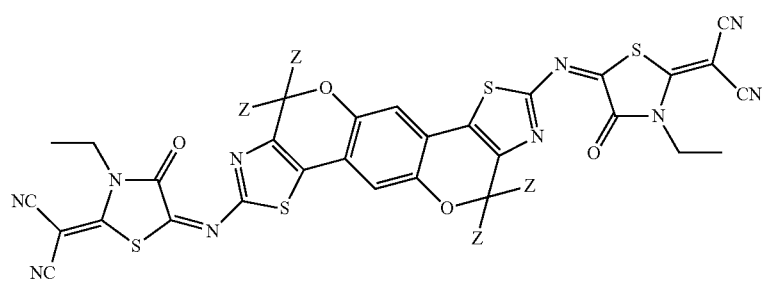

-continued
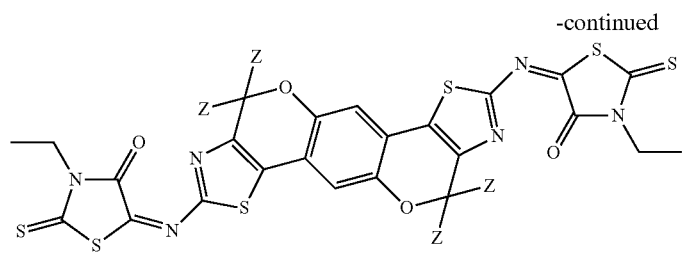
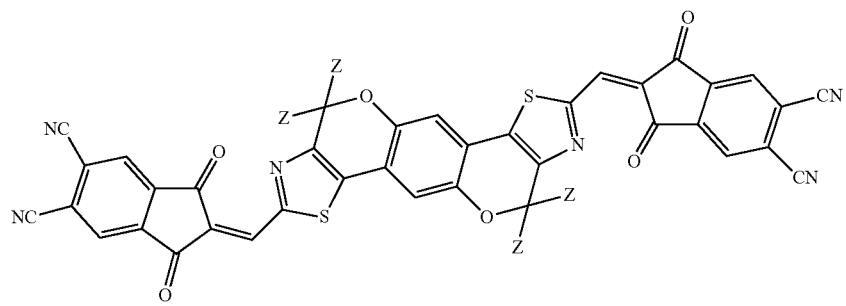
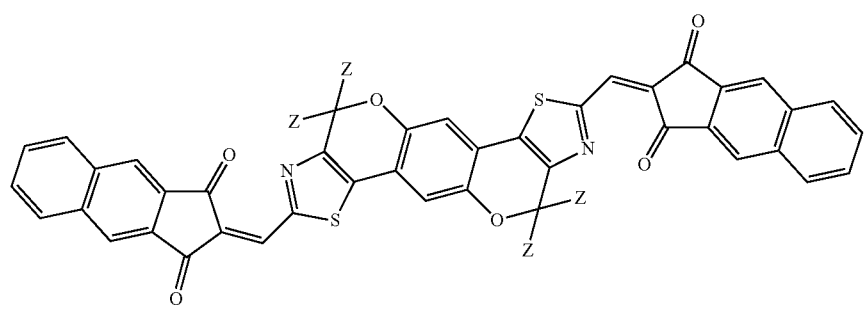
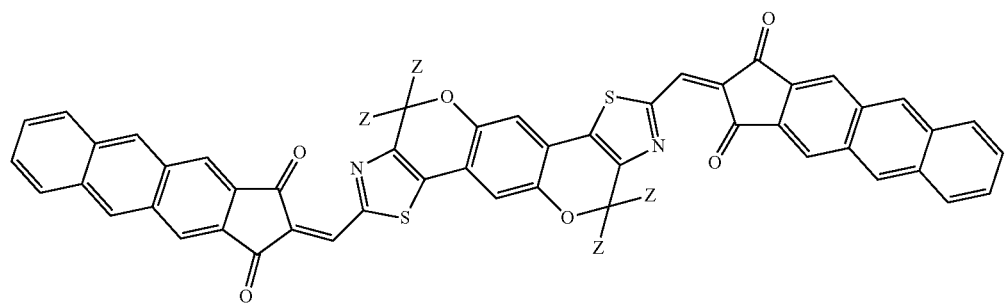
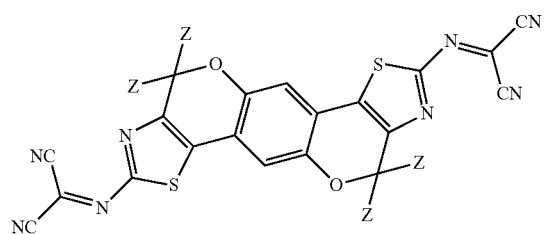
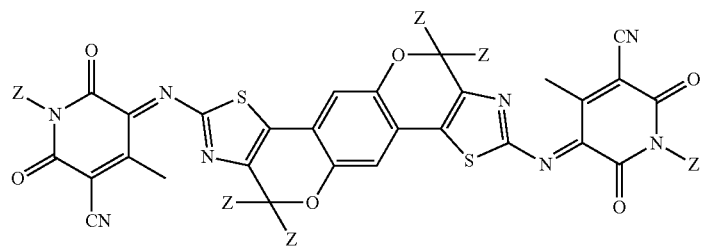

-continued
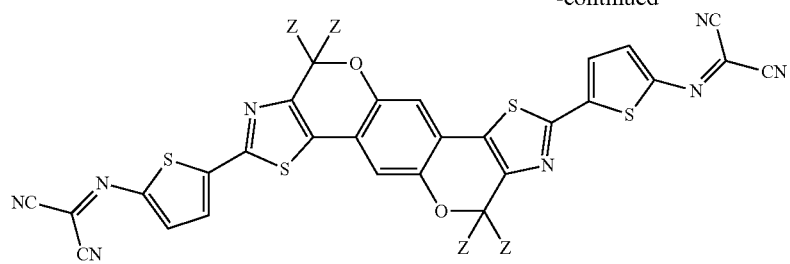
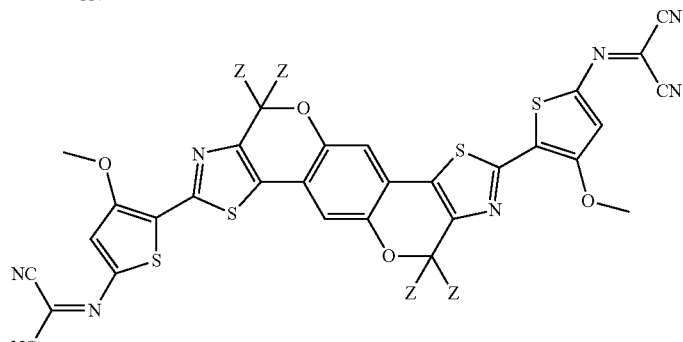
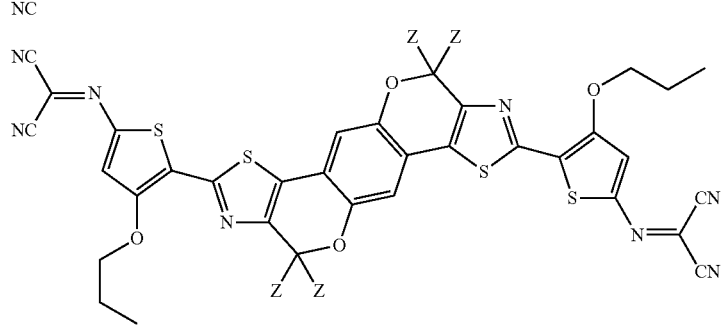
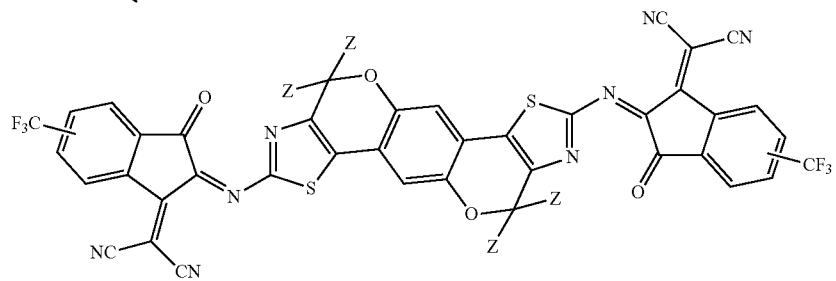
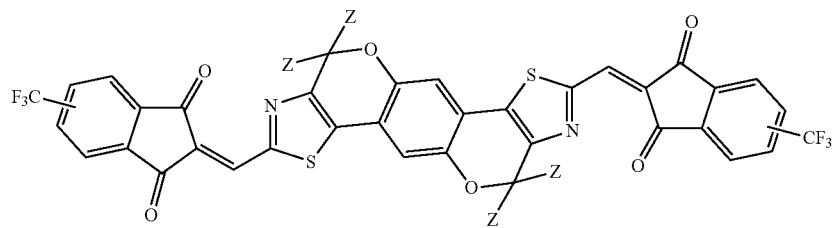
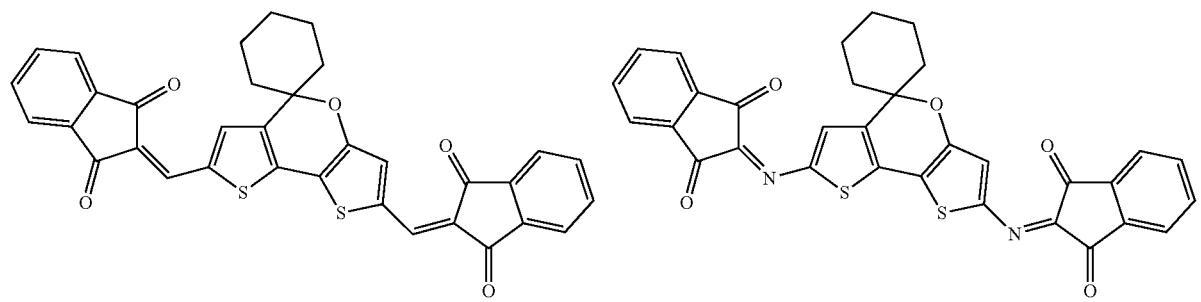

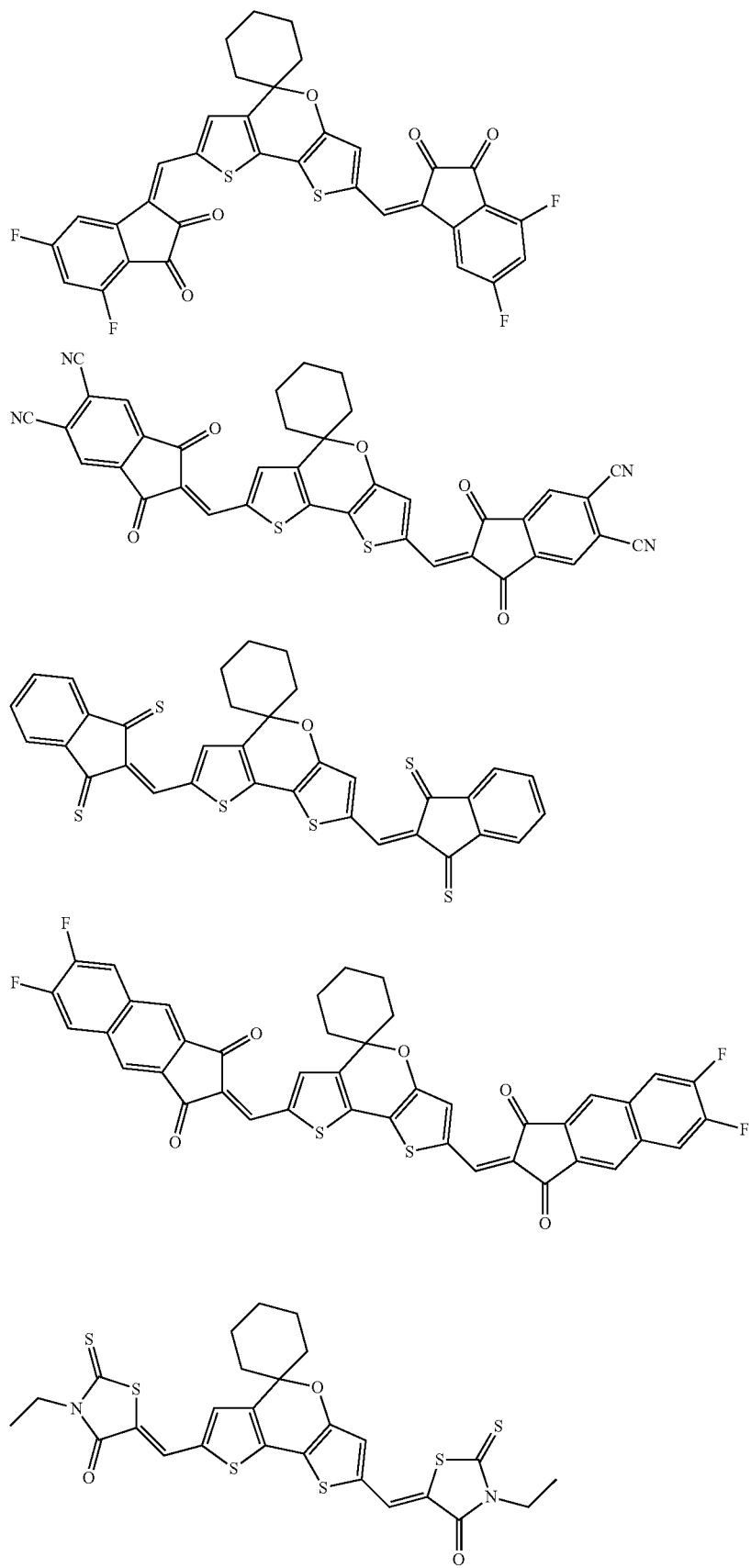

-continued
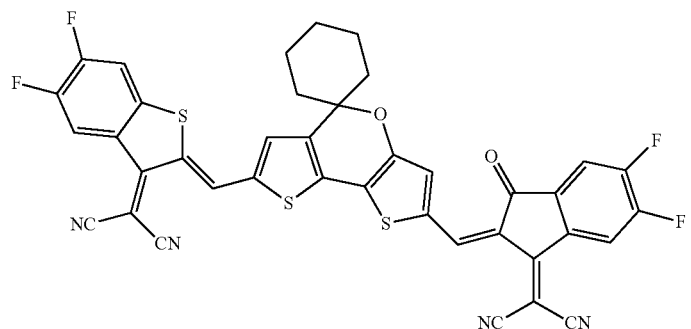
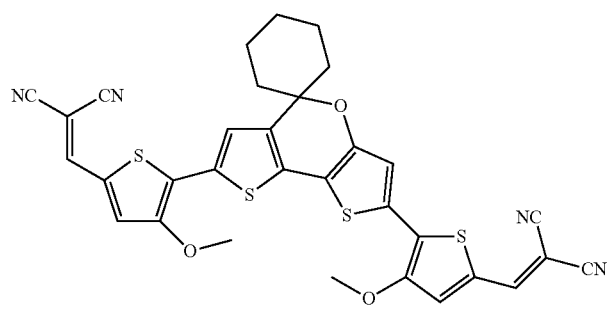
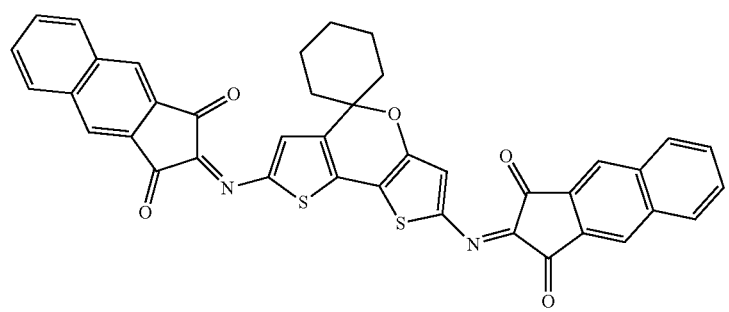
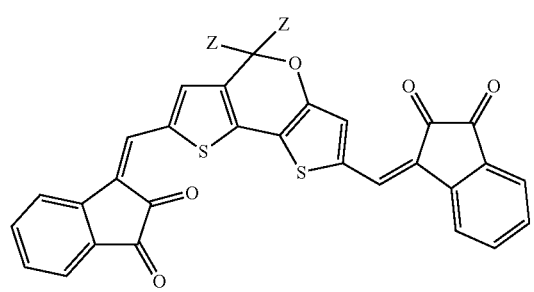
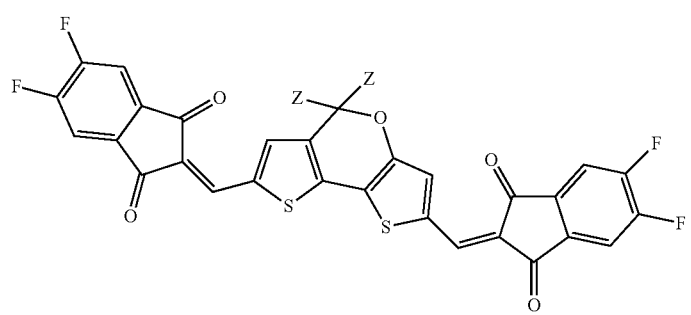

-continued
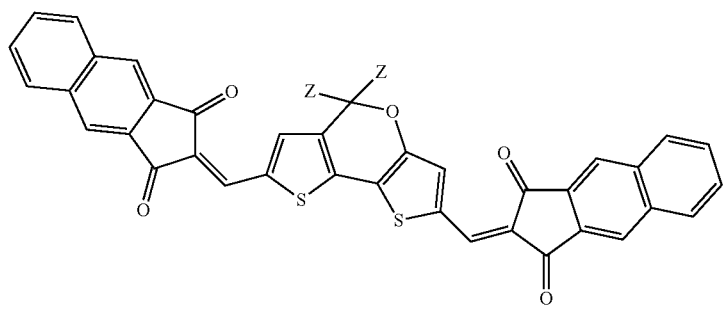
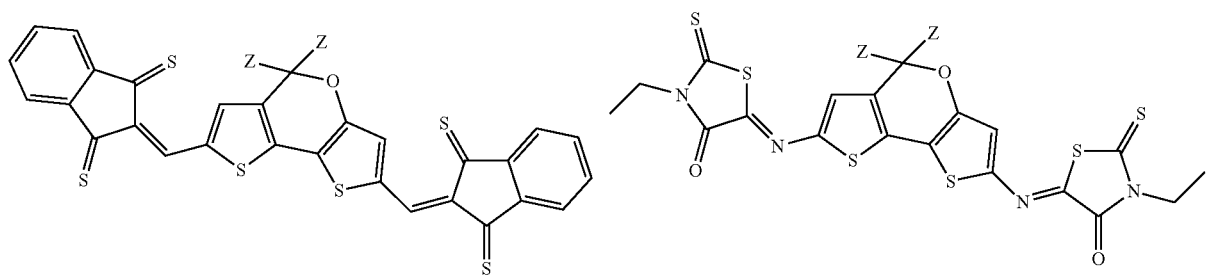
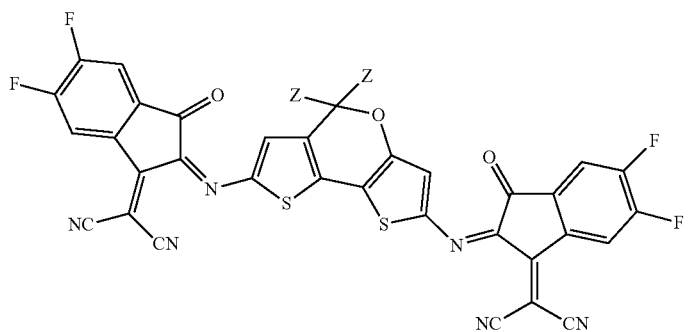
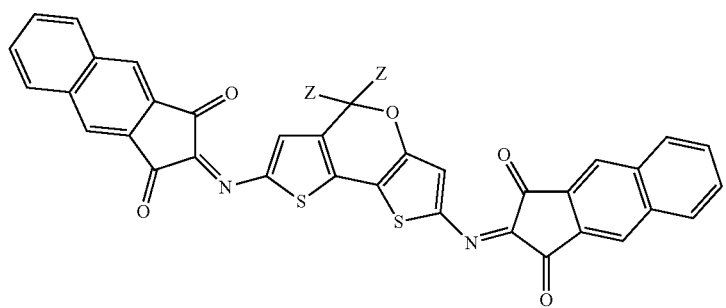
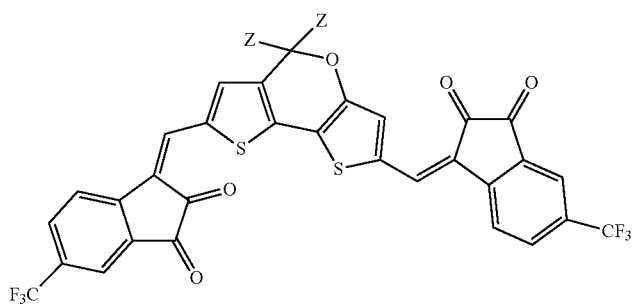

-continued
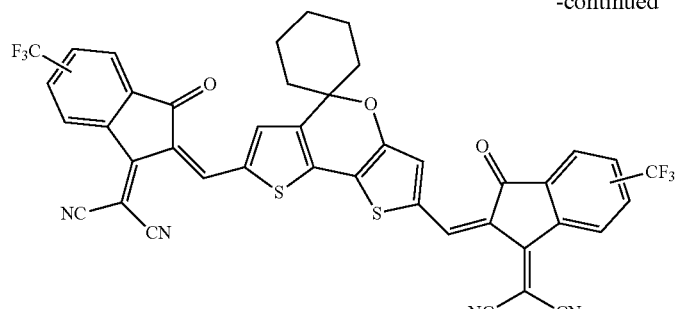
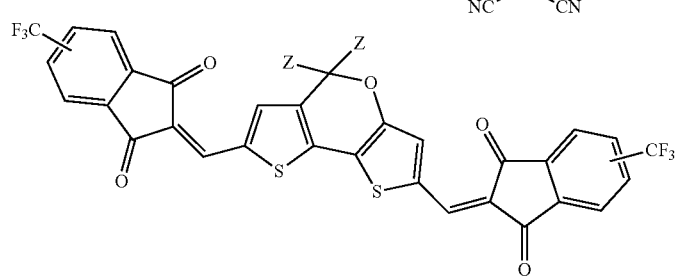
25
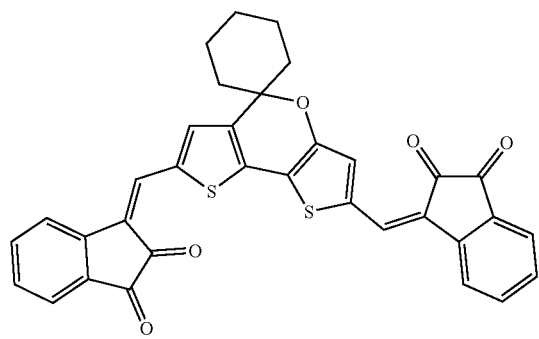
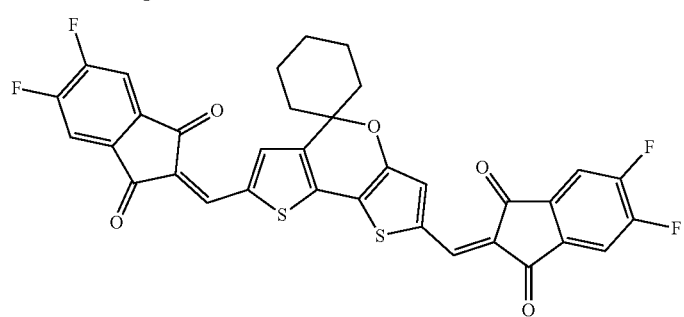
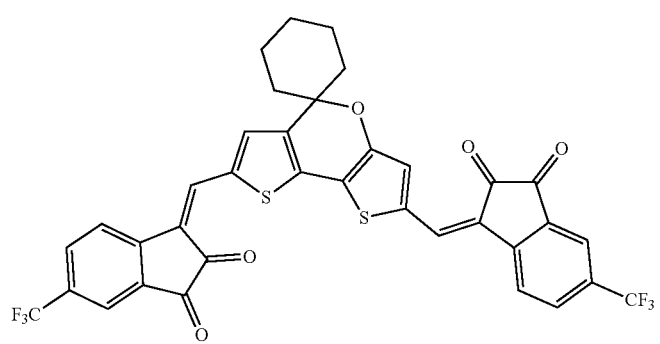

-continued
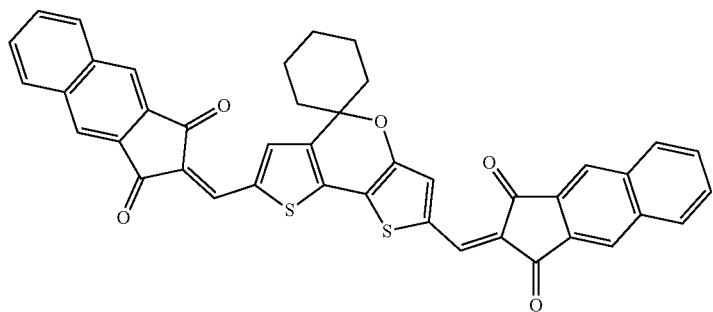
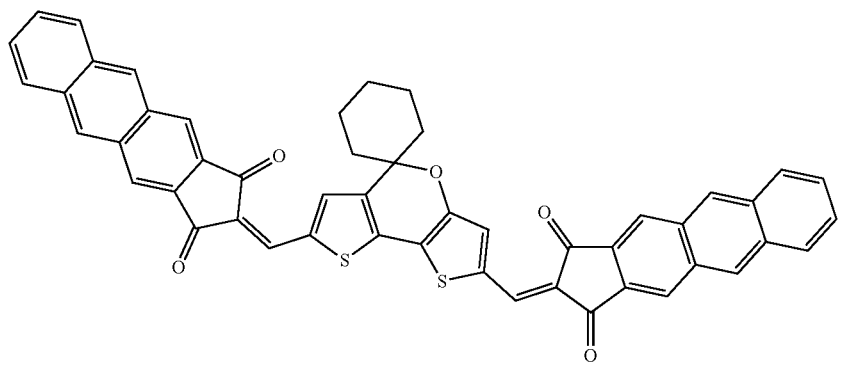
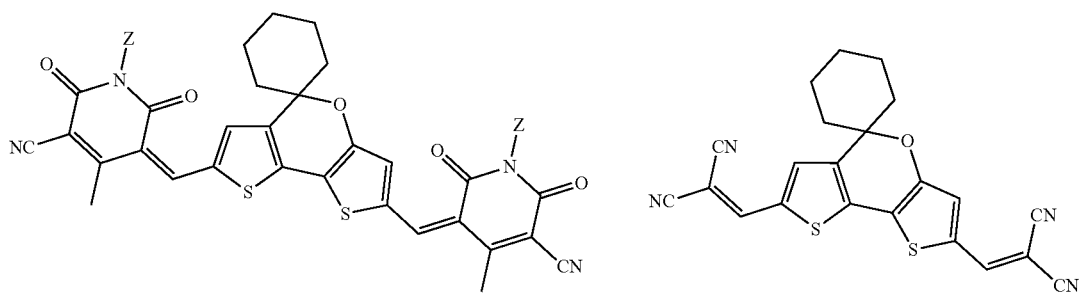
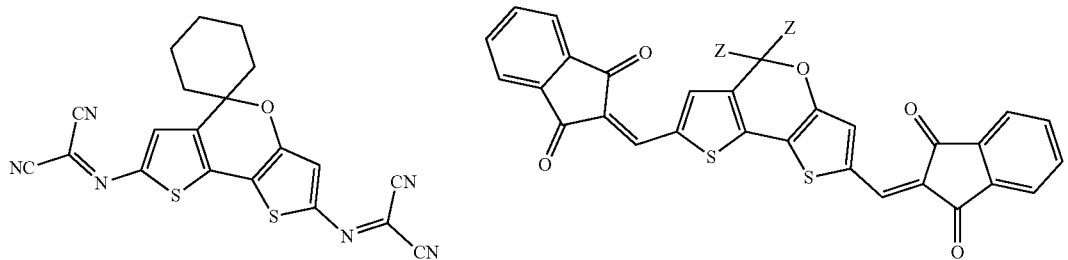
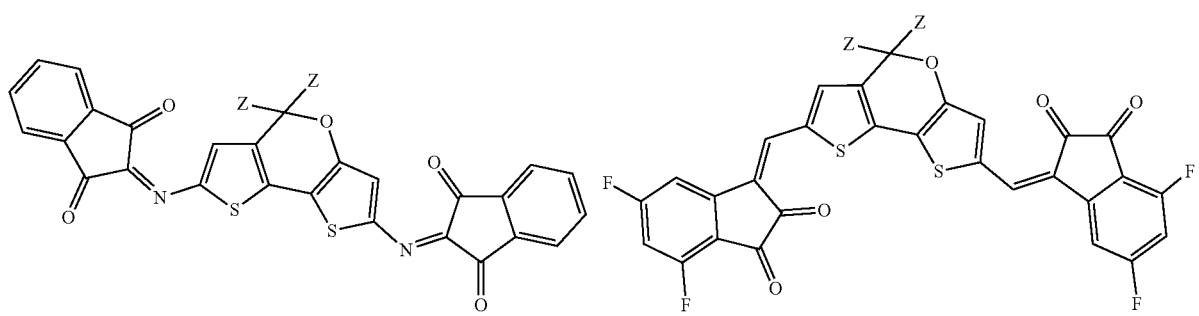

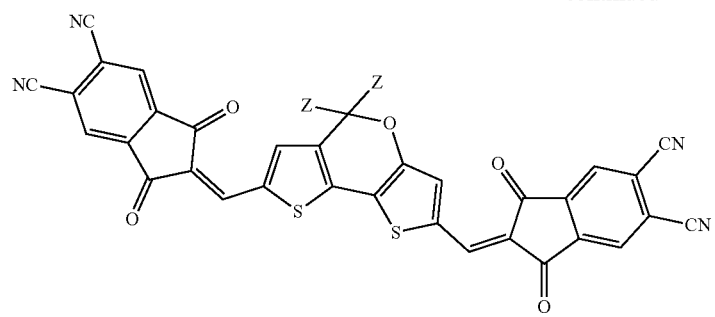
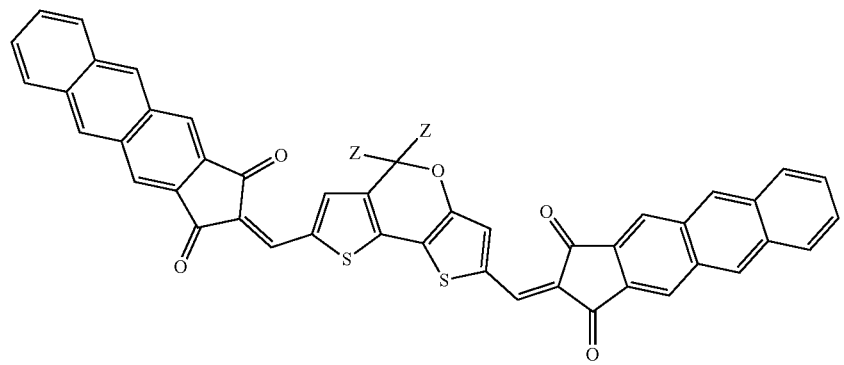
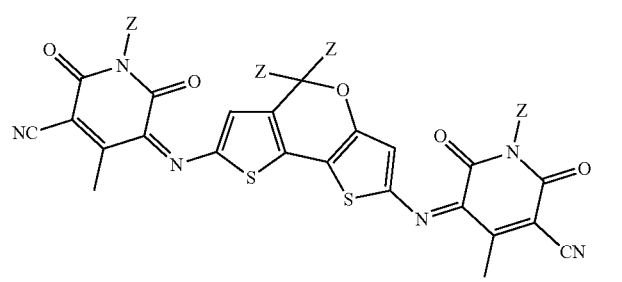
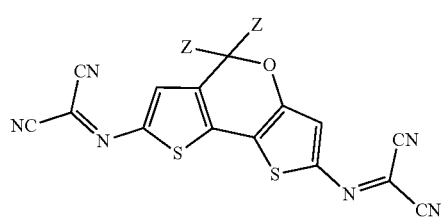
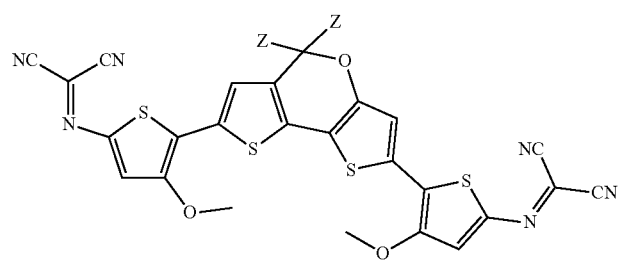
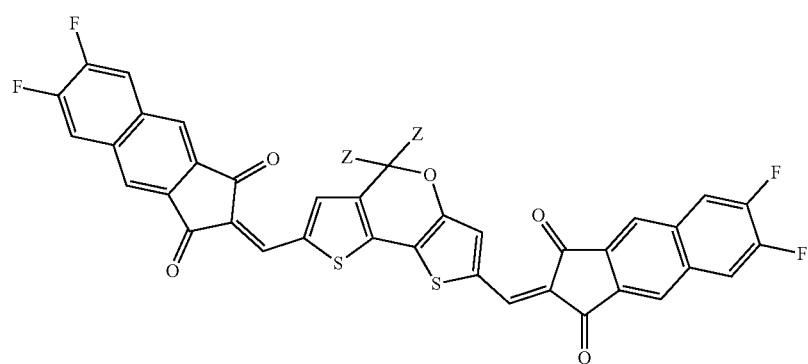

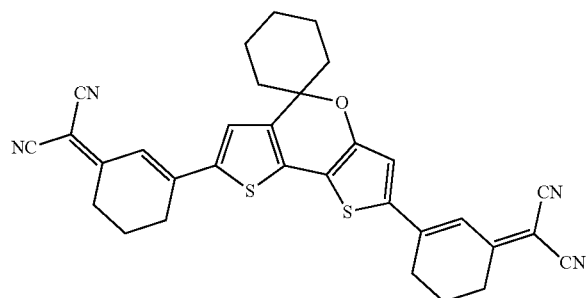
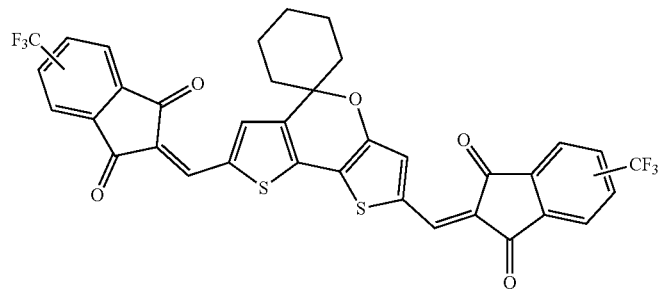
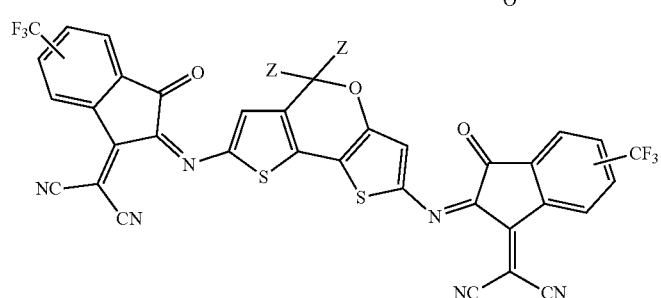
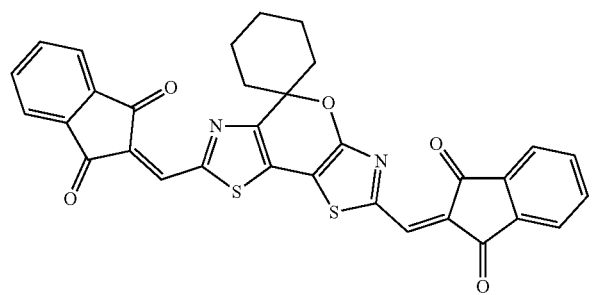
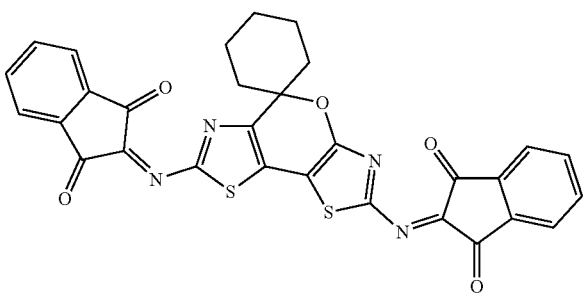
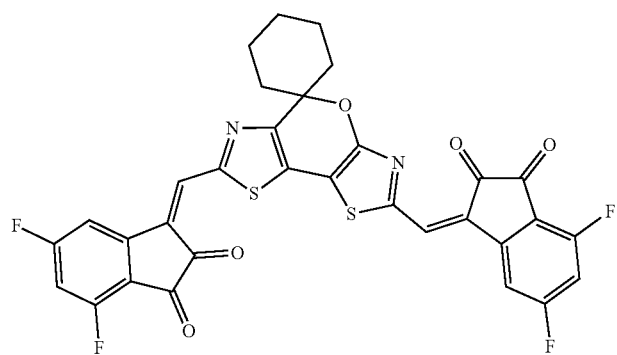

-continued
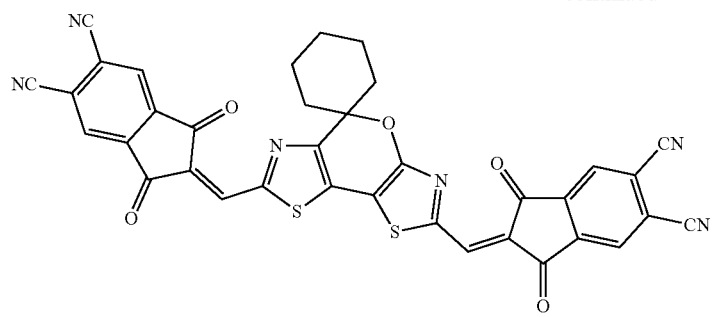
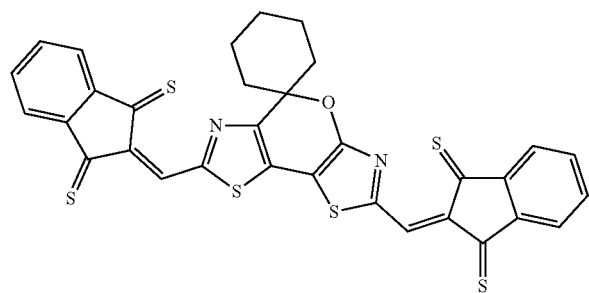
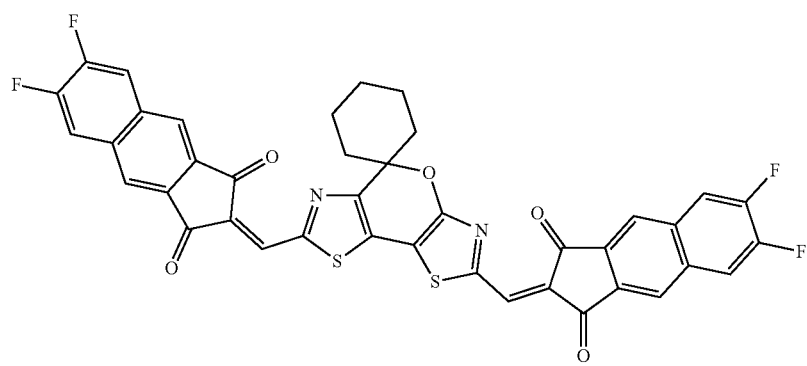
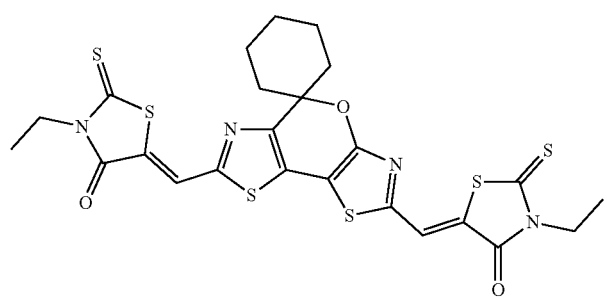
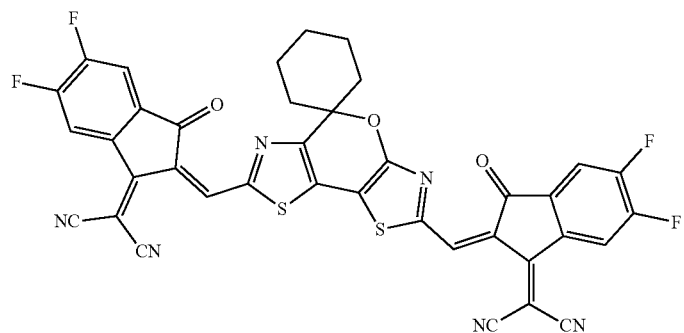

-continued
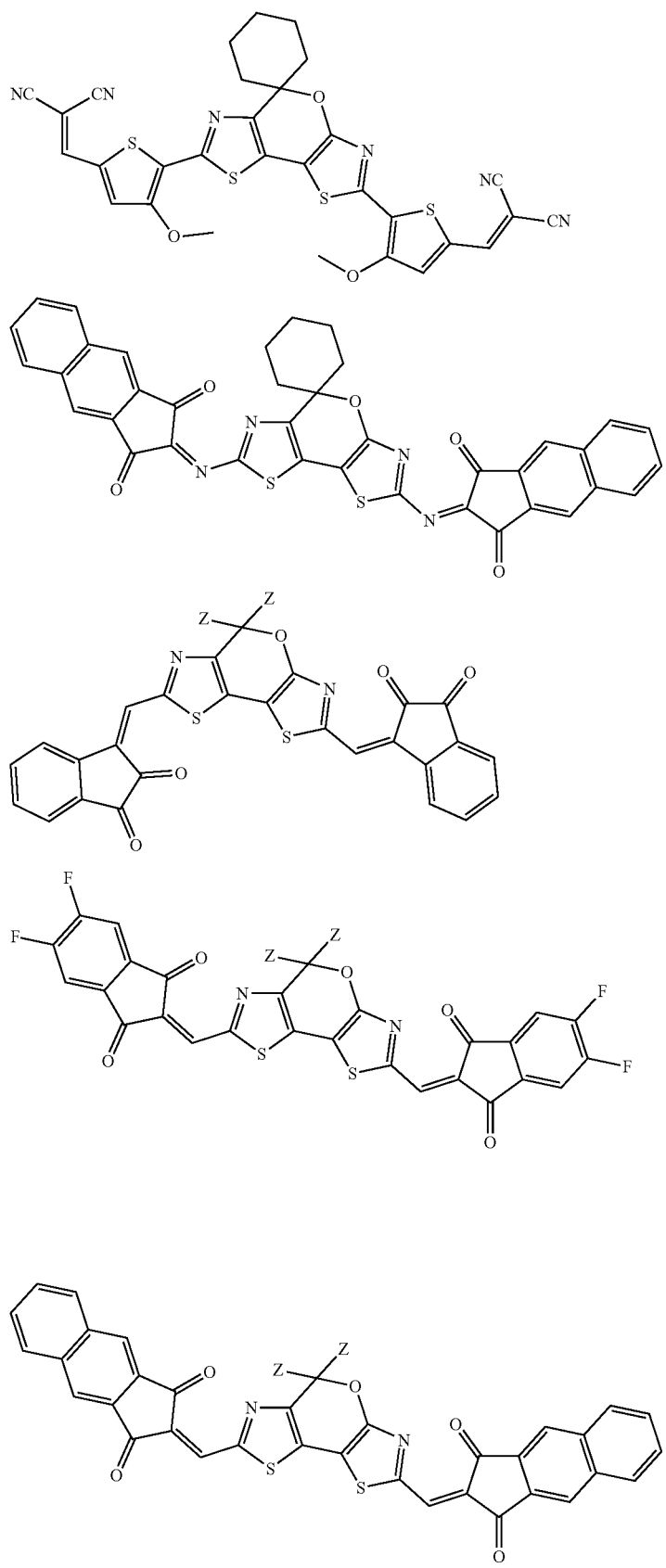

159
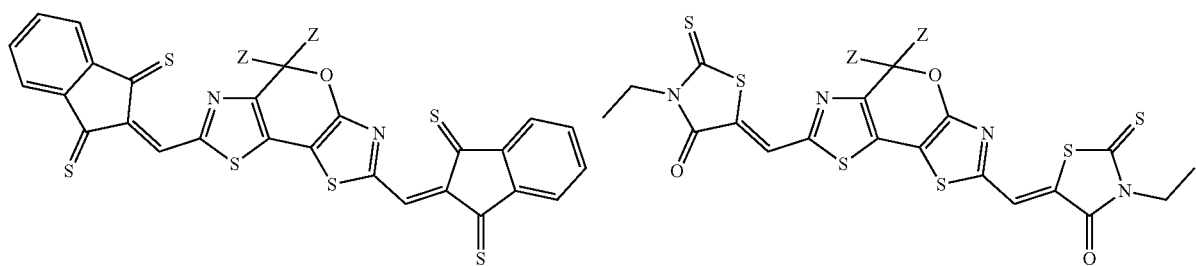
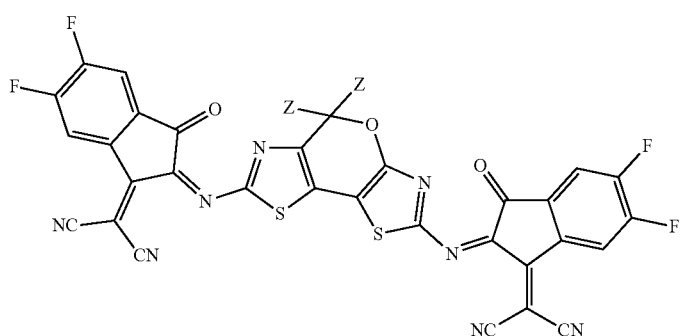
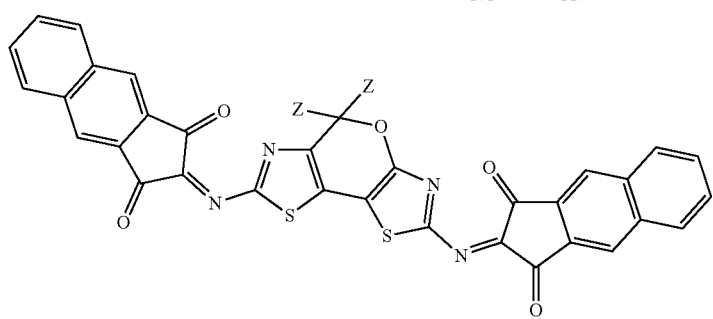
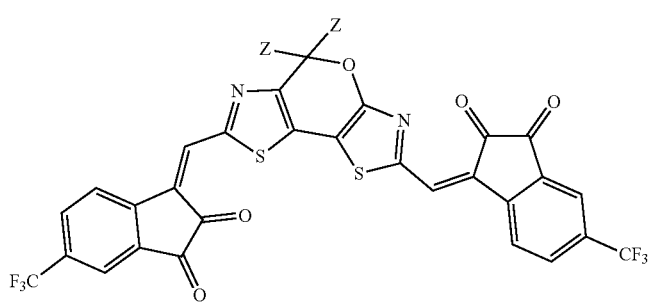
160
-continued
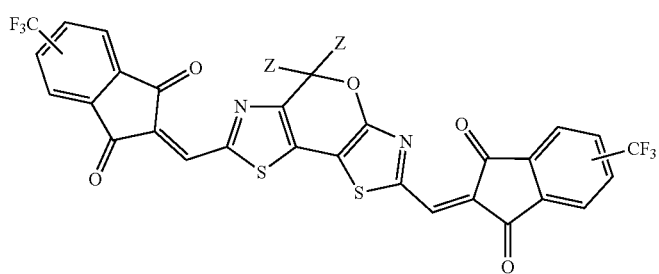

-continued
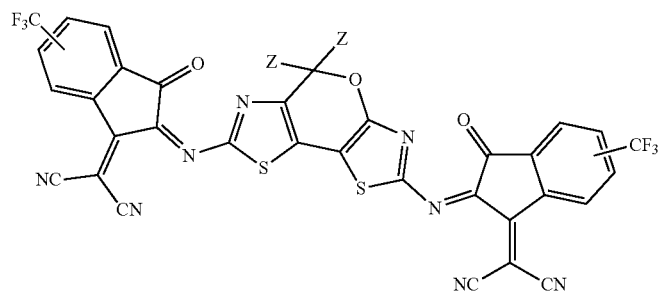
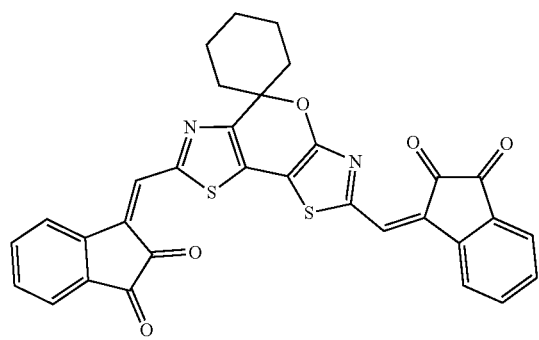
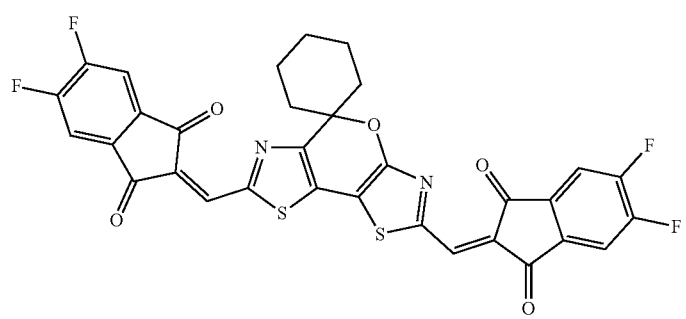
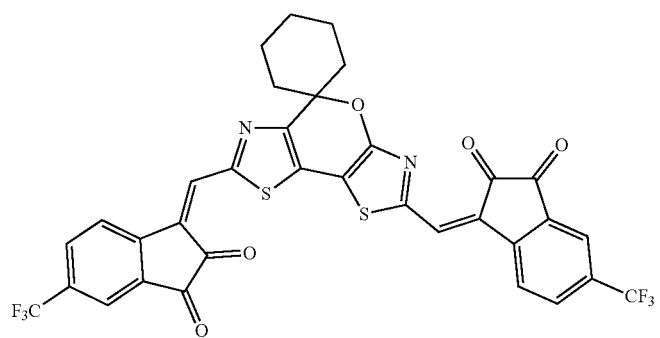
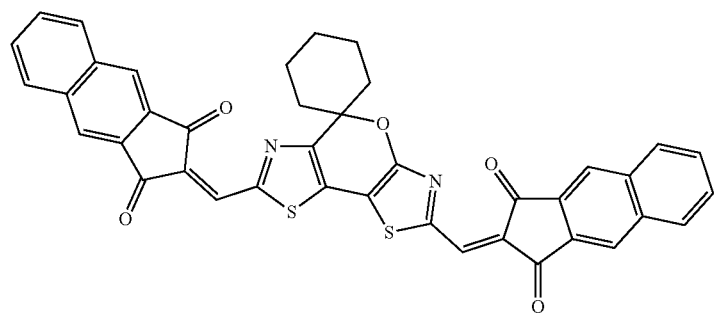

-continued
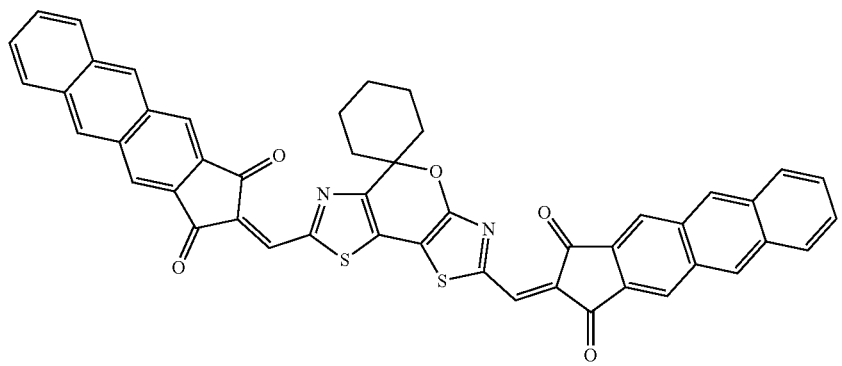
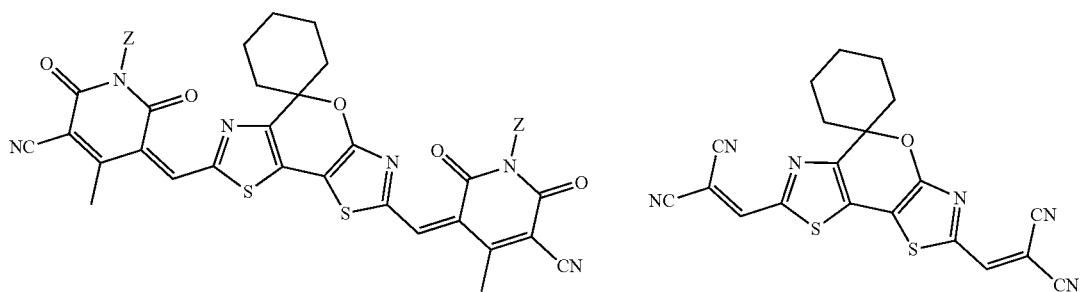
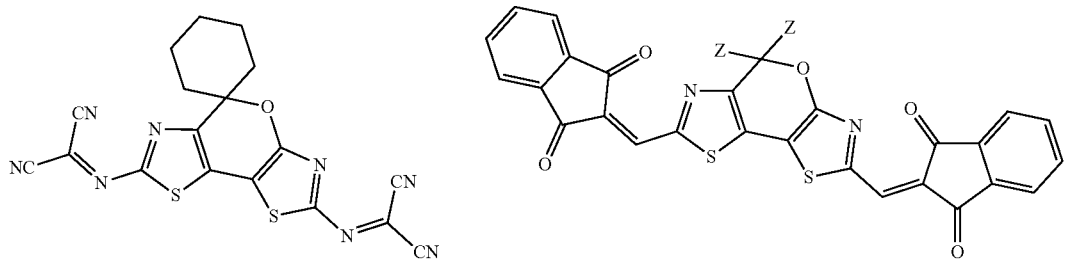
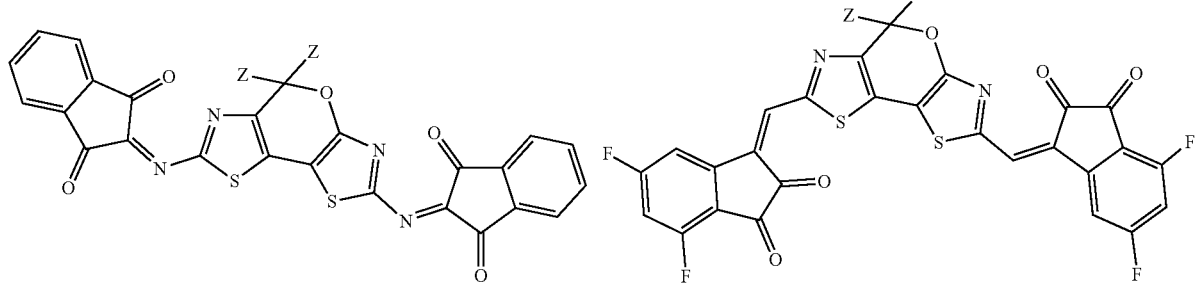
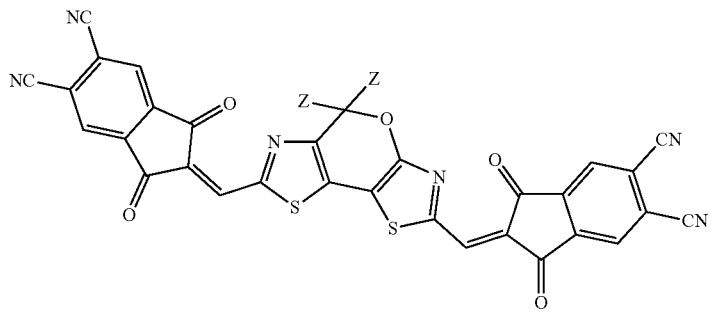

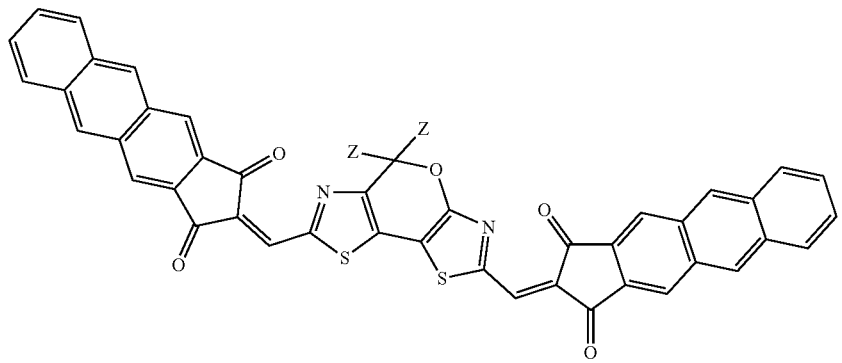
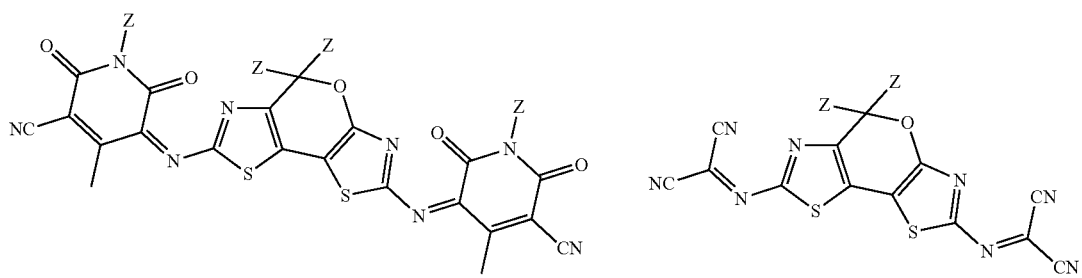
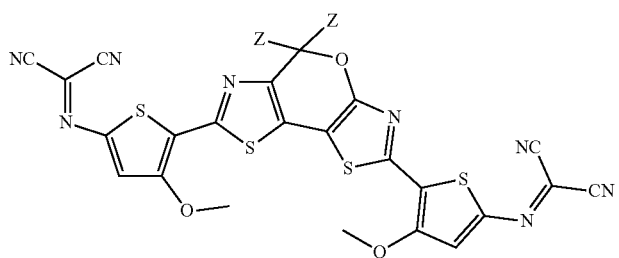
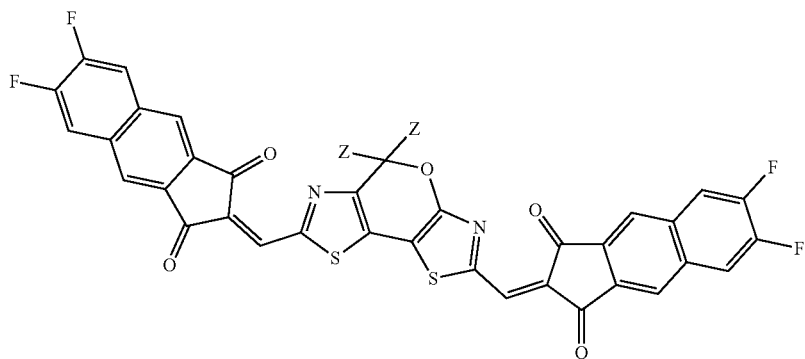
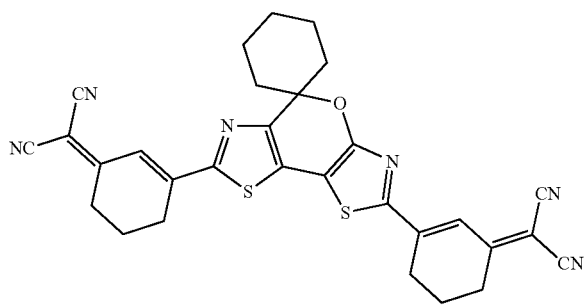

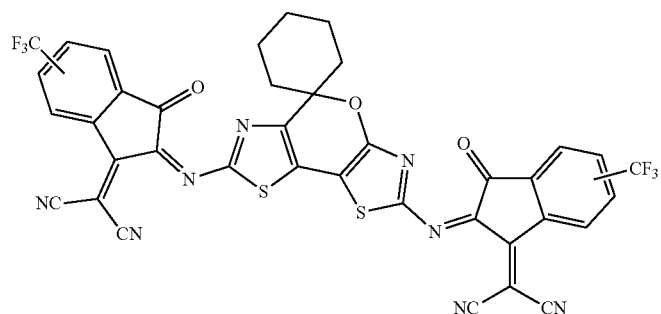
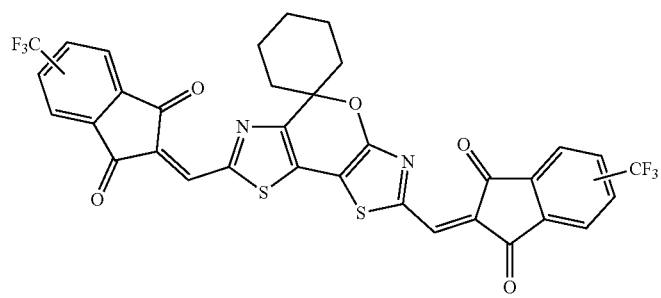
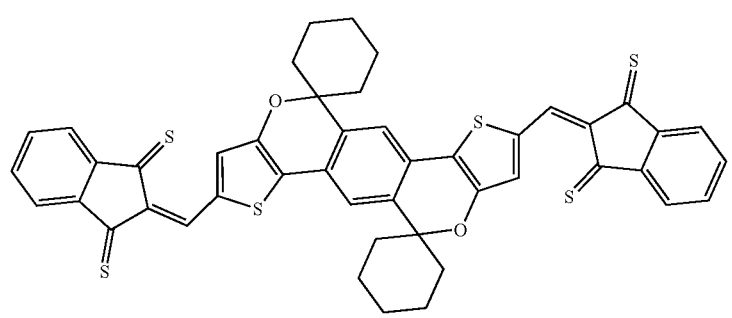
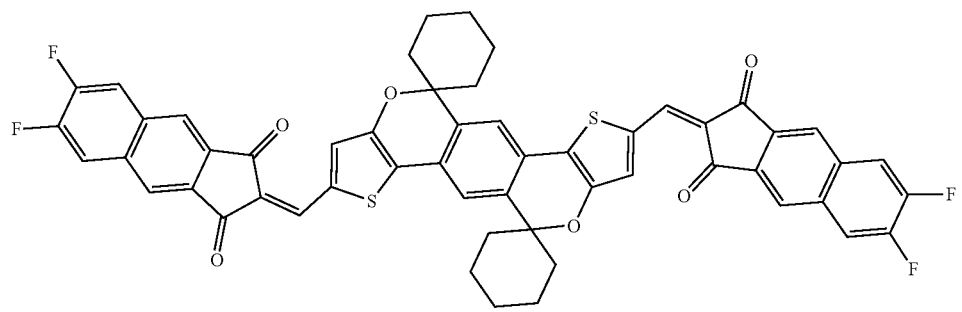
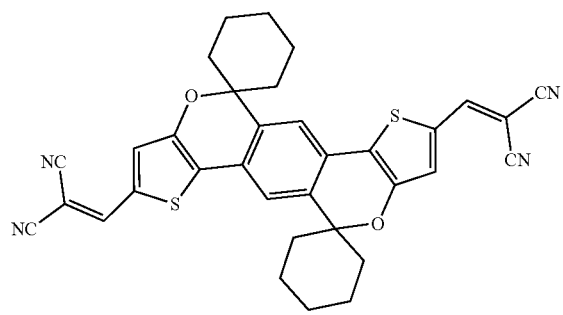
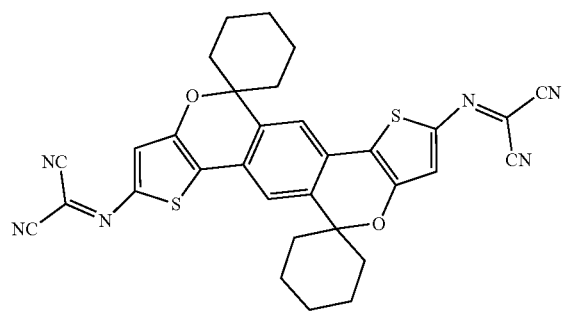

-continued
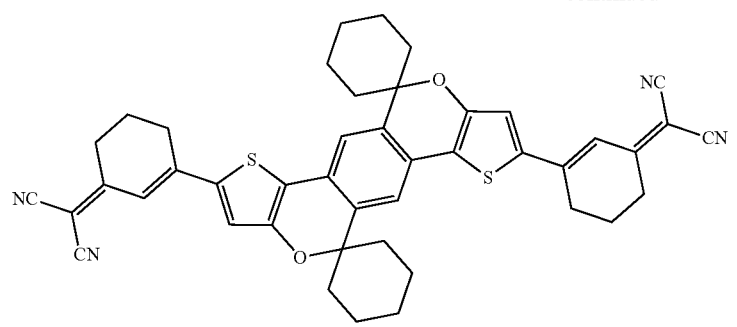
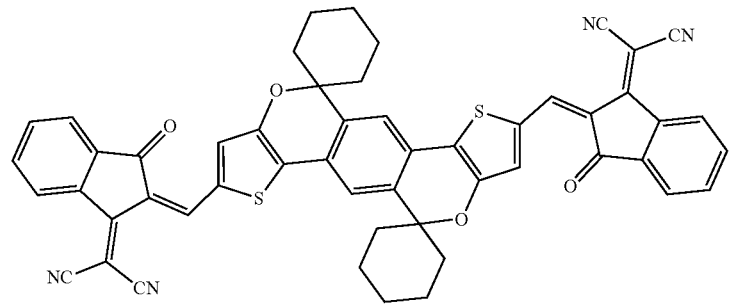
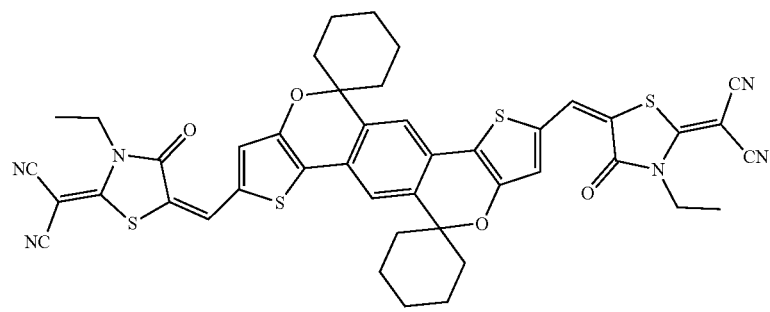
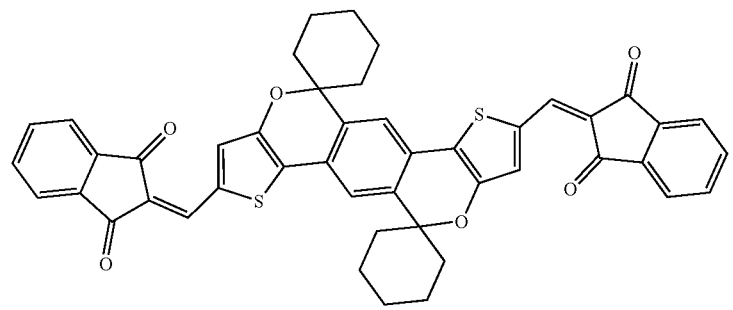
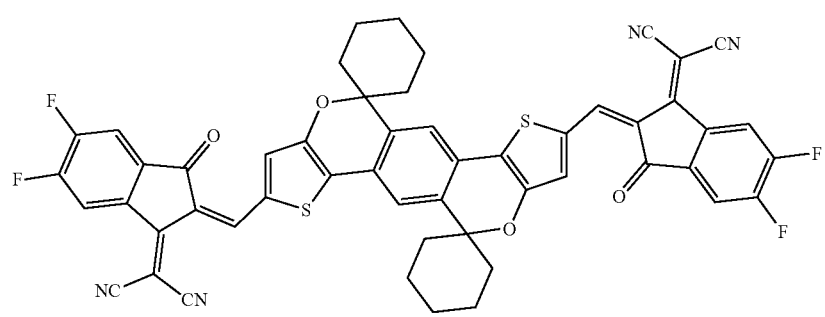

-continued
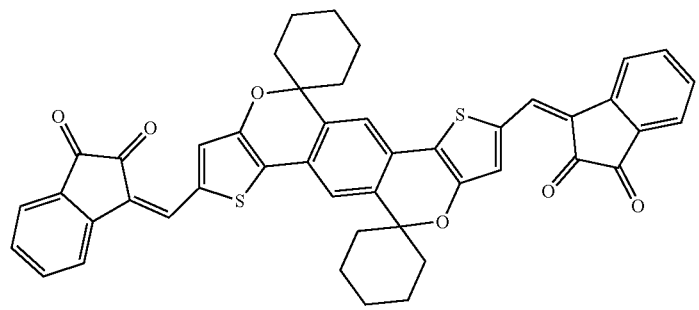
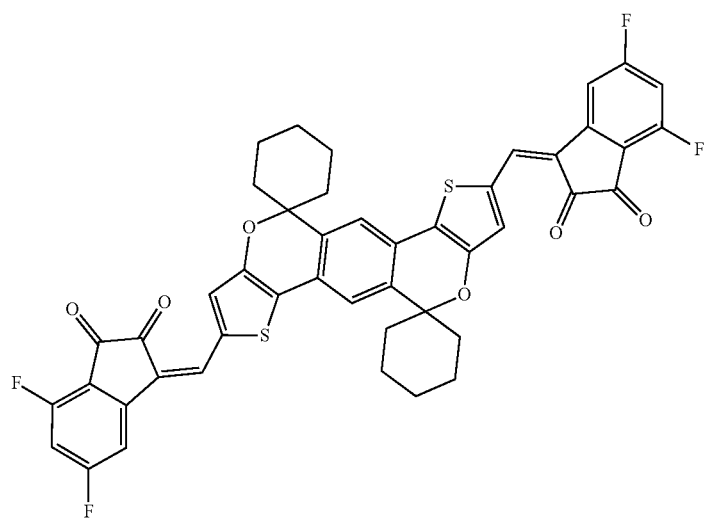
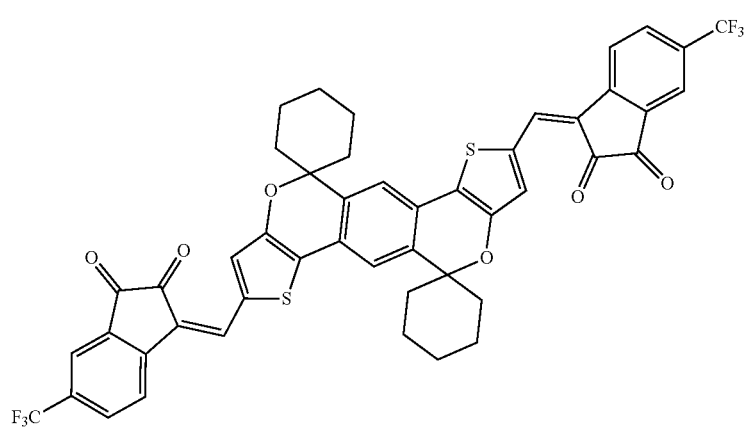
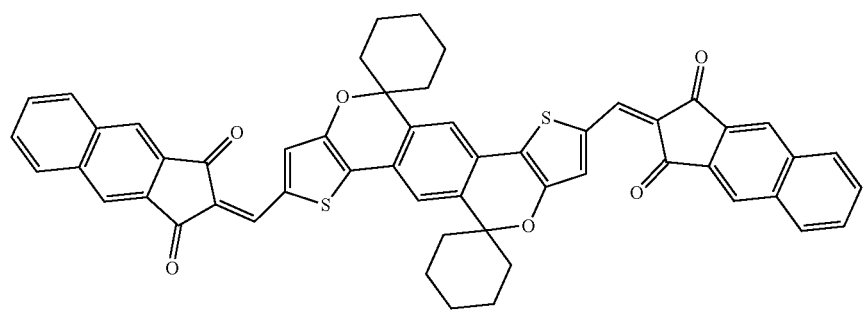

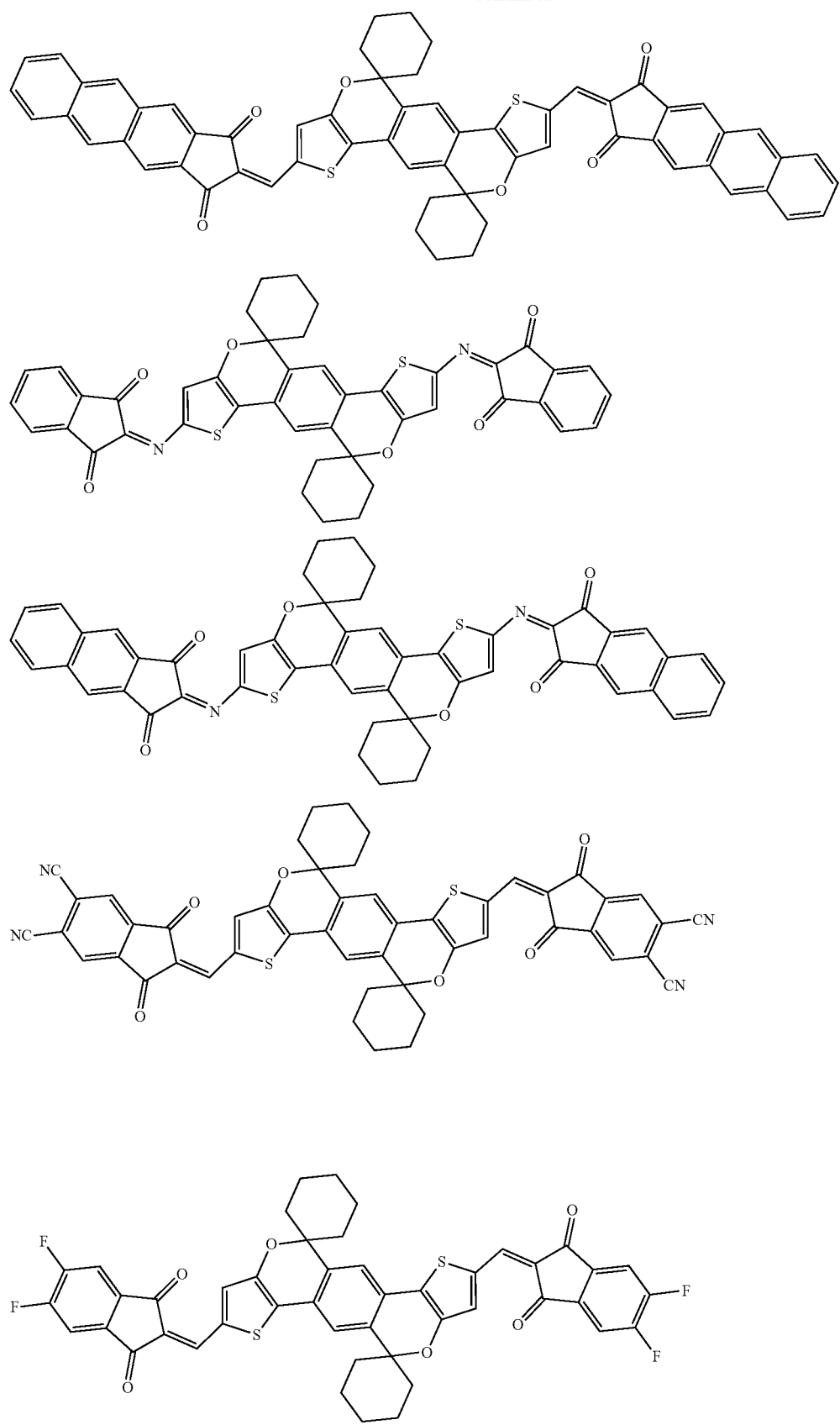

-continued
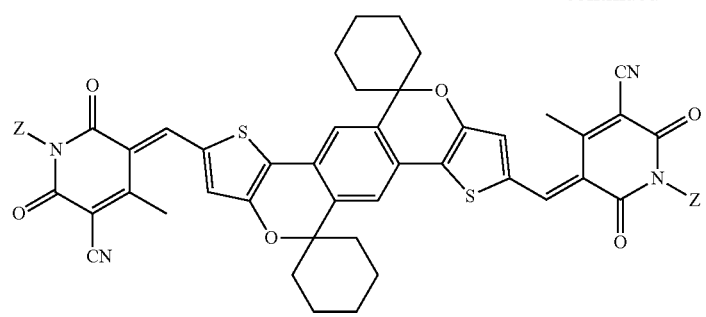
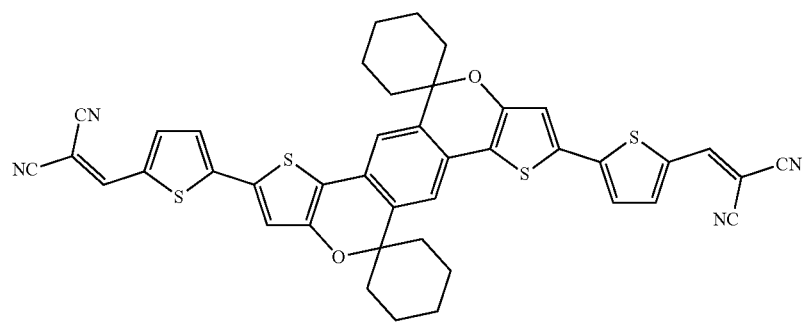
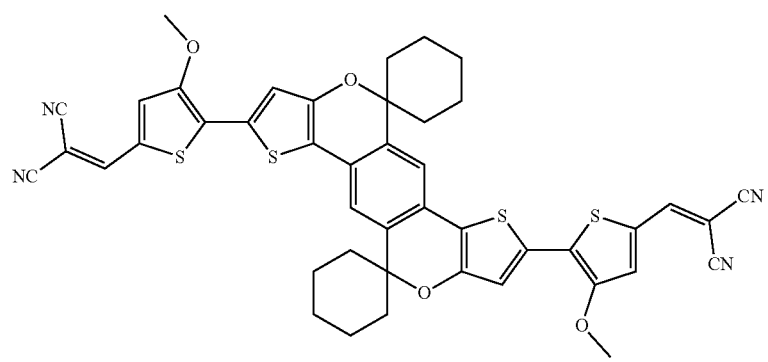
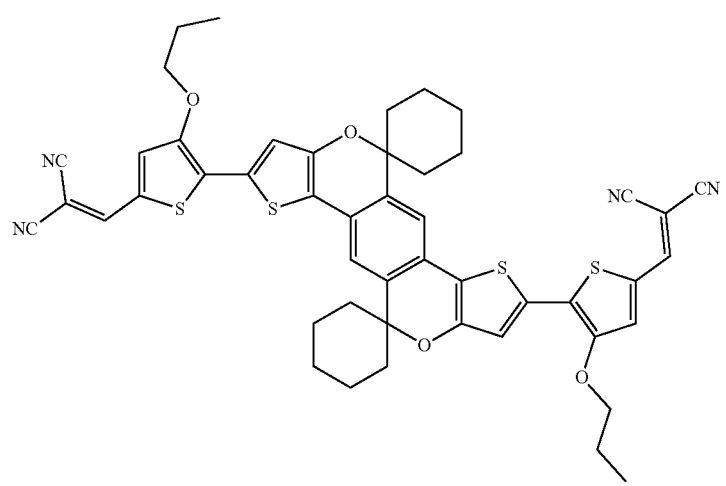

-continued
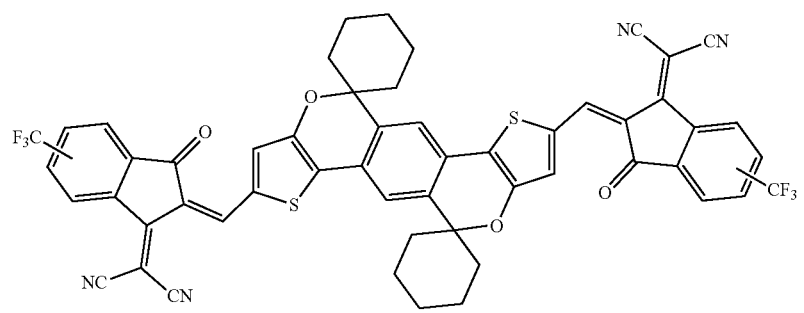
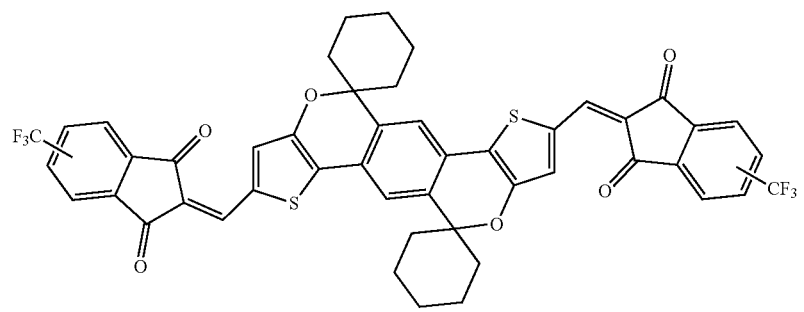
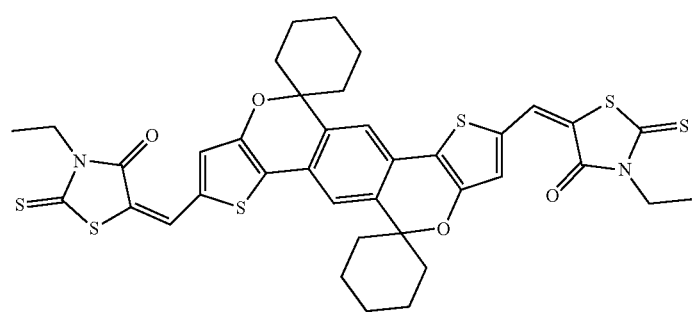
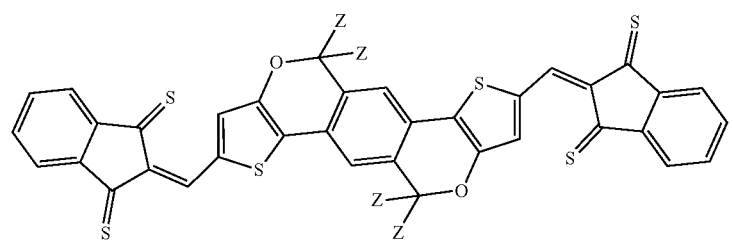
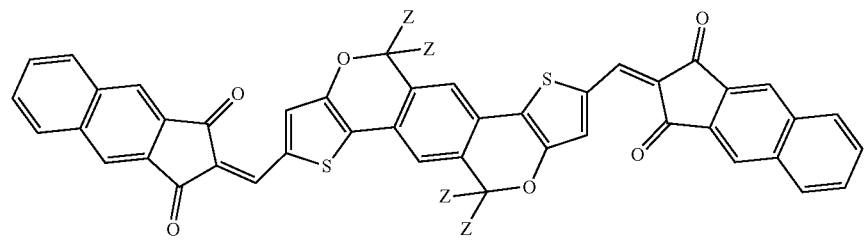
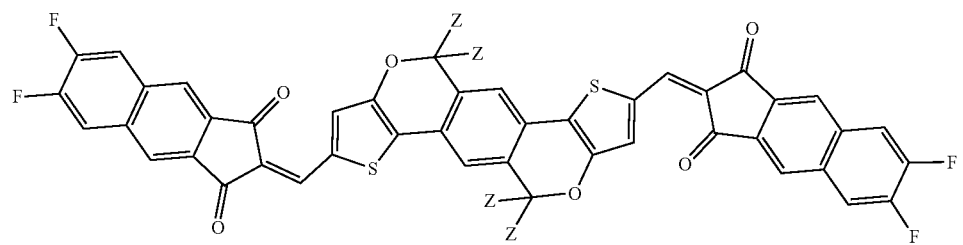

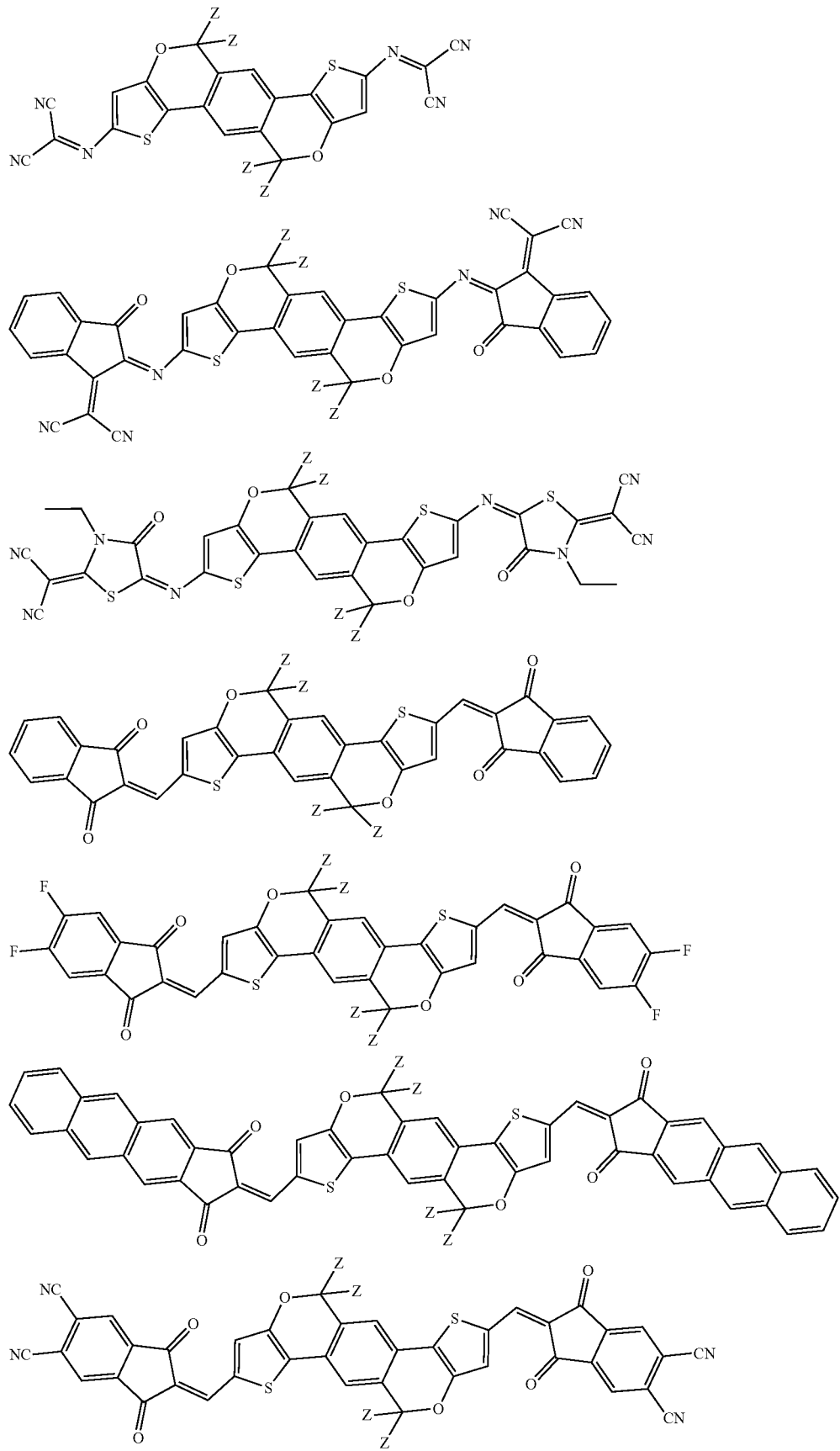

-continued
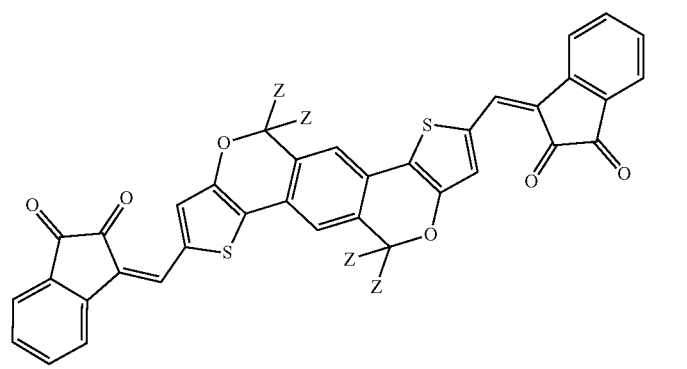
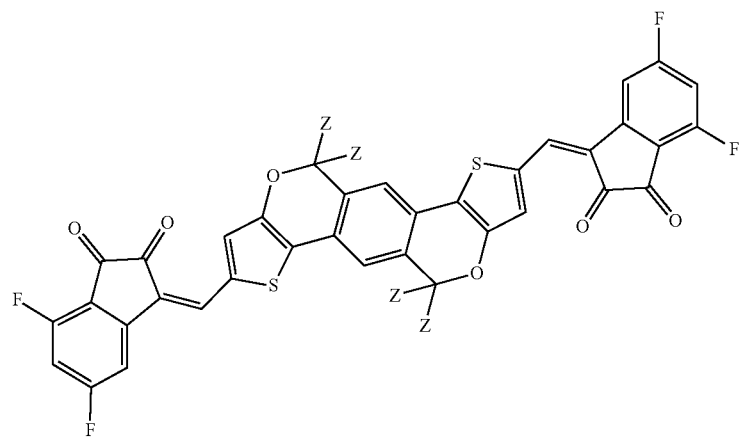
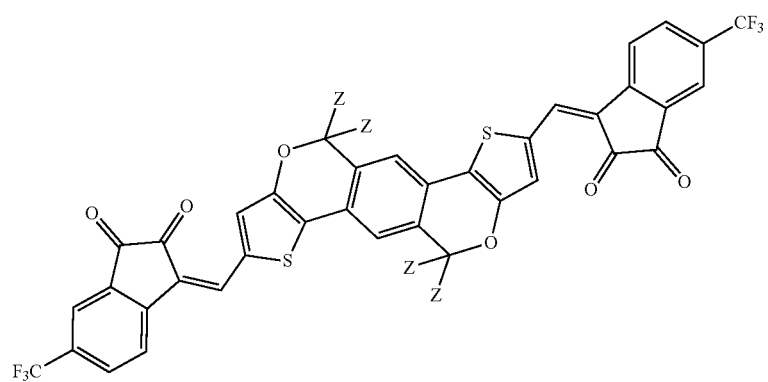
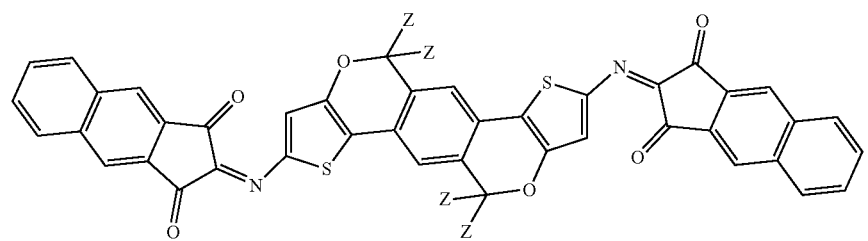
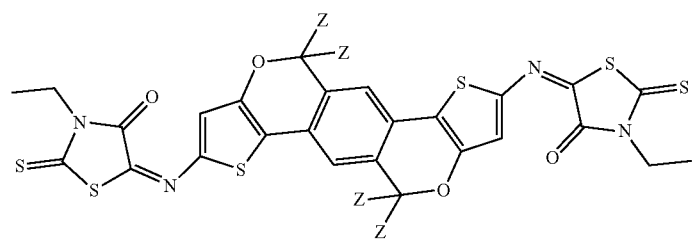

-continued
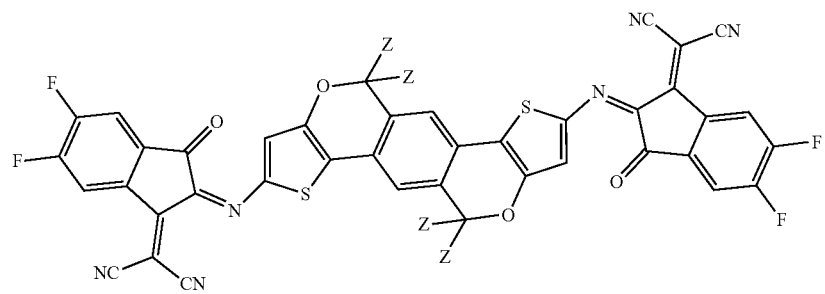
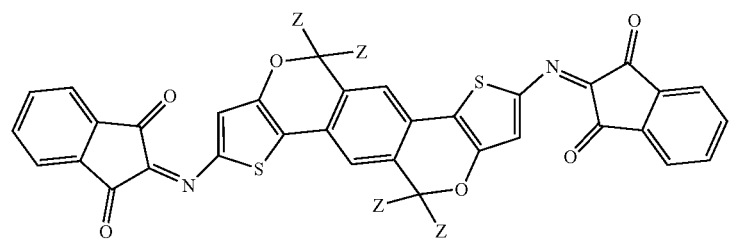
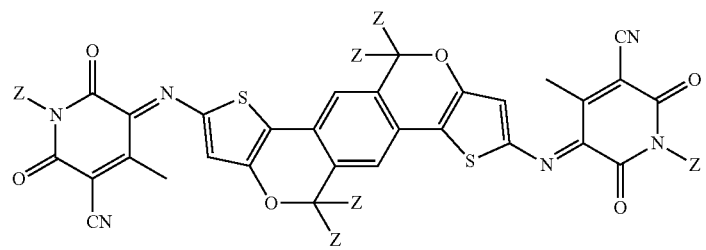
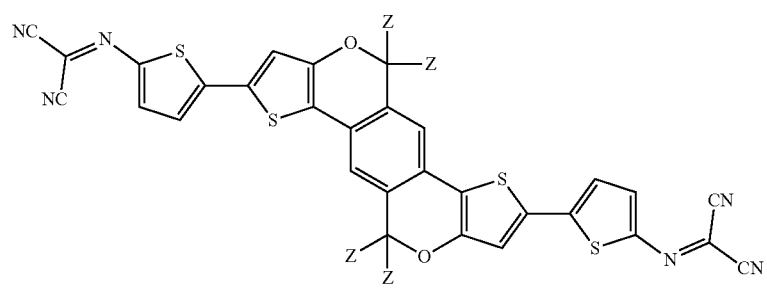
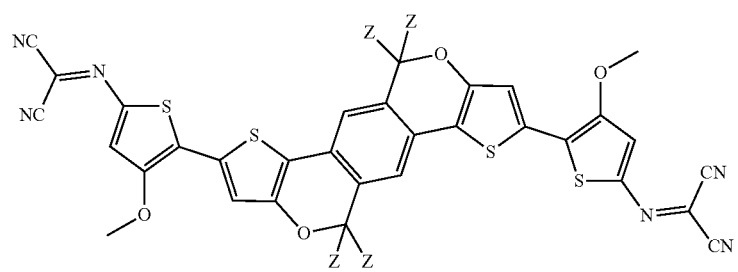
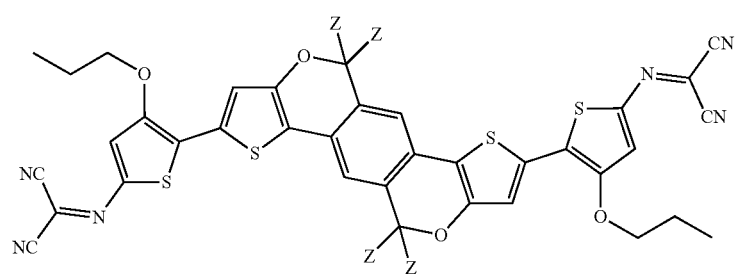

-continued
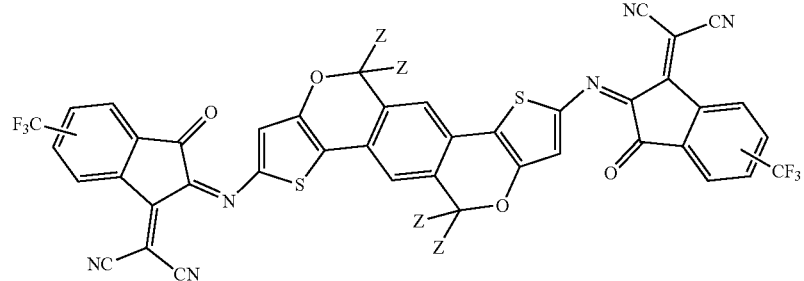
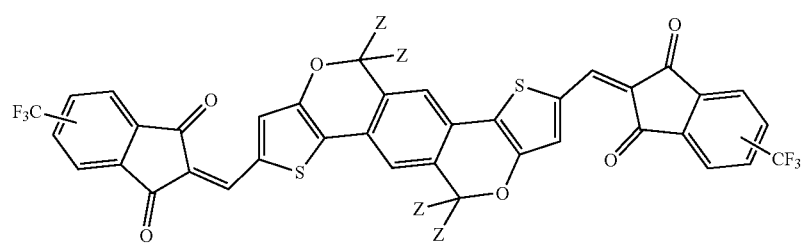
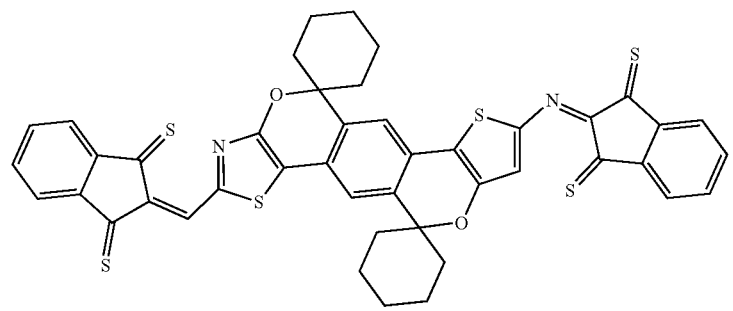
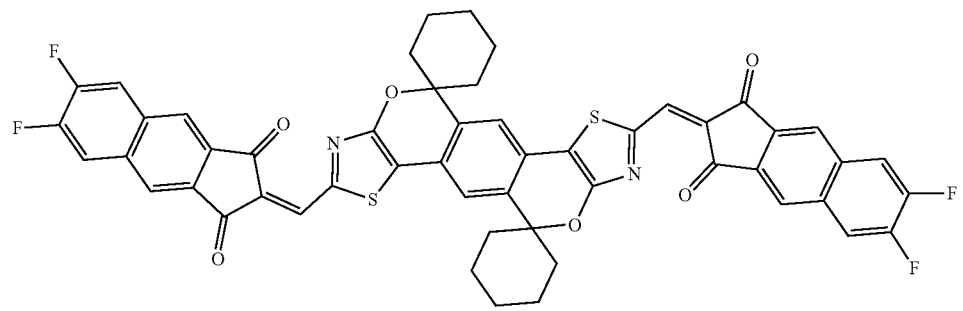
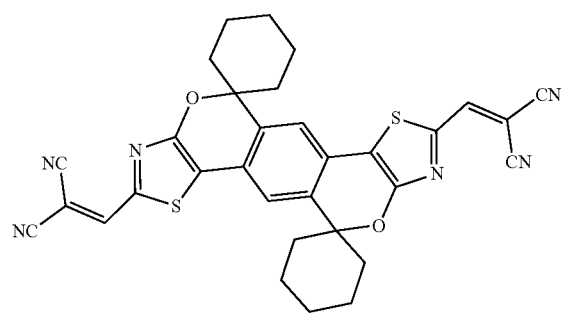
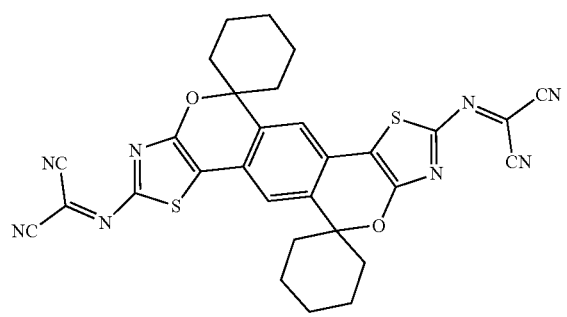

-continued
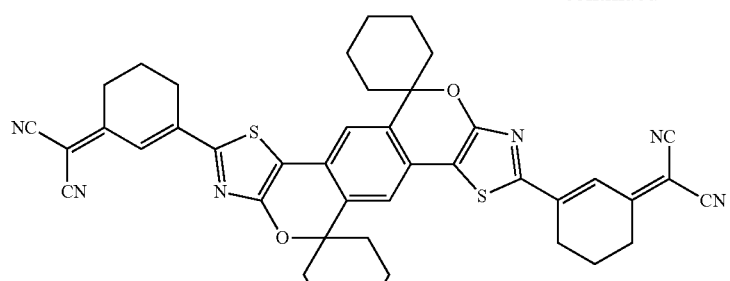
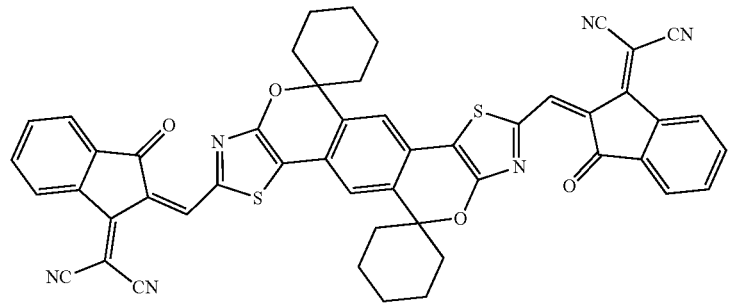
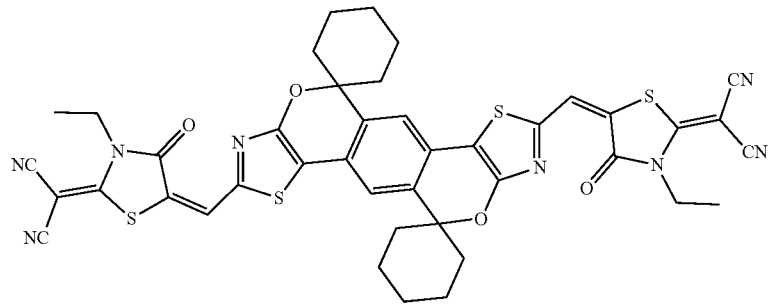
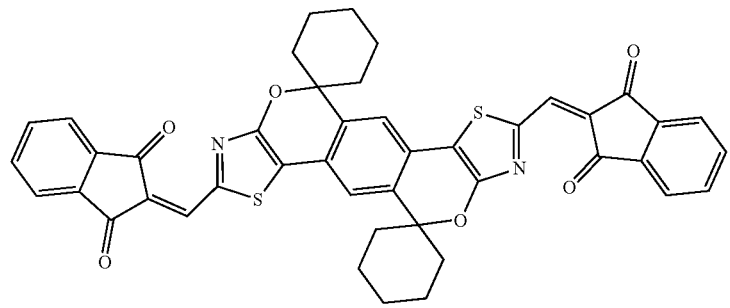
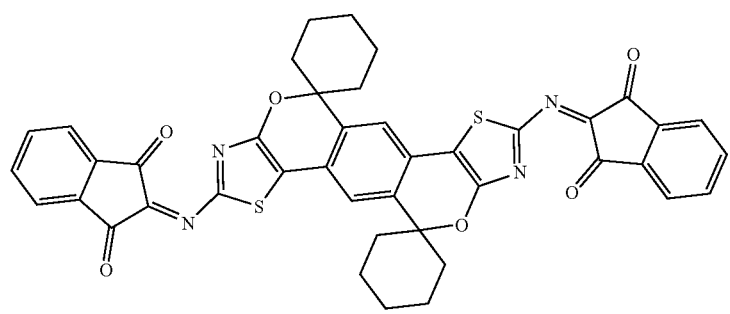

-continued
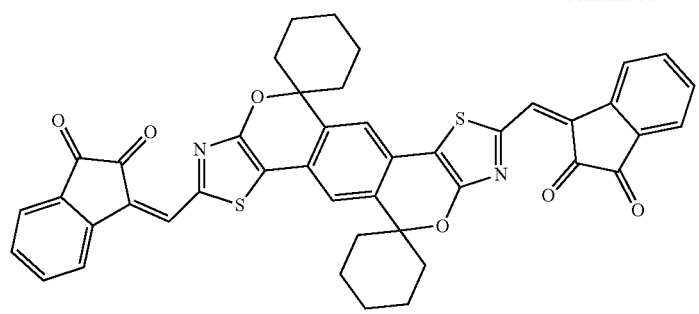
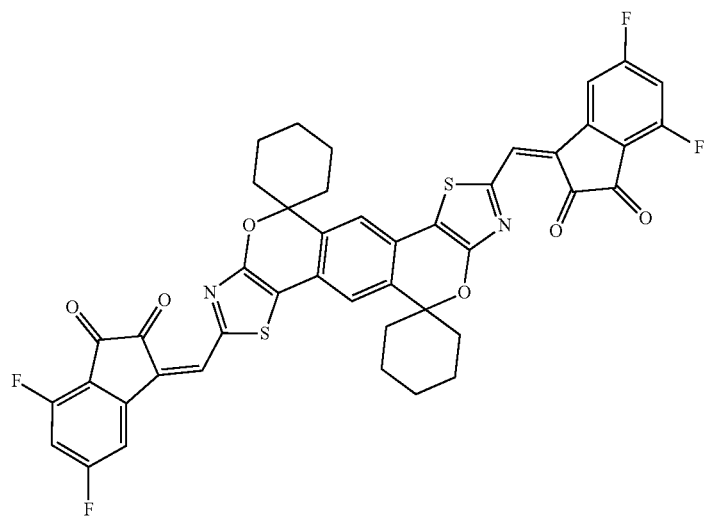
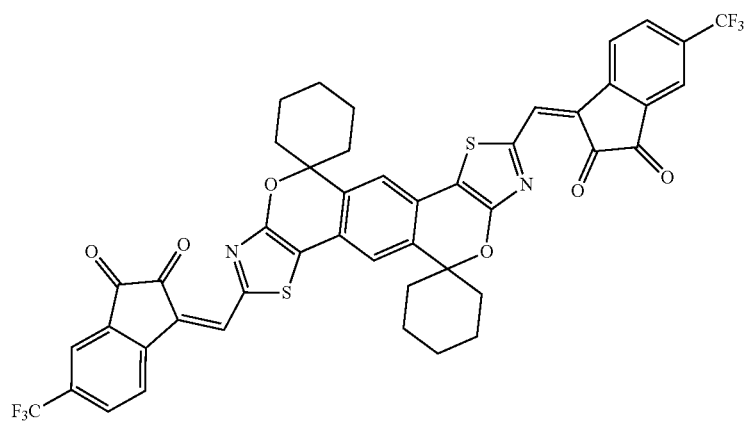
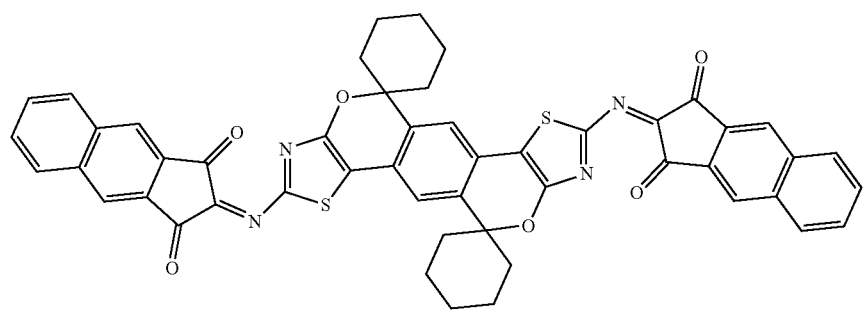

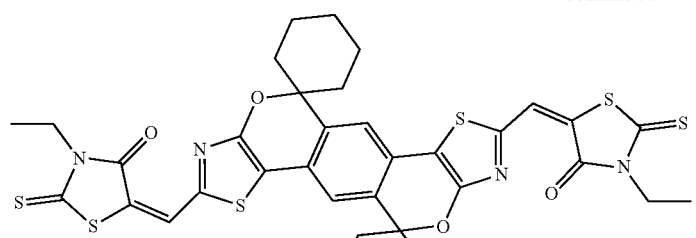
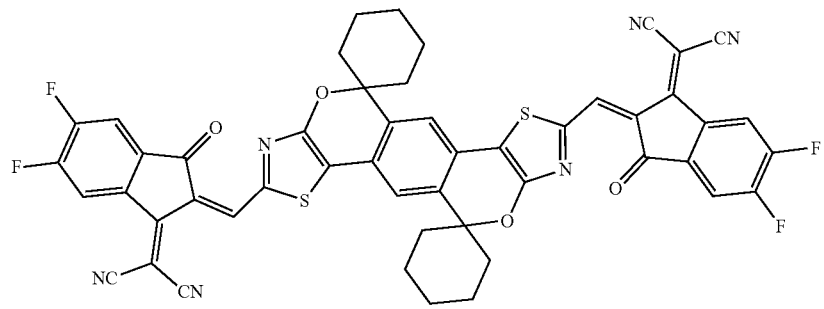
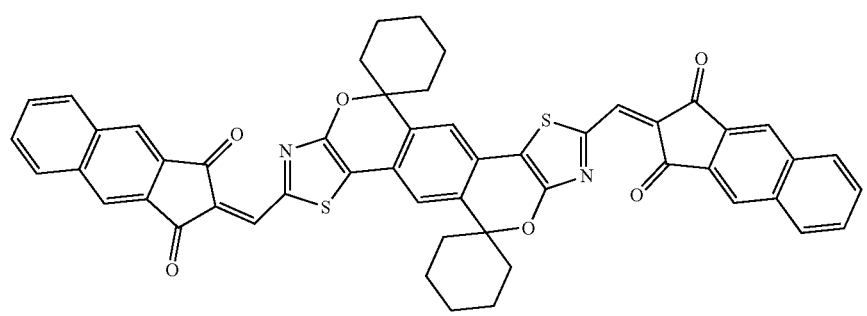
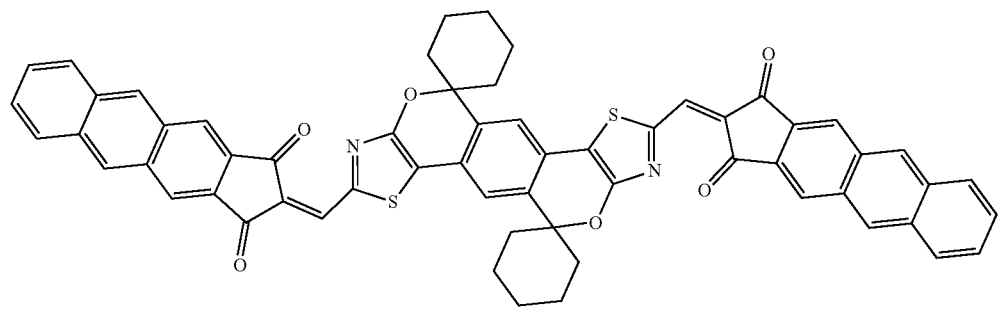
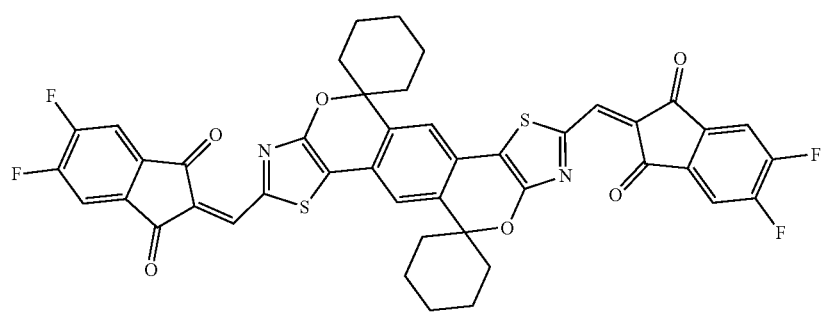

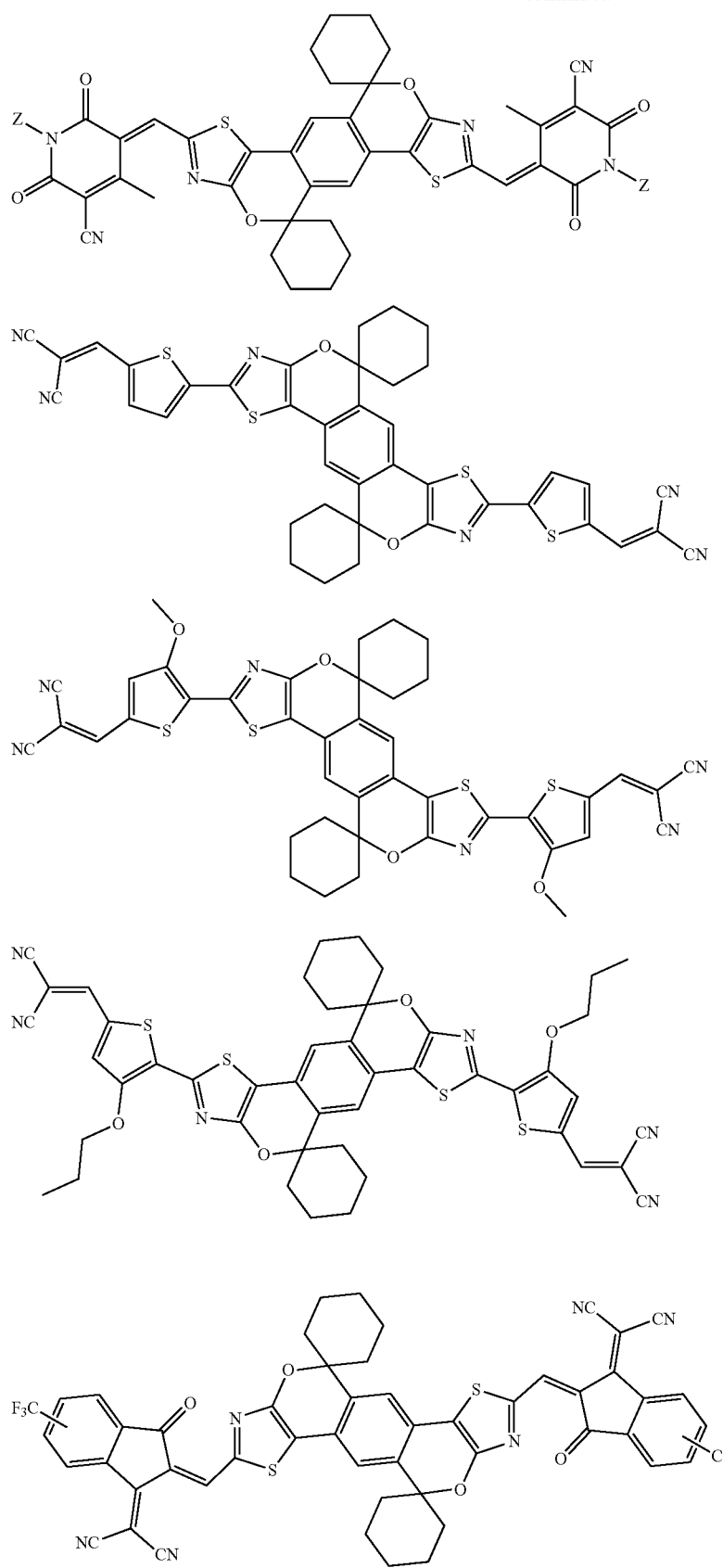

-continued
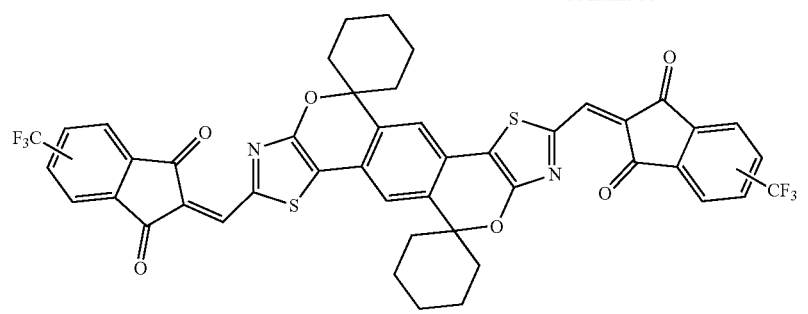
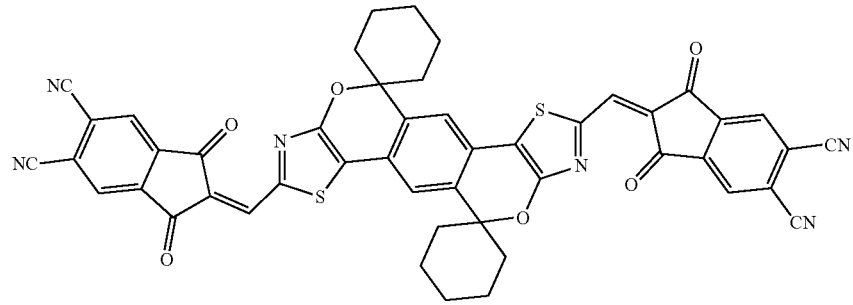
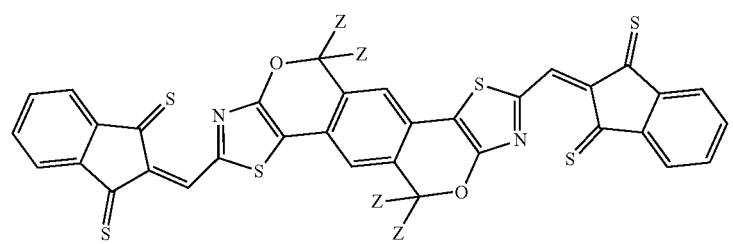
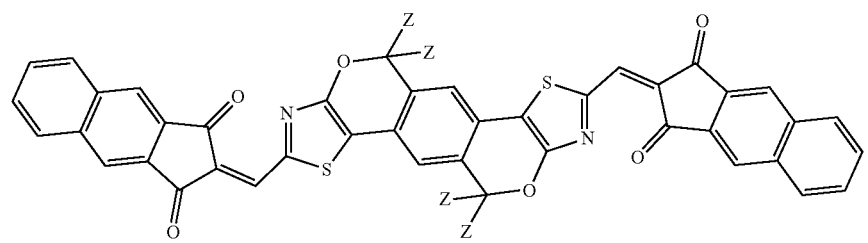
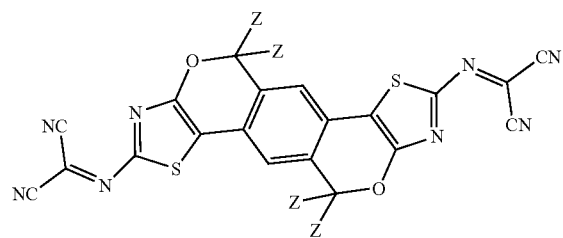
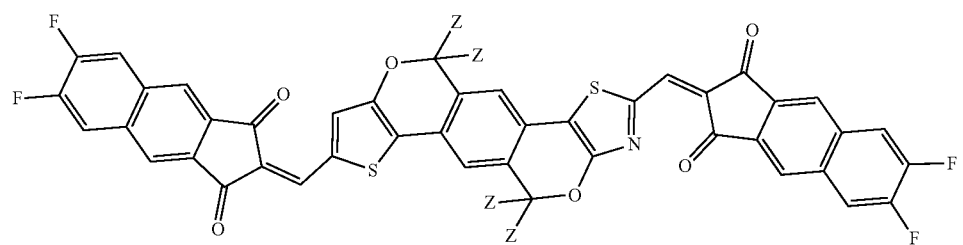

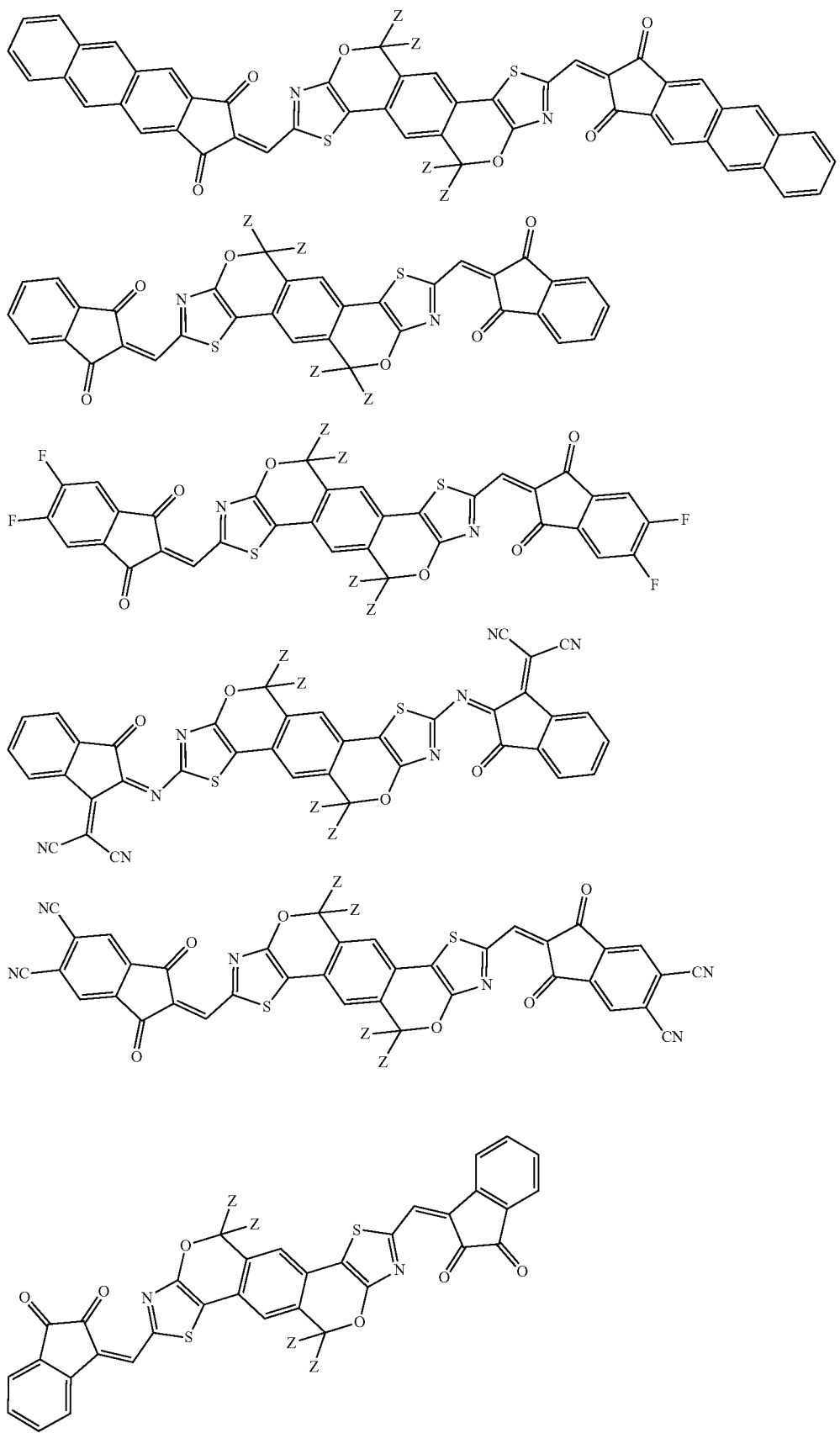

-continued
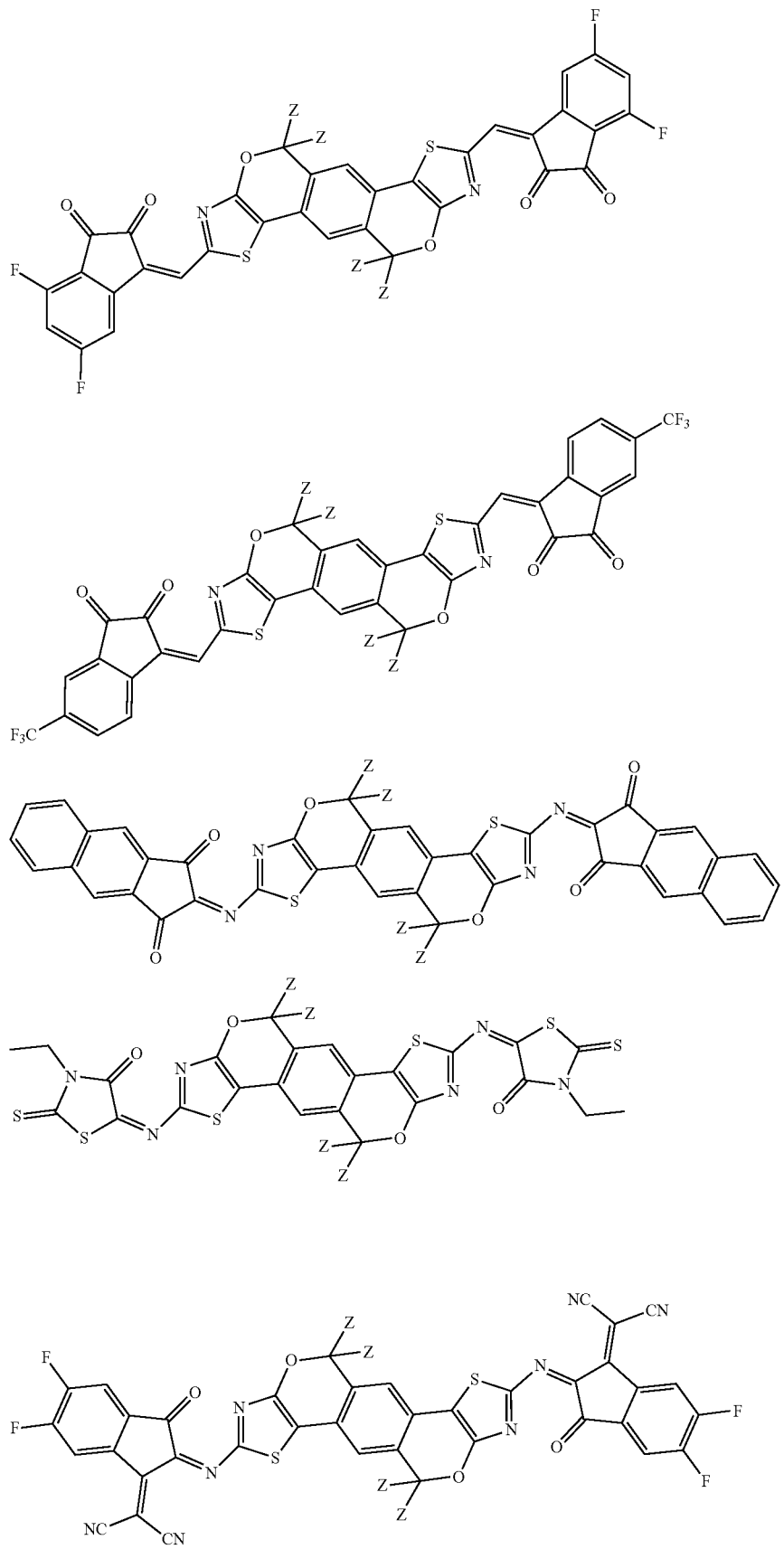

201
-continued
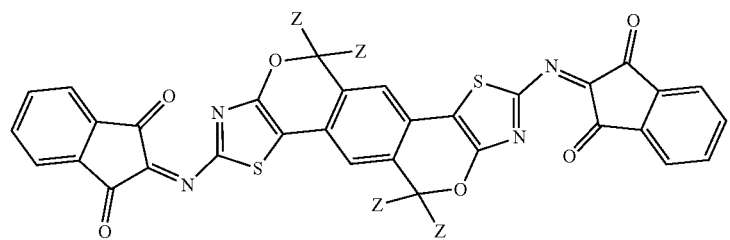
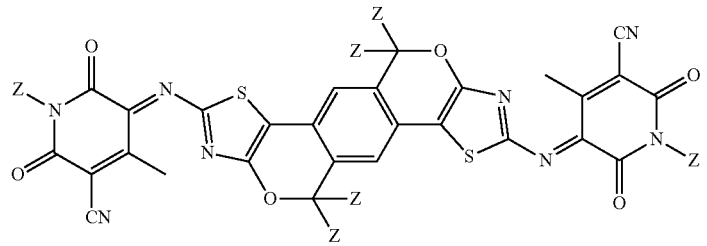
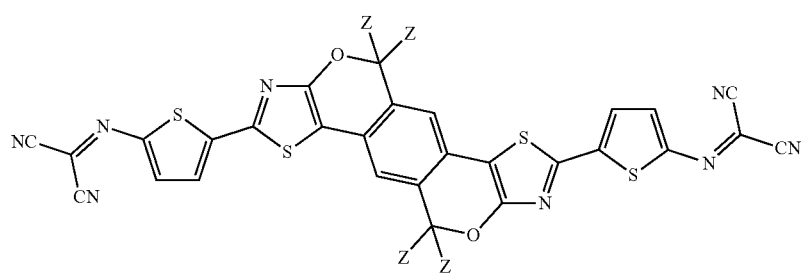
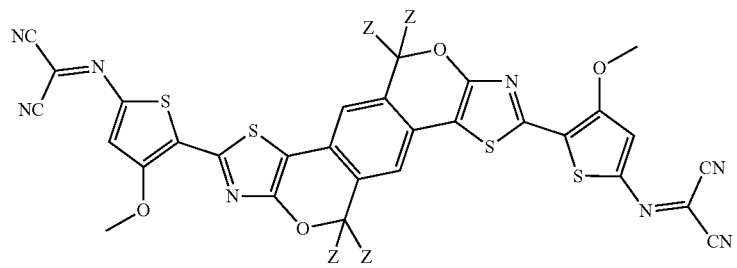
202
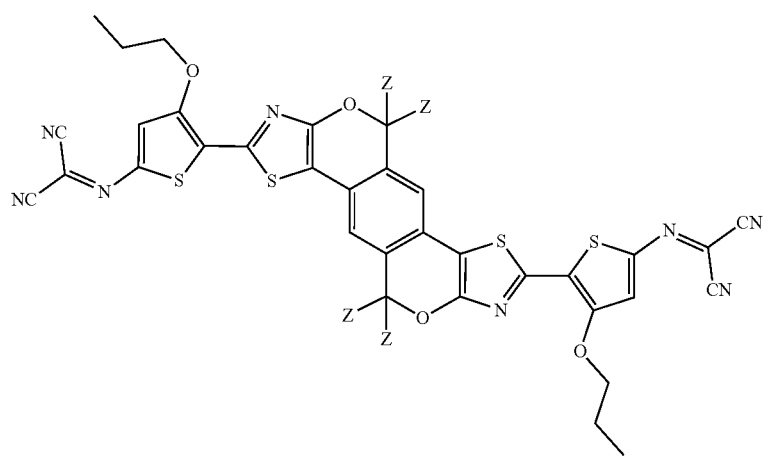

-continued
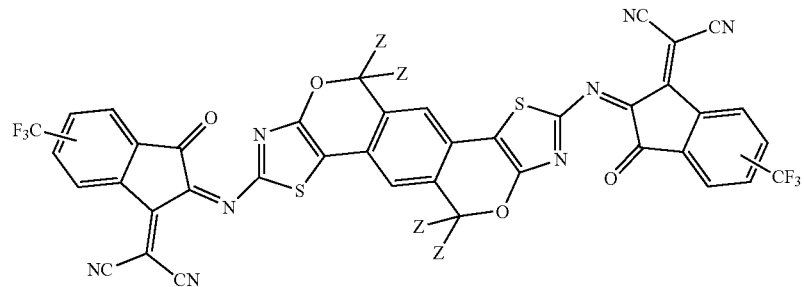
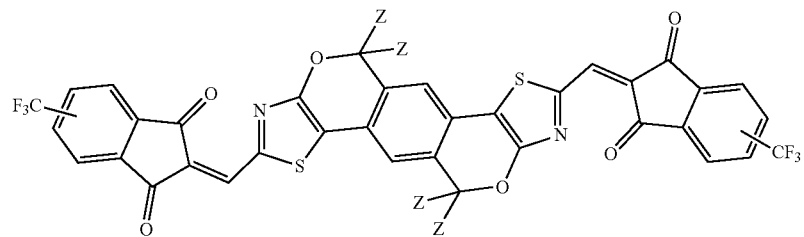
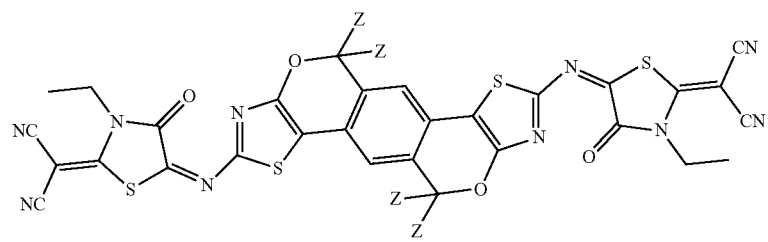
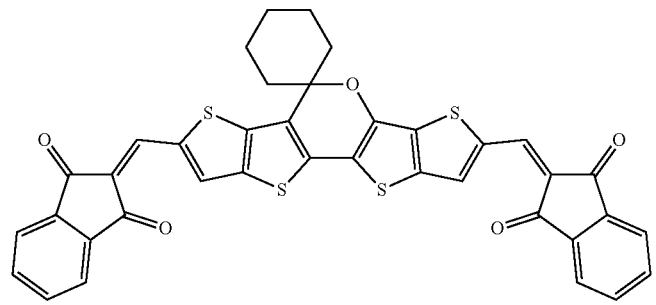
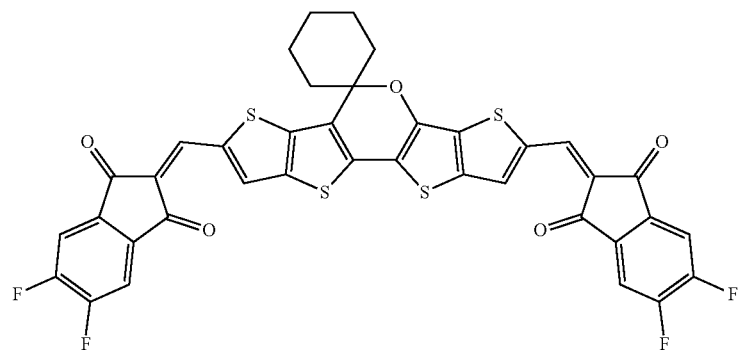
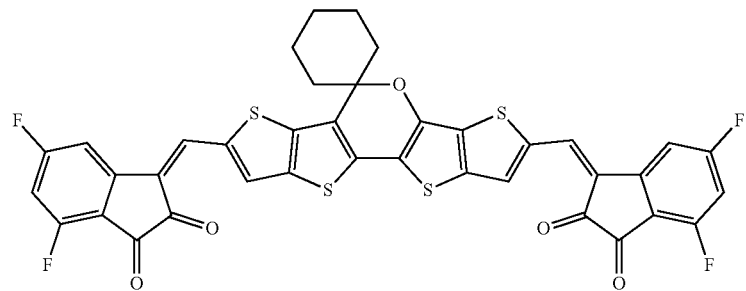

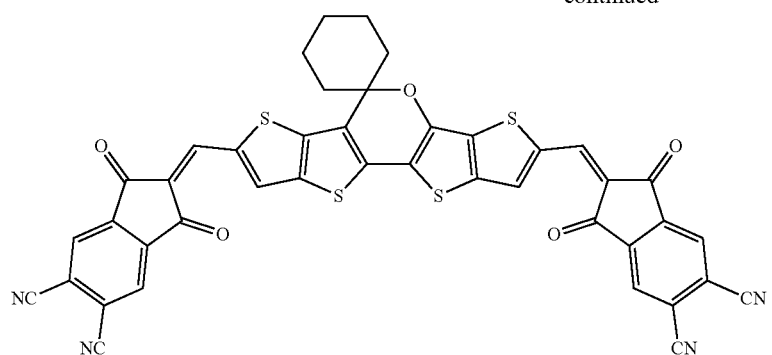
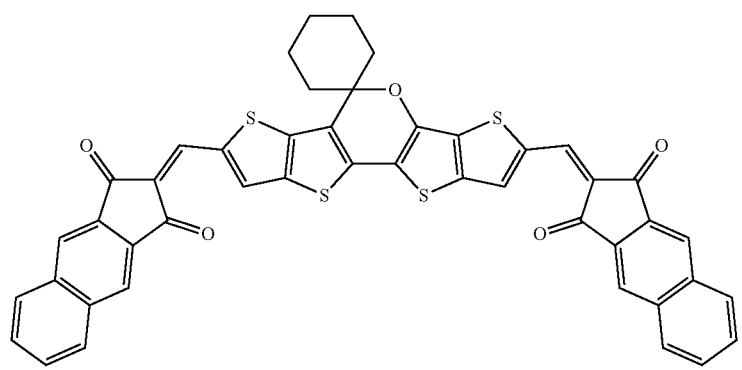
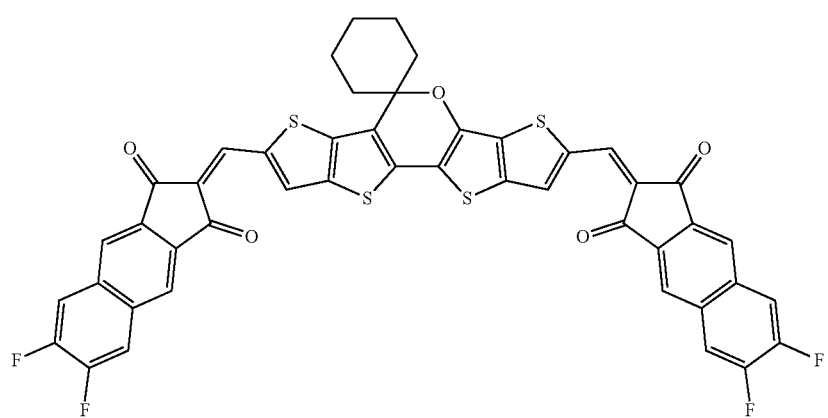
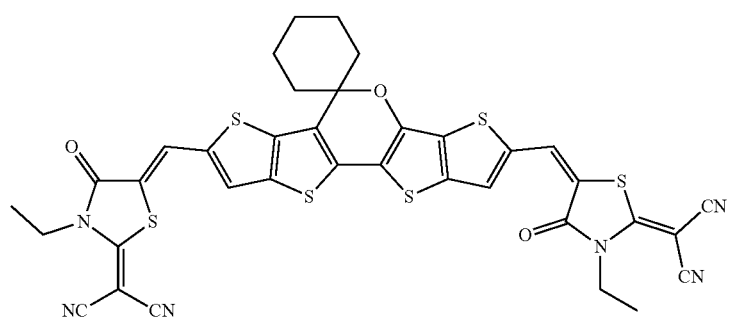

-continued
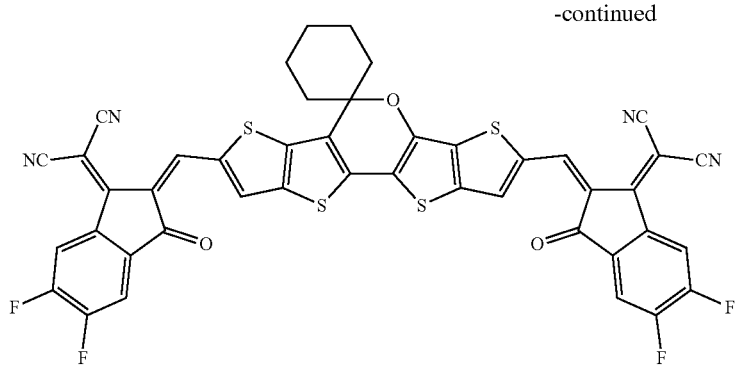
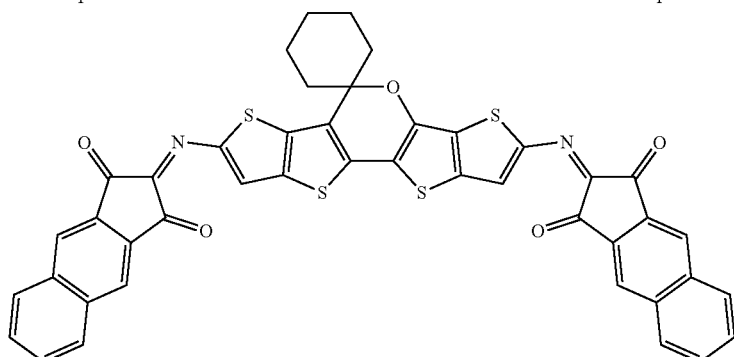
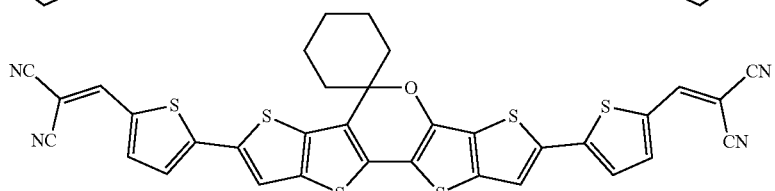
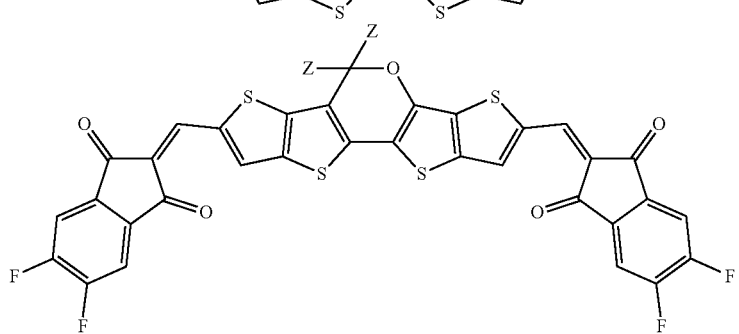
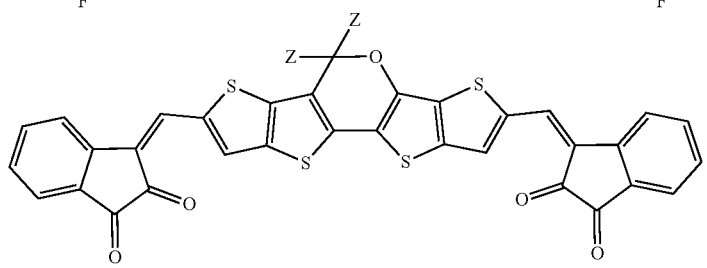
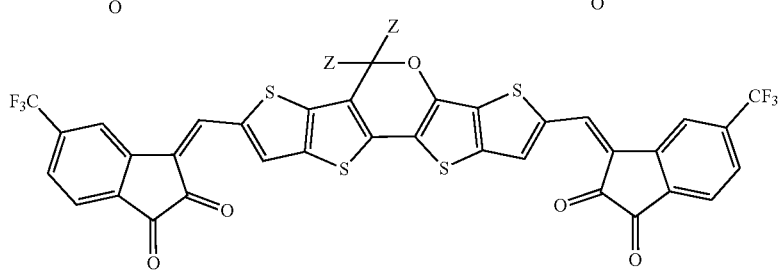

-continued
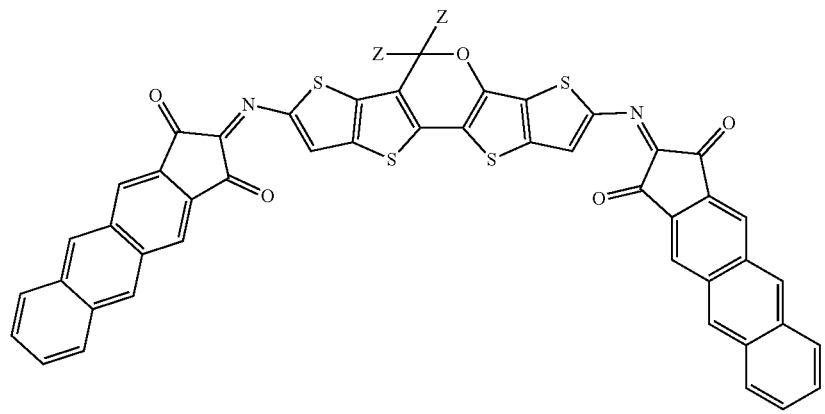
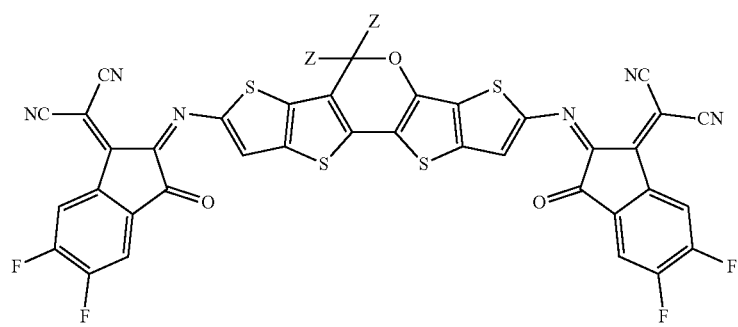
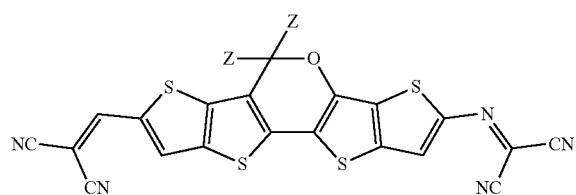
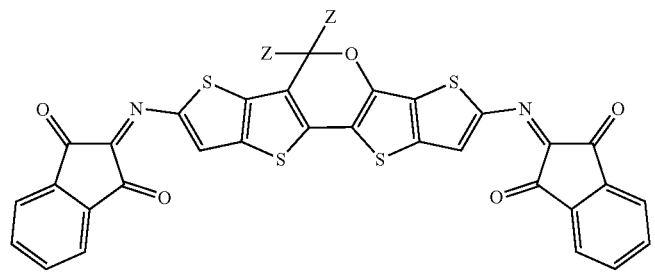
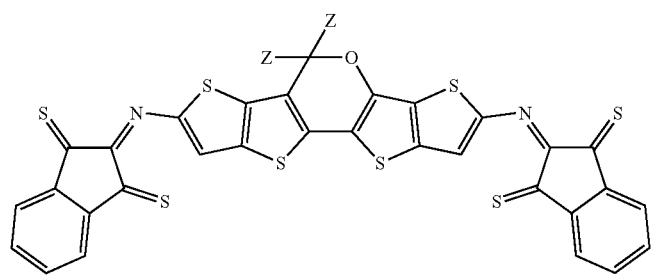
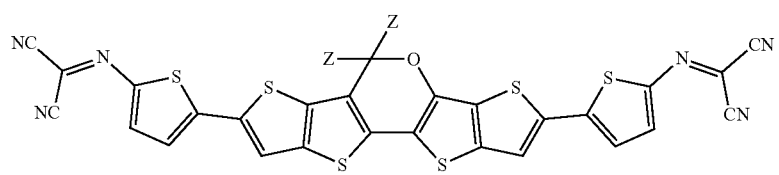

-continued
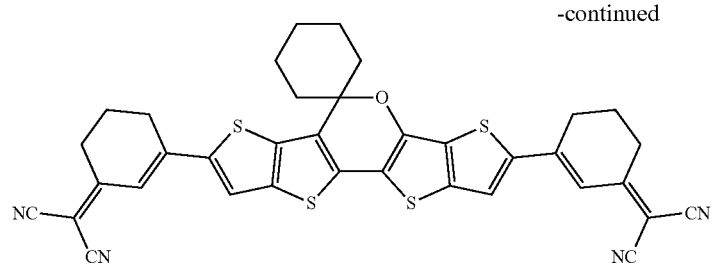
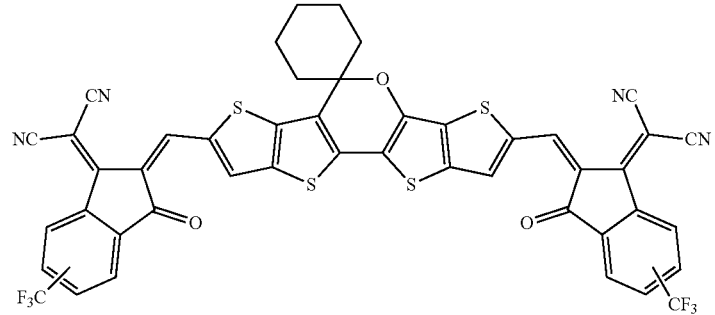
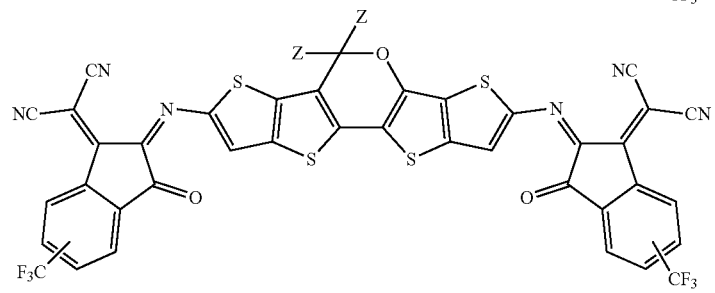
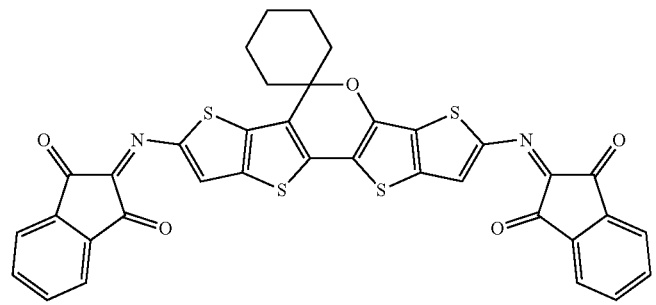
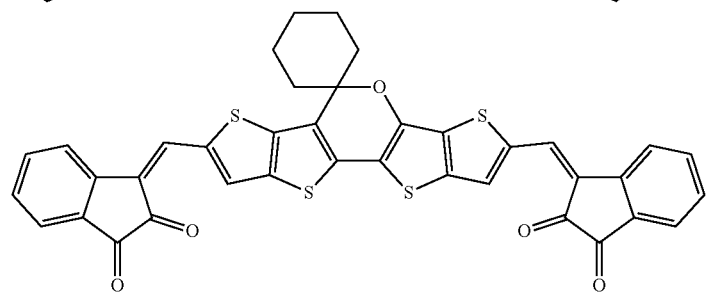
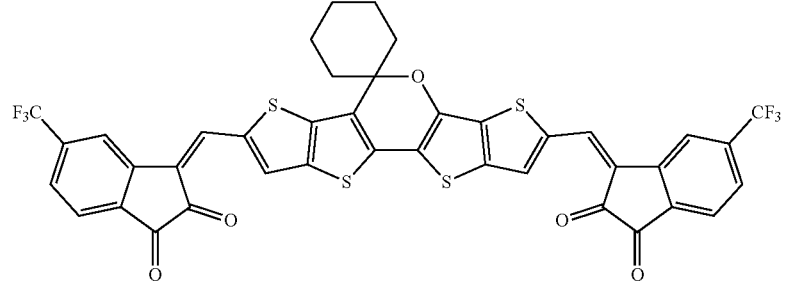

-continued
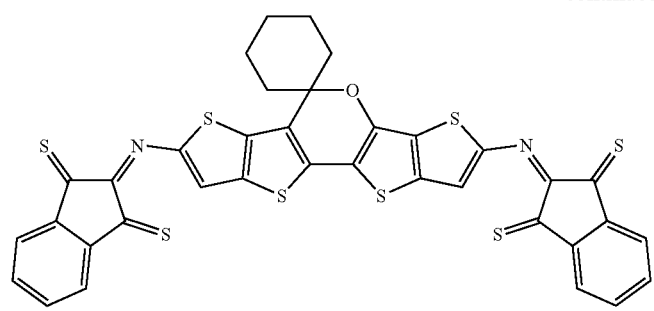
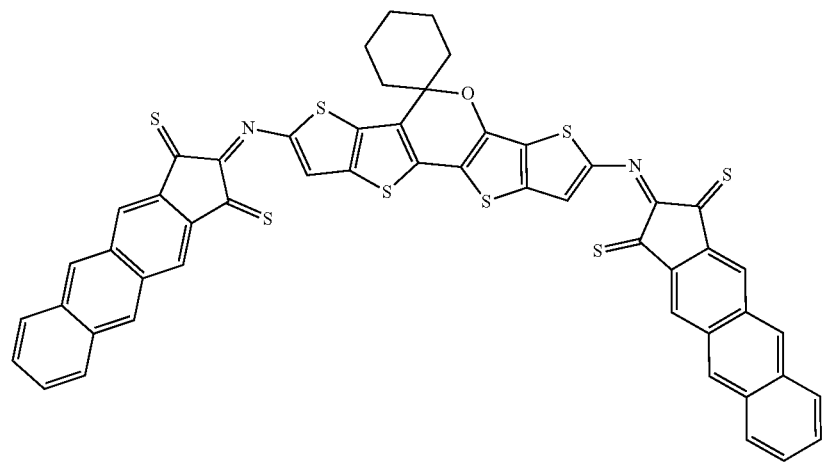
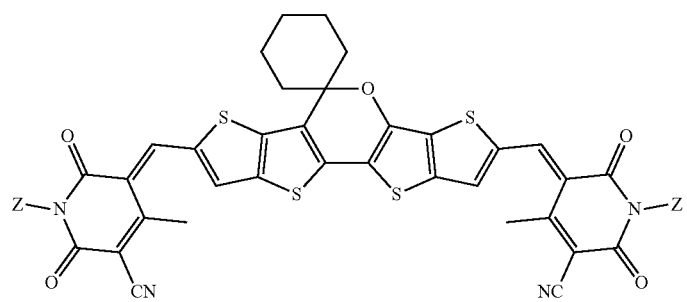
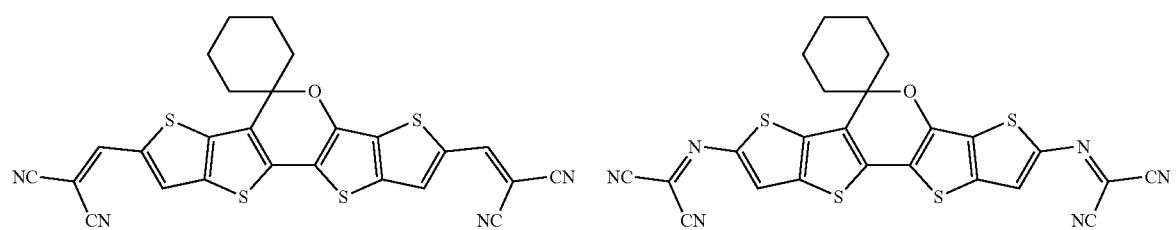
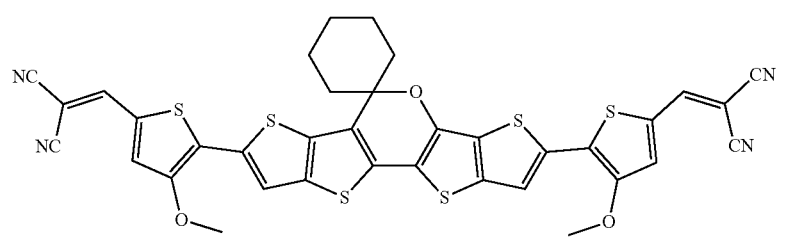

-continued
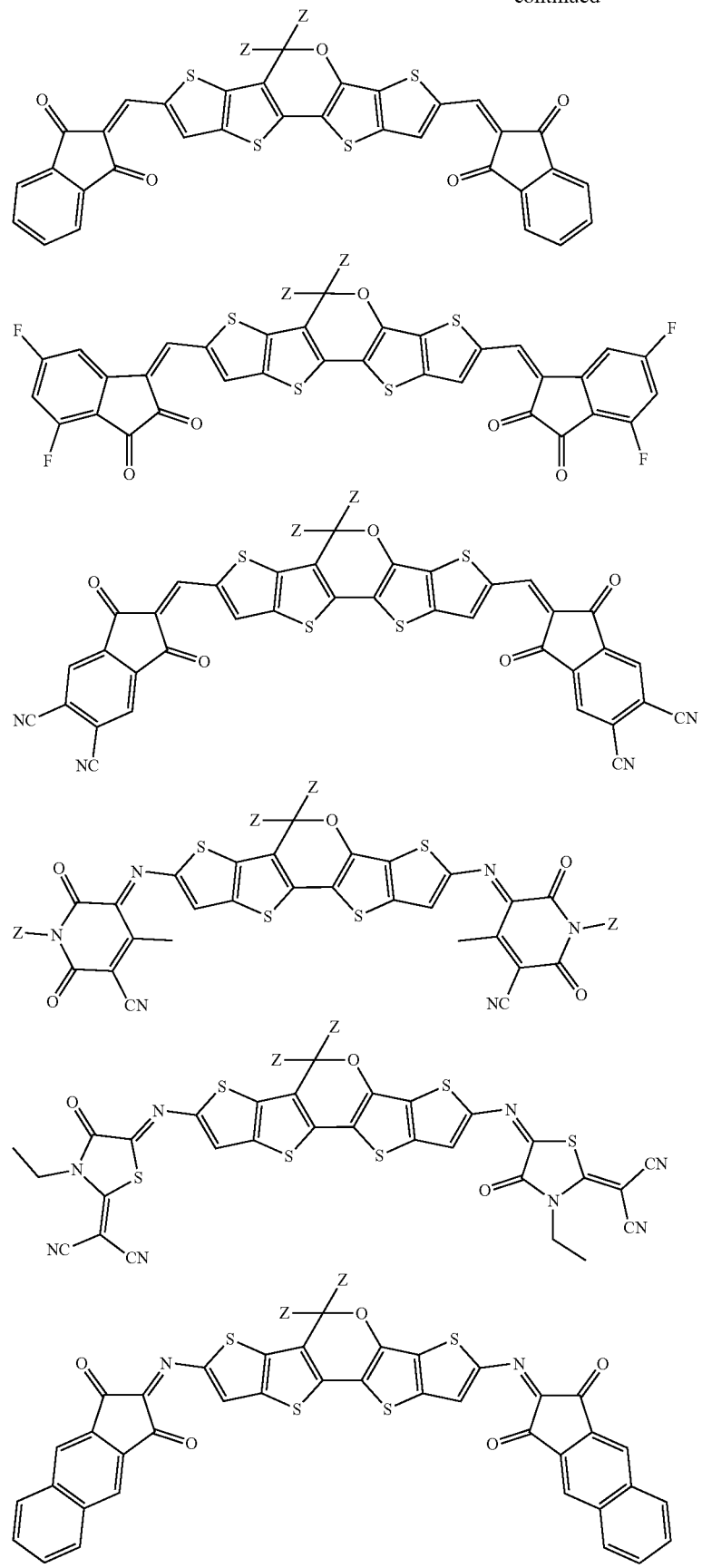

-continued
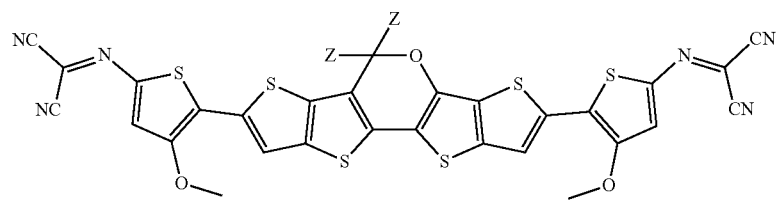
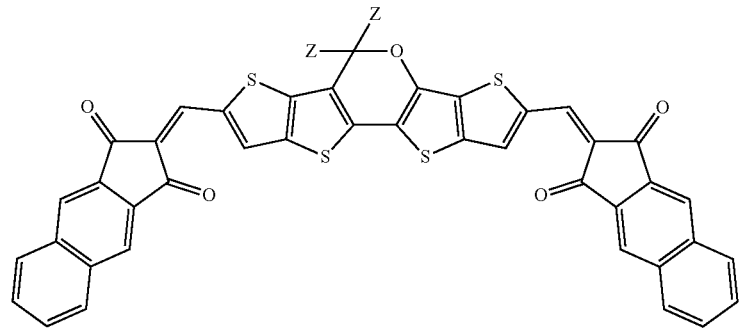
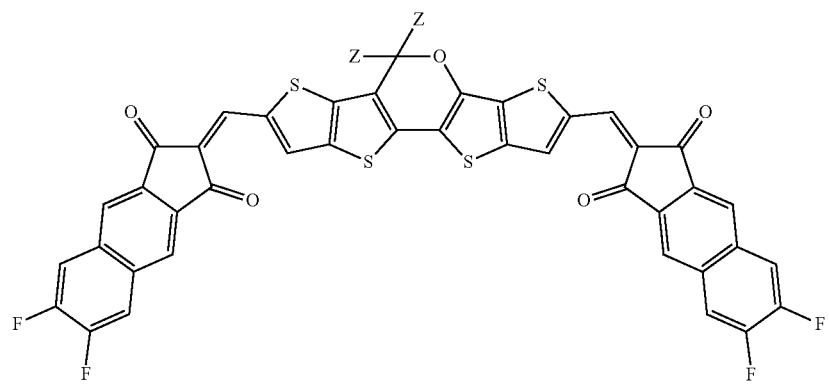
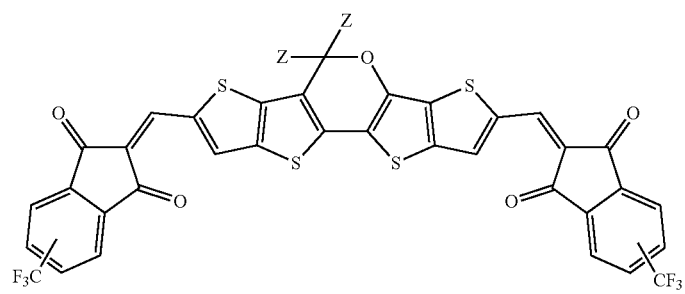
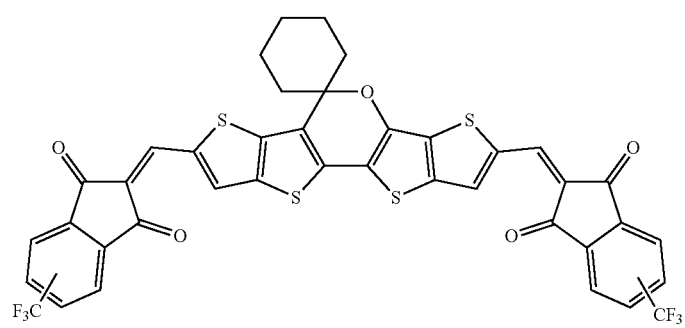

-continued
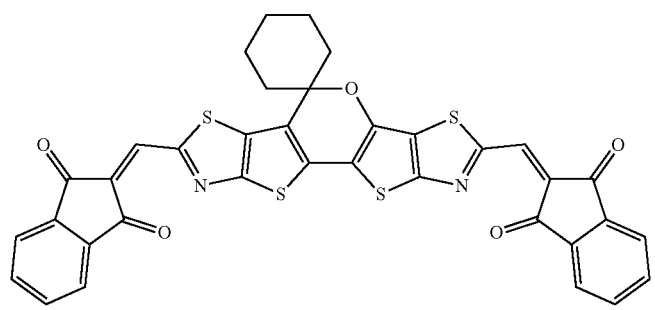
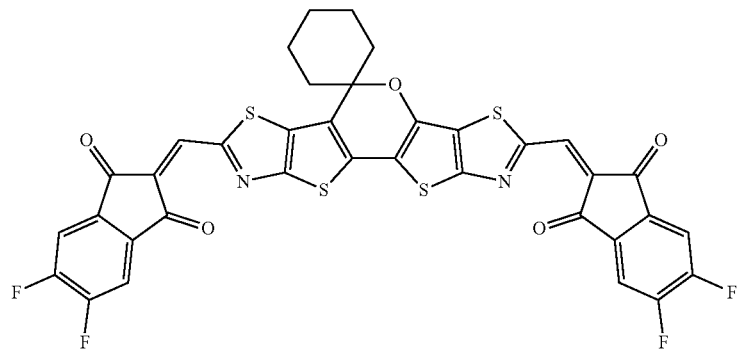
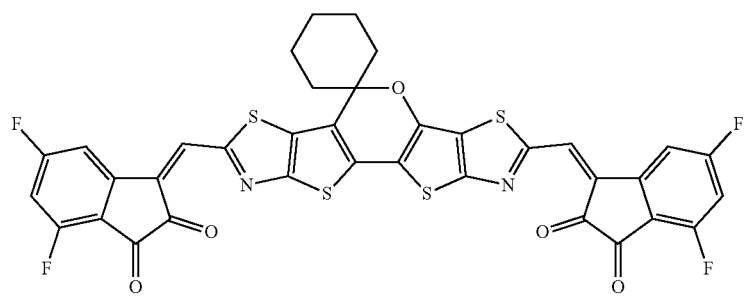
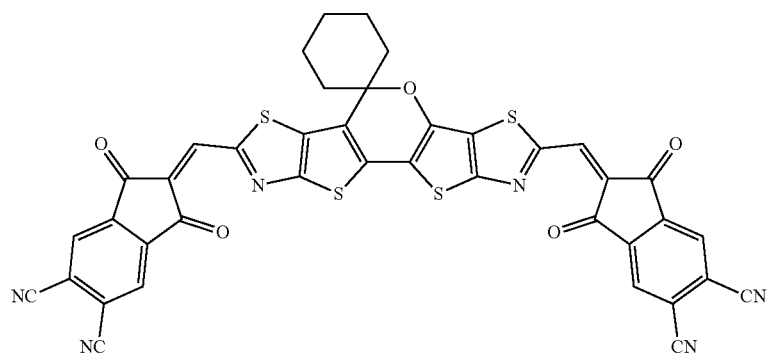
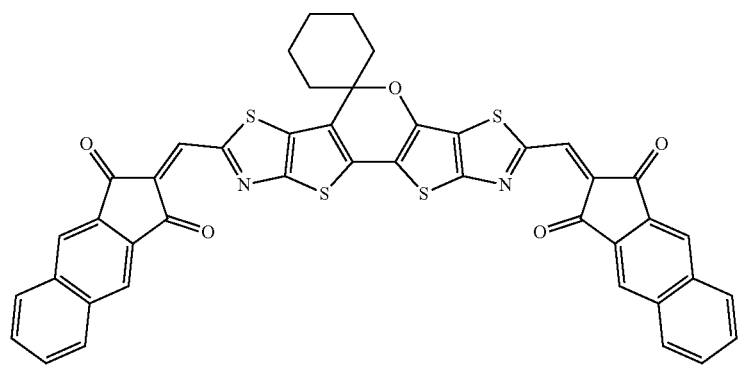

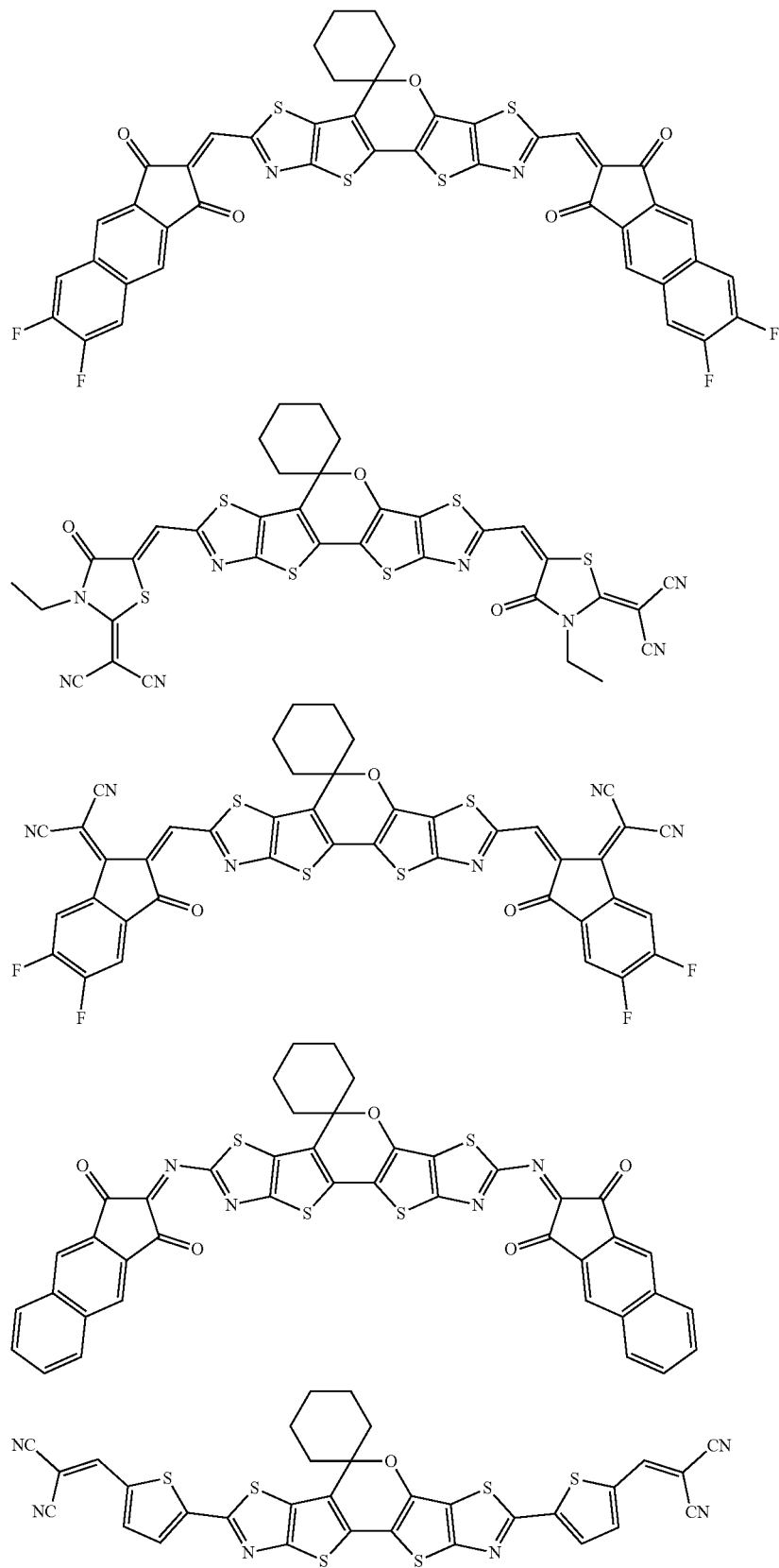

-continued
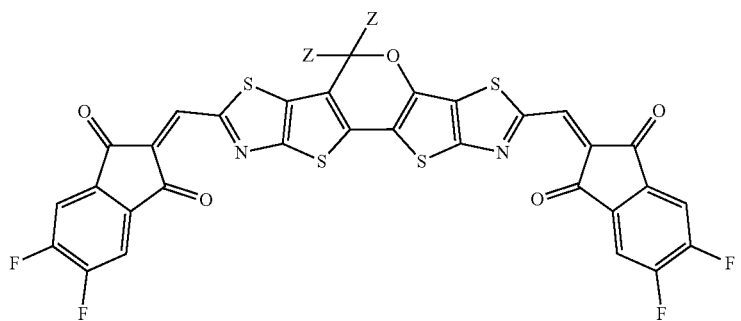
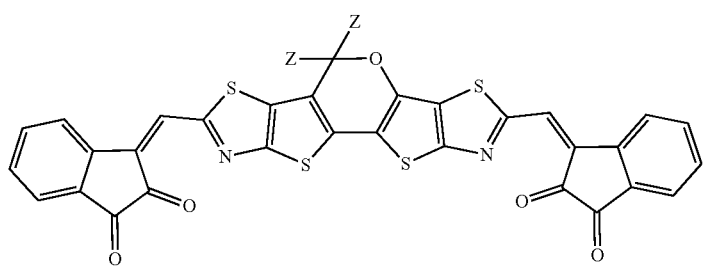
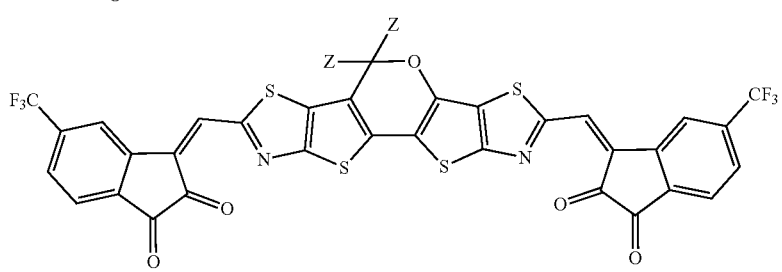
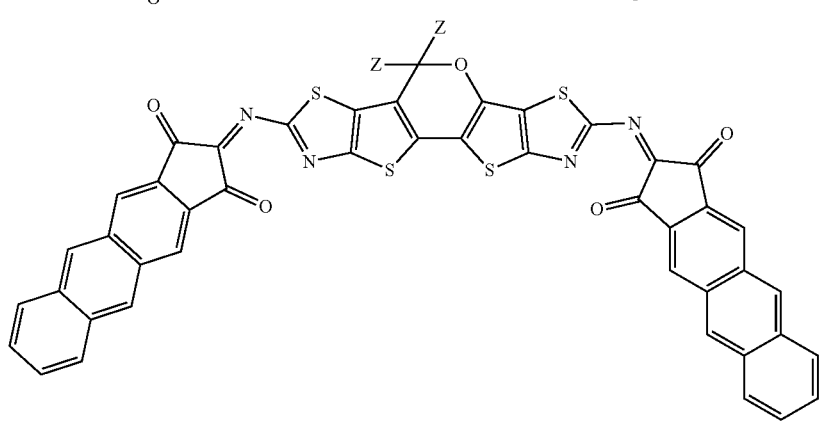
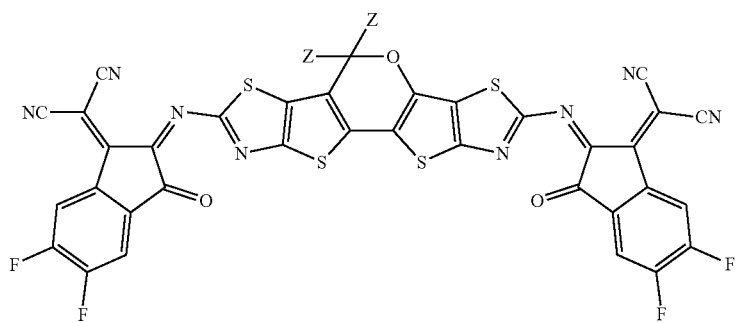

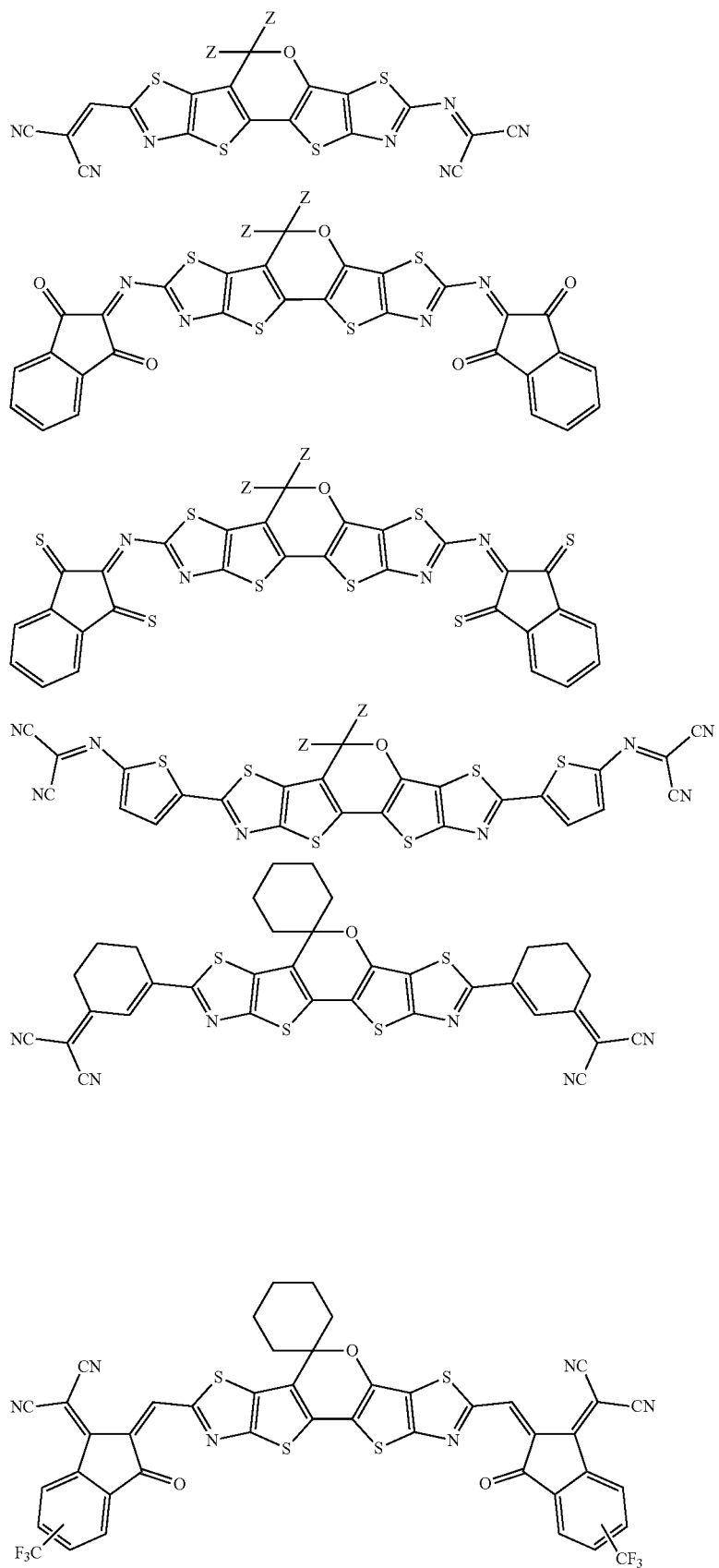

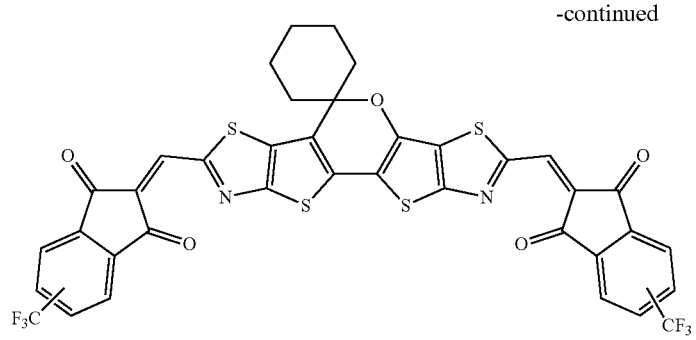
-continued
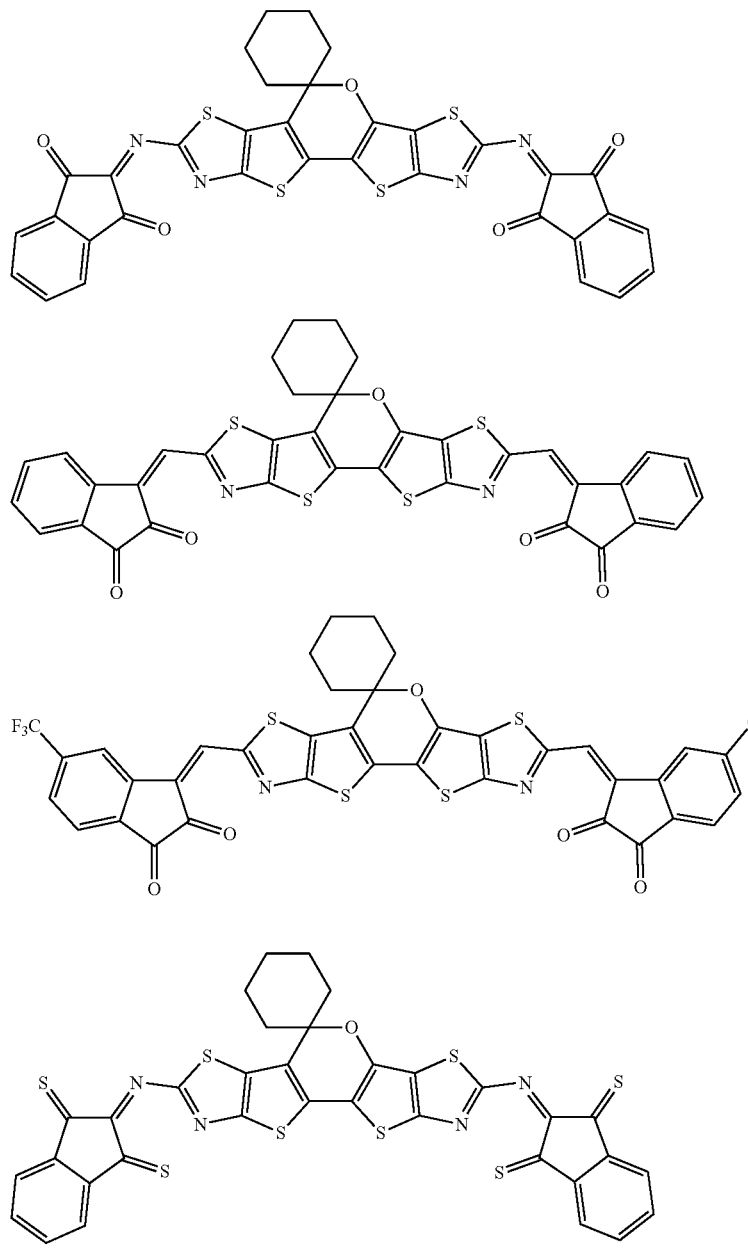

-continued
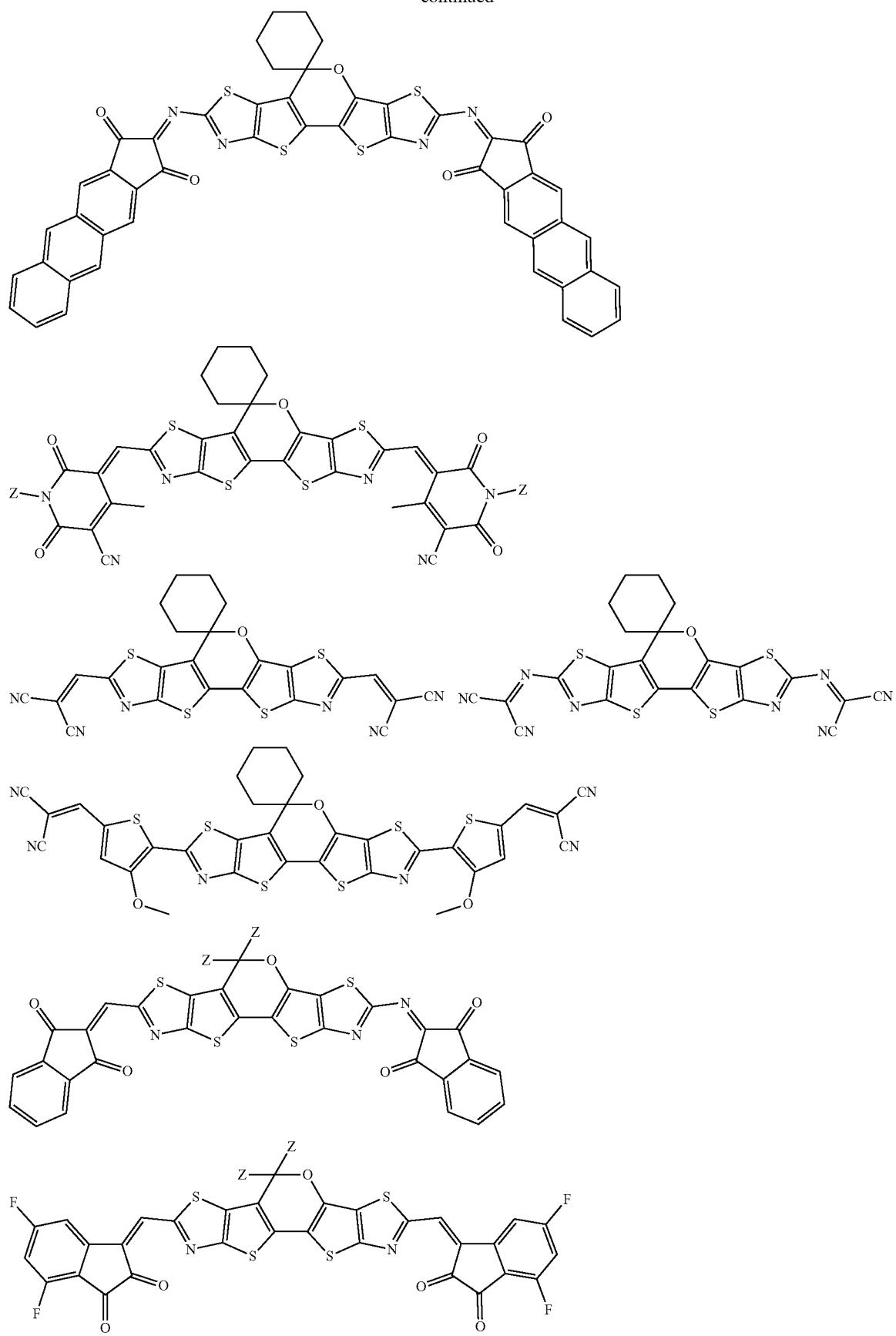

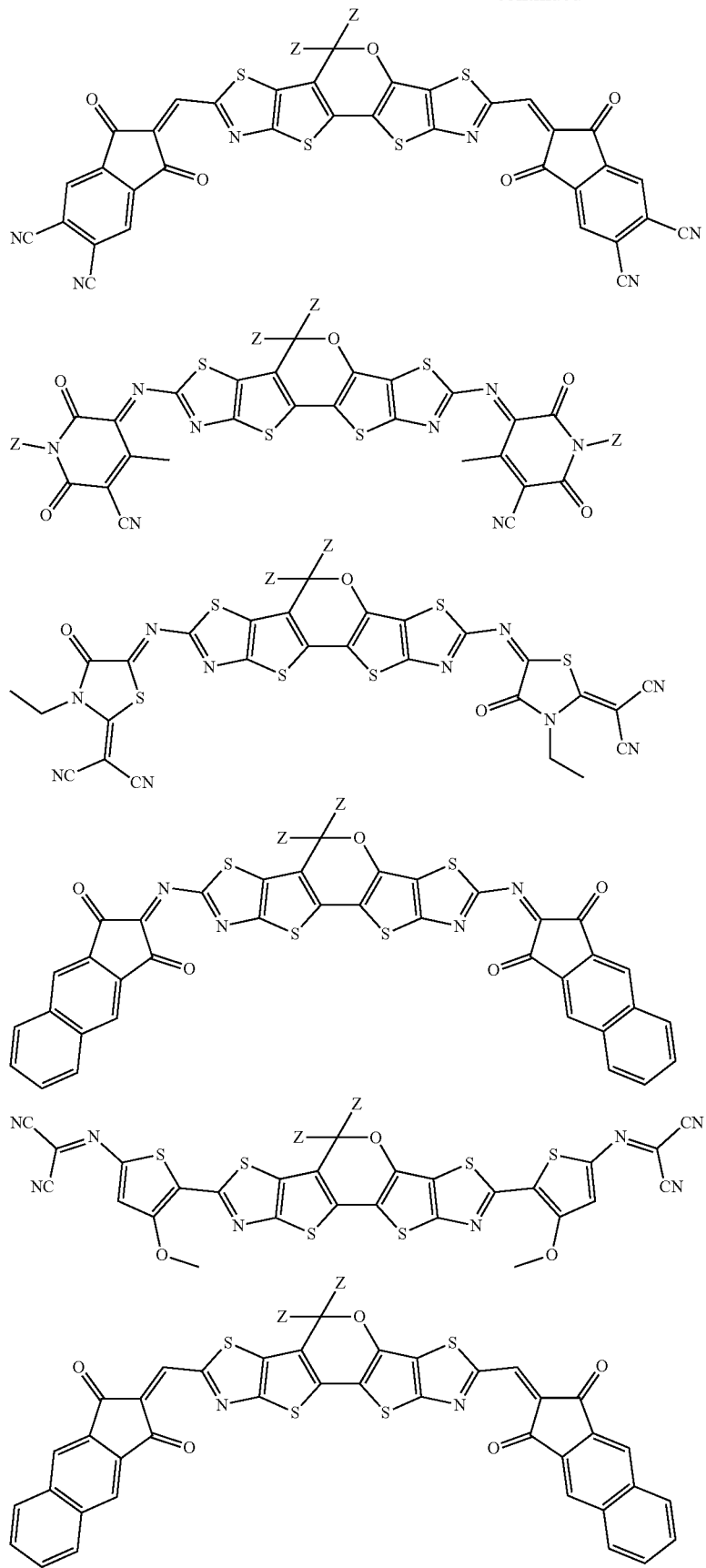

-continued
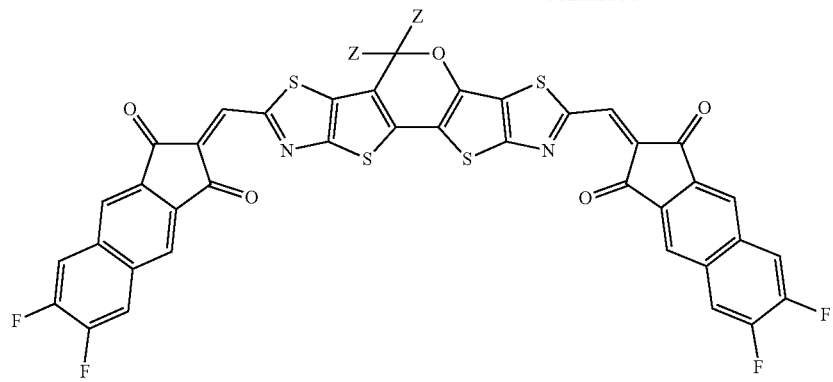
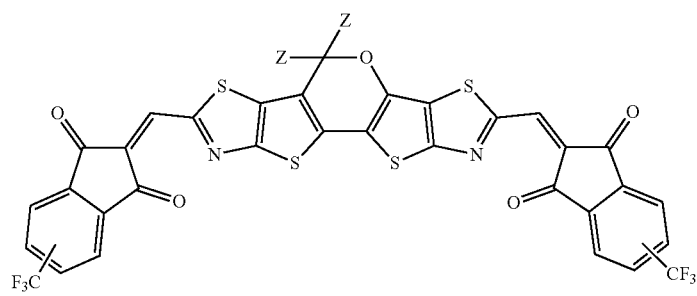
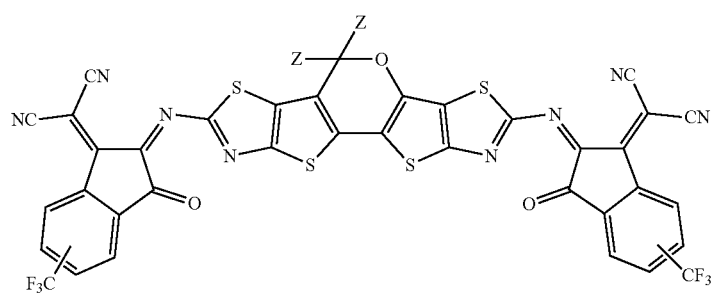
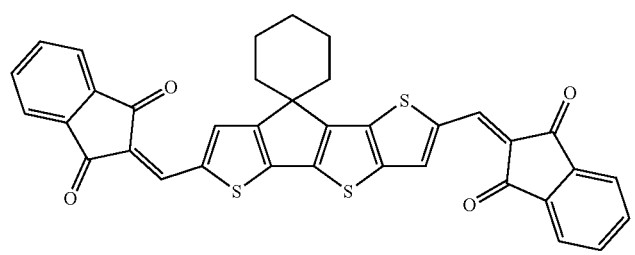
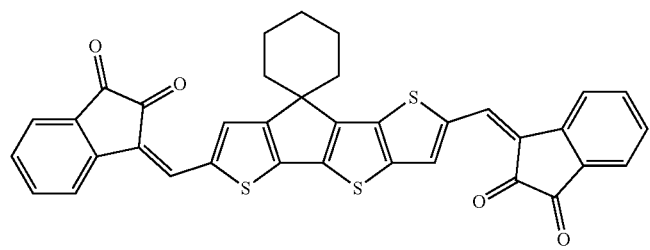
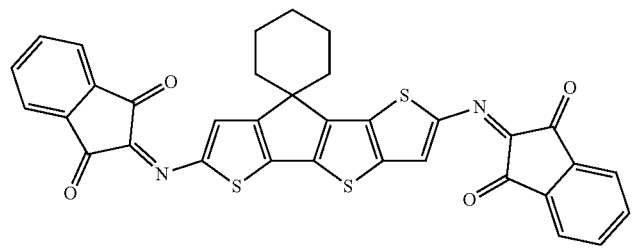

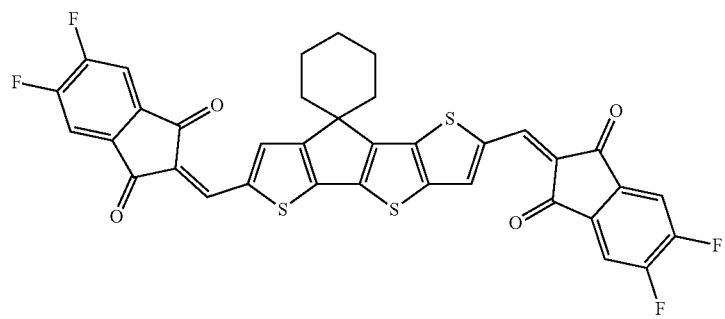
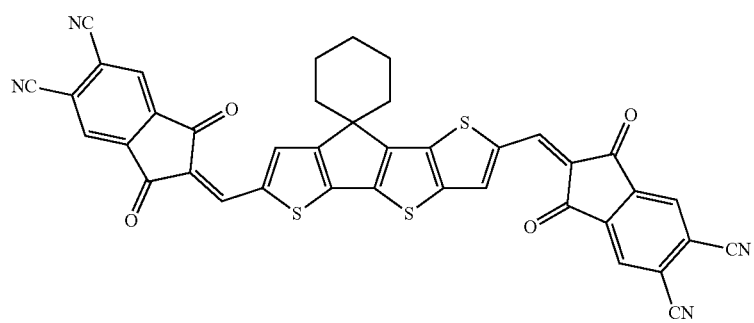
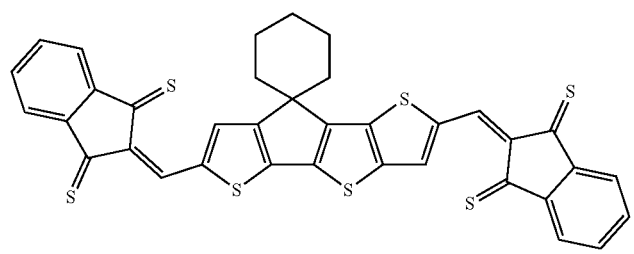
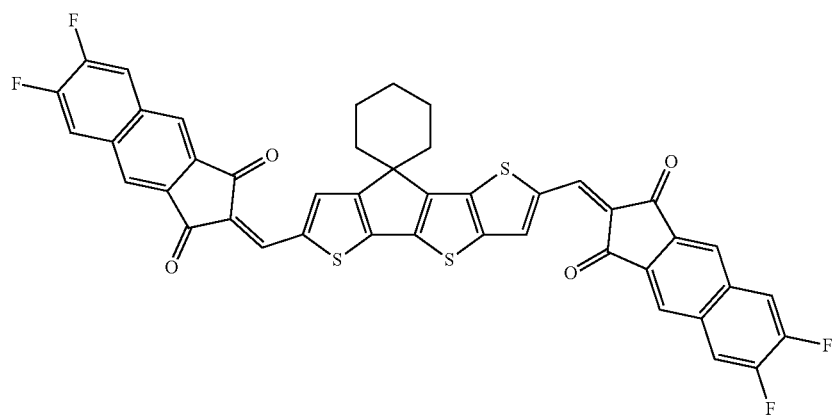
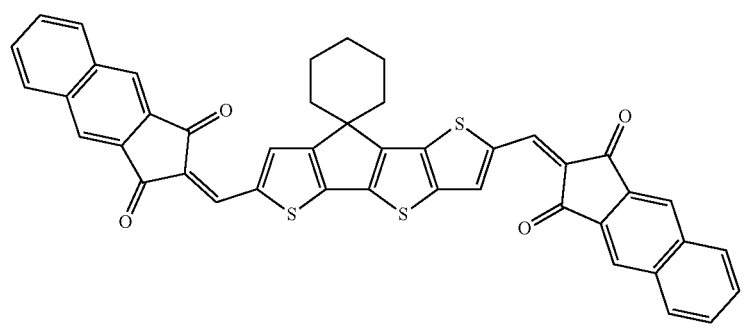

-continued
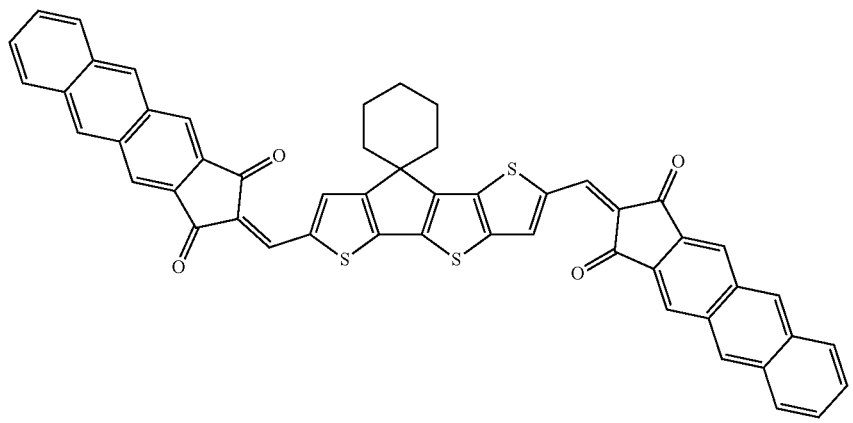
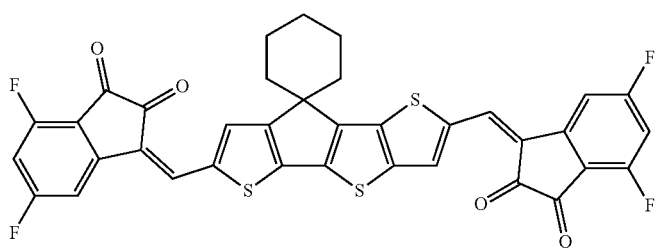
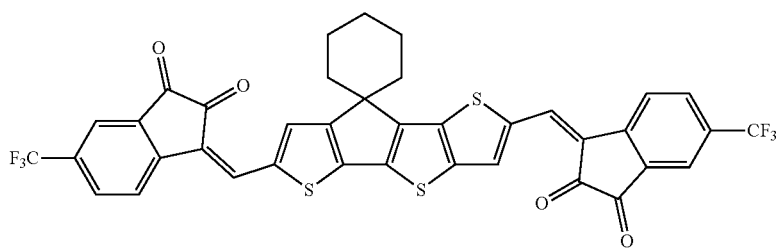
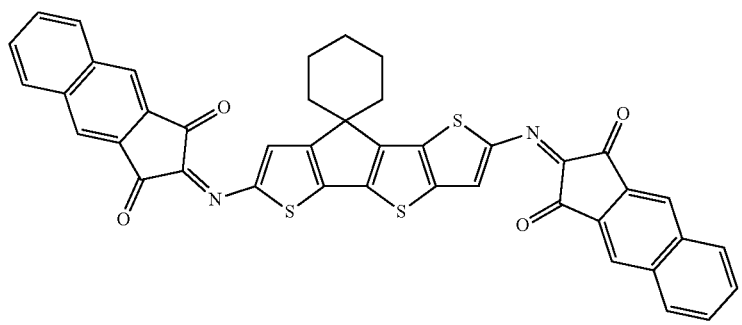
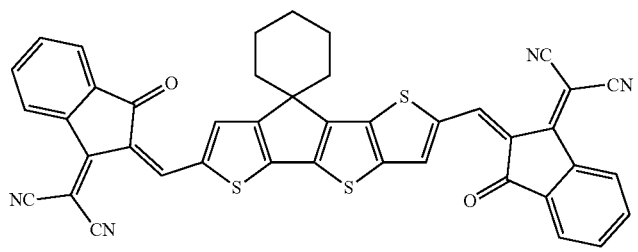

-continued
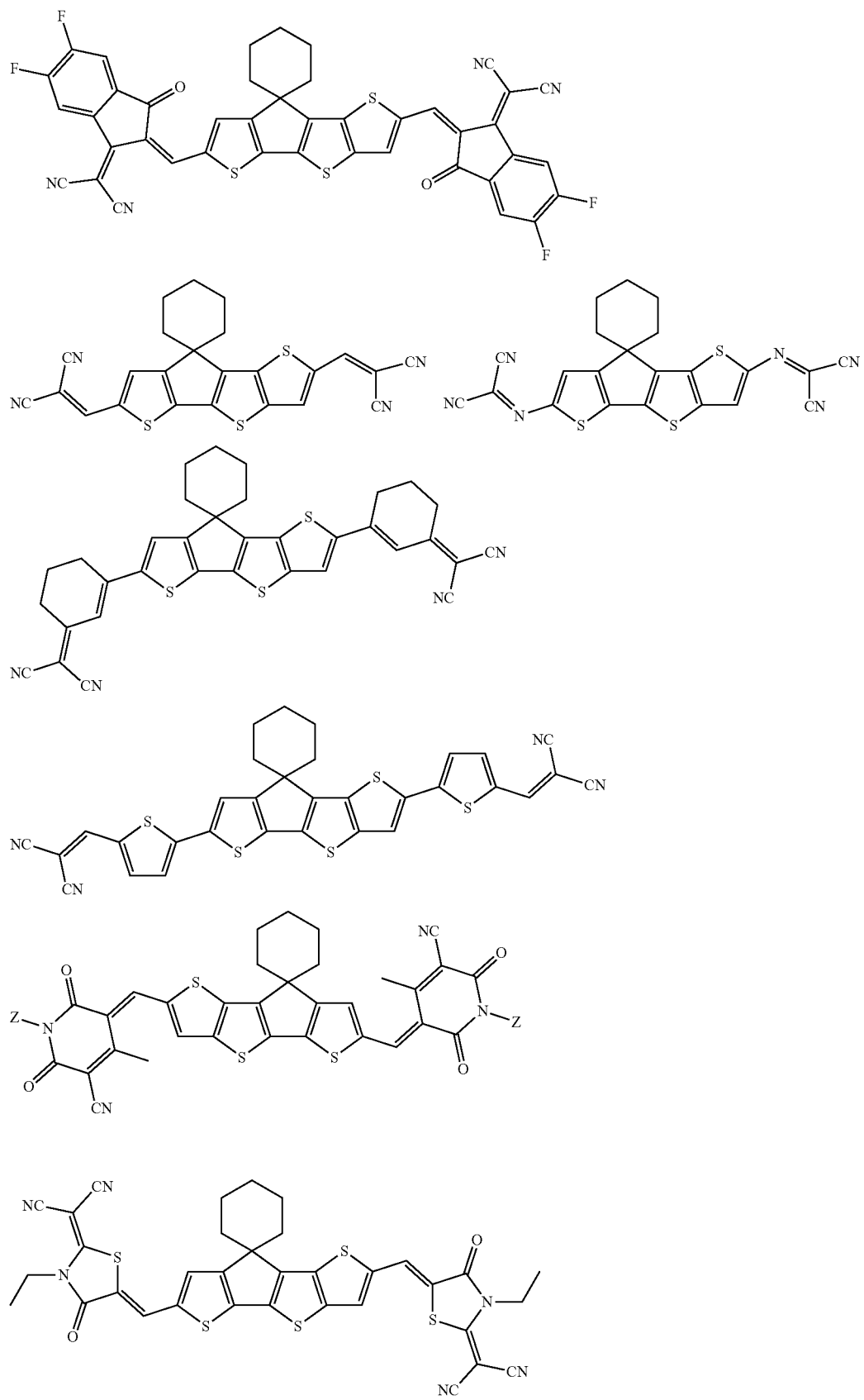

-continued
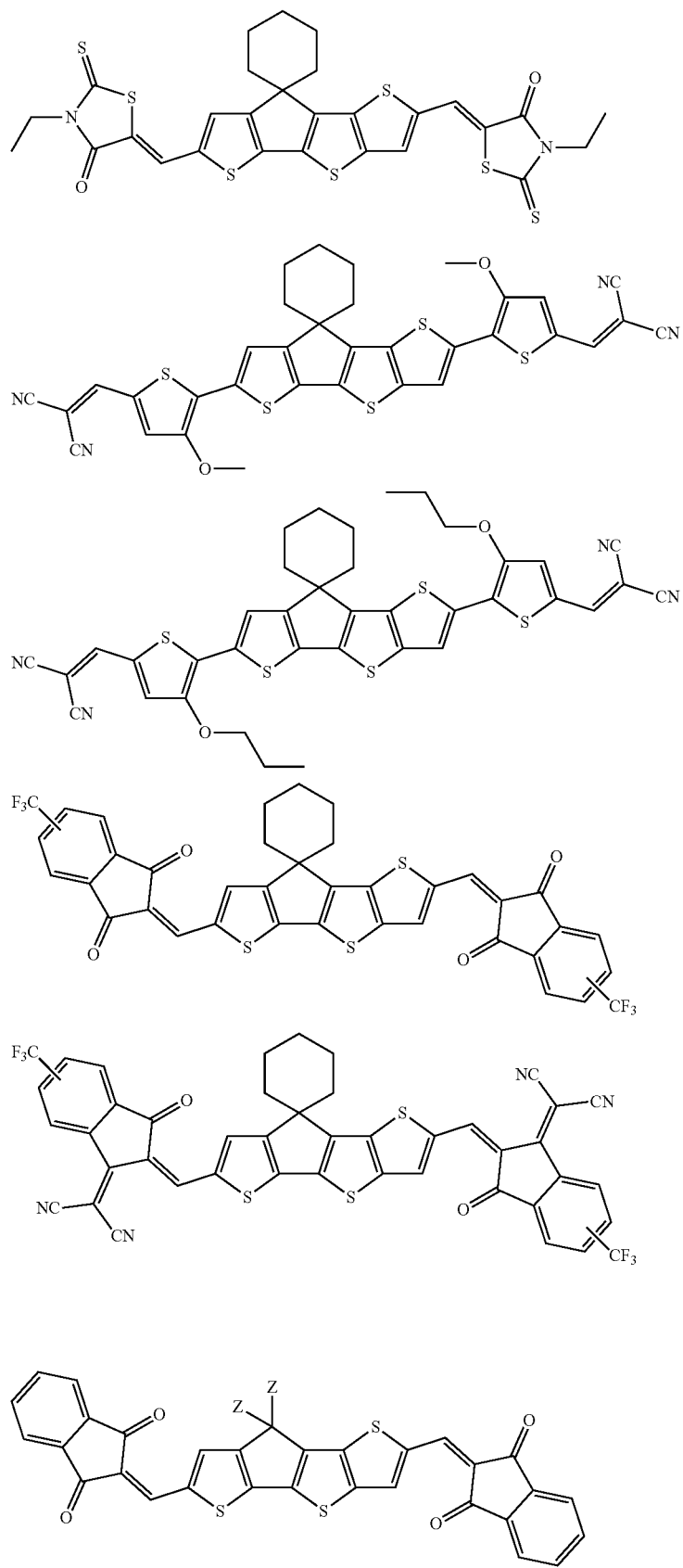

-continued
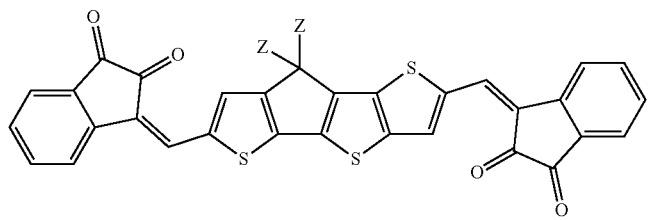
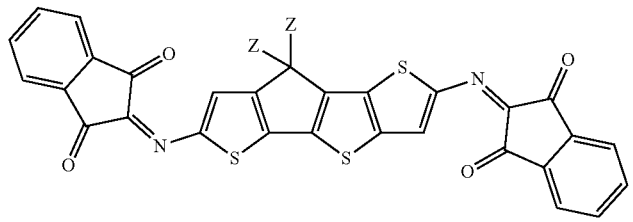
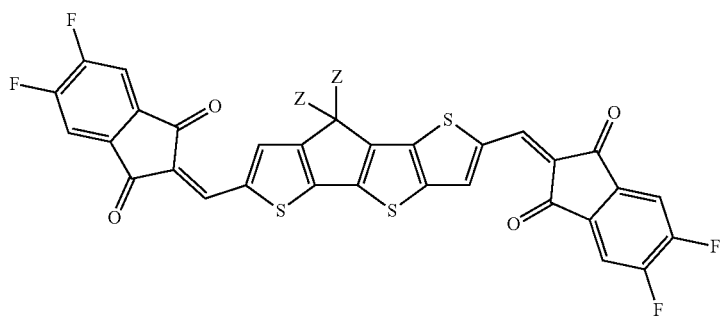
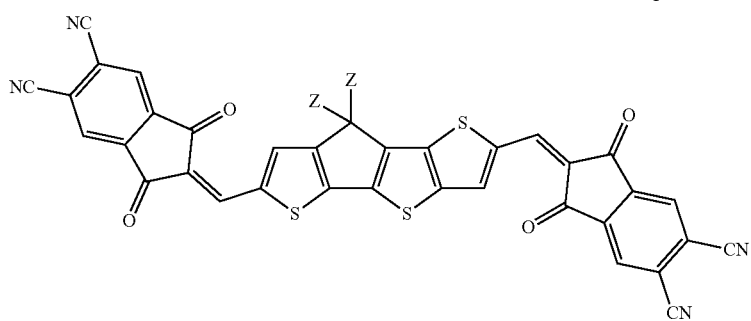
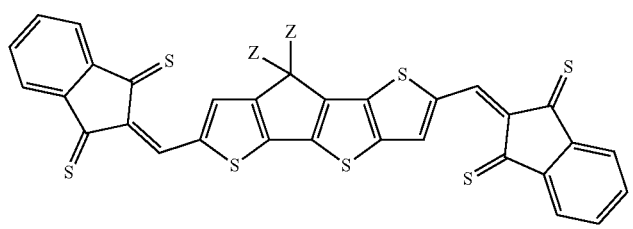
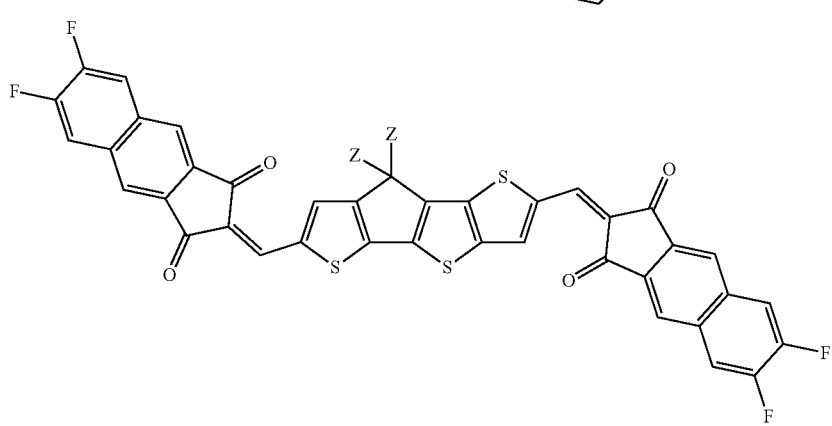

-continued
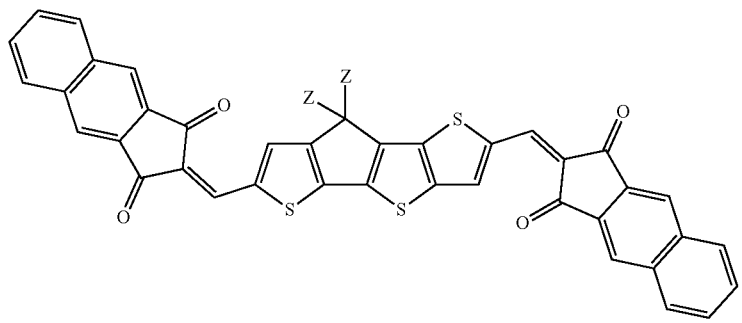
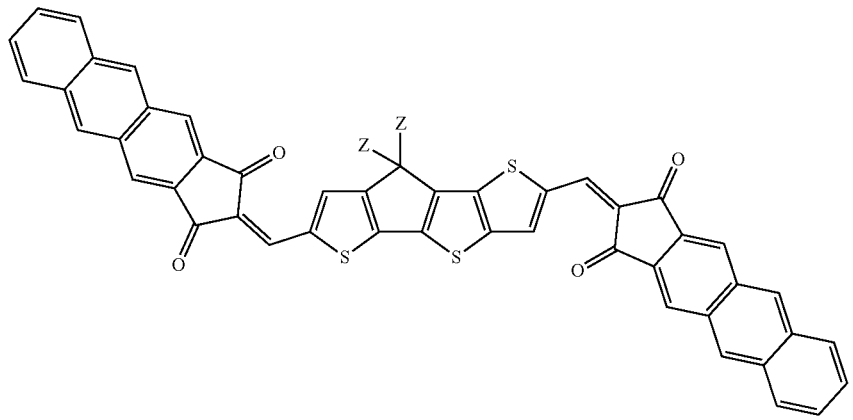
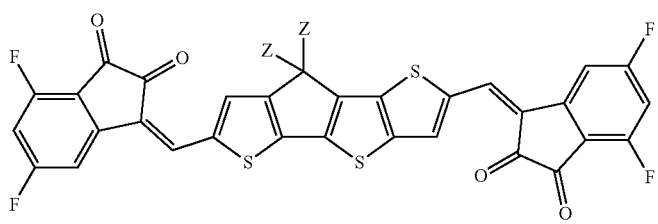
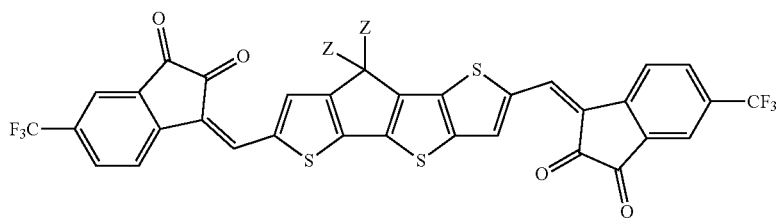
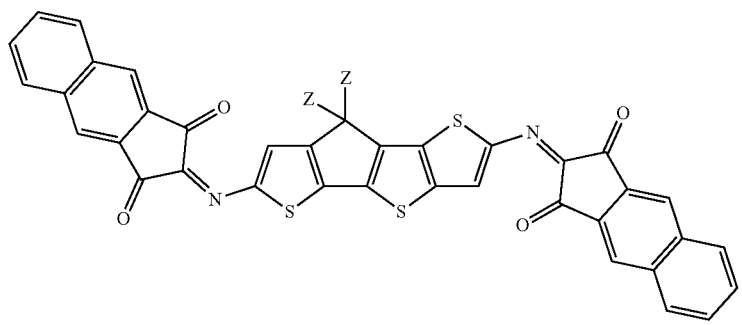
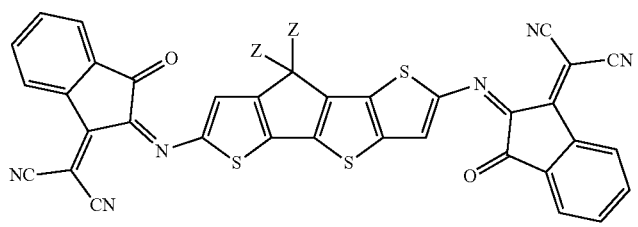

-continued
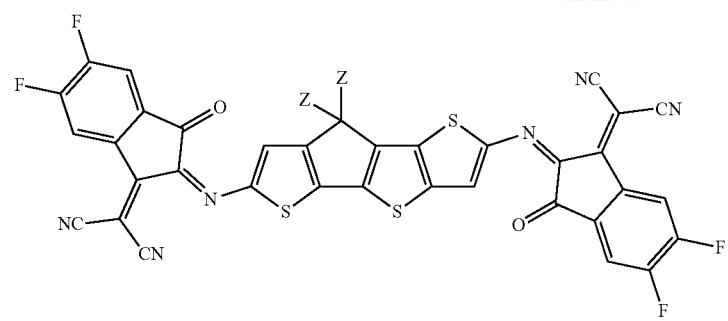
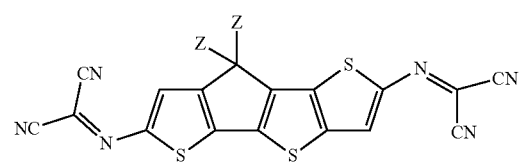
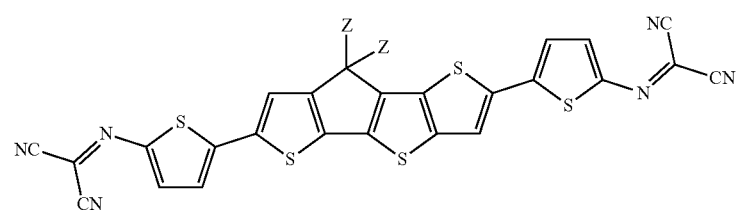
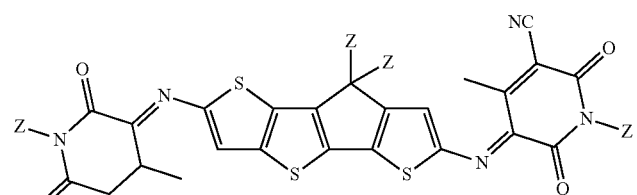
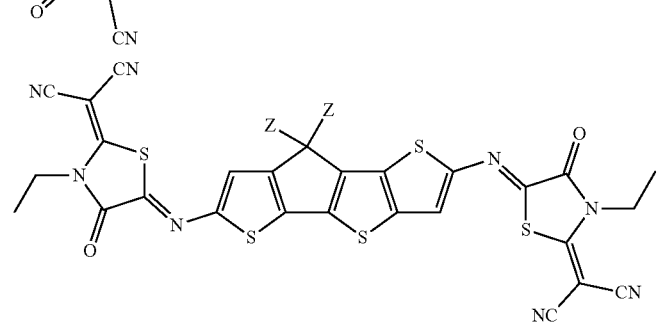
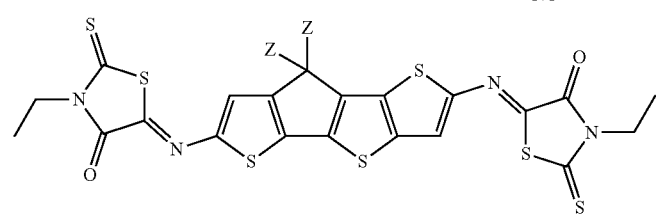
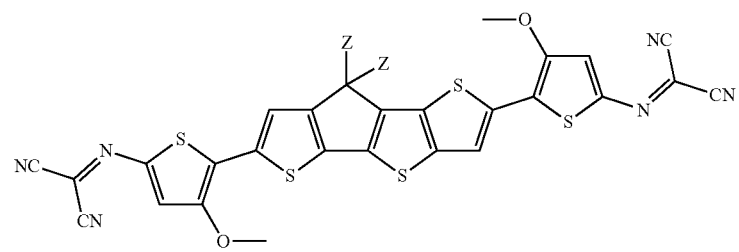

-continued
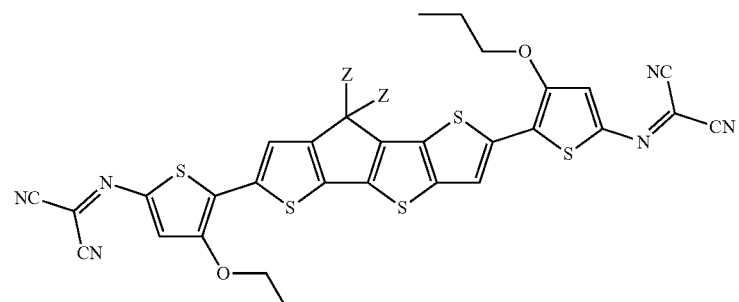
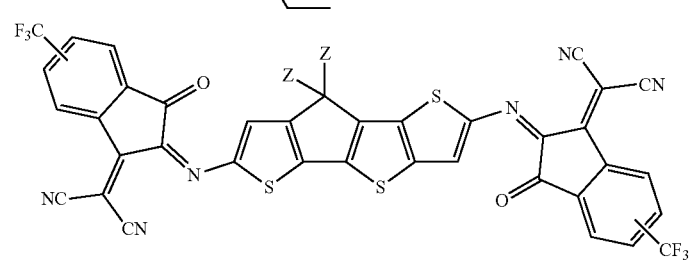
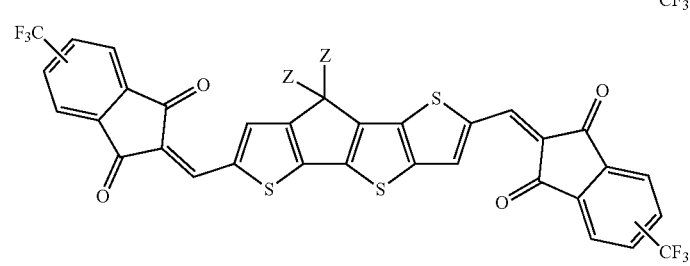
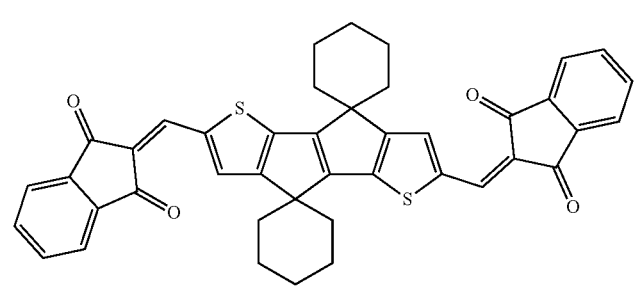
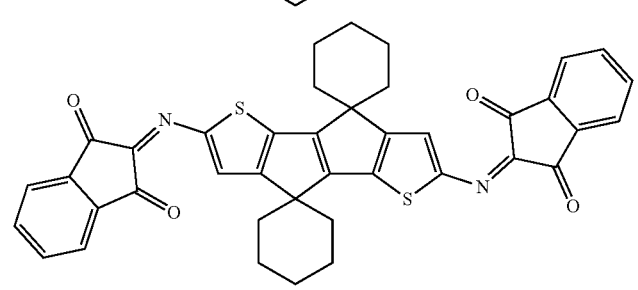
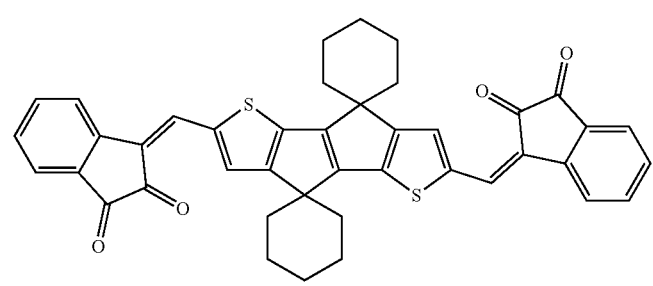

-continued
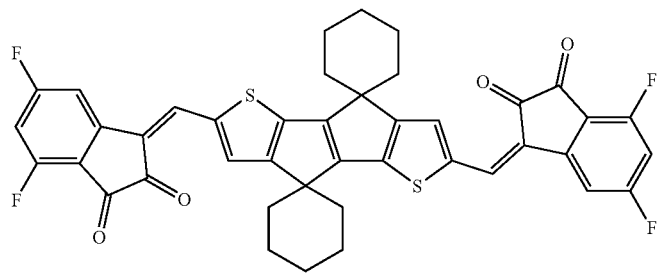
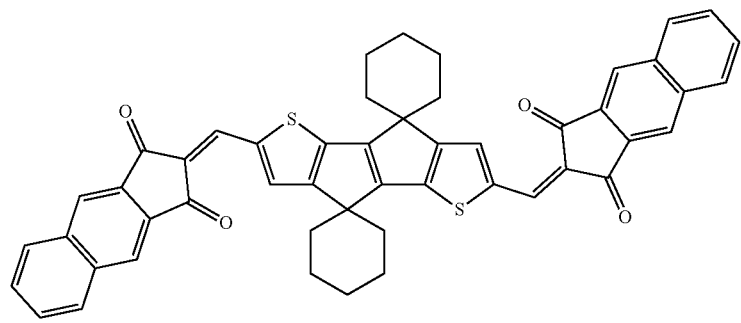
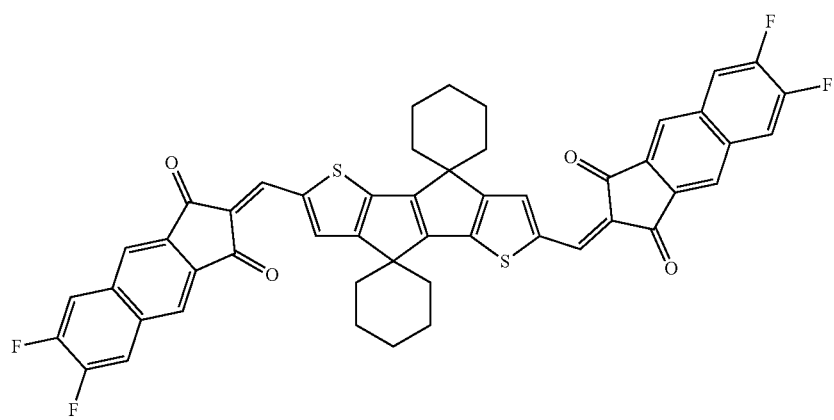
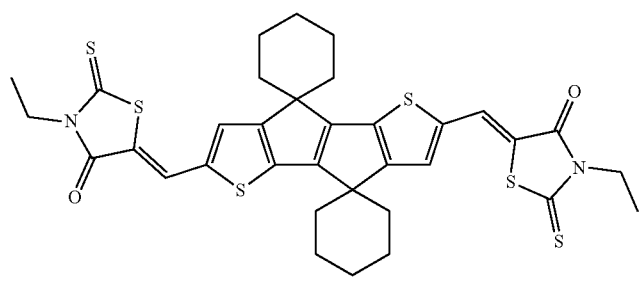
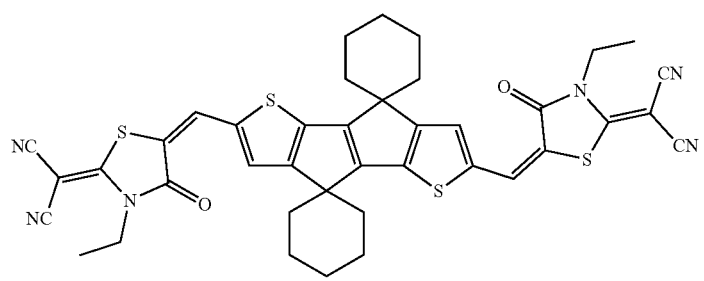

-continued
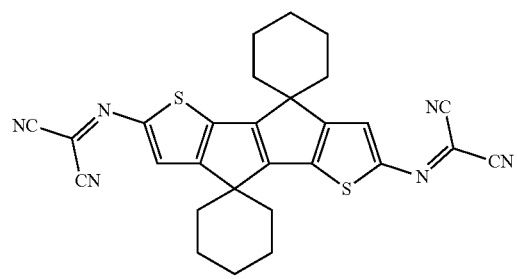
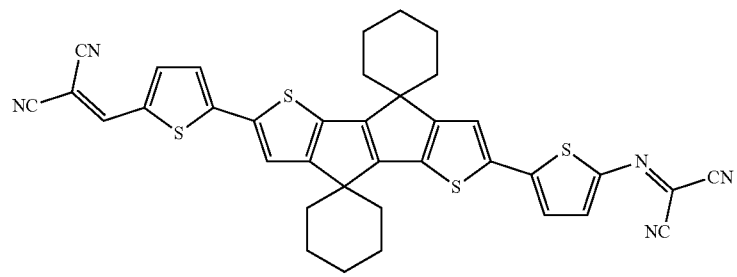
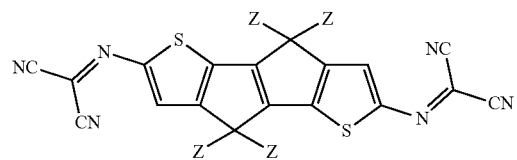
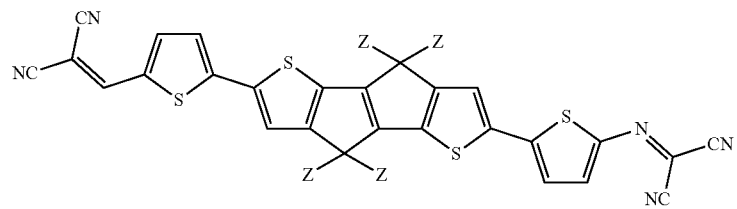
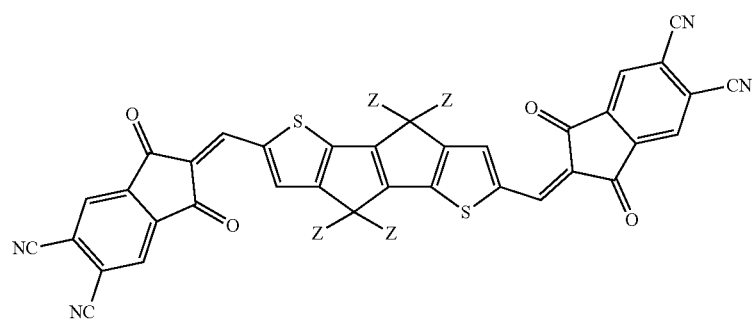
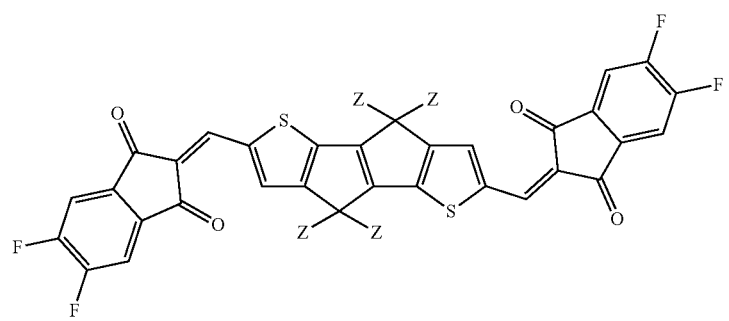

-continued
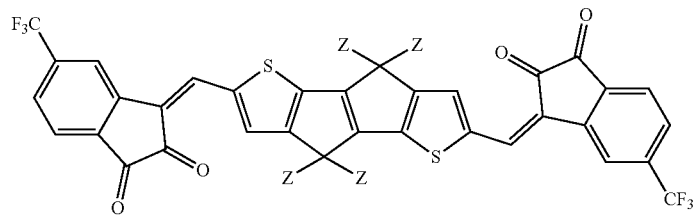
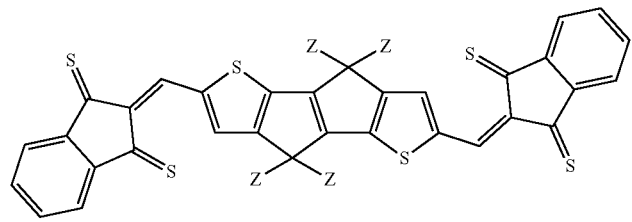
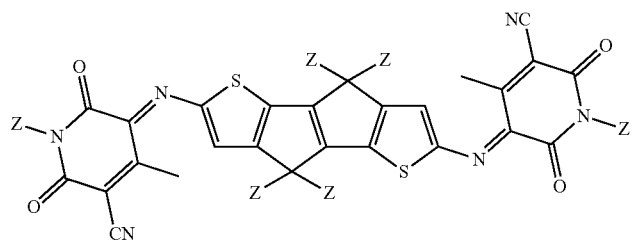
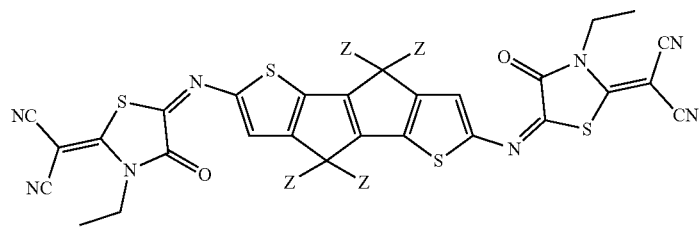
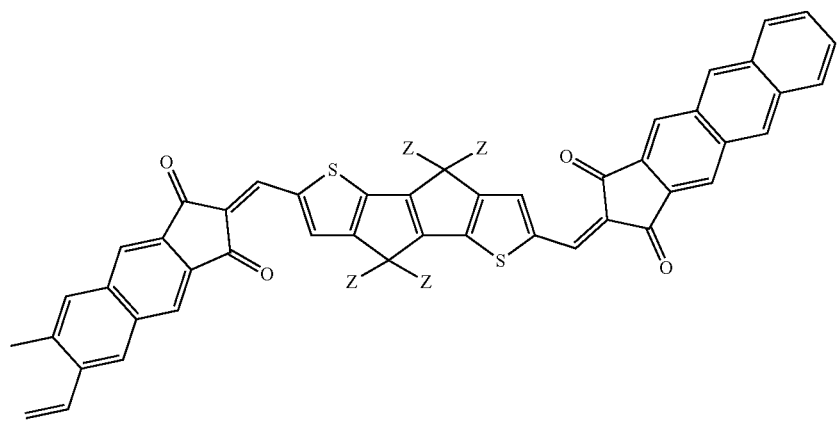
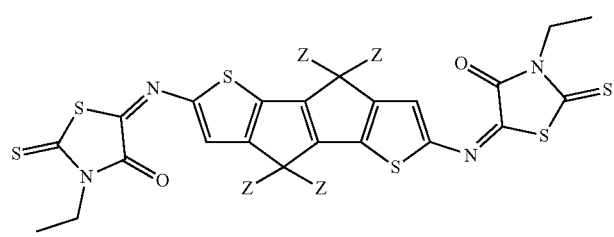

-continued
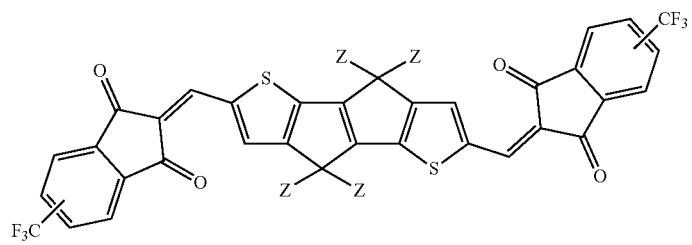
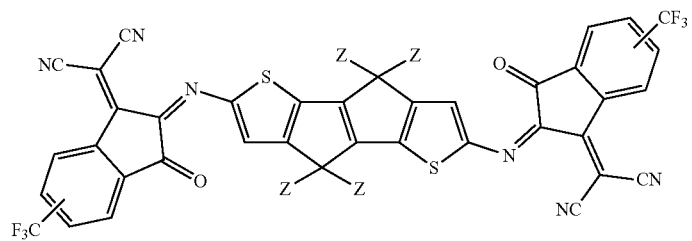
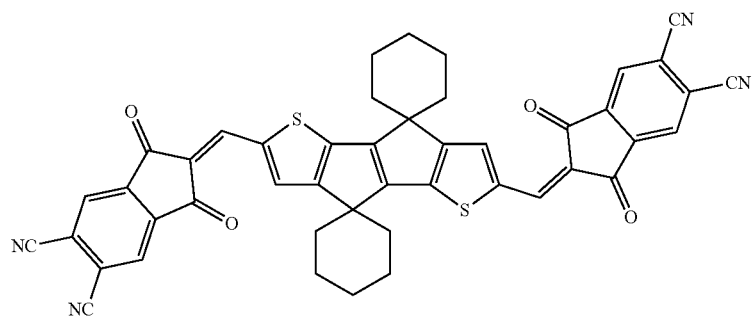
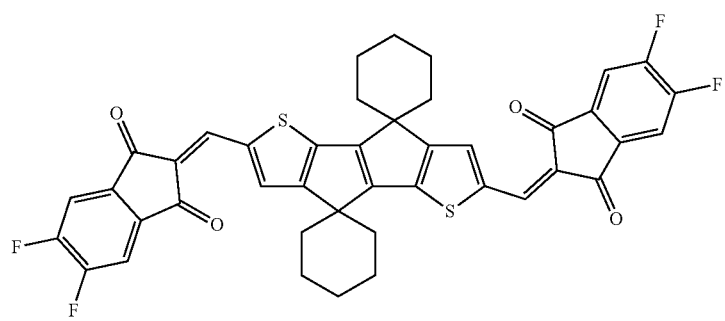
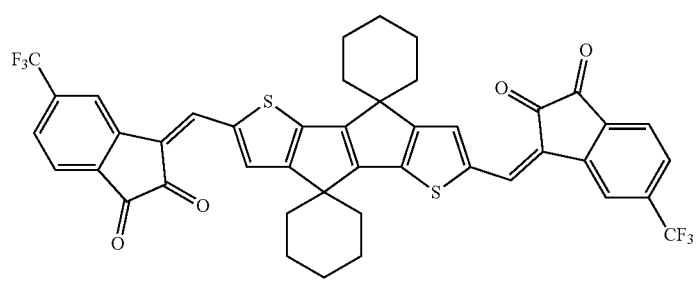
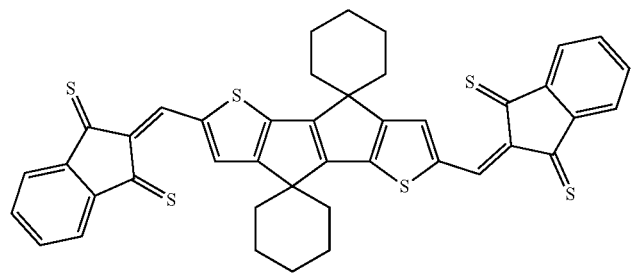

259 260
-continued
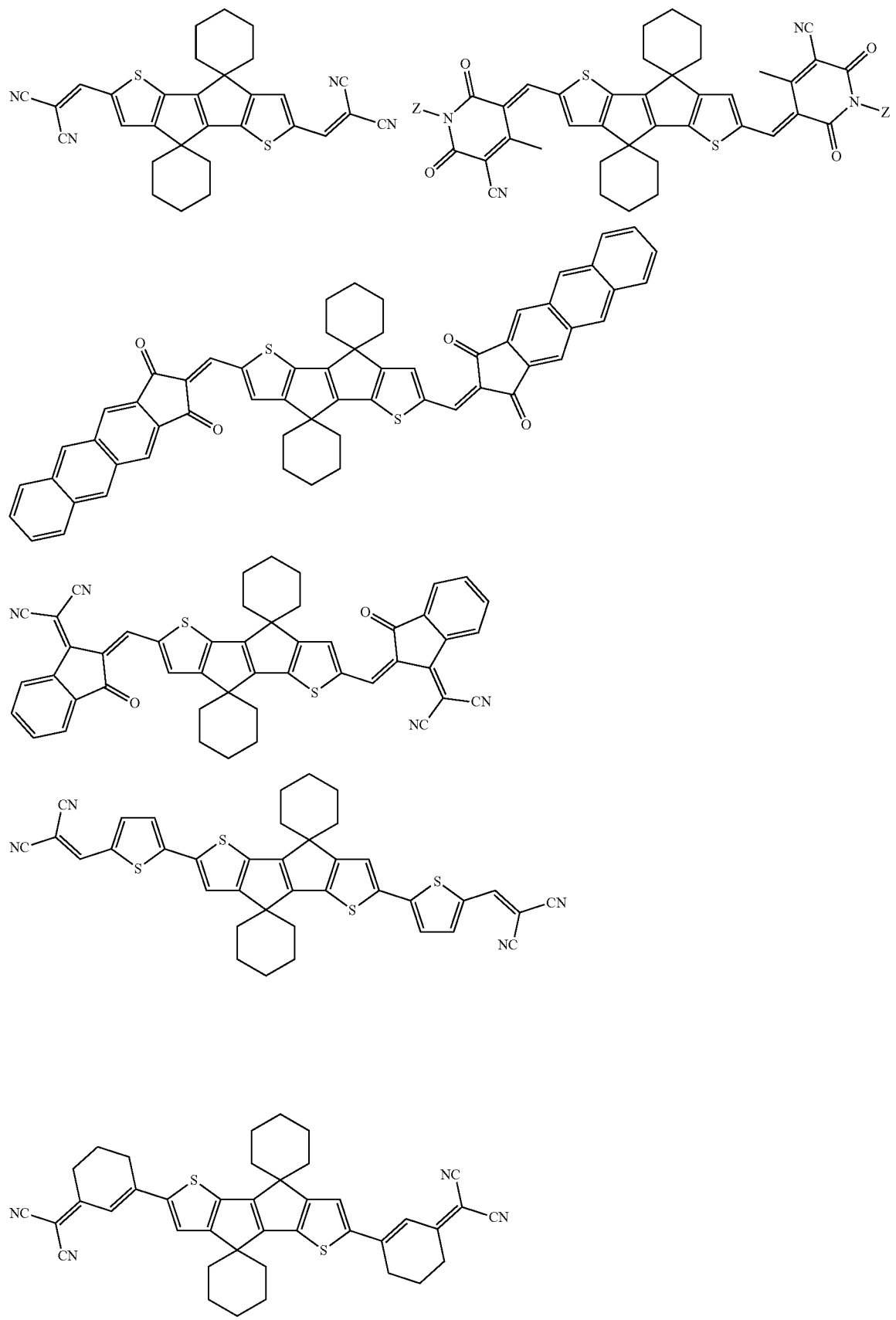

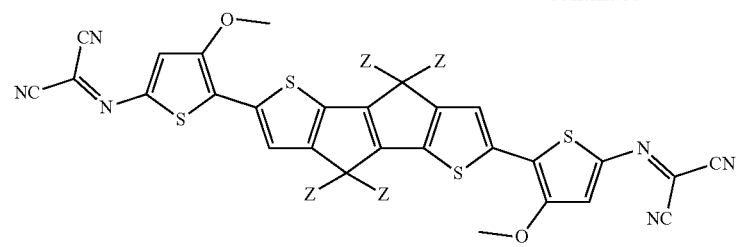
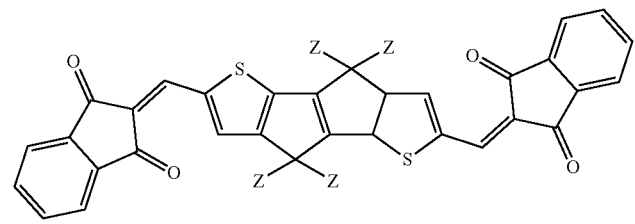
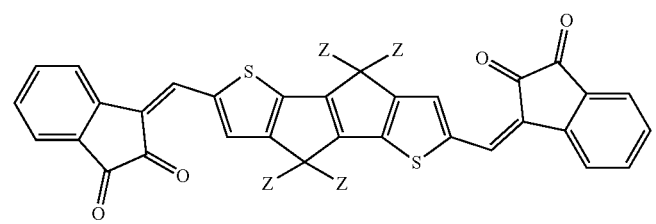
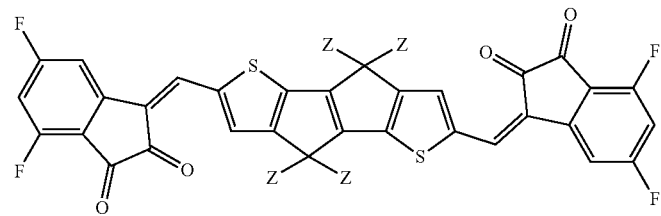
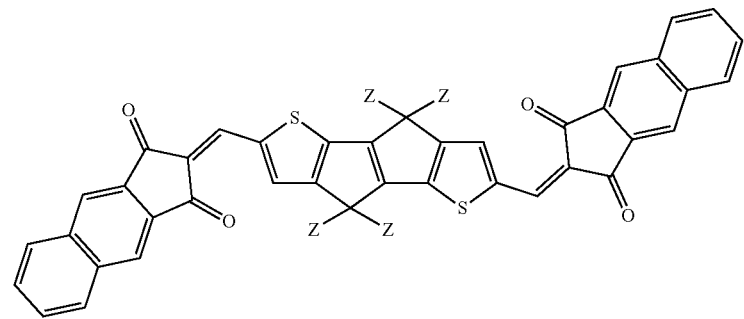
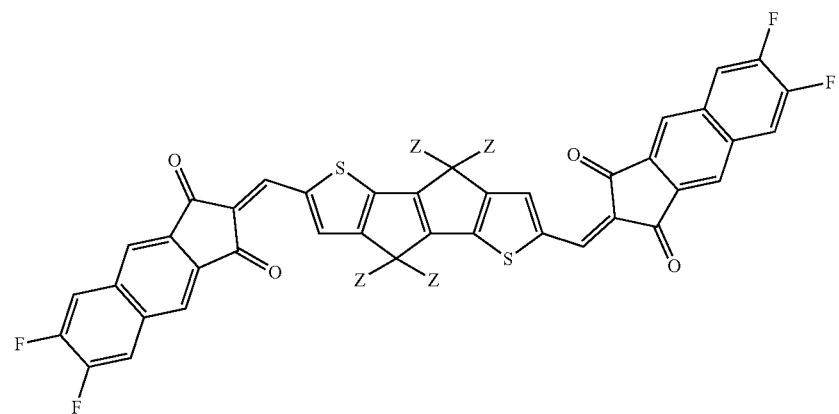

-continued
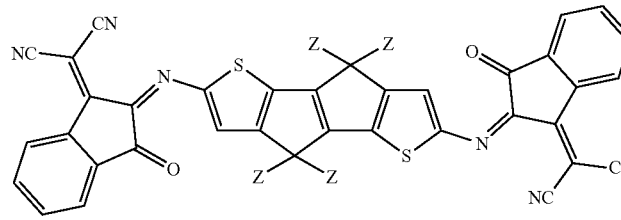
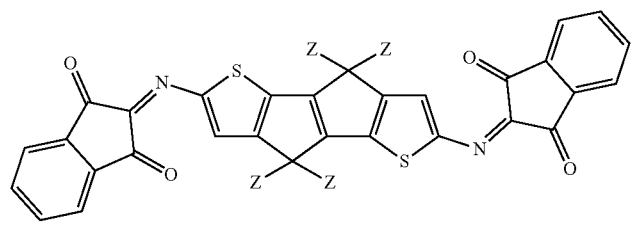
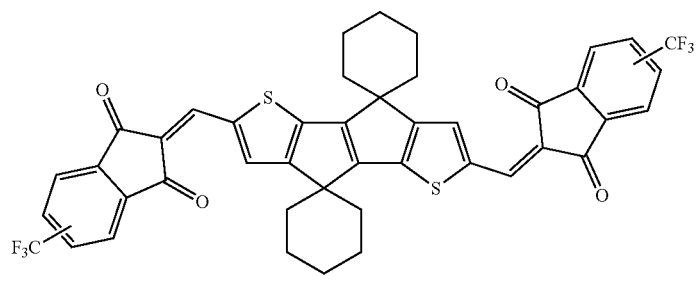
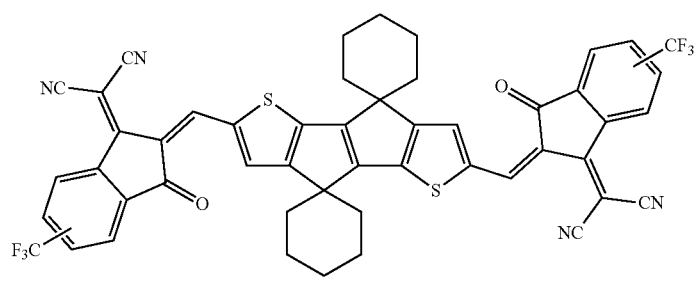

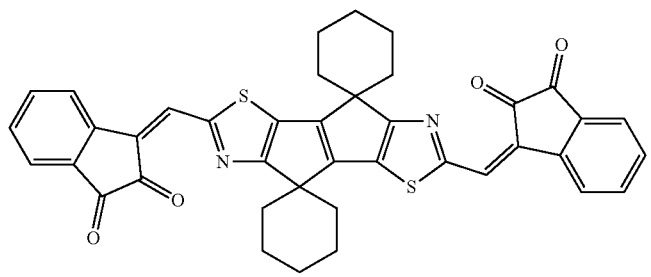
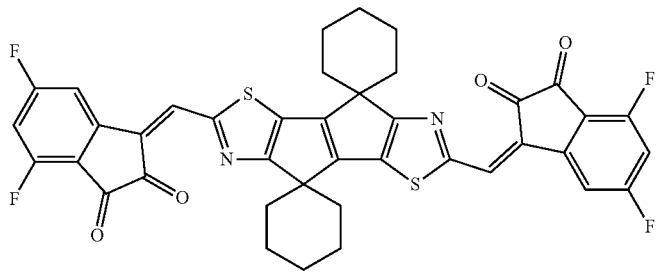
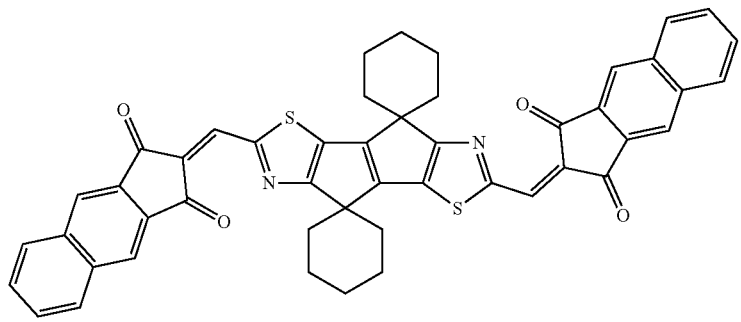
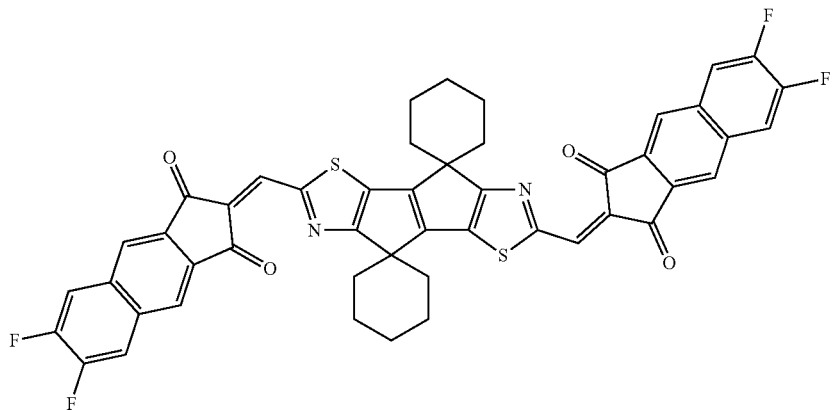
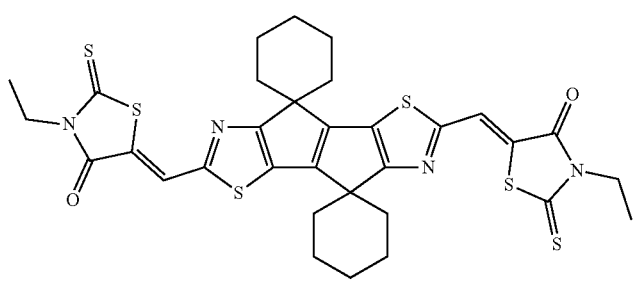

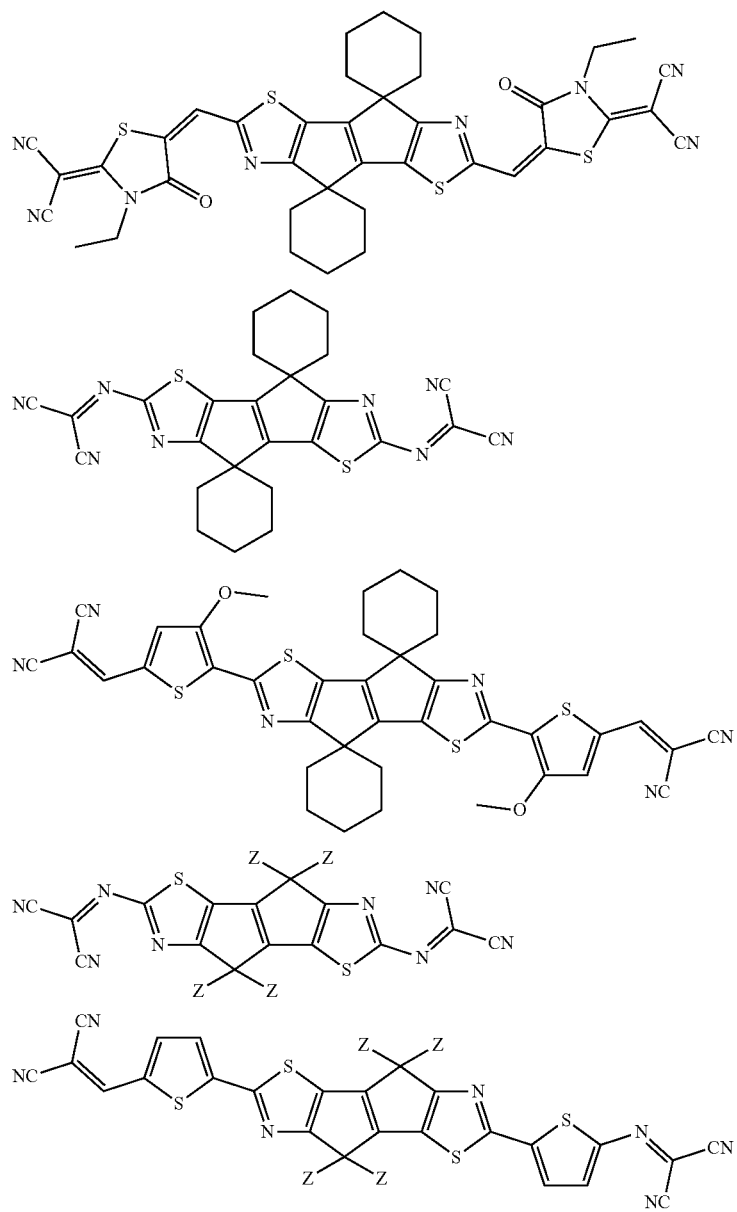
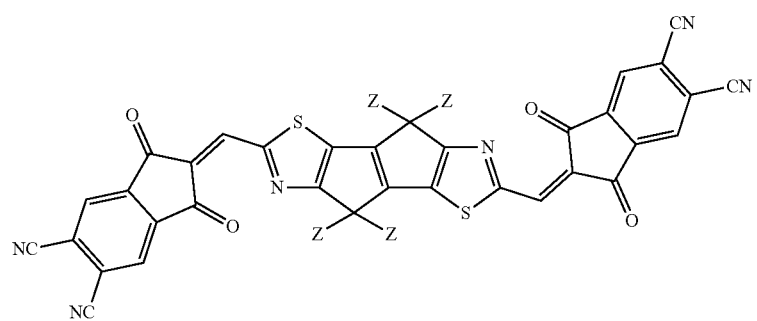

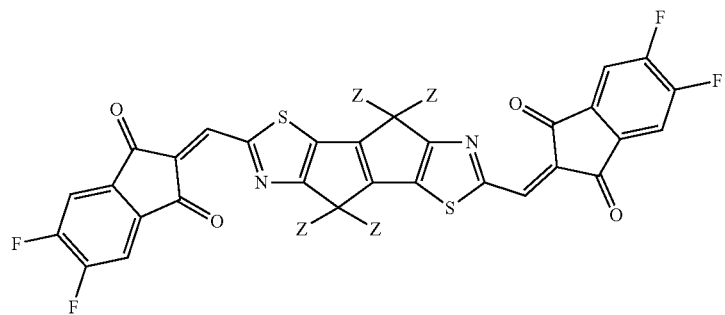
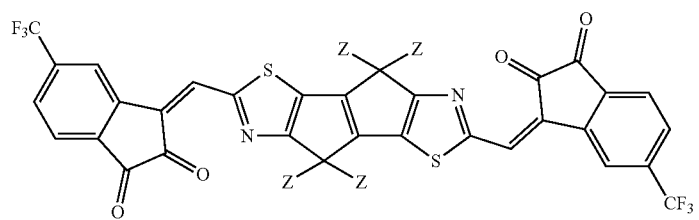
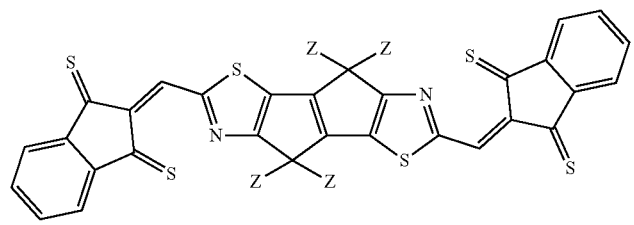
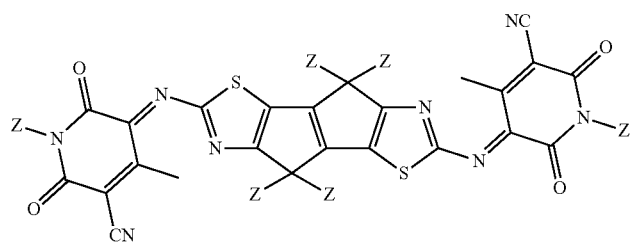
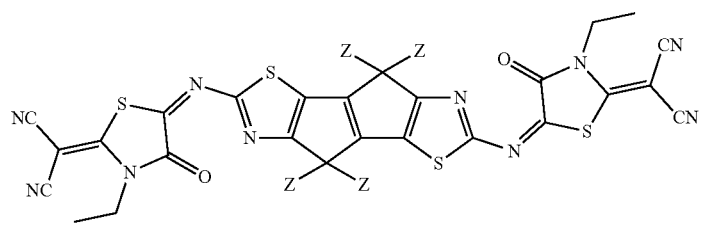
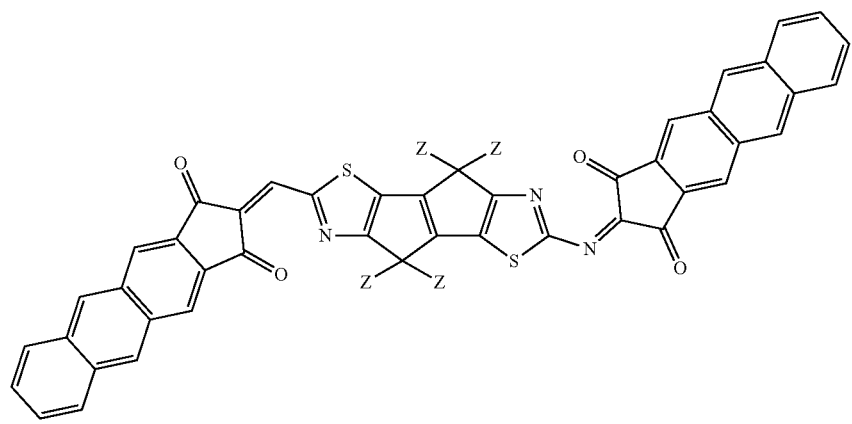

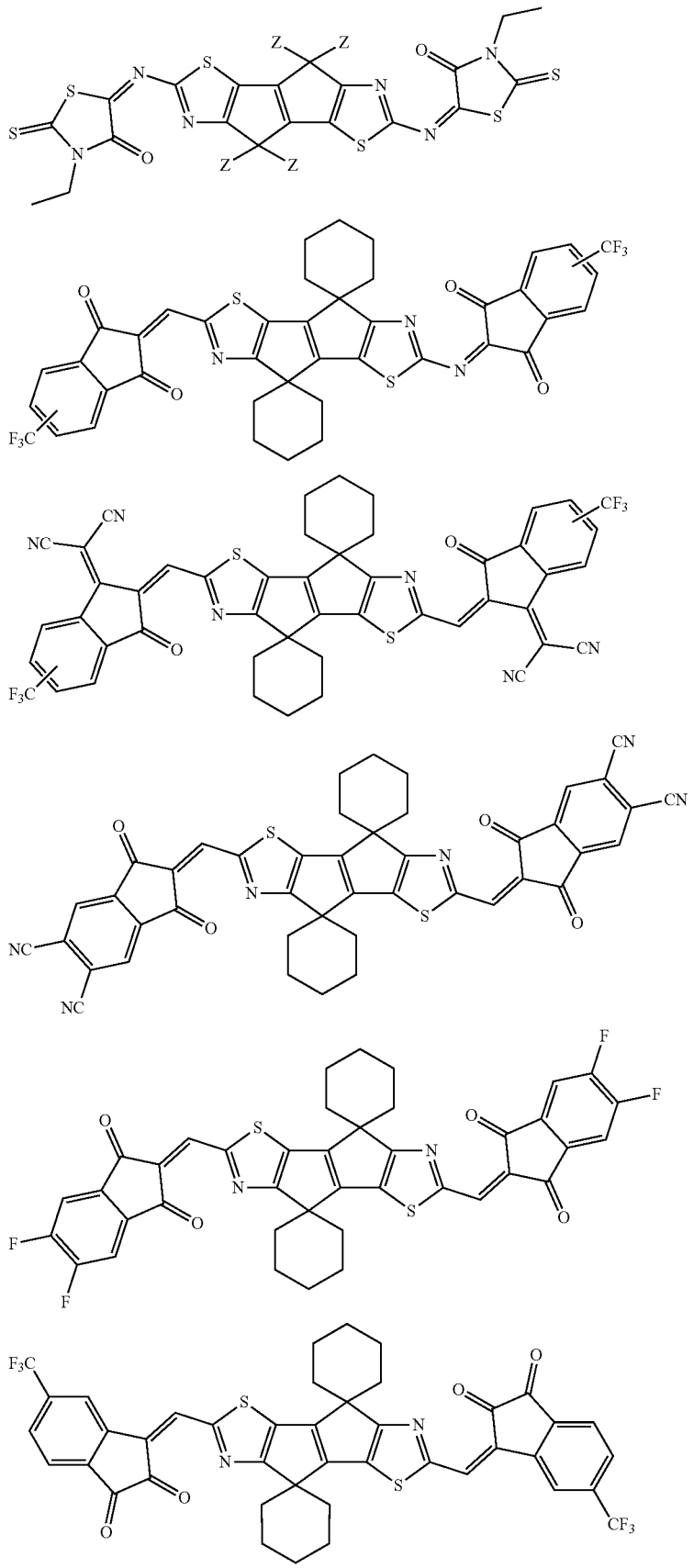

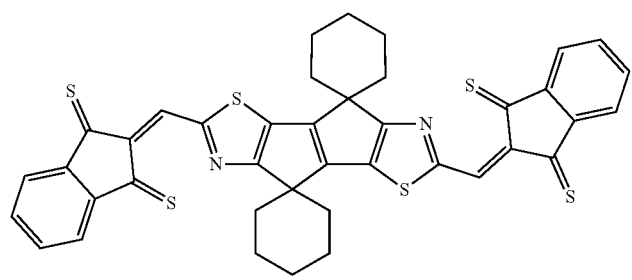
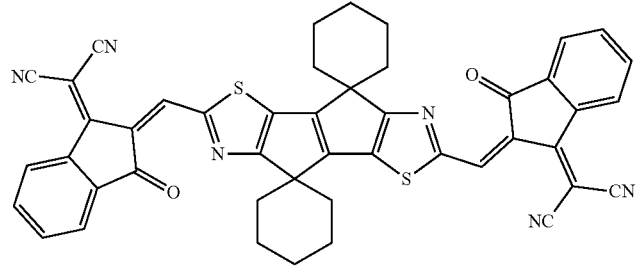
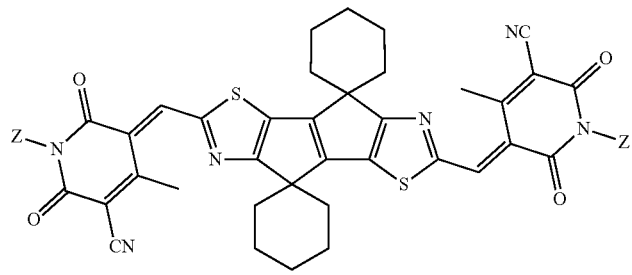
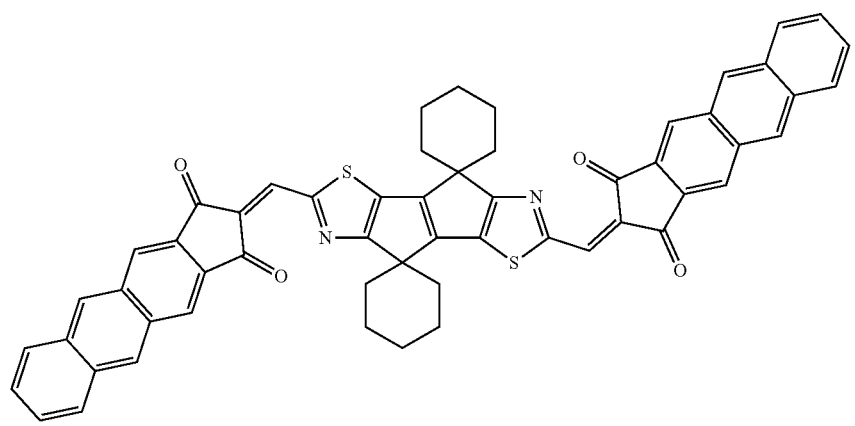
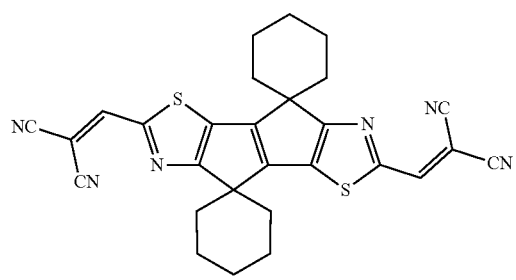

-continued
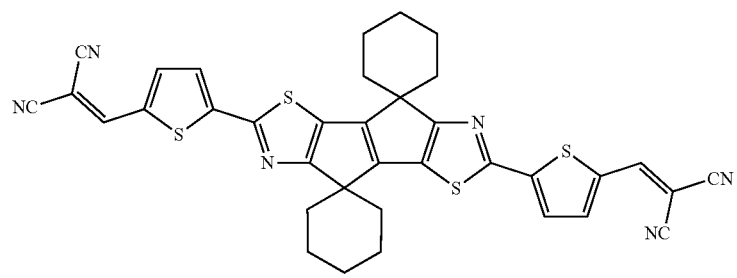
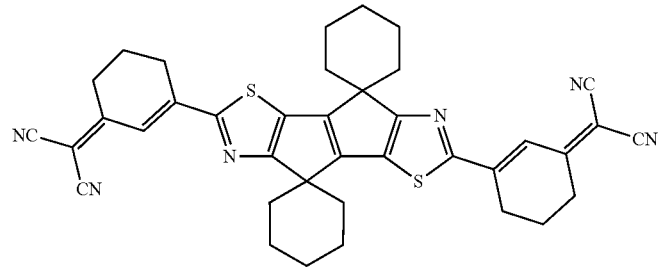
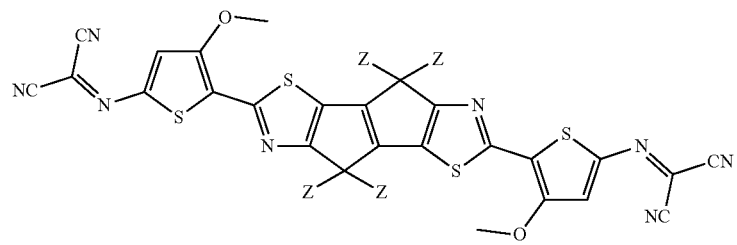
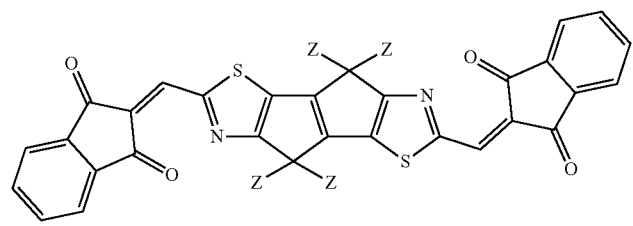
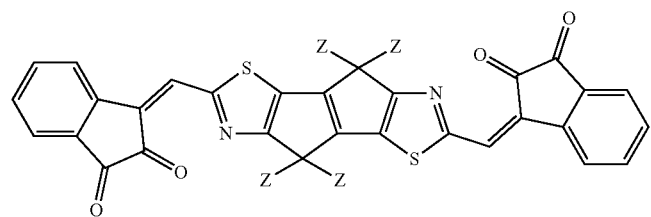
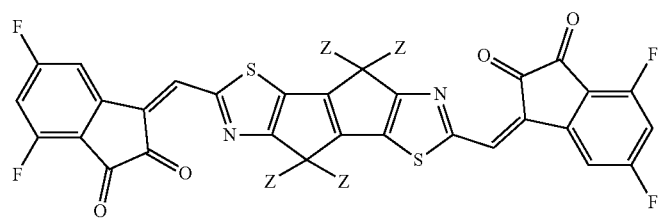

-continued
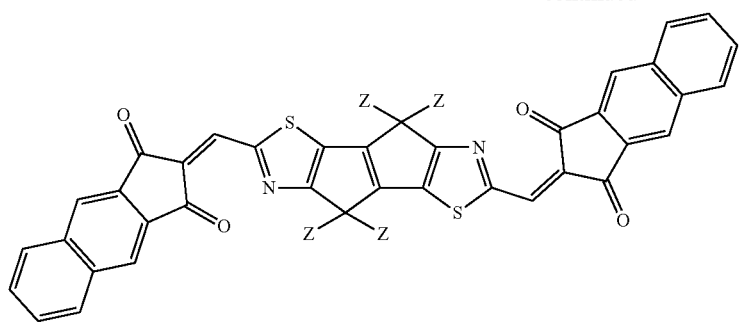
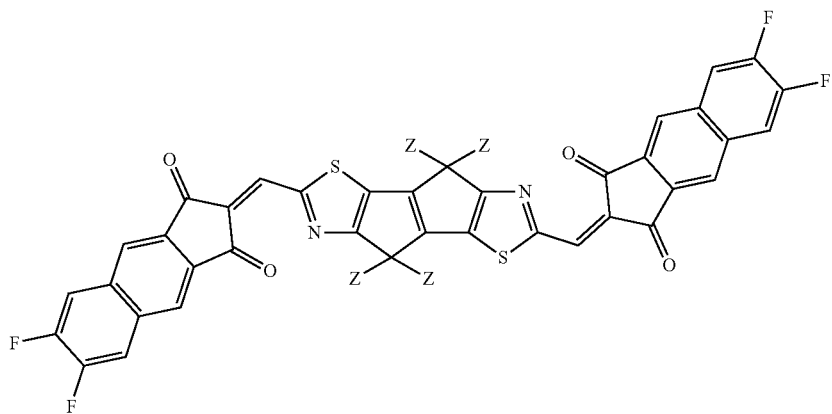
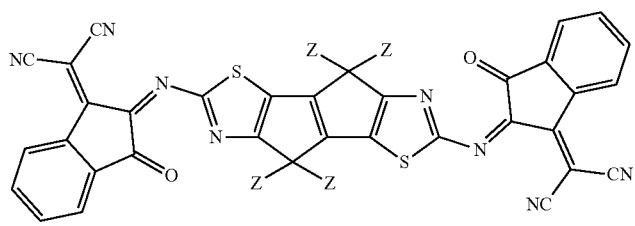
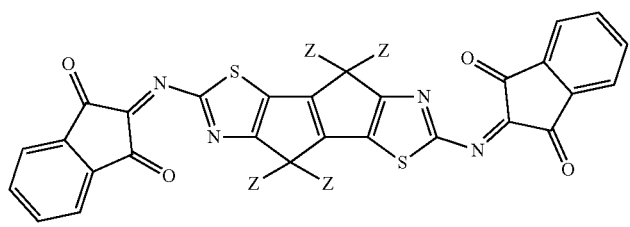
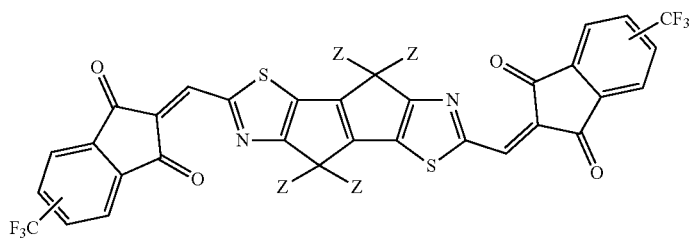
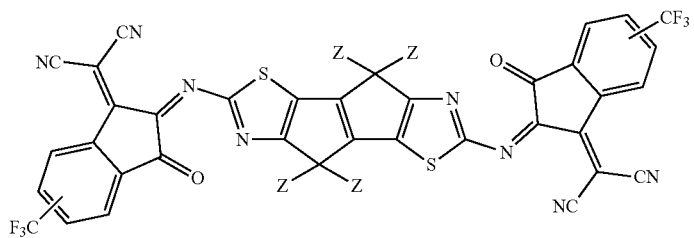

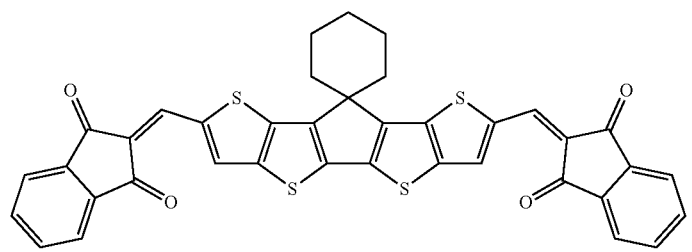
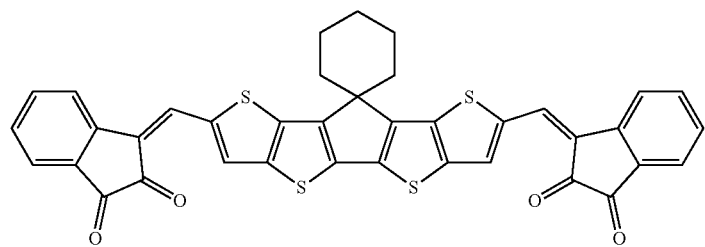
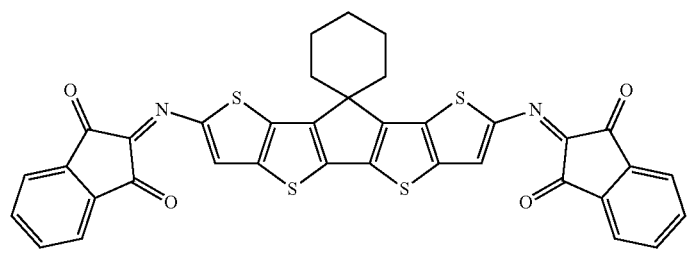
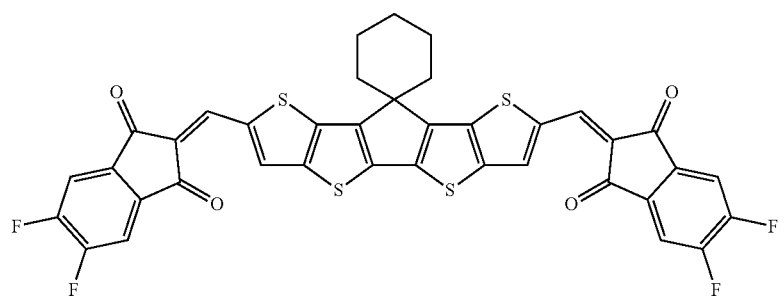
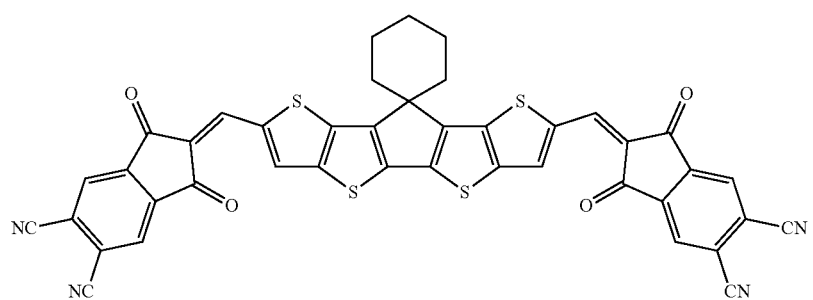
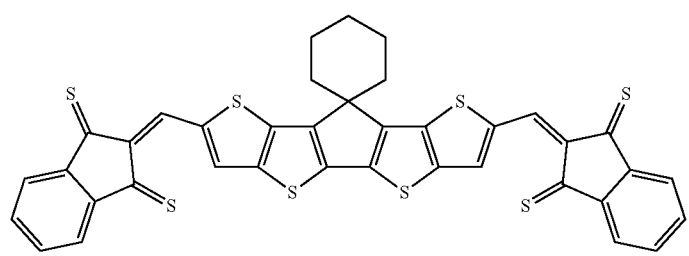

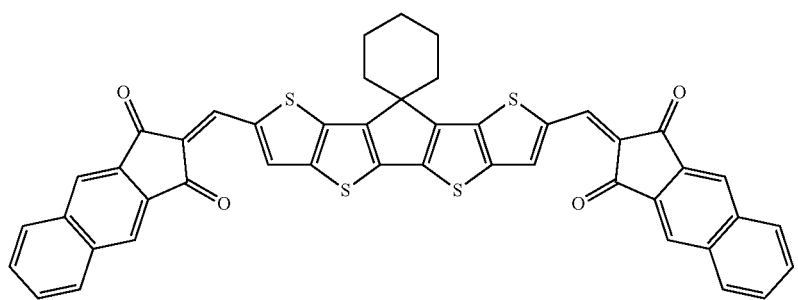
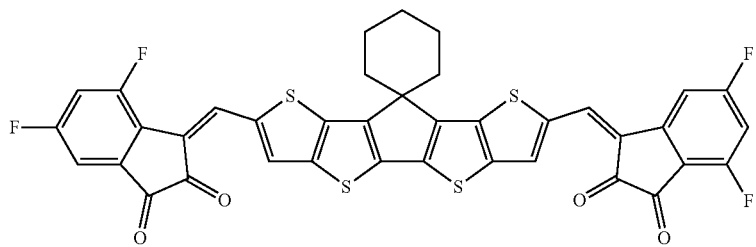
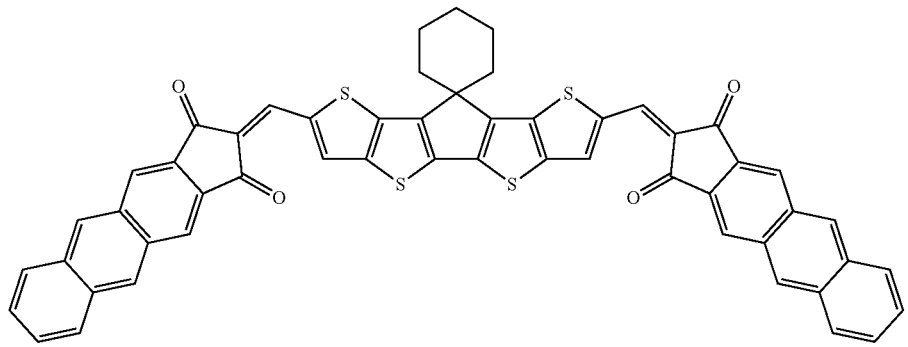
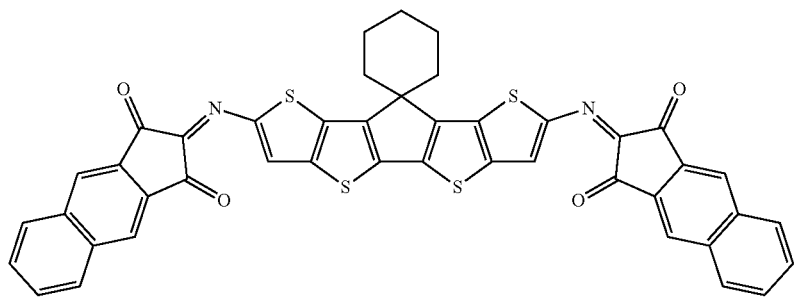
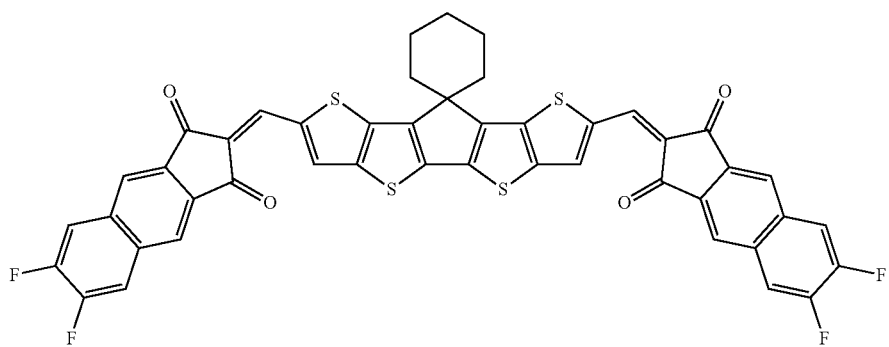

-continued
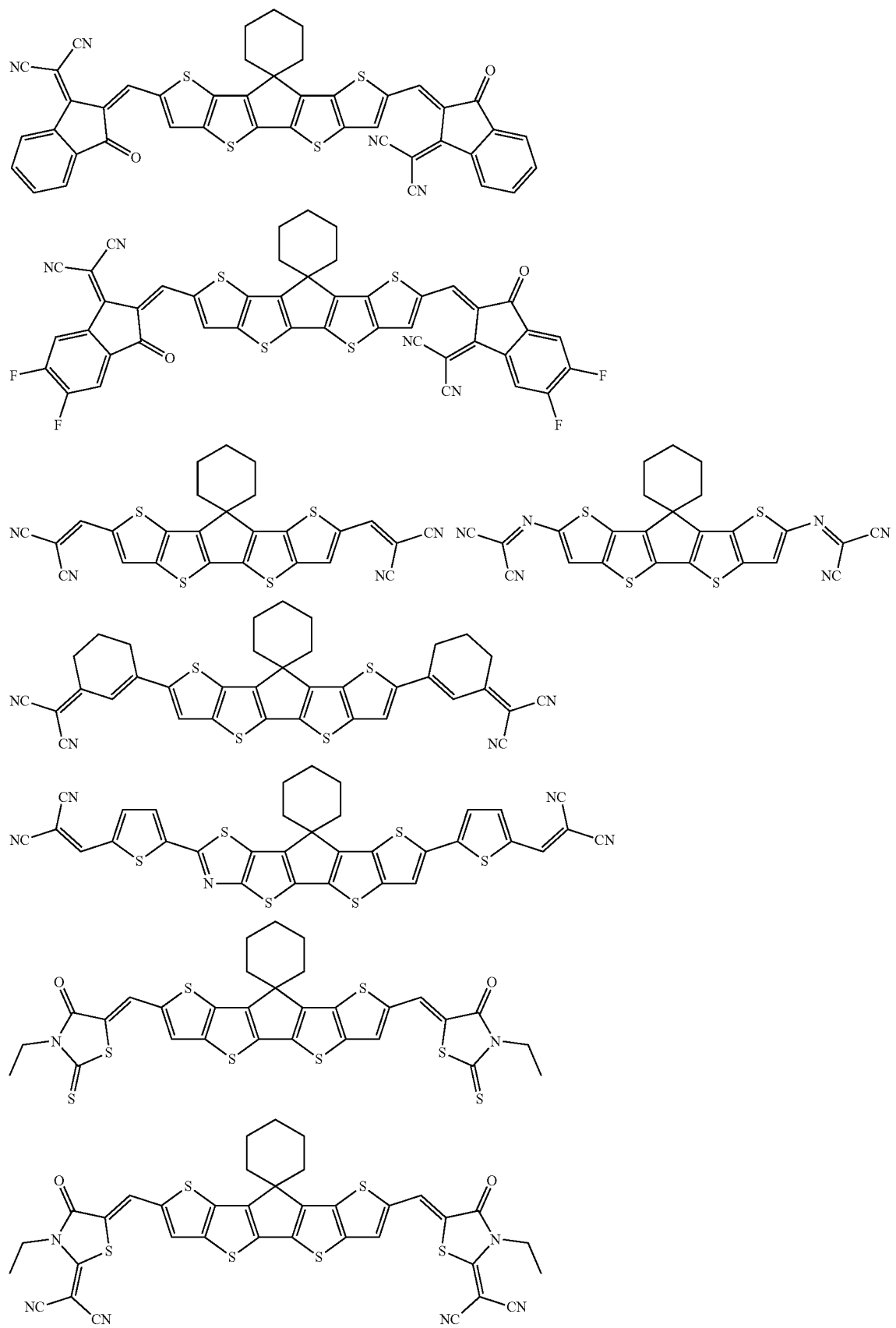

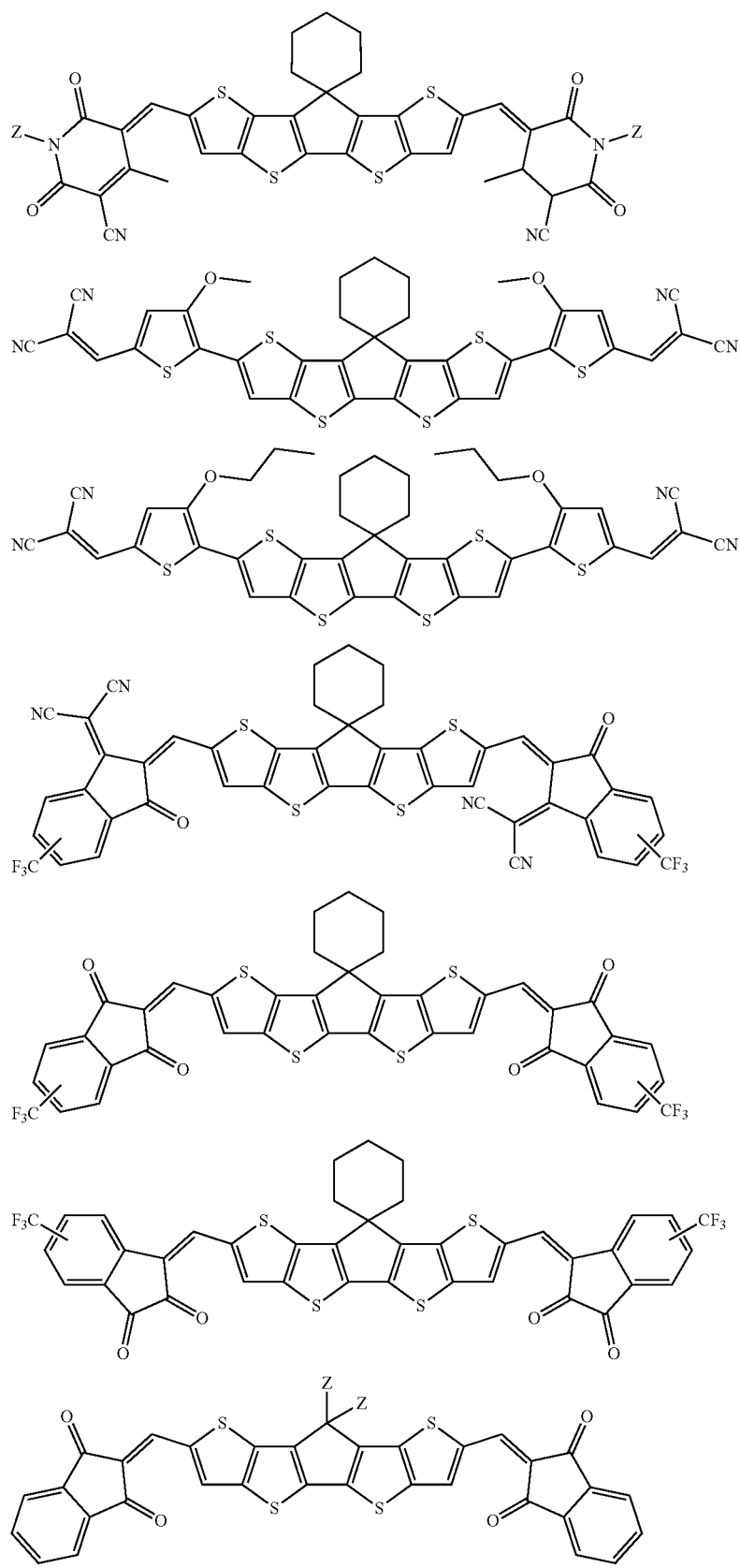

-continued
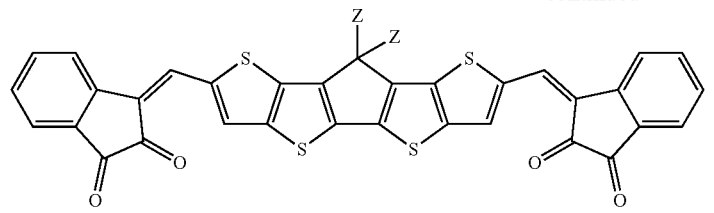
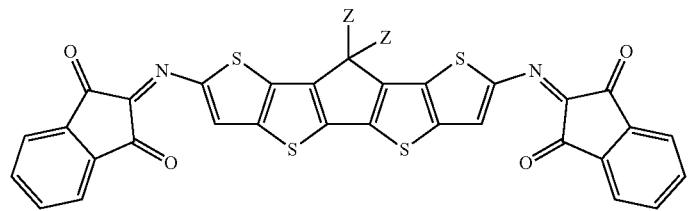
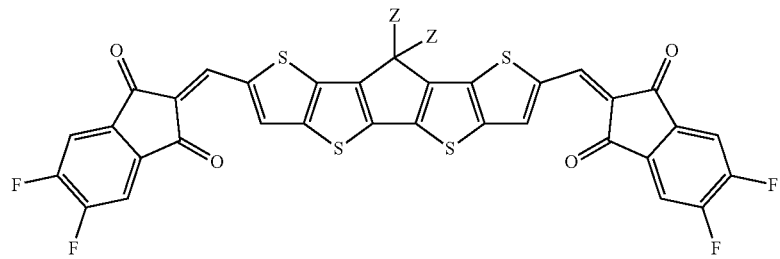
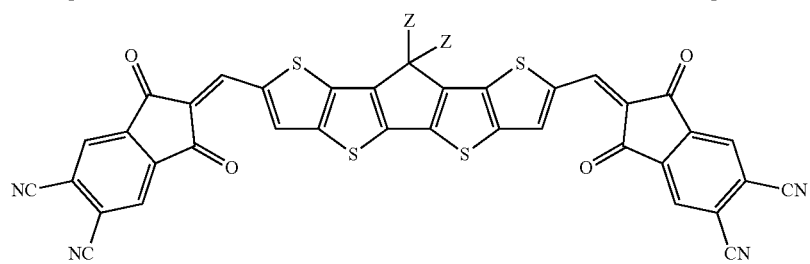
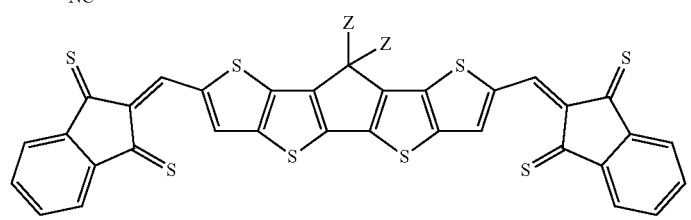
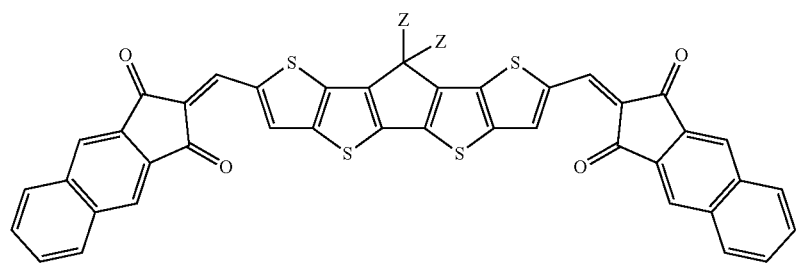
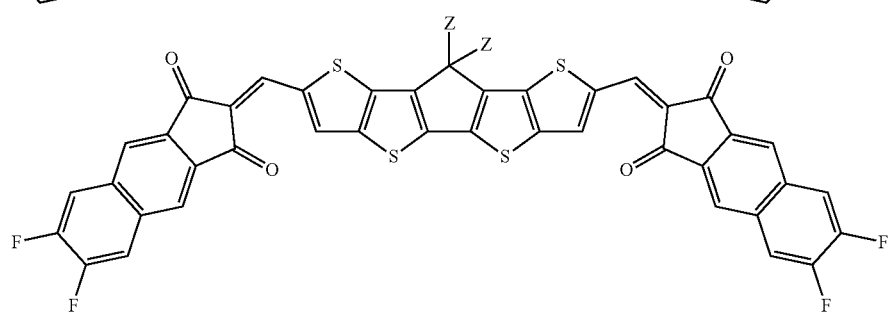

-continued
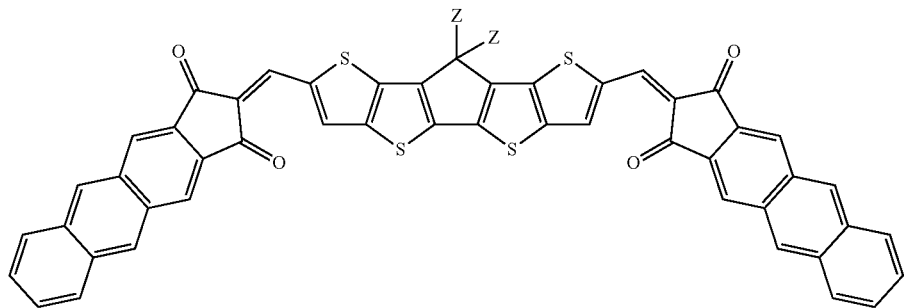
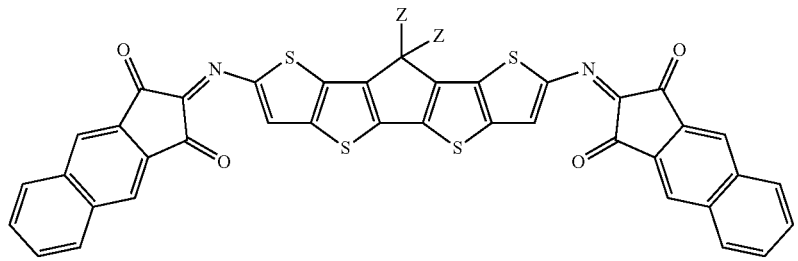
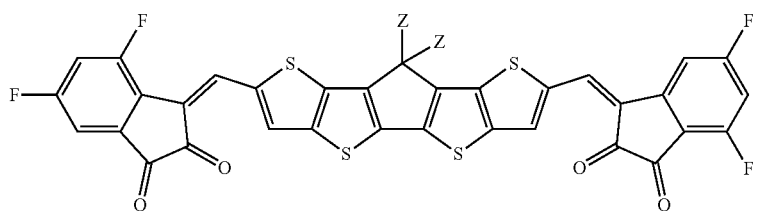
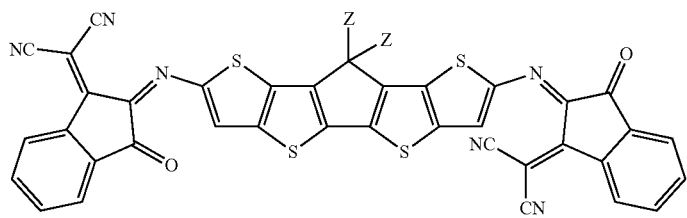
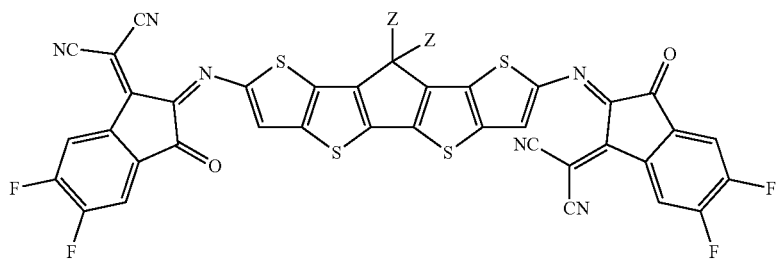
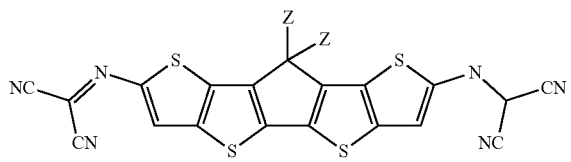
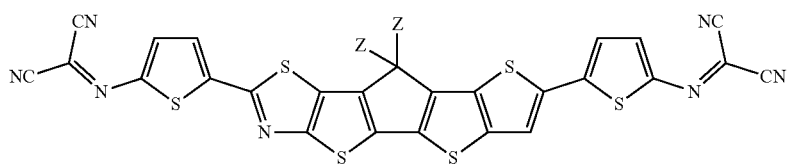

-continued
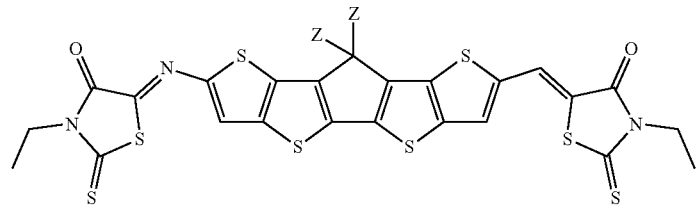
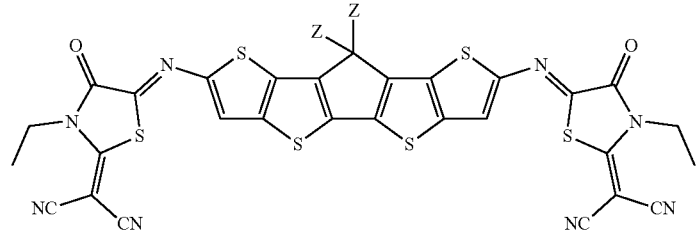
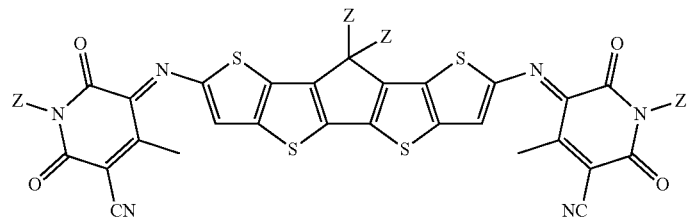
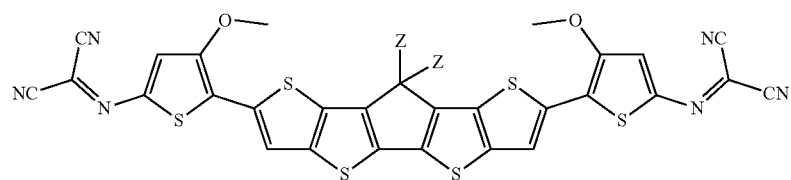
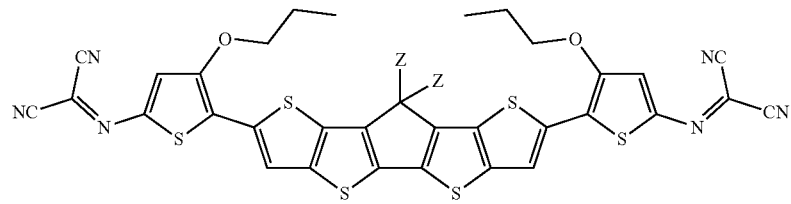
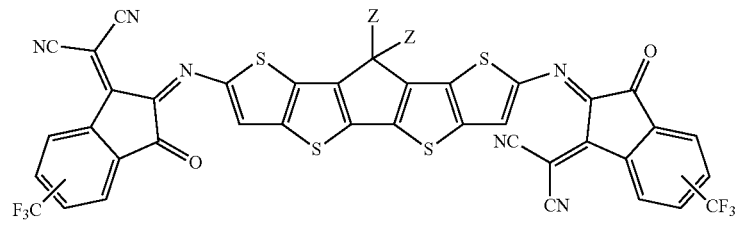
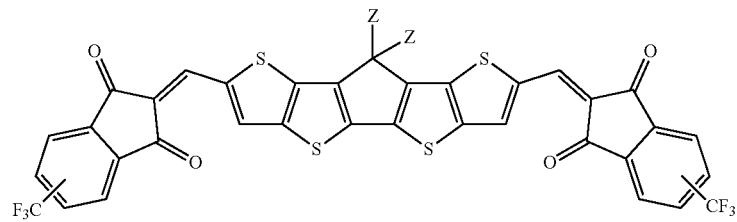
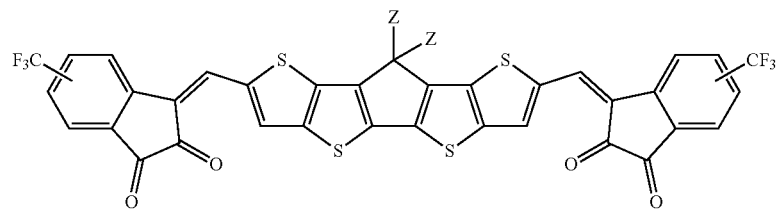

-continued
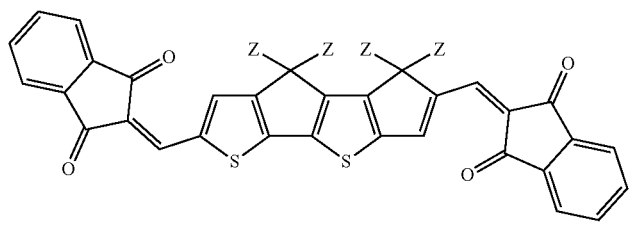
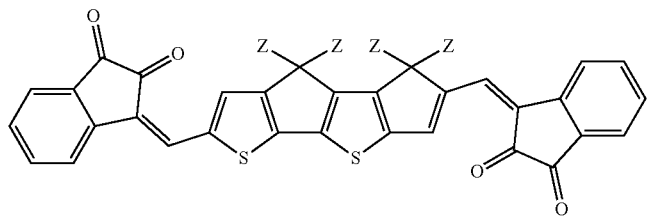
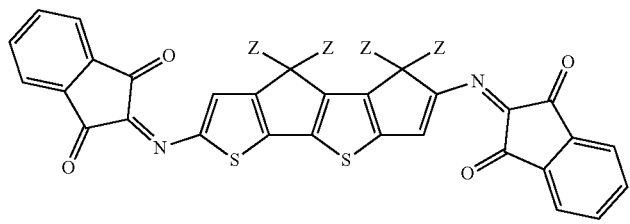
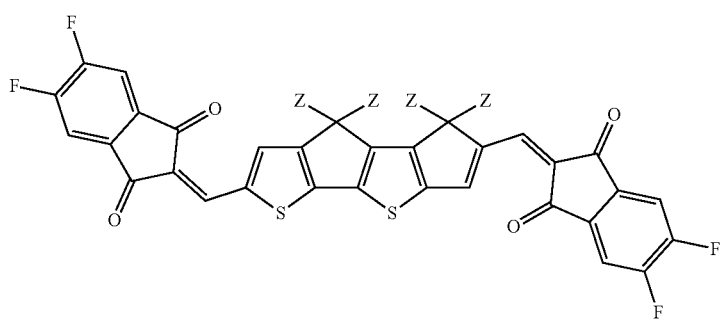
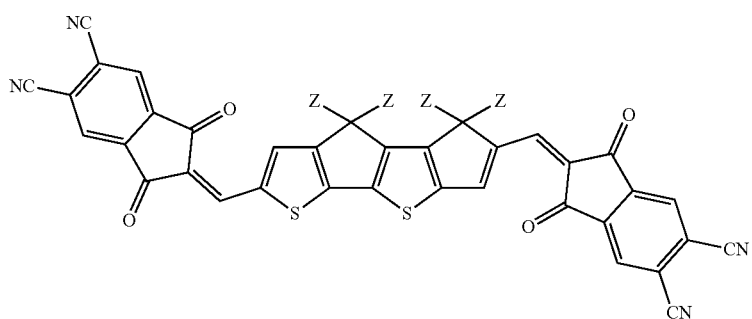
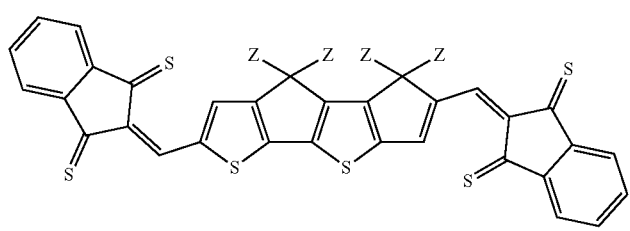

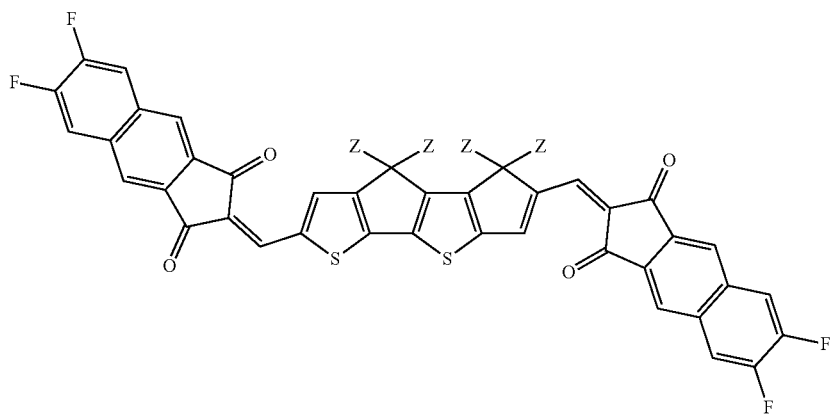
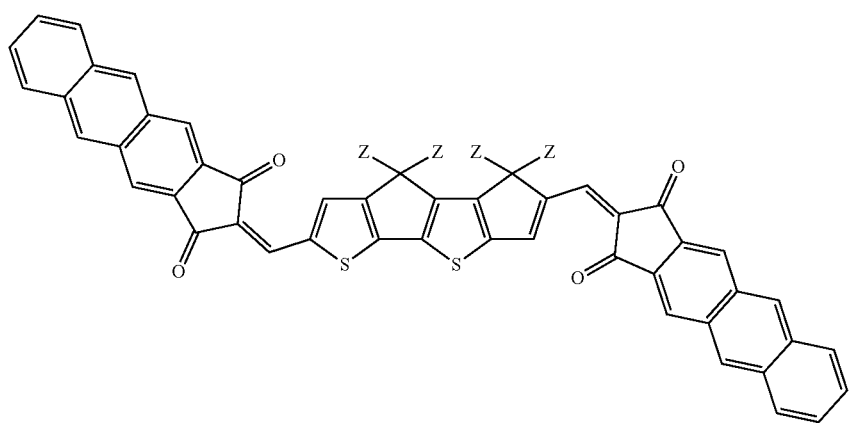
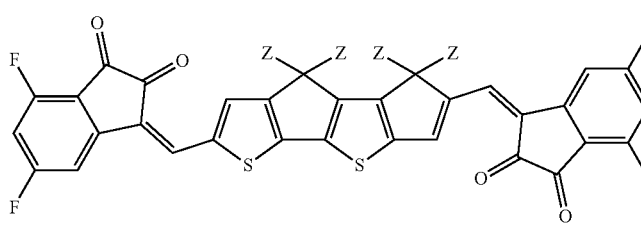
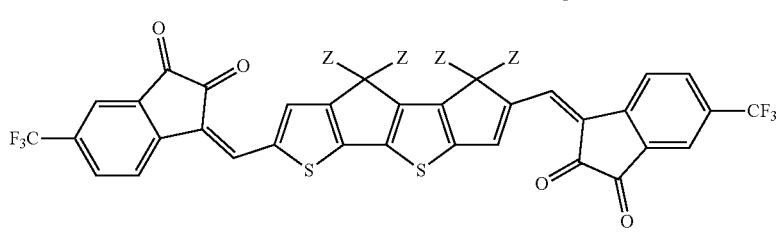
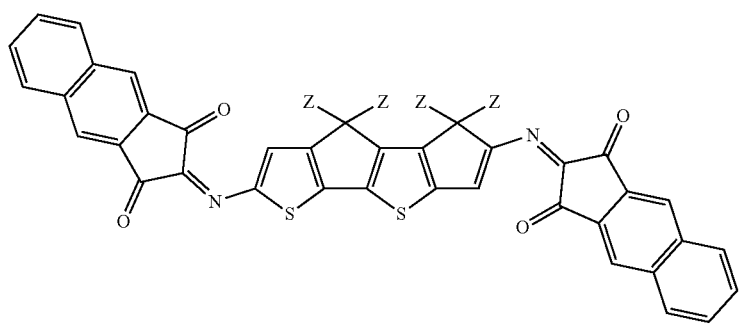

-continued
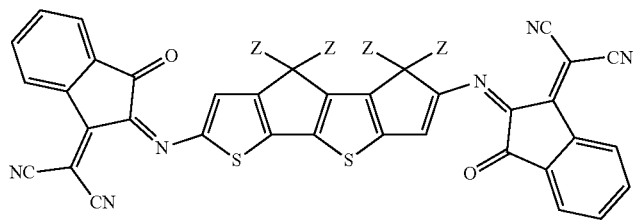
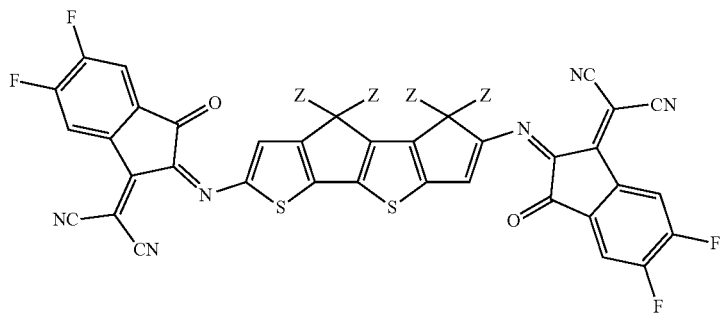
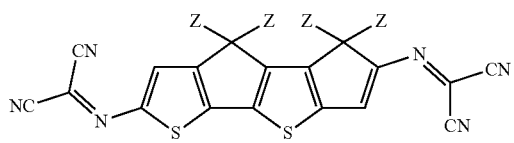
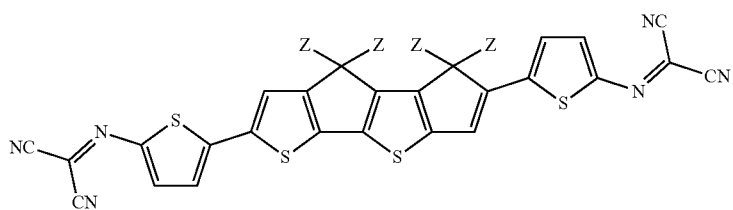
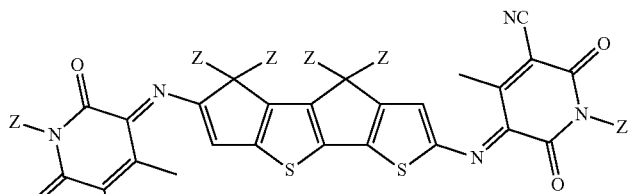
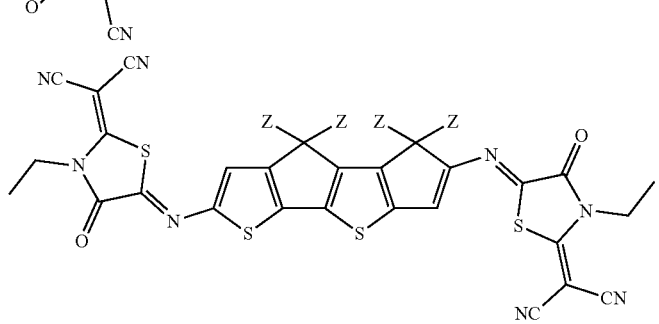
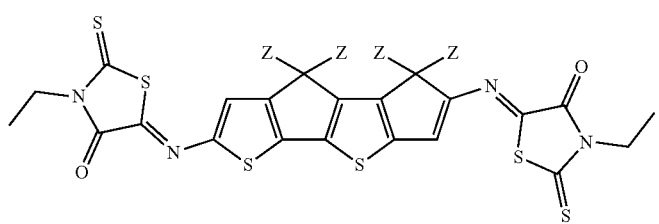

-continued
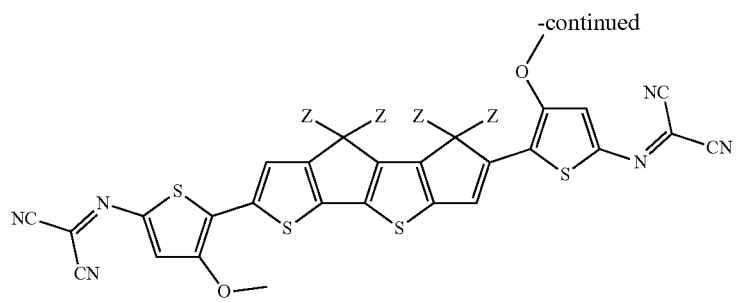
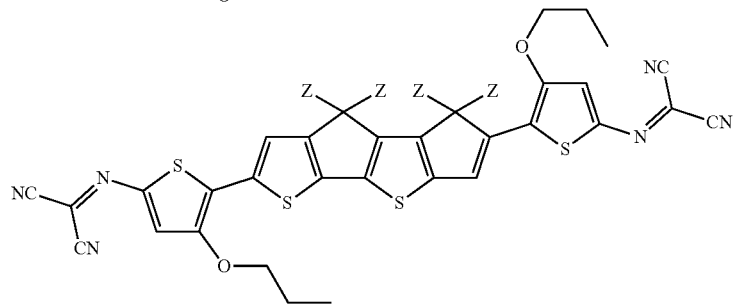
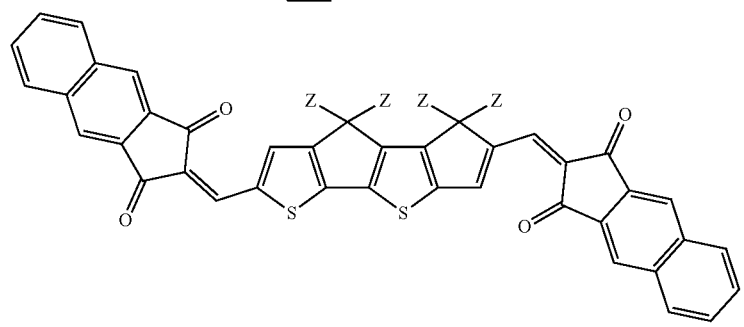
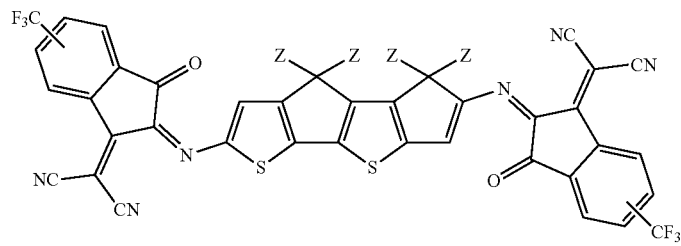
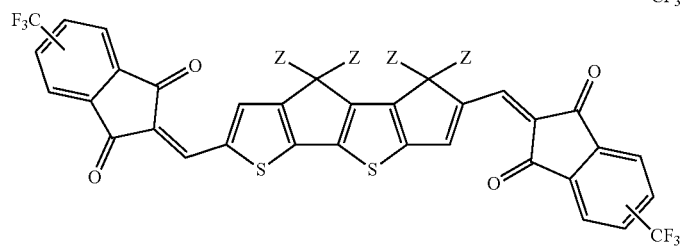
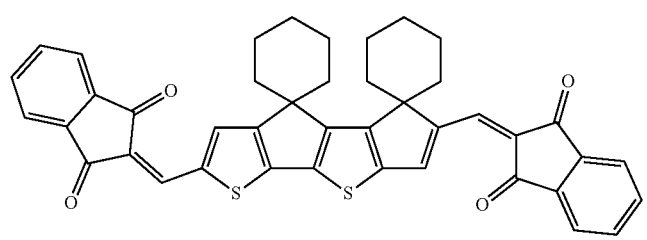

-continued
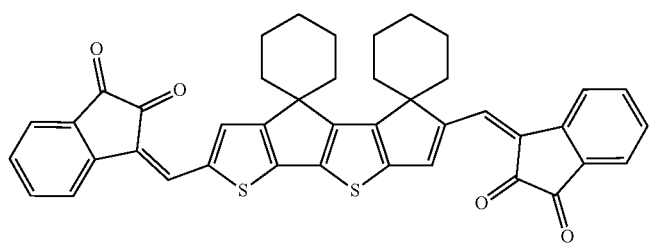
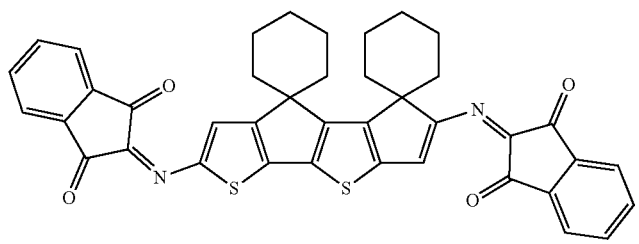
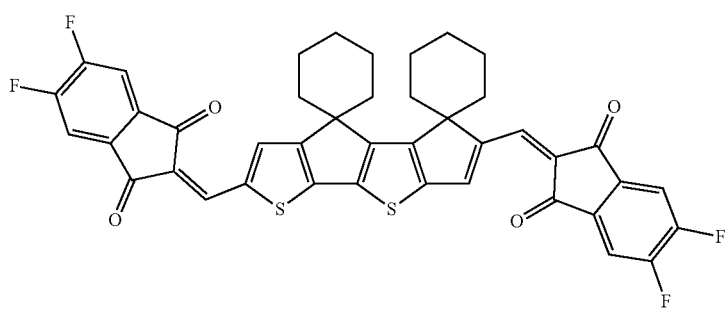
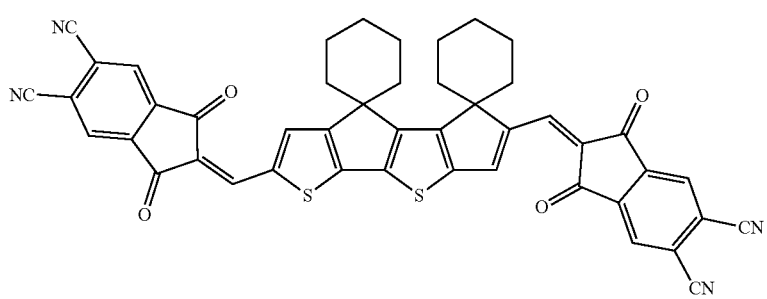
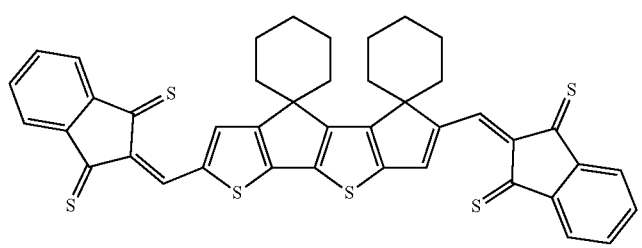
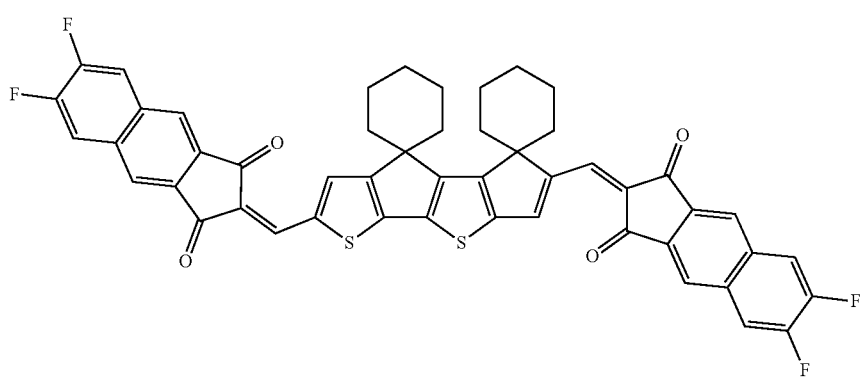

-continued
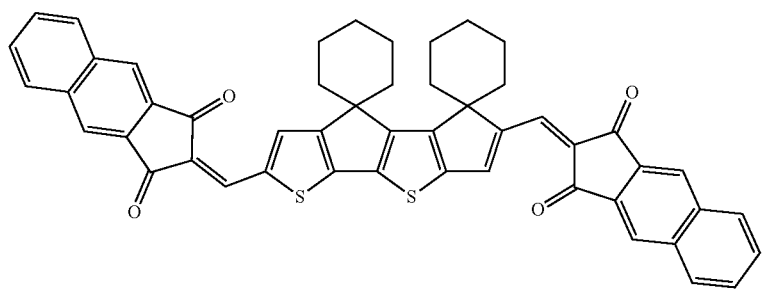
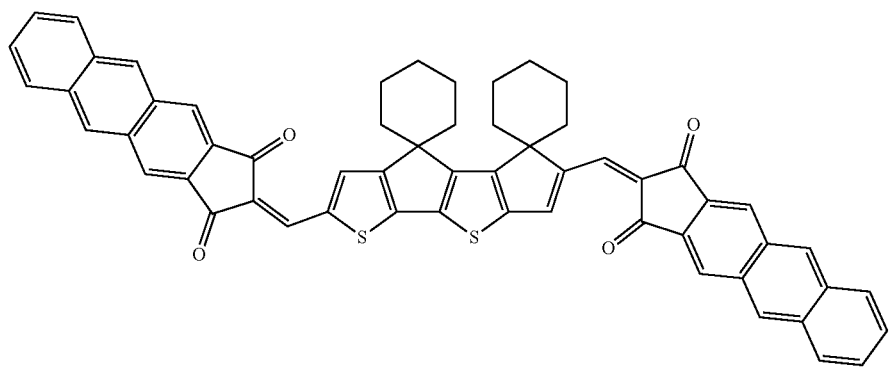
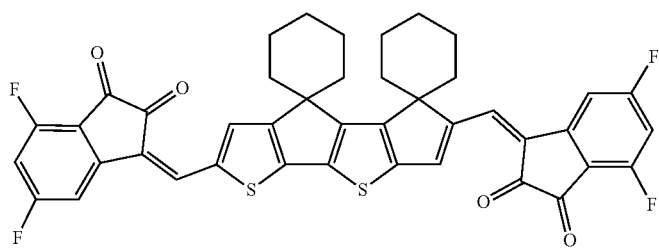
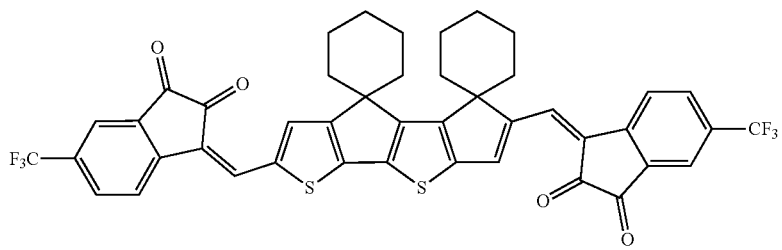
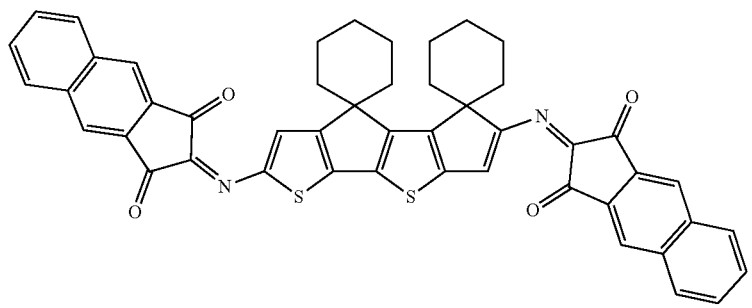
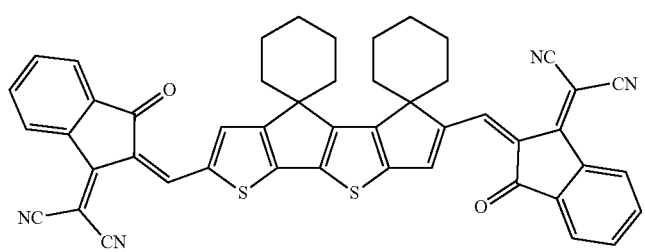

-continued
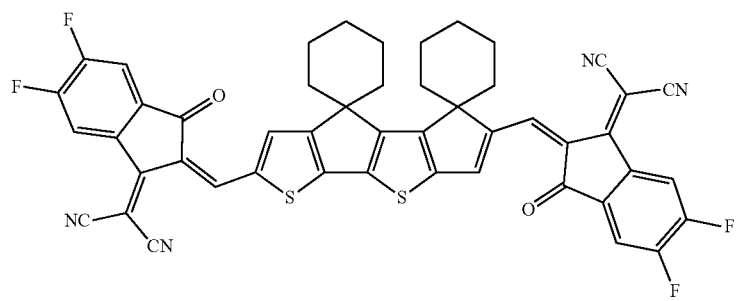
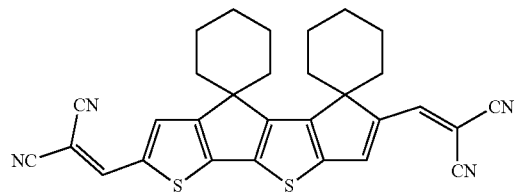
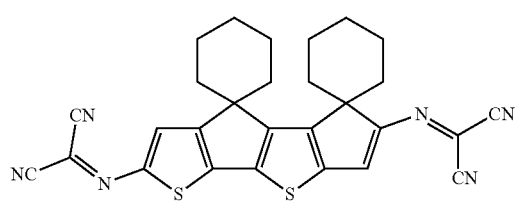
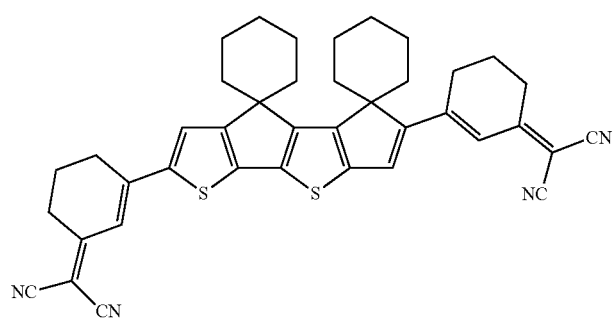
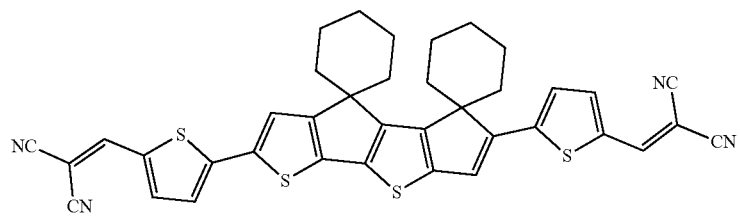
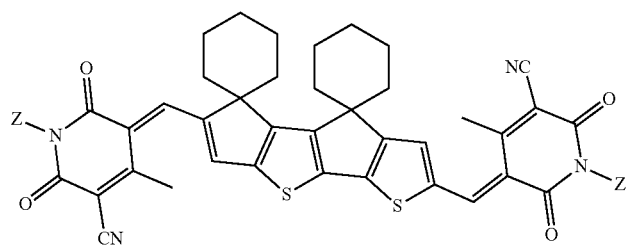
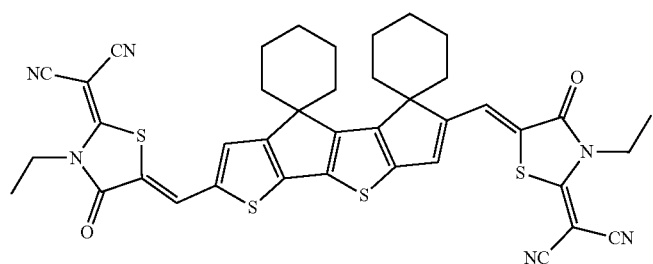

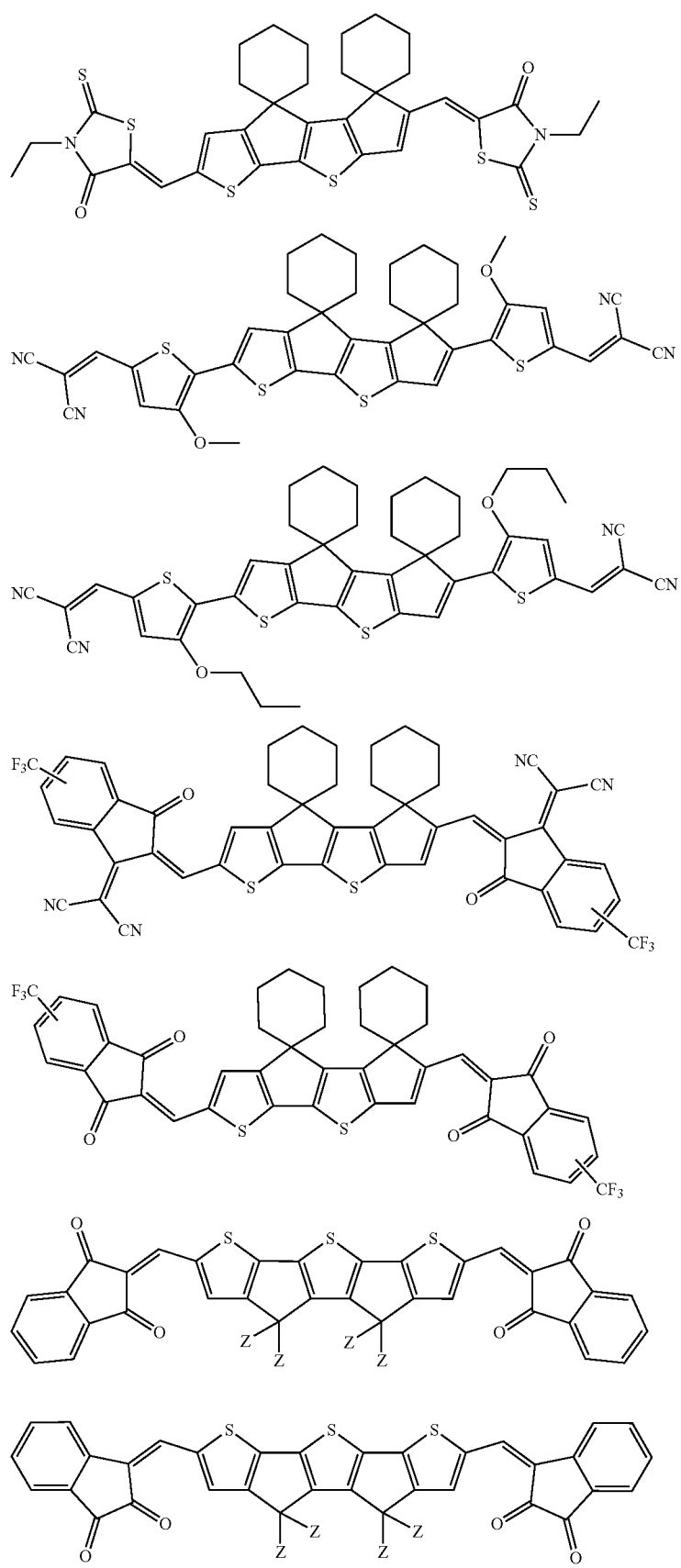

-continued
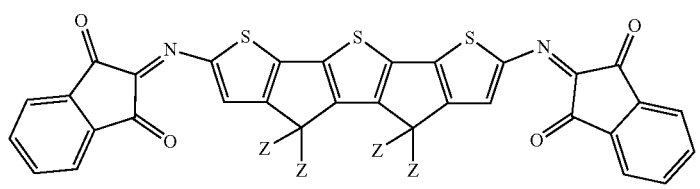
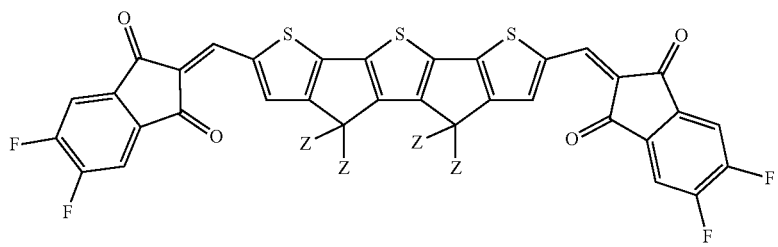
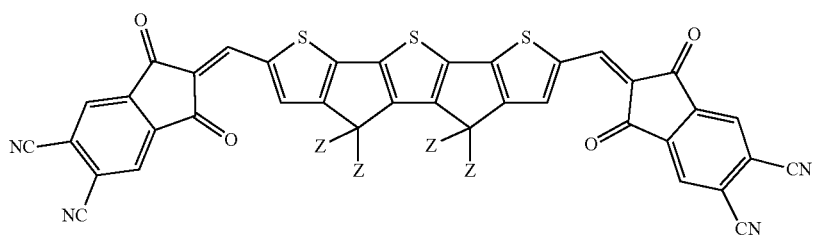
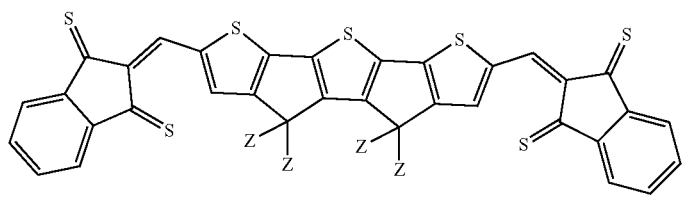
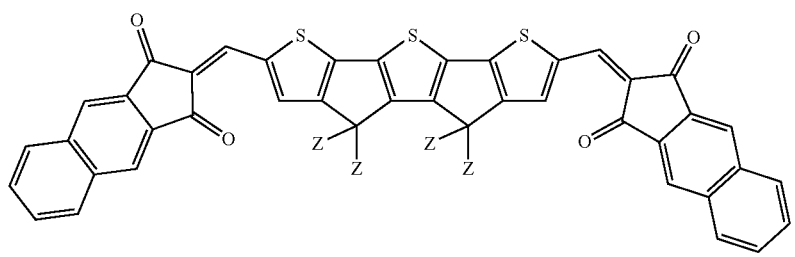
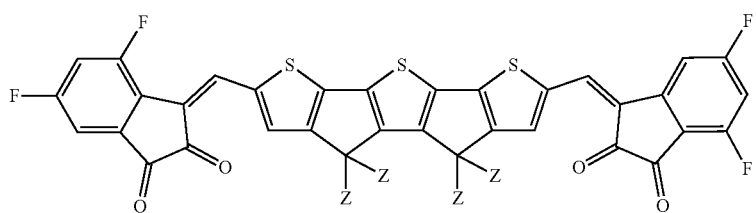
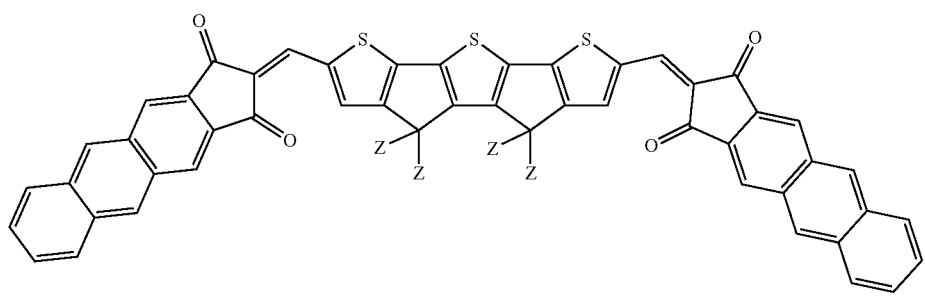

-continued
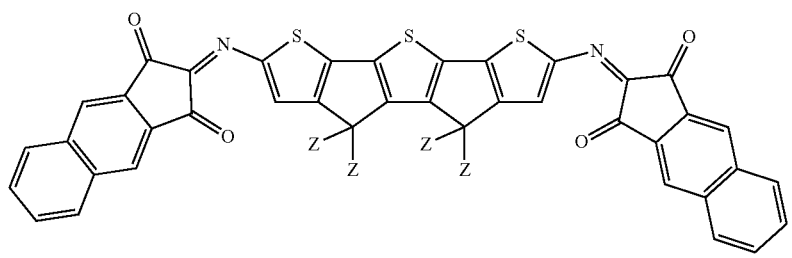
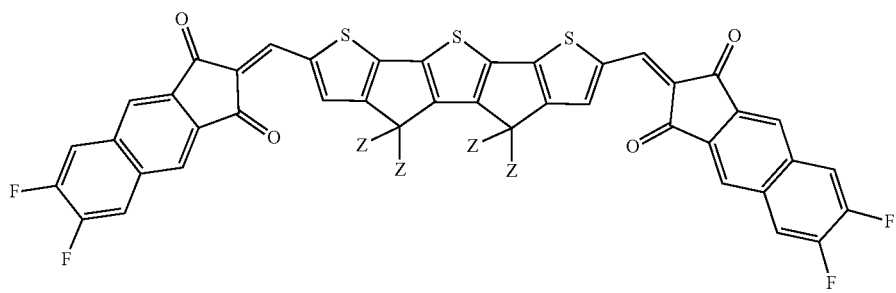
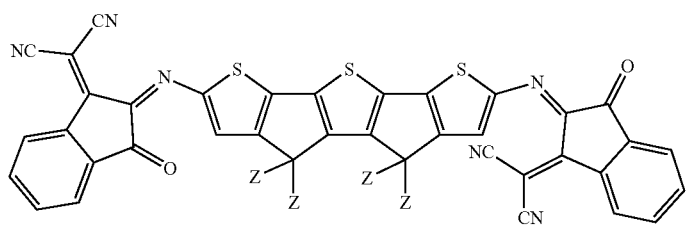
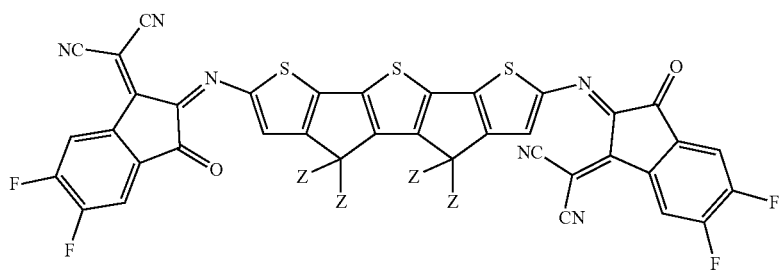
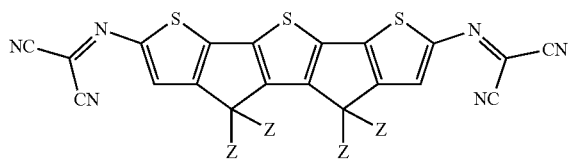
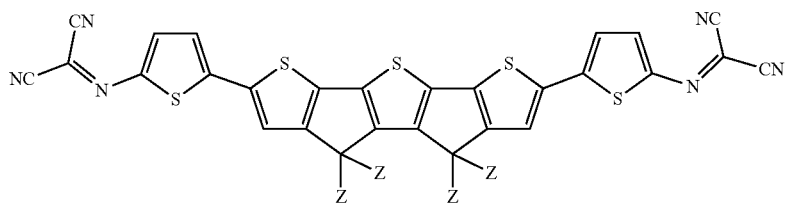
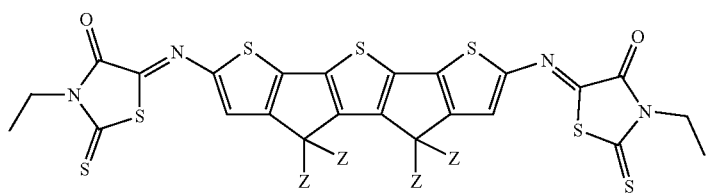

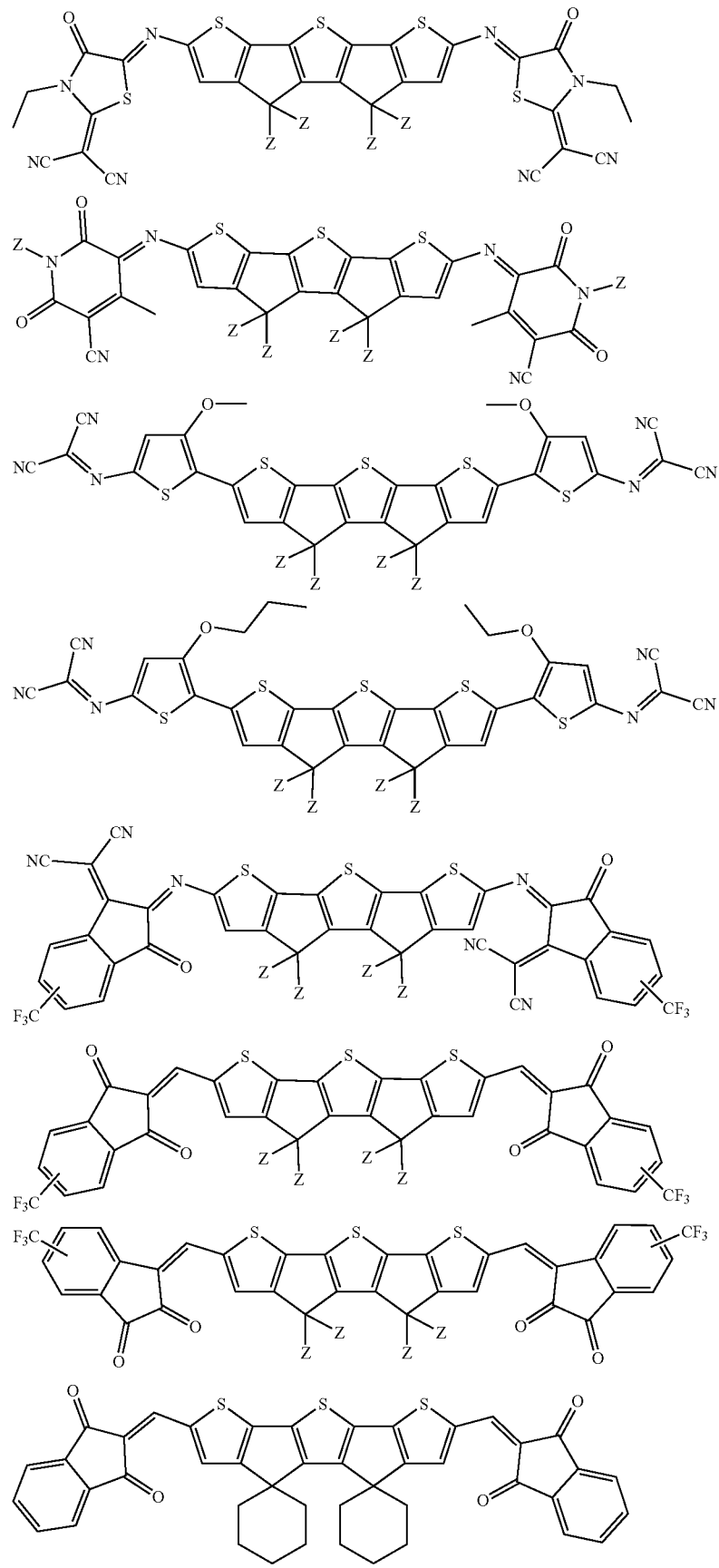
-continued

-continued
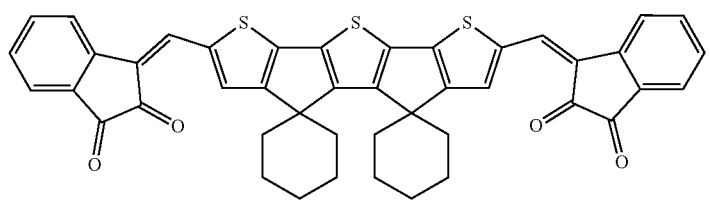
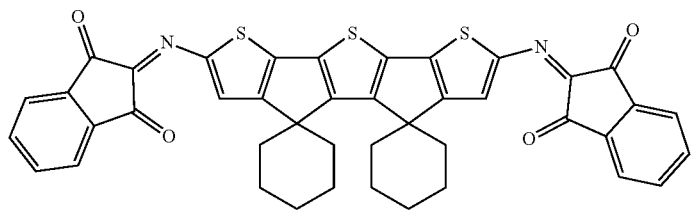
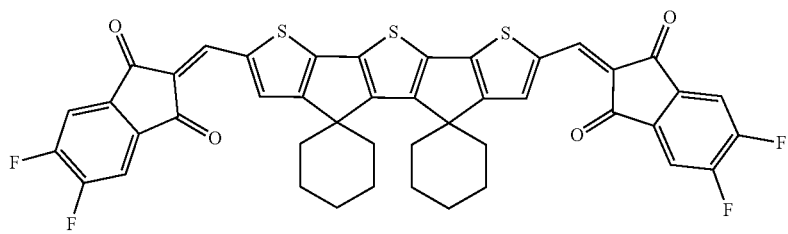
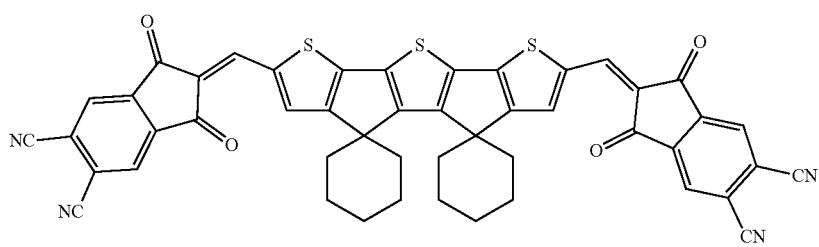
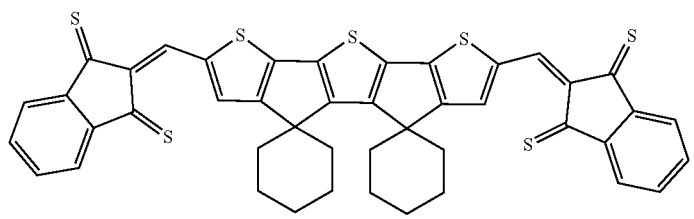
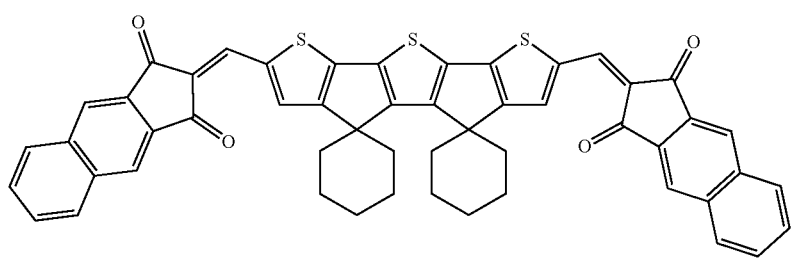
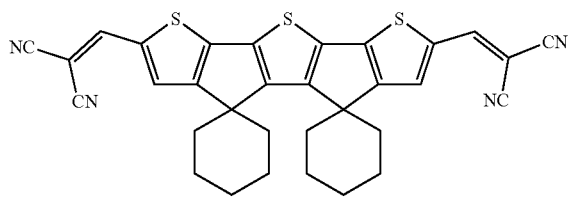

-continued
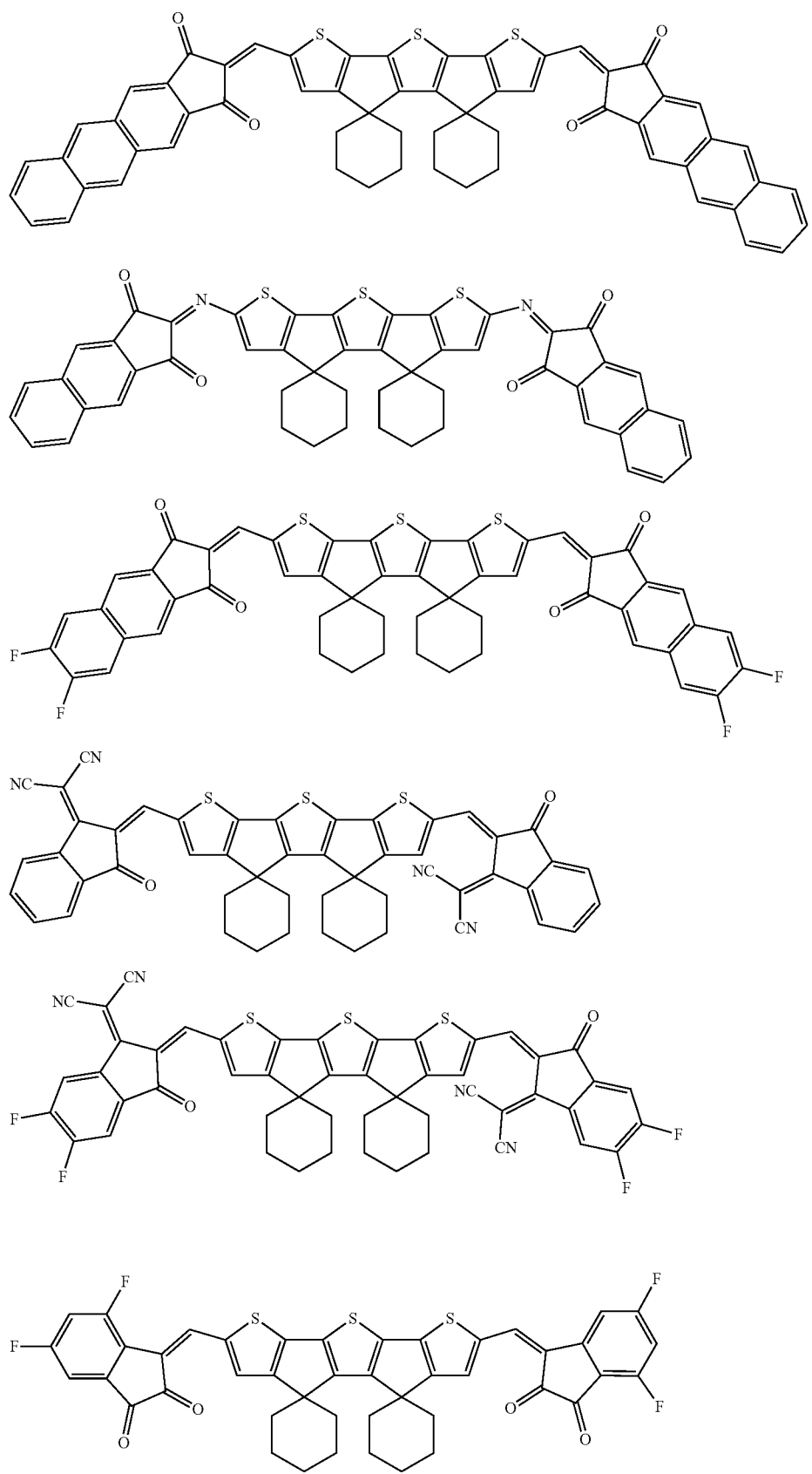

-continued
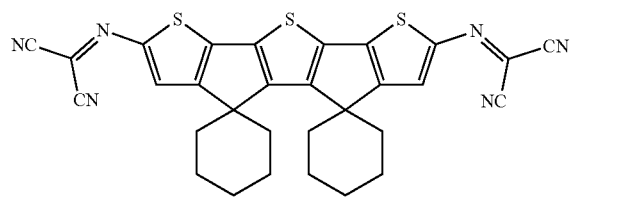
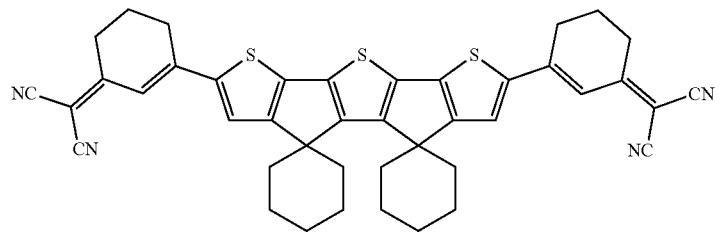
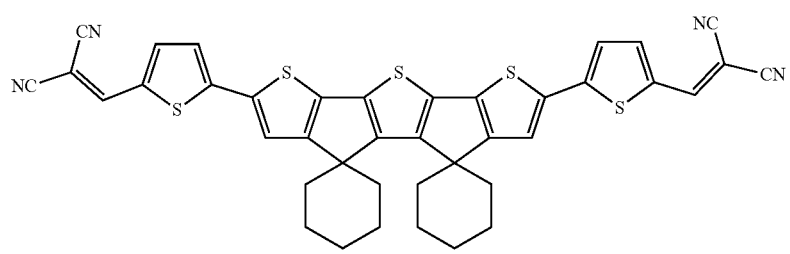
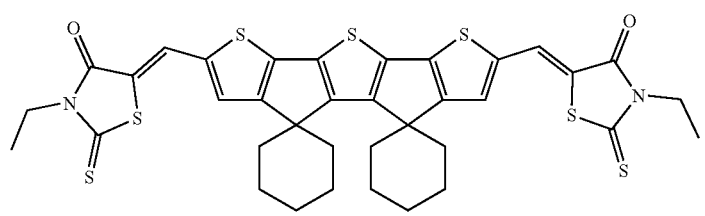
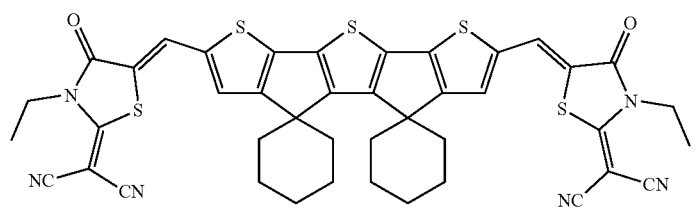
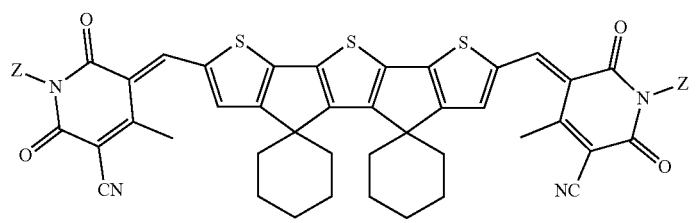
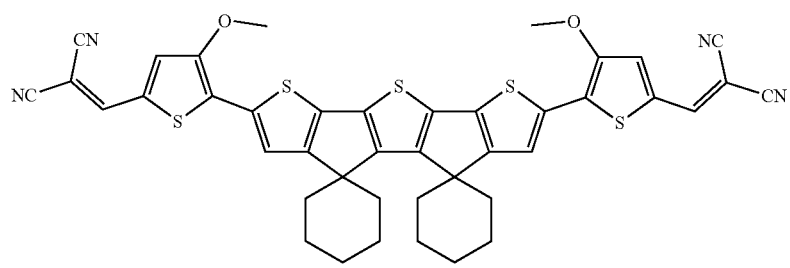

-continued
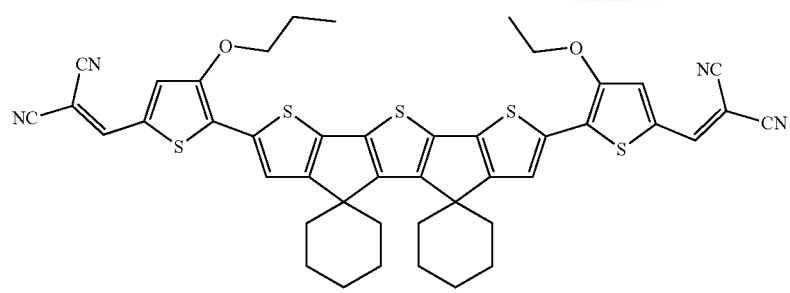
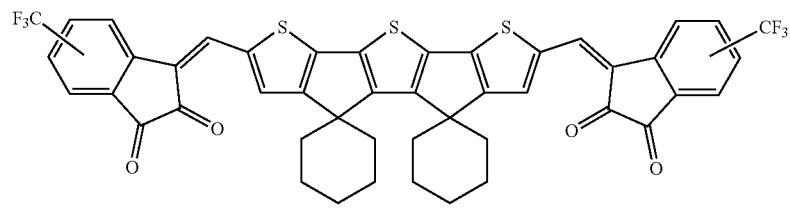
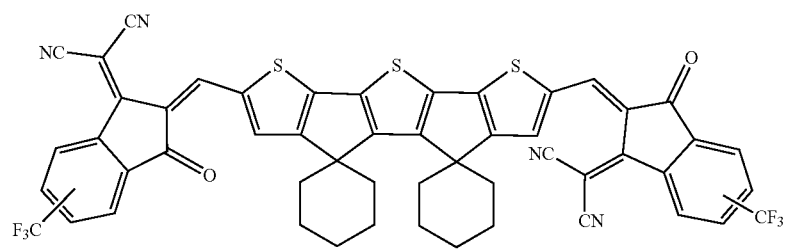
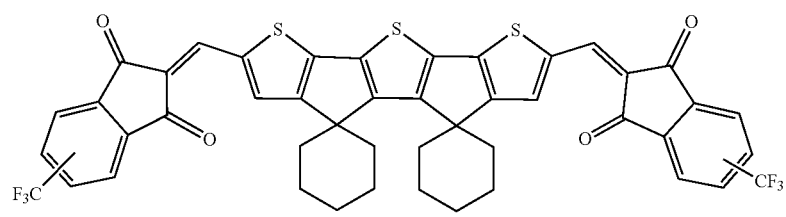
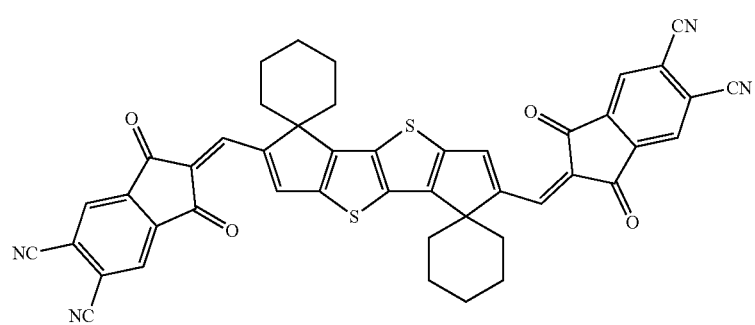
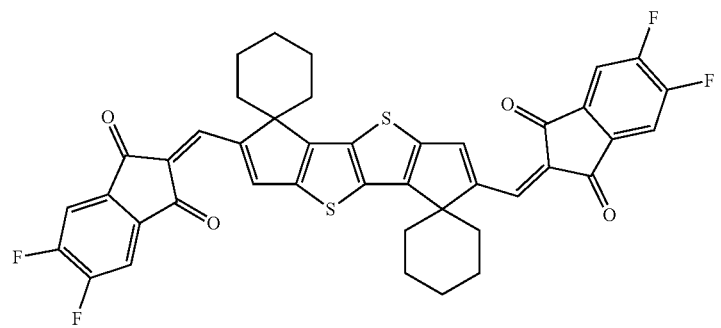

-continued
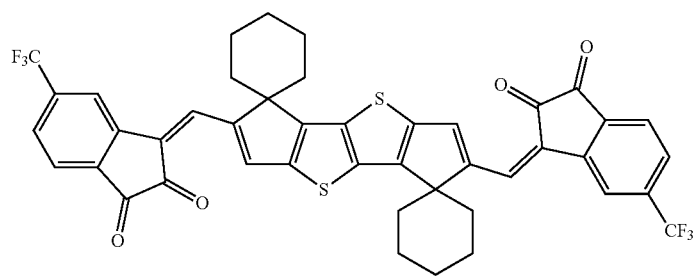
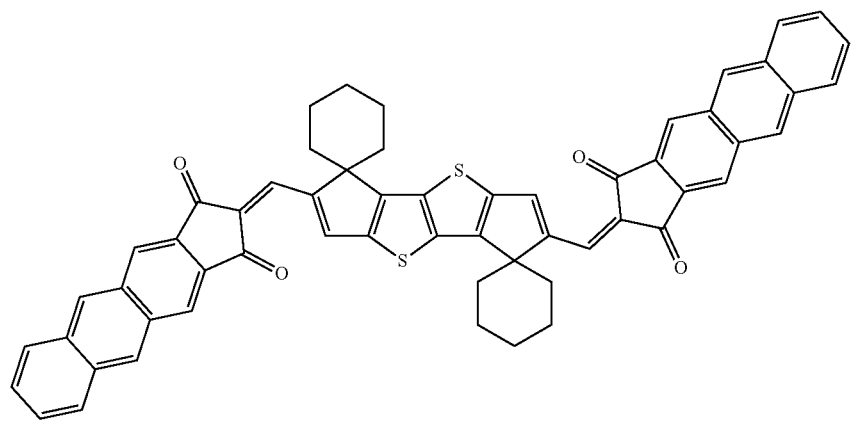
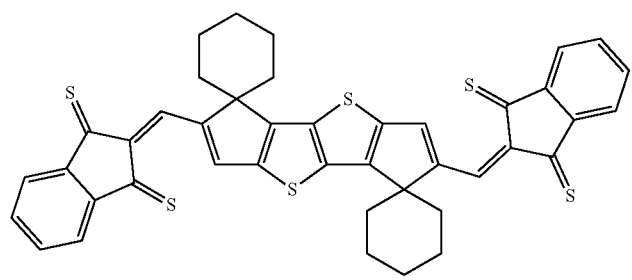
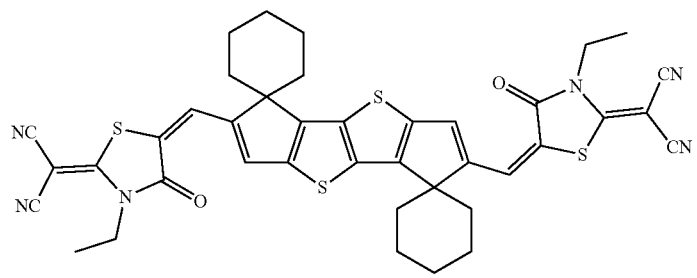
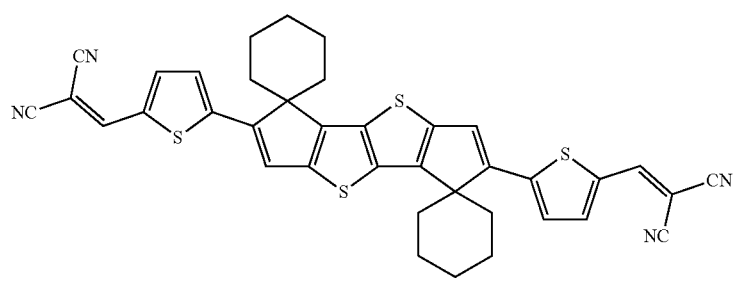

-continued
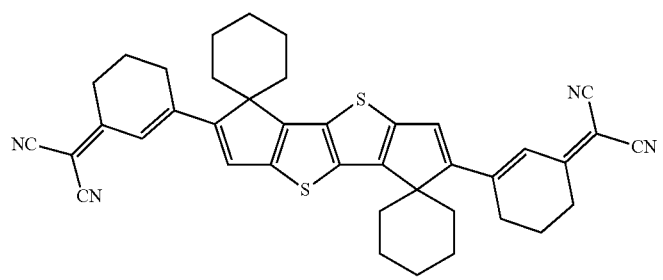
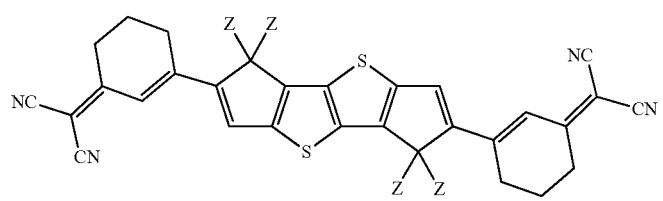
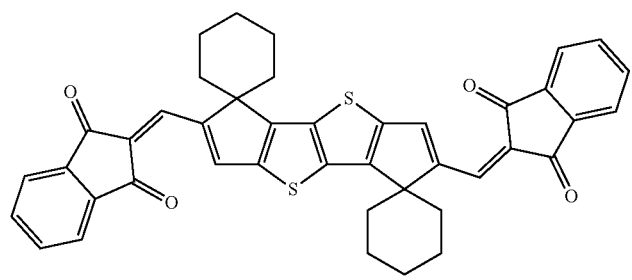
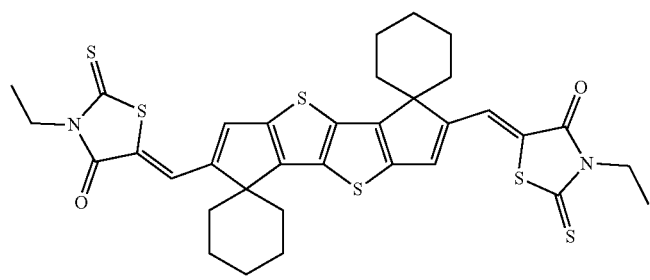
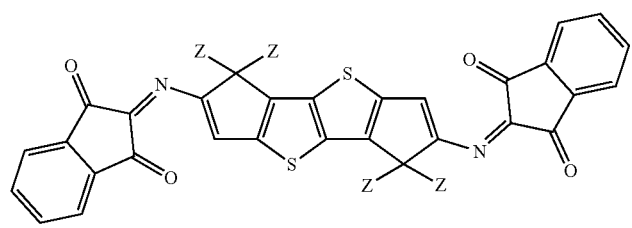
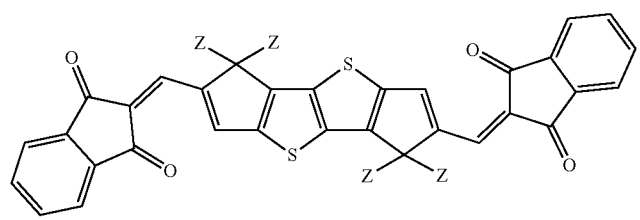

-continued
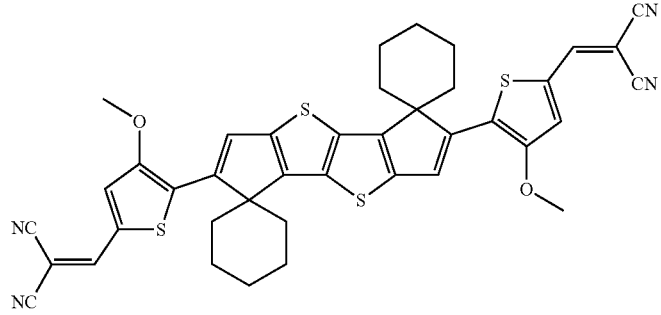
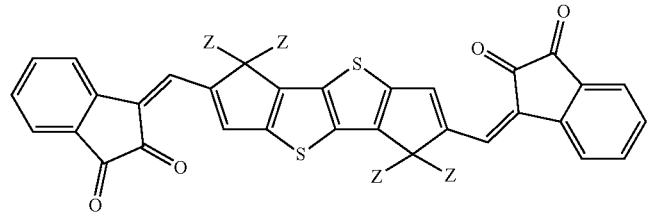
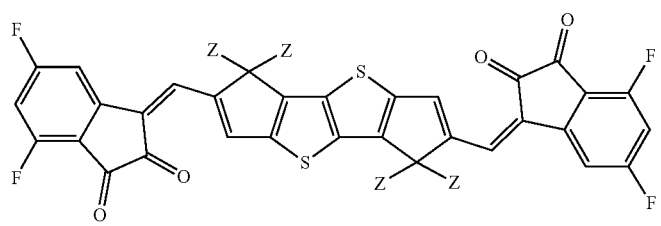
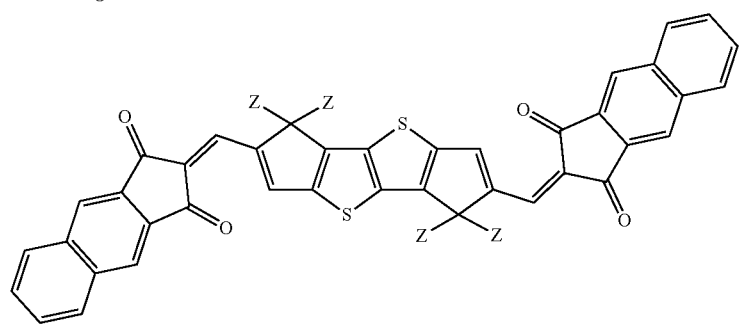
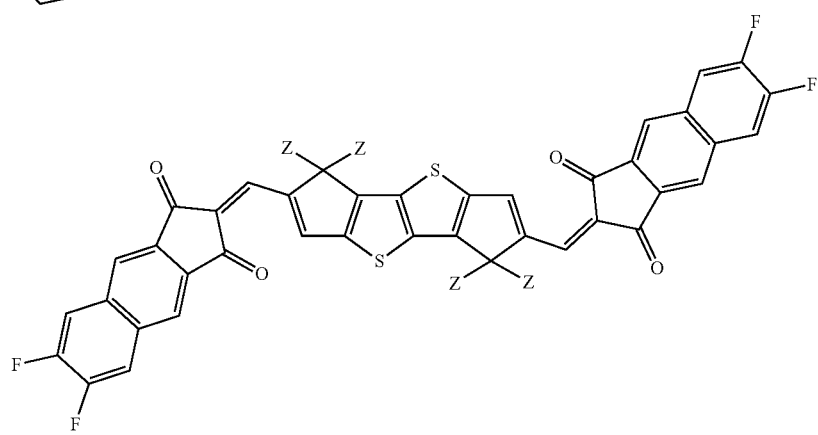
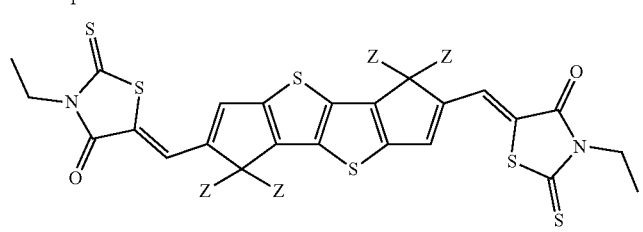

-continued
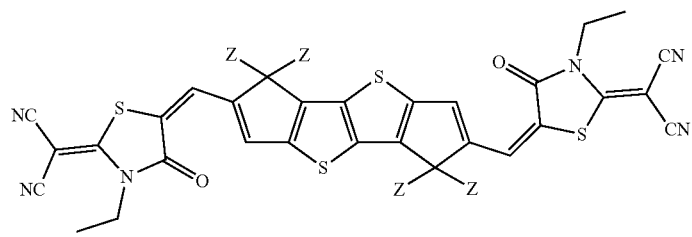
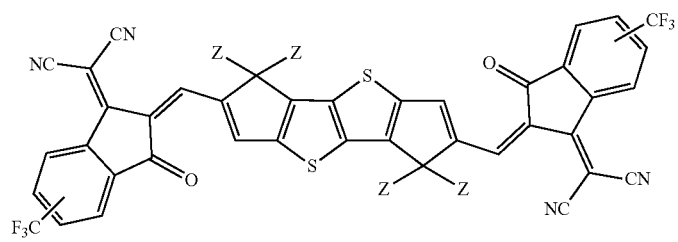
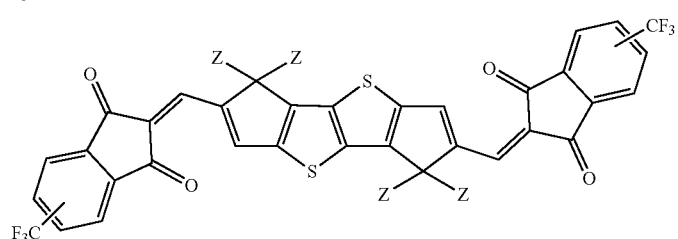
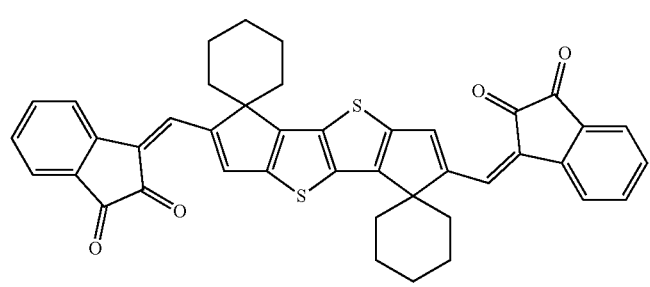
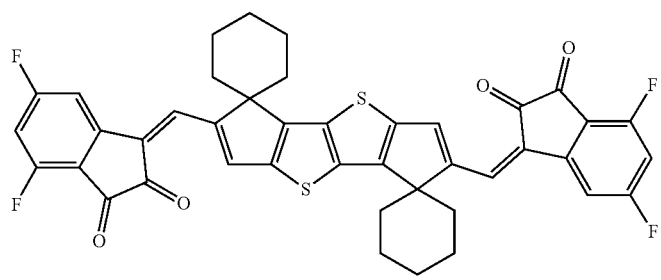
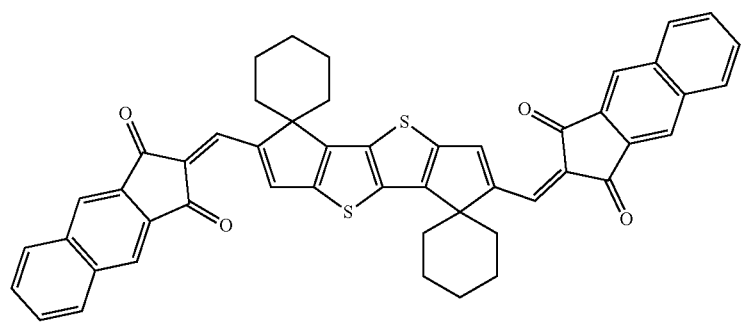

331
-continued
332
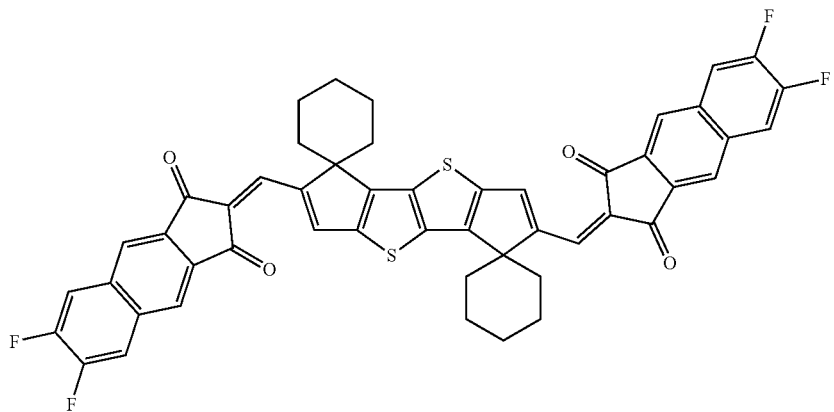
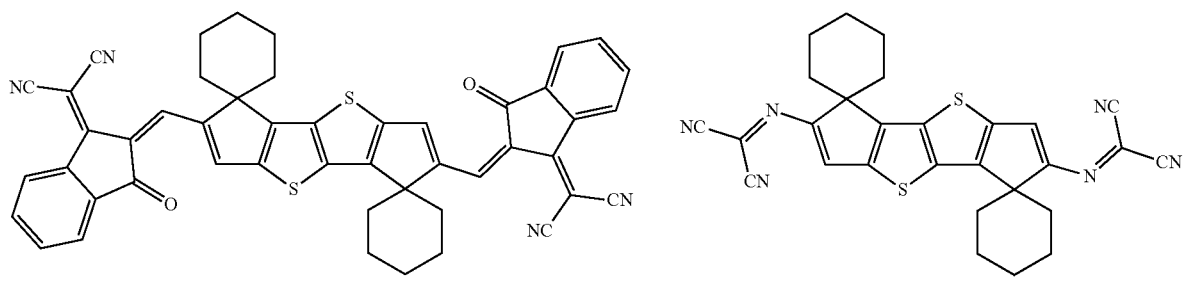
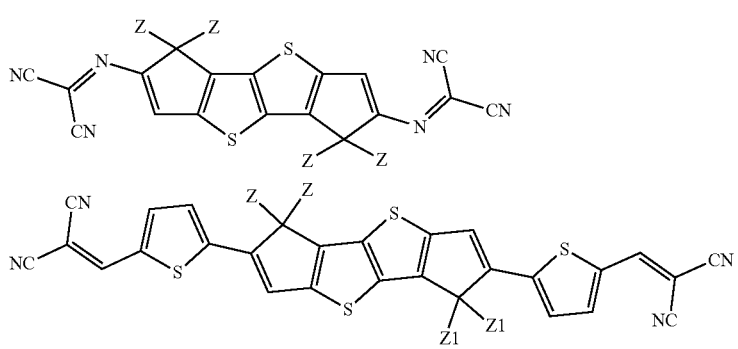
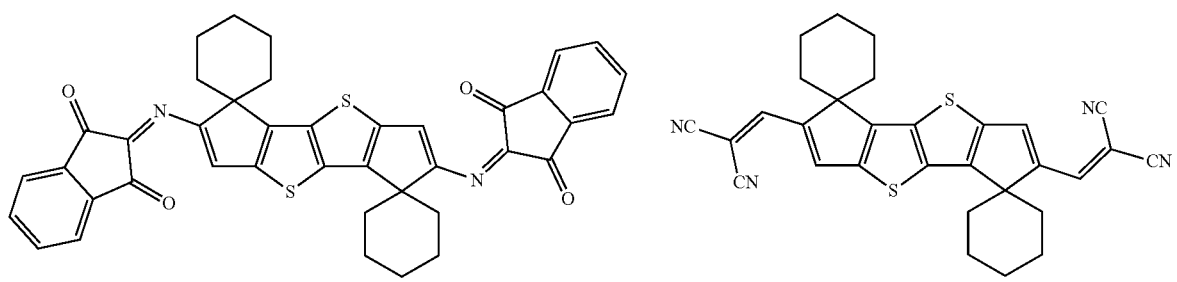
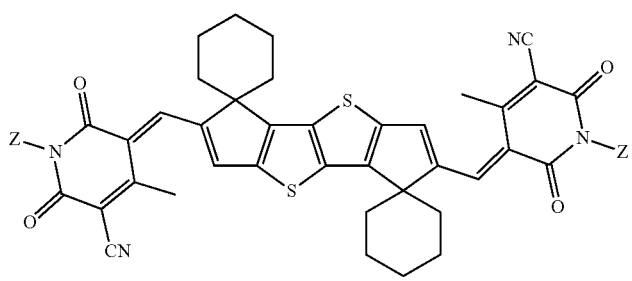

-continued
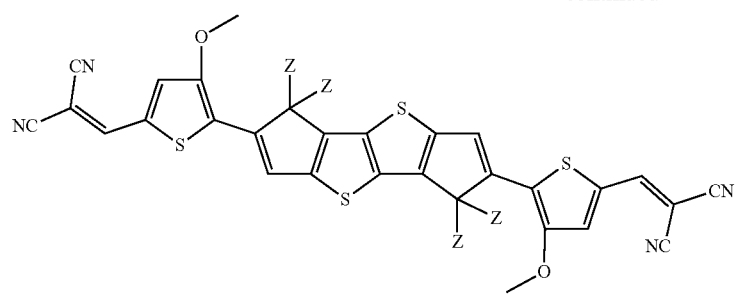
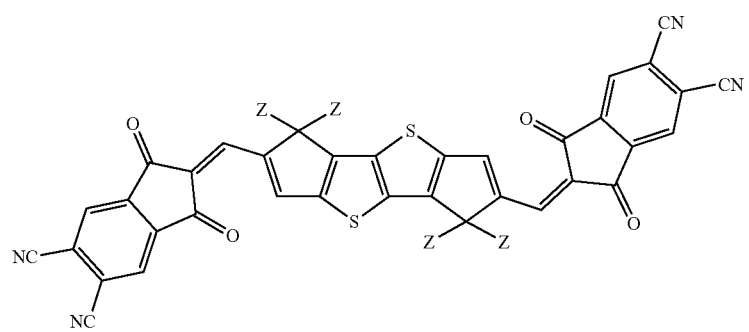
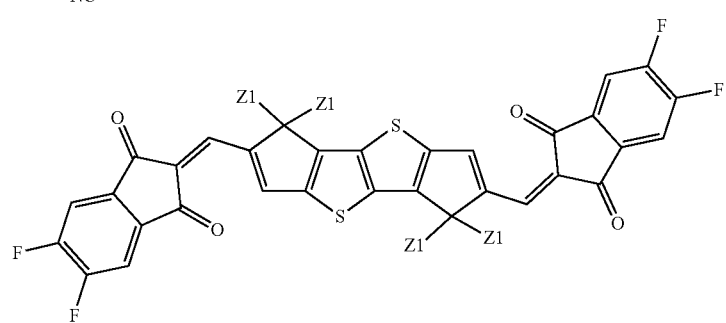
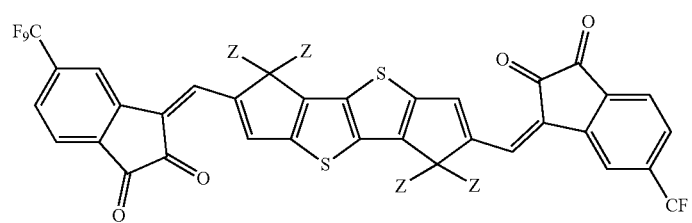
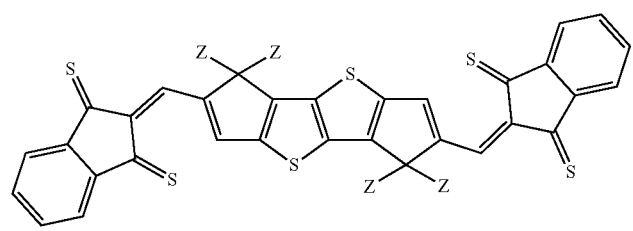

-continued
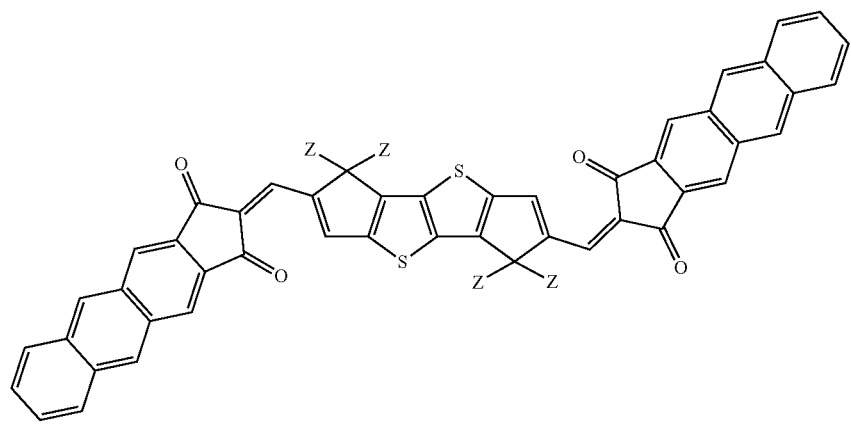
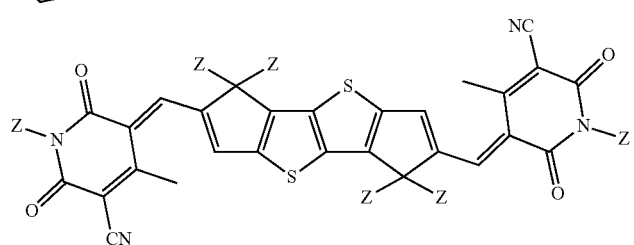
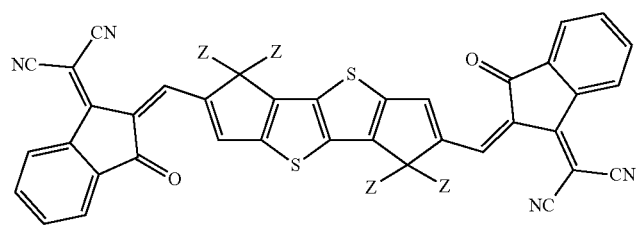
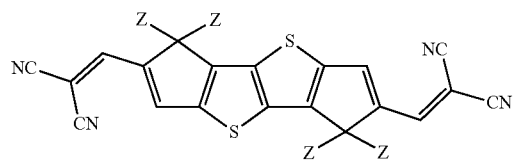
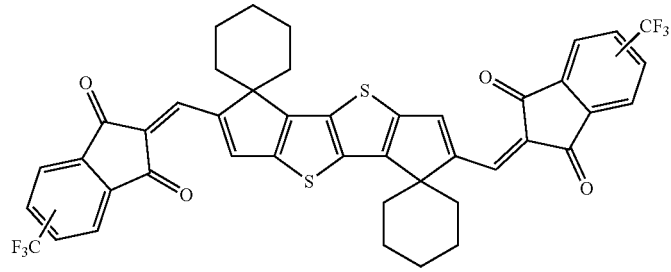
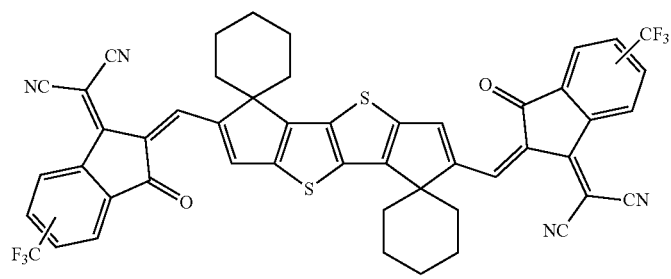

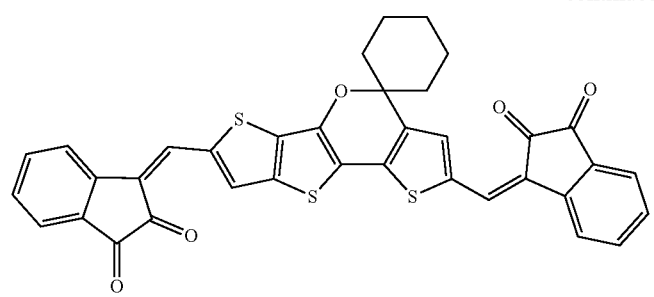
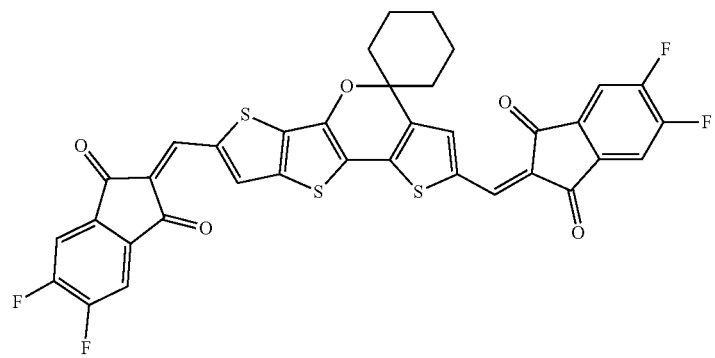
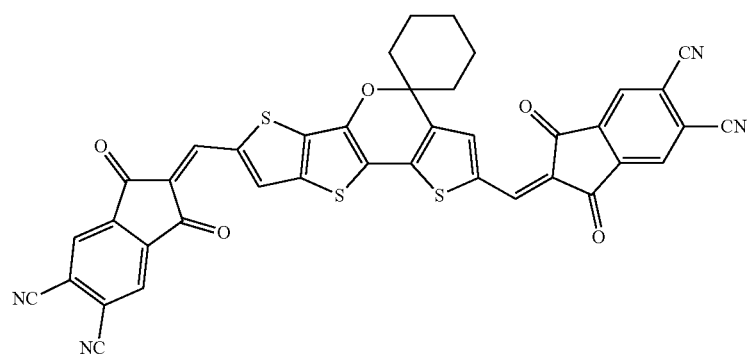
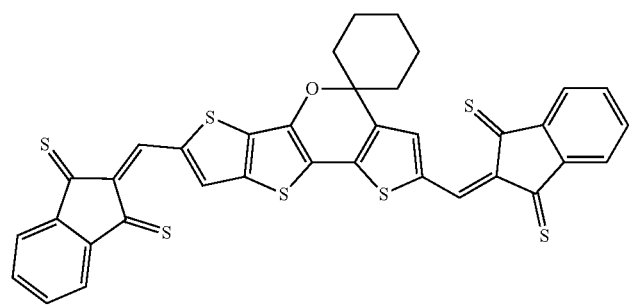
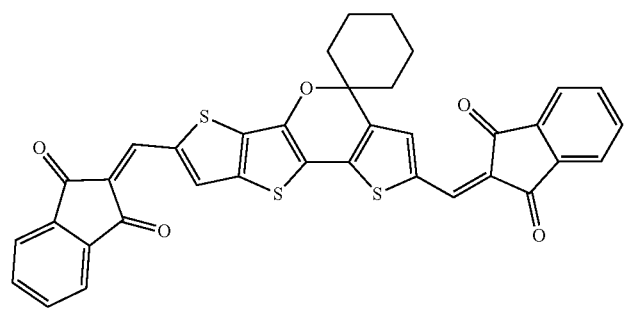

-continued
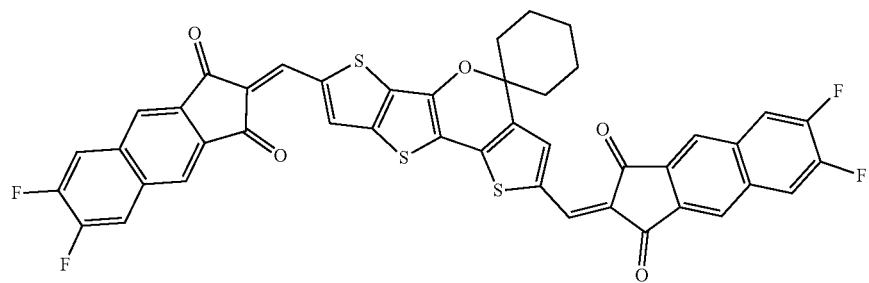
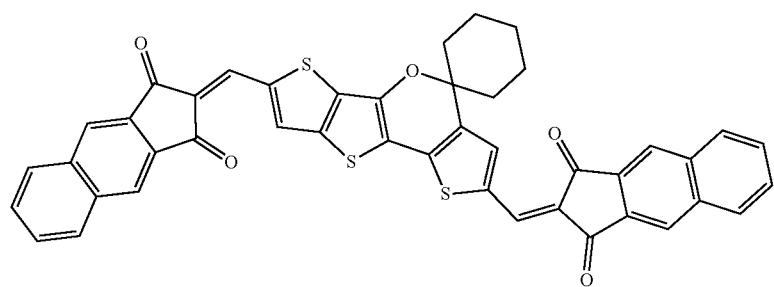
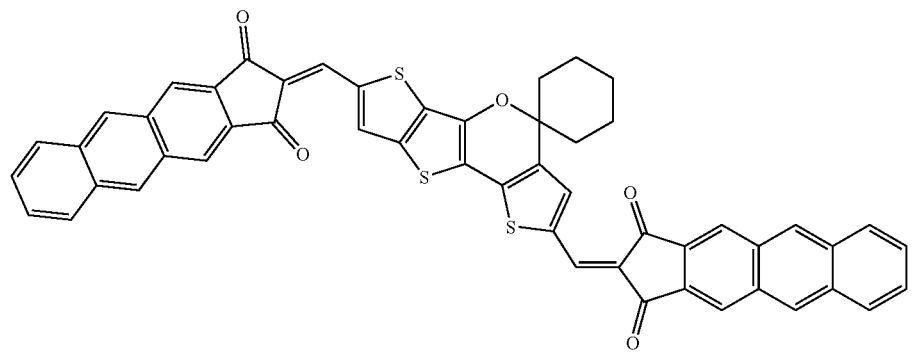
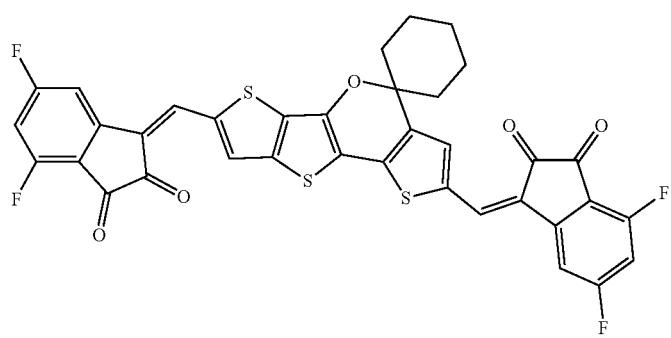
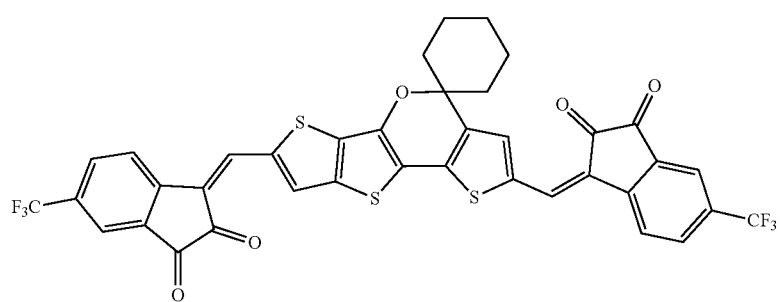

-continued
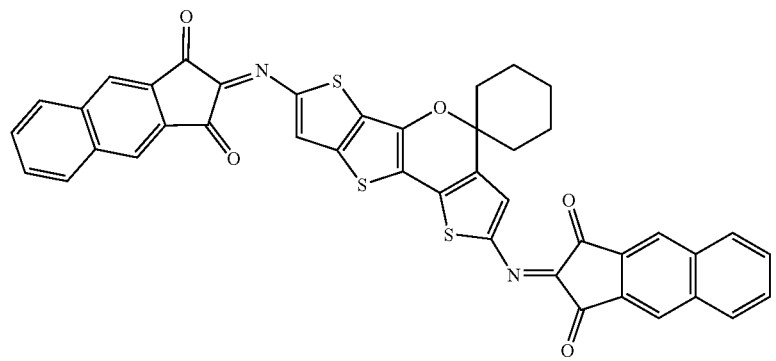
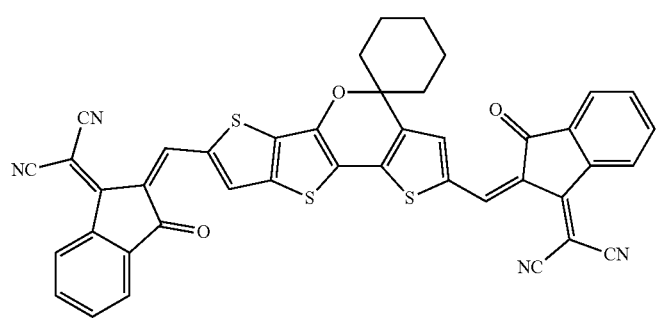 [SMILES: N#CC(C#N)=C1/C(=C/c2cc3c(s2)-c2sc4cc(/C=C5\C(=O)c6ccccc6C5=C(C#N)C#N)sc4c2OC32CCCCC2)C(=O)c2ccccc21]
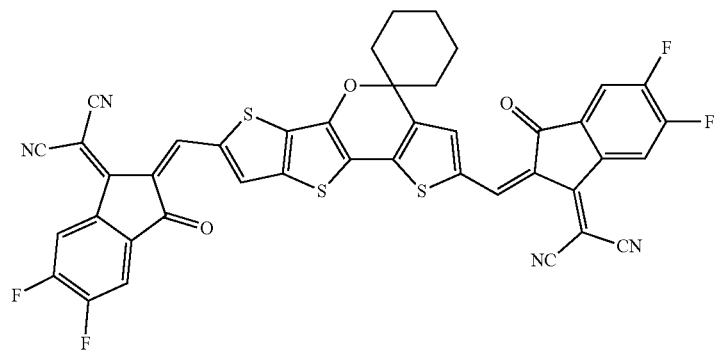
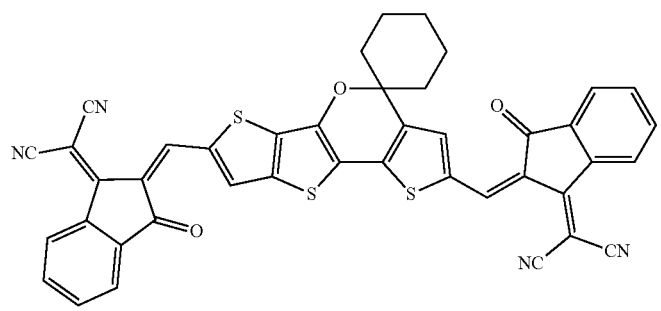
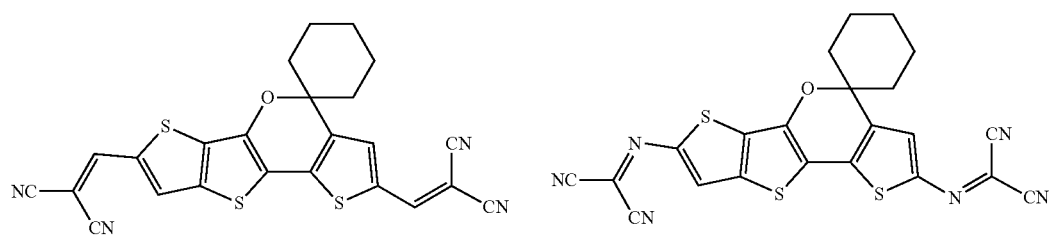

-continued
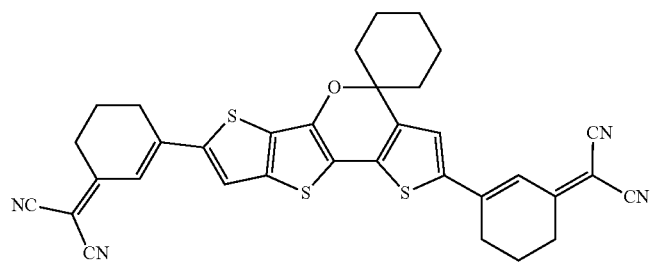
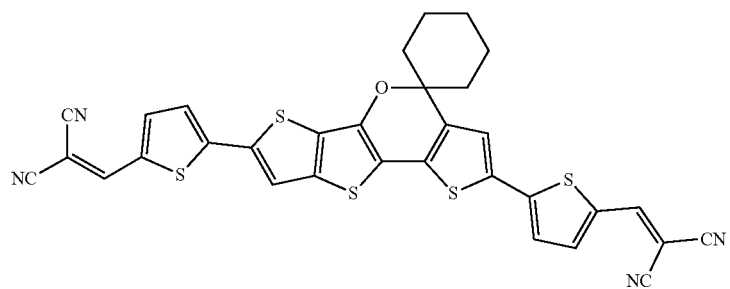
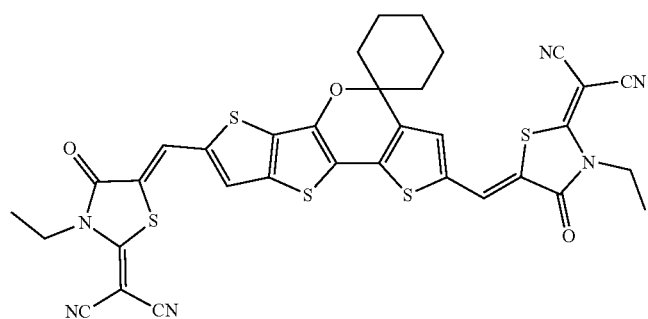
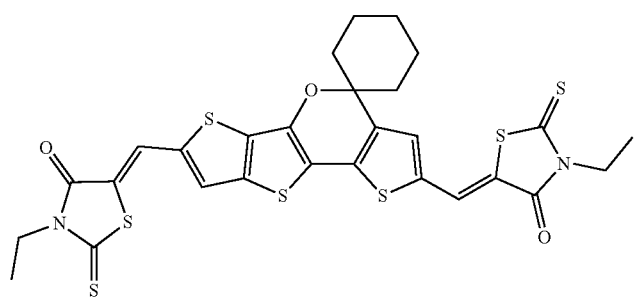
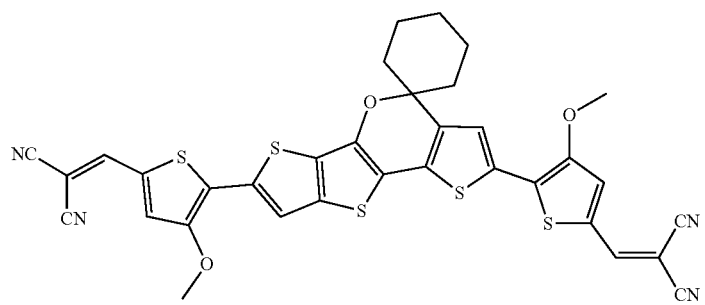

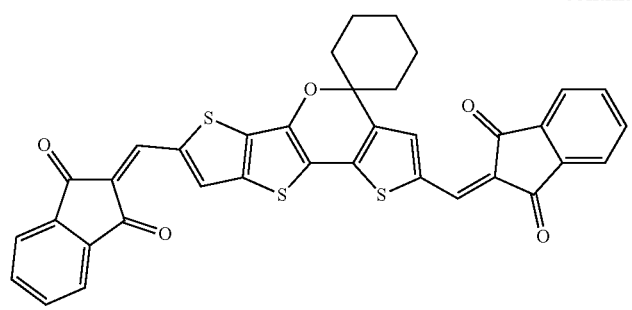
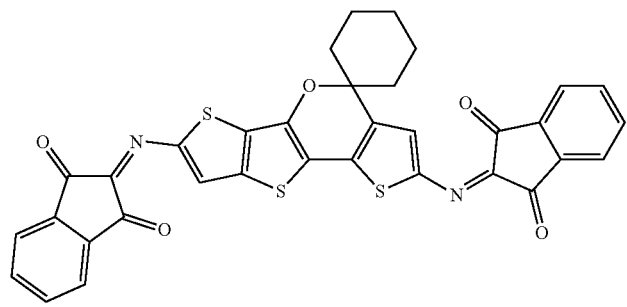
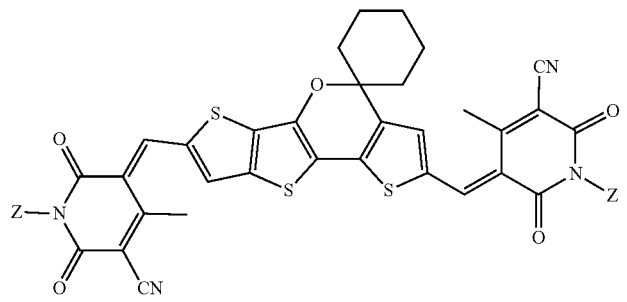
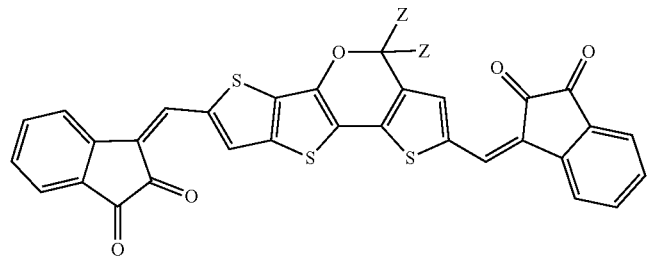
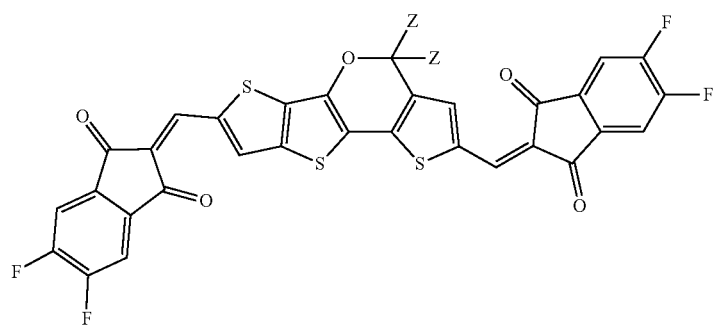

-continued
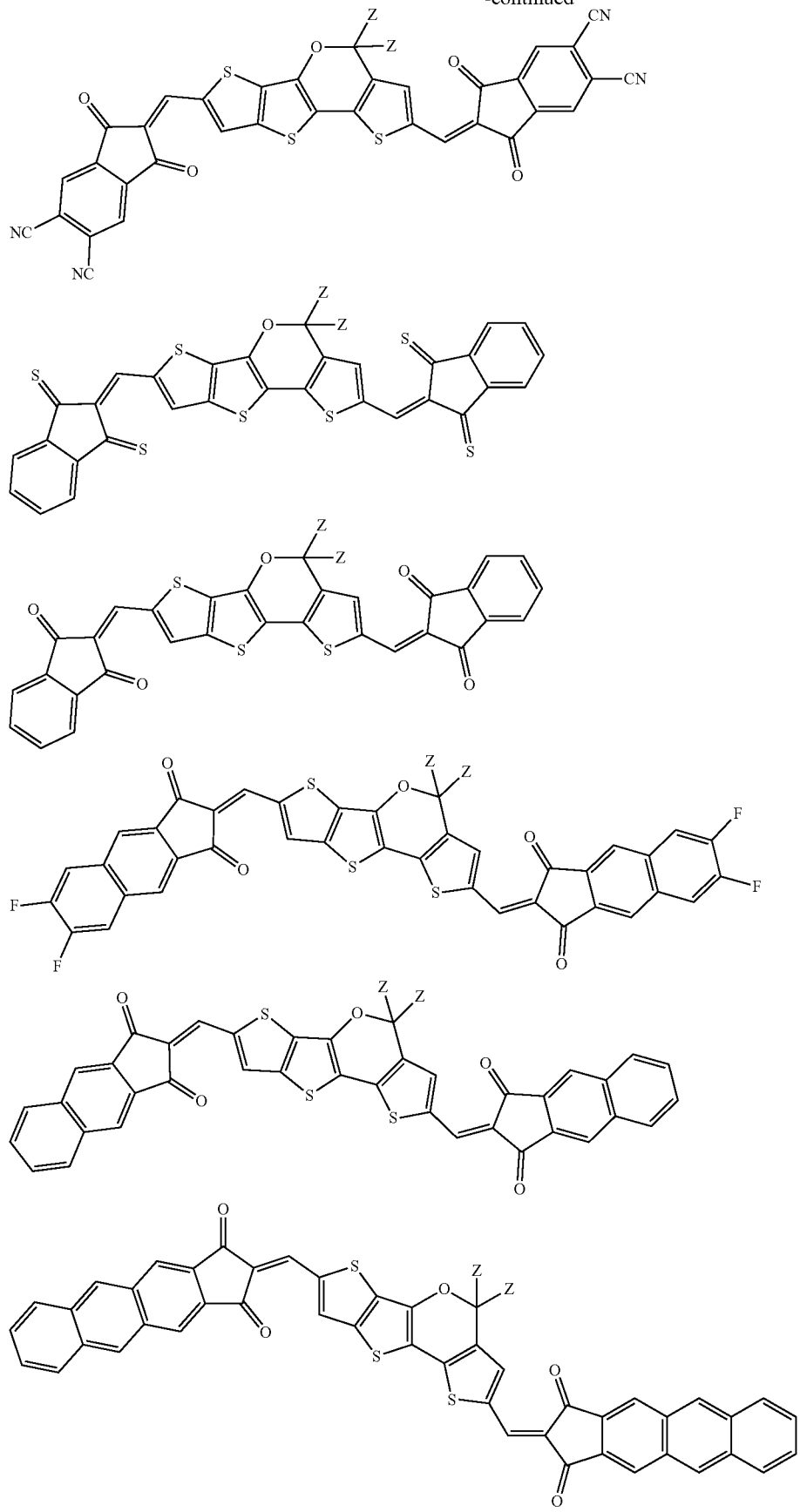

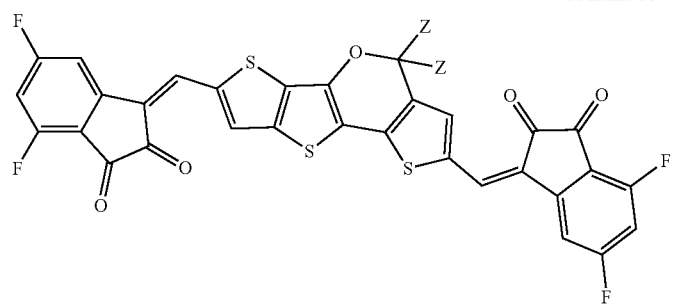
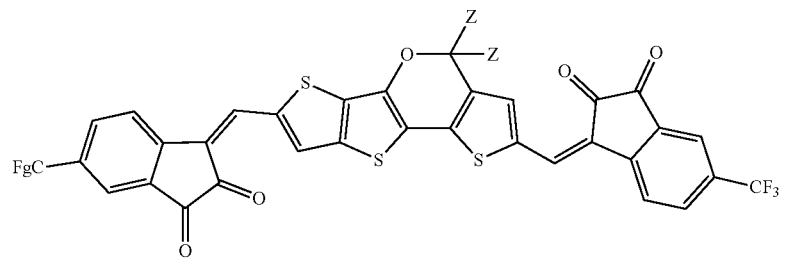
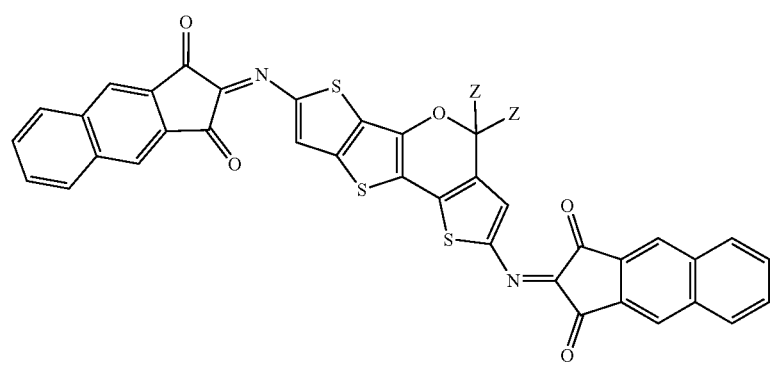
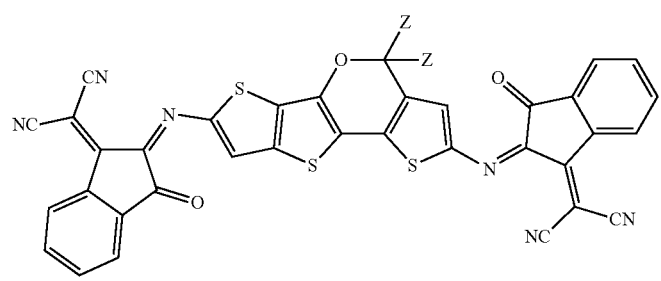
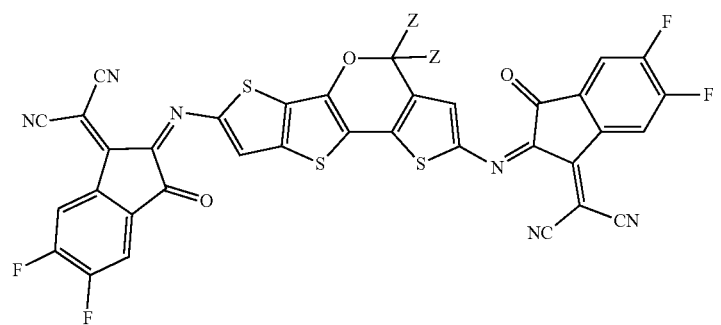

-continued
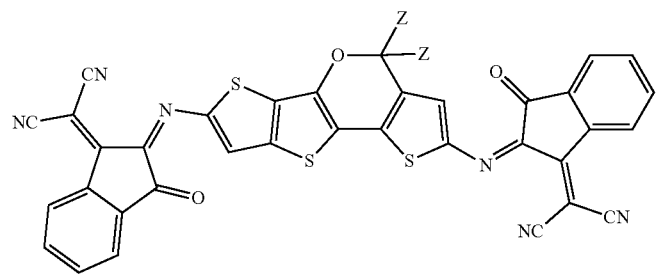
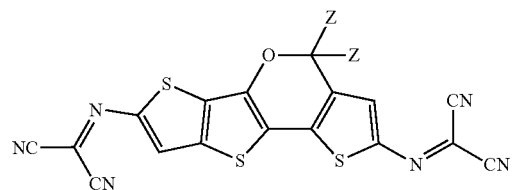
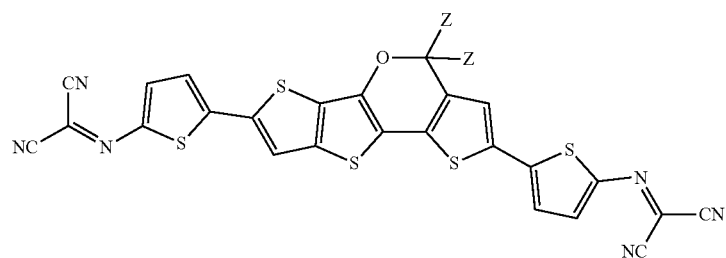
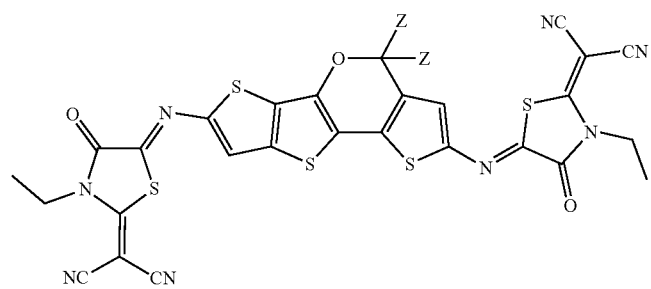
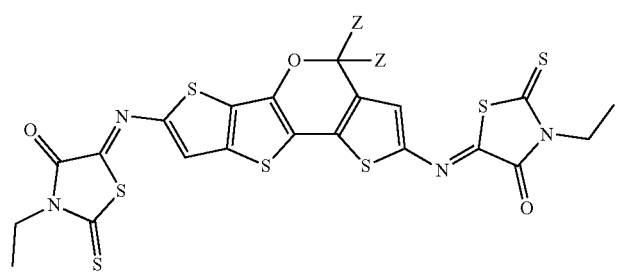
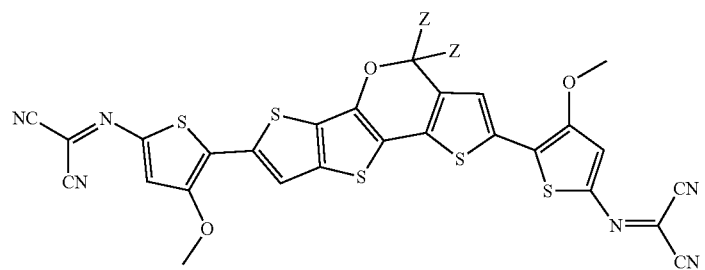

-continued
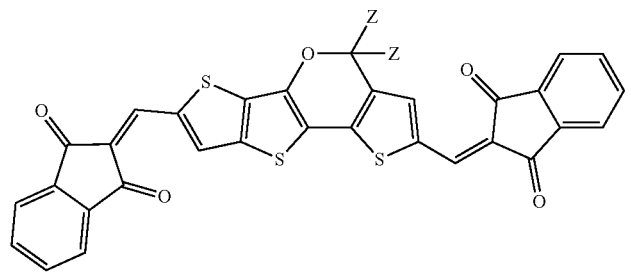
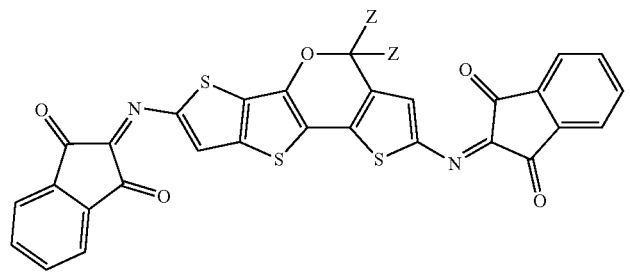
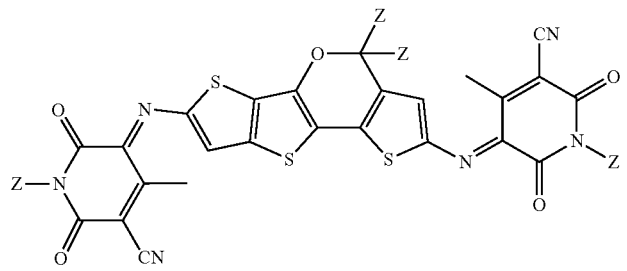
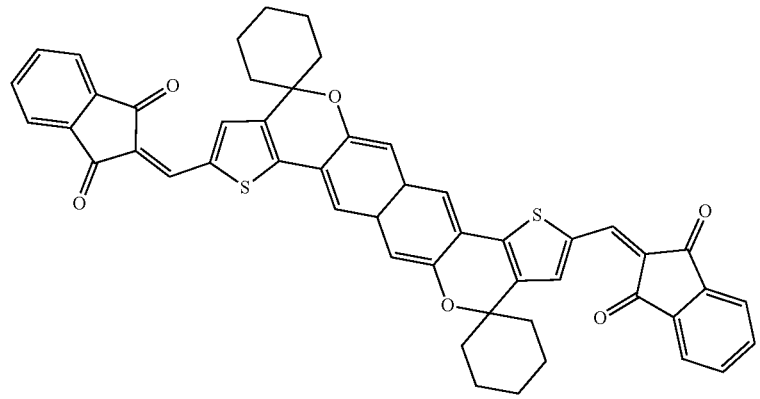
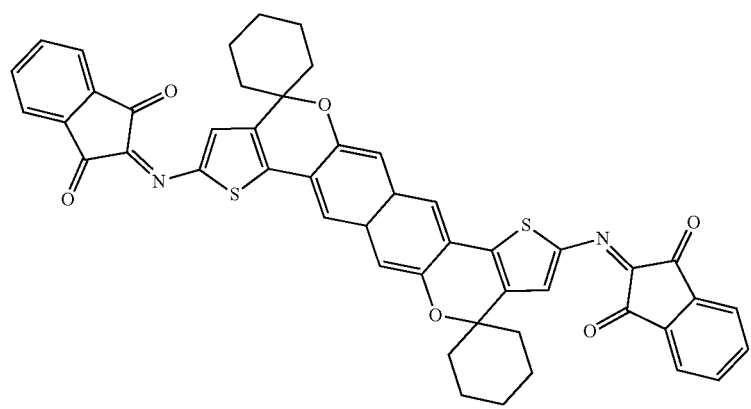

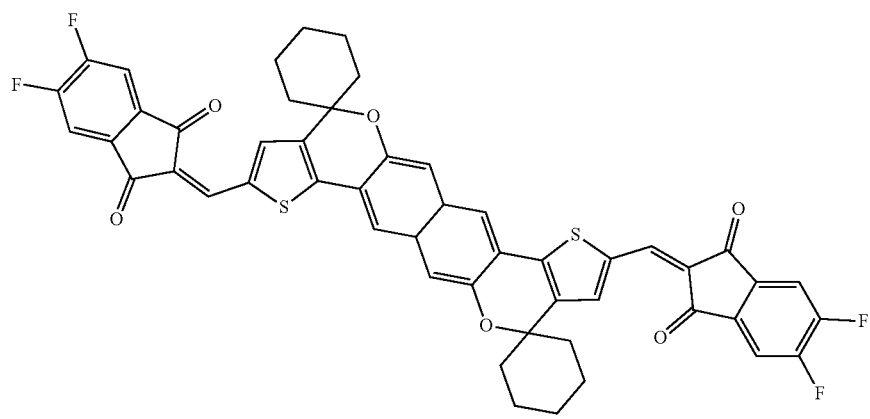
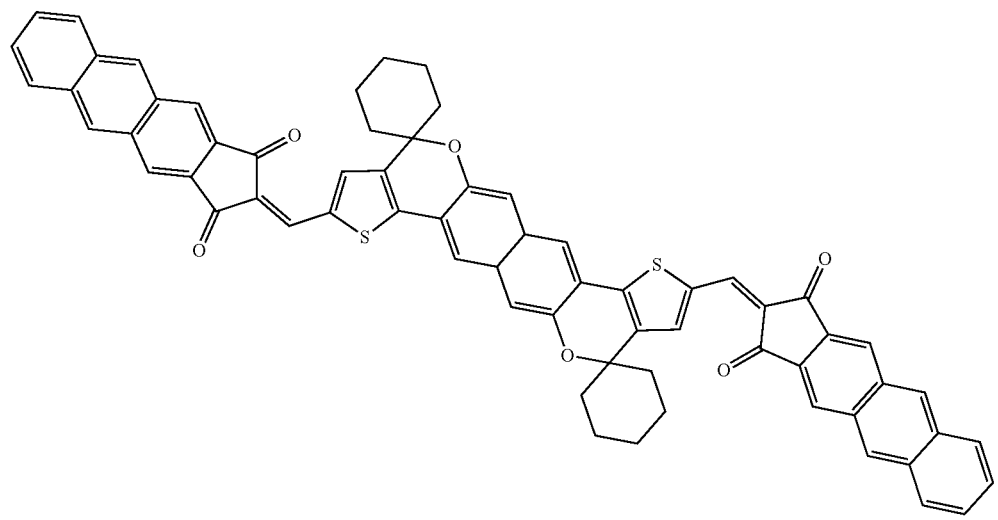
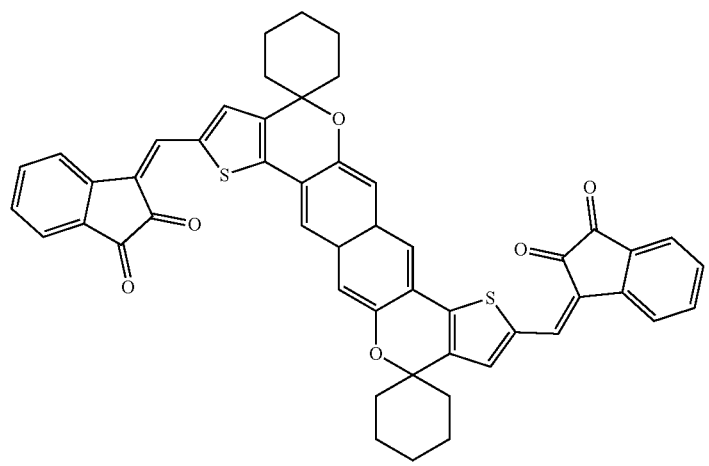

-continued
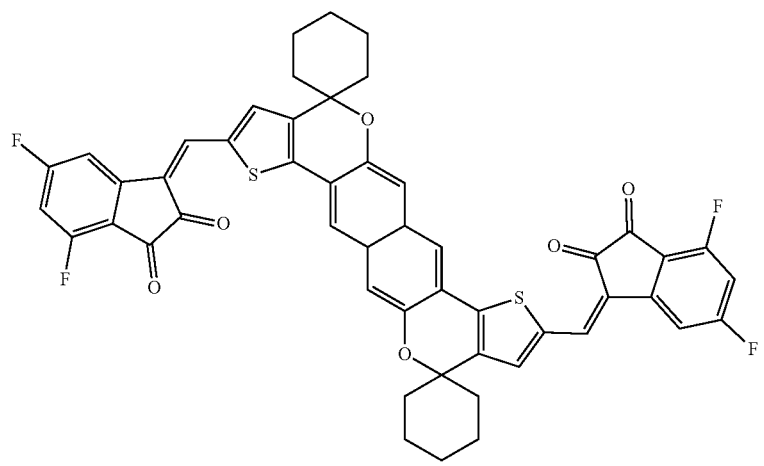
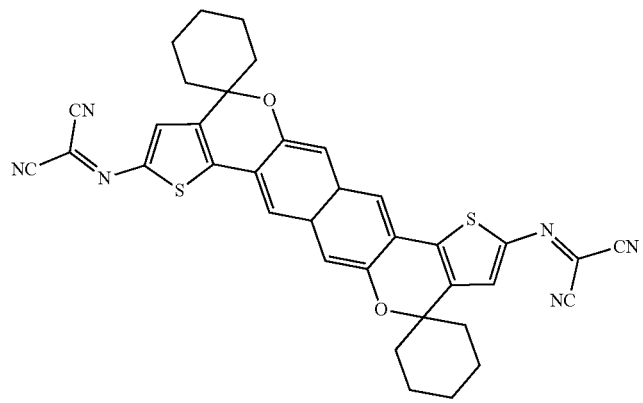
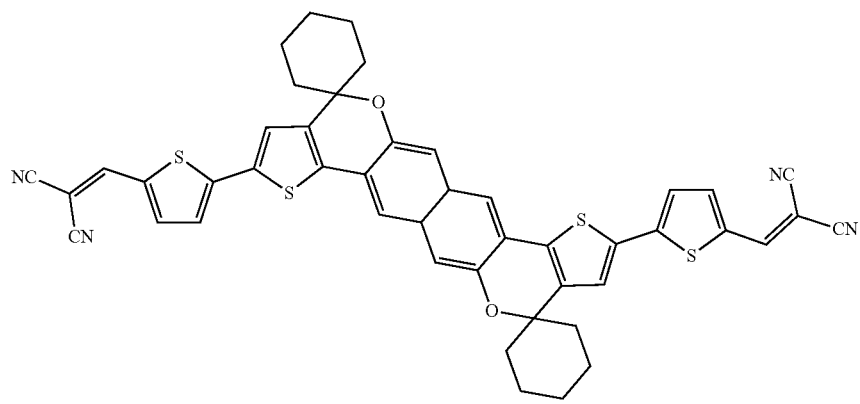
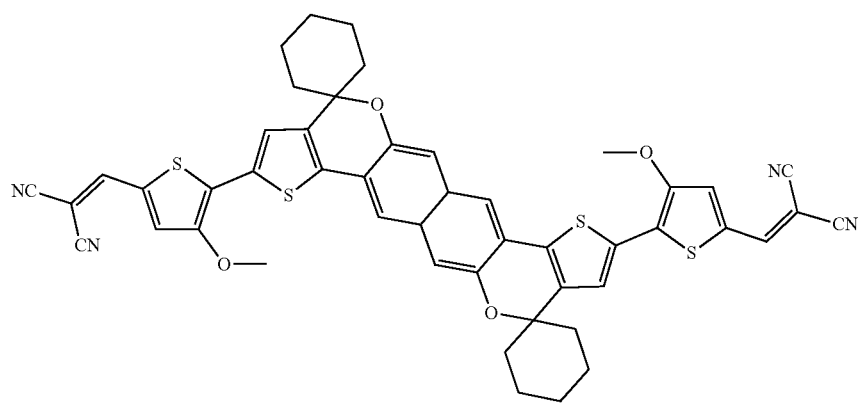

-continued
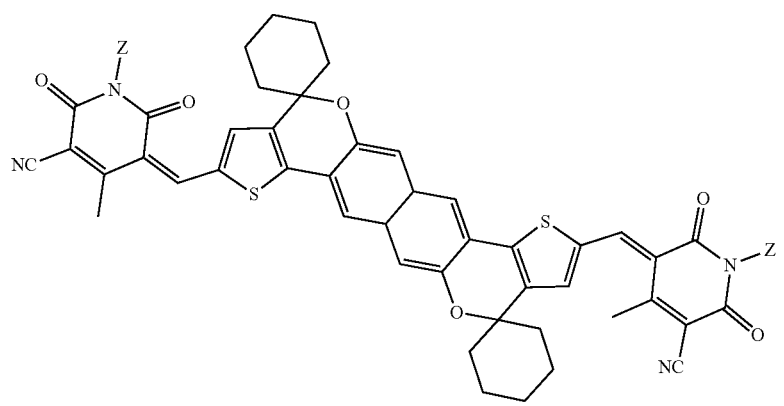
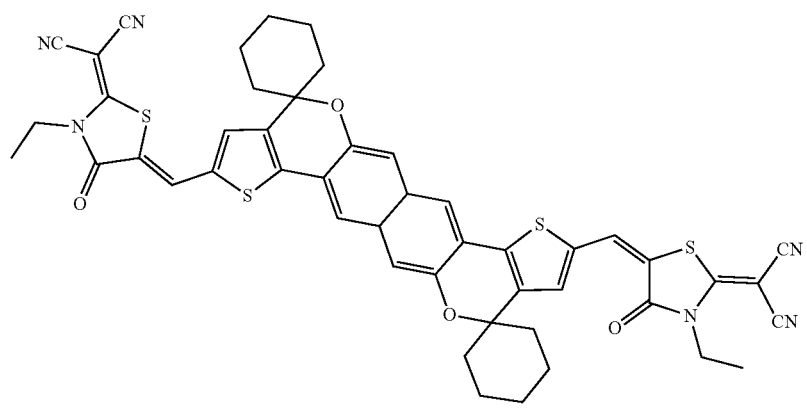
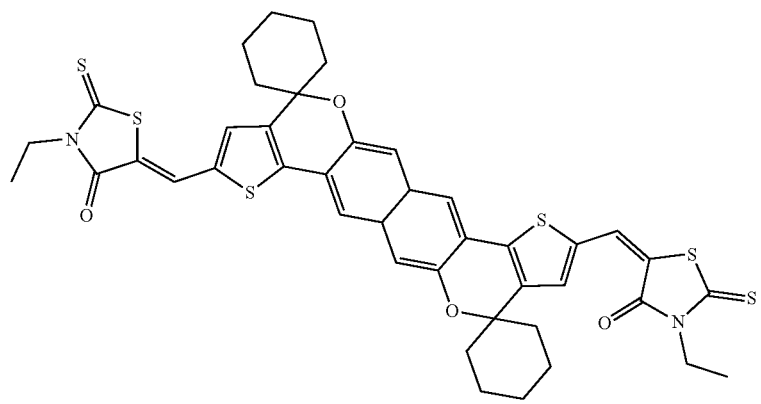
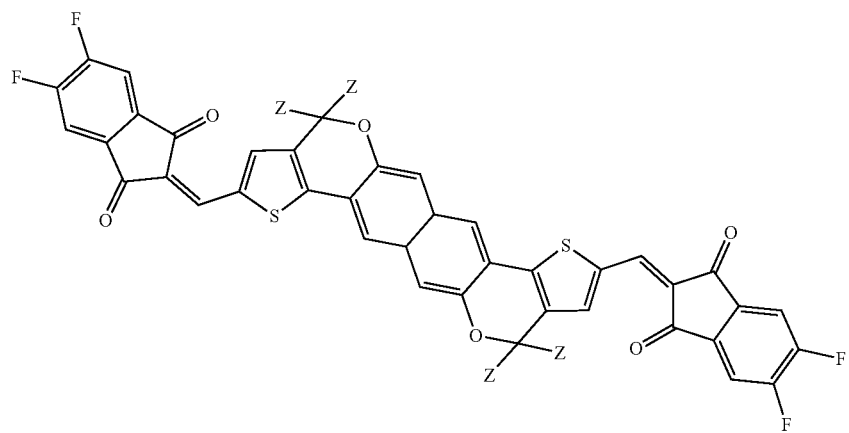

-continued
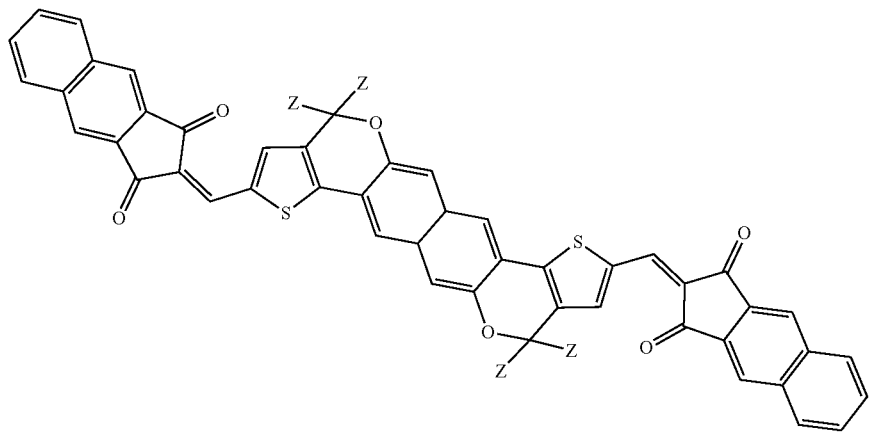
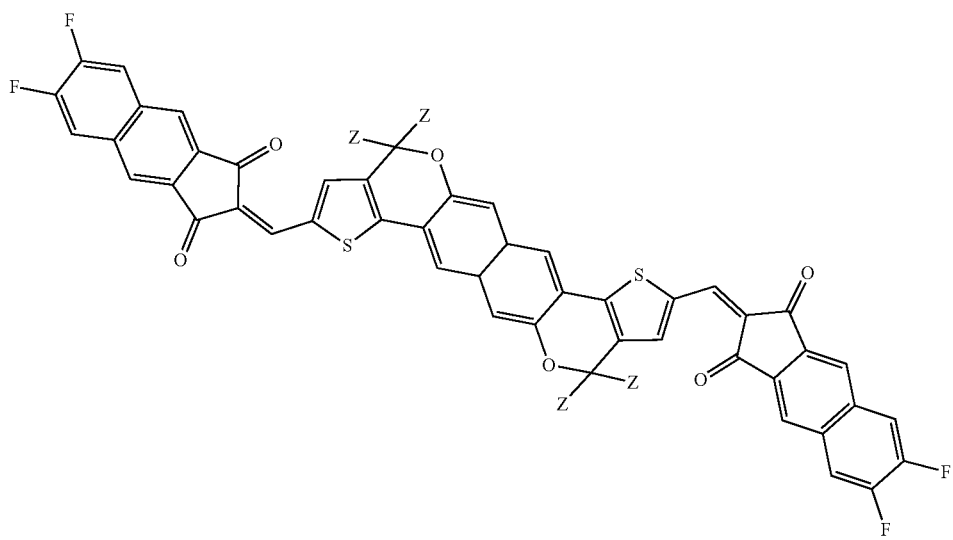
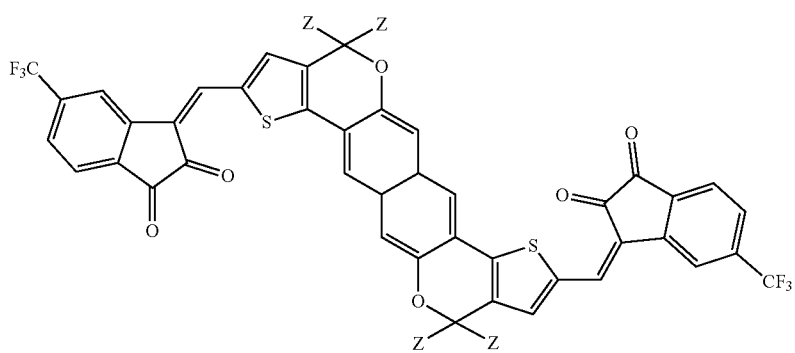
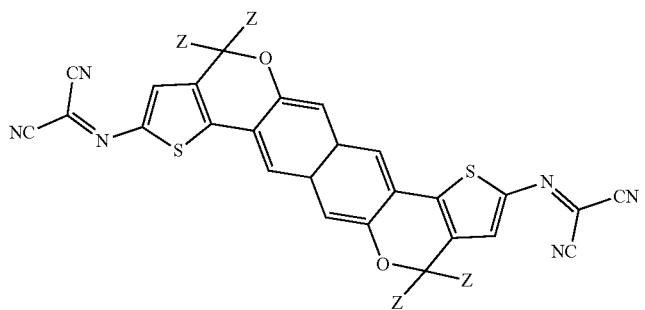

-continued
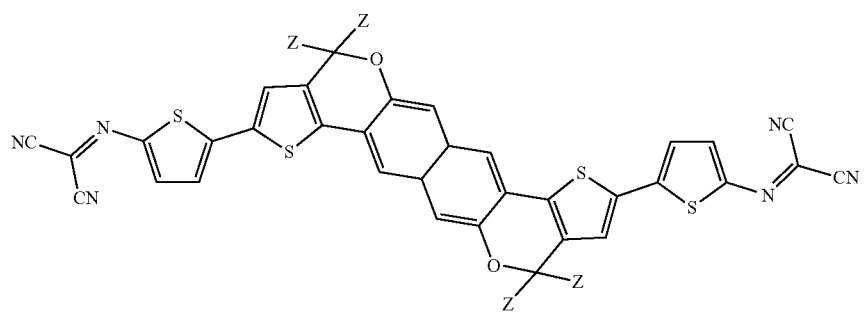
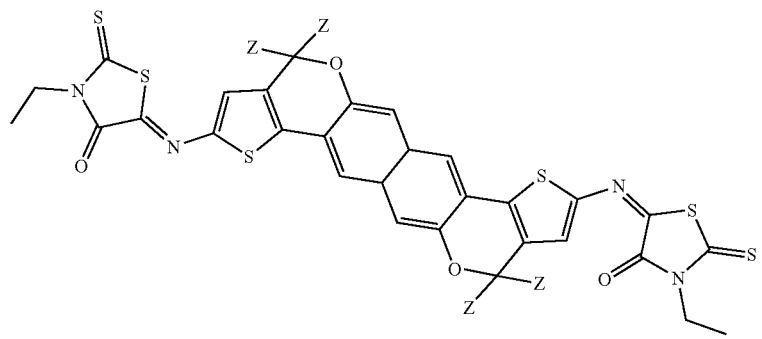
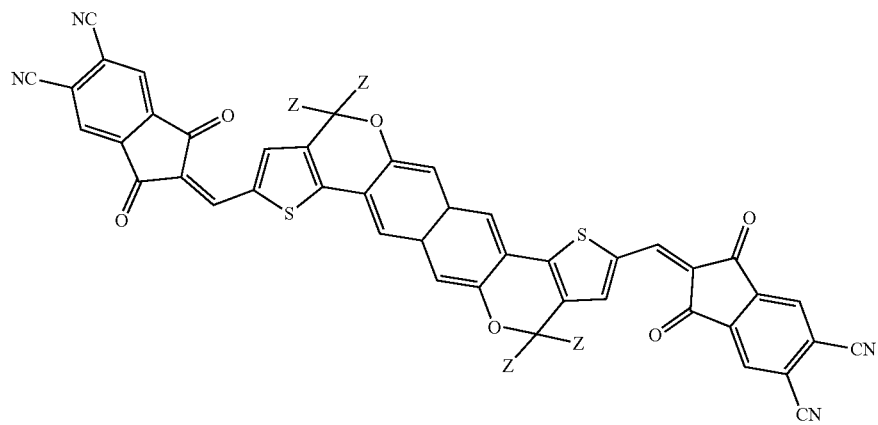
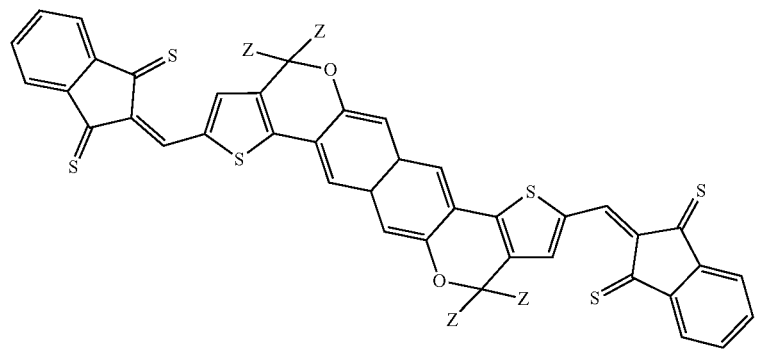

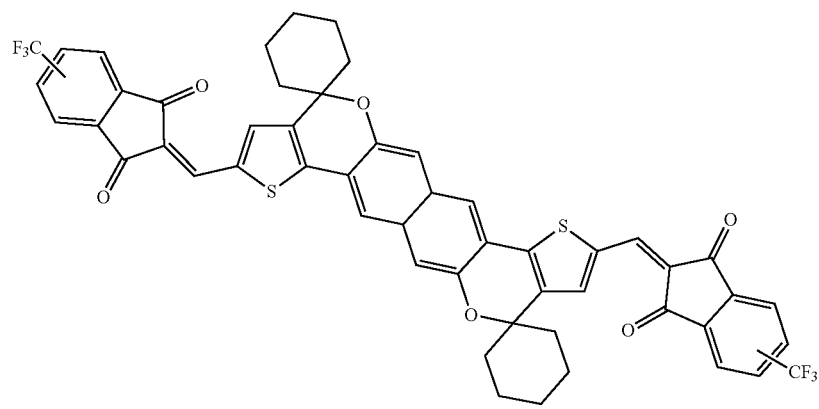
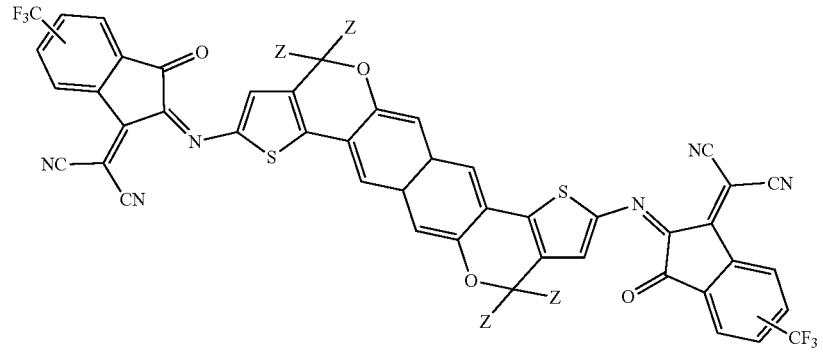
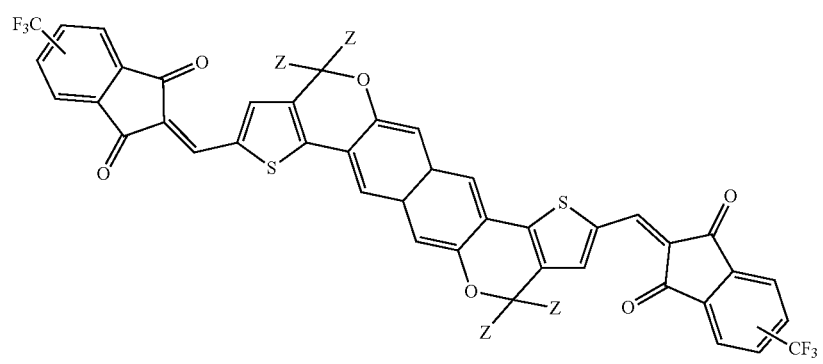
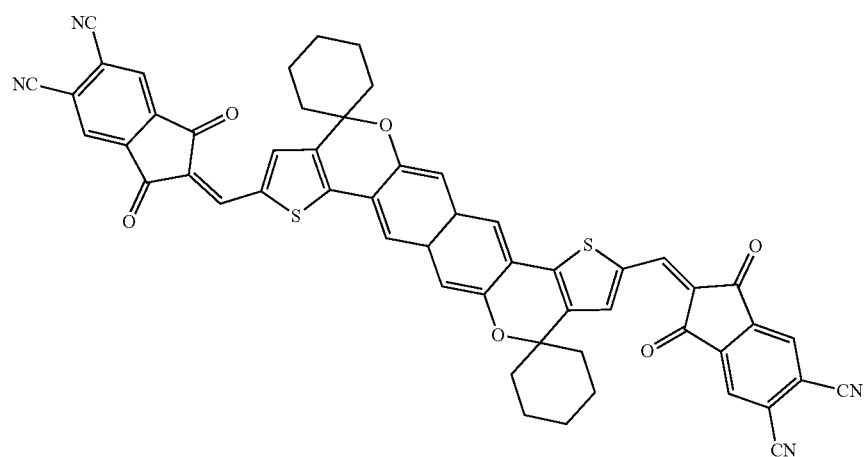

-continued
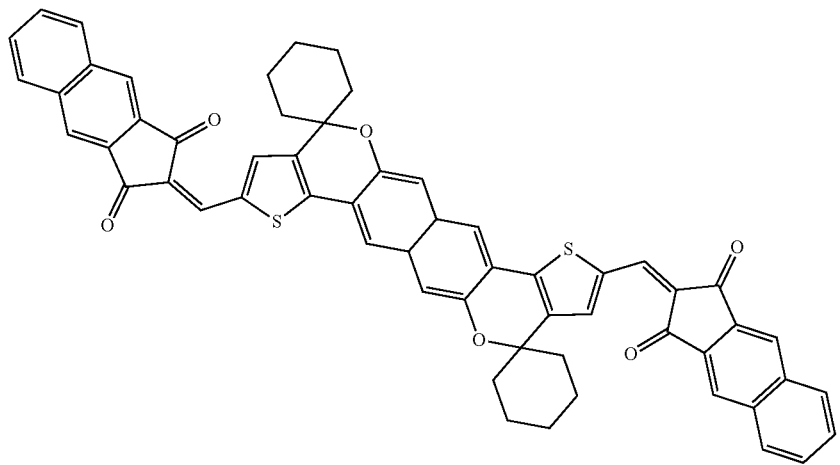
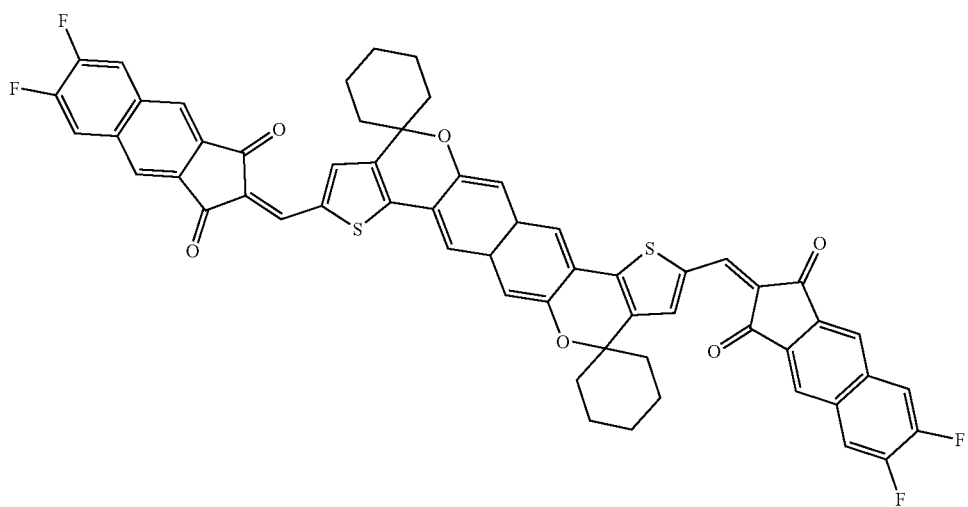
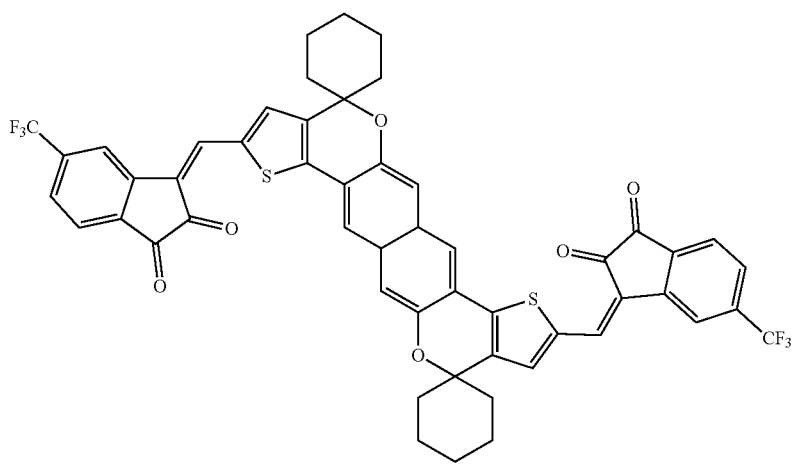

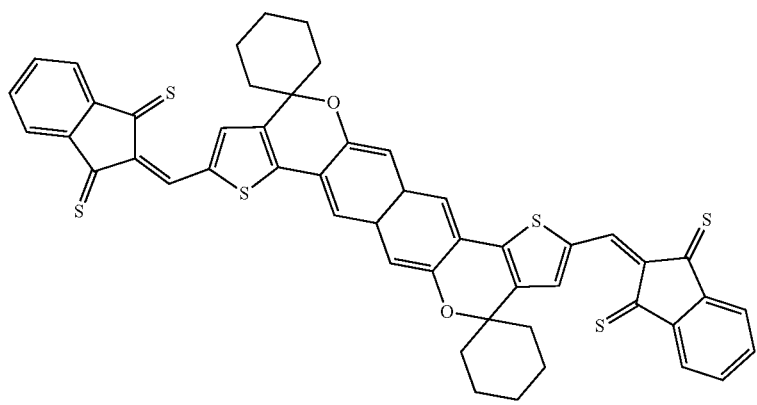
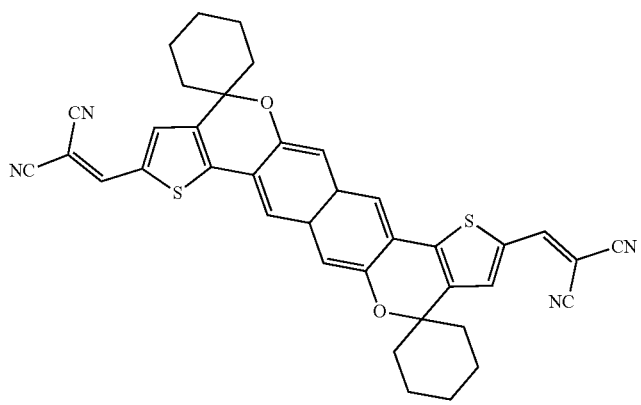
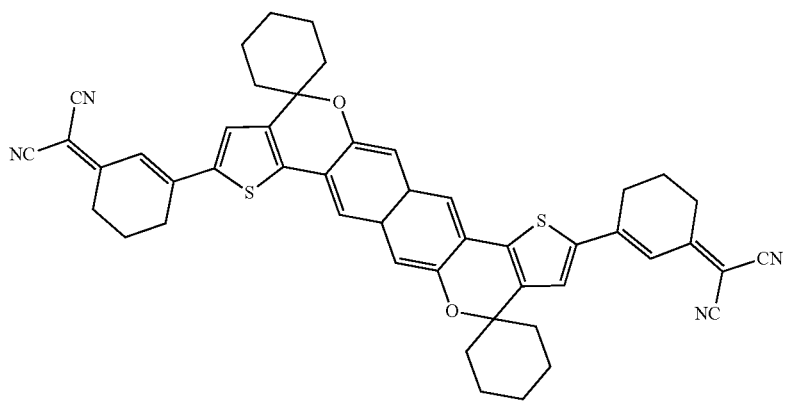
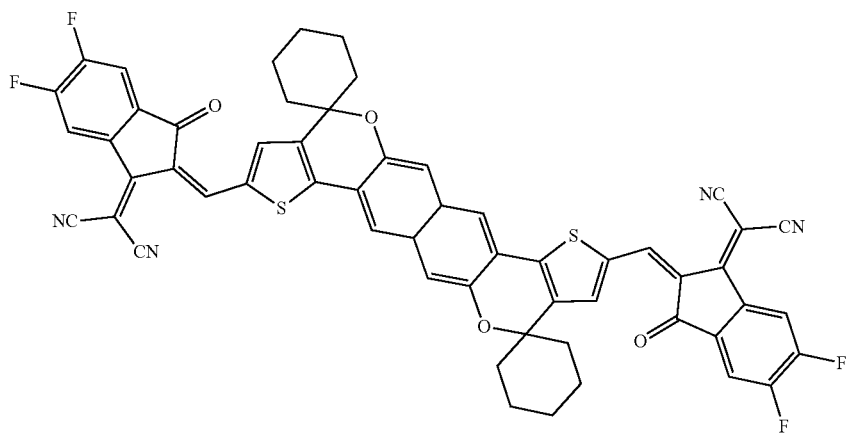

-continued
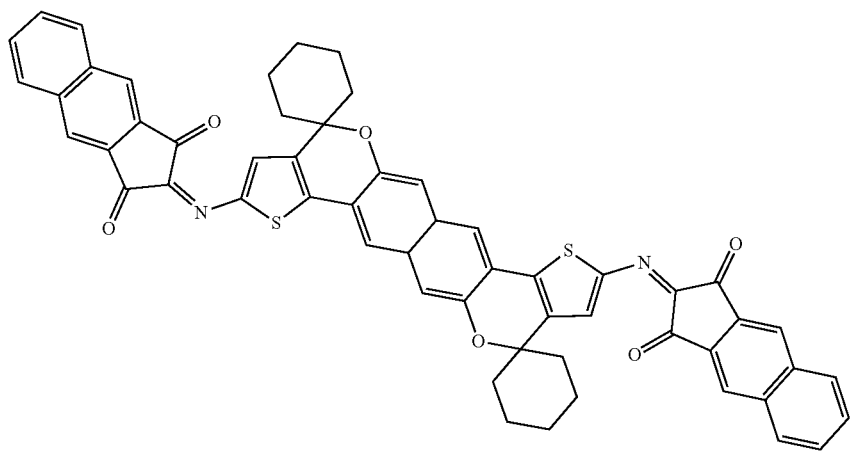
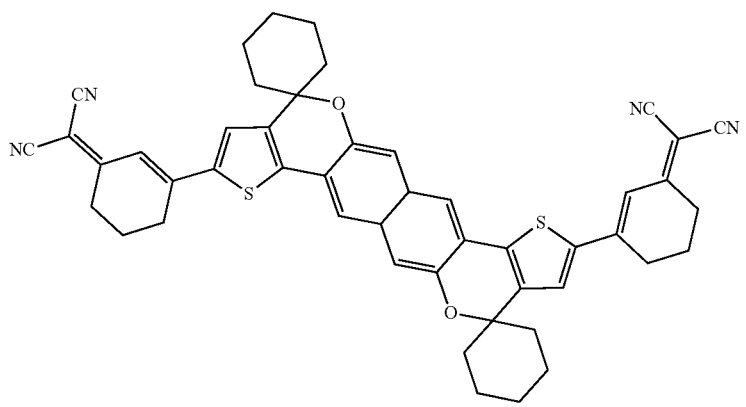
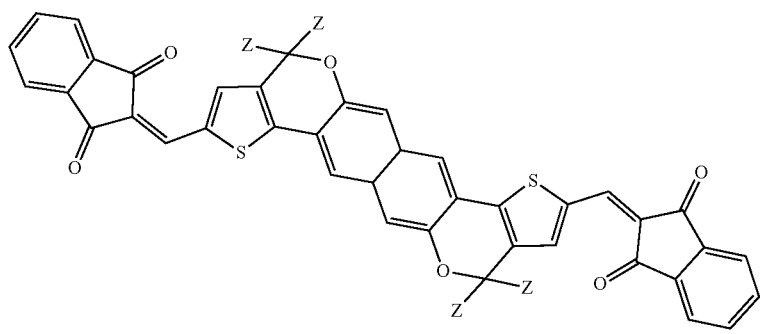
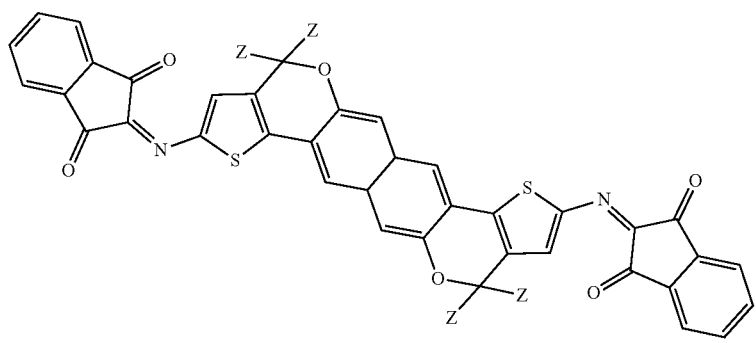

-continued
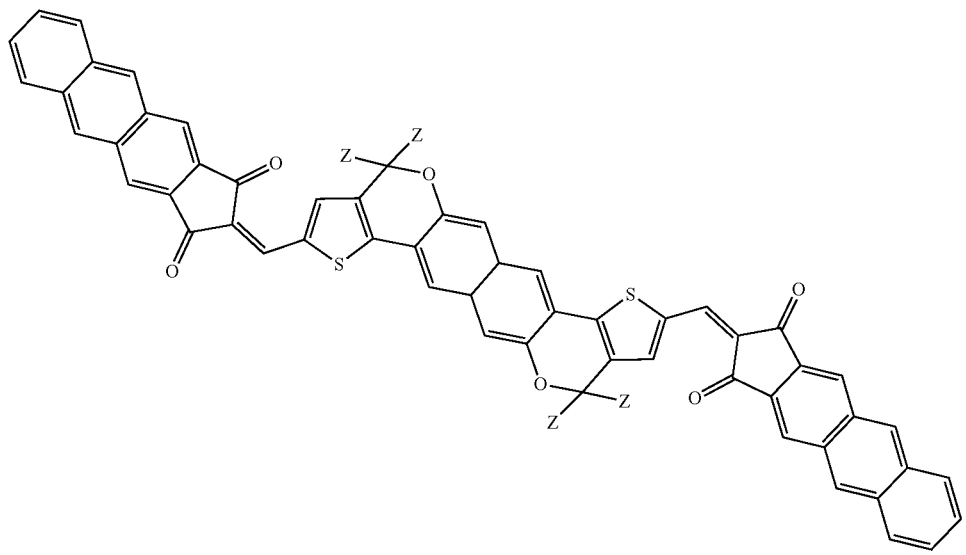
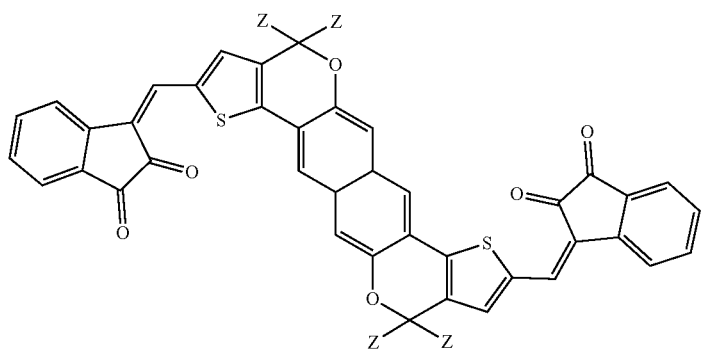
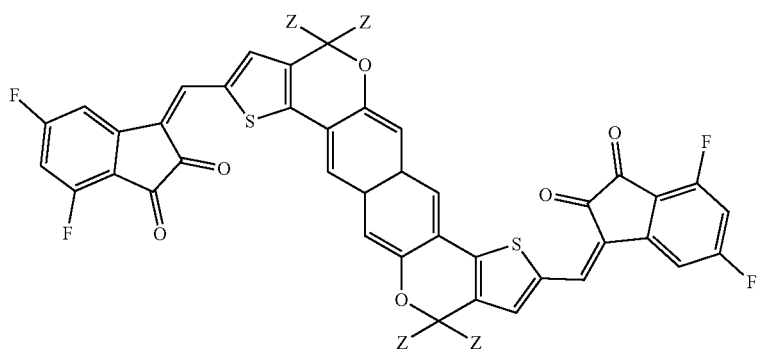
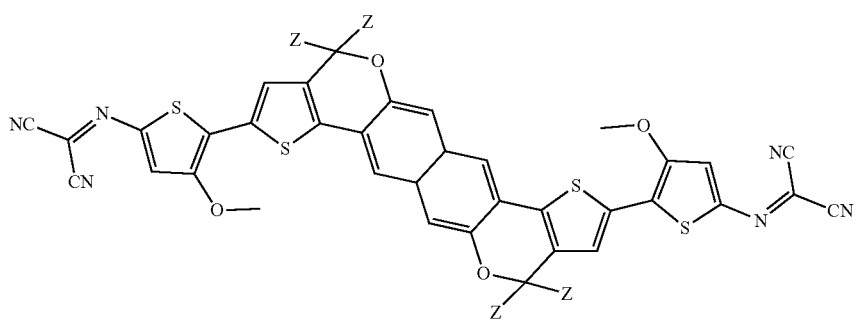

-continued
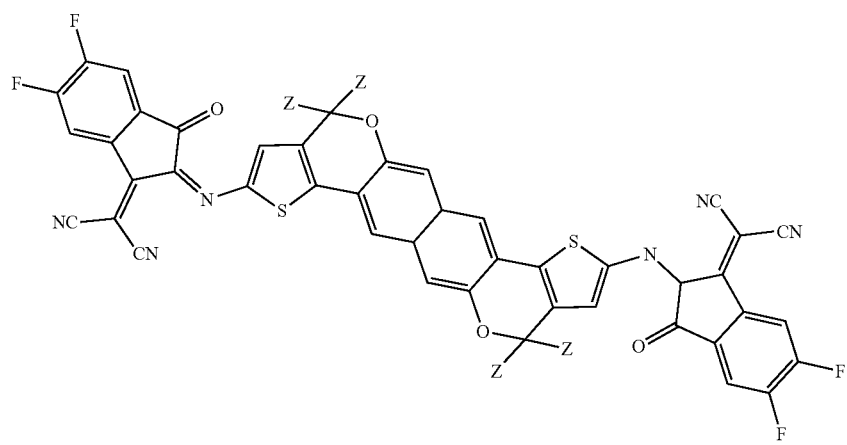
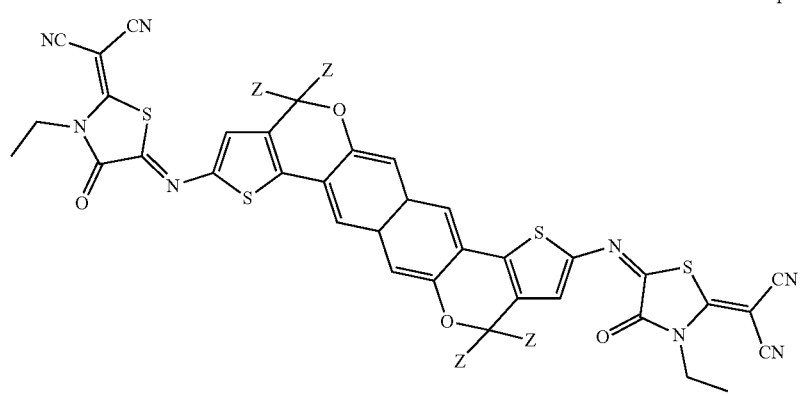
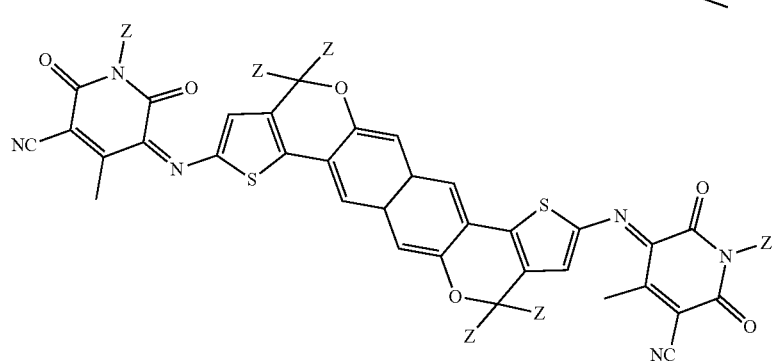
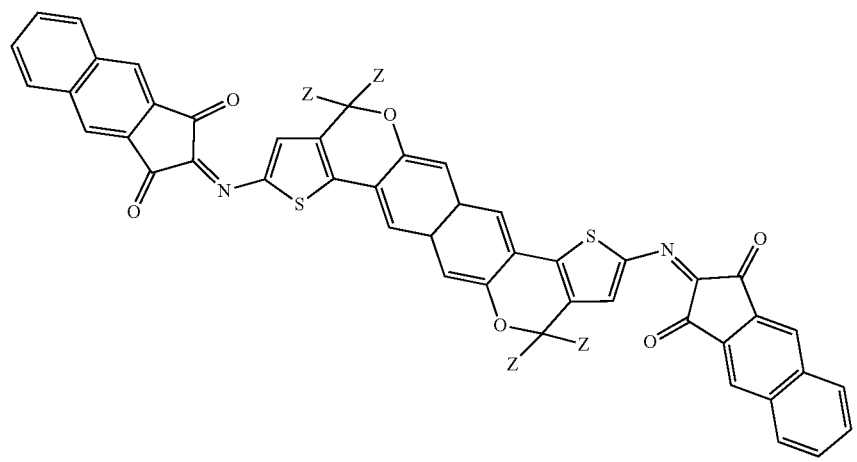

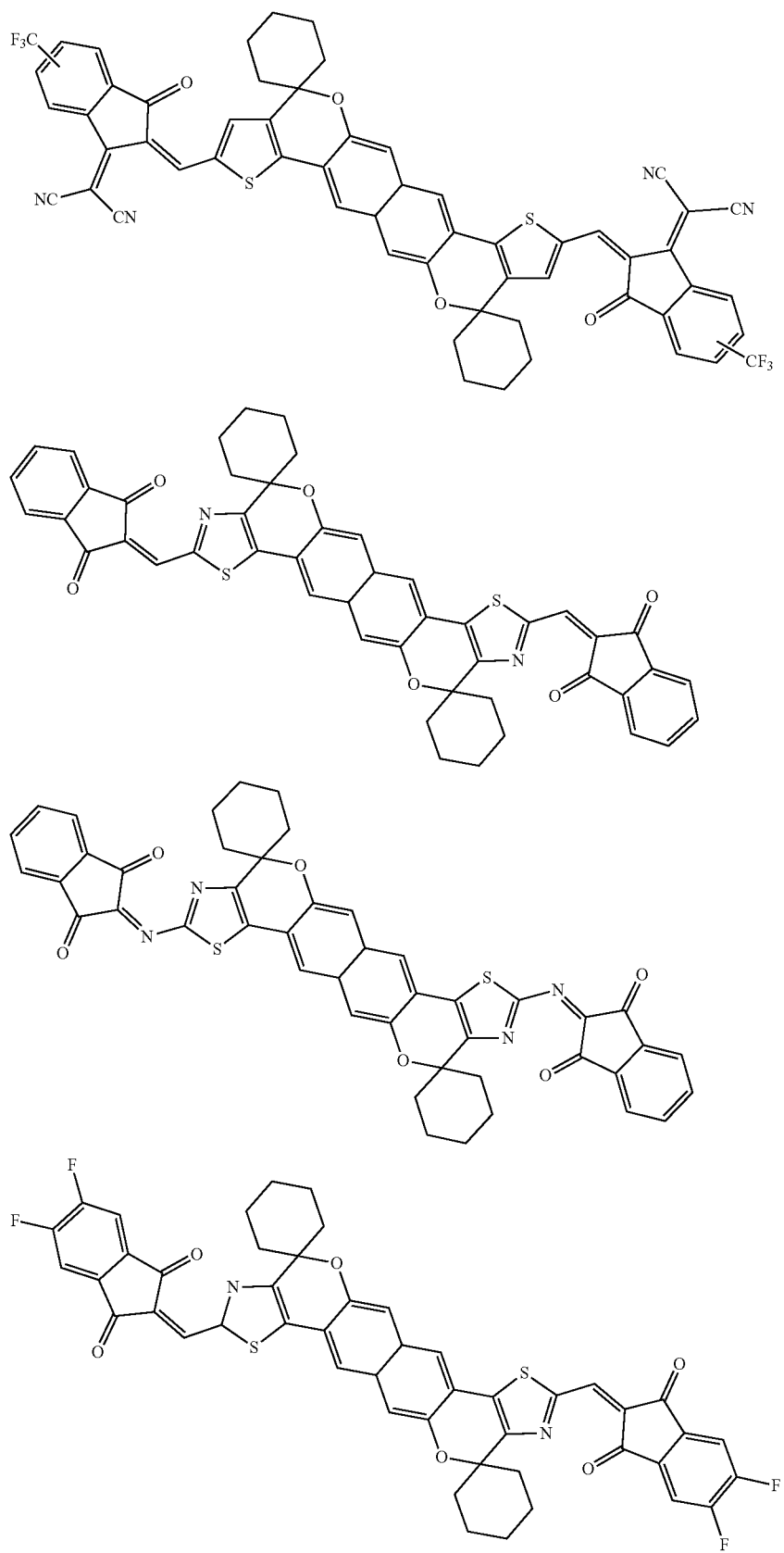

-continued
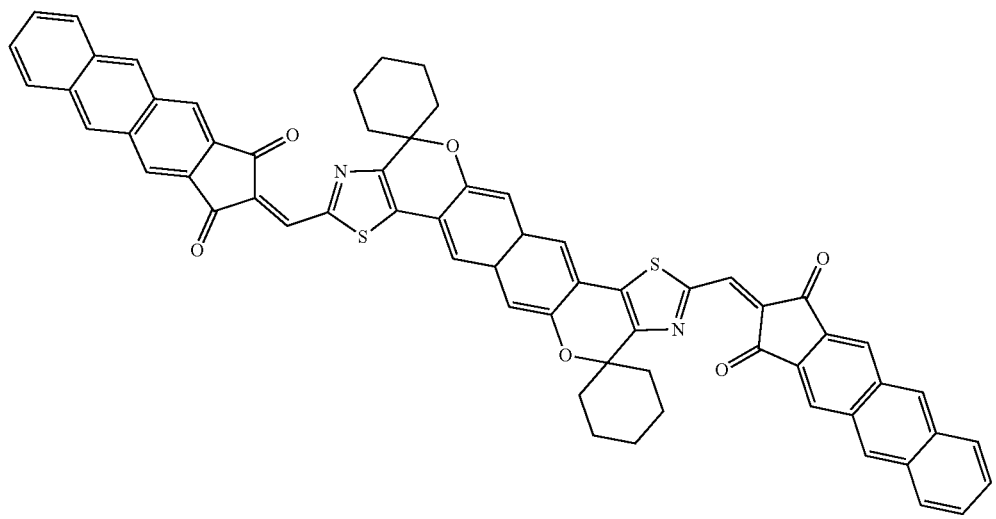
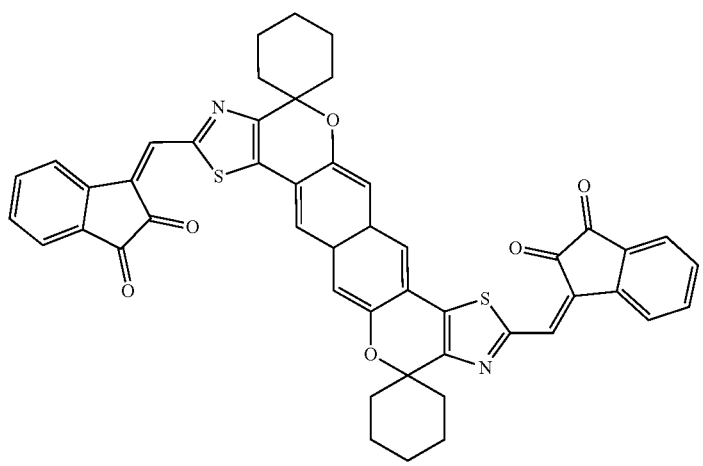
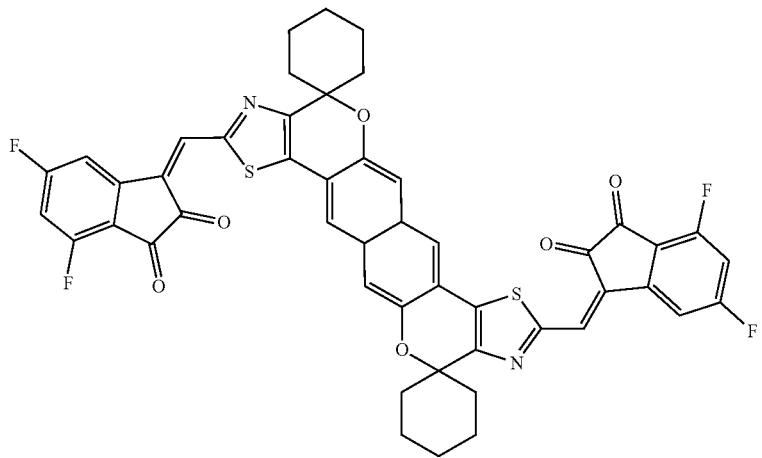

-continued
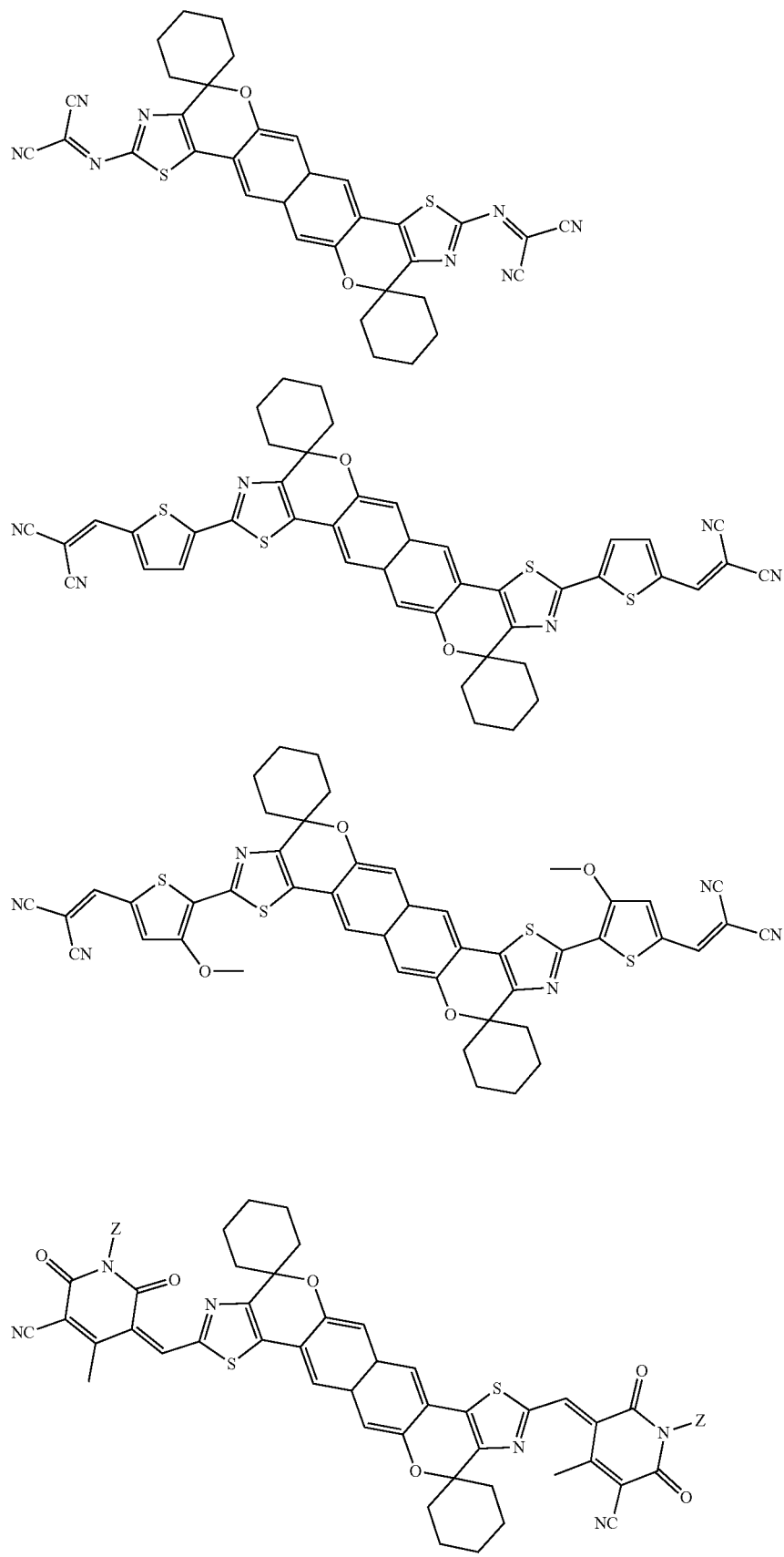

-continued
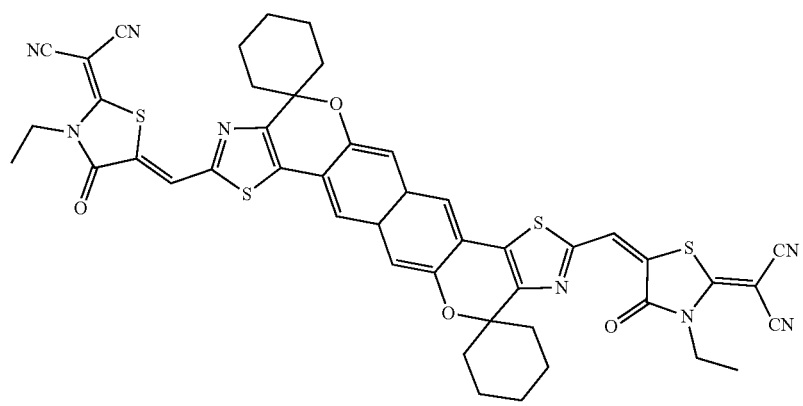
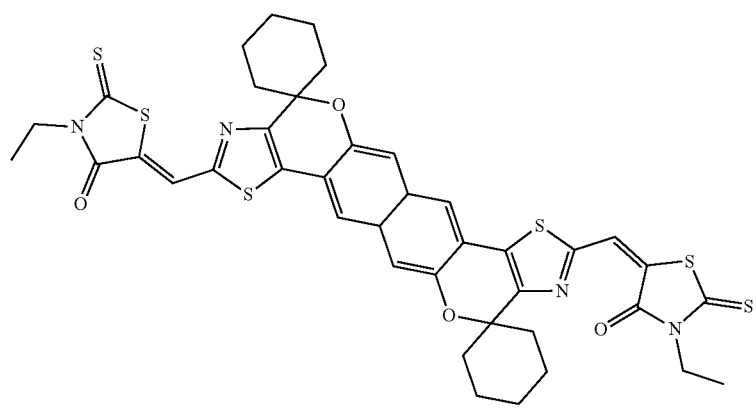
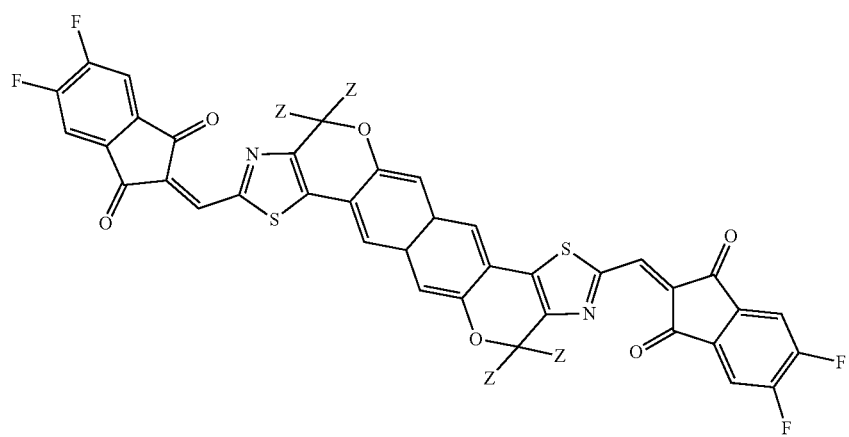
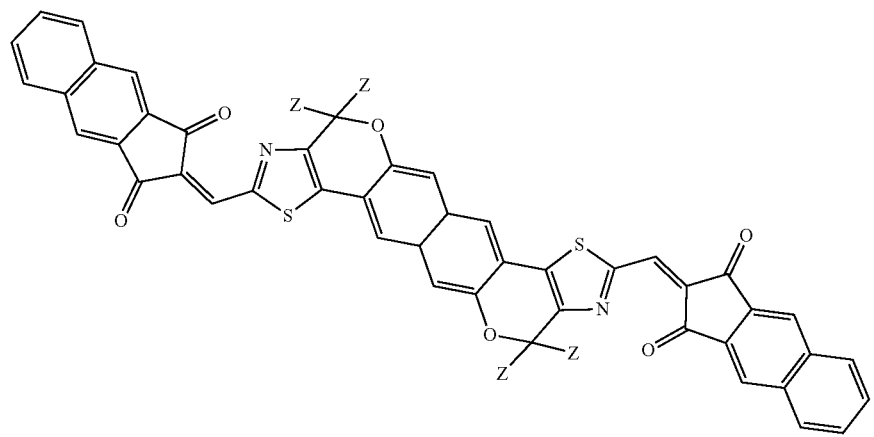

-continued
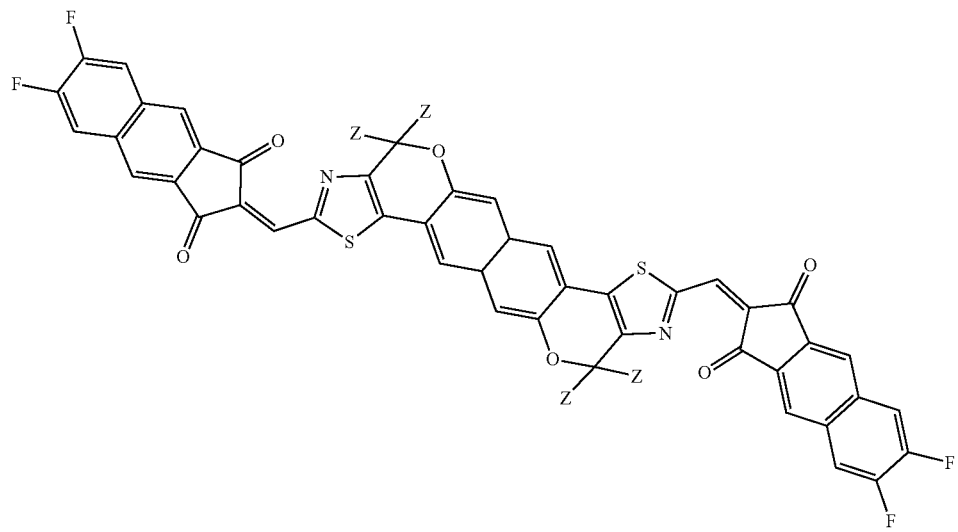
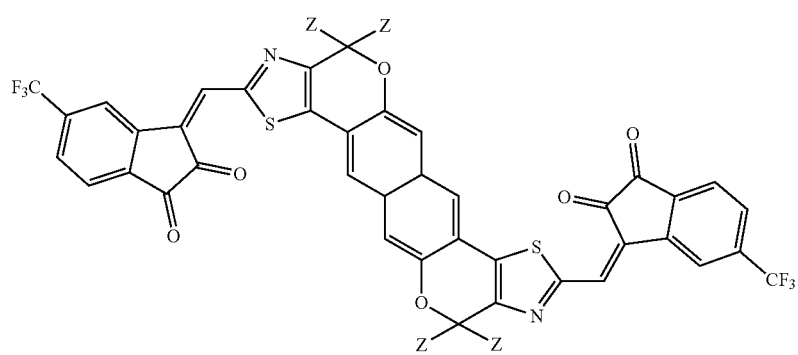
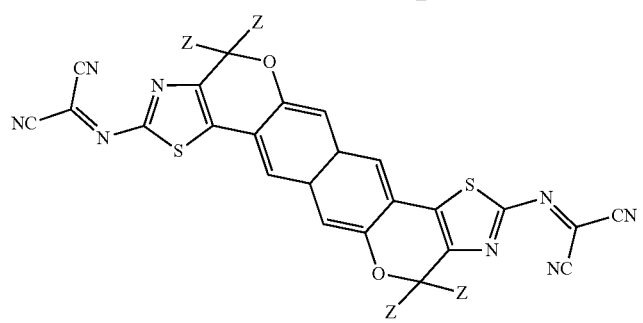
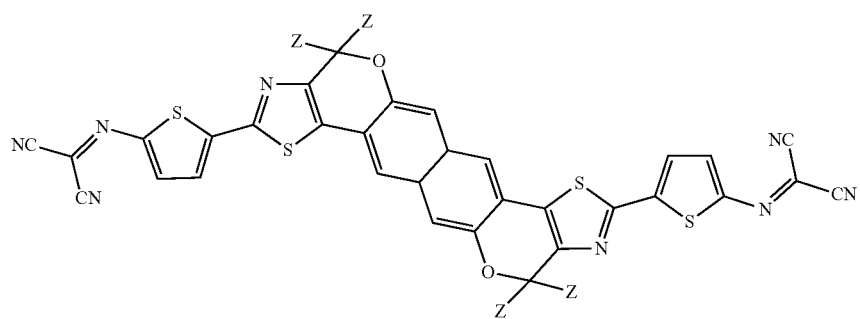

-continued
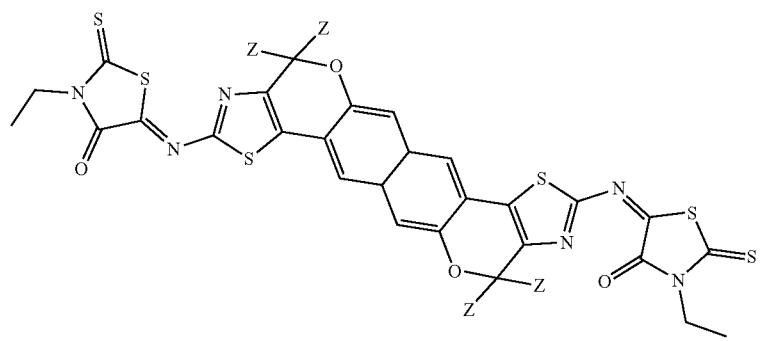
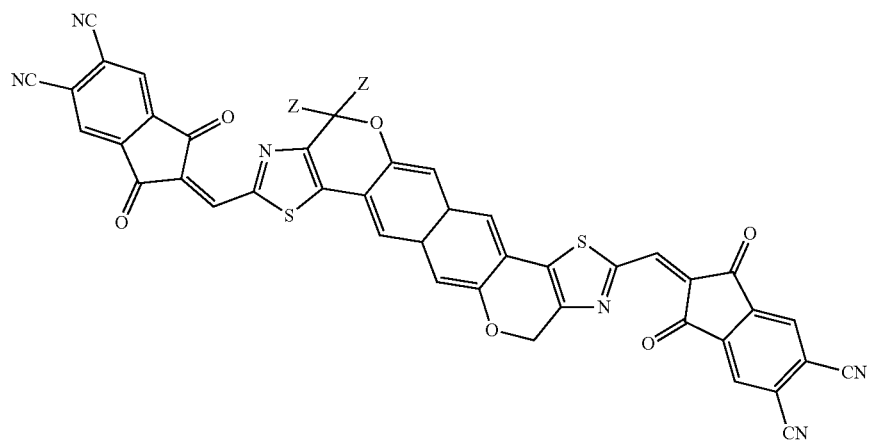
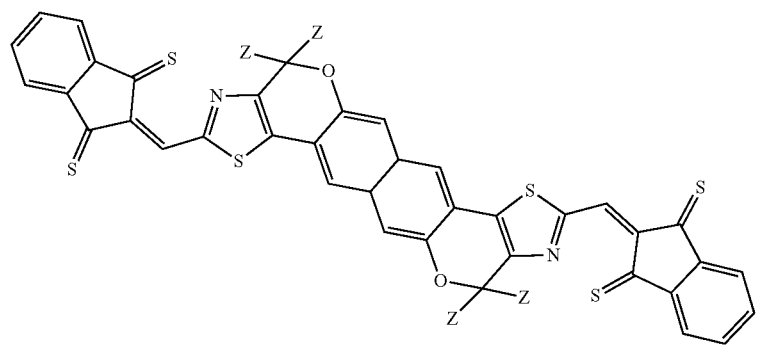
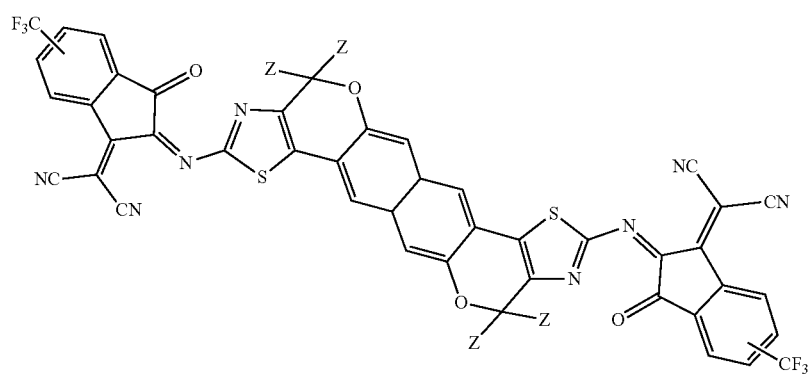

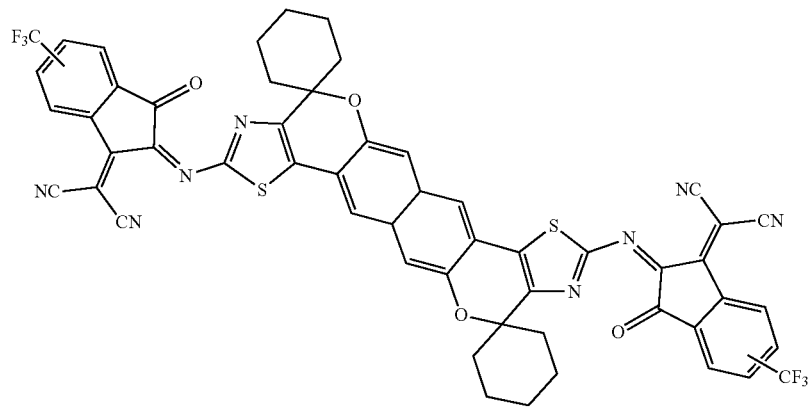
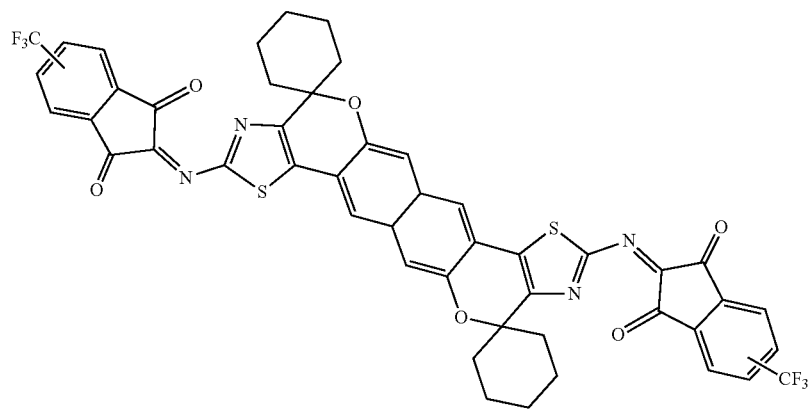
45
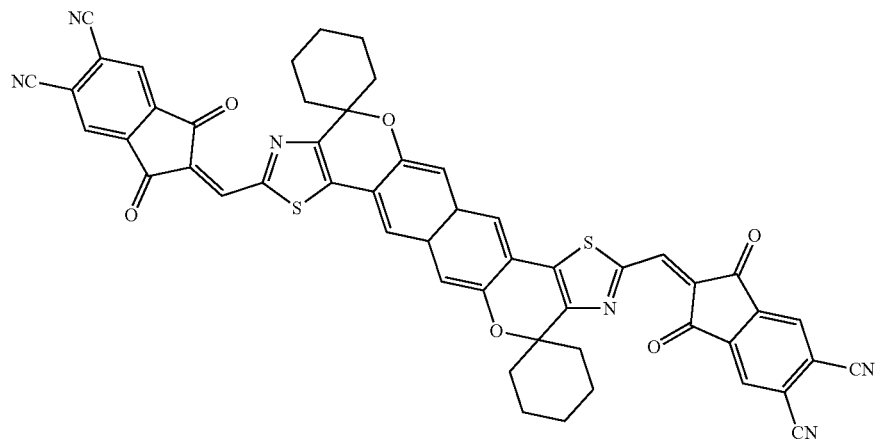

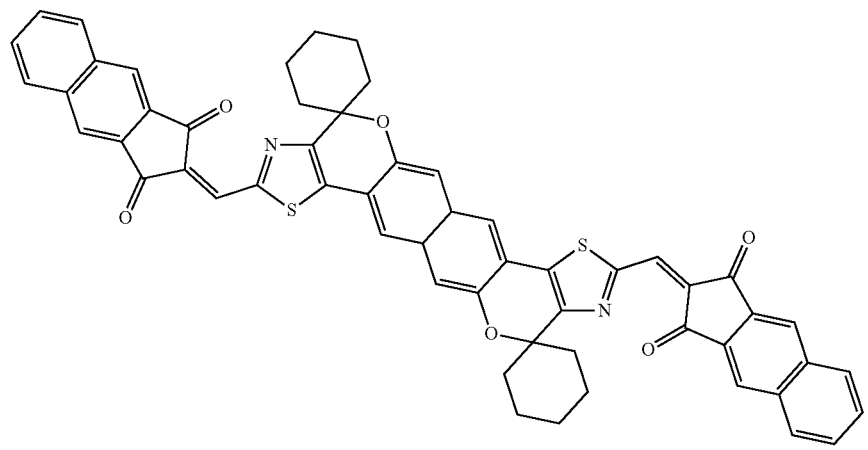
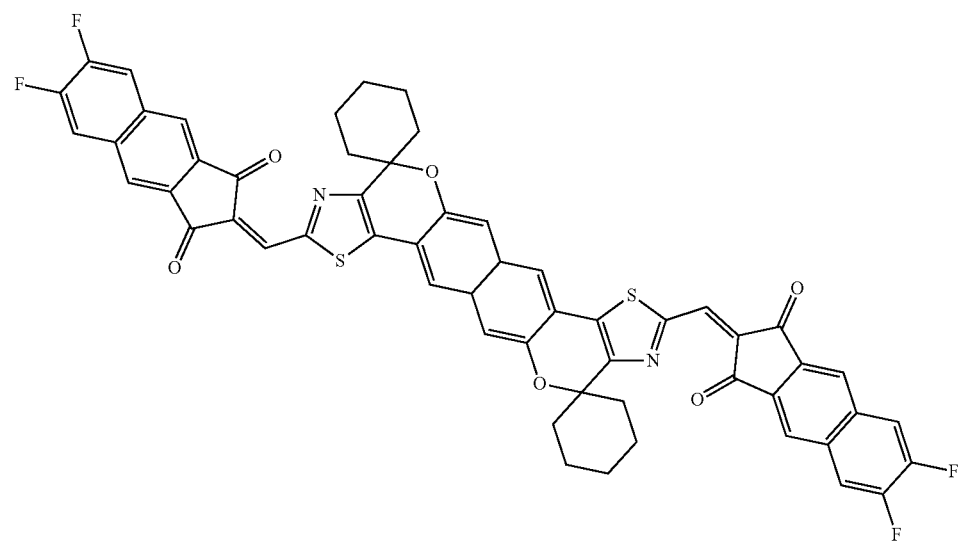
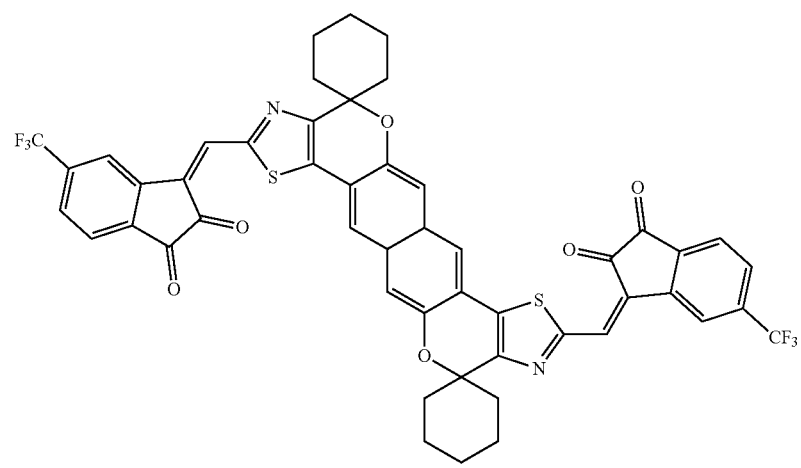

393
394
-continued
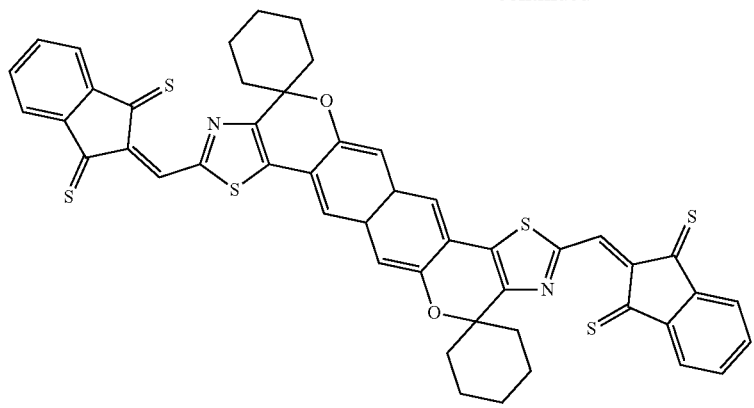
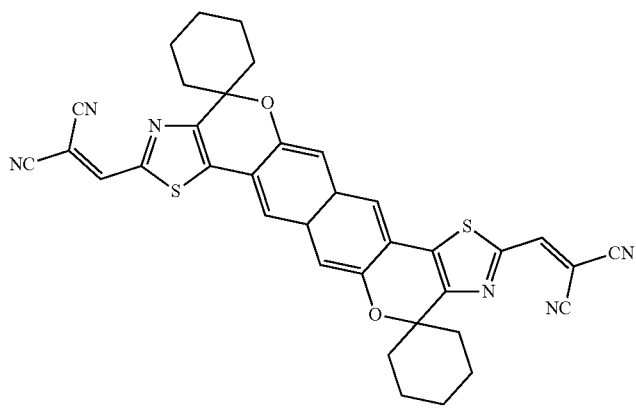
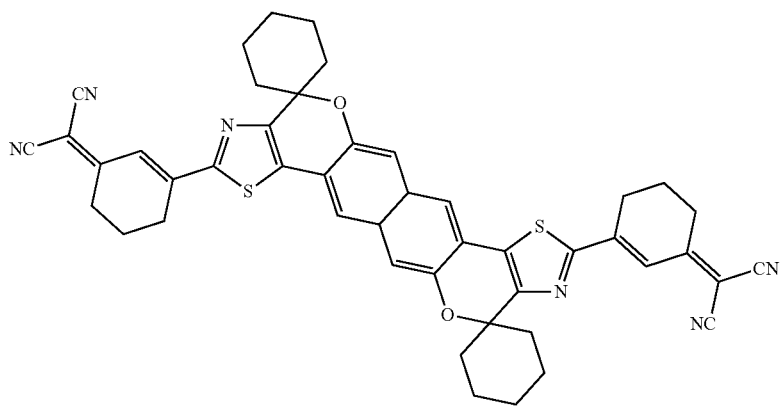
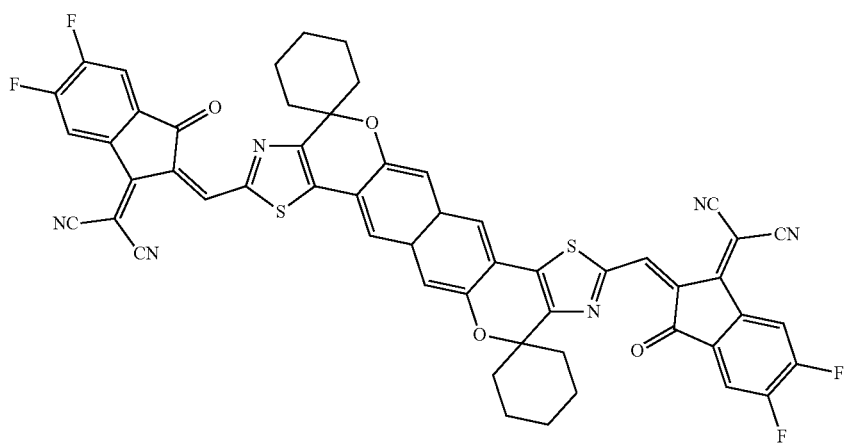

-continued
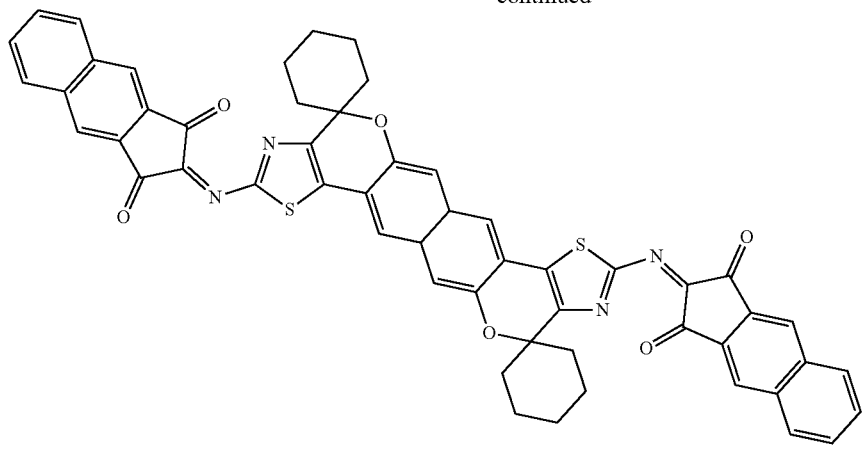
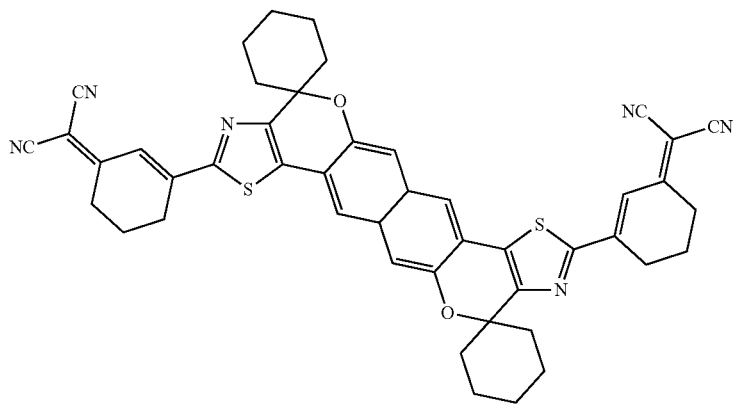
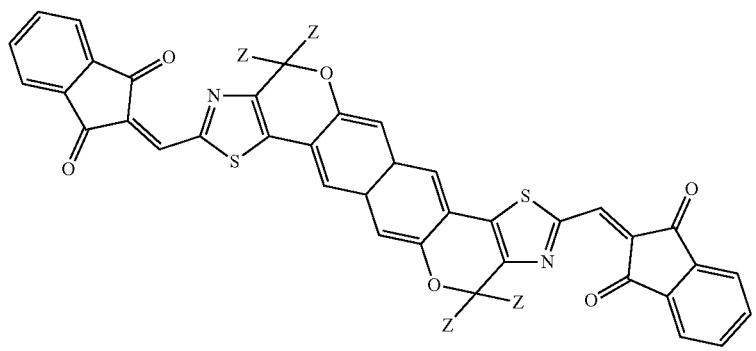
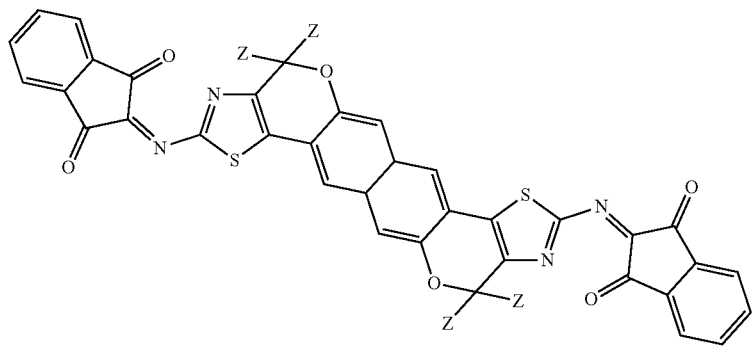

-continued
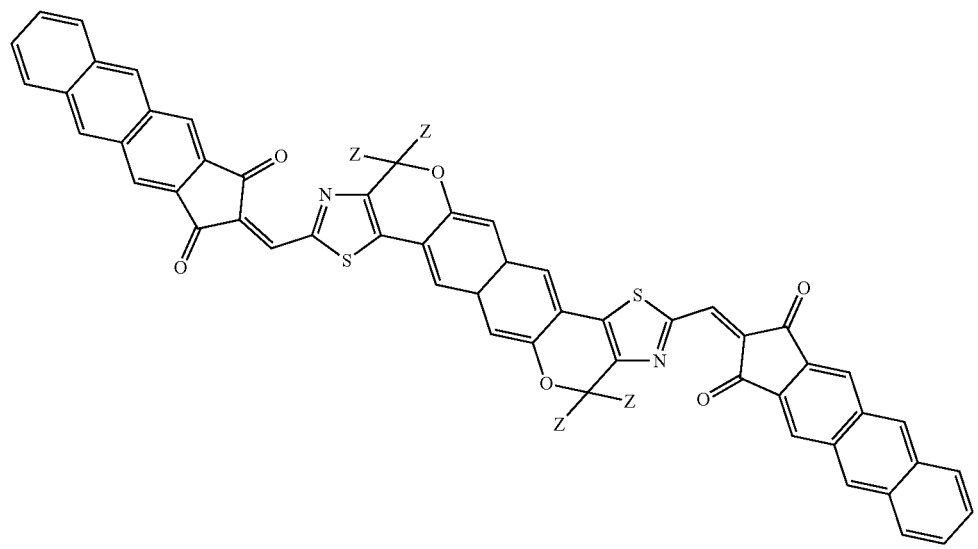
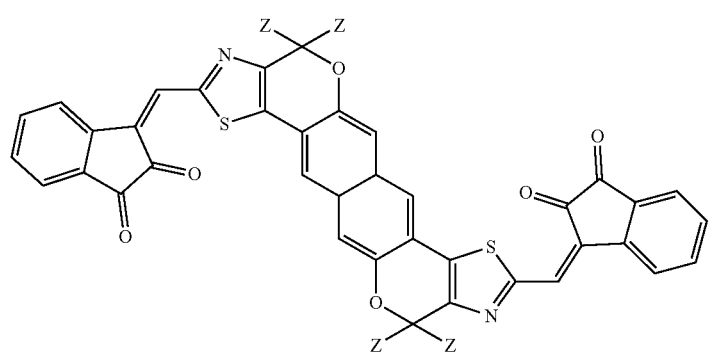
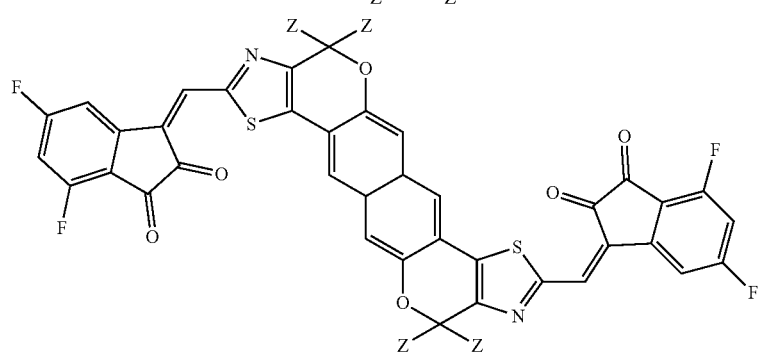
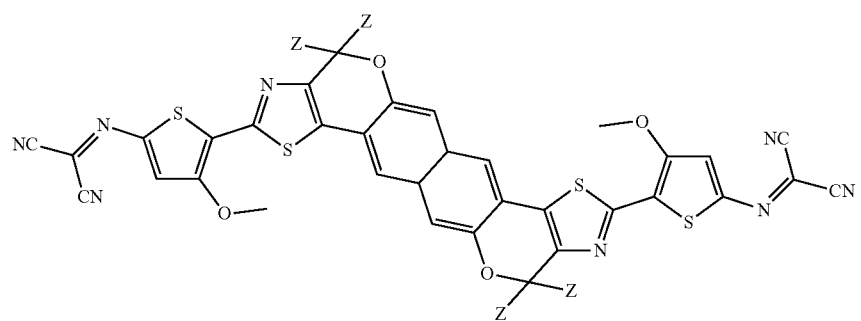

-continued
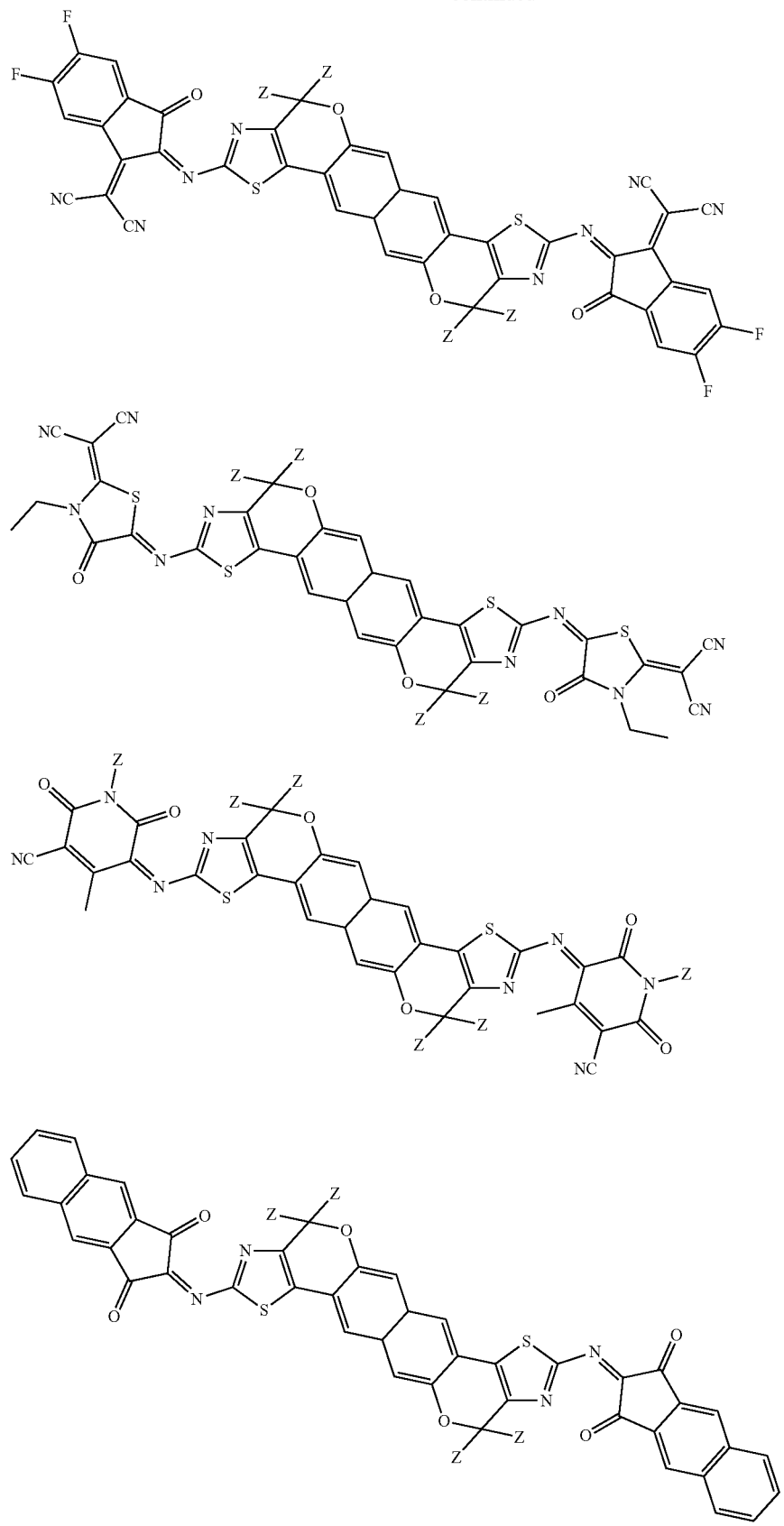

-continued
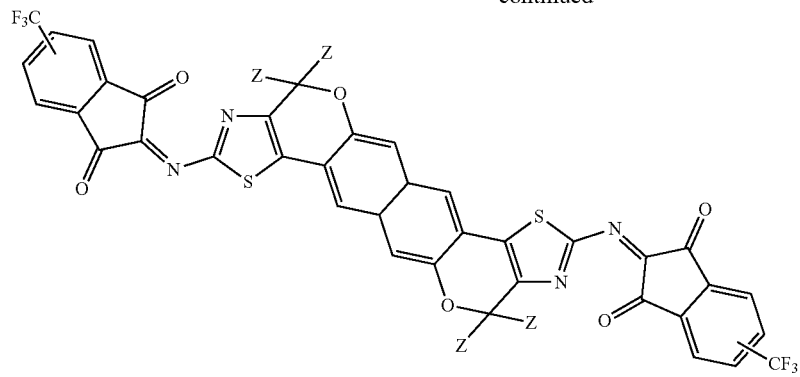
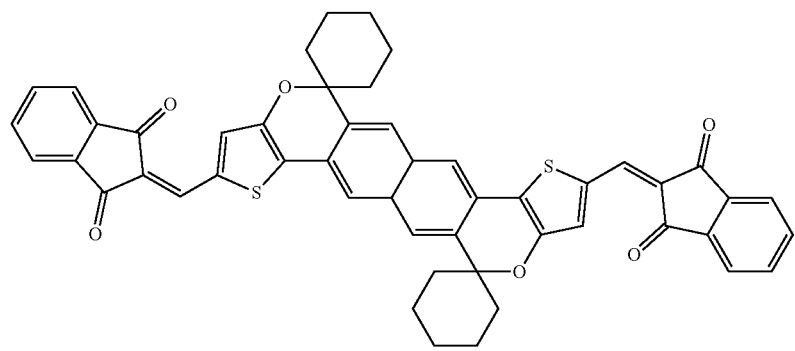
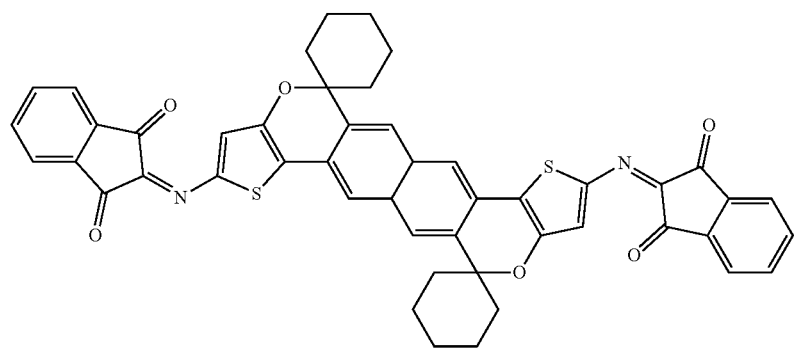
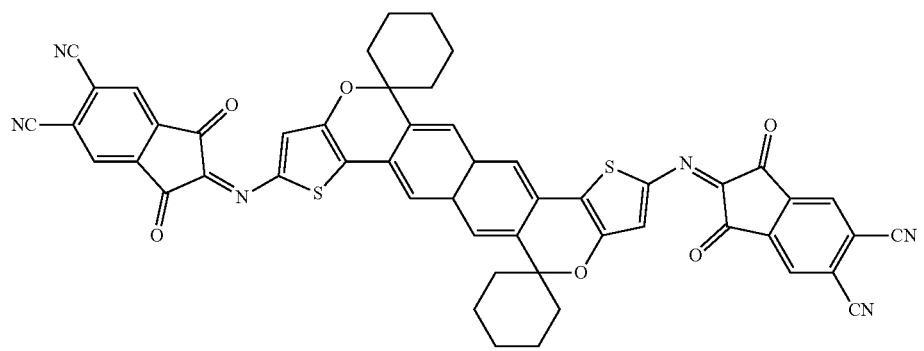

403                                                                                           404
-continued
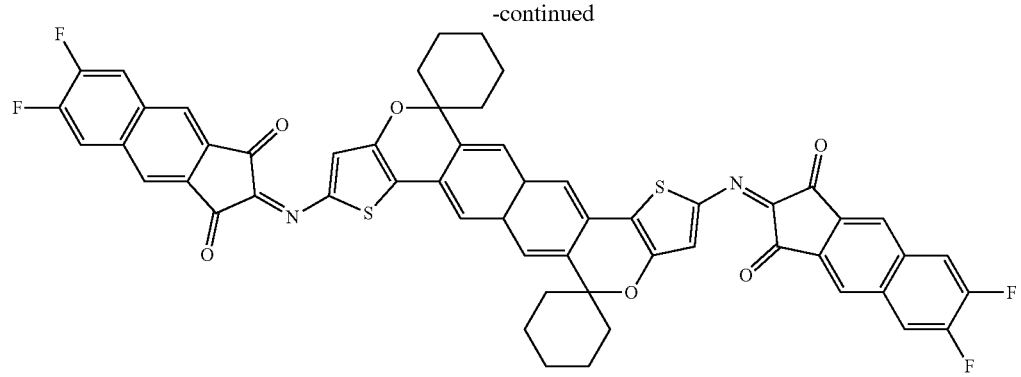
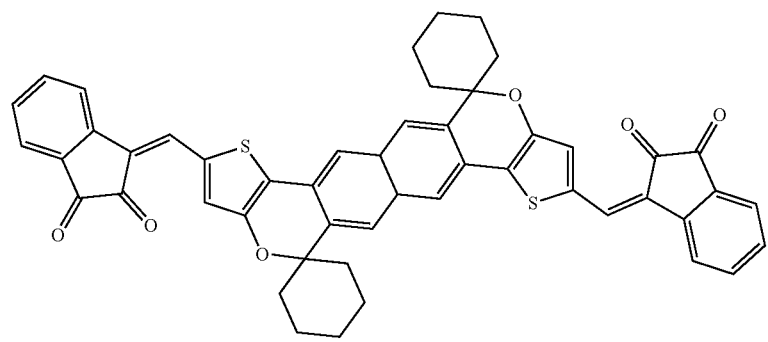
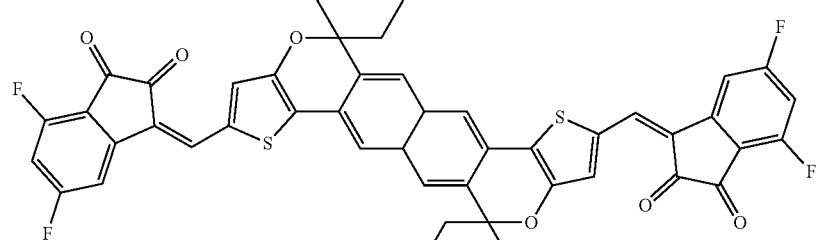
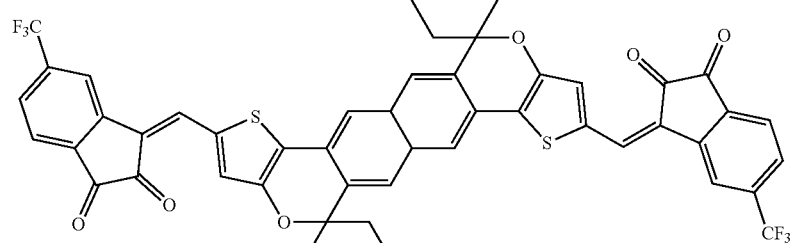
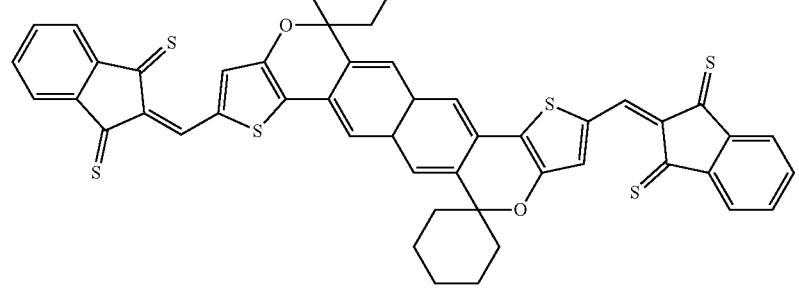

-continued
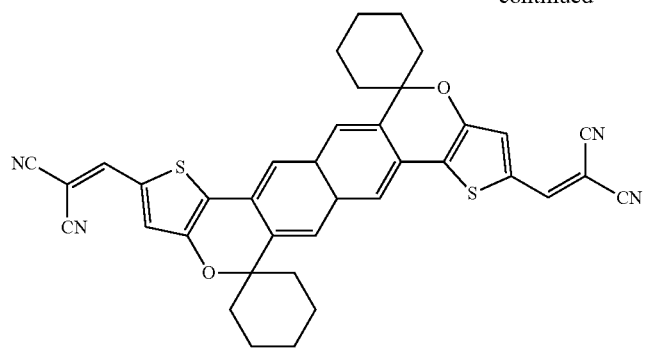
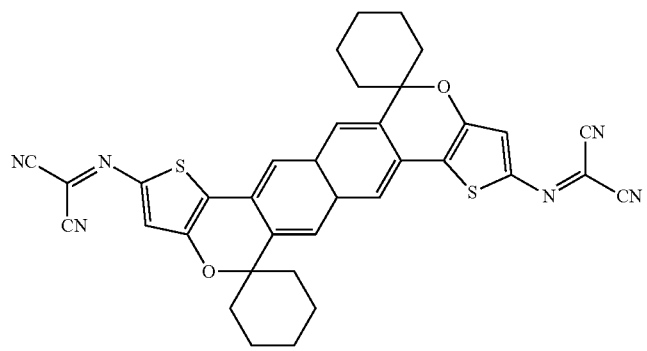
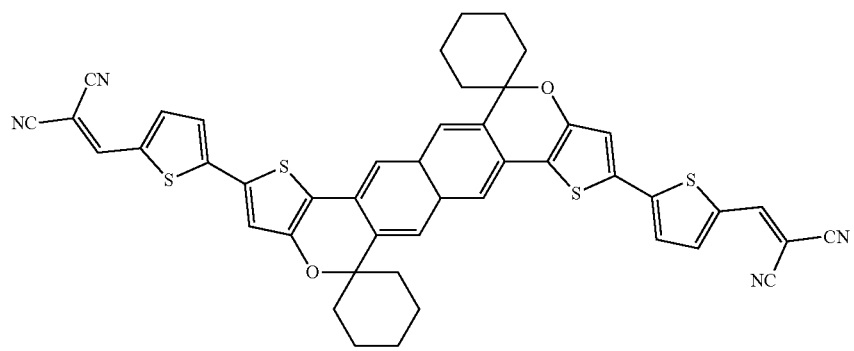
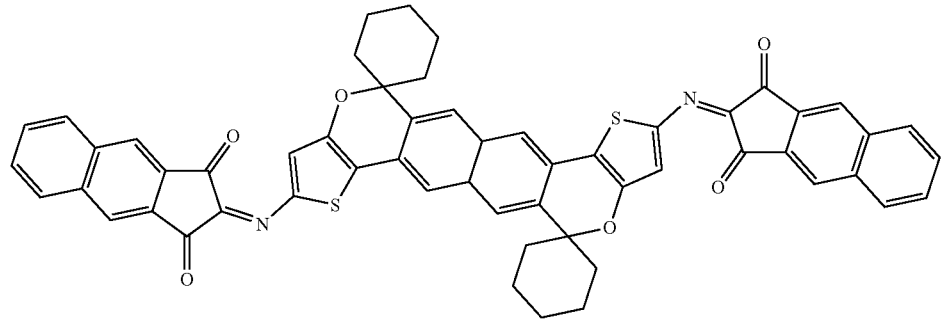
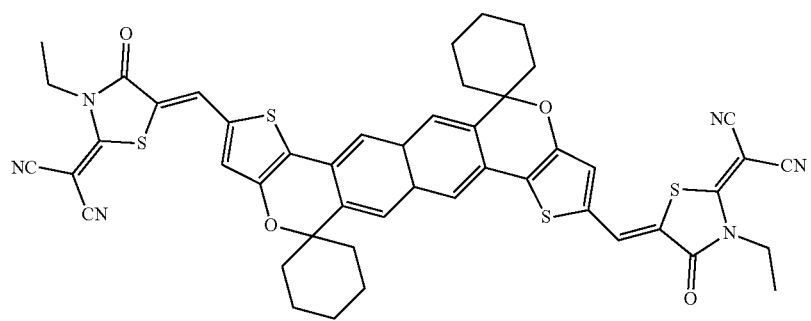

-continued
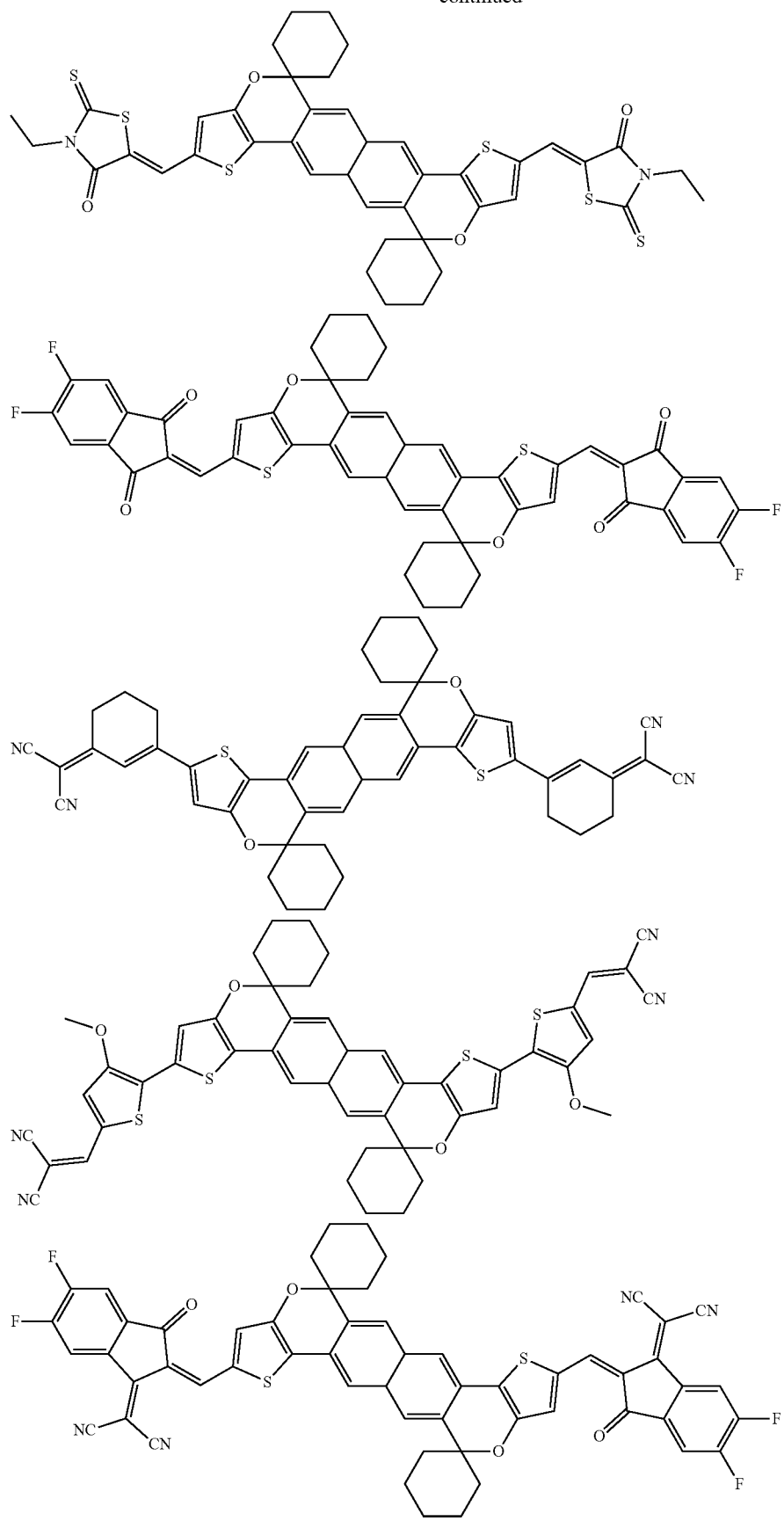

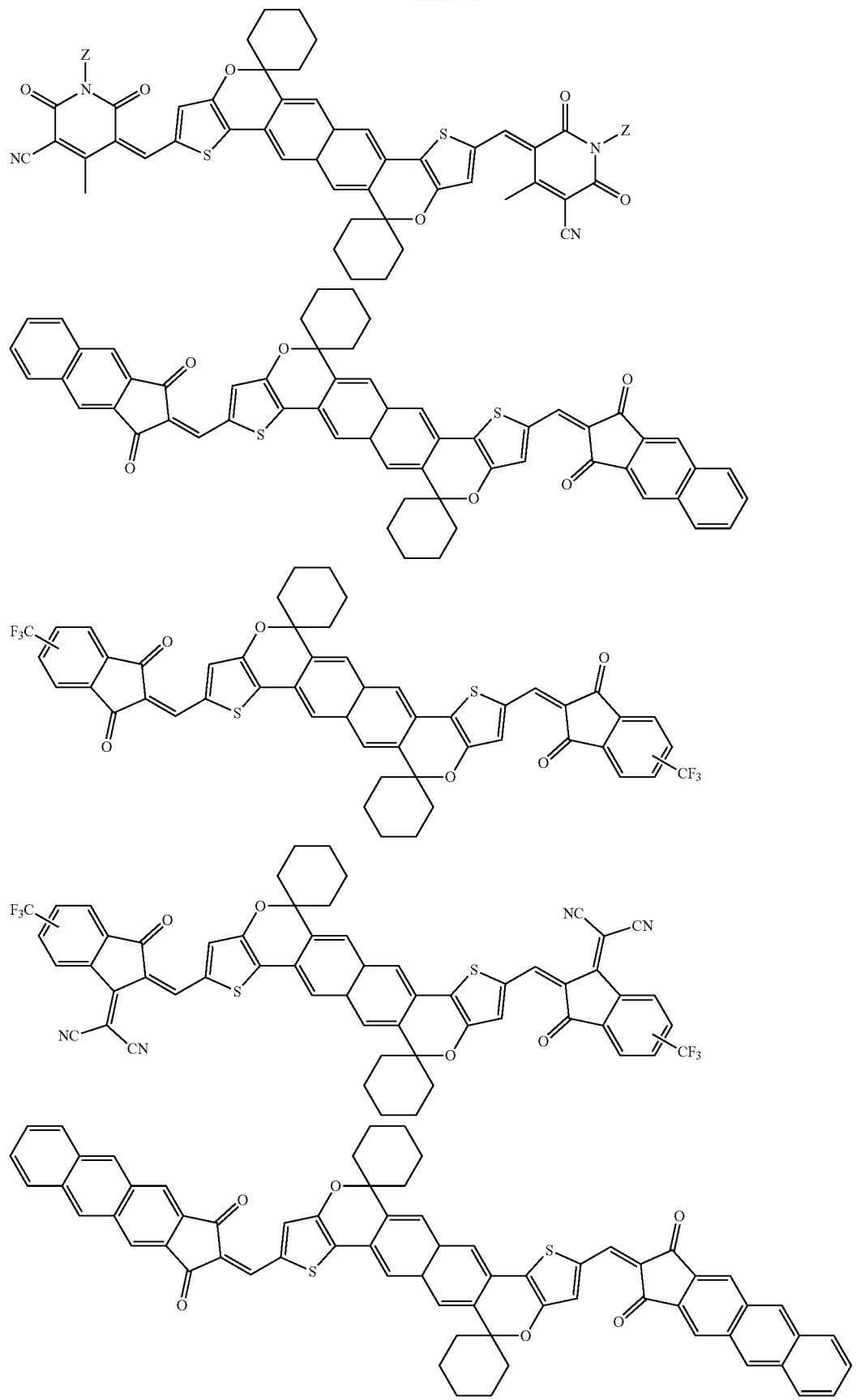

-continued
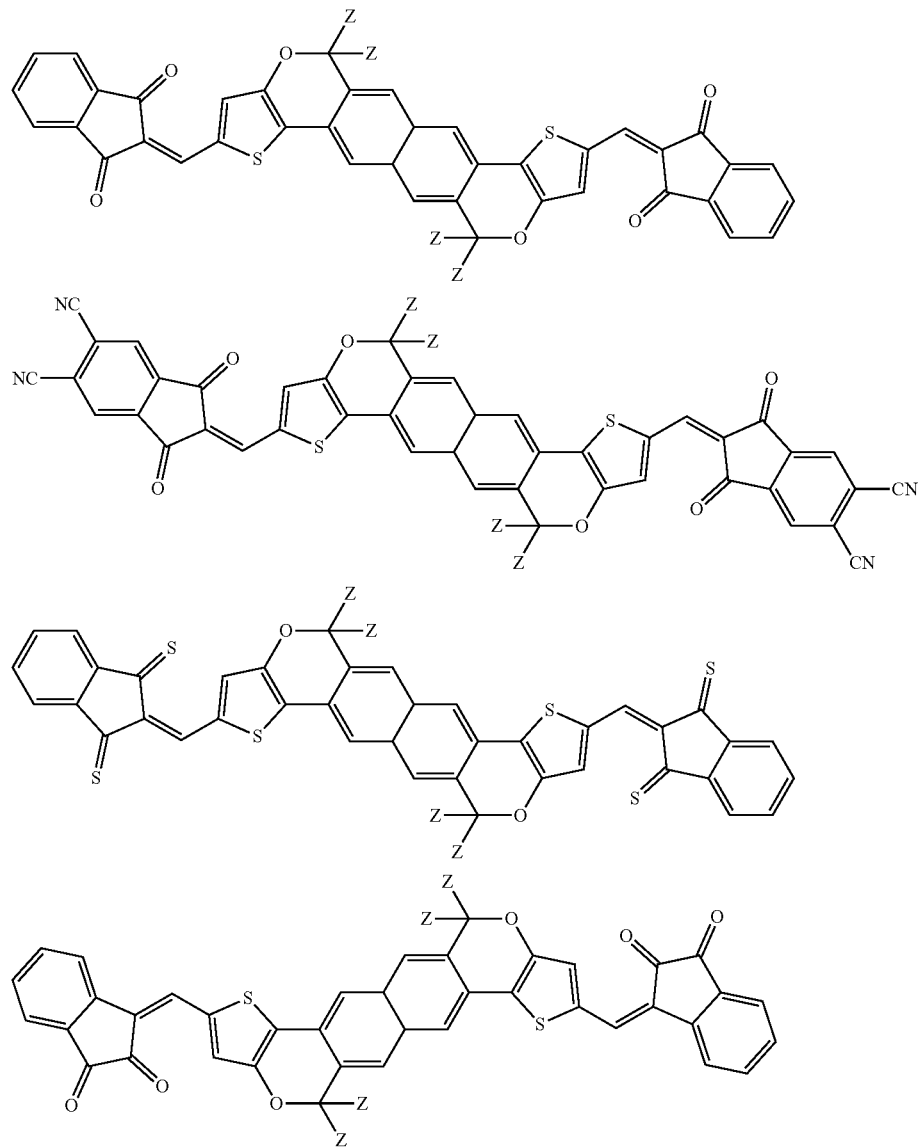
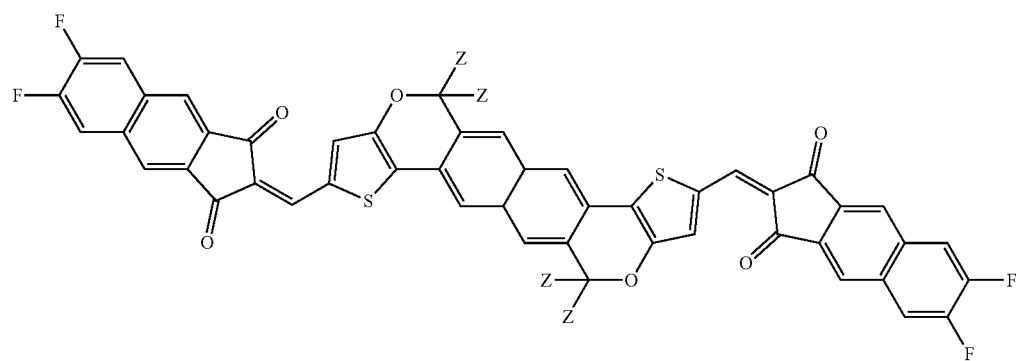

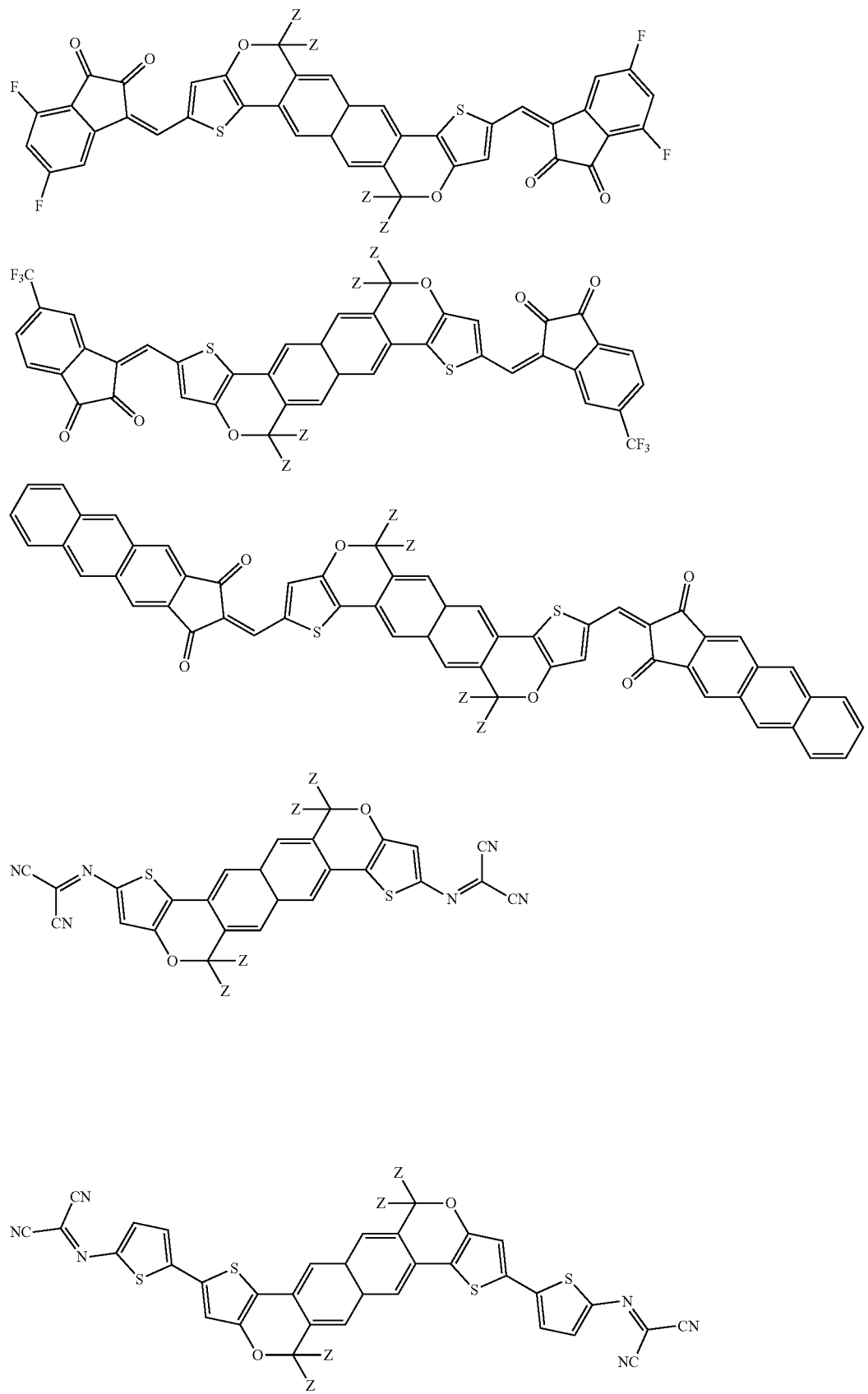

-continued
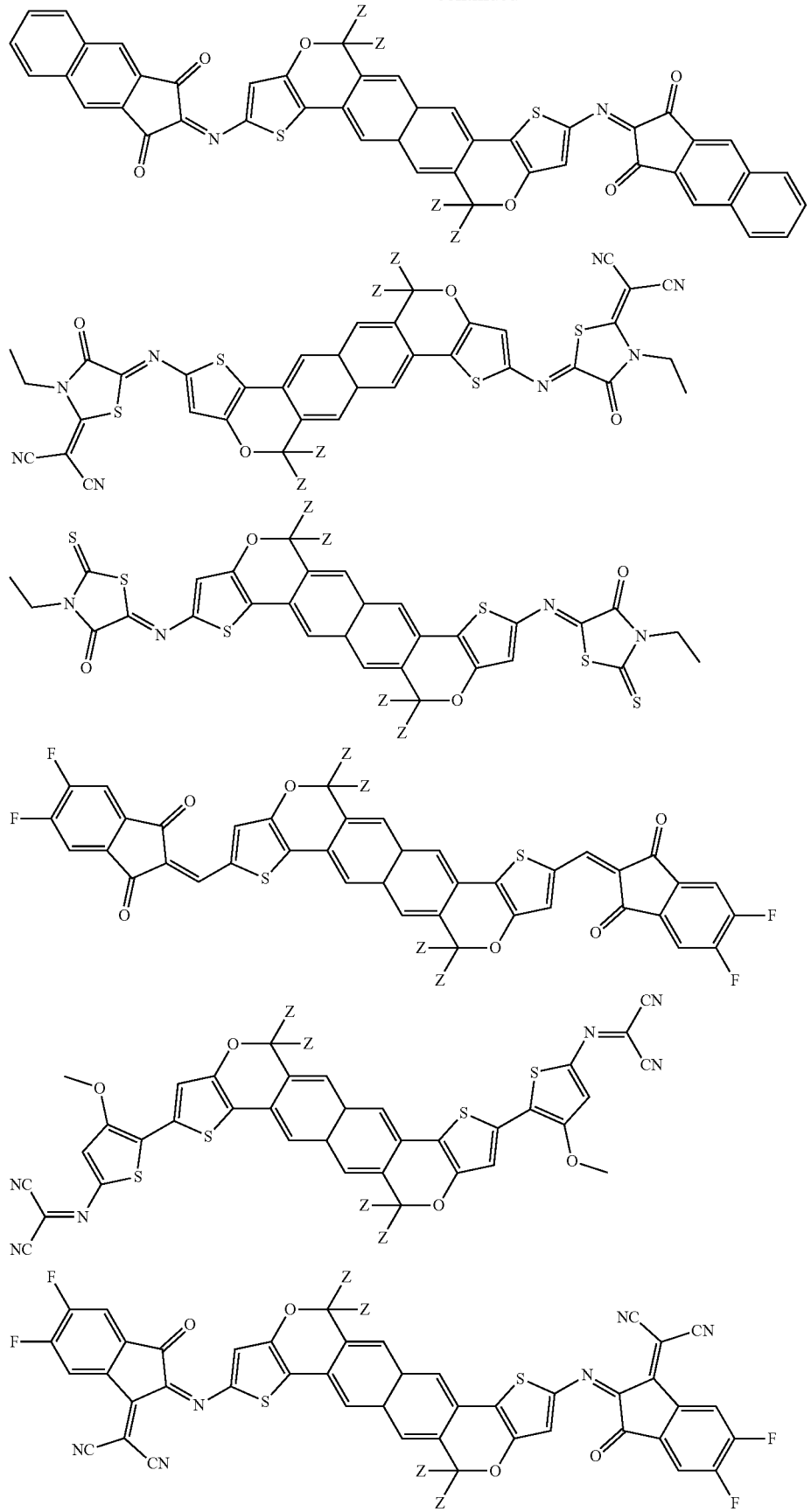

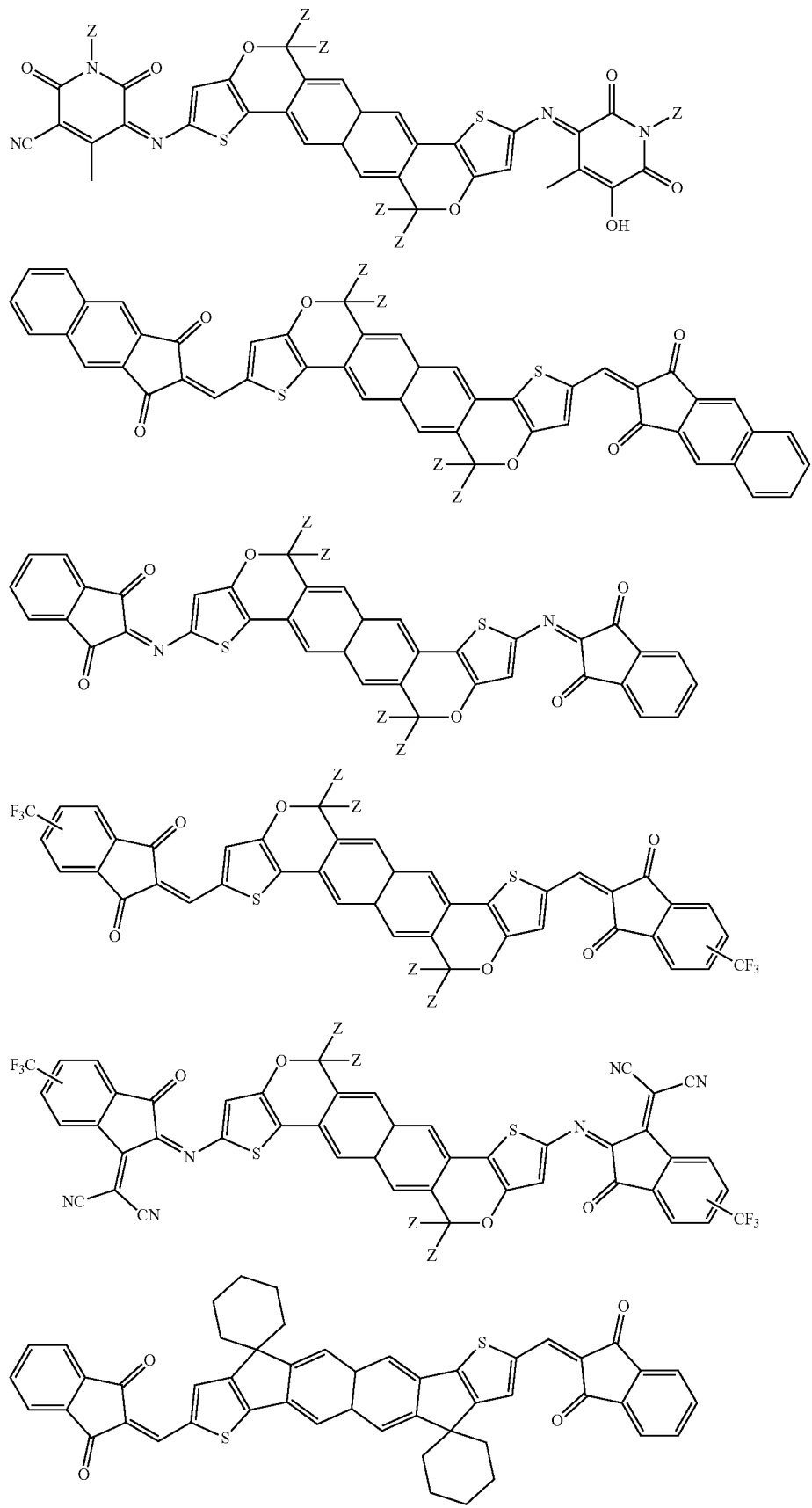

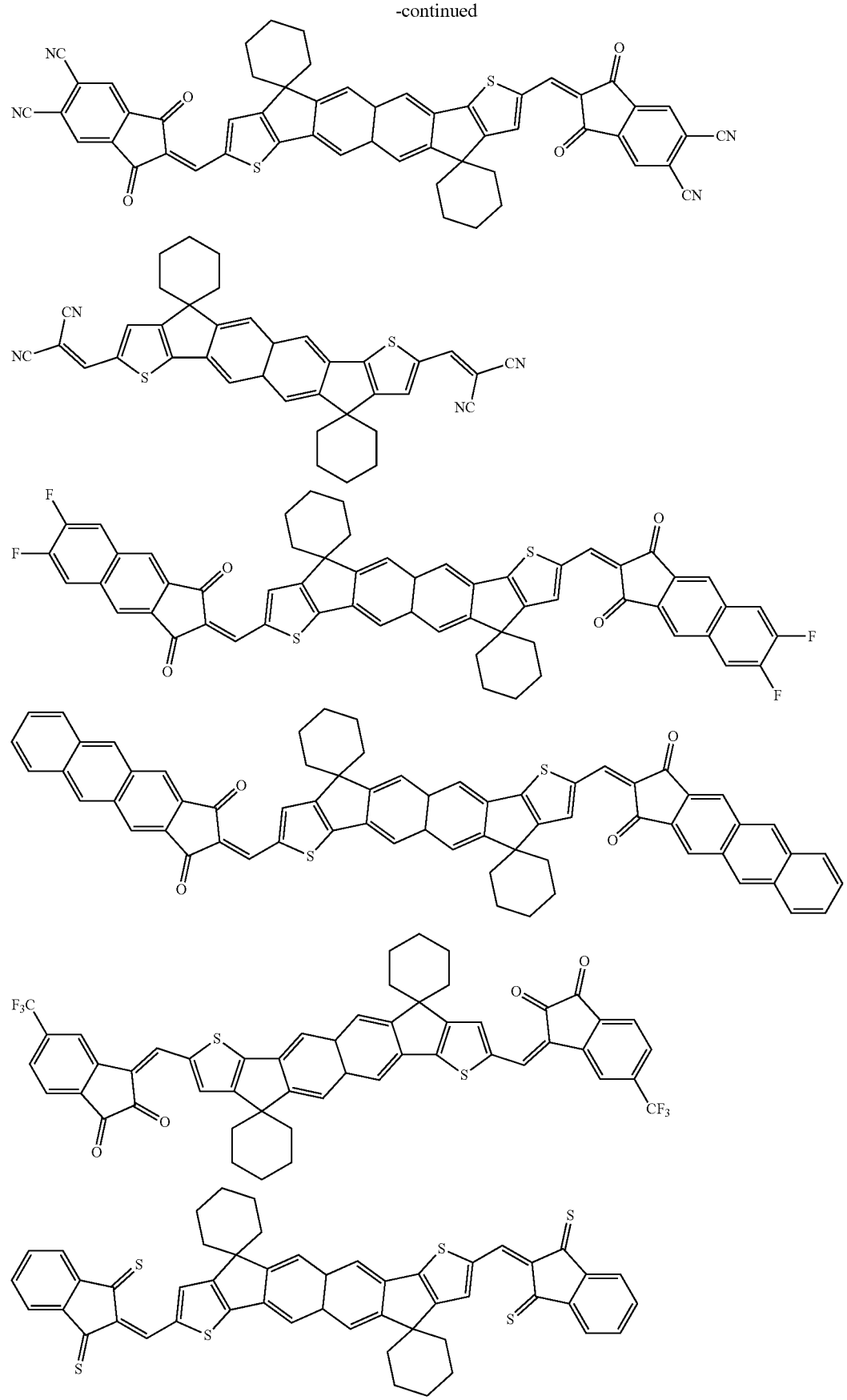

-continued
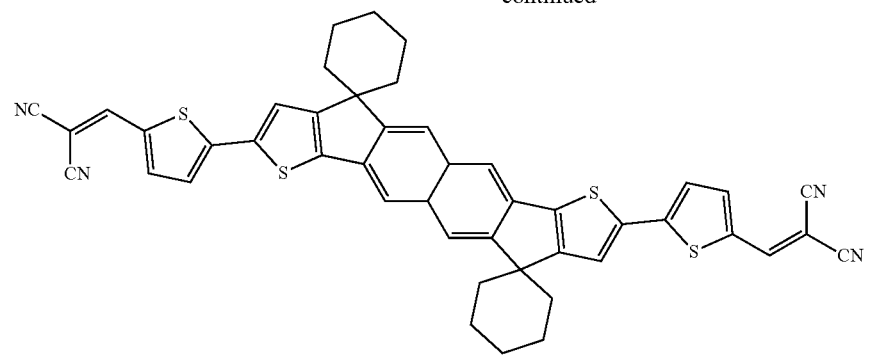
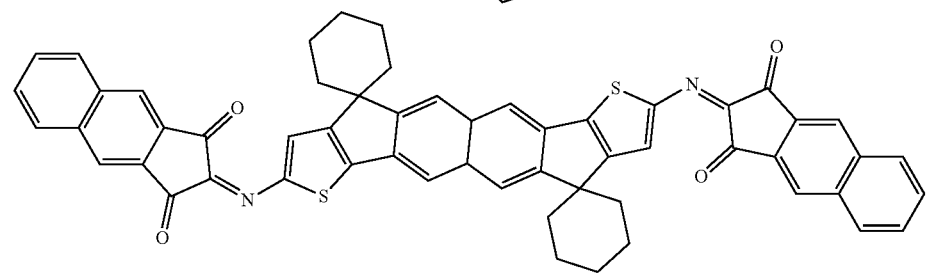
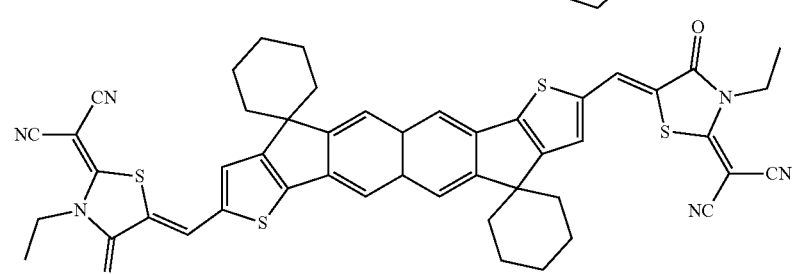
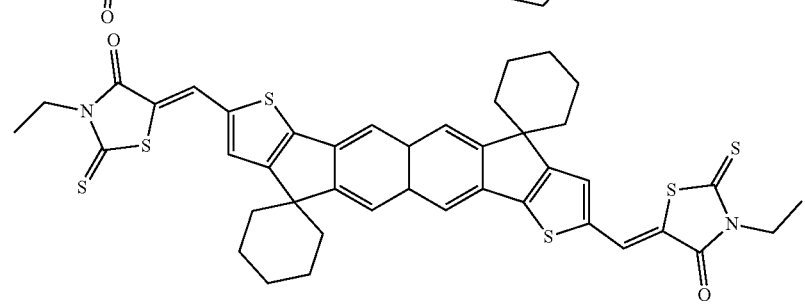
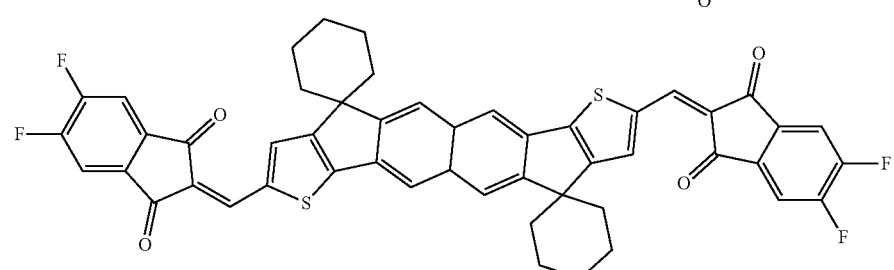
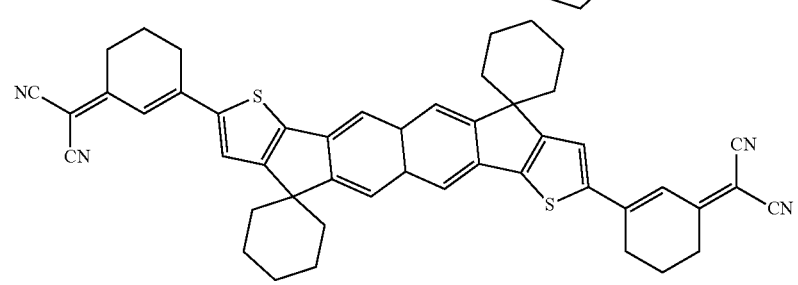

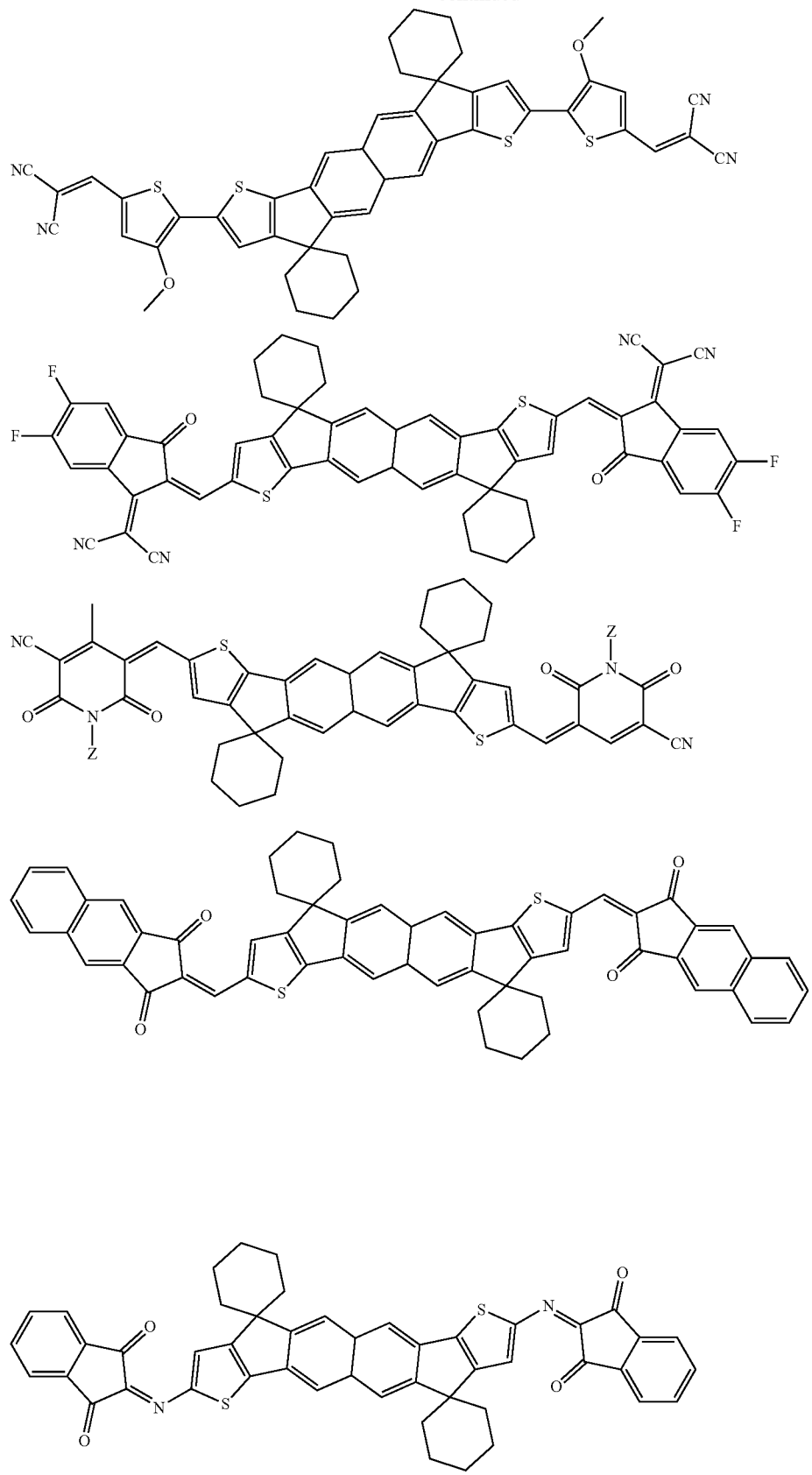

-continued
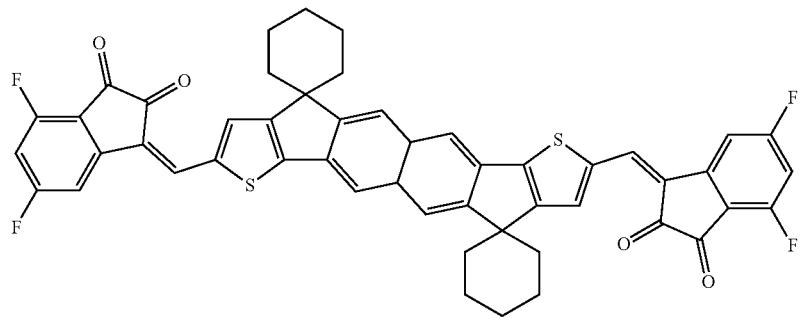
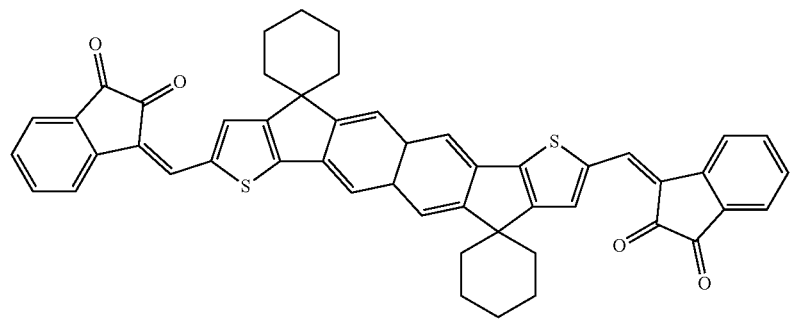
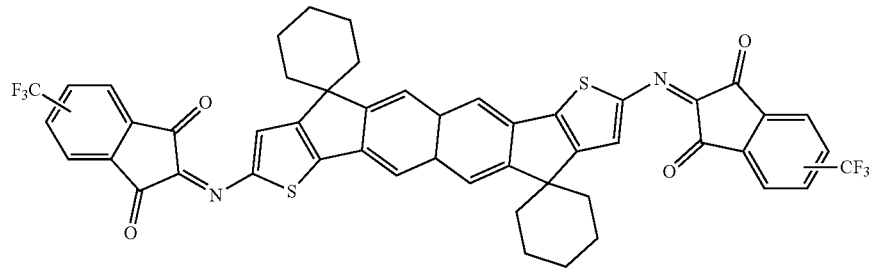
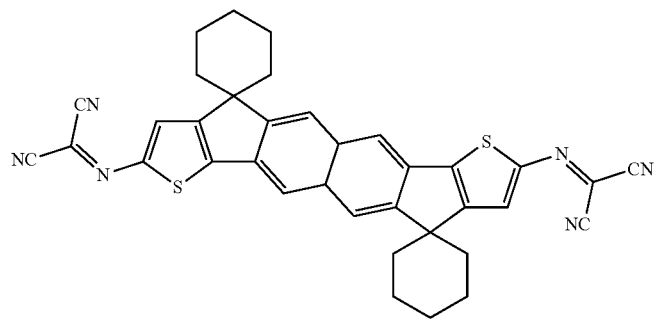
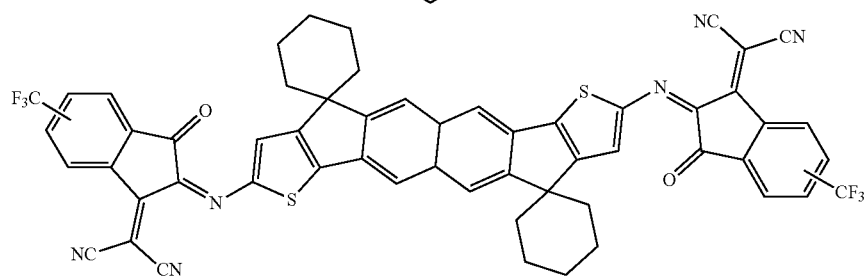
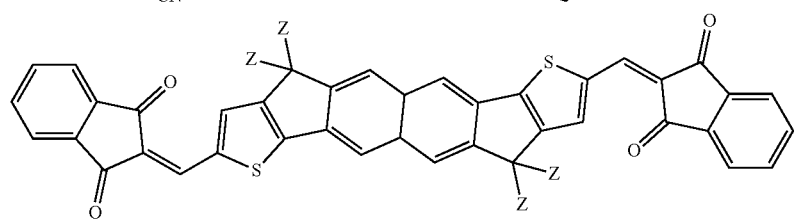

-continued
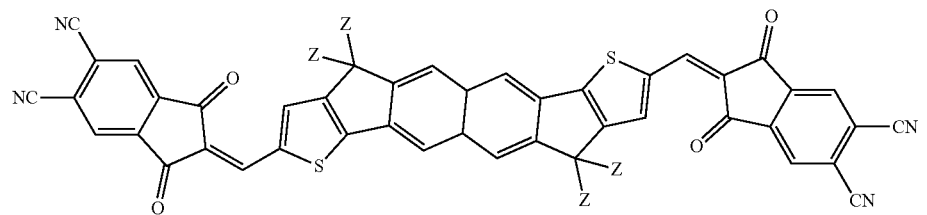
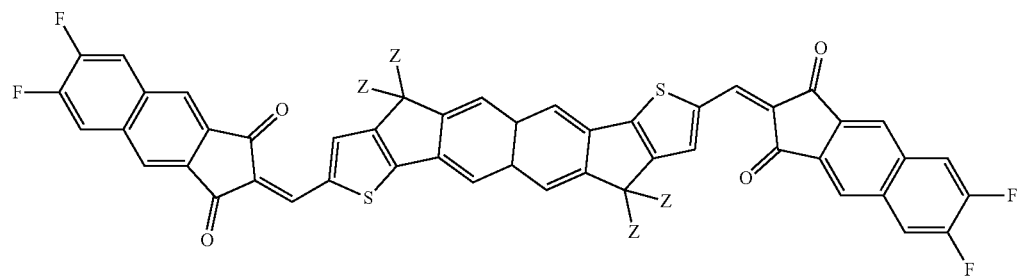
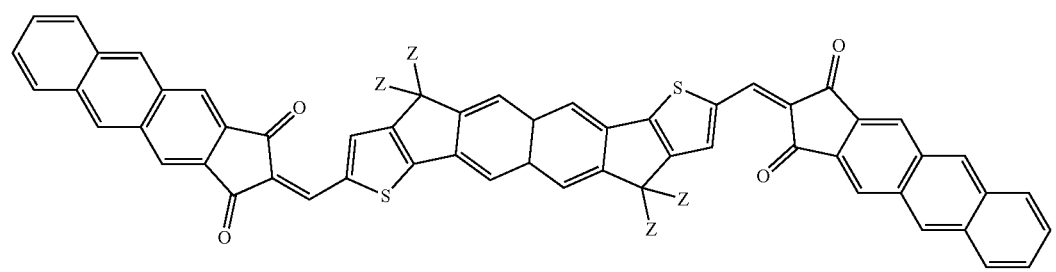
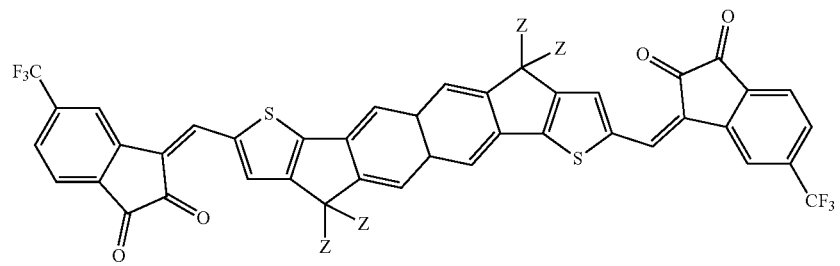
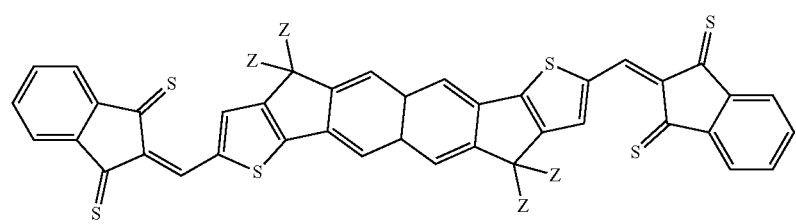
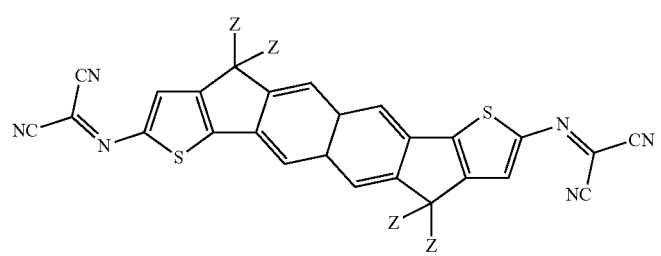

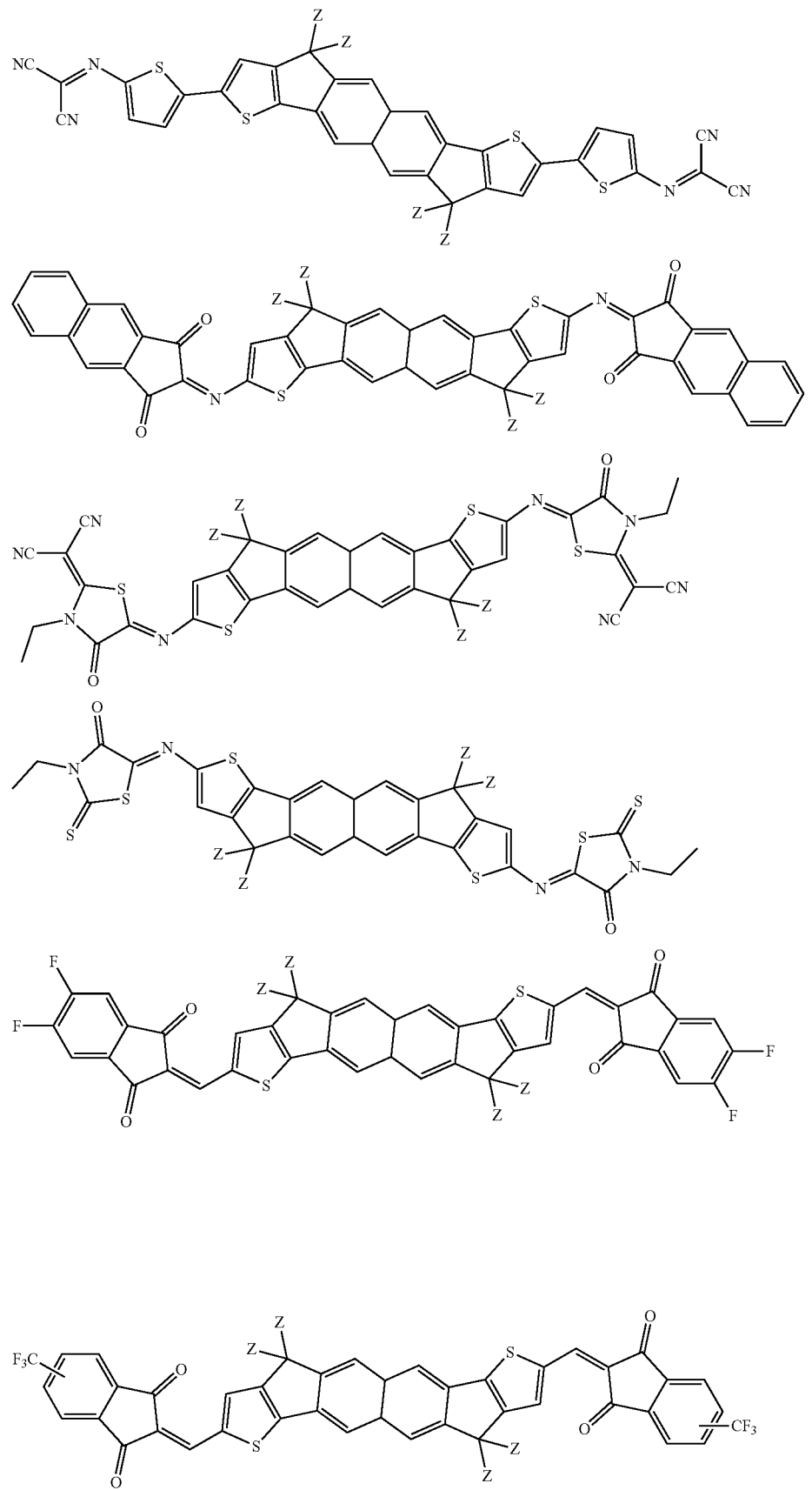

-continued
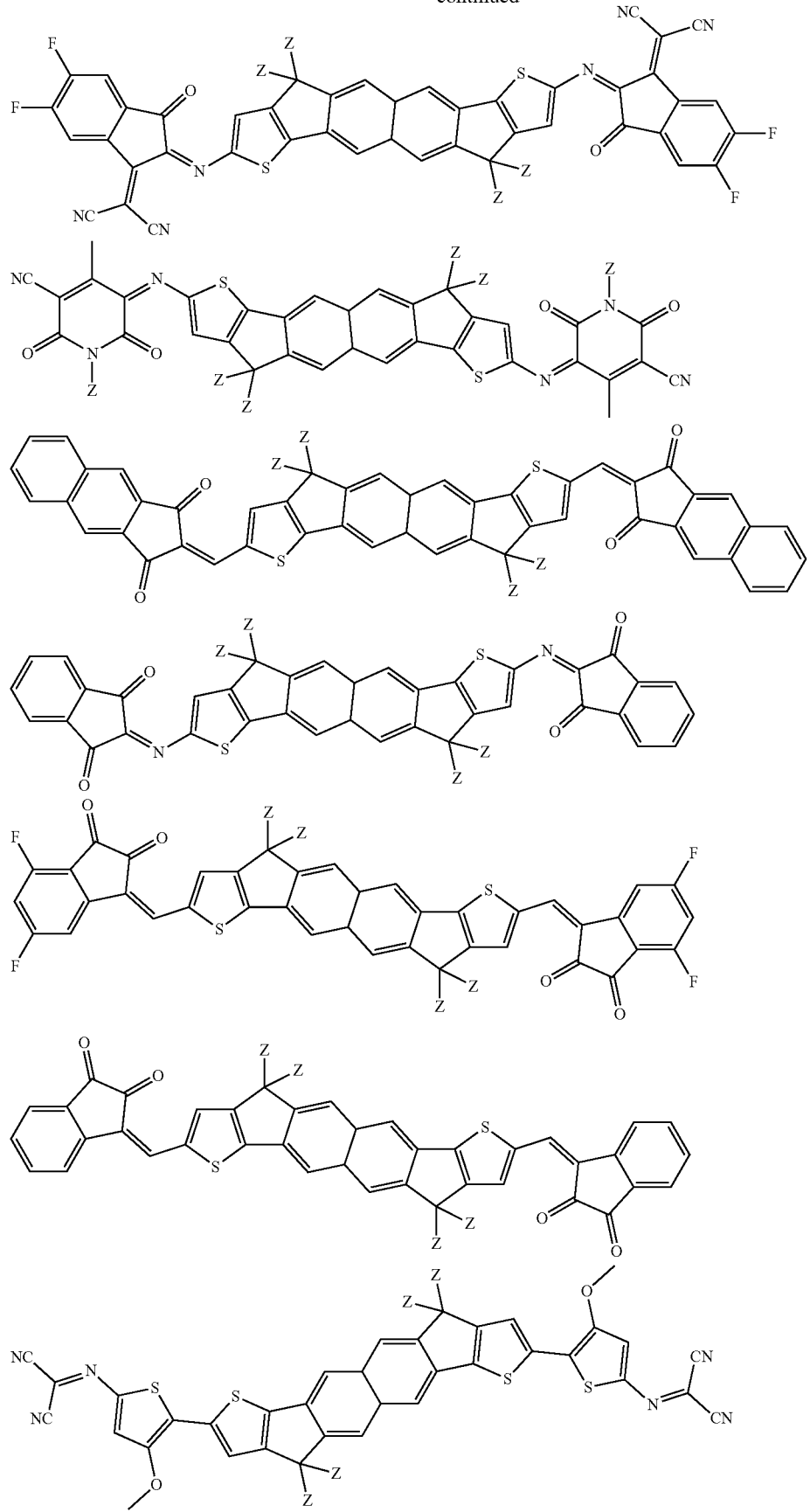

-continued
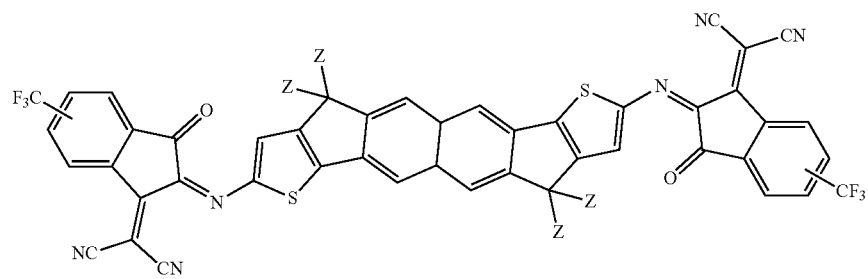
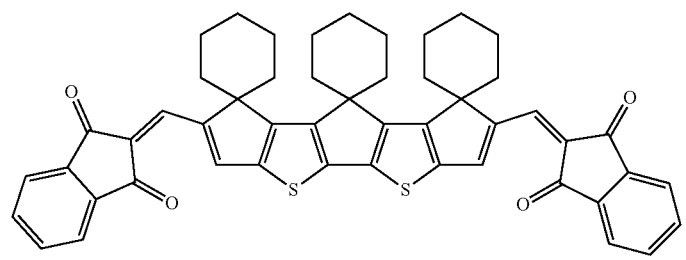
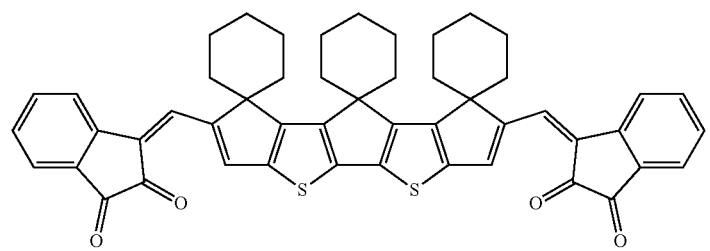
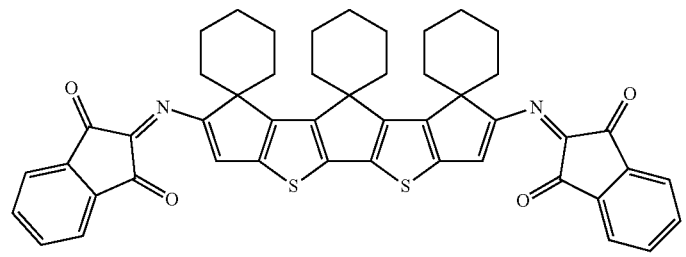
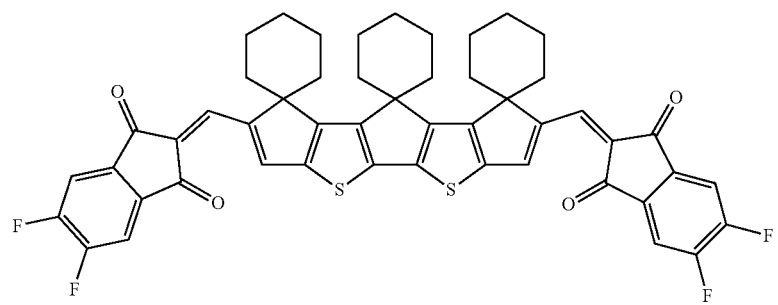
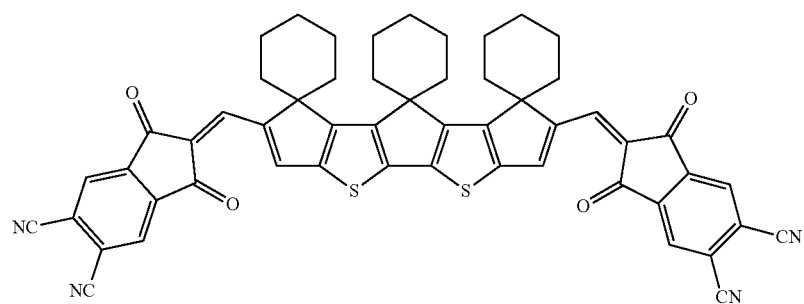

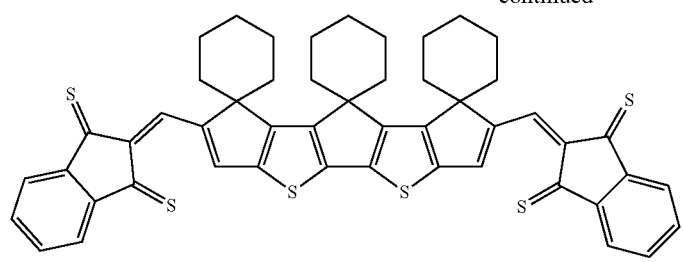
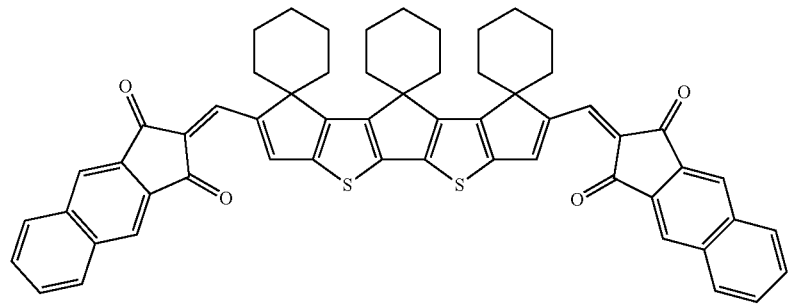
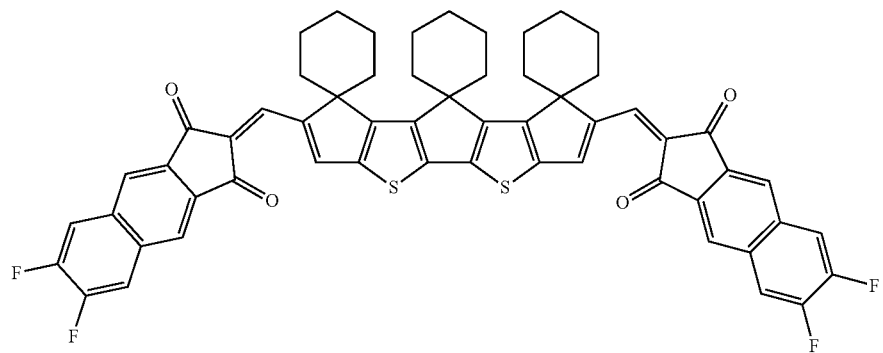
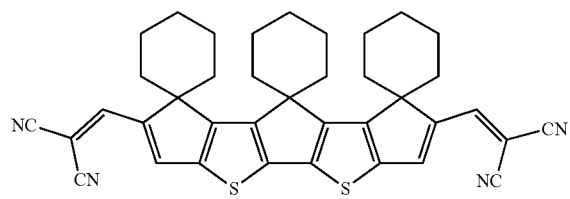
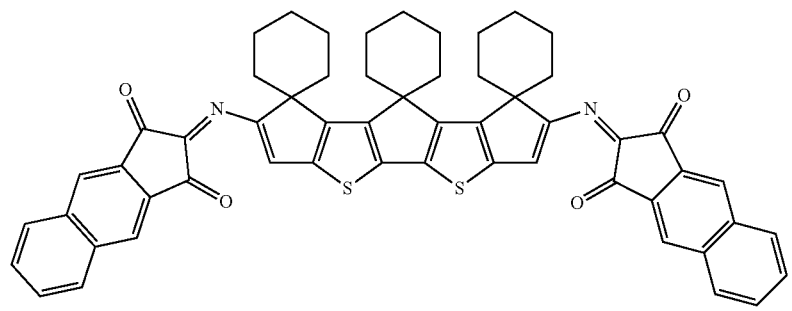
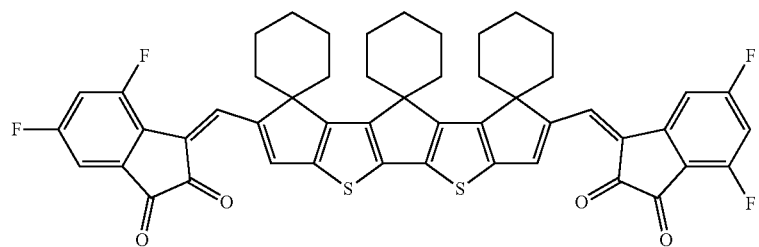

-continued
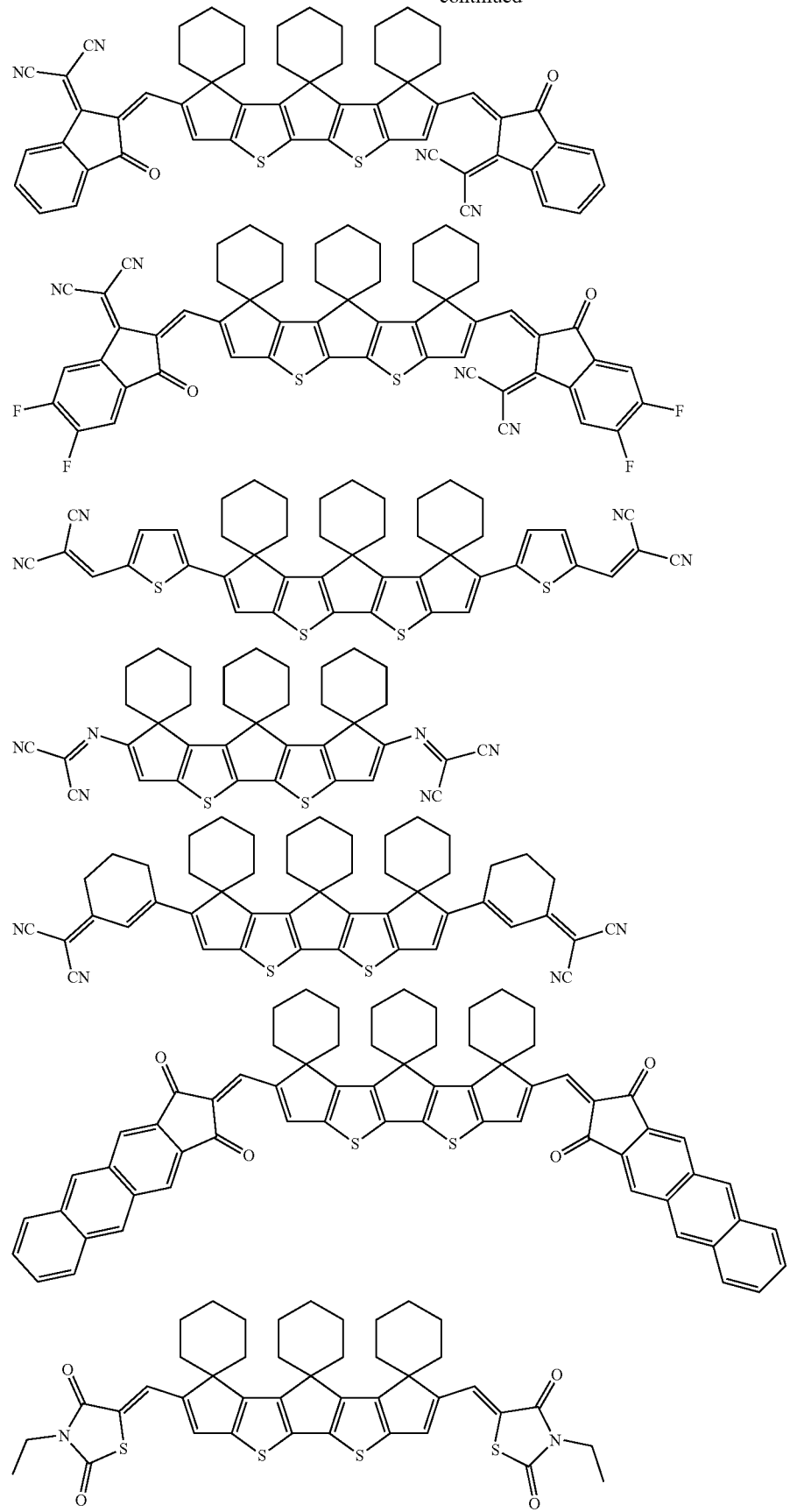

-continued
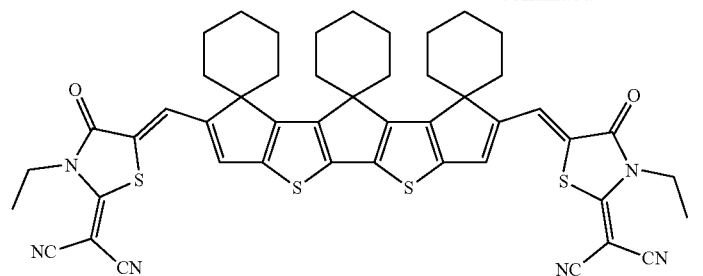
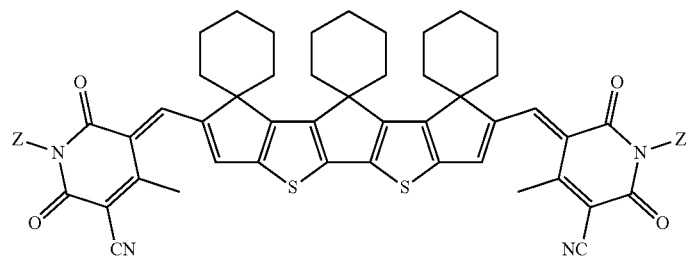
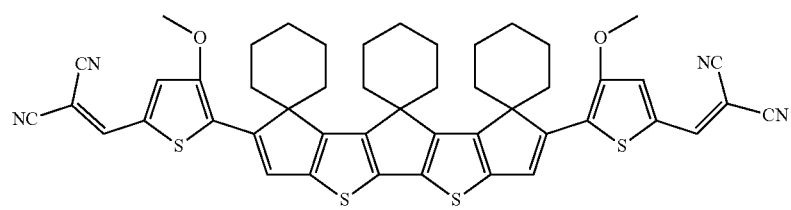
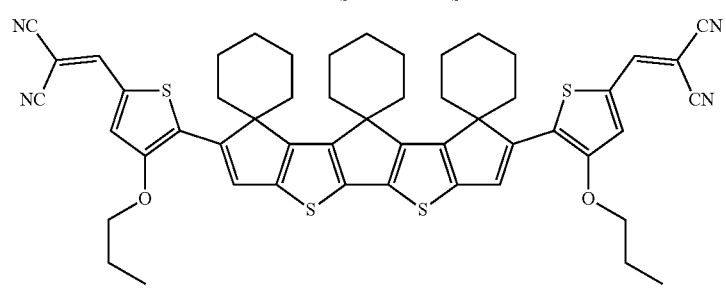
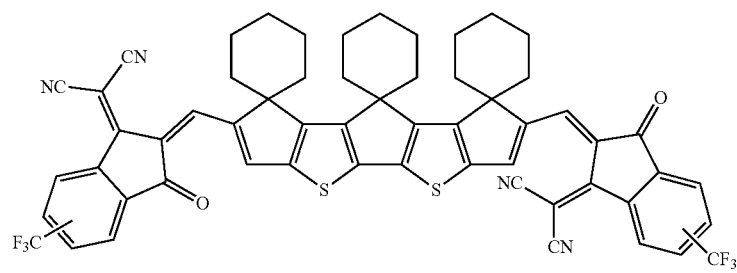
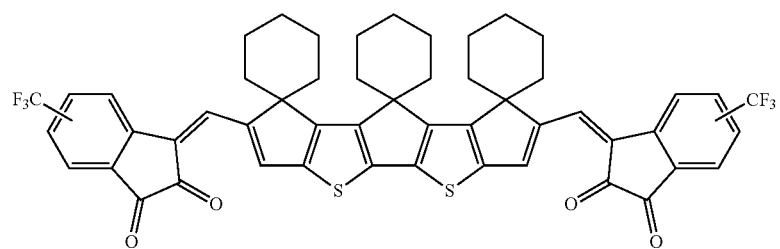

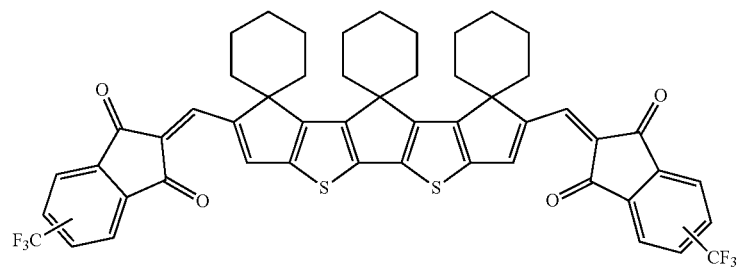
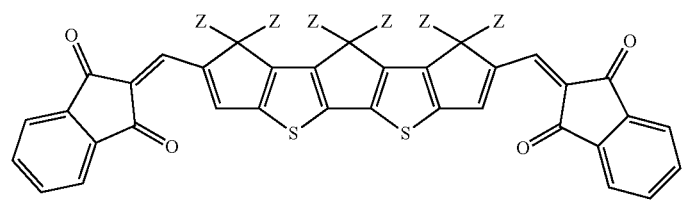
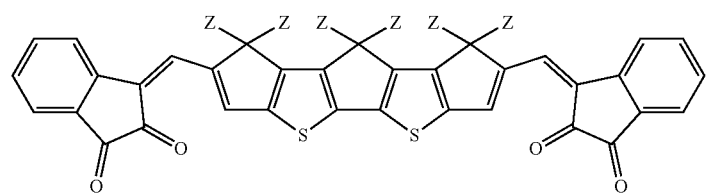
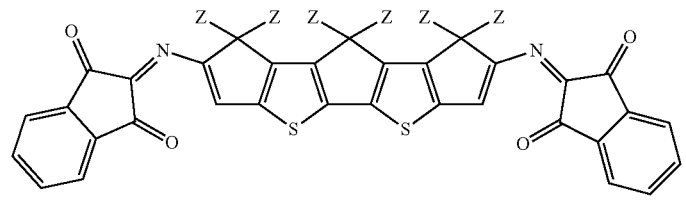
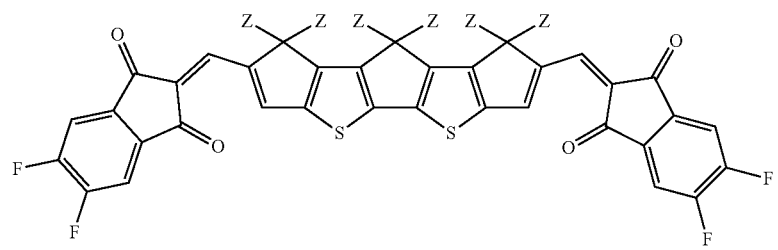
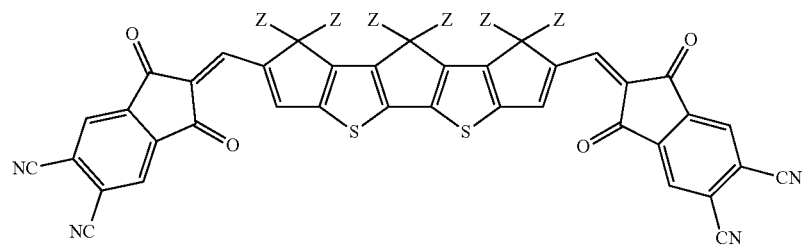
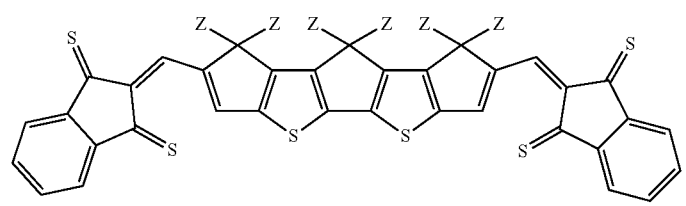

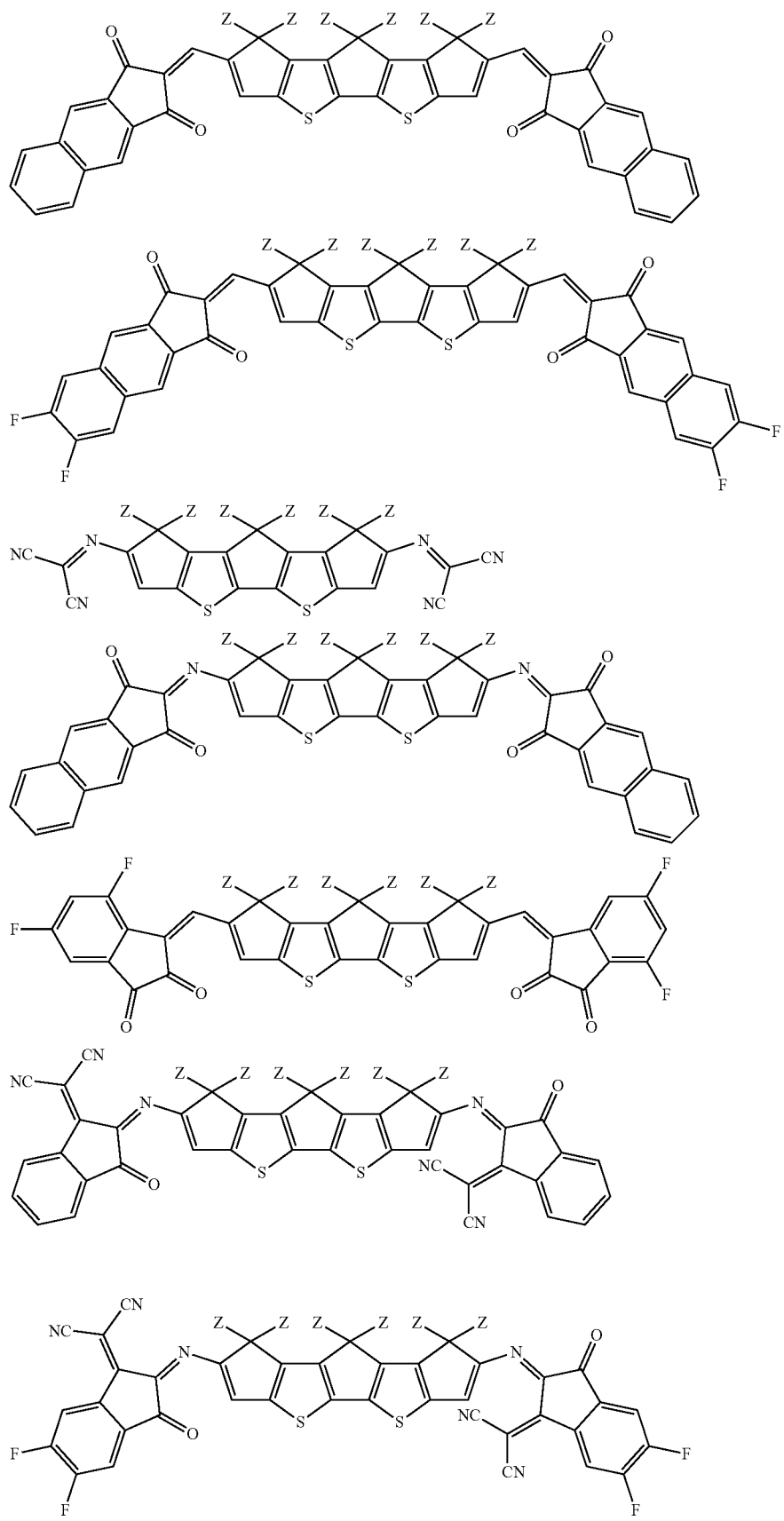

-continued
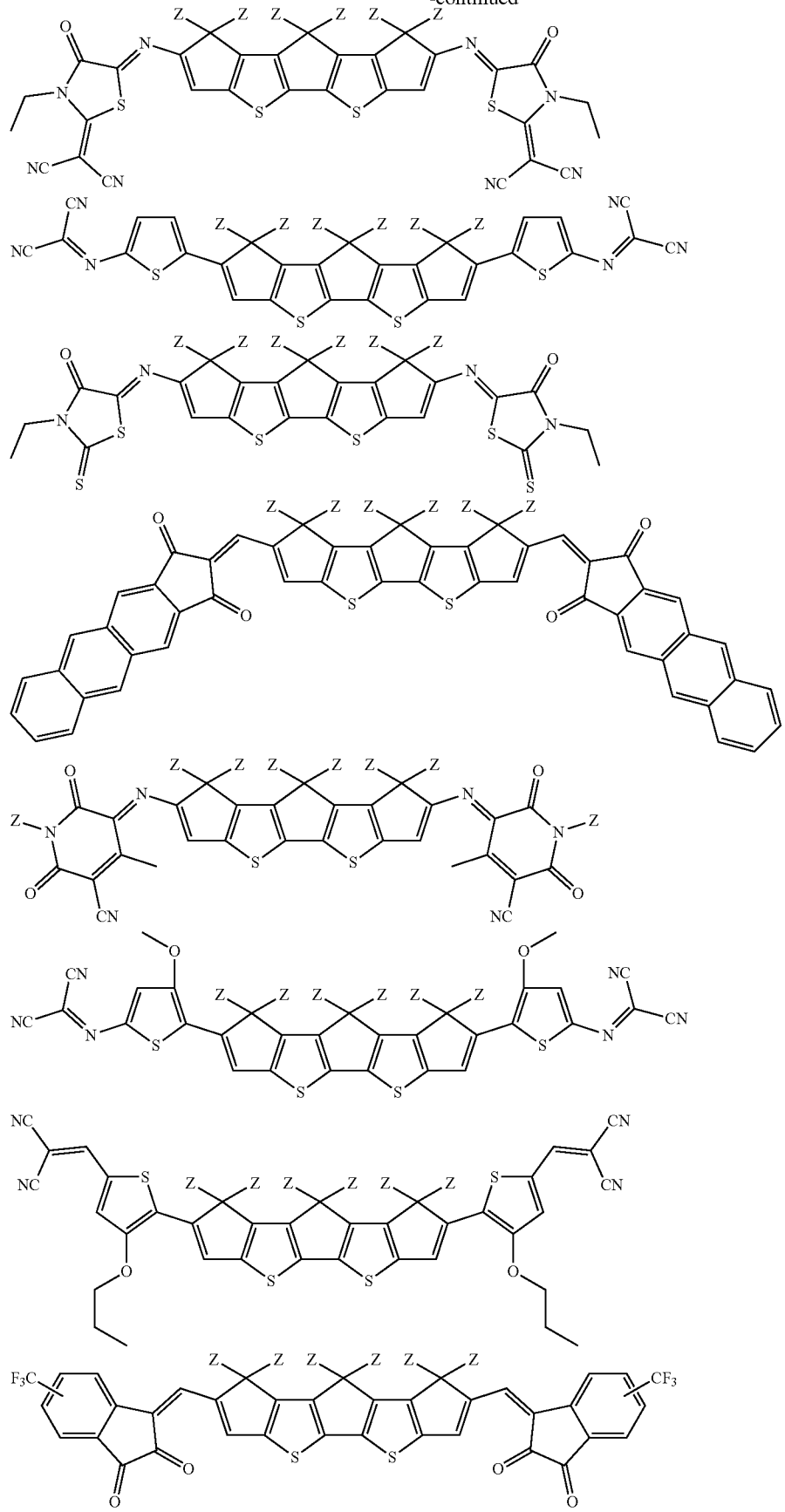

-continued
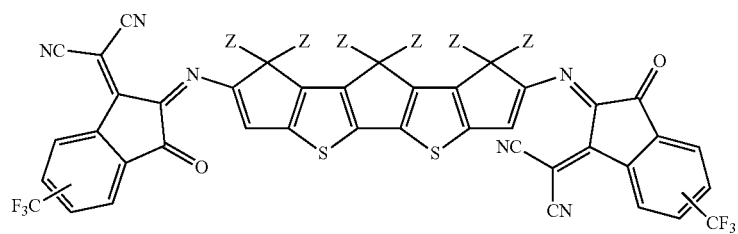
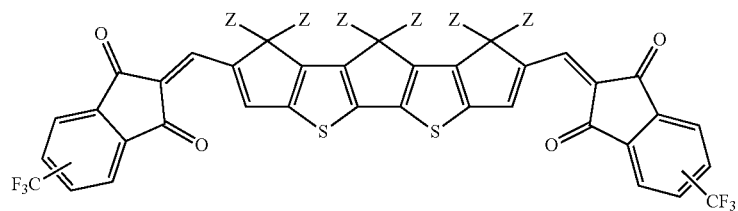
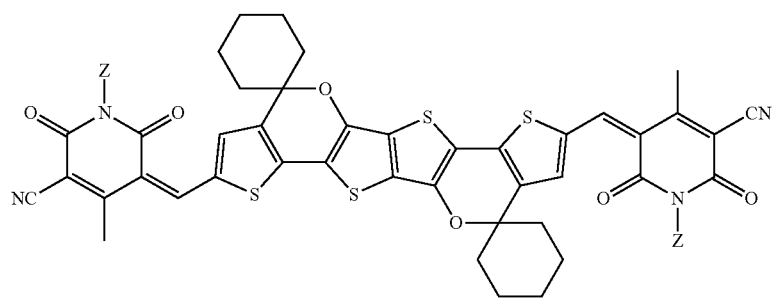
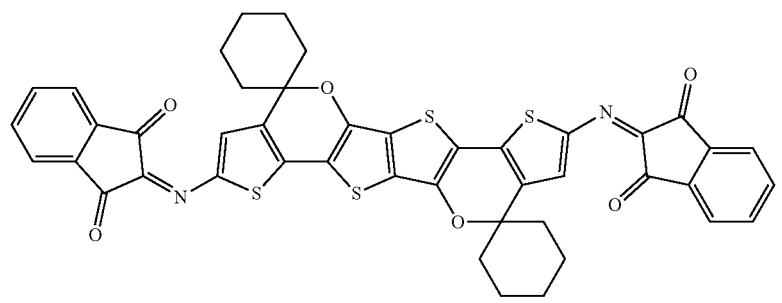
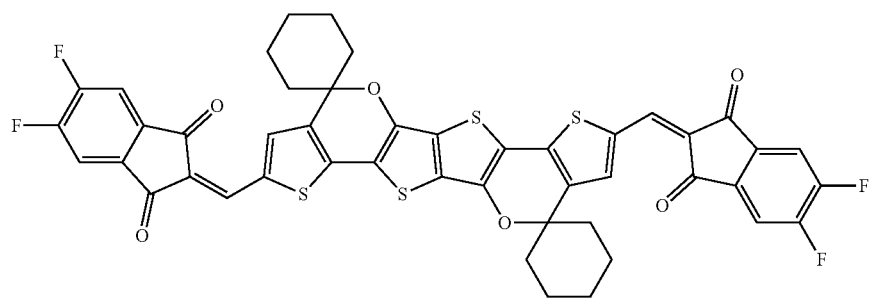
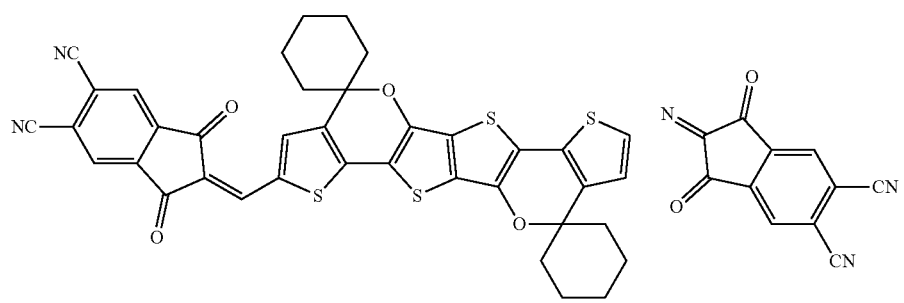

-continued
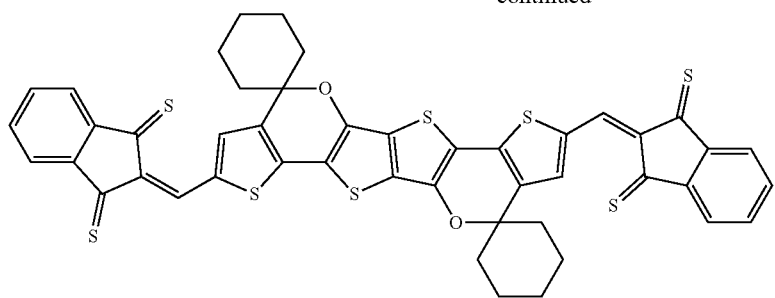
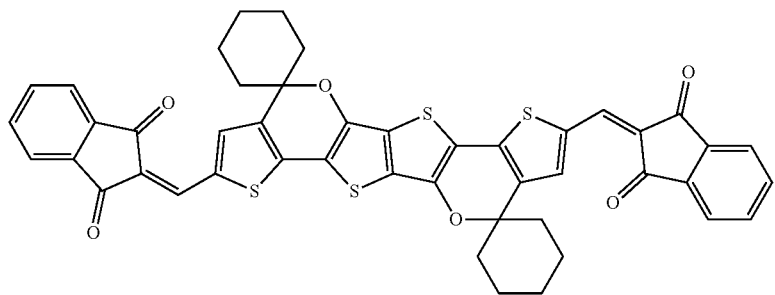
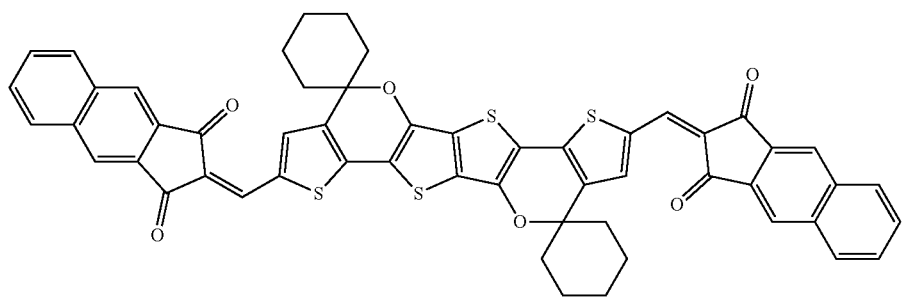
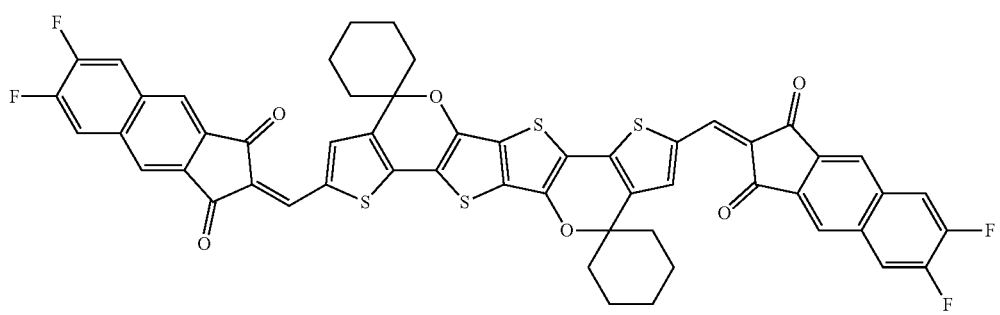
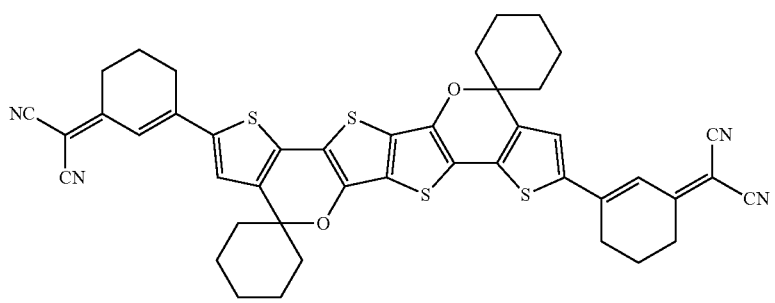

-continued
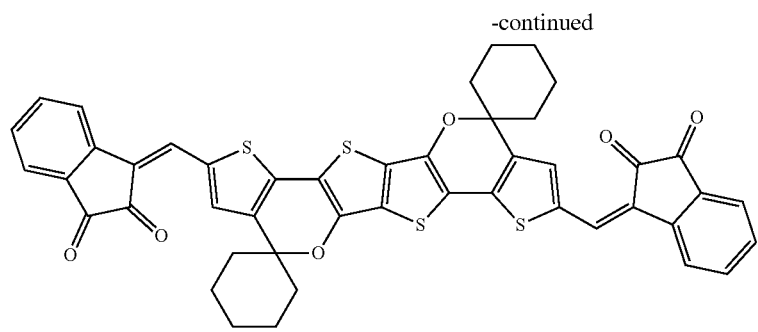
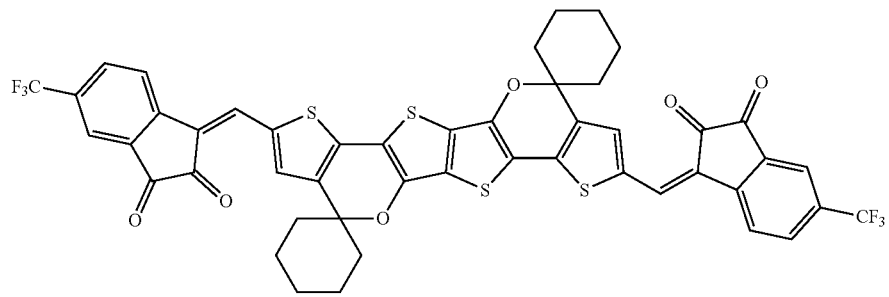
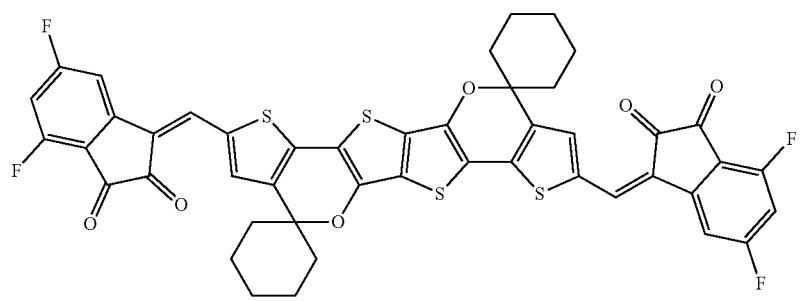
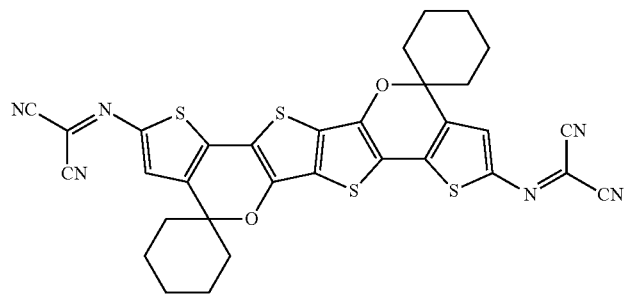
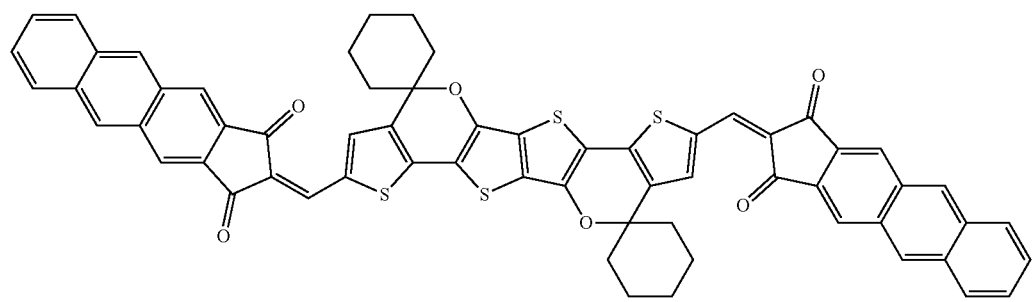

-continued
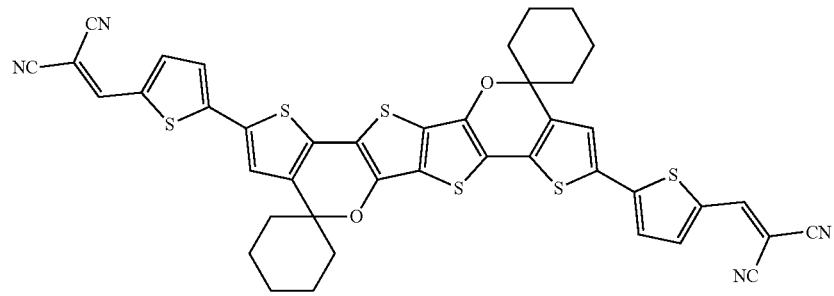
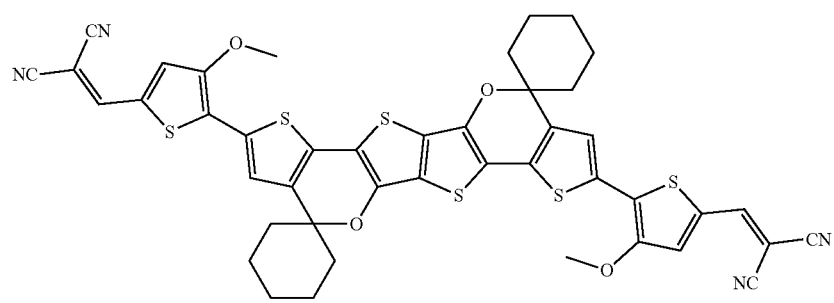
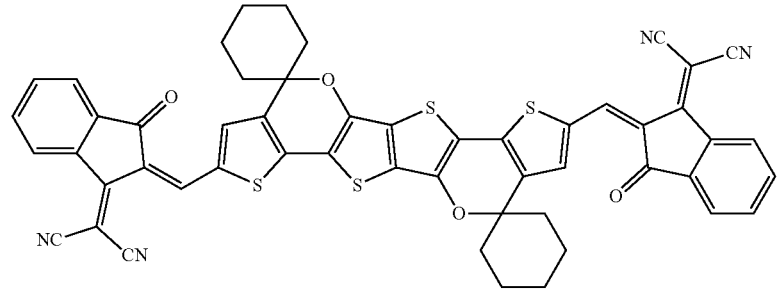
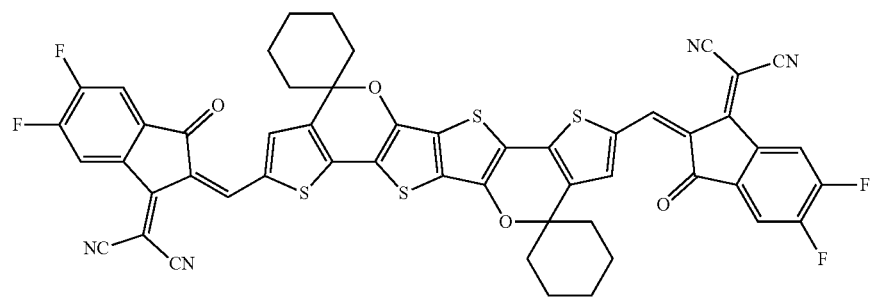
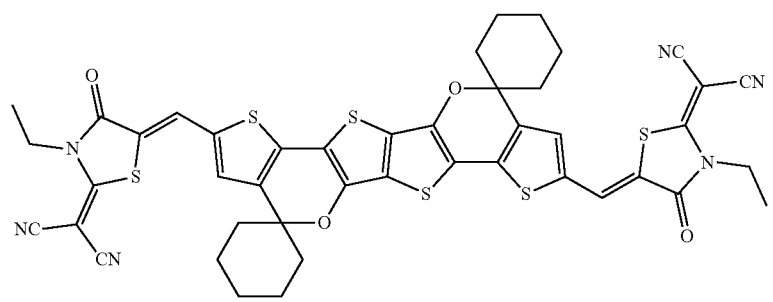

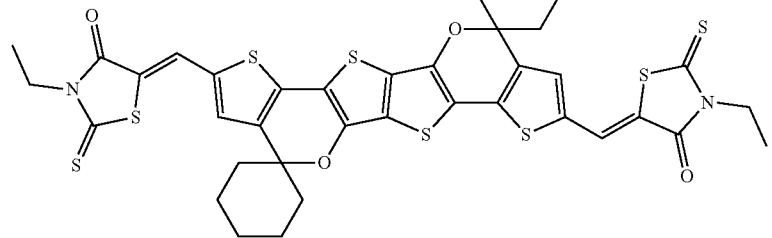
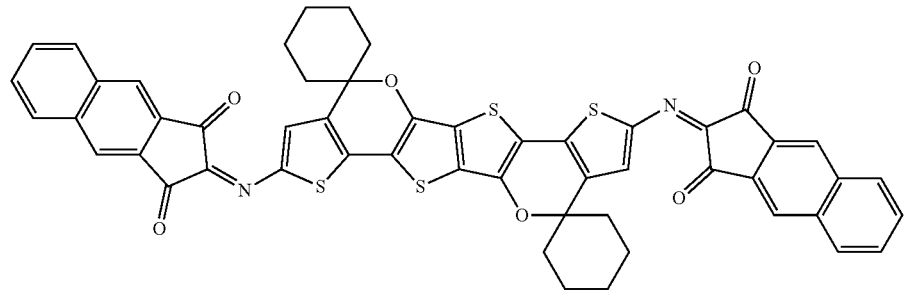
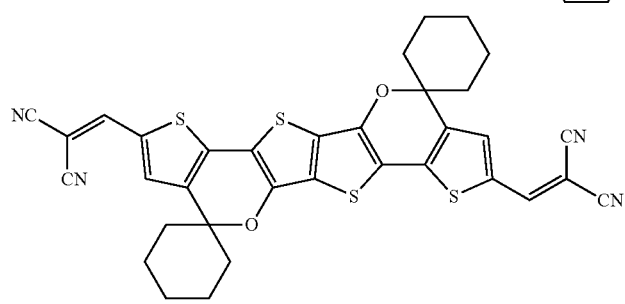
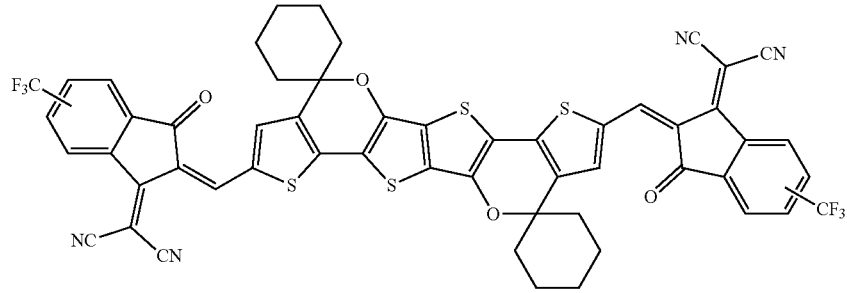
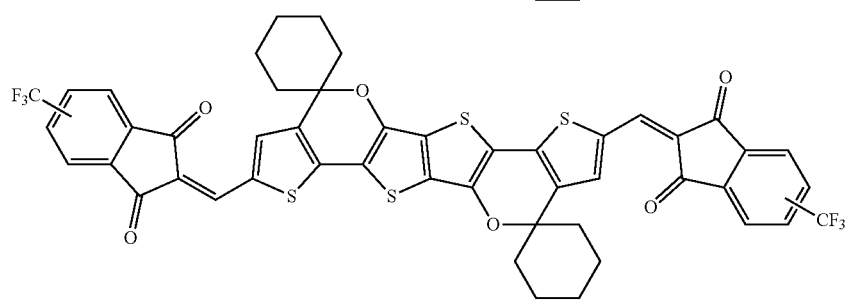
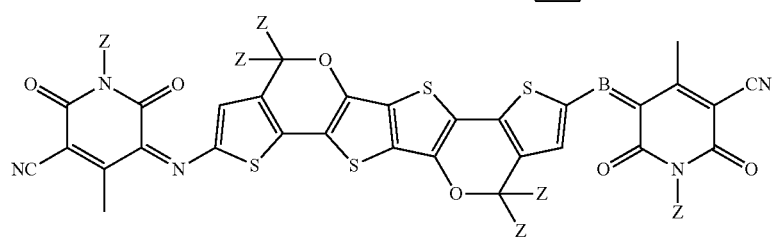

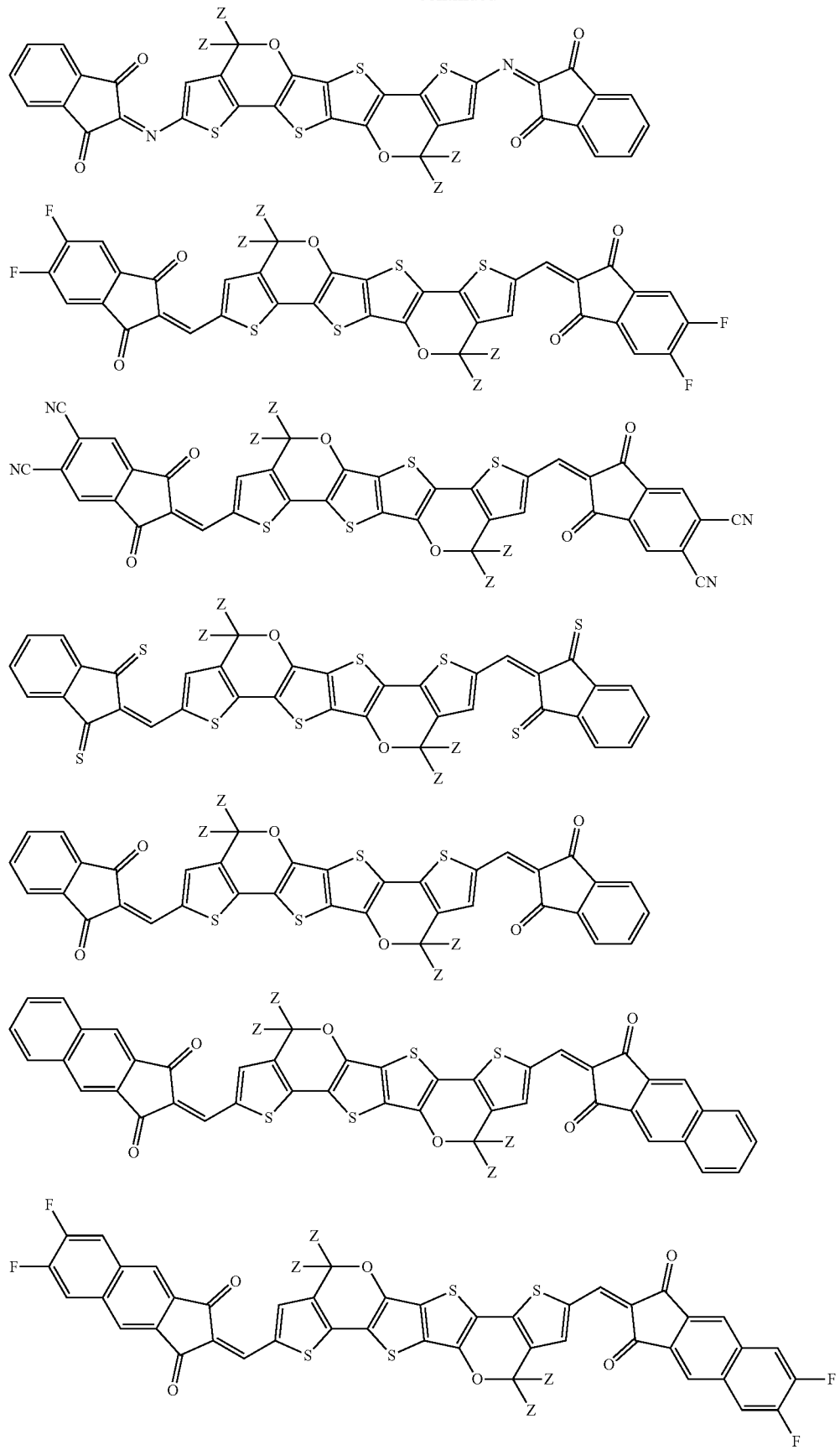

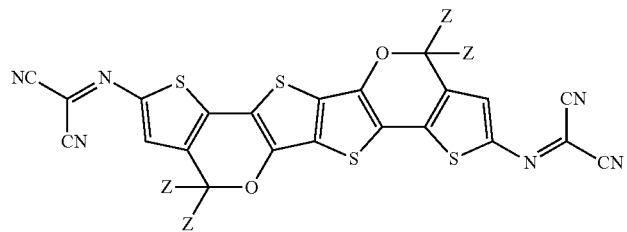
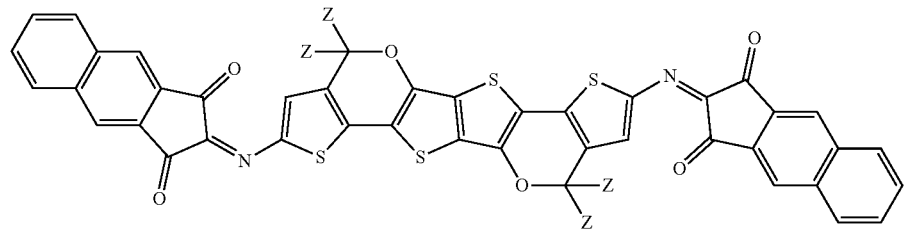
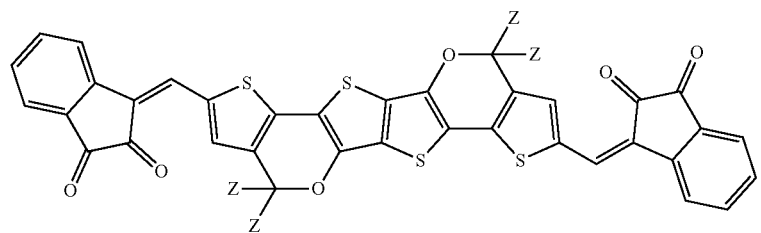
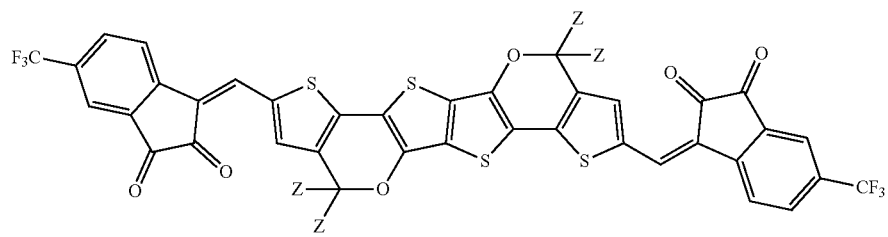
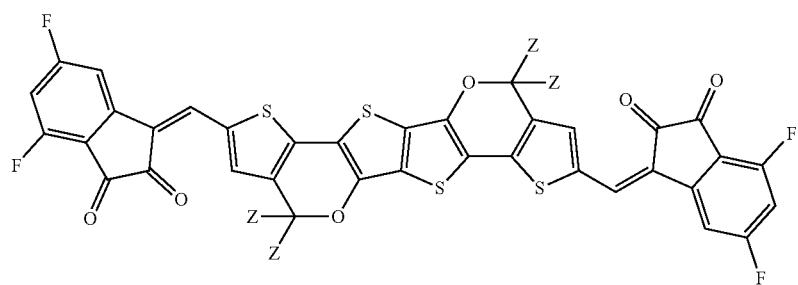
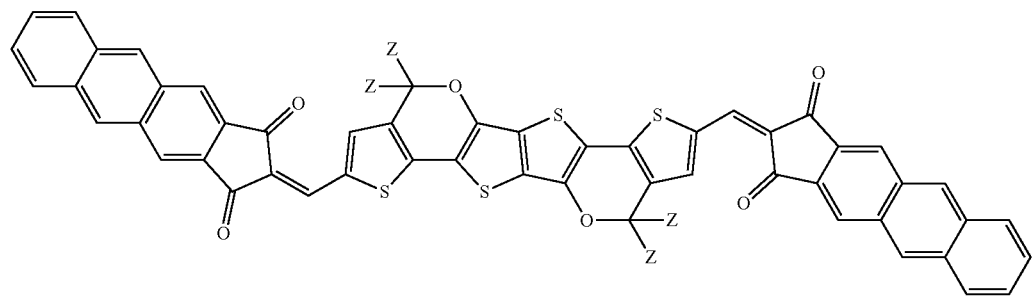

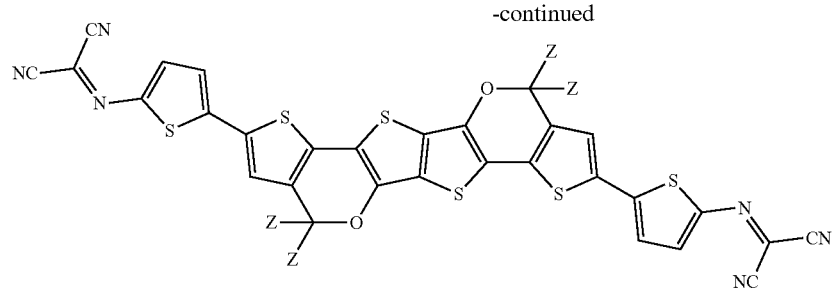
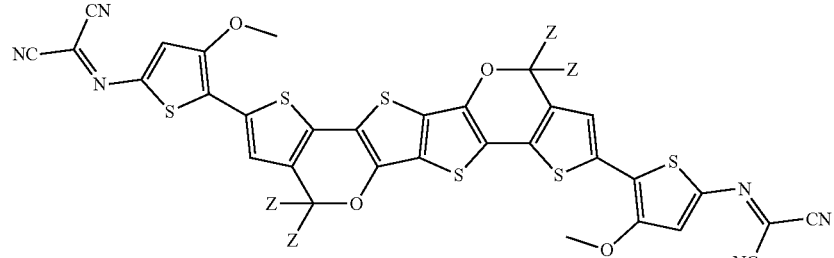
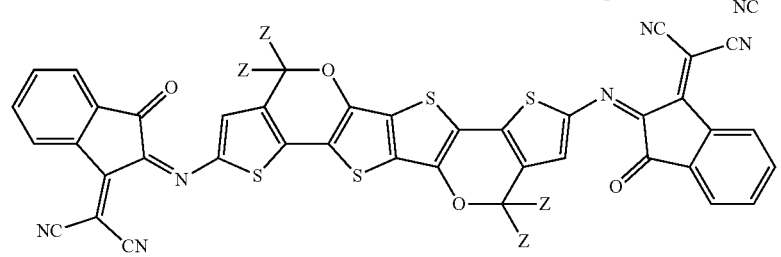
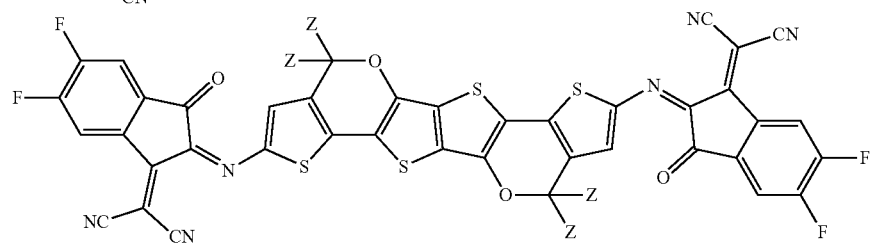
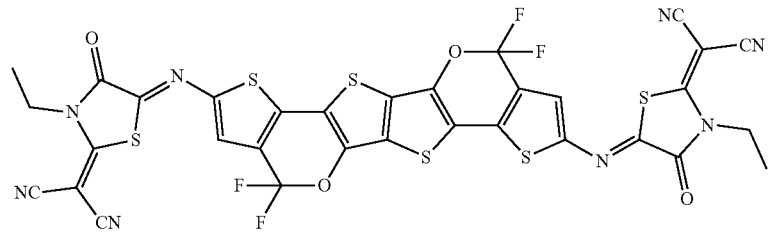
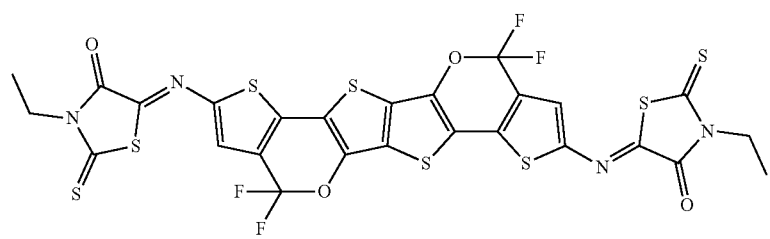
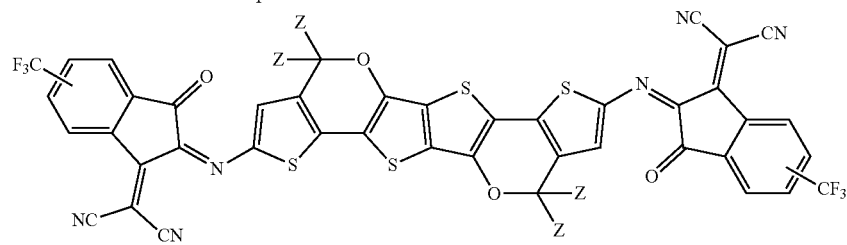

-continued
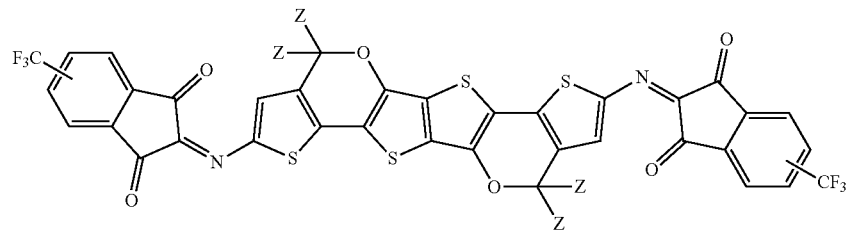
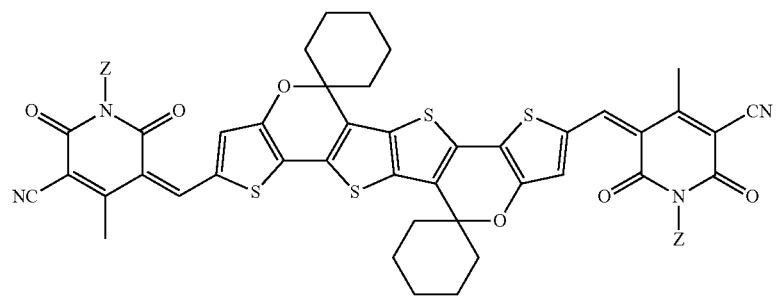
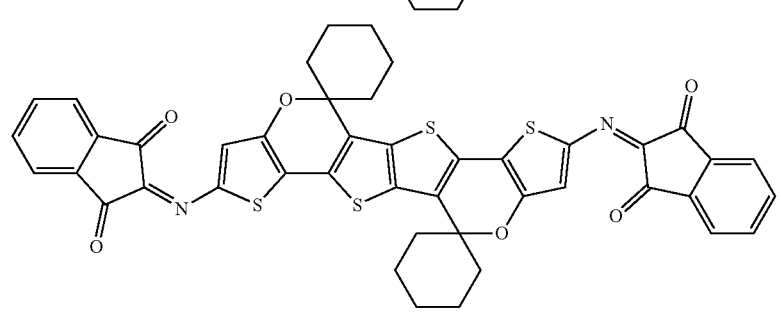
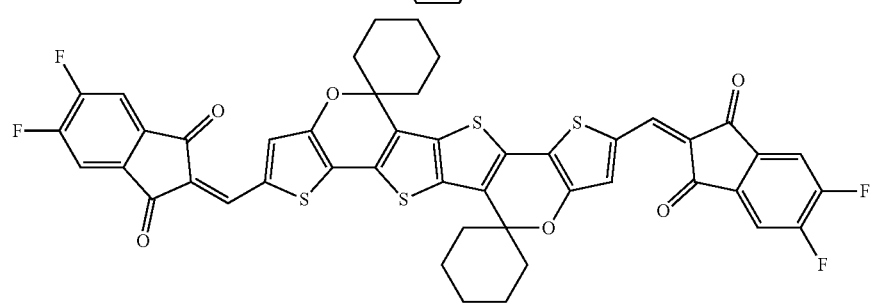
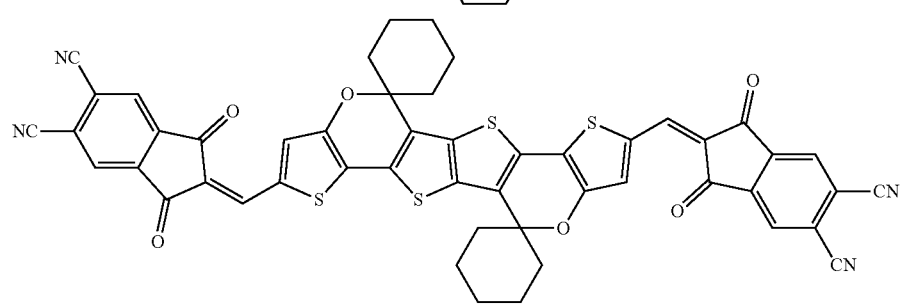
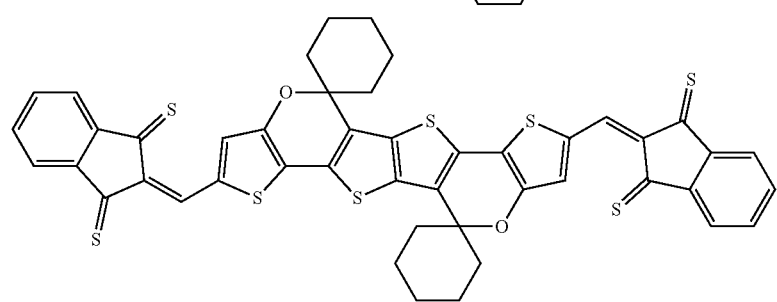

-continued
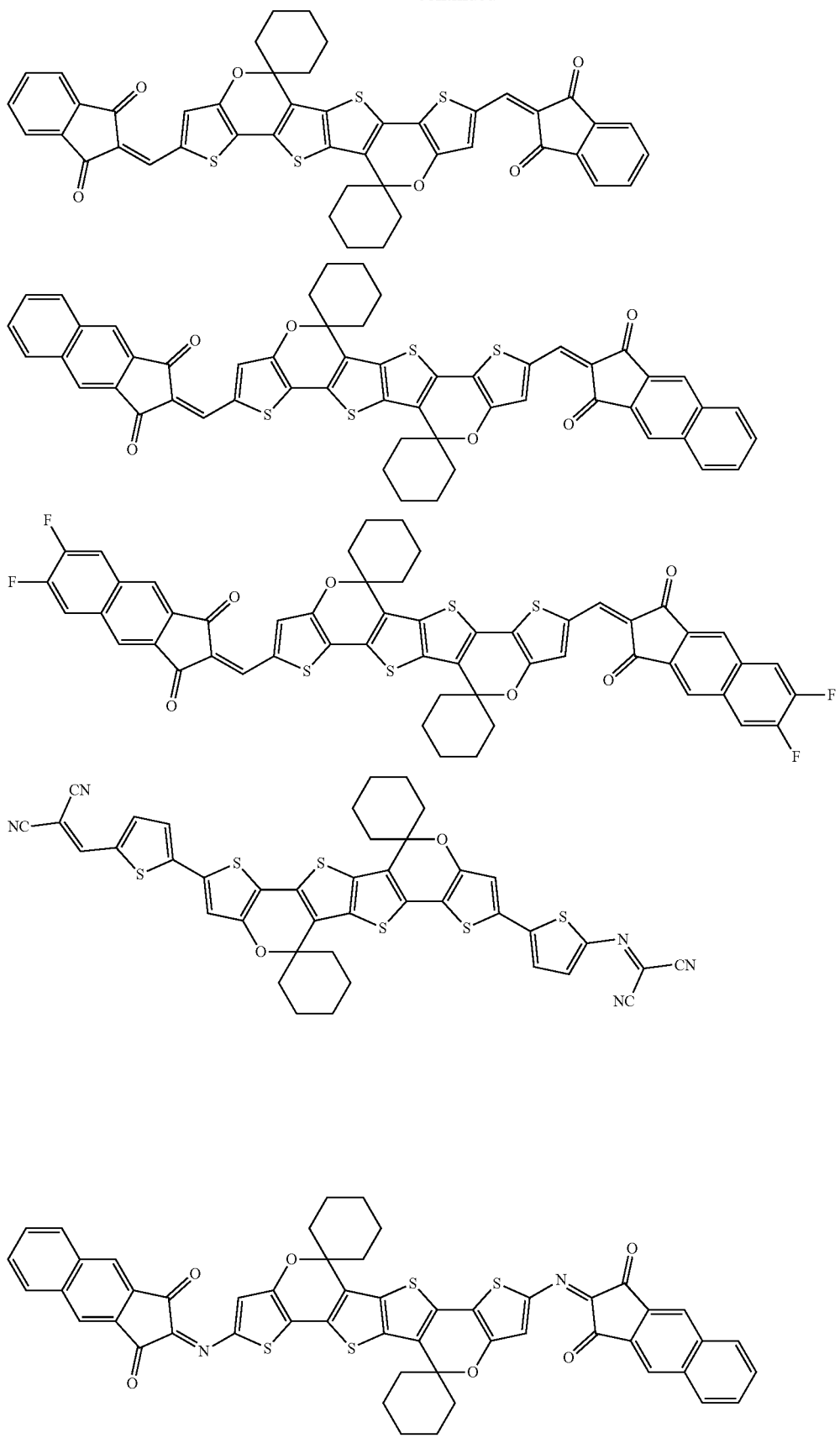

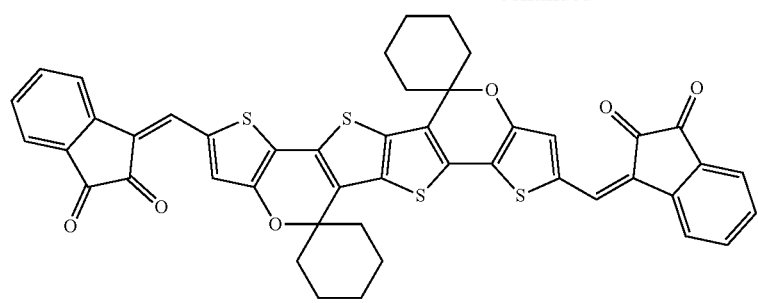
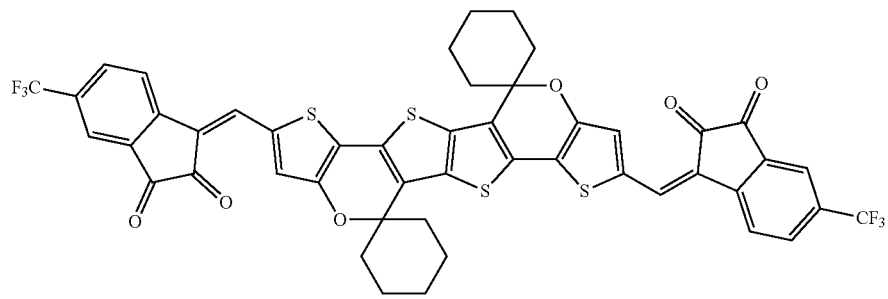
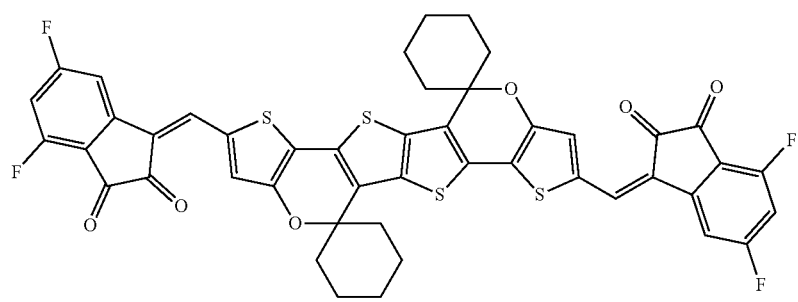
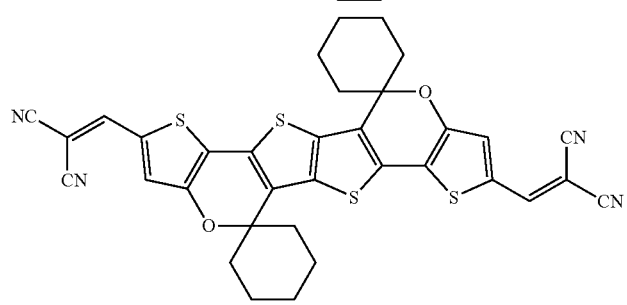
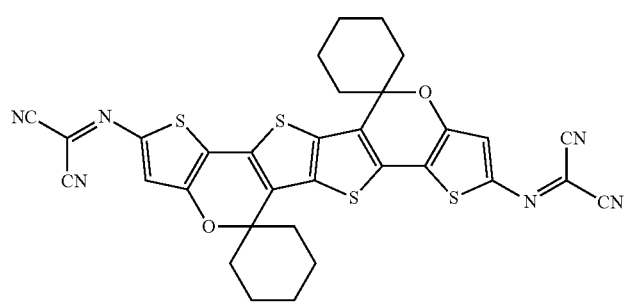

-continued
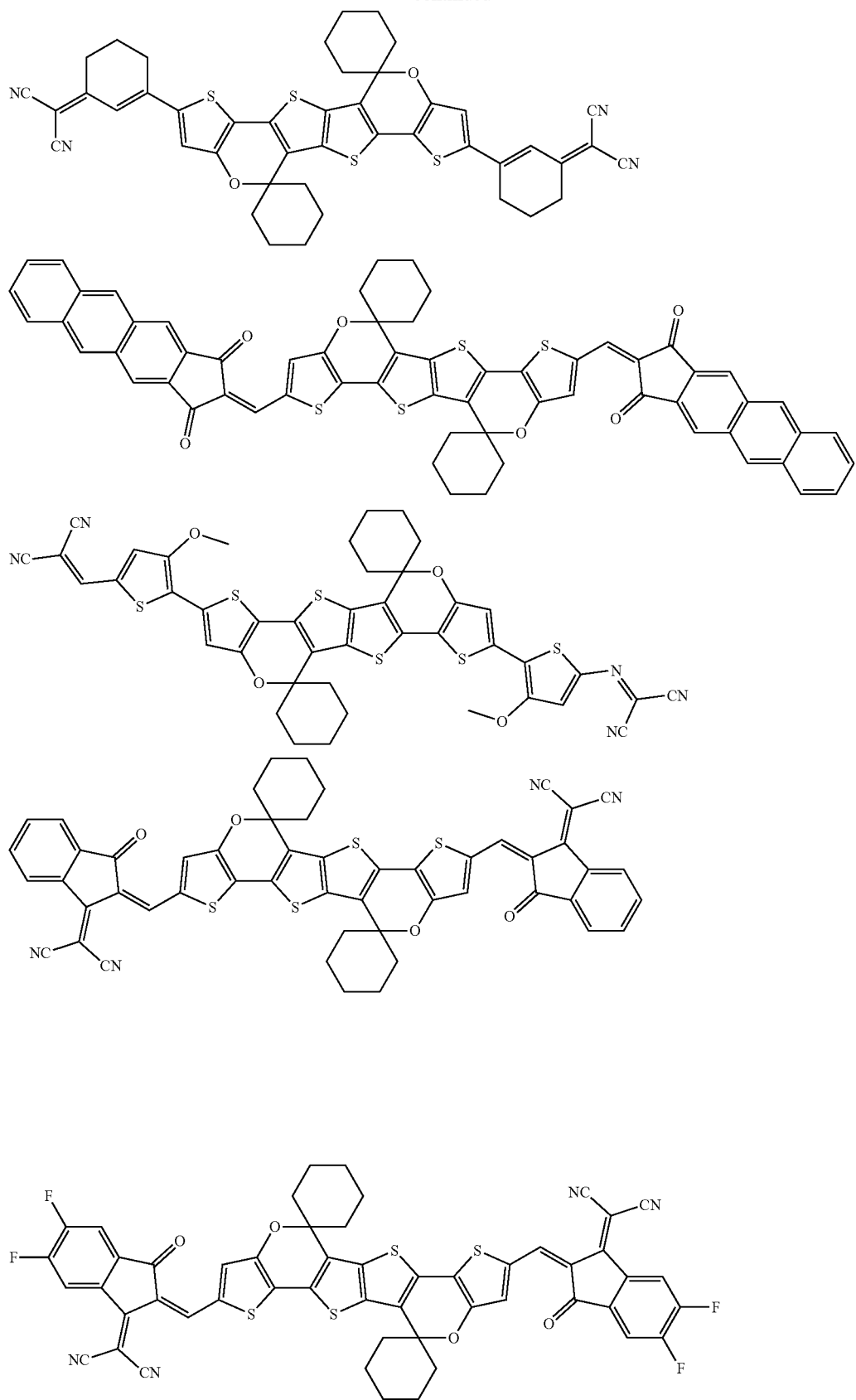

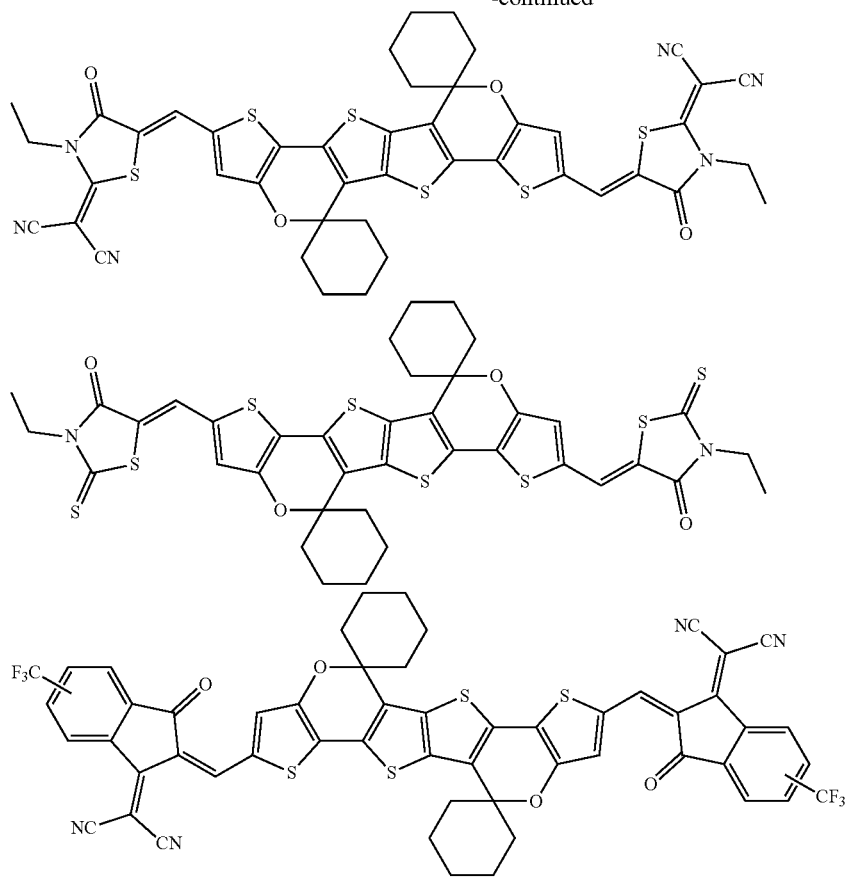
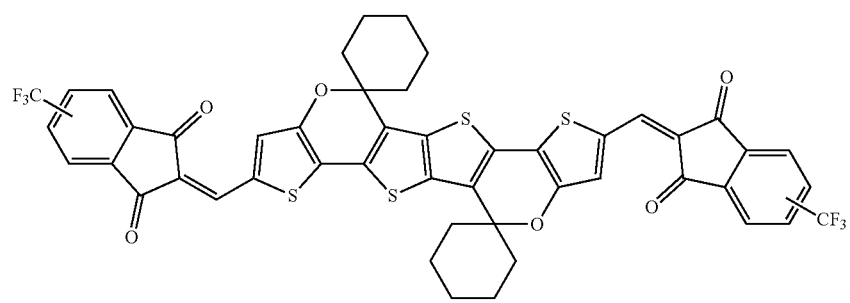
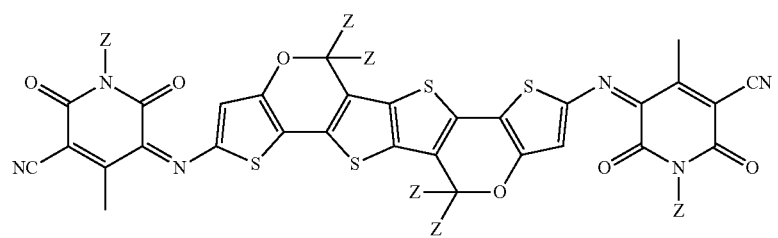

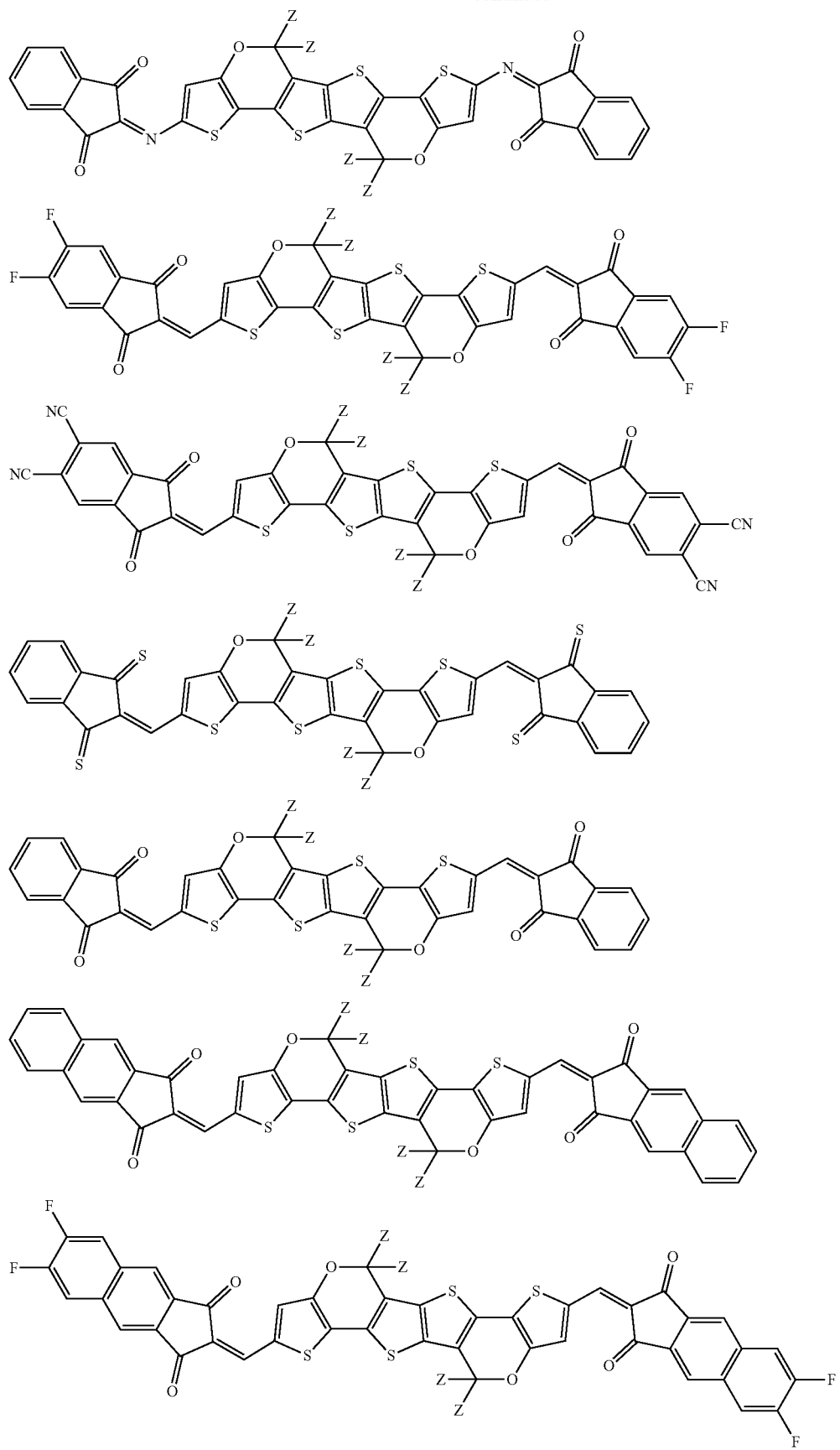

-continued
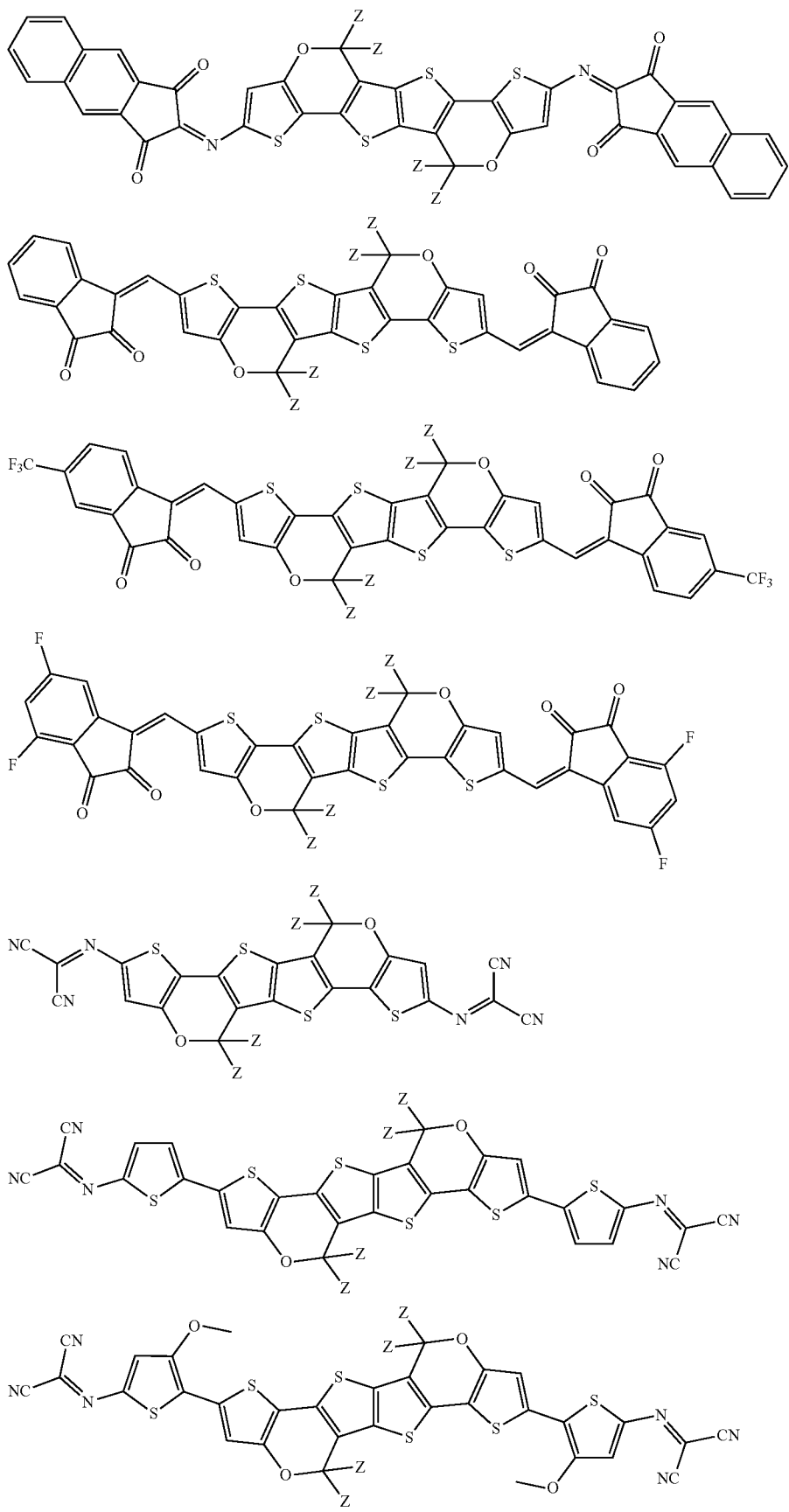

-continued
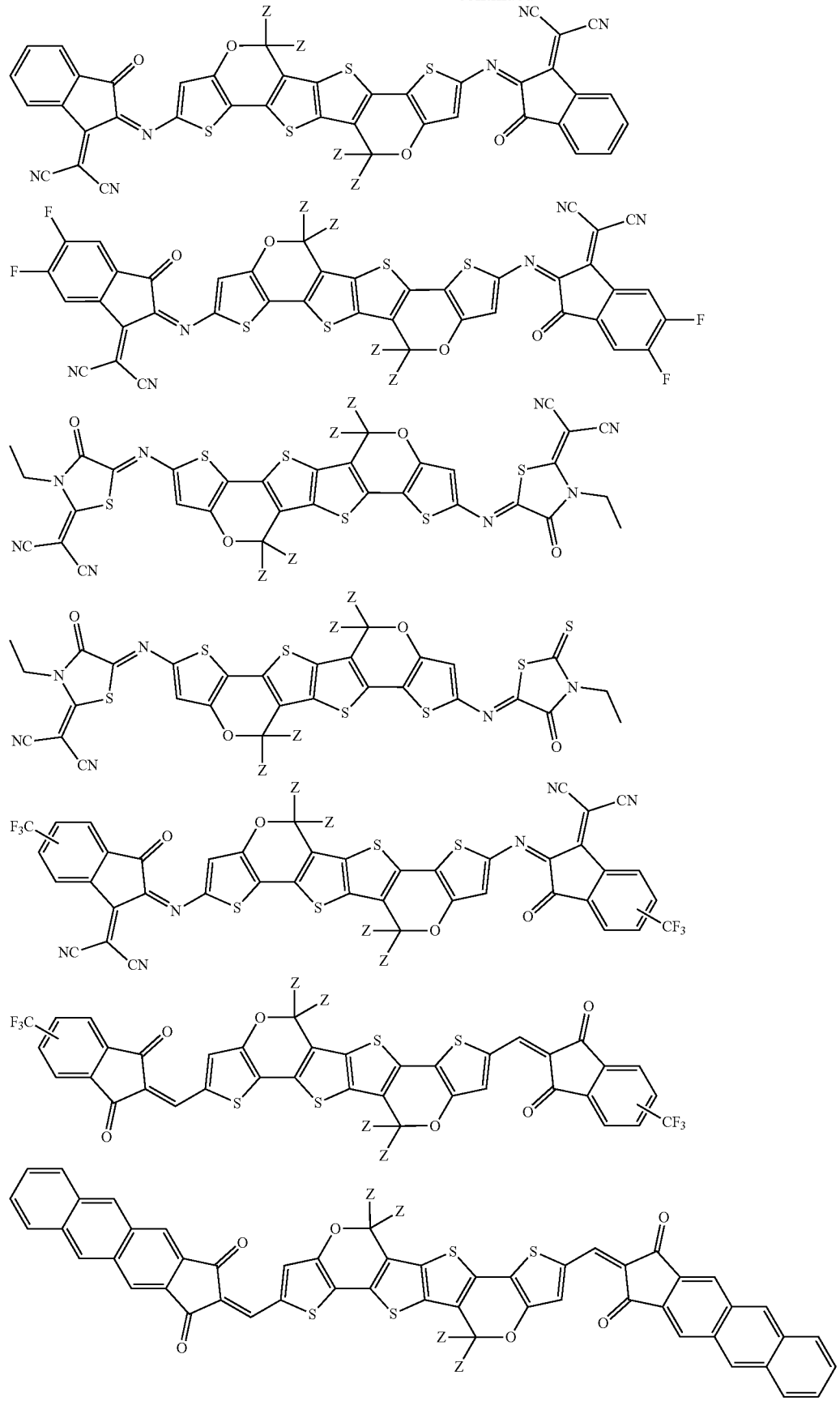

-continued
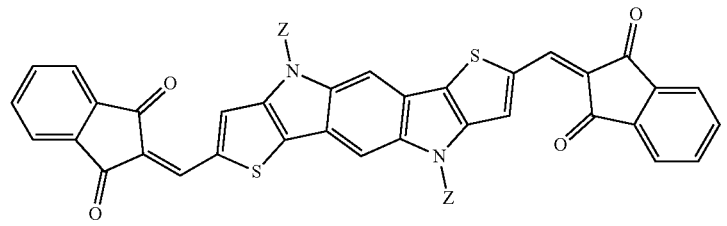
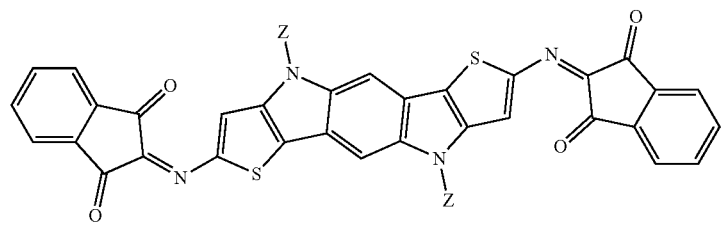
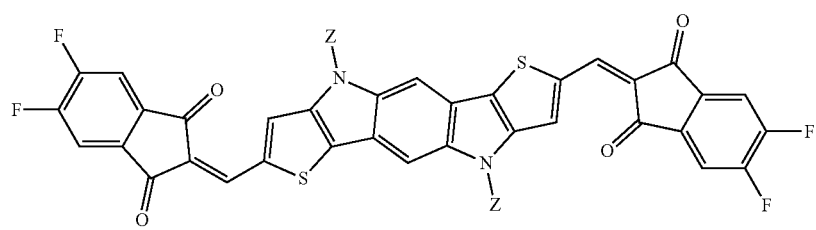
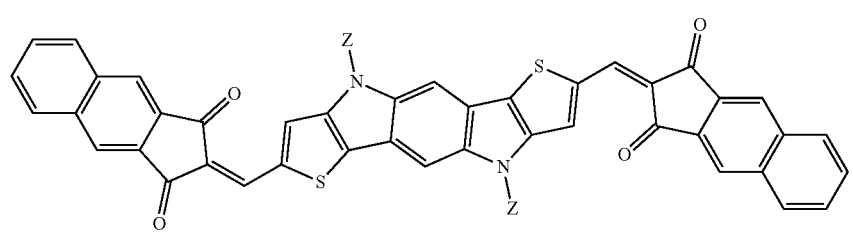
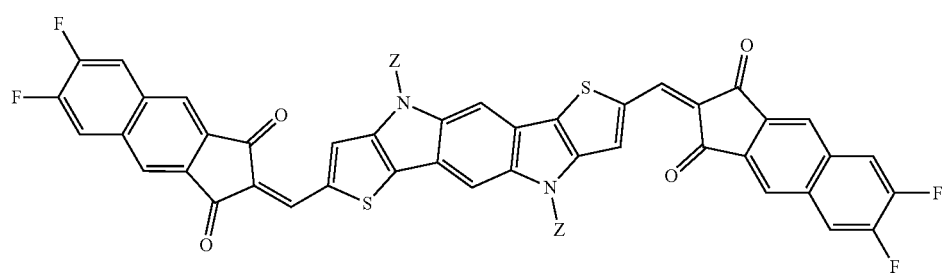
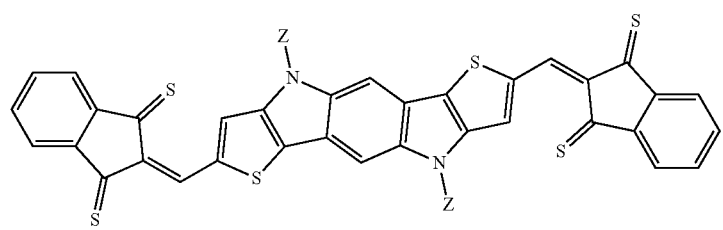
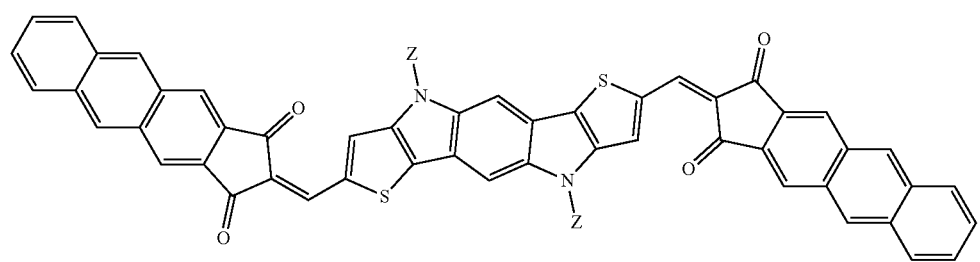

-continued
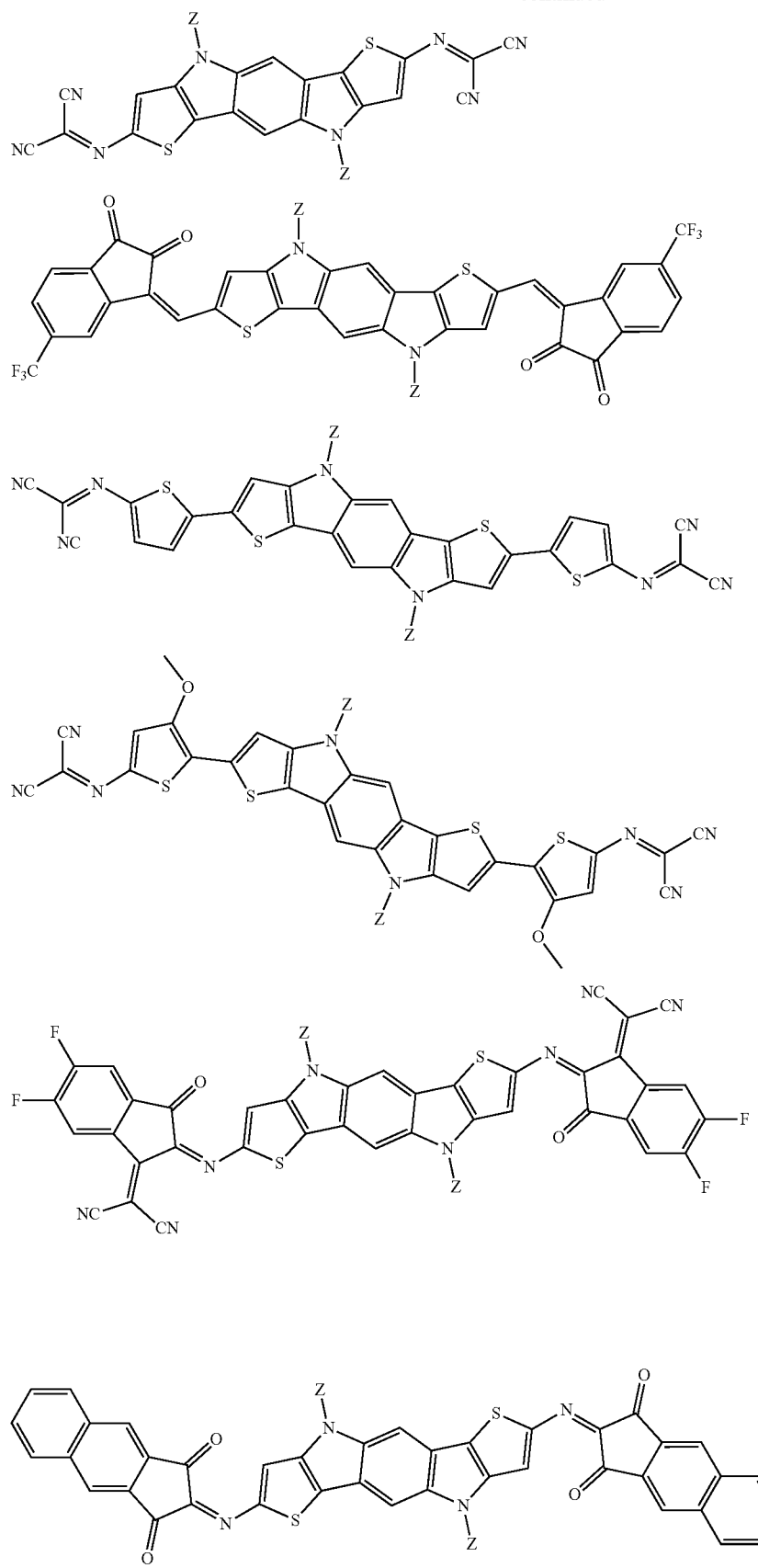

-continued
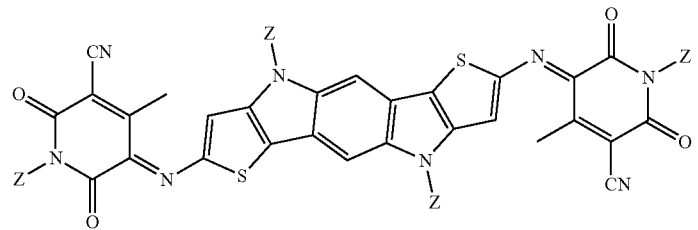
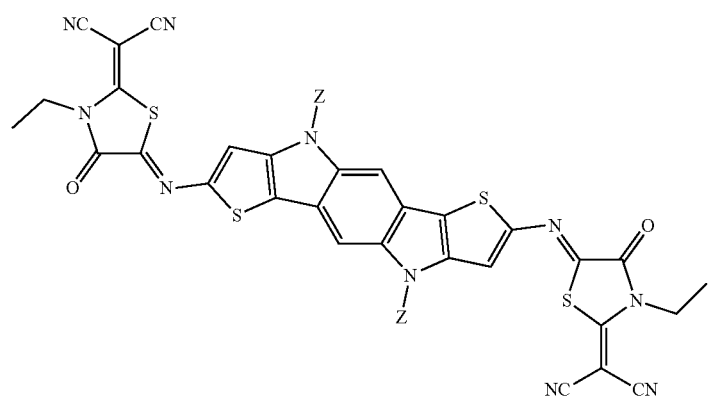
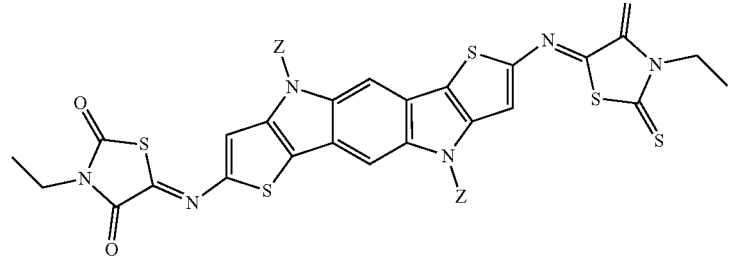
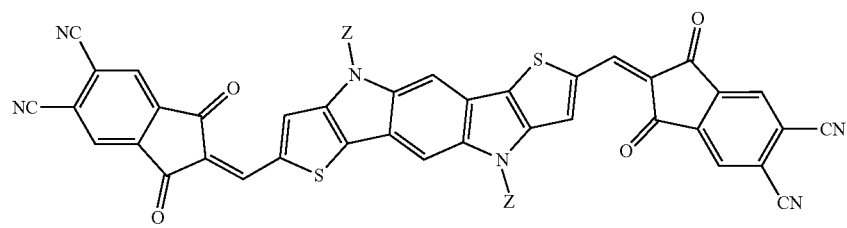
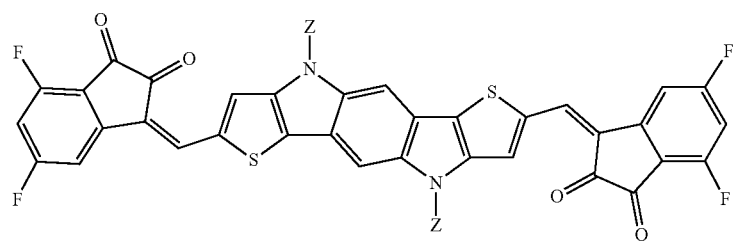
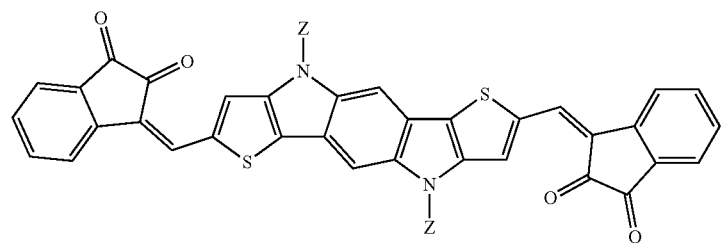

-continued
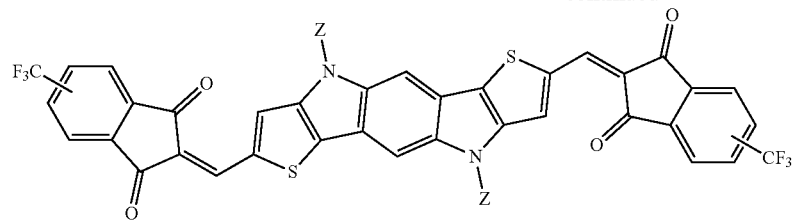
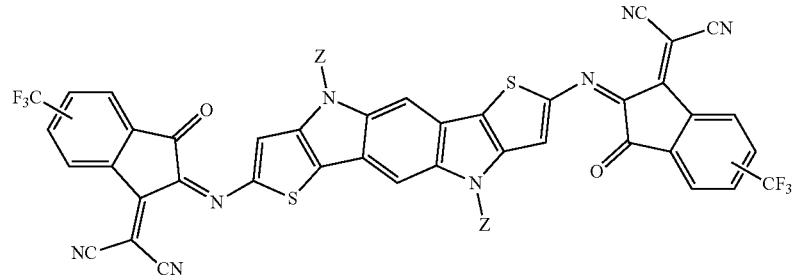
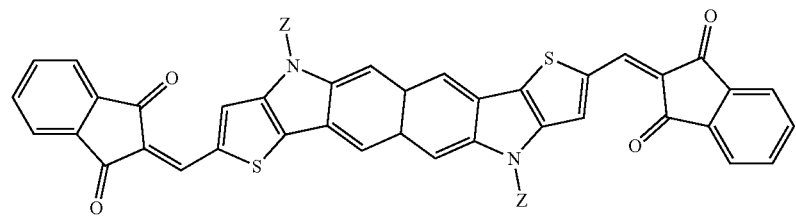
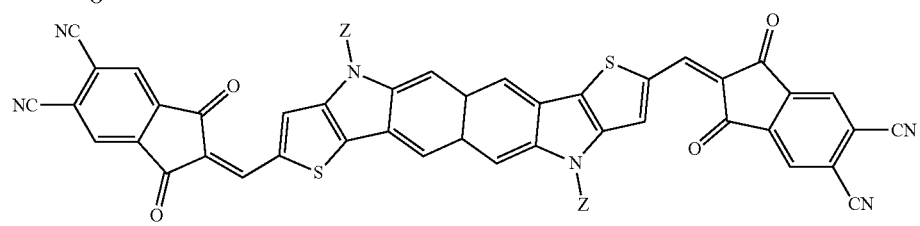
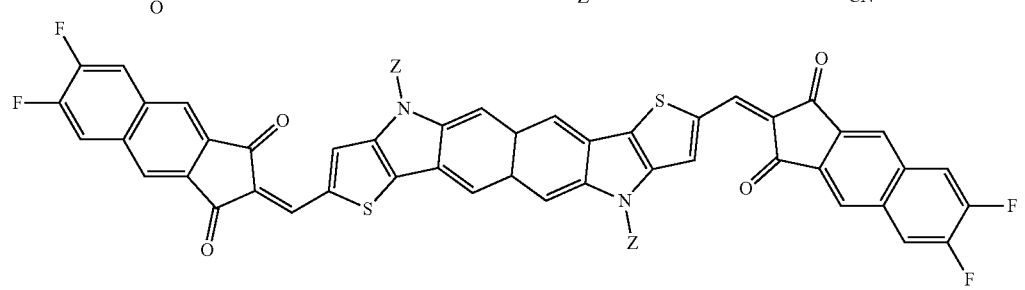
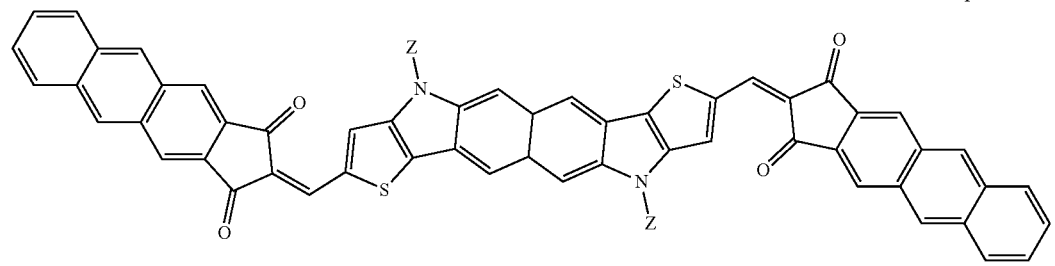
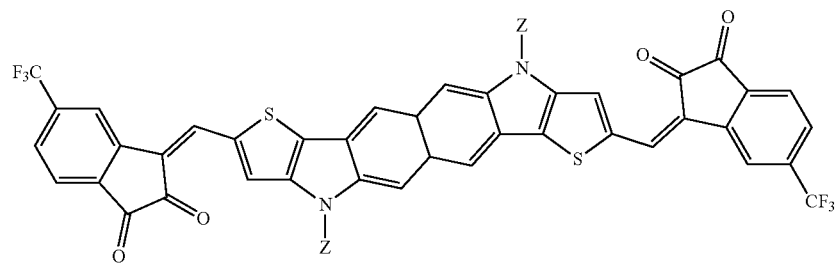

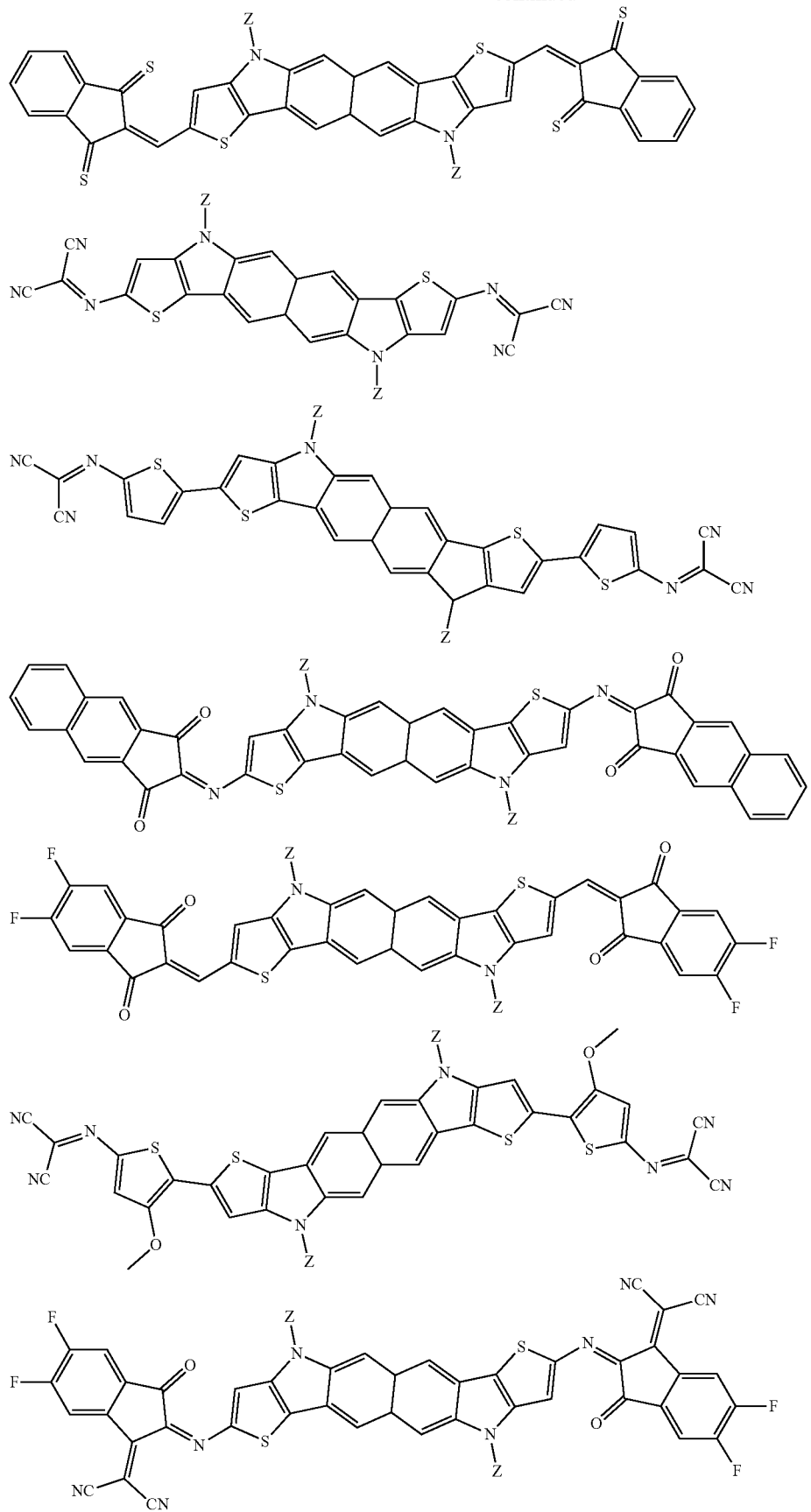

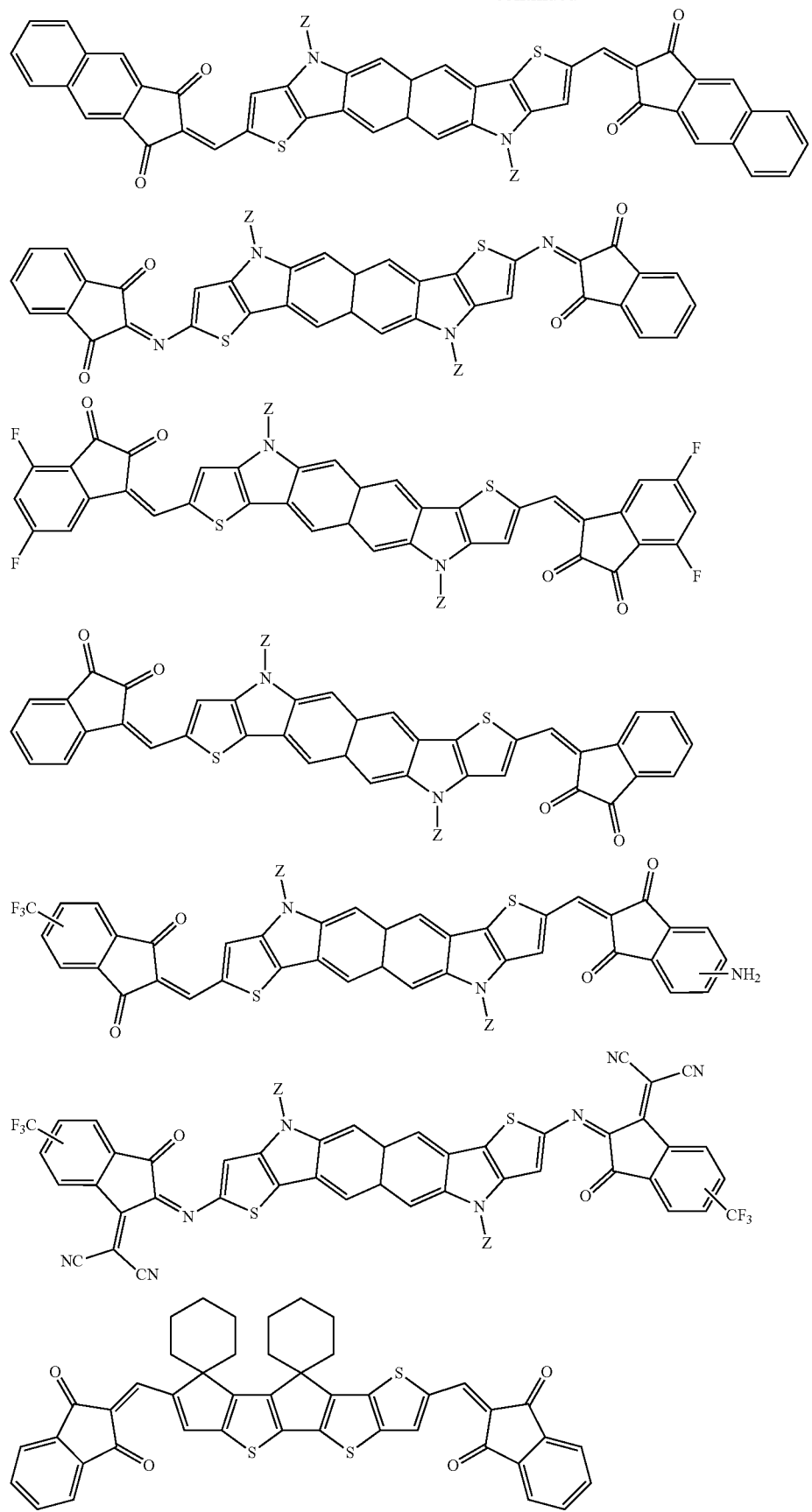

-continued
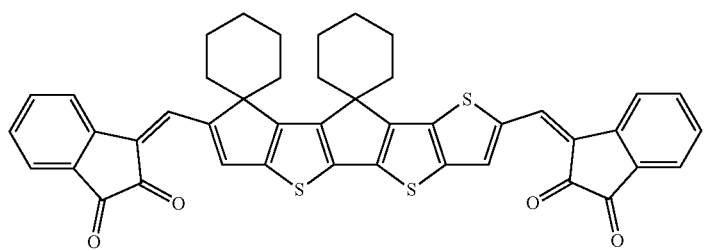
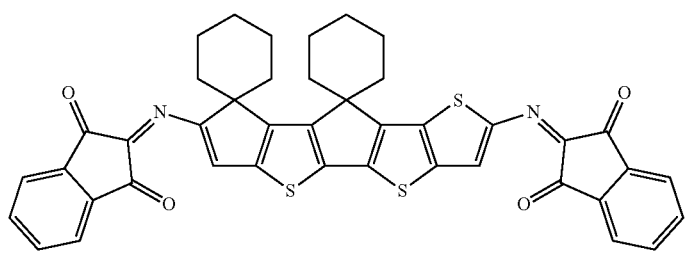
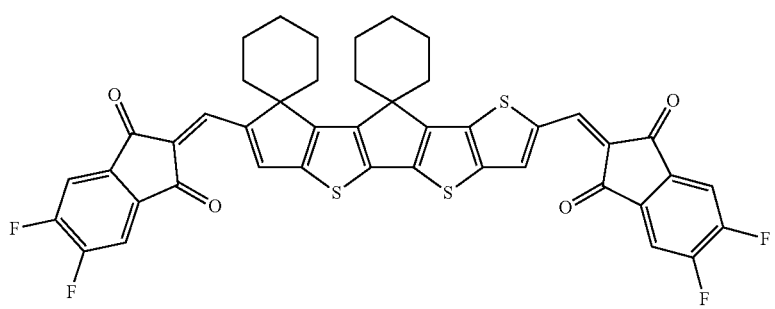
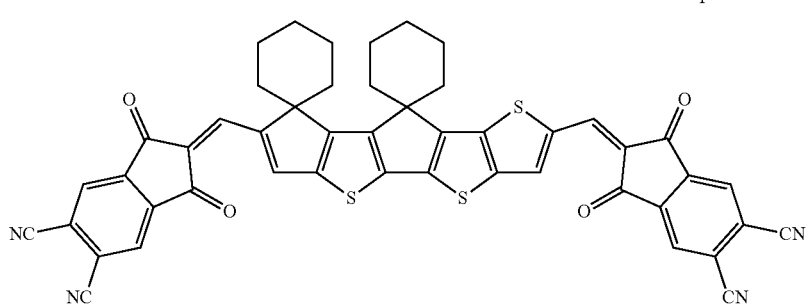
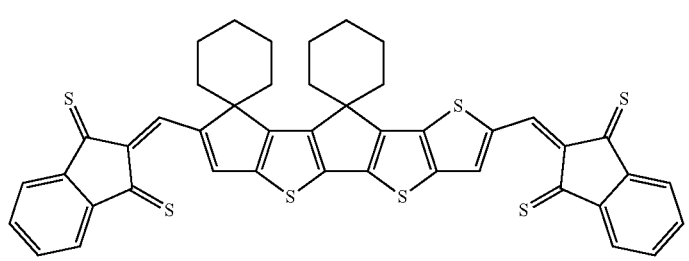
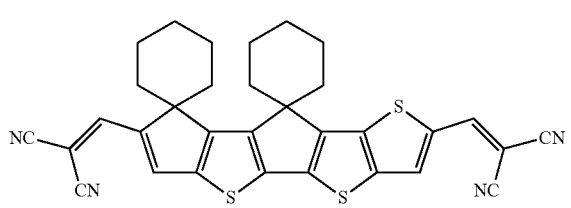

-continued
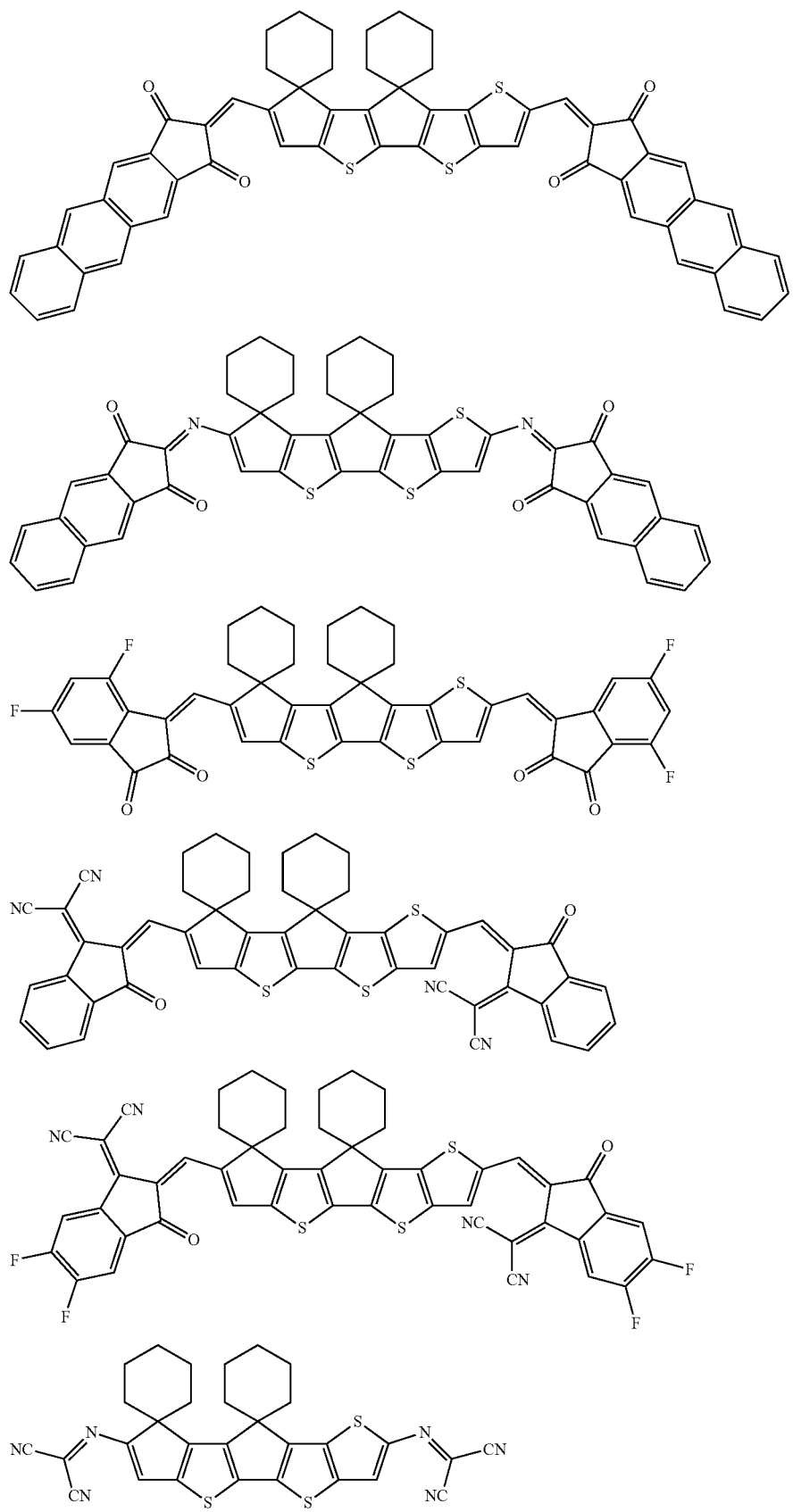

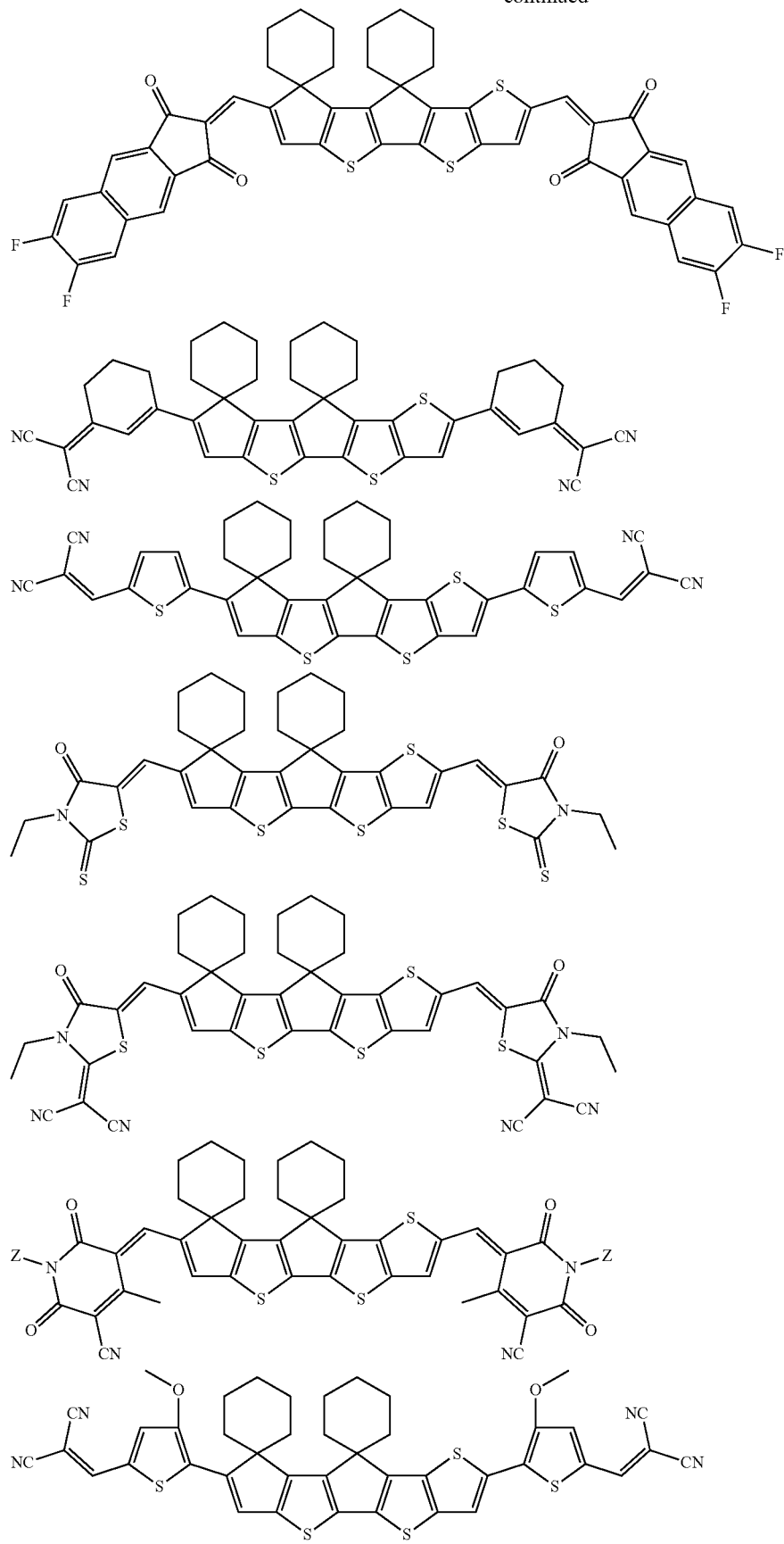

-continued
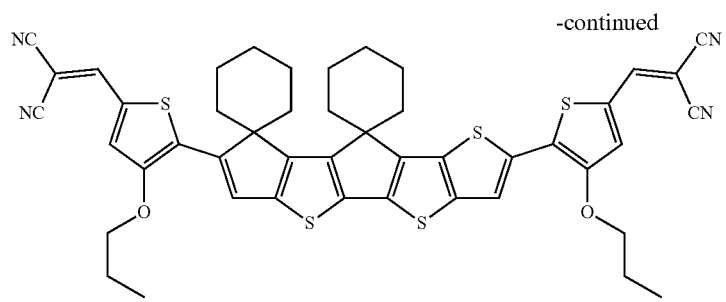
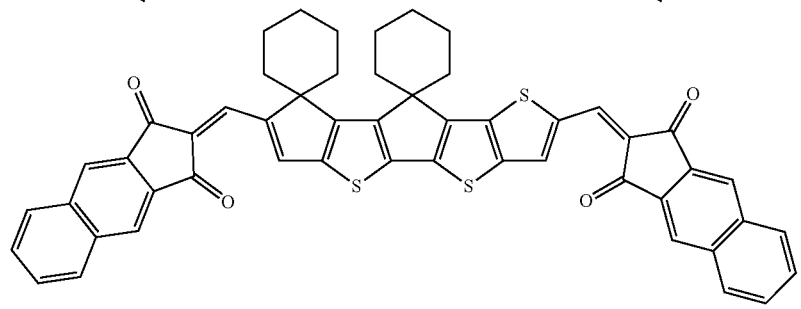
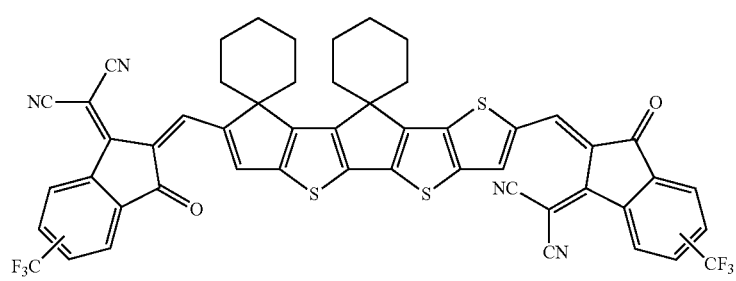
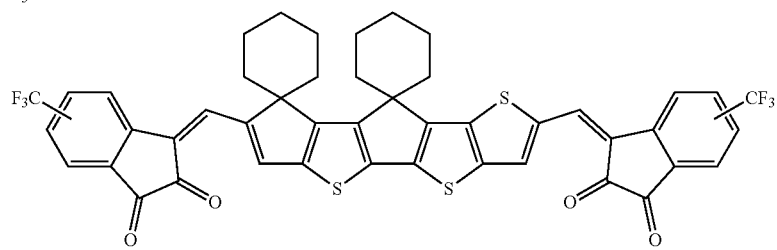
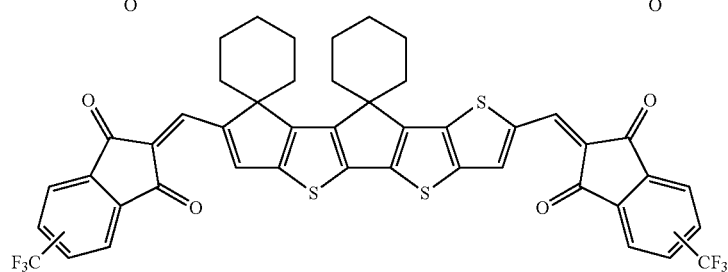
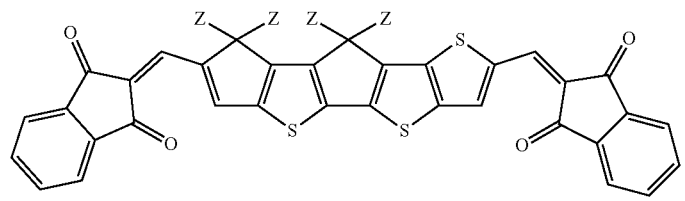
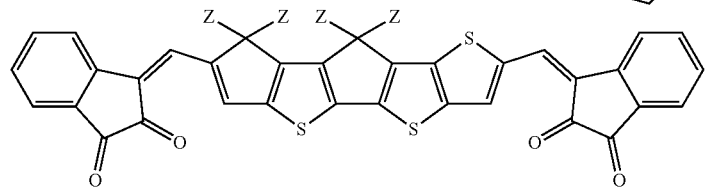

-continued
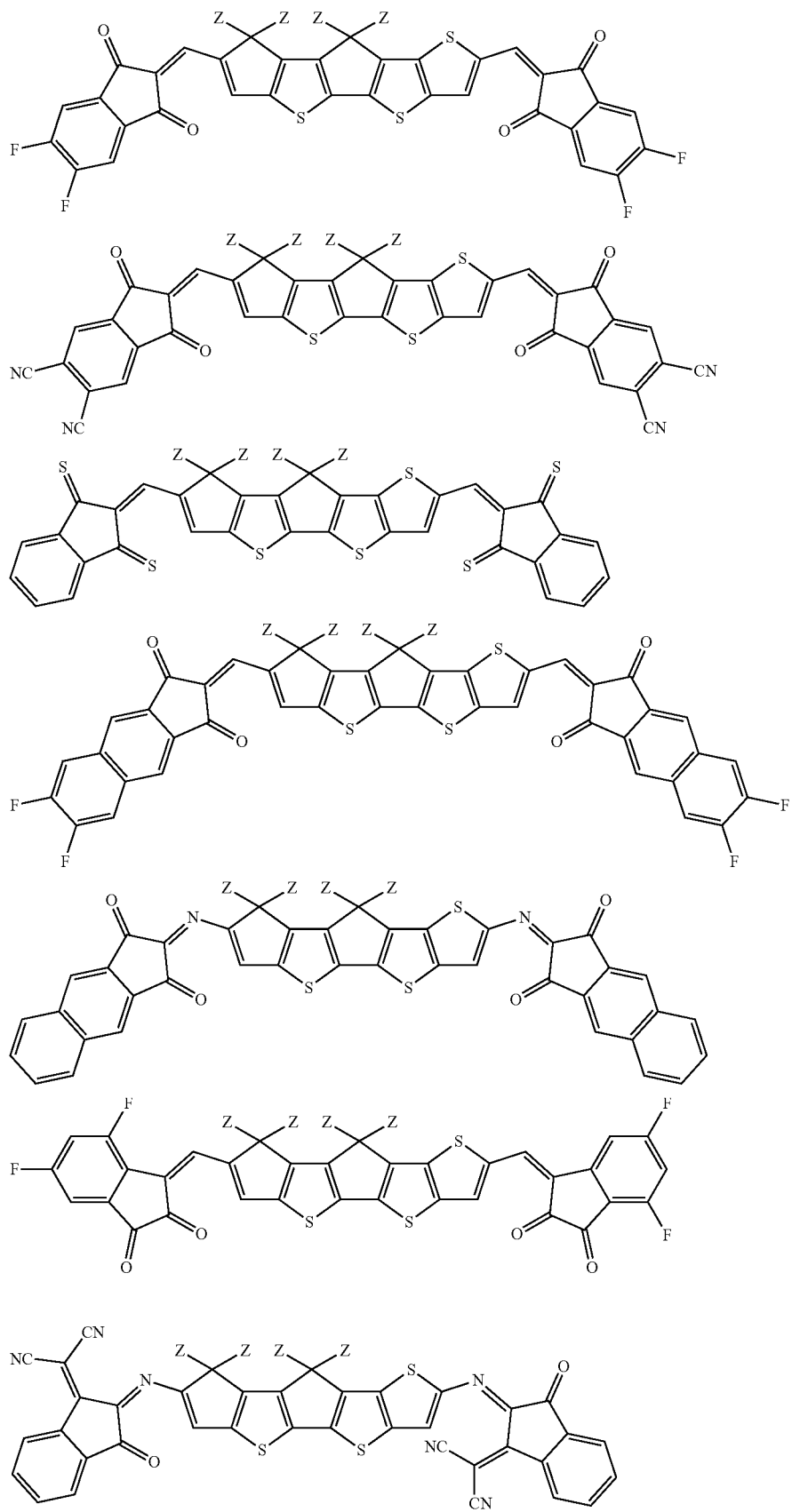

-continued
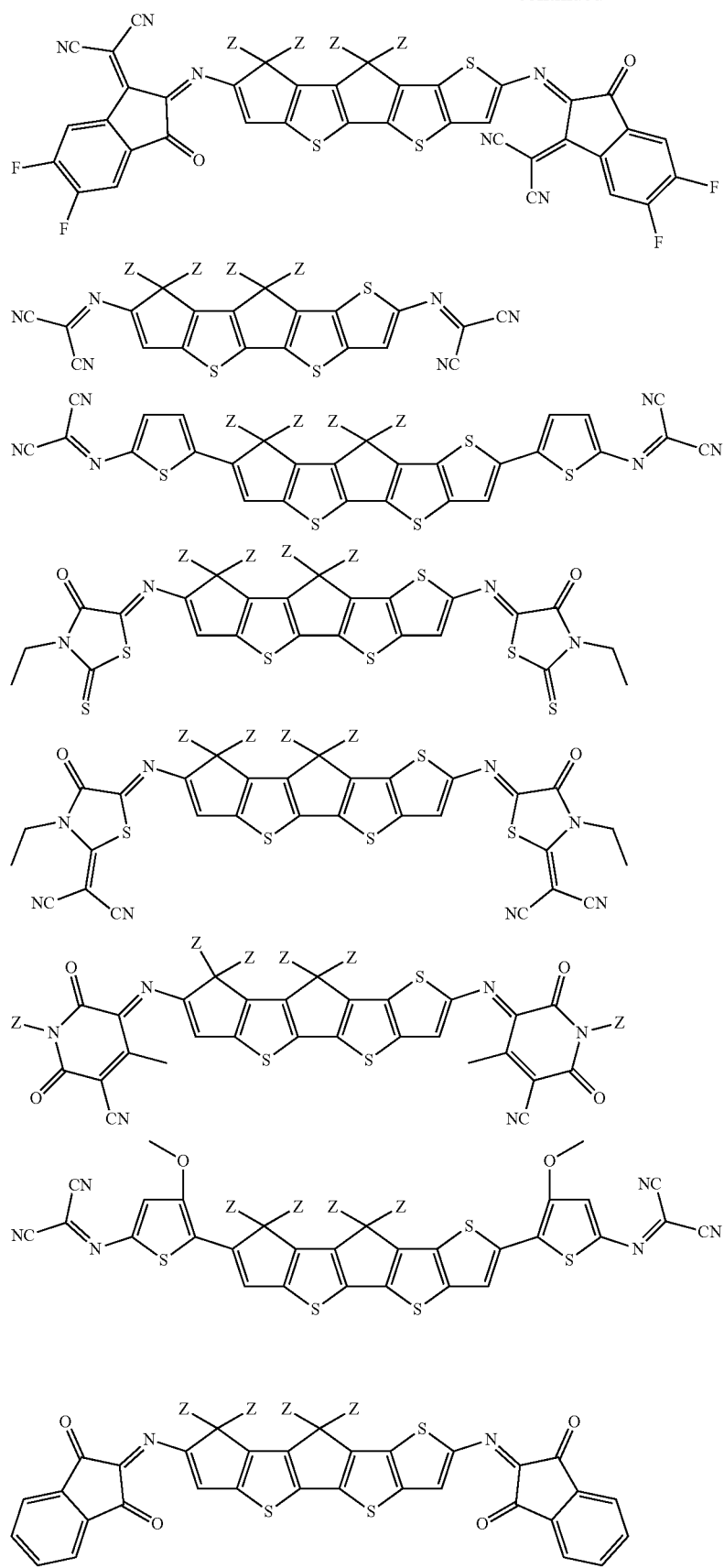

-continued
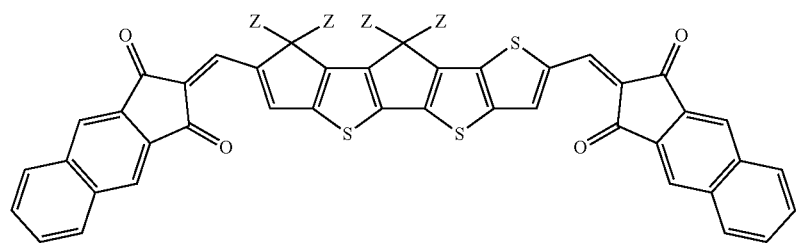
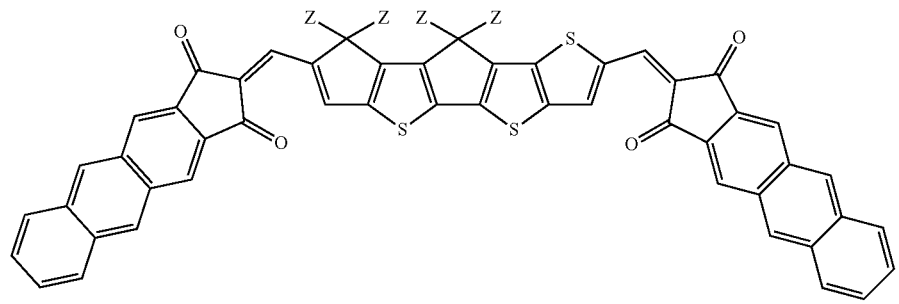
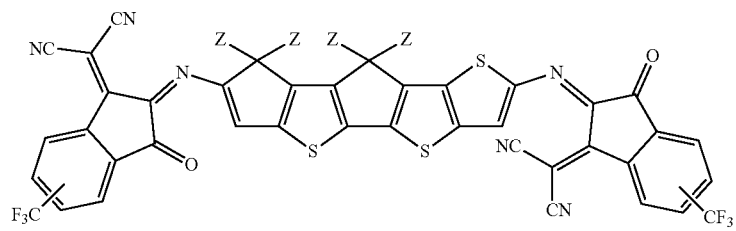
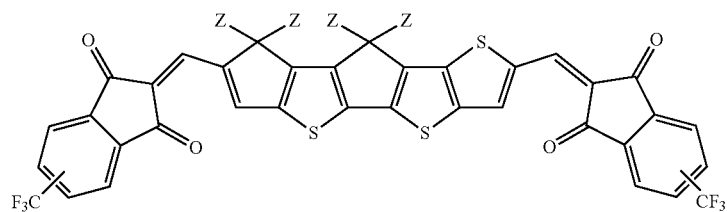
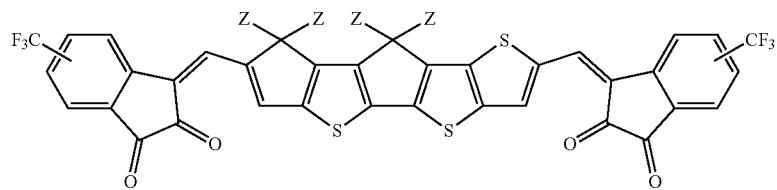
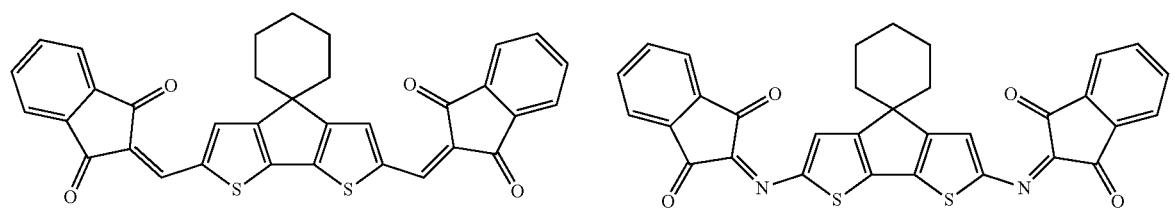
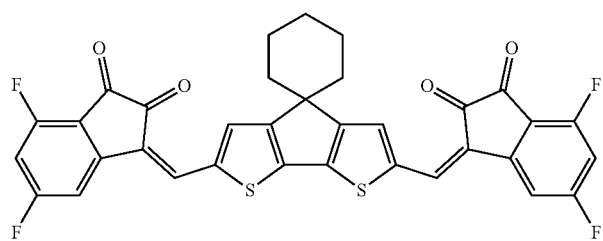

-continued
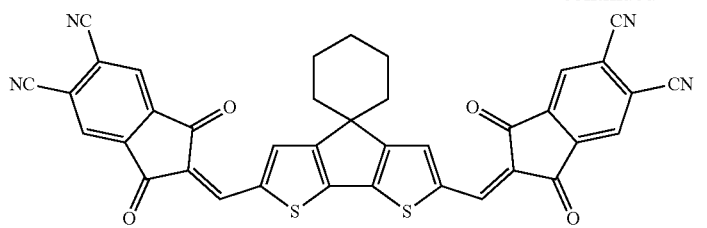
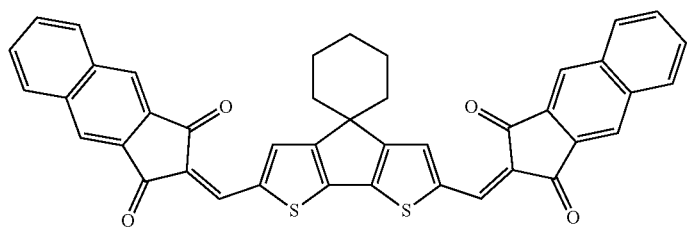
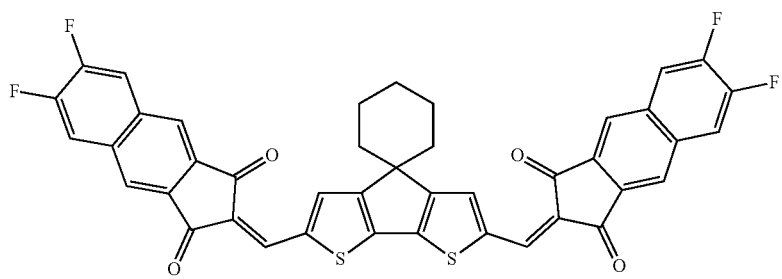
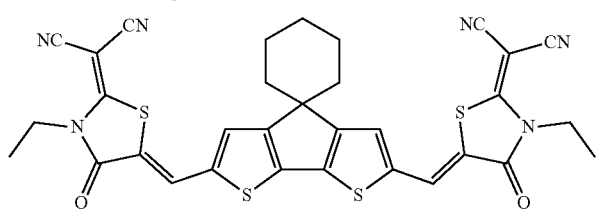
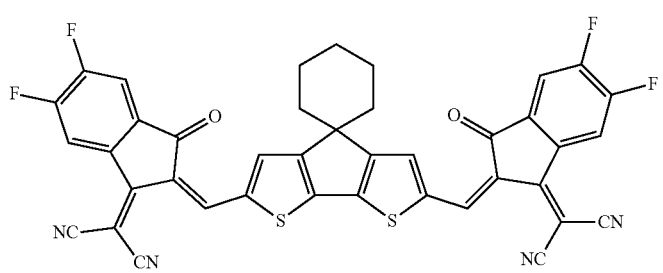
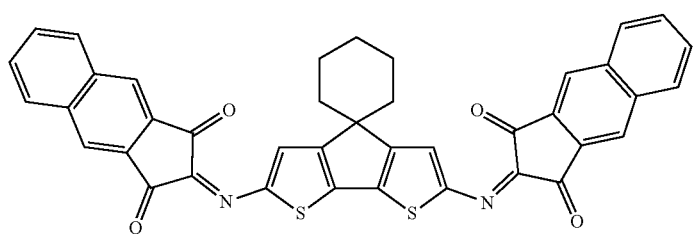
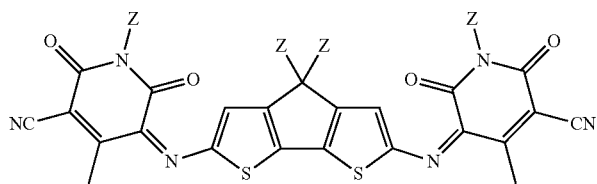

-continued
507
508
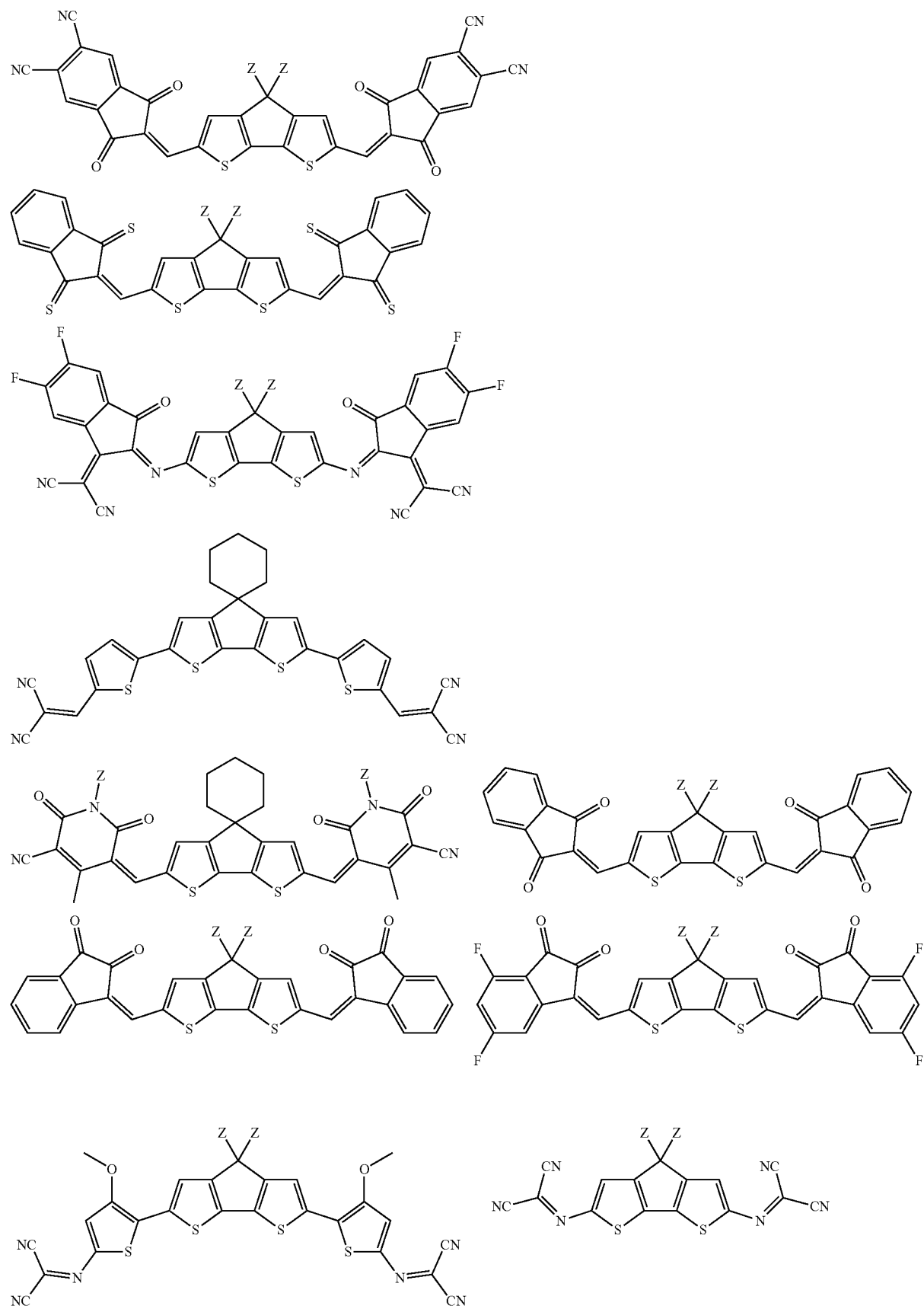

-continued
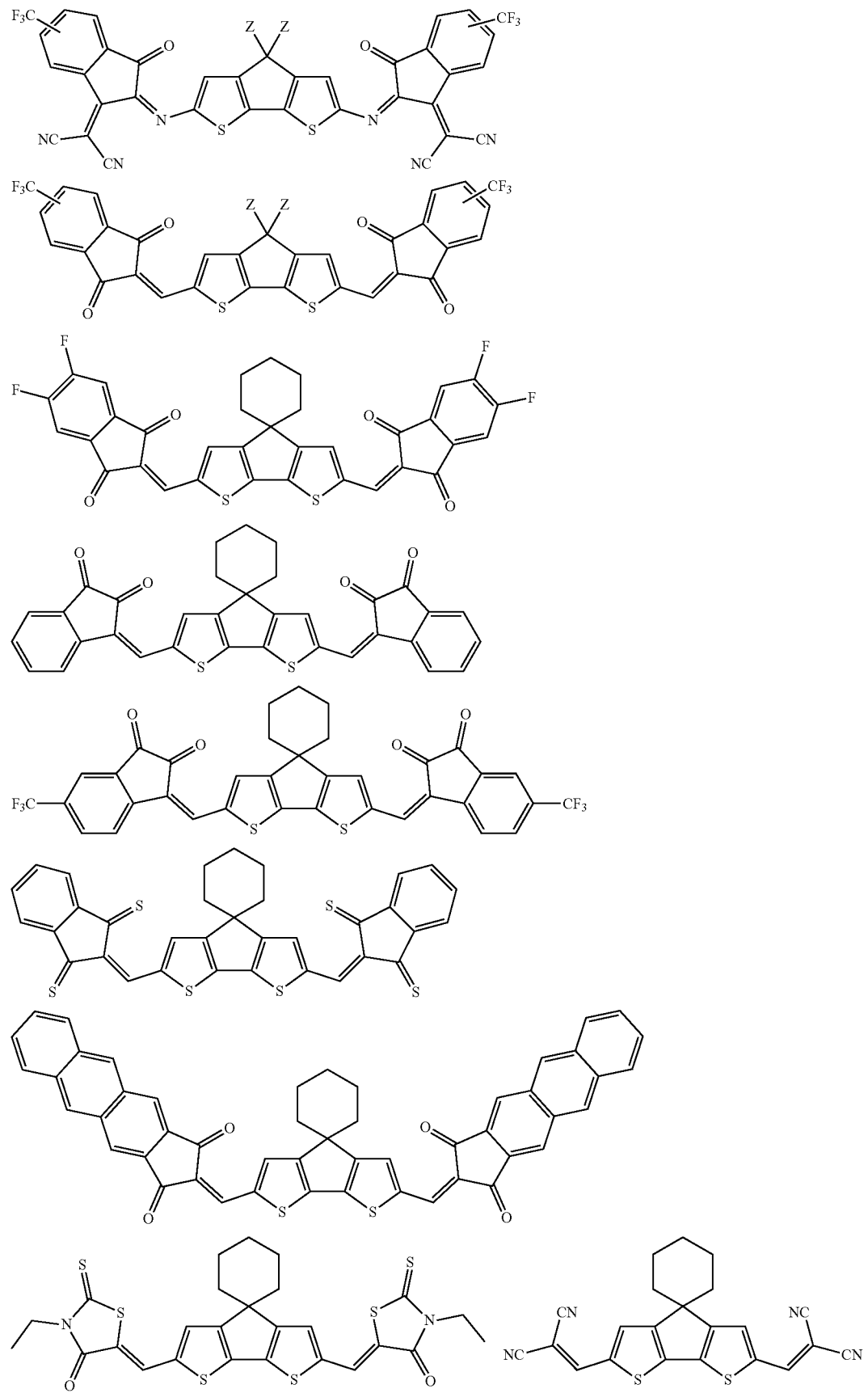

511
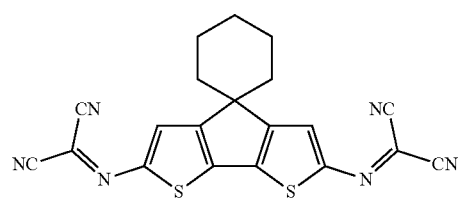
512
-continued
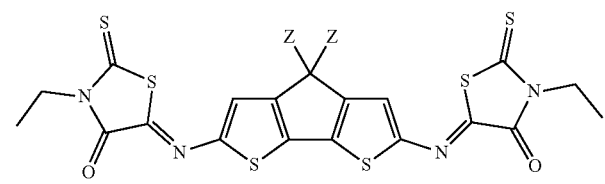
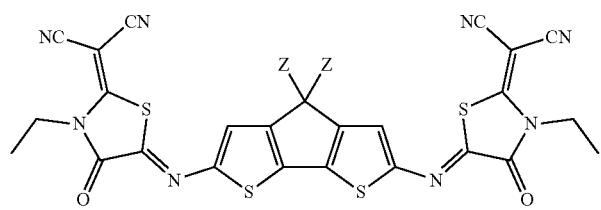
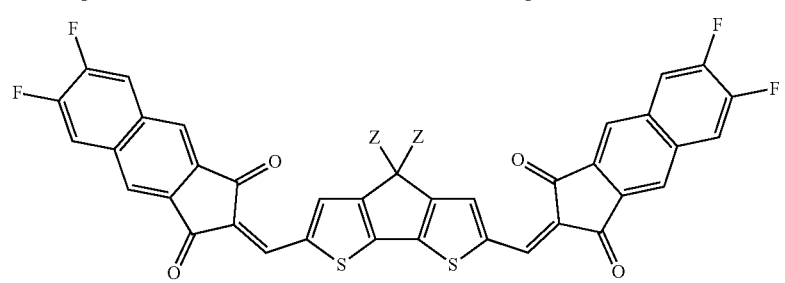
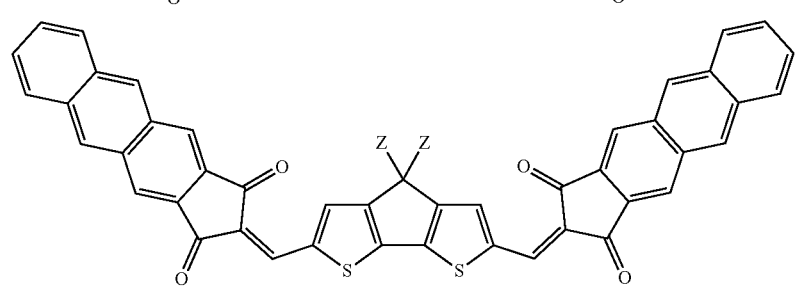
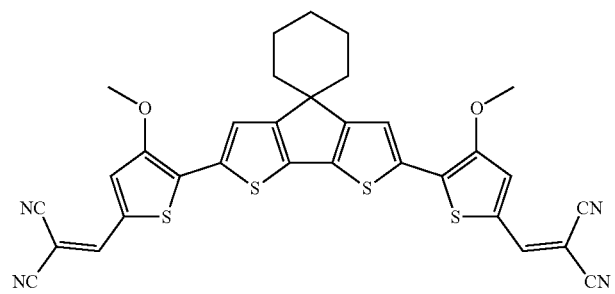
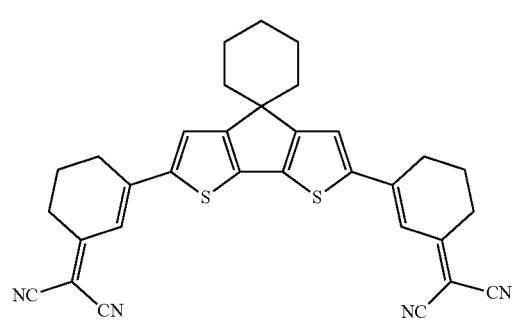
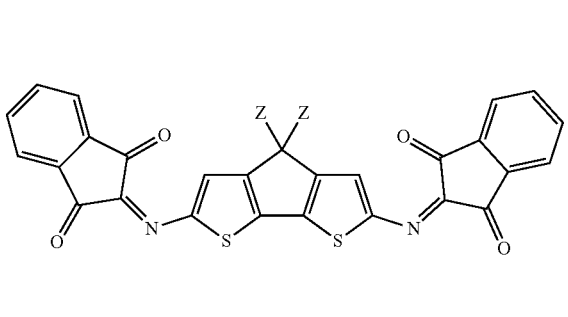

513 514
-continued
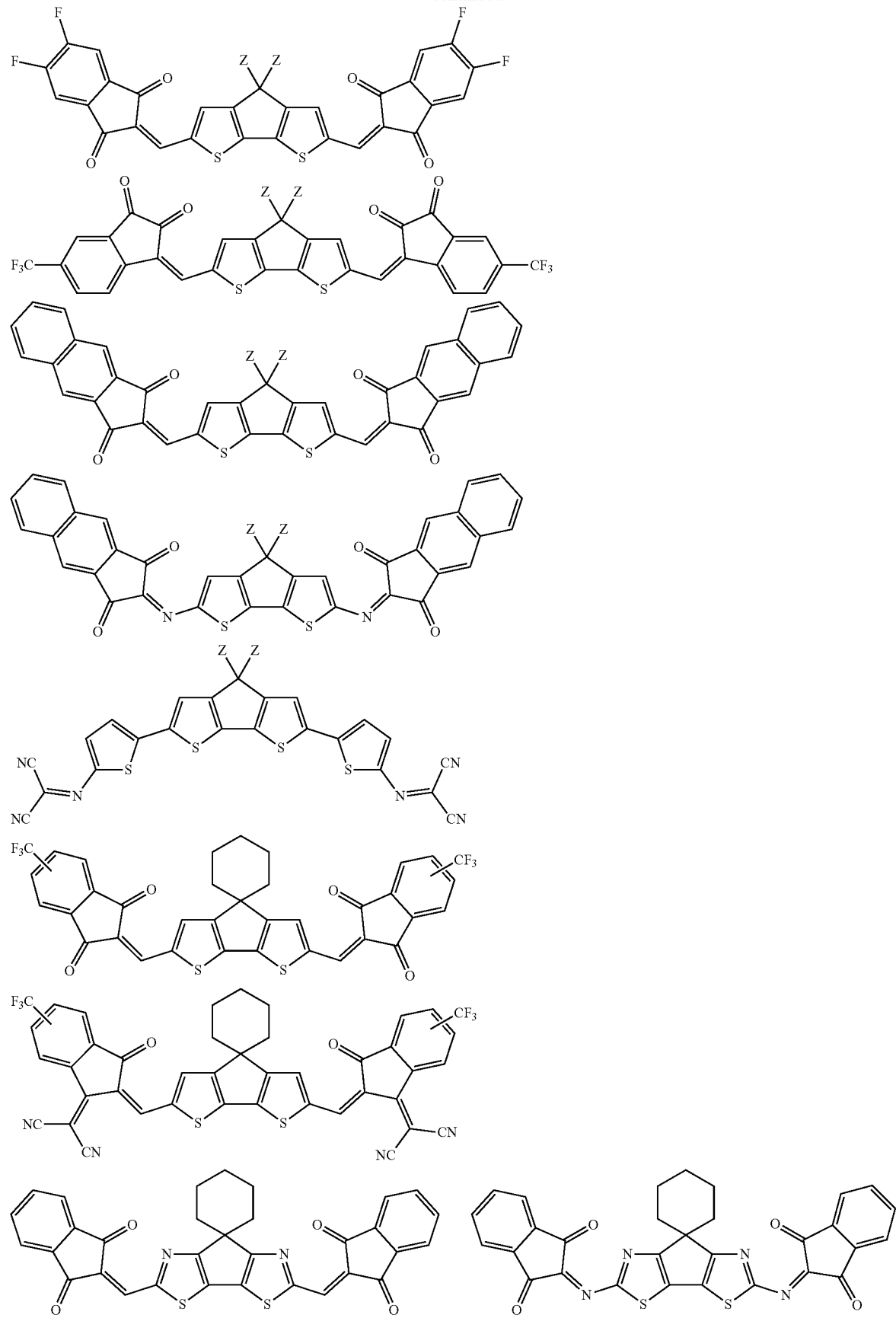

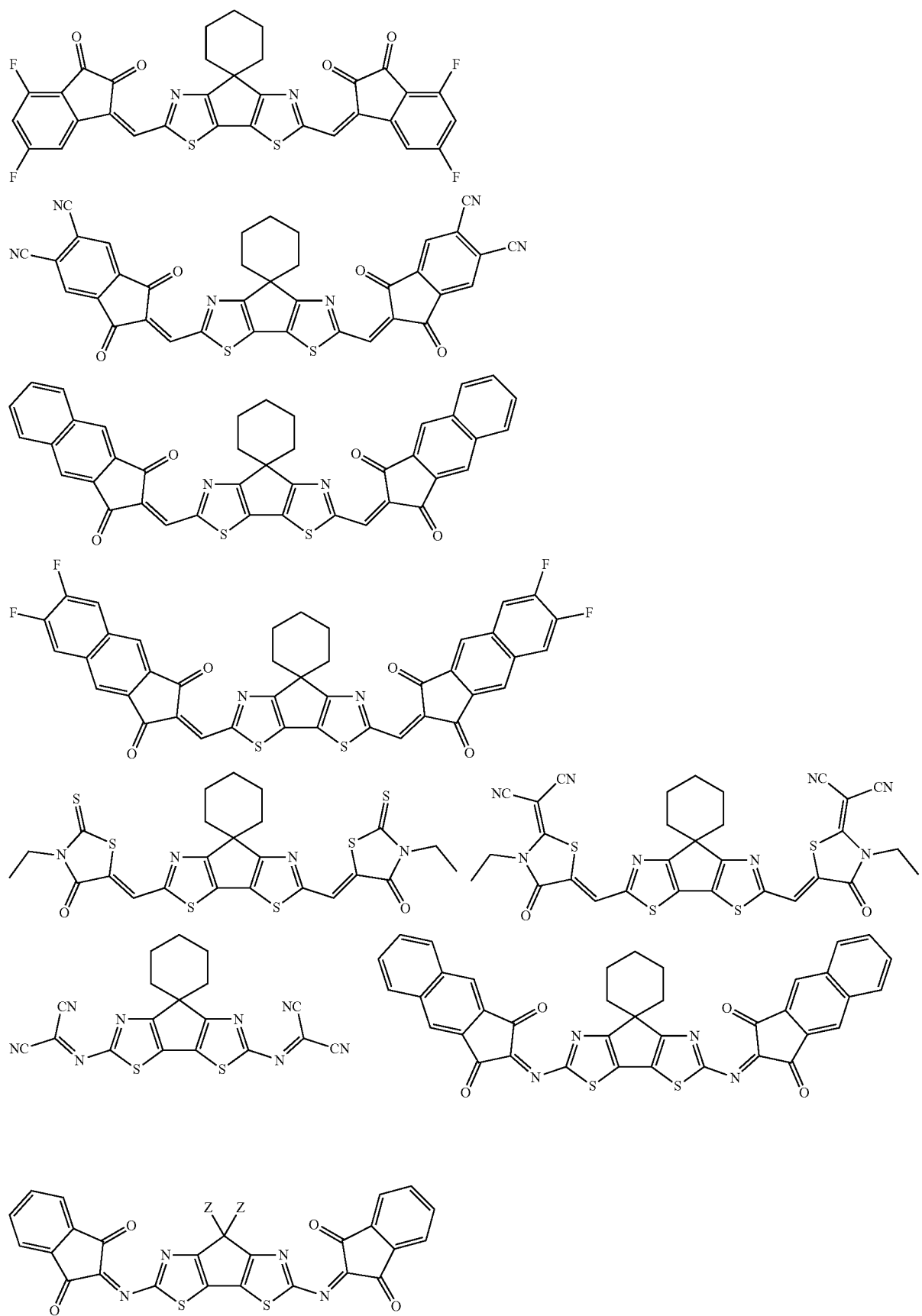

517 518
-continued
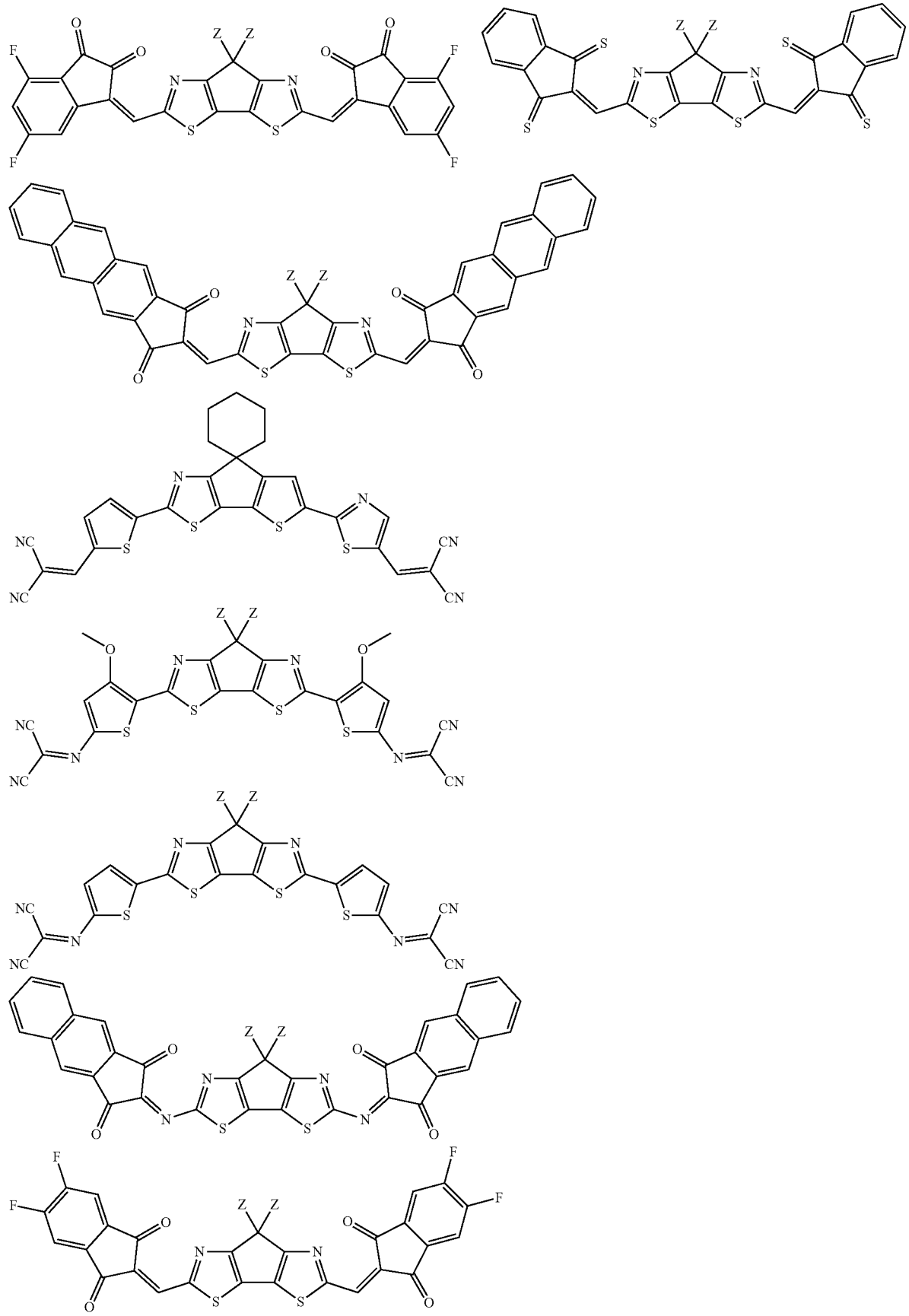

-continued
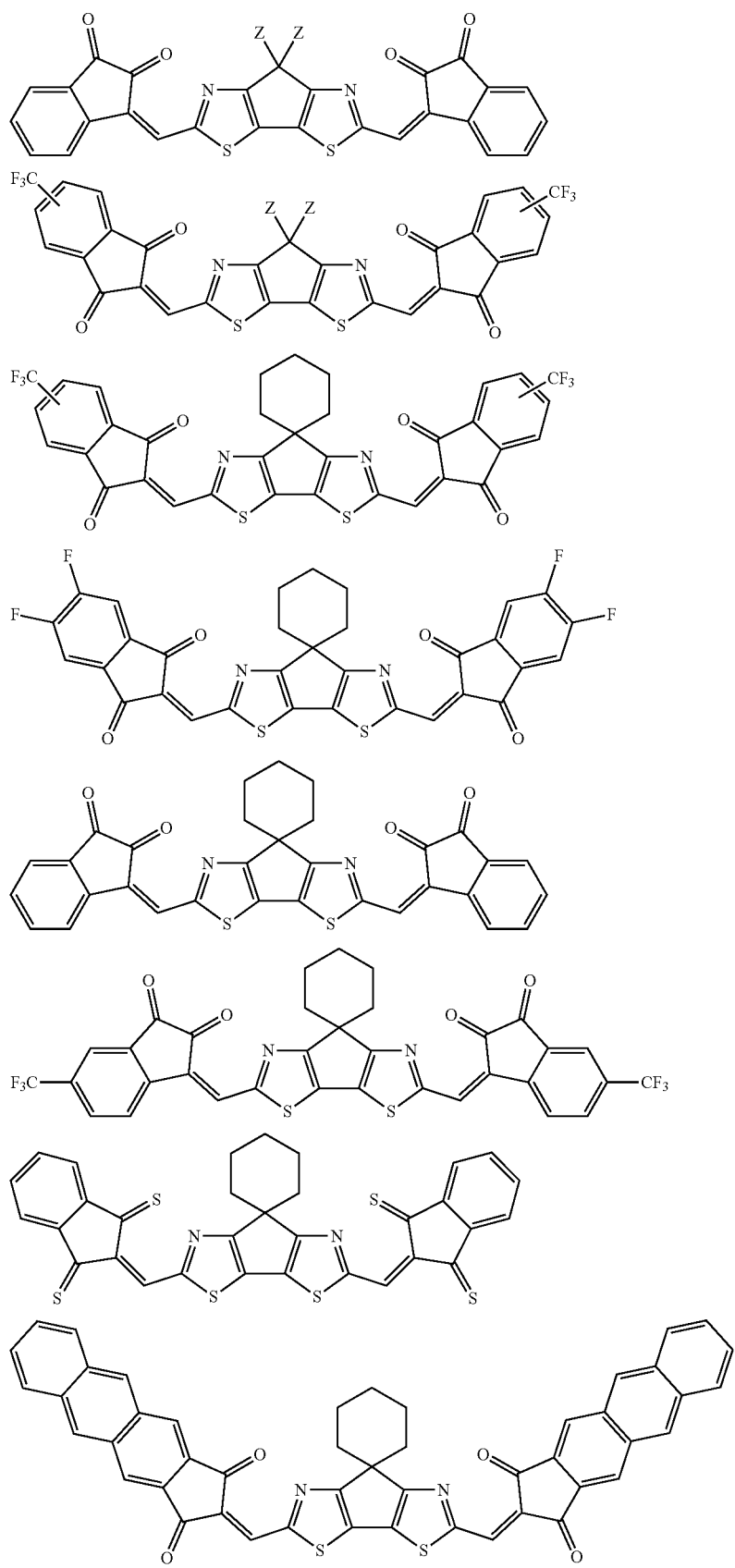

-continued
521
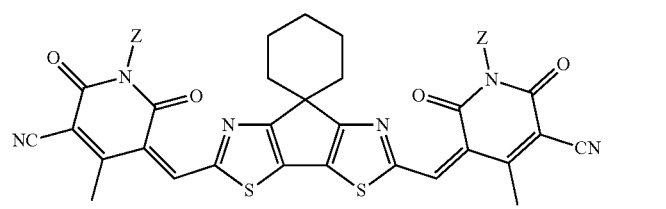
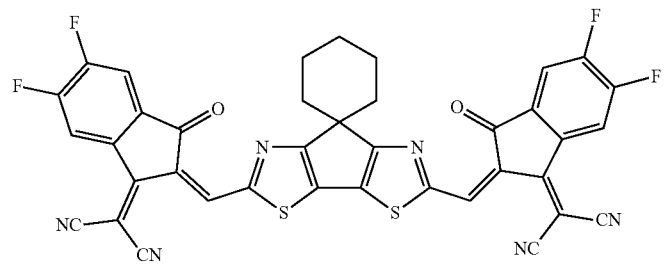
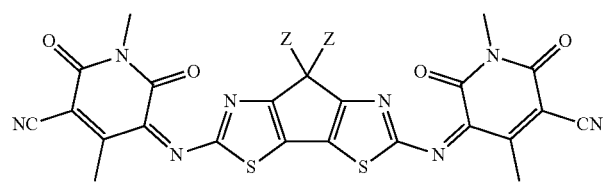
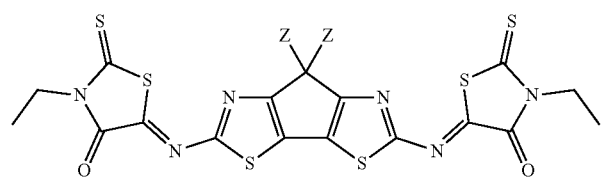
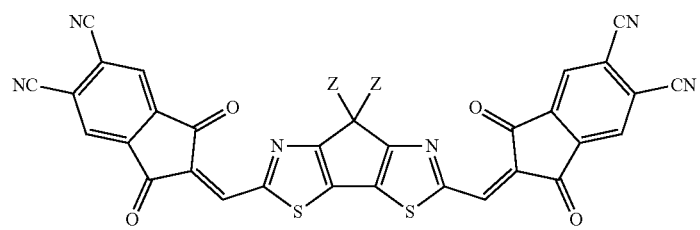
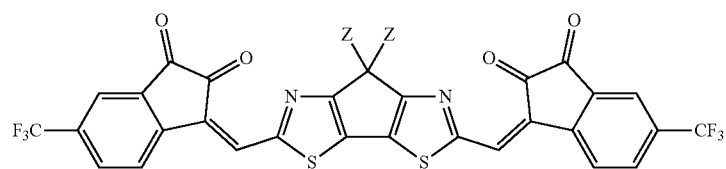
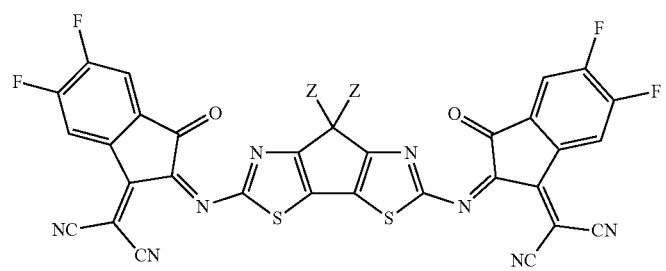
522
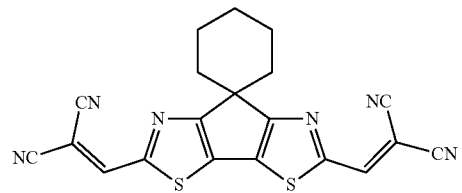
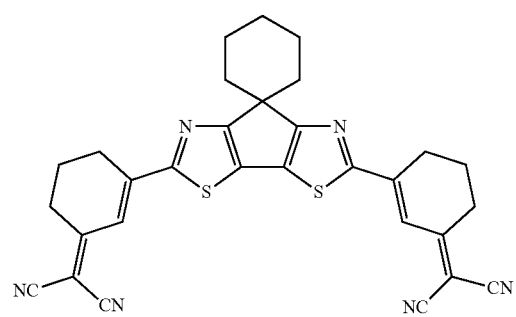

523 524
-continued
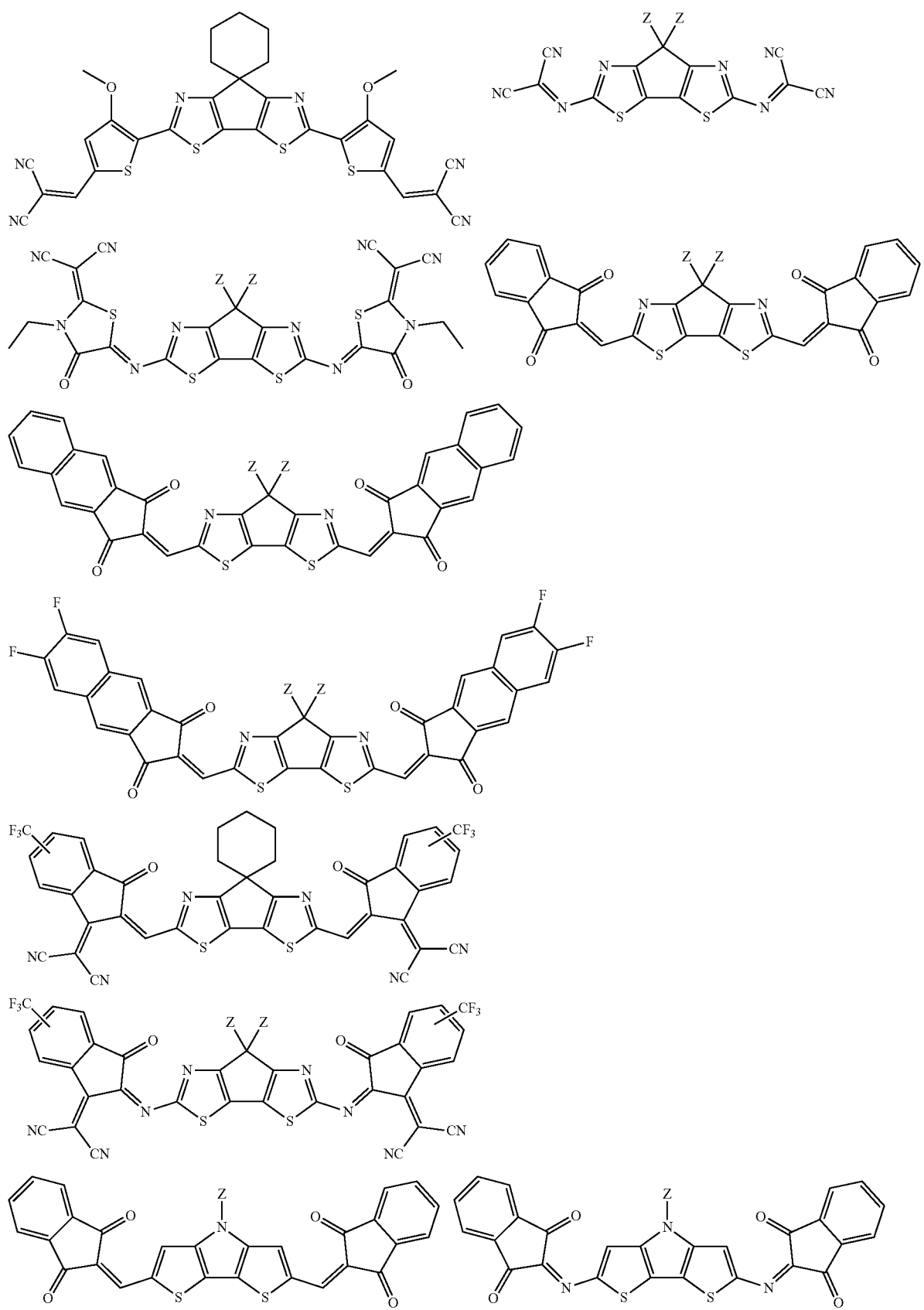

525
-continued
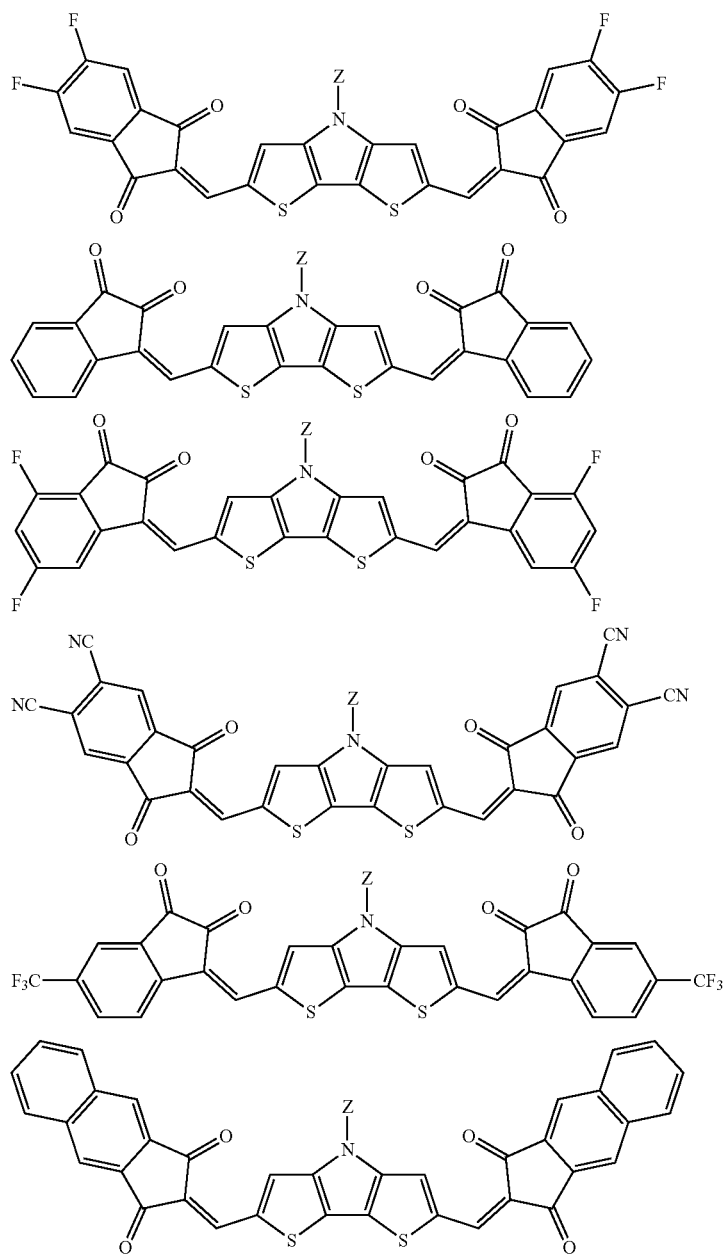
526
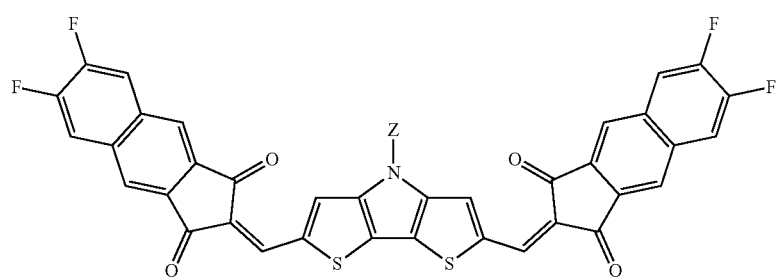

-continued
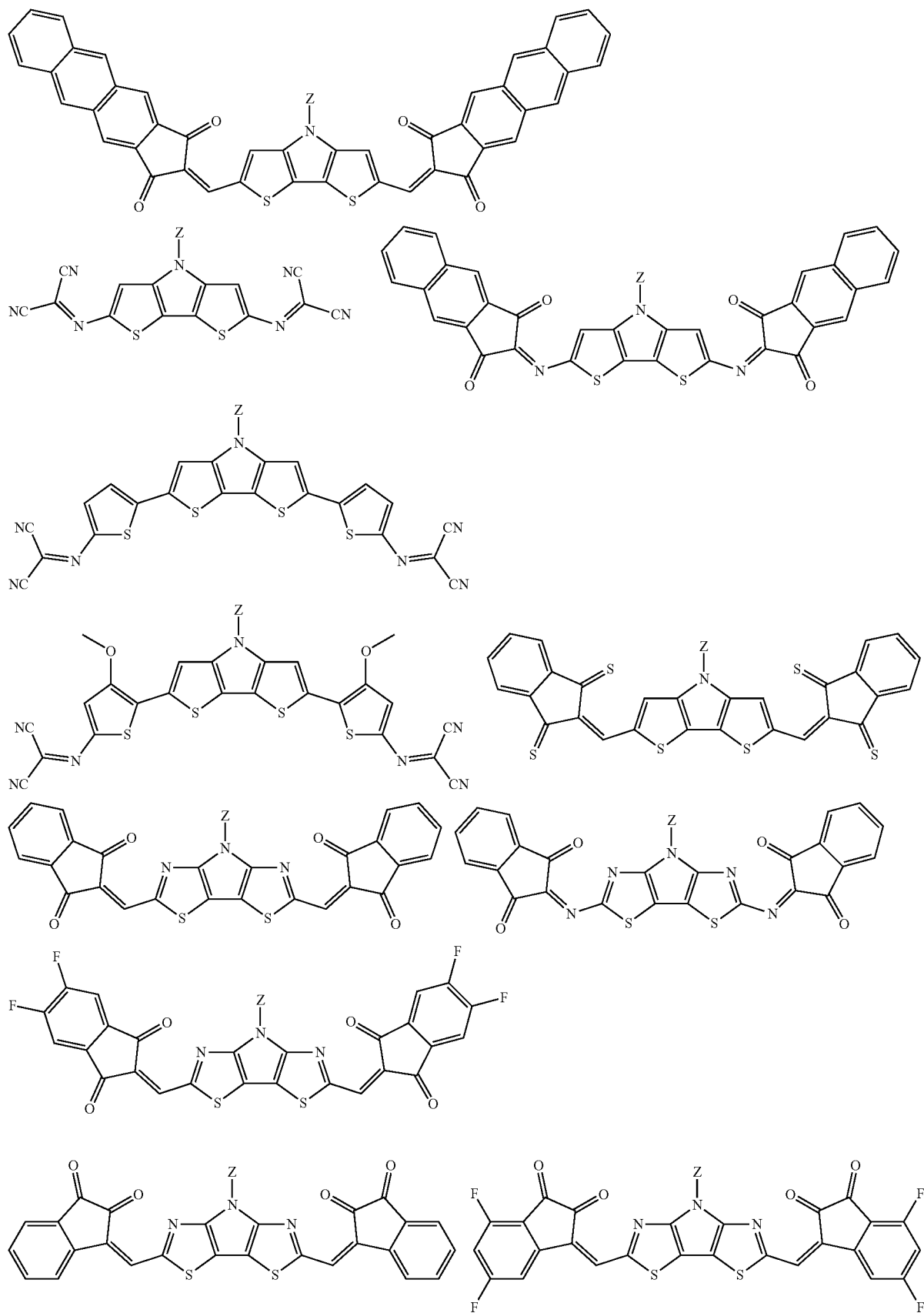

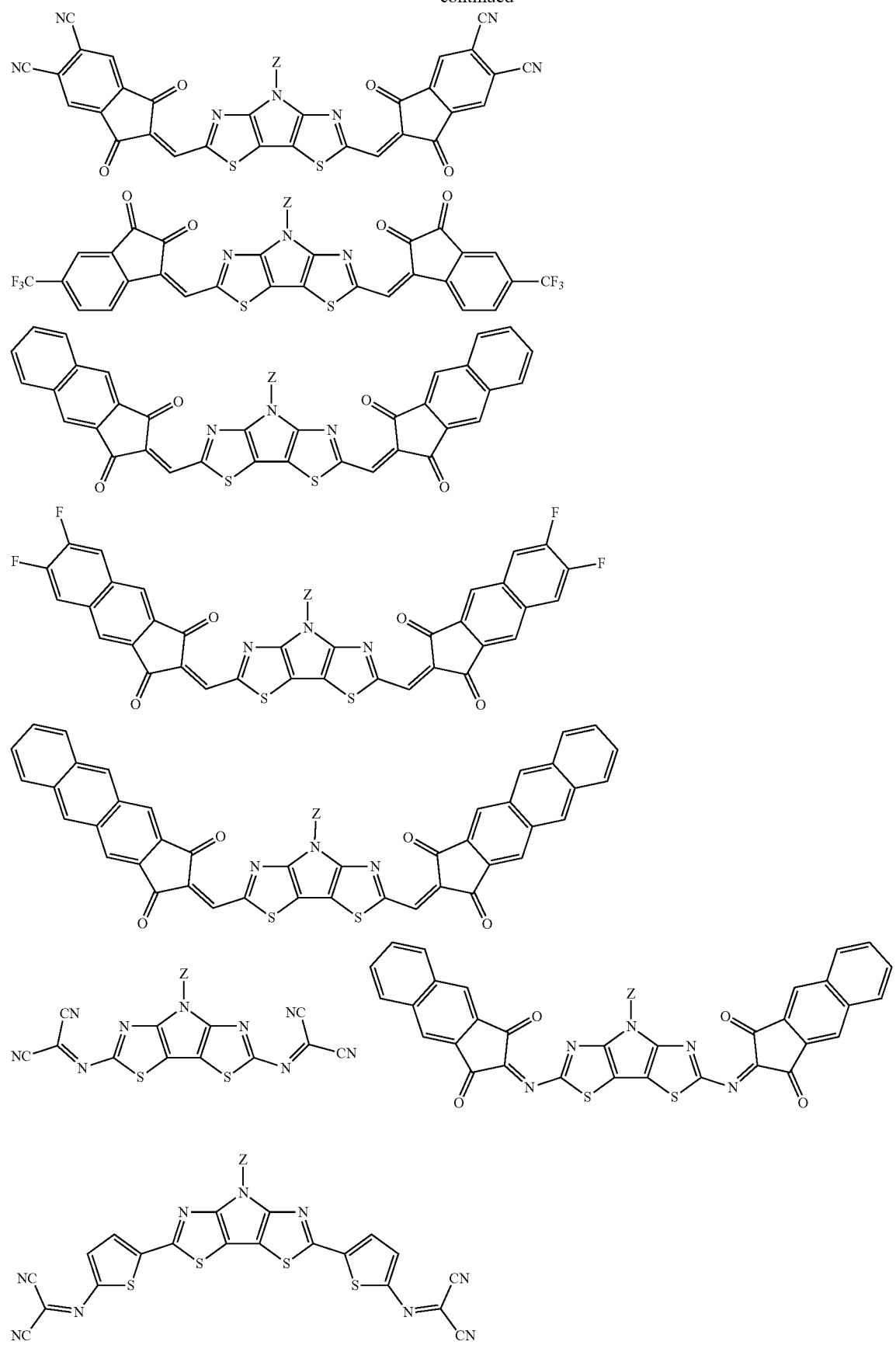

531 532
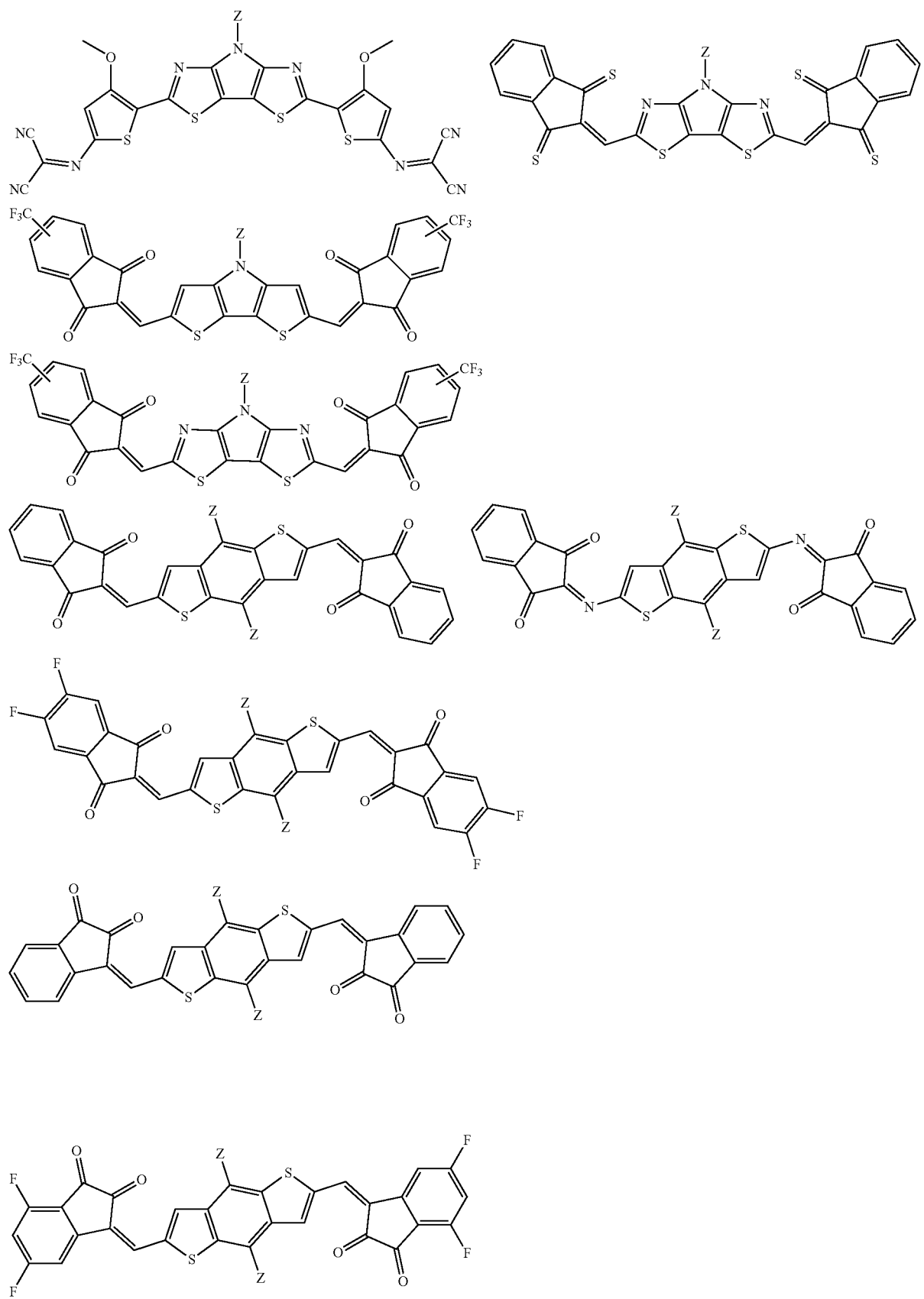

-continued
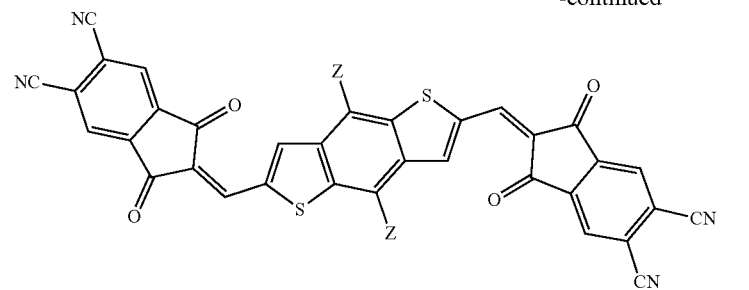
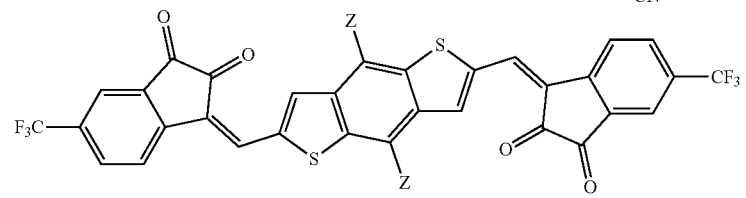
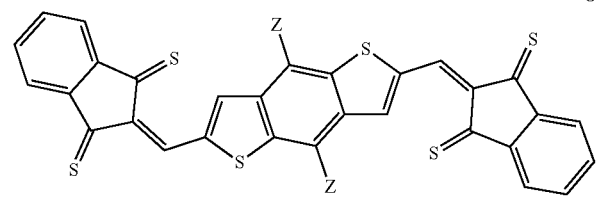
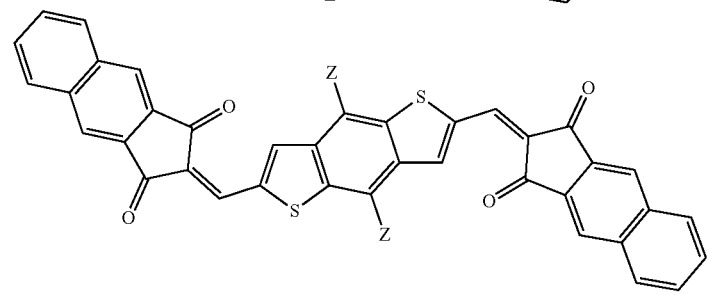
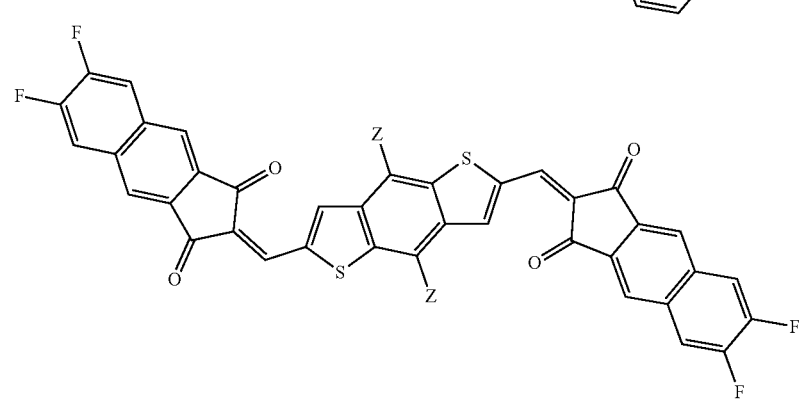
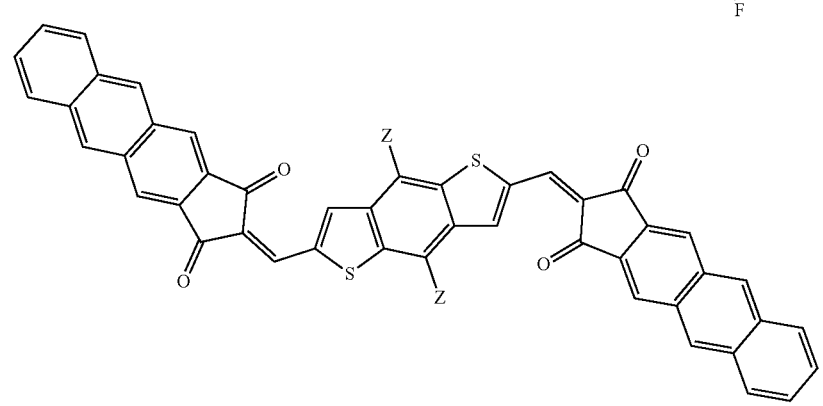

535 536
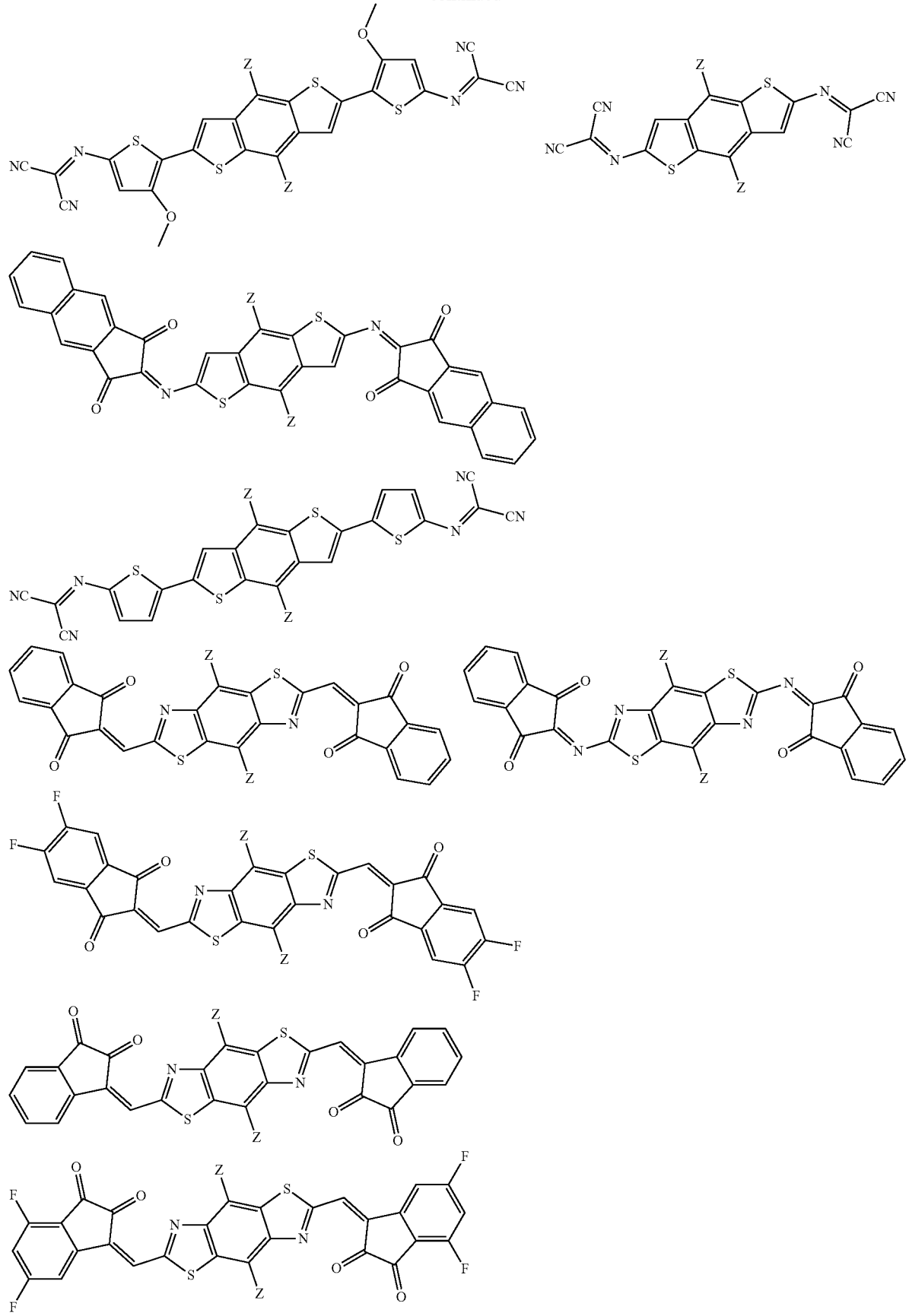

-continued
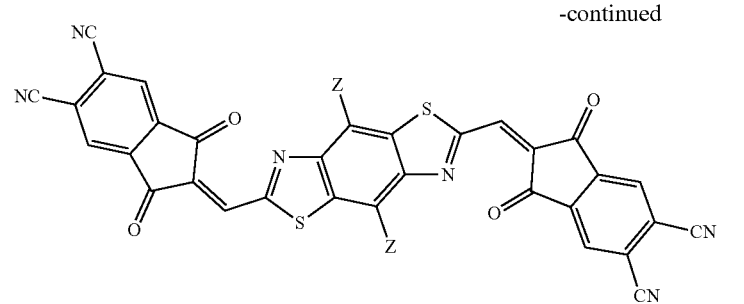
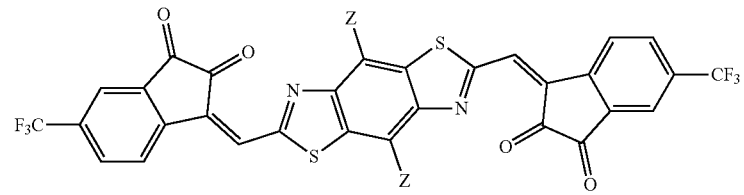
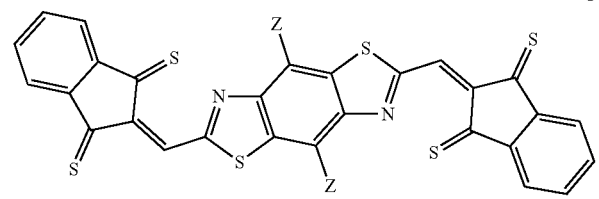
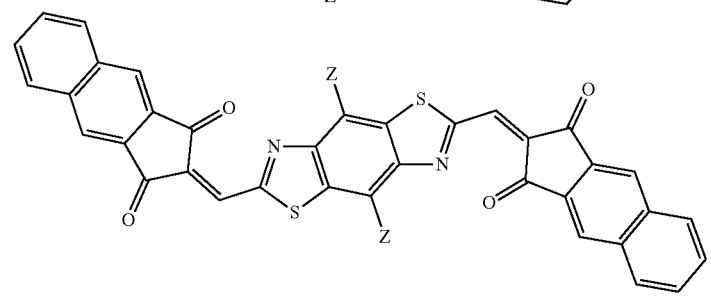
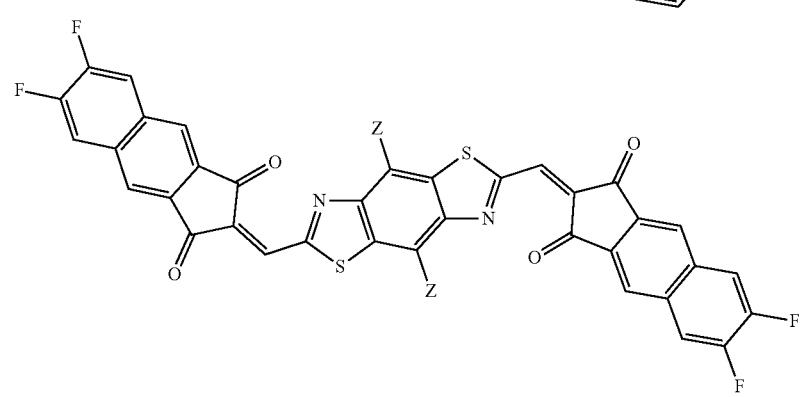
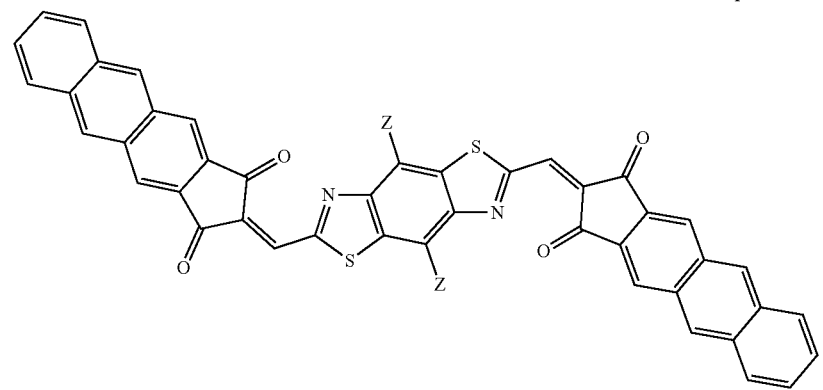

-continued
539 540
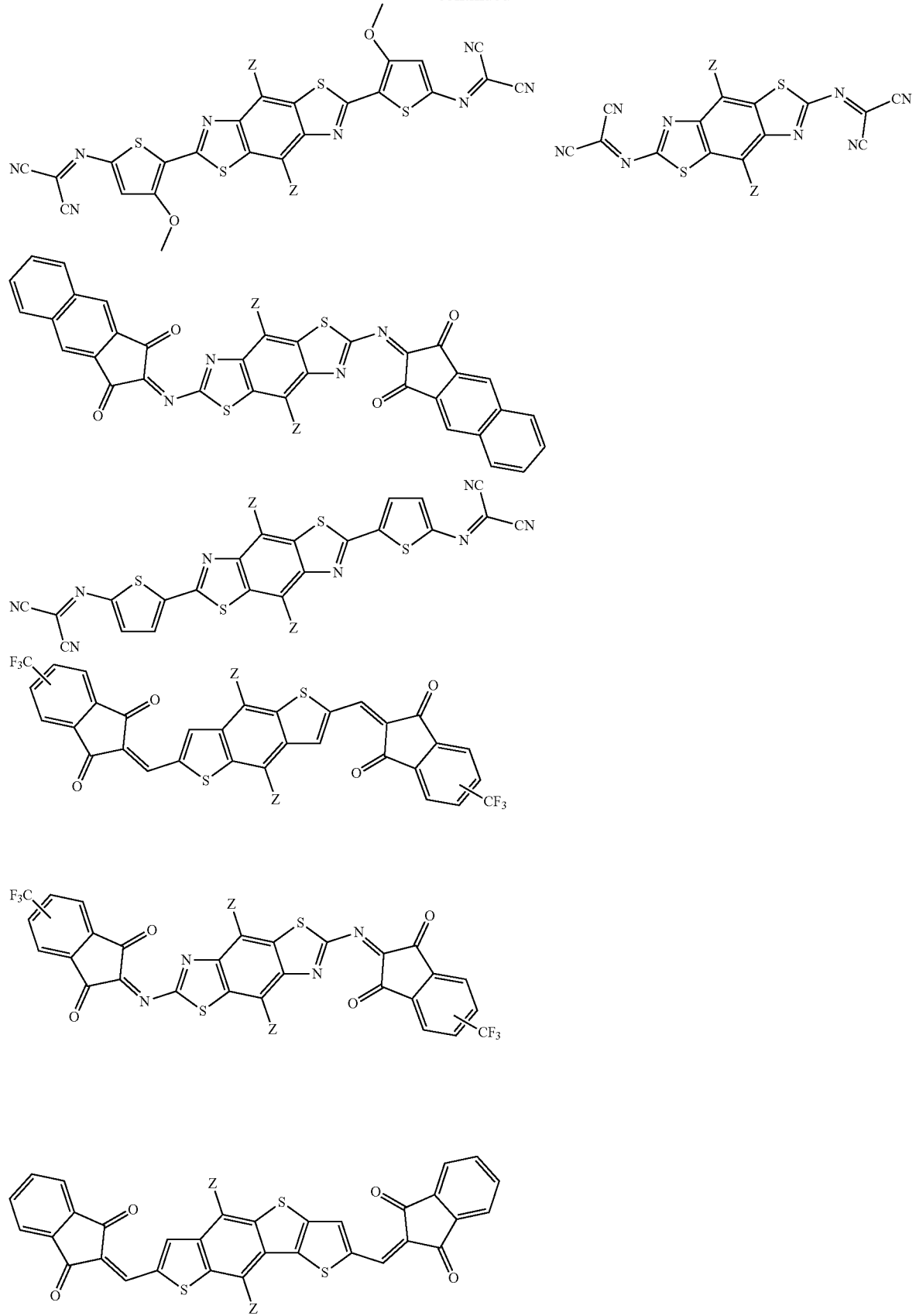

-continued
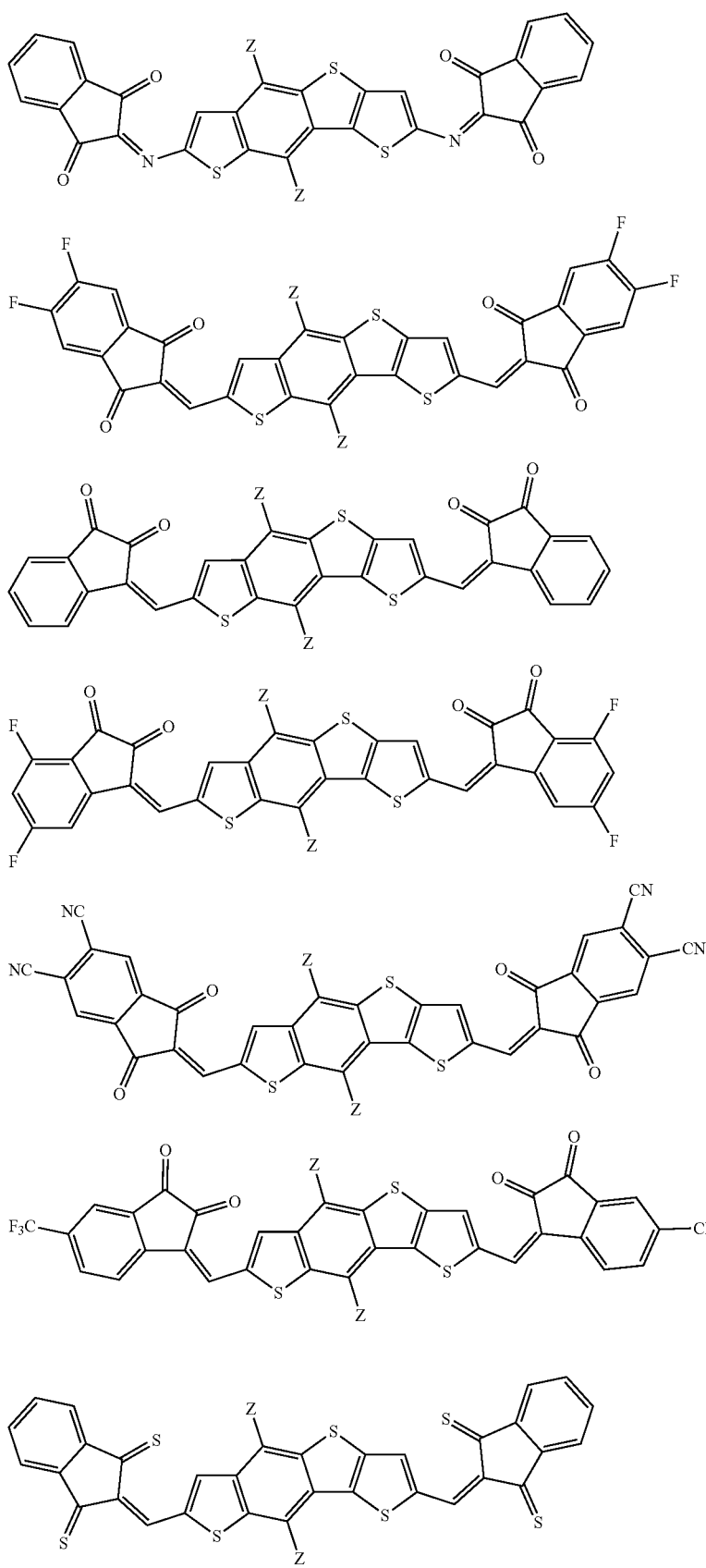

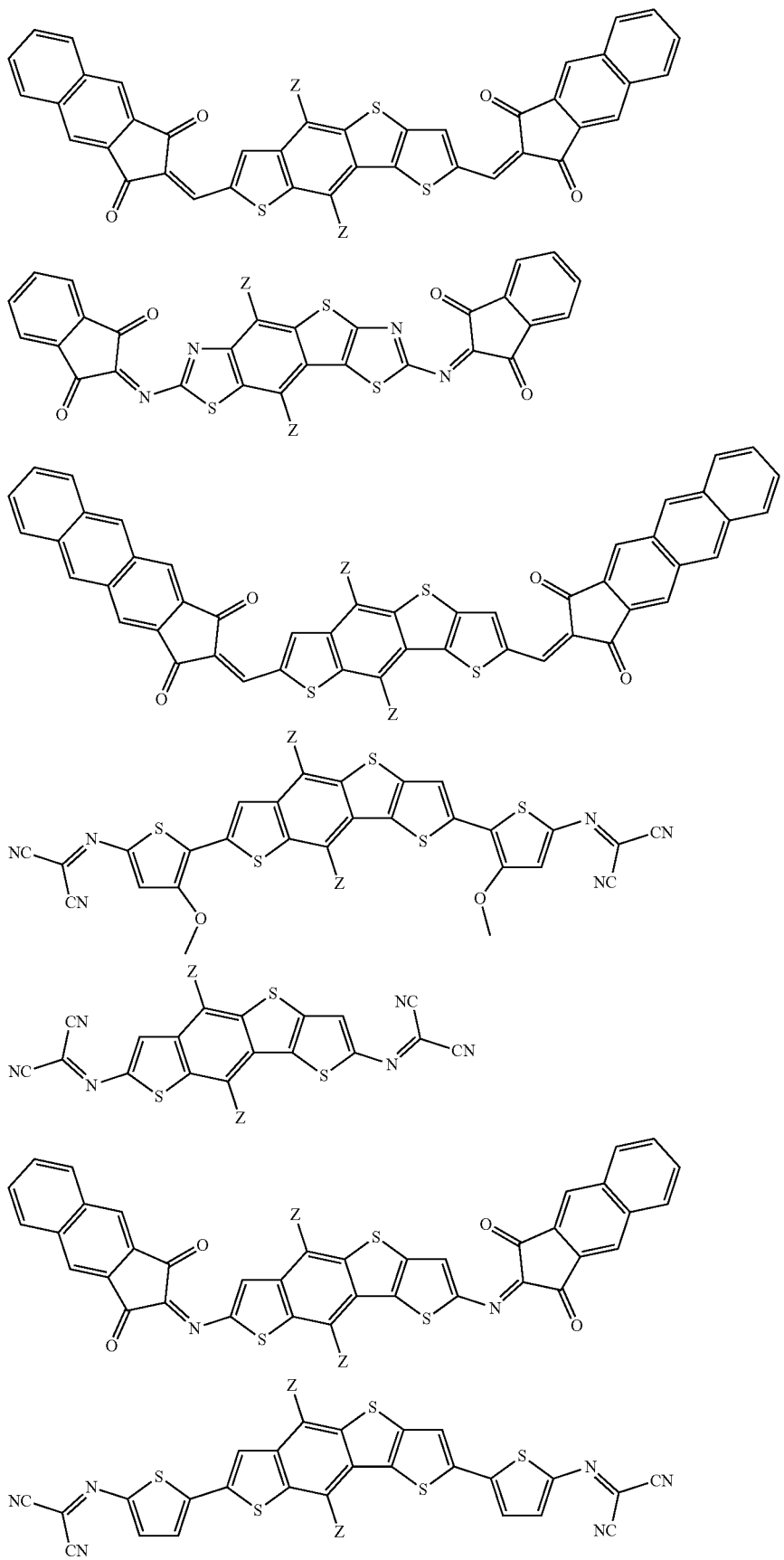

-continued
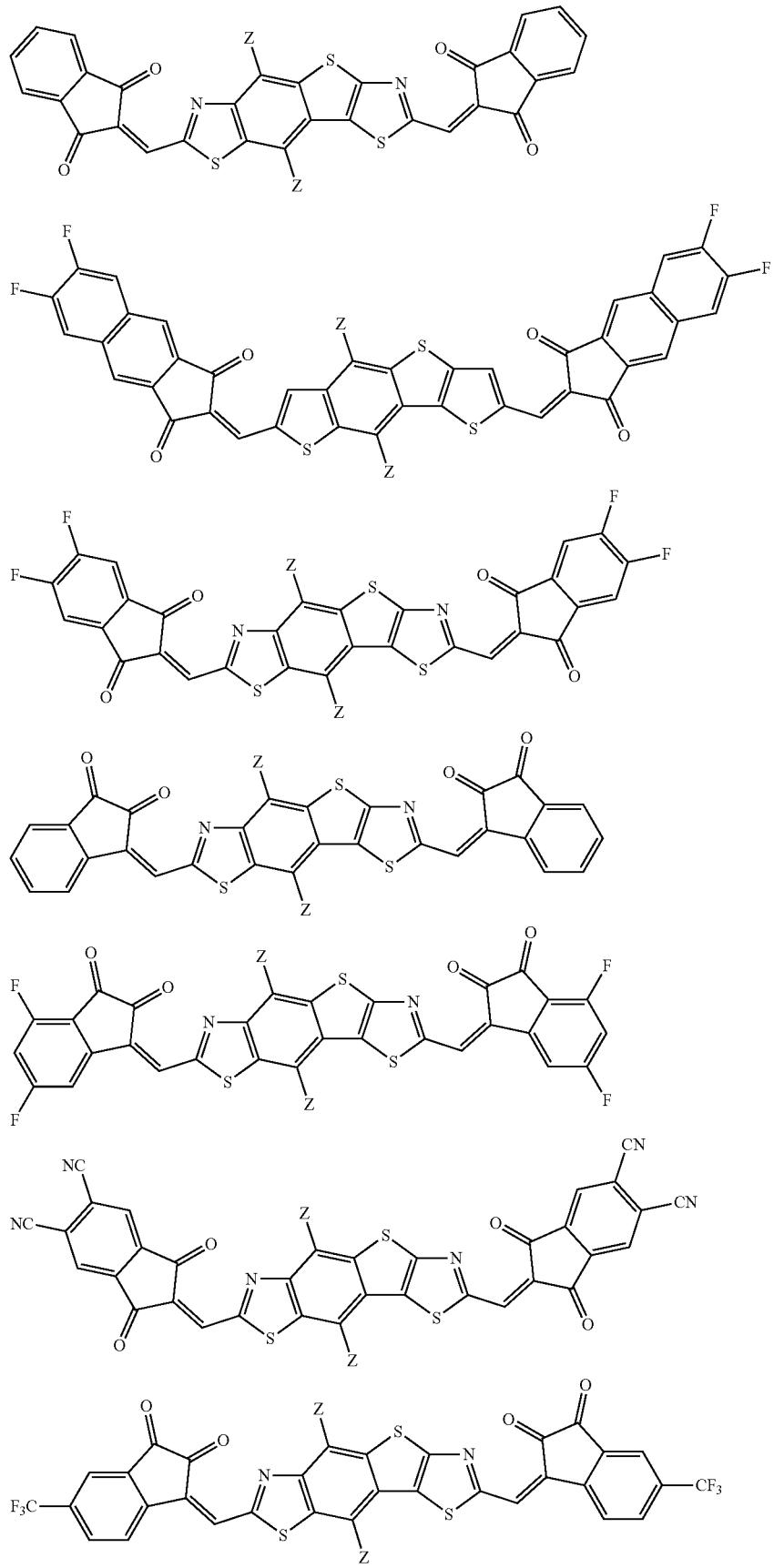

-continued
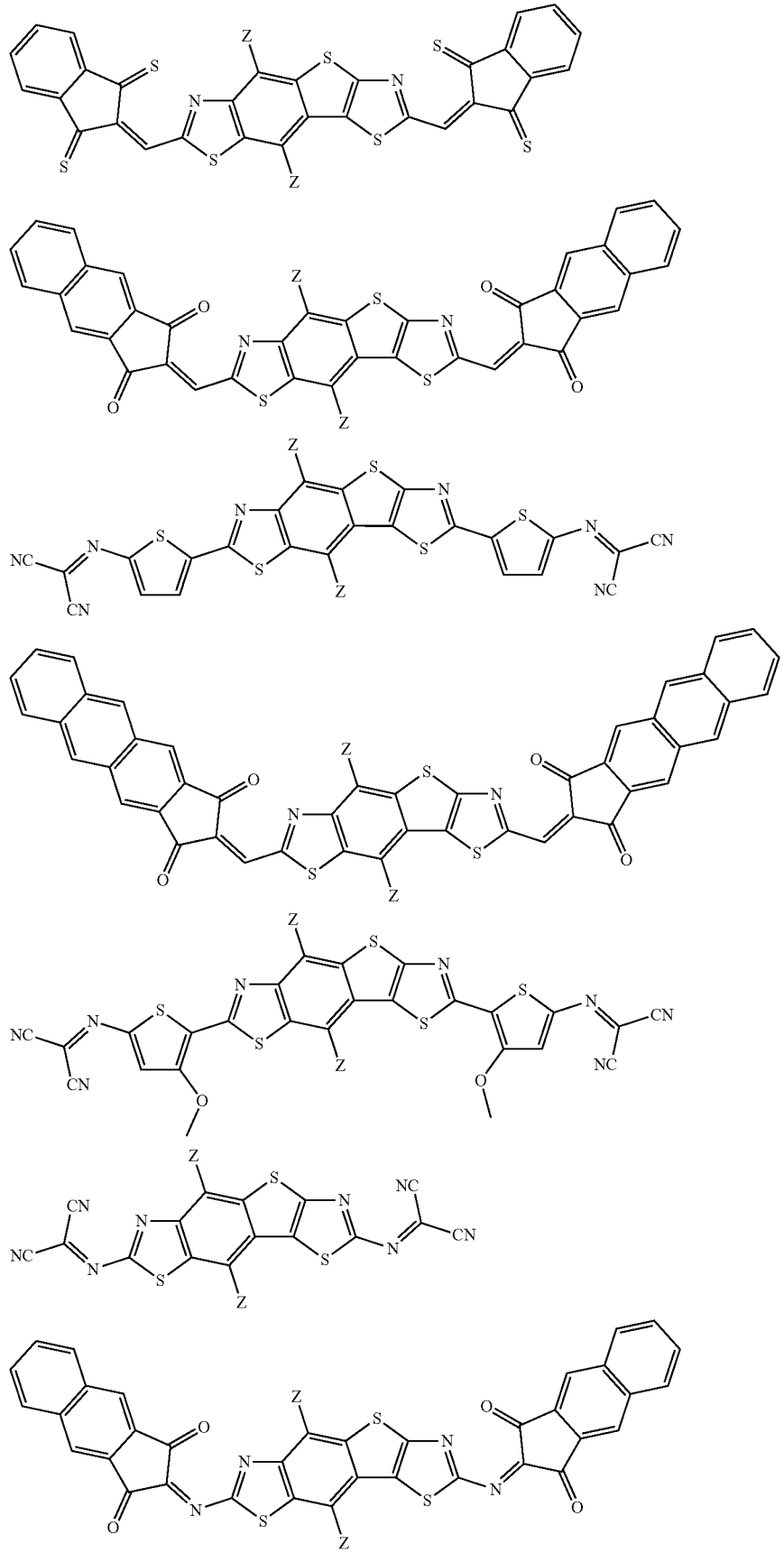

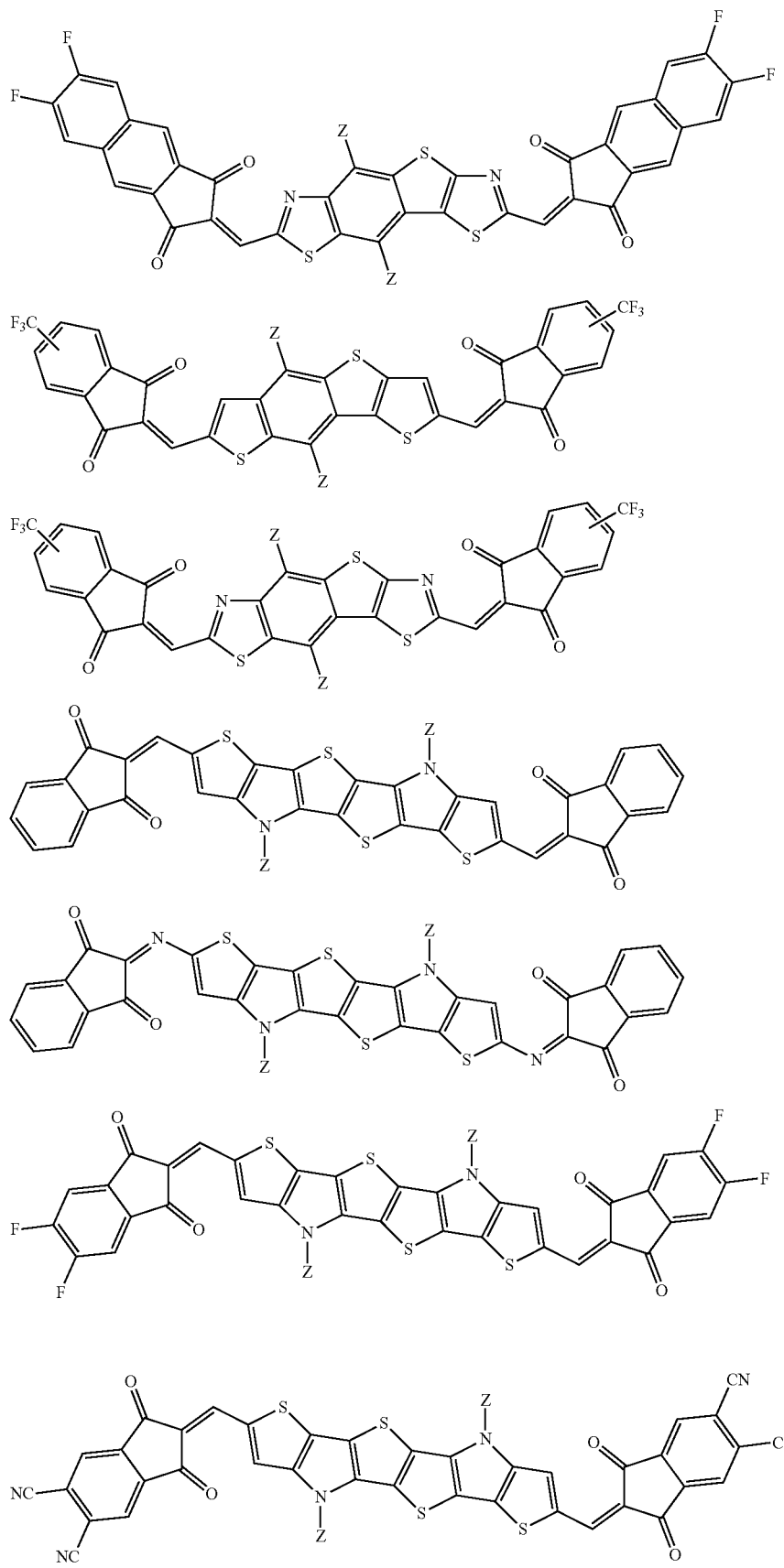

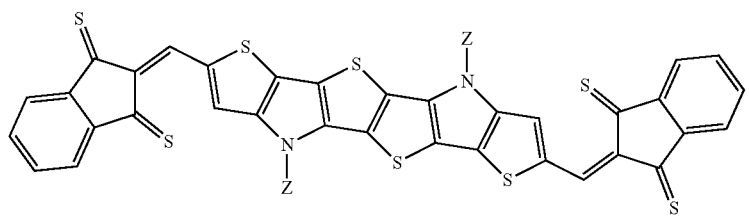
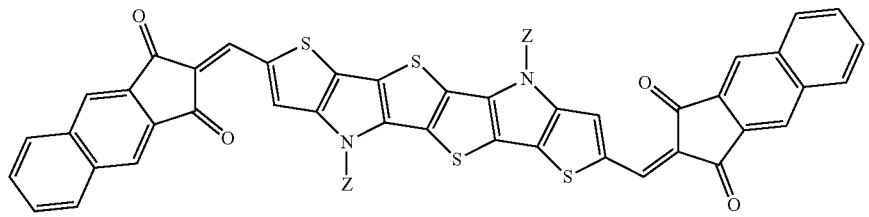
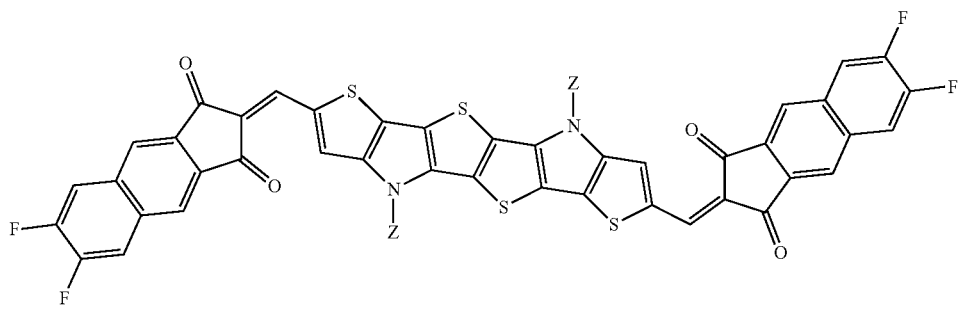
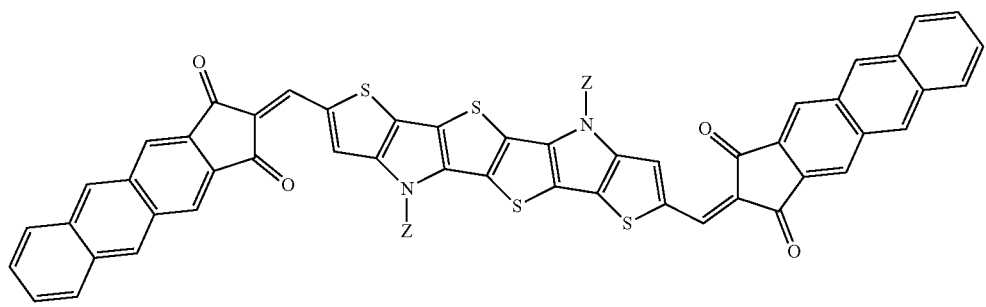
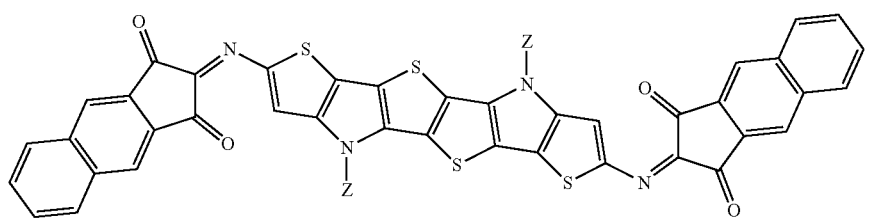
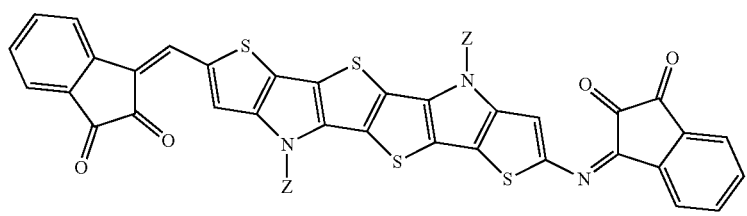

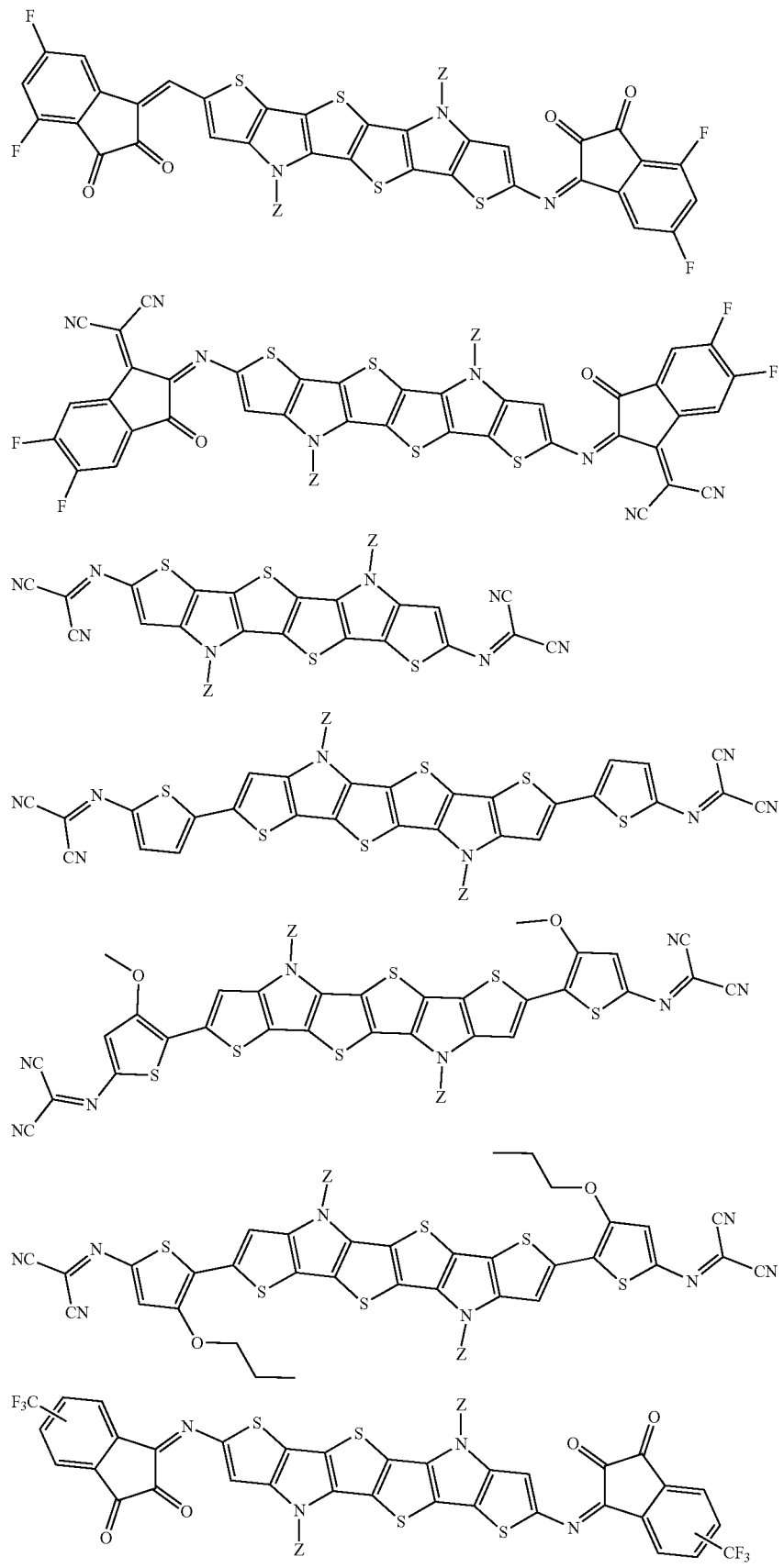

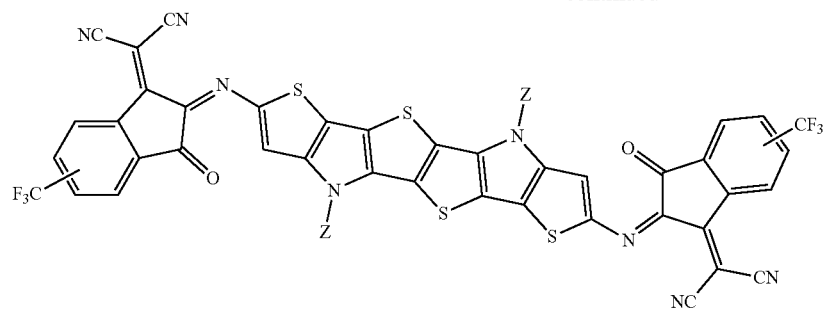
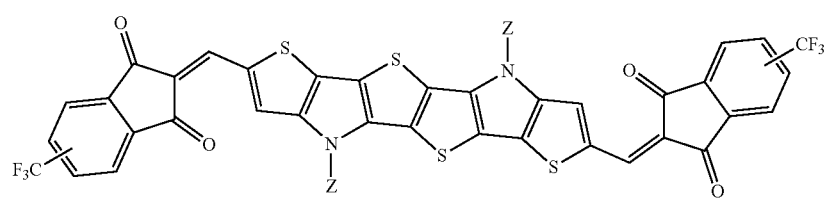
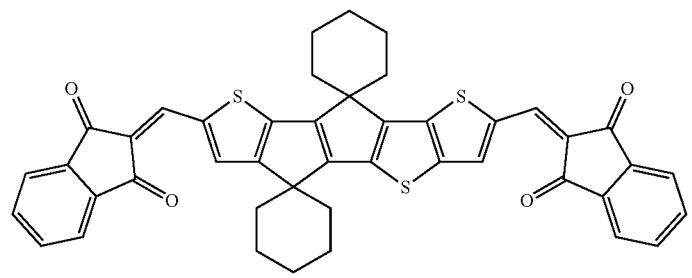
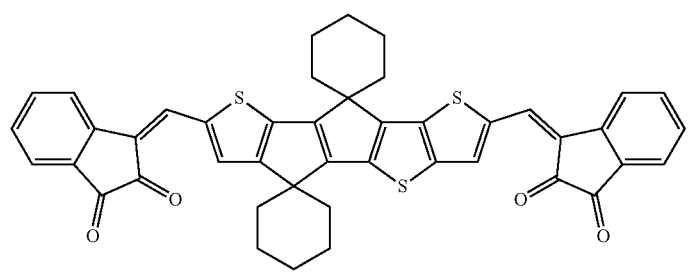
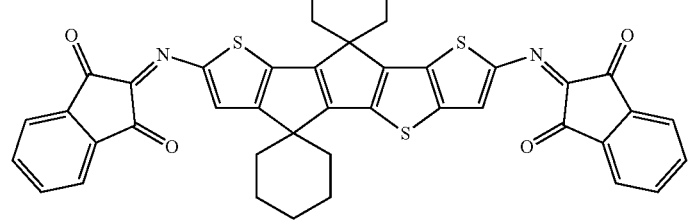
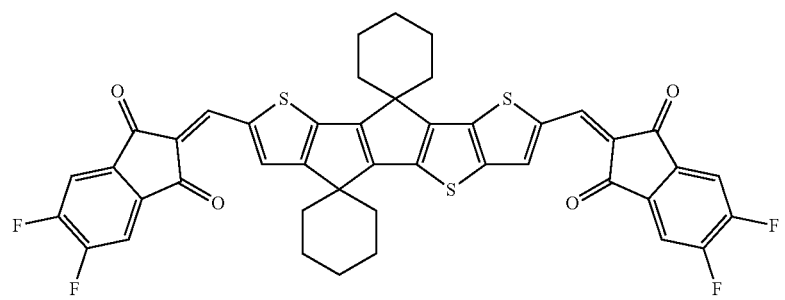

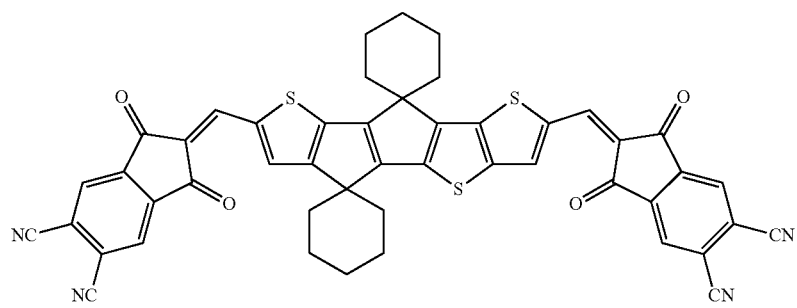
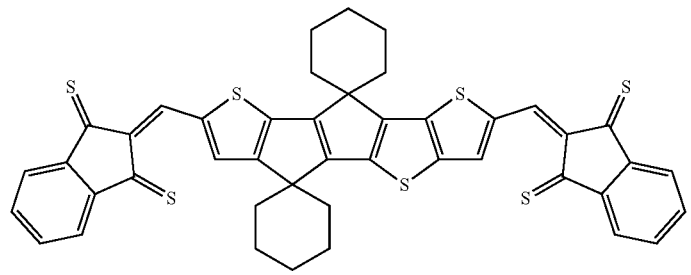
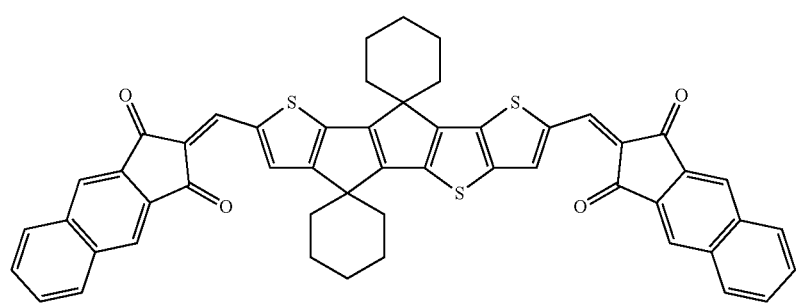
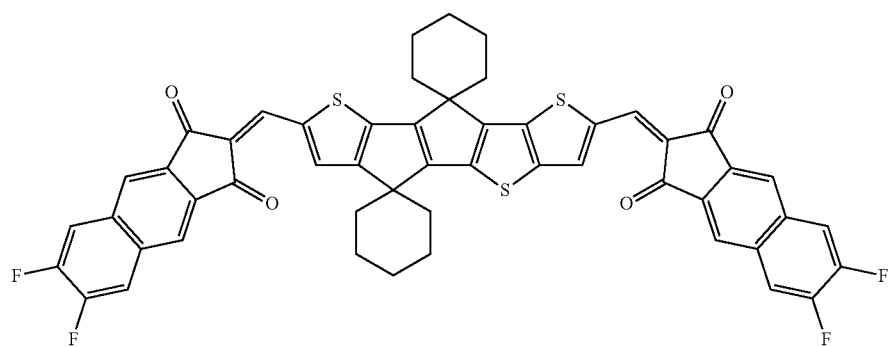
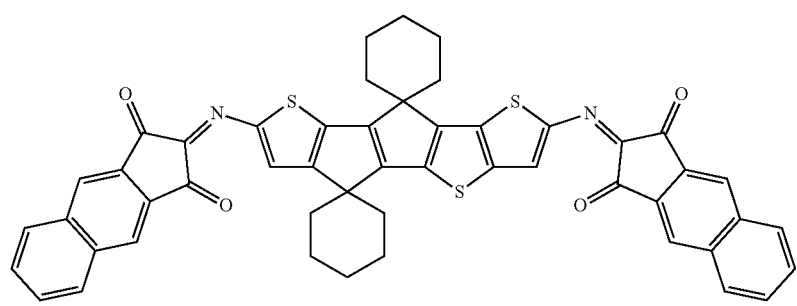

-continued
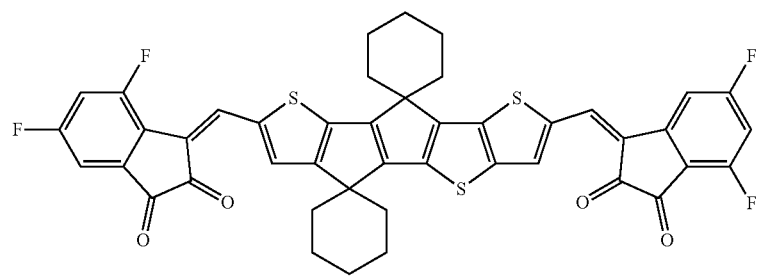
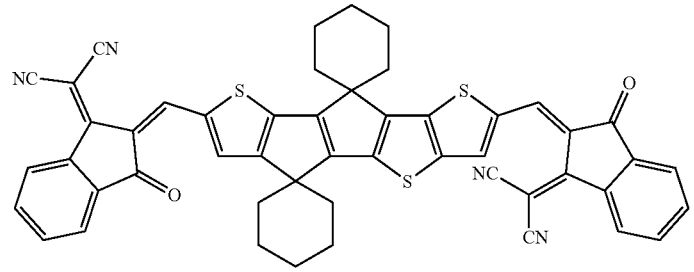
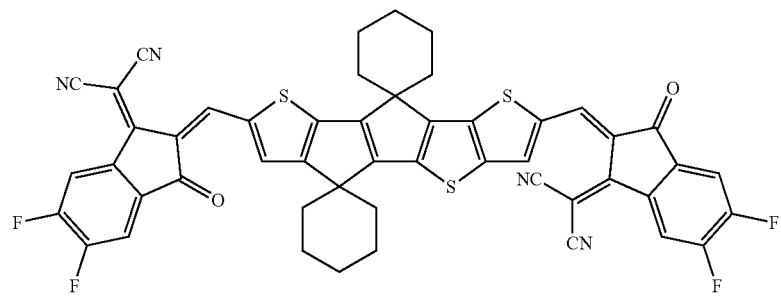
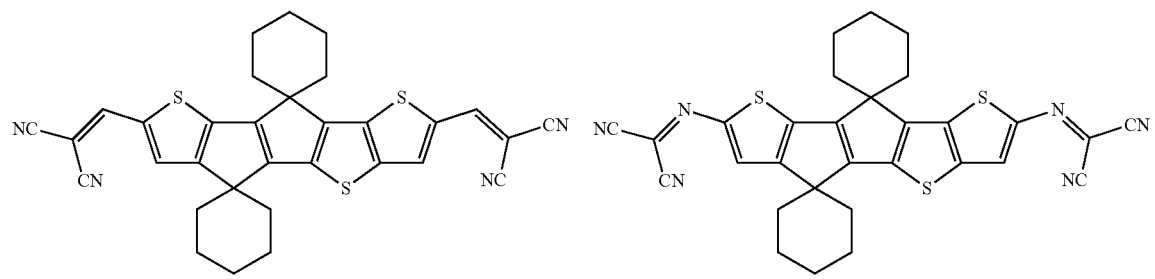
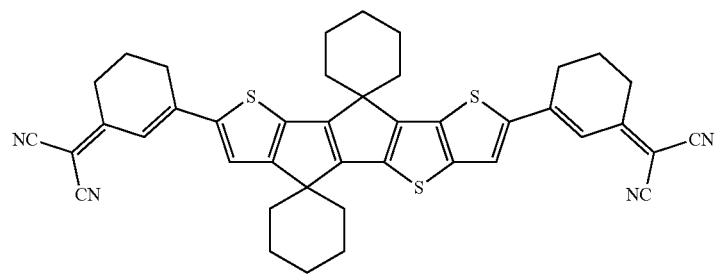
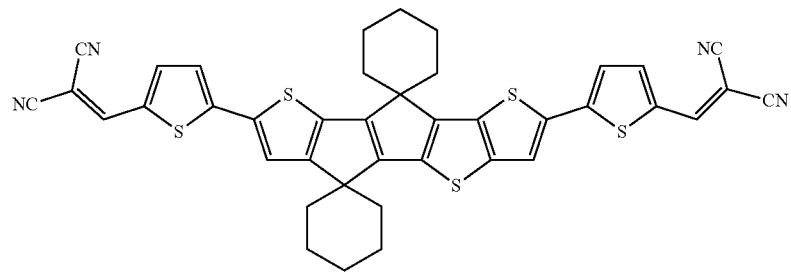

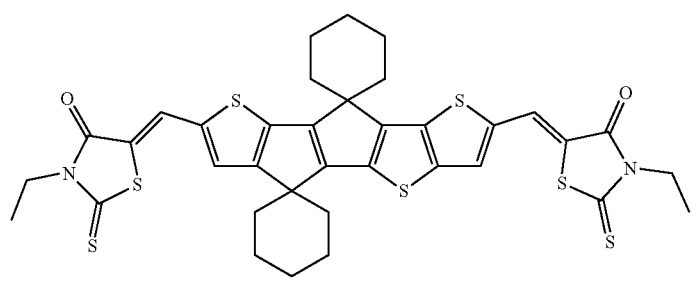
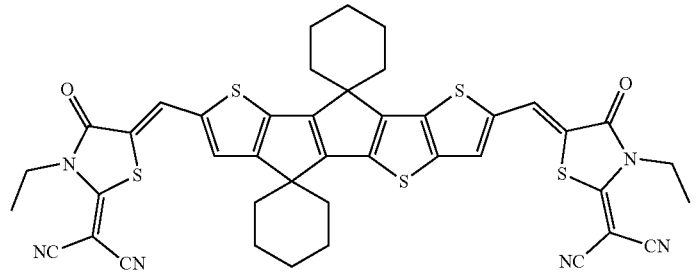
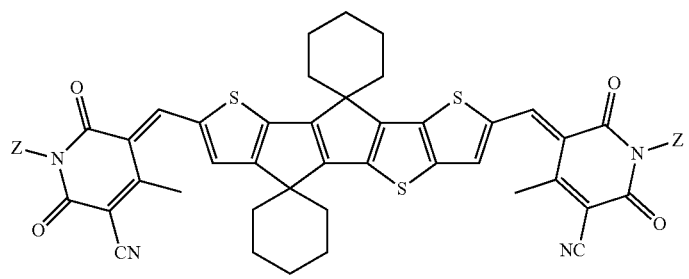
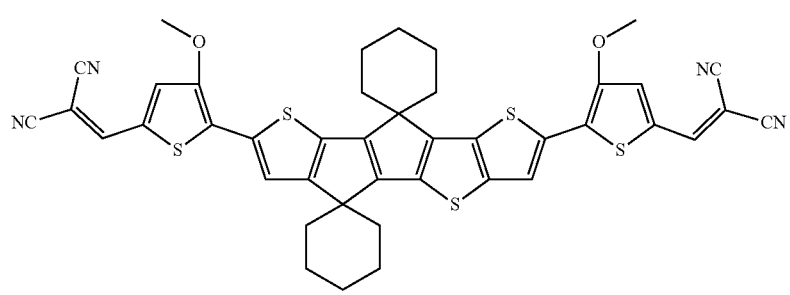
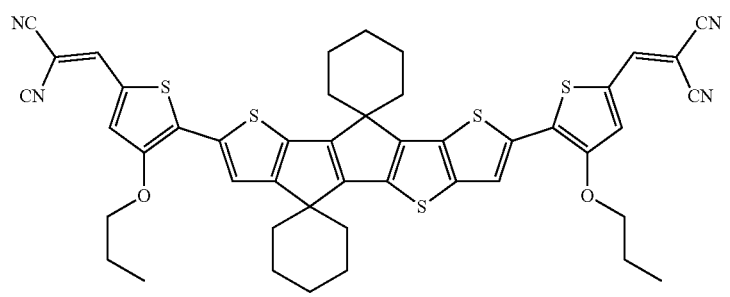

-continued
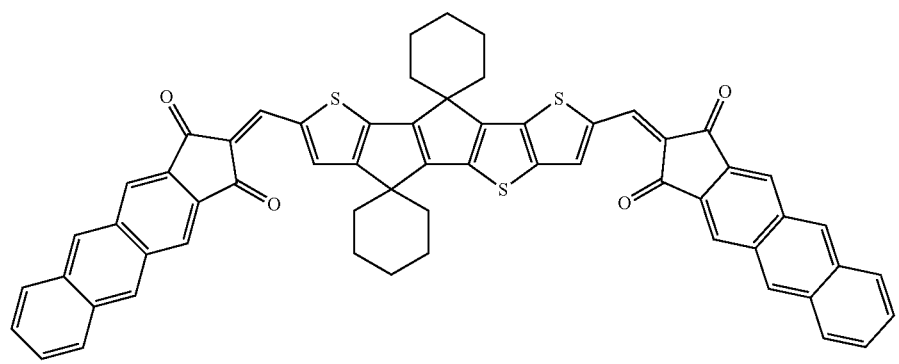
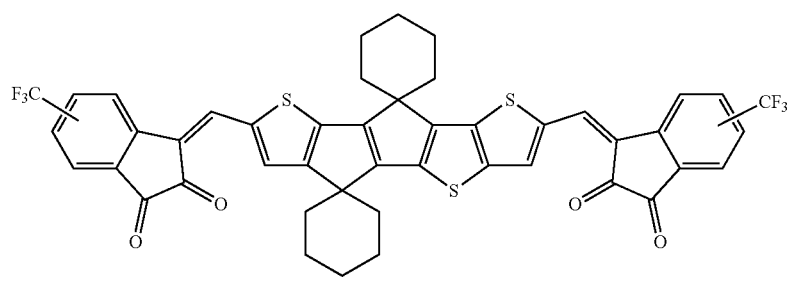
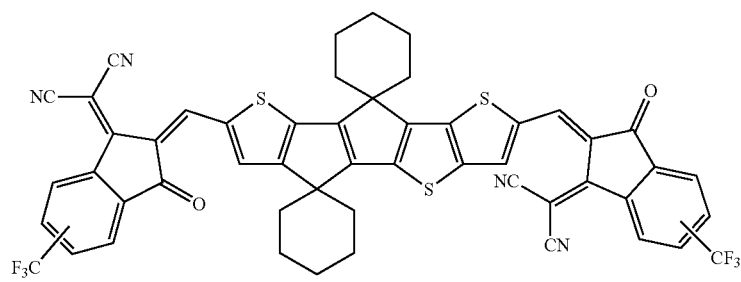
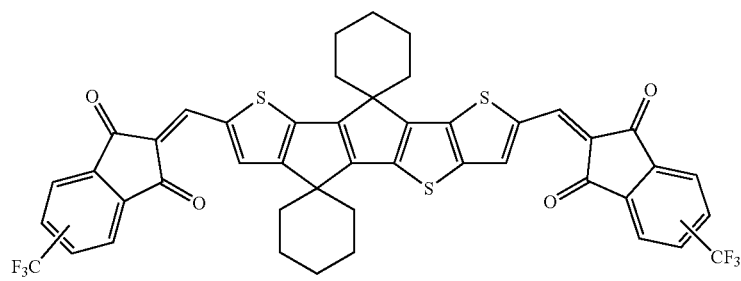
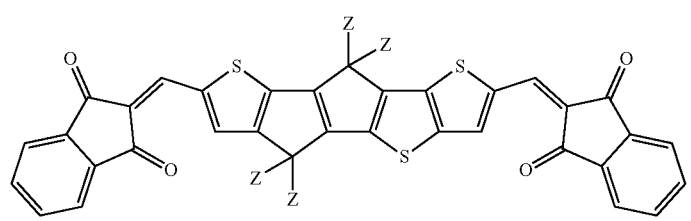
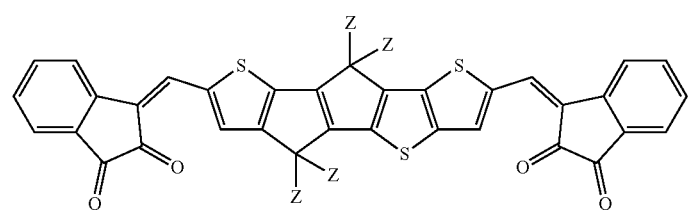

-continued
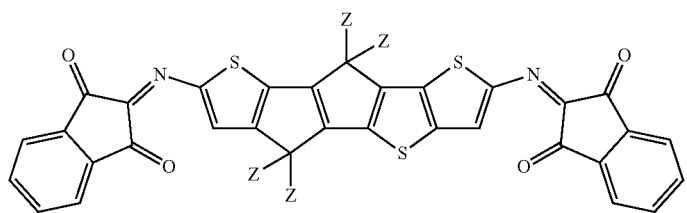
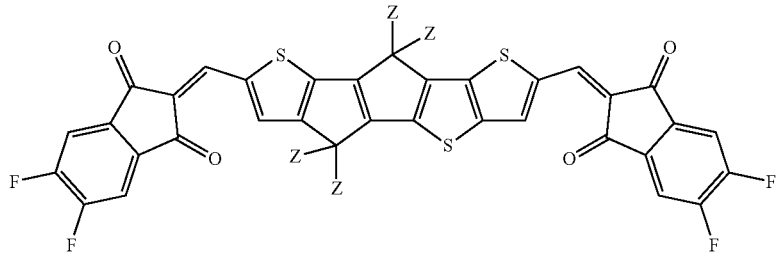
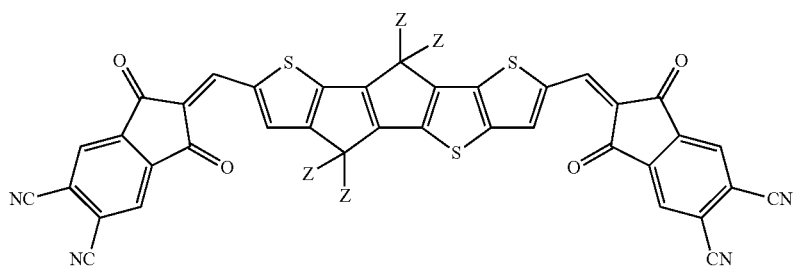
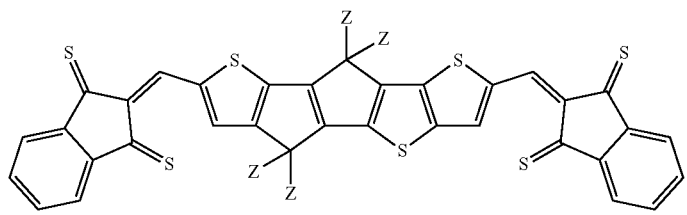
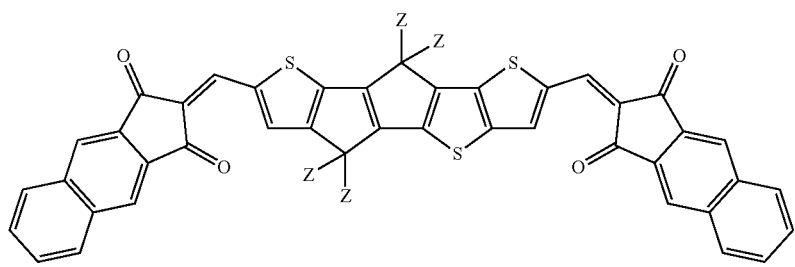
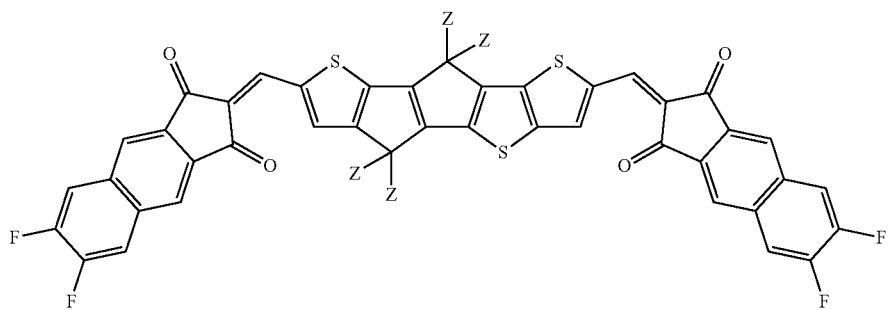

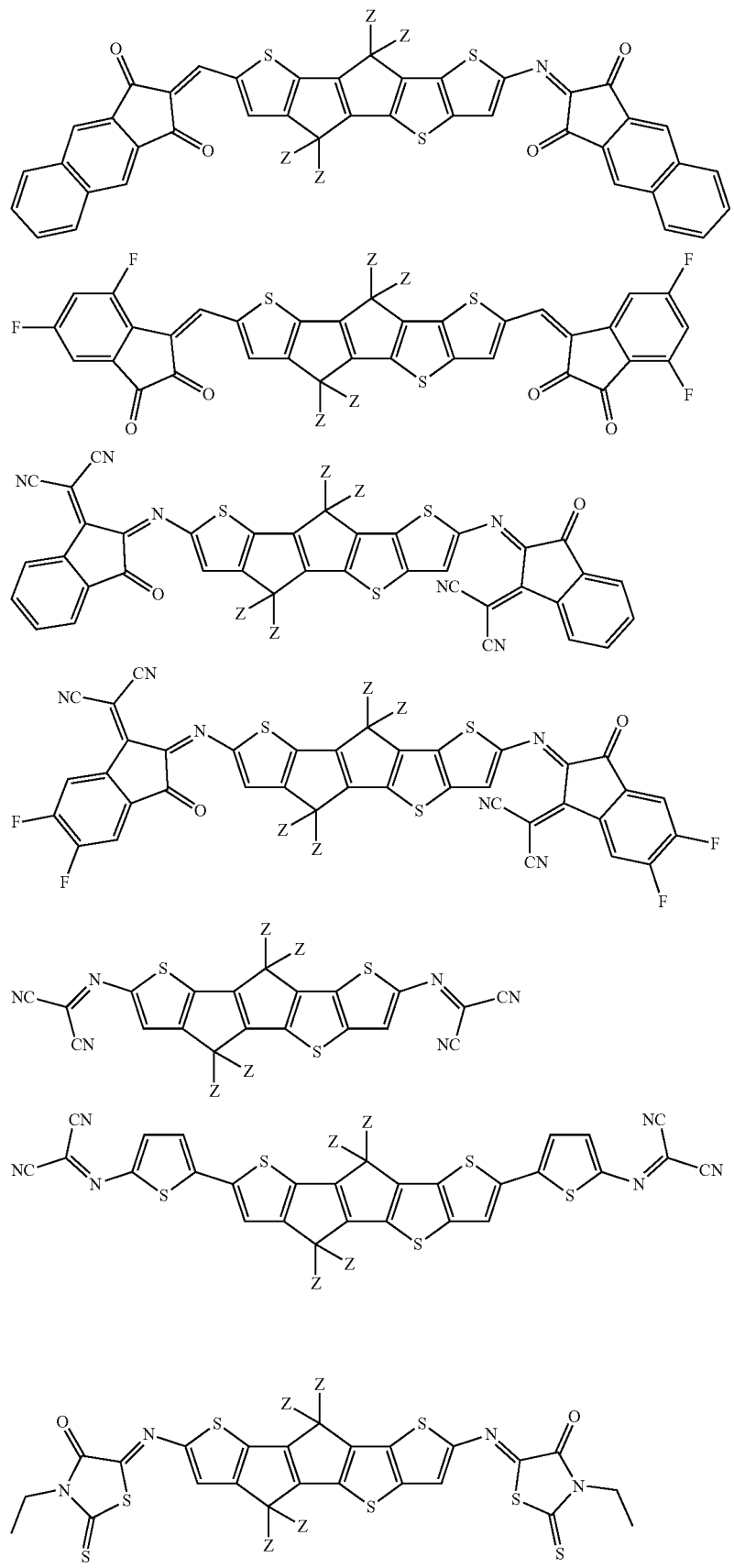

-continued
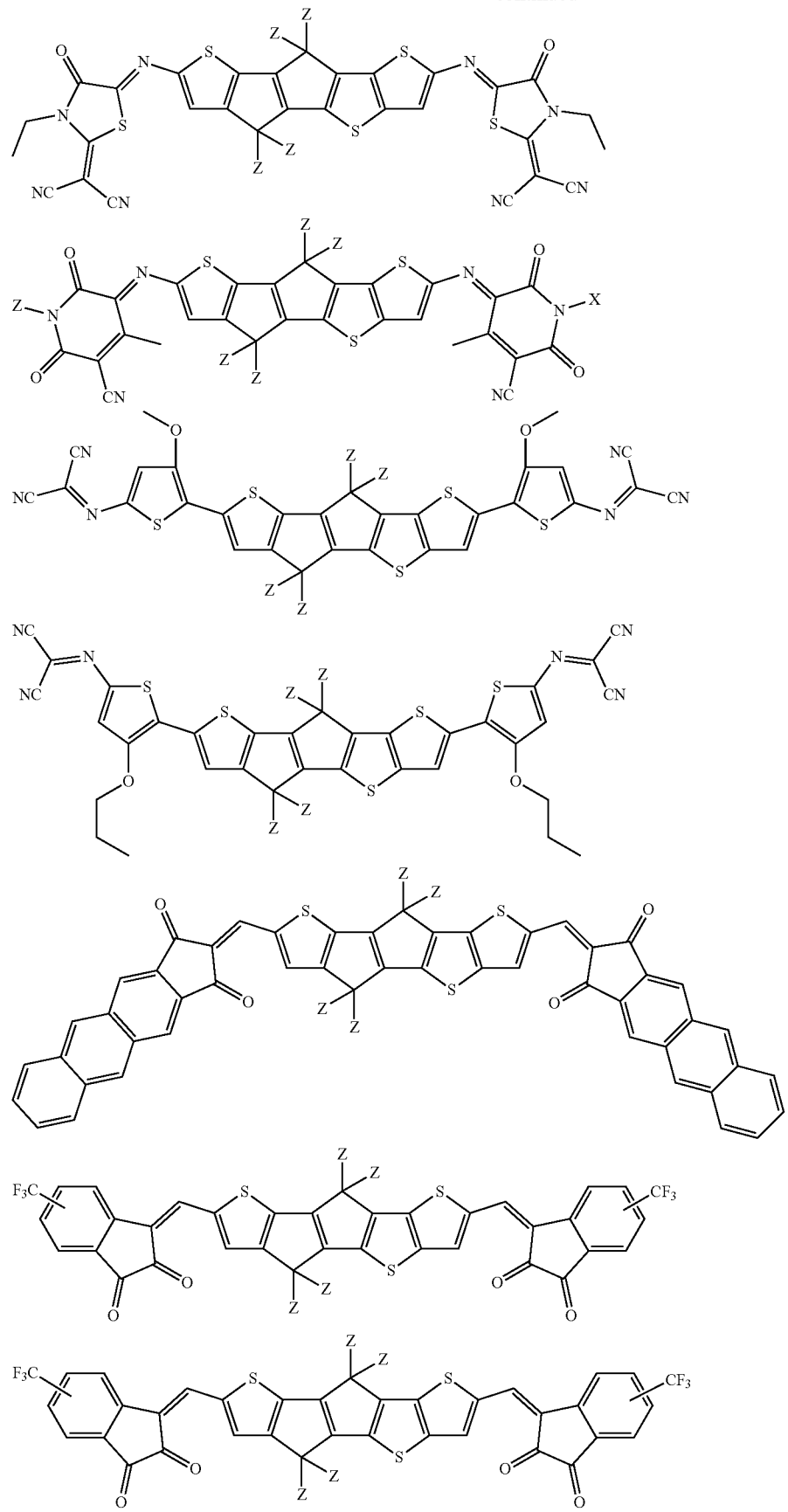

-continued
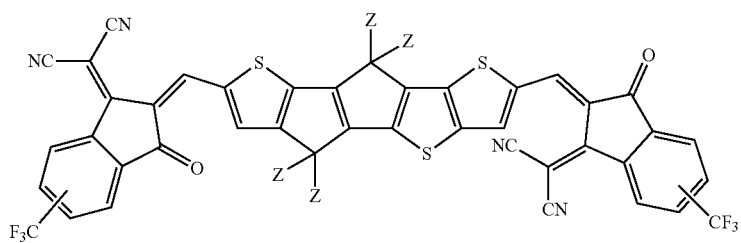
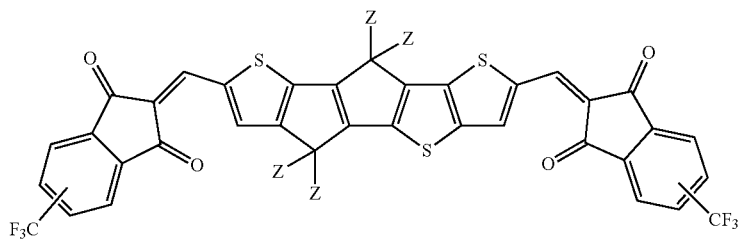
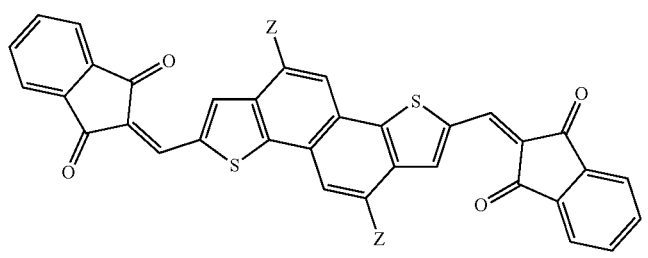
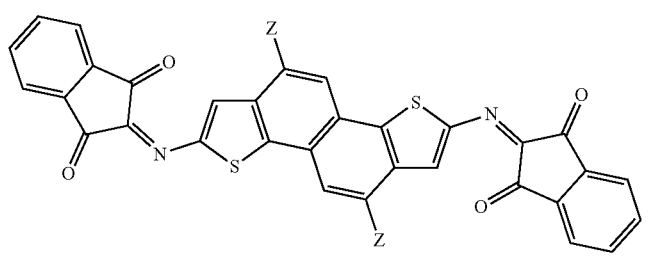
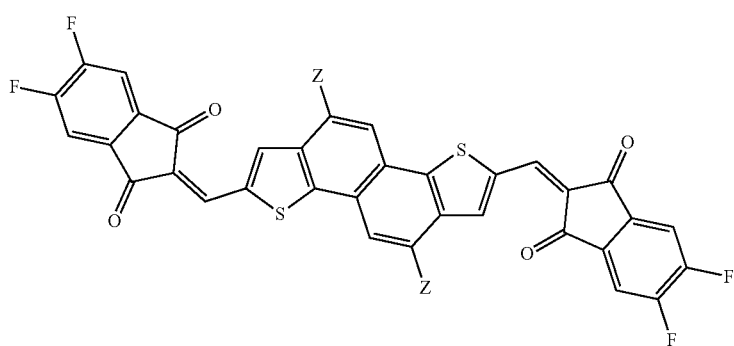
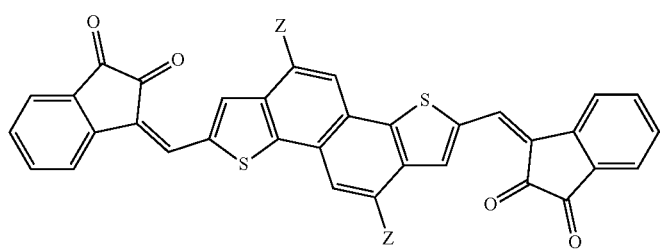

-continued
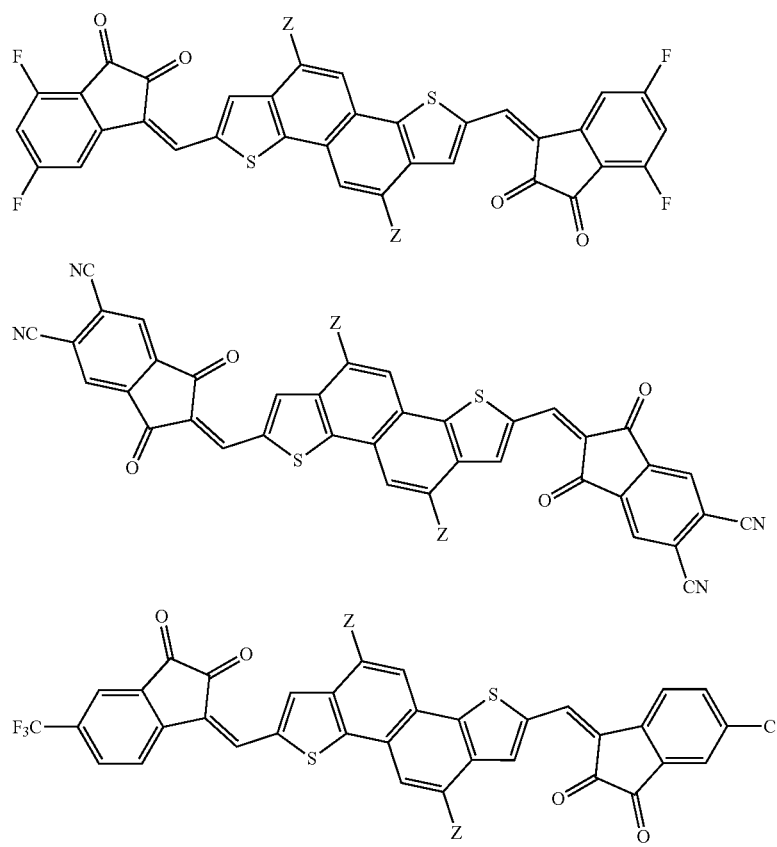
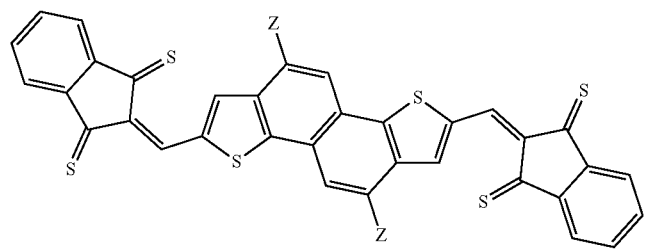
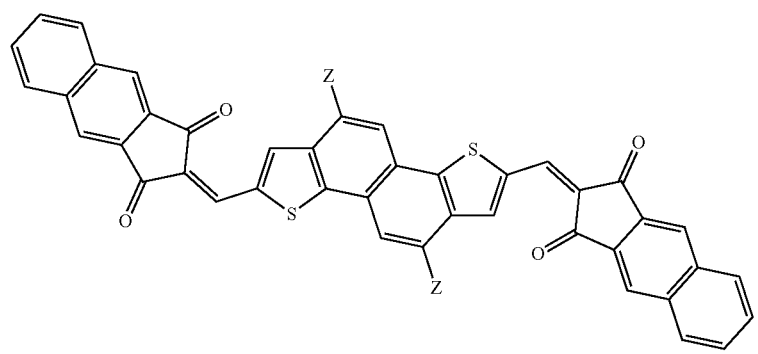

-continued
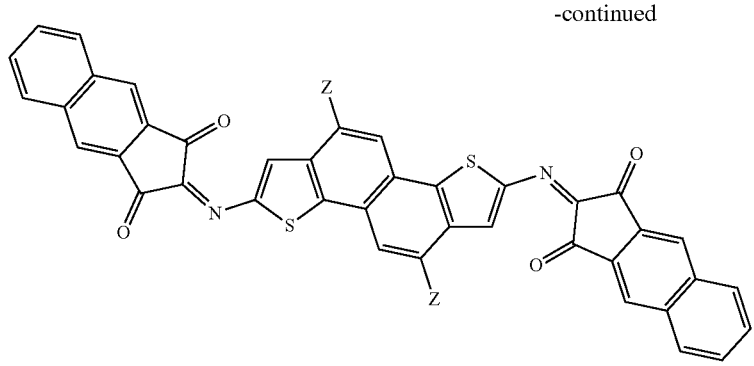
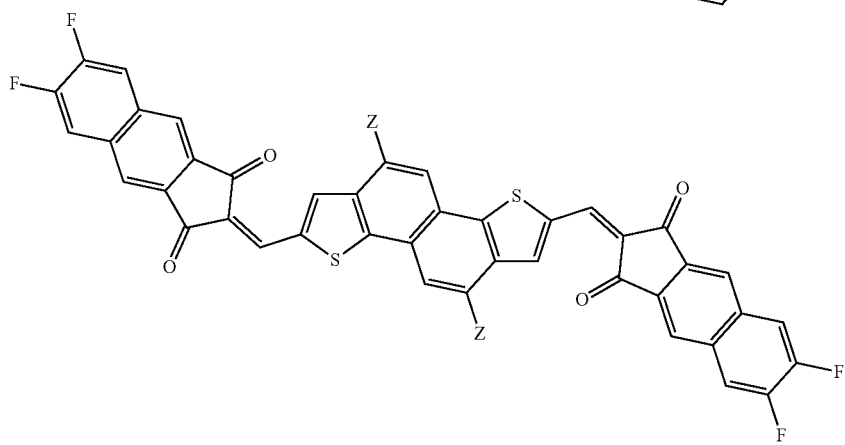
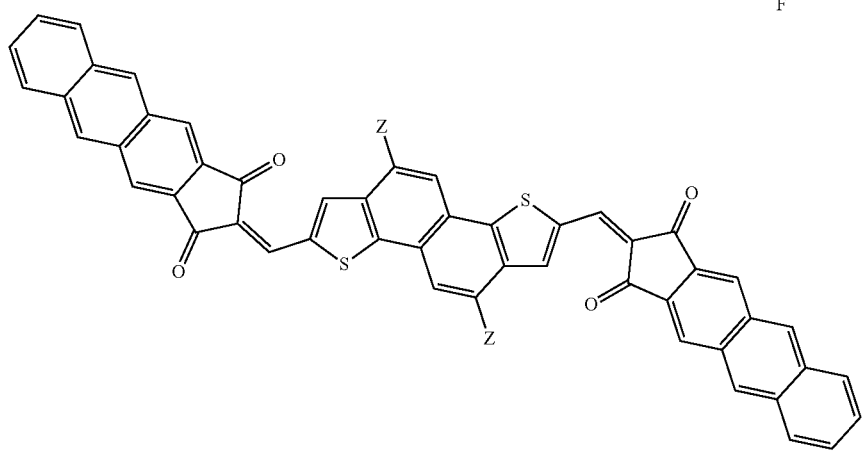
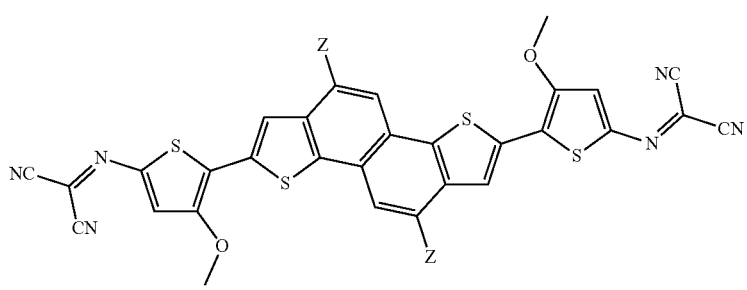
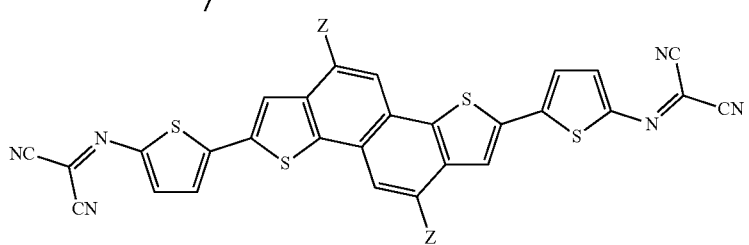

577 578
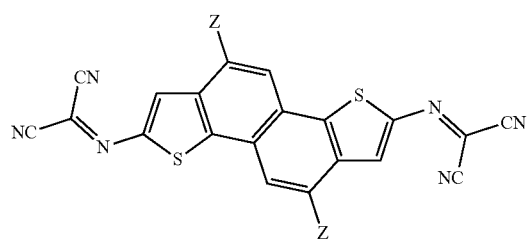
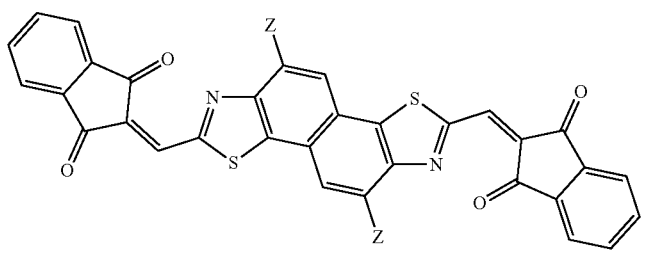
-continued
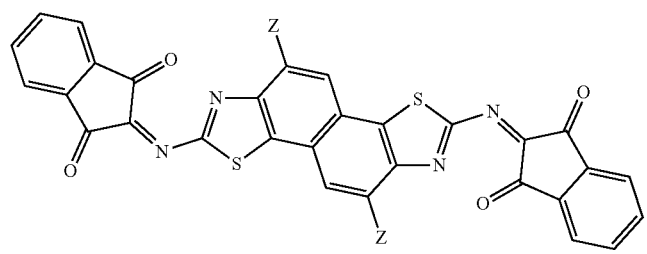
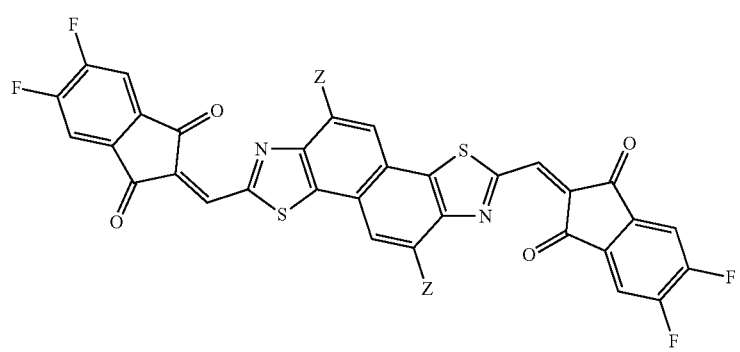
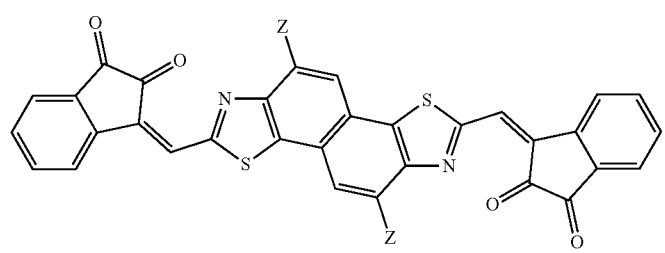
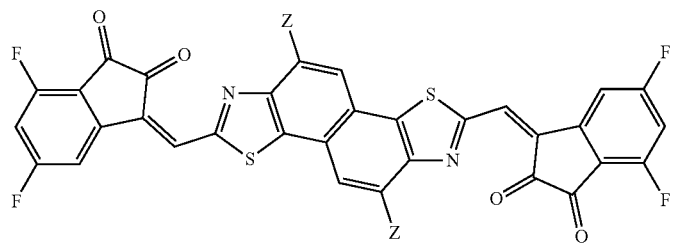
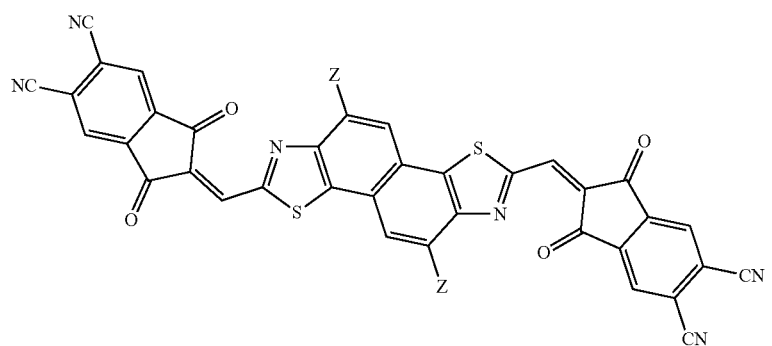

-continued
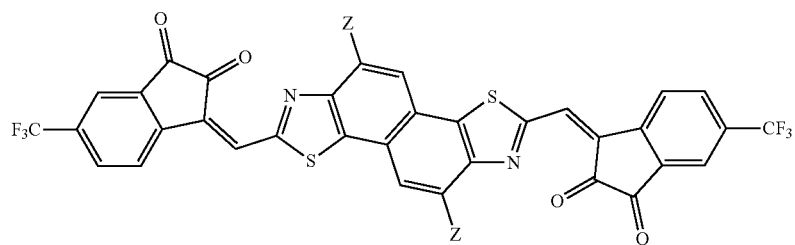
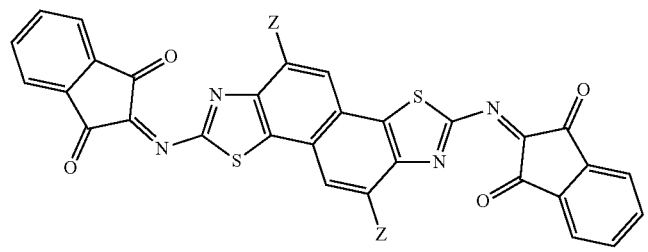
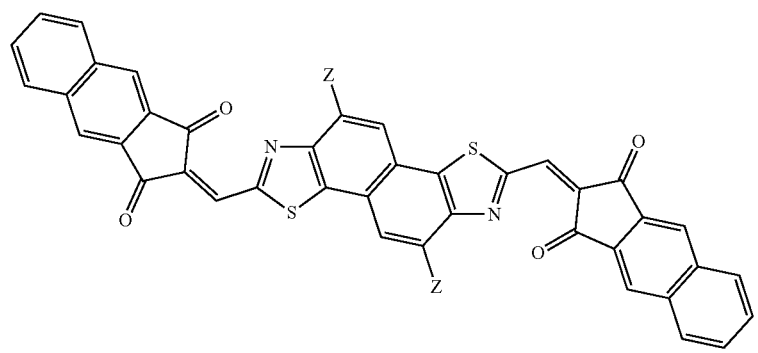
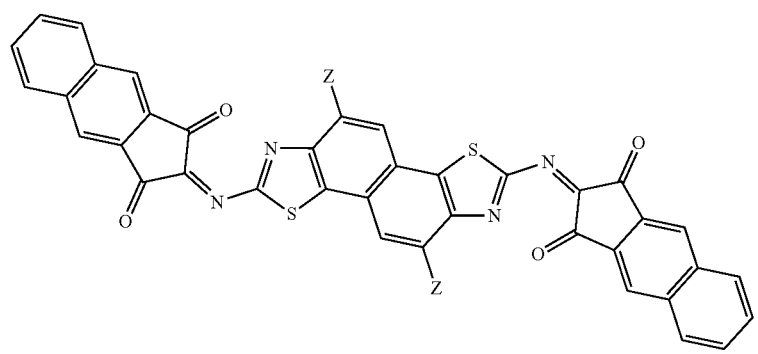
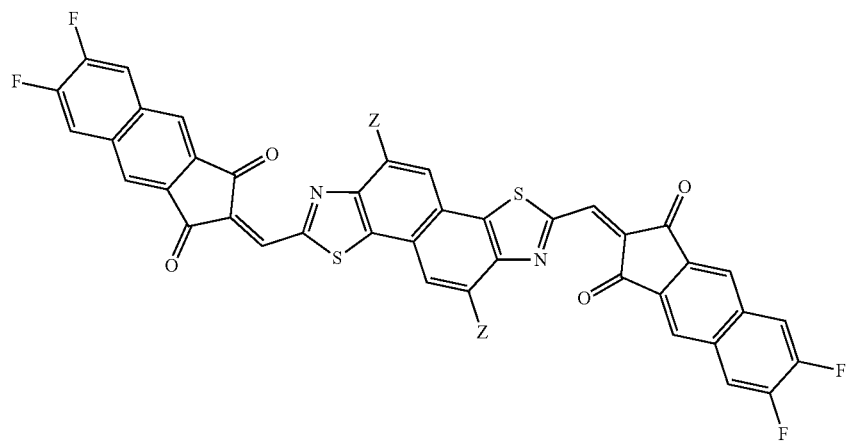

-continued
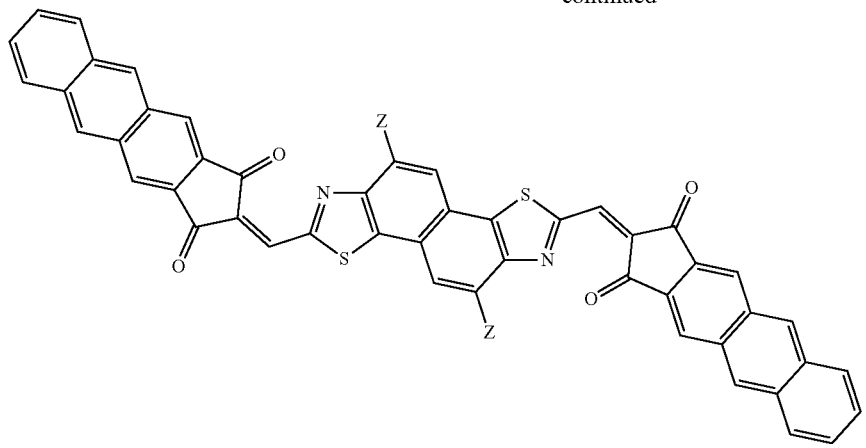
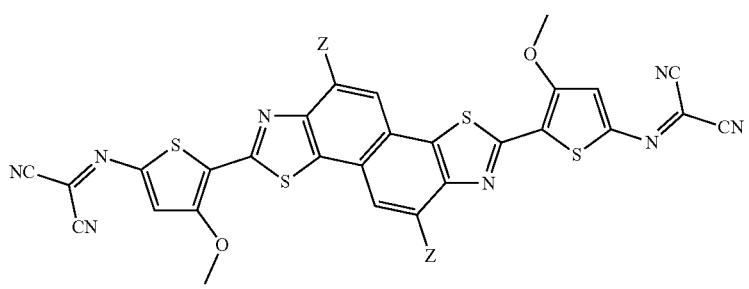
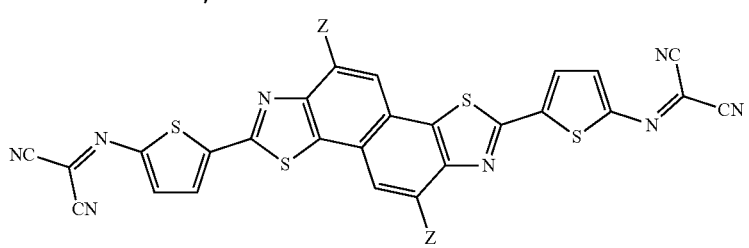
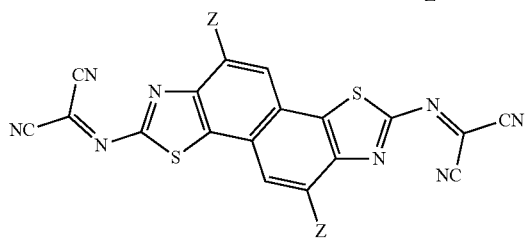
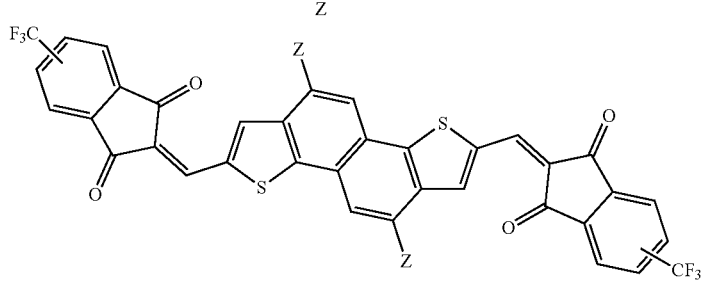
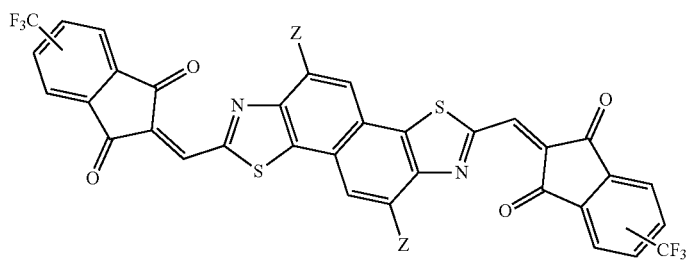

-continued
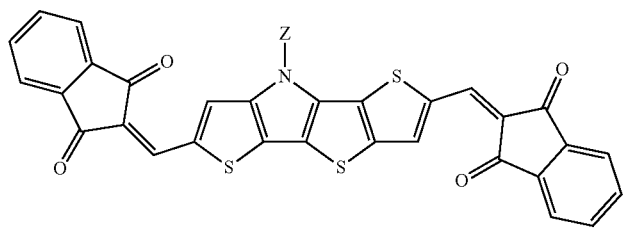
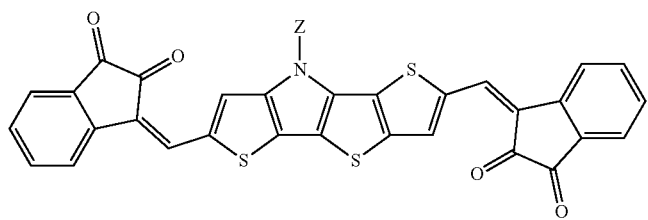
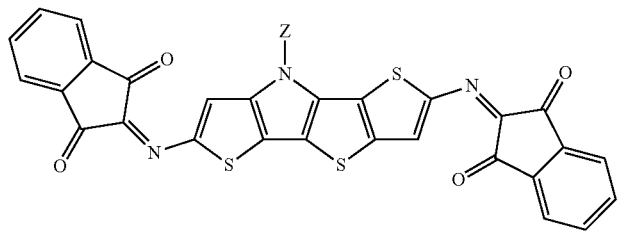
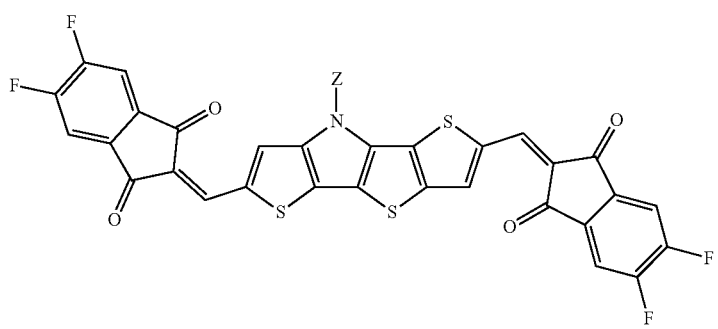
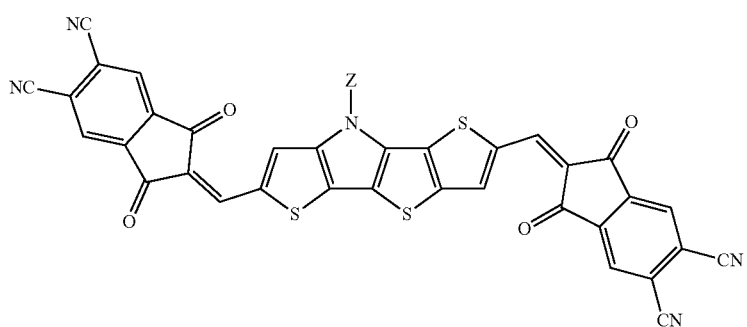
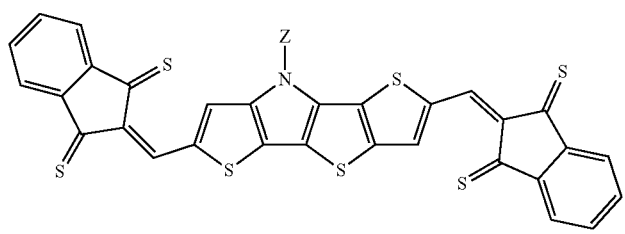

-continued
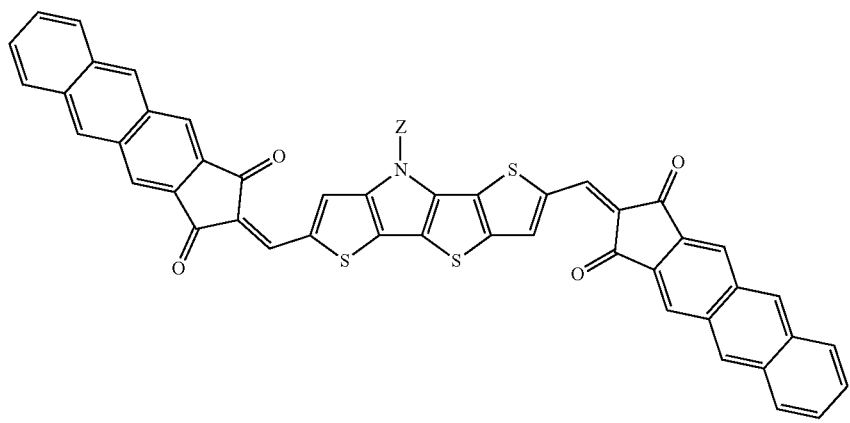
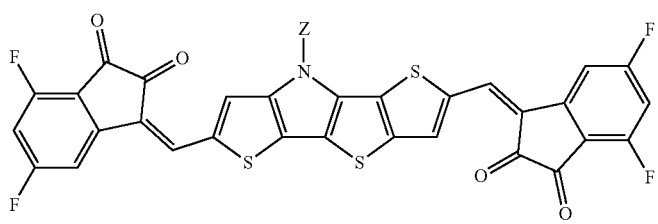
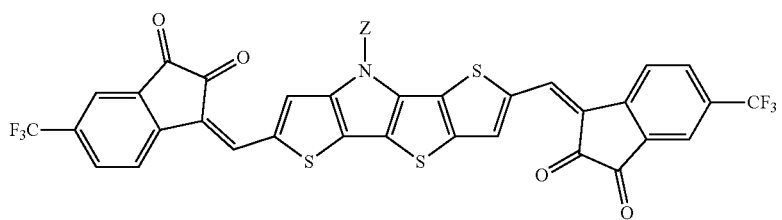
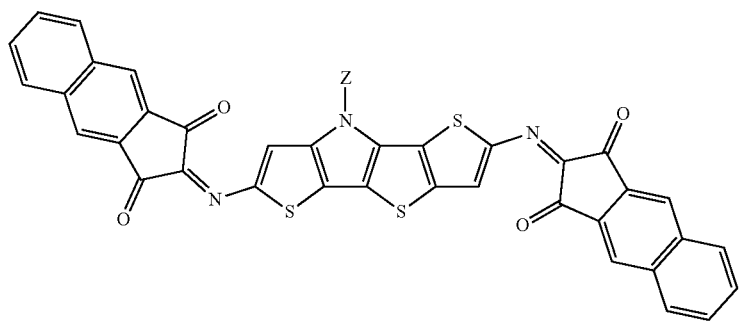
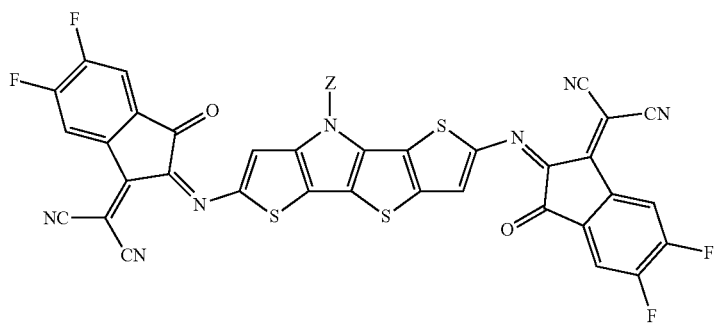
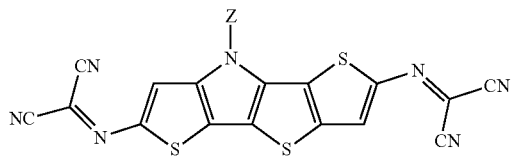

-continued
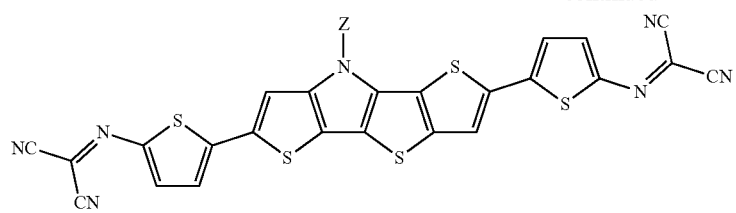
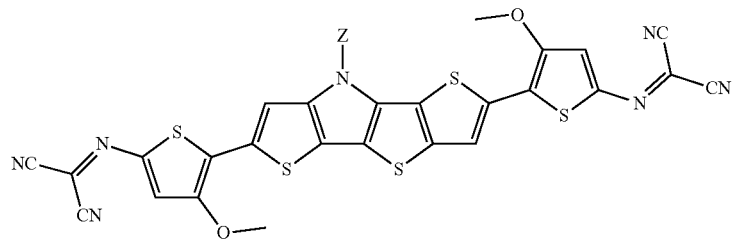
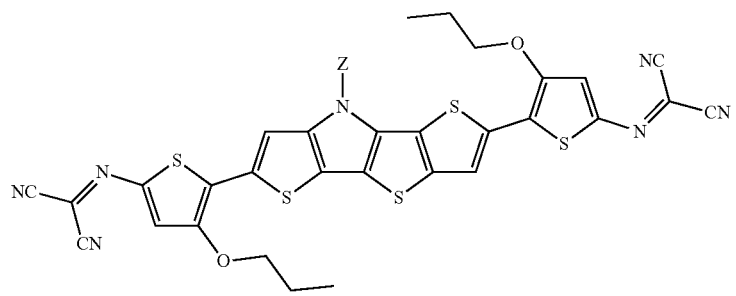
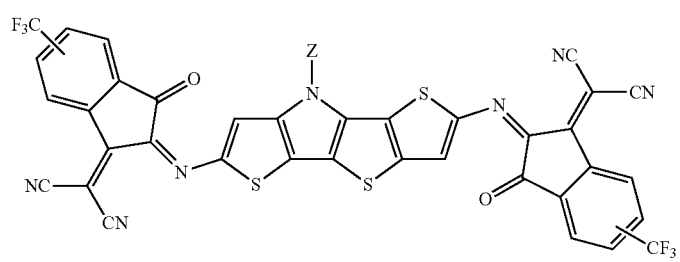
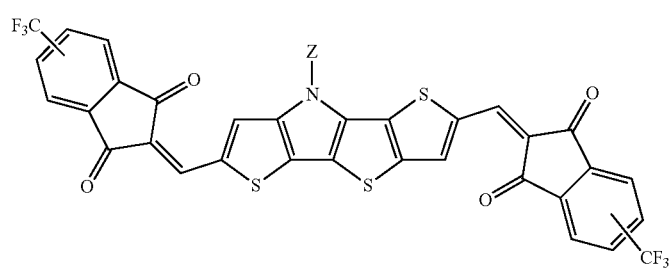
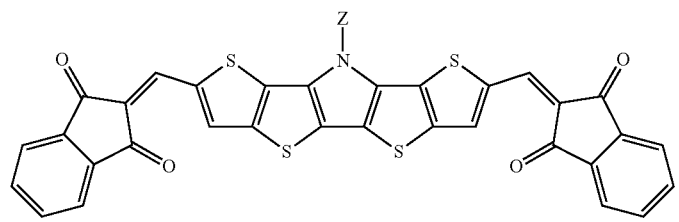
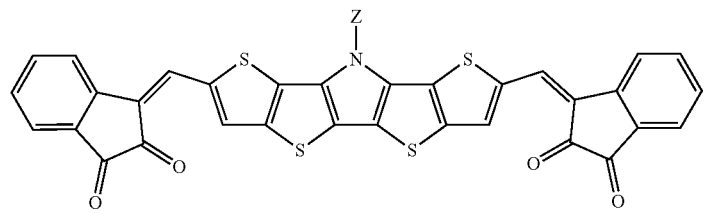

-continued
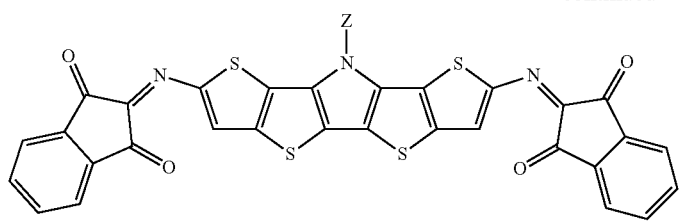
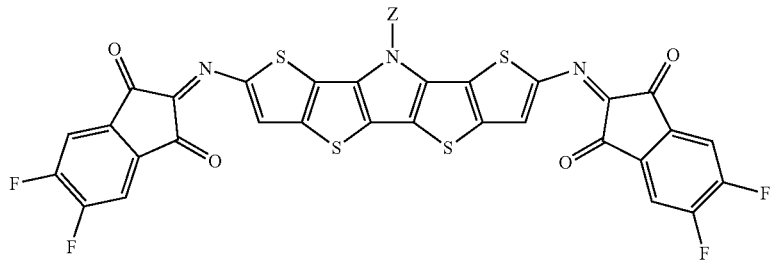
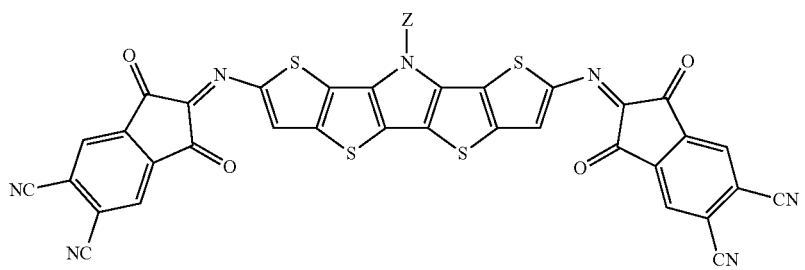
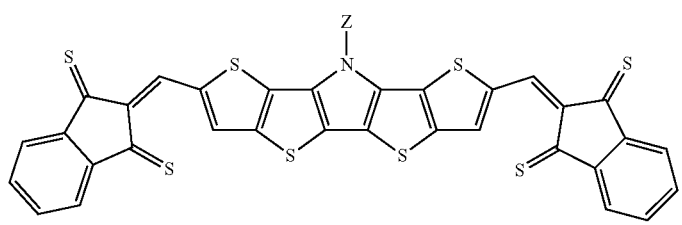
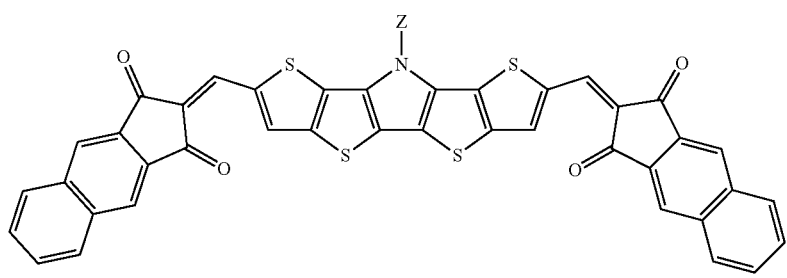
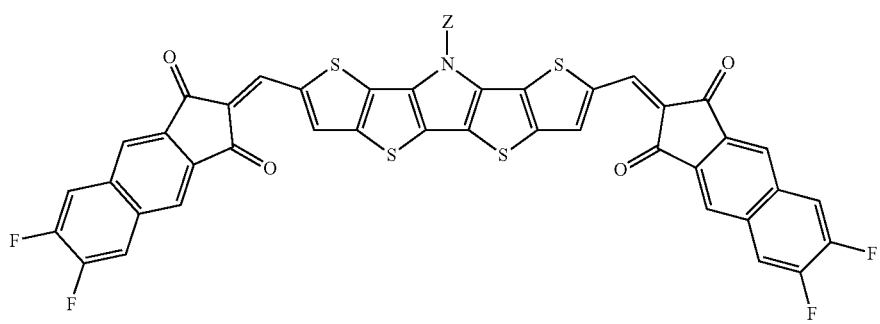

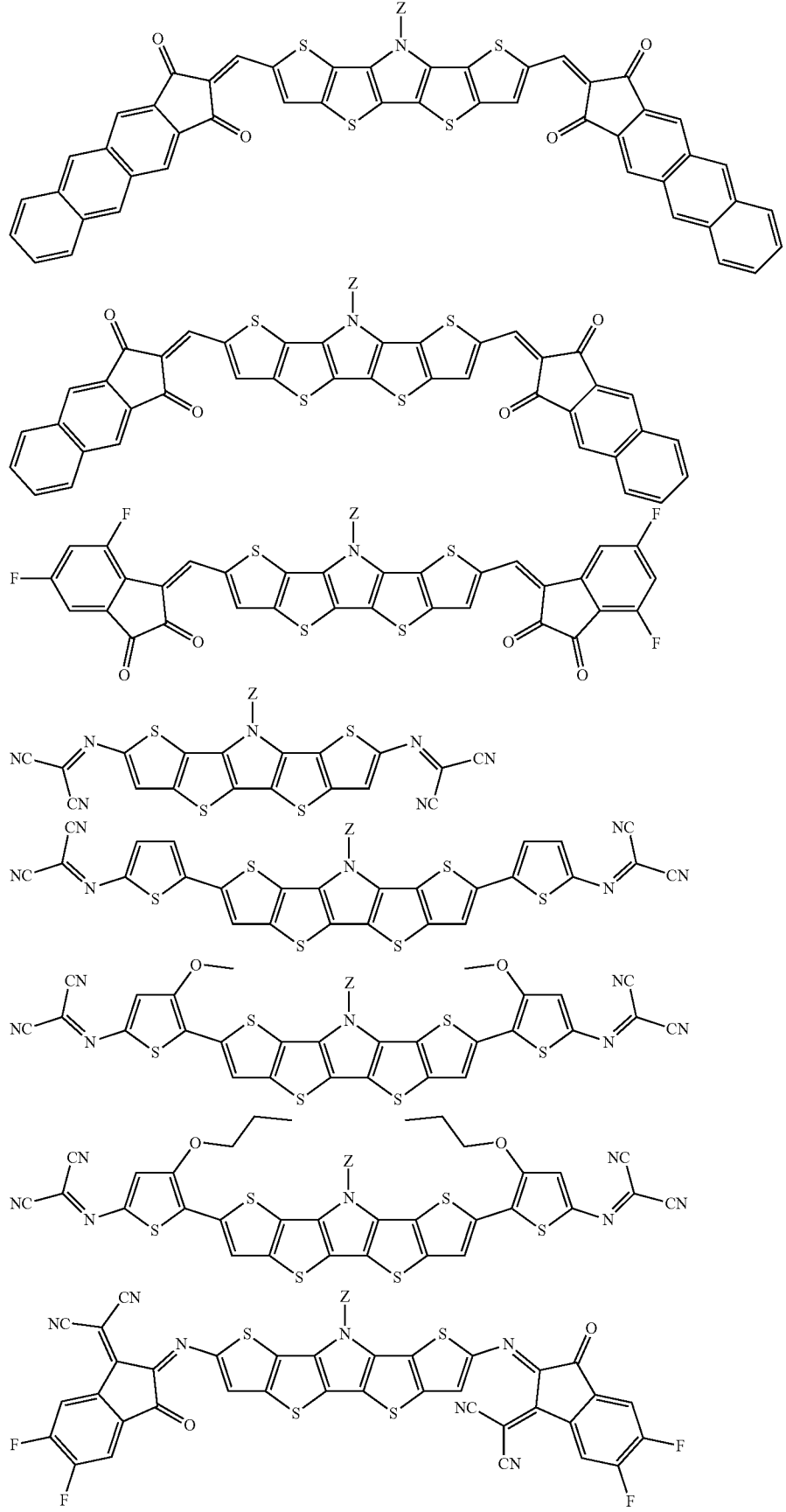

-continued
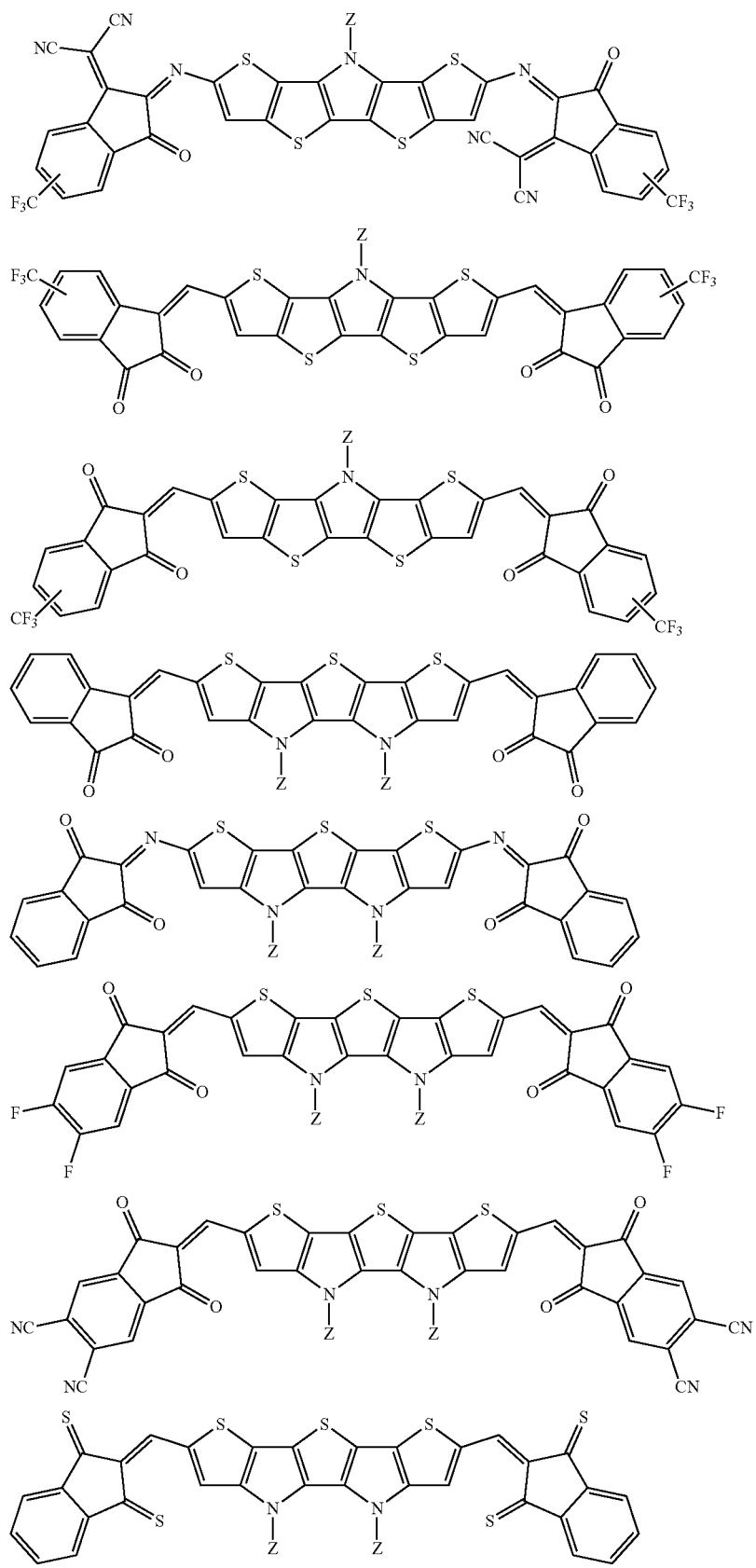

-continued
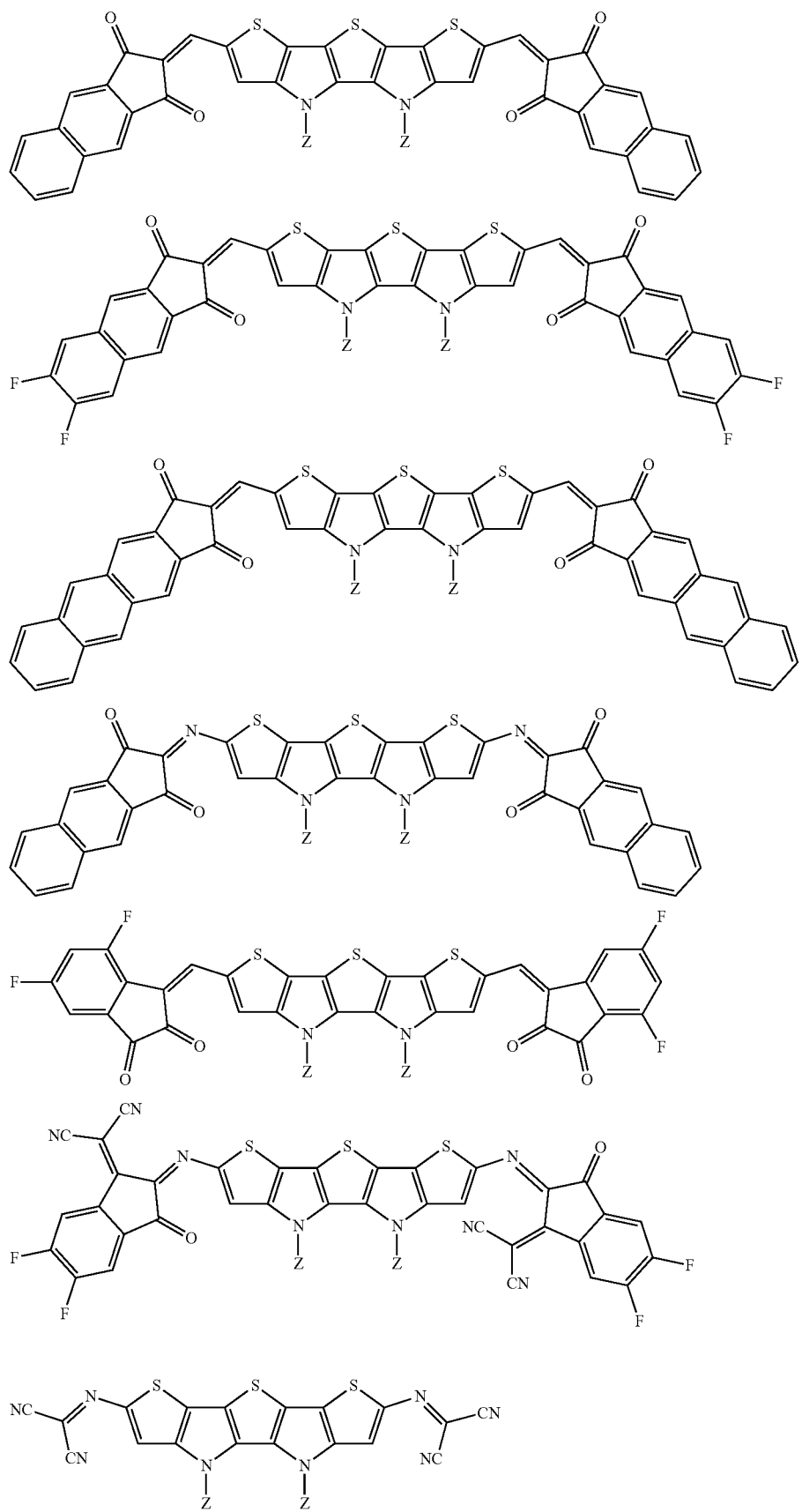

-continued
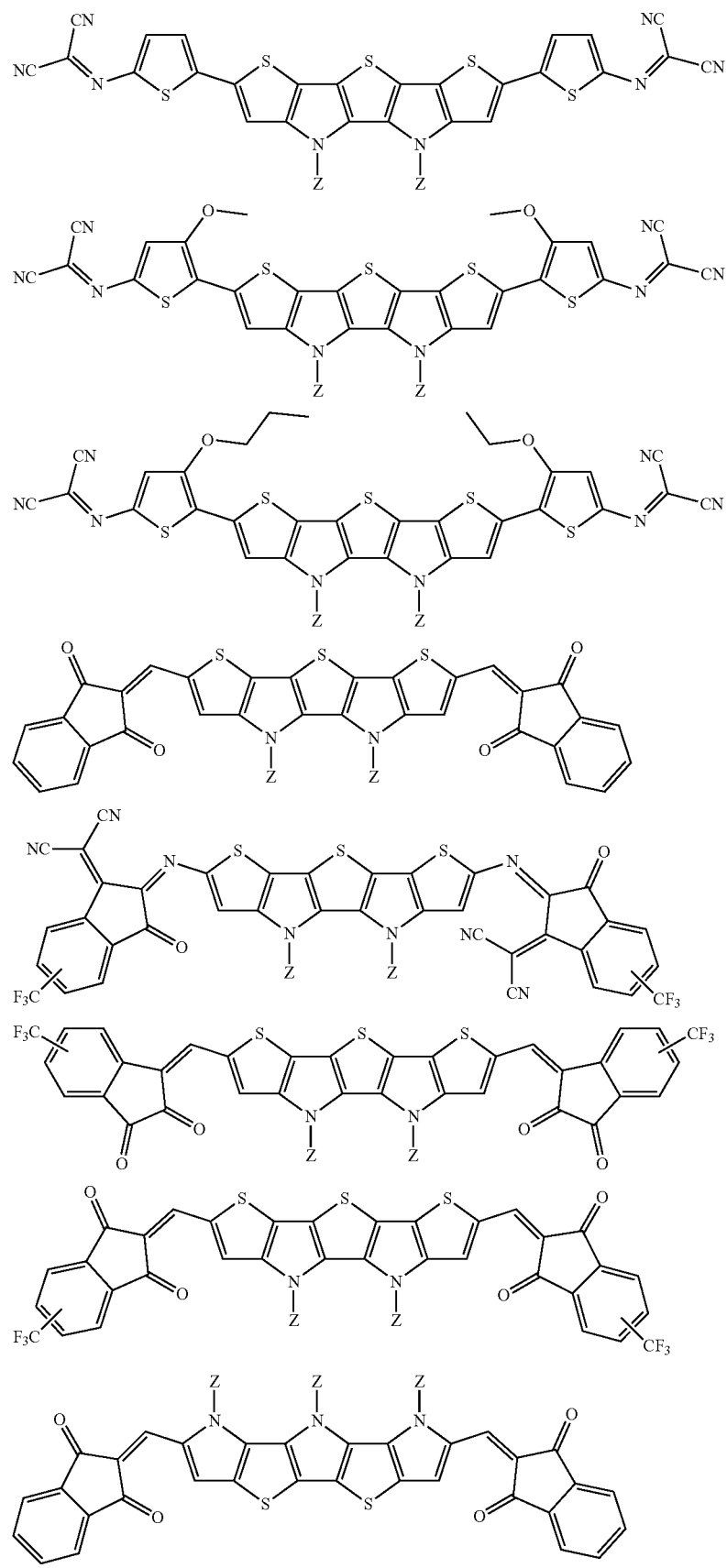

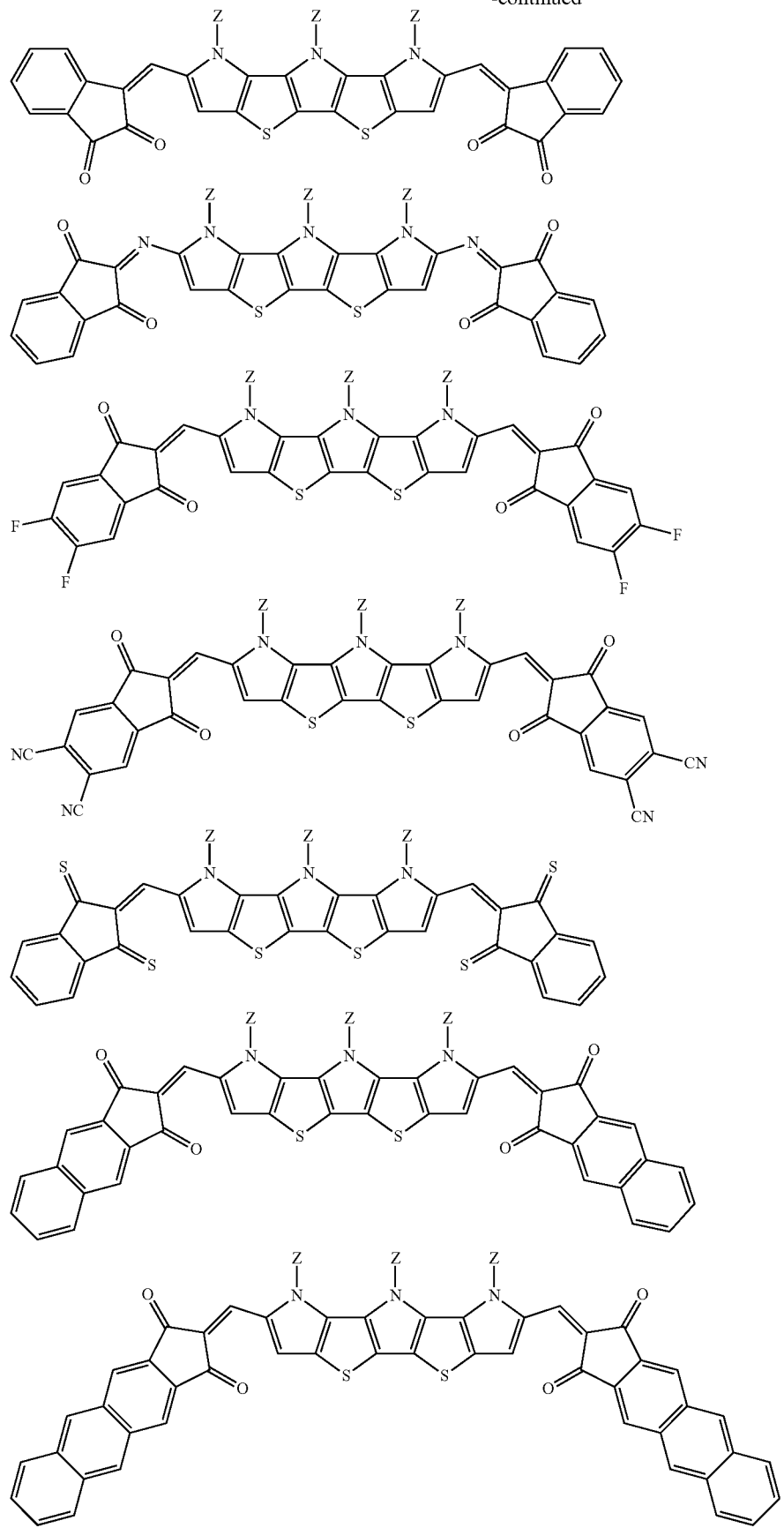

-continued
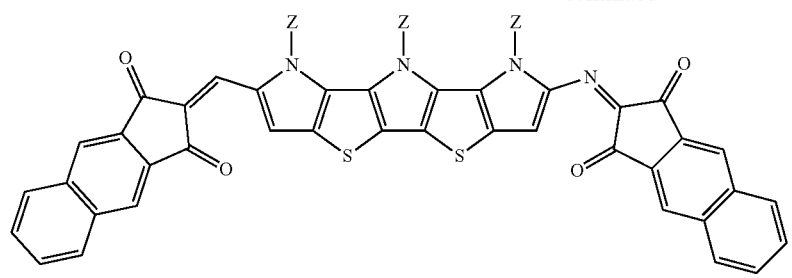
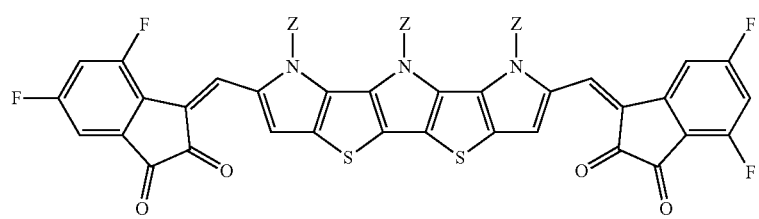
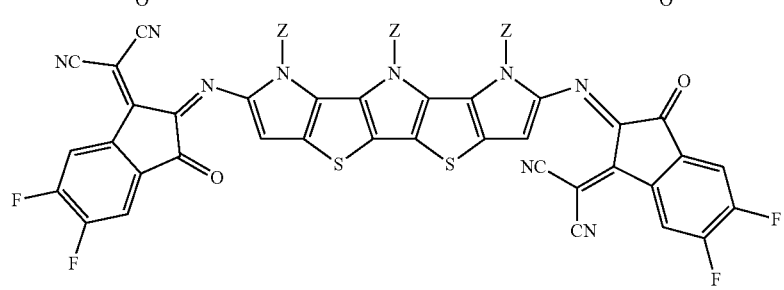
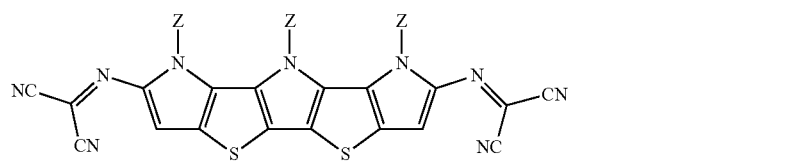
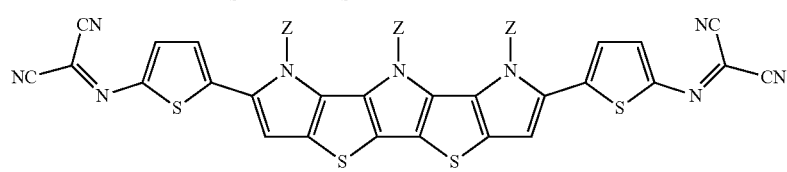
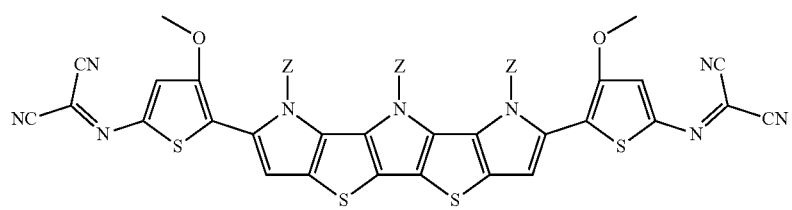
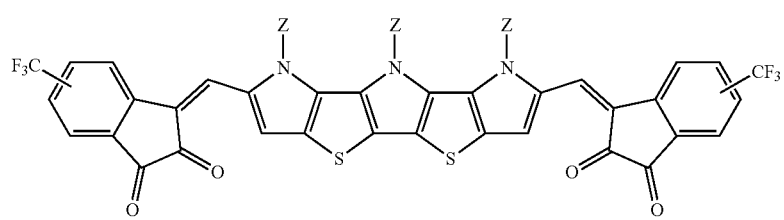

-continued
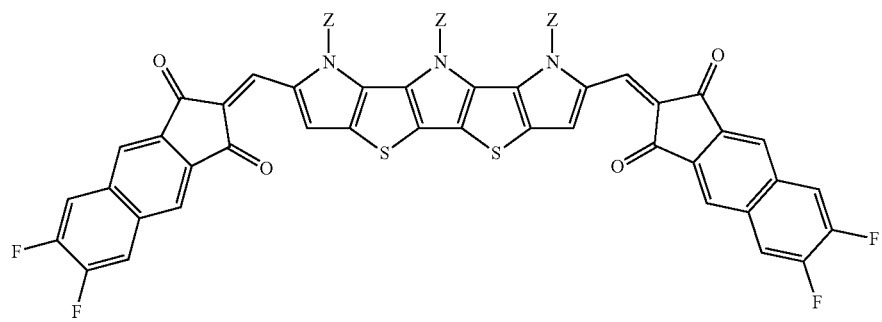
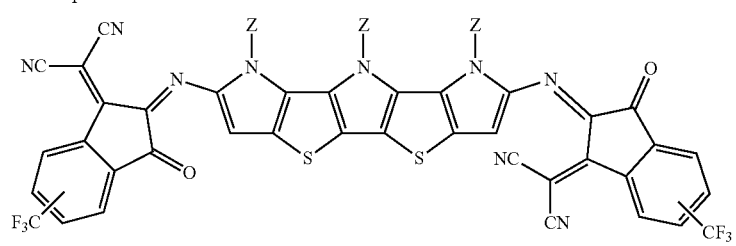
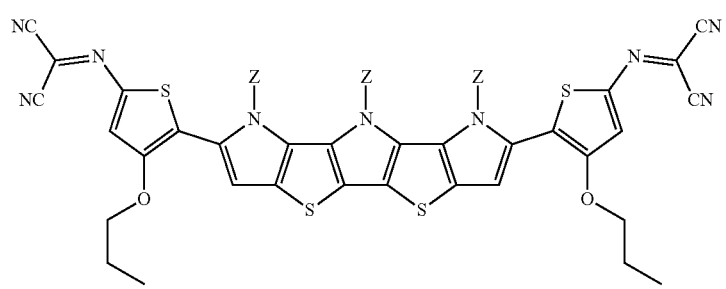
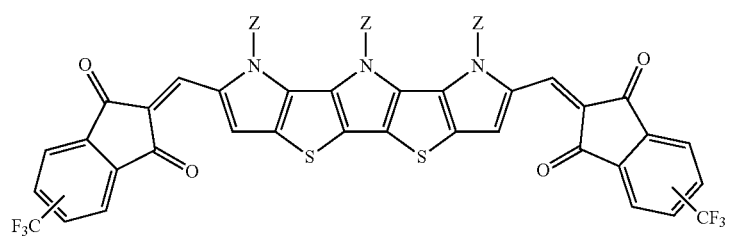
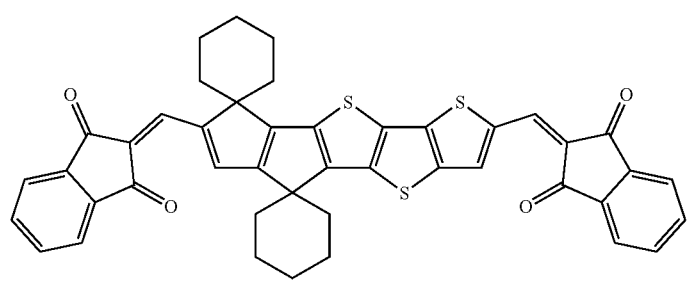
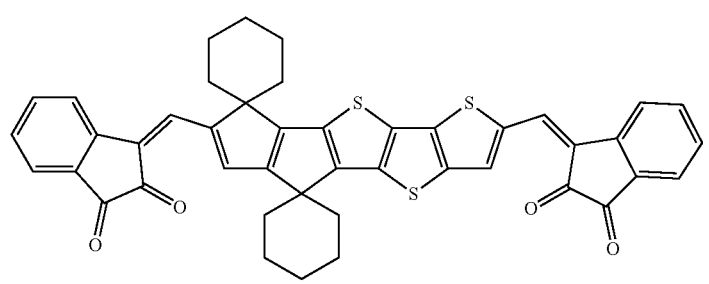

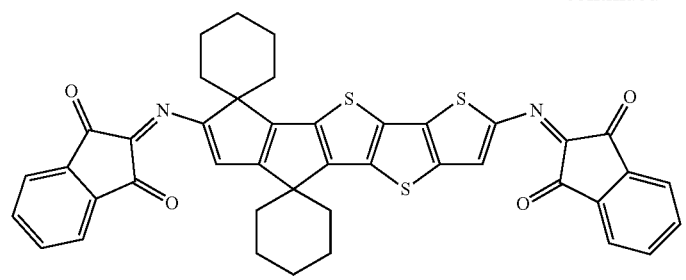
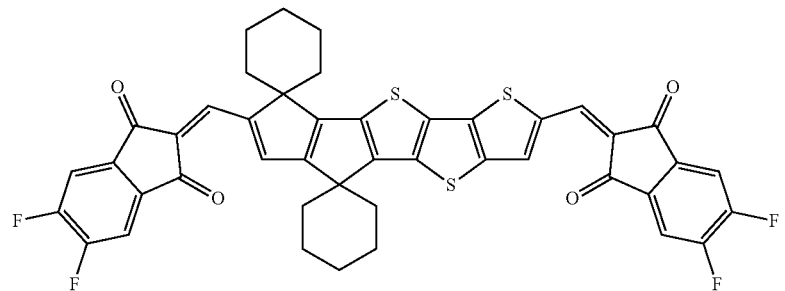
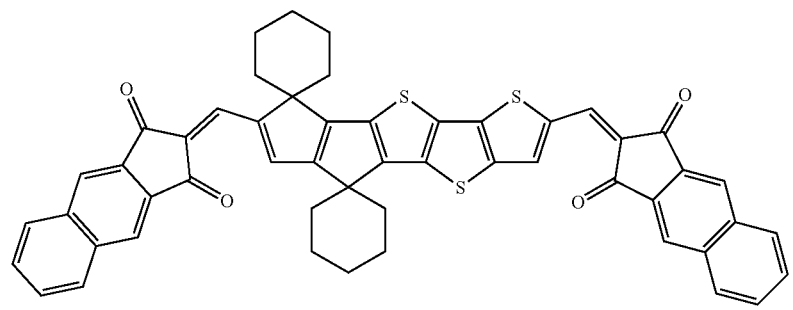
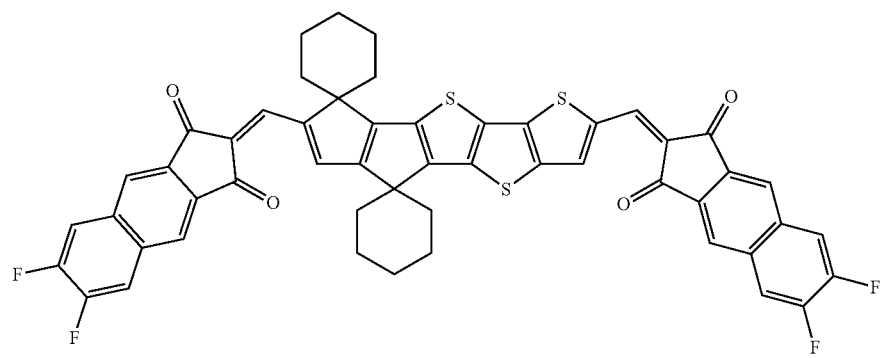
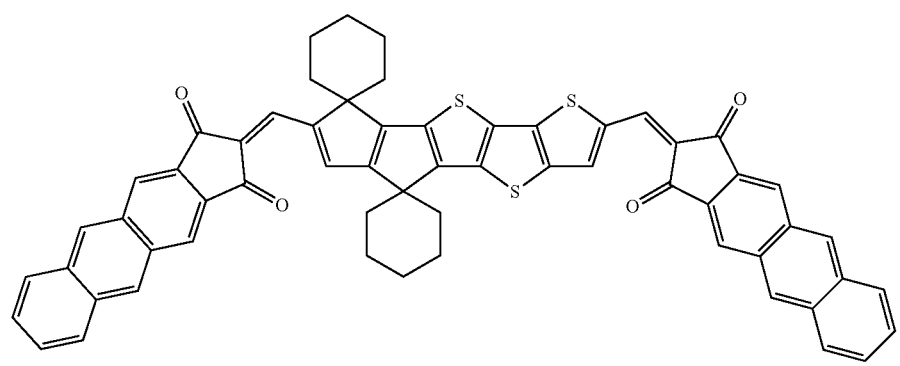

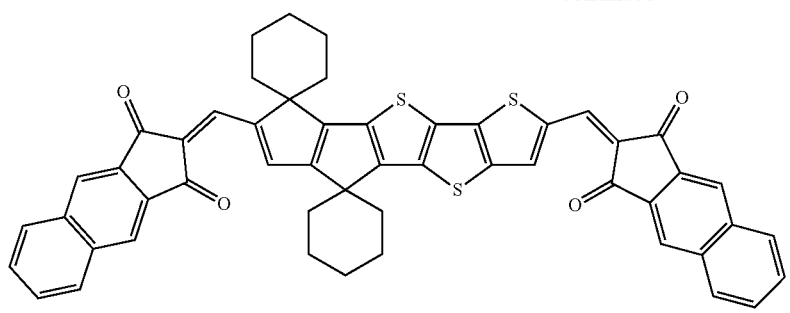
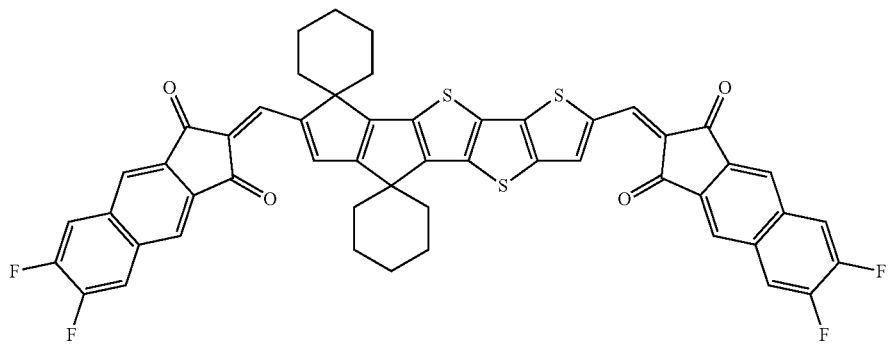
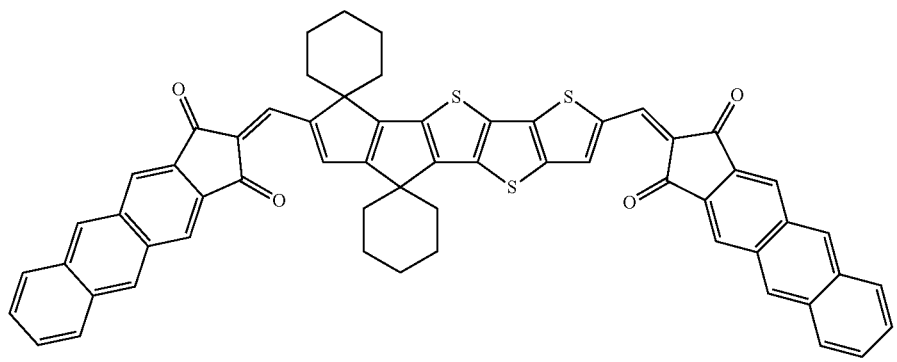
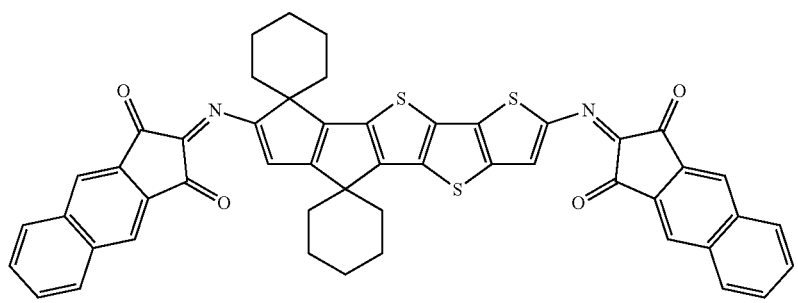
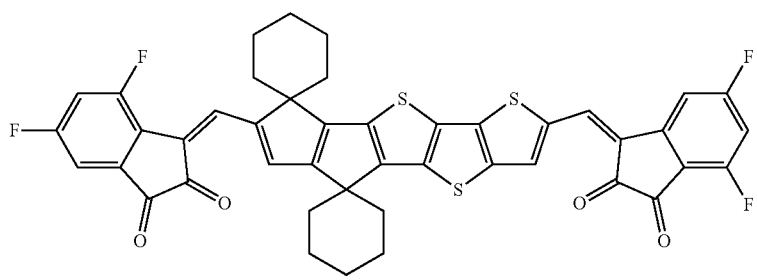

-continued
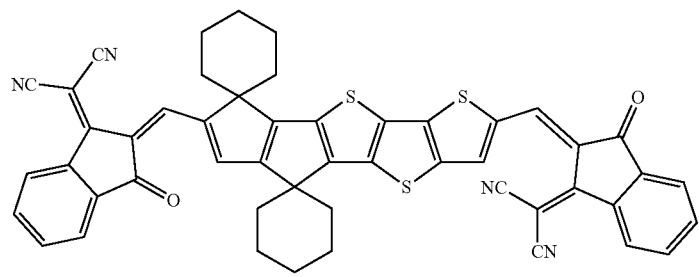
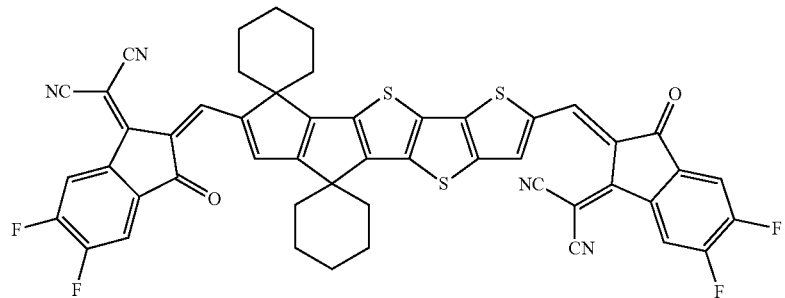
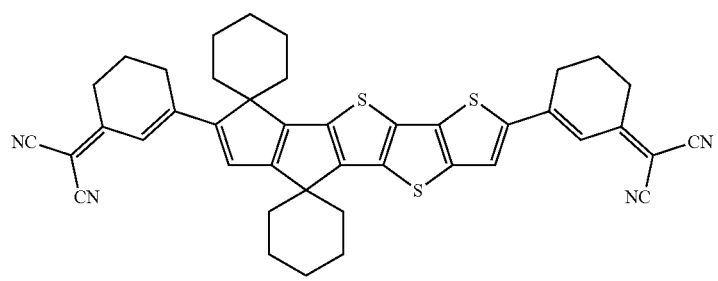
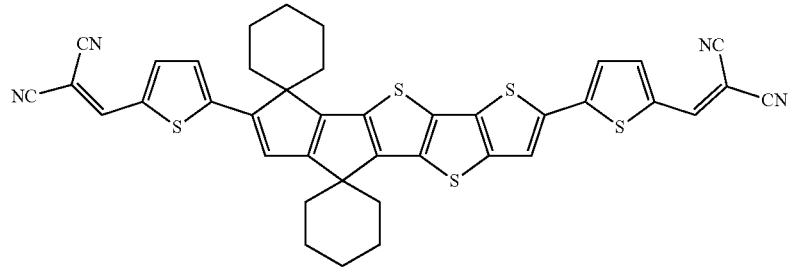
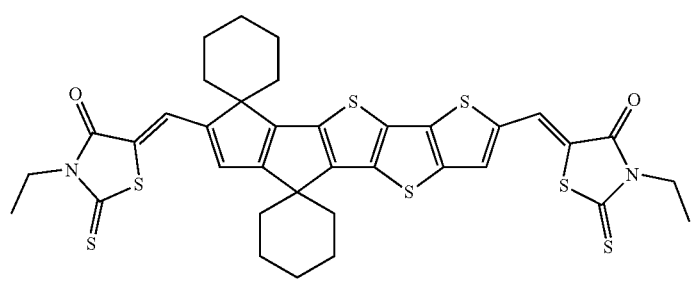
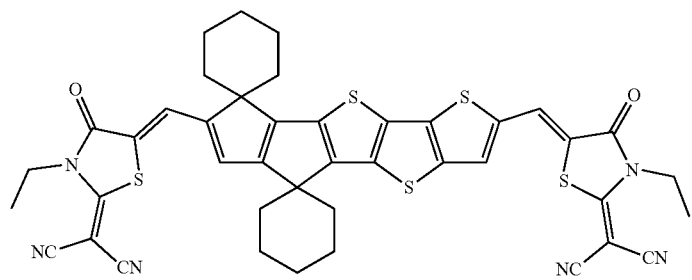

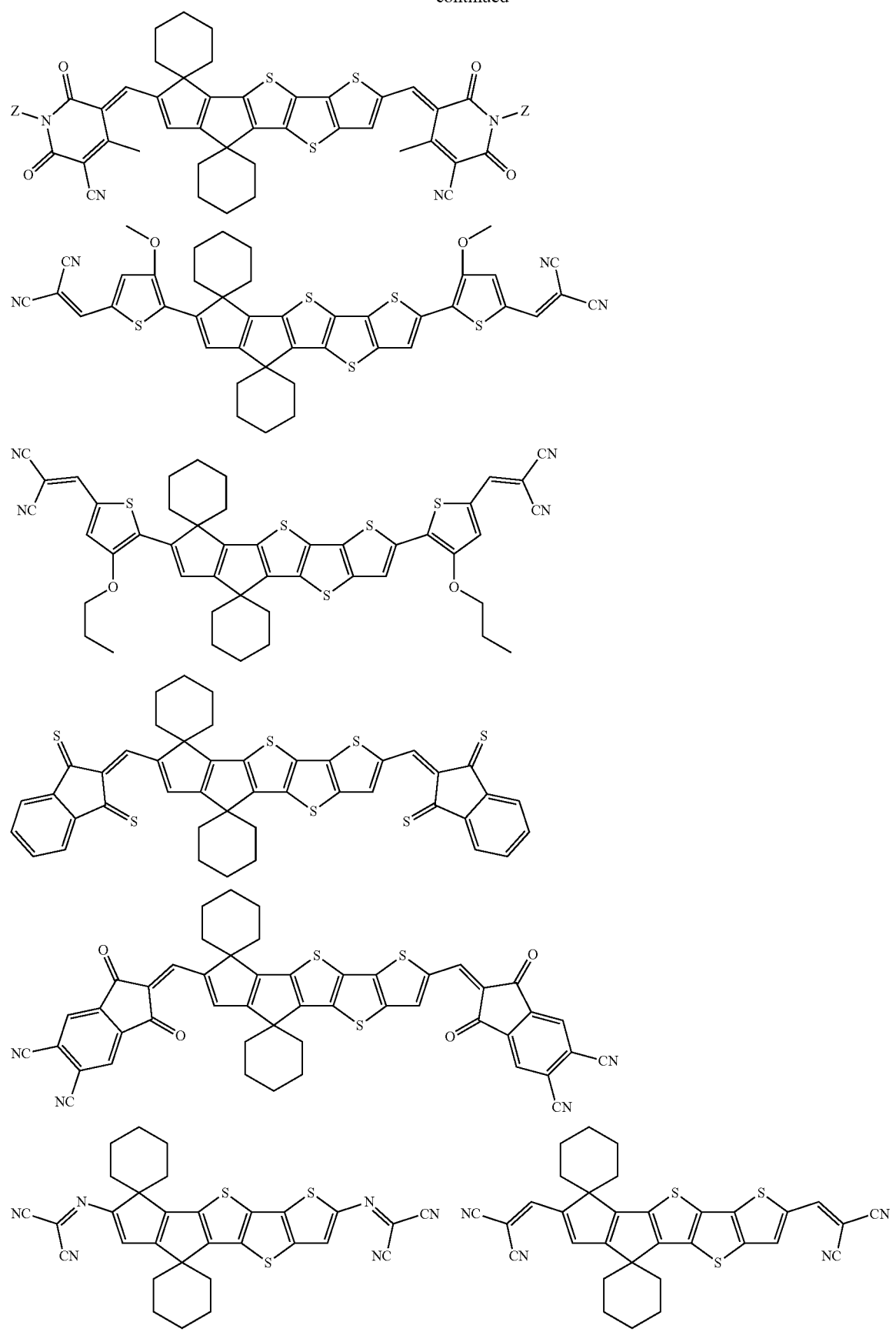

-continued
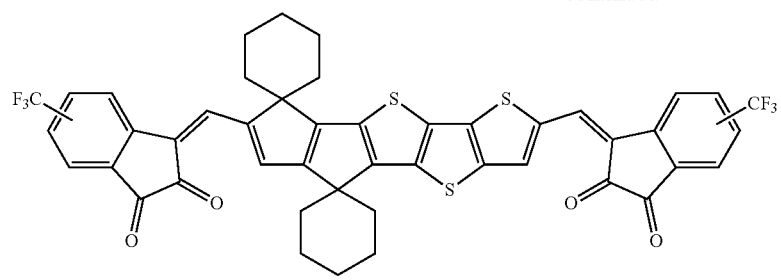
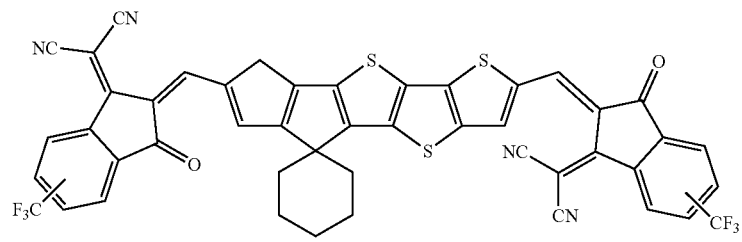
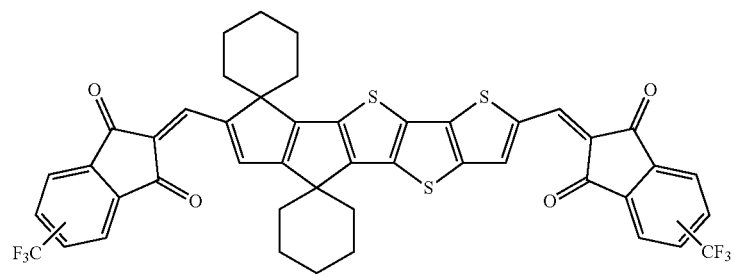
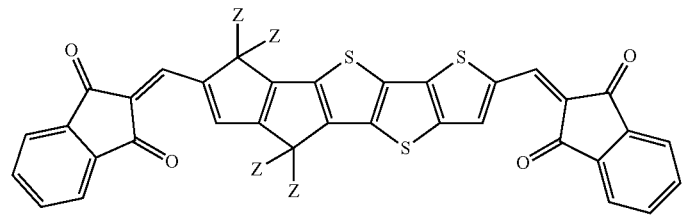
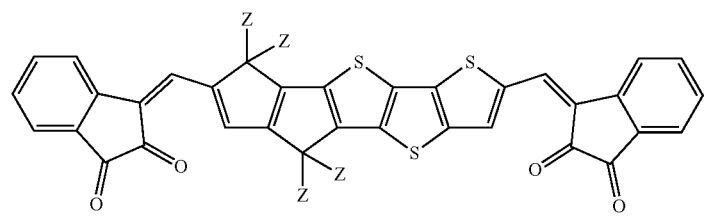
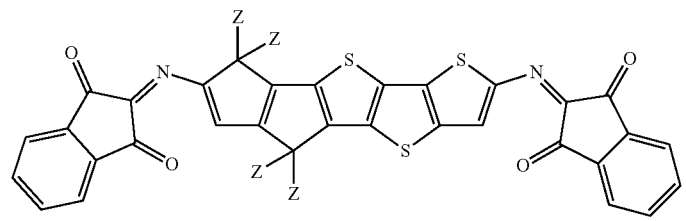
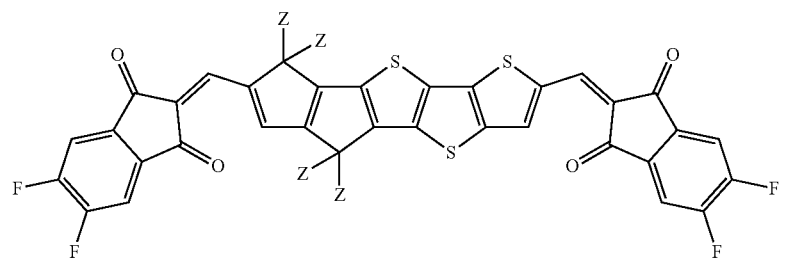

-continued
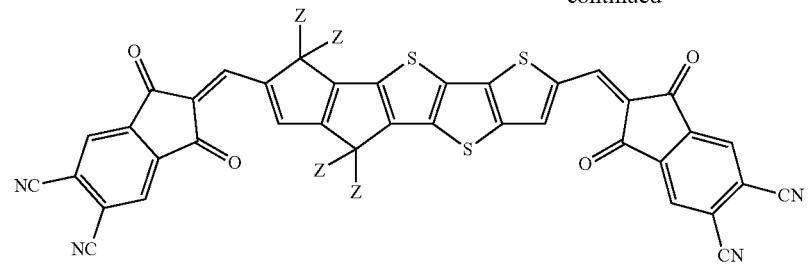
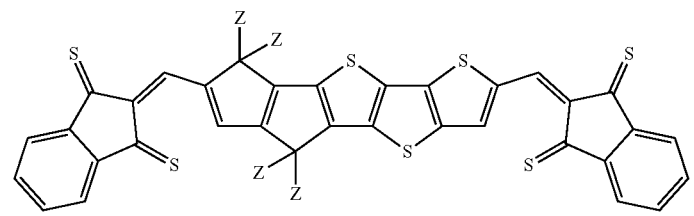
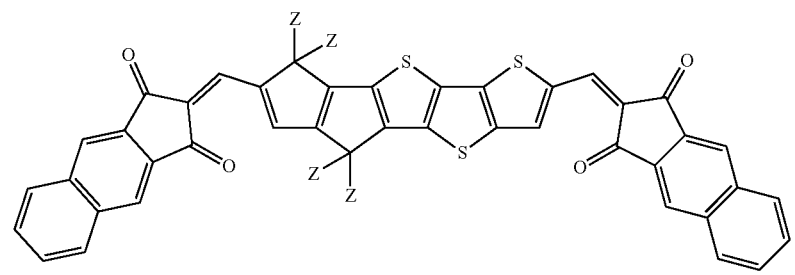
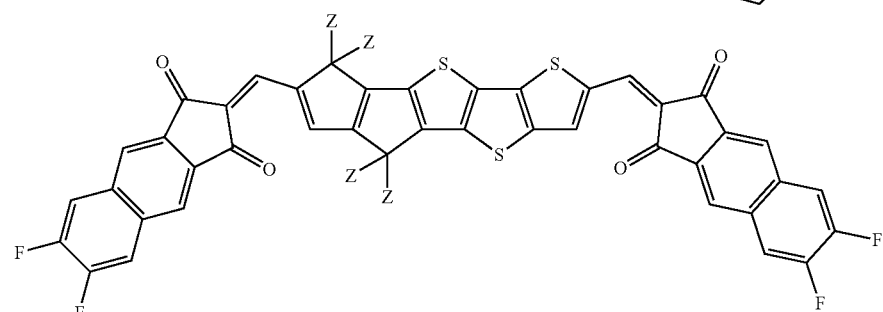
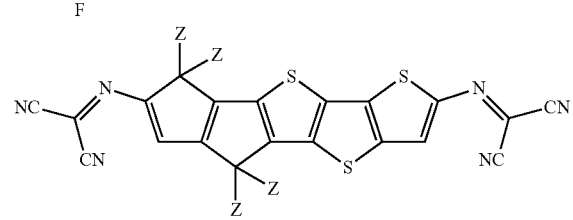
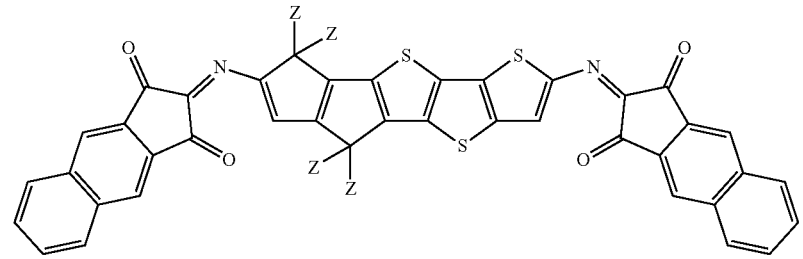
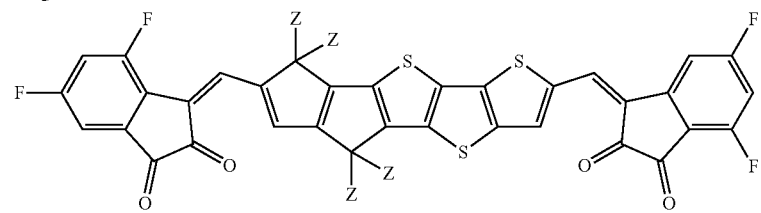

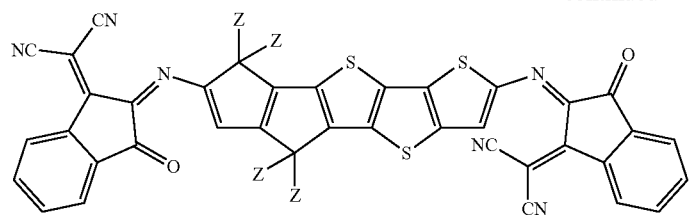
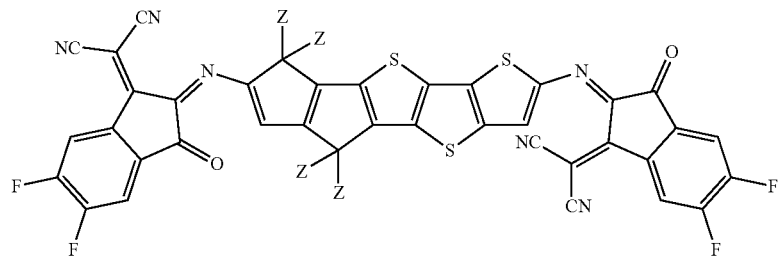
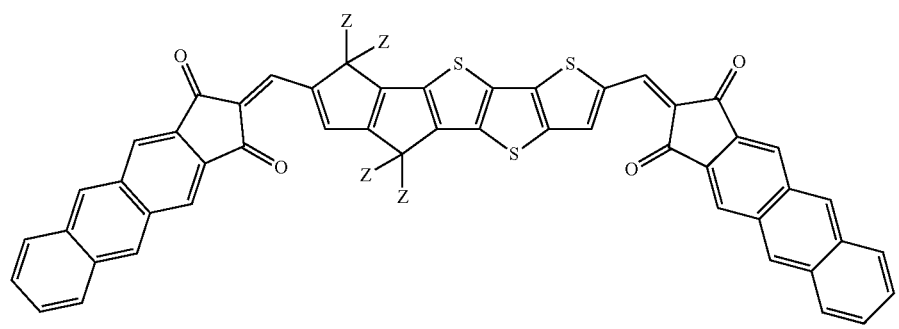
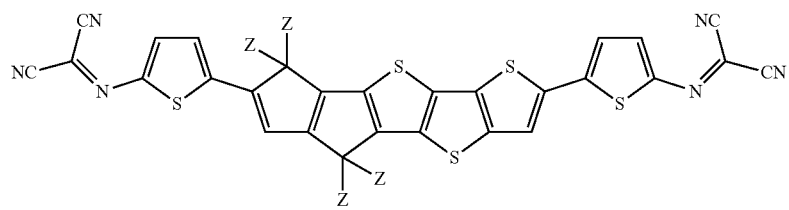
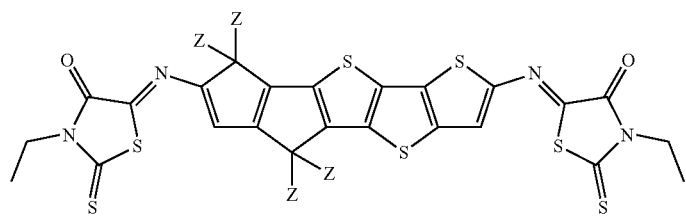
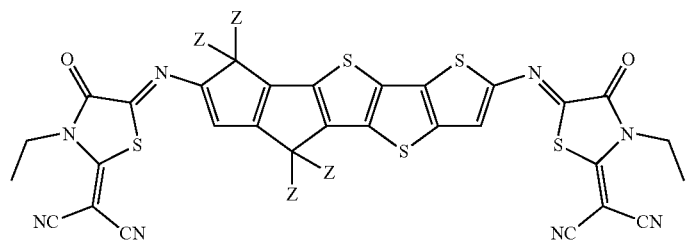
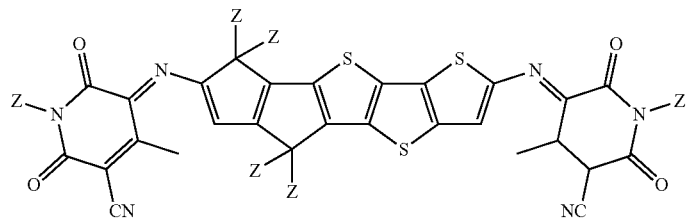

-continued
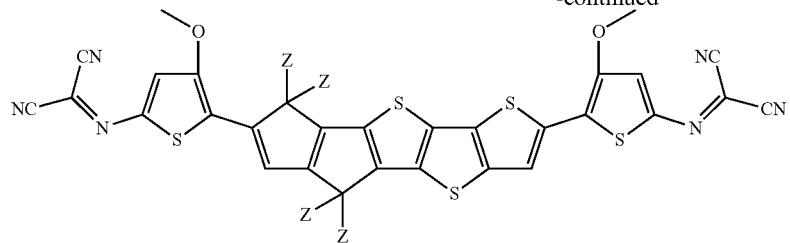
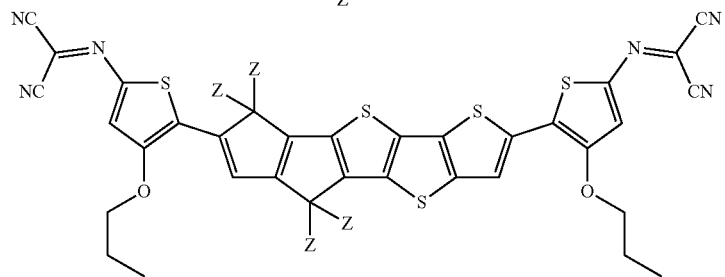
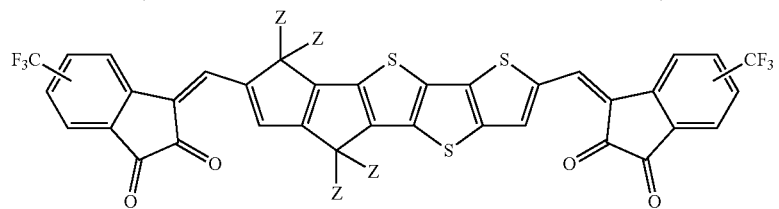
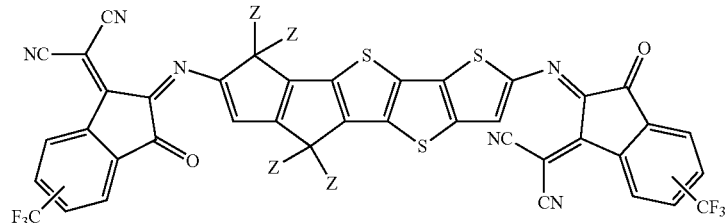
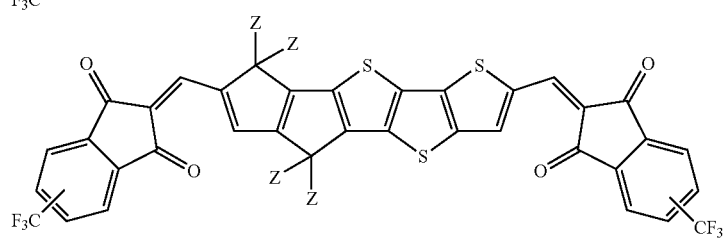
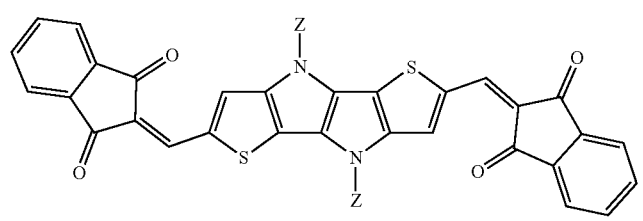
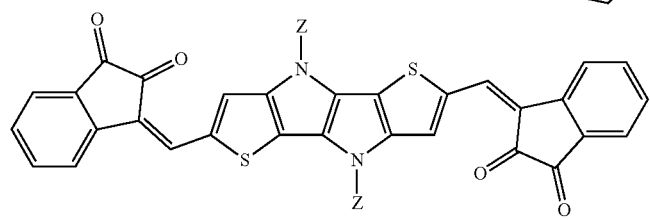

621
-continued
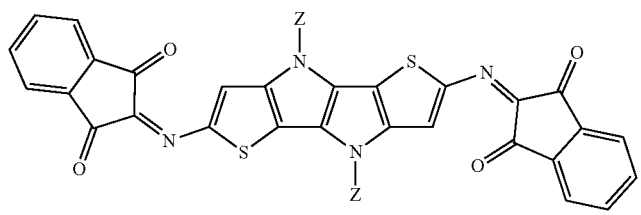
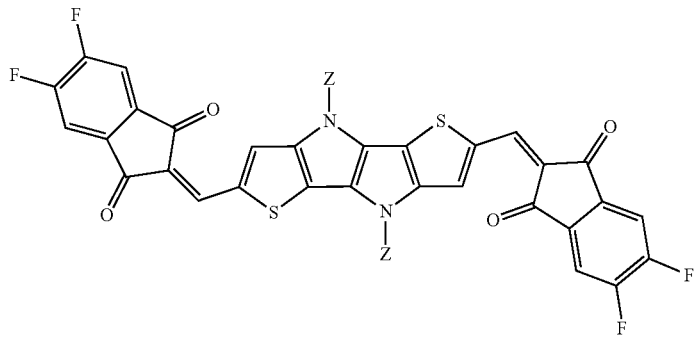
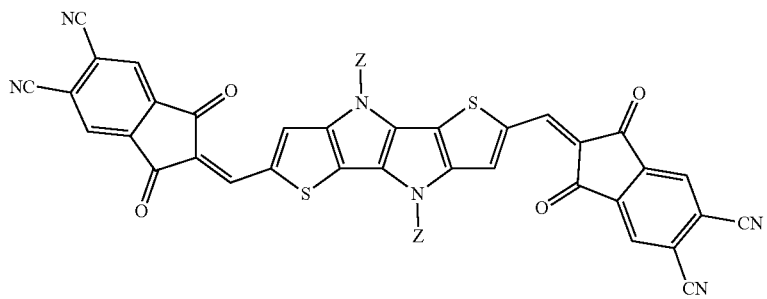
622
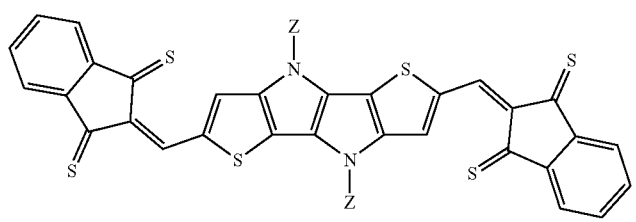
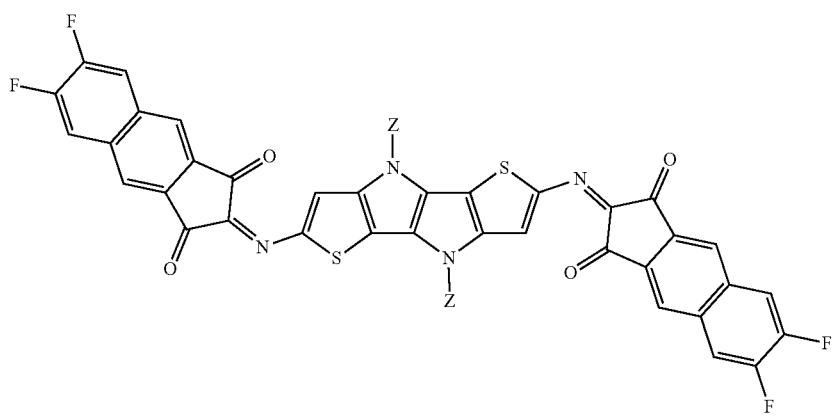

-continued
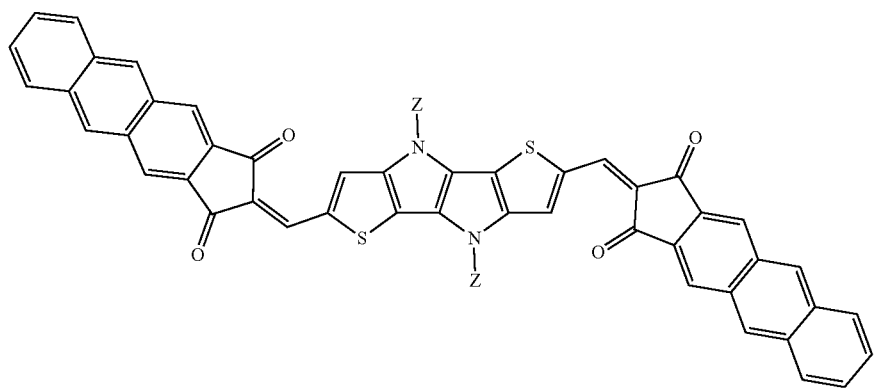
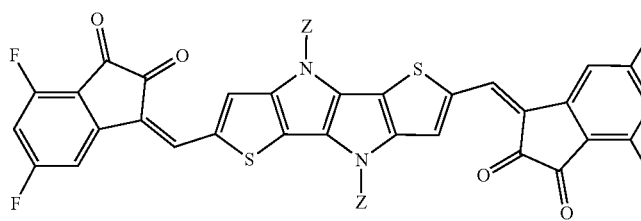
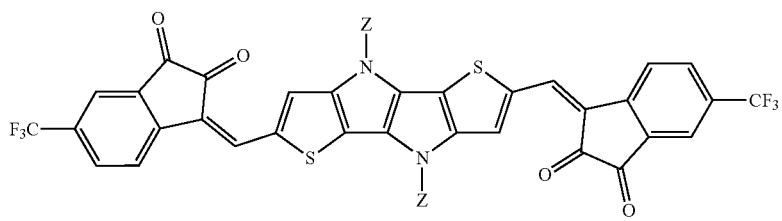
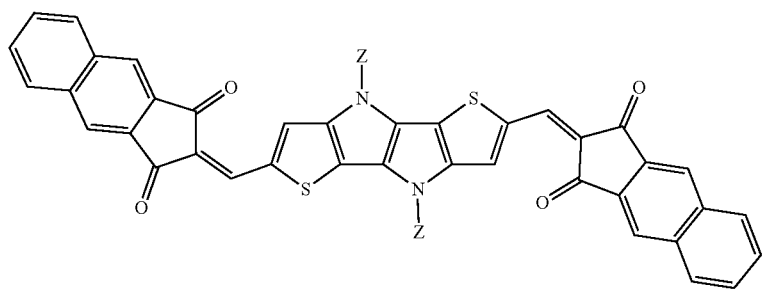
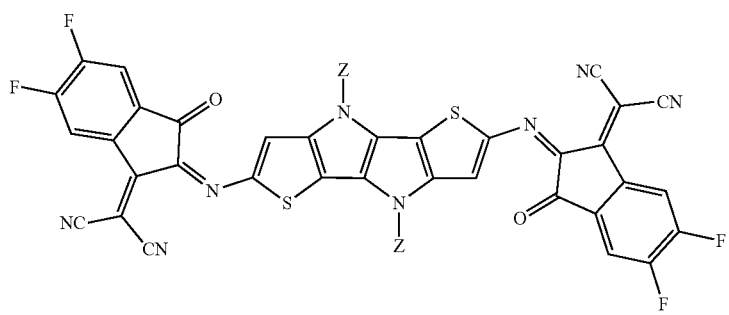
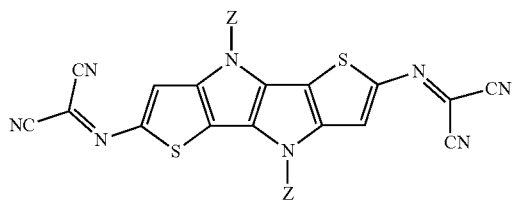

-continued
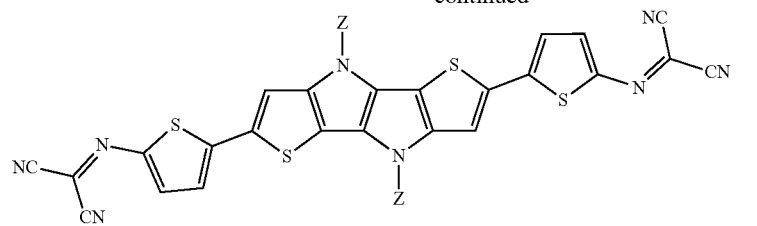
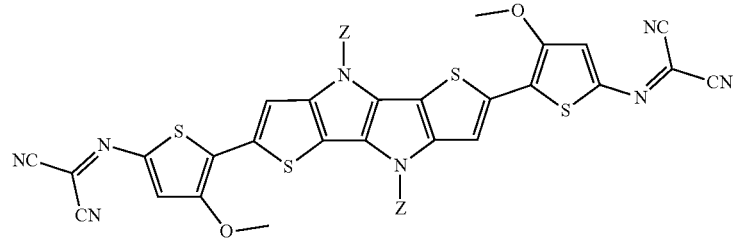
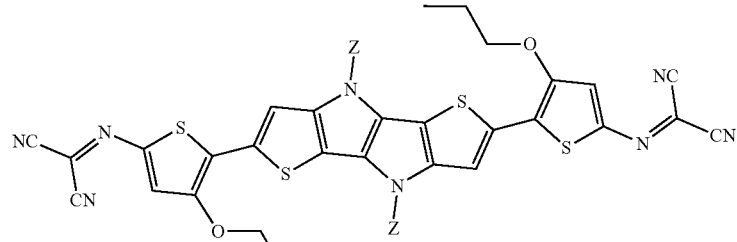
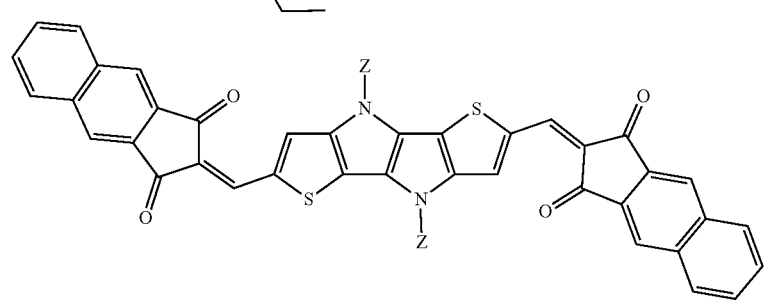
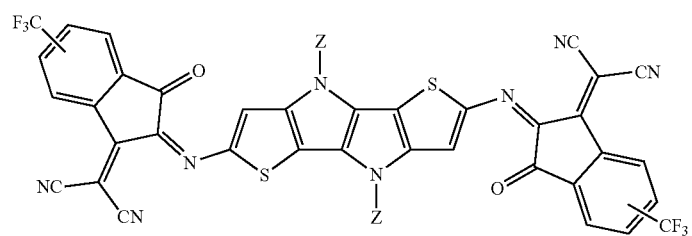
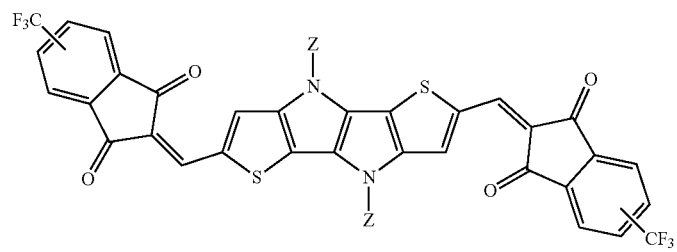
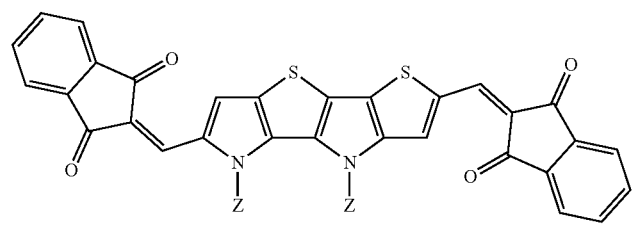

-continued
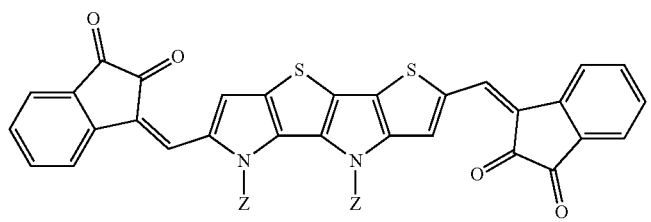
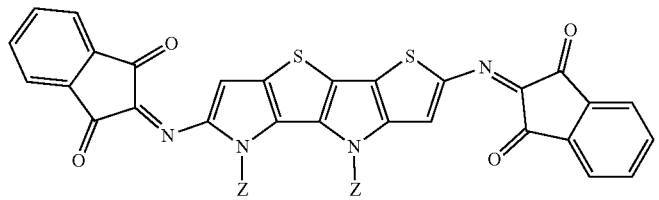
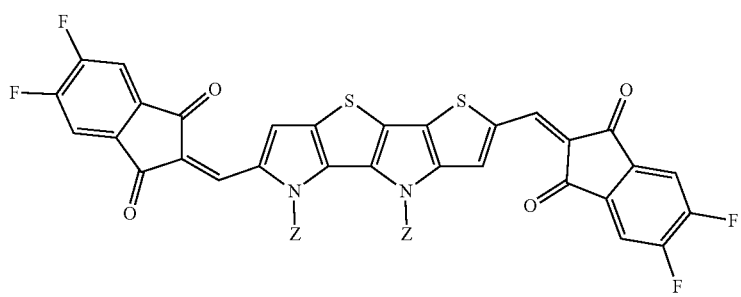
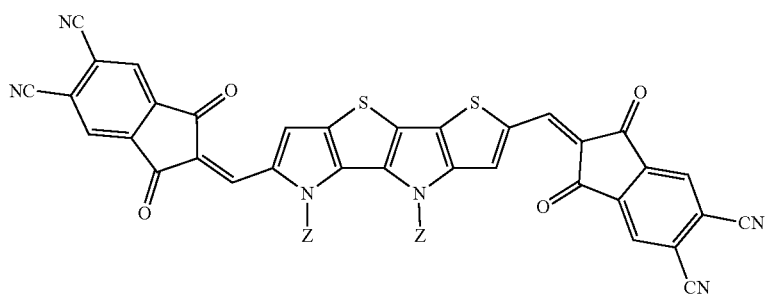
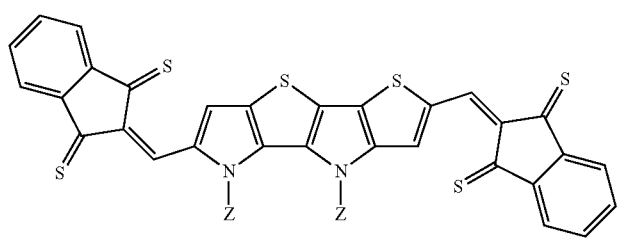
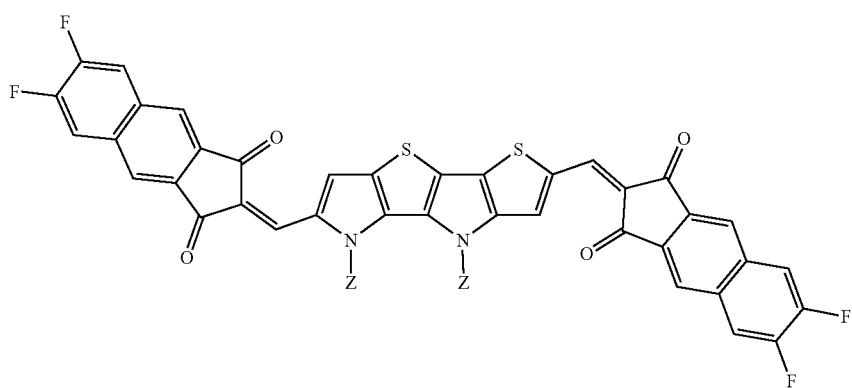

-continued
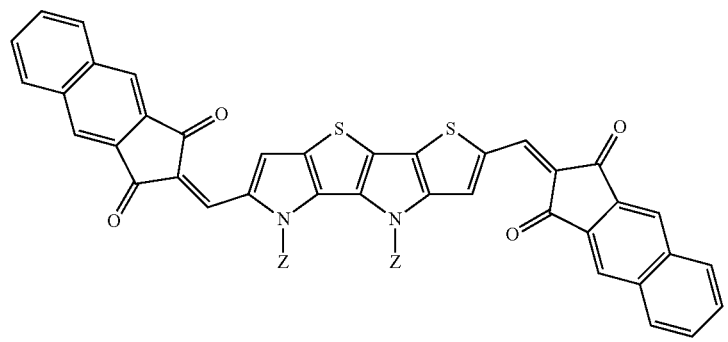
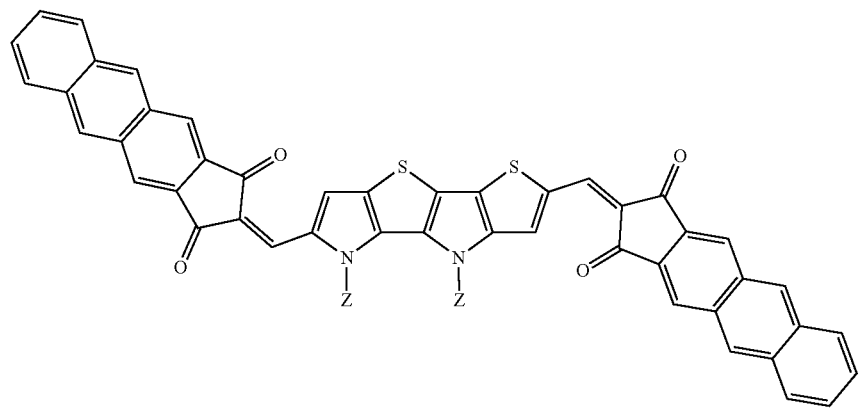
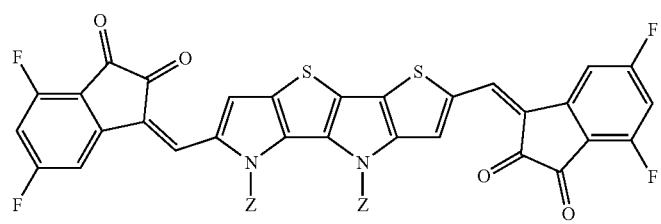
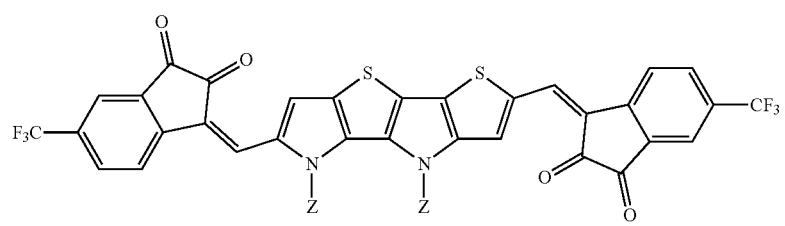
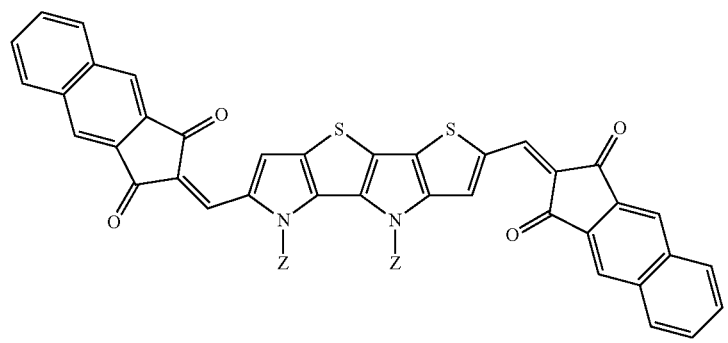

631 632
-continued
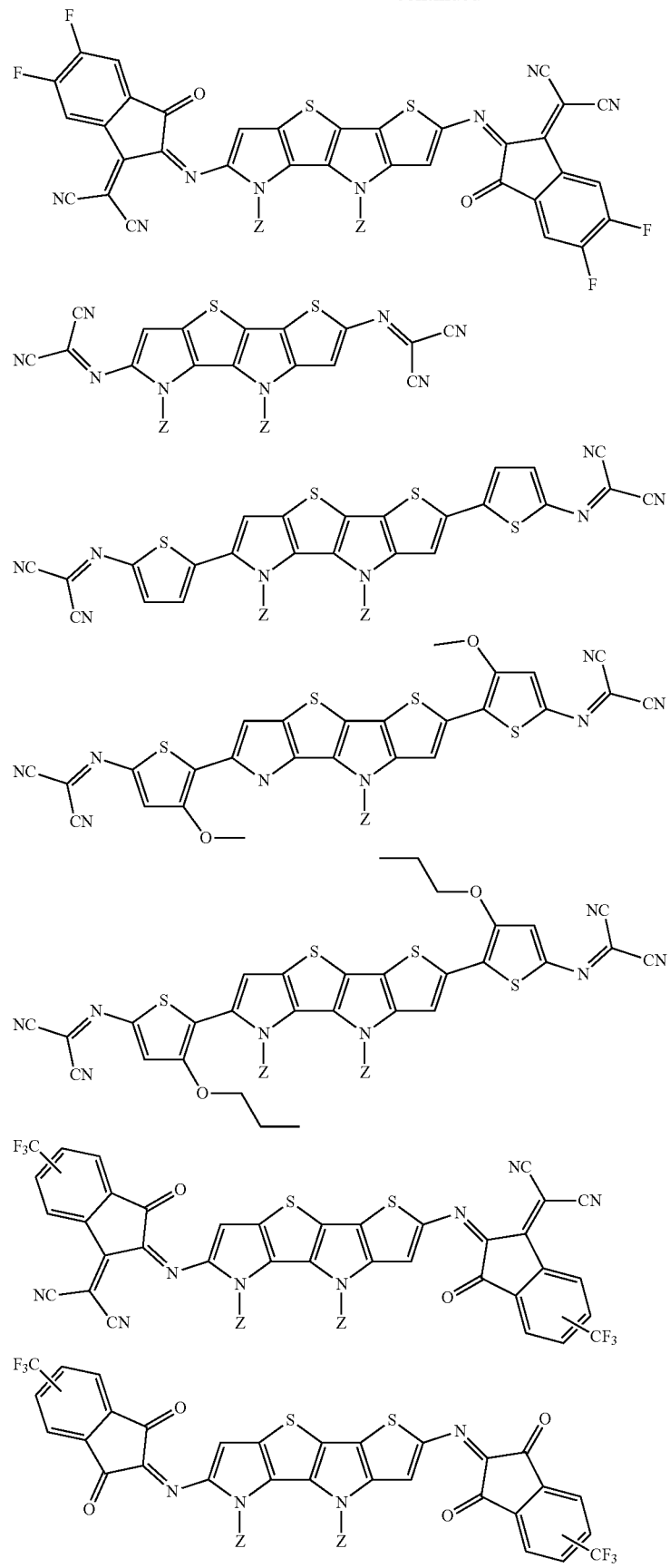

-continued
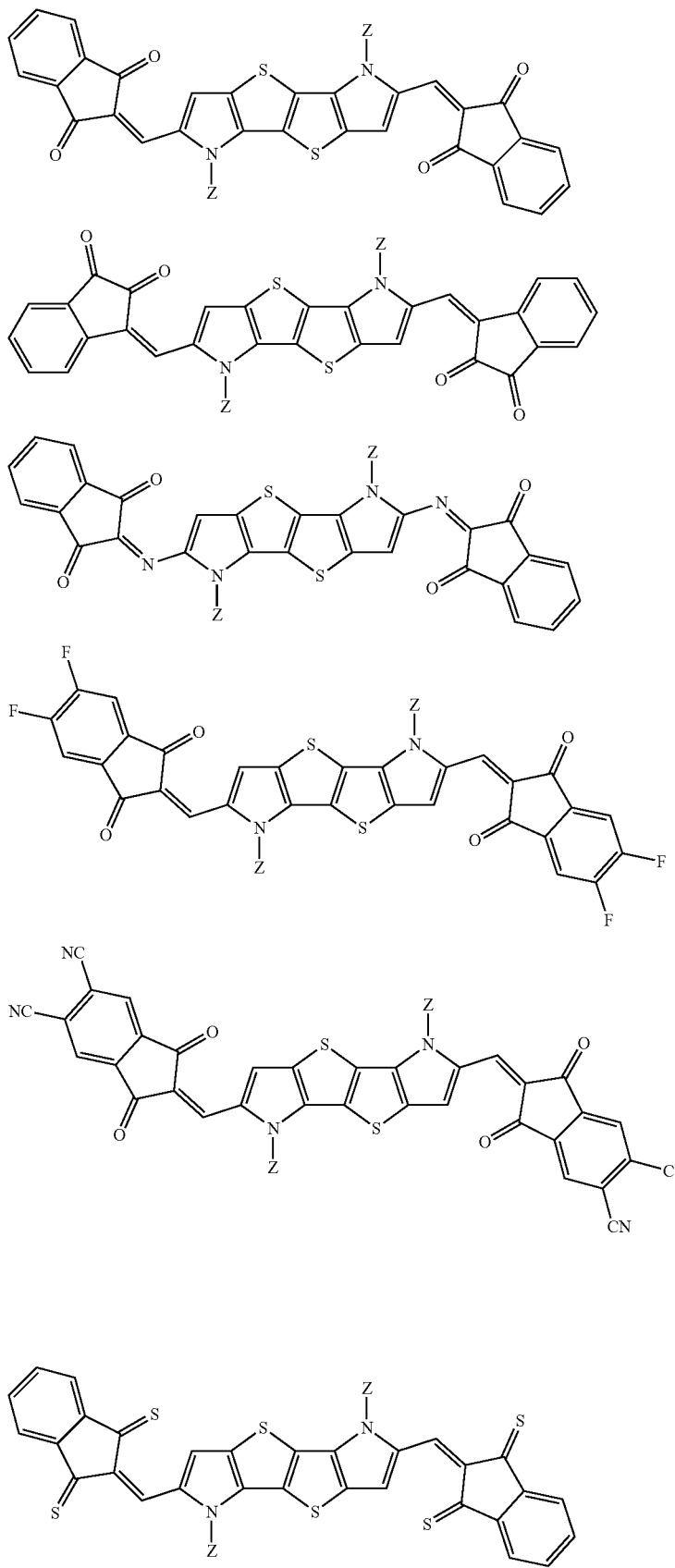

-continued
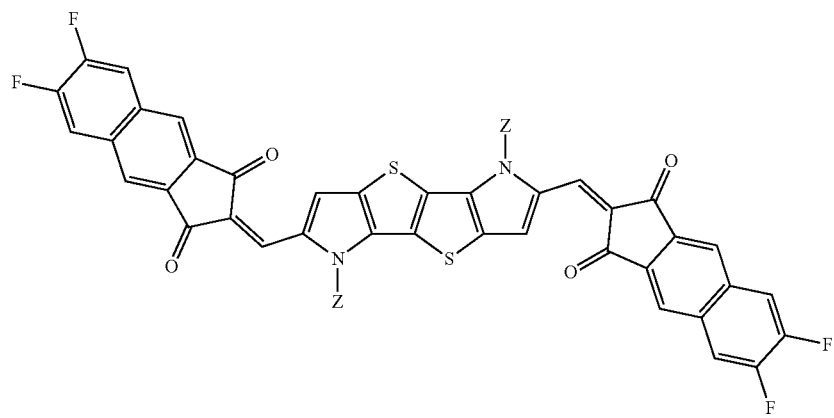
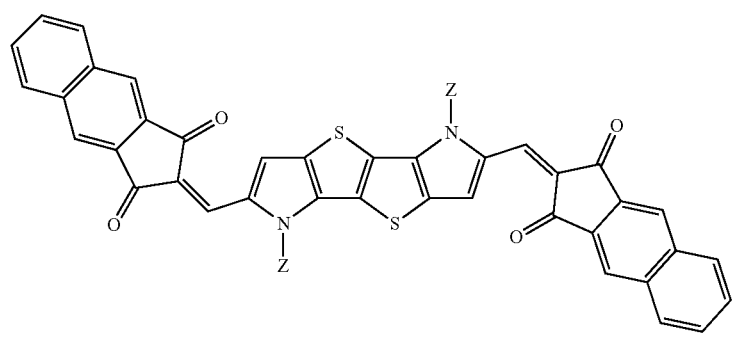
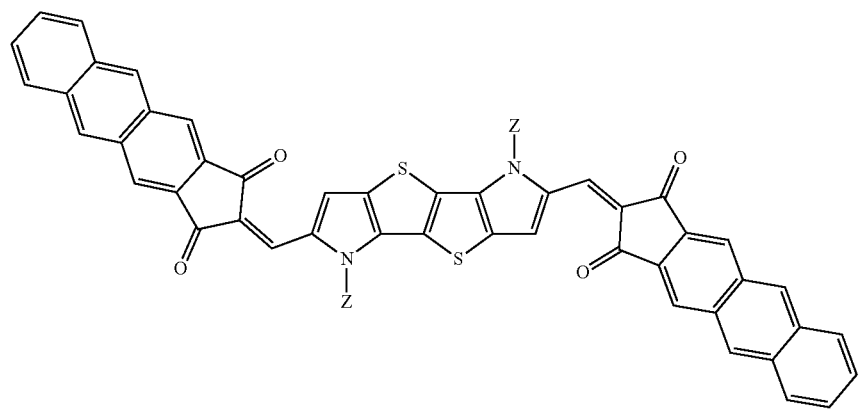
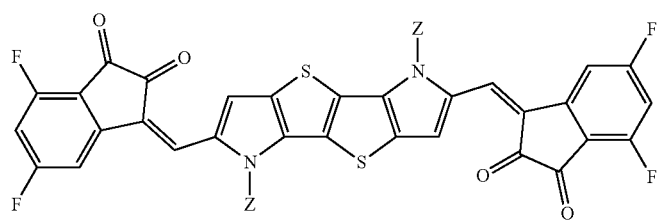
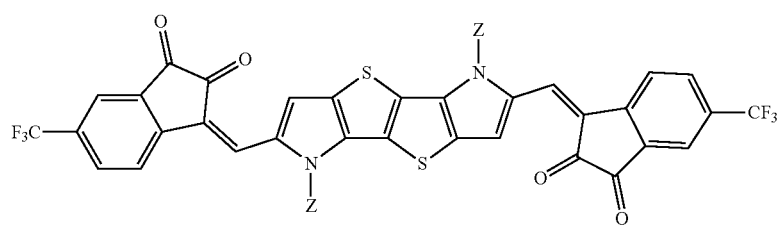

-continued
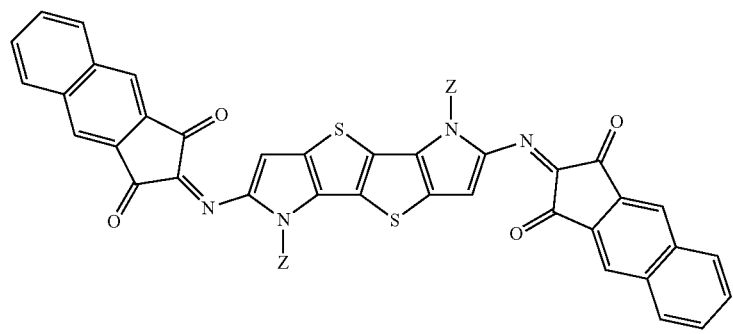
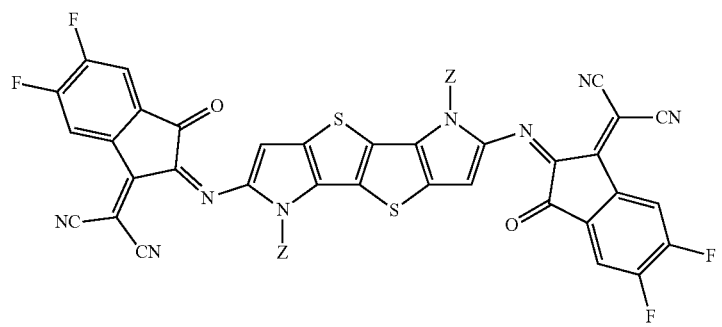
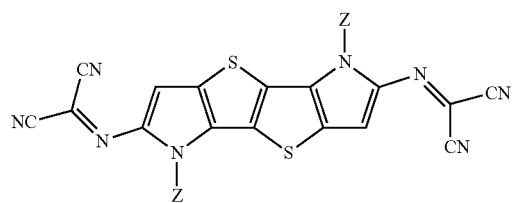
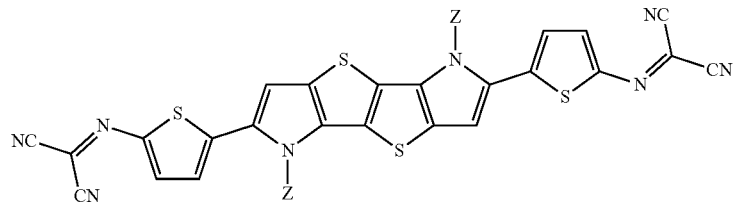
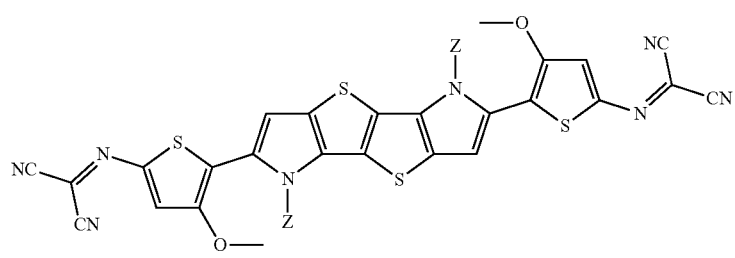
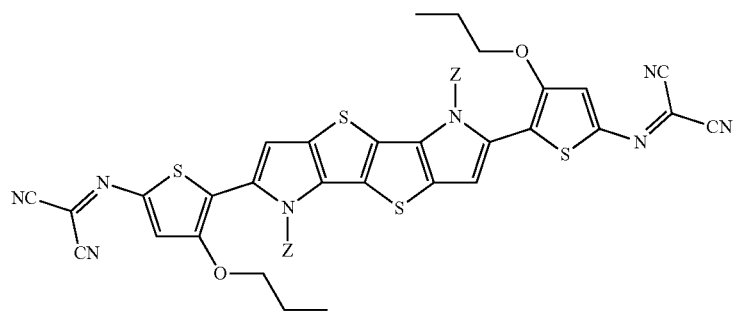

-continued
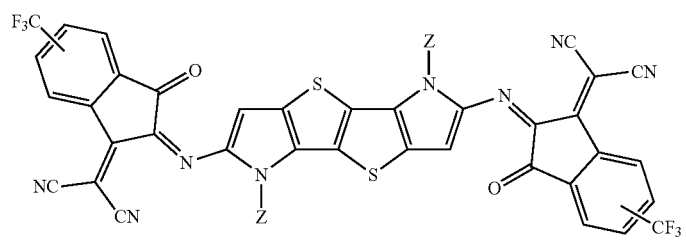
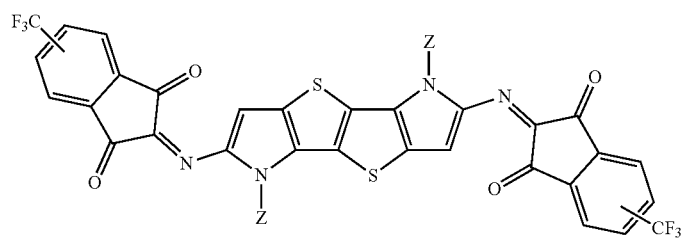
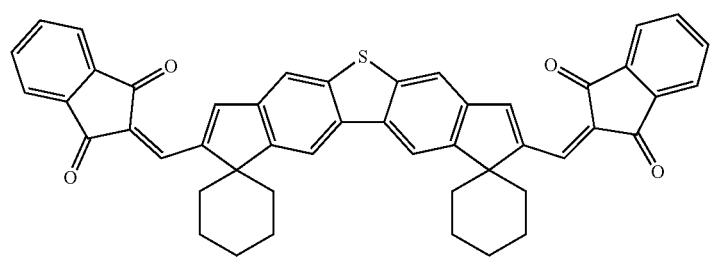
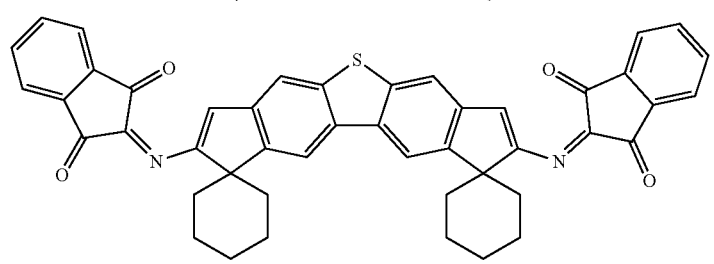
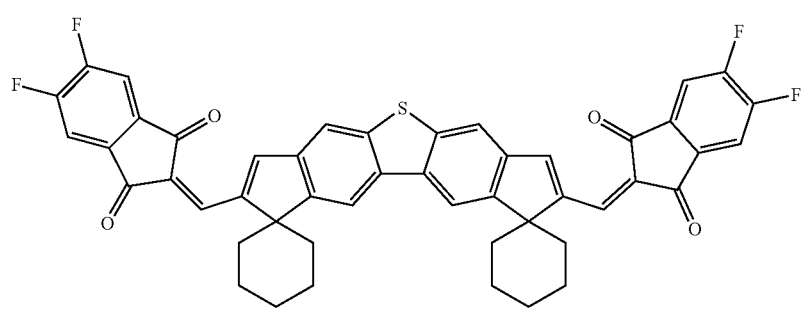
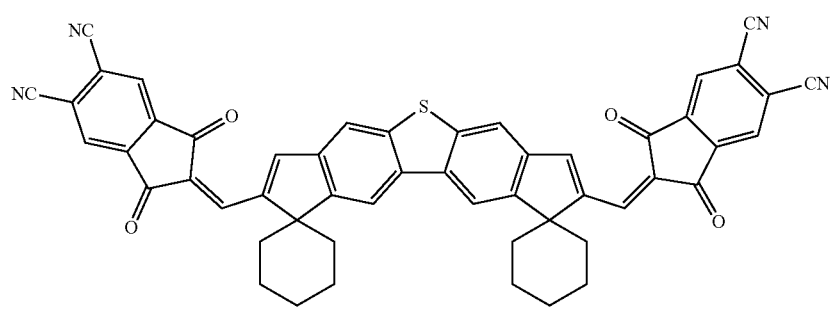

-continued
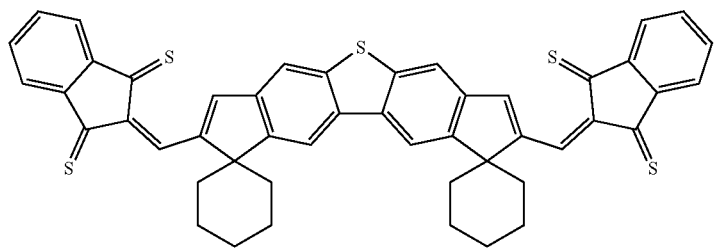
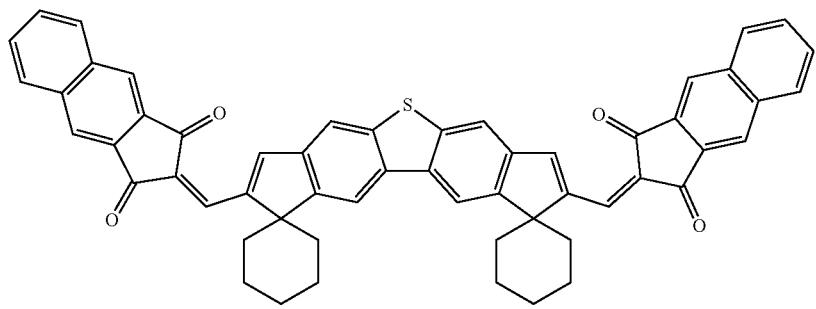
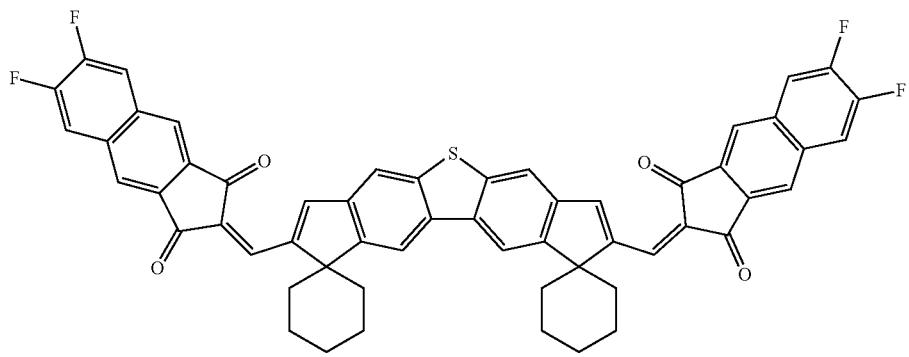
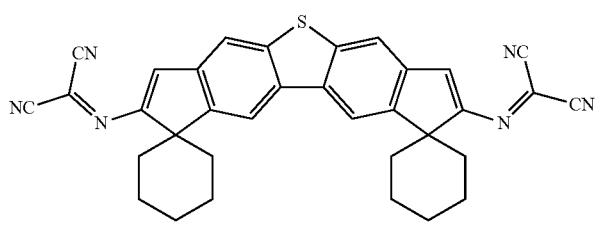
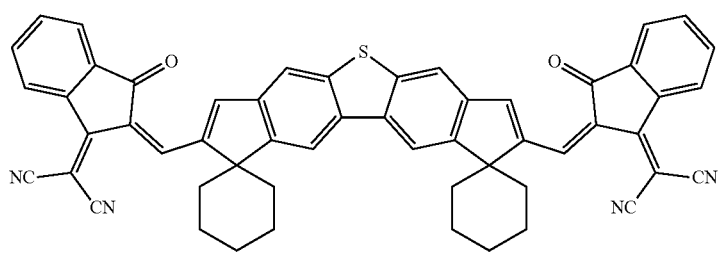
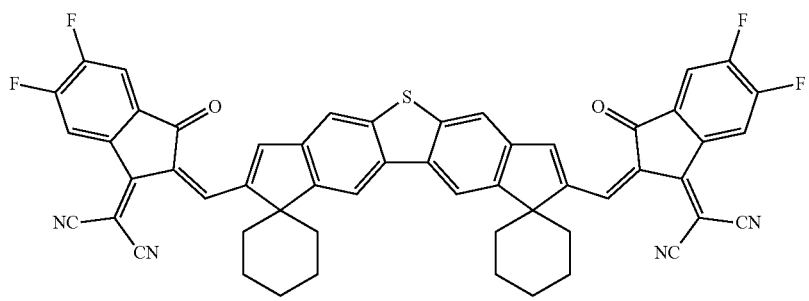

-continued
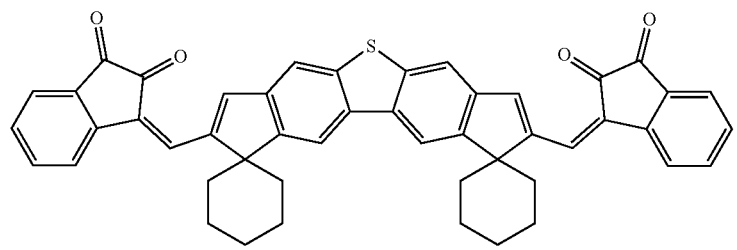
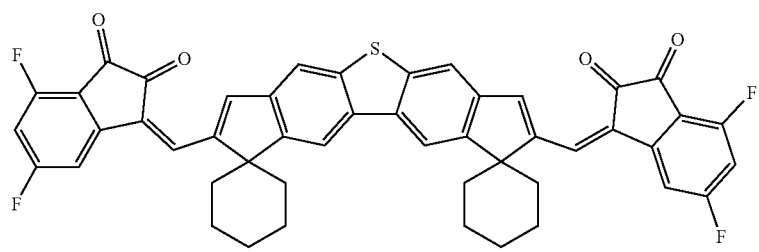
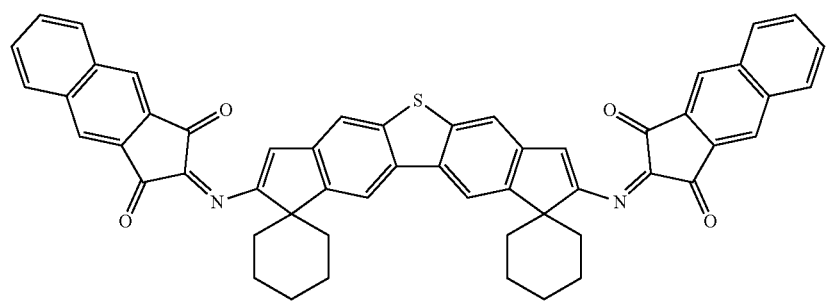
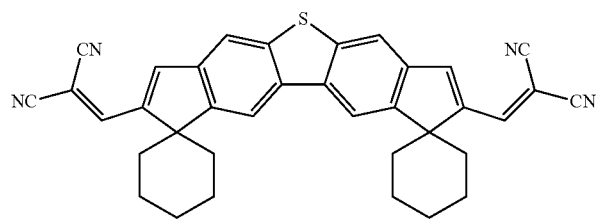
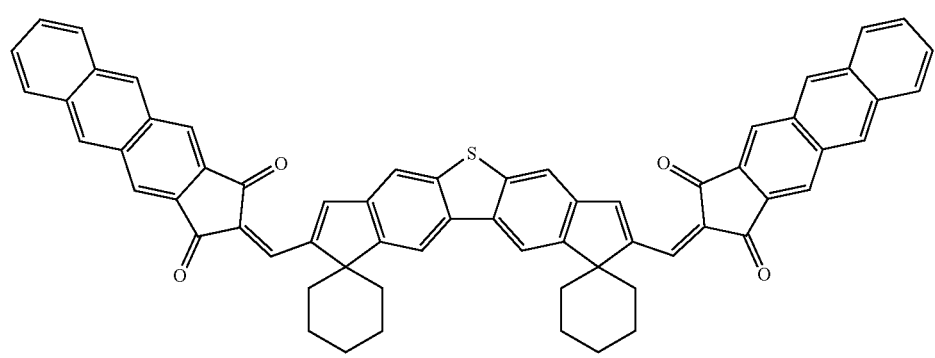
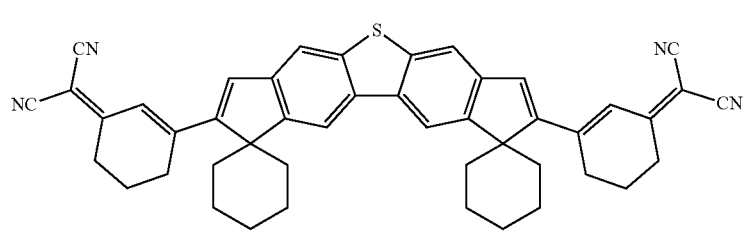

-continued
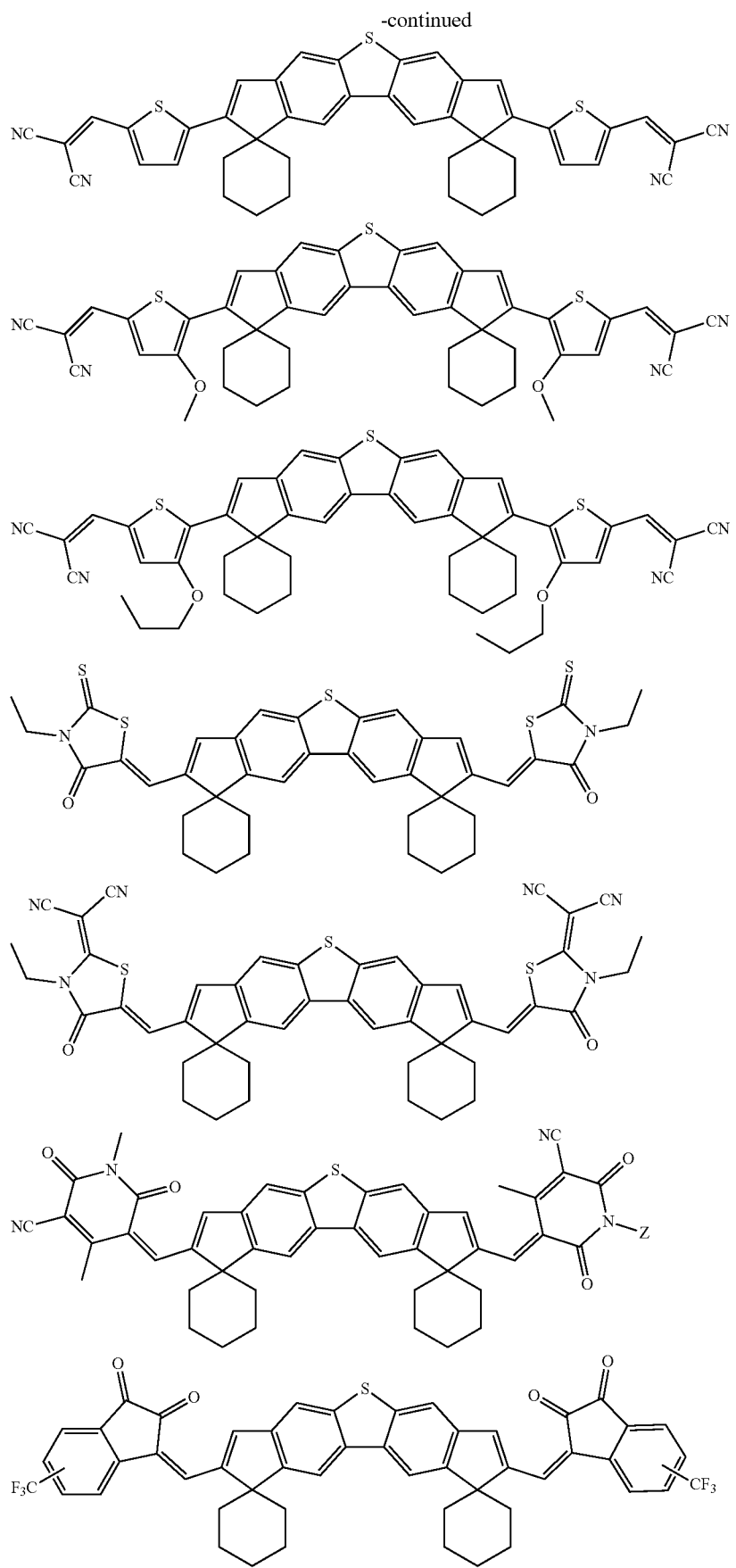

-continued
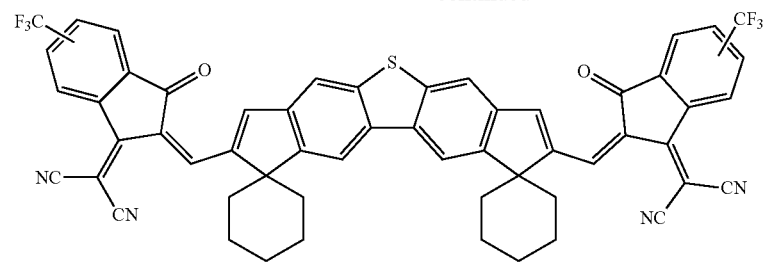
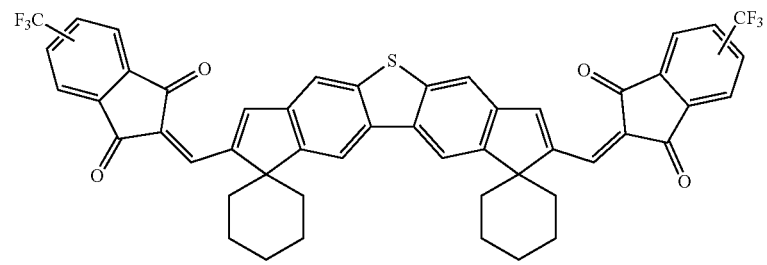
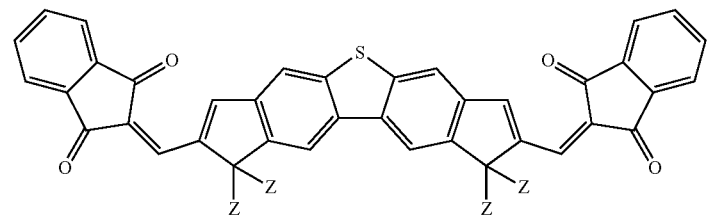
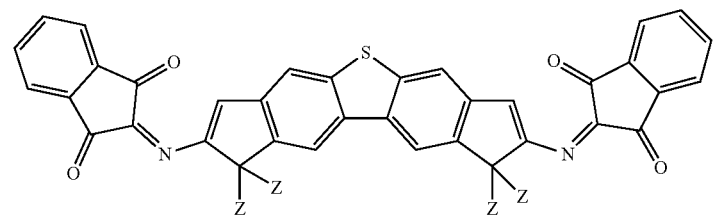
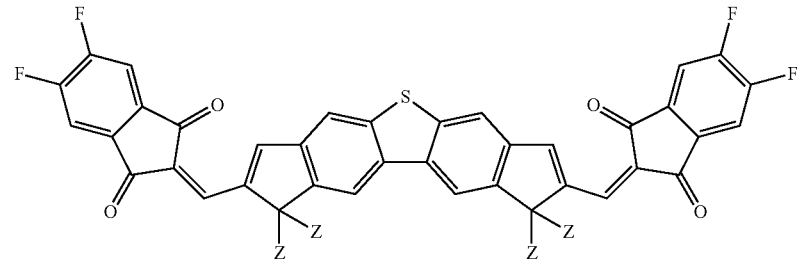
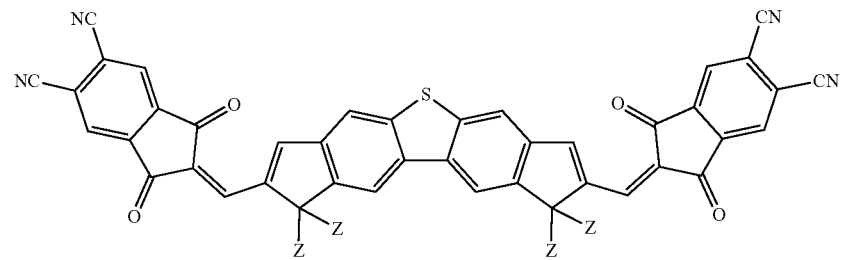
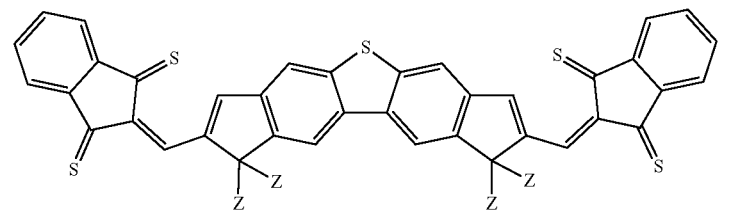

-continued
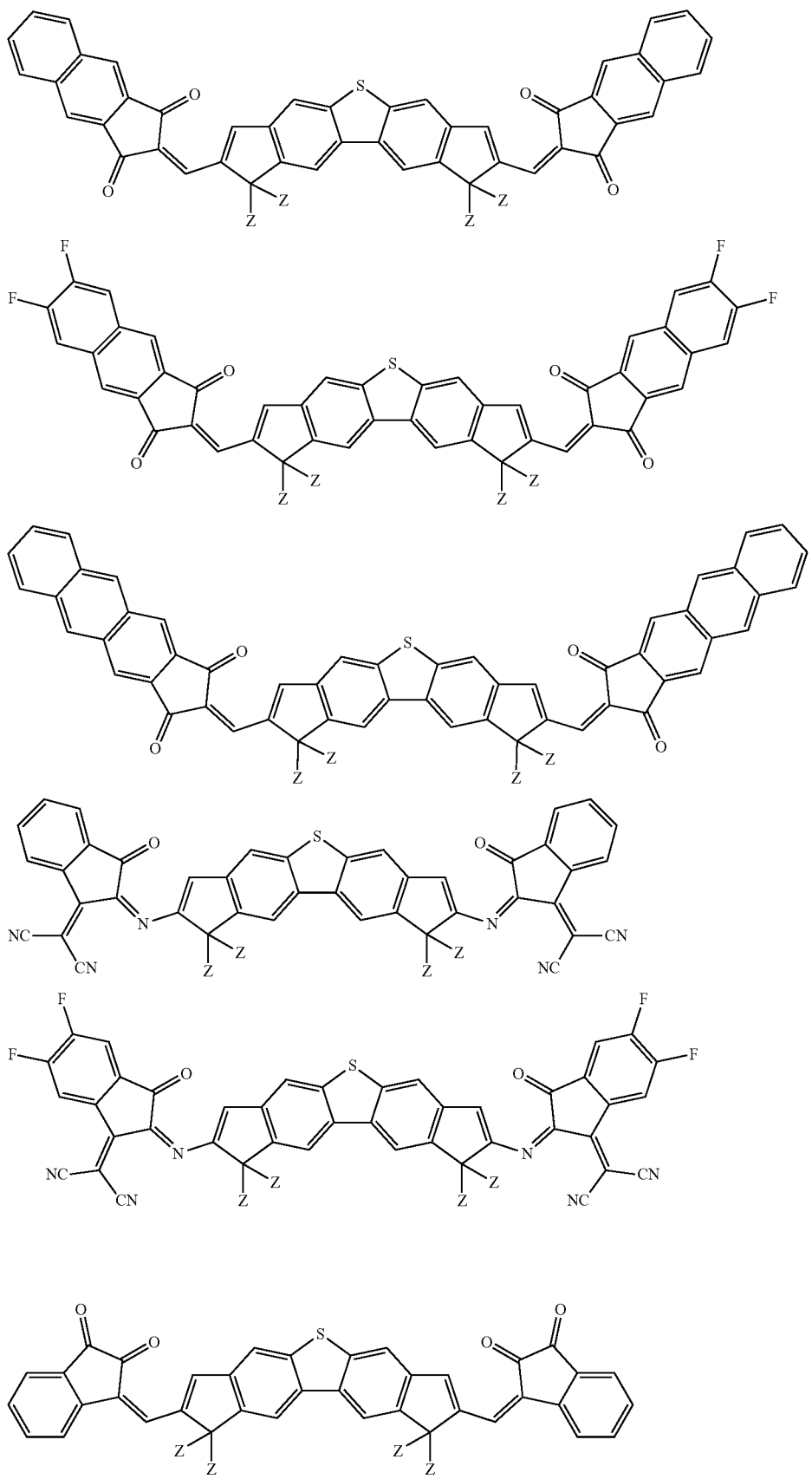

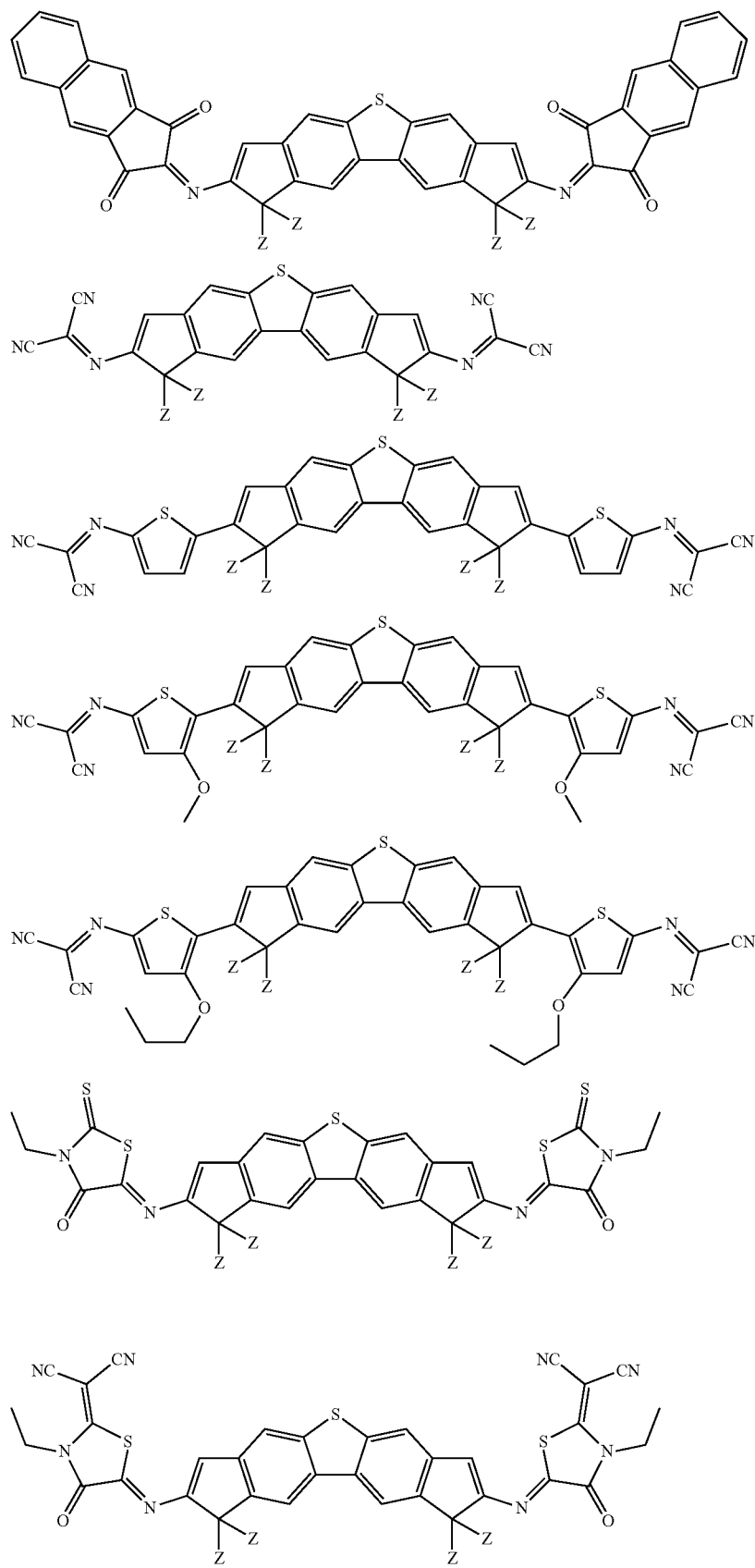

-continued
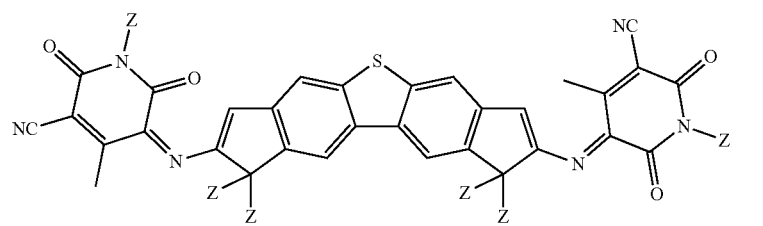
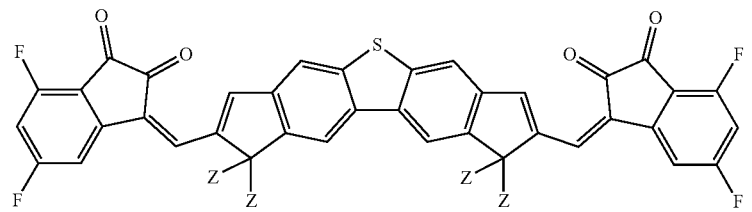
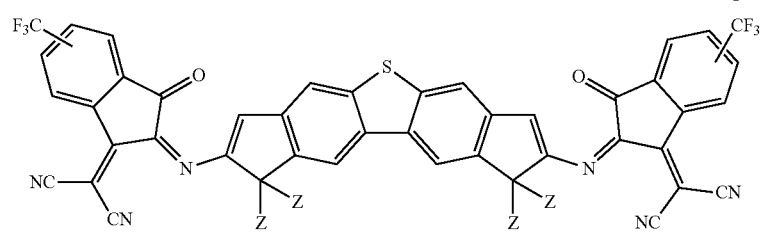
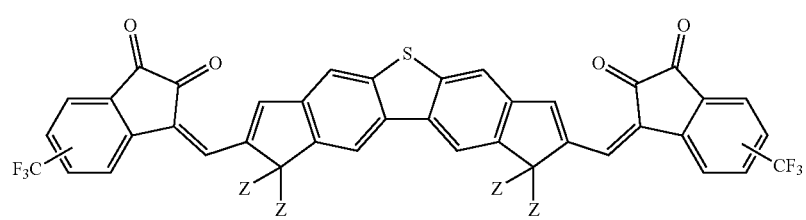
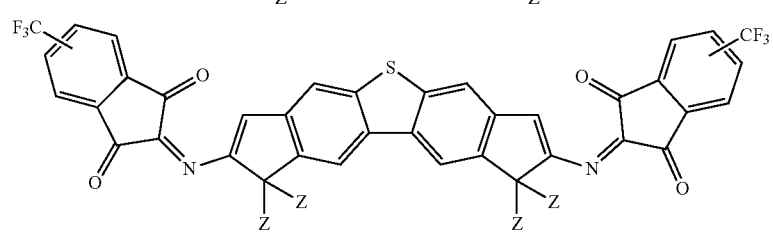
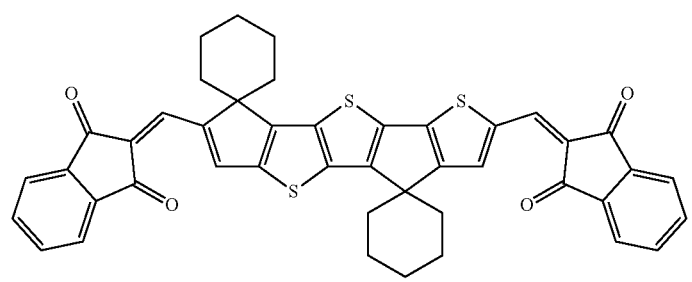
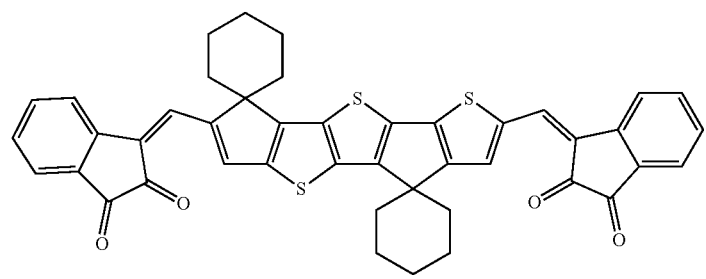

-continued
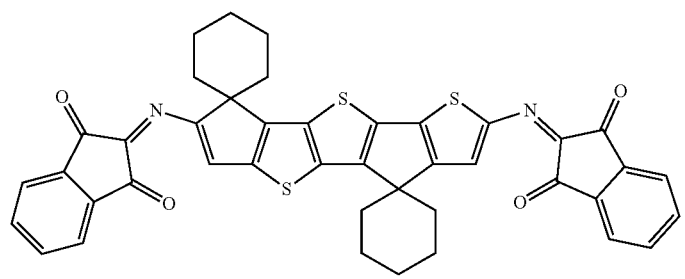
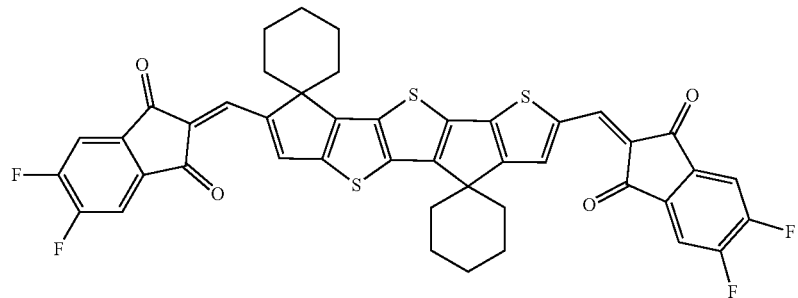
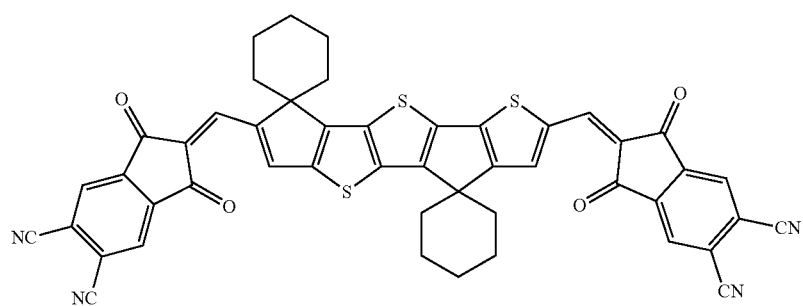
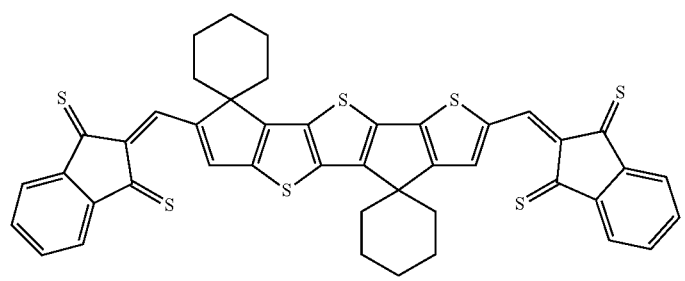
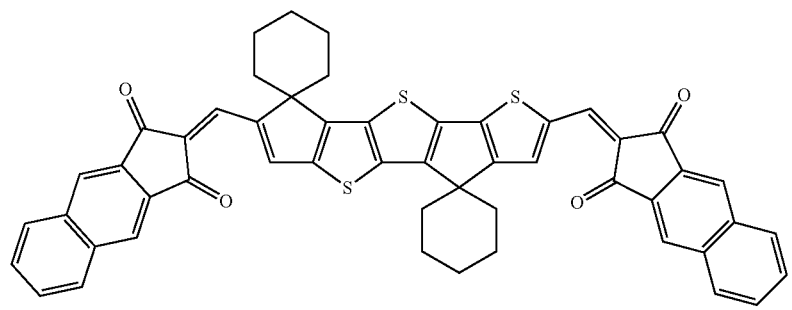

-continued
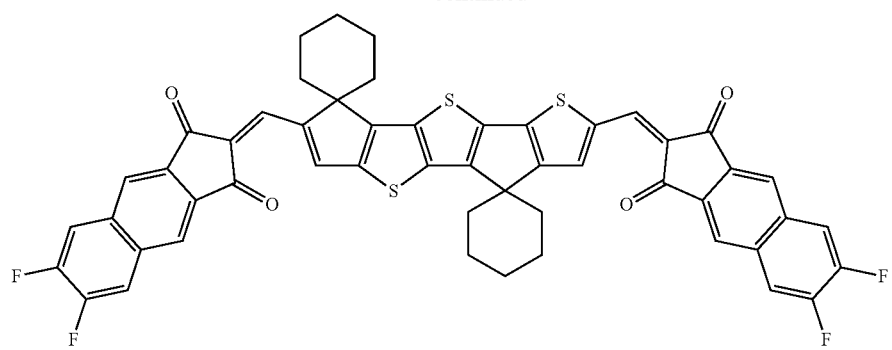
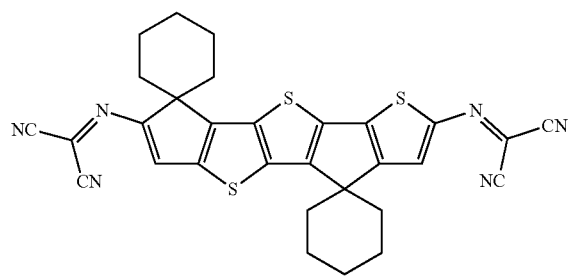
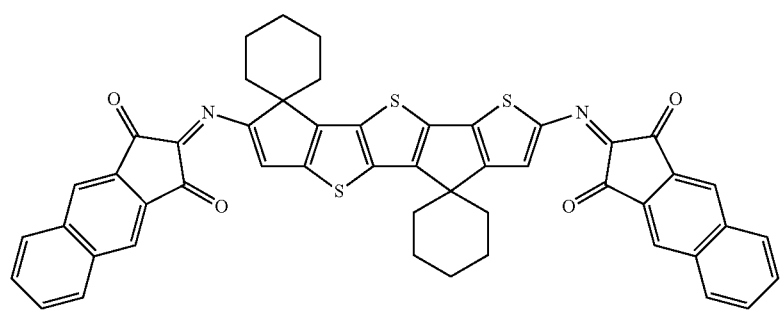
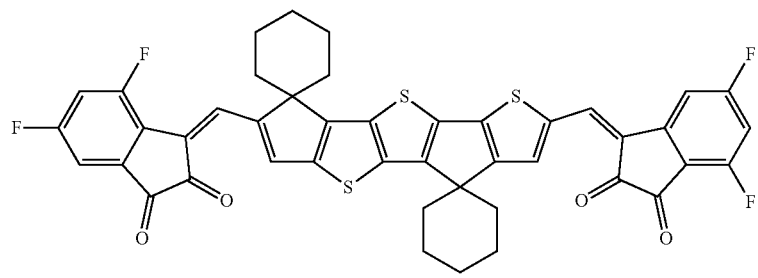
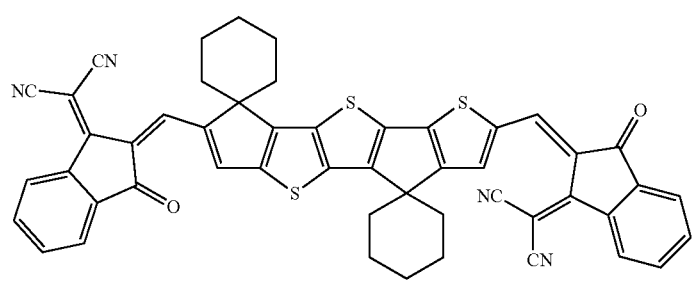

-continued
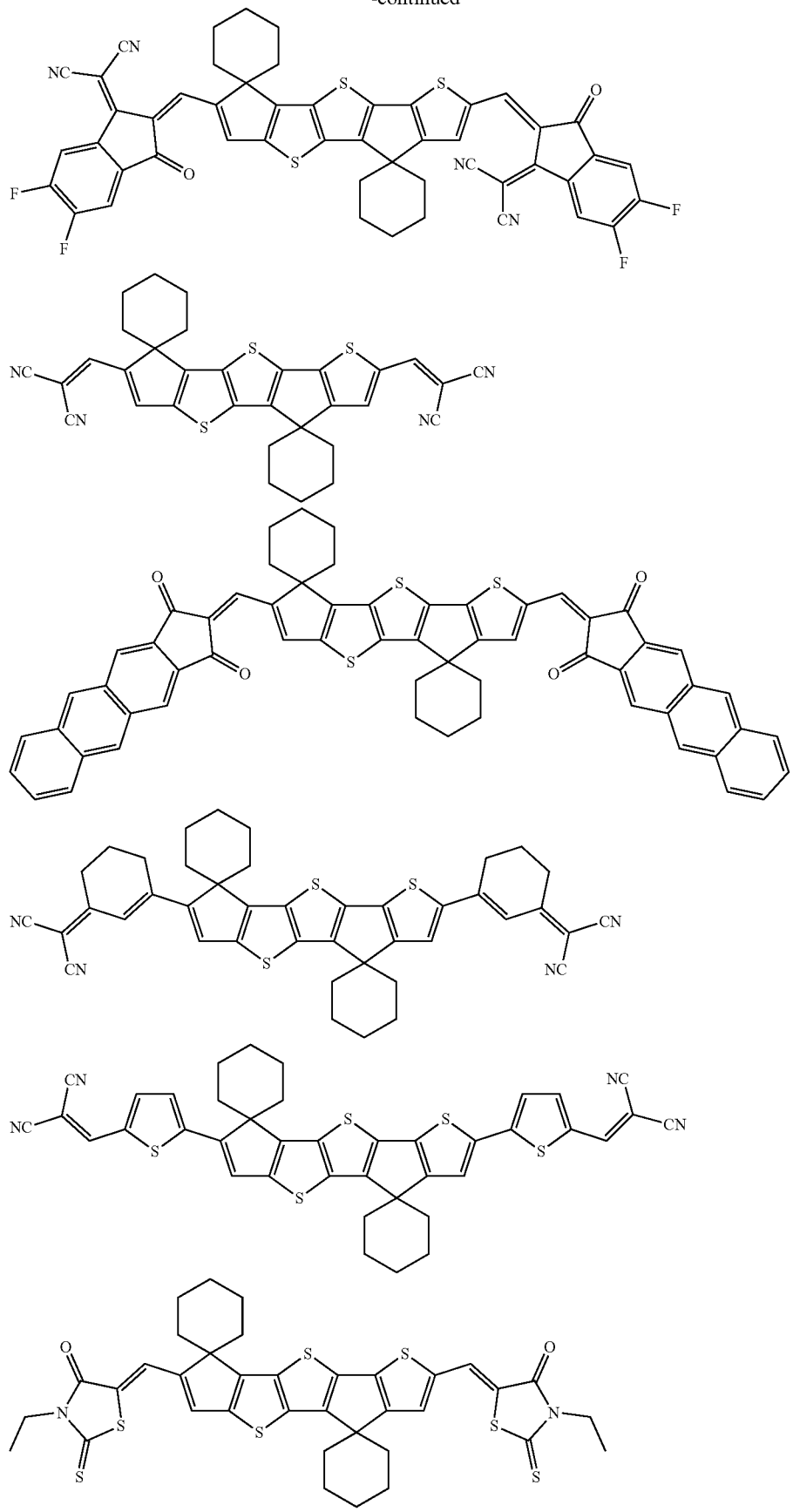

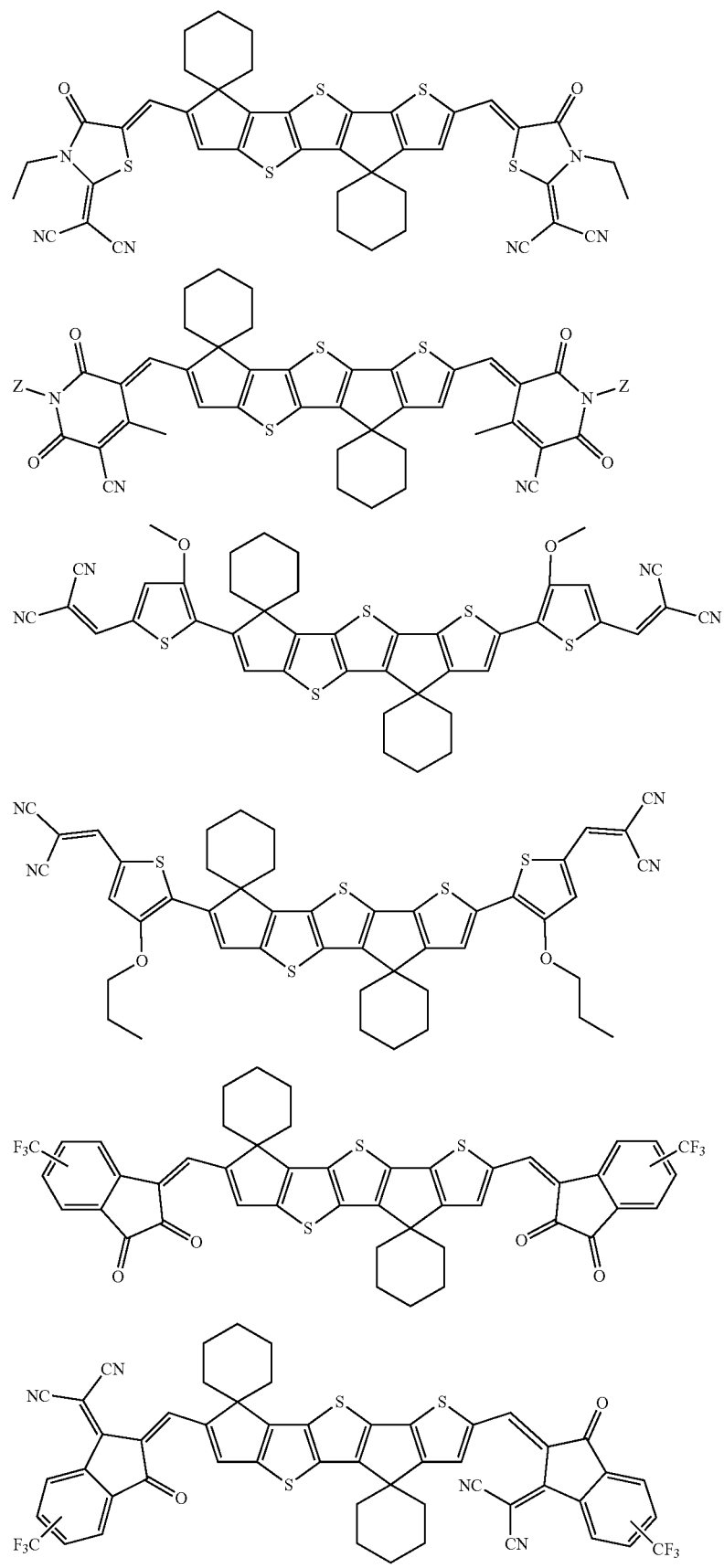

-continued
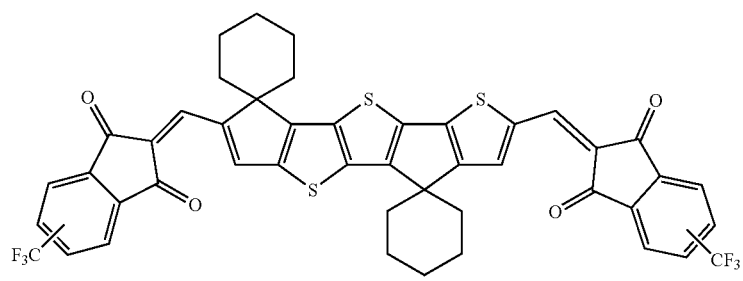
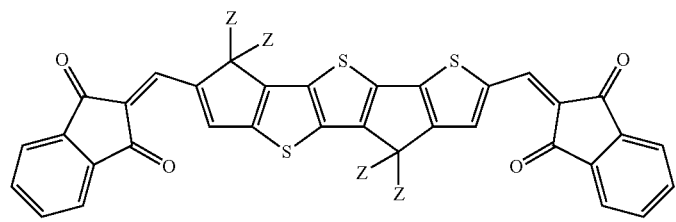
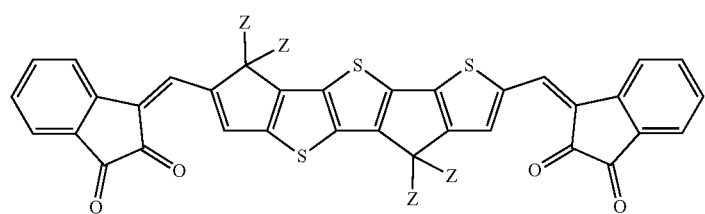
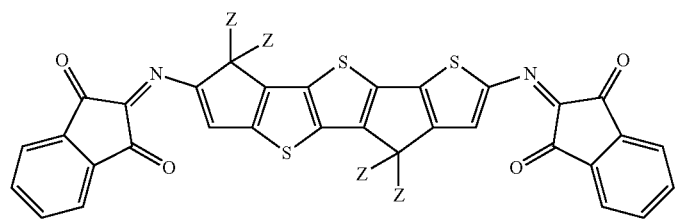
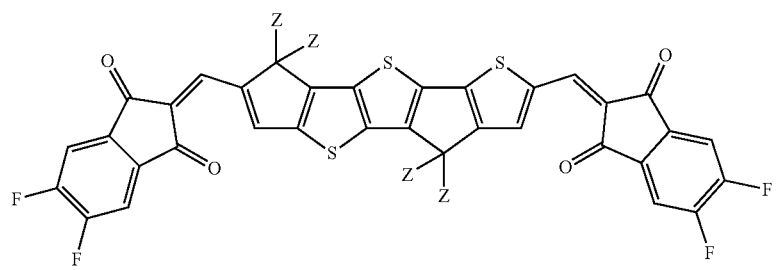
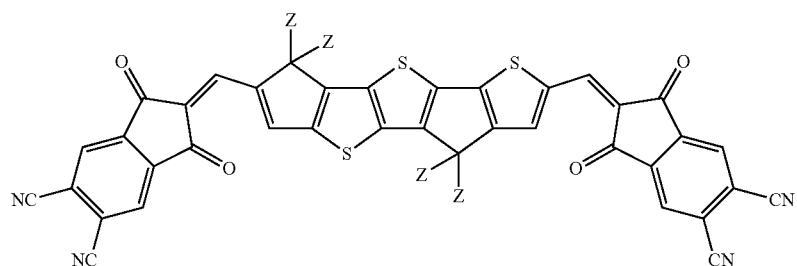
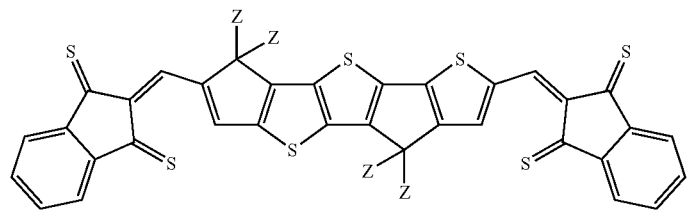

-continued
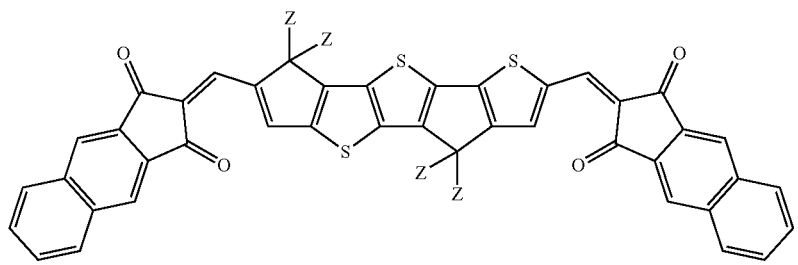
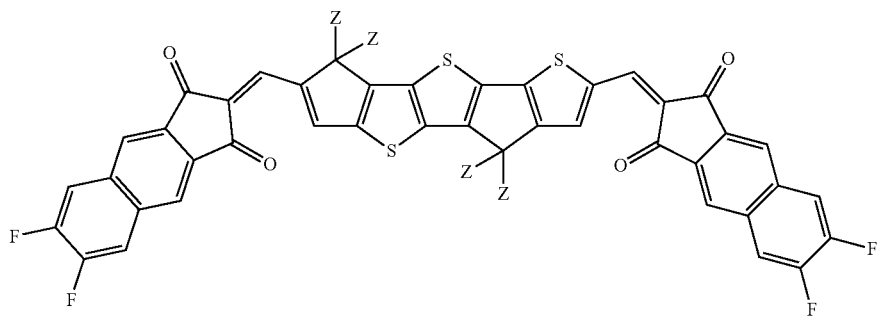
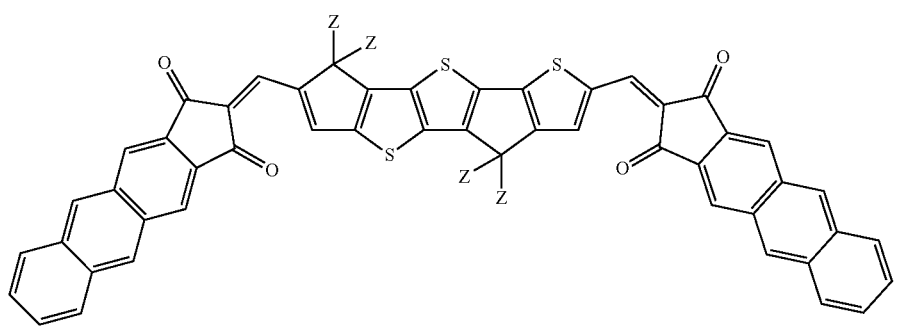
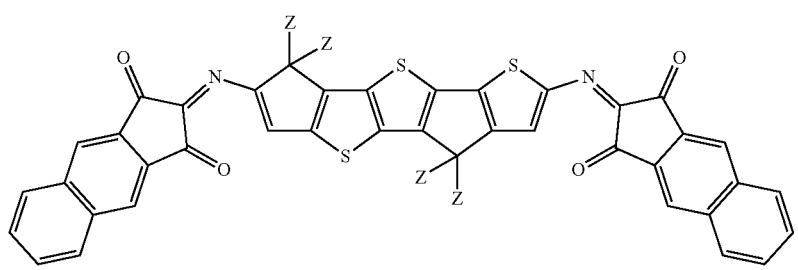
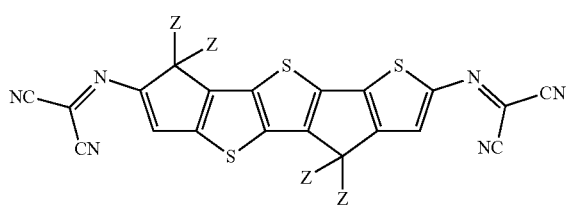
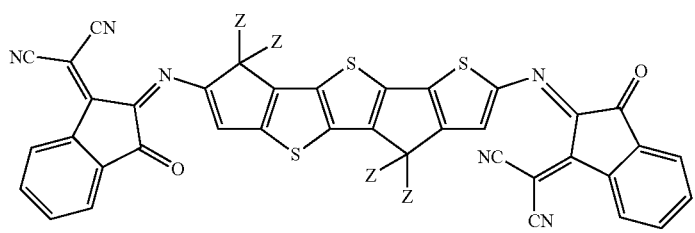

-continued
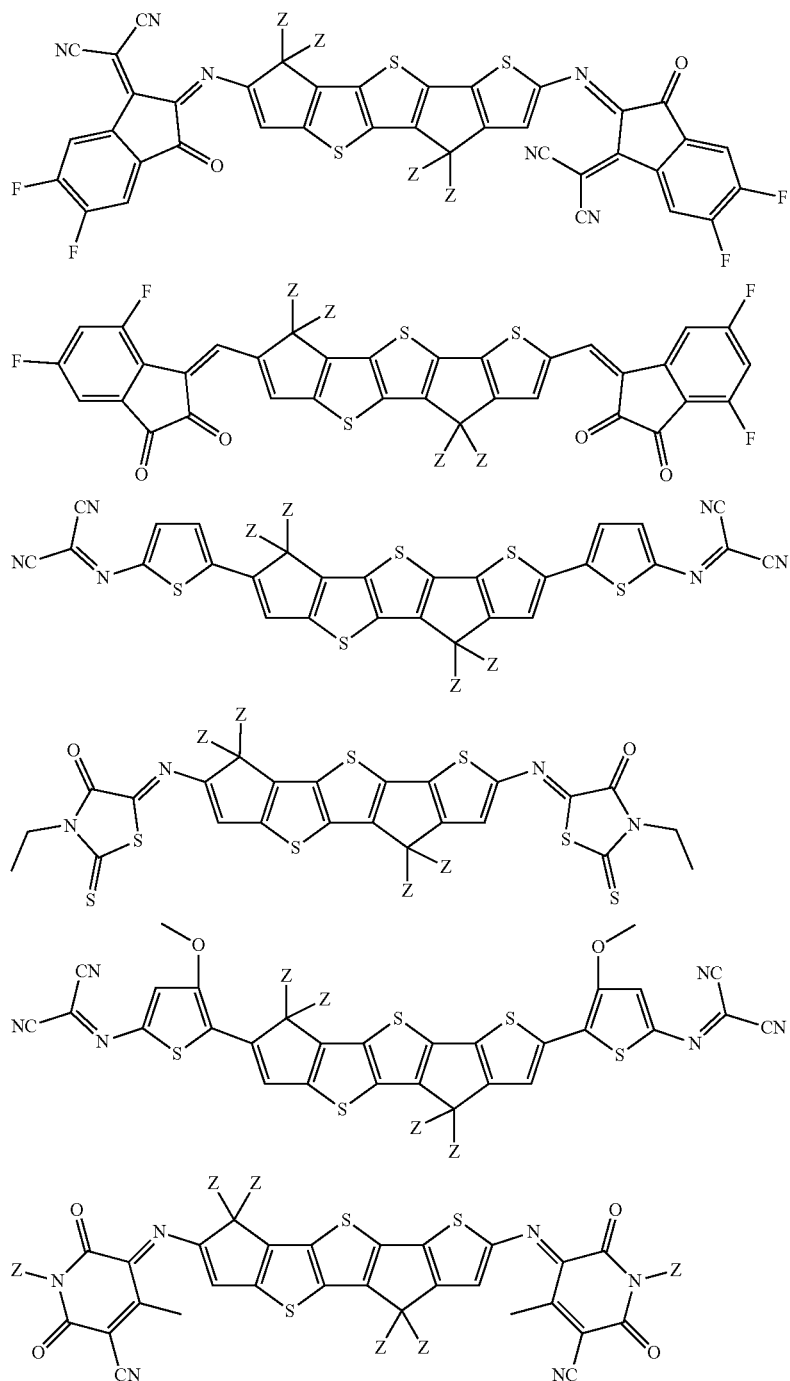
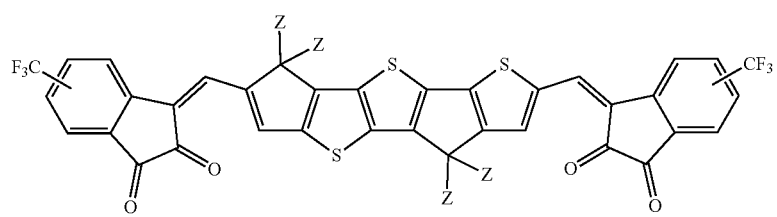

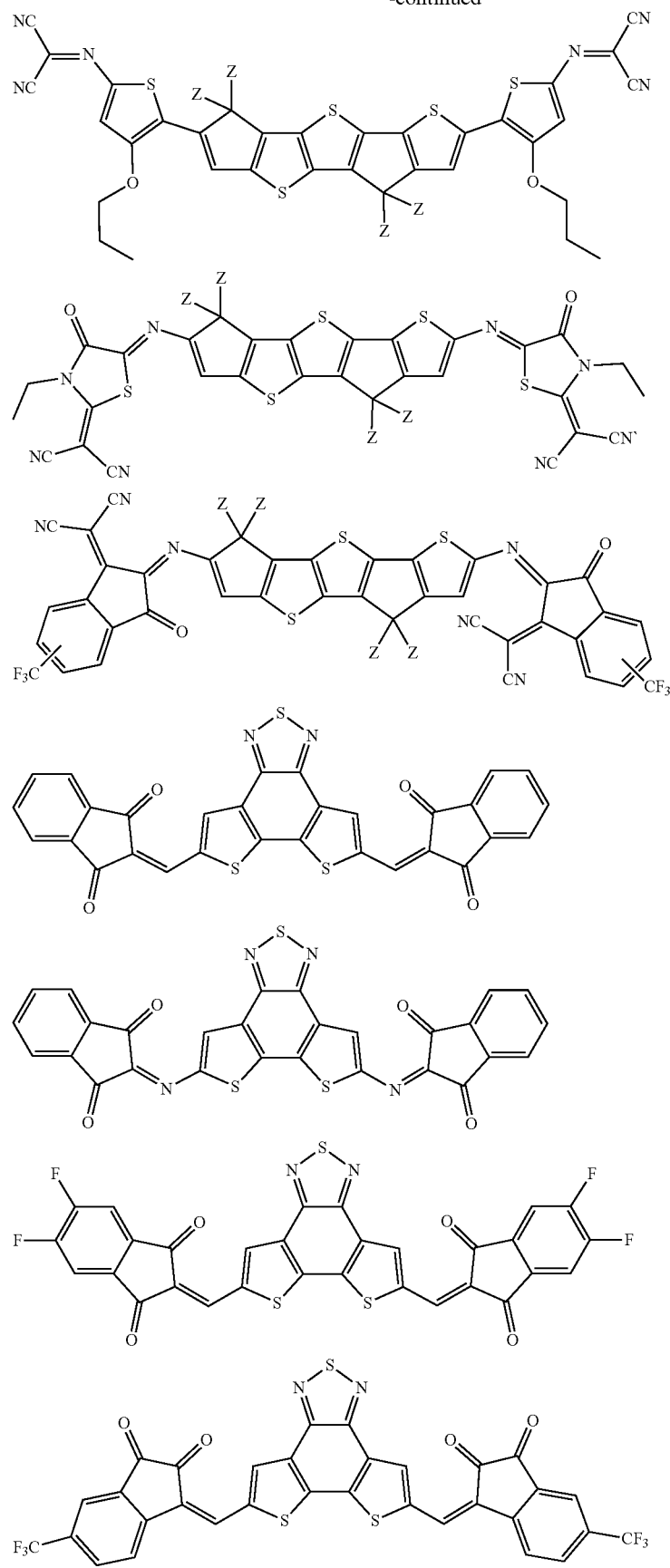

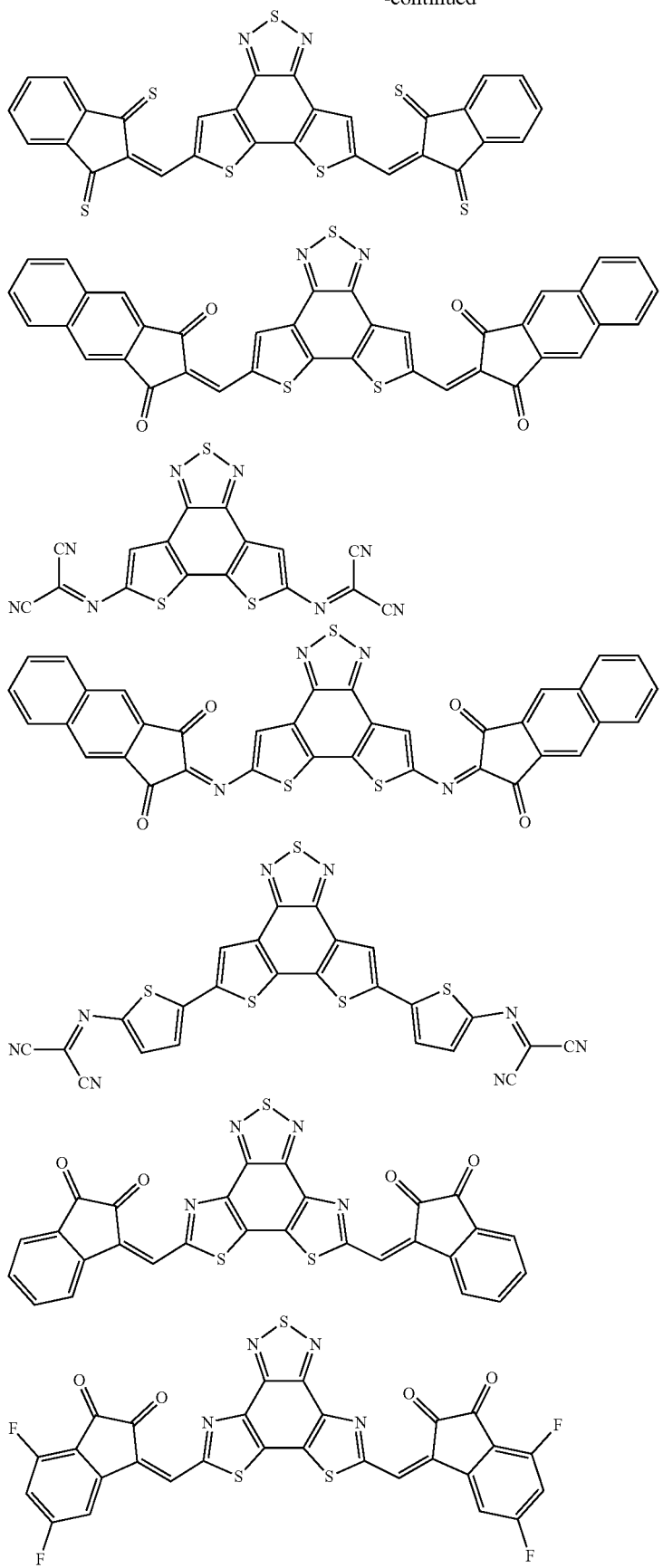

-continued
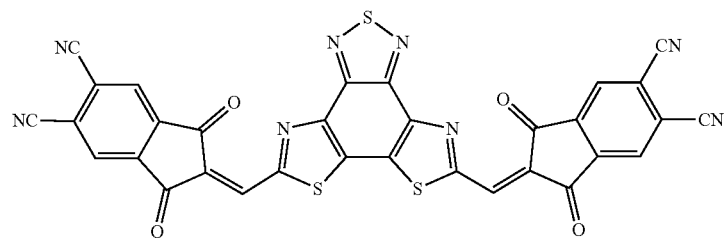
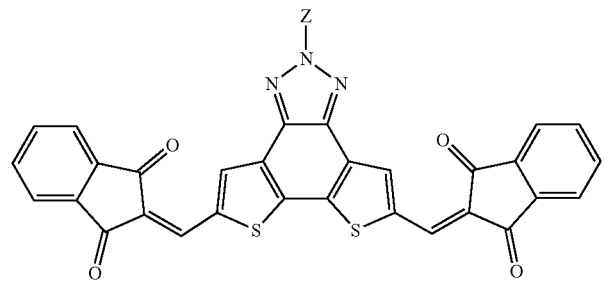
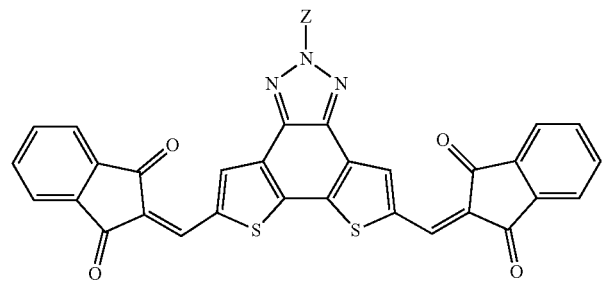
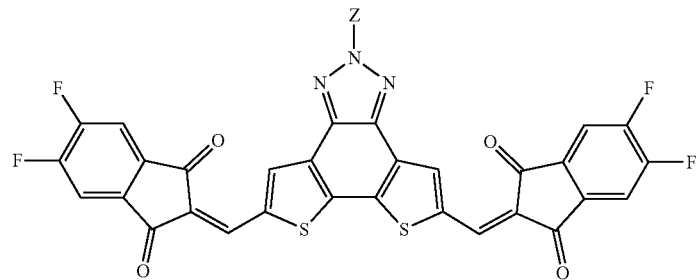
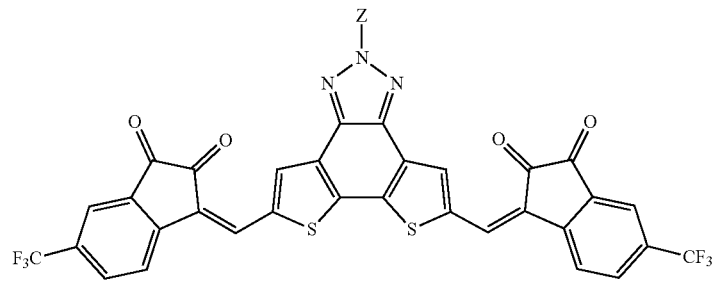
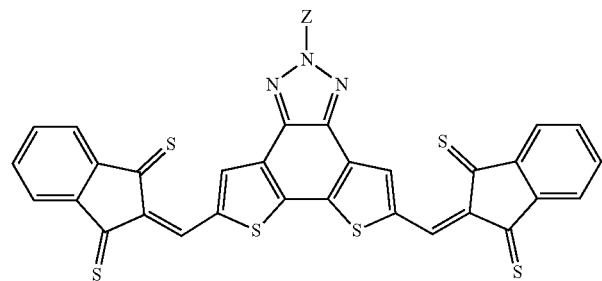

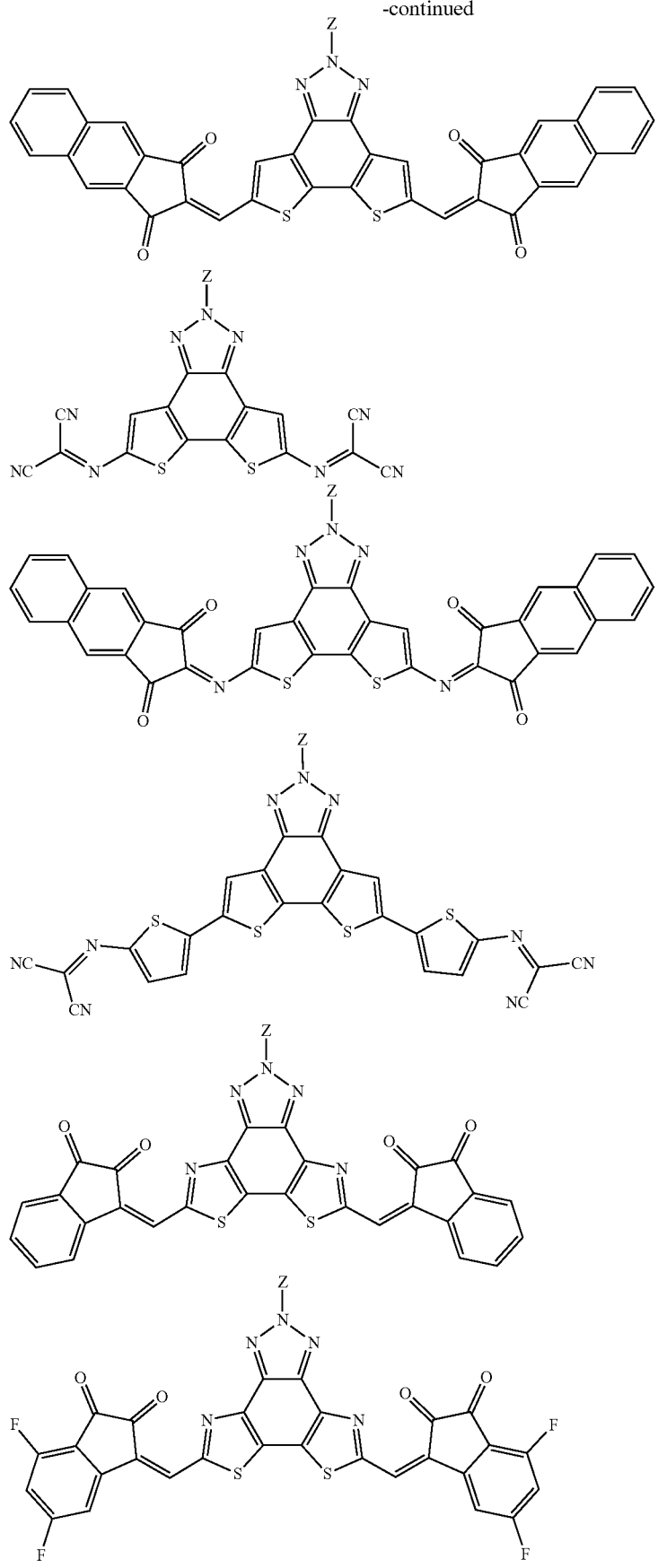

-continued
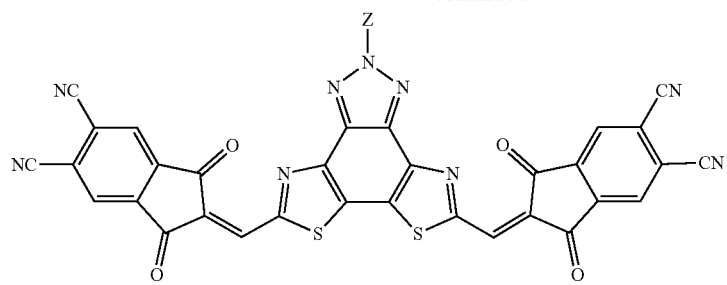
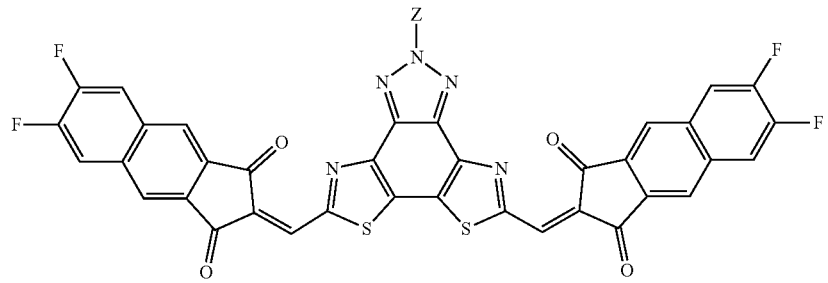
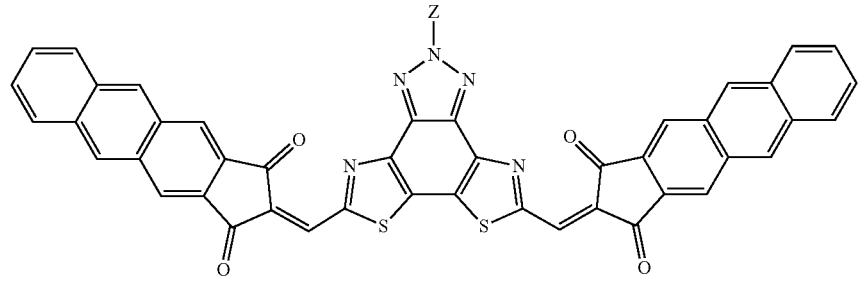
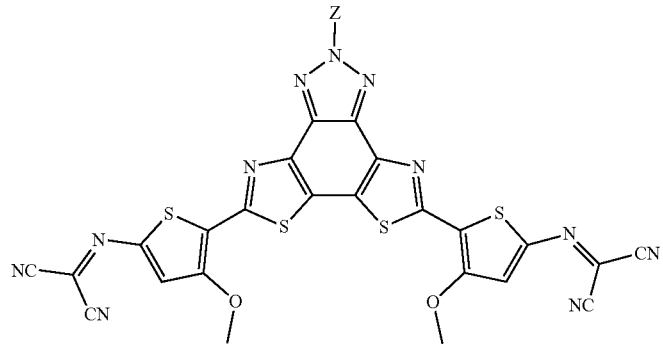
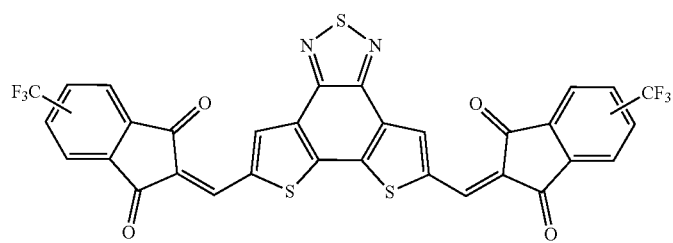
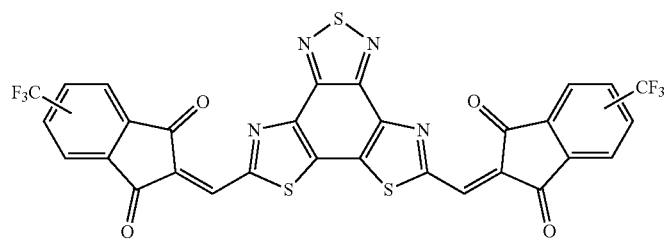

-continued
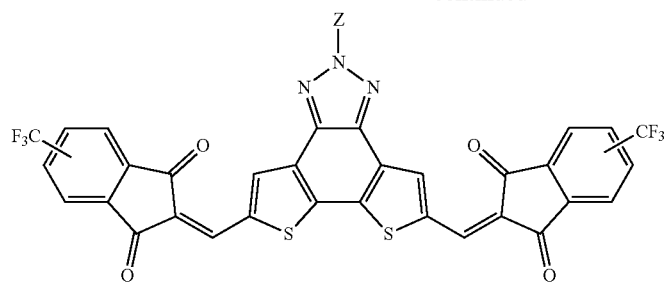
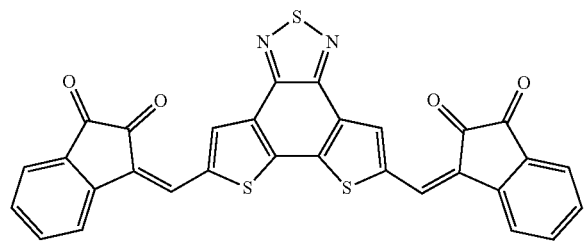
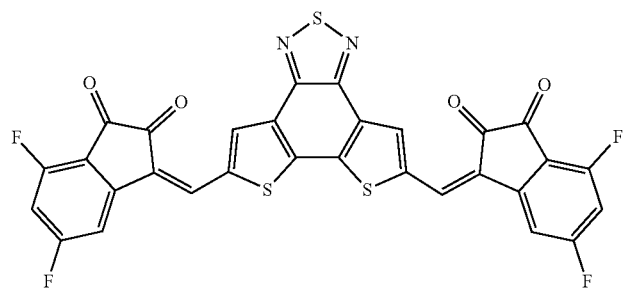
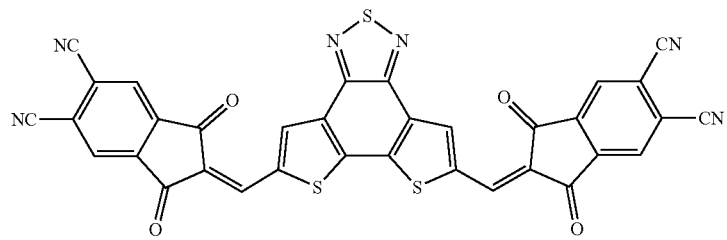
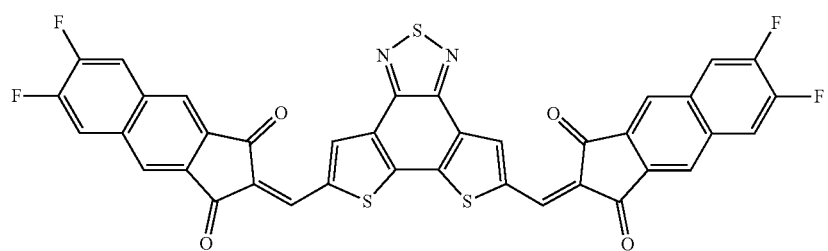
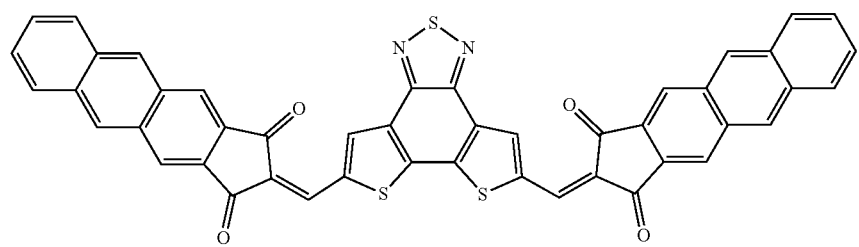

-continued
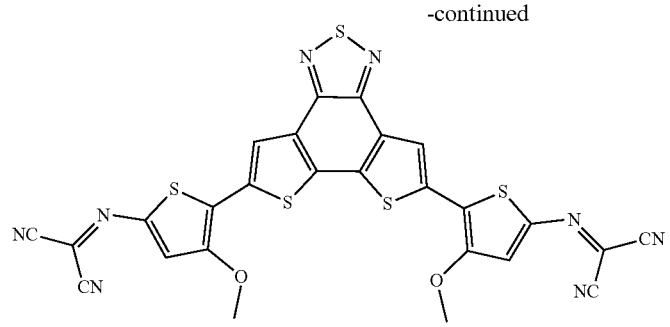
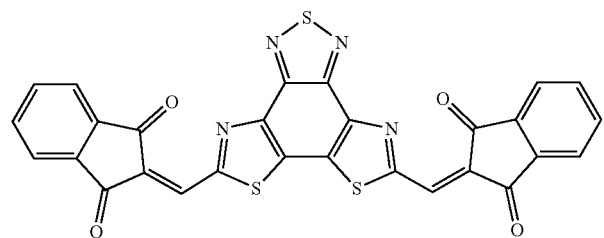
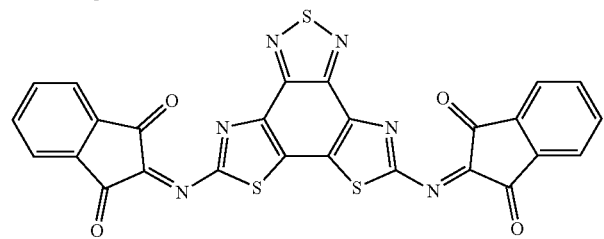
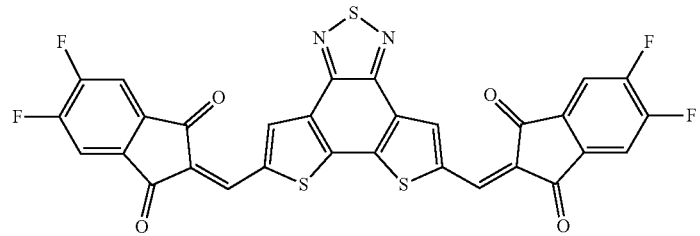
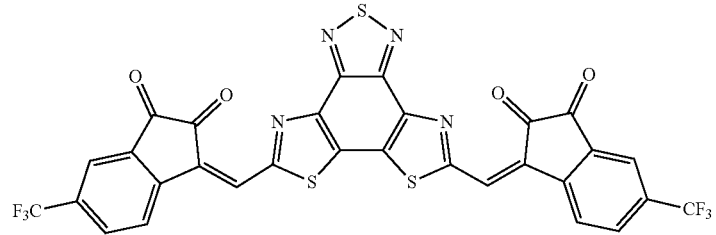
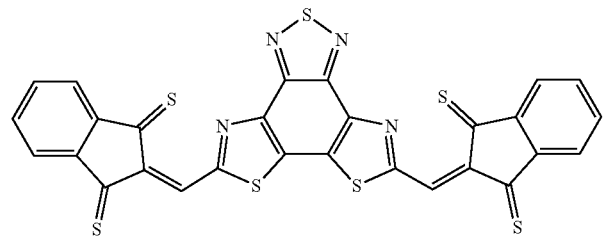
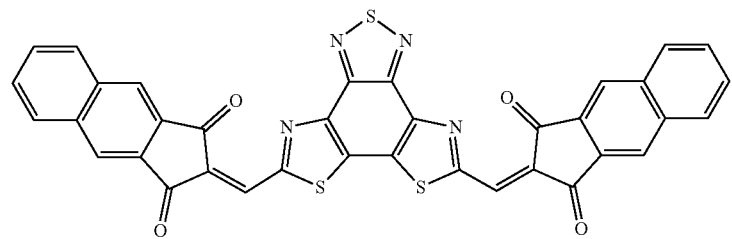

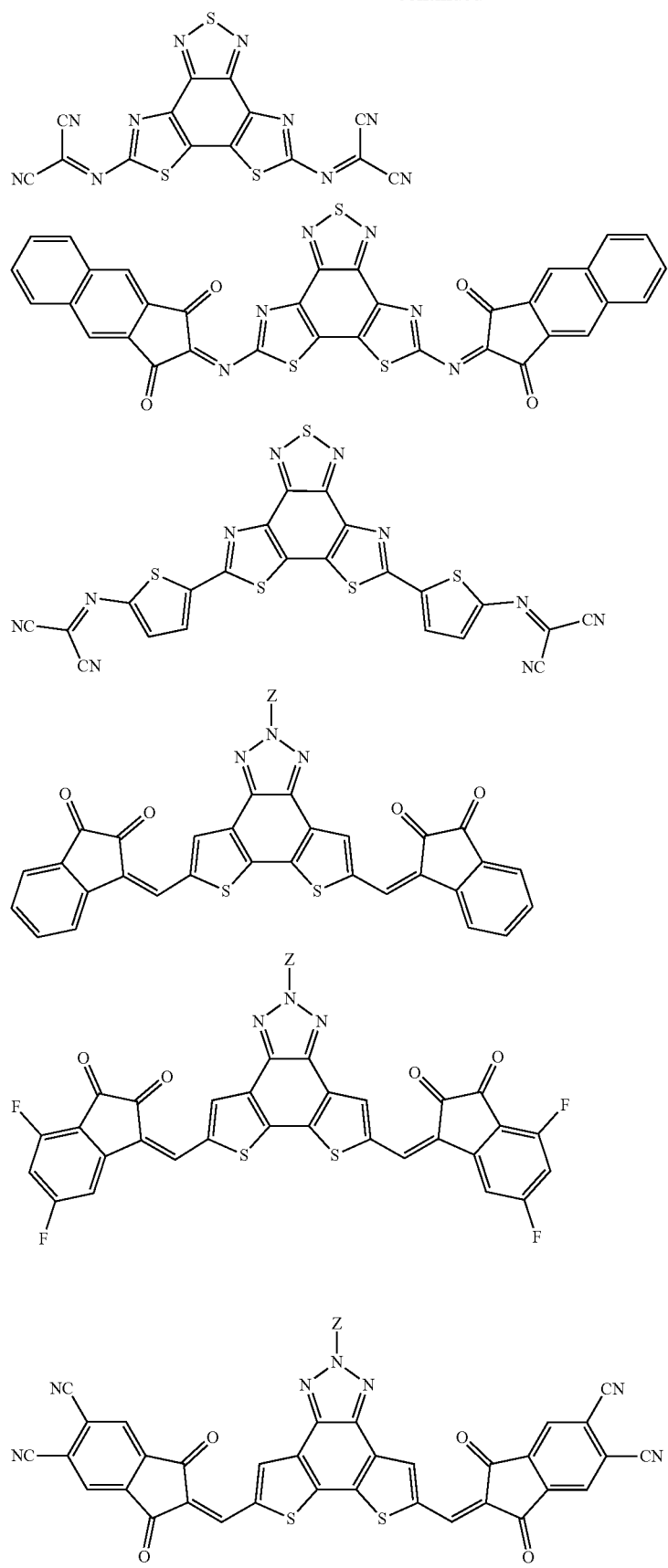

-continued
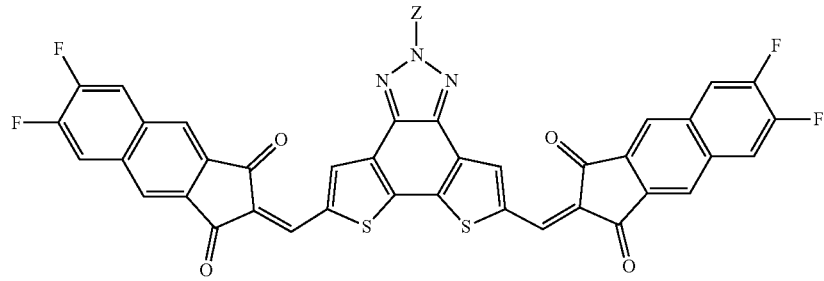
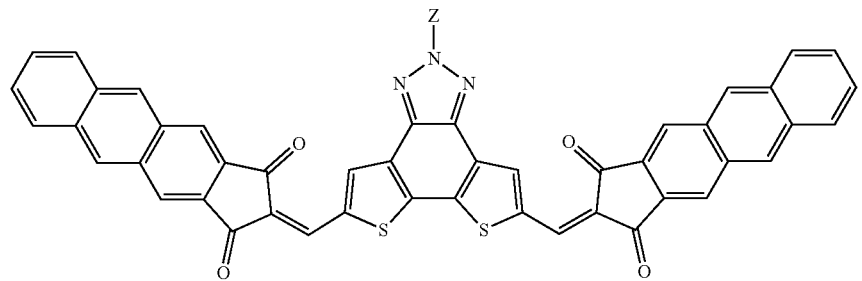
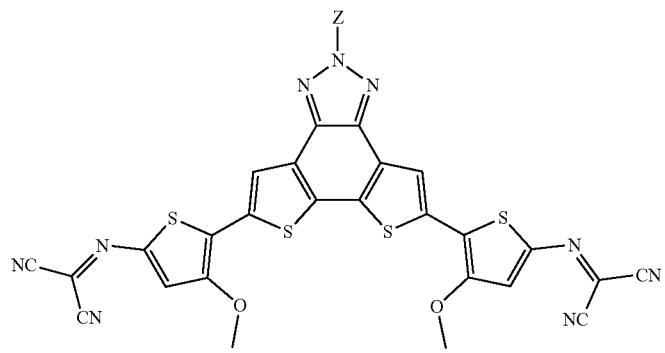
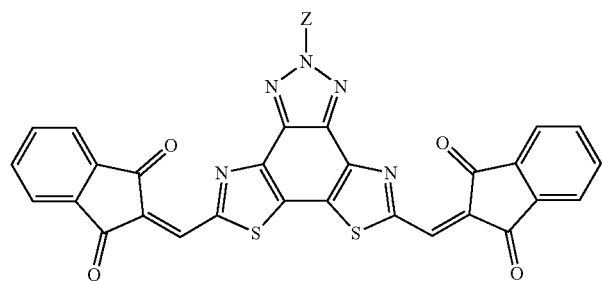
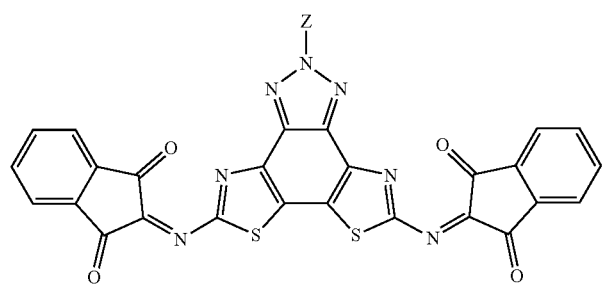

-continued
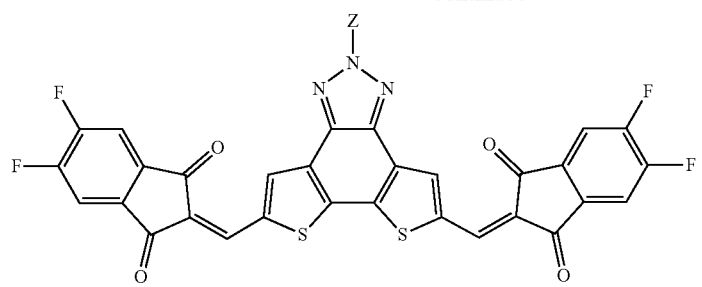
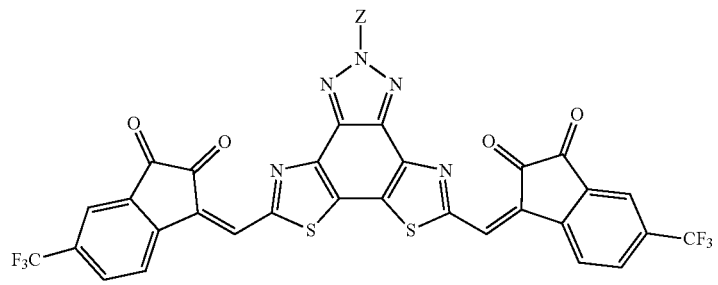
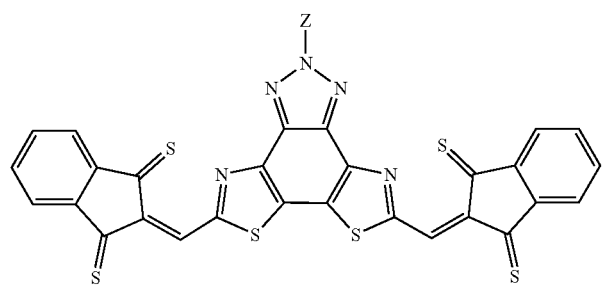
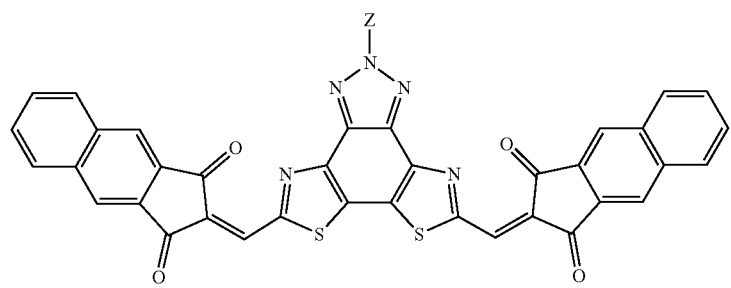
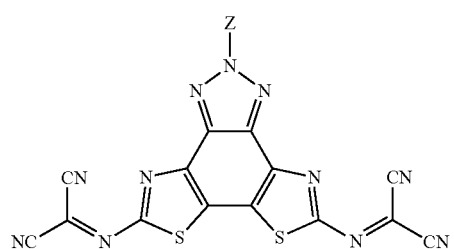
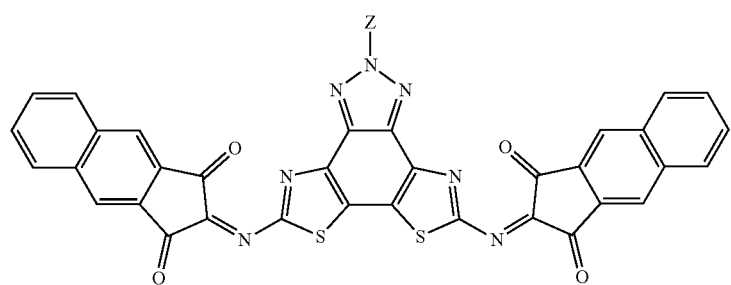

-continued
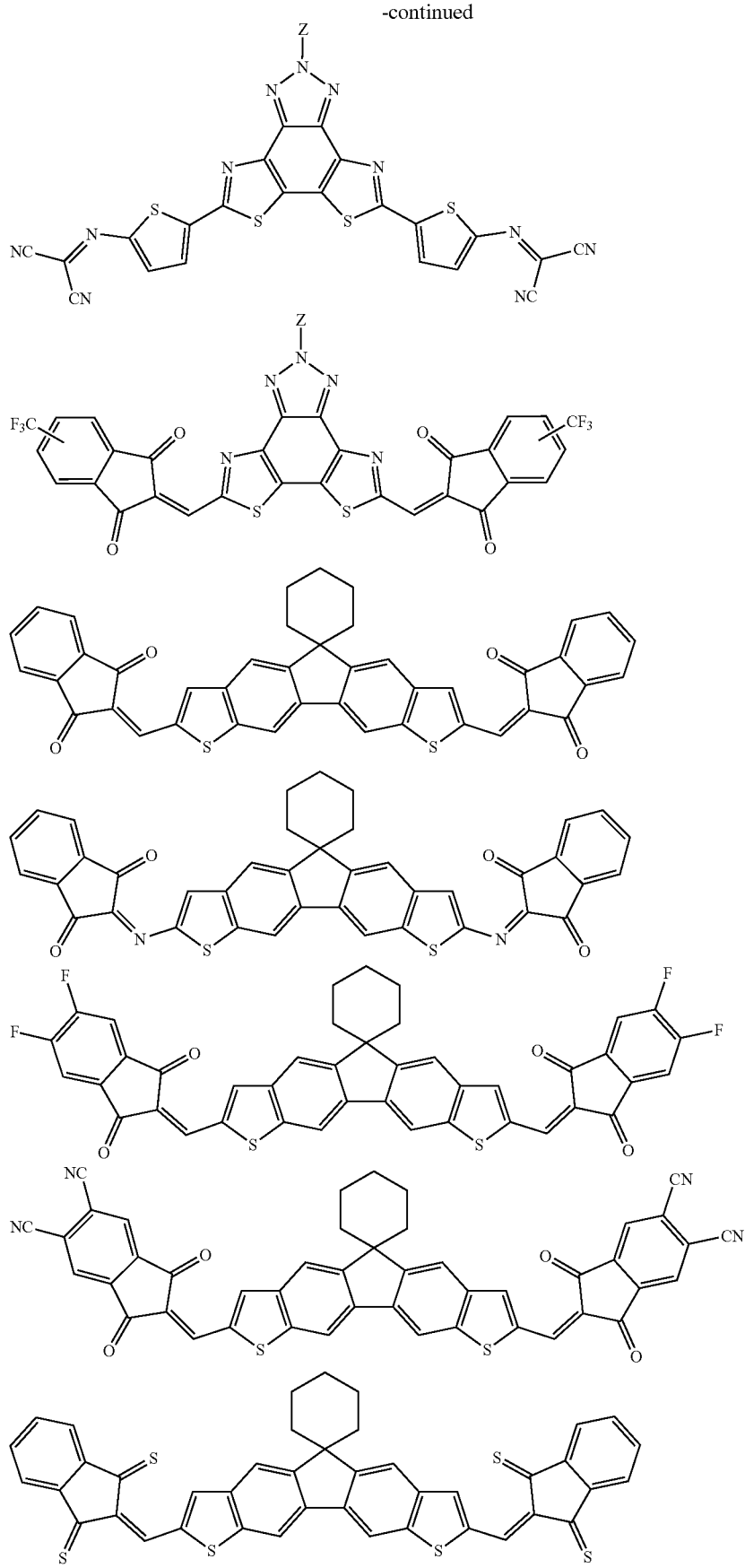

-continued
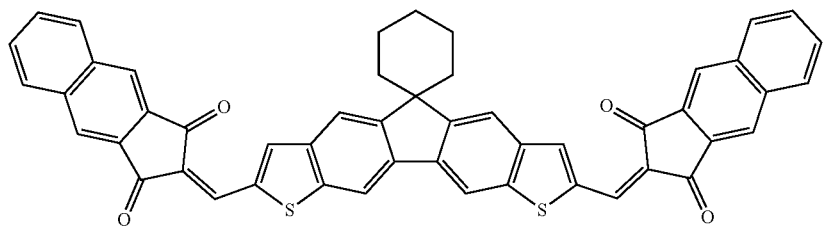
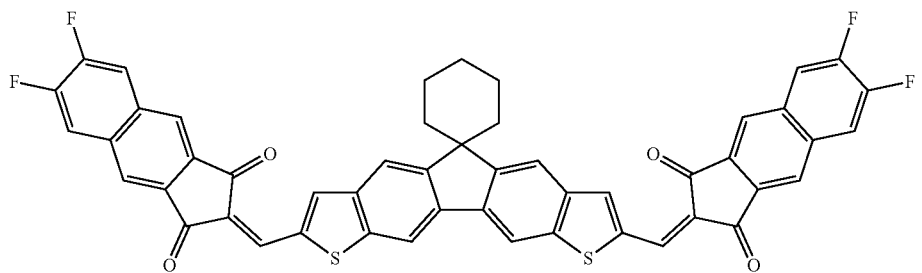
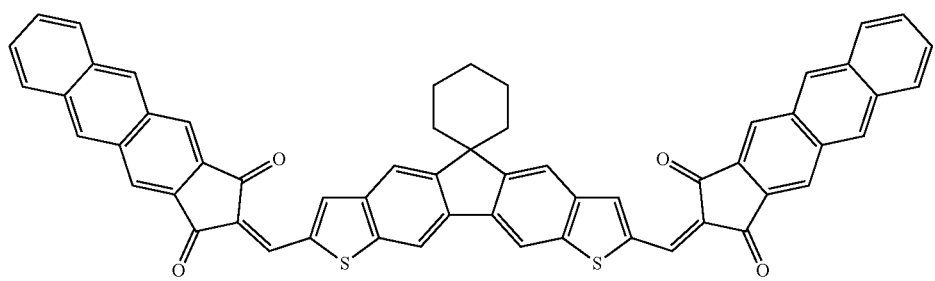
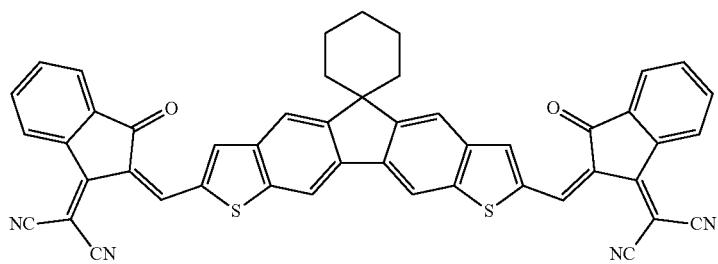
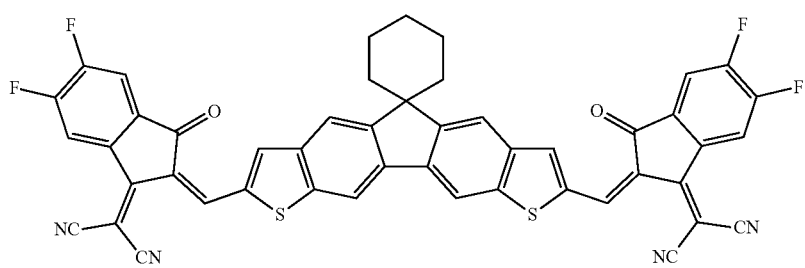
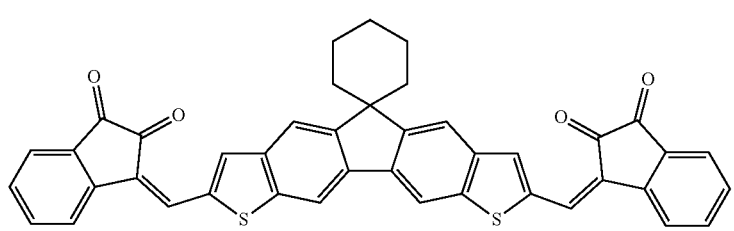

-continued
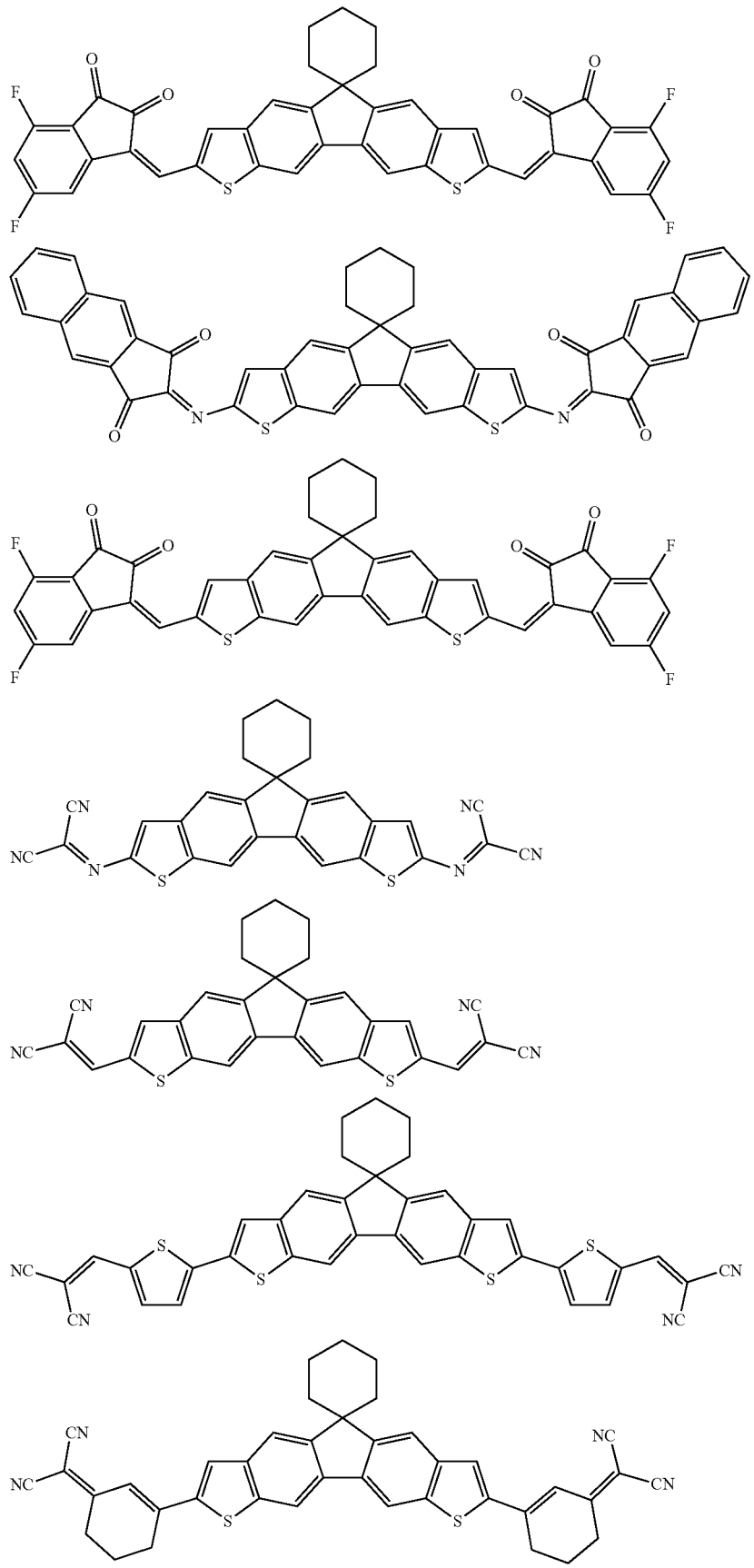

-continued
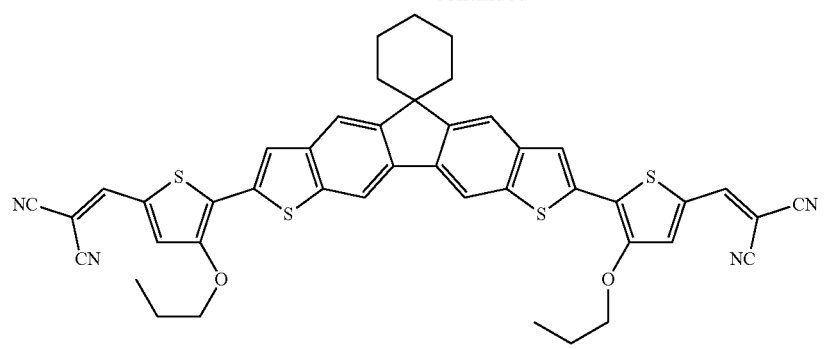
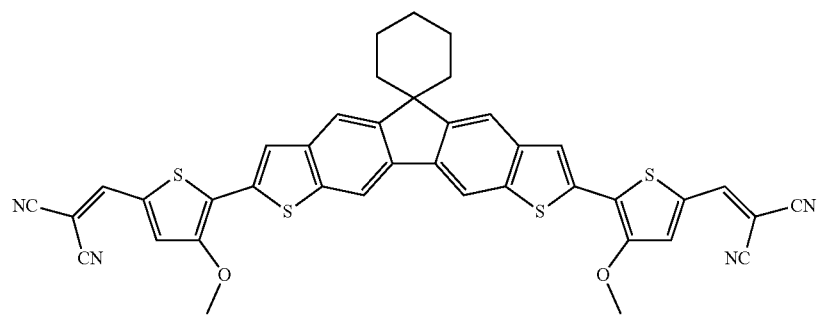
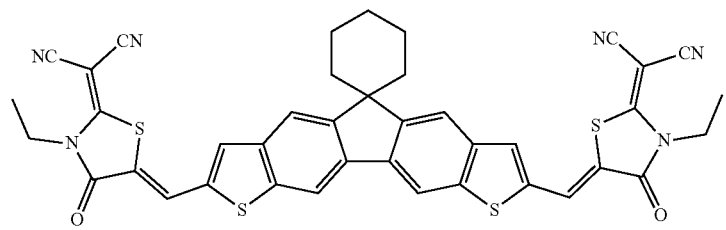
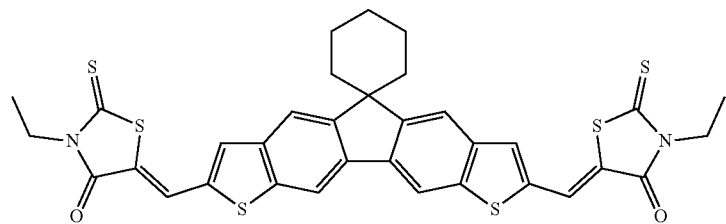
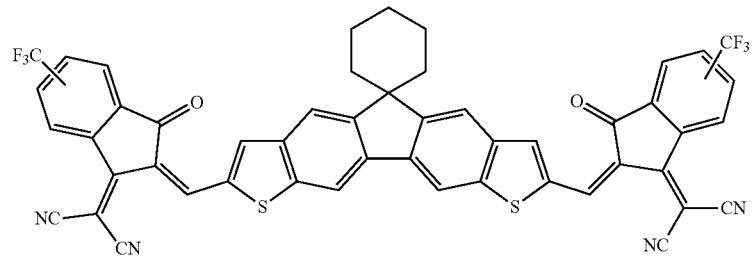
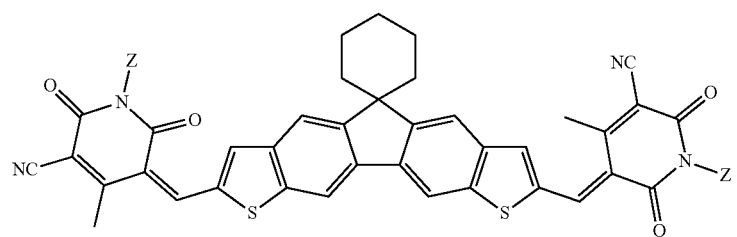

-continued
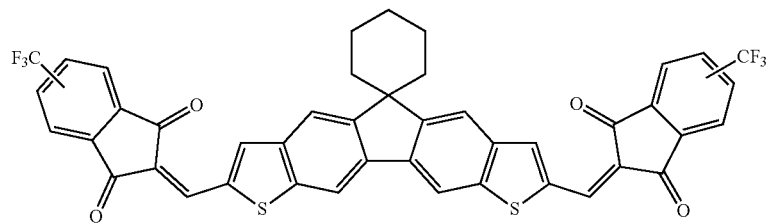
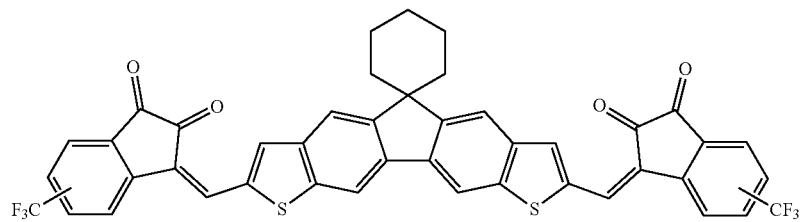
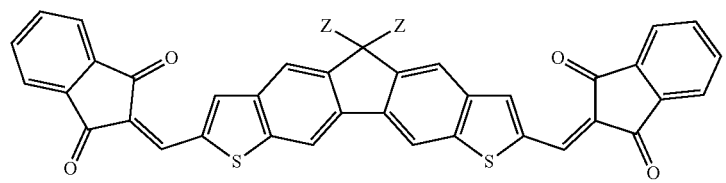
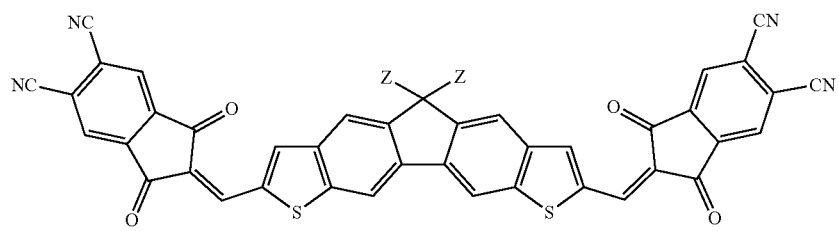
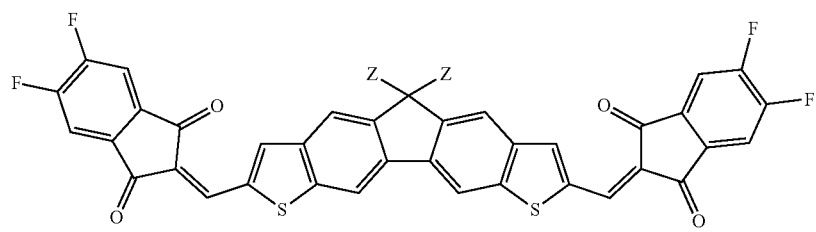
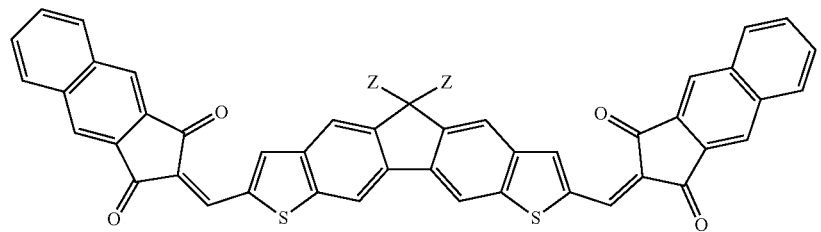
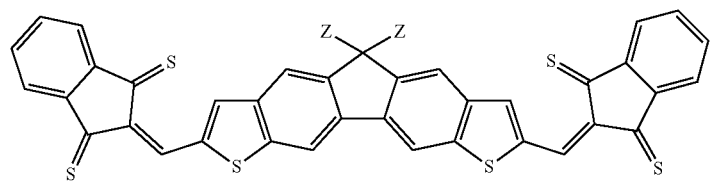

-continued
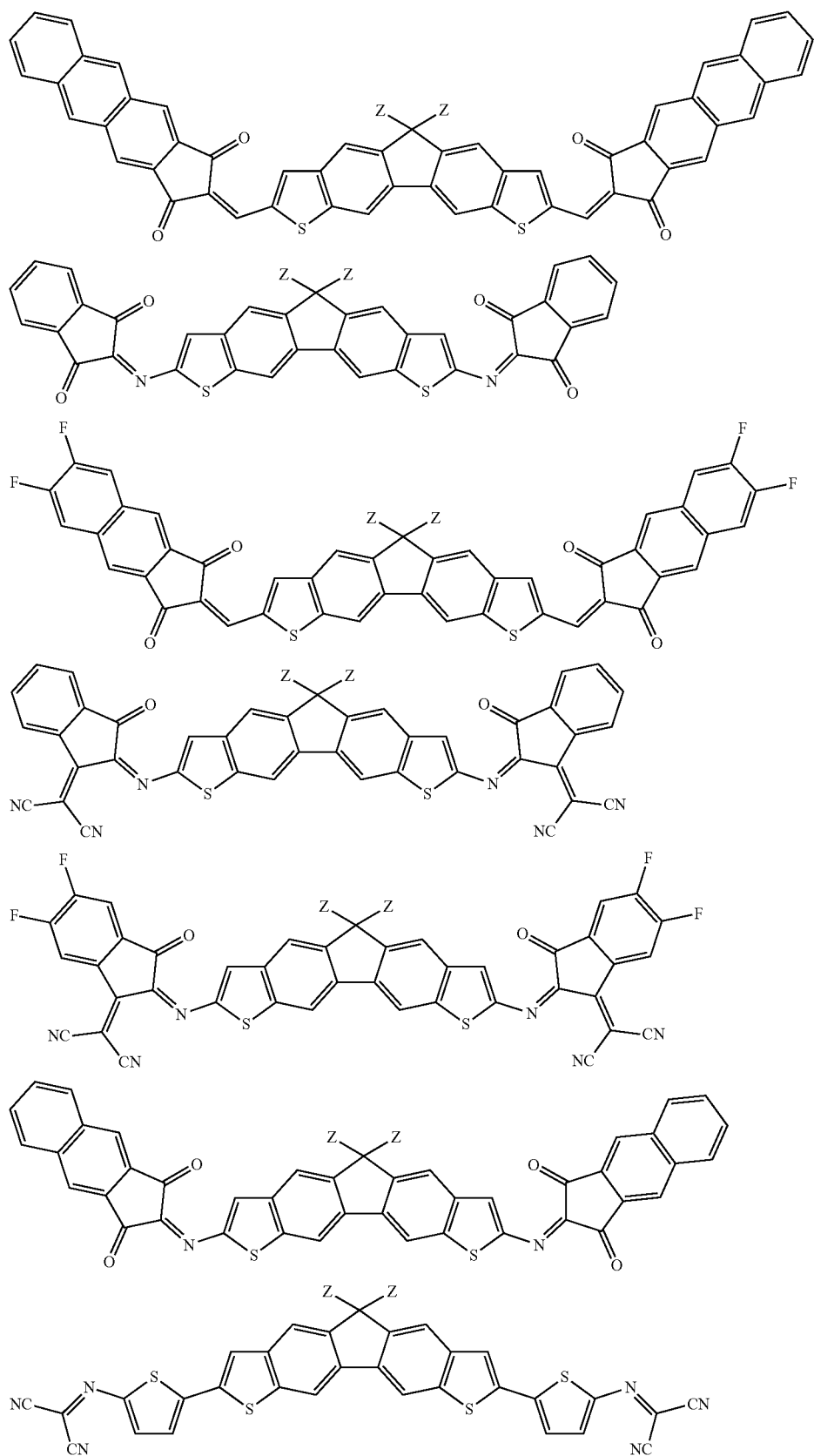

-continued
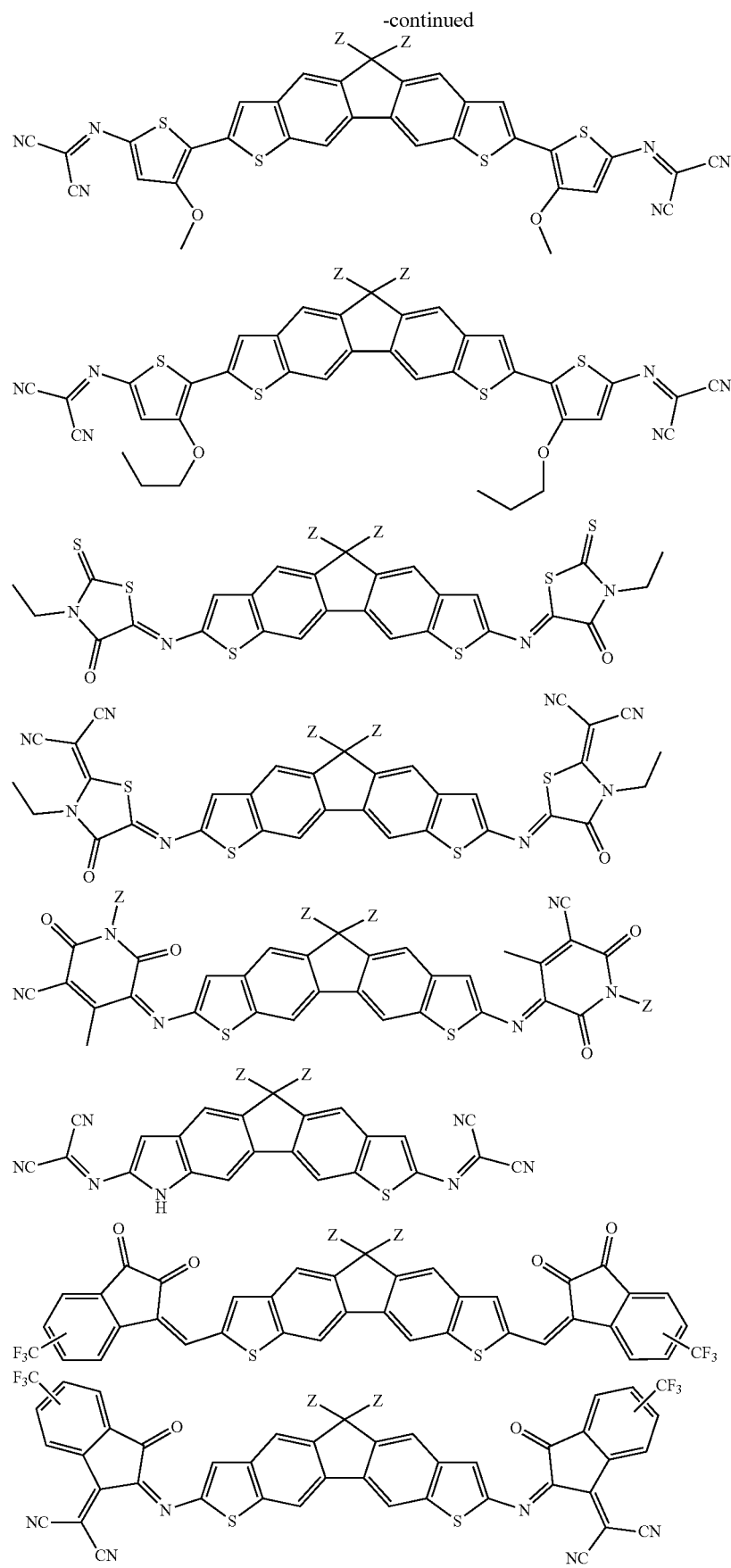

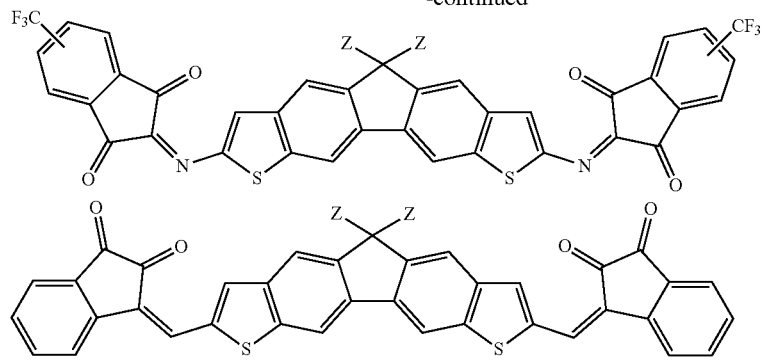
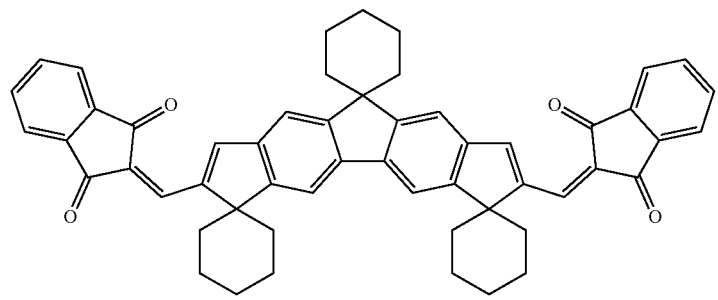
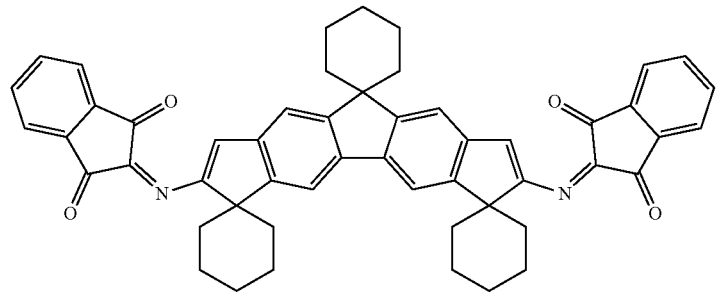
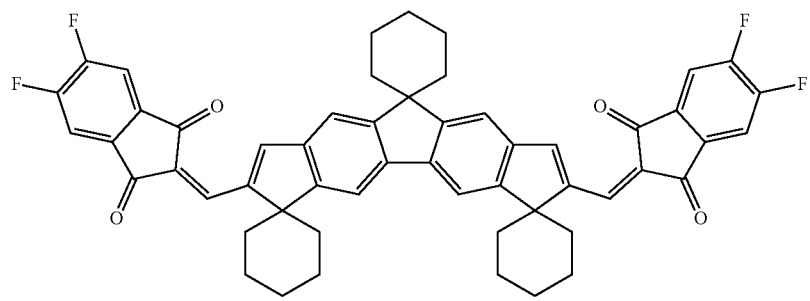
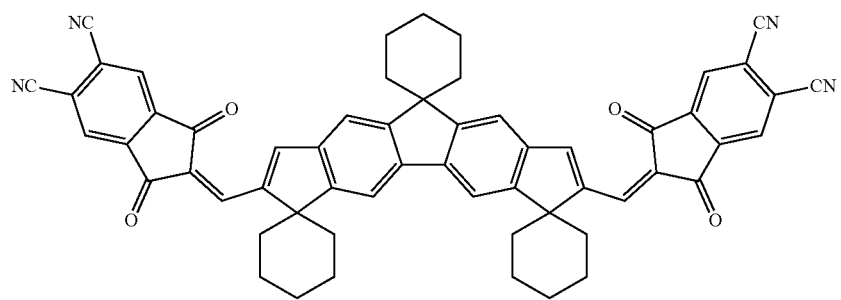

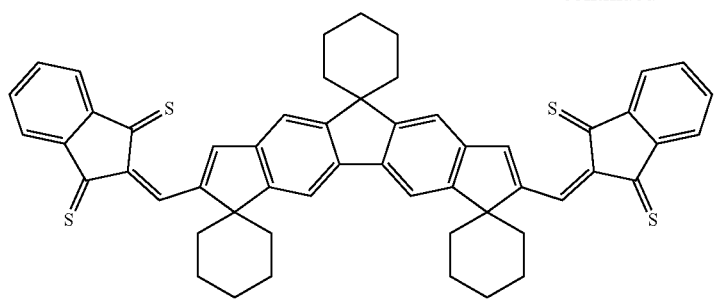
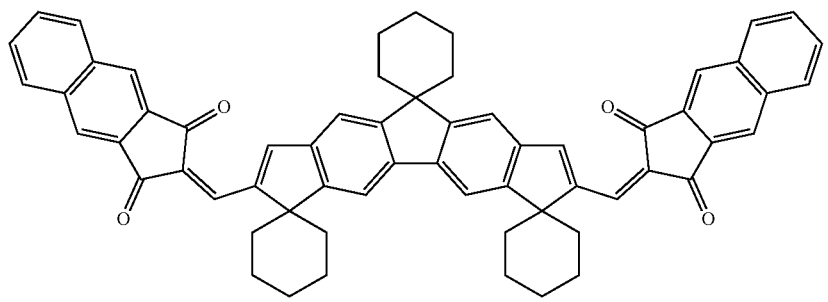
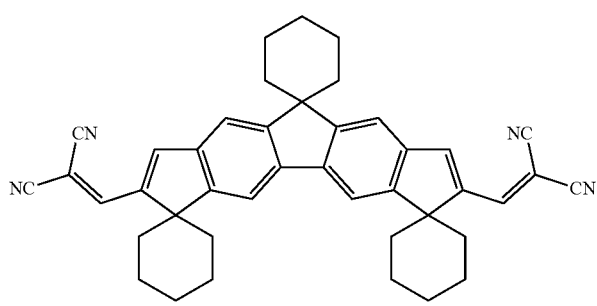
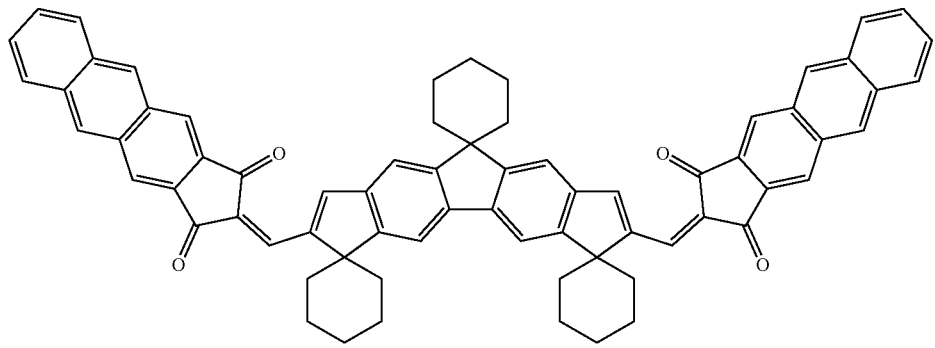
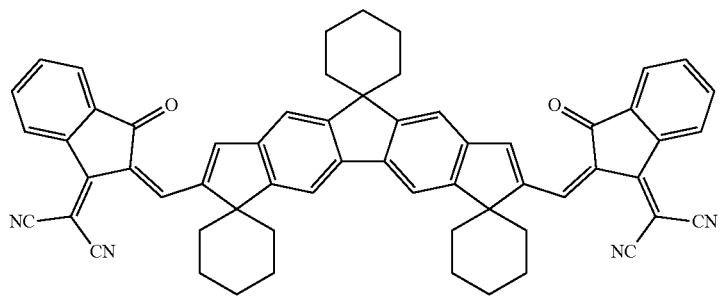

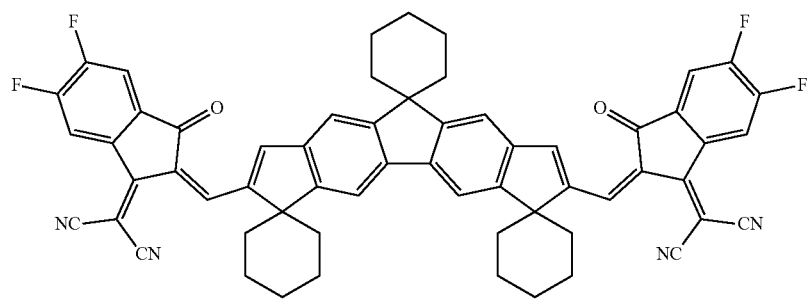
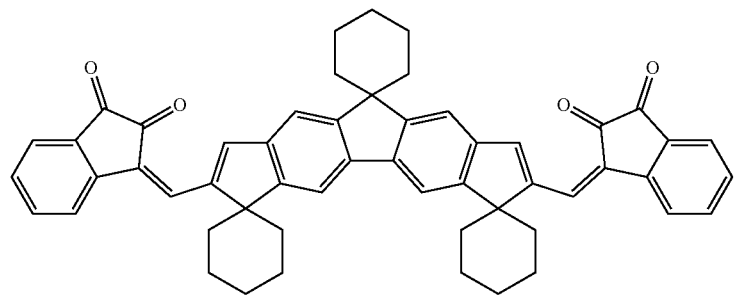
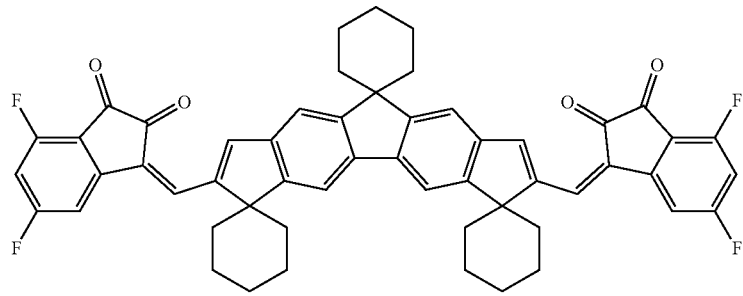
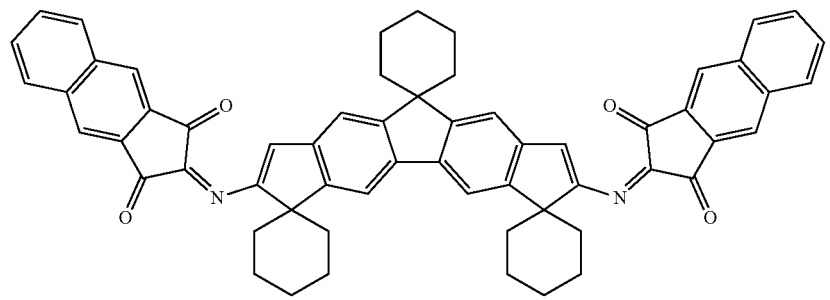
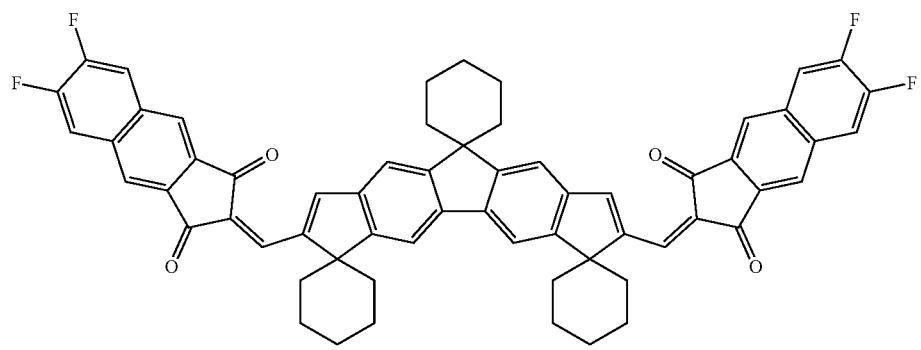

-continued
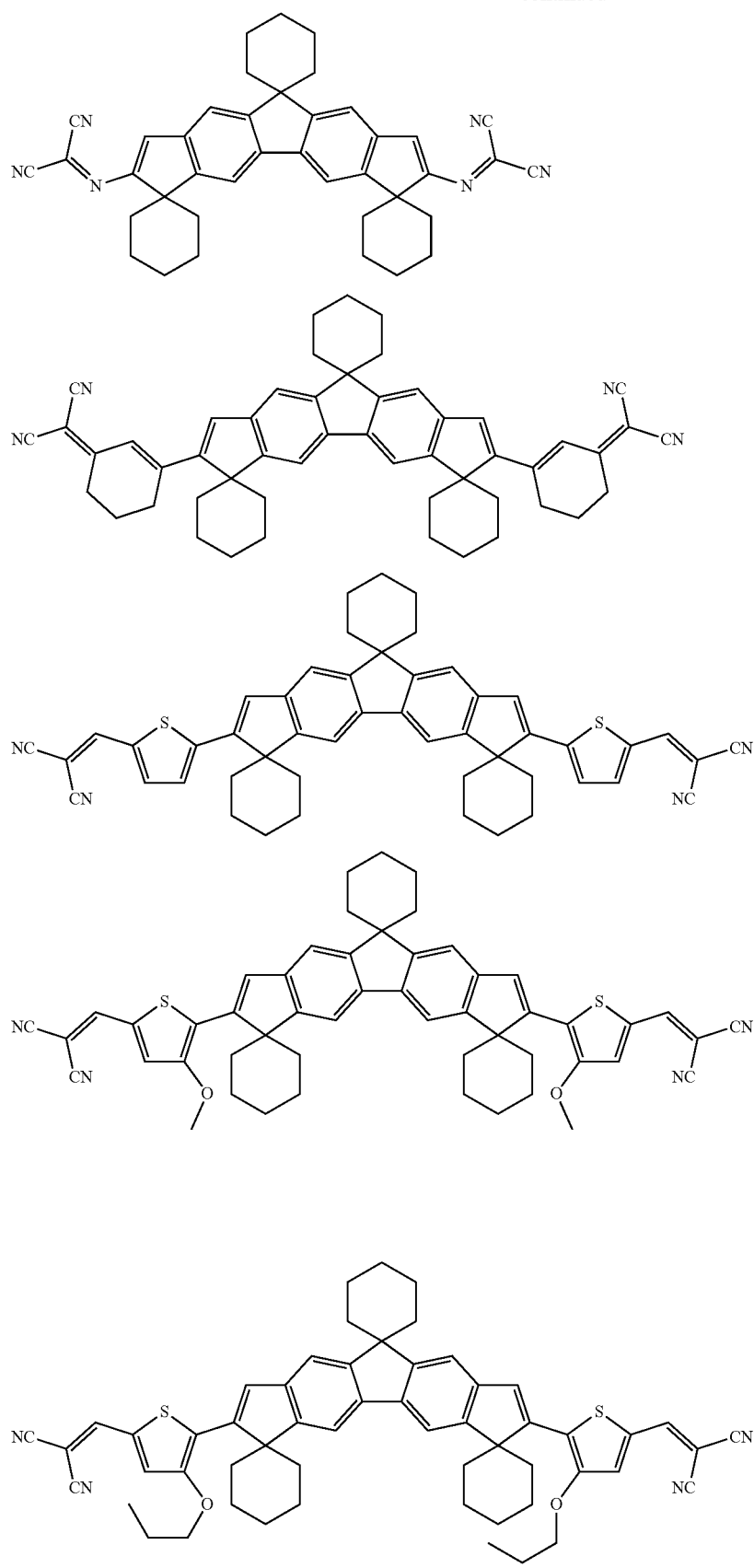

-continued
| 711 | 712 |
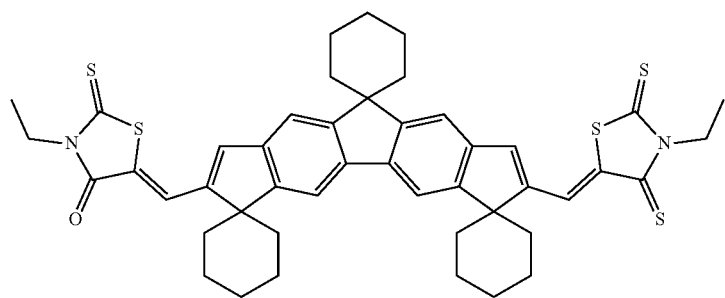
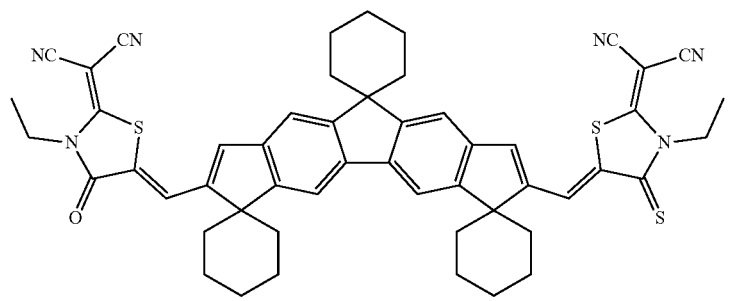
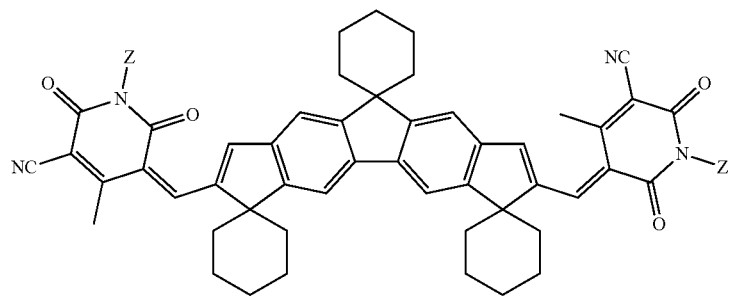
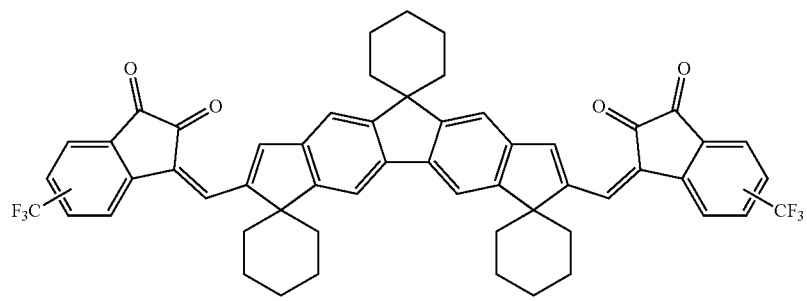
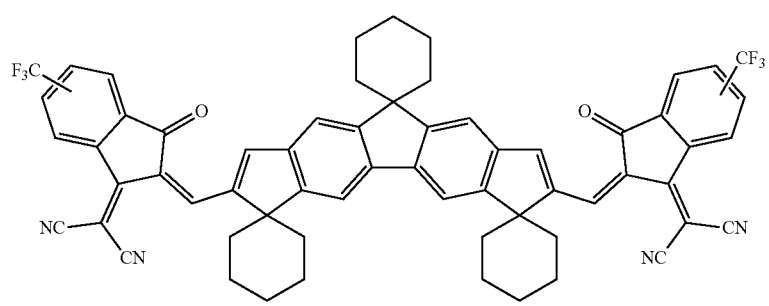

-continued
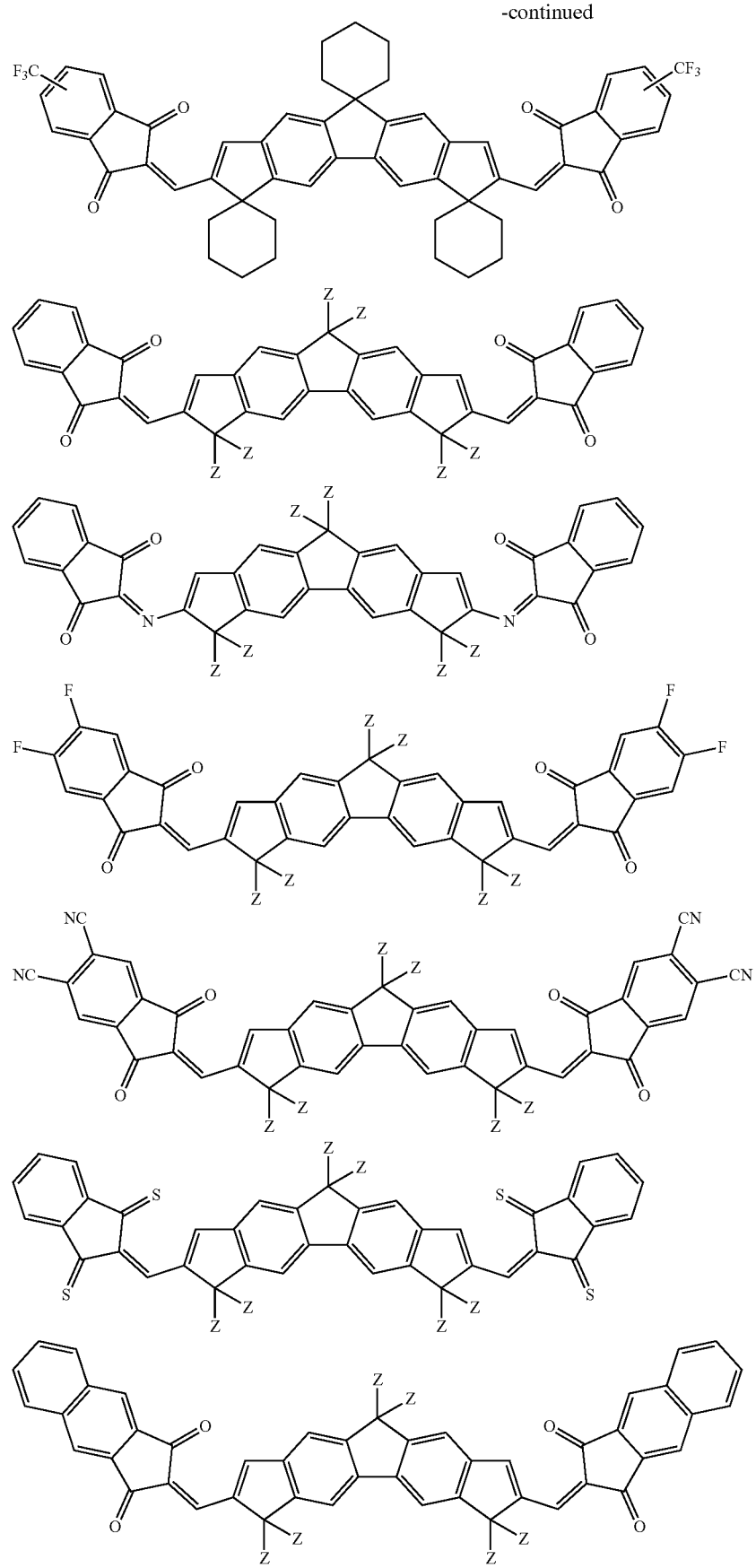

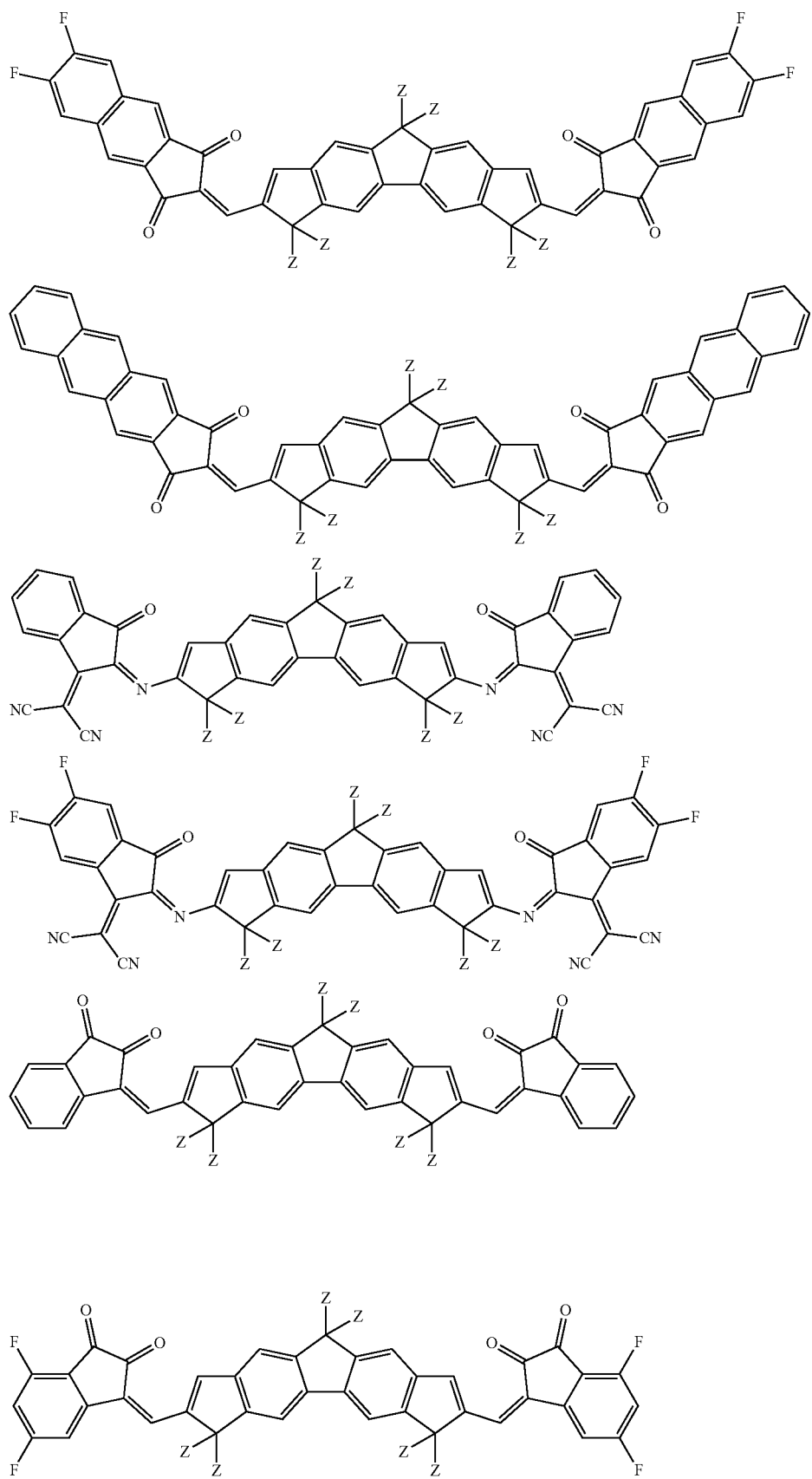

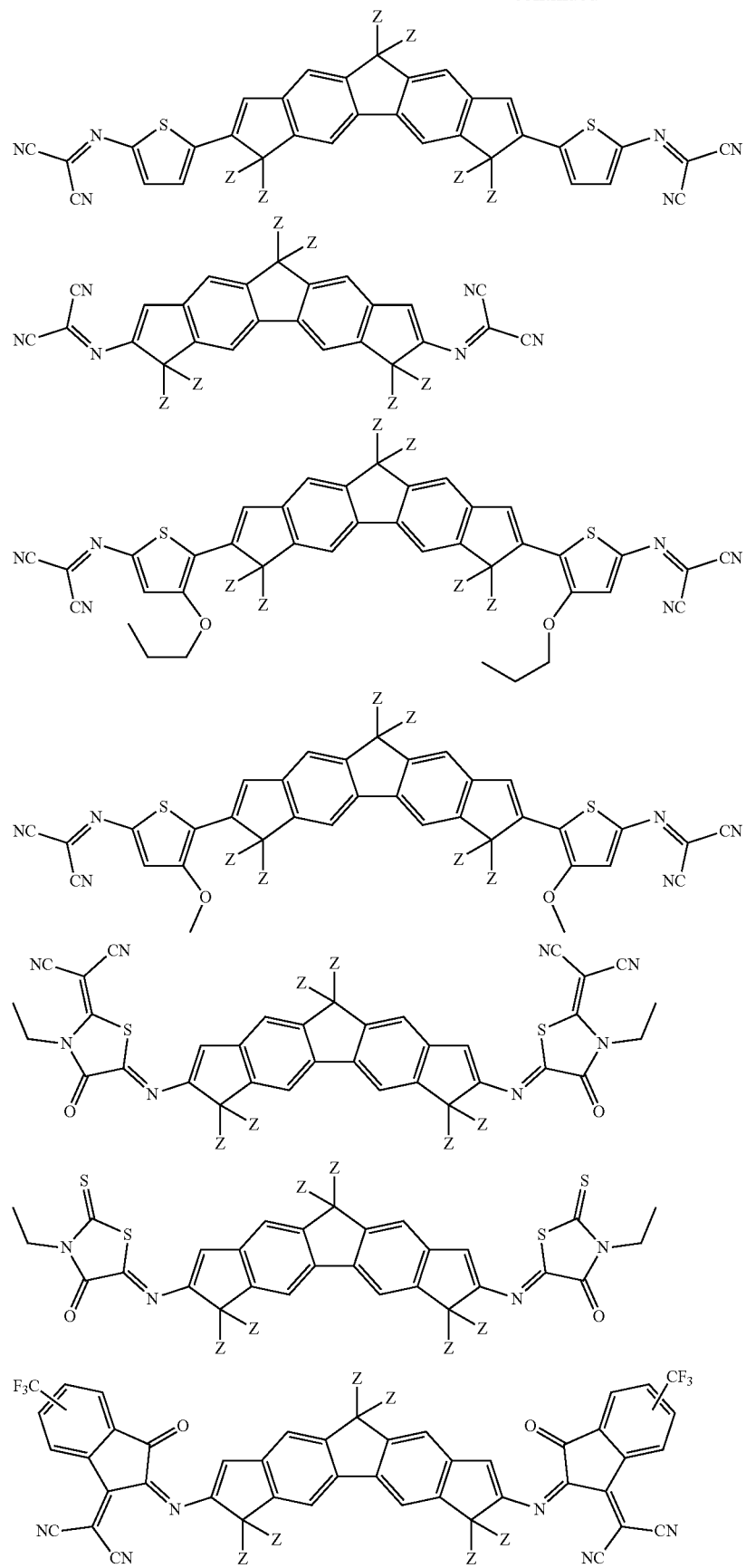
-continued

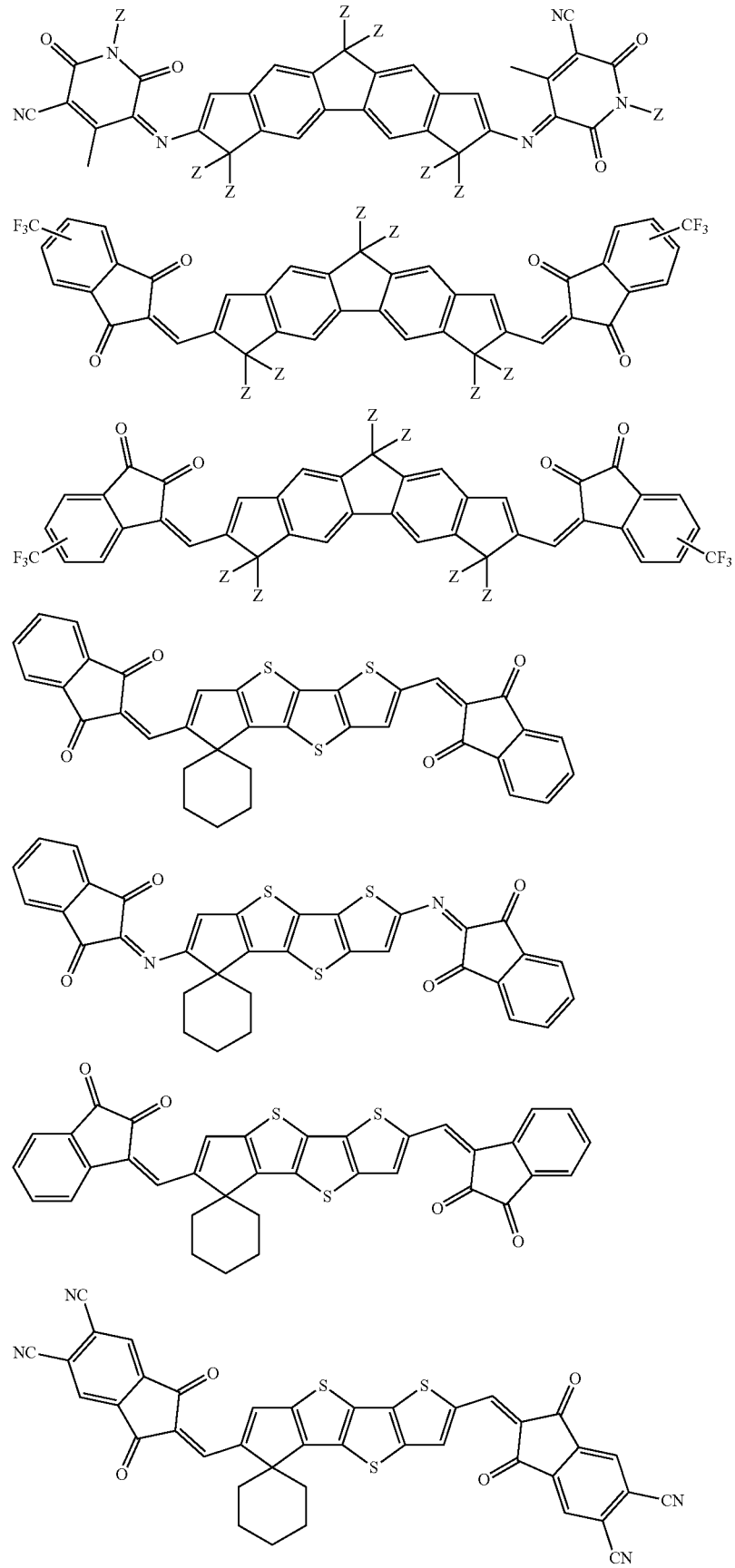

-continued
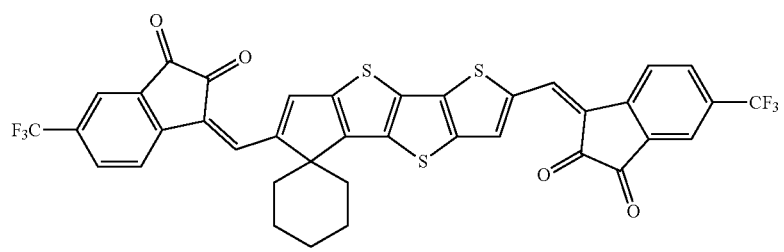
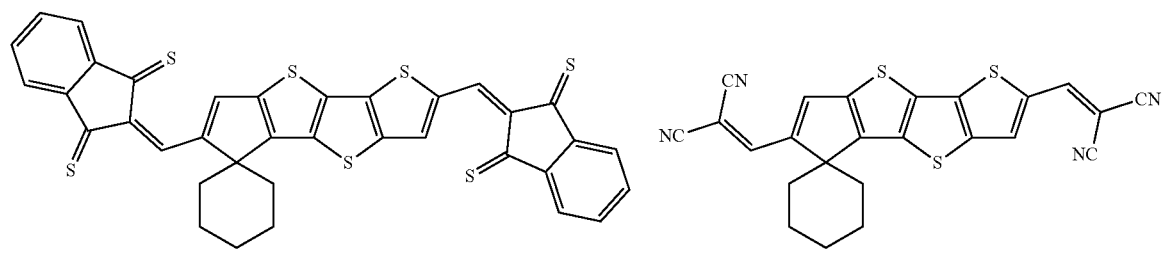
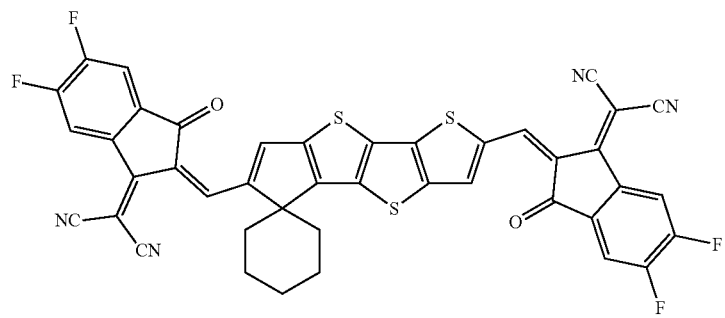
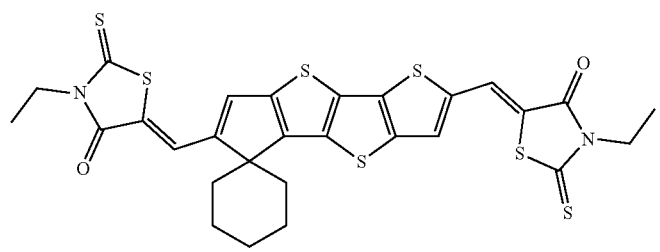
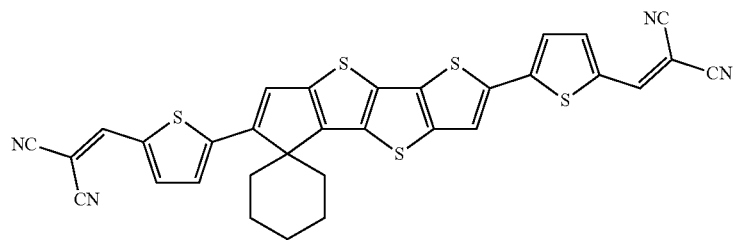
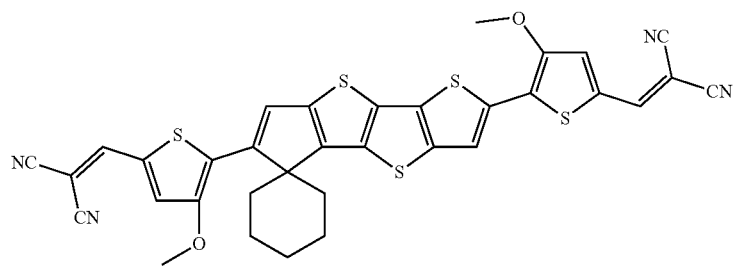

-continued
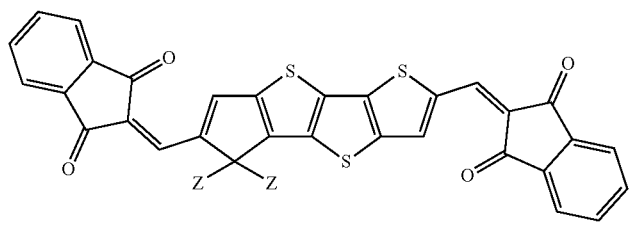
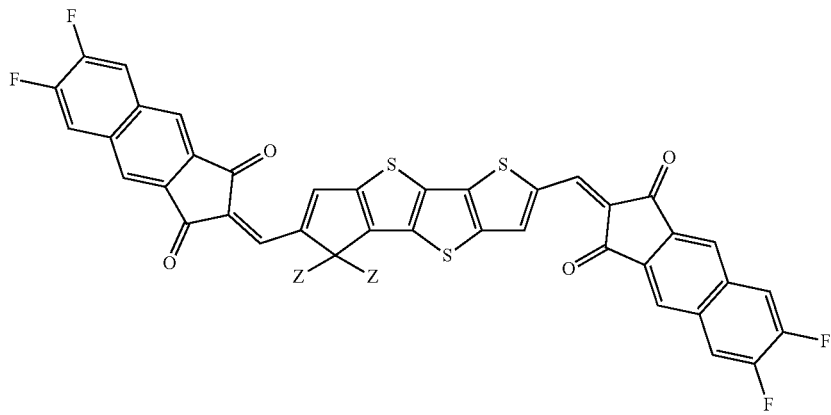
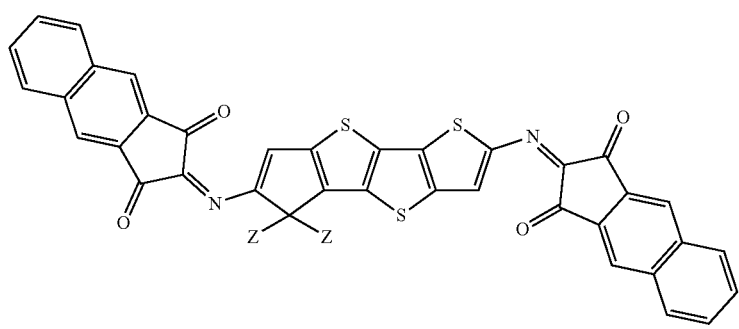
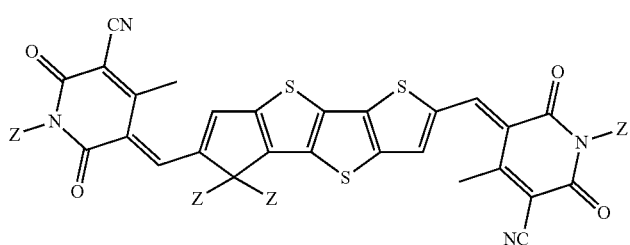
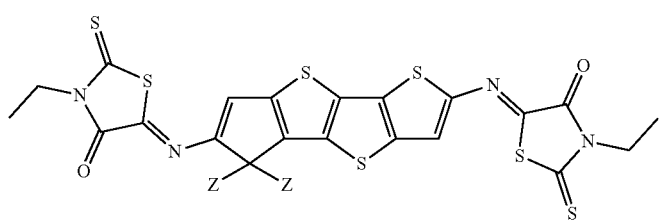
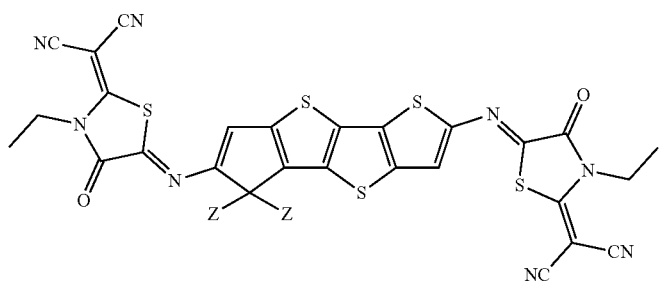

-continued
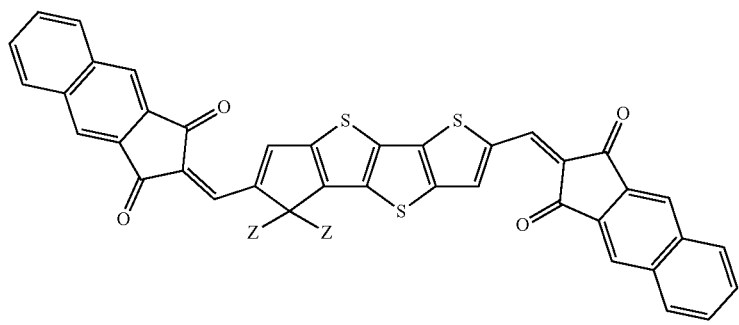
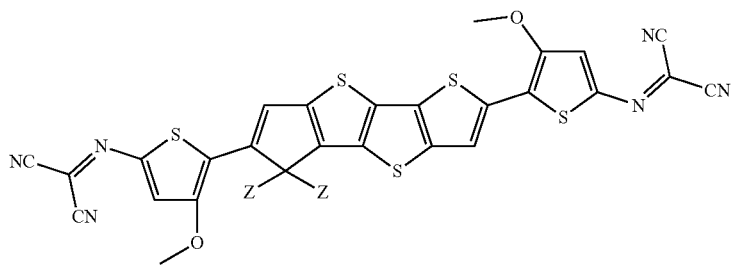
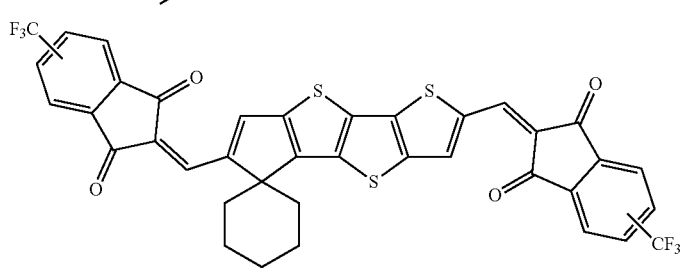
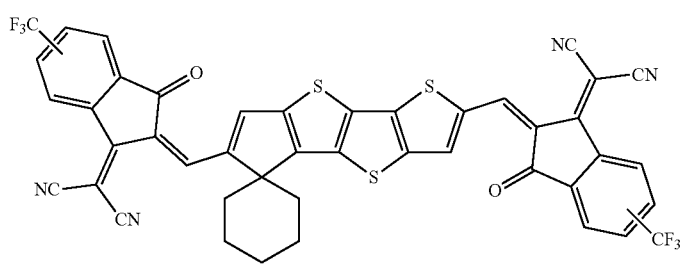
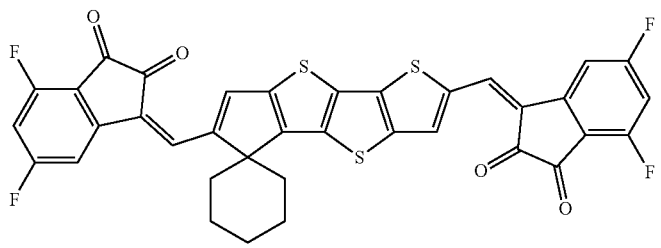

-continued
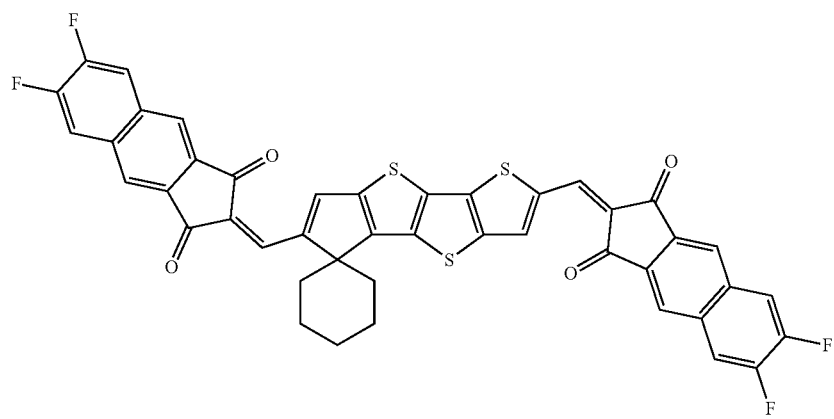
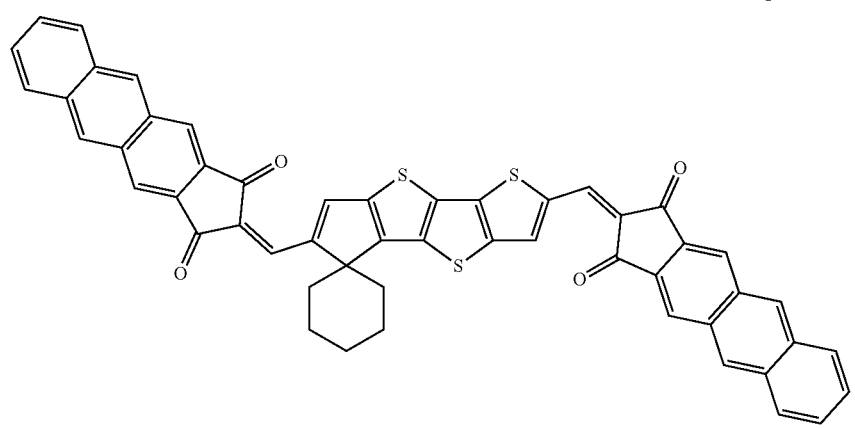
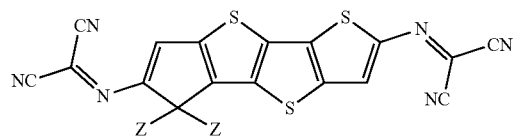
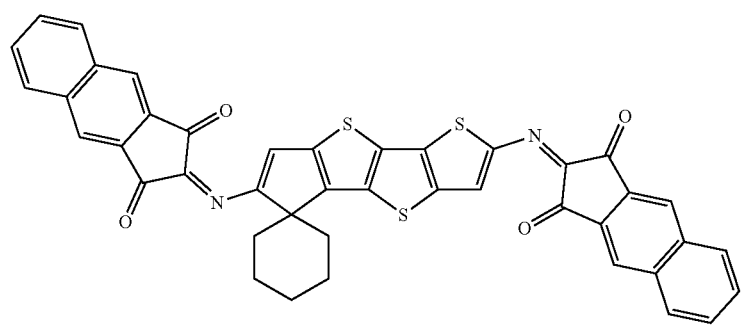
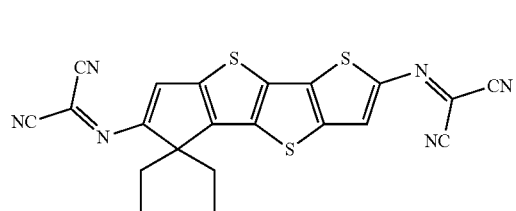
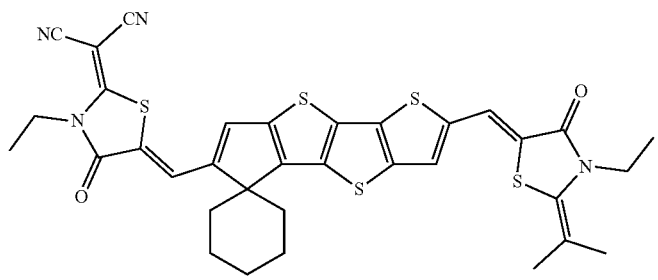

-continued
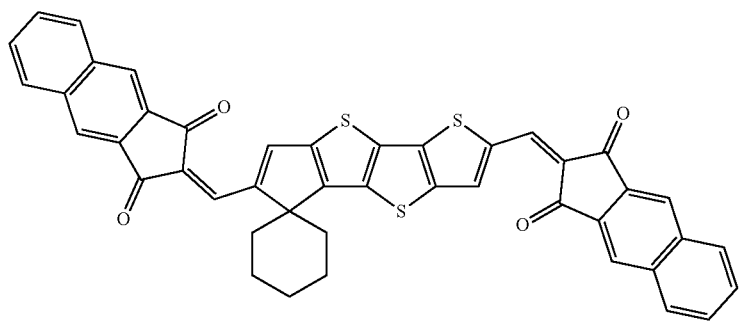
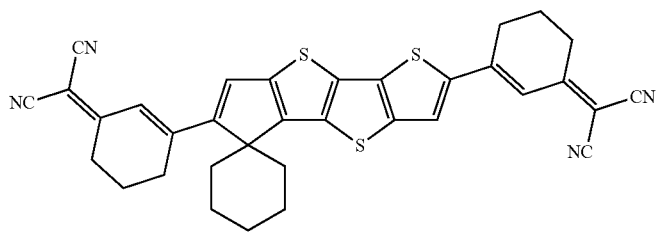
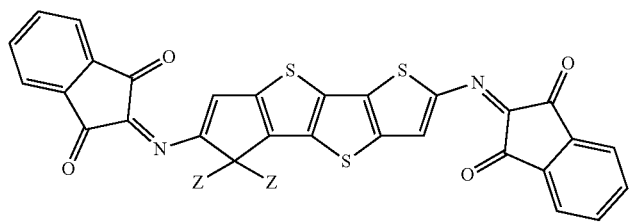
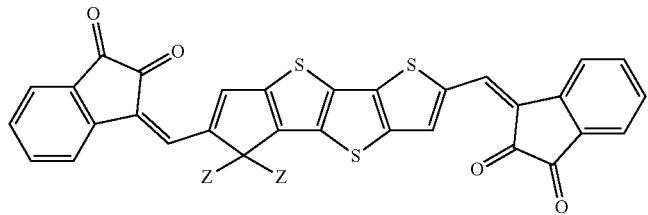
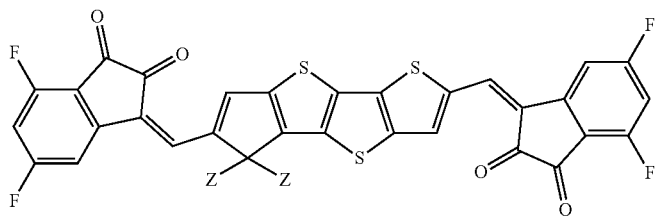
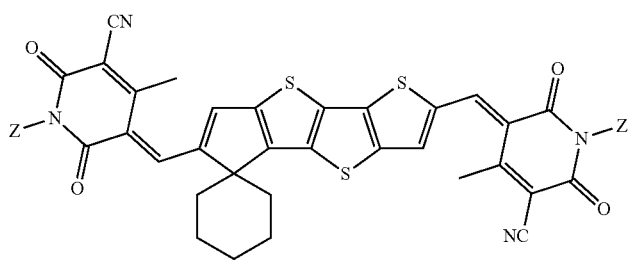
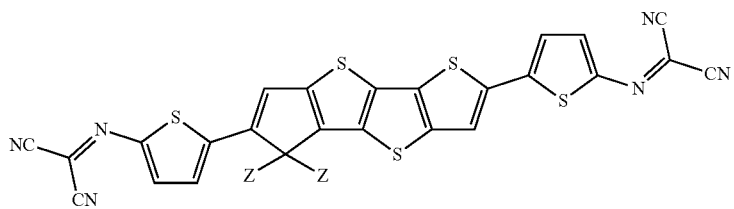

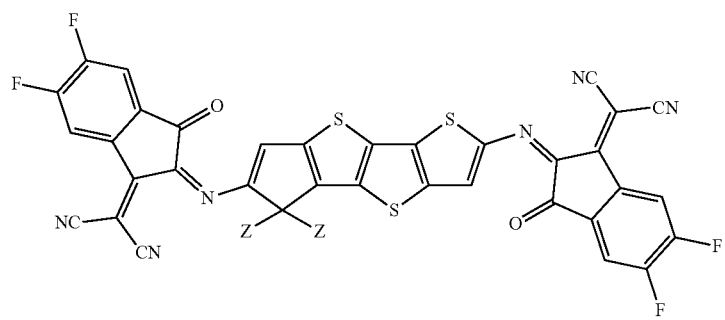
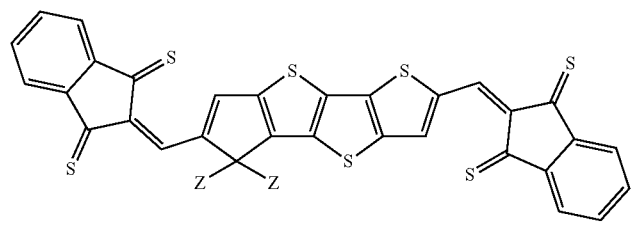
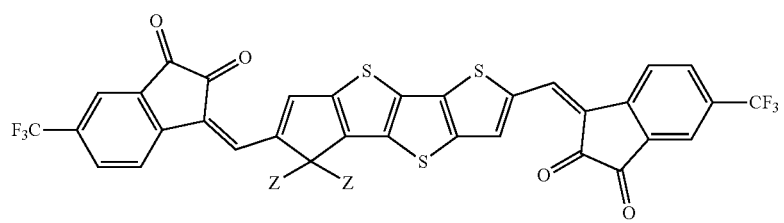
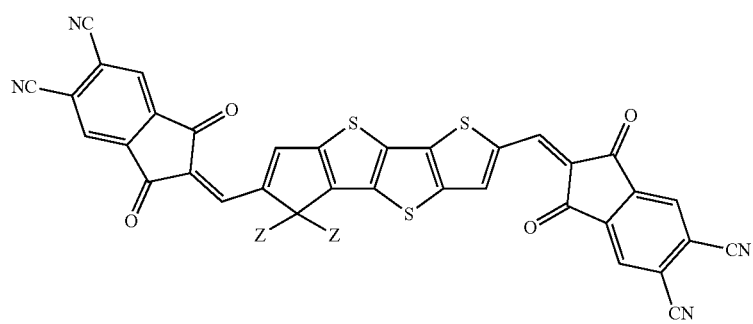
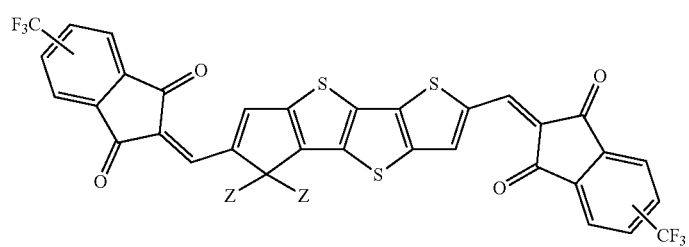
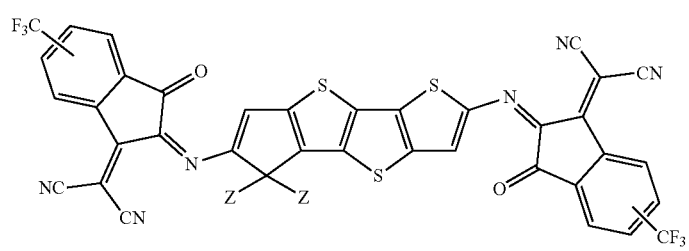

-continued
733
734
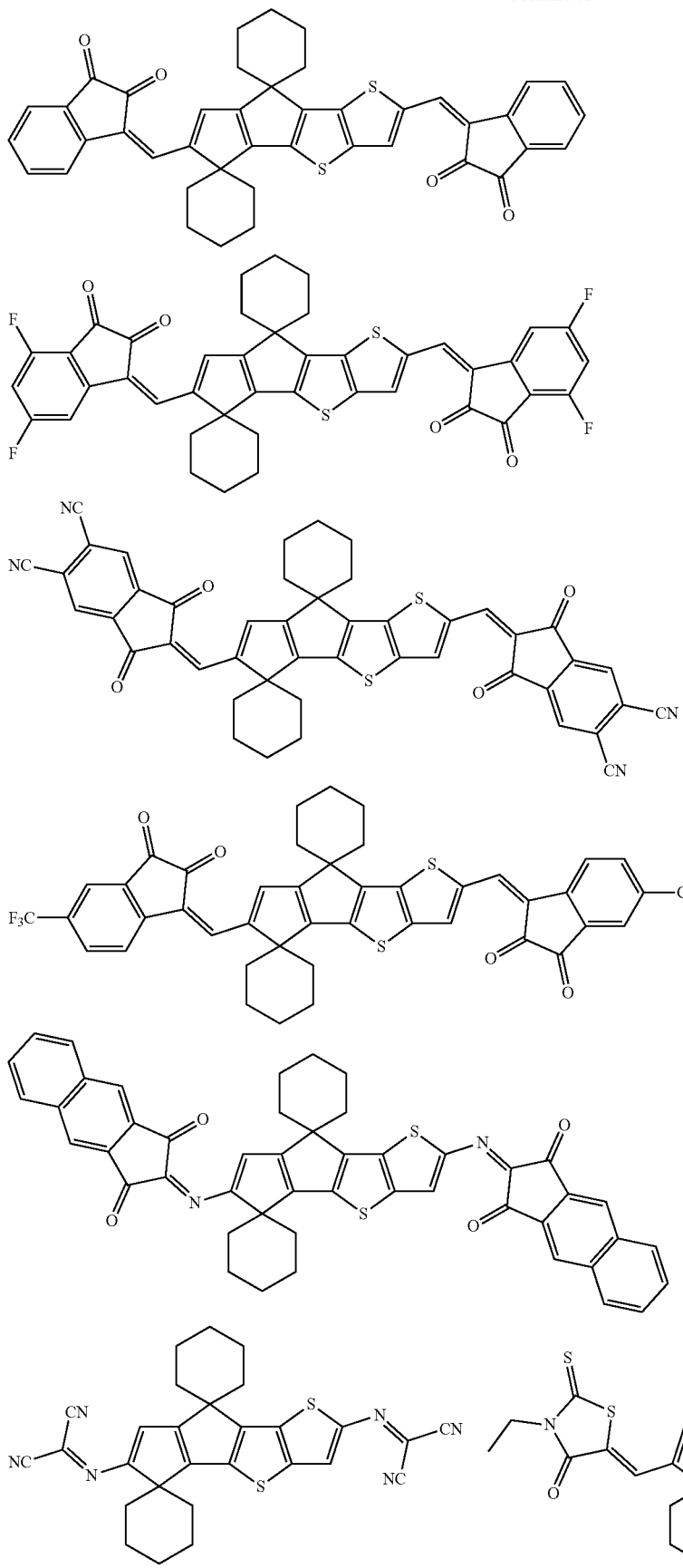

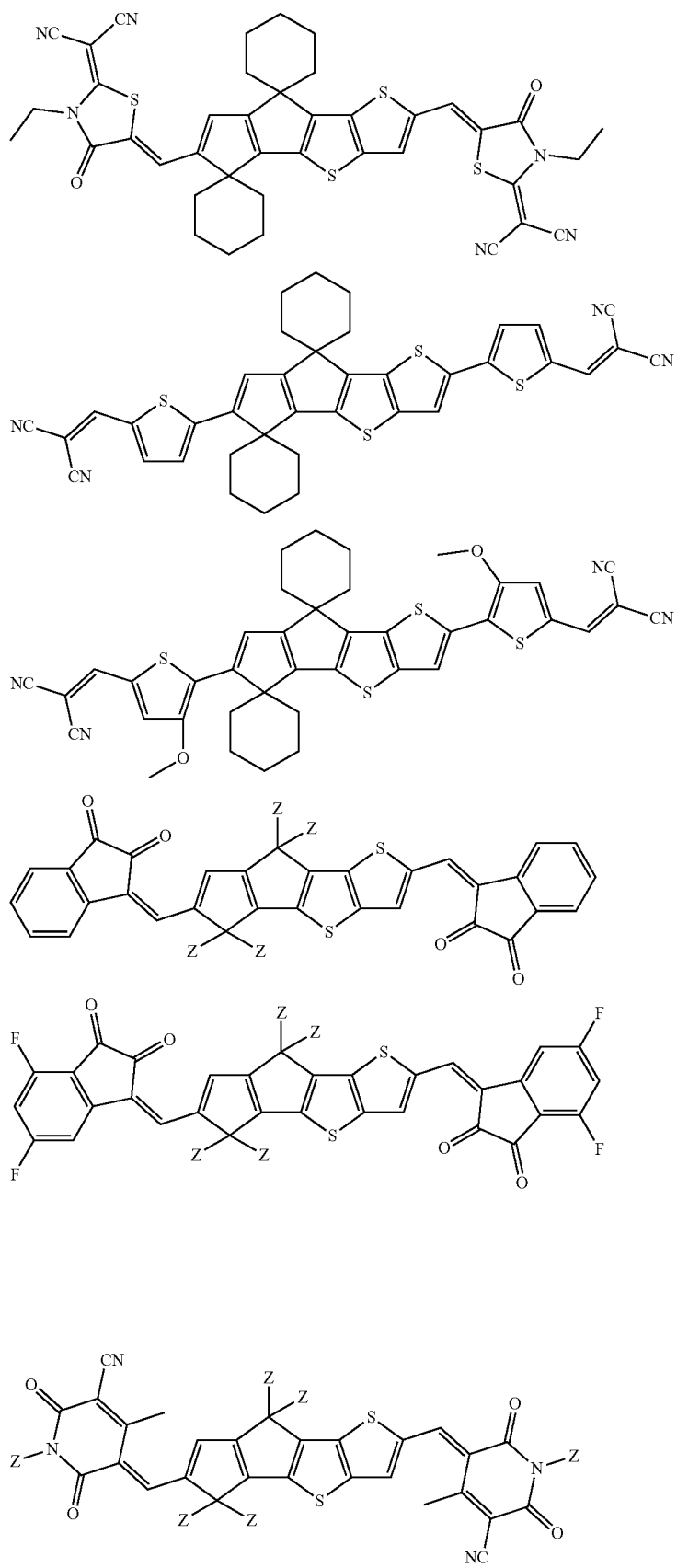

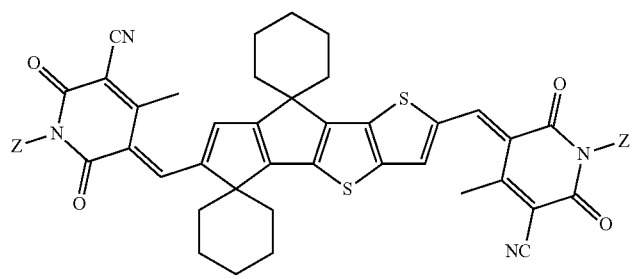
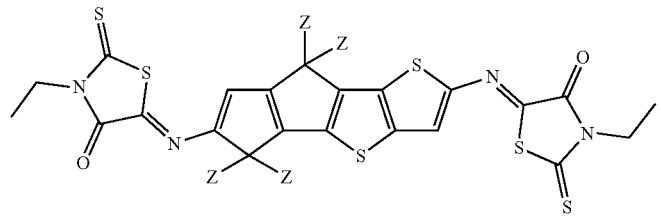
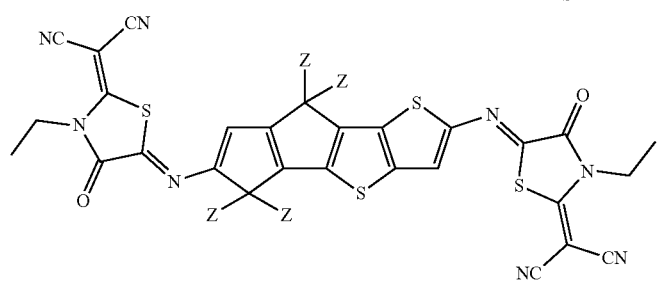
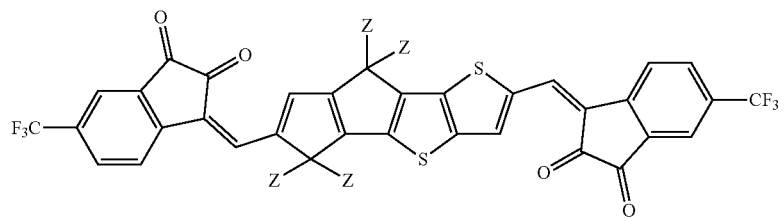
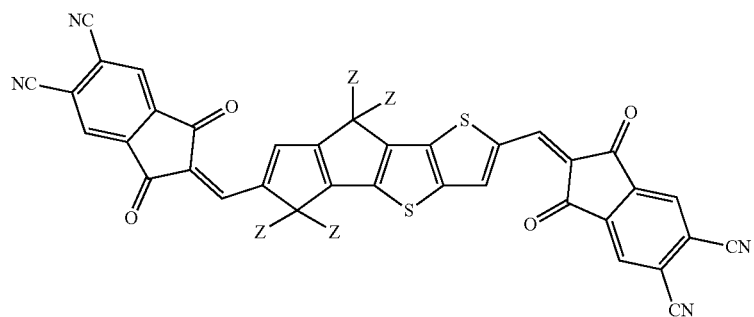
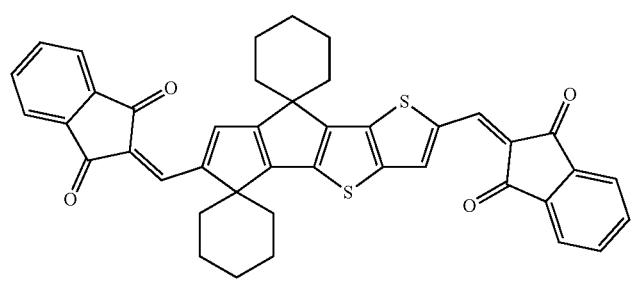 [SMILES: O=C1C(=CC2=CC3=C(c4sc5cc(C=C6C(=O)c7ccccc7C6=O)sc5c4C34CCCCC4)C23CCCCC3)C(=O)c2ccccc21]

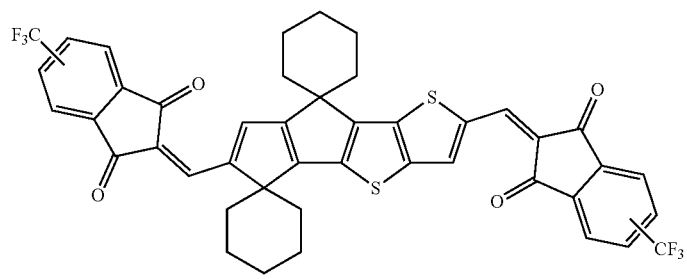
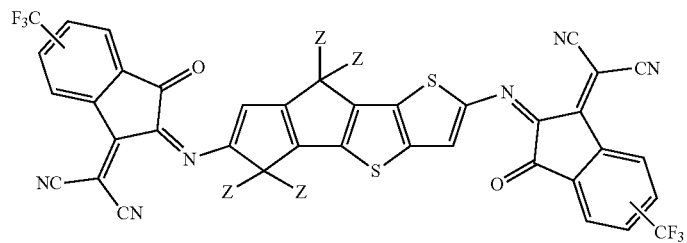
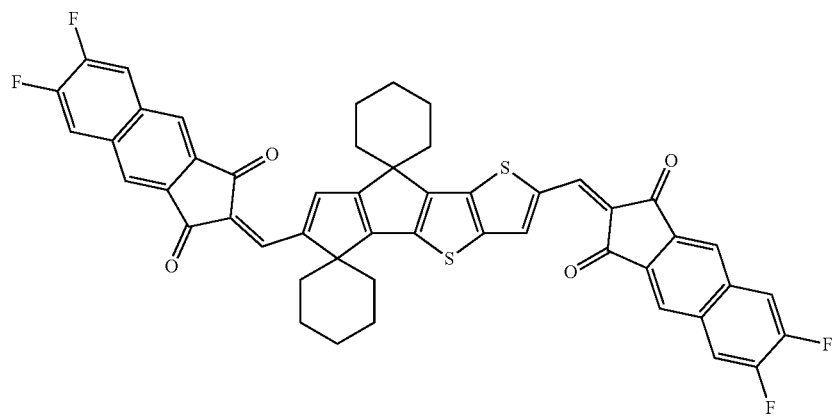
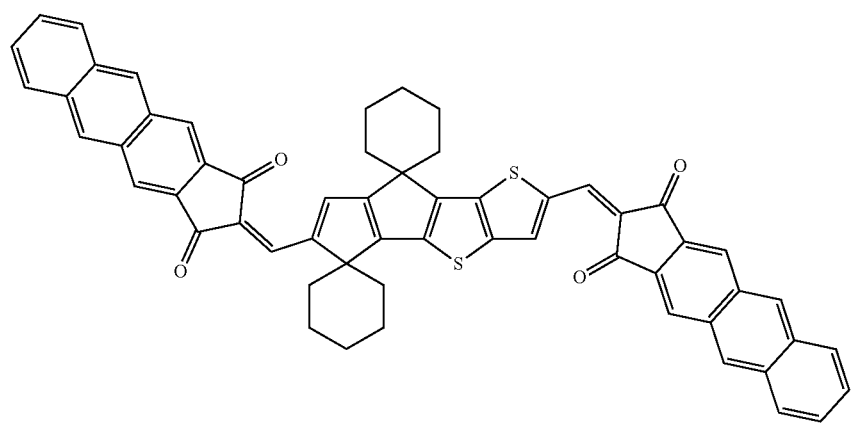
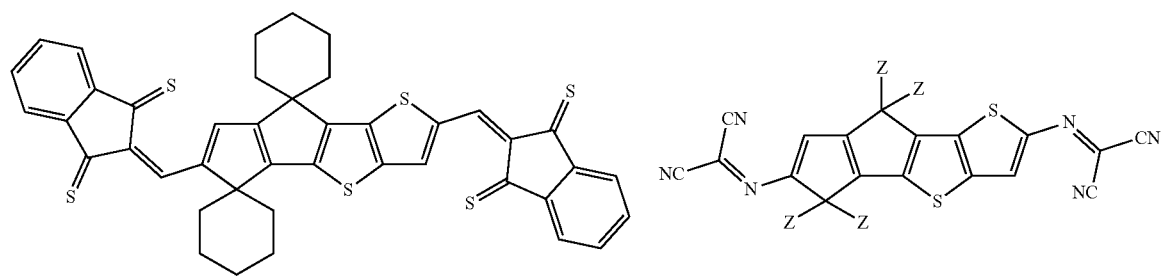

-continued
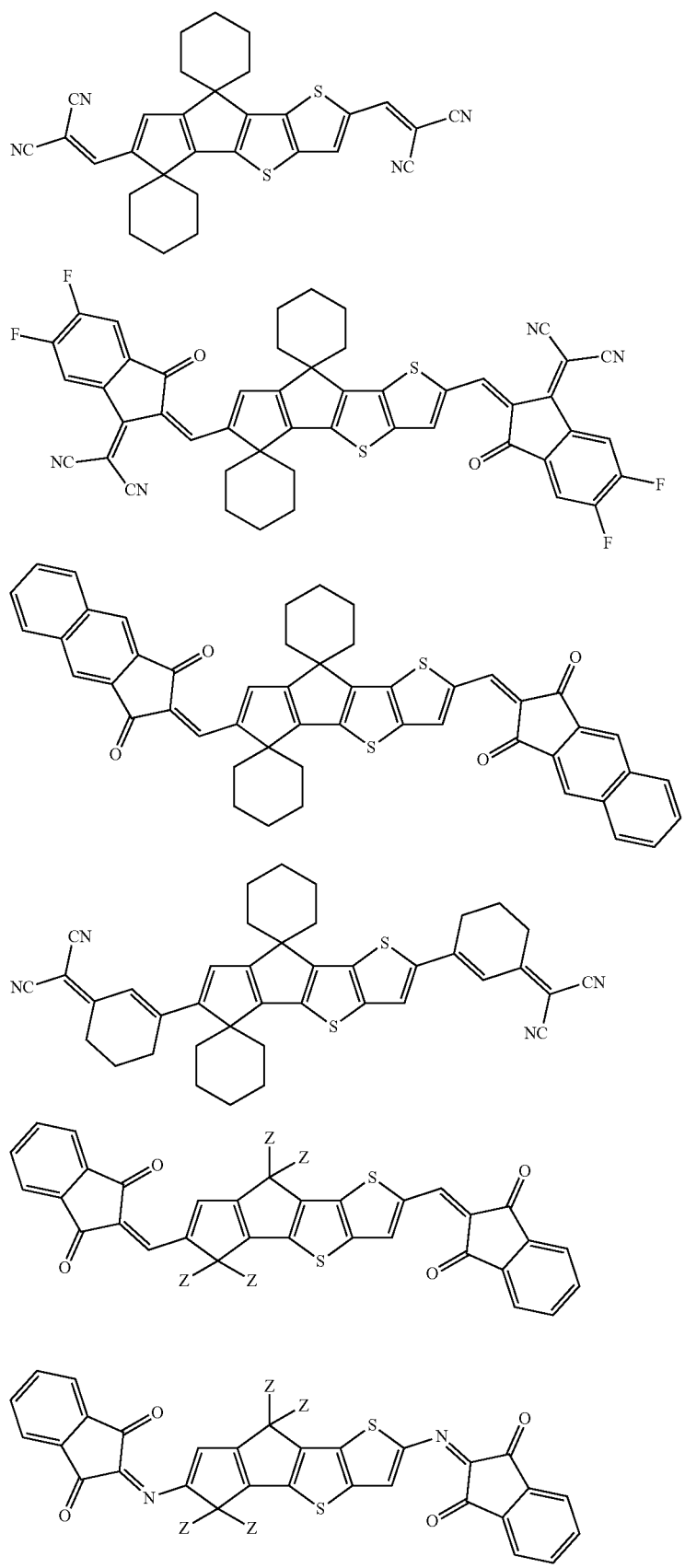

-continued
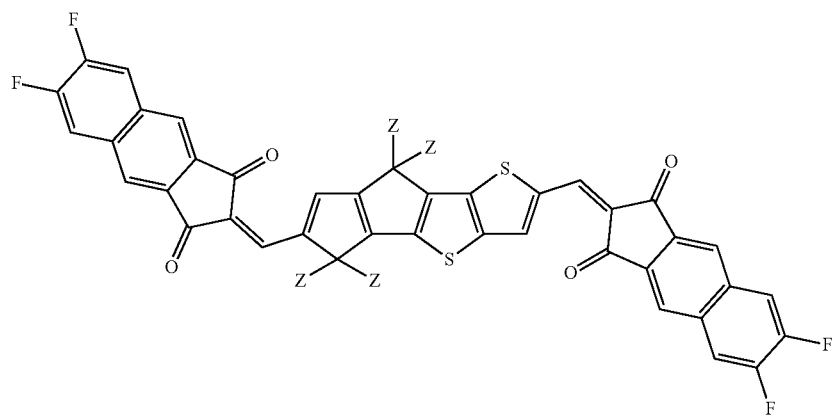
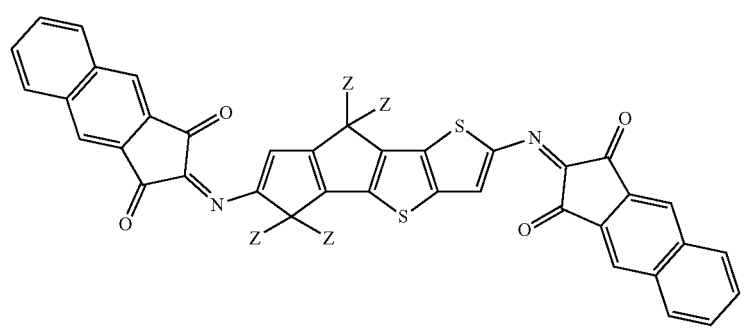
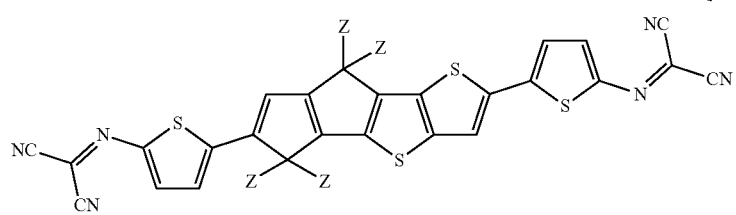
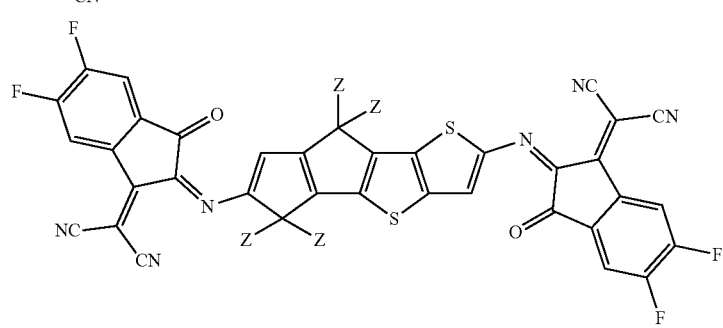
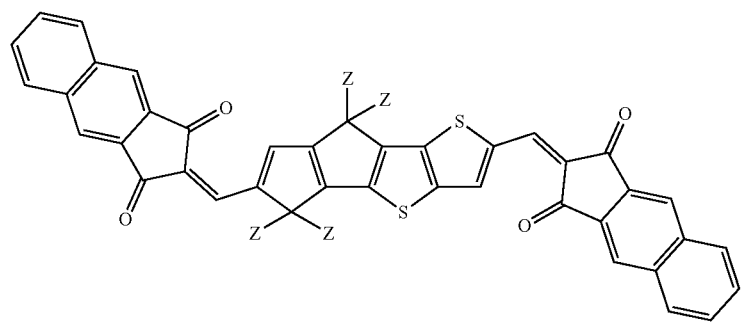

745 746
-continued
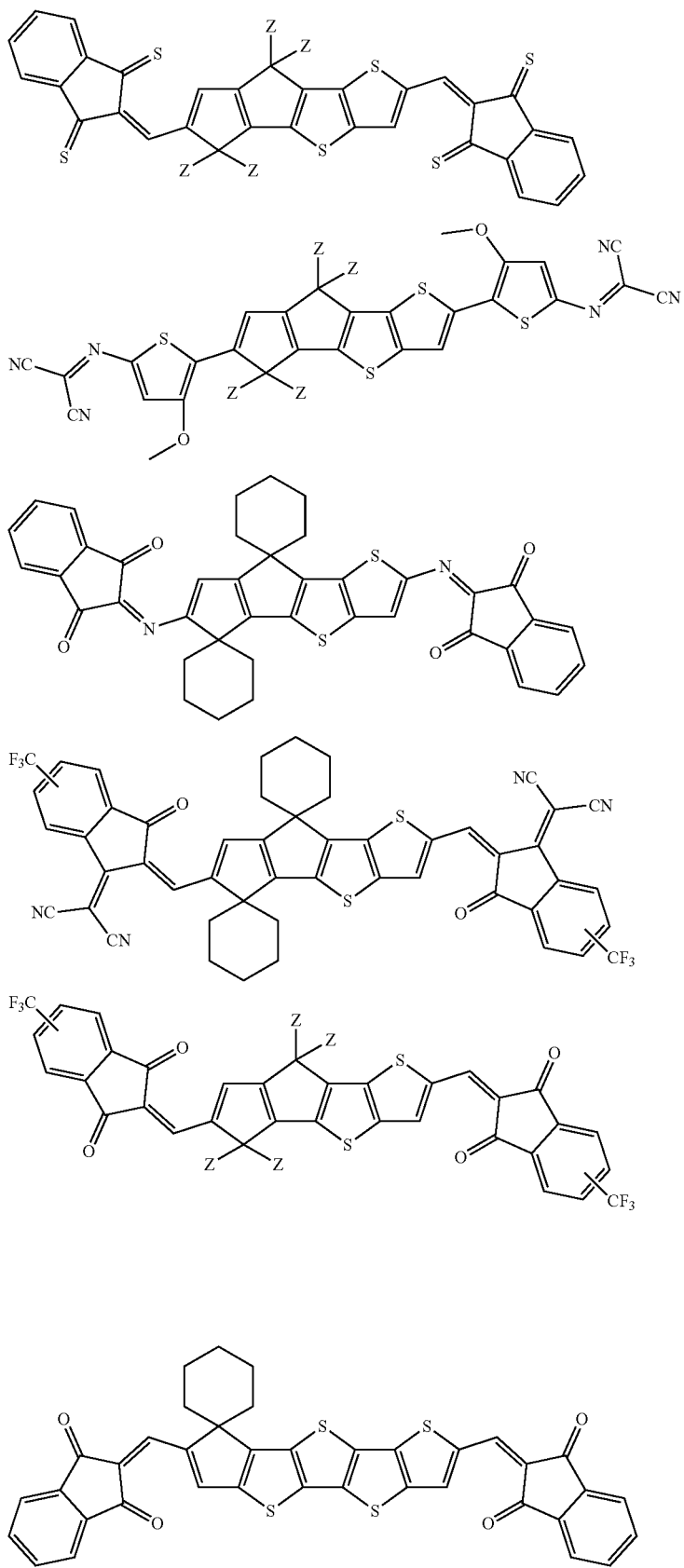

-continued
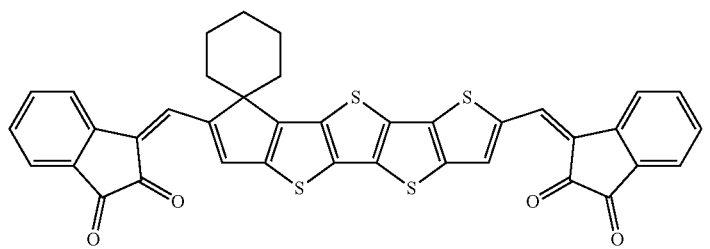
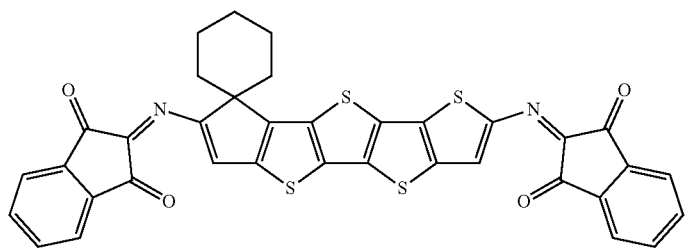
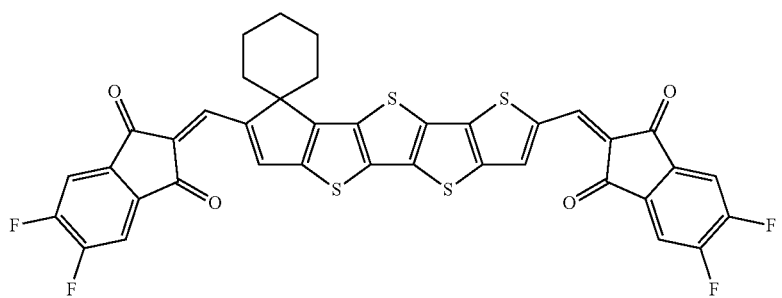
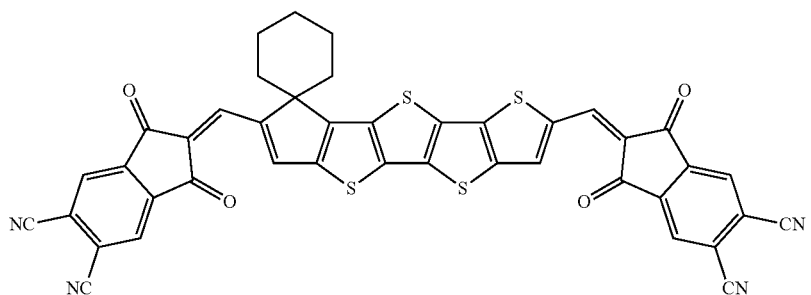
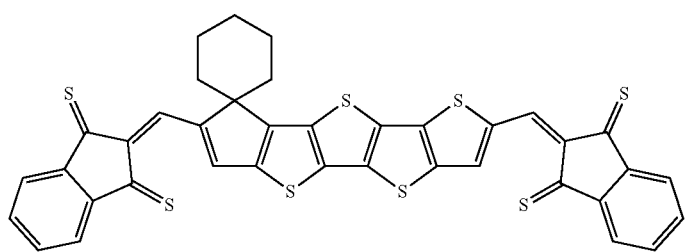
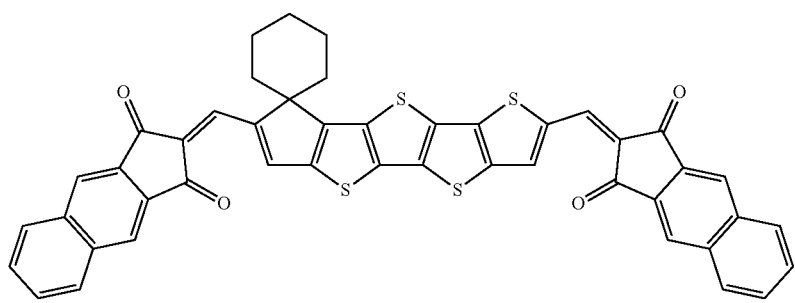

-continued
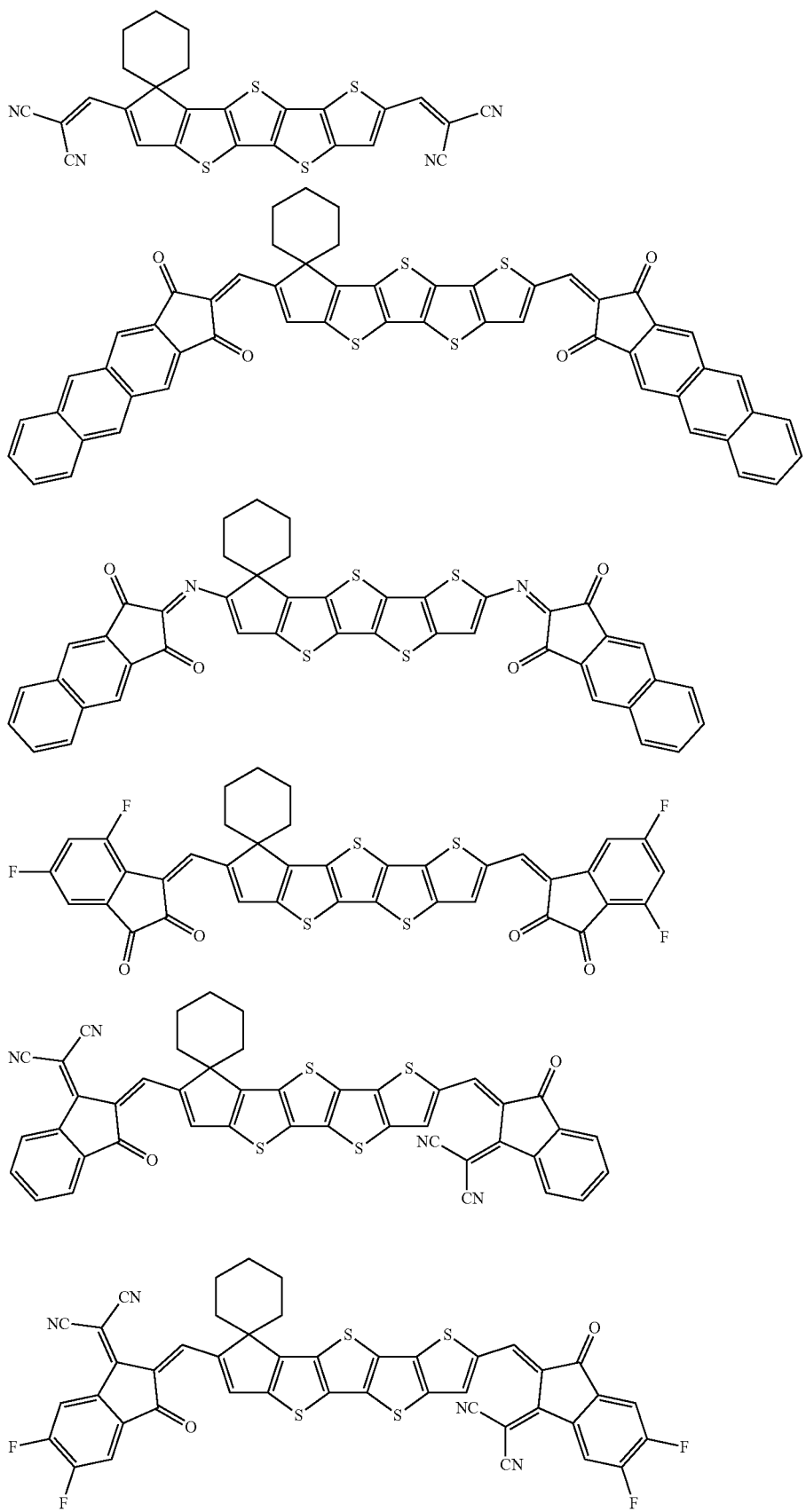

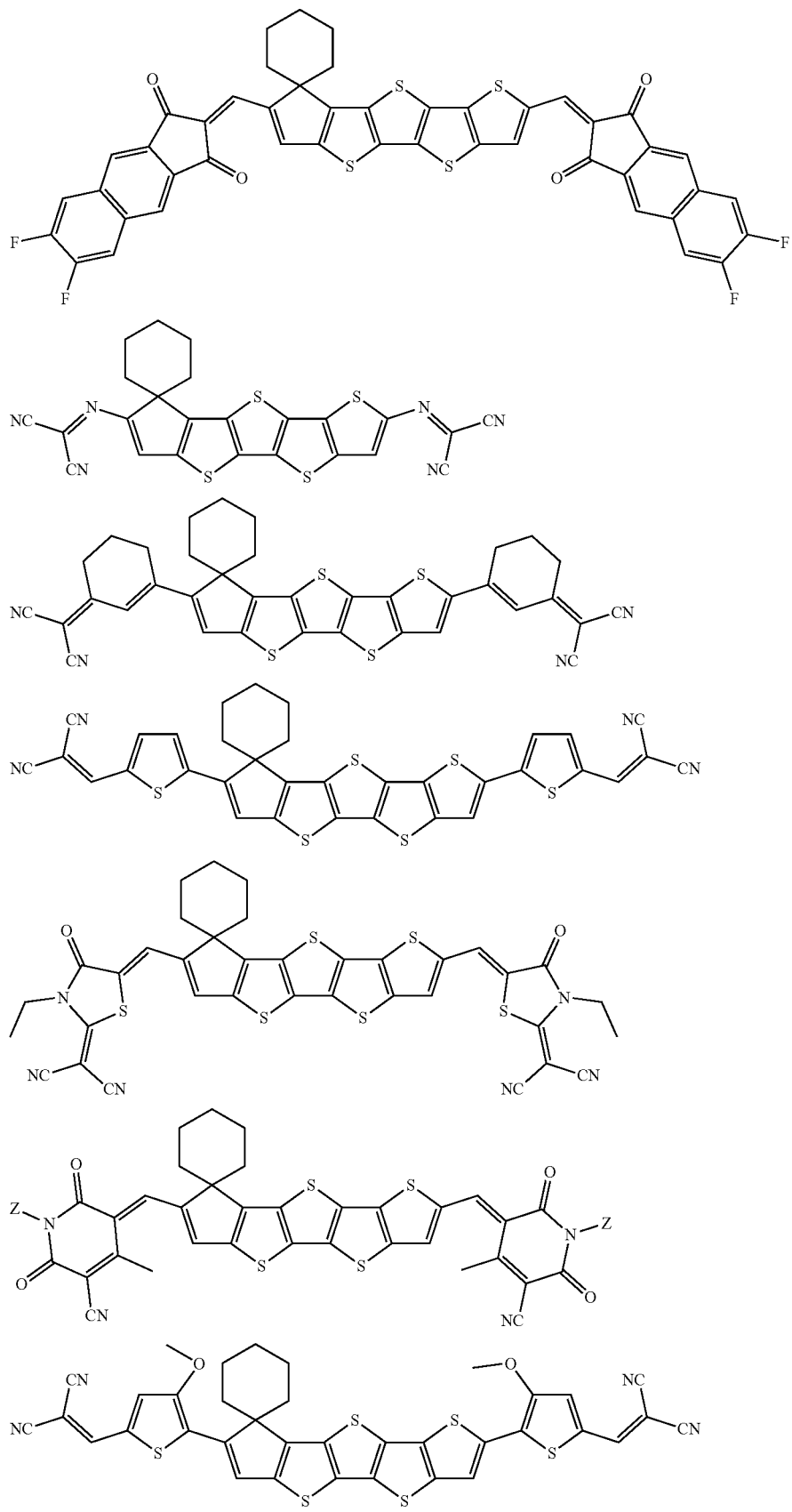

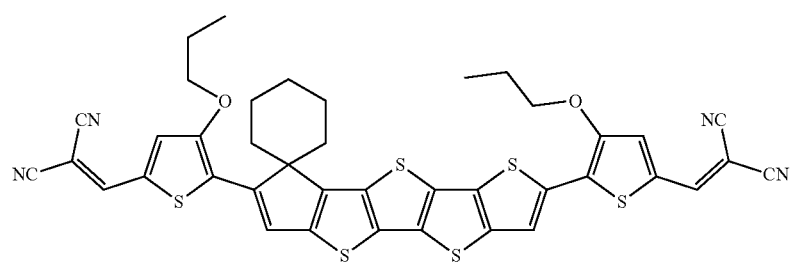
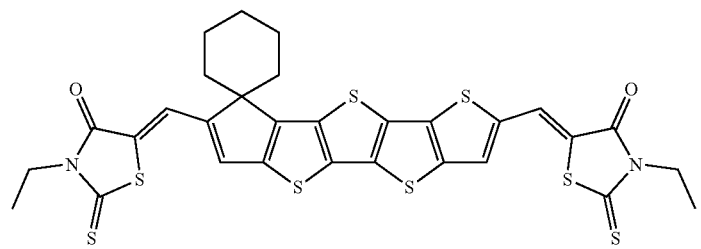
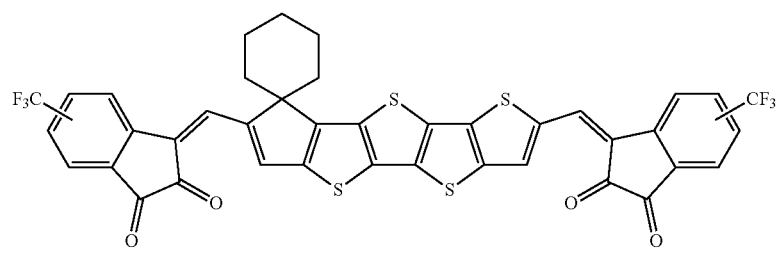
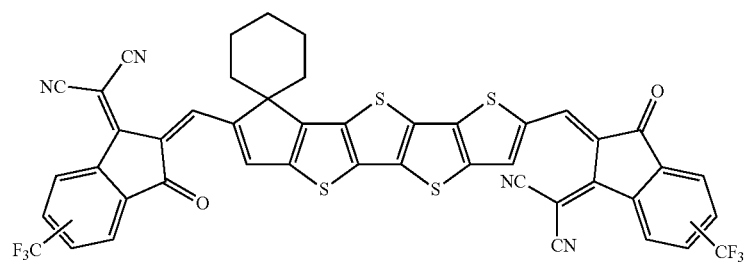
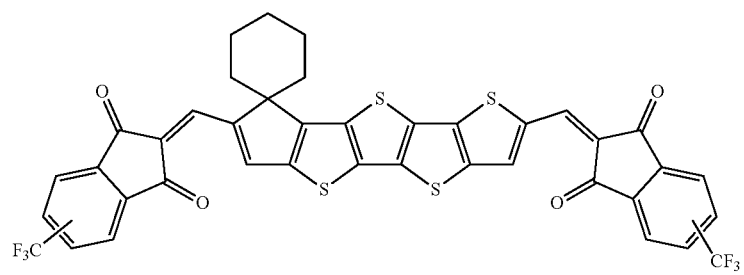
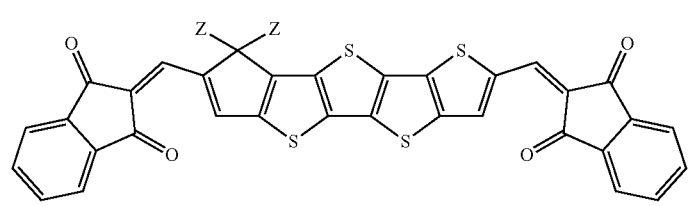
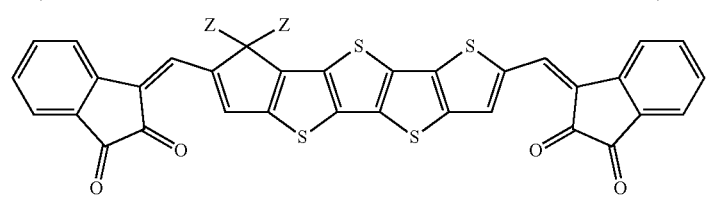

-continued
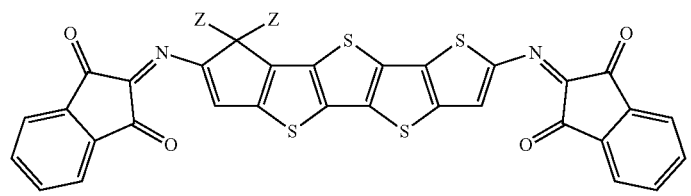
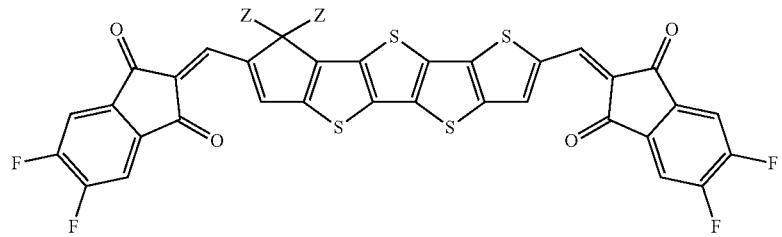
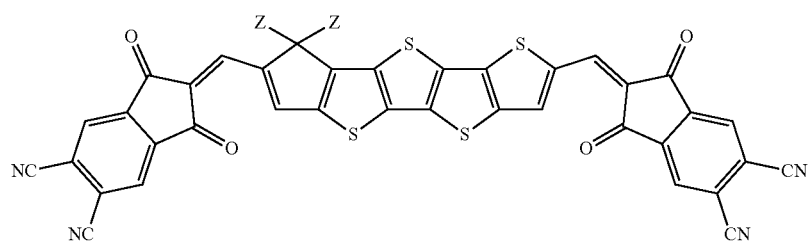
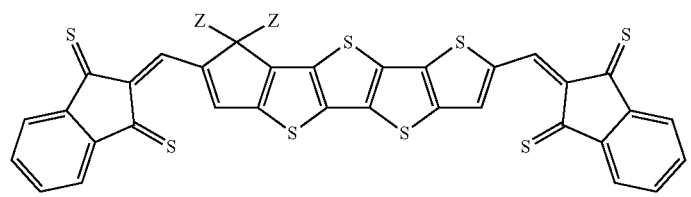
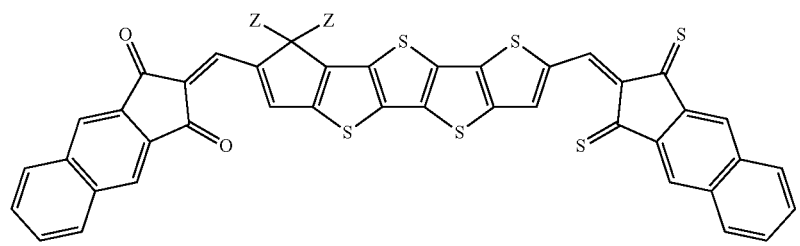
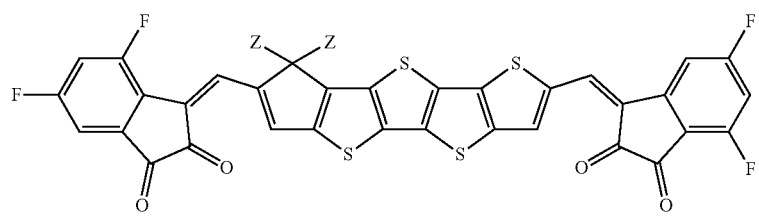
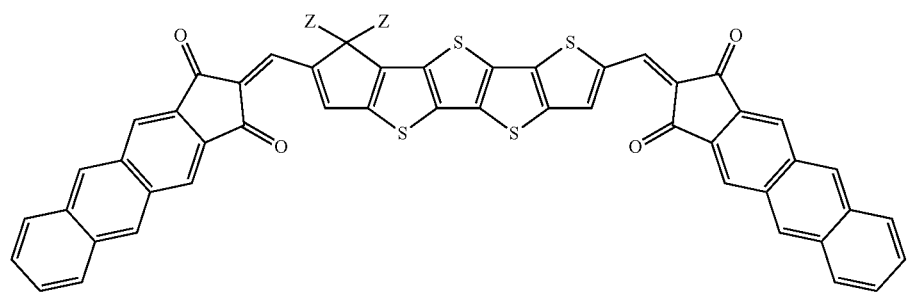

-continued
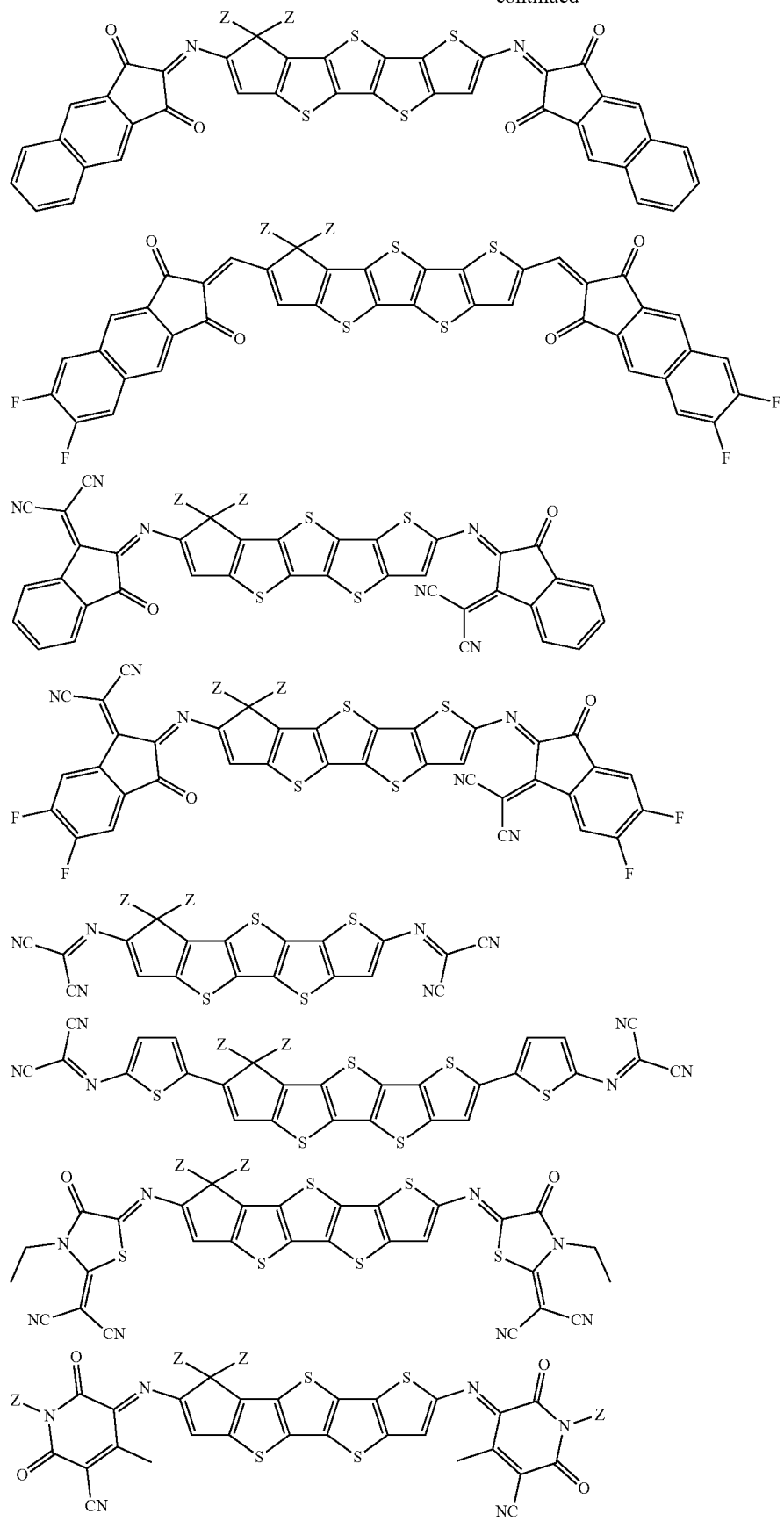

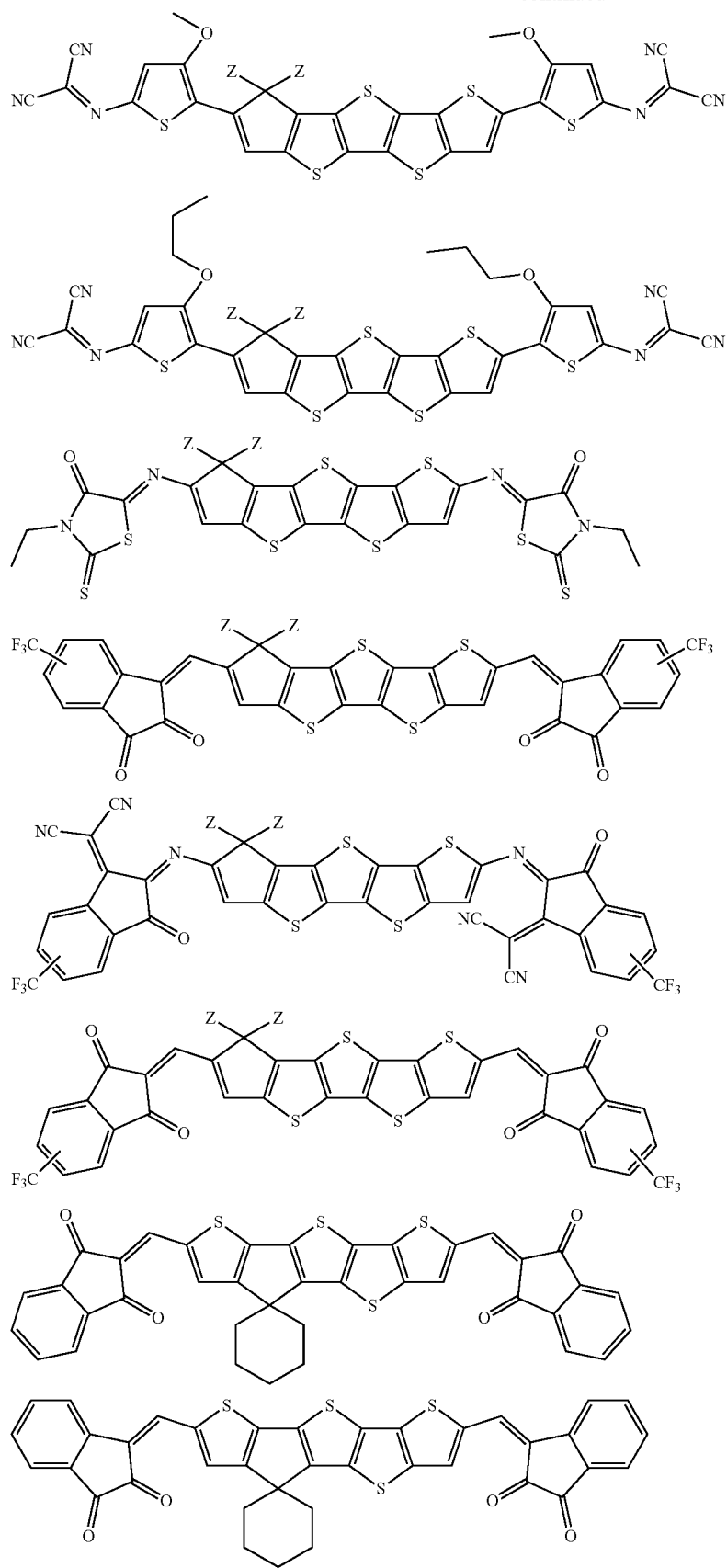

-continued
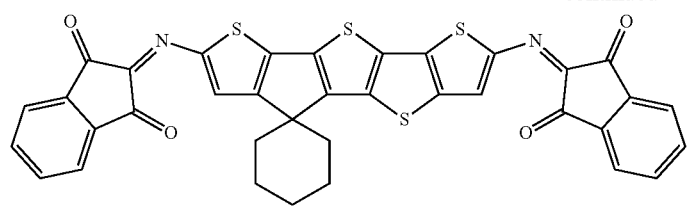
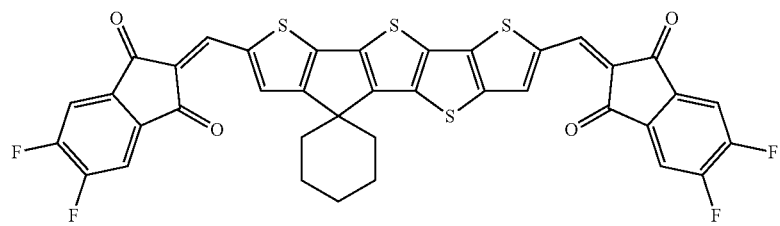
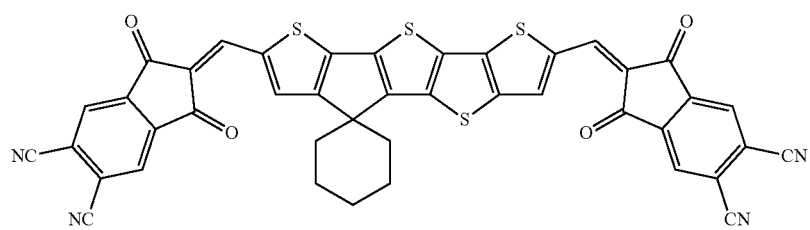
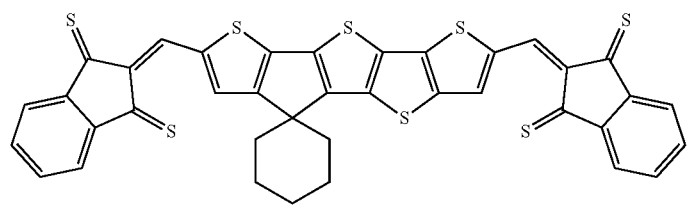
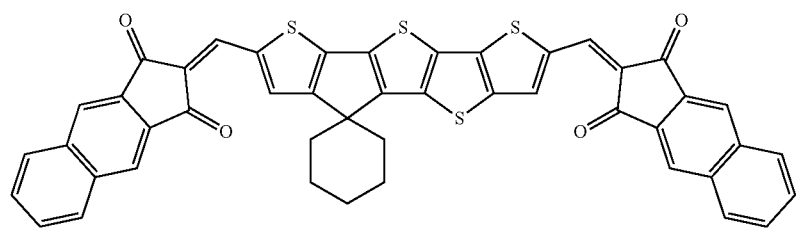
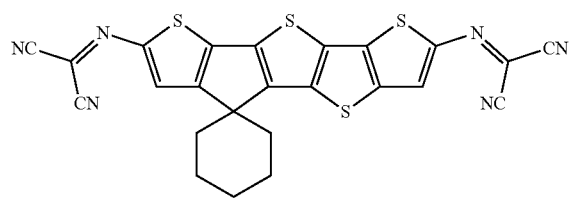
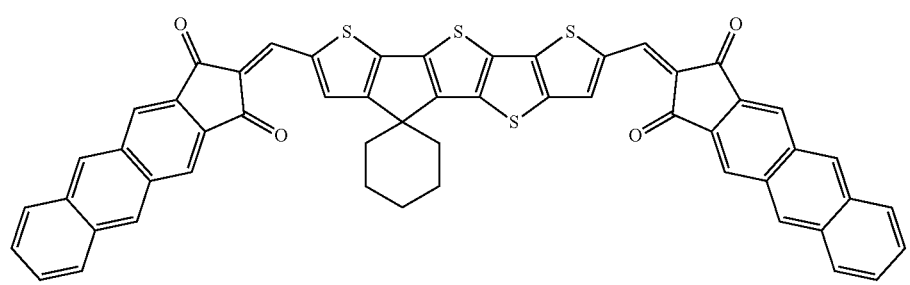

-continued
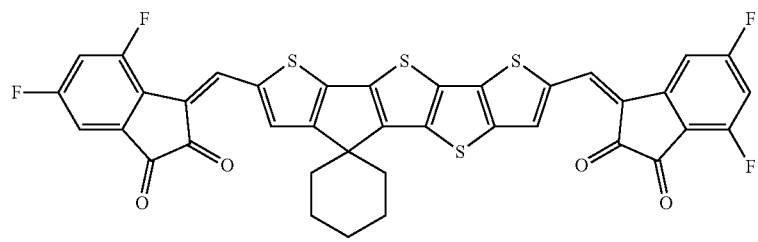
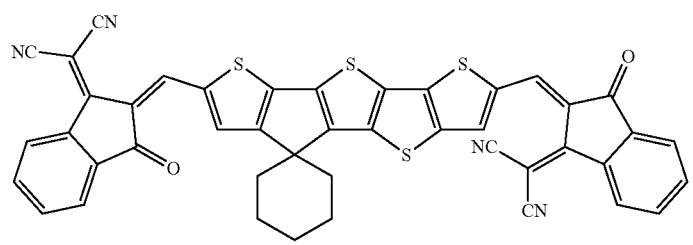
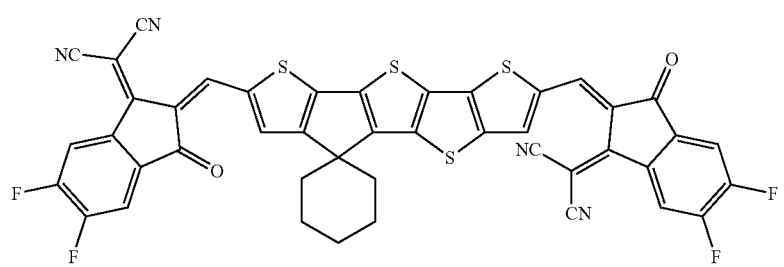
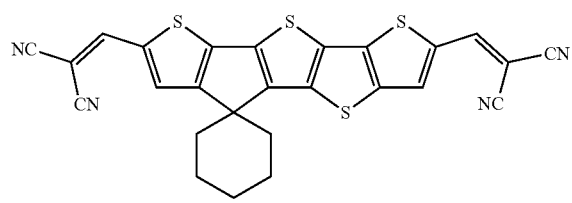
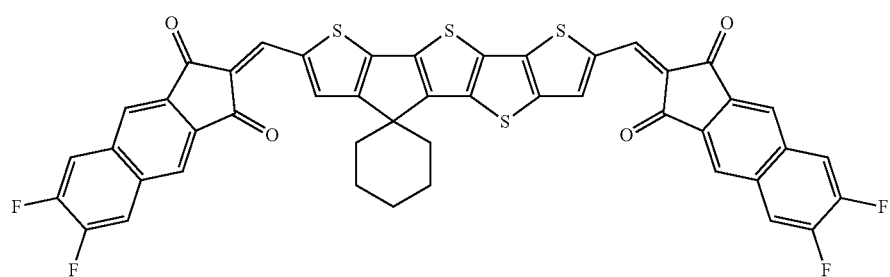
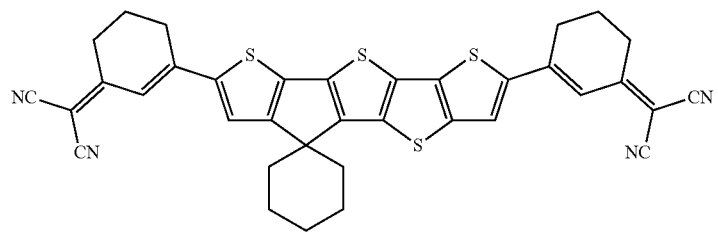
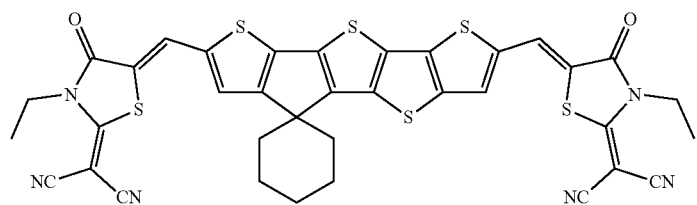

-continued
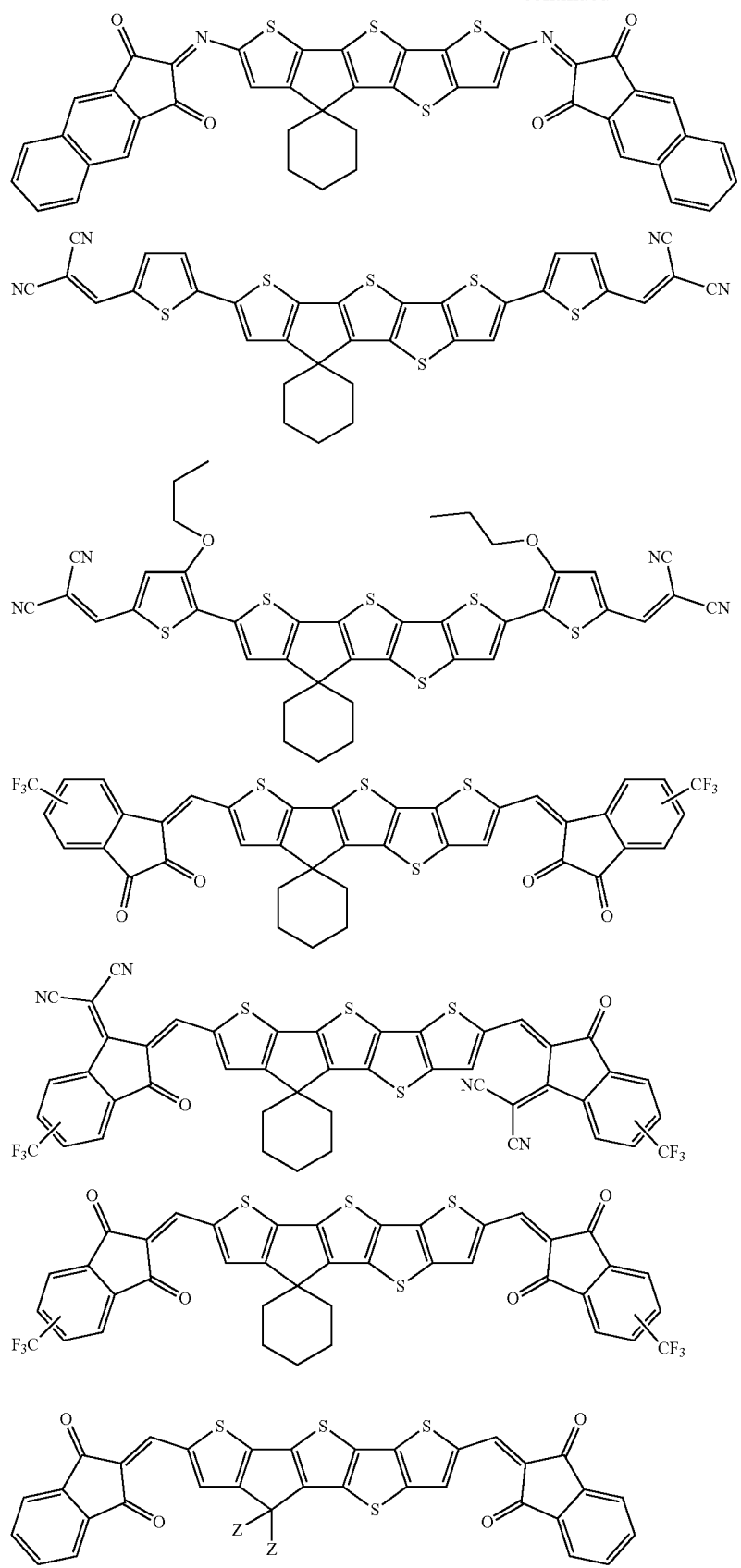

-continued
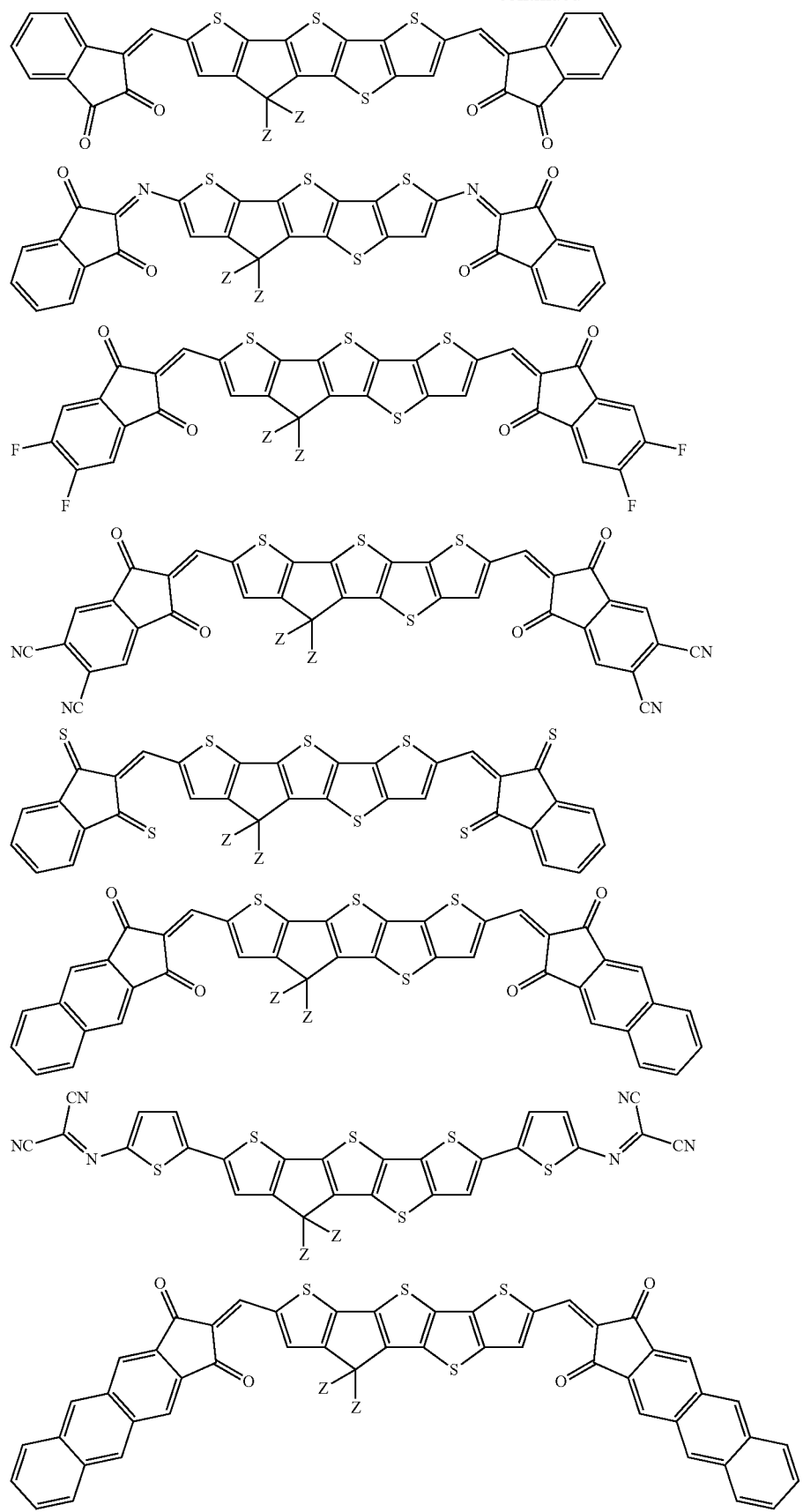

-continued
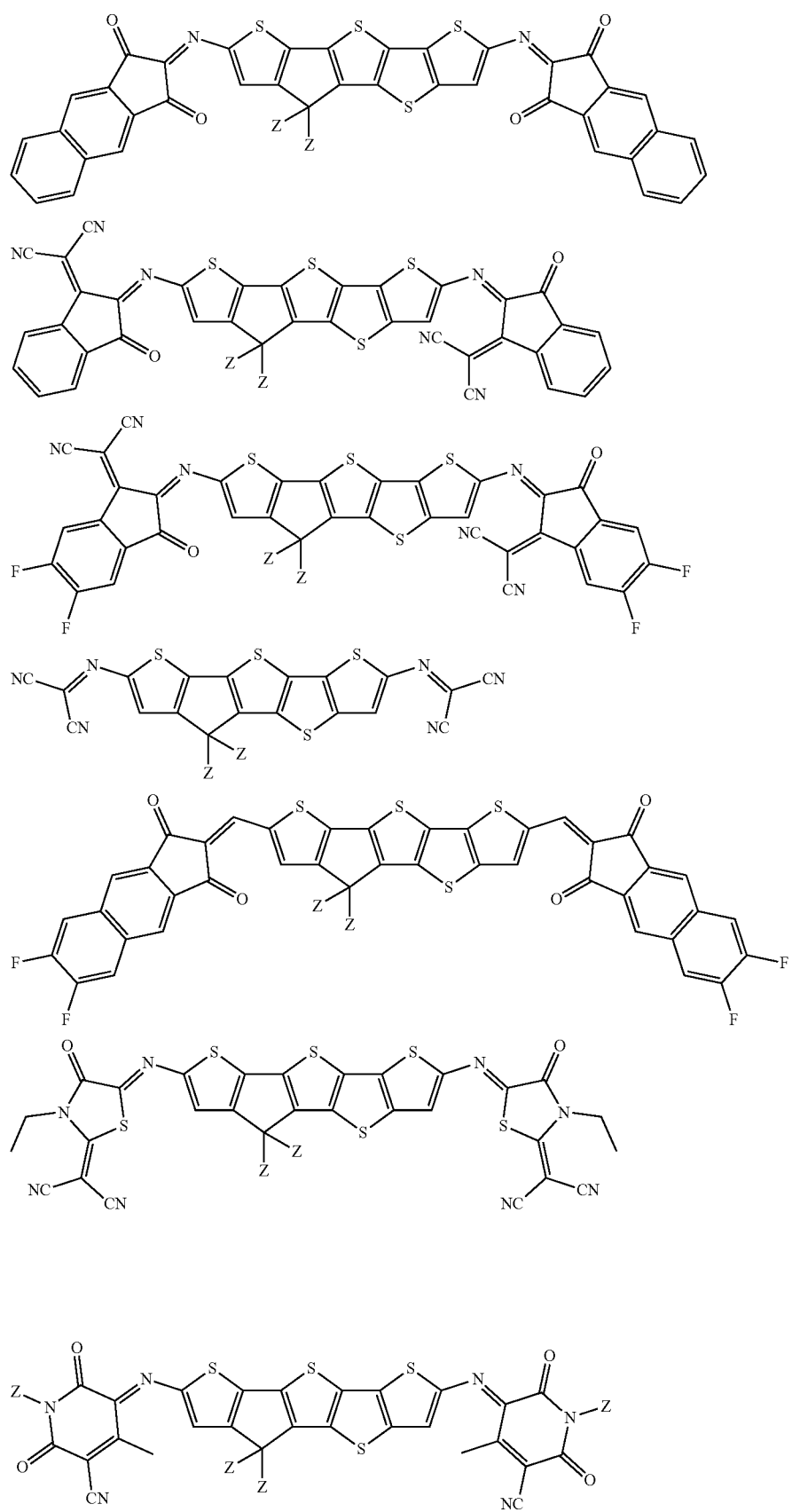

-continued
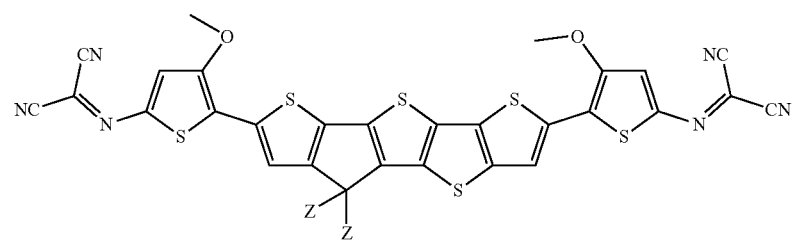
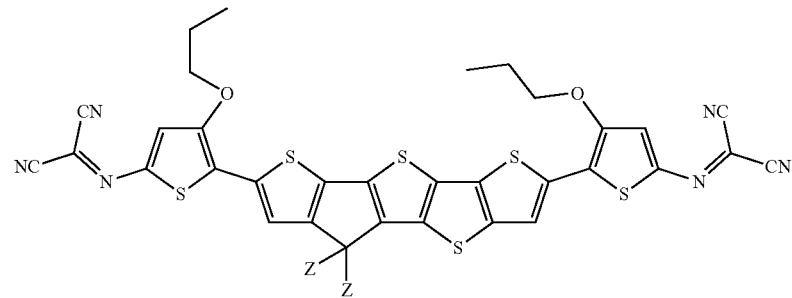
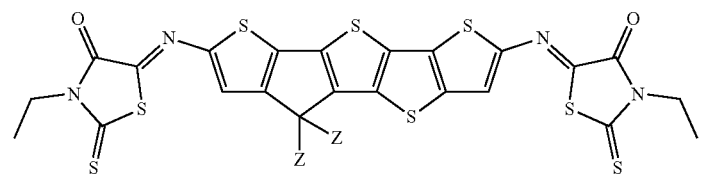
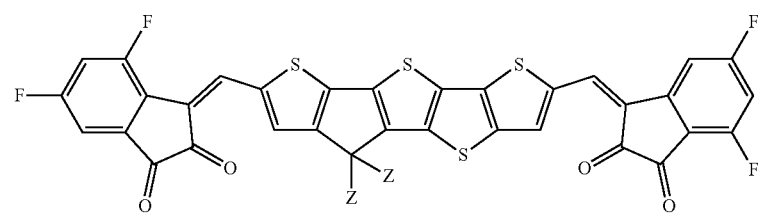
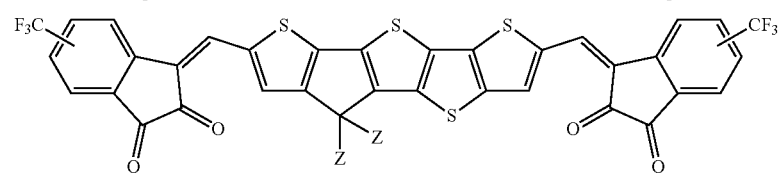
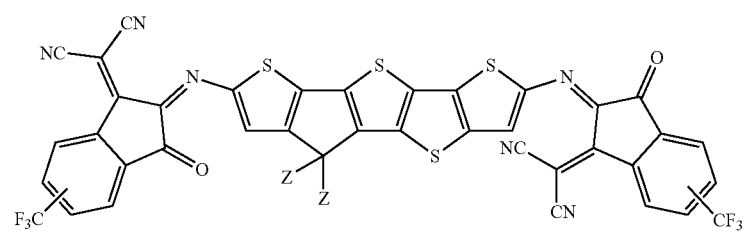
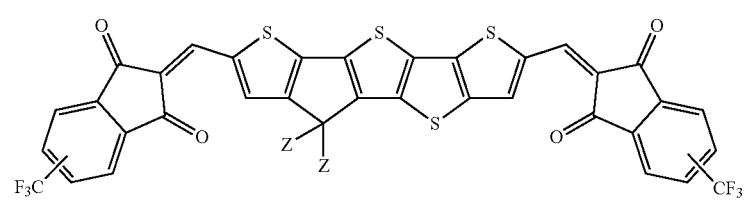

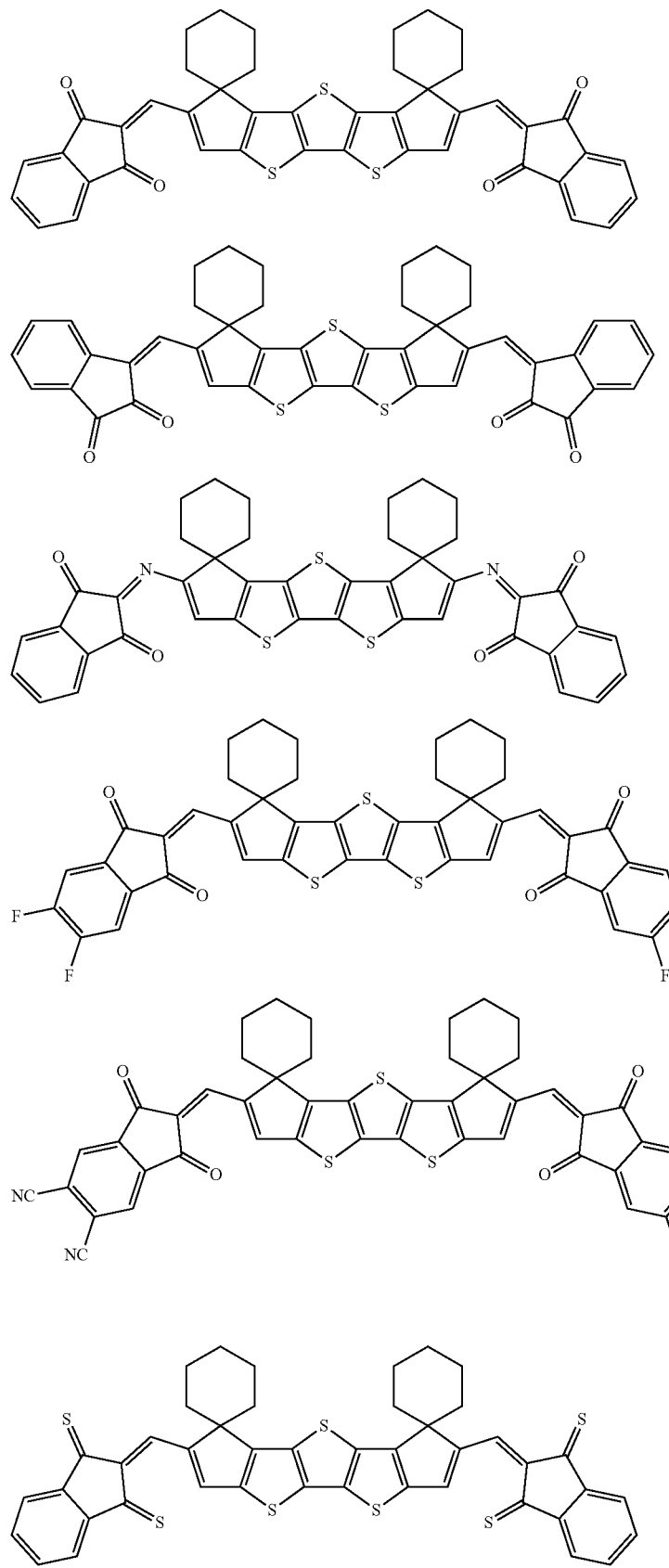

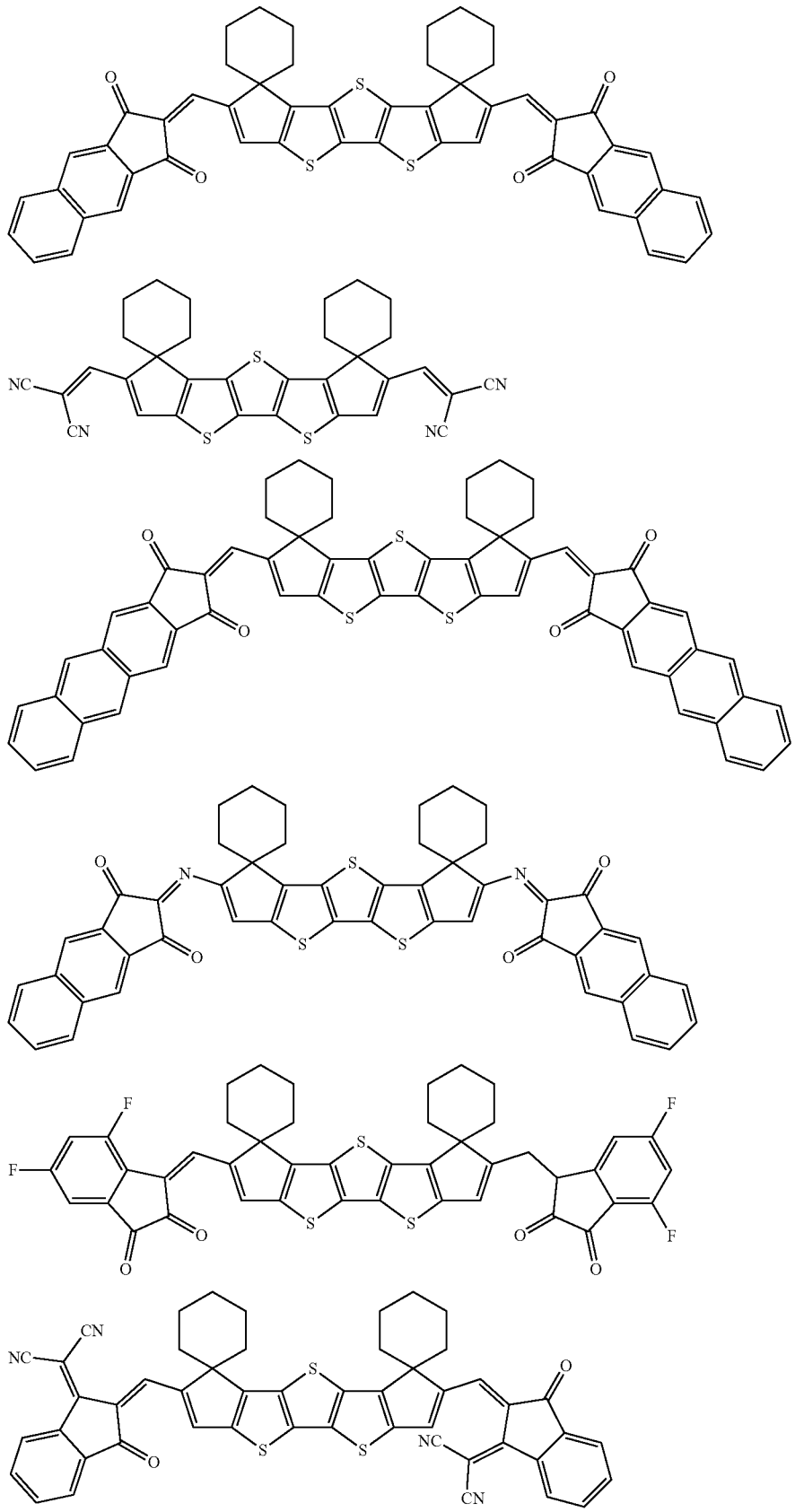

-continued
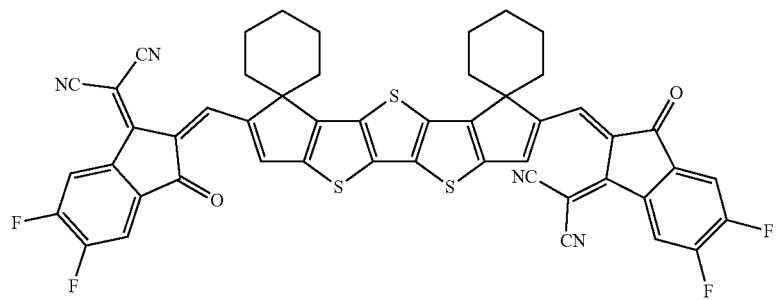
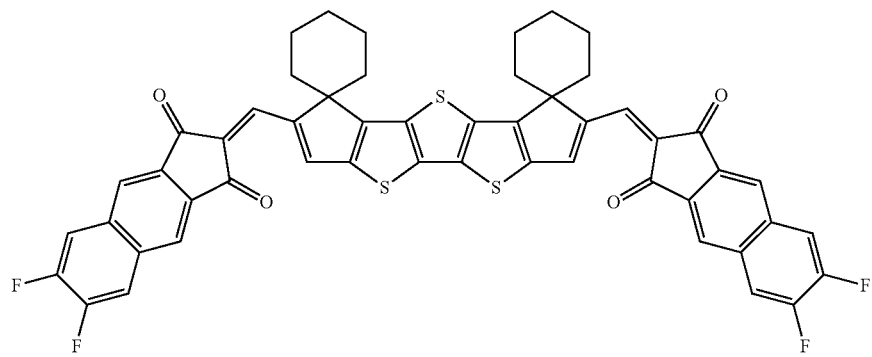
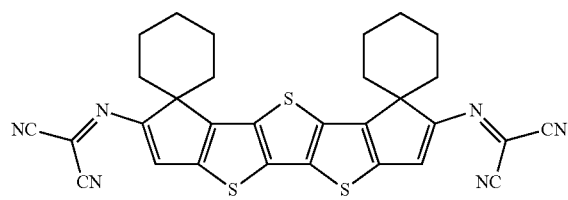
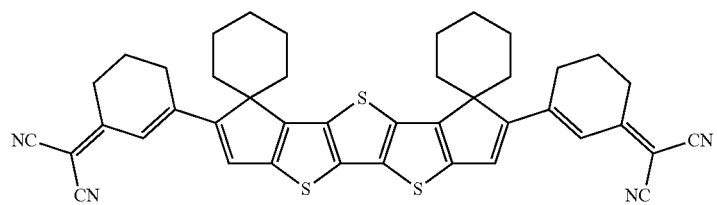
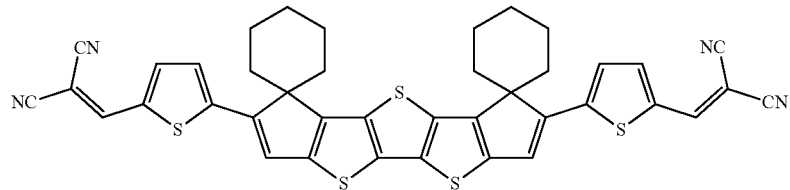
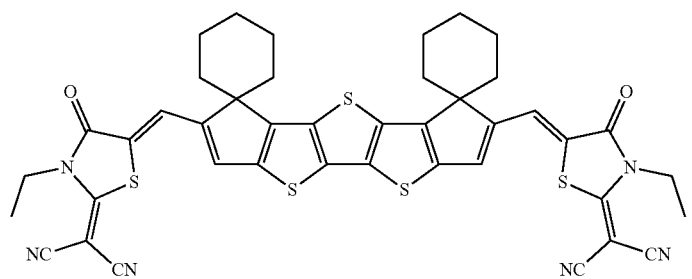

-continued
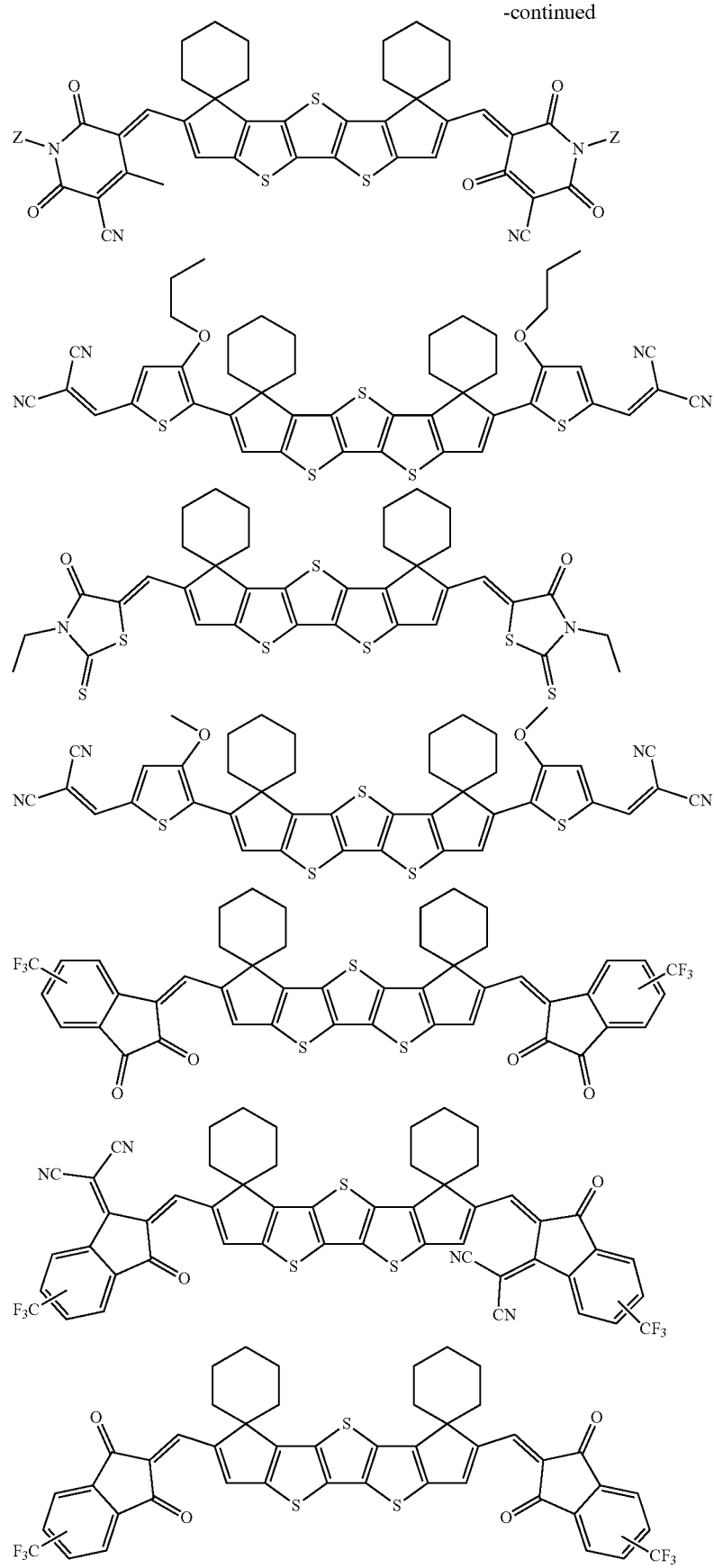

-continued
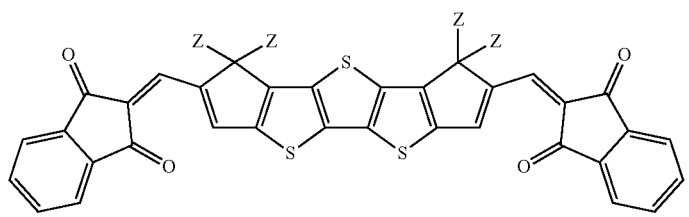
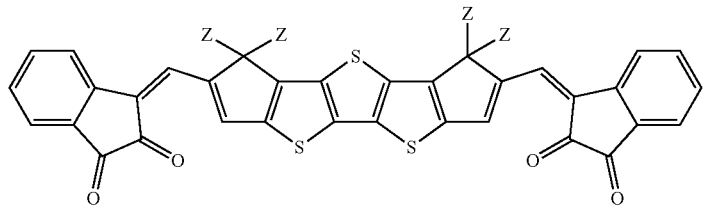
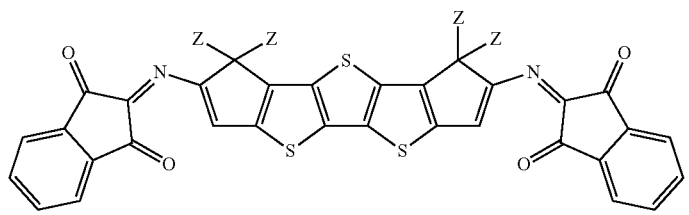
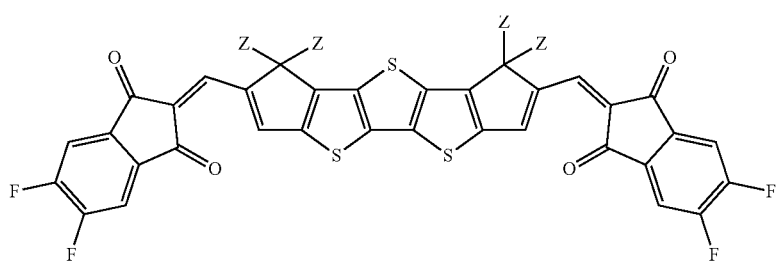
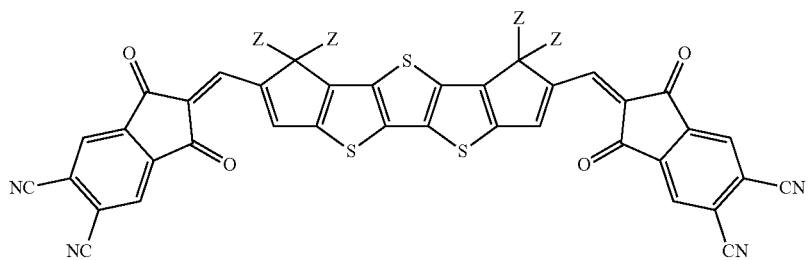
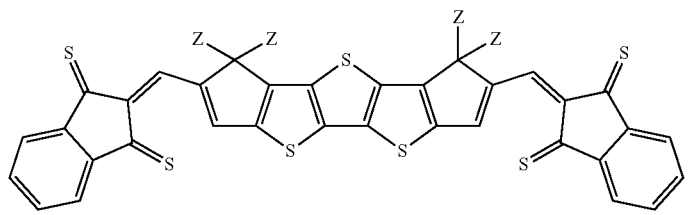
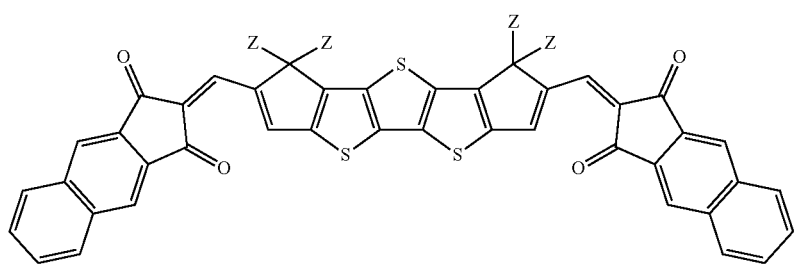

-continued
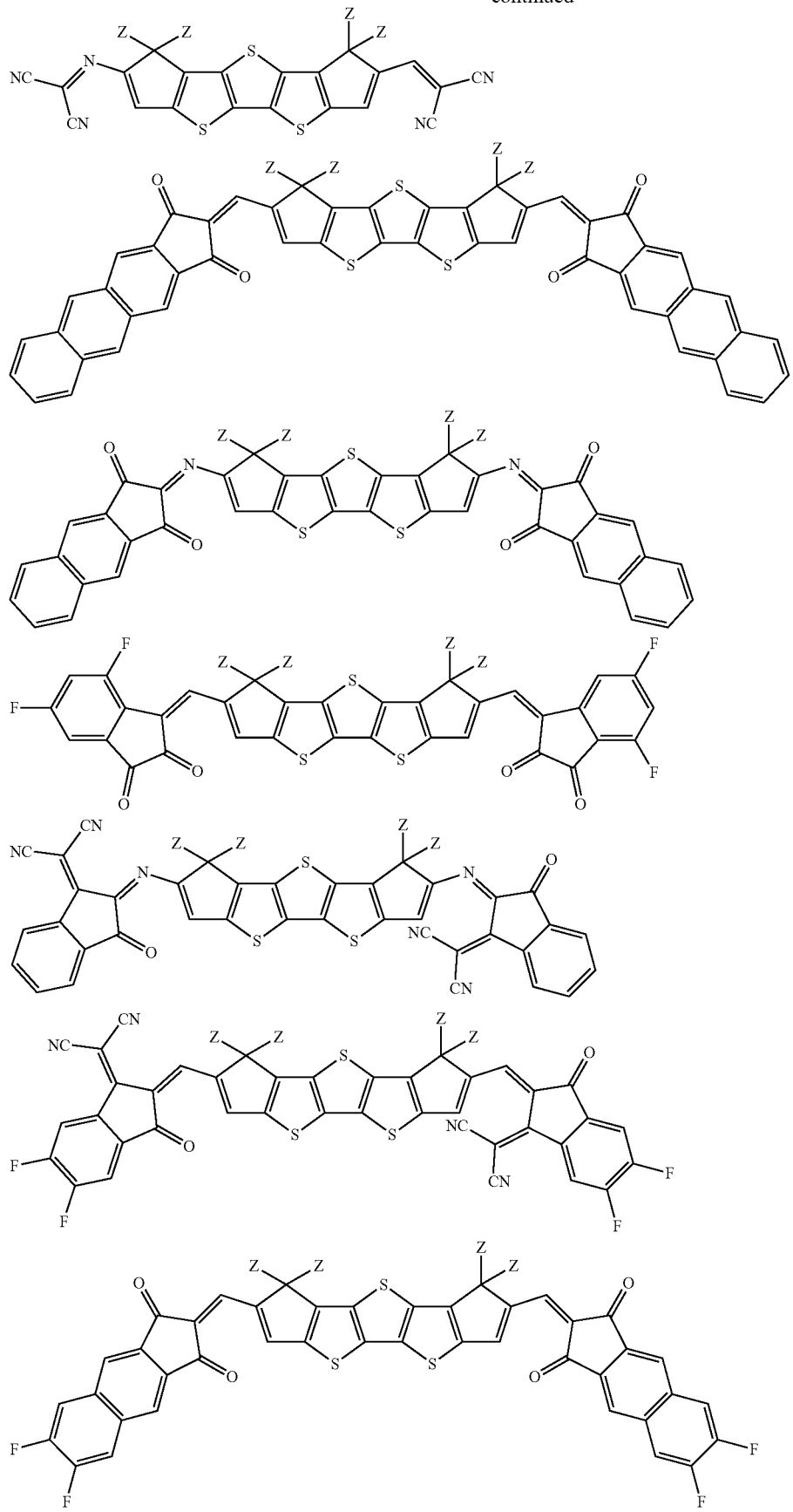

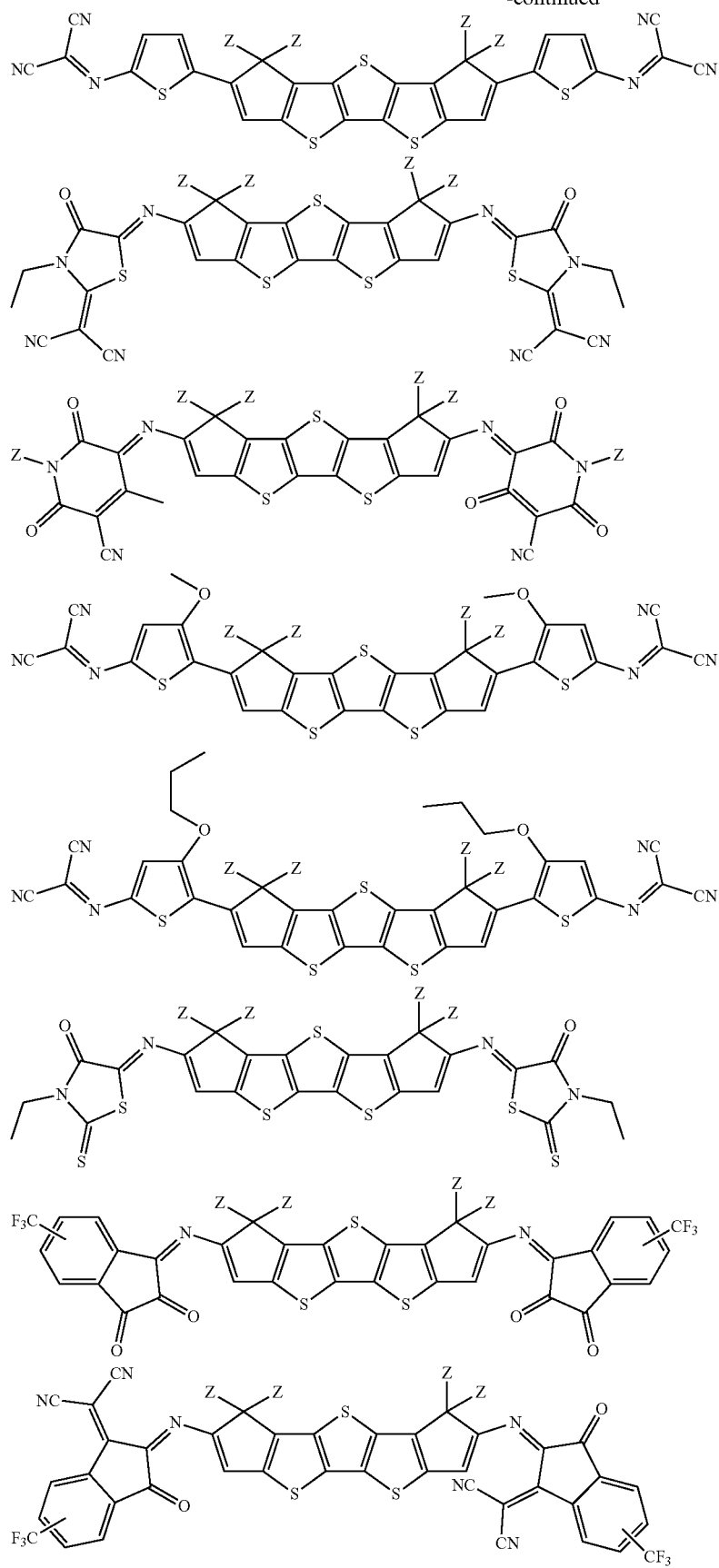

787 788
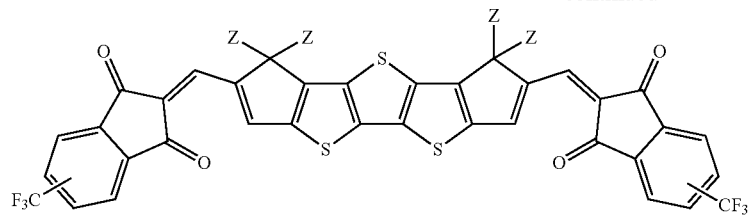
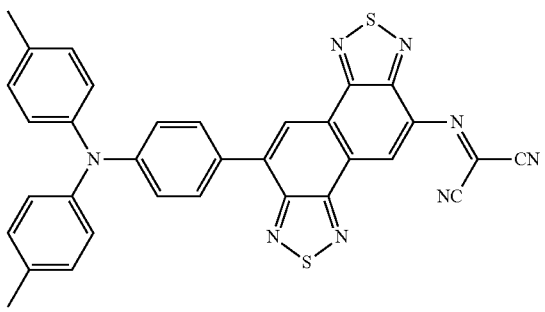
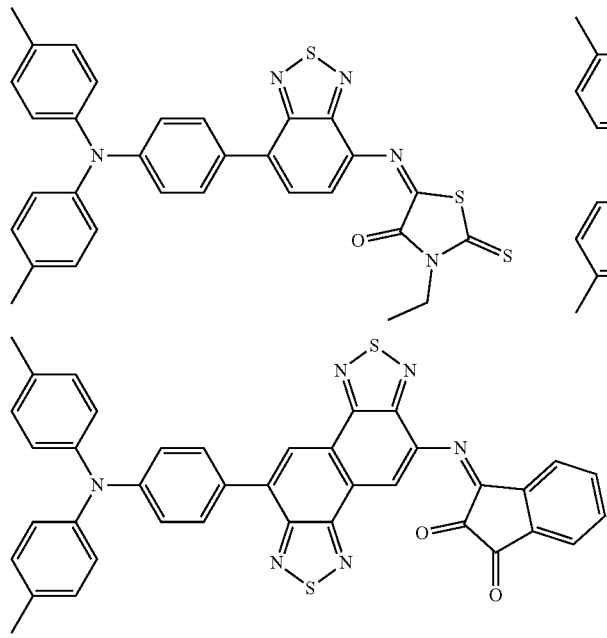
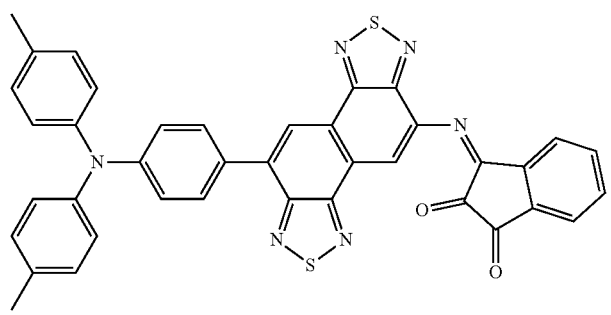
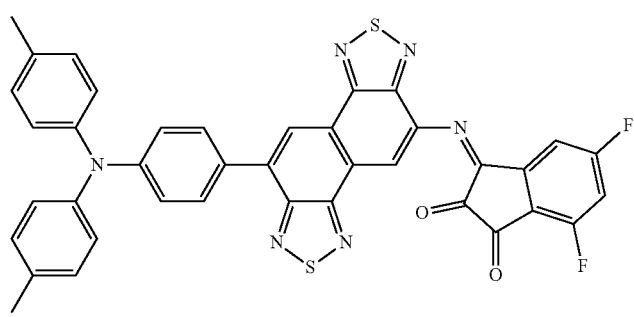
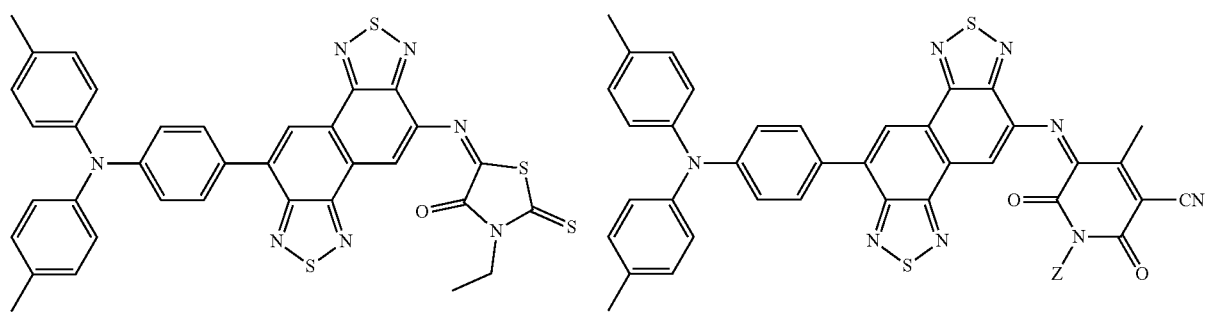

789 790
-continued
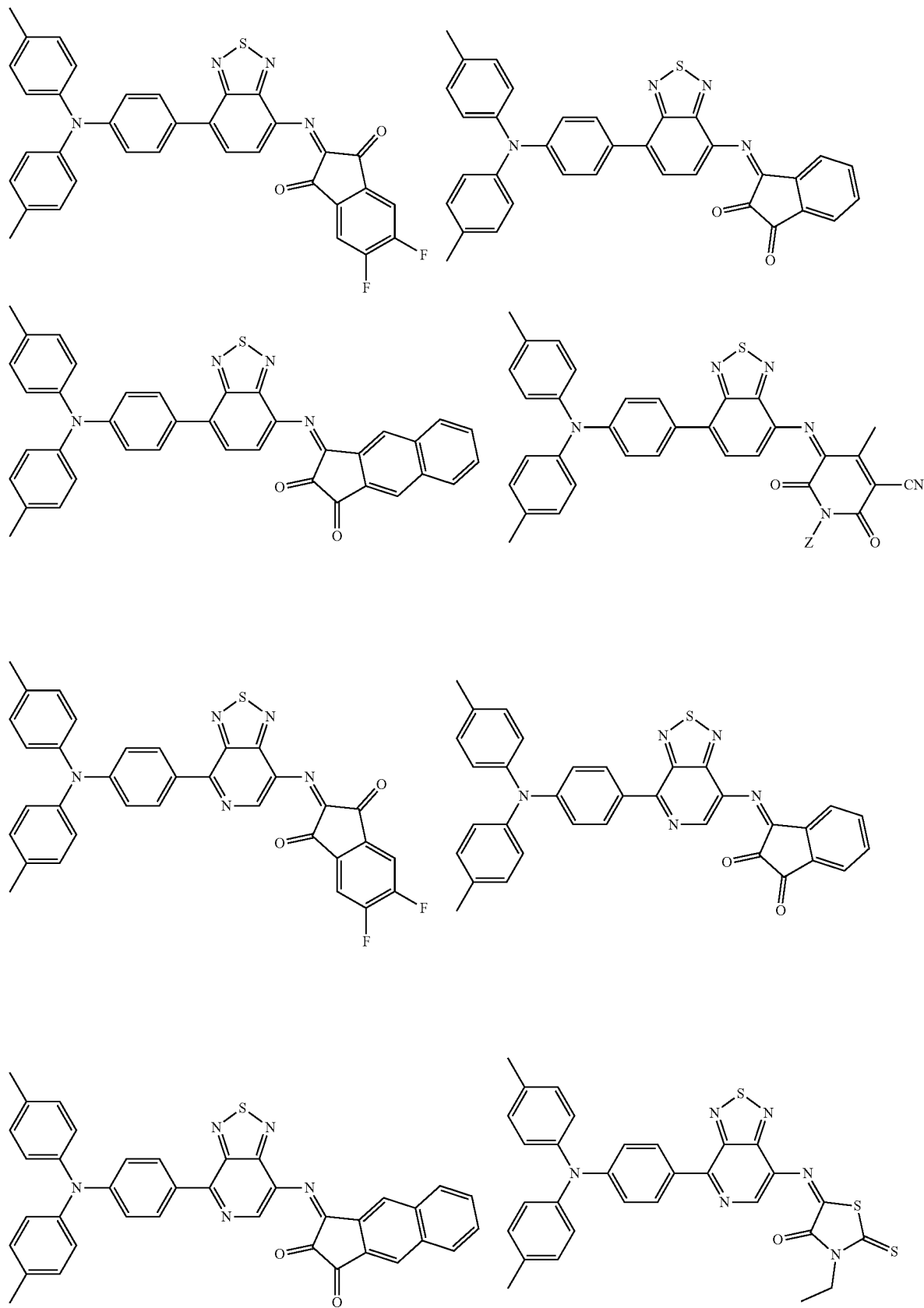

791 792
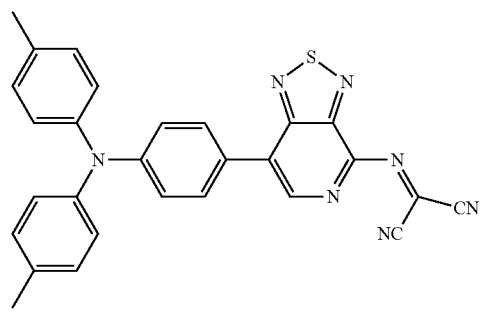
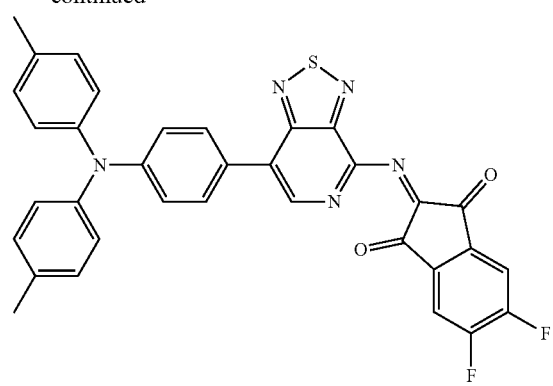
-continued
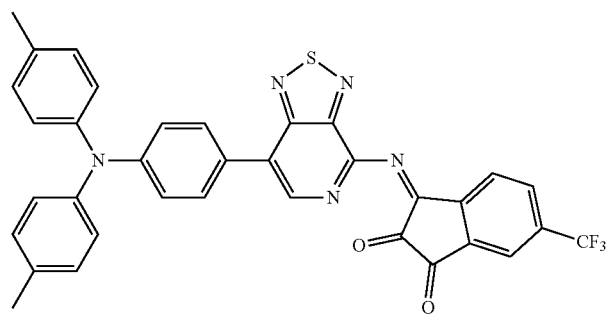
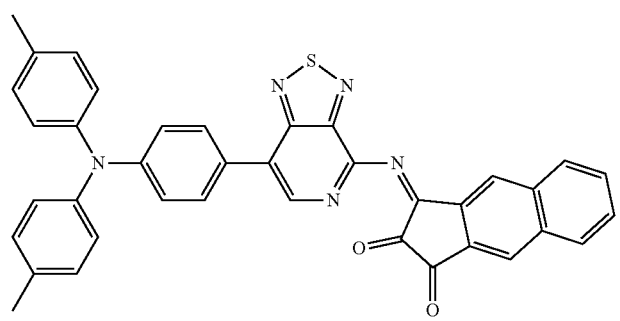
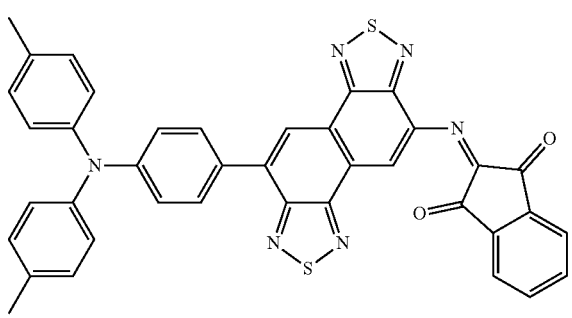
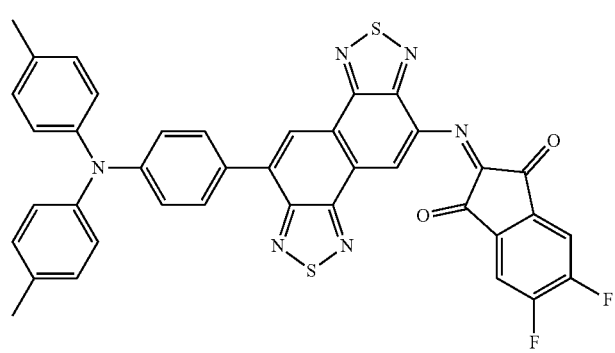
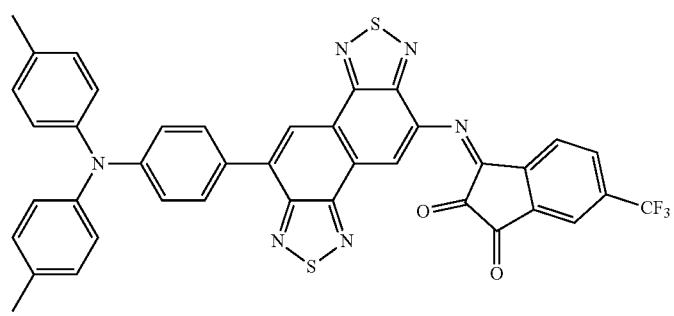

-continued
793
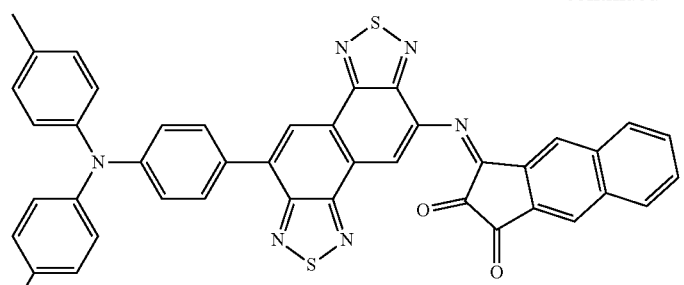
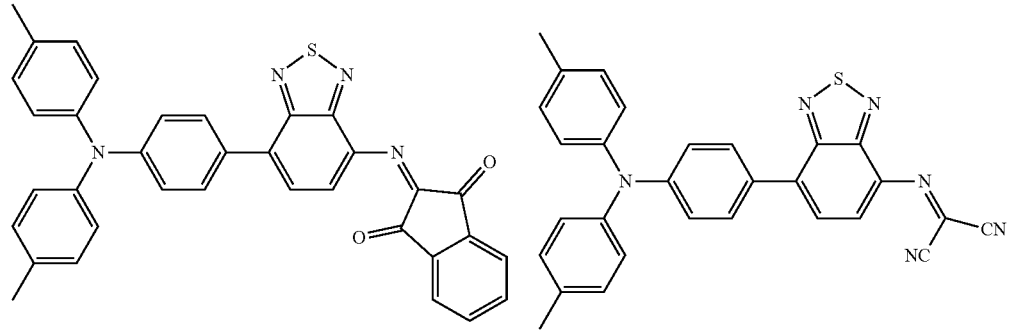
794
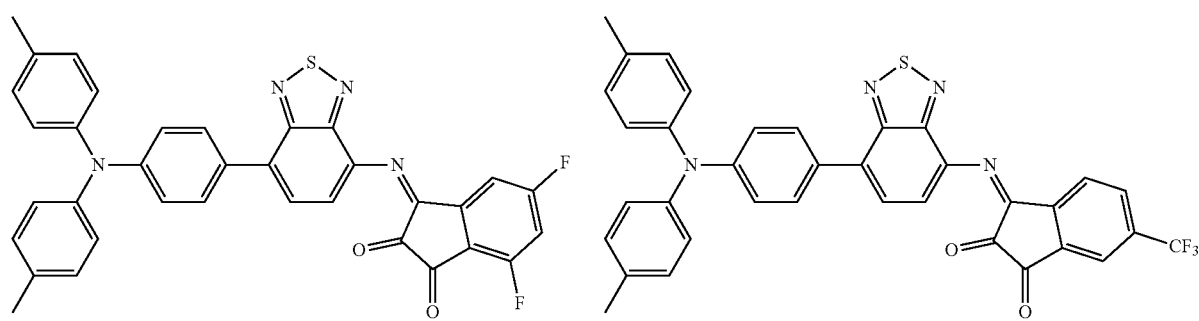
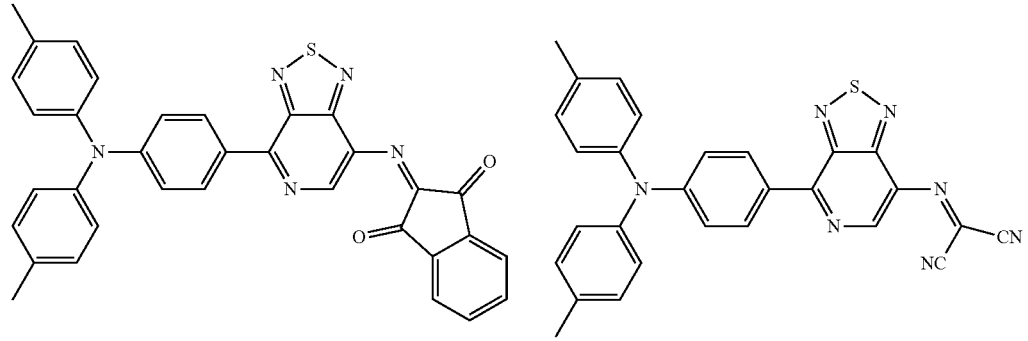
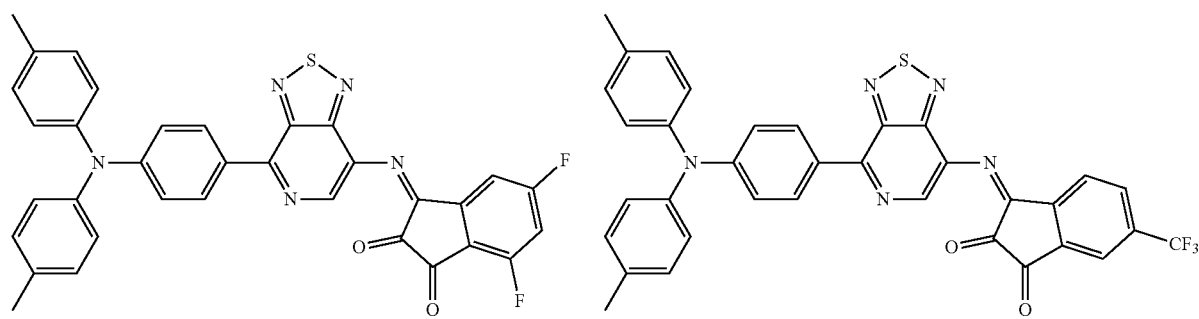

795 796
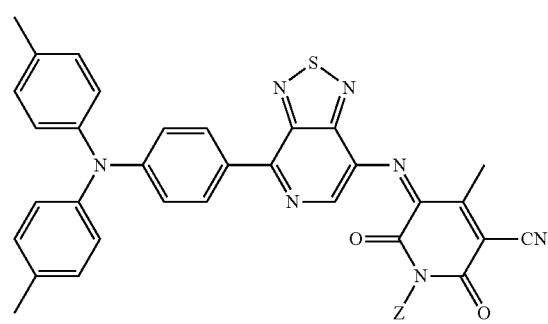
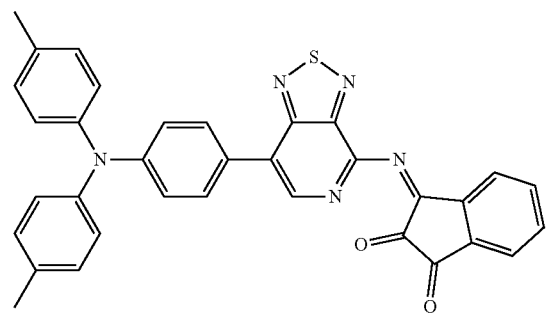
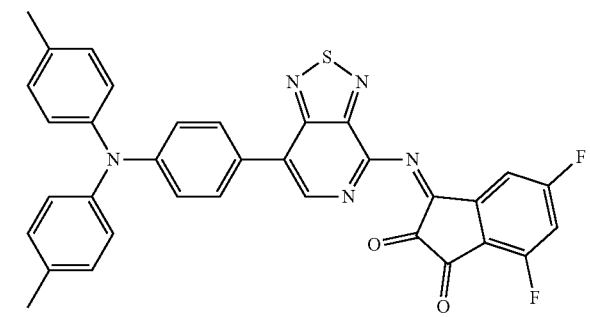
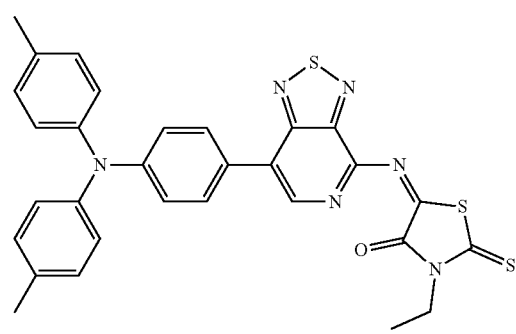
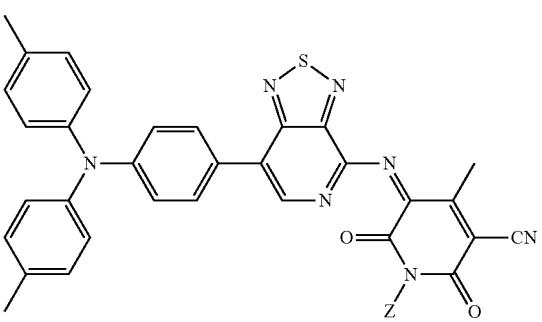
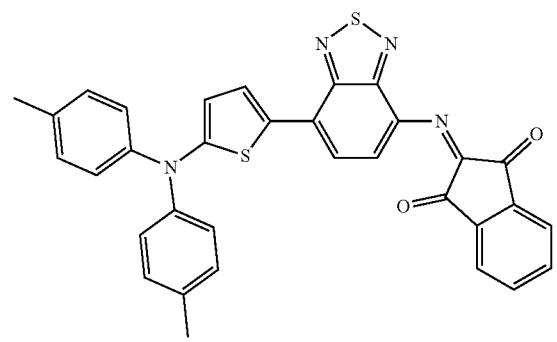
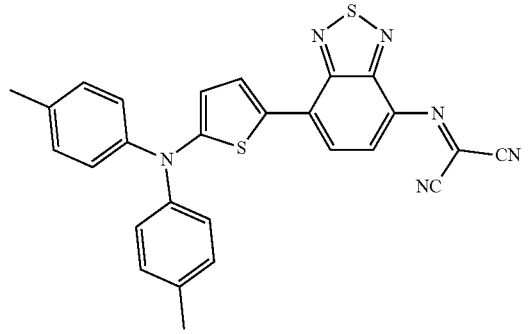
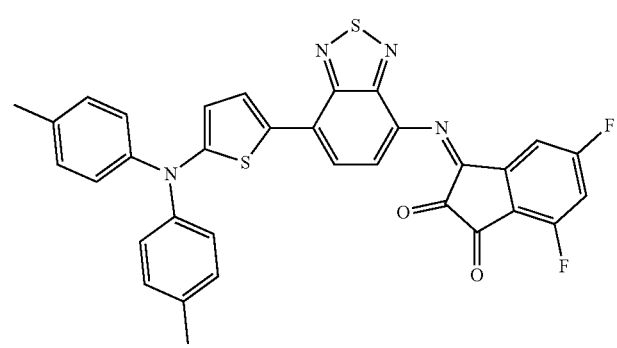

797 798
-continued
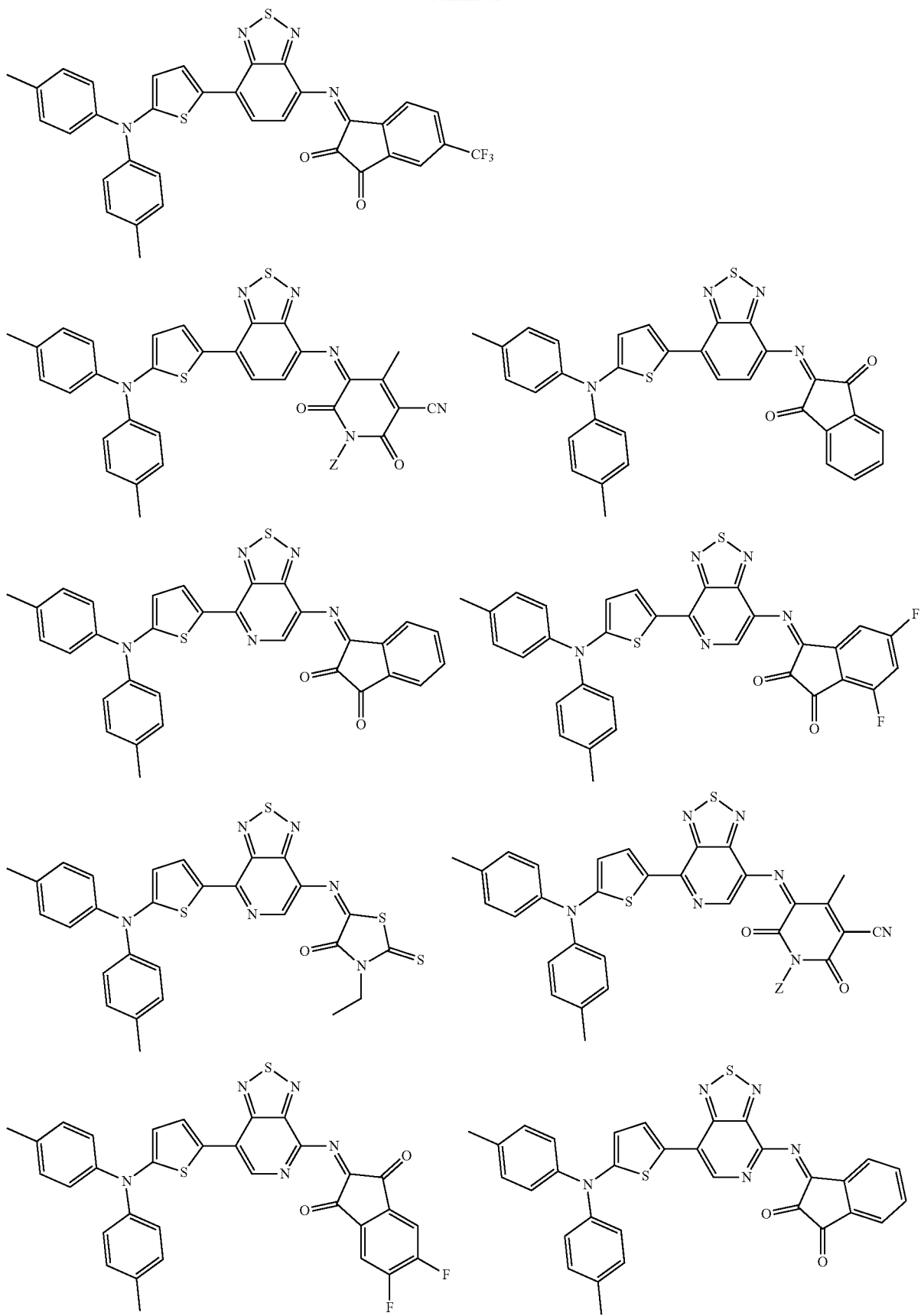

799
800
-continued
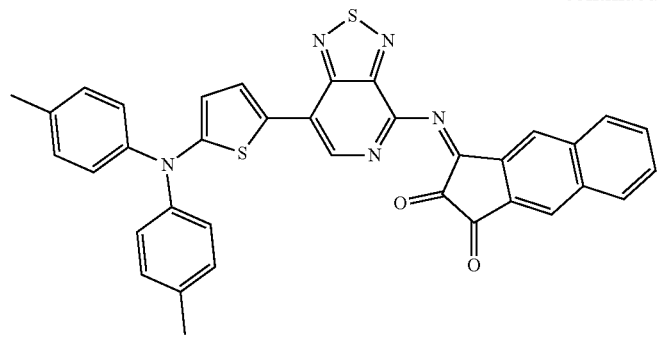
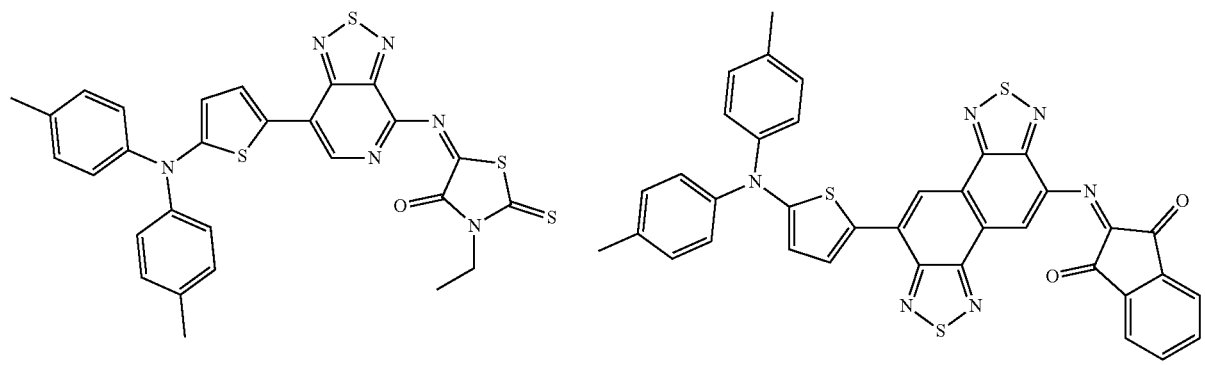
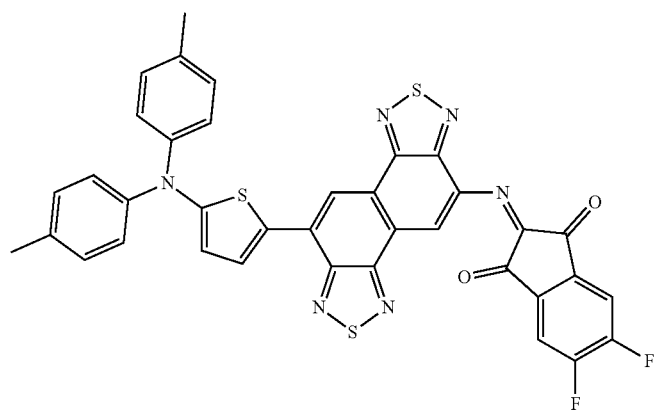
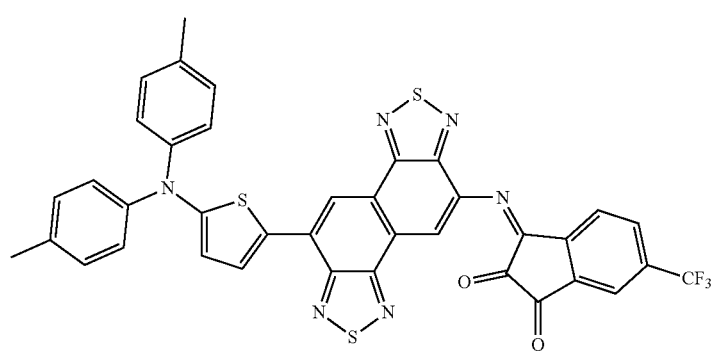

-continued
801
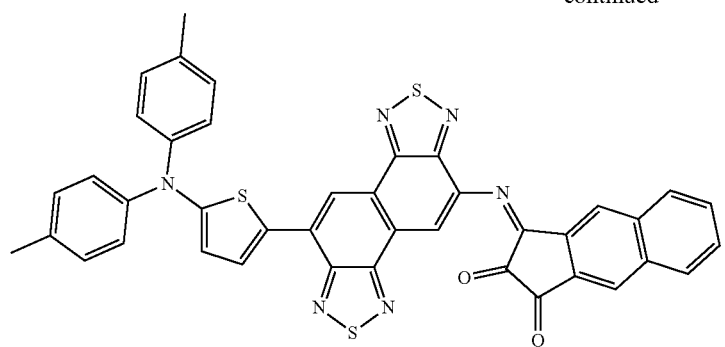
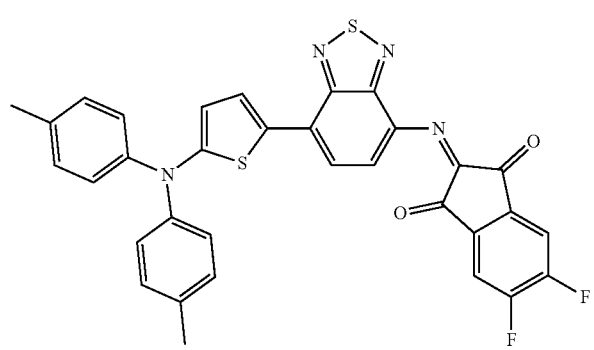
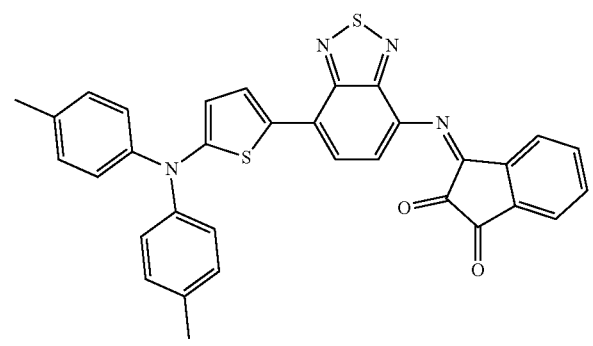
802
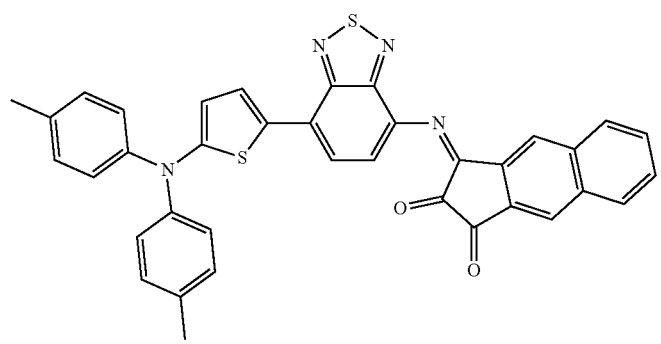
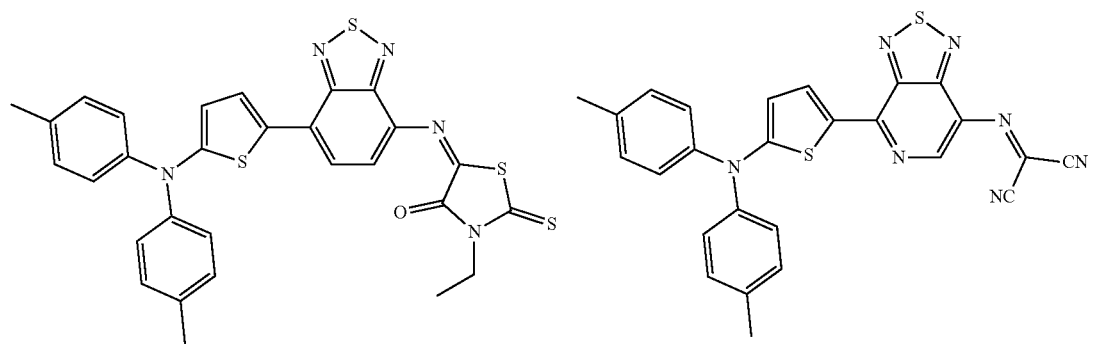
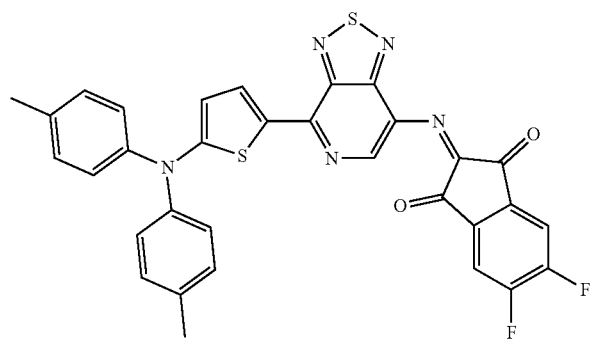

-continued
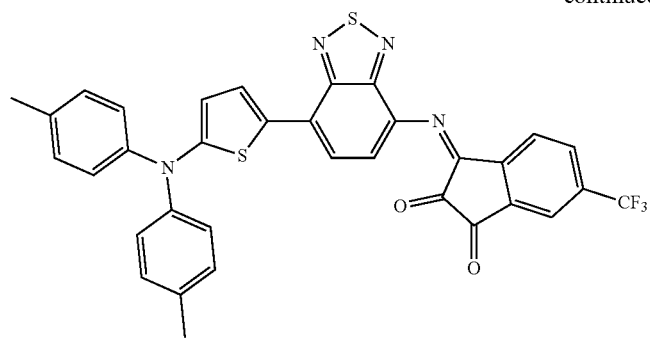
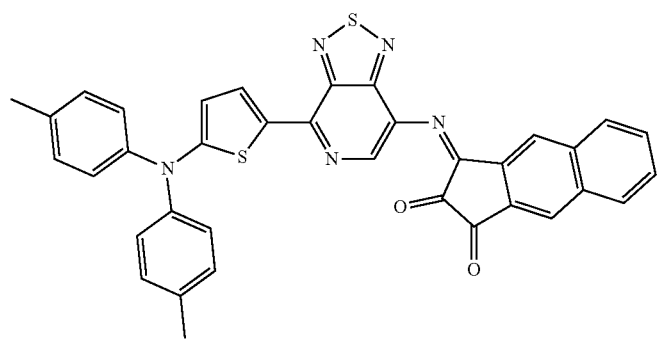
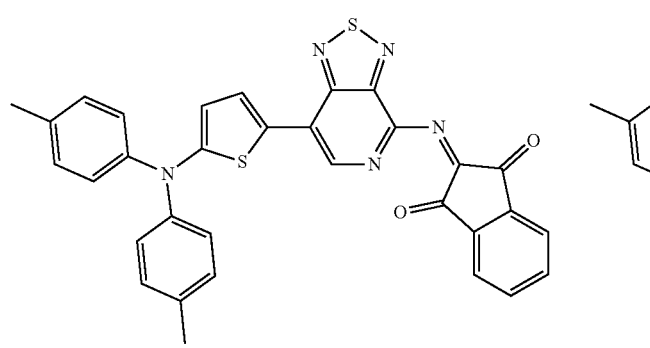
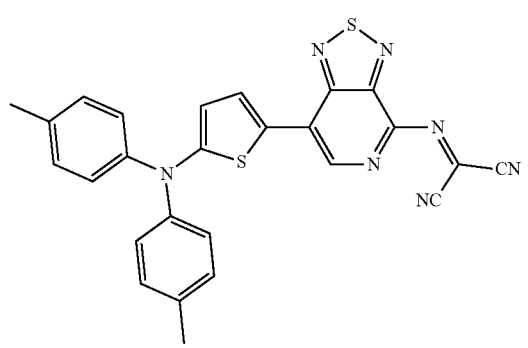
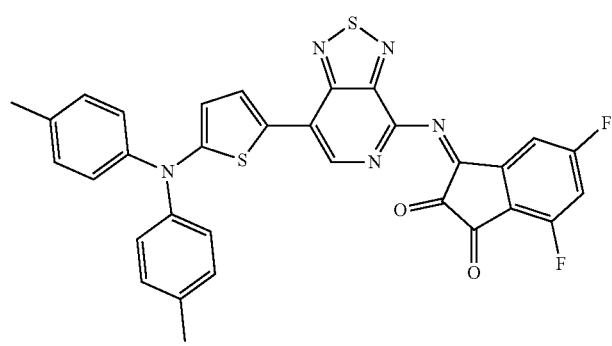
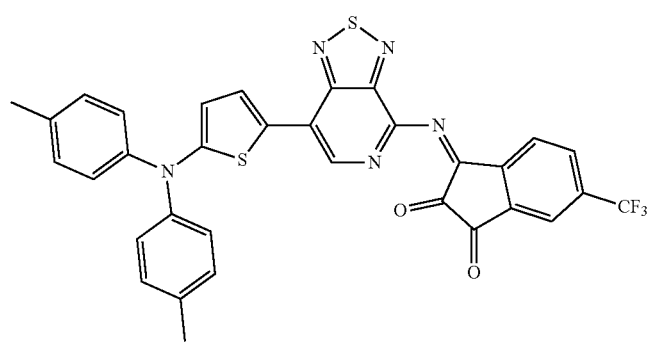

-continued
805 806
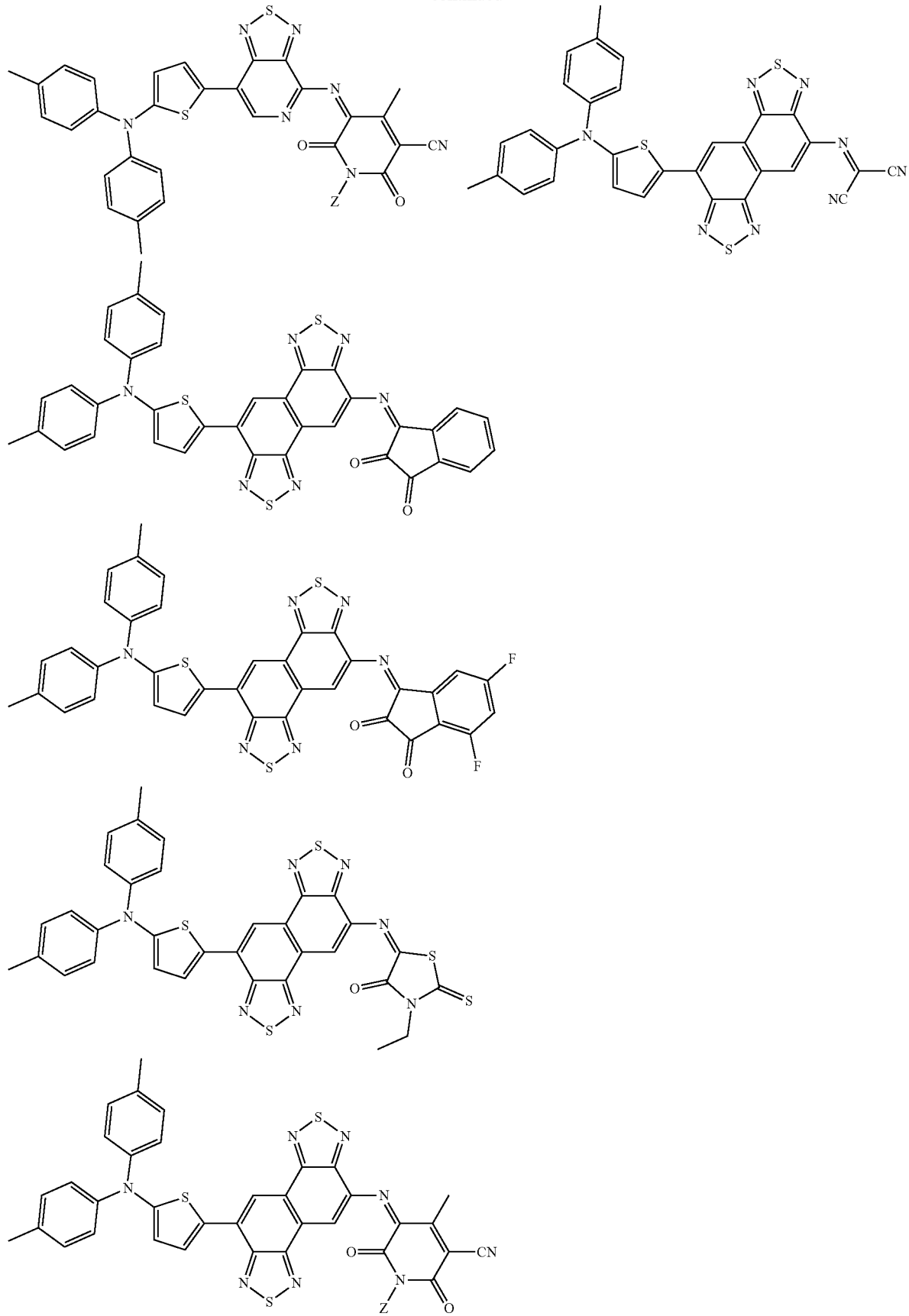

807 808
-continued
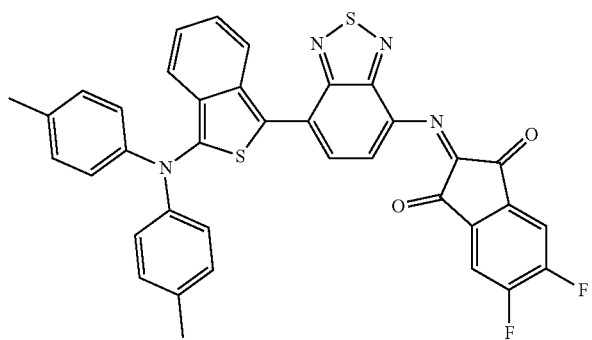
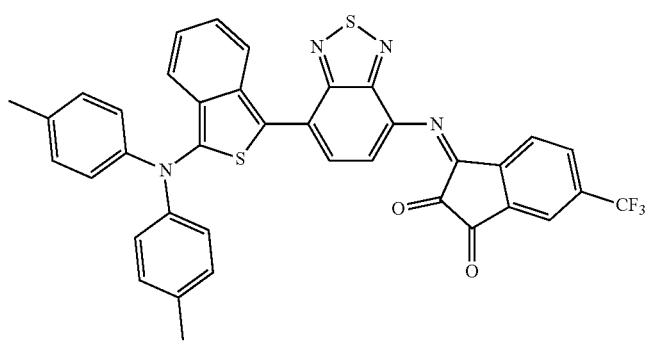
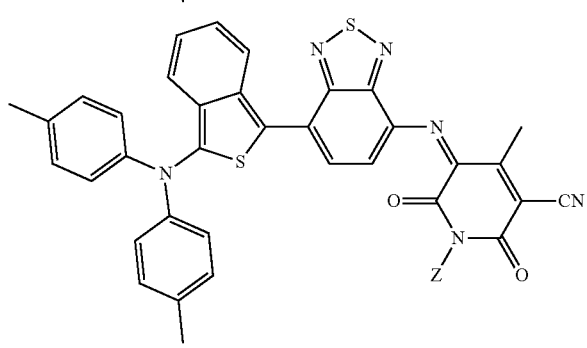
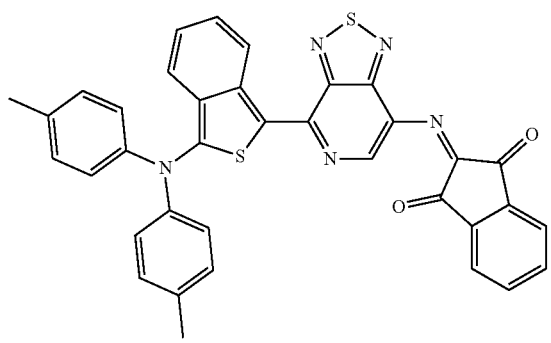
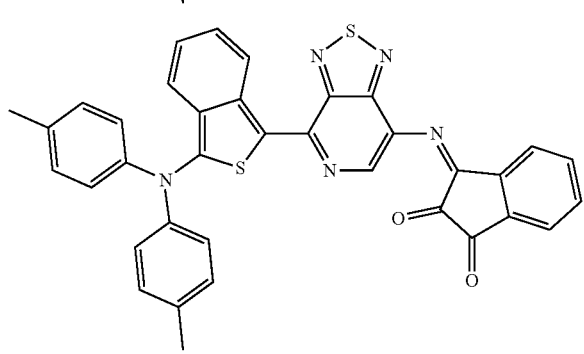
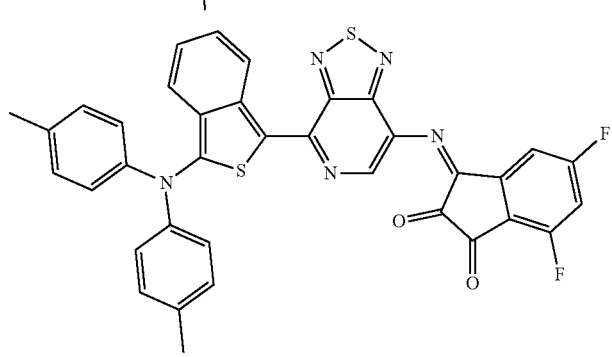
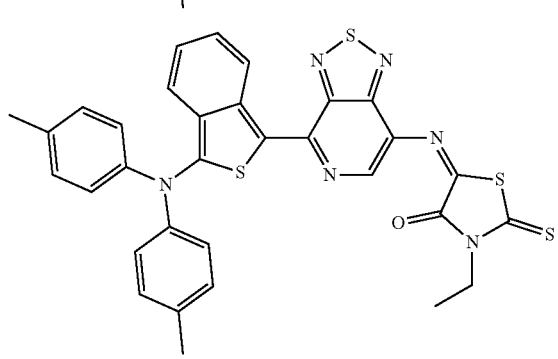
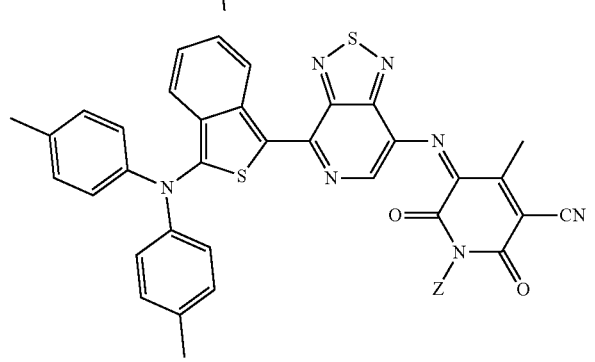

809 810
-continued
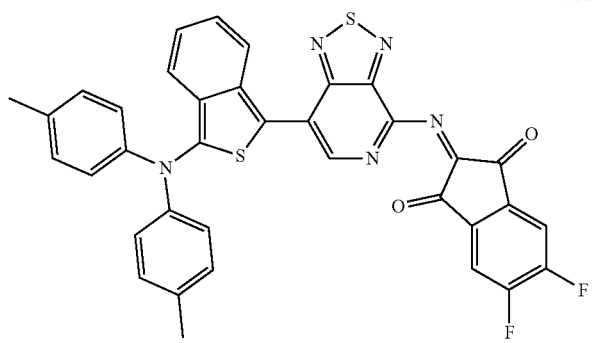
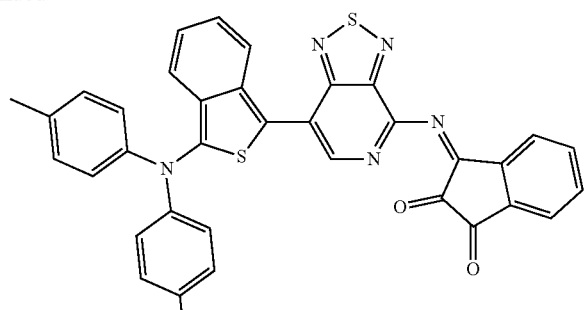
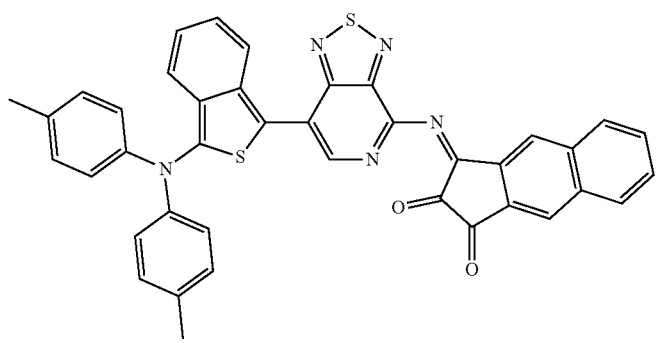
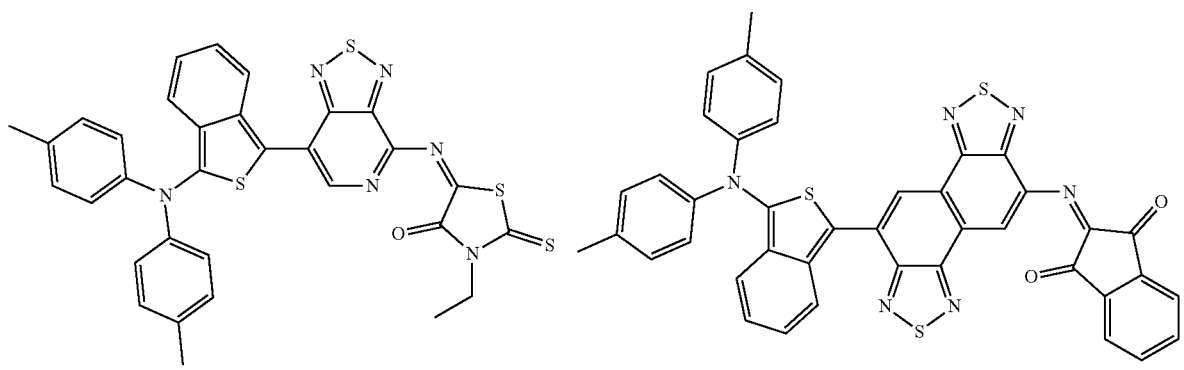
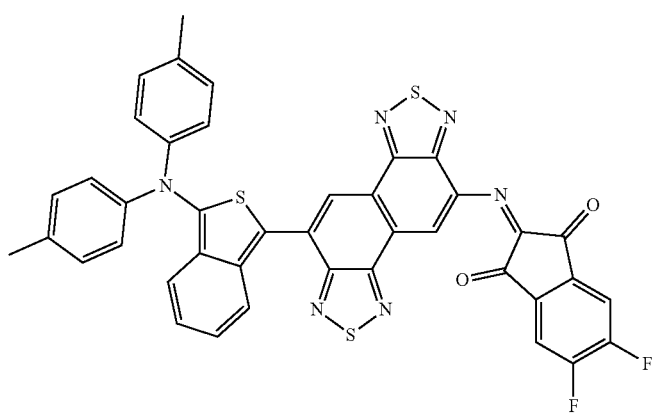

811                                    812
-continued
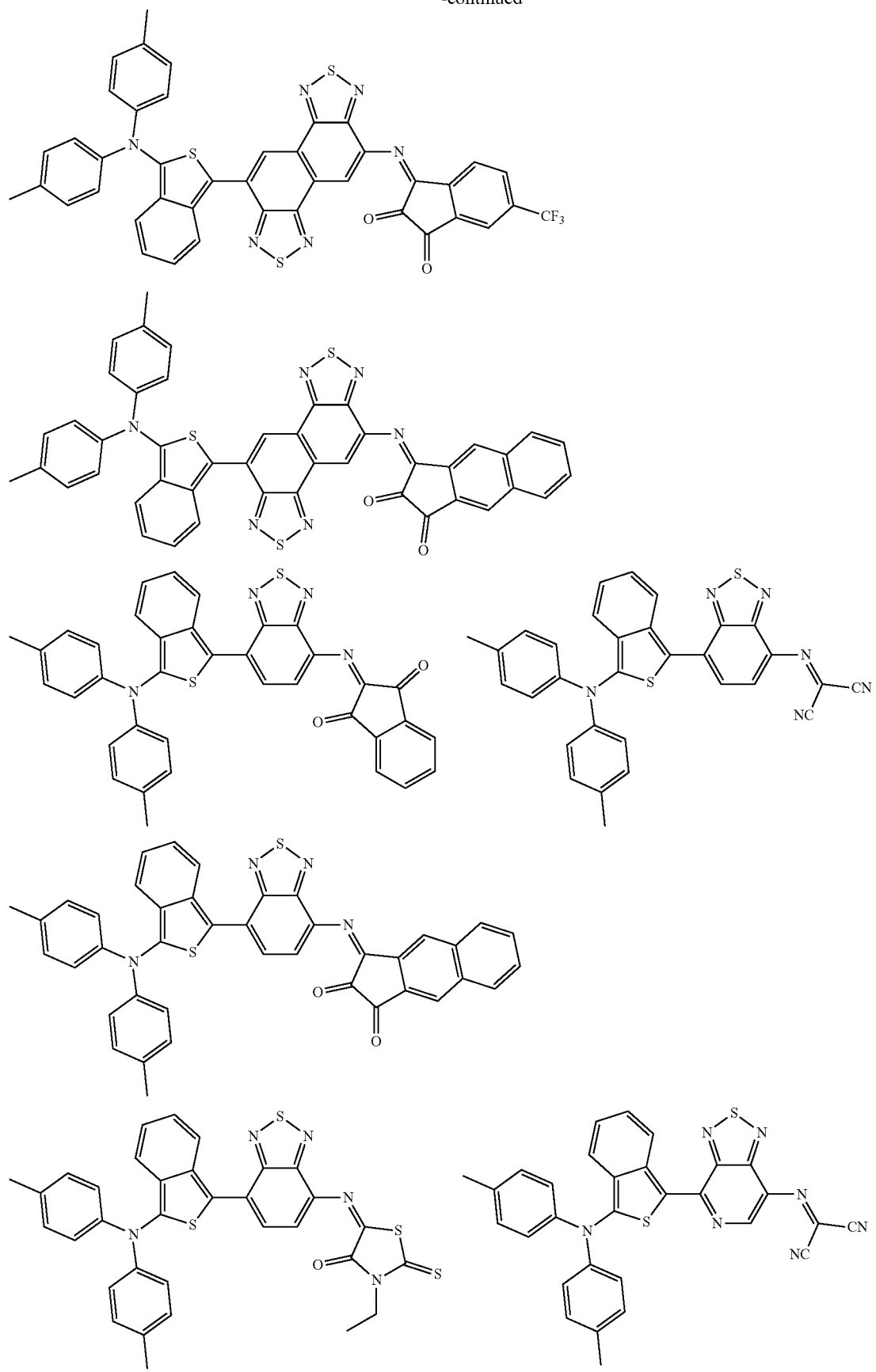

-continued
| 813 | 814 |
|---|---|
| 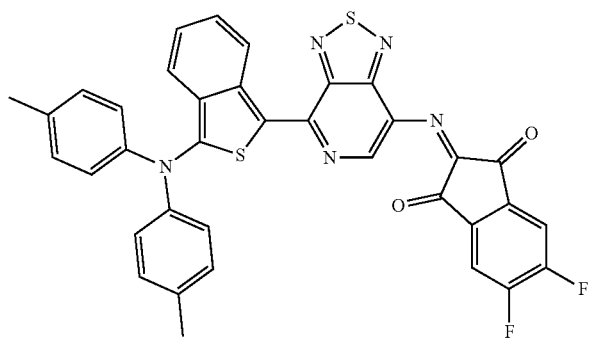 | |
| 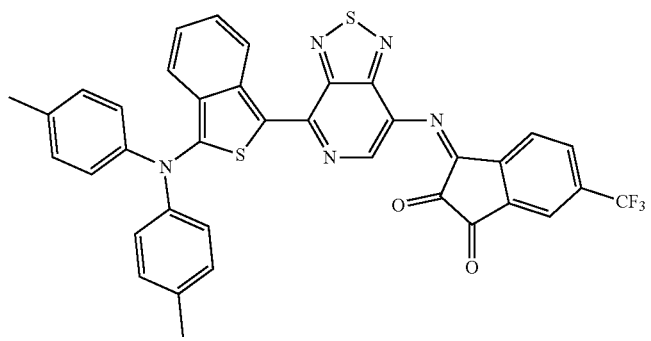 | |
| 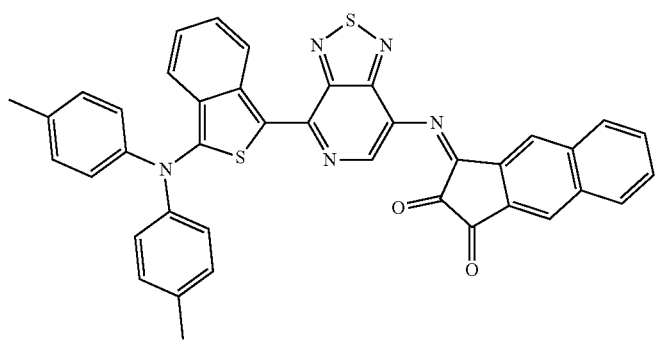 | |
| 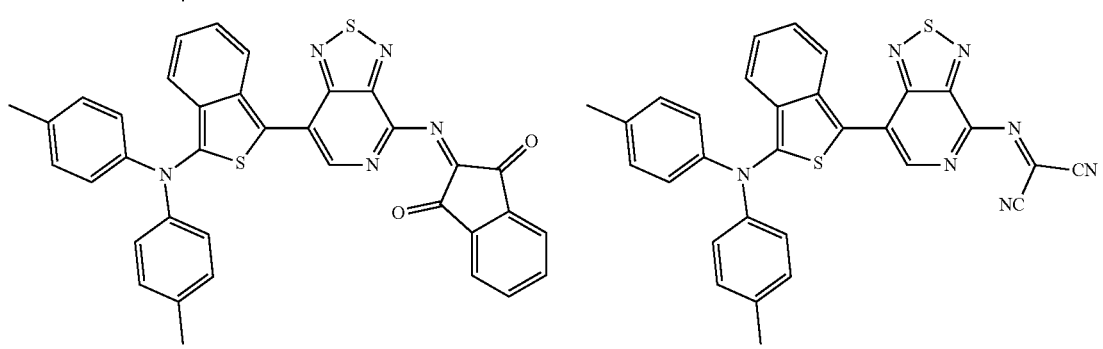 | |
| 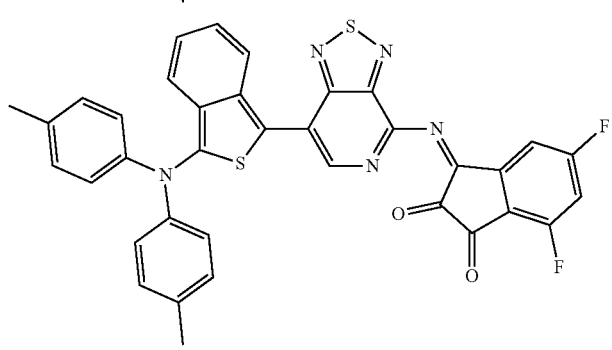 | |

815 816
-continued
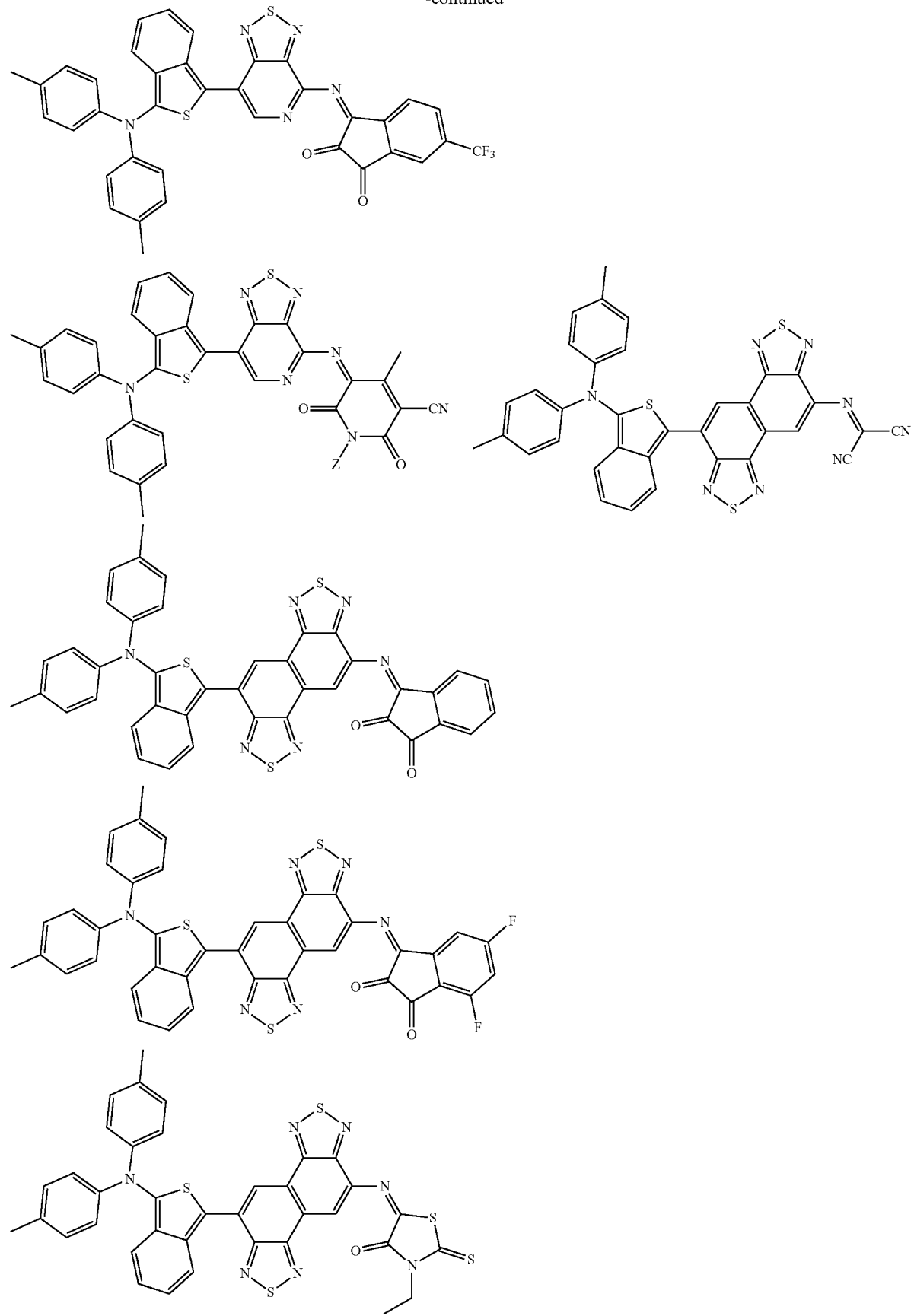

817 818
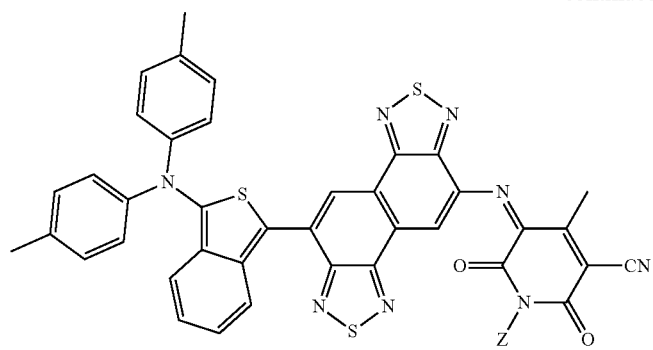
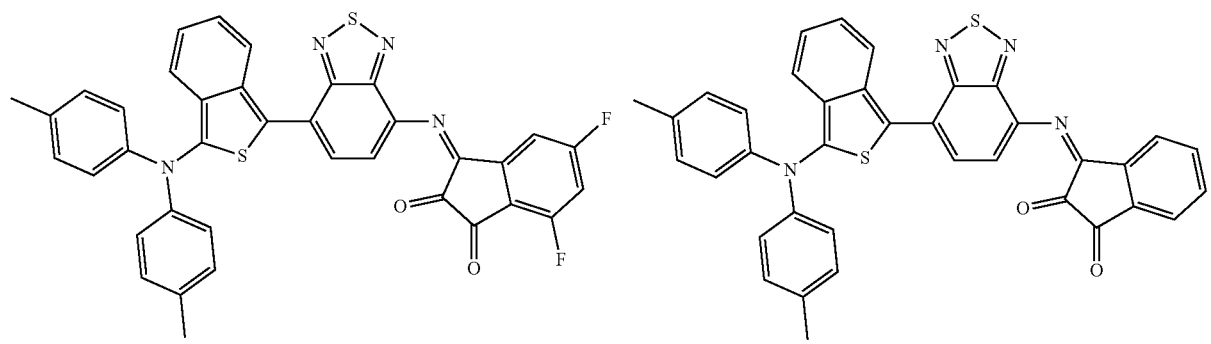
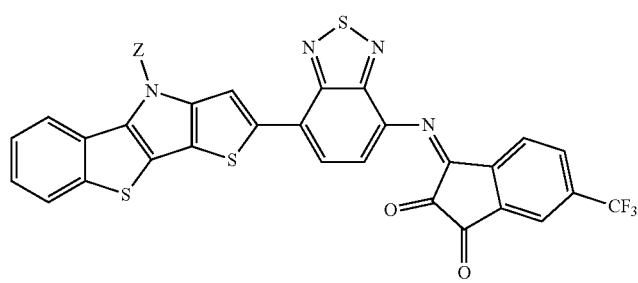
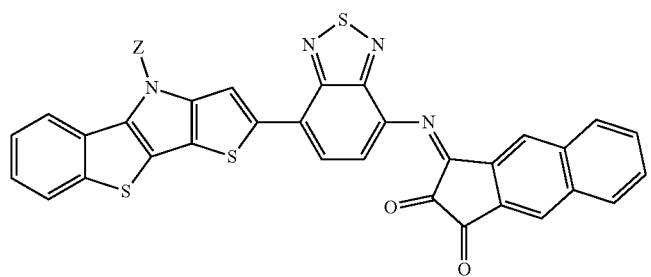
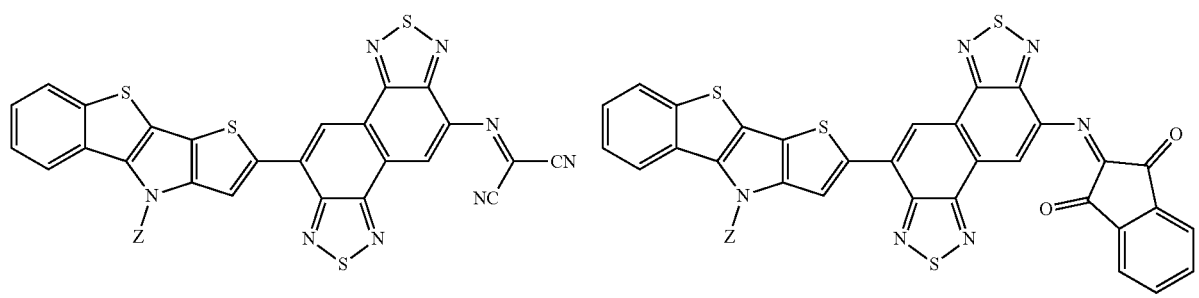

-continued
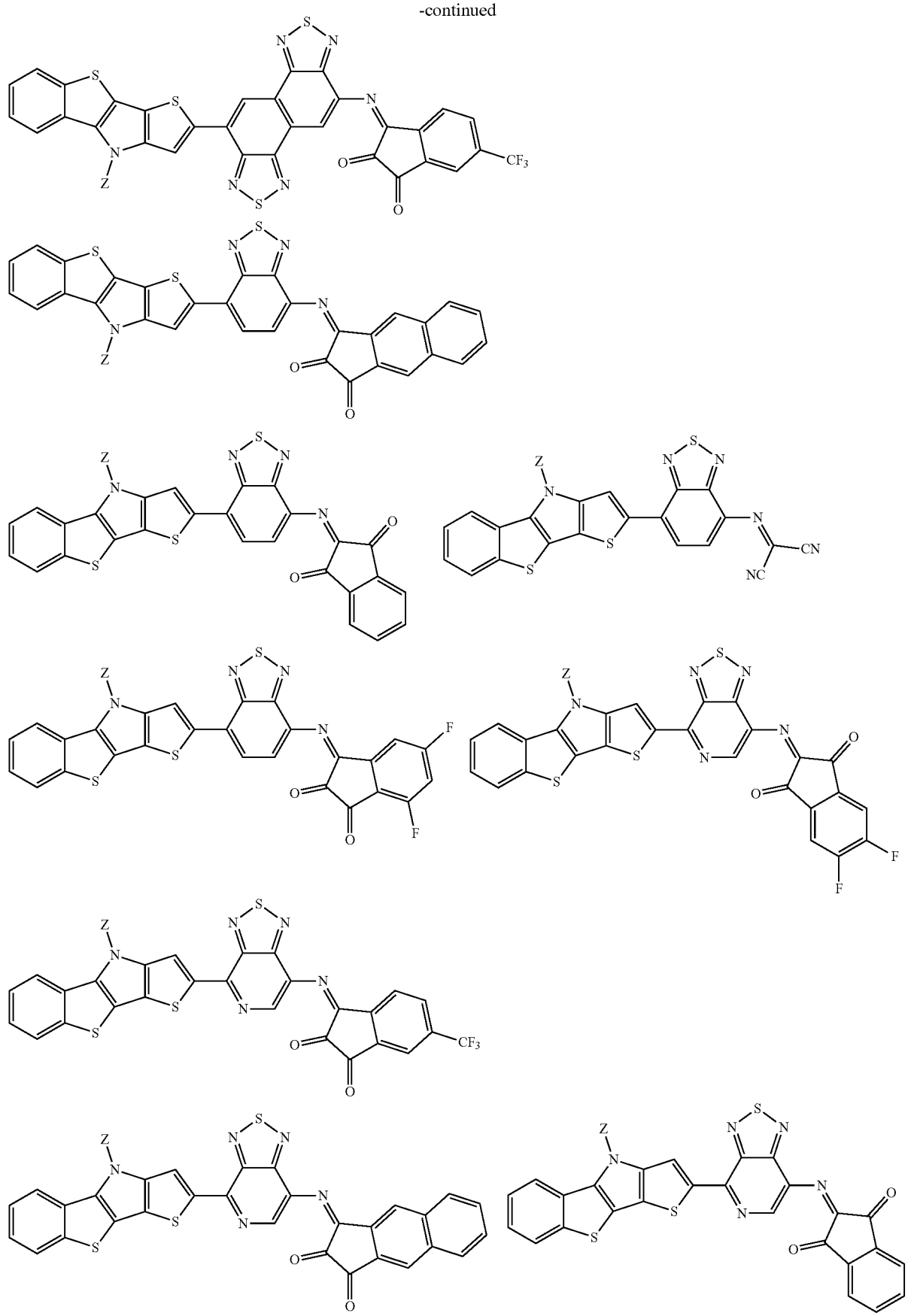

-continued
| 821 | 822 |
|---|---|
| 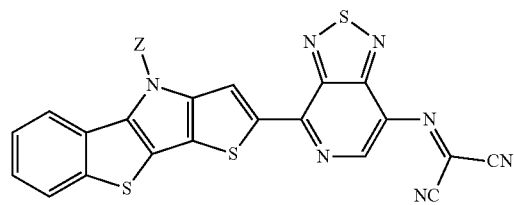 | 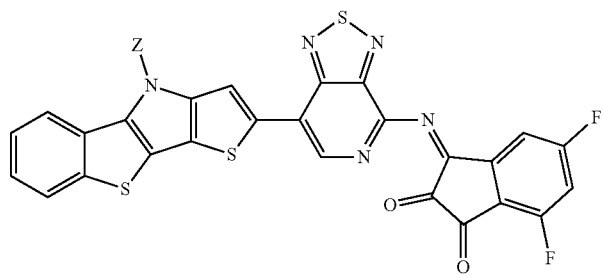 |
| 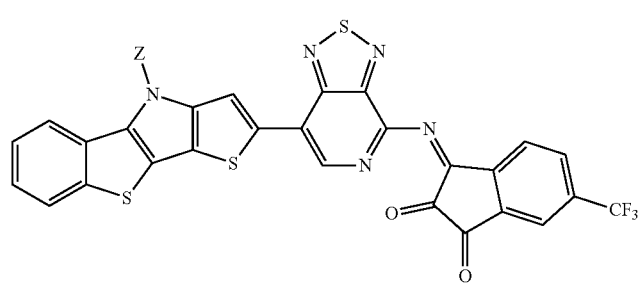 | |
| 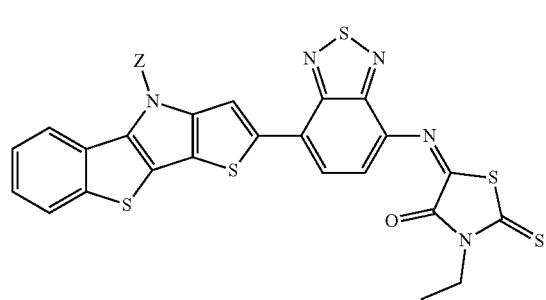 | 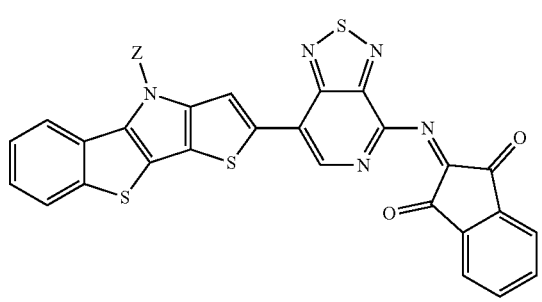 |
| 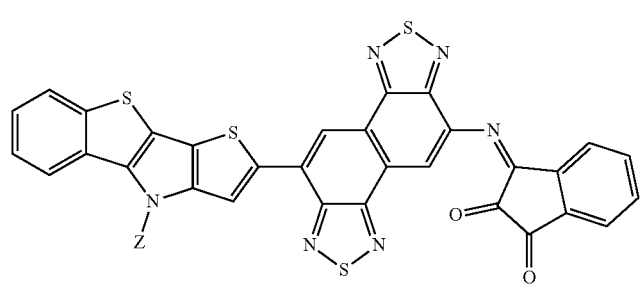 | 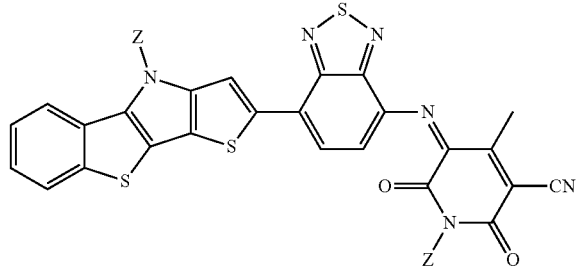 |
| 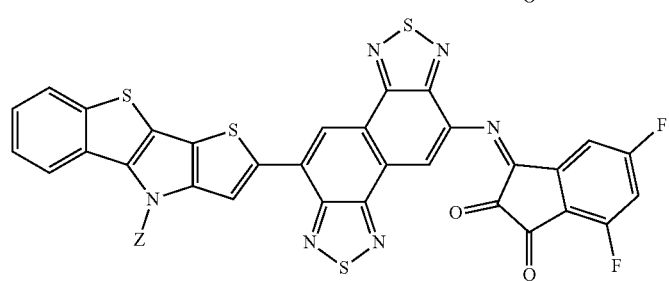 | |

-continued
823
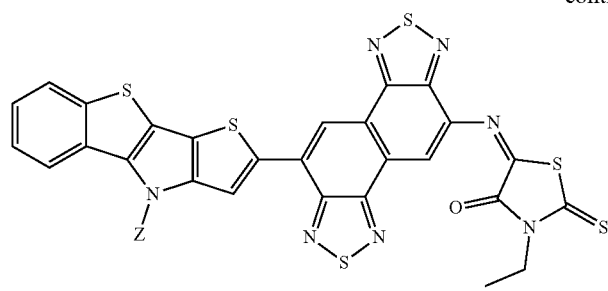
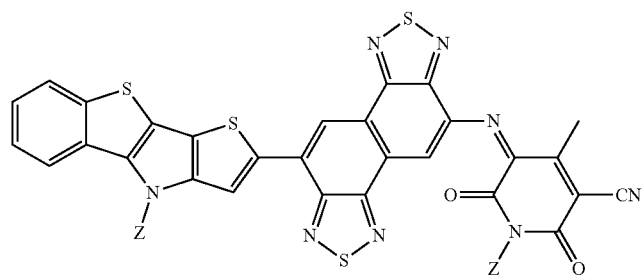
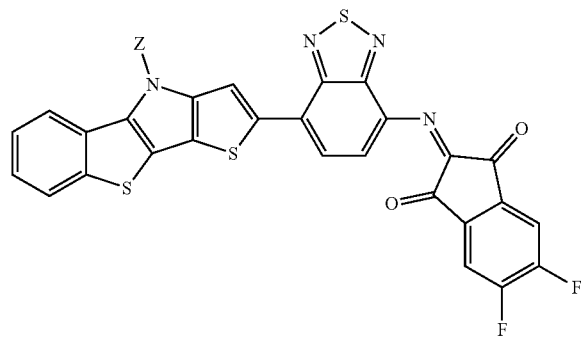
824
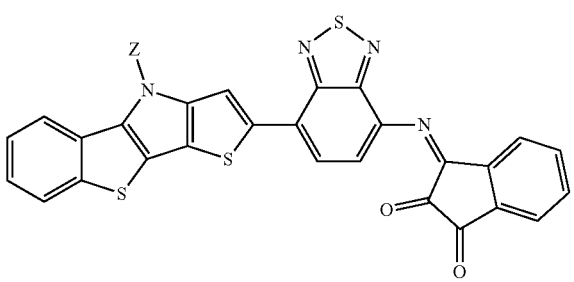
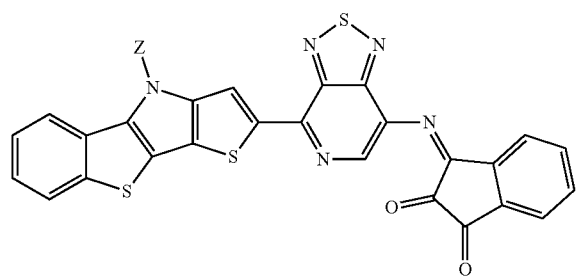
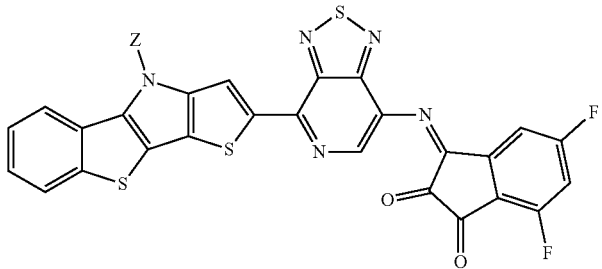
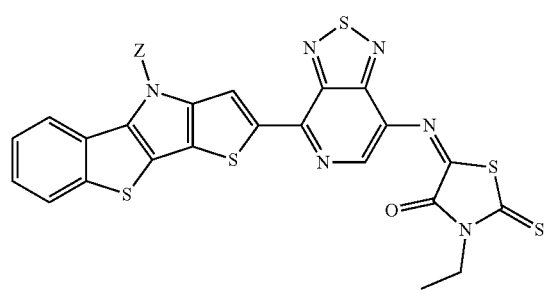
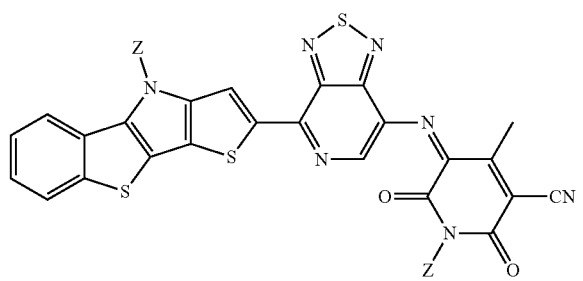

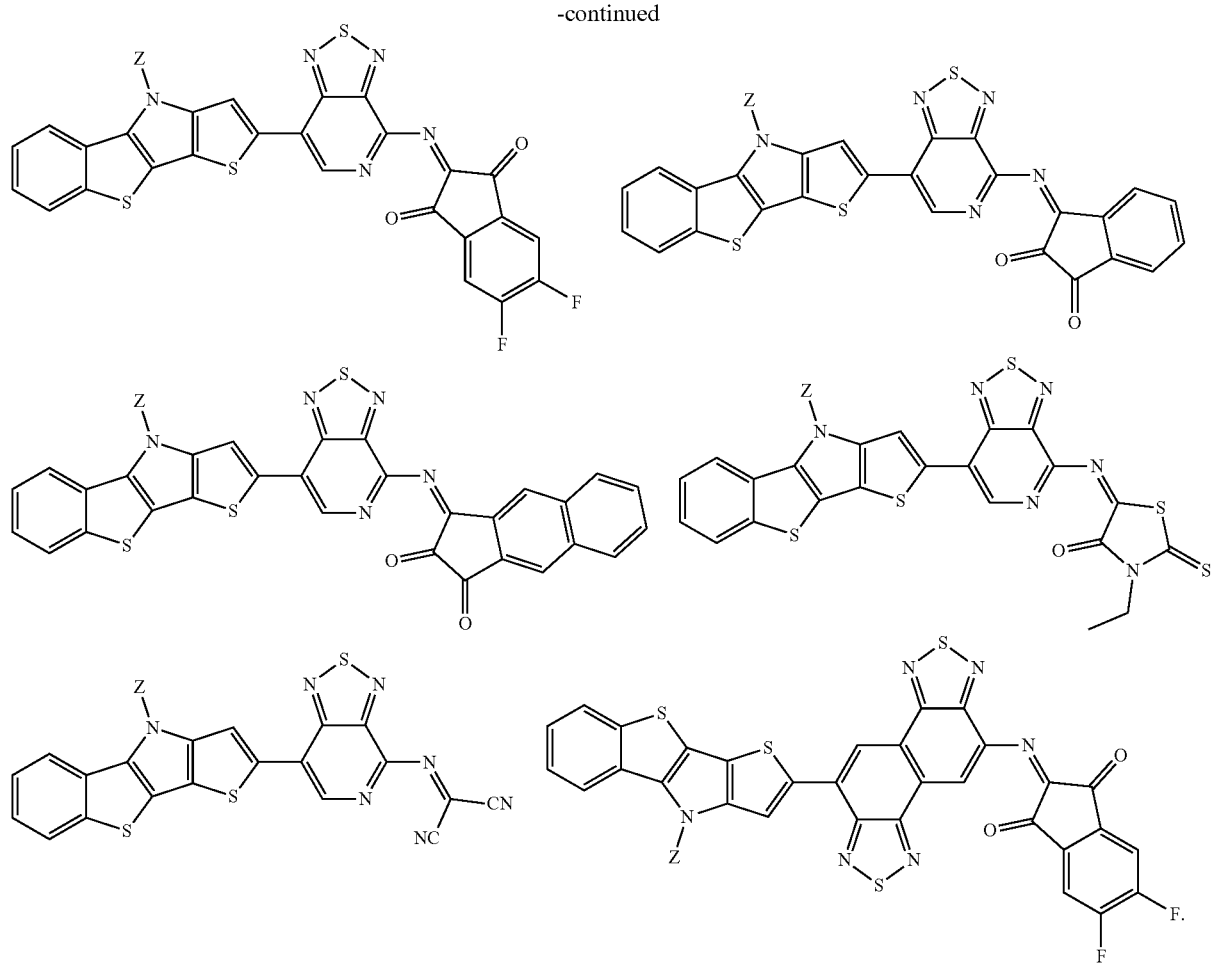

The disclosed photoactive compounds can be paired with a variety of other compounds to form a photovoltaic heterojunction. For example, when the photoactive compound is an electron acceptor compound, it can be paired with a counterpart electron donor material. As another example, when the photoactive compound is an electron donor compound, it can be paired with a counterpart electron acceptor material. A counterpart electron donor material may be a counterpart electron donor compound, for example, and may be different in some cases from the photoactive materials described herein. A counterpart electron acceptor material may be a counterpart electron donor compound, for example, and may be different in some cases from the photoactive materials described herein. In some cases, a photoactive layer may comprise one or multiple different electron donor compounds (e.g., blends of different photoactive compounds). In some cases, a photoactive layer may comprise one or multiple different electron acceptor compounds (e.g., blends of different photoactive compounds).

In some examples, the photoactive material of a device may contain a photoactive compound that is an electron acceptor compound described herein and the electron donor compound comprises a boron-dipyrromethene (BODIPY) compound, a phthalocyanine compound, a naphthalocyanine compound, a metal dithiolate (MDT) compound, or a dithiophene squarine compound. Combinations thereof may also be used. Examples of useful BODIPY compounds include, but are not limited to, those described in U.S. patent application Ser. No. 16/010,371, filed on Jun. 15, 2018, which is hereby incorporated by reference. Examples of useful phthalocyanine and naphthalocyanine compounds include, but are not limited to, those described in U.S. patent application Ser. No. 16/010,365, filed on Jun. 15, 2018, which is hereby incorporated by reference. Examples of useful MDT compounds include, but are not limited to, those described in U.S. patent application Ser. No. 16/010,369, filed on Jun. 15, 2018, which is hereby incorporated by reference. Examples of useful dithiophene squarine compounds include, but are not limited to, those described in U.S. patent application Ser. No. 16/010,374, filed on Jun. 15, 2018, which is hereby incorporated by reference. In some examples, a photoactive layer contains a BODIPY compound, a phthalocyanine compound, a naphthalocyanine compound, a MDT compound, a dithiophene squarine compound, or a combination thereof.

Aspects of the invention may be further understood by reference to the following non-limiting examples.

Example 1—Synthesis of Example Photoactive Compounds, Including Those Containing Core-Disrupted and Indandione Groups FIGS. 8-34 provide overview of various example synthetic schemes providing synthetic routes for various photoactive compounds, including core disrupted compounds and compounds containing indandione groups.

Figure 8:
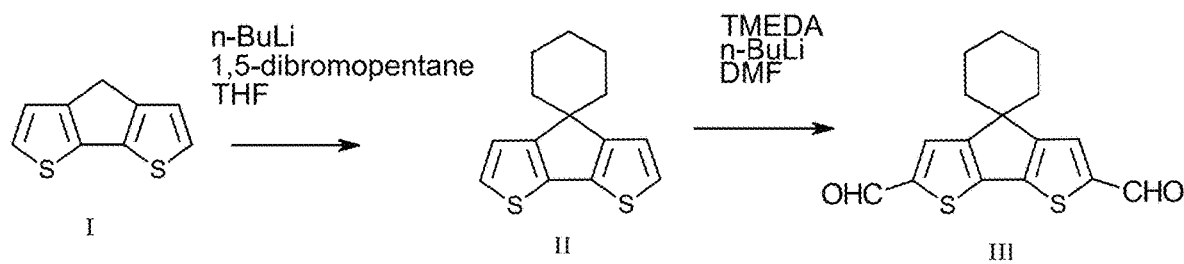
FIG. 8 provides a synthetic scheme for preparation of an example compound useful in preparing various core-disrupted photoactive compounds.

FIG. 8 provides a synthetic scheme for preparation of compound III by way of compound II.

Compound II: Flask 1: To a dry three neck flask 4H-Cyclopenta[1,2-b:5,4-b']di thiophene (10.08 g, 0.0565 mol) and 240 mL of anhydrous THF were added under nitrogen protection. The reaction flask was then cooled to −20° C. and n-BuLi (2.5 M in Hexanes, 22.4 mL, 0.056 mol) was added dropwise. Temperature was kept between −25° C. and −18° C. for 30 minutes under agitation with a magnetically coupled spinbar.

Flask 2: To a dry second three neck flask 1,5-dibromopentane was added to 80 mL of anhydrous THF, placed under nitrogen protection, and then cooled to −70° C. with a dry ice and acetone dewar flask. A dry addition funnel was added to one of the flask ports and the reaction mixture from Flask 1 was cannulated into the addition funnel added dropwise over the course of 30 minutes to the flask 2 at −70° C. This new reaction mixture was stirred for 30 minutes at −70° C. and 80 mL of anhydrous THF was rinsed through the addition funnel to further dilute the reaction. A second equivalent of n-BuLi was added dropwise (2.5 M in Hexanes, 22.4 mL, 0.056 mol) to this reaction mixture and allowed to stir for 30 minutes at −70° C. before gradual warming to room temperature over the course of 30 additional minutes. The reaction continued for 1 hour at room temperature before workup through addition to 600 mL of deionized water and 3× extractions of 300 mL of diethyl ether, drying over sodium sulfate, and concentration in vacuo to yield crude product. Purification was achieved via column chromatography on Silica-60 with Heptane to yield compound II (6.13 g, 44% yield).

Compound III: To a dry three neck flask compound II (0.40 g, 0.00162 mol) and 40 mL of anhydrous diethyl ether were added under nitrogen protection. TMEDA was added to the reaction mixture dropwise at room temperature, then the flask was cooled to −40° C. n-BuLi (2.5 M in Hexanes, 1.30 mL, 0.00325 mol) was added to the reaction mixture dropwise. The reaction mixture was allowed to warm to room temperature over 30 minutes and then was mixed for an additional 30 minutes at room temperature. The flask was then cooled to −40° C. and anhydrous DMF (0.50 mL, 0.00649 mol) was added. The reaction was allowed to mix for 30 minutes at −40° C. and was then warmed gradually to mix overnight at room temperature. Workup was accomplished by pouring the reaction mixture into 100 mL of 20% NH$_4$Cl (aq) solution, 3× extraction with dichloromethane, and drying over sodium sulfate to yield crude compound III. Purification by column chromatography on Silica-60 elutes with Dichloromethane-Heptane to yield compound III (0.348 g, 71% yield).

Figure 9:
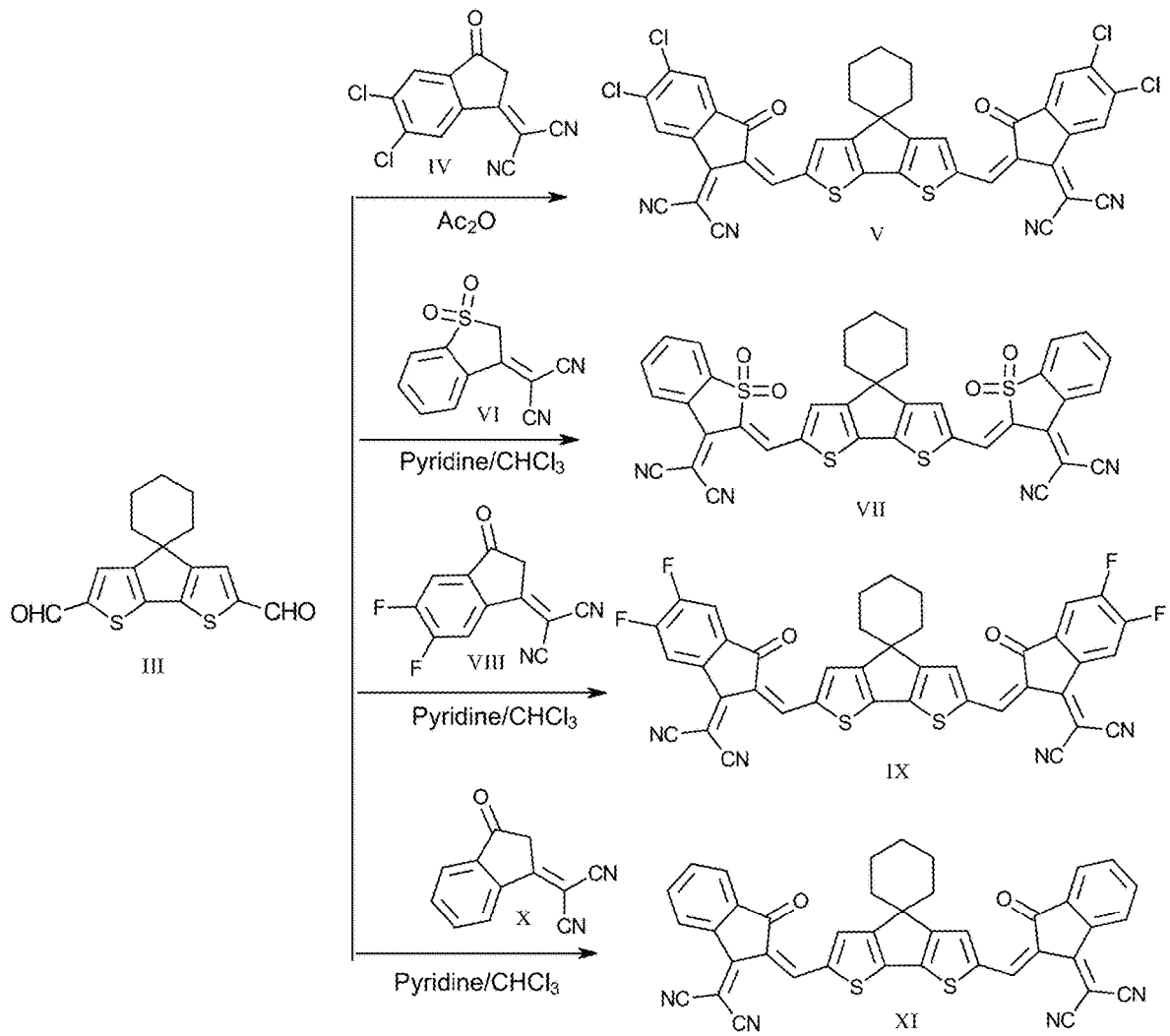
FIG. 9 provides synthetic schemes for preparation of various example core-disrupted photoactive compounds.

FIG. 9 provides synthetic schemes for preparation of various core-disrupted photoactive compounds:

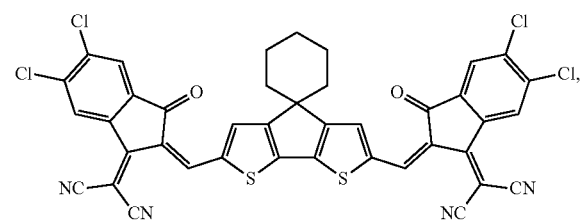

V

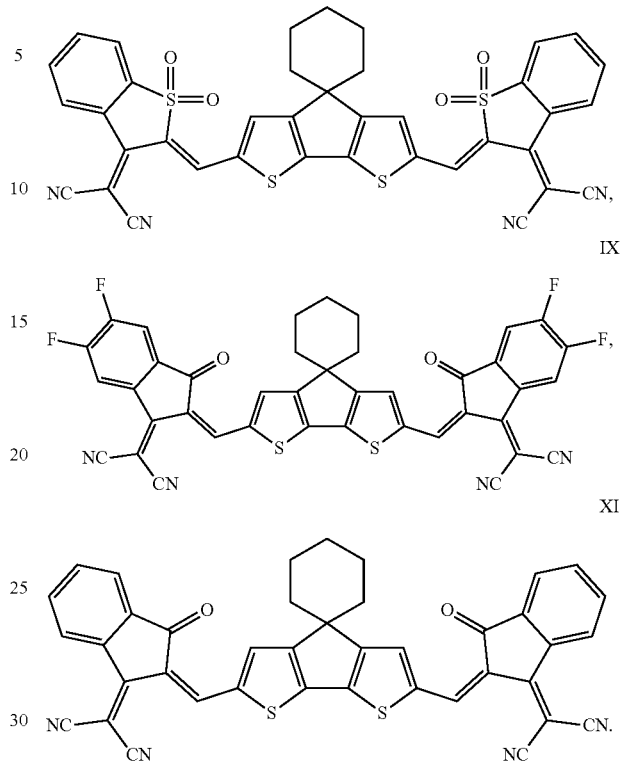

VII

IX

XI

Compound V: To a 3-neck flask equipped with a condenser and magnetic stir bar, compound III (0.15 g, 0.0005 mol), compound IV (0.43 g, 0.002 mol), and 60 mL of acetic anhydride were added. The flask was purged with nitrogen then stirred at room temperature for 30 minutes before being heated to 90° C. and stirred for an additional hour. 200 mL of water were added to the cooled reaction and the precipitate was filtered to obtain compound V. This compound was sublimed in 5% yield. $\lambda_{max}$ (DCM): 696 nm.

Compound VII: To a 3-neck flask equipped with a condenser and magnetic stir bar, compound III (1.0 eq) compound VI (4.0 eq), and anhydrous chloroform were added. The flask was purged with nitrogen then pyridine (20.0 eq) was added dropwise. The mixture was stirred at room temperature for 30 minutes then heated to reflux and stirred for 48 hours under nitrogen. The reaction mixture was cooled to room temperature, concentrated in vacuo, then resuspended in hot isopropanol. The suspension was filtered and washed with additional isopropanol then dried to obtain compound VII. This compound was sublimed in 0% yield. $\lambda_{max}$ (DCM): 682 nm.

Compound IX: To a 3-neck flask equipped with a condenser and magnetic stir bar, compound III (1.0 eq) compound VIII (4.0 eq), and anhydrous chloroform were added. The flask was purged with nitrogen then pyridine (20.0 eq) was added dropwise. The mixture was heated to reflux and stirred for 18 hours under nitrogen. The reaction mixture was cooled to room temperature then poured into 200 mL of cold methanol. The suspension was filtered then washed with additional methanol to afford compound IX as a shiny green solid with limited solubility in 80% yield. This compound was sublimed in 30% yield. $\lambda_{max}$ (DCM): 609 nm.

Compound XI: Compound XI was synthesized from compound III using the same method as used for compound IX, substituting compound X in place of compound VIII. Compound XI was sublimed in 13% yield. $\lambda_{max}$ (DCM): 676 nm.

Figure 10:
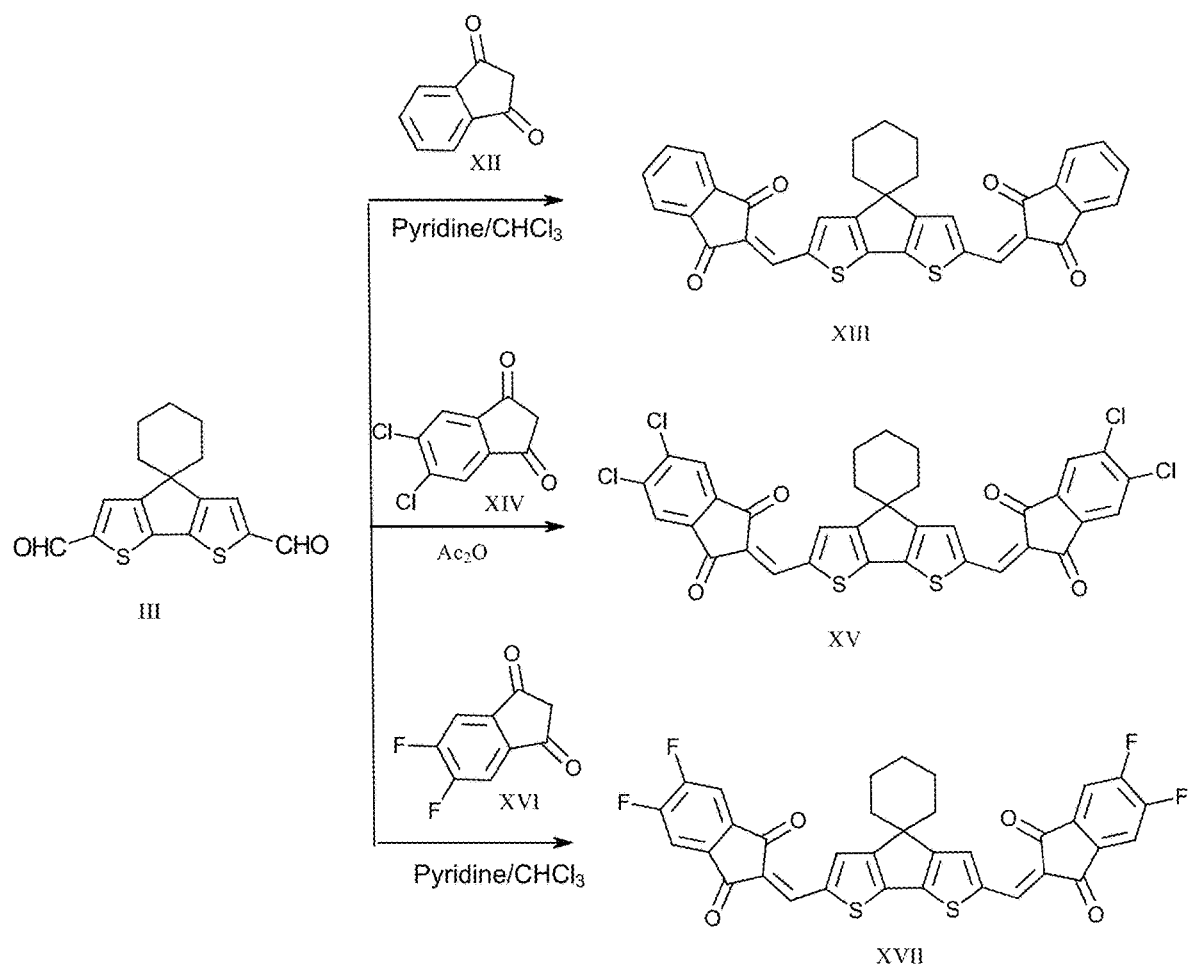
FIG. 10 provides synthetic schemes for preparation of various example core-disrupted photoactive compounds.

FIG. 10 provides synthetic schemes for preparation of various core-disrupted photoactive compounds:

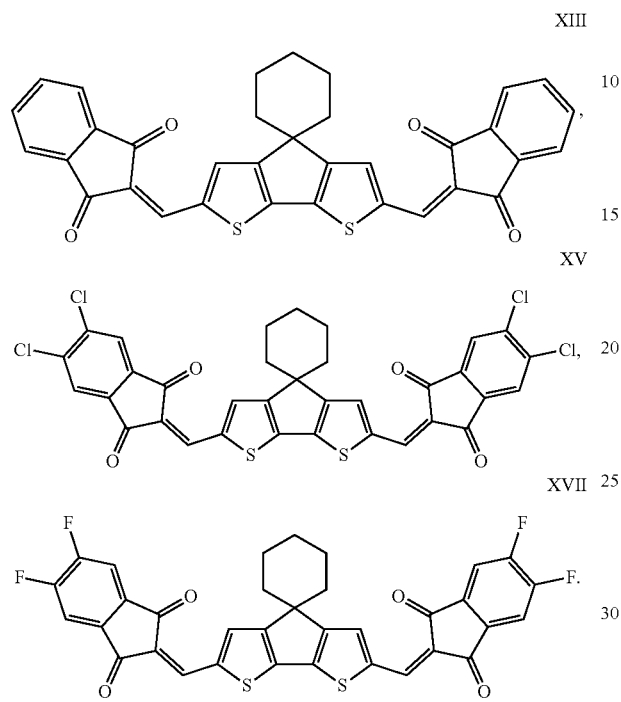

Compound XIII: Compound XIII was synthesized from compound III using the same method as used for compound IX, substituting compound XII in place of compound VIII. Compound XIII was sublimed in 65-85% yield. $\lambda_{max}$ (DCM): 593 nm.

Compound XV: Compound XV was synthesized from compound III using the same method as used for compound IX, substituting compound XIV in place of compound VIII, in 73% yield. Compound XV was sublimed in 9% yield. $\lambda_{max}$ (DCM): 611 nm.

Compound XVII: Compound XVII was synthesized from compound III using the same method as used for compound VII, substituting compound XVI in place of compound VI, in 99% yield. This compound was sublimed in 75-88% yield. $\lambda_{max}$ (DCM): 599 nm.

Figure 11:
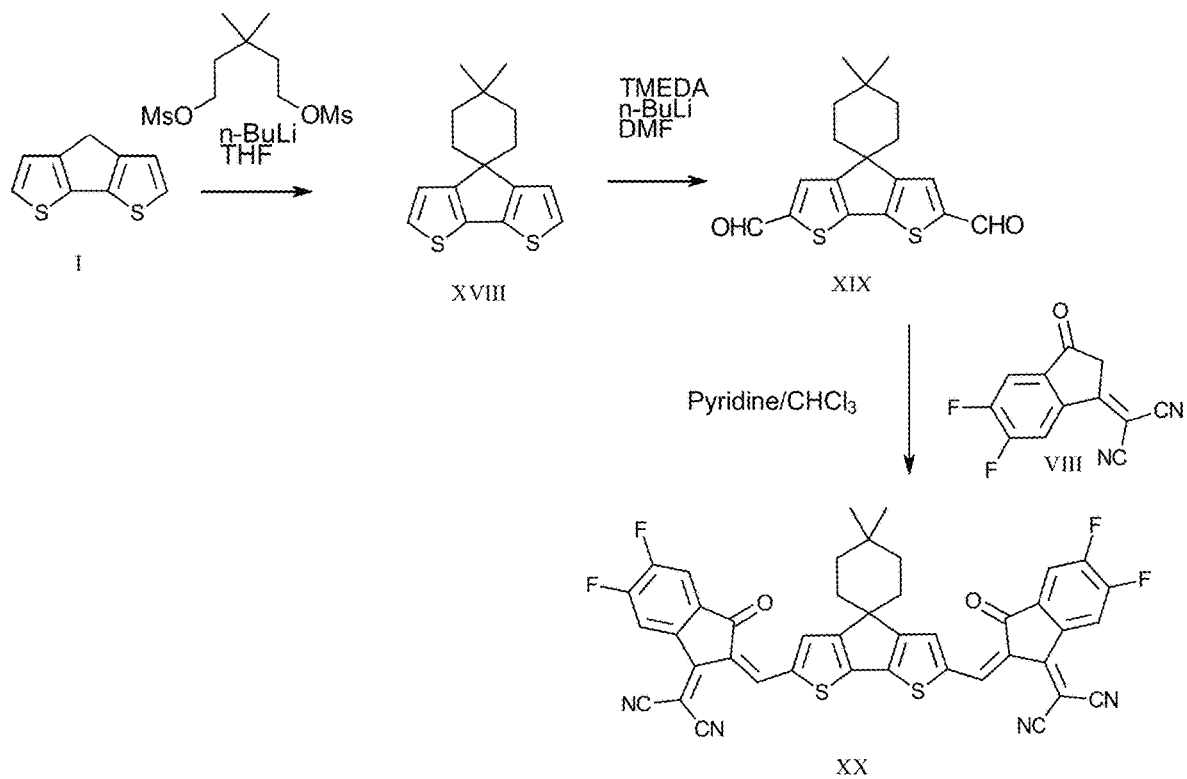
FIG. 11 provides a synthetic scheme for preparation of an example core-disrupted photoactive compound.

FIG. 11 provides a synthetic scheme for preparation of a core-disrupted photoactive compound:

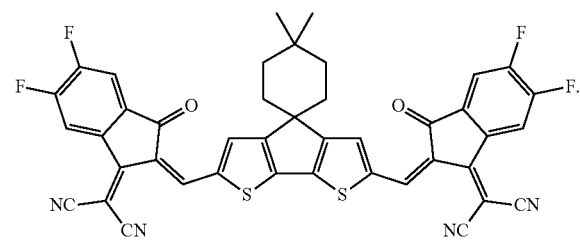

Compound XVIII was synthesized from compound I using the same method as used for compound II, substituting 1,5-Pentanediol, 3,3-dimethyl-, 1,5-dimethanesulfonate in place of 1,5-dibromopentane, in 55% yield.

Compound XIX was synthesized using the same method as used for compound III, substituting compound XVIII in place of compound II, in 51% yield.

Compound XX was synthesized from compound VIII using the same method as used for compound IX, substituting compound XIX in place of compound III, in 41% yield. Compound XX was sublimed in 12% yield.

Figure 12:
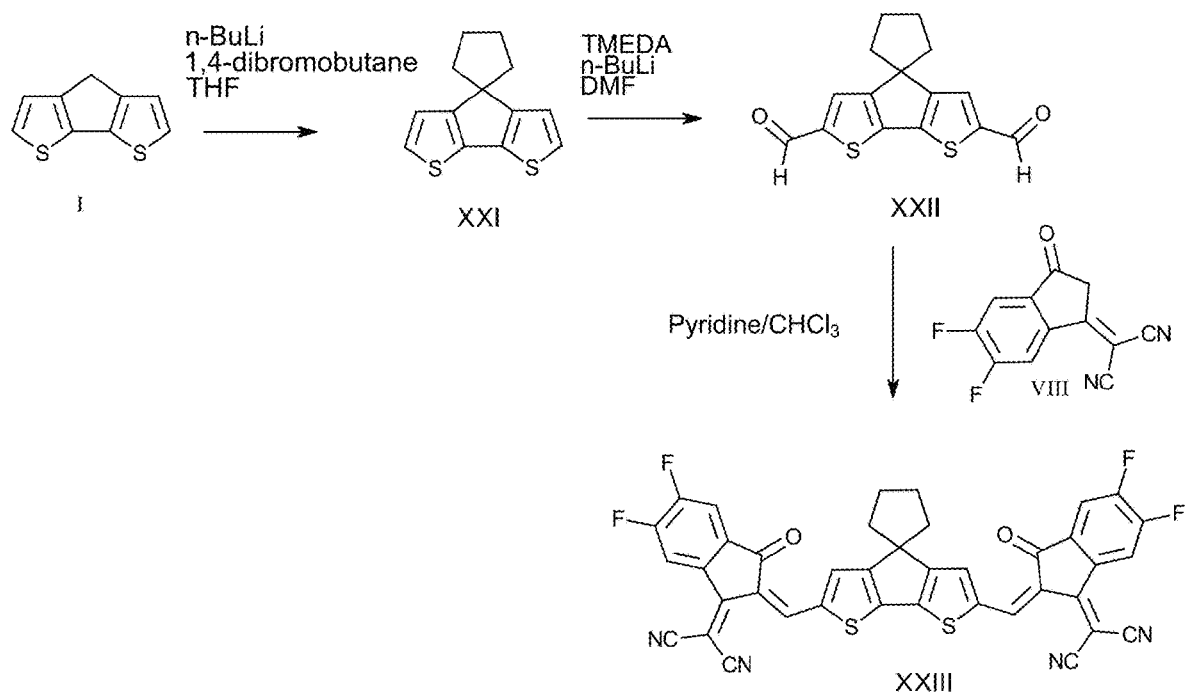
FIG. 12 provides a synthetic scheme for preparation of an example core-disrupted photoactive compound.

FIG. 12 provides a synthetic scheme for preparation of a core-disrupted photoactive compound:

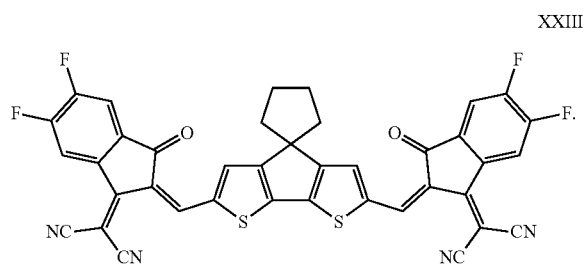 [SMILES: N#CC(C#N)=C1/C(=C/c2cc3c(s2)-c2sc(/C=C4\C(=O)c5cc(F)c(F)cc5C4=C(C#N)C#N)cc2C32CCCC2)C(=O)c2cc(F)c(F)cc21]

Compound XXI was synthesized from compound I using the same method as used for compound II, substituting 1,4-dibromobutane in place of 1,5-dibromopentane, in 69% yield.

Compound XXII was synthesized using the same method as used for compound III, substituting compound XXI in place of compound II, in 39% yield.

Compound XXIII was synthesized from compound VIII using the same method as used for compound IX, substituting compound XXII in place of compound III. Compound XXIII was sublimed in 12% yield. $\lambda_{max}$ (DCM): 686 nm.

Figure 13:
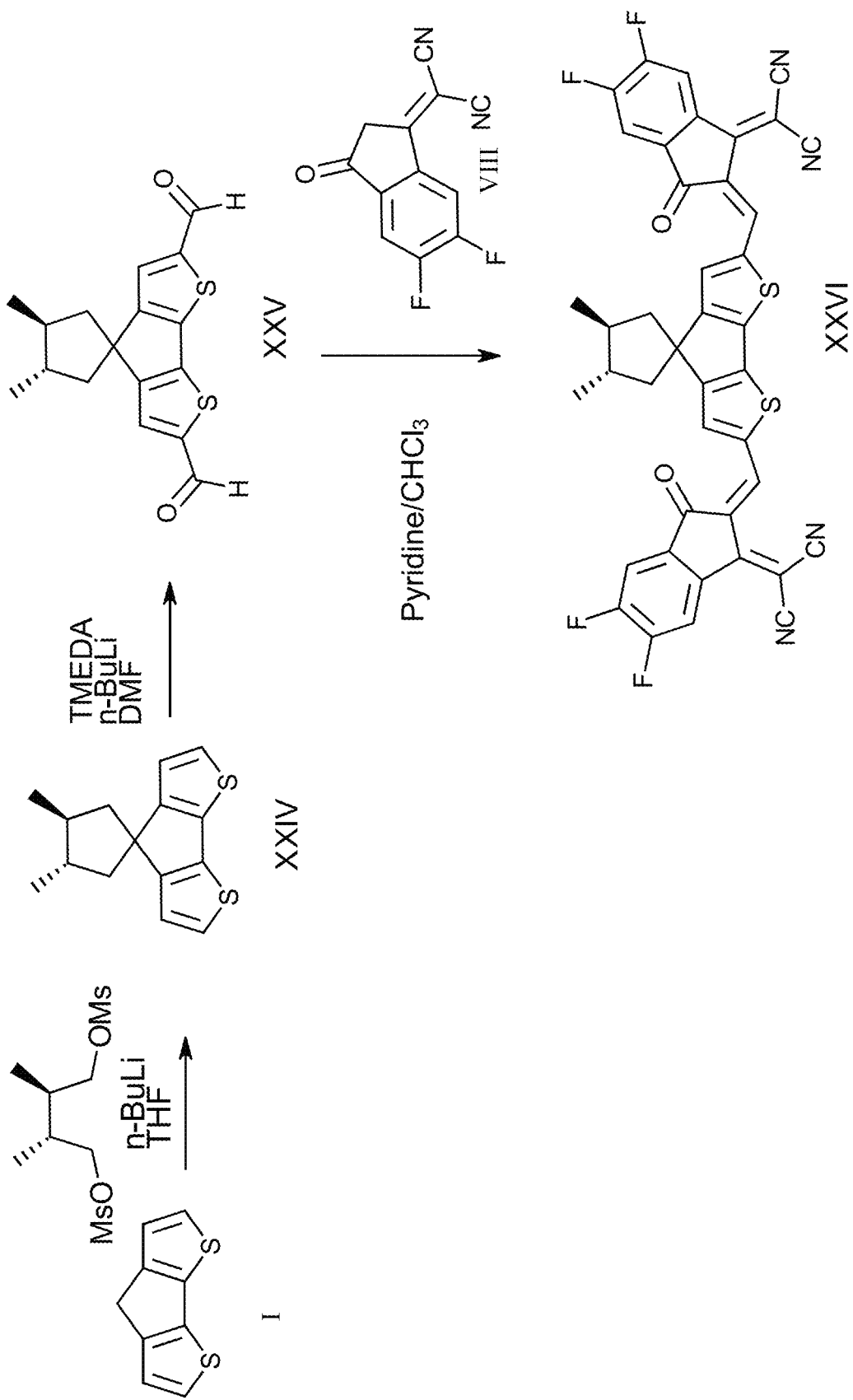
FIG. 13 provides a synthetic scheme for preparation of an example core-disrupted photoactive compound.

FIG. 13 provides a synthetic scheme for preparation of a core-disrupted photoactive compound:

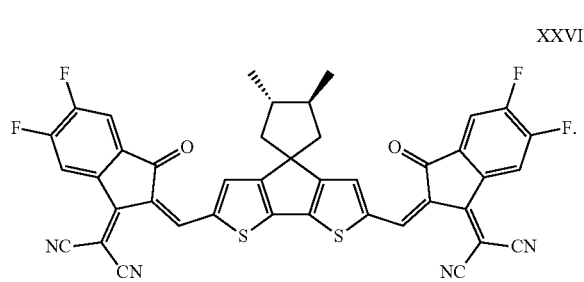 [SMILES: C[C@H]1CC2(C[C@@H]1C)c1cc(/C=C3\C(=O)c4cc(F)c(F)cc4C3=C(C#N)C#N)sc1-c1sc(/C=C3\C(=O)c4cc(F)c(F)cc4C3=C(C#N)C#N)cc12]

Compound XXIV was synthesized from compound I using the same method as used for compound II, substituting and 1,4-Butanediol, 2,3-dimethyldimethanesulfonate in place of 1,5-dibromopentane, in 53% yield.

Compound XXV was synthesized using the same method as used for compound III, substituting compound XXIV in place of compound II, in 51% yield.

Compound XXVI was synthesized from compound VIII using the same method as used for compound IX, substituting compound XXV in place of compound III, in 93% yield. Compound XXVI was sublimed in 5% yield. $\lambda_{max}$ (DCM): 680 nm.

Figure 14:
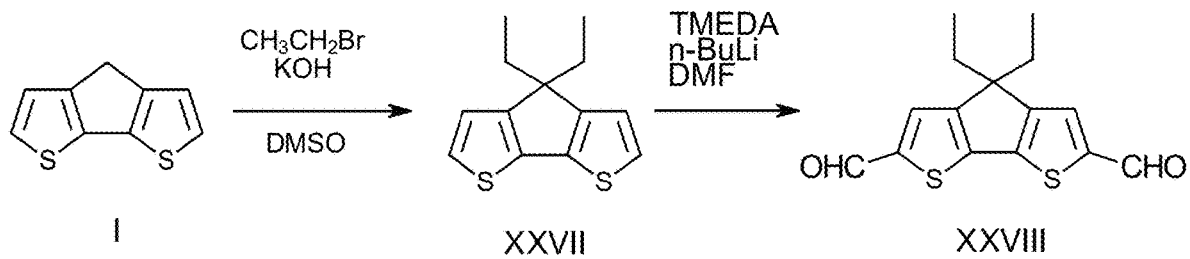
FIG. 14 provides a synthetic scheme for preparation of an example compound useful in preparing various photoactive compounds.

FIG. 14 provides a synthetic scheme for preparation of compound XXVIII by way of compound XXVII.

Compound XXVII: To a dry three neck flask compound I (9 g, 0.050 mol), potassium hydroxide (9.06 g, 0.162 mol), and 250 mL of anhydrous DMSO were added under nitrogen atmosphere. The reaction flask was purged with nitrogen and magnetically stirred at room temperature for a period of 45 minutes. Bromoethane (11.0 g, 0.101 mol) was added dropwise and the mixture was left to stir for 18 hours. The reaction mixture was diluted with ethyl acetate then washed with water followed by a saturated sodium chloride solution. The organic layer was dried over anhydrous MgSO$_4$ then filtered and concentrated in vacuo to yield the crude product as an oil. Purification was achieve via column chromatography on Silica-60 using a heptane/ethyl acetate gradient for elution to yield compound XXVII as an oil (11 g) in 93% yield.

Compound XXVIII was synthesized using the same method as used for compound III, substituting compound XXVII in place of compound II, in 79% yield.

Figure 15:
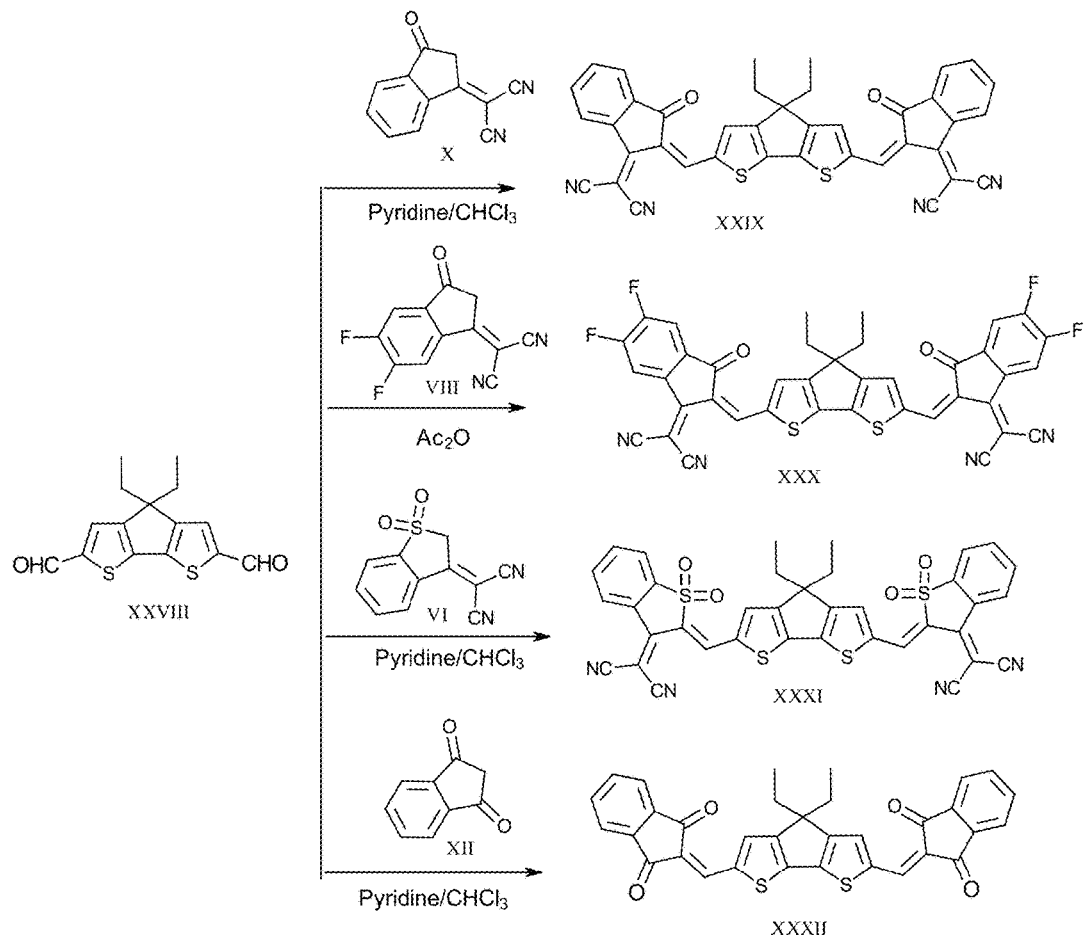
FIG. 15 provides synthetic schemes for preparation of various example photoactive compounds.

FIG. 15 provides synthetic schemes for preparation of various photoactive compounds:

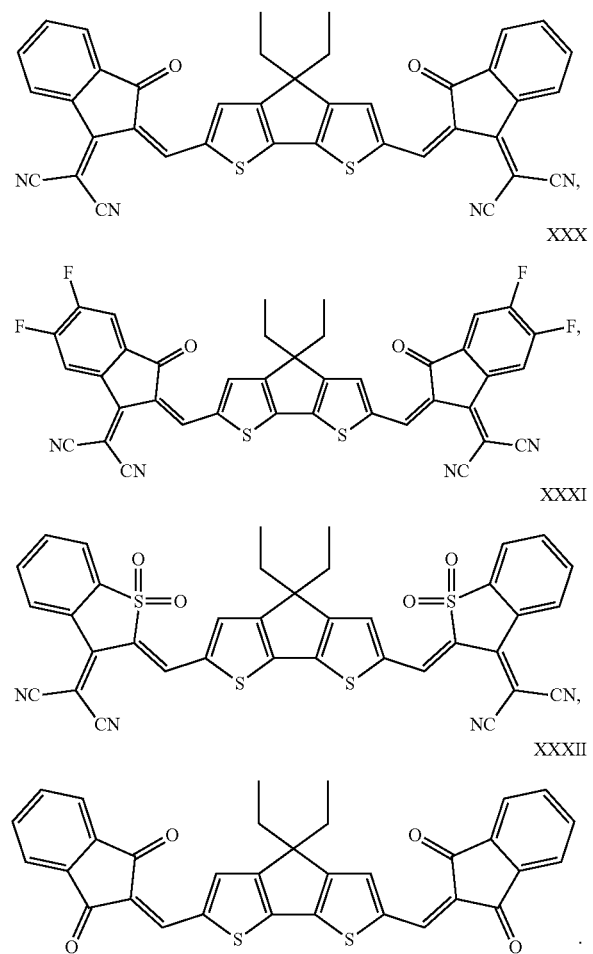

Compound XXIX was synthesized from compound X using the same method as used for compound XI, substituting compound XXVIII in place of compound III. $\lambda_{max}$ (DCM): 477 nm.

Compound XXX was synthesized using the same method as used for compound V, substituting compound XXVIII in place of compound III and compound VIII in place of compound IV, in 73% yield. $\lambda_{max}$ (DCM): 676 nm.

Compound XXXI: To a 3-neck flask equipped with a condenser and magnetic stir bar, compound XXVIII (0.5 g, 0.002 mol), compound VI (1.59 g, 0.007 mol), and 150 mL of anhydrous chloroform were added. The flask was purged with nitrogen then pyridine (1.63 g, 0.021 mol) was added dropwise. The mixture was stirred at room temperature for 30 minutes then heated to reflux and stirred for 18 hours under nitrogen. The reaction mixture was cooled to room temperature then poured into cold water. The biphasic mixture was extracted with dichloromethane. Organic layers were combined, dried over MgSO$_4$, filtered, and concentrated in vacuo to obtain compound XXXI as a dark solid (1.2 g, 98% yield). $\lambda_{max}$ (DCM): 614 nm.

Compound XXXII was synthesized using the same method as used for compound IX, substituting compound XXVIII in place of compound III and compound XII in place of compound VIII. Compound XXXII was sublimed in 30% yield.

Figure 16:
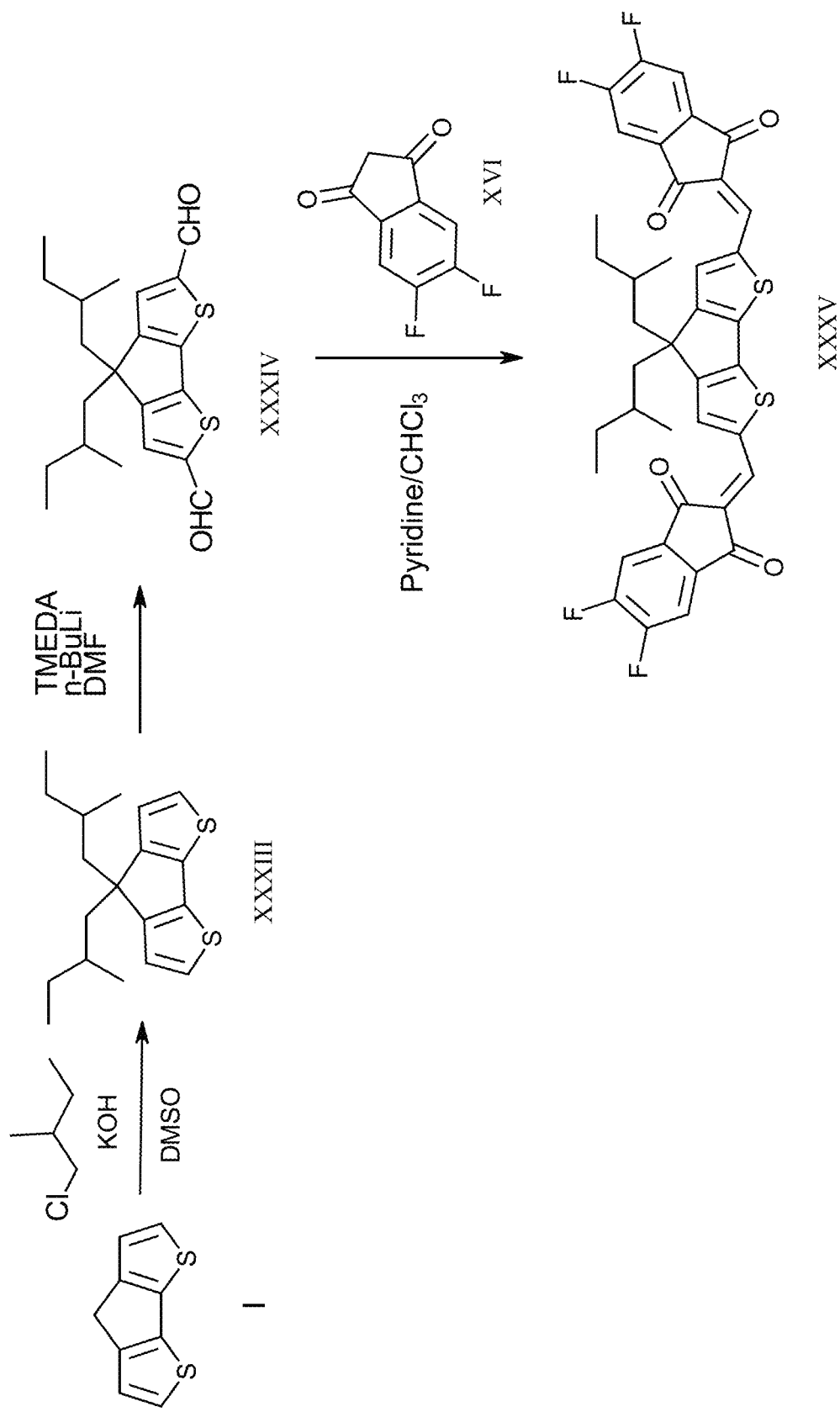
FIG. 16 provides a synthetic scheme for preparation of an example indandione-containing photoactive compound.

FIG. 16 provides a synthetic scheme for preparation of an indandione-containing photoactive compound:

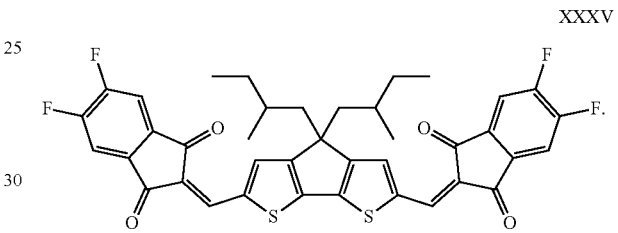

Compound XXXIII was synthesized from compound I using the same method as used for compound XXXVII, substituting 1-chloro-2-methylbutane in place of 1,5-dibromopentane, in 90% yield.

Compound XXXIV was synthesized using the same method as used for compound III, substituting compound XXXIII in place of compound II, in 84% yield.

Compound XXXV: A solution of compound XXXIV (6.37 g, 17.0 mmol, 1 eq) and XVI (12.38 g, 68.0 mmol, 4 eq) in chloroform (640 mL, 100 vol) was sparged with nitrogen for 5 minutes. Pyridine (20.6 mL, 20.2 g, 255 mmol, 15 eq) was added slowly over 2 minutes. The solution was then heated at 60° C. (reflux) for 30 hours. The suspension was cooled to 23° C. and filtered through a pad of Celite (18 g), which was rinsed with dichloromethane (3×100 mL). The combined filtrate was concentrated to dryness under reduced pressure to give a crude dark solid (18 g). The solid was suspended in dichloromethane (450 mL) at 40° C. (reflux) for 1 hour and filtered through a pad of Celite (18 g) rinsing with dichloromethane (2×100 mL). The filtrate was concentrated under reduced pressure to a volume of 200 mL. The solution was heated at 40° C. and treated with hexanes (360 mL) slowly over 1.5 hours. The suspension was cooled to 23° C. over 2 hours and the solid was collected by vacuum filtration and washed with a 2 to 1 mixture of hexanes and dichloromethane (3×50 mL). The filtrate was concentrated onto Celite (26 g) and purified on an automated Biotage system (Sorbtech 330 g column), eluting with a gradient of 50 to 100% dichloromethane/heptanes) to give compound XXXV (5.3 g) in 44% yield. This compound was sublimed in 60-80% yield.

Figure 17:
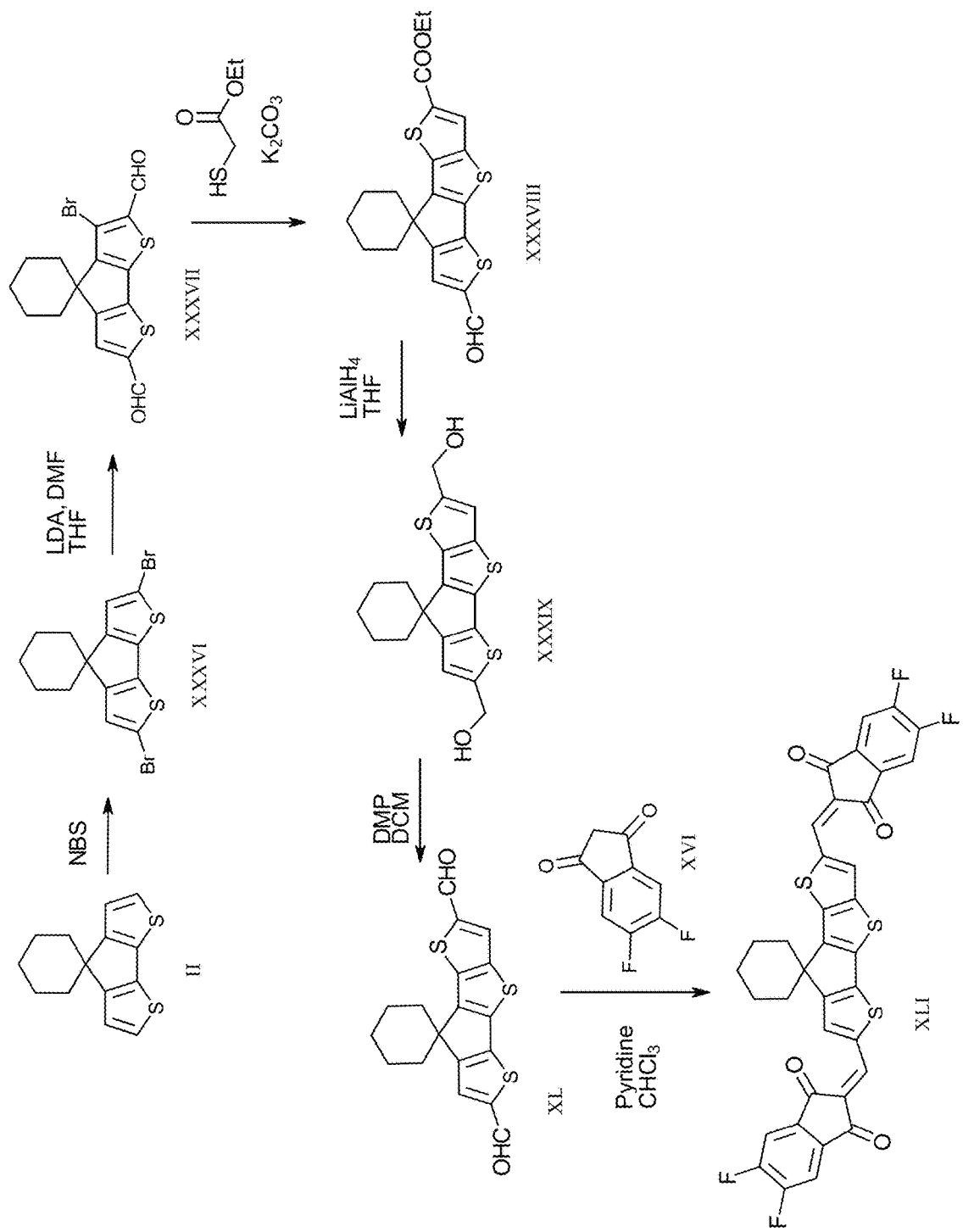
FIG. 17 provides a synthetic scheme for preparation of an example core-disrupted, indandione-containing photoactive compound.

FIG. 17 provides a synthetic scheme for preparation of a core-disrupted, indandione-containing photoactive compound:

XLI

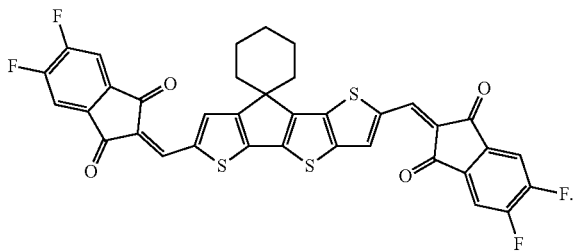

Compound XXXVI: Compound II (2.5 g, 1.0 eq) was dissolved in 67 mL of chloroform followed by addition of NBS (3.97 g, 2.2 eq) and the mixture was stirred in the dark for 12 hours. Upon completion, the reaction mixture was poured into water and the biphasic mixture was extracted with chloroform. Organic layers were combined, dried over MgSO$_4$, filtered, and concentrated. The crude material was dry loaded onto silica gel and purified by CombiFlash. Desired product was eluted with heptane to afford compound XXXVI as an orange solid (3.68 g, 89% yield).

Compound XXXVII: In an oven dried 3-neck RB flask equipped with nitrogen inlet diisopropylamine (2.65 g, 4.0 eq) was dissolved in dry THF (30 mL) and the reaction temp was adjusted to −78° C. followed by dropwise addition of n-butyl lithium (2.5 M, 9.8 mL, 4.0 eq) and the reaction was stirred at 0° C. for 30 mins to generate LDA. In another oven dried 100 mL 3-neck RB flask compound XXXVI was dissolved in dry THF (15 mL) and the reaction temp is adjusted to −78° C. followed by dropwise addition of LDA generated in other RB flask. The mixture was stirred for 30 min at this temperature, and then warmed to room temperature for 2 h. After the mixture was cooled to 0° C., anhydrous DMF (1.2 mL) was added, and the reaction stirred at this temperature for 30 min. Then the mixture was allowed to warm to room temperature for 1 h and water (30 mL) was added. The organics were extracted (3×30 mL DCM), dried by sodium sulfate, filtered and concentrated under reduced pressure. The residue was purified by silica gel chromatography using 24 g column eluted with DCM/Heptane to afford compound XXXVII as yellow solid (1.1 g, 47% yield).

Compound XXXVIII: In an oven dried 100 mL 3-neck RB flask equipped with nitrogen gas inlet, ethyl thioglycolate (0.9 g, 2.0 eq) was added dropwise to a mixture of compound XXXVII (1.4 g, 1.0 eq) and potassium carbonate (1.5 g, 3.0 eq) in DMF (10 mL) at 50° C. under argon. After addition, the mixture was stirred at this temperature for 24 h. TLC (DCM) showed completion of reaction. The reaction was quenched by adding water (50 mL). Yellow colored precipitate was filtered and purified by silica gel column eluted with Heptane/DCM. Appropriate fractions were combined, concentrated, and dried under high vacuum to get compound XXXVIII (1.05 g, 72% yield).

Compound XXXIX: Lithium aluminum hydride (0.30 g, 3.5 eq)) was suspended in 15 mL of THF and cooled to 0° C. followed by dropwise addition of compound XXXVIII (1.05 g, 1.0 eq)) dissolved in 30 mL THF. An additional 10 mL of THF was used to rinse and transfer residue from vials. The reaction was left to warm to room temperature and stirred overnight. The reaction was cooled to 0° C. and quenched by slow addition of water. Biphasic mixture was extracted with ether. Organic layers were combined, washed with brine, dried over MgSO$_4$, filtered and concentrated to yield a brown solid/foam. The crude material was purified by column chromatography and eluted with Heptanes:EtOAc to afford compound XXXIX as a light yellow solid (0.762 g, 94% yield).

Compound XL: Compound XXXIX (610 mg, 1.0 eq) was added to a dry 3-neck 100 mL flask followed by 50 mL of anhydrous DCM. DMP (Dess-Martin periodinane) (1.9 g, 2.6 eq)) was added portion-wise and the reaction was stirred under nitrogen overnight. The reaction mixture was diluted with ether and washed with 1 N NaOH followed by 1 M Na$_2$S$_2$O$_3$, saturated bicarb, and finally brine. The organic layer was dried over MgSO$_4$, filtered, and concentrated. The crude material was dry loaded onto silica gel and purified by column chromatography. Desired product was eluted with Heptane/EtOAc to afford Compound XL as a yellowish brown solid (343 mg, 57% yield).

Compound XLI: Compound XL (200 mg, 1.0 eq) was added to a 100 mL 3-neck flask followed by compound XVI (280 mg, 4.0 eq) and 40 mL of DCE. The mixture was purged with nitrogen at room temperature for 20 min then pyridine (0.85 mL, 12.0 eq) was added dropwise. The reaction was stirred at room temperature for an additional 20 min then heated to reflux and left to stir for 96 hours. The precipitate was filtered and washed with hot methanol to get compound XLI (120 mg. 49%). This compound was sublimed in 9% yield. $\lambda_{max}$ (DCM): 610 nm.

Figure 18:
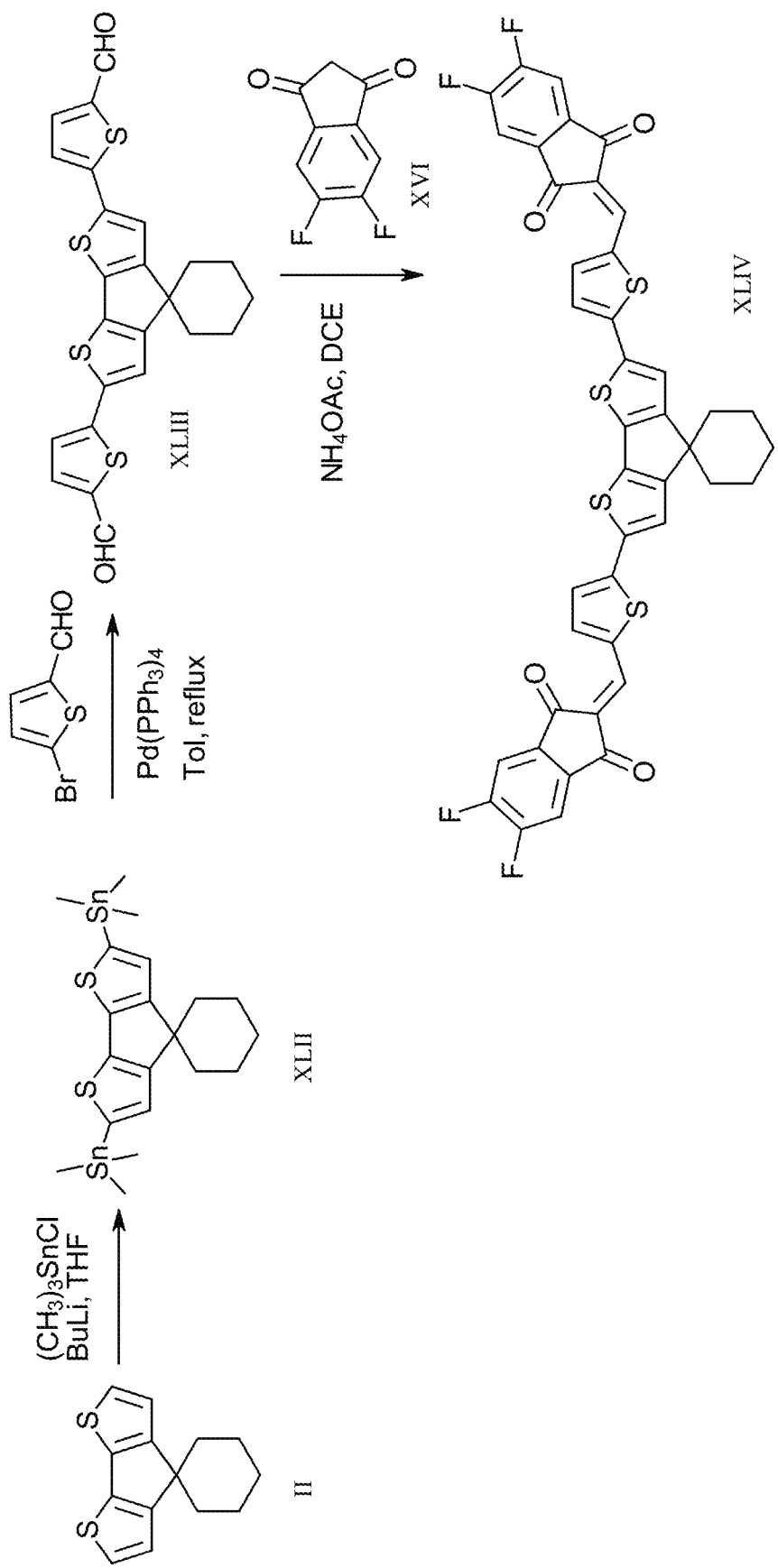
FIG. 18 provides a synthetic scheme for preparation of an example core-disrupted, indandione-containing photoactive compound.

FIG. 18 provides a synthetic scheme for preparation of a core-disrupted, indandione-containing photoactive compound including thiophene pi moieties:

XLIV

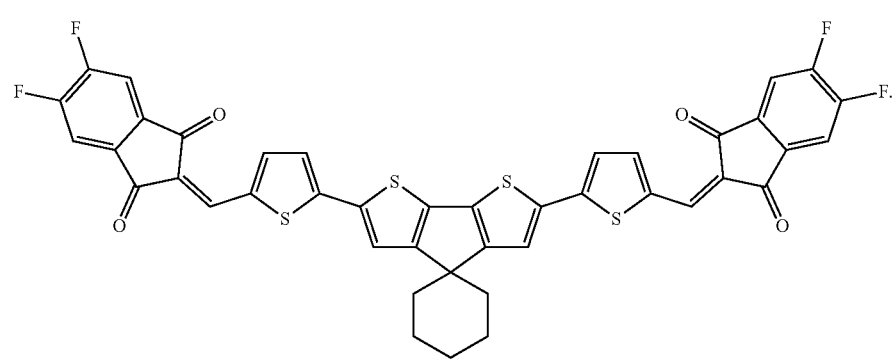

Compound XLII: In an oven dried 250 mL 3-neck RB flask, compound II (1.5 g, 1.0 eq) was dissolved in dry THF (70 mL) under nitrogen and the reaction temperature was adjusted to −78° C. followed by dropwise addition of n-butyl lithium (2.5 M, 5.1 mL, 2.1 eq). The reaction mixture was then stirred at −10 to 0° C. for 1 hr and then re-adjusted to −78° C. followed by dropwise addition of trimethyl tin (1 M solution, 18.3 mL, 3.0 eq). The reaction mixture was then stirred at RT. After 18 hrs the reaction was quenched by adding water. Organic layer was separated, and the aqueous layer was washed with ether (2×50 mL). Combined organic layers were dried over sodium sulfate and concentrated under vacuum to obtain compound XLII, which used as it is for next step.

Compound XLIII: In a 250 mL 3-neck RB flask equipped with nitrogen line and condenser, compound XLII (3.5 g, 1.0 eq) and compound 5-bromo-thiophene-2-carbaldeyde (2.34 g, 2.0 eq) were dissolved in dry toluene (200 mL) under nitrogen and the solution was purged with nitrogen for 30 mins followed by addition of Pd(PPh$_3$)$_4$ (0.7 g, 0.10 eq). The mixture was purged with nitrogen and refluxed for 18 hrs. TLC showed formation of two lower Rf yellow/red colored spots. The reaction mixture was concentrated under vacuum and purified by autoflash chromatography using 80 g silica gel column with DCM/EtOAc to obtain compound XLIII (1.7 g, 60% yield).

Compound XLIV: In an oven dried 500 mL 3-neck RB flask equipped with condenser and nitrogen inlet compound XLIII (0.5 g, 1.0 eq), compound XVII (1.0 g, 5.0 eq) and ammonium acetate (1.65 g, 20.0 eq) dry dichloroethane (200 mL) under nitrogen and the reaction mixture was refluxed at 83° C. for 3 weeks. The reaction mixture was cooled to RT and the dark green color solid was filtered. The solid obtained was washed with hot methanol and dried under high vacuum to get compound XLIV (0.85 g, 100% yield). This compound was sublimed in 12-17% yield. $\lambda_{max}$ (DCM): 654 nm.

Figure 19:
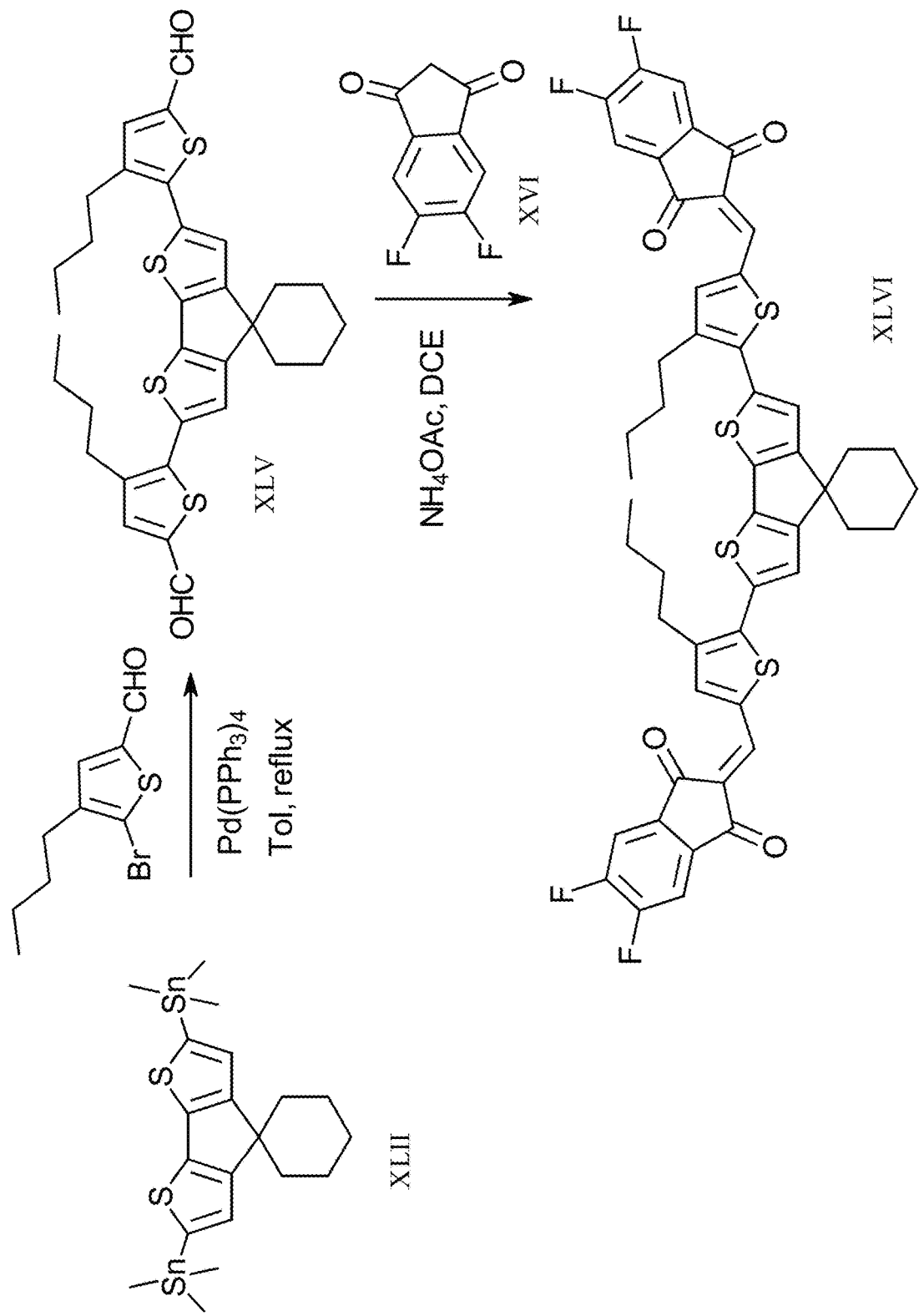
FIG. 19 provides a synthetic scheme for preparation of an example core-disrupted, indandione-containing photoactive compound.

FIG. 19 provides a synthetic scheme for preparation of a core-disrupted, indandione-containing photoactive compound:

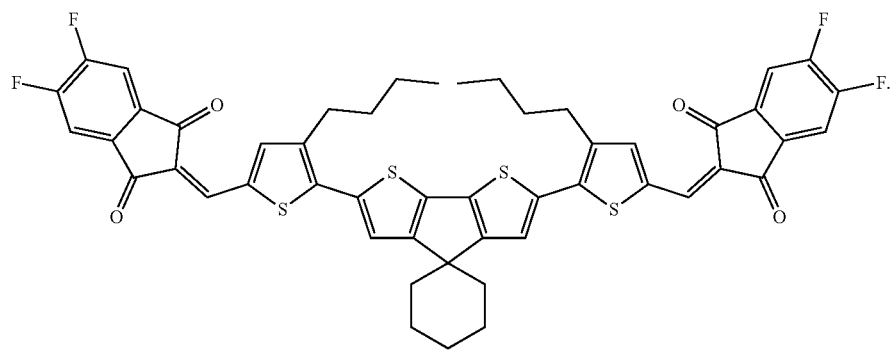

XLVI

Compound XLV was synthesized from compound XLII using the same method as used for compound XLIII, substituting 5-bromo-4-butyl-thiophene-2-carbaldehyde in place of 5-bromo-thiophene-2-carbaldeyde, in 19% yield.

Compound XLVI was synthesized from compound XVI using the same method as used for compound XVII, substituting compound XLV in place of compound III, in 100% yield. This compound was sublimed in 3% yield. $\lambda_{max}$ (DCM): 640 nm.

Figure 20:
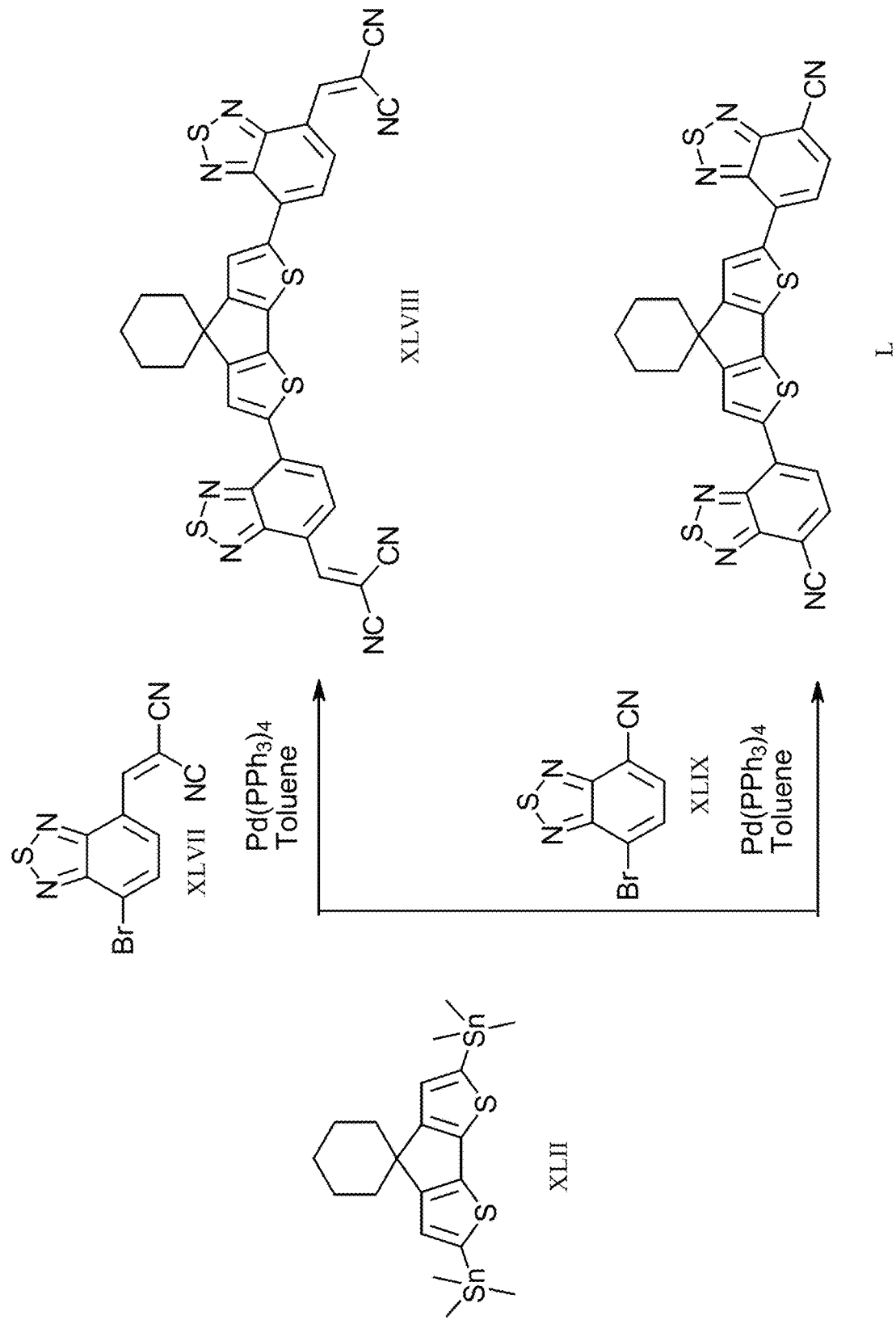
FIG. 20 provides synthetic schemes for preparation of example core-disrupted photoactive compounds.

FIG. 20 provides synthetic schemes for preparation of core-disrupted photoactive compounds:

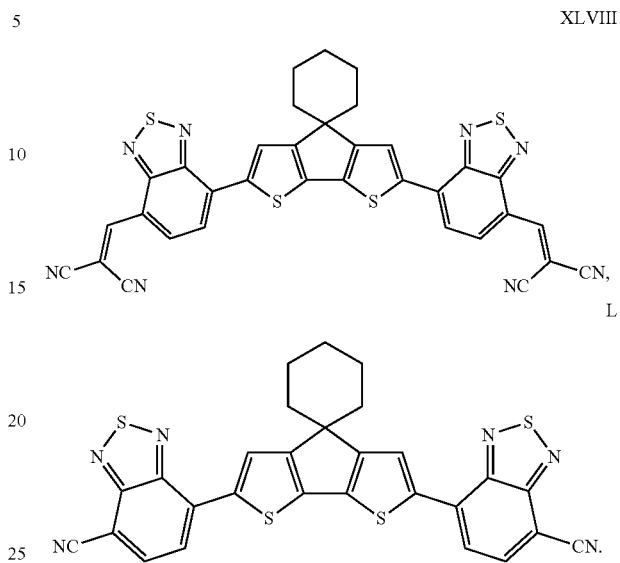

XLVIII

L

Compound XLVIII: Compound XLII (1.0 eq), XLVII (2.1 eq) and Pd(PPh$_3$)$_4$ (0.1 eq) were added to try toluene under nitrogen and the mixture was purged with nitrogen gas. The reaction mixture was then stirred at 110° C. for 24 hours. The solvent was distilled off under reduced vacuum and the residue was purified by silica gel column chromatography using dichloromethane to obtained compound XLVIII.

Compound L was synthesized from compound XLII using the same method as used for compound XLVIII, substituting compound XLIX in place of compound XLVII.

Figure 21:
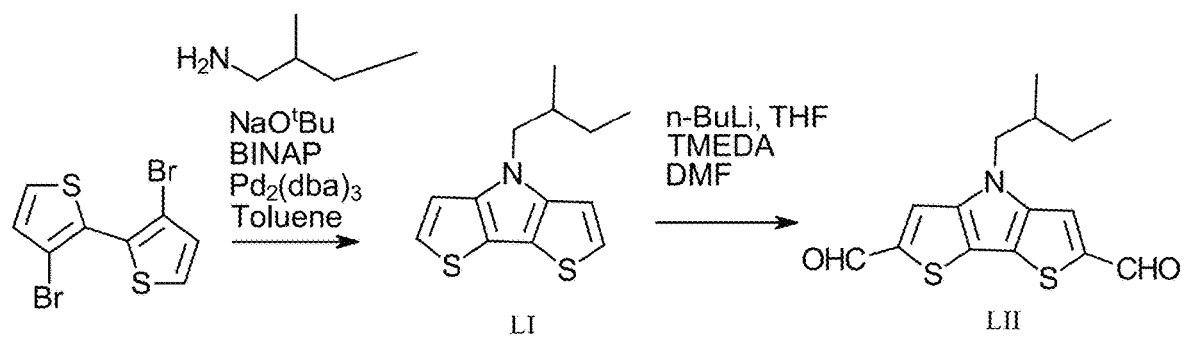
FIG. 21 provides a synthetic scheme for preparation of an example compound useful in preparing various photoactive compounds.

FIG. 21 provides a synthetic scheme for preparation of compound LII by way of compound LI.

Compound LI: A suspension of 3,3'-dibromo-2,2'-bithiophene (15 g, 1.0 eq), sodium tert-butoxide (10 g, 2.2 eq), Pd$_2$(dba)$_3$ (1.26 g, 0.03 eq) and BINAP (3.45 g, 0.12 eq) in anhydrous toluene was purged with nitrogen for 30 minutes followed by addition of 2-methylbutylamine (4.05 g, 1.0 eq) and the reaction mixture was refluxed at 110° C. for 48 hours under nitrogen atmosphere. The reaction mixture was then poured in water and extracted with dichloromethane (200 mL). The organic layer was separated, dried over sodium sulfate, and concentrated under vacuum. The crude material was purified by flash chromatography to obtain compound LI (9.6 g, 76% yield).

Compound LII: To a dry three neck flask Compound LI (4.3 g, 1.0 eq) and was dissolved in anhydrous THF under nitrogen atmosphere followed by addition of TMEDA (5.21 g, 2.6 eq). n-Butyl lithium (2.5 M, 18 mL, 2.6 eq) was then added dropwise and the reaction mix continued to stir at −40° C. for 30 min and then warmed to room temperature and the mixture was stirred at room temperature for 2 hr. The reaction mixture was cooled back to −40° C. followed by addition dry DMF (3.27 g, 2.6 eq) dropwise and stirred at room temperature overnight. Workup was accomplished by pouring the reaction mixture into 20% NH₄Cl (aq) solution, 3× extraction with dichloromethane, and drying over sodium sulfate to yield crude product. Purification was done by column chromatography on silica gel with Dichloromethane-Heptane to yield compound LII (2.5 g, 62% yield).

Figure 22:
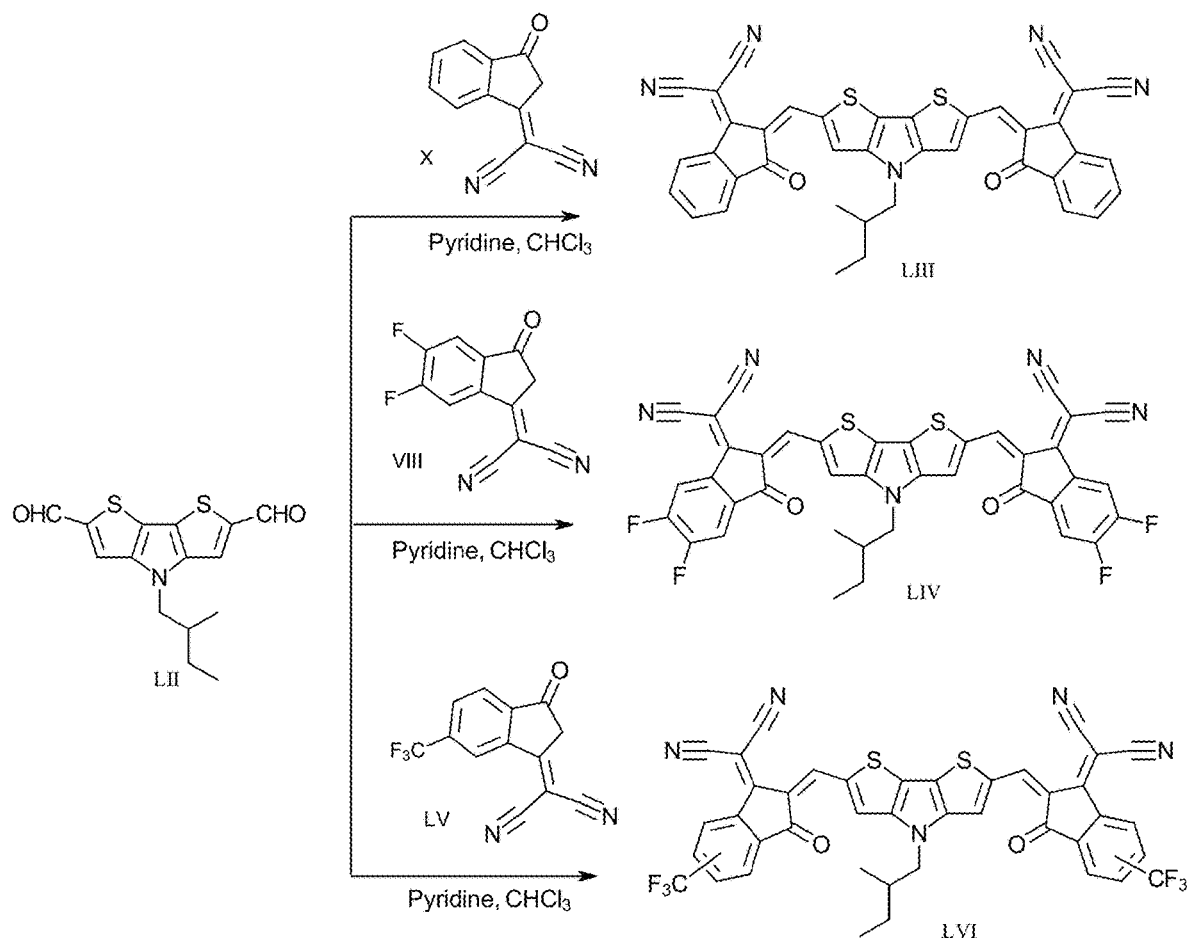
FIG. 22 provides synthetic schemes for preparation of various example photoactive compounds.

FIG. 22 provides synthetic schemes for preparation of various photoactive compounds:

LIII

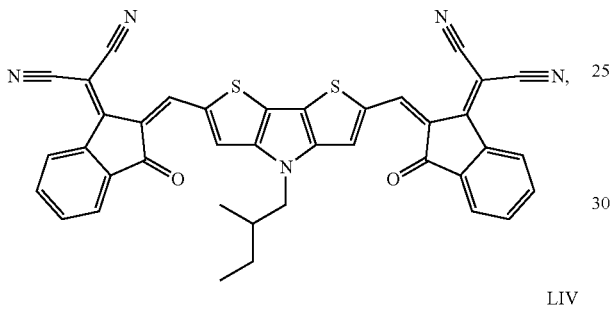

LIV

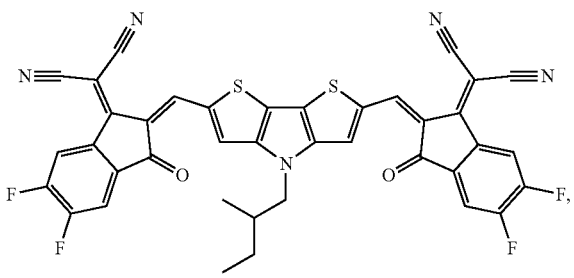

LVI

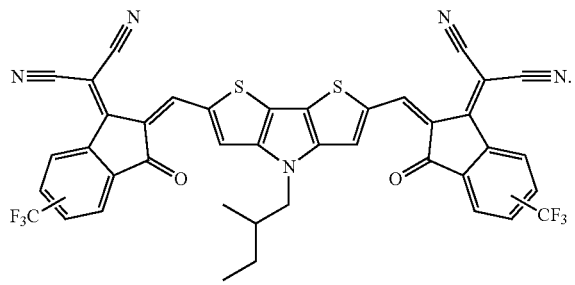

Compound LIII: Compound LII (1.0 eq) and X (4.0 eq) were mixed with anhydrous chloroform under nitrogen atmosphere followed by addition of pyridine (20 eq). The reaction mixture was refluxed for 48 hours and then cooled to room temperature. The precipitate was flirted and washed with hot isopropyl alcohol to afford compound IV (60% yield).

Compound LIV was synthesized from compound LII using the same method as used for compound LIII, substituting compound VIII in place of compound X, in 90% yield.

Compound LVI was synthesized using compound LII and LV using a similar method as used for compound LIII, substituting compound LV in place of compound X, in 75% yield.

Figure 23:
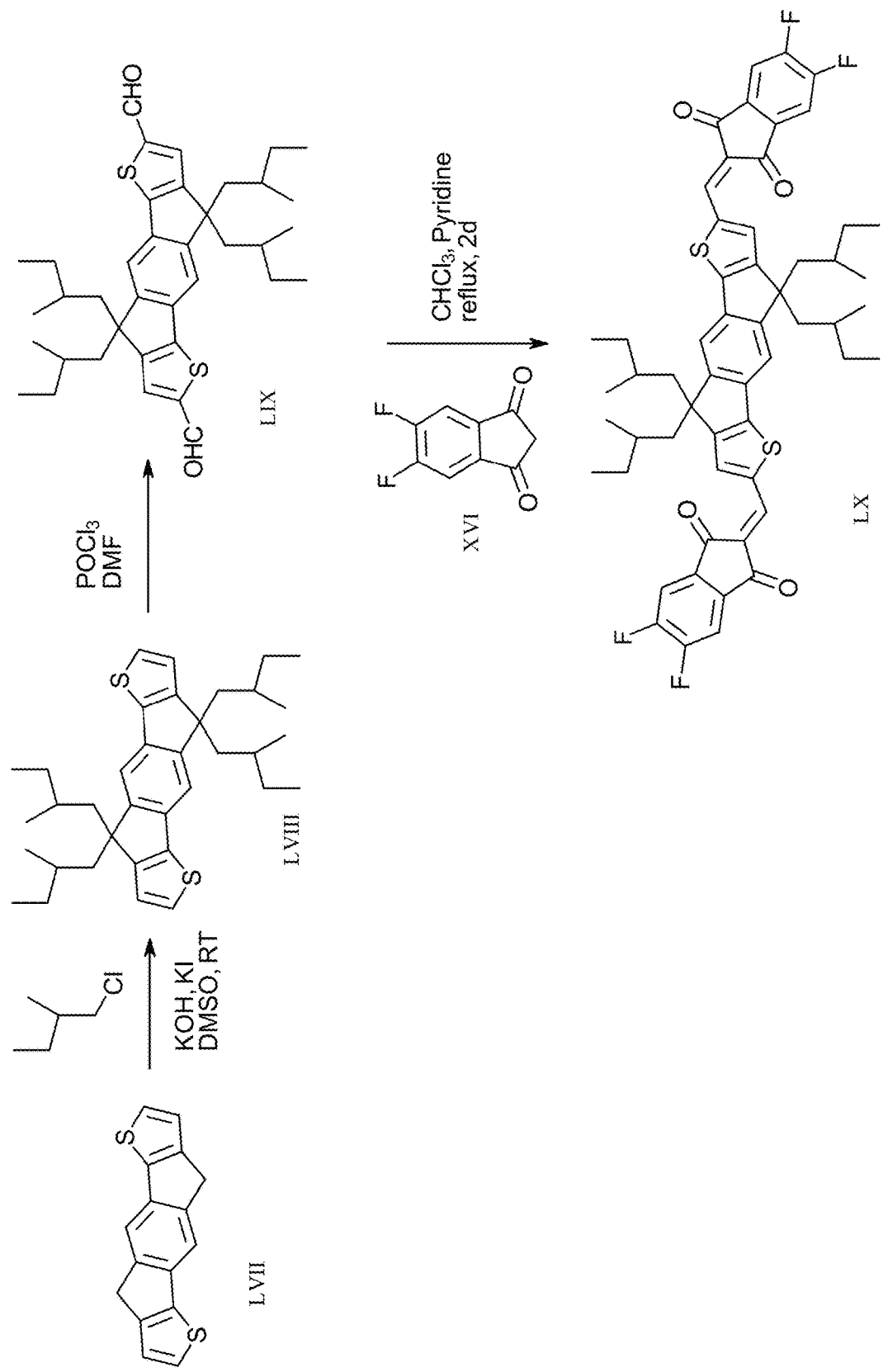
FIG. 23 provides a synthetic scheme for preparation of an example photoactive compound.

FIG. 23 provides a synthetic scheme for preparation of a photoactive compound:

LX

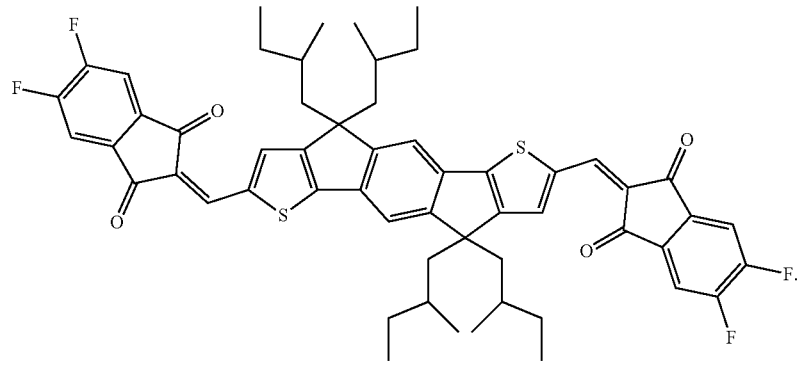

Compound LVIII: A suspension of compound LVII (1 eq), potassium hydroxide (7.5 eq) and potassium iodide (0.04 eq) in anhydrous dimethyl sulfoxide (25 vol) was sparged with nitrogen for 5 min. 1-Chloro-2-methylbutane (4.6 eq) was added slowly over 10 min under nitrogen. The resulting dark suspension was stirred at 21° C. for 18 hr. The reaction mixture was cooled to 10° C. Water (25 vol) was added dropwise over 5 min ($T_{max}$=14° C.). The mixture was then diluted further with water (25 vol) and extracted into heptane (60 vol, then 2×30 vol). The organics were combined and washed with water (25 vol), dried ($Na_2SO_4$) and filtered. The filtrates were concentrated in vacuo to give the crude product as a dark brown oil. Purification by flash column chromatography ($SiO_2$) eluting with heptane gave compound LVIII as a yellow oil that solidified on standing (67% yield).

Compound LIX: Phosphorus oxychloride (20 eq) was added dropwise over 20 min to an oven dried flask containing a solution of DMF (20 eq) in DCE (15 vol) under an atmosphere of nitrogen. The resulting yellow solution was stirred at ambient temperature for 3 hr. A solution of compound LVIII (1 eq) in dichloroethane (37.5 vol) was then added dropwise over 15 min (no exotherm observed). The solution was then heated to at 60° C. for 42 hr and then cooled to room temperature. The solvent was removed on the rotary evaporator. The resulting brown gum was quenched with ice-water (25 vol), then basified to ca. pH 8 with sat. sodium bicarbonate solution. The resulting suspension was then stirred at room temperature for 2 hr before extracting into DCM (50 vol, then 2×25 vol). The organics were dried ($Na_2SO_4$) and concentrated in vacuo to give the compound LIX as brown solid (72%).

Compound LX: A solution of compound LIX (1 eq) and XVI (4 eq) in chloroform (56 vol) was sparged with nitrogen for 5 min. Pyridine (15 eq) was then added causing a rise in temperature of 15.5° C. to 17.5° C. The mixture was then heated at reflux. After 48 hr, the dark purple reaction solution was cooled to room temperature. A small sample was removed, concentrated, and analysed by 1H NMR spectroscopy to show that all aldehydes had been consumed. The reaction mixture was concentrated on the rotary evaporator to provide crude product as a dark purple solid, which was further purified by hot methanol wash to get compound LX (90%). This compound was sublimed in 65% yield.

Compound LXI and compound LXII were synthesized using the same methods as compound LX, but different reagents were used in place of 1-chloro-2-methylbutane (e.g., chloromethane or p-chlorotoluene) and in place of compound XVI (e.g., compound X):

-continued

LXII

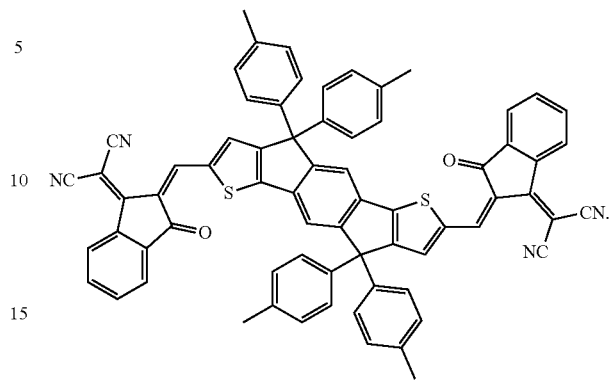

Figure 24:
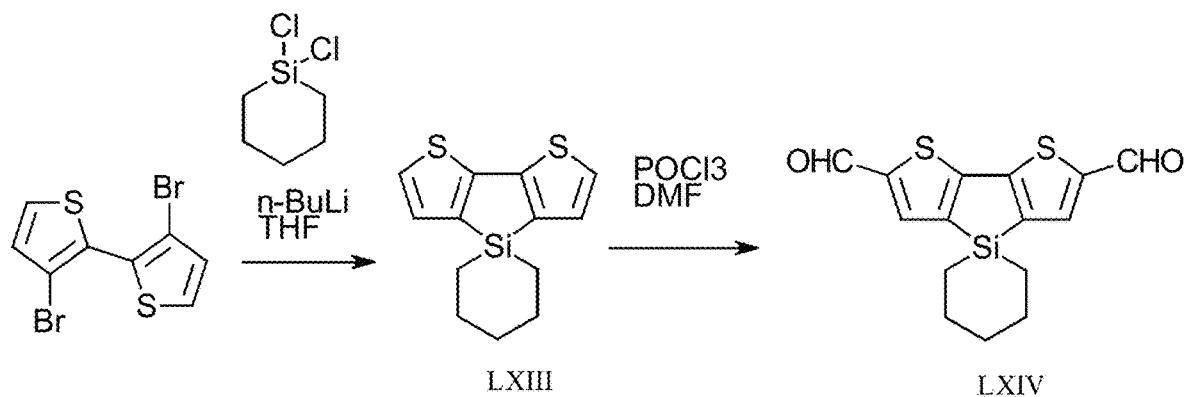
FIG. 24 provides a synthetic scheme for preparation of an example compound useful in preparing various core-disrupted photoactive compounds including a quaternary silicon center.

FIG. 24 provides a synthetic scheme for preparation of compound LXIV by way of compound LXIII.

Compound LXIII: n-Butyl lithium (2.0 eq) was added to dry THF in a 2-neck RB flask and the reaction mixture was cooled to -78° C. followed by dropwise addition of 3,3'-dibromo-2,2'-bithiophene (1.0 eq) dissolved in THF and the reaction mixture was stirred for 1 hour. A solution of dichlorosilane (1.1 eq) in THF was added to the reaction mixture keeping reaction temperature below -70° C. After addition, the reaction mixture was stirred at room temperature overnight. The reaction was then quenched by adding aqueous ammonium chloride and the product was extracted with ether and purified by column chromatography using heptane. The product obtained after chromatography was further purified by vacuum distillation at 390° C. to obtain compound LXIII in 12% yield.

Compound LXIV: Phosphorus oxychloride (10 eq) was added dropwise over 20 min to an oven dried flask containing a solution of DMF (20 eq) in DCE) under an atmosphere of nitrogen at 0° C. The resulting yellow solution was stirred at ambient temperature for 3 hr. A solution of compound LXIII (1 eq) in dichloroethane was then added dropwise over 15 min. The solution was then heated to 90° C. After 4 hours, the reaction mixture was cooled to room temperature and poured into saturated sodium acetate solution under ice bath. The product was extracted with dichloromethane. Organic layer was dried with sodium sulphate, concentrated under vacuum and purified by column chromatography to obtain compound LXIV in 60% yield.

Figure 25:
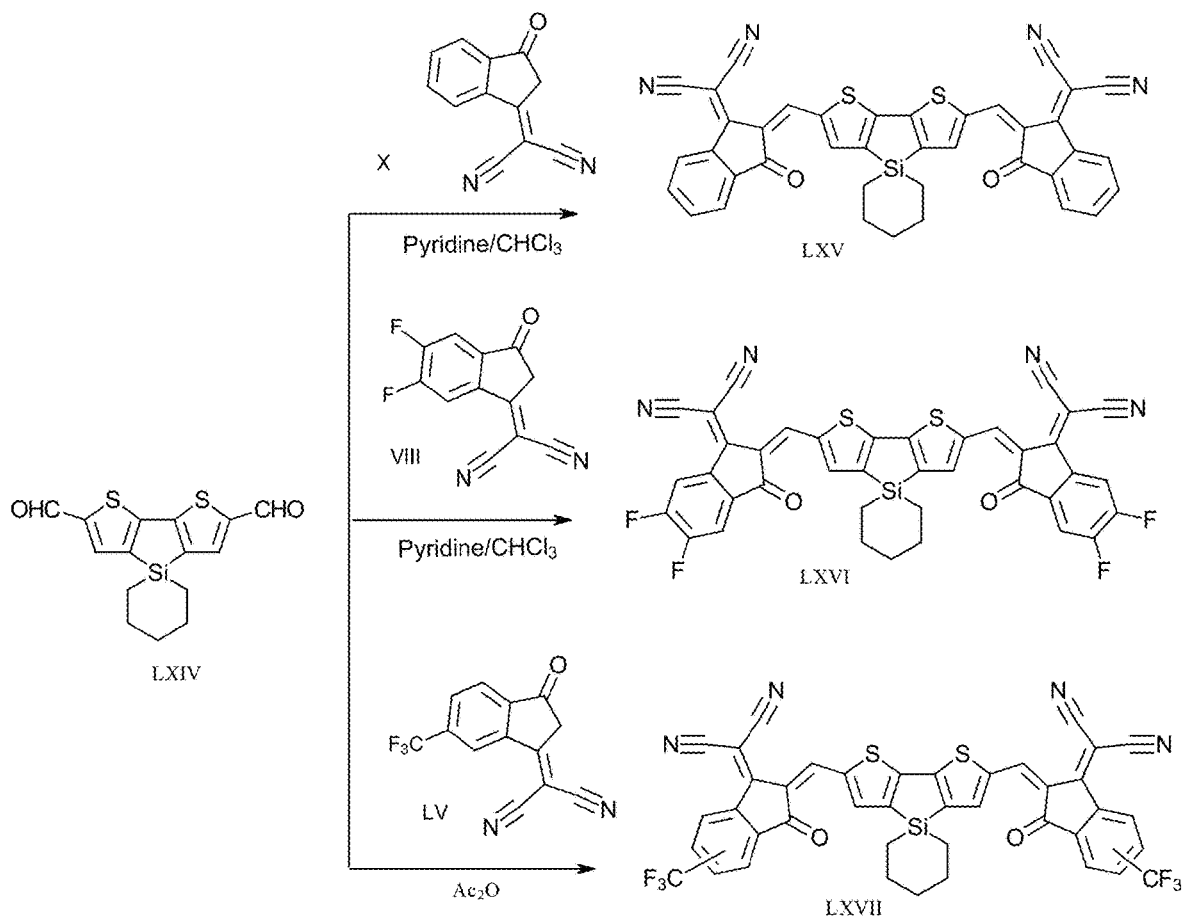
FIG. 25 provides synthetic schemes for preparation of various example core-disrupted photoactive compounds.

FIG. 25 provides synthetic schemes for preparation of various core-disrupted photoactive compounds:

LXI

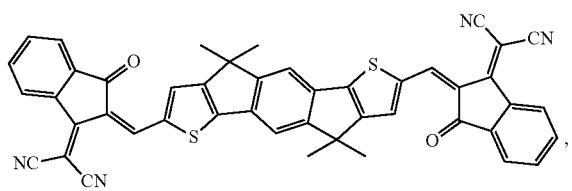

LXV

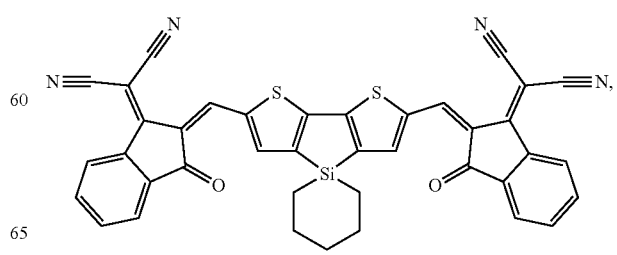

LXVI

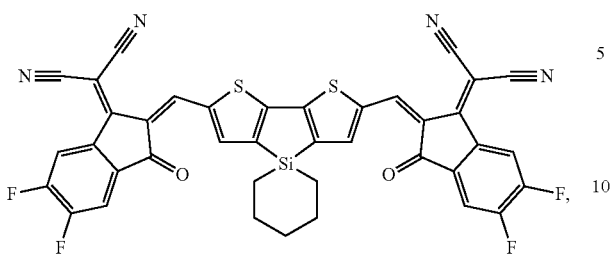

Figure 26:
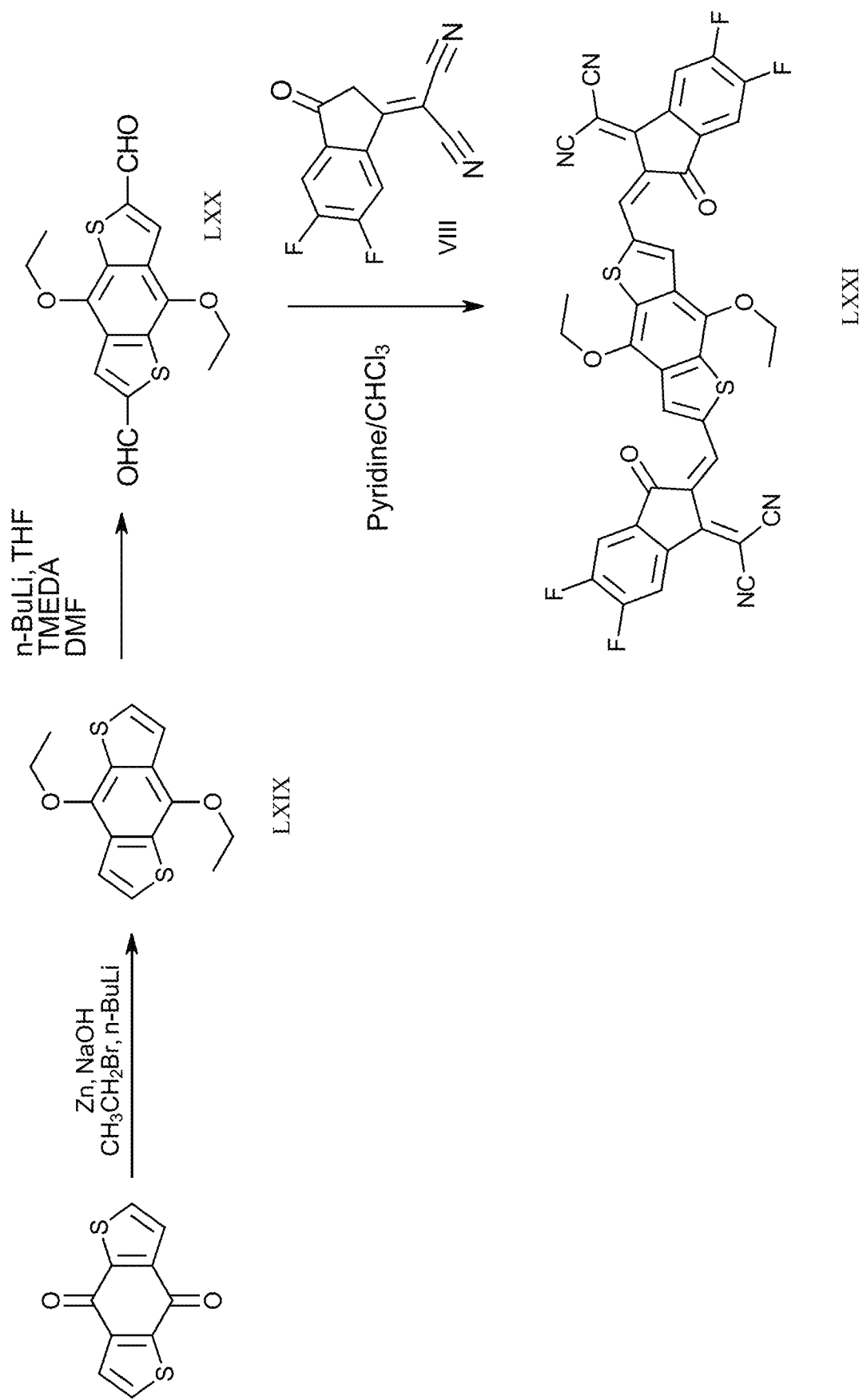
FIG. 26 provides a synthetic scheme for preparation of an example photoactive compound.

FIG. 26 provides a synthetic scheme for preparation of a photoactive compound:

LXXI

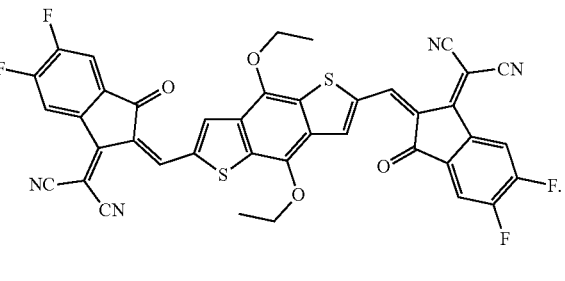

LXVII

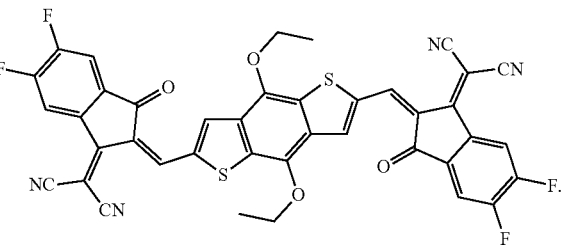

Compound LXV: Compound LXIV (1.0 eq) and X (4.0 eq) were refluxed with pyridine (15.0 eq) and chloroform for 48 hours. The reaction mixture was filtered while hot and the precipitate was washed with chloroform to obtained compound LXV in 82% yield. This compound was sublimed in 7% yield.

Compound LXVI was synthesized from compound LXIV using a similar method as used for compound LXV, substituting compound VIII in place of compound X. Compound LXVI was sublimed in 10% yield.

Compound LXVII: Compound LXIV (1.0 eq) and LV (4.0 eq) were mixed with acetic anhydride and the mixture was degassed with nitrogen. The reaction mixture was then stirred for 15 min at 50° C. followed by 4 hours at 80° C. The reaction mixture was then cooled to room temperature and filtered. The precipitate was washed with heptane and triturated with dichloromethane/methanol (8/2) to obtain compound LXVII (82%). This compound was sublimed in 11% yield.

Compound LXVIII was synthesized from compound LV using the same method as used for LXVII, substituting compound III in place of compound LXIV. Compound LXVIII was sublimed in 31% yield:

LXVIII

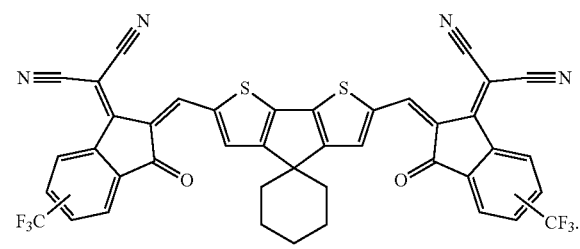

Compound LXIX: To a 3 neck-flask Benzo[1,2-b:4,5-b'] dithiophene-4,8-dione, zinc, sodium hydroxide, and 126 mL of water were added. The mixture was refluxed for 3 hours then cooled to room temperature. Bromoethane (4.45 g, 0.041 mol) and tetrabutylammonium bromide (0.44 g, 0.001 mol) were added and the reaction was refluxed for an additional 6 hours. The reaction was cooled to room temperature, diluted with water, and extracted with ethyl acetate. The organic layers were combined, dried over $MgSO_4$, filtered, and concentrated in vacuo to afford the crude product as an oil. Purification was achieved via column chromatography on Silica-60 with a heptane/dichloromethane gradient for elution to yield compound LXIX (2.37 g, 63% yield).

Compound LXX was synthesized using the same method as used for compound III, substituting compound LXIX in place of compound II, in 20% yield.

Compound LXXI was synthesized from compound VIII using the same method as used for compound IX, substituting compound LXX in place of compound III, in 80% yield. Compound LXIXI was sublimed in 0% yield. $\lambda_{max}$ (DCM): 494 nm.

Figure 27:
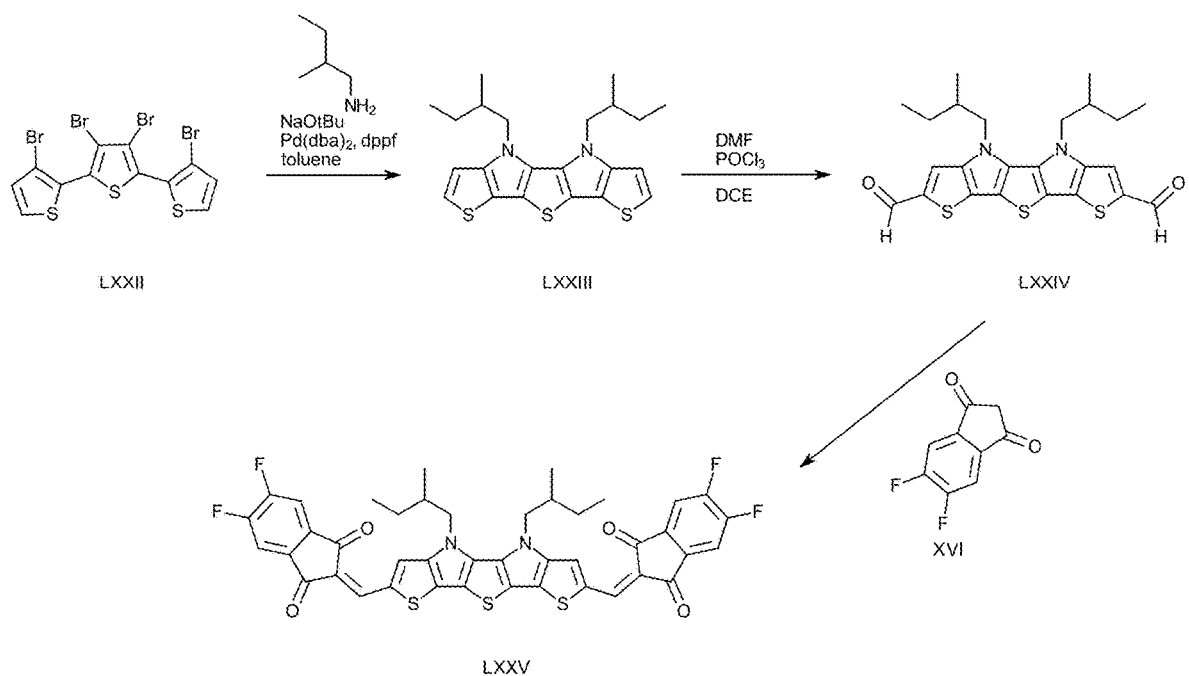
FIG. 27 provides a synthetic scheme for preparation of an example indandione containing photoactive compound.

FIGS. 27-34 provide overviews of various example synthetic schemes providing synthetic routes for various photoactive compounds, including compounds containing indandione groups. FIG. 27 provides a synthetic scheme for preparation of an indandione containing photoactive compound:

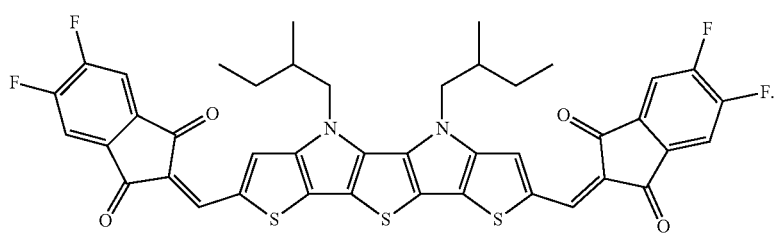

LXXV

Compound LXXIII: In an oven dried 2 L 3-neck flask equipped with nitrogen inlet and condenser, a solution of compound LXXII (30.0 g, 0.053 mol), sodium tert-butoxide (51.12 g, 0.005 mol), Pd(dba)$_2$ (3.06 g, 0.005 mol), and dppf (11.80 g, 0.021 mol) in 900 mL of dry toluene was stirred for 20 min at room temperature under nitrogen atmosphere. After addition of 2-methylbutylamine (13.91 g, 0.532 mol), the mixture was stirred at 110° C. for 20 h. The reaction was cooled to room temperature then diluted with water. The biphasic mixture was extracted with DCM. Organic layers were combined, dried over sodium sulphate, filtered, and concentrated in vacuo. The crude product was purified by autoflash chromatography using 330 g+125 g (stacked) silica gel columns eluted with Heptane/DCM to afford product as a white foam (10.3 g, 47% yield).

Compound LXXIV: A mixture of DMF (31 g, 0.4 mol) and POCl$_3$ (65 g, 0.4 mol) in 250 mL of dichloroethane was stirred for 2 h at room temperature. Compound LXXIII (7.0 g, 0.017 mol) dissolved in 1.2 L of DCE was added and the mixture was stirred at 60° C. for 4 d. TLC and LC-MS after mini work-up showed completion of reaction. The reaction mixture was concentrated under vacuum and residue was neutralized/hydrolyzed with satd. sod. Bicarb. until the pH is neutral. The red precipitate was filtered and washed with water. The wet crude material was stirred with DCM (700 mL) and dried with sod. sulfate. DCM solution was concentrated and slurried over silica gel (~40 g) and purified by autoflash chromatography using 330 g column eluted with DCM/EtOAc (0-20%). Appropriate fractions were combined and concentrated to get compound III (7.2 g, 90%) as orange solid.

Compound LXXV: In an oven dried 250 mL 3-neck flask equipped with condenser and nitrogen inlet compound LXXIV (1.5 g, 0.003 mol), compound XVI (2.9 g, 0.016 mol), and ammonium acetate (3.68 g, 0.048 mol) were dissolved in 800 mL dichloroethane under argon atmosphere. The solution was refluxed for 72 h. The reaction mixture was filtered hot and the green precipitate was washed with hot methanol to afford the desired product (200 mg, 42% yield). This compound was sublimed in 38% yield. $\lambda_{max}$ (DCM): 658 nm.

Figure 28:
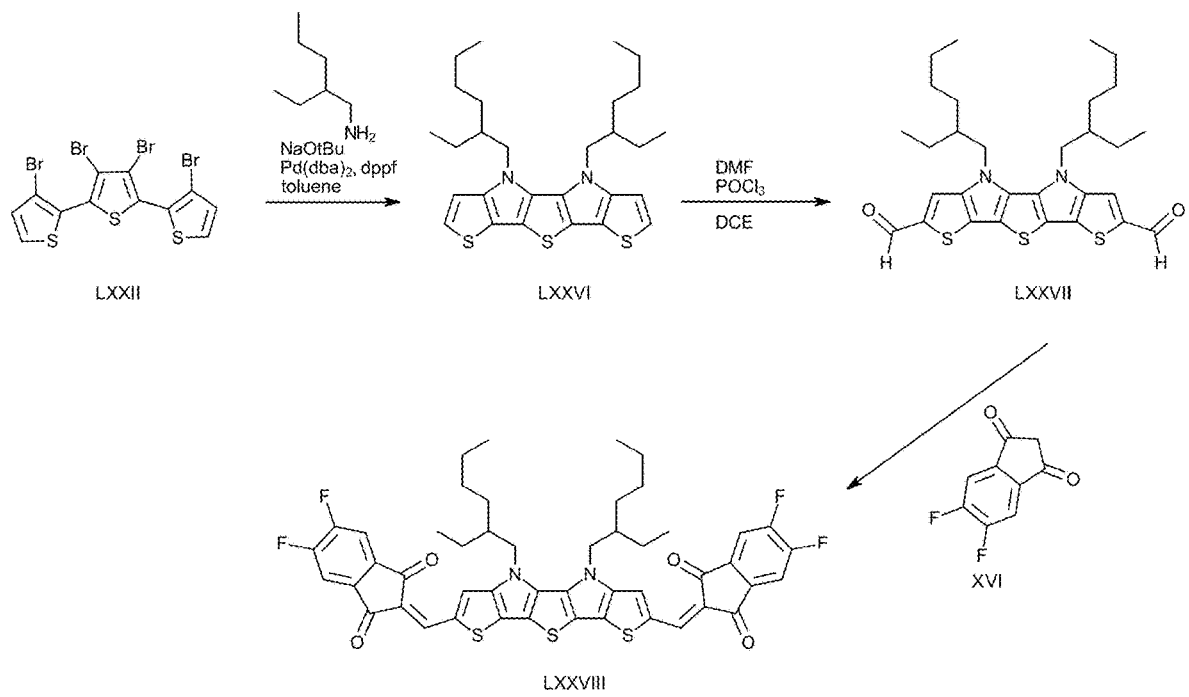
FIG. 28 provides a synthetic scheme for preparation of an example indandione containing photoactive compound.

FIG. 28 provides a synthetic scheme for preparation of an indandione containing photoactive compound:

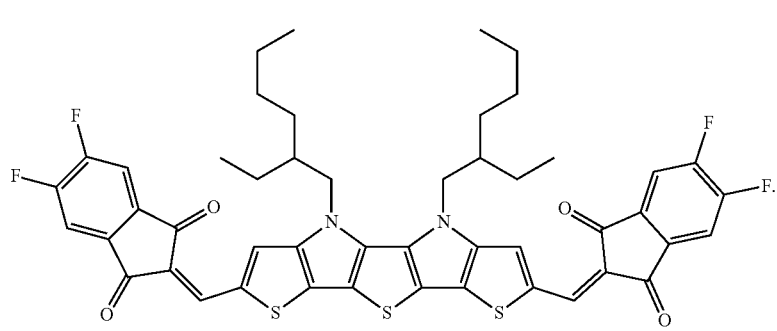

LXXVIII

Compound LXXVI: A mixture of compound LXXII (6.0 g, 10.6 mmol, 1.0 eq), sodium tert-butoxide (12.3 g, 127 mmol, 12 eq), Pd(dba)$_2$ (735 mg, 1.27 mmol, 0.12 eq), and dppf (2.95 g, 5.32 mmol, 0.5 eq) in toluene (220 mL) was sparged with argon for 30 minutes at room temperature. 2-Ethylhexylamine (7.0 mL, 42.6 mmol, 4 eq) was added and the mixture was heated at 110° C. for 20 hours. After cooling to room temperature, the reaction was diluted with water (100 mL). The aqueous layer was separated and extracted with dichloromethane (2×100 mL). The combined organic layers were dried over anhydrous sodium sulfate and concentrated under reduced pressure. The crude material was absorbed onto celite (60 g) and purified on a Büchi automated chromatography system (Sorbtech silica gel column, 330 g), eluting with a gradient of 0 to 30% dichloromethane in hexanes to give the product as a light yellow solid (2.1 g, 40% yield).

Compound LXXVII: Compound LXXVII was prepared as described in the synthesis of compound LXXIV, substituting compound LXXVI in place of compound LXXIII. The product was obtained in 86% yield.

Figure 29:
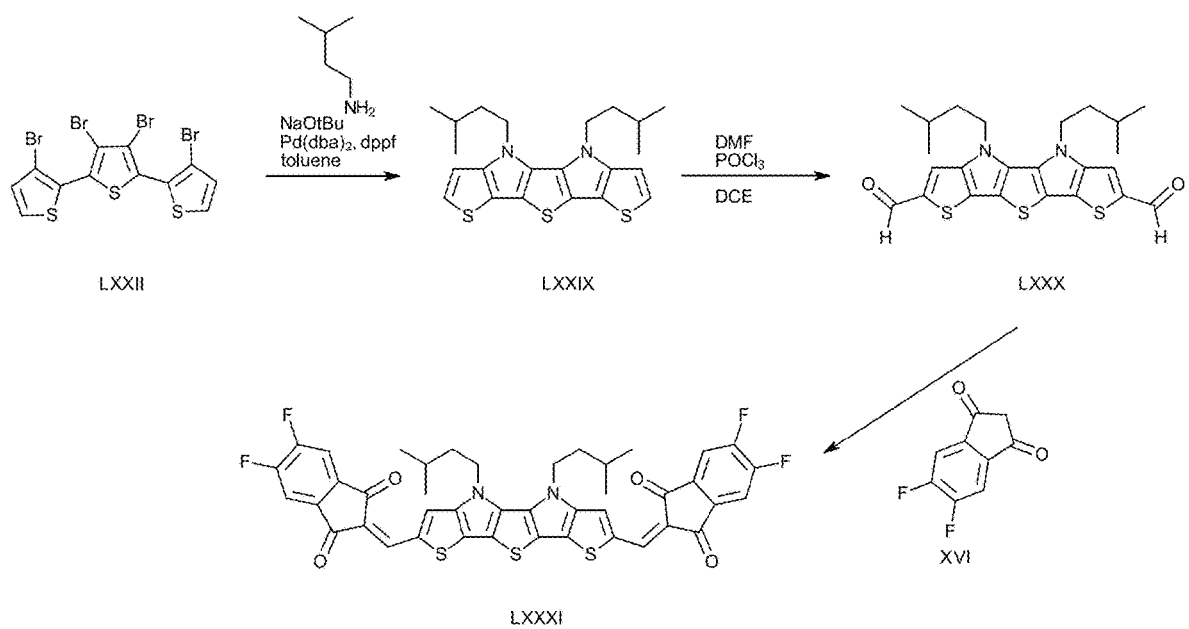
FIG. 29 provides a synthetic scheme for preparation of an example indandione containing photoactive compound.

Compound LXXVIII: Compound LXXVIII was prepared as described in the synthesis of compound LXXV, substituting compound LXXVII in place of compound LXXIV. The product was obtained in 74% yield. This compound was sublimed in 10% yield. $\lambda_{max}$ (DCM): 658 nm FIG. 29 provides a synthetic scheme for preparation of an indandione containing photoactive compound:

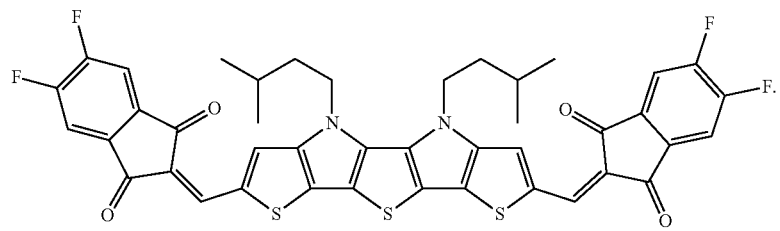

LXXXI

Compound LXXIX: A suspension of compound LXXII (15.55 g, 27.57 mmol, 1 eq), bis(dibenzylideneacetone) palladium (1.59 g, 2.76 mmol, 0.1 eq), 1,1'-bis(diphenylphosphino)ferrocene (6.11 g, 11.0 mmol, 0.4 eq) and sodium tert-butoxide (42.4 g, 441 mmol, 16 eq) in toluene (180 mL, 12 vol) was sparged with a stream of nitrogen for 10 minutes. The suspension was then stirred under nitrogen at 23° C. for 20 minutes. Isopentylamine (6.25 g, 8.32 mL, 71.68 mmol, 2.6 eq) was then added under nitrogen. The resulting suspension was heated at 104° C. for 16 hours. The suspension was cooled to 23° C. and treated slowly with ice water (100 mL). The biphasic mixture was filtered through a pad of Celite (20 g) and the layers were separated. The organic layer was concentrated under reduced pressure. The Celite pad was rinsed with dichloromethane (3×100 mL). The dichloromethane filtrate was combined with the above crude product and concentrated onto Celite (22 g). The solid was purified on an Interchim automated chromatography system (330 g Sorbtech), eluting with a gradient of 10 to 20% dichloromethane in heptanes to give a yellow solid (4.9 g). This material was triturated with methanol (20 mL) at 23° C. for 2 hours and the solid was collected by vacuum filtration, rinsed with methanol (2×5 mL) and dried under vacuum at 23° C. for 15 hours to afford the product as a light yellow solid (4.86 g, 42% yield).

Compound LXXX: Compound LXXX was prepared as described in the synthesis of compound LXXIV, substituting compound LXXIX in place of compound LXXIII (3.97 g, 75% yield).

Compound LXXXI: Compound LXXX (1.50 g, 3.19 mmol) was dissolved in dichloroethane (175 mL) at 75° C. Sodium sulfate (5 g) was added. The suspension was kept at 75° C. for 20 minutes and hot filtered into a 1-L 3-neck round-bottom flask rinsing with hot dichloroethane (75° C., 3×100 mL). 5,6-Difluoro-1H-indene-1,3(2H)-dione (2.90 g, 15.9 mmol, 5 eq), ammonium acetate (3.69 g, 47.85 mmol, 15 eq) and additional dichloroethane (275 mL) were added to the reaction. The solution was then heated at 81° C. (reflux) for 68 hours. Additional 5,6-difluoro-1H-indene-1, 3(2H)-dione (1.16 g, 6.38 mmol, 2 eq) and ammonium acetate (1.48 g, 19.1 mmol, 6 eq) were added. The suspension was heated at 81° C. (reflux) for 42 hours. The suspension was cooled to 23° C. over 2 hours and the solid was collected via vacuum filtration and rinsed with hot methanol (60° C., 3×30 mL). The solid (3.97 g) was triturated with chloroform (400 mL) at 23° C. for 20 hours. The solid was collected by vacuum filtration, rinsed with chloroform (3×20 mL) and further dried under vacuum oven at 50° C. for 5 hours to produce the product as a dark green solid in quantitative yield. This compound was sublimed in 23% yield.

Figure 30:
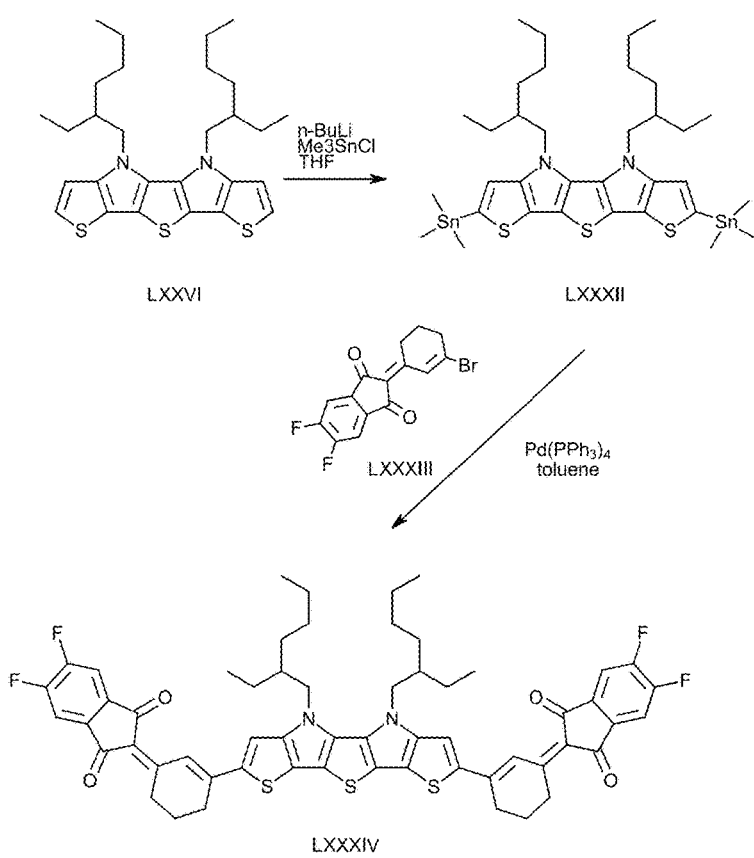
FIG. 30 provides a synthetic scheme for preparation of an example indandione containing photoactive compound.

FIG. 30 provides a synthetic scheme for preparation of an indandione containing photoactive compound:

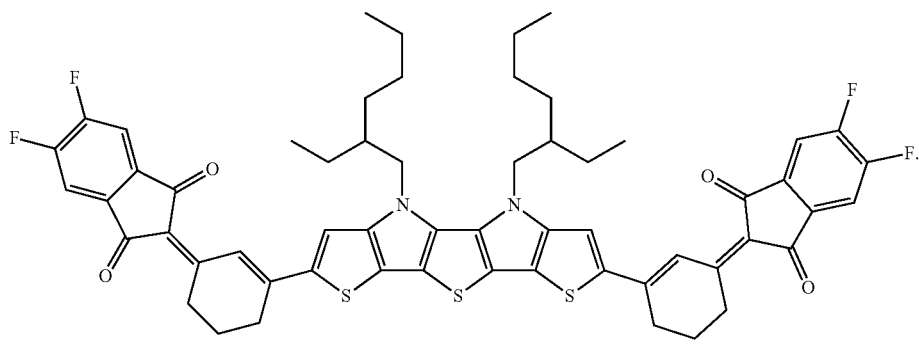

LXXXIV

Compound LXXXII: 2.5 M n-Butyl lithium in hexanes (3.1 mL, 7.82 mmol, 3 eq) was added dropwise over 15 minutes to a solution of compound LXXVI (1.3 g, 2.61 mmol, 1.0 eq) in anhydrous THF (60 mL) at −78° C. After stirring for 2 hours, 1 M trimethyl tin chloride in THF (10.5 mL, 10.5 mmol, 4 eq) was added dropwise over 15 minutes. After stirring for 30 minutes, the reaction was slowly warmed to room temperature and stirred overnight. The reaction was quenched with ice water (20 mL) and extracted with ether (3×50 mL). The combined organic layers were dried over sodium sulfate and concentrated under reduced pressure. The residue was dried under vacuum at 25° C. for 5 hours to give compound XII as a light brown oil (2.1 g, quantitative yield).

Compound LXXXIV: A mixture of compound LXXXII (1.3 g, 1.58 mmol, 1.0 eq), compound LXXXIII (1.6 g, 4.74 mmol, 3 eq), tetra-kistriphenylphosphine palladium (185 mg, 0.16 mmol, 0.1 eq), and copper (I) iodide (30 mg, 0.16 mmol, 0.1 eq) in toluene (16 mL) was sparged with argon for 15 minutes at room temperature. After heating at 110° C. overnight, the reaction was cooled to room temperature and concentrated under reduced pressure. The crude material was absorbed onto celite (40 g) and purified on a Büchi automated chromatography system (Sorbtech silica gel column, 120 g), eluting with a gradient of 20 to 100% dichloromethane in hexanes. The pure fractions were combined, concentrated and resultant solid was dried under vacuum at 50° C. overnight to give compound LXXXIV as a brown solid (970 mg, 60% yield). This compound was sublimed in 0% yield. $\lambda_{max}$ (DCM): 707 nm.

Figure 31:
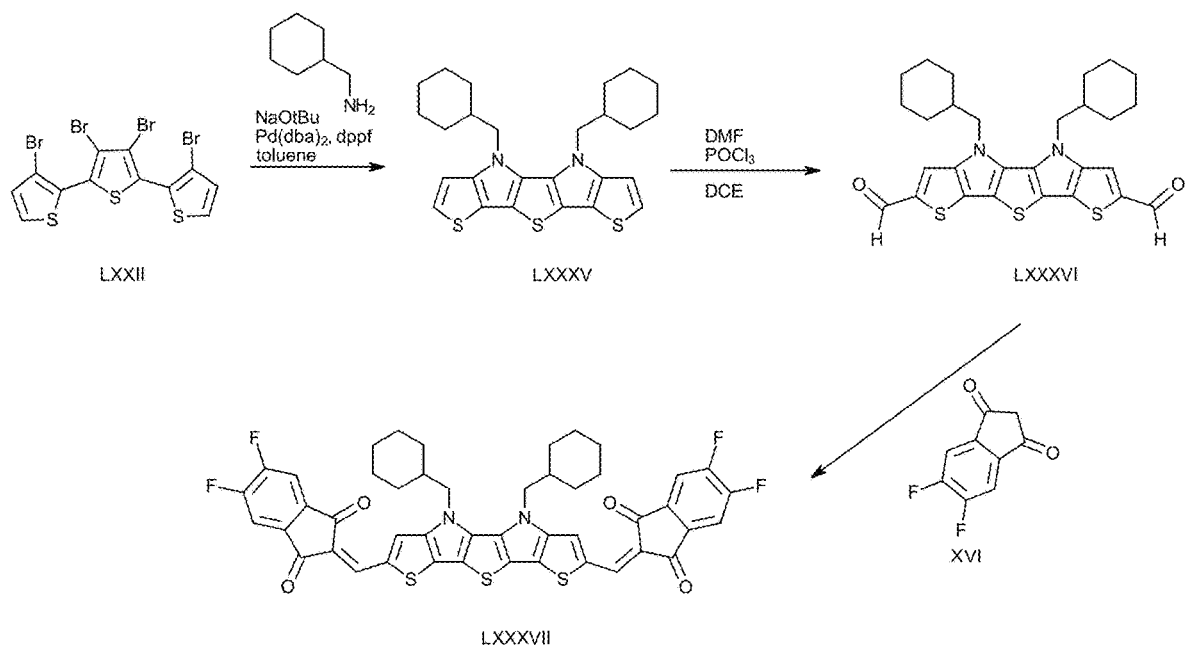
FIG. 31 provides a synthetic scheme for preparation of an example indandione containing photoactive compound.

FIG. 31 provides a synthetic scheme for preparation of an indandione containing photoactive compound:

gradient of 0 to 30% dichloromethane in hexanes. The product fractions were combined, concentrated, and chromatographed again using a Biotage automated chromatography system (Sorbtech 330 g, 60 μm silica gel column) eluting with a gradient of 10 to 20% dichloromethane in hexanes. The product was dried under vacuum at 50° C. overnight to give compound XV as a beige solid (2.73 g, 33% yield). Further trituration of the crude material with methanol provided pure product as a beige solid (1.502 g, 87% recovery yield).

Compound LXXXVI: Compound LXXXVI was synthesized using the same method as described for preparing

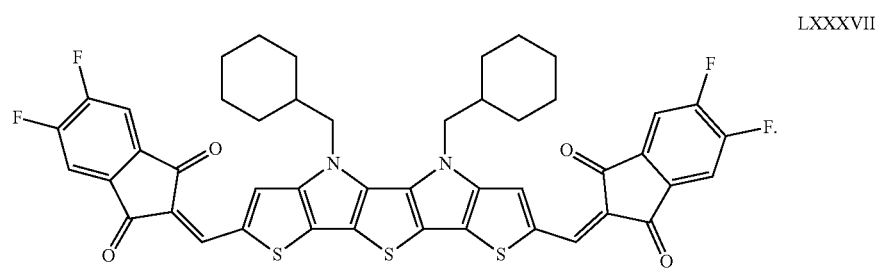 [SMILES: O=C1C(=Cc2cc3c(s2)c2sc4c5sc(C=C6C(=O)c7cc(F)c(F)cc7C6=O)cc5n(CC5CCCCC5)c4c2n3CC2CCCCC2)C(=O)c2cc(F)c(F)cc21]

LXXXVII

Compound LXXXV: A solution of compound LXXII (10 g, 17.73 mmol, 1.0 eq), cyclohexylmethylamine (4.41 g, 39.00 mmol, 2.2 eq), sodium tert-butoxide (10.22 g, 10.64 mmol, 6.0 eq) and 1,1'-bis(diphenylphosphino)ferrocene (0.20 g, 0.36 mmol, 0.02 eq) in anhydrous toluene (80.0 mL) was sparged with nitrogen for 20 minutes Bis(diphenylphosphino)ferrocene palladium dichloride-dichloromethane adduct (2.90 g, 3.55 mmol, 0.2 eq) was added and the mixture was stirred at 90° C. for 17 hours. After cooling to room temperature, the mixture was concentrated under reduced pressure, diluted with saturated ammonium chloride (100 mL), and extracted with dichloromethane (2×500 mL). The combined organic layers were washed with saturated brine (200 mL) and concentrated under reduced pressure after adding Celite (100 g). The resultant Celite mixture was purified on a Biotage automated chromatography system (Sorbtech 330 g, 60 μm silica gel column), eluting with a compound LXXIV, substituting compound LXXXV in place of compound LXXIII. Product was obtained in 91% yield.

Compound LXXXVII: Compound LXXII was synthesized using the same method as described for preparing compound LXXV, substituting compound LXXXVI in place of compound LXXIV. This compound was sublimed in 14% yield.

Figure 32:
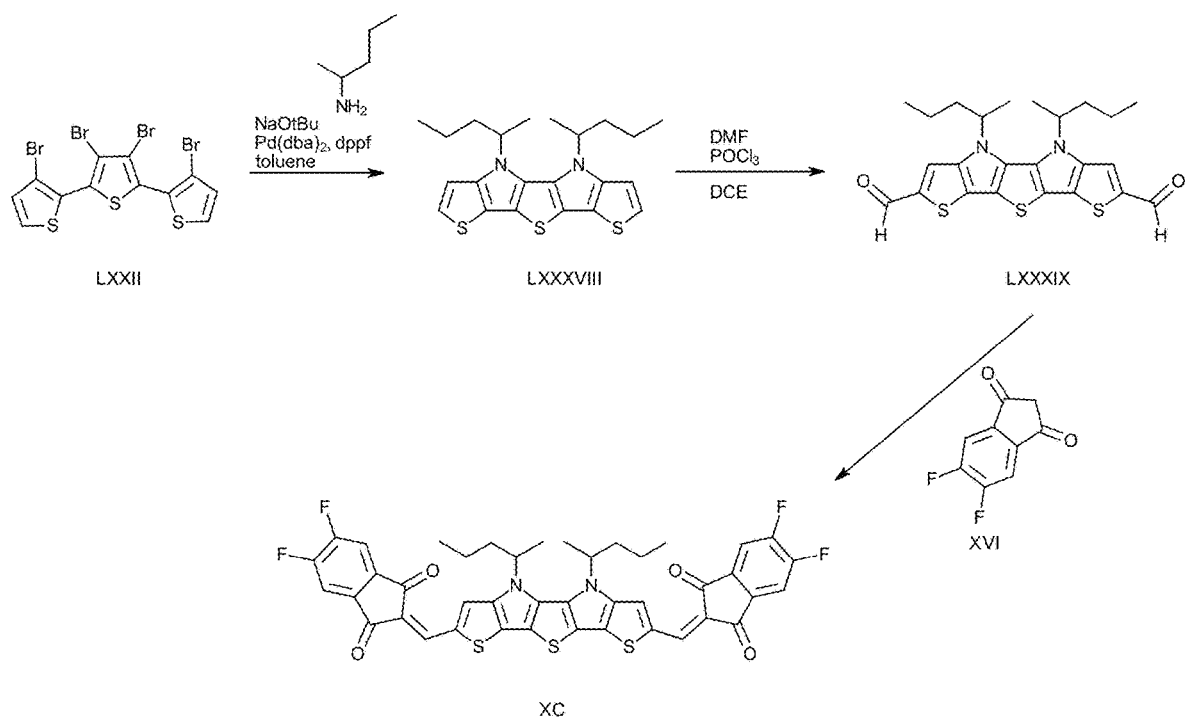
FIG. 32 provides a synthetic scheme for preparation of an example indandione containing photoactive compound.

FIG. 32 provides a synthetic scheme for preparation of an indandione containing photoactive compound:

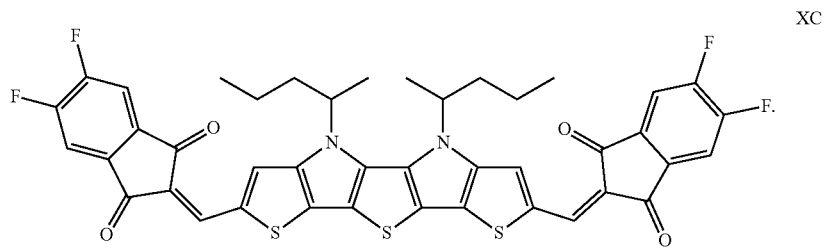 [SMILES: CCCC(C)n1c2cc(C=C3C(=O)c4cc(F)c(F)cc4C3=O)sc2c2sc3c4sc(C=C5C(=O)c6cc(F)c(F)cc6C5=O)cc4n(C(C)CCC)c3c21]

XC

Compound LXXXVIII: A solution of compound LXXII (8.6 g, 15.2 mmol, 1 eq) and pentan-2-amine (5 mL, 45.5 mmol, 3 eq) in toluene (200 mL) was sparged with nitrogen for 15 minutes. Concurrently, in another flask, a mixture of Pd(dba)$_2$ (0.9 g, 1.5 mmol, 0.1 eq) and dppf (3.4 g, 6.1 mmol, 0.4 eq) in toluene (100 mL) was sparged with nitrogen for 15 minutes and transferred via a canula to the first mixture. Sodium tert-butoxide (14.5 g, 152 mmol, 10 eq) was added to the mixture. After refluxing for 20 hours, the reaction mixture was cooled to room temperature and concentrated under reduced pressure. The residue was dissolved in dichloromethane (300 mL) and washed with water (250 mL). The aqueous layer was extracted with dichloromethane (2×150 mL). The combined organic layers were dried over sodium sulfate, filtered, and concentrated under reduced pressure. The residue was absorbed onto Celite (120 g) and purified on an Interchim automated chromatography system (Sorbtech 220 g silica column), eluting with a gradient of 0 to 20% dichloromethane in hexanes to give the product as a yellow solid (1.6 g, 26% yield).

Compound LXXXIX: Compound LXXXIX was synthesized using the same method as described for preparing compound LXXIV, substituting compound LXXXVIII in place of compound LXXIII. Product was obtained in 95% yield.

Compound XC: Compound XC was synthesized using the same method as described for preparing compound LXXV, substituting compound LXXXIX in place of compound LXXIV. Product was obtained in 47% yield. This compound was sublimed in 48% yield. $\lambda_{max}$ (DCM): 659 nm.

Figure 33:
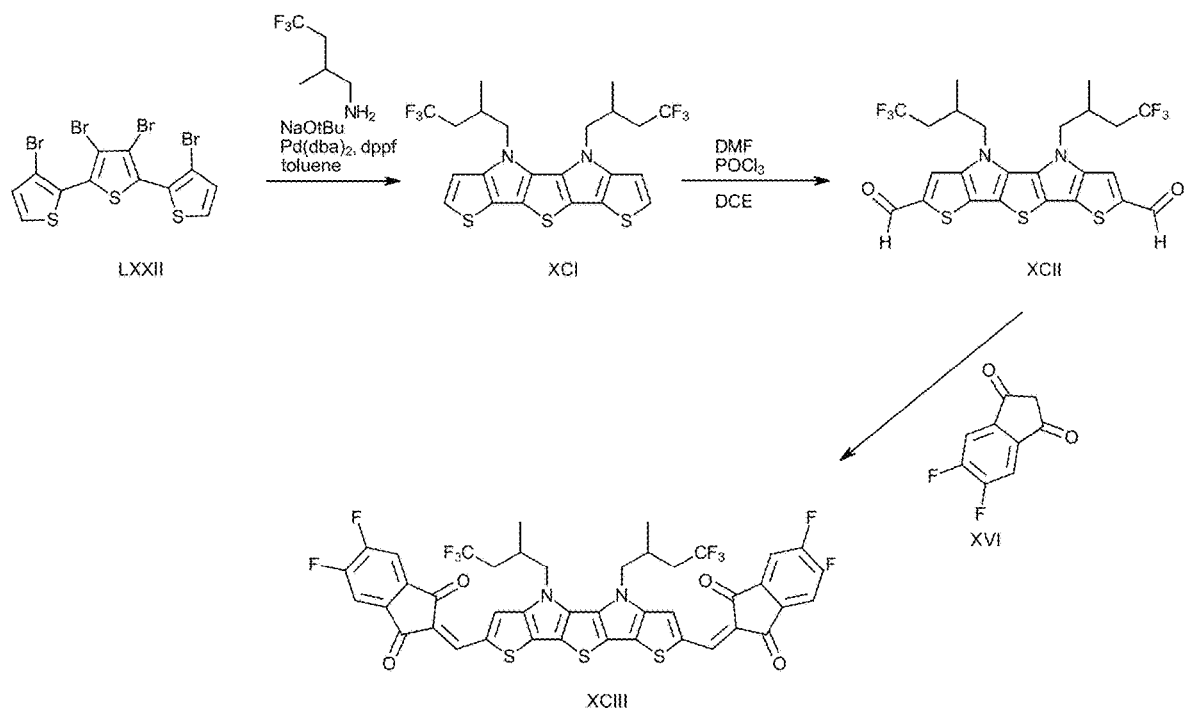
FIG. 33 provides a synthetic scheme for preparation of an example indandione containing photoactive compound.

FIG. 33 provides a synthetic scheme for preparation of an indandione containing photoactive compound:

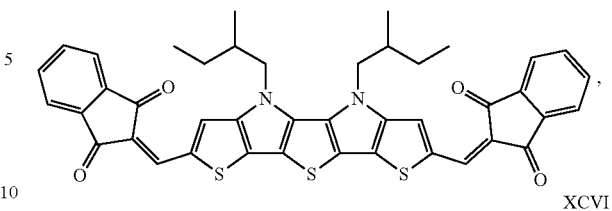

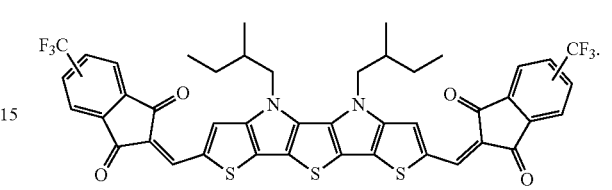

Compound XCIV: In an oven dried 1 L 3-neck flask equipped with condenser and nitrogen inlet compound LXXIV (2.05 g, 0.004 mol), compound XII (3.18 g, 0.022 mol), and ammonium acetate (5.04 g, 0.065 mol) were dissolved in 500 mL dichloroethane under nitrogen atmosphere. The solution was refluxed for about 48 hours then

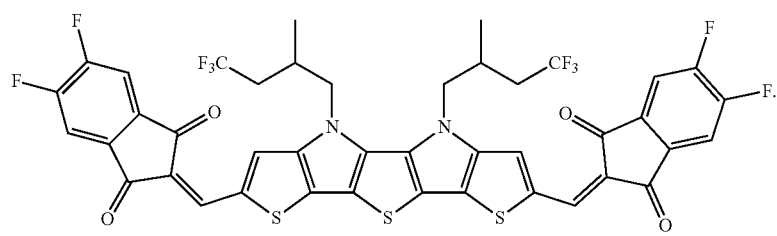

Compound XCI: In an oven dried 2 L 3-neck flask equipped with nitrogen inlet and condenser, a solution of compound LXII (3.0 g, 0.005 mol), sodium tert-butoxide (5.11 g, 0.053 mol), and Pd(dba)$_2$ (0.31 g, 0.001 mol), and dppf (1.18 g, 0.002 mol) in 90 mL of dry toluene was stirred for 20 min at room temperature under nitrogen atmosphere. After addition of 4,4,4-trifluoro-2-methylbutan-1-amine hydrochloride (2.83 g, 0.016 mol), the mixture was stirred at 110° C. for 20 h. The reaction was cooled to room temperature then diluted with water. The biphasic mixture was extracted with DCM (100 mL). Organic layers were combined, dried over sodium sulfate, and concentrated in vacuo. The crude product was purified by autoflash chromatography using 80 g silica gel column eluted with Heptane/DCM. Product was obtained as yellow solid (1.08 g, 39% yield).

Compound XCII: Compound XCII was synthesized using the same method as described for preparing compound LXXIV, substituting compound XCI in place of compound LXXIII. Product was obtained in 88% yield.

Compound XCIII: Compound XCIII was synthesized using the same method as described for preparing compound LXXV, substituting compound XCII in place of compound LXXIV. Product was obtained in quantitative yield. This compound was sublimed in 52% yield. $\lambda_{max}$ (DCM): 644 nm.

Figure 34:
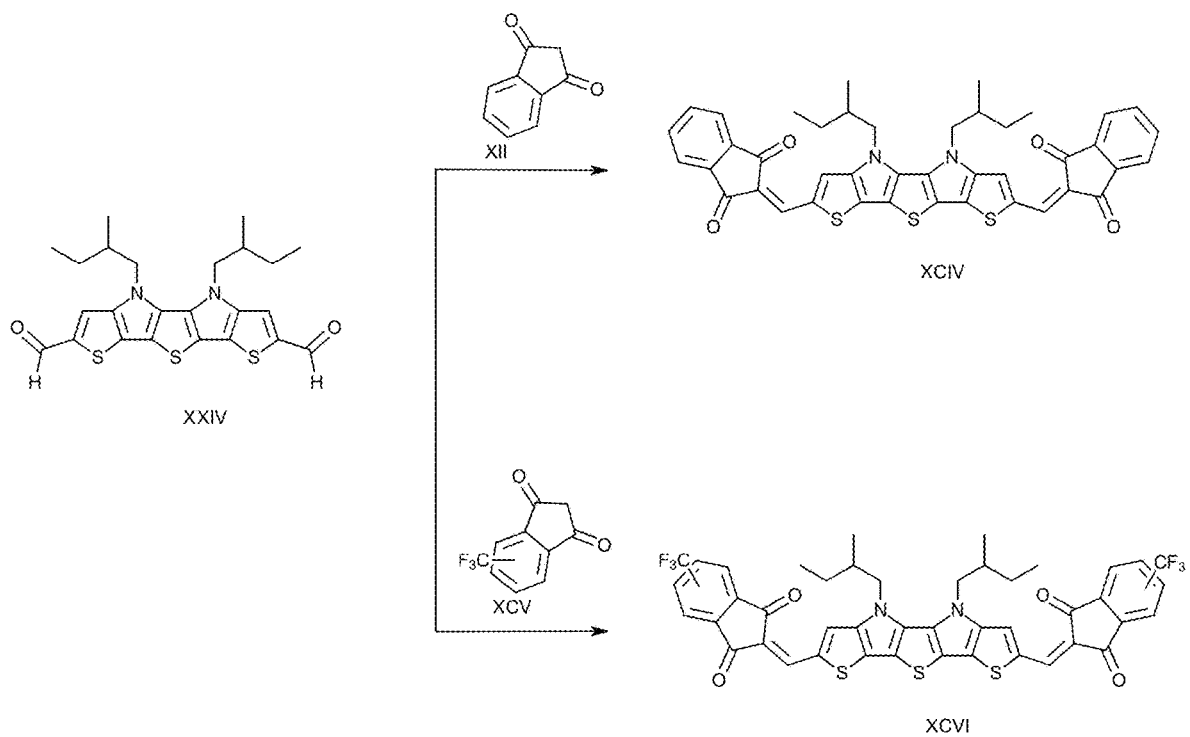
FIG. 34 provides synthetic schemes for preparation of example indandione containing photoactive compounds.

FIG. 34 provides synthetic schemes for preparation of indandione containing photoactive compounds:

cooled to room temperature. The green precipitate was filtered off and washed with hot methanol to afford the desired product (1.6 g, 50% yield). The filtrate was concentrated under vacuum and the residue was washed with a hot mixture of methanol (100 mL) and DCE (50 mL). The green solid obtained was dried under high vacuum at 60° C. overnight to obtain additional product with (1.75 g, 55% yield). This compound was sublimed in 40% yield. $\lambda_{max}$ (DCM): 646 nm.

Compound XCVI: In an oven dried 2 L 3-neck flask equipped with condenser and nitrogen inlet compound LXXIV (1.0 g, 0.002 mol), compound XCV (2.27 g, 0.011 mol), and ammonium acetate (4.09 g, 0.053 mol) were dissolved in 700 mL dichloroethane under argon atmosphere. The solution was refluxed for 2 days then cooled to room temperature and concentrated under vacuum to ¼ of its volume and diluted by methanol (300 mL). The resulting precipitate was filtered off and washed with hot methanol to afford desired product as a green solid (1.33 g, 72.7% yield). This compound was sublimed in 26% yield. $\lambda_{max}$ (DCM): 668 nm.

Figure 35:
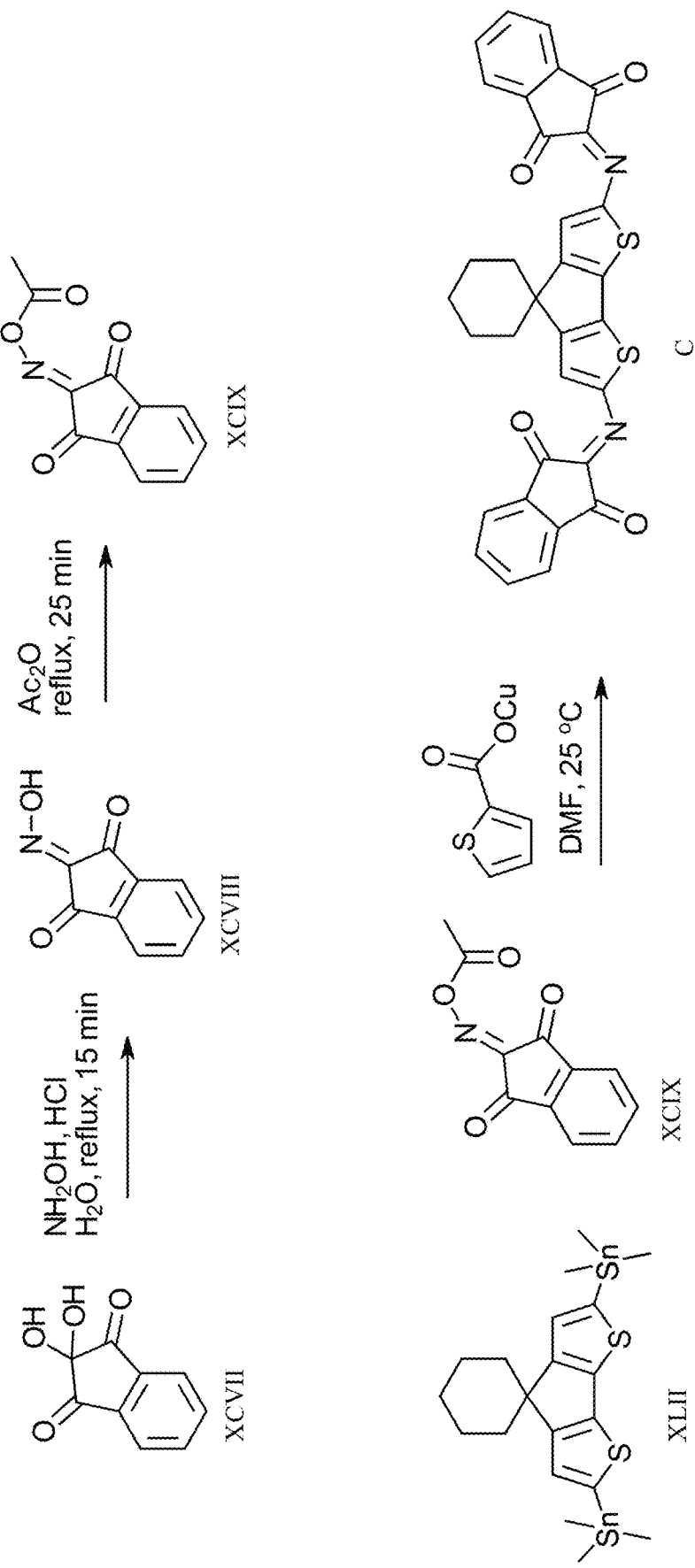
FIG. 35 provides a synthetic scheme showing preparation of an example photoactive compound in accordance with some examples.

Example 2—Synthesis of Example Core Disrupted Photoactive Compounds Containing Imine Linked Indandione Groups FIG. 35 provides an overview of an example synthetic scheme providing a synthetic route for a core disrupted photoactive compound containing imine linked indandione groups:

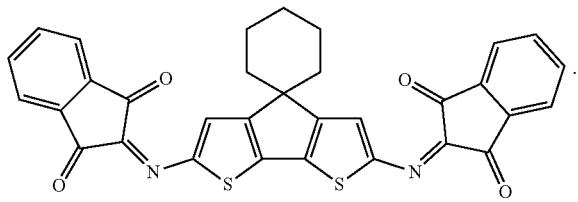

Synthesis of the compounds depicted in FIG. 35 was performed as follows:

Compound XCVIII: To a 40 mL scintillation vial attached to an adaptor with a reflux condenser in a heating block Ninhydrin (compound XCVII, 1.44 g, 0.00808 mol), Hydroxylamine HCl (0.60 g, 0.00863 mol), deionized water (14 mL), and a magnetic spinbar were added. The reaction mixture was heated quickly to 100° C. and allowed to reflux for 15 minutes under atmosphere. As the reaction progressed, the solids were dissolved and a yellow precipitate began to form. Workup was accomplished by cooling to room temperature, filtering, and washing with cold water to collect compound XCVIII in 90% yield (1.28 g).

Compound XCIX: To a 40 mL scintillation vial with a magnetically coupled spinbar in a heating block compound XCVIII (1.0 g, 0.0571 mol) and acetic anhydride (1.5 mL) were added. The mixture was heated to reflux, ~140° C. and the mixture began to completely melt together and mix at 70° C. The reaction was refluxed for 25 minutes and then rapidly cooled to room temperature. An ice bath was used to precipitate the product inside the vial, which was then washed with diethyl ether (10 mL, 4×) and petroleum ether to produce compound XCIX in in 93.0% yield (1.1532 g).

Compound C: To a dry three neck flask with an internal thermocouple and a magnetically coupled spinbar compound XLII (0.158 g, 0.000276 mol), compound XCIX (0.1 g, 0.00046 mol) CuTC (0.035 g, 0.000184 mol), and anhydrous THF (15 mL) were added under nitrogen protection. Mixture was sonicated to help dissolve CuTC and then mixed at room temperature for 16 hours. Solution was concentrated in vacuo and then washed with hot isopropyl alcohol 3× and then cold dichloromethane 2× to obtain compound C in 21.1% yield.

Example 3—Optical Properties of Imine-Linked Photoactive Compounds

Compounds XIII and C were synthesized according to the schemes described herein in Examples 1 and 2 to evaluate the difference in optical properties between a photoactive compound with an alkene linker and an analog core disrupted photoactive compound with an imine linker:

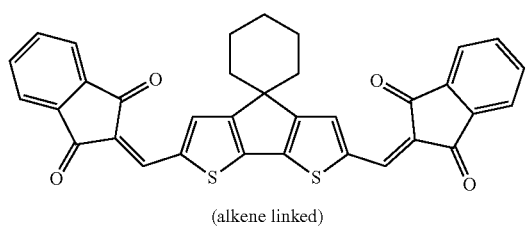

(alkene linked)

XIII and

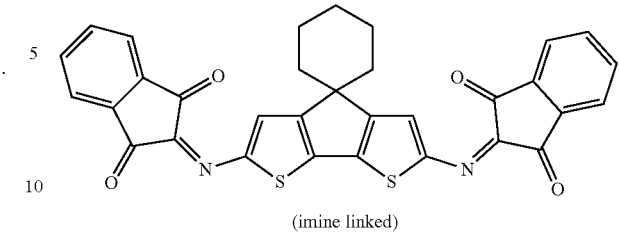

(imine linked)

C

Figure 36:
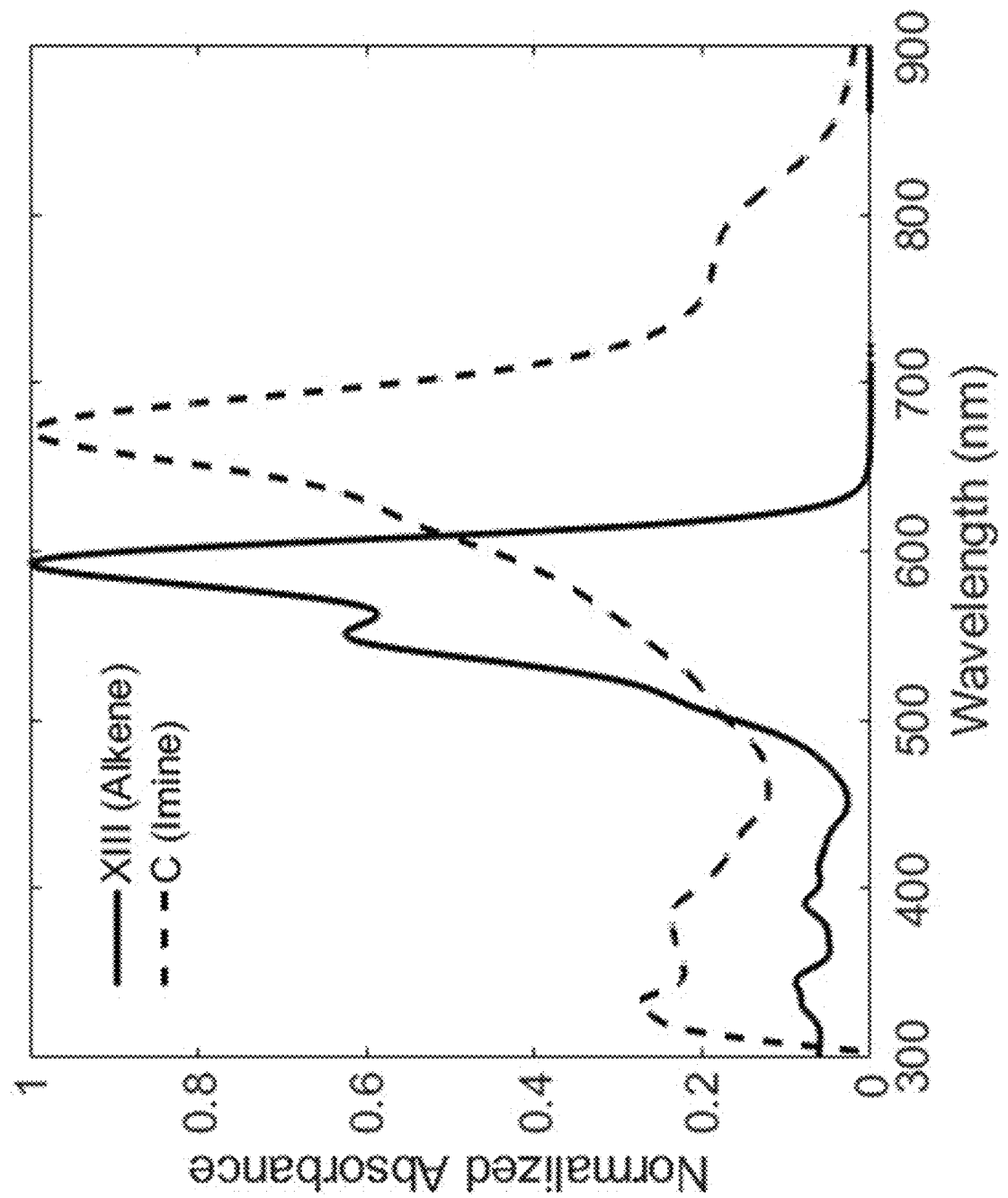
FIG. 36 provides a plot showing normalized absorbance by example photoactive compounds in accordance with some examples.

The compounds were dissolved into a solution at ~1 micromolar concentration and their ultraviolet-visible (UV-vis) absorption spectrum was obtained. FIG. 36 provides the normalized UV-vis absorbance profile, showing a peak absorbance by the alkene linked compound at about 590 nm and a peak absorbance by the imine linked compound at about 670 nm.

Example 4—Sublimation of Photoactive Compounds Containing Core Disruption and Indandiones Several photoactive compounds were synthesized according to the schemes described above in Example 1 to evaluate the difference in sublimation properties between photoactive compounds containing core disrupted donor moieties and non-disrupted donor moieties as well as the difference in sublimation properties between photoactive compounds containing indandione-based acceptor moieties and photoactive compounds containing dicyanomethyleneindanone-based acceptor moieties. The following core disrupted dicyanomethyleneindanone-based compounds were synthesized: compound V and compound IX. The following non-disrupted dicyanomethyleneindanone-based compounds were also synthesized: compound XXIX and compound XXX. The following core disrupted indandione-based compounds were also synthesized: compound XIII and compound XVII. The following non-disrupted indandione-based compounds were also synthesized: compound XXXII.

Figure 37:
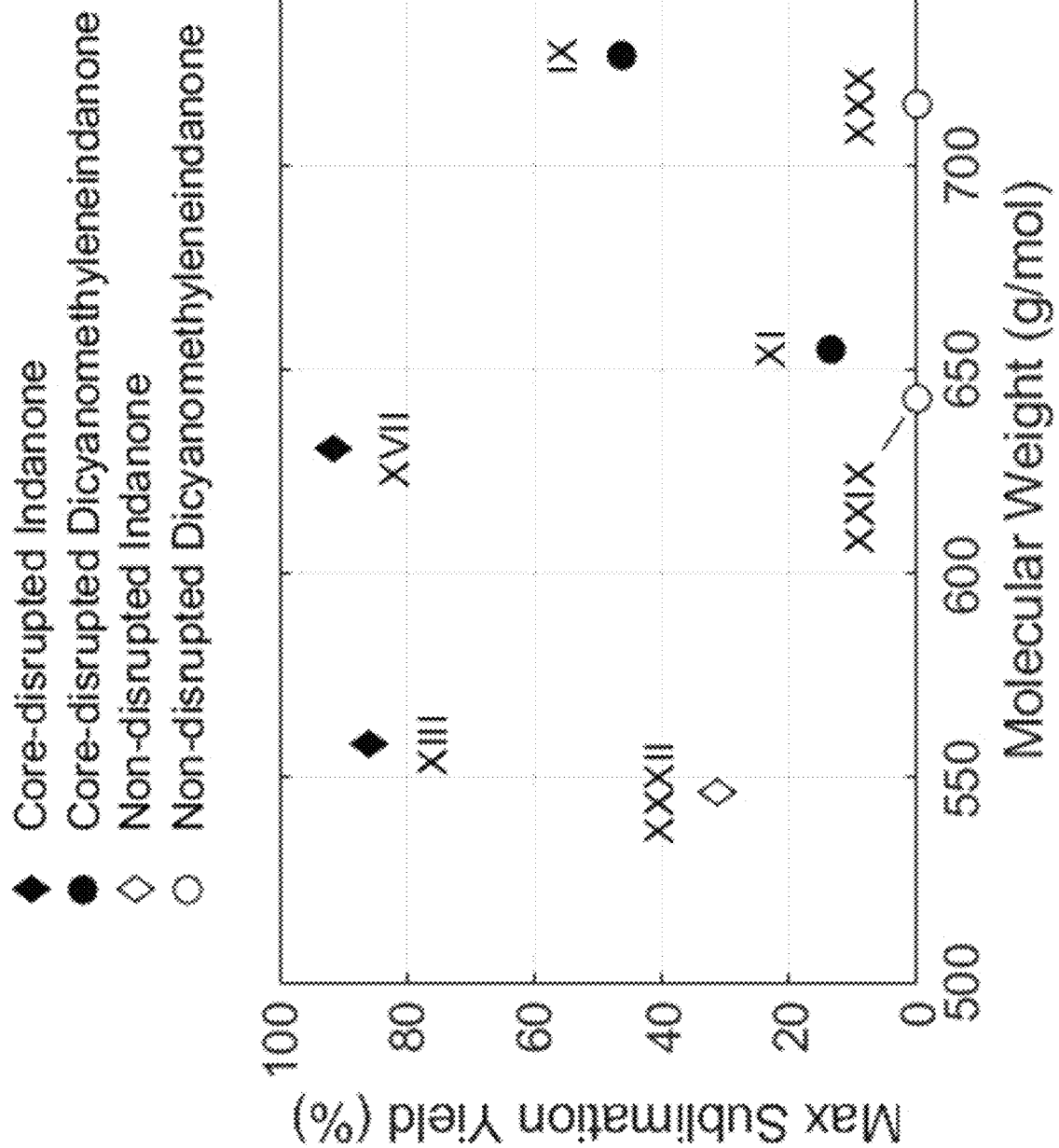
FIG. 37 provides a plot showing sublimation yield of example photoactive compounds in accordance with some examples.

The synthesized photoactive compounds were subjected to purification by vacuum sublimation and the results are summarized in FIG. 37, which shows a plot of the maximum sublimation yield of each compound as a function of molecular weight. Compound XI had a maximum sublimation yield of 13.5%, compound IX had a maximum sublimation yield of 46.3%, compound XXIX had a maximum sublimation yield of 0%, compound XXX had a maximum sublimation yield of 0%, compound XIII had a maximum sublimation yield of 85.7%, compound XVII had a maximum sublimation yield of 91.3%, and compound XXXII had a maximum sublimation yield of 31.1%, Sublimation yields of the non-disrupted photoactive compounds (empty points on FIG. 37) and the core disrupted photoactive compounds (filled points on FIG. 37) were compared to see the effects of core disruption at the electron donor moiety. The change from non-disrupted photoactive compounds XXIX, XXX, and XXXII to counterpart core disrupted photoactive compounds XI, IX, and XIII respectively showed increases in sublimation yield of 13.5%, 46.3%, and 54.6%. These results indicate that use of core-disruption in electron donor moieties may be a suitable technique for achieving high volatility and enable compatibility with physical vapor deposition.

Sublimation yields of the dicyanomethyleneindanone-based photoactive compounds (circular points on FIG. 37) and the indandione-based photoactive compounds (diamond points on FIG. 37) were compared to see the effects of the change of electron acceptor moiety from dicyanomethyleneindanone to indandione. The change from dicyanomethyleneindanone-based compounds XI, IX, and XXIX to counterpart indandione-based compounds XIII, XVII, and XXXII respectively showed increases in sublimation yield of 72.2%, 45%, and 31.1%. These results indicate that use of indandione in electron acceptor moieties may be a suitable technique for achieving high volatility and enable compatibility with physical vapor deposition.

Figure 38:
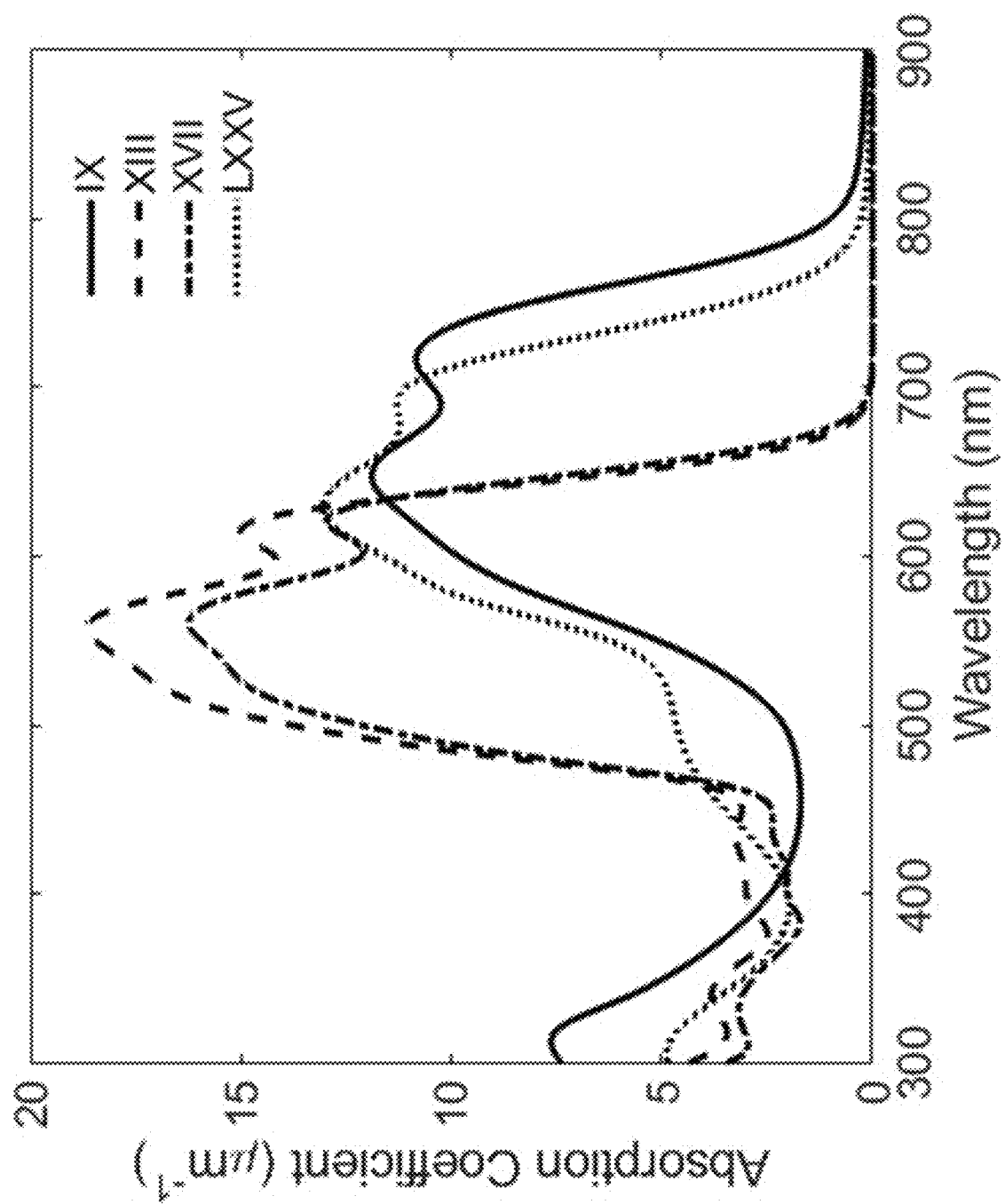
FIG. 38 provides absorption coefficients for example photoactive compounds for which transparent photovoltaic devices were constructed.

Example 5—Transparent Photovoltaic Devices Comprising Photoactive Compounds Containing Core Disruption and Indandiones FIG. 38 illustrates absorption coefficients for exemplary active layer materials that can be utilized in various examples described herein. The absorption coefficients were determined from films of compounds IX, XIII, XVII, and LXXV deposited through vacuum thermal evaporation. As illustrated in FIG. 38, the active layer materials can be characterized by strong absorption peaks in the red to NIR regions of the solar spectrum. Strong optical transitions at these long wavelengths confirm the preservation of molecular structure through the vacuum thermal evaporation process, in which similar molecules without core-disruption or indandione units may decompose. Although spectra of particular exemplary compounds are illustrated in FIG. 38, examples are not limited to the particular example compound and other photoactive compounds can be utilized in various examples and embodiments.

FIGS. 39A-D illustrate transparent photovoltaic device structures 3900-3903, according to several examples. Device structures 3900-3903 comprise either a bulk heterojunction (BHJ) or planar-mixed heterojunction (PMHJ) active layer between a top electrode and a bottom electrode that contains a core-disrupted compound or molecule as an active material, which may be formed on a substrate through vacuum thermal evaporation, as described herein. In some examples, the core-disrupted molecule also contains indandione acceptor groups. The ITO layer may correspond to the anode. The $MoO_3$ layer may function as a hole injection layer and may be considered part of the anode structure or as a buffer layer coupled to the anode. The para-sexiphenyl (p-6P) layer may be considered as a buffer layer coupled to the anode. The Ag layer may correspond to the cathode. The TPBi:$C_{60}$ layer may be considered part of the cathode structure or as a buffer layer coupled to the cathode. The TPBi layer may correspond to an optical layer or as an encapsulating layer to the cathode. Although a particular exemplary electron donor (or acceptor) is illustrated in FIG. 39, such a configuration is not limiting and other donors and/or acceptors can be utilized according to various examples.

FIG. 39A illustrates a transparent photovoltaic device structure 3900, according to one example. Device structure 3900 comprises a binary BHJ active layer between a top electrode and a bottom electrode that contains ClAlPc as an electron donor and a core-disrupted molecule, compound IX, as an electron acceptor, formed through vacuum thermal evaporation. In some examples, the ClAlPc:IX blend is maintained at a donor to acceptor ratio of 50:50.

FIG. 39B illustrates a transparent photovoltaic device structure 3901, according to one example. Device structure 3901 comprises a ternary BHJ active layer between a top electrode and a bottom electrode that contains TAPC and the core-disrupted and indandione-containing compound XIII as electron donors and fullerene $C_{60}$ as an electron acceptor, formed through vacuum thermal evaporation. In some examples, the TAPC:XIII:$C_{60}$ blend is maintained at a donor:donor:acceptor ratio of 10:10:80.

FIG. 39C illustrates a transparent photovoltaic device structure 3902, according to one example. Device structure 3902 comprises a PMHJ active layer between a top electrode and a bottom electrode that contains SubNc as an electron donor and the core-disrupted and indandione-containing compound XVII as an electron acceptor, formed through vacuum thermal evaporation. In some examples, the SubNc:XVII blend is maintained at a donor to acceptor ratio of 50:50, and thin layers of SubNc and XVII are coupled to the blend layer.

FIG. 39D illustrates a transparent photovoltaic device structure 3903, according to one example. Device structure 3903 comprises a binary BHJ active layer between a top electrode and a bottom electrode that contains the indandione-containing compound LXXV as an electron donor and fullerene $C_{70}$ as an electron acceptor, formed through vacuum thermal evaporation. In some examples, the LXXV:$C_{70}$ blend is maintained at a donor to acceptor ratio of 30:70.

Figure 40A:
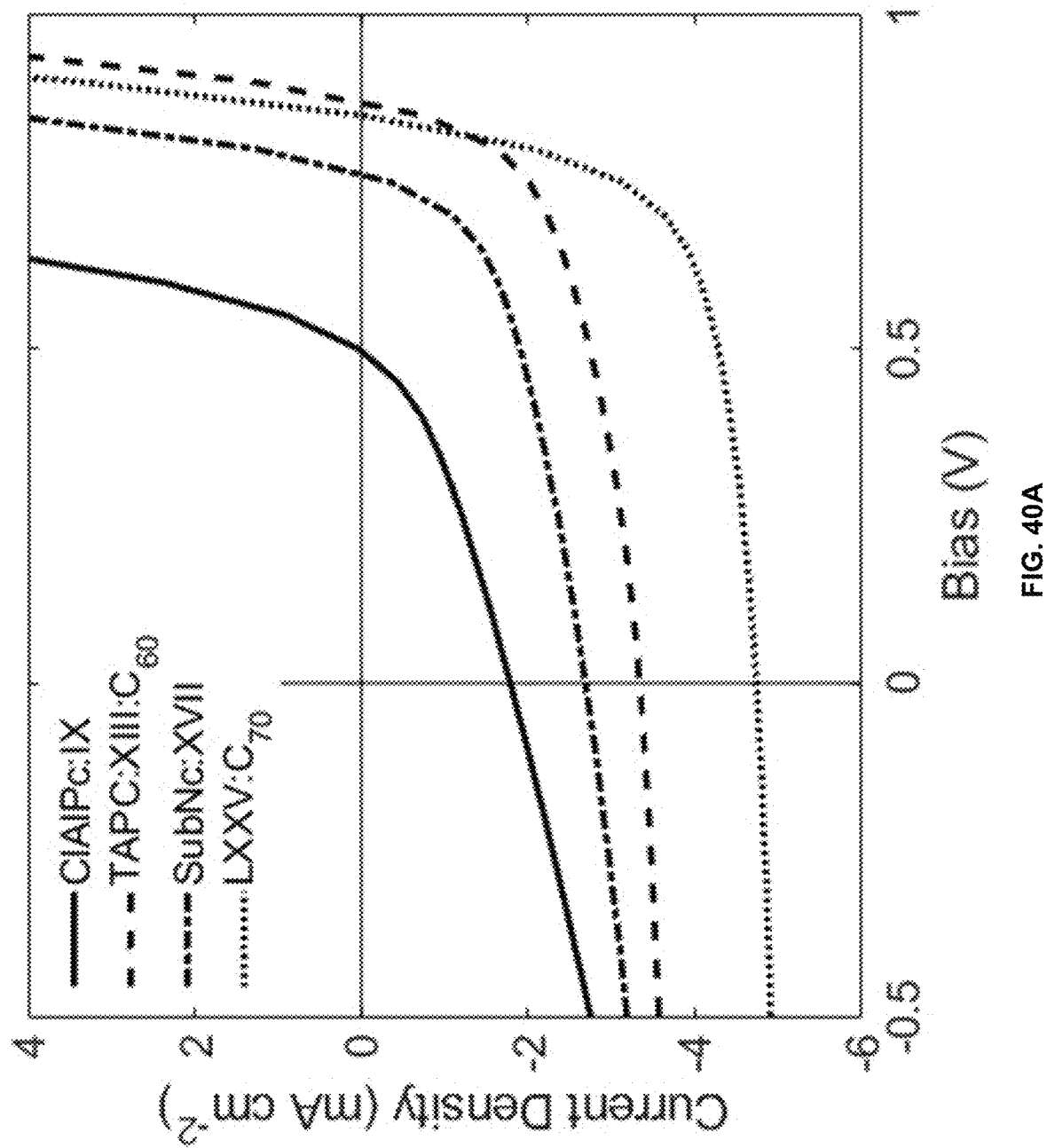
FIG. 40A provides a plot showing current density-voltage curves for the photovoltaic devices illustrated in FIGS. 39A-39D.
Figure 40B:
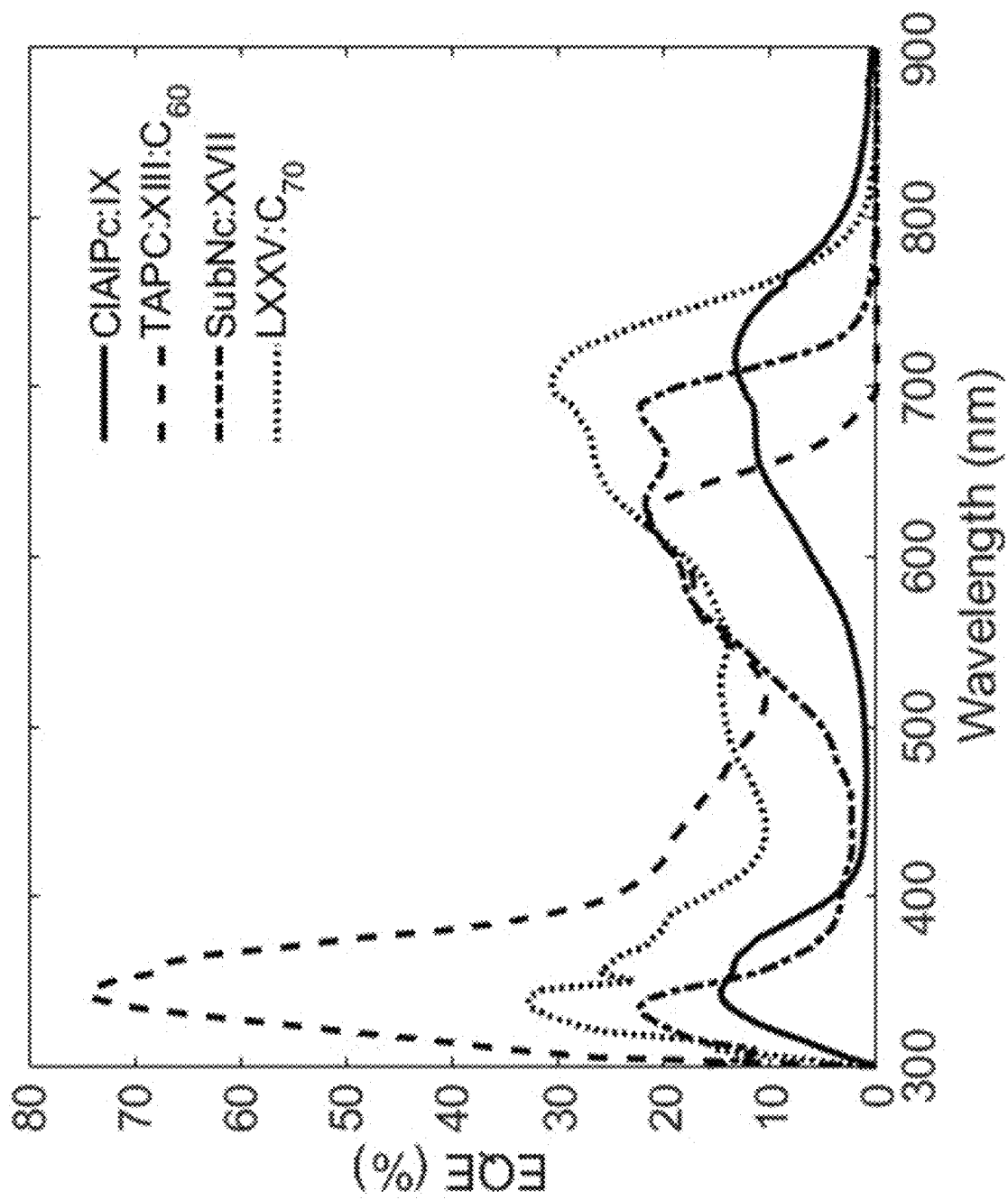
FIG. 40B provides a plot showing external quantum efficiency curves for the photovoltaic devices illustrated in FIGS. 39A-39D.
Figure 40C:
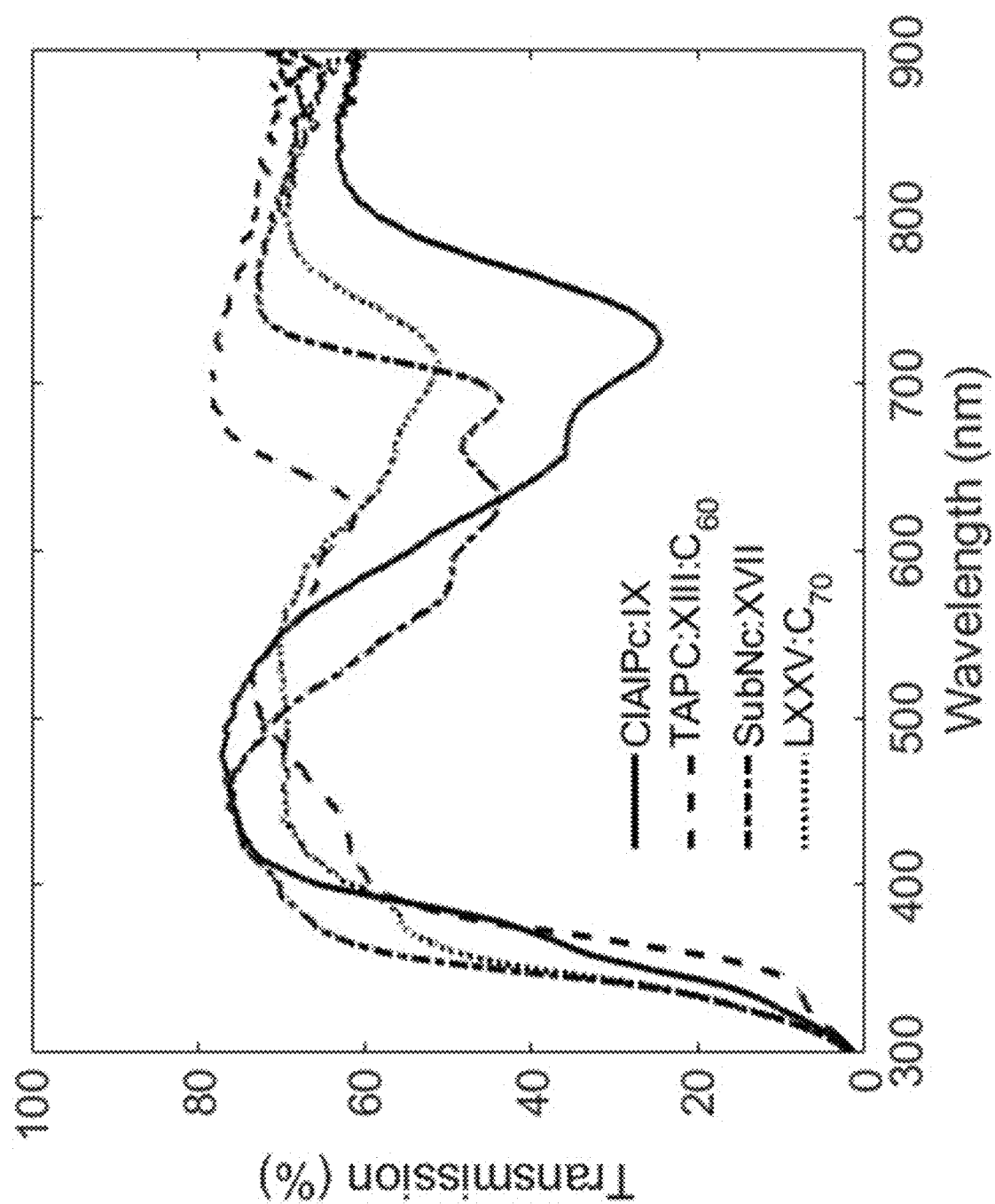
FIG. 40C provides a plot showing transmission spectra for the photovoltaic devices illustrated in FIGS. 39A-39D.

FIGS. 40A-C illustrate current density-voltage curves (FIG. 40A), external quantum efficiency (EQE) curves (FIG. 40B), and transmission spectra (FIG. 40C) for the device structures shown in FIGS. 39A-39D. Specifically, the solid lines correspond to device structure 3900, the dashed lines correspond to device structure 3901, the dash-dotted lines correspond to device structure 3902, and the dotted lines correspond to device structure 3903. As can be seen in FIG. 40A, all devices show strong rectification in forward-bias and photocurrent and power production under 1-sun illumination (AM1.5G spectrum) conditions. The photocurrents are confirmed to have significant contributions from the active compounds IX, XIII, XVII, and LXXV based on the EQE spectra in FIG. 40B and their corresponding absorption coefficients in FIG. 38. The transparency of the photovoltaic devices is confirmed by their transmission spectra in FIG. 40C.

Table 1 tabulates the electrical and optical device performance data from the current density-voltage curves (FIG. 40A) and transmission spectra (FIG. 40C) for the device structures shown in FIGS. 39A-39D. Specifically, the data for compound IX corresponds to device structure 3900, the data for compound XIII corresponds to device structure 3901, the data for compound XVII corresponds to device structure 3902, and the data for compound LXXV corresponds to device structure 3903. The core-disrupted or indandione-containing molecules are listed in terms of their function in the active layer (electron donor or electron acceptor), the other active materials paired with them, and the device parameters short-circuit current density ($J_{sc}$), open-circuit voltage ($V_{oc}$), fill factor (FF), power conversion efficiency (PCE), and average visible transmittance ($T_{vis}$). As can be seen, all devices 3900-3903 exhibit $T_{vis}$ values above 50%, highlighting the compatibility of the example molecules for transparent photovoltaics.

TABLE 1

Device Performance Summary

| Compound | Function | Pairing | $J_{sc}$ (mA cm$^{-2}$) | $V_{OC}$ (V) | FF | PCE (%) | $T_{vis}$ (%) |
|---|---|---|---|---|---|---|---|
| IX | Acceptor | ClAlPc | 1.79 | 0.50 | 0.36 | 0.32 | 65.9 |
| XIII | Donor | TAPC, $C_{60}$ | 3.33 | 0.87 | 0.54 | 1.57 | 68.4 |
| XVII | Acceptor | SubNc | 2.68 | 0.76 | 0.48 | 0.99 | 57.3 |
| LXXV | Donor | $C_{70}$ | 4.74 | 0.85 | 0.63 | 2.57 | 67.9 |

STATEMENTS REGARDING INCORPORATION BY REFERENCE AND VARIATIONS

All references throughout this disclosure, for example patent documents including issued or granted patents or equivalents; patent application publications; and non-patent literature documents or other source material; are hereby incorporated by reference herein in their entireties, as though individually incorporated by reference.

All patents and publications mentioned in this disclosure are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'".

Every formulation or combination of components described or exemplified can be used to practice the invention, unless otherwise stated. Specific names of materials are intended to be exemplary, as it is known that one of skill in the art can name the same material differently. It will be appreciated that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this disclosure. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Abbreviations that may be utilized in the present specification include:
p-6P: 1-phenyl-4-[4-[4-(4-phenylphenyl)phenyl]phenyl]benzene
TPBi: 2,2',2"-(1,3,5-Benzinetriyl)-tris(1-phenyl-1-H-benzimidazole)
ClAlPc: Chloro(29H,31H-phthalocyaninato)aluminum
SubNc: Chloro(subphthalocyaninato)boron
TAPC: 4,4'-Cyclohexylidenebis[N,N-bis(4-methylphenyl)benzenamine]

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred examples and embodiments and optional features, modification and variation of the concepts herein disclosed may be resorted to by those skilled in the art, and that such modifications and variations are considered within the scope of this disclosure as defined by the appended claims.

What is claimed is:

1. A photoactive compound having the formula:

A-D-A,

A-pi-D-A, or

A-pi-D-pi-A, wherein A is an electron acceptor moiety, wherein pi is a π-bridging moiety, wherein D is an electron donor moiety comprising a central core and one or more planarity disrupting moieties, Z, wherein each Z is bonded to a quaternary carbon center, Q, of the central core to form one or more Q-Z-Z moieties,

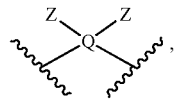

wherein the central core has a planar structure, wherein the one or more planarity disrupting moieties, Z, are conformationally locked in a configuration out of plane to the central core, and wherein at least one of the one or more Q-Z-Z moieties comprises

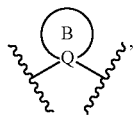

wherein B comprises one or more of the following groups or a heterocyclic analog thereof:

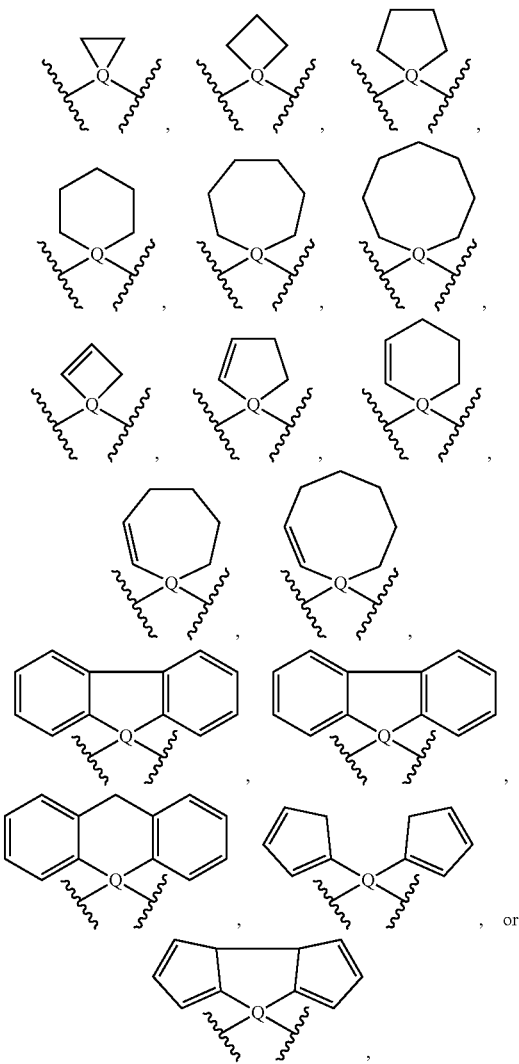

each of which is unsubstituted or substituted with one or more methyl, ethyl or fluoro, or trifluoromethyl groups.

2. The photoactive compound of claim 1, having a molecular weight of from 250 atomic mass units to 1200 atomic mass units.

3. The photoactive compound of claim 1, characterized by or exhibiting a sublimation purification yield by mass of 20% or greater.

4. The photoactive compound of claim 1, having a thermal decomposition temperature of from 200° ° C. to 500° C.

5. The photoactive compound of claim 1, exhibiting a bandgap of 0.5 eV to 4.0 eV.

6. The photoactive compound of claim 1, exhibiting a sublimation temperature of from 150° C. to 450° C. at pressures of from 0.2 Torr to 10-7 Torr.

7. The photoactive compound of claim 1, wherein the central core comprises an aromatic, heteroaromatic, polycyclic aromatic, or polycyclic heteroaromatic moiety including one or more 5-membered rings, one or more 6-membered rings, or a combination of one or more 5-membered rings and one or more 6-membered rings.

8. The photoactive compound of claim 1, wherein the central core comprises one or more quaternary carbons.

9. The photoactive compound of claim 1, wherein D comprises or has a formula of

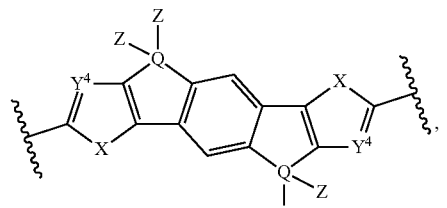

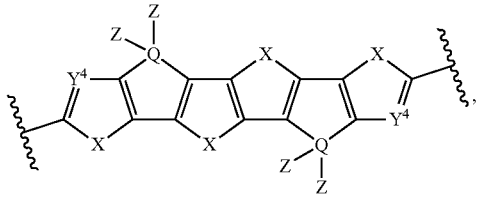

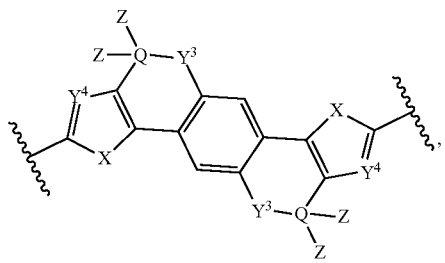

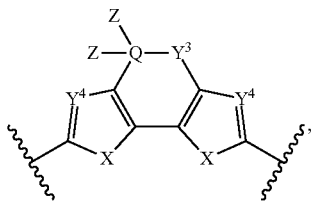

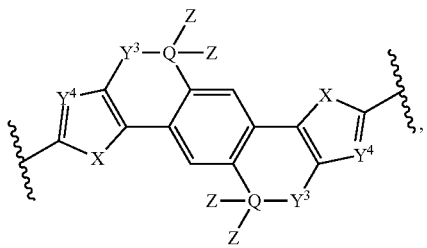

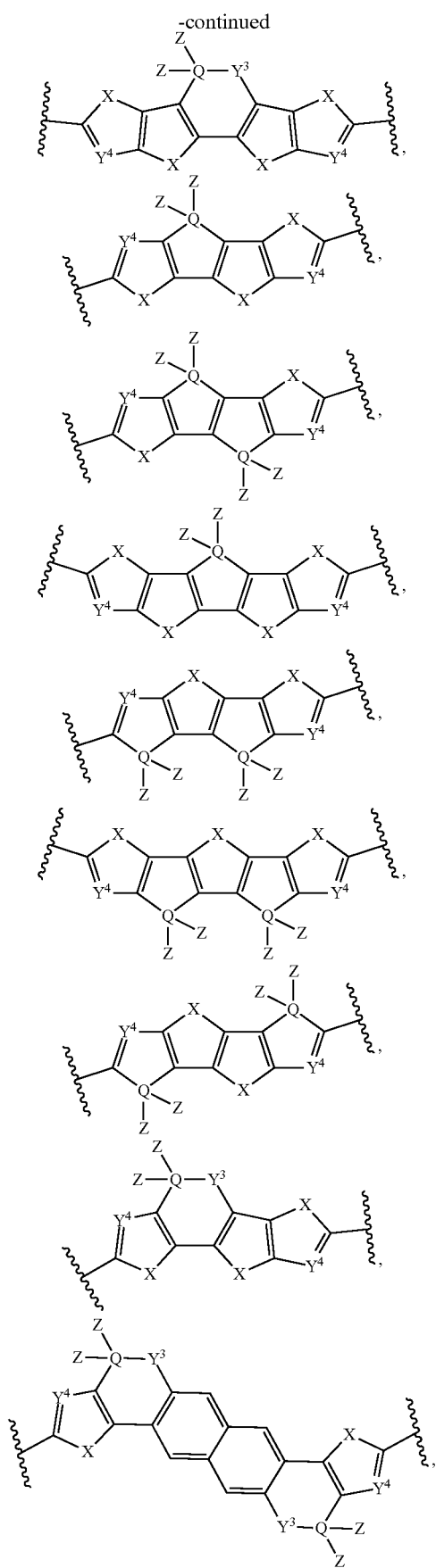
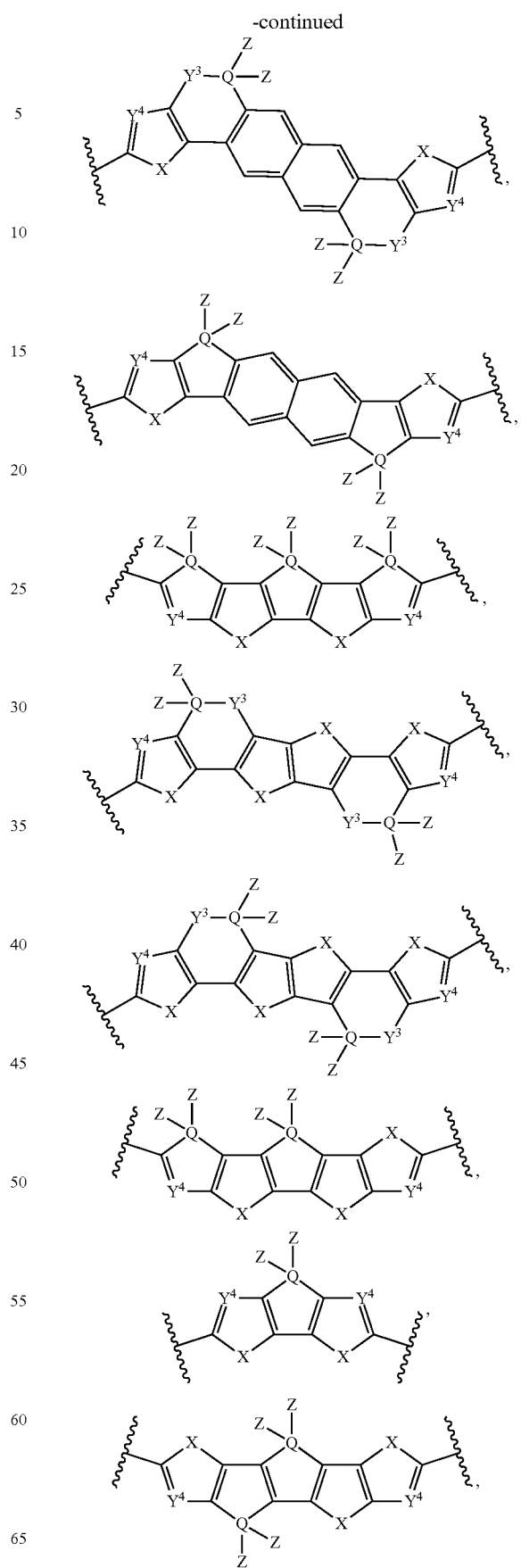

861

-continued

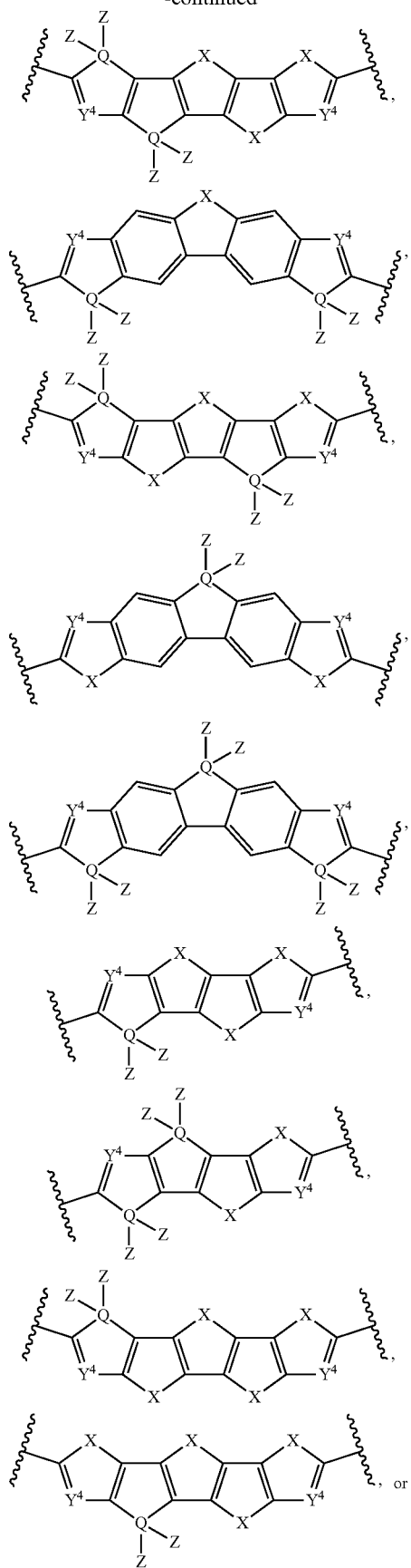

862

-continued

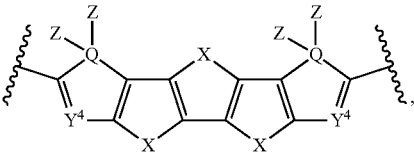

wherein Z is a planarity disrupting moiety, wherein each X is independently O, S, Se, NH, $NR^N$, $CH_2$, $C(R^N)_2$, $Si(R^N)_2$, or $Ge(R^N)_2$, wherein $R^N$ is a branched, cyclic, or straight chain alkyl or ester group having a molecular weight of from 15 amu to 100 amu, wherein $Y^3$ is independently O or S, and wherein $Y^4$ is independently CH, N, or $CR^N$.

10. The photoactive compound of claim 1,
wherein each Z is independently an unsubstituted or methyl, ethyl, fluoro, or trifluoromethyl substituted cycloalkyl group, an unsubstituted or methyl, ethyl, fluoro, or trifluoromethyl substituted cycloalkenyl group, an unsubstituted or methyl, ethyl, fluoro, or trifluoromethyl substituted cyclopentadienyl group, or an unsubstituted or methyl, ethyl, fluoro, or trifluoromethyl substituted phenyl group; or wherein ring group B comprises an unsubstituted or methyl, ethyl, fluoro, or trifluoromethyl substituted cycloalkyl group, an unsubstituted or methyl, ethyl, fluoro, or trifluoromethyl substituted cycloalkenyl group, an unsubstituted or methyl, ethyl, fluoro, or trifluoromethyl substituted cyclopentadienyl group, or an unsubstituted or methyl, ethyl, fluoro, or trifluoromethyl substituted phenyl group; or wherein ring group B comprises fused 5-membered rings that are unsubstituted or methyl, ethyl, fluoro, or trifluoromethyl substituted, fused 6-membered rings that are unsubstituted or methyl, ethyl, fluoro, or trifluoromethyl substituted, or fused 5-membered and 6-membered rings that are unsubstituted or methyl, ethyl, fluoro, or trifluoromethyl substituted; or wherein ring group B comprises a heterocyclic group or a fused heterocyclic group.

11. The photoactive compound of claim 1, wherein each A independently comprises:

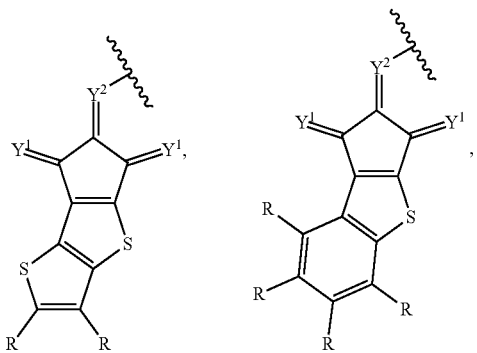

863
-continued
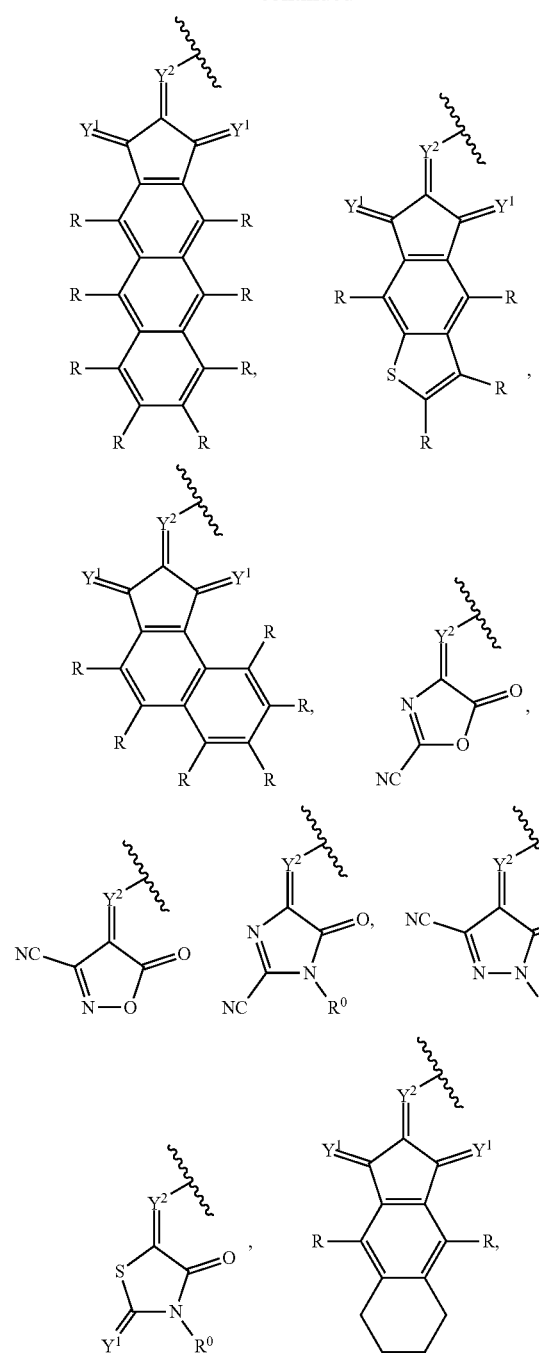
864
-continued
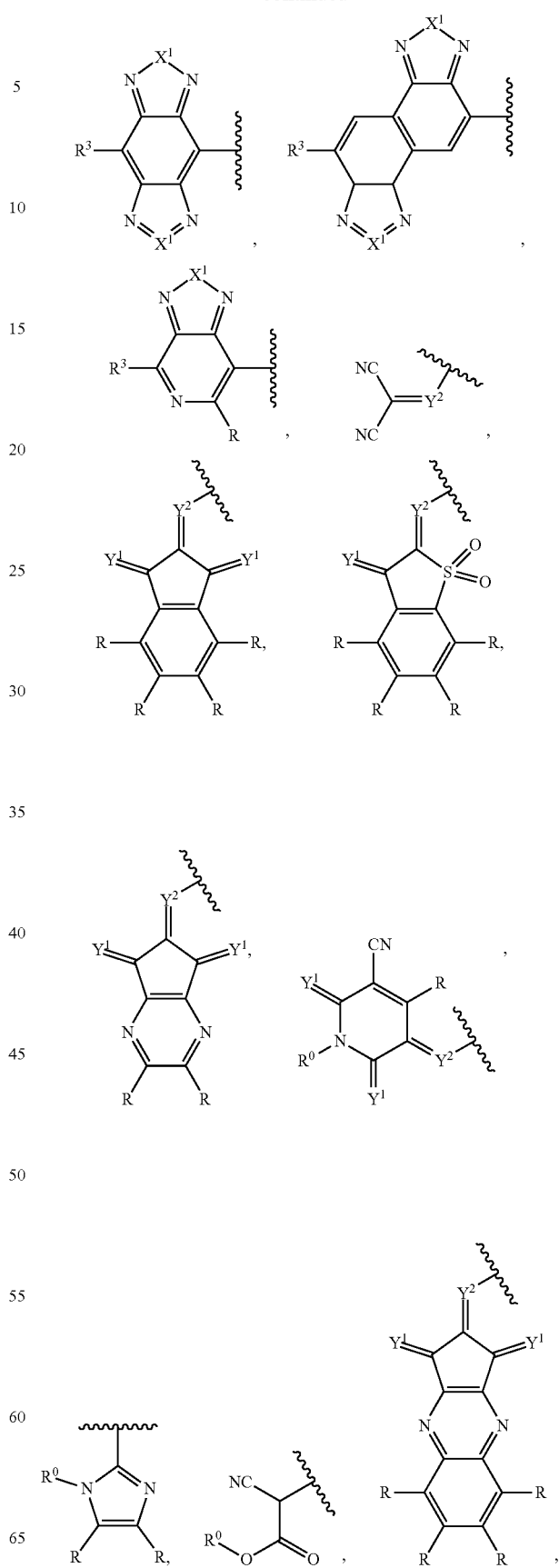

-continued

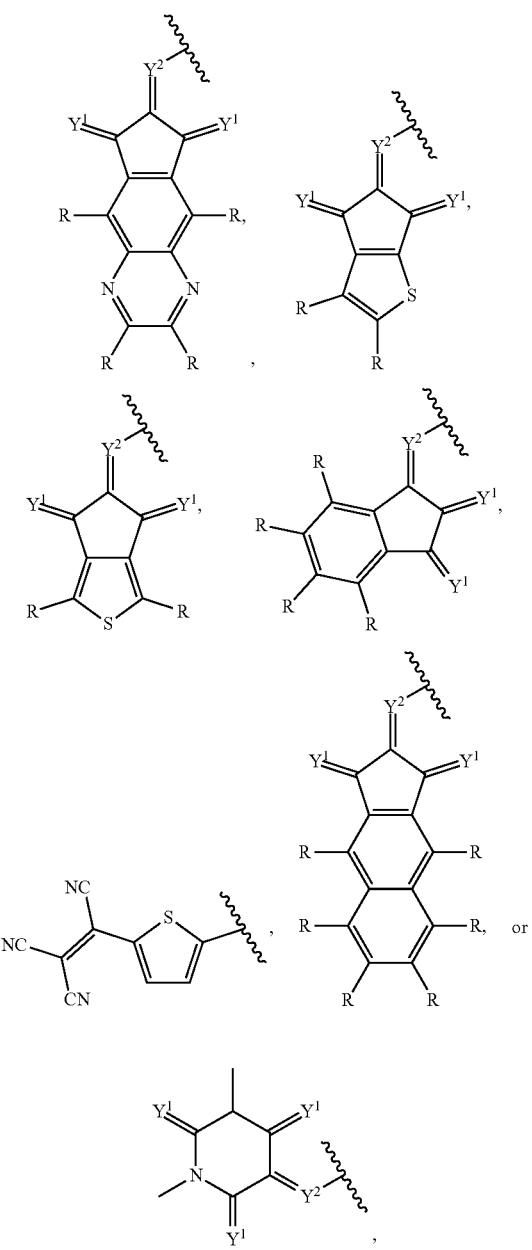

wherein each R is independently H, F, Cl, Br, I, $CH_3$, $CF_3$, or CN, wherein each $Y^1$ is independently $C(CN)_2$, O, S, or cyanoimine, and wherein $Y^2$ is CH or N or $Y^2$ is not present and the A is connected to a D moiety or a pi moiety by a double bond, wherein each $X^1$ is independently O, S, Se, or $NR^O$, wherein each $R^3$ is CN or $C(CN)_2$, and wherein $R^O$ is a branched or straight chain alkyl group having a molecular weight of from 15 amu to 100 amu.

12. The photoactive compound of claim 1, wherein at least one A comprises an indanone, an indandione, an indanthione, an indandithione, a dicyanomethyleneindanone, a bis(dicyanomethylidene)indan, or an aryl-substituted indanone, indandione, indanthione, indandithione, dicyanomethyleneindanone, or bis(dicyanomethylidene)indan.

13. The photoactive compound of claim 1, wherein at least one A comprises an imine bond linking the electron acceptor moiety to the electron donor moiety or the π-bridging moiety.

14. The photoactive compound of claim 1, wherein each pi independently comprises:

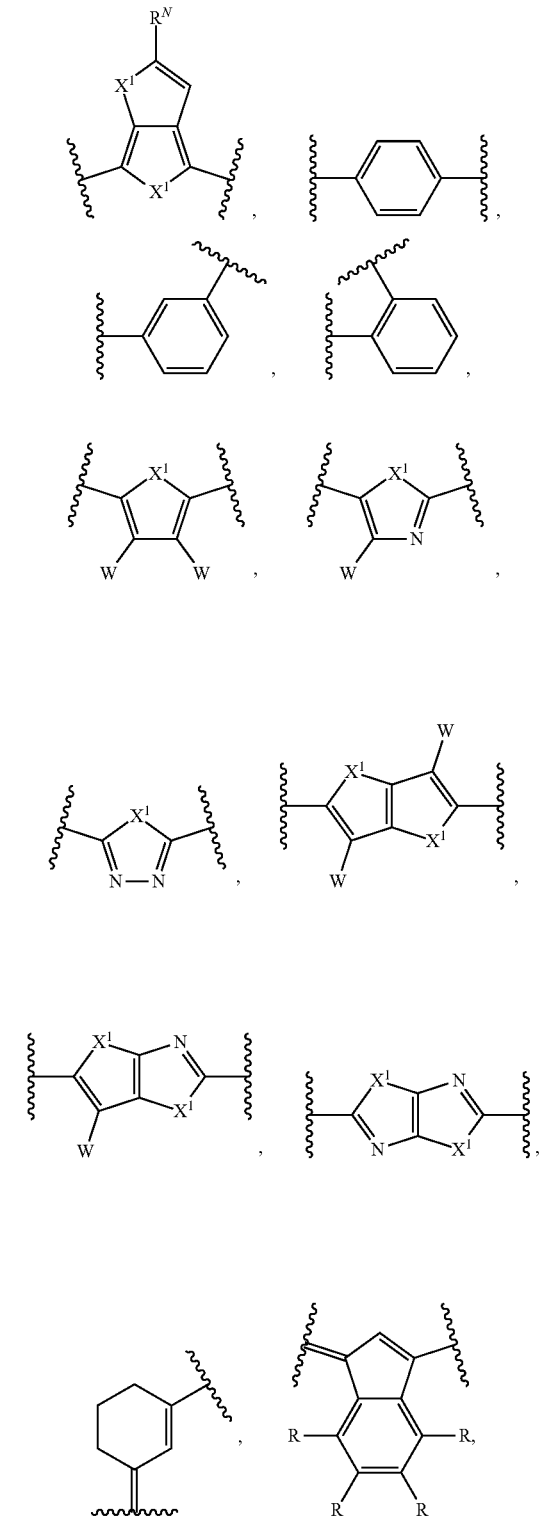

867
-continued

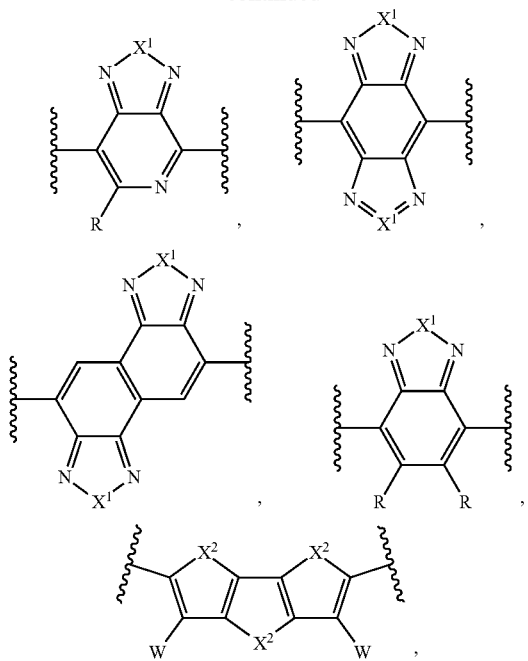

868
-continued

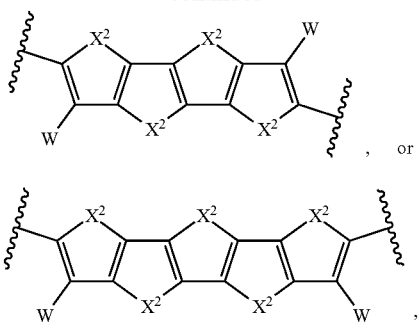

wherein each $X^1$ is independently O, S, Se, or $NR^N a$, wherein each R is independently H, F, Cl, Br, I, $CH_3$, $CF_3$, or CN, wherein each $X^2$ is independently O, S, Se, NH, $NR^N$, $CH_2$, or $C(R^N)_2$, wherein each W is independently H, F, or a branched or straight chain C1-C8 alkyl group or a branched or straight chain C1-C8 alkoxy group, and wherein each $R^N$ is independently a branched, cyclic, or straight chain alkyl or ester group having a molecular weight of from 15 amu to 100 amu.

15. The photoactive compound of claim 1, having a formula of

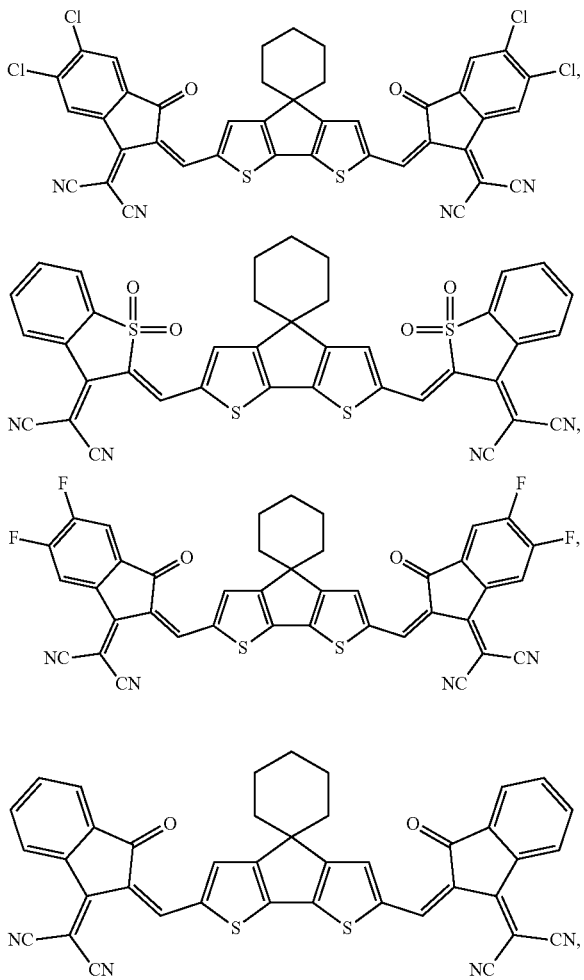

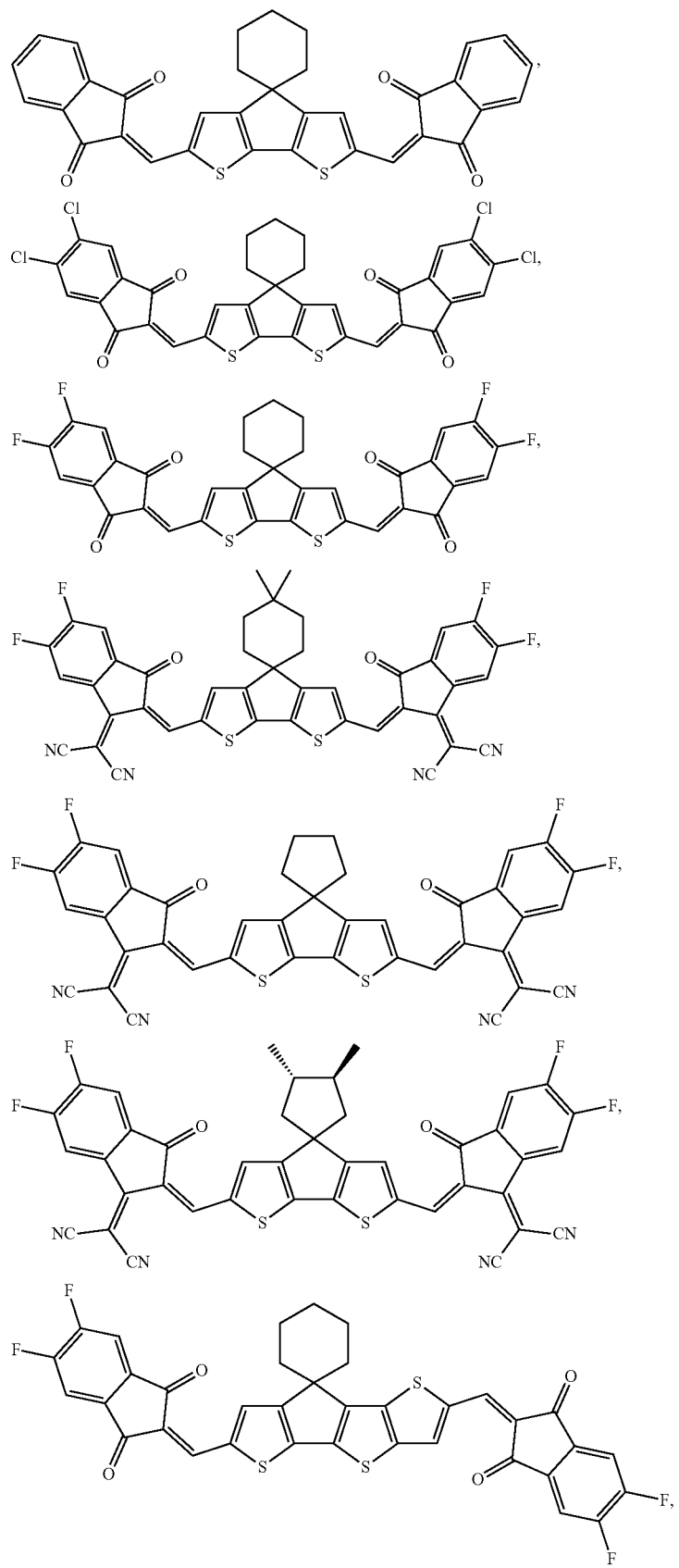

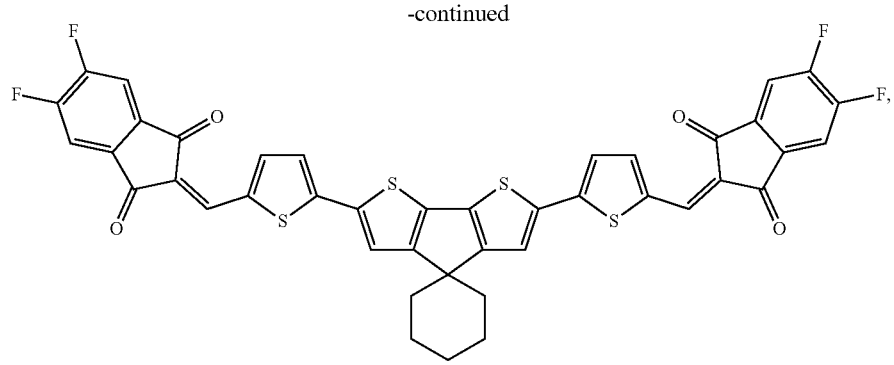
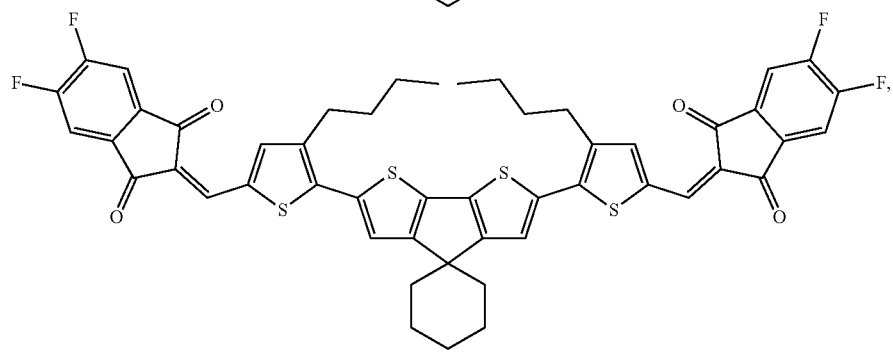
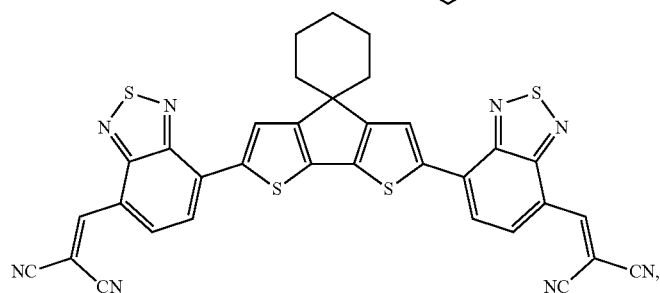
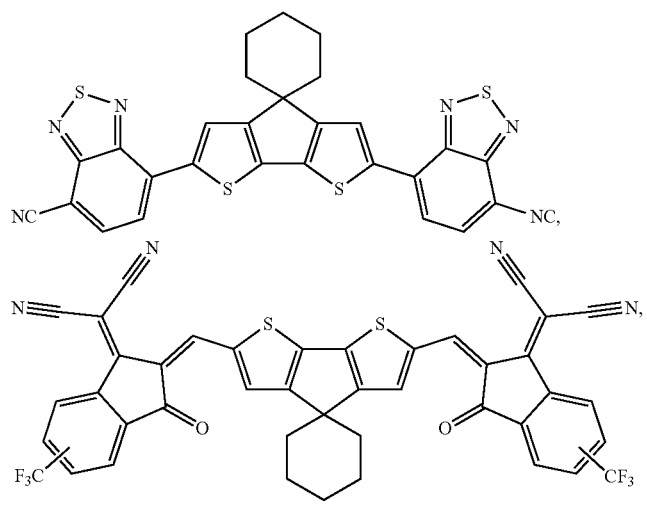
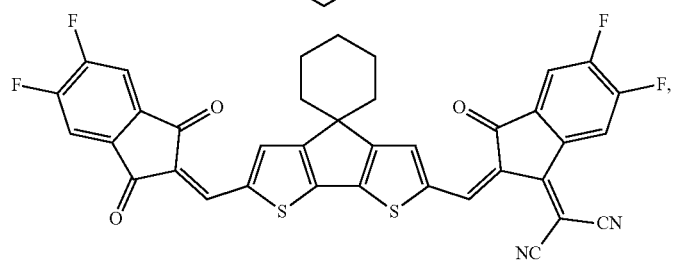

-continued
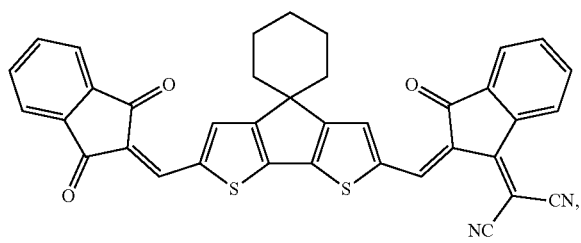
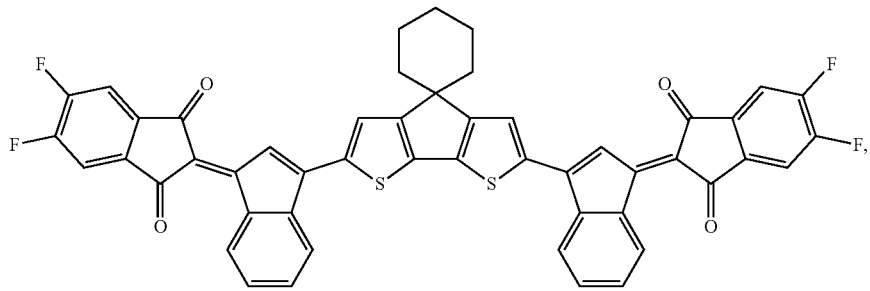
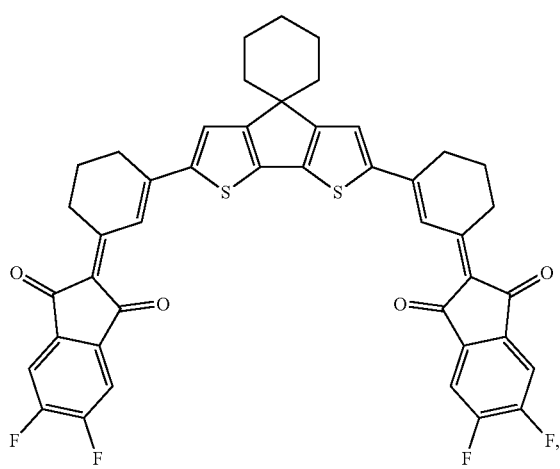
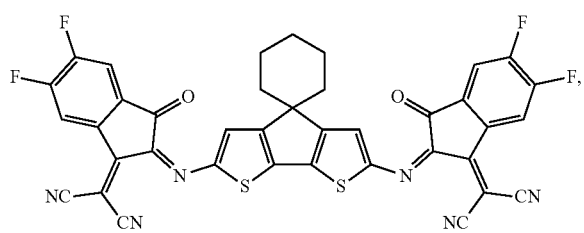
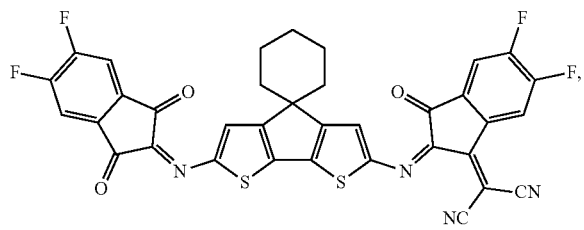
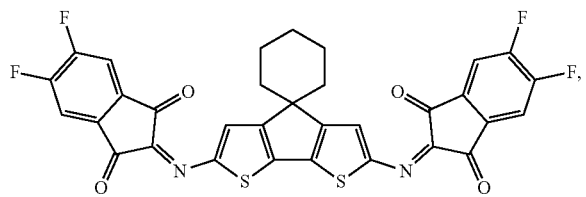

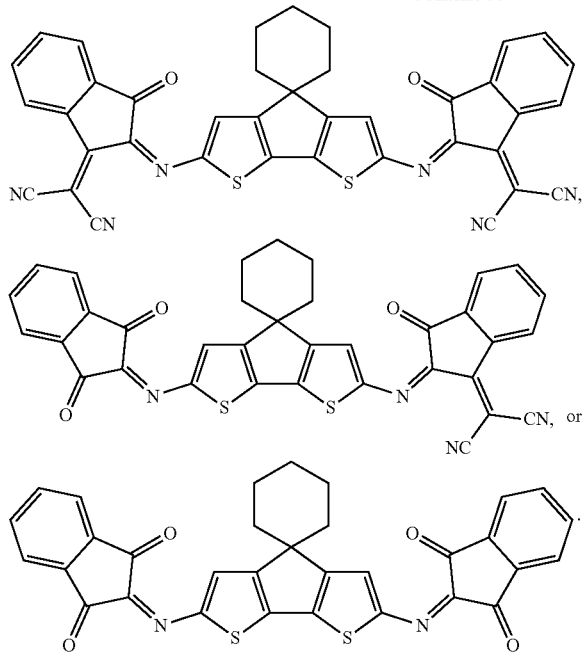

16. A photovoltaic device comprising:
a substrate;
a first electrode coupled to the substrate;
a second electrode above the first electrode;
a first photoactive layer between the first electrode and the second electrode, wherein the first photoactive layer comprises the photoactive compound of claim 1; and
a second photoactive layer between the first electrode and the second electrode, wherein the second photoactive layer comprises a counterpart electron donor material or a counterpart electron acceptor material, and wherein the first photoactive layer and the second photoactive layer correspond to separate photoactive layers, partially mixed photoactive layers, or a fully mixed photoactive layer.

17. The photovoltaic device of claim 16, wherein one or more or all of the substrate, the first electrode, the second electrode, the first photoactive layer, or the second photoactive layer is visibly transparent.

18. The photovoltaic device of claim 16, wherein one or more of the substrate, the first electrode, the second electrode, the first photoactive layer, or the second photoactive layer is partially transparent or opaque.

19. The photovoltaic device of claim 16, wherein the photoactive compound of claim 1 is an electron acceptor compound and wherein the second photoactive layer comprises a counterpart electron donor material.

20. The photovoltaic device of claim 16, wherein the photoactive compound of claim 1 is an electron donor compound and wherein the second photoactive layer comprises a counterpart electron acceptor material.

21. A method of making a photovoltaic device, the method comprising:
providing a substrate;
providing a first electrode coupled to the substrate;
depositing a photoactive layer over the first electrode and the substrate by a vapor deposition technique, the photoactive layer comprising the photoactive compound of claim 1; and
providing a second electrode over the photoactive layer.

22. The method of claim 21, wherein depositing the photoactive layer comprises depositing the photoactive compound using a thermal evaporation process.

23. The method of claim 21, wherein one or more or all of the substrate, the first electrode, the second electrode, or the photoactive layer is visibly transparent.

24. The method of claim 21, wherein one or more of the substrate, the first electrode, the second electrode, or the photoactive layer is partially transparent or opaque.

* * * * *